(12) United States Patent
Ishida et al.

(10) Patent No.: US 12,239,643 B2
(45) Date of Patent: *Mar. 4, 2025

(54) THERAPEUTIC AGENT FOR INFLAMMATORY DISEASES, AUTOIMMUNE DISEASES, FIBROTIC DISEASES, AND CANCER DISEASES

(71) Applicant: MEIJI SEIKA PHARMA CO., LTD., Tokyo (JP)

(72) Inventors: Natsuki Ishida, Yokohama (JP); Yuji Tabata, Yokohama (JP); Takashi Matsuhira, Yokohama (JP); Keiji Tamura, Yokohama (JP); Takeru Yamakawa, Tokyo (JP); Satoshi Isshiki, Odawara (JP); Yoshinari Wakiyama, Odawara (JP); Shohei Ouchi, Yokohama (JP)

(73) Assignee: MEIJI SEIKA PHARMA CO., LTD., Tokyo (JP)

( * ) Notice: Subject to any disclaimer, the term of this patent is extended or adjusted under 35 U.S.C. 154(b) by 963 days.

This patent is subject to a terminal disclaimer.

(21) Appl. No.: 17/255,560

(22) PCT Filed: Jun. 27, 2019

(86) PCT No.: PCT/JP2019/025526
§ 371 (c)(1),
(2) Date: Dec. 23, 2020

(87) PCT Pub. No.: WO2020/004521
PCT Pub. Date: Jan. 2, 2020

(65) Prior Publication Data
US 2021/0315892 A1  Oct. 14, 2021

(30) Foreign Application Priority Data
Jun. 27, 2018  (JP) .................... 2018-121442

(51) Int. Cl.
*A61K 31/4995* (2006.01)
*A61K 31/439* (2006.01)
(Continued)

(52) U.S. Cl.
CPC ........ *A61K 31/4995* (2013.01); *A61K 31/439* (2013.01); *A61K 31/5386* (2013.01);
(Continued)

(58) Field of Classification Search
CPC .................................................. A61K 31/439
See application file for complete search history.

(56) References Cited

U.S. PATENT DOCUMENTS 5,631,257 A   5/1997 Iwamatsu et al.
6,037,342 A   3/2000 Sato et al.
(Continued)

FOREIGN PATENT DOCUMENTS

JP  6-345744 A   12/1994
JP  10-29987 A   2/1998
(Continued)

OTHER PUBLICATIONS

Communication, dated Jan. 7, 2021, issued in International Application No. PCT/JP2019/025526.
International Search Report issued Aug. 20, 2019 in International Application No. PCT/JP2019/025526.
Clark et al., "Discovery of Novel-2((Pyridin-3-yloxy)methyl)piperazines as α7 Nicotinic Acetylcholine Receptor Modulators for the Treatment of Inflammatory Disorders", Journal of Medicinal Chemistry, 2014, vol. 57, pp. 3966-3983.
Halpin, "ABCD of the phosphodiesterase family: interaction and differential activity in COPD", International Journal of COPD, 2008, vol. 3, No. 4, pp. 543-561.
(Continued)

*Primary Examiner* — John S Kenyon
*Assistant Examiner* — Rehana Ismail
(74) *Attorney, Agent, or Firm* — Sughrue Mion, PLLC

(57) ABSTRACT

A therapeutic agent for treating at least one disease selected from the group consisting of inflammatory diseases, autoimmune diseases, fibrotic diseases, and cancer diseases, comprising: at least one selected from the group consisting of a compound represented by the following general formula (1) and pharmacologically acceptable salts thereof as an active ingredient.

[Chem. 1]

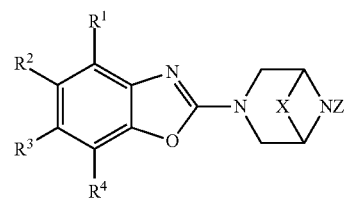

(1)

[In the formula (1),
$R^1$ and $R^2$ may be the same or different and each represents a hydrogen atom, a halogen atom, a hydroxyl group, a carboxy group, a cyano group, an optionally substituted $C_{1-6}$ alkyl group et al.; $R^3$ represents a hydrogen atom; $R^4$ represents an optionally substituted 4- to 10-membered monocyclic heterocyclic group containing 1 to 4 heteroatoms selected from an oxygen atom, a nitrogen atom, and a sulfur atom; X represents a group represented by the following formula: —$CH_2$—, —$CH_2$—$CH_2$—, —$CH_2$—$CH_2$—$CH_2$—, or —$CH_2$—O—$CH_2$—; and Z represents a hydrogen atom or a hydroxyl group.]

7 Claims, No Drawings

(51) Int. Cl.

| | |
|---|---|
| *A61K 31/5386* | (2006.01) |
| *A61P 17/04* | (2006.01) |
| *A61P 19/02* | (2006.01) |
| *A61P 19/04* | (2006.01) |
| *A61P 29/00* | (2006.01) |
| *A61P 35/00* | (2006.01) |
| *A61P 35/02* | (2006.01) |
| *A61P 37/06* | (2006.01) |

(52) U.S. Cl.
CPC ............... *A61P 17/04* (2018.01); *A61P 19/02* (2018.01); *A61P 19/04* (2018.01); *A61P 29/00* (2018.01); *A61P 35/00* (2018.01); *A61P 35/02* (2018.01); *A61P 37/06* (2018.01)

(56) References Cited

U.S. PATENT DOCUMENTS

| | | | |
|---|---|---|---|
| 6,297,246 | B1 | 10/2001 | Sato et al. |
| 6,333,328 | B1 | 12/2001 | Sato et al. |
| 6,403,791 | B1 | 6/2002 | Dyke et al. |
| 10,669,283 | B2 * | 6/2020 | Tamura ................ C07D 471/08 |
| 11,512,091 | B2 * | 11/2022 | Kumura ................ A61P 17/14 |
| 2001/0016579 | A1 | 8/2001 | Sato et al. |
| 2003/0013730 | A1 | 1/2003 | Sato et al. |
| 2016/0159783 | A1 | 6/2016 | Kikuchi et al. |

FOREIGN PATENT DOCUMENTS

| | | |
|---|---|---|
| JP | 2003-522771 A | 7/2003 |
| JP | 2018-16544 A | 2/2018 |
| WO | 2015/005429 A1 | 1/2015 |
| WO | 2018/124060 A1 | 7/2018 |
| WO | 2020/004517 A1 | 1/2020 |

OTHER PUBLICATIONS

Dyke et al., "Update on the therapeutic potential of PDE4 inhibitors", Expert Opin. Investig. Drugs, 2002, vol. 11, No. 1, pp. 1-13.
Huang et al., "Preferential inhibition of human phosphodiesterase 4 by ibudilast", Life Sciences, 2006, vol. 78, pp. 2663-2668.
Sadrai et al., "PDE4 Inhibition Suppresses IL-17-Associated Immunity in Dry Eye Disease", Investigative Ophthalmology & Visual Science, Jun. 2012, vol. 53, No. 7, pp. 3584-3591.
Cortijo et al., "Roflumilast, a phosphodiesterase 4 inhibitor, alleviates bleomycin-induced lung injury", British Journal of Pharmacology, 2009, vol. 156, pp. 534-544.
Selige et al., "The Differential Impact of PDE4 Subtypes in Human Lung Fibroblasts on Cytokine-Induced Proliferation and Myofibroblast Conversion", Journal of Cellular Physiology, 2011, vol. 226, pp. 1970-1980.
Maier et al., "Inhibition of phosphodiesterase 4 (PED4) reduces dermal fibrosis by interfering with the release of interleukin-6 from M2 macrophages", Ann Rheum Dis, 2017, vol. 76, pp. 1133-1141.
Moellmann et al., "The PDE4 inhibitor roflumilast reduces weight gain by increasing energy expenditure and leads to improved glucose metabolism", Diabetes Obes Metab, 2017, vol. 19, pp. 496-508.
Nio et al., "Phosphodiesterase 4 inhibitor and phosphodiesterase 5 inhibitor combination therapy has antifibrotic and anti-inflammatory effects in mdx mice with Duchenne muscular dystrophy", The FASEB Journal, 2017, vol. 31, pp. 5307-5320.
Tsunoda et al., "Inhibition of Phosphodiesterase-4 (PDE4) activity triggers luminal apoptosis and AKT dephosphorylation in a 3-D colonic-crypt model", Molecular Cancer, 2012, vol. 11, No. 46, pp. 1-12.
Pullamsetti et al., "Phosphodiesterase-4 promotes proliferation and angiogenesis of lung cancer by crosstalk with HIF", Oncogene, 2013, vol. 32, pp. 1121-1134.
Sengupta et al., "Treating brain tumors with PDE4 inhibitors", Trends in Pharmacological Sciences, Jun. 2011, vol. 32, No. 6, pp. 337-344.
Ogawa et al., "Inhibition of PDE4 phosphodiesterase activity induces growth suppression, apoptosis, glucocorticoid sensitivity, p53 and p21WAF1/CIP1 proteins in human acute lymphoblastic cells", Blood, 2002, vol. 89, pp. 3390-3397.
Park et al., "Resveratrol Ameliorates Aging-Related Metabolic Phenotypes by Inhibiting cAMP Phosphodiesterases", Cell, vol. 148, pp. 421-433.
Richter et al., "PDE4 as a target for cognition enhancement", Expert Opin Ther Targets, Sep. 2013, vol. 17, No. 9, pp. 1011-1027.
Spina, "PDE4 inhibitors: current status", British Journal of Pharmacology, 2008, vol. 155, pp. 308-315.
Rolan et al., "Ibudilast : a review of its pharmacology, efficacy and safety in respiratory and neurological disease", Expert Opinion on Pharmacotherapy, 2009, vol. 10, pp. 2897-2904.
Sakuma et al., "Effects of Topical Application of Ibudilast for Seasonal Allergic Conjunctivitis in Patients Wearing Soft Contact Lenses", Eye & Contact Lens, 2009, vol. 5, pp. 251-254.
Goodman et al., "Ibudilast for the treatment of multiple sclerosis", Expert Opinion on Investigational Drugs, 2016, vol. 25, No. 10, pp. 1231-1237.
Rabe et al., "Update on roflumilast, a phosphodiesterase 4 inhibitor for the treatment of chronic obstructive pulmonary disease", British Journal of Pharmacology, 2011, vol. 163, pp. 53-67.
Maurice et al., "Advances in targeting cyclic nucleotide phosphodiesterases", Nature Reviews, Apr. 2014, vol. 13, pp. 290-314.
Wouters et al., "Effect of the Phosphodiesterase 4 Inhibitor Roflumilast on Glucose Metabolism in Patients with Treatment-Naive, Newly Diagnosed Type 2 Diabetes Mellitus", J Clin Endocrinol Metab, Sep. 2012, vol. 97, No. 9, pp. #1720-E1725.
Poole et al., "Apremilast: First Global Approval", Drugs, 2014, vol. 74, pp. 825-837.
Shrager, Summer Meeting of the American Academy of Dermatology (AAD), 2016, Abstract 2070.
Huff et al., "Repigmentation of Tenacious Vitiligo on Apremilast", Case Reports in Dermatological Medicine, 2017, vol. 2017, pp. 1-3, Article ID 2386234.
Weber et al., "Apremilast in the treatment of moderate to severe hidradenitis suppurativa: A case series of 9 patients", J Am Acad Dermatol, 2017, vol. 76, No. 6, pp. 1189-1191.
Hafner et al., "Apremilast Is Effective in Lichen Planus Mucosae-Associated Stenotic Esophagitis", Case Rep Dermatol, 2016, vol. 8, pp. 224-226.
Paller et al., "Efficacy and safety of crisaborole ointment, a novel, nonsteroidal phosphodiesterase 4 (PDE4) inhibitor for the topical treatment of atopic dermatitis (AD) in children and adults", J Am Acad Dermatol, 2016, vol. 75, No. 3, pp. 494-503.
Kumar et al., "Phosphodiesterase 4-targeted treatments for autoimmune diseases", BMC Medicine, 2013, vol. 11, No. 96, pp. 1-8.
Communication, dated Jan. 24, 2022, issued by the Indian Patent Office in Indian Application No. 202037055282.

* cited by examiner

THERAPEUTIC AGENT FOR INFLAMMATORY DISEASES, AUTOIMMUNE DISEASES, FIBROTIC DISEASES, AND CANCER DISEASES

CROSS-REFERENCE TO RELATED APPLICATIONS

This application is a National Stage of International Application No. PCT/JP2019/025526, filed Jun. 27, 2019, which claims priority under U.S.C. § 119(a) to Japanese Patent Application No. JP2018-121442, filed Jun. 27, 2018.

TECHNICAL FIELD

The present invention relates to therapeutic agents for inflammatory diseases, autoimmune diseases, fibrotic diseases, and cancer diseases, and more specifically relates to therapeutic agents for inflammatory diseases, autoimmune diseases, fibrotic diseases, and cancer diseases containing compounds having PDE4 inhibitory activity.

RELATED BACKGROUND ART

Phosphodiesterase (PDE) is known as an important enzyme which inactivates cyclic nucleotides (cAMP and cGMP) being second messengers by hydrolyzing one side of phosphodiester bonds present in the cyclic nucleotides. PDEs which break down cAMP are classified into several isoforms. Among these, type IV phosphodiesterase (PDE4) is one of the principal cAMP-breaking enzymes present in many inflammatory cells, immune cells, blood, and organs such as the brain and the lungs (Non-Patent Document 1: International Journal of Chronic Obstructive Pulmonary Disease, 2008, 3(4), pp. 543-561).

A PDE4 inhibitor containing a compound having PDE4 inhibitory activity (PDE4 inhibitor) reduces the production and the release of various inflammatory cytokines such as TNF-α and IL-23, and therefore is known to be effective for the treatment of various inflammatory diseases involving TNF-α and the like (Non-Patent Document 2: Expert Opinion on Investigational Drugs, 2002, 11(1), pp. 1-13). In addition, the PDE4 inhibitor is reported to have an effect not only on respiratory inflammatory diseases (asthma and chronic obstructive pulmonary disease (COPD)) but also on dermal inflammatory diseases (psoriasis and atopic dermatitis), and moreover is reported to have a potential to produce an effect on eye inflammatory diseases such as allergic conjunctivitis and dry eye (see Non-Patent Document 3: Life Sciences, 2006, 78, pp. 2663-2668; see Non-Patent Document 4: Investigative Ophthalmology & Visual Science, 2012, 53, pp. 3584-3591), and mental illnesses such as depressive disorder and dysmnesia (see Non-Patent Document 2). Furthermore, in animal models, the PDE4 inhibitor is also suggested to be effective on interstitial pneumonia such as idiopathic pulmonary fibrosis (Non-Patent Document 5: British Journal of Pharmacology, 2009, 156, pp. 534-544). What is more, the PDE4 inhibitor is suggested to be effective on various fibrosis (Non-Patent Document 6: Journal of Cellular Physiology, 2011, 226, pp. 1970-1980), on systemic sclerosis being a type of fibrosis (Non-Patent Document 7: Annals of the Rheumatic Diseases 2017, 76, pp. 1133-1141), on non-alcoholic steatohepatitis (see Non-Patent Document 8: Diabetes Obes Metab., 2017, 19, pp. 496-508), and on muscular dystrophy (see Non-Patent Document 9: The FASEB Journal, 2017, 31, pp. 5307-5320) because the PDE4 is involved in the functions of fibroblasts.

It has been known in recent years that expression levels of the PDE4 are excessively high in cells derived from patients with colorectal cancer, and its inhibitor has antitumor activity (Non-Patent Document 10: Molecular Cancer, 2012, 11:46). There has been also reported that the PDE4 is involved in the growth of lung cancer and angiogenesis, and its inhibitor has a potential to produce an effect on lung cancer as well (Non-Patent Document 11: Oncogene, 2013, 32, pp. 1121-1134) and is a possible candidate for a promising method for treating brain tumors (Non-Patent Document 12: Trends in Pharmacological Sciences, June 2011, Vol. 32, No. 6, pp. 337-344) and acute lymphocytic leukemia (Non-Patent Document 13: Blood, May 2002, Vol. 99, No. 9, pp 0.3390-3397), for example. Thus, the PDE4 inhibitor might be effective on various types of cancer.

There has been also reported that the PDE4 inhibitor might be effective on metabolic diseases such as obesity and diabetes (Non-Patent Document 14: Cell 148, February 2012, pp. 421-433) and on cognitive disorders caused by aging, Alzheimer's disease, Parkinson's disease, schizophrenia, and Huntington's disease (Non-Patent Document 15: Expert Opinion on Therapeutic Targets, September 2013, 17(9), pp. 1011-1027).

Theophylline, which is known as a non-selective PDE inhibitor, has conventionally been used for the treatment of asthma (Non-Patent Document 16: British Journal of Pharmacology, 2008, 155, pp. 308-315). In addition, ibudilast, a non-selective PDE inhibitor, shows a treatment effect on bronchial asthma and cerebrovascular diseases thanks to its anti-inflammatory action and vasodilation action (Non-Patent Document 17: Expert Opinion on Pharmacotherapy, 2009, 10, pp. 2897-2904) and is used for allergic conjunctivitis (eye lotion) (Non-Patent Document 18: Eye Contact Lens, September 2009, Vol. 35, No. 5, pp. 251-254). Ibudilast is also expected to produce an effect on multiple sclerosis and neuropathic pain (Non-Patent Document 19: Expert Opinion on Investigational Drugs, 2016, Vol. 25, No. 10, pp. 1231-1237). Roflumilast, which is a strong oral PDE4 inhibitor, has been approved and used in Europe and the United States, as a drug applied to chronic obstructive pulmonary disease (COPD) (Non-Patent Document 20: British Journal of Pharmacology, 2011, 163, pp. 53-67). In animal models, roflumilast has been also suggested to be effective on interstitial pneumonia such as idiopathic pulmonary fibrosis (see Non-Patent Document 5) and non-alcoholic steatohepatitis (see Non-Patent Document 8). Moreover, clinical trials have been carried out for obesity, dementia, and atopic dermatitis (Non-Patent Document 21: Nature Reviews Drug Discovery, April 2014, Vol. 13, pp. 290-314). Furthermore, an effect has been reported of lowering blood sugar levels of patients with diabetes (Non-Patent Document 22: The Journal of Clinical Endocrinology & Metabolism, September 2012, 97 (9), pp. 1720-1725). In recent years, apremilast, which is an oral PDE4 inhibitor too, has been approved and widely used in Europe and the United States as a medication for the treatment of psoriatic arthritis and psoriasis vulgaris, and its clinical trials have been carried out for acne, ankylosing spondylitis, rheumatism, Behcet's disease, ulcerative colitis, atopic dermatitis, alopecia areata, vitiligo, hidradenitis suppurativa, and lichen planus (see Non-Patent Document 20 and Non-Patent Document 23: Drugs, 2014, 74, pp. 825-837, Non-Patent Document 24: Summer Meeting of the American Academy of Dermatology (AAD) 2016, Abstract 4070, Non-Patent Document 25: Case Reports in Dermatological Medicine 2017, Article ID 2386234, Non-Patent Document 26: J Am Acad Dermatol 2017, 76, 6, pp. 1189-1191, and Non-Patent Document 27: Case Rep Dermatol 2016, 8, pp. 224-226). Clinical trials of crisaborole, which is a topical PDE4 inhibitor, have been reported in that crisaborole has an effect on atopic dermatitis of children and adults (Non-Patent Document 28: Journal of the American Academy of Dermatology, September 2016, Vol. 75, No. 3, pp. 494-503). Clinical trials of the PDE4 inhibitor have been carried out for various inflammatory diseases (inflammatory bowel diseases such as Crohn's disease and ulcerative colitis, multiple sclerosis, rheumatism, sarcoidosis, Behcet's disease, and rhinitis) in addition to the above. Also, non-clinical studies have also pointed out a possibility that the PDE4 inhibitor might be effective on systemic lupus erythematosus. Further, many compounds having PDE4 inhibitory activity have a central action and have been reported to have an effect on depressive disorder, Parkinson's disease, learning disability, dysmnesia, and Alzheimer's disease (Non-Patent Document 2 and Non-Patent Document 29: BMC Medicine, 2013, 11:96).

As described above, it is considered that the compound having PDE4 inhibitory activity may be effective for various diseases such as asthma, COPD, various fibrosis such as interstitial pneumonia, idiopathic pulmonary fibrosis, systemic sclerosis, non-alcoholic steatohepatitis, and muscular dystrophy, inflammatory bowel diseases such as Crohn's disease and ulcerative colitis, multiple sclerosis, rheumatism, ankylosing spondylitis, acne, atopic dermatitis, alopecia areata, vitiligo, hidradenitis suppurativa, lichen planus, allergic conjunctivitis, dry eye, rhinitis, psoriatic arthritis, psoriasis vulgaris, sarcoidosis, Behcet's disease, systemic lupus erythematosus, cerebrovascular disease, neuropathic pain, depressive disorder, cognitive disorders, learning disability, Parkinson's disease, Alzheimer's disease, Huntington's disease, schizophrenia, various types of cancer (such as colorectal cancer, lung cancer, hematologic cancer, and brain tumor), and metabolic diseases (such as diabetes and obesity).

Japanese Patent Application Publication No. Hei 6-345744 (Patent Document 1) and Japanese Patent Application Publication No. Hei 10-29987 (Patent Document 2) have reported the activity of a benzoxazole derivative on serotonin 5-$HT_3$. Additionally, International Publication No. Wo 2015/005429 (Patent Document 3) has reported a benzoxazole derivative which has a PDE4 inhibitory activity. However, the substituent at position 2 in each of these benzoxazole derivatives is a monocyclic heterocycle.

CITATION LIST

Patent Literature

[PTL 1] Japanese Unexamined Patent Application Publication No. Hei 6-345744
[PTL 2] Japanese Unexamined Patent Application Publication No. Hei 10-29987
[PTL 3] International Publication No. WO2015/005429

Non Patent Literatures

[NPL 1] Halpin D. M G., International Journal of Chronic Obstructive Pulmonary Disease, 2008, 3(4), pp. 543-561
[NPL 2] Dyke H. J. and Montana J. G., Expert Opinion on Investigational Drugs, 2002, 11(1), pp. 1-13
[NPL 3] Huang Z et al. Life Sciences, 2006, 78, pp. 2663-2
[NPL 4] Sadrai et al., Investigative Ophthalmology & Visual Science, 2012, 53, pp. 3584-3591
[NPL 5] Cortijo J. et al., British Journal of Pharmacology, 2009, 156, pp. 534-544
[NPL 6] Selige J. et al., Journal of Cellular Physiology, 2011, 226, pp. 1970-1980
[NPL 7] Maier C. et al., Annals of the Rheumatic Diseases 2017, 76, pp. 1133-1141
[NPL 8] Moellmann J et al., Diabetes Obes Metab., 2017, 19, pp. 496-508
[NPL 9] Nio Y. et al., The FASEB Journal, 2017, 31, pp. 5307-5320
[NPL 10] Tsunoda T. et al., Molecular Cancer, 2012, 11:46
[NPL 11] Pullamsetti S. S. et al., Oncogene, 2013, 32, pp. 1121-1134
[NPL 12] Sengupta R. et al., Trends in Pharmacological Sciences, June 2011, Vol. 32, No. 6, pp. 337-344
[NPL 13] Ogawa R. et al., Blood, May 2002, Vol. 99, No. 9, pp. 3390-3397
[NPL 14] Park S.-J. et al., Cell 148, February 2012, pp. 421-433, 2012
[NPL 15] Richter W. et al., Expert Opinion on Therapeutic Targets, September 2013, 17(9), pp. 1011-1027
[NPL 16] Spina D., British Journal of Pharmacology, 2008, 155, pp. 308-315
[NPL 17] Rolan P. et al., Expert Opinion on Pharmacotherapy, 2009, 10, pp. 2897-2904
[NPL 18] Sakuma K. et al., Eye Contact Lens, September 2009, Vol. 35, No. 5, pp. 251-254
[NPL 19] Goodman A. D. et al., Expert Opinion on Investigational Drugs, 2016, Vol. 25, No. 10, pp. 1231-1237
[NPL 20] Rabe K. F., British Journal of Pharmacology, 2011, 163, pp. 53-67
[NPL 21] Maurice D. H. et al., Nature Reviews Drug Discovery, April 2014, Vol. 13, pp. 290-314
[NPL 22] Wouters E. F. W. et al., The Journal of Clinical Endocrinology & Metabolism, September 2012, 97 (9), pp. 1720-1725
[NPL 23] Poole R. M. et al., Drugs, 2014, 74, pp. 825-837
[NPL 24] Shrager D., Summer Meeting of the American Academy of Dermatology (AAD) 2016, Abstract 4070
[NPL 25] Huff S. B and Gottwald L. D., Case Reports in Dermatological Medicine 2017, Article ID 2386234
[NPL 26] Weber P. et al., J Am Acad Dermatol 2017, 76, 6, pp. 1189-1191
[NPL 27] Hafner J. et al., Case Rep Dermatol 2016, 8, pp. 224-226
[NPL 28] Paller A. S. et al., Journal of the American Academy of Dermatology, September 2016, Vol. 75, No. 3, pp. 494-503
[NPL 29] Kumar N. et al., BMC Medicine, 2013, 11:96

SUMMARY OF INVENTION

Technical Problem

Conventional PDE4 inhibitors cannot be said to have sufficient efficacy by PDE4 inhibitory activity during oral administration and topical administration, and are not always effective against the various diseases described above, for which PDE4 inhibitors are considered to be effective. Furthermore, it is not fully clear which disease the compounds having various PDE4 inhibitory activities were effective against.

The present invention has been made in view of the above-described problems of the related art, and an object thereof is to provide a therapeutic agent containing a compound having excellent PDE4 inhibitory activity and useful for treating inflammatory diseases, autoimmune diseases, fibrotic diseases, and cancer diseases.

Means for Solving the Problems

The present inventors have made earnest studies to solve the above problems, and have found as a result that a benzoxazole derivative having a bicyclic piperazine ring and a pharmacologically acceptable salt thereof have excellent PDE4 inhibitory activity, and are useful in the treatment of inflammatory diseases, autoimmune diseases, fibrotic diseases, and cancer diseases. Thus, the present invention has been completed.

Specifically, the present invention is

[1]

A therapeutic agent for treating at least one disease selected from the group consisting of inflammatory diseases, autoimmune diseases, fibrotic diseases, and cancer diseases, comprising: at least one selected from the group consisting of a compound represented by the following general formula (1) and pharmacologically acceptable salts thereof as an active ingredient.

[Chem. 1]

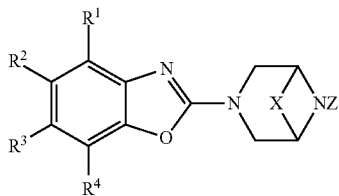

(1)

[In the formula (1), $R^1$ and $R^2$ may be the same or different and each represents a hydrogen atom, a halogen atom, a hydroxyl group, a carboxy group, a cyano group, an optionally substituted $C_{1-6}$ alkyl group, an optionally substituted $C_{3-7}$ cycloalkyl group, an optionally substituted $C_{6-10}$ monocyclic or polycyclic aryl group, an optionally substituted $C_{7-11}$ monocyclic or polycyclic aralkyl group, an optionally substituted 4- to 10-membered monocyclic or bicyclic aromatic heterocyclic group containing 1 to 4 heteroatoms selected from an oxygen atom, a nitrogen atom, and a sulfur atom, an optionally substituted 4- to 10-membered monocyclic or bicyclic nonaromatic heterocyclic group containing 1 to 4 heteroatoms selected from an oxygen atom, a nitrogen atom, and a sulfur atom, an optionally substituted di-$C_{1-6}$ alkyl amino group, an optionally substituted $C_{3-7}$ cycloalkyl amino group, an optionally substituted $C_{1-6}$ acylamino group, an optionally substituted $C_{1-6}$ alkyloxy group, an optionally substituted $C_{2-6}$ alkenyloxy group, an optionally substituted $C_{1-6}$ alkyloxy-$C_{1-6}$ alkyl group, an optionally substituted $C_{3-7}$ cycloalkyloxy group, an optionally substituted $C_{6-10}$ monocyclic or polycyclic aryloxy group, an optionally substituted $C_{7-11}$ monocyclic or polycyclic aralkyloxy group, an optionally substituted 4- to 10-membered monocyclic or bicyclic aromatic heterocyclyloxy group containing 1 to 4 heteroatoms selected from an oxygen atom, a nitrogen atom, and a sulfur atom, an optionally substituted 4- to 10-membered monocyclic or bicyclic nonaromatic heterocyclyloxy group containing 1 to 4 heteroatoms selected from an oxygen atom, a nitrogen atom, and a sulfur atom, an optionally substituted $C_{1-6}$ alkylthio group, an optionally substituted $C_{1-6}$ alkylsulfonyl group, an optionally substituted $C_{1-6}$ alkylsulfinyl group, an optionally substituted mono-$C_{1-6}$ alkylsulfamoyl group, an optionally substituted di-$C_{1-6}$ alkylsulfamoyl group [two $C_{1-6}$ alkyl groups in the di-$C_{1-6}$ alkylsulfamoyl group may form a pyrrolidin-1-yl group or a morpholino group with an adjacent nitrogen atom], a sulfamoyl group, an optionally substituted $C_{1-6}$ alkylcarbonyl group, an optionally substituted 1-($C_{1-6}$ alkyloxy)imino-$C_{1-6}$ alkyl group, an aminocarbonyl group, an optionally substituted mono-$C_{1-6}$ alkylaminocarbonyl group, an optionally substituted di-$C_{1-6}$ alkylaminocarbonyl group, an optionally substituted $C_{3-7}$ cycloalkylaminocarbonyl group, an optionally substituted $C_{7-11}$ monocyclic or polycyclic aralkylaminocarbonyl group, an optionally substituted $C_{1-6}$ alkyloxycarbonyl group, or an optionally substituted hydroxyaminocarbonyl group, $R^3$ represents a hydrogen atom, $R^4$ represents an optionally substituted 4- to 10-membered monocyclic heterocyclic group containing 1 to 4 heteroatoms selected from an oxygen atom, a nitrogen atom, and a sulfur atom, X represents a group represented by the following formula: —$CH_2$—, —$CH_2$—$CH_2$—, —$CH_2$—$CH_2$—$CH_2$—, or —$CH_2$—O—$CH_2$—, and Z represents a hydrogen atom or a hydroxyl group.]

[2]

The therapeutic agent according to [1], wherein the compound represented by the general formula (1) is a compound in which $R^1$ represents a hydrogen atom, a halogen atom, a hydroxyl group, a carboxy group, a cyano group, an optionally substituted $C_{1-6}$ alkyl group, an optionally substituted $C_{3-7}$ cycloalkyl group, an optionally substituted 4- to 10-membered monocyclic aromatic heterocyclic group containing 1 to 4 heteroatoms selected from an oxygen atom, a nitrogen atom, and a sulfur atom, an optionally substituted 4- to 10-membered monocyclic nonaromatic heterocyclic group containing 1 to 4 heteroatoms selected from an oxygen atom, a nitrogen atom, and a sulfur atom, an optionally substituted $C_{1-6}$ acylamino group, an optionally substituted $C_{1-6}$ alkyloxy group, an optionally substituted $C_{1-6}$ alkyloxy-$C_{1-6}$ alkyl group, an optionally substituted $C_{3-7}$ cycloalkyloxy group, an optionally substituted 4- to 10-membered monocyclic aromatic heterocyclyloxy group containing 1 to 4 heteroatoms selected from an oxygen atom, a nitrogen atom, and a sulfur atom, an optionally substituted 4- to 10-membered monocyclic nonaromatic heterocyclyloxy group containing 1 to 4 heteroatoms selected from an oxygen atom, a nitrogen atom, and a sulfur atom, an optionally substituted $C_{1-6}$ alkylthio group, an optionally substituted $C_{1-6}$ alkylsulfonyl group, an optionally substituted $C_{1-6}$ alkylsulfinyl group, an optionally substituted mono-$C_{1-6}$ alkylsulfamoyl group, an optionally substituted di-$C_{1-6}$ alkylsulfamoyl group [two $C_{1-6}$ alkyl groups in the di-$C_{1-6}$ alkylsulfamoyl group may form a pyrrolidin-1-yl group or a morpholino group with an adjacent nitrogen atom], a sulfamoyl group, an optionally substituted $C_{1-6}$ alkylcarbonyl group, an optionally substituted 1-($C_{1-6}$ alkyloxy)imino-$C_{1-6}$ alkyl group, an aminocarbonyl group, an optionally substituted mono-$C_{1-6}$ alkylaminocarbonyl group, an optionally substituted di-$C_{1-6}$ alkylaminocarbonyl group, an optionally substituted $C_{3-7}$ cycloalkylaminocarbonyl group, an optionally substituted $C_{7-11}$ monocyclic aralkylaminocarbonyl group, an optionally substituted $C_{1-6}$ alkyloxycarbonyl group, or an optionally substituted hydroxyaminocarbonyl group, and $R^2$ represents a hydrogen atom, a halogen atom, a hydroxyl group, a carboxy group, a cyano group, an optionally substituted $C_{1-6}$ alkyl group, an optionally substituted 4- to 10-membered monocyclic aromatic heterocyclic group containing 1 to 4 heteroatoms selected from an oxygen atom, a nitrogen atom, and a sulfur atom, an optionally substituted 4- to 10-membered monocyclic nonaromatic heterocyclic group containing 1 to 4 heteroatoms selected from an oxygen atom, a nitrogen atom, and a sulfur atom, an optionally substituted $C_{1-6}$ acylamino group, an optionally substituted $C_{1-6}$ alkyloxy group, an optionally substituted $C_{2-6}$ alkenyloxy group, an optionally substituted $C_{1-6}$ alkyloxy-$C_{1-6}$ alkyl group, an optionally substituted $C_{3-7}$ cycloalkyloxy group, an optionally substituted 4- to 10-membered monocyclic aromatic heterocyclyloxy group containing 1 to 4 heteroatoms selected from an oxygen atom, a nitrogen atom, and a sulfur atom, an optionally substituted 4- to 10-membered monocyclic nonaromatic heterocyclyloxy group containing 1 to 4 heteroatoms selected from an oxygen atom, a nitrogen atom, and a sulfur atom, an optionally substituted $C_{1-6}$ alkylthio group, an optionally substituted $C_{1-6}$ alkylsulfonyl group, an optionally substituted $C_{1-6}$ alkylsulfinyl group, an optionally substituted mono-$C_{1-6}$ alkylsulfamoyl group, an optionally substituted di-$C_{1-6}$ alkylsulfamoyl group, a sulfamoyl group, an optionally substituted $C_{1-6}$ alkylcarbonyl group, an optionally substituted 1-($C_{1-6}$ alkyloxy)imino-$C_{1-6}$ alkyl group, an aminocarbonyl group, an optionally substituted mono-$C_{1-6}$ alkylaminocarbonyl group, an optionally substituted di-$C_{1-6}$ alkylaminocarbonyl group, an optionally substituted $C_{3-7}$ cycloalkylaminocarbonyl group, an optionally substituted $C_{7-11}$ monocyclic or polycyclic aralkylaminocarbonyl group, or an optionally substituted $C_{1-6}$ alkyloxycarbonyl group.

[3]

The therapeutic agent according to [1], wherein the compound represented by the general formula (1) is a compound in which $R^1$ represents a hydrogen atom, a halogen atom, a hydroxyl group, a carboxy group, a cyano group, an optionally substituted $C_{1-6}$ alkyl group, an optionally substituted $C_{3-7}$ cycloalkyl group, an optionally substituted 4- to 10-membered monocyclic aromatic heterocyclic group containing 1 to 4 heteroatoms selected from an oxygen atom, a nitrogen atom, and a sulfur atom, an optionally substituted 4- to 10-membered monocyclic nonaromatic heterocyclic group containing 1 to 4 heteroatoms selected from an oxygen atom, a nitrogen atom, and a sulfur atom, an optionally substituted $C_{1-6}$ acylamino group, an optionally substituted $C_{1-6}$ alkyloxy group, an optionally substituted $C_{1-6}$ alkyloxy-$C_{1-6}$ alkyl group, an optionally substituted $C_{3-7}$ cycloalkyloxy group, an optionally substituted 4- to 10-membered monocyclic aromatic heterocyclyloxy group containing 1 to 4 heteroatoms selected from an oxygen atom, a nitrogen atom, and a sulfur atom, an optionally substituted 4- to 10-membered monocyclic nonaromatic heterocycly-loxy group containing 1 to 4 heteroatoms selected from an oxygen atom, a nitrogen atom, and a sulfur atom, an optionally substituted $C_{1-6}$ alkylthio group, an optionally substituted $C_{1-6}$ alkylsulfonyl group, an optionally substituted $C_{1-6}$ alkylsulfinyl group, an optionally substituted mono-$C_{1-6}$ alkylsulfamoyl group, an optionally substituted di-$C_{1-6}$ alkylsulfamoyl group [two $C_{1-6}$ alkyl groups in the di-$C_{1-6}$ alkylsulfamoyl group may form a pyrrolidin-1-yl group or a morpholino group with an adjacent nitrogen atom], a sulfamoyl group, an optionally substituted $C_{1-6}$ alkylcarbonyl group, an optionally substituted 1-($C_{1-6}$ alkyloxy)imino-$C_{1-6}$ alkyl group, an aminocarbonyl group, an optionally substituted mono-$C_{1-6}$ alkylaminocarbonyl group, an optionally substituted di-$C_{1-6}$ alkylaminocarbonyl group, an optionally substituted $C_{3-7}$ cycloalkylaminocarbonyl group, an optionally substituted $C_{7-11}$ monocyclic aralkylaminocarbonyl group, an optionally substituted $C_{1-6}$ alkyloxycarbonyl group, or an optionally substituted hydroxyaminocarbonyl group, and $R^2$ represents a hydrogen atom.

[4]

The therapeutic agent according to [1], wherein the compound represented by the general formula (1) is a compound in which $R^1$ represents a hydrogen atom, and $R^2$ represents a hydrogen atom, a halogen atom, a hydroxyl group, a carboxy group, a cyano group, an optionally substituted $C_{1-6}$ alkyl group, an optionally substituted 4- to 10-membered monocyclic aromatic heterocyclic group containing 1 to 4 heteroatoms selected from an oxygen atom, a nitrogen atom, and a sulfur atom, an optionally substituted $C_{1-6}$ acylamino group, an optionally substituted $C_{1-6}$ alkyloxy group, an optionally substituted $C_{2-6}$ alkenyloxy group, an optionally substituted $C_{1-6}$ alkyloxy-$C_{1-6}$ alkyl group, an optionally substituted $C_{3-7}$ cycloalkyloxy group, an optionally substituted 4- to 10-membered monocyclic aromatic heterocyclyloxy group containing 1 to 4 heteroatoms selected from an oxygen atom, a nitrogen atom, and a sulfur atom, an optionally substituted 4- to 10-membered monocyclic nonaromatic heterocyclyloxy group containing 1 to 4 heteroatoms selected from an oxygen atom, a nitrogen atom, and a sulfur atom, an optionally substituted $C_{1-6}$ alkylthio group, an optionally substituted $C_{1-6}$ alkylsulfonyl group, an optionally substituted $C_{1-6}$ alkylsulfinyl group, an optionally substituted mono-$C_{1-6}$ alkylsulfamoyl group, an optionally substituted di-$C_{1-6}$ alkylsulfamoyl group, a sulfamoyl group, an optionally substituted $C_{1-6}$ alkylcarbonyl group, an aminocarbonyl group, an optionally substituted 1-($C_{1-6}$ alkyloxy)imino-$C_{1-6}$ alkyl group, an aminocarbonyl group, an optionally substituted mono-$C_{1-6}$ alkylaminocarbonyl group, an optionally substituted di-$C_{1-6}$ alkylaminocarbonyl group, an optionally substituted $C_{3-7}$ cycloalkylaminocarbonyl group, an optionally substituted $C_{7-11}$ monocyclic or polycyclic aralkylaminocarbonyl group, or an optionally substituted $C_{1-6}$ alkyloxycarbonyl group.

[5]

The therapeutic agent according to [1], wherein the compound represented by the general formula (1) is a compound represented by the following general formula (11).

[Chem. 2]

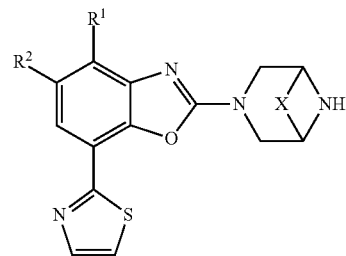

(11)

[in the formula (11), $R^1$ represents an optionally substituted $C_{1-6}$ alkyl group, or an optionally substituted $C_{1-6}$ alkyloxy group, $R^2$ represents a hydrogen atom, a halogen atom, an optionally substituted $C_{1-6}$ alkyl group, or an optionally substituted $C_{1-6}$ alkylcarbonyl group, and X represents a group represented by the following formula: —CH₂—, —CH₂—CH₂—, —CH₂—CH₂—CH₂—, or —CH₂—O—CH₂—]

[6]

The therapeutic agent according to any one of [1] to [5], wherein PDE4 inhibitory activity of the at least one selected from the group consisting of the compound represented by the general formula (1) and the pharmacologically acceptable salts thereof is 11 nM or less at a concentration (IC50) that inhibits PDE4 activity by 50%.

[7]

The therapeutic agent according to [1], wherein the compound represented by the general formula (1) is
2-(3,8-diazabicyclo[3.2.1]octan-3-yl)-5-chloro-7-(thiazol-2-yl)-4-(trifluoromethoxy)benzo[d]oxazole,
2-(3,9-diazabicyclo[3.3.1]nonan-3-yl)-5-chloro-7-(thiazol-2-yl)-4-(trifluoromethoxy)benzo[d]oxazole,
2-(3,6-diazabicyclo[3.1.1]heptan-3-yl)-5-chloro-7-(thiazol-2-yl)-4-(trifluoromethoxy)benzo[d]oxazole,
7-(5-chloro-7-(thiazol-2-yl)-4-(trifluoromethoxy)benzo[d]oxazol-2-yl)-3-oxa-7,9-diazabicyclo[3.3.1]nonane,
2-(3,8-diazabicyclo[3.2.1]octan-3-yl)-5-chloro-7-(1H-pyrazol-1-yl)-4-(trifluoromethoxy)benzo[d]oxazole,
2-(3,8-diazabicyclo[3.2.1]octan-3-yl)-5-chloro-7-(furan-2-yl)-4-(trifluoromethoxy)benzo[d]oxazole,
2-(3,8-diazabicyclo[3.2.1]octan-3-yl)-5-chloro-7-(pyridin-2-yl)-4-(trifluoromethoxy)benzo[d]oxazole,
2-(3,8-diazabicyclo[3.2.1]octan-3-yl)-5-chloro-7-(thiazol-4-yl)-4-(trifluoromethoxy)benzo[d]oxazole,
2-(3,8-diazabicyclo[3.2.1]octan-3-yl)-5-chloro-7-(oxazol-2-yl)-4-(trifluoromethoxy)benzo[d]oxazole,
2-(3,8-diazabicyclo[3.2.1]octan-3-yl)-5-chloro-7-(5-fluoropyridin-2-yl)-4-(trifluoromethoxy)benzo[d]oxazole,
2-(3,8-diazabicyclo[3.2.1]octan-3-yl)-5-chloro-7-(pyridin-2-yl)-4-(trifluoromethyl)benzo[d]oxazole,
2-(3,9-diazabicyclo[3.3.1]nonan-3-yl)-5-chloro-7-(pyridin-2-yl)-4-(trifluoromethyl)benzo[d]oxazole,
2-(3,6-diazabicyclo[3.1.1]heptan-3-yl)-5-chloro-7-(pyridin-2-yl)-4-(trifluoromethyl)benzo[d]oxazole,
7-(5-chloro-7-(pyridin-2-yl)-4-(trifluoromethyl)benzo[d]oxazol-2-yl)-3-oxa-7,9-diazabicyclo[3.3.1]nonane,
2-(3,8-diazabicyclo[3.2.1]octan-3-yl)-5-chloro-7-(1H-pyrazol-1-yl)-4-(trifluoromethyl)benzo[d]oxazole,
2-(3,9-diazabicyclo[3.3.1]nonan-3-yl)-5-chloro-7-(1H-pyrazol-1-yl)-4-(trifluoromethyl)benzo[d]oxazole,
2-(3,6-diazabicyclo[3.1.1]heptan-3-yl)-5-chloro-7-(1H-pyrazol-1-yl)-4-(trifluoromethyl)benzo[d]oxazole,
7-(5-chloro-7-(1H-pyrazol-1-yl)-4-(trifluoromethyl)benzo[d]oxazol-2-yl)-3-oxa-7,9-diazabicyclo[3.3.1]nonane,
7-(5-chloro-7-(thiazol-2-yl)-4-(trifluoromethyl)benzo[d]oxazol-2-yl)-3-oxa-7,9-diazabicyclo[3.3.1]nonane,
2-(3,8-diazabicyclo[3.2.1]octan-3-yl)-5-chloro-7-(thiazol-2-yl)-4-(trifluoromethyl)benzo[d]oxazole,
2-(3,8-diazabicyclo[3.2.1]octan-3-yl)-5-isopropyl-7-(thiazol-2-yl)benzo[d]oxazole,
2-(3,6-diazabicyclo[3.1.1]heptan-3-yl)-5-isopropyl-7-(thiazol-2-yl)benzo[d]oxazole,
7-(5-isopropyl-7-(thiazol-2-yl)benzo[d]oxazol-2-yl)-3-oxa-7,9-diazabicyclo[3.3.1]nonane,
2-(3,9-diazabicyclo[3.3.1]nonan-3-yl)-5-isopropyl-7-(thiazol-2-yl)benzo[d]oxazole,
2-(3,8-diazabicyclo[3.2.1]octan-3-yl)-4-methyl-7-(thiazol-2-yl)benzo[d]oxazole,
2-(3,6-diazabicyclo[3.1.1]heptan-3-yl)-4-methyl-7-(thiazol-2-yl)benzo[d]oxazole,
2-(3,9-diazabicyclo[3.3.1]nonan-3-yl)-4-methyl-7-(thiazol-2-yl)benzo[d]oxazole,
2-(3,8-diazabicyclo[3.2.1]octan-3-yl)-7-(thiazol-2-yl)-4-(trifluoromethoxy)benzo[d]oxazole,
2-(3,6-diazabicyclo[3.1.1]heptan-3-yl)-7-(thiazol-2-yl)-4-(trifluoromethoxy)benzo[d]oxazole,
2-(3,9-diazabicyclo[3.3.1]nonan-3-yl)-7-(thiazol-2-yl)-4-(trifluoromethoxy)benzo[d]oxazole,
2-(3,8-diazabicyclo[3.2.1]octan-3-yl)-7-(thiazol-2-yl)-4-(trifluoromethyl)benzo[d]oxazole,
2-(3,6-diazabicyclo[3.1.1]heptan-3-yl)-7-(thiazol-2-yl)-4-(trifluoromethyl)benzo[d]oxazole,
2-(3,9-diazabicyclo[3.3.1]nonan-3-yl)-7-(thiazol-2-yl)-4-(trifluoromethyl)benzo[d]oxazole,
N-(2-(3,9-diazabicyclo[3.3.1]nonan-3-yl)-7-(thiazol-2-yl)benzo[d]oxazol-4-yl)acetamide,
N-(2-(3,6-diazabicyclo[3.1.1]heptan-3-yl)-7-(thiazol-2-yl)benzo[d]oxazol-4-yl)acetamide,
2-(3,8-diazabicyclo[3.2.1]octan-3-yl)-4-chloro-7-(thiazol-2-yl)benzo[d]oxazole,
2-(3,6-diazabicyclo[3.1.1]heptan-3-yl)-4-chloro-7-(thiazol-2-yl)benzo[d]oxazole,
2-(3,9-diazabicyclo[3.3.1]nonan-3-yl)-4-chloro-7-(thiazol-2-yl)benzo[d]oxazole,
2-(3,8-diazabicyclo[3.2.1]octan-3-yl)-5-(methylthio)-7-(thiazol-2-yl)benzo[d]oxazole,
2-(3,6-diazabicyclo[3.1.1]heptan-3-yl)-5-(methylthio)-7-(thiazol-2-yl)benzo[d]oxazole,
2-(3,9-diazabicyclo[3.3.1]nonan-3-yl)-5-(methylthio)-7-(thiazol-2-yl)benzo[d]oxazole,
2-(3,8-diazabicyclo[3.2.1]octan-3-yl)-5-(methylsulfonyl)-7-(thiazol-2-yl)benzo[d]oxazole,
2-(3,6-diazabicyclo[3.1.1]heptan-3-yl)-5-(methylsulfonyl)-7-(thiazol-2-yl)benzo[d]oxazole,
2-(3,9-diazabicyclo[3.3.1]nonan-3-yl)-5-(methylsulfonyl)-7-(thiazol-2-yl)benzo[d]oxazole,
2-(3,8-diazabicyclo[3.2.1]octan-3-yl)-5-(methylsulfinyl)-7-(thiazol-2-yl)benzo[d]oxazole,
2-(3,6-diazabicyclo[3.1.1]heptan-3-yl)-5-(methylsulfinyl)-7-(thiazol-2-yl)benzo[d]oxazole,
2-(3,9-diazabicyclo[3.3.1]nonan-3-yl)-5-(methylsulfinyl)-7-(thiazol-2-yl)benzo[d]oxazole,
N-(2-(3,9-diazabicyclo[3.3.1]nonan-3-yl)-7-(thiazol-2-yl)benzo[d]oxazol-5-yl)acetamide,
N-(2-(3,6-diazabicyclo[3.1.1]heptan-3-yl)-7-(thiazol-2-yl)benzo[d]oxazol-5-yl)acetamide,
N-(2-(3,8-diazabicyclo[3.2.1]octan-3-yl)-7-(thiazol-2-yl)benzo[d]oxazol-5-yl)acetamide,
2-(3,8-diazabicyclo[3.2.1]octan-3-yl)-7-(thiazol-2-yl)-5-(trifluoromethyl)benzo[d]oxazole,
2-(3,6-diazabicyclo[3.1.1]heptan-3-yl)-7-(thiazol-2-yl)-5-(trifluoromethyl)benzo[d]oxazole,
2-(3,9-diazabicyclo[3.3.1]nonan-3-yl)-7-(thiazol-2-yl)-5-(trifluoromethyl)benzo[d]oxazole,
2-(3,8-diazabicyclo[3.2.1]octan-3-yl)-7-(thiazol-2-yl)-5-(trifluoromethoxy)benzo[d]oxazole,
2-(3,9-diazabicyclo[3.3.1]nonan-3-yl)-7-(thiazol-2-yl)-5-(trifluoromethoxy)benzo[d]oxazole,
2-(3,6-diazabicyclo[3.1.1]heptan-3-yl)-7-(thiazol-2-yl)-5-(trifluoromethoxy)benzo[d]oxazole,
2-(3,8-diazabicyclo[3.2.1]octan-3-yl)-7-(thiazol-2-yl)benzo[d]oxazole-5-sulfonamide,
2-(3,6-diazabicyclo[3.1.1]heptan-3-yl)-7-(thiazol-2-yl)benzo[d]oxazole-5-sulfonamide,
2-(3,9-diazabicyclo[3.3.1]nonan-3-yl)-7-(thiazol-2-yl)benzo[d]oxazole-5-sulfonamide,
2-(3,8-diazabicyclo[3.2.1]octan-3-yl)-5-methoxy-7-(thiazol-2-yl)benzo[d]oxazole, 2-(3,6-diazabicyclo[3.1.1]heptan-3-yl)-5-methoxy-7-(thiazol-2-yl)benzo[d]oxazole,
2-(3,9-diazabicyclo[3.3.1]nonan-3-yl)-5-methoxy-7-(thiazol-2-yl)benzo[d]oxazole,
2-(3,8-diazabicyclo[3.2.1]octan-3-yl)-7-(thiazol-2-yl)benzo[d]oxazol-5-ol,
2-(3,6-diazabicyclo[3.1.1]heptan-3-yl)-7-(thiazol-2-yl)benzo[d]oxazol-5-ol,
2-(3,9-diazabicyclo[3.3.1]nonan-3-yl)-7-(thiazol-2-yl)benzo[d]oxazol-5-ol,
2-(3,8-diazabicyclo[3.2.1]octan-3-yl)-7-(thiazol-2-yl)-5-(2,2,2-trifluoroethoxy)benzo[d]oxazole,
2-(3,6-diazabicyclo[3.1.1]heptan-3-yl)-7-(thiazol-2-yl)-5-(2,2,2-trifluoroethoxy)benzo[d]oxazole,
2-(3,8-diazabicyclo[3.2.1]octan-3-yl)-5-isopropoxy-7-(thiazol-2-yl)benzo[d]oxazole,
2-(3,8-diazabicyclo[3.2.1]octan-3-yl)-5-(2-methoxyethoxy)-7-(thiazol-2-yl)benzo[d]oxazole,
2-(3,8-diazabicyclo[3.2.1]octan-3-yl)-5-(oxetan-3-ylmethoxy)-7-(thiazol-2-yl)benzo[d]oxazole,
2-(((2-(3,8-diazabicyclo[3.2.1]octan-3-yl)-7-(thiazol-2-yl)benzo[d]oxazol-5-yl)oxy)methyl)propane-1,3-diol,
5-(allyloxy)-2-(3,8-diazabicyclo[3.2.1]octan-3-yl)-7-(thiazol-2-yl)benzo[d]oxazole,
2-((2-(3,8-diazabicyclo[3.2.1]octan-3-yl)-7-(thiazol-2-yl)benzo[d]oxazol-5-yl)oxy)acetonitrile,
2-((2-(3,8-diazabicyclo[3.2.1]octan-3-yl)-7-(thiazol-2-yl)benzo[d]oxazol-5-yl)oxy)acetic acid,
2-(3,8-diazabicyclo[3.2.1]octan-3-yl)-4-methoxy-7-(thiazol-2-yl)benzo[d]oxazole,
2-(3,6-diazabicyclo[3.1.1]heptan-3-yl)-4-methoxy-7-(thiazol-2-yl)benzo[d]oxazole,
2-(3,9-diazabicyclo[3.3.1]nonan-3-yl)-4-methoxy-7-(thiazol-2-yl)benzo[d]oxazole,
2-(3,8-diazabicyclo[3.2.1]octan-3-yl)-7-(thiazol-2-yl)benzo[d]oxazol-4-ol,
2-(3,6-diazabicyclo[3.1.1]heptan-3-yl)-7-(thiazol-2-yl)benzo[d]oxazol-4-ol,
2-(3,9-diazabicyclo[3.3.1]nonan-3-yl)-7-(thiazol-2-yl)benzo[d]oxazol-4-ol,
2-(3,8-diazabicyclo[3.2.1]octan-3-yl)-4-cyclobutoxy-7-(thiazol-2-yl)benzo[d]oxazole,
2-((2-(3,8-diazabicyclo[3.2.1]octan-3-yl)-7-(thiazol-2-yl)benzo[d]oxazol-4-yl)oxy)acetonitrile,
1-((2-(3,8-diazabicyclo[3.2.1]octan-3-yl)-7-(thiazol-2-yl)benzo[d]oxazol-4-yl)oxy)-3-methoxypropan-2-ol,
2-(3,8-diazabicyclo[3.2.1]octan-3-yl)-4-((tetrahydrofuran-3-yl)oxy)-7-(thiazol-2-yl)benzo[d]oxazole,
2-(3,8-diazabicyclo[3.2.1]octan-3-yl)-4,7-di(thiazol-2-yl)benzo[d]oxazole,
ethyl 2-(3,8-diazabicyclo[3.2.1]octan-3-yl)-7-(thiazol-2-yl)benzo[d]oxazole-5-carboxylate,
ethyl 2-(3,6-diazabicyclo[3.1.1]heptan-3-yl)-7-(thiazol-2-yl)benzo[d]oxazole-5-carboxylate,
ethyl 2-(3-oxa-7,9-diazabicyclo[3.3.1]nonan-7-yl)-7-(thiazol-2-yl)benzo[d]oxazole-5-carboxylate,
ethyl 2-(3,9-diazabicyclo[3.3.1]nonan-3-yl)-7-(thiazol-2-yl)benzo[d]oxazole-5-carboxylate,
ethyl 2-(3,8-diazabicyclo[3.2.1]octan-3-yl)-7-(1H-pyrazol-1-yl)benzo[d]oxazole-5-carboxylate,
ethyl 2-(3,6-diazabicyclo[3.1.1]heptan-3-yl)-7-(1H-pyrazol-1-yl)benzo[d]oxazole-5-carboxylate,
ethyl 2-(3-oxa-7,9-diazabicyclo[3.3.1]nonan-7-yl)-7-(1H-pyrazol-1-yl)benzo[d]oxazole-5-carboxylate,
ethyl 2-(3,9-diazabicyclo[3.3.1]nonan-3-yl)-7-(1H-pyrazol-1-yl)benzo[d]oxazole-5-carboxylate,
2-(2-(3,8-diazabicyclo[3.2.1]octan-3-yl)-7-(thiazol-2-yl)benzo[d]oxazol-5-yl)propan-2-ol,
2-(2-(3,6-diazabicyclo[3.1.1]heptan-3-yl)-7-(thiazol-2-yl)benzo[d]oxazol-5-yl)propan-2-ol,
2-(3,6-diazabicyclo[3.1.1]heptan-3-yl)-5-(2-methoxypropan-2-yl)-7-(thiazol-2-yl)benzo[d]oxazole,
2-(3,8-diazabicyclo[3.2.1]octan-3-yl)-5-(2-methoxypropan-2-yl)-7-(thiazol-2-yl)benzo[d]oxazole,
2-(3,8-diazabicyclo[3.2.1]octan-3-yl)-N,N-dimethyl-7-(thiazol-2-yl)benzo[d]oxazole-5-carboxamide,
(2-(3,8-diazabicyclo[3.2.1]octan-3-yl)-7-(thiazol-2-yl)benzo[d]oxazol-5-yl) (morpholino)methanone,
(2-(3,8-diazabicyclo[3.2.1]octan-3-yl)-7-(thiazol-2-yl)benzo[d]oxazol-5-yl)(piperidin-1-yl)methanone,
(2-(3,8-diazabicyclo[3.2.1]octan-3-yl)-7-(thiazol-2-yl)benzo[d]oxazol-5-yl)(azetidin-1-yl)methanone,
N-benzyl-2-(3,8-diazabicyclo[3.2.1]octan-3-yl)-7-(thiazol-2-yl)benzo[d]oxazole-5-carboxamide,
2-(3,8-diazabicyclo[3.2.1]octan-3-yl)-7-(thiazol-2-yl)benzo[d]oxazole-5-carboxamide,
2-(3,8-diazabicyclo[3.2.1]octan-3-yl)-N-methyl-7-(thiazol-2-yl)benzo[d]oxazole-5-carboxamide,
N-(2-(3,8-diazabicyclo[3.2.1]octan-3-yl)-7-(thiazol-2-yl)benzo[d]oxazol-5-yl)-N-methylacetamide,
2-(3,8-diazabicyclo[3.2.1]octan-3-yl)-5-(morpholinomethyl)-7-(thiazol-2-yl)benzo[d]oxazole,
1-(2-(3,8-diazabicyclo[3.2.1]octan-3-yl)-7-(thiazol-2-yl)benzo[d]oxazol-5-yl)-N,N-dimethylmethanamine,
2-(3,8-diazabicyclo[3.2.1]octan-3-yl)-7-(thiazol-2-yl)-5-(1,1,1-trifluoro-2-methoxypropan-2-yl)benzo[d]oxazole,
2-(3,6-diazabicyclo[3.1.1]heptan-3-yl)-7-(thiazol-2-yl)-5-(1,1,1-trifluoro-2-methoxypropan-2-yl)benzo[d]oxazole,
1-(2-(3,8-diazabicyclo[3.2.1]octan-3-yl)-7-(thiazol-2-yl)benzo[d]oxazol-5-yl)ethan-1-one,
1-(2-(3,6-diazabicyclo[3.1.1]heptan-3-yl)-7-(thiazol-2-yl)benzo[d]oxazol-5-yl)ethan-1-one,
1-(2-(3,8-diazabicyclo[3.2.1]octan-3-yl)-7-(thiazol-2-yl)benzo[d]oxazol-5-yl)-2,2-difluoroethan-1-ol,
2-(3,8-diazabicyclo[3.2.1]octan-3-yl)-5-(2,2-difluoro-1-methoxyethyl)-7-(thiazol-2-yl)benzo[d]oxazole,
1-(2-(3,8-diazabicyclo[3.2.1]octan-3-yl)-7-(thiazol-2-yl)benzo[d]oxazol-5-yl)ethan-1-ol,
1-(2-(3,6-diazabicyclo[3.1.1]heptan-3-yl)-7-(thiazol-2-yl)benzo[d]oxazol-5-yl)ethan-1-ol,
2-(3,8-diazabicyclo[3.2.1]octan-3-yl)-5-(1-methoxyethyl)-7-(thiazol-2-yl)benzo[d]oxazole,
2-(3,6-diazabicyclo[3.1.1]heptan-3-yl)-5-(1-methoxyethyl)-7-(thiazol-2-yl)benzo[d]oxazole,
(2-(3,9-diazabicyclo[3.3.1]nonan-3-yl)-7-(thiazol-2-yl)benzo[d]oxazol-4-yl)methanol,
(2-(3,6-diazabicyclo[3.1.1]hepan-3-yl)-7-(thiazol-2-yl)benzo[d]oxazol-4-yl)methanol,
(2-(3,8-diazabicyclo[3.2.1]octan-3-yl)-7-(thiazol-2-yl)benzo[d]oxazol-4-yl)methanol,
ethyl 2-(3,8-diazabicyclo[3.2.1]octan-3-yl)-7-(thiazol-2-yl)benzo[d]oxazole-4-carboxylate,
ethyl 2-(3,6-diazabicyclo[3.1.1]heptan-3-yl)-7-(thiazol-2-yl)benzo[d]oxazole-4-carboxylate,
ethyl 2-(3,9-diazabicyclo[3.3.1]nonan-3-yl)-7-(thiazol-2-yl)benzo[d]oxazole-4-carboxylate,
2-(3,8-diazabicyclo[3.2.1]octan-3-yl)-N,N-dimethyl-7-(thiazol-2-yl)benzo[d]oxazole-4-carboxamide,
(2-(3,8-diazabicyclo[3.2.1]octan-3-yl)-7-(thiazol-2-yl)benzo[d]oxazol-4-yl) (morpholino)methanone,
(2-(3,8-diazabicyclo[3.2.1]octan-3-yl)-7-(thiazol-2-yl)benzo[d]oxazol-4-yl)(piperidin-1-yl)methanone, 1-(2-(3,8-diazabicyclo[3.2.1]octan-3-yl)-7-(thiazol-2-yl)
benzo[d]oxazol-4-yl)-2,2,2-trifluoroethan-1-ol,
(R)-1-(2-(3,8-diazabicyclo[3.2.1]octan-3-yl)-7-(thiazol-2-
yl)benzo[d]oxazol-4-yl)-2,2,2-trifluoroethan-1-ol,
(S)-1-(2-(3,8-diazabicyclo[3.2.1]octan-3-yl)-7-(thiazol-2-
yl)benzo[d]oxazol-4-yl)-2,2,2-trifluoroethan-1-ol,
1-(2-(3,6-diazabicyclo[3.1.1]heptan-3-yl)-7-(thiazol-2-yl)
benzo[d]oxazol-4-yl)-2,2,2-trifluoroethan-1-ol,
(R)-1-(2-(3,6-diazabicyclo[3.1.1]heptan-3-yl)-7-(thiazol-2-
yl)benzo[d]oxazol-4-yl)-2,2,2-trifluoroethan-1-ol,
(S)-1-(2-(3,6-diazabicyclo[3.1.1]heptan-3-yl)-7-(thiazol-2-
yl)benzo[d]oxazol-4-yl)-2,2,2-trifluoroethan-1-ol,
2-(3,6-diazabicyclo[3.1.1]heptan-3-yl)-7-(thiazol-2-yl)-4-
(2,2,2-trifluoro-1-methoxyethyl)benzo[d]oxazole,
(R)-2-(3,6-diazabicyclo[3.1.1]heptan-3-yl)-7-(thiazol-2-yl)-
4-(2,2,2-trifluoro-1-methoxyethyl)benzo[d]oxazole,
(S)-2-(3,6-diazabicyclo[3.1.1]heptan-3-yl)-7-(thiazol-2-yl)-
4-(2,2,2-trifluoro-1-methoxyethyl)benzo[d]oxazole,
1-(2-(3,6-diazabicyclo[3.1.1]heptan-3-yl)-7-(thiazol-2-yl)
benzo[d]oxazol-4-yl)-2,2-difluoroethan-1-ol,
2-(2-(3,6-diazabicyclo[3.1.1]heptan-3-yl)-7-(thiazol-2-yl)
benzo[d]oxazol-4-yl)-1,1-difluoropropan-2-ol,
(R)-2-(2-(3,6-diazabicyclo[3.1.1]heptan-3-yl)-7-(thiazol-2-
yl)benzo[d]oxazol-4-yl)-1,1-difluoropropan-2-ol,
(S)-2-(2-(3,6-diazabicyclo[3.1.1]heptan-3-yl)-7-(thiazol-2-
yl)benzo[d]oxazol-4-yl)-1,1-difluoropropan-2-ol,
1-(1-(2-(3,6-diazabicyclo[3.1.1]heptan-3-yl)-7-(thiazol-2-
yl)benzo[d]oxazol-4-yl)-2,2-difluoroethoxy)-2-methyl-
propan-2-ol,
1-(2-(3,8-diazabicyclo[3.2.1]octan-3-yl)-7-(thiazol-2-yl)
benzo[d]oxazol-4-yl)-2,2-difluoroethan-1-ol,
2-(2-(3,8-diazabicyclo[3.2.1]octan-3-yl)-7-(thiazol-2-yl)
benzo[d]oxazol-4-yl)-1,1-difluoropropan-2-ol,
2-(3,6-diazabicyclo[3.1.1]heptan-3-yl)-4-(2,2-difluoro-1-
methoxyethyl)-7-(thiazol-2-yl)benzo[d]oxazole,
2-(3,8-diazabicyclo[3.2.1]octan-3-yl)-4-(2,2-difluoro-1-
methoxyethyl)-7-(thiazol-2-yl)benzo[d]oxazole,
1-(2-(3,8-diazabicyclo[3.2.1]octan-3-yl)-7-(thiazol-2-yl)
benzo[d]oxazol-4-yl)ethan-1-ol,
1-(2-(3,6-diazabicyclo[3.1.1]heptan-3-yl)-7-(thiazol-2-yl)
benzo[d]oxazol-5-yl)-2,2,2-trifluoroethan-1-ol,
1-(2-(3,9-diazabicyclo[3.3.1]nonan-3-yl)-7-(thiazol-2-yl)
benzo[d]oxazol-5-yl)-2,2,2-trifluoroethan-1-ol,
1-(2-(3,8-diazabicyclo[3.2.1]octan-3-yl)-7-(thiazol-2-yl)
benzo[d]oxazol-5-yl)-2,2,2-trifluoroethan-1-ol,
(R)-1-(2-(3,8-diazabicyclo[3.2.1]octan-3-yl)-7-(thiazol-2-yl)
benzo[d]oxazol-5-yl)-2,2,2-trifluoroethan-1-ol,
(S)-1-(2-(3,8-diazabicyclo[3.2.1]octan-3-yl)-7-(thiazol-2-yl)
benzo[d]oxazol-5-yl)-2,2,2-trifluoroethan-1-ol,
1-(2-(3,8-diazabicyclo[3.2.1]octan-3-yl)-7-(1H-pyrazol-1-
yl)benzo[d]oxazol-5-yl)-2,2,2-trifluoroethan-1-ol,
1-(2-(3,8-diazabicyclo[3.2.1]octan-3-yl)-7-(thiazol-2-yl)
benzo[d]oxazol-5-yl)-2,2,2-trifluoroethyl acetate,
2-(3,8-diazabicyclo[3.2.1]octan-3-yl)-7-(thiazol-2-yl)-5-(2,
2,2-trifluoro-1-methoxyethyl)benzo[d]oxazole,
(R)-2-(3,8-diazabicyclo[3.2.1]octan-3-yl)-7-(thiazol-2-yl)-
5-(2,2,2-trifluoro-1-methoxyethyl)benzo[d]oxazole,
(S)-2-(3,8-diazabicyclo[3.2.1]octan-3-yl)-7-(thiazol-2-yl)-
5-(2,2,2-trifluoro-1-methoxyethyl)benzo[d]oxazole,
2-(3,6-diazabicyclo[3.1.1]heptan-3-yl)-7-(thiazol-2-yl)-5-
(2,2,2-trifluoro-1-methoxyethyl)benzo[d]oxazole,
2-(3,9-diazabicyclo[3.3.1]nonan-3-yl)-7-(thiazol-2-yl)-5-(2,
2,2-trifluoro-1-methoxyethyl)benzo[d]oxazole,
2-(3,8-diazabicyclo[3.2.1]octan-3-yl)-7-(thiazol-2-yl)-5-(2,
2,2-trifluoro-1-(2,2,2-trifluoroethoxy)ethyl)benzo[d]oxa-
zole,
2-(3,8-diazabicyclo[3.2.1]octan-3-yl)-7-(thiazol-2-yl)-5-(2,
2,2-trifluoro-1-(2-methoxyethoxy)ethyl)benzo[d]oxazole,
2-(3,8-diazabicyclo[3.2.1]octan-3-yl)-5-(1-ethoxy-2,2,2-tri-
fluoroethyl)-7-(thiazol-2-yl)benzo[d]oxazole,
2-(1-(2-(3,8-diazabicyclo[3.2.1]octan-3-yl)-7-(thiazol-2-yl)
benzo[d]oxazol-5-yl)-2,2,2-trifluoroethoxy)ethan-1-ol,
2-(3,6-diazabicyclo[3.1.1]heptan-3-yl)-5-(1-ethoxy-2,2,2-
trifluoroethyl)-7-(thiazol-2-yl)benzo[d]oxazole,
2-(3,6-diazabicyclo[3.1.1]heptan-3-yl)-7-(thiazol-2-yl)-5-
(2,2,2-trifluoro-1-(2,2,2-trifluoroethoxy)ethyl)benzo[d]
oxazole,
2-(1-(2-(3,6-diazabicyclo[3.1.1]heptan-3-yl)-7-(thiazol-2-
yl)benzo[d]oxazol-5-yl)-2,2,2-trifluoroethoxy)acetoni-
trile,
2-(1-(2-(3,8-diazabicyclo[3.2.1]octan-3-yl)-7-(thiazol-2-yl)
benzo[d]oxazol-5-yl)-2,2,2-trifluoroethoxy)acetonitrile,
2-(3,6-diazabicyclo[3.1.1]heptan-3-yl)-7-(thiazol-2-yl)-5-
(2,2,2-trifluoro-1-(2-methoxyethoxy)ethyl)benzo[d]oxa-
zole,
1-(1-(2-(3,8-diazabicyclo[3.2.1]octan-3-yl)-7-(thiazol-2-yl)
benzo[d]oxazol-5-yl)-2,2,2-trifluoroethoxy)propan-2-ol,
1-(2-(3,9-diazabicyclo[3.3.1]nonan-3-yl)-7-(thiazol-2-yl)
benzo[d]oxazol-5-yl)-2,2,2-trifluoroethane-1,1-diol,
1-(2-(3,8-diazabicyclo[3.2.1]octan-3-yl)-7-(thiazol-2-yl)
benzo[d]oxazol-5-yl)-2,2,2-trifluoroethane-1,1-diol,
1-(2-(3,6-diazabicyclo[3.1.1]heptan-3-yl)-7-(thiazol-2-yl)
benzo[d]oxazol-5-yl)-2,2,2-trifluoroethane-1,1-diol,
2-(2-(3,8-diazabicyclo[3.2.1]octan-3-yl)-7-(thiazol-2-yl)
benzo[d]oxazol-5-yl)-1,1,1-trifluoropropan-2-ol,
2-(2-(3,6-diazabicyclo[3.1.1]heptan-3-yl)-7-(thiazol-2-yl)
benzo[d]oxazol-5-yl)-1,1,1-trifluoropropan-2-ol,
2-(2-(3,9-diazabicyclo[3.3.1]nonan-3-yl)-7-(thiazol-2-yl)
benzo[d]oxazol-5-yl)-1,1,1-trifluoropropan-2-ol,
2-(2-(3,9-diazabicyclo[3.3.1]nonan-3-yl)-7-(thiazol-2-yl)-
5-(1,1,1-trifluoro-2-methoxypropan-2-yl)benzo[d]oxa-
zole,
ethyl 2-(3,8-diazabicyclo[3.2.1]octan-3-yl)-7-(thiazol-2-yl)-
4-(trifluoromethyl)benzo[d]oxazole-5-carboxylate,
ethyl 2-(3,9-diazabicyclo[3.3.1]nonan-3-yl)-7-(thiazol-2-
yl)-4-(trifluoromethyl)benzo[d]oxazole-5-carboxylate,
ethyl 2-(3,6-diazabicyclo[3.1.1]heptan-3-yl)-7-(thiazol-2-
yl)-4-(trifluoromethyl)benzo[d]oxazole-5-carboxylate,
2-(2-(3,9-diazabicyclo[3.3.1]nonan-3-yl)-7-(thiazol-2-yl)-
4-(trifluoromethyl)benzo[d]oxazol-5-yl)propan-2-ol,
2-(3,8-diazabicyclo[3.2.1]octan-3-yl)-5-(methoxymethyl)-
7-(thiazol-2-yl)-4-(trifluoromethyl)benzo[d]oxazole,
(2-(3,8-diazabicyclo[3.2.1]octan-3-yl)-7-(thiazol-2-yl)-4-
(trifluoromethyl)benzo[d]oxazol-5-yl)methanol,
2-(3,8-diazabicyclo[3.2.1]octan-3-yl)-5-(2-methoxypropan-
2-yl)-7-(thiazol-2-yl)-4-(trifluoromethyl)benzo[d]oxa-
zole,
2-(3,6-diazabicyclo[3.1.1]heptan-3-yl)-5-(2-methoxypro-
pan-2-yl)-7-(thiazol-2-yl)-4-(trifluoromethyl)benzo[d]
oxazole,
2-(2-(3,8-diazabicyclo[3.2.1]octan-3-yl)-7-(thiazol-2-yl)-4-
(trifluoromethyl)benzo[d]oxazol-5-yl)propan-2-ol,
2-(2-(3,6-diazabicyclo[3.1.1]heptan-3-yl)-7-(thiazol-2-yl)-
4-(trifluoromethyl)benzo[d]oxazol-5-yl)propan-2-ol,
1-(2-(3,8-diazabicyclo[3.2.1]octan-3-yl)-7-(thiazol-2-yl)-4-
(trifluoromethyl)benzo[d]oxazol-5-yl)ethan-1-one,
1-(2-(3,6-diazabicyclo[3.1.1]heptan-3-yl)-7-(thiazol-2-yl)-
4-(trifluoromethyl)benzo[d]oxazol-5-yl)ethan-1-one,
1-(2-(3,8-diazabicyclo[3.2.1]octan-3-yl)-7-(thiazol-2-yl)-4-
(trifluoromethyl)benzo[d]oxazol-5-yl)ethan-1-ol,
1-(2-(3,6-diazabicyclo[3.1.1]heptan-3-yl)-7-(thiazol-2-yl)-
4-(trifluoromethyl)benzo[d]oxazol-5-yl)ethan-1-ol, 1-(2-(3,8-diazabicyclo[3.2.1]octan-3-yl)-7-(thiazol-2-yl)-4-(trifluoromethyl)benzo[d]oxazol-5-yl)-2,2-difluoroethan-1-ol,
2-(3,8-diazabicyclo[3.2.1]octan-3-yl)-5-(1-methoxyethyl)-7-(thiazol-2-yl)-4-(trifluoromethyl)benzo[d]oxazole,
2-(3,6-diazabicyclo[3.1.1]heptan-3-yl)-5-(1-methoxyethyl)-7-(thiazol-2-yl)-4-(trifluoromethyl)benzo[d]oxazole,
ethyl 2-(3,8-diazabicyclo[3.2.1]octan-3-yl)-7-(thiazol-2-yl)-4-(trifluoromethoxy)benzo[d]oxazole-5-carboxylate,
ethyl 2-(3,6-diazabicyclo[3.1.1]heptan-3-yl)-7-(thiazol-2-yl)-4-(trifluoromethoxy)benzo[d]oxazole-5-carboxylate,
ethyl 2-(3,9-diazabicyclo[3.3.1]nonan-3-yl)-7-(thiazol-2-yl)-4-(trifluoromethoxy)benzo[d]oxazole-5-carboxylate,
2-(3,8-diazabicyclo[3.2.1]octan-3-yl)-7-(thiazol-2-yl)-4-(trifluoromethoxy)benzo[d]oxazole-5-carboxylic acid,
2-(3,6-diazabicyclo[3.1.1]heptan-3-yl)-7-(thiazol-2-yl)-4-(trifluoromethoxy)benzo[d]oxazole-5-carboxylic acid,
2-(3,9-diazabicyclo[3.3.1]nonan-3-yl)-7-(thiazol-2-yl)-4-(trifluoromethoxy)benzo[d]oxazole-5-carboxylic acid,
2-(2-(3,8-diazabicyclo[3.2.1]octan-3-yl)-7-(thiazol-2-yl)-4-(trifluoromethoxy)benzo[d]oxazol-5-yl)propan-2-ol,
2-(2-(3,6-diazabicyclo[3.1.1]heptan-3-yl)-7-(thiazol-2-yl)-4-(trifluoromethoxy)benzo[d]oxazol-5-yl)propan-2-ol,
2-(2-(3,9-diazabicyclo[3.3.1]nonan-3-yl)-7-(thiazol-2-yl)-4-(trifluoromethoxy)benzo[d]oxazol-5-yl)propan-2-ol,
2-(3,8-diazabicyclo[3.2.1]octan-3-yl)-5-(2-methoxypropan-2-yl)-7-(thiazol-2-yl)-4-(trifluoromethoxy)benzo[d]oxazole,
2-(3,6-diazabicyclo[3.1.1]heptan-3-yl)-5-(2-methoxypropan-2-yl)-7-(thiazol-2-yl)-4-(trifluoromethoxy)benzo[d]oxazole,
2-(3,9-diazabicyclo[3.3.1]nonan-3-yl)-5-(2-methoxypropan-2-yl)-7-(thiazol-2-yl)-4-(trifluoromethoxy)benzo[d]oxazole,
(2-(3,8-diazabicyclo[3.2.1]octan-3-yl)-7-(thiazol-2-yl)-4-(trifluoromethoxy)benzo[d]oxazol-5-yl)(azetidin-1-yl)methanone,
2-(3,8-diazabicyclo[3.2.1]octan-3-yl)-N-(2-hydroxyethyl)-N-methyl-7-(thiazol-2-yl)-4-(trifluoromethoxy)benzo[d]oxazole-5-carboxamide,
(2-(3,8-diazabicyclo[3.2.1]octan-3-yl)-7-(thiazol-2-yl)-4-(trifluoromethoxy)benzo[d]oxazol-5-yl)(3-hydroxy-3-(trifluoromethyl)azetidin-1-yl)methanone, (2-(3,8-diazabicyclo[3.2.1]octan-3-yl)-7-(thiazol-2-yl)-4-(trifluoromethoxy)benzo[d]oxazol-5-yl)methanol,
1-(2-(3,8-diazabicyclo[3.2.1]octan-3-yl)-7-(thiazol-2-yl)-4-(trifluoromethoxy)benzo[d]oxazol-5-yl)ethan-1-ol
1-(2-(3,6-diazabicyclo[3.1.1]heptan-3-yl)-7-(thiazol-2-yl)-4-(trifluoromethoxy)benzo[d]oxazol-5-yl)ethan-1-ol,
(R)-1-(2-(3,6-diazabicyclo[3.1.1]heptan-3-yl)-7-(thiazol-2-yl)-4-(trifluoromethoxy)benzo[d]oxazol-5-yl)ethan-1-ol,
(S)-1-(2-(3,6-diazabicyclo[3.1.1]heptan-3-yl)-7-(thiazol-2-yl)-4-(trifluoromethoxy)benzo[d]oxazol-5-yl)ethan-1-ol,
1-(2-(3,8-diazabicyclo[3.2.1]octan-3-yl)-7-(thiazol-2-yl)-4-(trifluoromethoxy)benzo[d]oxazol-5-yl)propan-1-ol,
1-(2-(3,8-diazabicyclo[3.2.1]octan-3-yl)-7-(thiazol-2-yl)-4-(trifluoromethoxy)benzo[d]oxazol-5-yl)-2-methylpropan-1-ol,
1-(2-(3,8-diazabicyclo[3.2.1]octan-3-yl)-7-(thiazol-2-yl)-4-(trifluoromethoxy)benzo[d]oxazol-5-yl)-2,2-difluoroethan-1-ol,
(R)-1-(2-(3,8-diazabicyclo[3.2.1]octan-3-yl)-7-(thiazol-2-yl)-4-(trifluoromethoxy)benzo[d]oxazol-5-yl)-2,2-difluoroethan-1-ol,
(S)-1-(2-(3,8-diazabicyclo[3.2.1]octan-3-yl)-7-(thiazol-2-yl)-4-(trifluoromethoxy)benzo[d]oxazol-5-yl)-2,2-difluoroethan-1-ol,
1-(2-(3,6-diazabicyclo[3.1.1]heptan-3-yl)-7-(thiazol-2-yl)-4-(trifluoromethoxy)benzo[d]oxazol-5-yl)-2,2-difluoroethan-1-ol,
(R)-1-(2-(3,6-diazabicyclo[3.1.1]heptan-3-yl)-7-(thiazol-2-yl)-4-(trifluoromethoxy)benzo[d]oxazol-5-yl)-2,2-difluoroethan-1-ol,
(S)-1-(2-(3,6-diazabicyclo[3.1.1]heptan-3-yl)-7-(thiazol-2-yl)-4-(trifluoromethoxy)benzo[d]oxazol-5-yl)-2,2-difluoroethan-1-ol,
2-(3,6-diazabicyclo[3.1.1]heptan-3-yl)-5-(2,2-difluoro-1-methoxyethyl)-7-(thiazol-2-yl)-4-(trifluoromethoxy)benzo[d]oxazole,
2-(3,8-diazabicyclo[3.2.1]octan-3-yl)-5-(2,2-difluoro-1-methoxyethyl)-7-(thiazol-2-yl)-4-(trifluoromethoxy)benzo[d]oxazole,
2-(3,8-diazabicyclo[3.2.1]octan-3-yl)-5-(1-methoxyethyl)-7-(thiazol-2-yl)-4-(trifluoromethoxy)benzo[d]oxazole,
2-(3,6-diazabicyclo[3.1.1]heptan-3-yl)-5-(1-methoxyethyl)-7-(thiazol-2-yl)-4-(trifluoromethoxy)benzo[d]oxazole,
1-(2-(3,6-diazabicyclo[3.1.1]heptan-3-yl)-7-(thiazol-2-yl)-4-(trifluoromethoxy)benzo[d]oxazol-5-yl)ethan-1-one,
1-(2-(3,8-diazabicyclo[3.2.1]octan-3-yl)-7-(thiazol-2-yl)-4-(trifluoromethoxy)benzo[d]oxazol-5-yl)ethan-1-one,
2-(3,6-diazabicyclo[3.1.1]heptan-3-yl)-7-(thiazol-2-yl)-5-(1,1,1-trifluoro-2-methoxypropan-2-yl)-4-(trifluoromethoxy)benzo[d]oxazole,
2-(3,8-diazabicyclo[3.2.1]octan-3-yl)-7-(thiazol-2-yl)-5-(1,1,1-trifluoro-2-methoxypropan-2-yl)-4-(trifluoromethoxy)benzo[d]oxazole,
2-(2-(3,6-diazabicyclo[3.1.1]heptan-3-yl)-7-(thiazol-2-yl)-4-(trifluoromethoxy)benzo[d]oxazol-5-yl)-1,1,1-trifluoropropan-2-ol,
2-(2-(3,8-diazabicyclo[3.2.1]octan-3-yl)-7-(thiazol-2-yl)-4-(trifluoromethoxy)benzo[d]oxazol-5-yl)-1,1,1-trifluoropropan-2-ol,
(E)-1-(2-(3,8-diazabicyclo[3.2.1]octan-3-yl)-7-(thiazol-2-yl)-4-(trifluoromethoxy)benzo[d]oxazol-5-yl)ethan-1-one O-methyloxime,
(Z)-1-(2-(3,8-diazabicyclo[3.2.1]octan-3-yl)-7-(thiazol-2-yl)-4-(trifluoromethoxy)benzo[d]oxazol-5-yl)ethan-1-one O-methyloxime,
(E)-1-(2-(3,6-diazabicyclo[3.1.1]heptan-3-yl)-7-(thiazol-2-yl)-4-(trifluoromethoxy)benzo[d]oxazol-5-yl)ethan-1-one O-methyloxime,
(Z)-1-(2-(3,6-diazabicyclo[3.1.1]heptan-3-yl)-7-(thiazol-2-yl)-4-(trifluoromethoxy)benzo[d]oxazol-5-yl)ethan-1-one O-methyloxime,
2-(3,8-diazabicyclo[3.2.1]octan-3-yl)-4-(1-ethoxy-2,2,2-trifluoroethyl)-7-(thiazol-2-yl)benzo[d]oxazole,
2-(3,8-diazabicyclo[3.2.1]octan-3-yl)-7-(thiazol-2-yl)-4-(2,2,2-trifluoro-1-(2,2,2-trifluoroethoxy)ethyl)benzo[d]oxazole,
2-(3,8-diazabicyclo[3.2.1]octan-3-yl)-7-(thiazol-2-yl)-4-(2,2,2-trifluoro-1-methoxyethyl)benzo[d]oxazole,
2-(3,6-diazabicyclo[3.1.1]heptan-3-yl)-7-(thiazol-2-yl)-4-(2,2,2-trifluoro-1-(2,2,2-trifluoroethoxy)ethyl)benzo[d]oxazole,
2-(3,6-diazabicyclo[3.1.1]heptan-3-yl)-4-(1-ethoxy-2,2,2-trifluoroethyl)-7-(thiazol-2-yl)benzo[d]oxazole,
2-(1-(2-(3,8-diazabicyclo[3.2.1]octan-3-yl)-7-(thiazol-2-yl)benzo[d]oxazol-4-yl)-2,2,2-trifluoroethoxy)ethan-1-ol,
2-(1-(2-(3,6-diazabicyclo[3.1.1]heptan-3-yl)-7-(thiazol-2-yl)benzo[d]oxazol-4-yl)-2,2,2-trifluoroethoxy)acetonitrile,
2-(1-(2-(3,6-diazabicyclo[3.1.1]heptan-3-yl)-7-(thiazol-2-yl)benzo[d]oxazol-4-yl)-2,2,2-trifluoroethoxy)ethan-1-ol, 2-(1-(2-(3,8-diazabicyclo[3.2.1]octan-3-yl)-7-(thiazol-2-yl) benzo[d]oxazol-4-yl)-2,2,2-trifluoroethoxy)acetonitrile,
2-(3,6-diazabicyclo[3.1.1]heptan-3-yl)-7-(thiazol-2-yl)-4-(2,2,2-trifluoro-1-(2-methoxyethoxy)ethyl)benzo[d]oxazole,
4-(1-((1H-tetrazol-5-yl)methoxy)-2,2,2-trifluoroethyl)-2-(3,8-diazabicyclo[3.2.1]octan-3-yl)-7-(thiazol-2-yl)benzo[d]oxazole,
4-(1-((1H-tetrazol-5-yl)methoxy)-2,2,2-trifluoroethyl)-2-(3,6-diazabicyclo[3.1.1]heptan-3-yl)-7-(thiazol-2-yl)benzo[d]oxazole,
1-((1-(2-(3,6-diazabicyclo[3.1.1]heptan-3-yl)-7-(thiazol-2-yl)benzo[d]oxazol-4-yl)-2,2,2-trifluoroethoxy)methyl)cyclopropan-1-ol,
1-(2-(3,8-diazabicyclo[3.2.1]octan-3-yl)-7-(thiazol-2-yl) benzo[d]oxazol-4-yl)-2,2,2-trifluoroethane-1,1-diol,
2-(2-(3,6-diazabicyclo[3.1.1]heptan-3-yl)-7-(thiazol-2-yl) benzo[d]oxazol-4-yl)-1,1,1-trifluoropropan-2-ol,
(R)-2-(2-(3,6-diazabicyclo[3.1.1]heptan-3-yl)-7-(thiazol-2-yl)benzo[d]oxazol-4-yl)-1,1,1-trifluoropropan-2-ol,
(S)-2-(2-(3,6-diazabicyclo[3.1.1]heptan-3-yl)-7-(thiazol-2-yl)benzo[d]oxazol-4-yl)-1,1,1-trifluoropropan-2-ol,
2-(3,6-diazabicyclo[3.1.1]heptan-3-yl)-7-(thiazol-2-yl)-4-(1,1,1-trifluoro-2-methoxypropan-2-yl)benzo[d]oxazole,
2-(2-(3,8-diazabicyclo[3.2.1]octan-3-yl)-7-(thiazol-2-yl) benzo[d]oxazol-4-yl)-1,1,1-trifluoropropan-2-ol,
methyl 2-(3,8-diazabicyclo[3.2.1]octan-3-yl)-7-(thiazol-2-yl)benzo[d]oxazole-4-carboxylate,
2-(3,8-diazabicyclo[3.2.1]octan-3-yl)-7-(thiazol-2-yl)benzo[d]oxazole-4-carboxylic acid,
2-(2-(3,6-diazabicyclo[3.1.1]heptan-3-yl)-7-(thiazol-2-yl) benzo[d]oxazol-4-yl)propan-2-ol,
2-(2-(3,8-diazabicyclo[3.2.1]octan-3-yl)-7-(thiazol-2-yl) benzo[d]oxazol-4-yl)propan-2-ol,
1-(2-(3,9-diazabicyclo[3.3.1]nonan-3-yl)-7-(thiazol-2-yl) benzo[d]oxazol-4-yl)ethan-1-ol,
1-(2-(3,6-diazabicyclo[3.1.1]heptan-3-yl)-7-(thiazol-2-yl) benzo[d]oxazol-4-yl)ethan-1-ol,
2-(3,6-diazabicyclo[3.1.1]heptan-3-yl)-4-(1-methoxyethyl)-7-(thiazol-2-yl)benzo[d]oxazole,
2-(3,8-diazabicyclo[3.2.1]octan-3-yl)-4-(1-methoxyethyl)-7-(thiazol-2-yl)benzo[d]oxazole,
2-(3,9-diazabicyclo[3.3.1]nonan-3-yl)-4-(1-methoxyethyl)-7-(thiazol-2-yl)benzo[d]oxazole,
1-(2-(3,6-diazabicyclo[3.1.1]heptan-3-yl)-7-(thiazol-2-yl) benzo[d]oxazol-4-yl)ethan-1-one,
1-(2-(3,8-diazabicyclo[3.2.1]octan-3-yl)-7-(thiazol-2-yl) benzo[d]oxazol-4-yl)ethan-1-one,
1-((2-(3,6-diazabicyclo[3.1.1]heptan-3-yl)-7-(thiazol-2-yl) benzo[d]oxazol-4-yl)oxy)-1,1-difluoro-2-methylpropan-2-ol,
2-((2-(3,6-diazabicyclo[3.1.1]heptan-3-yl)-7-(thiazol-2-yl) benzo[d]oxazol-4-yl)oxy)-2,2-difluoroethan-1-ol,
1-((2-(3,6-diazabicyclo[3.1.1]heptan-3-yl)-7-(thiazol-2-yl) benzo[d]oxazol-4-yl)oxy)-1,1-difluoropropan-2-ol,
(R)-1-((2-(3,6-diazabicyclo[3.1.1]heptan-3-yl)-7-(thiazol-2-yl)benzo[d]oxazol-4-yl)oxy)-1,1-difluoropropan-2-ol,
(S)-1-((2-(3,6-diazabicyclo[3.1.1]heptan-3-yl)-7-(thiazol-2-yl)benzo[d]oxazol-4-yl)oxy)-1,1-difluoropropan-2-ol,
2-(1-(2-(3,6-diazabicyclo[3.1.1]heptan-3-yl)-7-(thiazol-2-yl)benzo[d]oxazol-4-yl)-2,2,2-trifluoroethoxy)acetic acid,
2-(3,8-diazabicyclo[3.2.1]octan-3-yl)-4-((tetrahydro-2H-pyran-4-yl)oxy)-7-(thiazol-2-yl)benzo[d]oxazole,
1-(1-(2-(3,6-diazabicyclo[3.1.1]heptan-3-yl)-7-(thiazol-2-yl)benzo[d]oxazol-4-yl)-2,2,2-trifluoroethoxy)-2-methylpropan-2-ol,
2-(1-(2-(3,6-diazabicyclo[3.1.1]heptan-3-yl)-7-(thiazol-2-yl)benzo[d]oxazol-4-yl)-2,2,2-trifluoroethoxy)acetamide,
1-(1-(2-(3,6-diazabicyclo[3.1.1]heptan-3-yl)-7-(thiazol-2-yl)benzo[d]oxazol-4-yl)-2,2,2-trifluoroethoxy)-1,1-difluoro-2-methylpropan-2-ol,
2-(1-(2-(3,6-diazabicyclo[3.1.1]heptan-3-yl)-7-(thiazol-2-yl)benzo[d]oxazol-4-yl)-2,2,2-trifluoroethoxy)-2,2-difluoroethan-1-ol,
1-((2-(3,6-diazabicyclo[3.1.1]heptan-3-yl)-7-(thiazol-2-yl) benzo[d]oxazol-4-yl)oxy)propan-2-ol,
1-(1-(2-(3,6-diazabicyclo[3.1.1]heptan-3-yl)-7-(thiazol-2-yl)benzo[d]oxazol-4-yl)-2,2,2-trifluoroethoxy)propan-2-ol,
2-(3,8-diazabicyclo[3.2.1]octan-3-yl)-4-((tetrahydro-2H-pyran-3-yl)oxy)-7-(thiazol-2-yl)benzo[d]oxazole,
2-(3,8-diazabicyclo[3.2.1]octan-3-yl)-4-(difluoromethoxy)-7-(thiazol-2-yl)benzo[d]oxazole,
1-((2-(3,8-diazabicyclo[3.2.1]octan-3-yl)-7-(thiazol-2-yl) benzo[d]oxazol-4-yl)oxy)-2-methylpropan-2-ol,
1-(1-(2-(3,6-diazabicyclo[3.1.1]heptan-3-yl)-7-(thiazol-2-yl)benzo[d]oxazol-4-yl)-2,2,2-trifluoroethoxy)-1,1-difluoropropan-2-ol,
3-((2-(3,6-diazabicyclo[3.1.1]heptan-3-yl)-7-(thiazol-2-yl) benzo[d]oxazol-4-yl)oxy)cyclobutane-1-carbonitrile,
2-(3-((2-(3,6-diazabicyclo[3.1.1]heptan-3-yl)-7-(thiazol-2-yl)benzo[d]oxazol-4-yl)oxy)cyclobutyl)propan-2-ol,
2-((2-(3,6-diazabicyclo[3.1.1]heptan-3-yl)-7-(thiazol-2-yl) benzo[d]oxazol-4-yl)oxy)-2-methylpropan-1-ol,
1-(2-(3,6-diazabicyclo[3.1.1]heptan-3-yl)-7-(thiazol-2-yl)-4-(trifluoromethoxy)benzo[d]oxazol-5-yl)cyclopropan-1-ol,
1-(2-(3,8-diazabicyclo[3.2.1]octan-3-yl)-7-(thiazol-2-yl)-4-(trifluoromethoxy)benzo[d]oxazol-5-yl)cyclopropan-1-ol,
3-((2-(3,6-diazabicyclo[3.1.1]heptan-3-yl)-7-(thiazol-2-yl) benzo[d]oxazol-4-yl)oxy)-1,1,1-trifluoropropan-2-ol,
2-(3,6-diazabicyclo[3.1.1]heptan-3-yl)-4-(difluoromethoxy)-7-(thiazol-2-yl)benzo[d]oxazole,
1-((2-(3,6-diazabicyclo[3.1.1]heptan-3-yl)-7-(thiazol-2-yl) benzo[d]oxazol-4-yl)oxy)-2-methylpropan-2-ol,
3-(1-(2-(3,6-diazabicyclo[3.1.1]heptan-3-yl)-7-(thiazol-2-yl)benzo[d]oxazol-4-yl)-2,2,2-trifluoroethoxy)-2,3-dimethylbutan-2-ol,
2-(3,6-diazabicyclo[3.1.1]heptan-3-yl)-7-(thiazol-2-yl)-4-(2,2,2-trifluoro-1-(2-methoxy-2-methylpropoxy)ethyl) benzo[d]oxazole,
2-(3,6-diazabicyclo[3.1.1]heptan-3-yl)-7-(thiazol-2-yl)-4-(2,2,2-trifluoro-1-((1-methoxycyclopropyl)methoxy) ethyl)benzo[d]oxazole,
2-(3,6-diazabicyclo[3.1.1]heptan-3-yl)-5-(1-methoxycyclopropyl)-7-(thiazol-2-yl)-4-(trifluoromethoxy)benzo[d]oxazole,
1-(1-(2-(3,6-diazabicyclo[3.1.1]heptan-3-yl)-7-(thiazol-4-yl)benzo[d]oxazol-4-yl)-2,2,2-trifluoroethoxy)-2-methylpropan-2-ol,
3-((2-(3,6-diazabicyclo[3.1.1]heptan-3-yl)-7-(thiazol-2-yl) benzo[d]oxazol-4-yl)oxy)cyclobutan-1-ol,
1-((1-(2-(3,6-diazabicyclo[3.1.1]heptan-3-yl)-7-(thiazol-4-yl)benzo[d]oxazol-4-yl)-2,2,2-trifluoroethoxy)methyl) cyclopropan-1-ol,
2-(3,6-diazabicyclo[3.1.1]heptan-3-yl)-5-(2-methoxypropan-2-yl)-7-(thiazol-4-yl)-4-(trifluoromethoxy)benzo[d] oxazole,
2-(2-(3,6-diazabicyclo[3.1.1]heptan-3-yl)-7-(thiazol-4-yl)-4-(trifluoromethoxy)benzo[d]oxazol-5-yl)propan-2-ol, 1-((2-(3,6-diazabicyclo[3.1.1]heptan-3-yl)-7-(pyridin-2-yl)benzo[d]oxazol-4-yl)oxy)-1,1-difluoro-2-methylpropan-2-ol,
1-((2-(3,6-diazabicyclo[3.1.1]heptan-3-yl)-7-(oxazol-2-yl)benzo[d]oxazol-4-yl)oxy)-1,1-difluoro-2-methylpropan-2-ol,
2-(2-(3,8-diazabicyclo[3.2.1]octan-3-yl)-7-(thiazol-4-yl)-4-(trifluoromethoxy)benzo[d]oxazol-5-yl)propan-2-ol
2-(3,6-diazabicyclo[3.1.1]heptan-3-yl)-4-((tetrahydro-2H-pyran-4-yl)oxy)-7-(thiazol-2-yl)benzo[d]oxazole,
4-((2-(3,6-diazabicyclo[3.1.1]heptan-3-yl)-7-(thiazol-2-yl)benzo[d]oxazol-4-yl)oxy)-4,4-difluoro-2-methylbutan-2-ol,
2-(3,8-diazabicyclo[3.2.1]octan-3-yl)-5-(2-methoxypropan-2-yl)-7-(thiazol-4-yl)-4-(trifluoromethoxy)benzo[d]oxazole,
1-(2-(3,6-diazabicyclo[3.1.1]heptan-3-yl)-7-(thiazol-4-yl)-4-(trifluoromethoxy)benzo[d]oxazol-5-yl)cyclopropan-1-ol,
1-(2-(3,6-diazabicyclo[3.1.1]heptan-3-yl)-7-(thiazol-4-yl)-4-(trifluoromethoxy)benzo[d]oxazol-5-yl)-2,2-difluoroethan-1-ol,
(R)-1-(2-(3,6-diazabicyclo[3.1.1]heptan-3-yl)-7-(thiazol-4-yl)-4-(trifluoromethoxy)benzo[d]oxazol-5-yl)-2,2-difluoroethan-1-ol,
(S)-1-(2-(3,6-diazabicyclo[3.1.1]heptan-3-yl)-7-(thiazol-4-yl)-4-(trifluoromethoxy)benzo[d]oxazol-5-yl)-2,2-difluoroethan-1-ol,
1-(2-(3,8-diazabicyclo[3.2.1]octan-3-yl)-7-(thiazol-4-yl)-4-(trifluoromethoxy)benzo[d]oxazol-5-yl)-2,2-difluoroethan-1-ol,
(R)-1-(2-(3,8-diazabicyclo[3.2.1]octan-3-yl)-7-(thiazol-4-yl)-4-(trifluoromethoxy)benzo[d]oxazol-5-yl)-2,2-difluoroethan-1-ol,
(S)-1-(2-(3,8-diazabicyclo[3.2.1]octan-3-yl)-7-(thiazol-4-yl)-4-(trifluoromethoxy)benzo[d]oxazol-5-yl)-2,2-difluoroethan-1-ol,
1-((2-(3,6-diazabicyclo[3.1.1]heptan-3-yl)-7-(1H-pyrazol-1-yl)benzo[d]oxazol-4-yl)oxy)-1,1-difluoro-2-methylpropan-2-ol,
4-((2-(3,6-diazabicyclo[3.1.1]heptan-3-yl)-7-(thiazol-2-yl)benzo[d]oxazol-4-yl)oxy)cyclohexan-1-ol,
1-((2-(3,6-diazabicyclo[3.1.1]heptan-3-yl)-7-(4-methylthiazol-2-yl)benzo[d]oxazol-4-yl)oxy)-1,1-difluoro-2-methylpropan-2-ol,
1-((2-(3,6-diazabicyclo[3.1.1]heptan-3-yl)-7-(thiazol-4-yl)benzo[d]oxazol-4-yl)oxy)-1,1-difluoro-2-methylpropan-2-ol,
1-((2-(3,8-diazabicyclo[3.2.1]octan-3-yl)-7-(thiazol-4-yl)benzo[d]oxazol-4-yl)oxy)-1,1-difluoro-2-methylpropan-2-ol,
1-((2-(3,6-diazabicyclo[3.1.1]heptan-3-yl)-7-(thiazol-4-yl)benzo[d]oxazol-4-yl)oxy)-1,1-difluoropropan-2-ol,
1-((2-(3,8-diazabicyclo[3.2.1]octan-3-yl)-7-(thiazol-4-yl)benzo[d]oxazol-4-yl)oxy)-1,1-difluoropropan-2-ol,
2-((2-(3,6-diazabicyclo[3.1.1]heptan-3-yl)-7-(thiazol-4-yl)benzo[d]oxazol-4-yl)oxy)-2,2-difluoroethan-1-ol,
2-((2-(3,8-diazabicyclo[3.2.1]octan-3-yl)-7-(thiazol-4-yl)benzo[d]oxazol-4-yl)oxy)-2,2-difluoroethan-1-ol,
3-((2-(3,6-diazabicyclo[3.1.1]heptan-3-yl)-7-(thiazol-2-yl)benzo[d]oxazol-4-yl)oxy)-4,4,4-trifluoro-2-methylbutan-2-ol,
4-((2-(3,6-diazabicyclo[3.1.1]heptan-3-yl)-7-(thiazol-2-yl)benzo[d]oxazol-4-yl)oxy)tetrahydro-2H-thiopyran 1,1-dioxide,
2-((2-(3,6-diazabicyclo[3.1.1]heptan-3-yl)-7-(pyridin-2-yl)benzo[d]oxazol-4-yl)oxy)-2,2-difluoroethan-1-ol,
1-((2-(3,8-diazabicyclo[3.2.1]octan-3-yl)-7-(1H-pyrazol-1-yl)benzo[d]oxazol-4-yl)oxy)-1,1-difluoro-2-methylpropan-2-ol,
1-((2-(3,8-diazabicyclo[3.2.1]octan-3-yl)-7-(pyridin-2-yl)benzo[d]oxazol-4-yl)oxy)-1,1-difluoro-2-methylpropan-2-ol,
1-((2-(3,8-diazabicyclo[3.2.1]octan-3-yl)-7-(4-methylthiazol-2-yl)benzo[d]oxazol-4-yl)oxy)-1,1-difluoro-2-methylpropan-2-ol,
2-((2-(3,6-diazabicyclo[3.1.1]heptan-3-yl)-7-(5-fluoropyridin-2-yl)benzo[d]oxazol-4-yl)oxy)-2,2-difluoroethan-1-ol,
2-((2-(3,6-diazabicyclo[3.1.1]heptan-3-yl)-7-(1H-pyrazol-1-yl)benzo[d]oxazol-4-yl)oxy)-2,2-difluoroethan-1-ol,
1-((2-(3,8-diazabicyclo[3.2.1]octan-3-yl)-7-(oxazol-2-yl)benzo[d]oxazol-4-yl)oxy)-1,1-difluoro-2-methylpropan-2-ol,
1-((2-(3,8-diazabicyclo[3.2.1]octan-3-yl)-7-(2H-1,2,3-triazol-2-yl)benzo[d]oxazol-4-yl)oxy)-1,1-difluoro-2-methylpropan-2-ol,
2-(3,6-diazabicyclo[3.1.1]heptan-3-yl)-4-(((S)-tetrahydrofuran-3-yl)oxy)-7-(thiazol-2-yl)benzo[d]oxazole,
2-(3,6-diazabicyclo[3.1.1]heptan-3-yl)-4-(((R)-tetrahydrofuran-3-yl)oxy)-7-(thiazol-2-yl)benzo[d]oxazole,
2-(3,6-diazabicyclo[3.1.1]heptan-3-yl)-4-(oxetan-3-yloxy)-7-(thiazol-2-yl)benzo[d]oxazole,
3-((2-(3,6-diazabicyclo[3.1.1]heptan-3-yl)-7-(thiazol-2-yl)benzo[d]oxazol-4-yl)oxy)-3,3-difluoro-2-methylpropane-1,2-diol,
1-((2-(3,8-diazabicyclo[3.2.1]octan-3-yl)-7-(1,2,4-thiadiazol-5-yl)benzo[d]oxazol-4-yl)oxy)-1,1-difluoro-2-methylpropan-2-ol,
1-((2-(3,8-diazabicyclo[3.2.1]octan-3-yl)-7-(1-methyl-1H-pyrazol-3-yl)benzo[d]oxazol-4-yl)oxy)-1,1-difluoro-2-methylpropan-2-ol,
1-((2-(3,6-diazabicyclo[3.1.1]heptan-3-yl)-7-(5-fluoropyridin-2-yl)benzo[d]oxazol-4-yl)oxy)-1,1-difluoro-2-methylpropan-2-ol,
1-((2-(3,8-diazabicyclo[3.2.1]octan-3-yl)-7-(pyrimidin-2-yl)benzo[d]oxazol-4-yl)oxy)-1,1-difluoro-2-methylpropan-2-ol,
1-((2-(3,8-diazabicyclo[3.2.1]octan-3-yl)-7-(isothiazol-3-yl)benzo[d]oxazol-4-yl)oxy)-1,1-difluoro-2-methylpropan-2-ol,
1-((2-(3,8-diazabicyclo[3.2.1]octan-3-yl)-7-(5-fluoropyridin-2-yl)benzo[d]oxazol-4-yl)oxy)-1,1-difluoro-2-methylpropan-2-ol,
1-((2-(3,8-diazabicyclo[3.2.1]octan-3-yl)-7-(3-methyl-1,2,4-thiadiazol-5-yl)benzo[d]oxazol-4-yl)oxy)-1,1-difluoro-2-methylpropan-2-ol,
2-(3,6-diazabicyclo[3.1.1]heptan-3-yl)-7-(thiazol-2-yl)-4-((trifluoromethyl)sulfonyl)benzo[d]oxazole,
2-(3,6-diazabicyclo[3.1.1]heptan-3-yl)-7-(thiazol-2-yl)benzo[d]oxazole-4-carbonitrile,
2-(3,6-diazabicyclo[3.1.1]heptan-3-yl)-7-(thiazol-2-yl)-4-((5-(trifluoromethyl)pyridin-2-yl)oxy)benzo[d]oxazole,
2-(3,6-diazabicyclo[3.1.1]heptan-3-yl)-4-(pyridin-2-yloxy)-7-(thiazol-2-yl)benzo[d]oxazole,
2-(3,6-diazabicyclo[3.1.1]heptan-3-yl)-4-(pyrimidin-2-yloxy)-7-(thiazol-2-yl)benzo[d]oxazole,
2-(3,6-diazabicyclo[3.1.1]heptan-3-yl)-4-(pyrazin-2-yloxy)-7-(thiazol-2-yl)benzo[d]oxazole,
2-(3,6-diazabicyclo[3.1.1]heptan-3-yl)-4-((6-methyl-4-(trifluoromethyl)pyridazin-3-yl)oxy)-7-(thiazol-2-yl)benzo[d]oxazole,
(6-((2-(3,6-diazabicyclo[3.1.1]heptan-3-yl)-7-(thiazol-2-yl)benzo[d]oxazol-4-yl)oxy)pyridin-3-yl)methanol, (6-((2-(3,6-diazabicyclo[3.1.1]heptan-3-yl)-7-(thiazol-2-yl)benzo[d]oxazol-4-yl)oxy)-5-(trifluoromethyl)pyridin-3-yl)methanol, 2-(3,6-diazabicyclo[3.1.1]heptan-3-yl)-7-(thiazol-2-yl)-4-((5-(trifluoromethoxy)pyridin-2-yl)oxy)benzo[d]oxazole, 2-(3,6-diazabicyclo[3.1.1]heptan-3-yl)-4-cyclopropyl-7-(thiazol-2-yl)benzo[d]oxazole, 2-(3,6-diazabicyclo[3.1.1]heptan-3-yl)-4-(methylthio)-7-(thiazol-2-yl)benzo[d]oxazole, 2-(3,6-diazabicyclo[3.1.1]heptan-3-yl)-4-(methylsulfinyl)-7-(thiazol-2-yl)benzo[d]oxazole, 2-(3,6-diazabicyclo[3.1.1]heptan-3-yl)-4-(methylsulfonyl)-7-(thiazol-2-yl)benzo[d]oxazole, 2-((2-(3,6-diazabicyclo[3.1.1]heptan-3-yl)-7-(thiazol-2-yl)benzo[d]oxazol-4-yl)thio)ethan-1-ol, 2-((2-(3,6-diazabicyclo[3.1.1]heptan-3-yl)-7-(thiazol-2-yl)benzo[d]oxazol-4-yl)sulfinyl)ethan-1-ol, 2-((2-(3,6-diazabicyclo[3.1.1]heptan-3-yl)-7-(thiazol-2-yl)benzo[d]oxazol-4-yl)sulfonyl)ethan-1-ol, 2-(3,6-diazabicyclo[3.1.1]heptan-3-yl)-4-((1,1-difluoroallyl)oxy)-7-(thiazol-2-yl)benzo[d]oxazole, 2-(3,6-diazabicyclo[3.1.1]heptan-3-yl)-4-((5-(methylsulfonyl)pyridin-2-yl)oxy)-7-(thiazol-2-yl)benzo[d]oxazole, 2-(3,6-diazabicyclo[3.1.1]heptan-3-yl)-N-(2-methoxyethyl)-7-(thiazol-2-yl)benzo[d]oxazole-4-carboxamide, 2-(3,6-diazabicyclo[3.1.1]heptan-3-yl)-7-(thiazol-2-yl)benzo[d]oxazole-4-carboxamide, 2-(3,6-diazabicyclo[3.1.1]heptan-3-yl)-N-(2-hydroxyethyl)-7-(thiazol-2-yl)benzo[d]oxazole-4-carboxamide, 2-(3,6-diazabicyclo[3.1.1]heptan-3-yl)-N-(2-hydroxyethyl)-N-methyl-7-(thiazol-2-yl)benzo[d]oxazole-4-carboxamide, 2-(3,6-diazabicyclo[3.1.1]heptan-3-yl)-N-cyclopropyl-7-(thiazol-2-yl)benzo[d]oxazole-4-carboxamide, 2-(3,6-diazabicyclo[3.1.1]heptan-3-yl)-N-ethyl-7-(thiazol-2-yl)benzo[d]oxazole-4-carboxamide, (2-(3,6-diazabicyclo[3.1.1]heptan-3-yl)-7-(thiazol-2-yl)benzo[d]oxazol-4-yl) (morpholino)methanone, (2-(3,6-diazabicyclo[3.1.1]heptan-3-yl)-7-(thiazol-2-yl)benzo[d]oxazol-4-yl) (pyrrolidin-1-yl)methanone, N-benzyl-2-(3,6-diazabicyclo[3.1.1]heptan-3-yl)-7-(thiazol-2-yl)benzo[d]oxazole-4-carboxamide, 1-((2-(3,6-diazabicyclo[3.1.1]heptan-3-yl)-7-(thiazol-2-yl)benzo[d]oxazol-4-yl)oxy)-1,1-difluoro-3-methylbutan-2-ol, 1-((2-(3,6-diazabicyclo[3.1.1]heptan-3-yl)-7-(5-chloropyridin-2-yl)benzo[d]oxazol-4-yl)oxy)-1,1-difluoro-2-methylpropan-2-ol, (R)-3-((2-(3,6-diazabicyclo[3.1.1]heptan-3-yl)-7-(thiazol-2-yl)benzo[d]oxazol-4-yl)oxy)-3,3-difluoro-2-methylpropane-1,2-diol, (S)-3-((2-(3,6-diazabicyclo[3.1.1]heptan-3-yl)-7-(thiazol-2-yl)benzo[d]oxazol-4-yl)oxy)-3,3-difluoro-2-methylpropane-1,2-diol, 2-(3,6-diazabicyclo[3.1.1]heptan-3-yl)-7-(thiazol-2-yl)benzo[d]oxazole-4-carboxylic acid, 2-(3,6-diazabicyclo[3.1.1]heptan-3-yl)-N-hydroxy-7-(thiazol-2-yl)benzo[d]oxazole-4-carboxamide, 3-(5-(2-hydroxypropan-2-yl)-7-(thiazol-2-yl)-4-(trifluoromethoxy)benzo[d]oxazol-2-yl)-3,8-diazabicyclo[3.2.1]octan-8-ol, 2-(3,6-diazabicyclo[3.1.1]heptan-3-yl)-4-morpholino-7-(thiazol-2-yl)benzo[d]oxazole, 3-((2-(3,6-diazabicyclo[3.1.1]heptan-3-yl)-7-(thiazol-2-yl)benzo[d]oxazol-4-yl)oxy)-3,3-difluoropropane-1,2-diol, 3-(4-(1,1-difluoro-2-hydroxy-2-methylpropoxy)-7-(thiazol-2-yl)benzo[d]oxazol-2-yl)-3,6-diazabicyclo[3.1.1]heptan-6-ol, (R)-3-(4-(1,1-difluoro-2-hydroxypropoxy)-7-(thiazol-2-yl)benzo[d]oxazol-2-yl)-3,6-diazabicyclo[3.1.1]heptan-6-ol, (S)-3-(4-(1,1-difluoro-2-hydroxypropoxy)-7-(thiazol-2-yl)benzo[d]oxazol-2-yl)-3,6-diazabicyclo[3.1.1]heptan-6-ol, 3-(4-(1,1-difluoro-2-hydroxyethoxy)-7-(thiazol-2-yl)benzo[d]oxazol-2-yl)-3,6-diazabicyclo[3.1.1]heptan-6-ol, 3-(5-chloro-7-(thiazol-2-yl)-4-(trifluoromethoxy)benzo[d]oxazol-2-yl)-3,8-diazabicyclo[3.2.1]octan-8-ol, (2-((2-(3,6-diazabicyclo[3.1.1]heptan-3-yl)-7-(thiazol-2-yl)benzo[d]oxazol-4-yl)oxy)pyridin-3-yl)methanol, 1-((2-(3,6-diazabicyclo[3.1.1]heptan-3-yl)-7-(thiazol-2-yl)benzo[d]oxazol-4-yl)oxy)-1,1-difluoropropane-2,2-diol, (R)-3-(7-(thiazol-2-yl)-4-(2,2,2-trifluoro-1-hydroxyethyl)benzo[d]oxazol-2-yl)-3,8-diazabicyclo[3.2.1]octan-8-ol, (S)-3-(7-(thiazol-2-yl)-4-(2,2,2-trifluoro-1-hydroxyethyl)benzo[d]oxazol-2-yl)-3,8-diazabicyclo[3.2.1]octan-8-ol, 3-(7-(thiazol-2-yl)-4-(trifluoromethoxy)benzo[d]oxazol-2-yl)-3,6-diazabicyclo[3.1.1]heptan-6-ol, 3-(5-(2-hydroxypropan-2-yl)-7-(thiazol-2-yl)-4-(trifluoromethyl)benzo[d]oxazol-2-yl)-3,8-diazabicyclo[3.2.1]octan-8-ol, 2-(3,6-diazabicyclo[3.1.1]heptan-3-yl)-7-(thiazol-2-yl)benzo[d]oxazole, 3-(5-(1-hydroxyethyl)-7-(thiazol-2-yl)-4-(trifluoromethoxy)benzo[d]oxazol-2-yl)-3,8-diazabicyclo[3.2.1]octan-8-ol, 3-(5-(1-hydroxyethyl)-7-(thiazol-2-yl)-4-(trifluoromethyl)benzo[d]oxazol-2-yl)-3,8-diazabicyclo[3.2.1]octan-8-ol, 2-(3,6-diazabicyclo[3.1.1]heptan-3-yl)-N-(2-hydroxyethyl)-7-(thiazol-2-yl)benzo[d]oxazole-4-sulfonamide, 2-(3,6-diazabicyclo[3.1.1]heptan-3-yl)-N-methyl-7-(thiazol-2-yl)benzo[d]oxazole-4-sulfonamide, 2-(3,6-diazabicyclo[3.1.1]heptan-3-yl)-N-(2-methoxyethyl)-7-(thiazol-2-yl)benzo[d]oxazole-4-sulfonamide, 2-(3,6-diazabicyclo[3.1.1]heptan-3-yl)-N,N-dimethyl-7-(thiazol-2-yl)benzo[d]oxazole-4-sulfonamide, 2-(3,6-diazabicyclo[3.1.1]heptan-3-yl)-N-(2-hydroxyethyl)-N-methyl-7-(thiazol-2-yl)benzo[d]oxazole-4-sulfonamide, 2-(3,6-diazabicyclo[3.1.1]heptan-3-yl)-4-(pyrrolidin-1-ylsulfonyl)-7-(thiazol-2-yl)benzo[d]oxazole, 2-(3,6-diazabicyclo[3.1.1]heptan-3-yl)-4-(morpholinosulfonyl)-7-(thiazol-2-yl)benzo[d]oxazole, 2-(3,6-diazabicyclo[3.1.1]heptan-3-yl)-4-(1,1-difluoro-2-methoxyethoxy)-7-(thiazol-2-yl)benzo[d]oxazole, 2-(3,6-diazabicyclo[3.1.1]heptan-3-yl)-4-(1,1-difluoro-2-methoxy-2-methylpropoxy)-7-(thiazol-2-yl)benzo[d]oxazole, 1-((2-(3,6-diazabicyclo[3.1.1]heptan-3-yl)-7-(1-methyl-1H-pyrazol-3-yl)benzo[d]oxazol-4-yl)oxy)-1,1-difluoro-2-methylpropan-2-ol, 1-((2-(3,6-diazabicyclo[3.1.1]heptan-3-yl)-7-(thiazol-2-yl)benzo[d]oxazol-4-yl)oxy)-1,1-difluorobutan-2-ol, 2-(3,6-diazabicyclo[3.1.1]heptan-3-yl)-7-(thiazol-2-yl)benzo[d]oxazole-4-sulfonamide, 1-(2-(3,6-diazabicyclo[3.1.1]heptan-3-yl)-7-(thiazol-2-yl)benzo[d]oxazol-4-yl)piperidin-4-ol, 4-(2-(3,6-diazabicyclo[3.1.1]heptan-3-yl)-7-(thiazol-2-yl)benzo[d]oxazol-4-yl)thiomorpholine 1,1-dioxide, 1-((2-(3,6-diazabicyclo[3.1.1]heptan-3-yl)-5-bromo-7-(thiazol-2-yl)benzo[d]oxazol-4-yl)oxy)-1,1-difluoro-2-methylpropan-2-ol, 1-((2-(3,6-diazabicyclo[3.1.1]heptan-3-yl)-5-chloro-7-(thiazol-2-yl)benzo[d]oxazol-4-yl)oxy)-1,1-difluoro-2-methylpropan-2-ol, 2-((2-(3,6-diazabicyclo[3.1.1]heptan-3-yl)-5-chloro-7-(thiazol-2-yl)benzo[d]oxazol-4-yl)oxy)-2,2-difluoroethan-1-ol,
2-(3,6-diazabicyclo[3.1.1]heptan-3-yl)-4-(1,1-difluoropropoxy)-7-(thiazol-2-yl)benzo[d]oxazole,
4-(benzo[d]oxazol-2-yldifluoromethoxy)-2-(3,6-diazabicyclo[3.1.1]heptan-3-yl)-7-(thiazol-2-yl)benzo[d]oxazole,
2-((2-(3,8-diazabicyclo[3.2.1]octan-3-yl)-7-(thiazol-2-yl)benzo[d]oxazol-4-yl)oxy)-2,2-difluoroethan-1-ol,
1-((2-(3,8-diazabicyclo[3.2.1]octan-3-yl)-7-(thiazol-2-yl)benzo[d]oxazol-4-yl)oxy)-1,1-difluoro-2-methylpropan-2-ol,
2-(3,6-diazabicyclo[3.1.1]heptan-3-yl)-4-((1,1-difluoro-3-(pyridin-3-yl)allyl)oxy)-7-(thiazol-2-yl)benzo[d]oxazole,
2-((2-(3,6-diazabicyclo[3.1.1]heptan-3-yl)-7-(thiazol-2-yl)benzo[d]oxazol-4-yl)oxy)-2,2-difluoro-N-(2-hydroxyethyl)-N-methylacetamide,
2-((2-(3,6-diazabicyclo[3.1.1]heptan-3-yl)-7-(thiazol-2-yl)benzo[d]oxazol-4-yl)oxy)-2,2-difluoro-N,N-dimethylacetamide,
2-((2-(3,6-diazabicyclo[3.1.1]heptan-3-yl)-7-(thiazol-2-yl)benzo[d]oxazol-4-yl)oxy)-2,2-difluoro-1-morpholinoethan-1-one,
2-((2-(3,6-diazabicyclo[3.1.1]heptan-3-yl)-7-(thiazol-2-yl)benzo[d]oxazol-4-yl)oxy)-2,2-difluoroacetamide,
2-((2-(3,6-diazabicyclo[3.1.1]heptan-3-yl)-7-(thiazol-2-yl)benzo[d]oxazol-4-yl)oxy)-2,2-difluoro-N-(2-hydroxyethyl)acetamide,
2-((2-(3,6-diazabicyclo[3.1.1]heptan-3-yl)-7-(thiazol-2-yl)benzo[d]oxazol-4-yl)oxy)-2,2-difluoro-1-(3-hydroxyazetidin-1-yl)ethan-1-one,
2-(3,6-diazabicyclo[3.1.1]heptan-3-yl)-7-(thiazol-2-yl)-5-((5-(trifluoromethyl)pyridin-2-yl)oxy)benzo[d]oxazole,
2-(3,6-diazabicyclo[3.1.1]heptan-3-yl)-4-cyclobutyl-7-(thiazol-2-yl)benzo[d]oxazole,
2-(3,6-diazabicyclo[3.1.1]heptan-3-yl)-4-(pyrrolidin-1-yl)-7-(thiazol-2-yl)benzo[d]oxazole,
(6-((2-(3,6-diazabicyclo[3.1.1]heptan-3-yl)-7-(thiazol-2-yl)benzo[d]oxazol-5-yl)oxy)pyridin-3-yl)methanol,
2-(3,6-diazabicyclo[3.1.1]heptan-3-yl)-7-(thiazol-2-yl)benzo[d]oxazole-5-carbonitrile,
2-(3,6-diazabicyclo[3.1.1]heptan-3-yl)-5-(pyridin-3-yl)-7-(thiazol-2-yl)benzo[d]oxazole, or
2-(3,6-diazabicyclo[3.1.1]heptan-3-yl)-5-cyclobutoxy-7-(thiazol-2-yl)benzo[d]oxazole.

[8]

A method for treating at least one disease selected from the group consisting of inflammatory diseases, autoimmune diseases, fibrotic diseases, and cancer diseases, comprising: administering to a patient the therapeutic agent according to any one of [1] to [7].

[9]

The therapeutic agent according to any one of [1] to [7], used for treatment of at least one disease selected from the group consisting of inflammatory diseases, autoimmune diseases, fibrotic diseases, and cancer diseases.

Effects of the Invention

The present invention makes it possible to provide a therapeutic agent containing a compound having excellent PDE4 inhibitory activity and useful for treating inflammatory diseases, autoimmune diseases, fibrotic diseases, and cancer diseases.

DETAILED DESCRIPTION OF THE PREFERRED EMBODIMENTS

Hereinafter, the present invention is described in detail based on its preferred embodiments. Note that in the following description, the same or corresponding elements are given the same reference numerals and overlapping explanations thereof are omitted.

The therapeutic agent of the present invention is a therapeutic agent for treating at least one disease selected from the group consisting of inflammatory diseases, autoimmune diseases, fibrotic diseases, and cancer diseases, containing a compound represented by the following general formula (1) and/or a pharmacologically acceptable salt thereof as an active ingredient.

[Chem. 3]

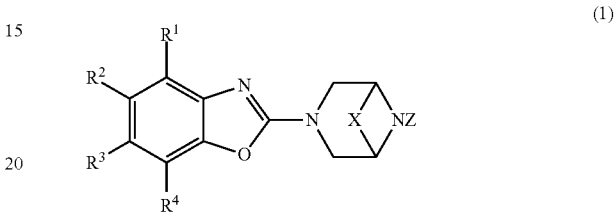

(1)

In the general formula (1), the halogen atom means a fluorine atom, a chlorine atom, a bromine atom, or an iodine atom, or preferably a fluorine atom or a chlorine atom.

In the general formula (1), the $C_{1-6}$ alkyl group means a linear chain or a branched chain alkyl group having 1 to 6 carbon atoms. The $C_{1-6}$ alkyl group is, for example, a methyl group, an ethyl group, an n-propyl group, an isopropyl group, an n-butyl group, an isobutyl group, a tert-butyl group, an n-pentyl group, an isoamyl group, or an n-hexyl group, preferably a linear chain or a branched chain $C_{1-4}$ alkyl group having 1 to 4 carbon atoms, or more preferably a methyl group, an ethyl group, an n-propyl group, an isopropyl group, or an n-butyl group.

In the general formula (1), the $C_{3-7}$ cycloalkyl group means a cyclic alkyl group having 3 to 7 carbon atoms. The $C_{3-7}$ cycloalkyl group is, for example, a cyclopropyl group, a cyclobutyl group, a cyclopentyl group, a cyclohexyl group, or a cycloheptyl group, preferably $C_{3-6}$ cycloalkyl group having 3 to 6 carbon atoms, or more preferably a cyclopropyl group, a cyclobutyl group, a cyclopentyl group, or a cyclohexyl group.

In the general formula (1), the $C_{6-10}$ monocyclic or polycyclic aryl group means a monocyclic aromatic hydrocarbon group or polycyclic aromatic hydrocarbon group having 6 to 10 carbon atoms. The $C_{6-10}$ monocyclic or polycyclic aryl group is, for example, a phenyl group or a naphthyl group, preferably monocyclic, or more preferably a phenyl group.

In the general formula (1), the $C_{7-11}$ monocyclic or polycyclic aralkyl group means a group having 7 to 11 carbon atoms, which is formed by substituting one hydrogen atom of the $C_{1-6}$ alkyl group with a monocyclic aromatic hydrocarbon group or polycyclic aromatic hydrocarbon group (the $C_{6-10}$ monocyclic or polycyclic aryl group) having 6 to 10 carbon atoms. The $C_{7-11}$ monocyclic or polycyclic aralkyl group is, for example, a benzyl group or a naphthylmethyl group, preferably monocyclic, or more preferably a benzyl group.

In the general formula (1), the 4- to 10-membered monocyclic or bicyclic aromatic heterocyclic group means a 4- to 10-membered monocyclic aromatic heterocycle or bicyclic aromatic heterocycle containing 1 to 4 heteroatoms selected from an oxygen atom, a nitrogen atom, and a sulfur atom. The 4- to 10-membered monocyclic or bicyclic aromatic heterocyclic group is, for example, a pyrrolyl group, a furanyl group, a thienyl group, a pyrazolyl group, an oxazolyl group, an isoxazolyl group, an oxadiazolyl group, a thiazolyl group, an isothiazolyl group, a thiadiazolyl group, an imidazolyl group, a triazolyl group, a pyridyl group, a pyrimidinyl group, a pyridazinyl group, a pyradinyl group, a tetrazolyl group, a quinolyl group, or an isoquinolyl group, preferably monocyclic, or more preferably a furanyl group, a thienyl group, a pyrazolyl group, an oxazolyl group, an isoxazolyl group, an oxadiazolyl group, a thiazolyl group, an isothiazolyl group, an imidazolyl group, a triazolyl group, a pyridyl group, or a pyrimidinyl group.

In the general formula (1), the 4- to 10-membered monocyclic or bicyclic nonaromatic heterocyclic group means a 4- to 10-membered monocyclic nonaromatic heterocycle or bicyclic nonaromatic heterocycle containing 1 to 4 heteroatoms selected from an oxygen atom, a nitrogen atom, and a sulfur atom. The 4- to 10-membered monocyclic or bicyclic nonaromatic heterocyclic group is, for example, a tetrahydrofuranyl group, a tetrahydropyranyl, a tetrahydro-2H-thiopyranyl group, an oxetanyl group, a pyrrolidinyl group, a piperidyl group, a piperazinyl group, an oxazolidinyl group, a morpholinyl group, an aziridinyl group, an azetidinyl group, a thiomorpholinyl group, or a tetrahydroquinolyl group, preferably monocyclic, or more preferably a tetrahydrofuranyl group, a tetrahydropyranyl, a tetrahydro-2H-thiopyranyl group, an oxetanyl group, a pyrrolidinyl group, a piperidyl group, a piperazinyl group, a morpholinyl group, or an azetidinyl group.

In the general formula (1), the di-$C_{1-6}$ alkyl amino group means a group which is formed by substituting two hydrogen atoms of the amino group with the $C_{1-6}$ alkyl groups. The di-$C_{1-6}$ alkyl amino group is, for example, a dimethylamino group, a diethylamino group, or a methylethylamino group, preferably a di-$C_{1-3}$ alkyl amino group in which the alkyl group has 1 to 3 carbon atoms, or more preferably a dimethylamino group or a diethylamino group.

In the general formula (1), the $C_{3-7}$ cycloalkyl amino group means a group which is formed by substituting one or two (one, preferably) hydrogen atoms of the amino group with the $C_{3-7}$ cycloalkyl group(s). The $C_{3-7}$ cycloalkyl amino group is, for example, a cyclobutylamino group, a cyclopentylamino group, or a cyclohexylamino group, preferably a $C_{3-6}$ cycloalkyl amino group in which the cycloalkyl group has 3 to 6 carbon atoms, or more preferably a cyclobutylamino group or a cyclopentylamino group.

In the general formula (1), the $C_{1-6}$ acylamino group means an amide group (group represented by the formula: R—CO—NH—) having one $C_{1-6}$ alkyl group (represented by the formula: R—) described above. The $C_{1-6}$ acylamino group is, for example, an acetamide group, an propionylamino group, a butyrylamino group, an isobutyrylamino group, a valerylamino group, or an isovalerylamino group, preferably a $C_{1-3}$ acylamino group in which the alkyl group has 1 to 3 carbon atoms, or more preferably an acetamide group, an propionylamino group, a butyrylamino group, or an isobutyrylamino group.

In the general formula (1), the $C_{1-6}$ alkyloxy group means a group which is formed by bonding one $C_{1-6}$ alkyl group described above to an oxygen atom. The $C_1$-6 alkyloxy group is, for example, a methoxy group, an ethoxy group, an n-propoxy group, an isopropoxy group, an n-butoxy group, an isobutoxy group, a tert-butoxy group, an n-pentyloxy group, an isopentyloxy group, a tert-pentyloxy group, a neopentyloxy group, a (3-methylbutan-2-yl)oxy group, an n-hexyloxy group, a (4-methylpentyl)oxy group, a 3,3-dimethylbutoxy group, a (2-methylpentan-2-yl)oxy group, a (2,3-dimethylbutan-2-yl)oxy group, or a (3,3-dimethylbutan-2-yl)oxy group, preferably a $C_{1-5}$ alkyloxy group in which the alkyl group has 1 to 5 carbon atoms, or more preferably a methoxy group, an ethoxy group, an n-propoxy group, an isopropoxy group, an n-butoxy group, an isobutoxy group, an n-pentyloxy group, an isopentyloxy group, a tert-pentyloxy group, or a (3-methylbutan-2-yl)oxy group.

In the general formula (1), the $C_{2-6}$ alkenyloxy group means a group which is formed by bonding one unsaturated hydrocarbon group having 2 to 6 carbon atoms to an oxygen atom. The $C_{2-6}$ alkenyloxy group is, for example, a vinyloxy group, an allyloxy group, or an isopropenyloxy group, preferably a $C_{2-3}$ alkenyloxy group in which the unsaturated hydrocarbon group has 2 or 3 carbon atoms, or more preferably an allyloxy group.

In the general formula (1), the $C_{1-6}$ alkyloxy-$C_{1-6}$ alkyl group means a group which is formed by substituting one or more (one, preferably) hydrogen atoms of the $C_{1-6}$ alkyl group with the $C_{1-6}$ alkyloxy group(s). The $C_{1-6}$ alkyloxy-$C_{1-6}$ alkyl group is, for example, a methoxymethyl group, a methoxyethyl group, an ethoxymethyl group, an ethoxyethyl group, an n-propoxymethyl group, an n-propoxyethyl group, an isopropoxymethyl group, an isopropoxyethyl group, an n-butoxymethyl group, an isobutoxymethyl group, an n-pentyloxymethyl group, or an n-hexyloxymethyl group, preferably a $C_{1-s}$ alkyloxy-$C_{1-3}$ alkyl group in which the alkyl group has 1 to 3 carbon atoms and the alkyloxy group has 1 to 5 carbon atoms, or more preferably a methoxymethyl group, a methoxyethyl group, an ethoxymethyl group, an ethoxyethyl group, an n-propoxymethyl group, an isopropoxymethyl group, an n-butoxymethyl group, or an isobutoxymethyl group.

In the general formula (1), the $C_{3-7}$ cycloalkyloxy group means a group which is formed by bonding one $C_{3-7}$ cycloalkyl group described above to an oxygen atom. The $C_{3-7}$ cycloalkyloxy group is, for example, a cyclopropyloxy group, a cyclobutyloxy group, a cyclopentyloxy group, or a cyclohexyloxy group, preferably a $C_{3-6}$ cycloalkyloxy group in which the cycloalkyl group has 3 to 6 carbon atoms, or more preferably a cyclopropyloxy group, a cyclobutyloxy group, a cyclopentyloxy group, or a cyclohexyloxy group.

In the general formula (1), the $C_{6-10}$ monocyclic or polycyclic aryloxy group means a group which is formed by bonding one $C_{6-10}$ monocyclic or polycyclic aryl group described above to an oxygen atom. The $C_6$-10 monocyclic or polycyclic aryloxy group is, for example, a phenyloxy group or a naphthyloxy group, preferably monocyclic, or more preferably a phenyloxy group.

In the general formula (1), the $C_{7-11}$ monocyclic or polycyclic aralkyloxy group means a group which is formed by bonding one $C_{7-11}$ monocyclic or polycyclic aralkyl group described above to an oxygen atom. The $C_{7-11}$ monocyclic or polycyclic aralkyloxy group is, for example, a benzyloxy group or a naphthylmethyloxy group, preferably monocyclic, or more preferably a benzyloxy group.

In the general formula (1), the 4- to 10-membered monocyclic or bicyclic aromatic heterocyclyloxy group means a group which is formed by bonding one 4- to 10-membered monocyclic or bicyclic aromatic heterocyclic group described above to an oxygen atom. The 4- to 10-membered monocyclic or bicyclic aromatic heterocyclyloxy group is, for example, a thiazolyloxy group, an oxazolyloxy group, a pyridiloxy group, a pyrimidinyloxy group, a pyrazinyloxy group, or a pyridazinyloxy group, preferably monochyclic, or more preferably a pyridiloxy group, a pyrimidinyloxy group, a pyrazinyloxy group, or a pyridazinyloxy group.

In the general formula (1), the 4- to 10-membered monocyclic or bicyclic nonaromatic heterocyclyloxy group means a group which is formed by bonding one 4- to 10-membered monocyclic or bicyclic nonaromatic heterocyclyl group described above to an oxygen atom. The 4- to 10-membered monocyclic or bicyclic nonaromatic heterocyclyloxy group is, for example, an oxetanyloxy group, a tetrahydrofuranyloxy group, a tetrahydropyranyloxy group, or a 1,1-dioxidotetrahydro-2H-thiopyran-4-yloxy group, preferably monocyclic, or more preferably an oxetanyloxy group, a tetrahydrofuranyloxy group, a tetrahydropyranyloxy group, or a 1,1-dioxidotetrahydro-2H-thiopyran-4-yloxy group.

In the general formula (1), the $C_{1-6}$ alkylthio group means a group which is formed by bonding one $C_{1-6}$ alkyl group described above to a sulfur atom. The $C_{1-6}$ alkylthio group is, for example, a methylthio group, an ethylthio group, a propylthio group, or an isopropylthio group, preferably a $C_{1-3}$ alkylthio group in which the alkyl group has 1 to 3 carbon atoms, or more preferably a methylthio group or an ethylthio group.

In the general formula (1), the $C_{1-6}$ alkylsulfonyl group means a sulfonyl group (group represented by the formula: R—SO$_2$—) having the $C_{1-6}$ alkyl group (represented by the formula: R—) described above. The $C_{1-6}$ alkylsulfonyl group is, for example, a methylsulfonyl group, an ethylsulfonyl group, or a propylsulfonyl group, preferably a $C_{1-3}$ alkylsulfonyl group in which the alkyl group has 1 to 3 carbon atoms, or more preferably a methylsulfonyl group or an ethylsulfonyl group.

In the general formula (1), the $C_{1-6}$ alkylsulfinyl group means a sulfinyl group (group represented by the formula: R—SO—) having the $C_{1-6}$ alkyl group (represented by the formula: R—) described above. The $C_{1-6}$ alkylsulfinyl group is, for example, a methylsulfinyl group, an ethylsulfinyl group, or a propylsulfinyl group, preferably a $C_{1-3}$ alkylsulfinyl group in which the alkyl group has 1 to 3 carbon atoms, or more preferably a methylsulfinyl group or an ethylsulfinyl group.

In the general formula (1), the mono-$C_{1-6}$ alkylsulfamoyl group means a group (group represented by the formula: R—NH—SO$_2$—) which is formed by substituting one hydrogen atom of the sulfamoyl group with the $C_{1-6}$ alkyl group (represented by the formula: R—). The mono-$C_{1-6}$ alkylsulfamoyl group is, for example, a methylsulfamoyl group, an ethylsulfamoyl group, or a propylsulfamoyl group, preferably a mono-$C_{1-3}$ alkylsulfamoyl group in which the alkyl group has 1 to 3 carbon atoms, or more preferably a methylsulfamoyl group.

In the general formula (1), the di-$C_{1-6}$ alkylsulfamoyl group means a group (group represented by the formula: R—NR'—SO$_2$—) which is formed by substituting two hydrogen atoms of the sulfamoyl group with the $C_{1-6}$ alkyl groups (represented by the formulae: R— and R'—). The di-$C_{1-6}$ alkylsulfamoyl group is, for example, a dimethylsulfamoyl group, a diethylsulfamoyl group, a dipropylsulfamoyl group, or a methylethylsulfamoyl group, preferably a di-$C_{1-3}$ alkylsulfamoyl group in which the alkyl group has 1 to 3 carbon atoms, or preferably a dimethylsulfamoyl group. As the di-$C_{1-6}$ alkylsulfamoyl group of the present invention, two $C_{1-6}$ alkyl groups (R, R') in the di-$C_{1-6}$ alkylsulfamoyl group may form a pyrrolidin-1-yl group or a morpholino group with an adjacent nitrogen atom.

In the general formula (1), the $C_{1-6}$ alkylcarbonyl group means a group which is formed by bonding one $C_{1-6}$ alkyl group described above to a carbonyl group. The $C_{1-6}$ alkylcarbonyl group is, for example, an acetyl group, an ethylcarbonyl group, a propylcarbonyl group, or a butylcarbonyl group, preferably a $C_{1-3}$ alkylcarbonyl group in which the alkyl group has 1 to 3 carbon atoms, or more preferably an acetyl group.

In the general formula (1), the 1-($C_{1-6}$ alkyloxy)imino-$C_{1-6}$ alkyl group means a group (represented by the formula: —C(—R)=N—OR') which is formed by substituting the $C_{1-6}$ alkyloxy group (represented by the formula: —OR') for one hydrogen atom bonded to the nitrogen atom of an imino-$C_{1-6}$ alkyl group (represented by the formula: —C(—R)=NH) being an imino group bonded with the $C_{1-6}$ alkyl group (represented by the formula: R—). The 1-($C_{1-6}$ alkyloxy)imino-$C_{1-6}$ alkyl group is, for example, a 1-(methoxy)iminoethyl group, a 1-(ethoxy)iminoethyl group, or a 1-(methoxy)iminopropyl group, preferably a 1-($C_{1-3}$ alkyloxy)imino-$C_{1-3}$ alkyl group in which the alkyl group has 1 to 3 carbon atoms, or more preferably a 1-(methoxy)iminoethyl group.

In the general formula (1), the mono-$C_{1-6}$ alkylaminocarbonyl group means a group which is formed by substituting one hydrogen atom of an aminocarbonyl group with the $C_{1-6}$ alkyl group. The mono-$C_{1-6}$ alkylaminocarbonyl group is, for example, a methylaminocarbonyl group, an ethylaminocarbonyl group, or a propylaminocarbonyl group, preferably a mono-$C_{1-3}$ alkylaminocarbonyl group in which the alkyl group has 1 to 3 carbon atoms, or more preferably a methylaminocarbonyl group or an ethylaminocarbonyl group.

In the general formula (1), the di-$C_{1-6}$ alkylaminocarbonyl group means a group which is formed by substituting two hydrogen atoms of an aminocarbonyl group with the $C_{1-6}$ alkyl groups. The di-$C_{1-6}$ alkylaminocarbonyl group is, for example, a dimethylaminocarbonyl group, a diethylaminocarbonyl group, or a dipropylaminocarbonyl group, preferably a di-$C_{1-3}$ alkylaminocarbonyl group in which the alkyl group has 1 to 3 carbon atoms, or more preferably a dimethylaminocarbonyl group or a diethylaminocarbonyl group.

In the general formula (1), the $C_{3-7}$ cycloalkylaminocarbonyl group means a group which is formed by substituting one or two (one, preferably) hydrogen atoms of an aminocarbonyl group with the $C_{3-7}$ cycloalkyl group(s). The $C_{3-7}$ cycloalkylaminocarbonyl group is, for example, a cyclobutylaminocarbonyl group, a cyclopentylaminocarbonyl group, or a cyclohexylaminocarbonyl group, preferably a $C_{4-6}$ cycloalkylaminocarbonyl group in which the cycloalkyl group has 4 to 6 carbon atoms, or more preferably a cyclobutylaminocarbonyl group or a cyclohexylaminocarbonyl group.

In the general formula (1), the $C_{7-11}$ monocyclic or polycyclic aralkylaminocarbonyl group means a group which is formed by substituting one or two (one, preferably) hydrogen atoms of an aminocarbonyl group with the $C_{7-11}$ monocyclic or polycyclic aralkyl group(s). The $C_{7-11}$ monocyclic or polycyclic aralkylaminocarbonyl group is preferably monocyclic, for example a benzylaminocarbonyl group.

In the general formula (1), the $C_{1-6}$ alkyloxycarbonyl group means a group which is formed by bonding one $C_{1-6}$ alkyloxy group described above to a carbonyl group. The $C_{1-6}$ alkyloxycarbonyl group is, for example, a methoxycarbonyl group, an ethoxycarbonyl group, or an isopropoxycarbonyl group, preferably a $C_{1-3}$ alkyloxycarbonyl group in which the alkyloxy group has 1 to 3 carbon atoms, or more preferably a methoxycarbonyl group or an ethoxycarbonyl group.

In the general formula (1), the hydroxyaminocarbonyl group means a group which is formed by substituting one or two (one, preferably) hydrogen atoms of an aminocarbonyl group with hydroxyl group(s).

In the general formula (1), "optionally substituted" means that each group may be further substituted by one or more substituents. The substituent in the case of substitution may be any group which can be substituted for the corresponding group and may be, for example, a halogen atom; a carboxy group; a cyano group; a hydroxyl group; a $C_{1-6}$ alkyl group optionally substituted with one or more halogen atom; a $C_{2-6}$ alkenyl group optionally substituted with 4- to 10-membered monocyclic aromatic heterocyclic group containing 1 to 4 heteroatoms selected from an oxygen atom, a nitrogen atom, and a sulfur atom; a $C_{3-6}$ cycloalkyl group; a hydroxy-$C_{1-6}$ alkyl group; a $C_{1-6}$ alkyloxy group optionally substituted with one or more halogen atom; a carbamoyl group; an aminocarbonyl group; a $C_{1-6}$ alkylcarbonyl group, an oxo group, a nitro group, a mono-$C_{1-6}$ alkyl amino group optionally substituted with one or more hydroxyl group; a di-$C_{1-6}$ alkyl amino group optionally substituted with one or more hydroxyl group; a $C_{1-6}$ alkylthio group; a $C_{1-6}$ alkylsulfonyl group; a $C_{6-10}$ aryl group (monocyclic or polycyclic (monocyclic, preferably)); or a 4- to 10-membered monocyclic or bicyclic heterocyclic group (aromatic or nonaromatic, optionally substituted with a $C_{1-6}$ alkyl group or hydroxyl group) containing 1 to 4 heteroatoms selected from an oxygen atom, a nitrogen atom, and a sulfur atom. Note that the hydroxy-$C_{1-6}$ alkyl group means a group which is formed by substituting one or more (one, preferably) hydrogen atoms of the $C_{1-6}$ alkyl group with hydroxyl group(s), and is, for example, a hydroxymethyl group, a 1-hydroxyethyl group, or a 2-hydroxypropan-2-yl group.

Consider the case where the substituent is a halogen atom. The $C_{1-6}$ alkyl group substituted with fluorine atoms is, for example, a trifluoromethyl group, a trifluoroethyl group, a difluoromethyl group, or a difluoroethyl group. The $C_{1-6}$ alkyloxy group substituted with fluorine atoms is, for example, a trifluoromethoxy group, a difluoromethoxy group, or a trifluoroethoxy group. The $C_{1-6}$ alkyloxy-$C_{1-6}$ alkyl group substituted with fluorine atoms is, for example, a 2,2,2-trifluoro-1-methoxyethyl group, a 1-ethoxy-2,2,2-trifluoroethyl group, or a 2,2,2-trifluoro-1-(2,2,2-trifluoroethoxy)ethyl group.

Consider the case where the substituent is a hydroxyl group. The $C_{1-6}$ alkyloxy group substituted with a hydroxyl group is, for example, a 2-hydroxy-2-methylpropoxy group or a 2-hydroxypropoxy group. The $C_{1-6}$ alkylthio group substituted with a hydroxyl group is, for example, a (2-hydroxyethyl)thio group. The $C_1$-6 alkylsulfonyl group substituted with a hydroxyl group is, for example, a (2-hydroxyethyl)sulfonyl group.

Consider the case where the substituents are a halogen atom and a hydroxyl group. The $C_{1-6}$ alkyloxy group substituted with a fluorine atom and a hydroxyl group is, for example, a 1,1-difluoro-2-hydroxyethoxy group, a 1,1-difluoro-2-hydroxypropoxy group, a 1,1-difluoro-2-hydroxy-2-methylpropoxy group, or a 1,1-difluoro-3-hydroxypropoxy group. The $C_{1-6}$ alkyl group substituted with a fluorine atom and a hydroxyl group is, for example, a 2,2,2-trifluoro-1-hydroxyethyl group, a 1,1,1-trifluoro-2-hydroxypropan-2-yl group, a 2,2-difluoro-1-hydroxyethyl group, or a 1,1-difluoro-2-hydroxypropan-2-yl group. In addition, the $C_{1-6}$ alkyloxy-$C_{1-6}$ alkyl group substituted with a fluorine atom and a hydroxyl group is, for example, a 2,2,2-trifluoro-1-(2-hydroxyethoxy)ethyl group or a 2,2,2-trifluoro-1-((1-hydroxycyclopropyl)methoxy)ethyl group.

Consider the case where the substituents are a halogen atom and a cyano group. The $C_{1-6}$ alkyloxy-$C_{1-6}$ alkyl group substituted with a halogen atom and a cyano group is, for example, a 1-(cyanomethoxy)-2,2,2-trifluoroethyl group.

Consider the case where the substituent is an oxo group. The tetrahydro-2H-thiopyranyl group substituted with the oxo group is, for example, a 1,1-dioxidotetrahydro-2H-thiopyranyl group.

In the present invention, in the general formula (1), $R^1$ and $R^2$ may be the same or different and each represents a hydrogen atom, a halogen atom, a hydroxyl group, a carboxy group, a cyano group, an optionally substituted $C_{1-6}$ alkyl group, an optionally substituted $C_{3-7}$ cycloalkyl group, an optionally substituted $C_{6-10}$ monocyclic or polycyclic aryl group, an optionally substituted $C_{7-11}$ monocyclic or polycyclic aralkyl group, an optionally substituted 4- to 10-membered monocyclic or bicyclic aromatic heterocyclic group containing 1 to 4 heteroatoms selected from an oxygen atom, a nitrogen atom, and a sulfur atom, an optionally substituted 4- to 10-membered monocyclic or bicyclic nonaromatic heterocyclic group containing 1 to 4 heteroatoms selected from an oxygen atom, a nitrogen atom, and a sulfur atom, an optionally substituted di-$C_{1-6}$ alkyl amino group, an optionally substituted $C_{3-7}$ cycloalkyl amino group, an optionally substituted $C_{1-6}$ acylamino group, an optionally substituted $C_{1-6}$ alkyloxy group, an optionally substituted $C_{2-6}$ alkenyloxy group, an optionally substituted $C_{1-6}$ alkyloxy-$C_{1-6}$ alkyl group, an optionally substituted $C_{3-7}$ cycloalkyloxy group, an optionally substituted $C_{6-10}$ monocyclic or polycyclic aryloxy group, an optionally substituted $C_{7-11}$ monocyclic or polycyclic aralkyloxy group, an optionally substituted 4- to 10-membered monocyclic or bicyclic aromatic heterocyclyloxy group containing 1 to 4 heteroatoms selected from an oxygen atom, a nitrogen atom, and a sulfur atom, an optionally substituted 4- to 10-membered monocyclic or bicyclic nonaromatic heterocyclyloxy group containing 1 to 4 heteroatoms selected from an oxygen atom, a nitrogen atom, and a sulfur atom, an optionally substituted $C_{1-6}$ alkylthio group, an optionally substituted $C_{1-6}$ alkylsulfonyl group, an optionally substituted $C_{1-6}$ alkylsulfinyl group, an optionally substituted mono-$C_{1-6}$ alkylsulfamoyl group, an optionally substituted di-$C_{1-6}$ alkylsulfamoyl group [two $C_{1-6}$ alkyl groups in the di-$C_{1-6}$ alkylsulfamoyl group may form a pyrrolidin-1-yl group or a morpholino group with an adjacent nitrogen atom], a sulfamoyl group, an optionally substituted $C_{1-6}$ alkylcarbonyl group, an optionally substituted 1-($C_{1-6}$ alkyloxy)imino-$C_{1-6}$ alkyl group, an aminocarbonyl group, an optionally substituted mono-$C_{1-6}$ alkylaminocarbonyl group, an optionally substituted di-$C_{1-6}$ alkylaminocarbonyl group, an optionally substituted $C_{3-7}$ cycloalkylaminocarbonyl group, an optionally substituted $C_{7-11}$ monocyclic or polycyclic aralkylaminocarbonyl group, an optionally substituted $C_{1-6}$ alkyloxycarbonyl group, or an optionally substituted hydroxyaminocarbonyl group.

In the present invention, the group represented by $R^1$ in the general formula (1) is preferably a hydrogen atom, a fluorine atom, a chlorine atom, a carboxy group, a cyano group, a methyl group, an ethyl group, an isopropyl group, a trifluoromethyl group, a difluoromethyl group, a hydroxymethyl group, a methoxymethyl group, a 2-hydroxypropan-2-yl group, a morpholinomethyl group, a (dimethylamino)methyl group, a 2,2,2-trifluoro-1-hydroxyethyl group, a 2,2,2-trifluoro-1-methoxyethyl group, a 1,1,1-trifluoro-2-hydroxypropan-2-yl group, a 2,2-difluoro-1-hydroxyethyl group, a 2,2-difluoro-1-methoxyethyl group, a 1,1-difluoro-2-hydroxypropan-2-yl group, a 1,1,1-trifluoro-2-methoxypropan-2-yl group, a 1-hydroxyethyl group, a 1-hydroxypropyl group, a 1-hydroxy-2-methylpropyl group, a 1-methoxyethyl group, a 2-methoxypropan-2-yl group, a 1-acetoxy-2,2,2-trifluoroethyl group, a 2,2,2-trifluoro-1-(2,2,2-trifluoroethoxy)ethyl group, a 2,2,2-trifluoro-1-(2-methoxyethoxy)ethyl group, a 1-ethoxy-2,2,2-trifluoroethyl group, a 2,2,2-trifluoro-1-(2-hydroxyethoxy)ethyl group, a 2,2,2-trifluoro-1,1-dihydroxyethyl group, a 1-(cyanomethoxy)-2,2,2-trifluoroethyl group, a 2,2,2-trifluoro-1-(2-hydroxypropoxy)ethyl group, a 2,2,2-trifluoro-1-(2-hydroxy-2-methylpropoxy)ethyl group, a 2,2,2-trifluoro-1-((1-hydroxycyclopropyl)methoxy)ethyl group, a 2,2,2-trifluoro-1-((1-hydroxypropan-2-yl)oxy)ethyl group, a 2,2,2-trifluoro-1-((1-hydroxy-2-methylpropan-2-yl)oxy)ethyl group, a 1-(1,1-difluoro-2-hydroxypropoxy)-2,2,2-trifluoroethyl group, a 1-(1,1-difluoro-2-hydroxy-2-methylpropoxy)-2,2,2-trifluoroethyl group, a 1-(difluoro(1-hydroxycyclopropyl)methoxy)-2,2,2-trifluoroethyl group, a 1-(carboxymethoxy)-2,2,2-trifluoroethyl group, a 1-(2-amino-2-oxoethoxy)-2,2,2-trifluoroethyl group, a 2,2,2-trifluoro-1-((methylsulfonyl)methoxy)ethyl group, a 2,2,2-trifluoro-1-(sulfamoylmethoxy)ethyl group, a 1,1,1-trifluoro-3-hydroxypropan-2-yl group, a 1,1,1,4,4,4-hexafluoro-3-hydroxybutan-2-yl group, a 1-((1,3-dihydroxypropan-2-yl)oxy)-2,2,2-trifluoroethyl group, a 1,1,1-trifluoro-3-hydroxybutan-2-yl group, a 1,1,1-trifluoro-3-oxobutan-2-yl group, a 1,1,1,4,4,4-hexafluoro-3-oxobutan-2-yl group, a 1,1,1-trifluoro-3,4-dihydroxybutan-2-yl group, a 1,1,1-trifluoro-4-hydroxy-3-oxobutan-2-yl group, a 1-((2H-tetrazol-5-yl)methoxy)-2,2,2-trifluoroethyl group, a 1-((2H-tetrazol-5-yl)methoxy)-2,2-difluoroethyl group, a 1-hydroxy-3-(methylsulfonyl)propyl group, a 2,2-difluoro-1-hydroxy-3-(methylsulfonyl)propyl group, a 3-(ethylsulfonyl)-1-hydroxypropyl group, a 3-(ethylsulfonyl)-2,2-difluoro-1-hydroxypropyl group, a 1-hydroxy-3-(isopropylsulfonyl)propyl group, a 2,2-difluoro-1-hydroxy-3-(isopropylsulfonyl)propyl group, a 2,2,2-trifluoro-1-(2-morpholino-2-oxoethoxy)ethyl group, a 1-hydroxy-2-morpholinoethyl group, a 2,2-difluoro-1-hydroxy-2-morpholinoethyl group, a 1-carboxy-2,2-difluoro-1-hydroxyethyl group, a 1-carboxy-2,2,2-trifluoro-1-hydroxyethyl group, a 2,2-difluoro-1-hydroxy-1-(2H-tetrazol-5-yl)ethyl group, a 2,2,2-trifluoro-1-hydroxy-1-(2H-tetrazol-5-yl)ethyl group, a 1,1-difluoro-3-hydroxypropan-2-yl group, a 1,1-difluoro-3-hydroxy-3-methylbutan-2-yl group, a 1,1,1-trifluoro-3-hydroxy-3-methylbutan-2-yl group, a 3-cyano-1,1,1-trifluoro-2-hydroxypropan-2-yl group, a 1,3-dihydroxypropyl group, a 1-hydroxy-3-methoxypropyl group, a 4,4,4-trifluoro-1,3-dihydroxybutyl group, a 1,3-dihydroxybutyl group, a 1,3-dihydroxy-3-methylbutyl group, a cyclopropyl (hydroxy)methyl group, a carboxy(hydroxy)methyl group, a hydroxy (2H-tetrazol-5-yl)methyl group, a hydroxy (3-hydroxycyclobutyl)methyl group, a 3-amino-1-hydroxy-3-oxopropyl group, a 1-hydroxy-2-(methylsulfonamide)ethyl group, a 2-cyanoethyl group, a 1,2-dihydroxyethyl group, a 3,3,3-trifluoro-1,2-dihydroxypropyl group, a 3,3,3-trifluoro-1-hydroxy-2-oxopropyl group, a 3,3,3-trifluoro-1-hydroxypropyl group, a 3,3,3-trifluoro-2-hydroxypropyl group, a 3,3,3-trifluoro-2-oxopropyl group, a 1-hydroxy-3-oxobutyl group, a cyclopropyl group, a cyclobutyl group, a cyclopentyl group, a phenyl group, a benzyl group, a thiazol-2-yl group, a 1H-pyrazol-1-yl group, a 5-methylthiazol-2-yl group, a 5-methoxycarbonylthiazol-2-yl group, a 5-hydroxymethylthiazol-2-yl group, a 5-(1-hydroxyethyl)thiazol-2-yl group, a 5-(2-hydroxypropan-2-yl)thiazol-2-yl group, a 5-(N,N-dimethylaminomethyl)thiazol-2-yl group, a 5-methylthiazol-4-yl group, an oxazol-2-yl group, an oxazol-4-yl group, a 5-methyloxazol-4-yl group, a 1H-imidazol-1-yl group, a 2,5-dimethyl-1H-imidazol-1-yl group, a 1H-imidazol-4-yl group, a 1-methyl-1H-imidazol-2-yl group, a 1-methyl-1H-imidazol-4-yl group, a pyridin-2-yl group, a pyridin-3-yl group, a pyridin-4-yl group, a 3,5-dimethylpyridin-4-yl group, a 6-hydroxypyridin-2-yl group, a 5-hydroxypyridin-2-yl group, a 4-hydroxypyridin-2-yl group, a 3-hydroxypyridin-2-yl group, a 6-methoxypyridin-2-yl group, a 5-methoxypyridin-2-yl group, a 4-methoxypyridin-2-yl group, a 3-methoxypyridin-2-yl group, a pyrimidin-2-yl group, a pyrimidin-4-yl group, a 1,3,5-triazin-2-yl group, a tetrahydrofuran-2-yl group, a tetrahydrofuran-3-yl group, a tetrahydropyran-2-yl group, a tetrahydropyran-3-yl group, a tetrahydropyran-4-yl group, an oxetanyl group, a pyrrolidin-1-yl-1-yl group, a piperidin-1-yl group, a piperazin-1-yl group, a morpholin-4-yl group, an azetidin-1-yl group, a 4-hydroxypiperidin-1-yl group, a 3-hydroxypyrrolidin-1-yl group, a 3-hydroxyazetidin-1-yl group, a dimethylamino group, a diethylamino group, a methylethylamino group, a cyclobutylamino group, a cyclopentylamino group, a cyclohexylamino group, an acetamide group, an N-methylacetamide group, an propionylamino group, a butyrylamino group, an isobutyrylamino group, a valerylamino group, an isovalerylamino group, a methoxy group, an ethoxy group, an n-propoxy group, an isopropoxy group, an n-butoxy group, an isobutoxy group, a trifluoromethoxy group, a difluoromethoxy group, a 2,2,2-trifluoroethoxy group, a cyanomethoxy group, a carboxymethoxy group, a 2-hydroxyethoxy group, a 2-methoxyethoxy group, a 2-hydroxypropoxy group, a 2-hydroxy-2-methylpropoxy group, a (1-hydroxycyclopropyl)methoxy group, a 1,1-difluoro-2-hydroxy-2-methylpropoxy group, a difluoro(1-hydroxycyclopropyl)methoxy group, a 1,1-difluoro-2-hydroxyethoxy group, a (1,1,1-trifluoro-3-hydroxypropan-2-yl)oxy group, a 3,3,3-trifluoro-2-hydroxypropoxy group, a 2,2-difluoro-2-hydroxyethoxy group, a 2-(trifluoromethoxy)ethoxy group, a (1,3-dihydroxypropan-2-yl)oxy group, a (1-hydroxy-3-(trifluoromethoxy)propan-2-yl)oxy group, a 2-oxopropoxy group, a 1,1-difluoro-2-oxopropoxy group, a (1,1,1-trifluoro-3-oxobutan-2-yl)oxy group, a 3,3,3-trifluoro-2-oxopropoxy group, a 1,1-difluoro-2-hydroxypropoxy group, a (1,1,1-trifluoro-3-hydroxybutan-2-yl)oxy group, an oxetan-3-yl methoxy group, a 3-hydroxy-2-(hydroxymethyl)propoxy group, an allyloxy group, a cyclobutoxy group, a (methylsulfonyl)methoxy group, a (ethylsulfonyl)methoxy group, a (isopropylsulfonyl)methoxy group, a (2H-tetrazol-5-yl)methoxy group, a 2-amino-2-oxoethoxy group, a cyanodifluoromethoxy group, a carboxydifluoromethoxy group, a difluoro(2H-tetrazol-5-yl)methoxy group, a difluoro(methylsulfonyl)methoxy group, a 2-carboxyethoxy group, a 2-cyanoethoxy group, a 2-(methylsulfonyl)ethoxy group, a 2-morpholinoethoxy group, a 3-hydroxycyclobutoxy group, a 3-cyanocyclobutoxy group, a 3-carboxycyclobutoxy group, a 3-(methylsulfonyl)cyclobutoxy group, 3-(2H-tetrazol-5-yl)cyclobutoxy group, a (4-hydroxycyclohexyl)oxy group, a 2-hydroxy-3-methoxypropoxy group, a phenyloxy group, a benzyloxy group, a thiazol-5-yloxy group, a thiazol-4-yloxy group, a pyridin-4-yloxy group, a pyridin-3-yl oxy group, a methylthio group, a methylsulfonyl group, a methylsulfinyl group, a methylsulfamoyl group, a dimethylsulfamoyl group, a sulfamoyl group, an acetyl group, a 2,2-difluoroacetyl group, a 1-(methoxyimino)ethyl group, a carbamoyl group, a dimethylcarbamoyl group, a morpholine-4-carbonyl group, a piperidine-1-carbonyl group, an azetidine-1-carbonyl group, a benzylcarbamoyl group, a methylcarbamoyl group, a 3-hydroxy-3-(trifluoromethyl) azetidine-1-carbonyl group, a methoxycarbonyl group, an ethoxycarbonyl group, a (tetrahydro-2H-pyran-4-yl)oxy group, a 1-(1,1-difluoro-2-hydroxyethoxy)-2,2,2-trifluoroethyl group, a tetrahydro-2H-pyran-3-yl)oxy group, a 3-(2-hydroxypropan-2-yl)cyclobutoxy group, a (1-hydroxy-2-methylpropan-2-yl)oxy group, a 2,2,2-trifluoro-1-((3-hydroxy-2,3-dimethylbutan-2-yl)oxy)ethyl group, a 2,2,2-trifluoro-1-(2-methoxy-2-methylpropoxy)ethyl group, a 2,2,2-trifluoro-1-((1-methoxycyclopropyl)methoxy)ethyl group, a 1,1-difluoro-3-hydroxy-3-methylbutoxy group, a (1,1-dioxido tetrahydro-2H-thiopyran-4-yl)oxy) group, an oxetan-3-yl oxy group, a 1,1-difluoro-2,3-dihydroxy-2-methylpropoxy group, a (trifluoromethyl)sulfonyl group, a (5-(trifluoromethyl)pyridin-2-yl)oxy group, a pyridin-2-yloxy group, a pyrimidin-2-yloxy group, a pyrazin-2-yloxy group, a (6-methyl-4-(trifluoromethyl)pyridazin-3-yl)oxy group, a (5-(hydroxymethyl)pyridin-2-yl)oxy group, a (5-(hydroxymethyl)-3-(trifluoromethyl)pyridin-2-yl)oxy group, a (5-(trifluoromethoxy)pyridin-2-yl)oxy group, a (2-hydroxyethyl)thio group, a (2-hydroxyethyl)sulfinyl group, a (2-hydroxyethyl)sulfonyl group, a (1,1-difluoroallyl)oxy group, a (5-(methylsulfonyl)pyridin-2-yl)oxy group, a (2-methoxyethyl)carbamoyl group, a (2-hydroxyethyl)carbamoyl group, a (2-hydroxyethyl) (methyl)carbamoyl group, a cyclopropylcarbamoyl group, an ethylcarbamoyl group, a pyrrolidine-1-carbonyl group, a hydroxy carbamoyl group, a 1,1-difluoro-2,3-dihydroxypropoxy group, a 3-((hydroxymethyl)pyridin-2-yl)oxy group, a 1,1-difluoro-2,2-dihydroxypropoxy group, an N-(2-hydroxyethyl)sulfamoyl group, an N-(2-methoxyethyl)sulfamoyl group, an N-(2-hydroxyethyl)-N-methylsulfamoyl group, a pyrrolidin-1-ylsulfonyl group, a morpholinosulfonyl group, a 1,1-difluoro-2-methoxyethoxy group, a 1,1-difluoro-2-methoxy-2-methylpropoxy group, a 1,1-difluoro-2-hydroxybutoxy group, a 1,1-dioxidothio morpholino group, a 1,1-difluoropropoxy group, or a 1,1-difluoro-2-hydroxy-3-methylbutoxy group, or more preferably a hydrogen atom, a chlorine atom, a carboxy group, a methyl group, a trifluoromethyl group, a hydroxymethyl group, a 2-hydroxypropan-2-yl group, a 2,2,2-trifluoro-1-hydroxyethyl group, a 2,2,2-trifluoro-1-methoxyethyl group, a 1,1,1-trifluoro-2-hydroxypropan-2-yl group, a 2,2-difluoro-1-hydroxyethyl group, a 2,2-difluoro-1-methoxyethyl group, a 1,1-difluoro-2-hydroxypropan-2-yl group, a 1,1,1-trifluoro-2-methoxypropan-2-yl group, a 1-hydroxyethyl group, a 1-methoxyethyl group, a 2-methoxypropan-2-yl group, a 2,2,2-trifluoro-1-(2,2,2-trifluoroethoxy)ethyl group, a 2,2,2-trifluoro-1-(2-methoxyethoxy)ethyl group, a 1-ethoxy-2,2,2-trifluoroethyl group, a 2,2,2-trifluoro-1-(2-hydroxyethoxy)ethyl group, a 2,2,2-trifluoro-1,1-dihydroxyethyl group, a 1-(cyanomethoxy)-2,2,2-trifluoroethyl group, a 2,2,2-trifluoro-1-(2-hydroxypropoxy)ethyl group, a 2,2,2-trifluoro-1-(2-hydroxy-2-methylpropoxy)ethyl group, a 2,2,2-trifluoro-1-((1-hydroxycyclopropyl)methoxy)ethyl group, a 2,2,2-trifluoro-1-((1-hydroxypropan-2-yl)oxy)ethyl group, a 2,2,2-trifluoro-1-((1-hydroxy-2-methylpropan-2-yl)oxy)ethyl group, a 1-(1,1-difluoro-2-hydroxypropoxy)-2,2,2-trifluoroethyl group, a 1-(1,1-difluoro-2-hydroxy-2-methylpropoxy)-2,2,2-trifluoroethyl group, a 1-(difluoro(1-hydroxycyclopropyl)methoxy)-2,2,2-trifluoroethyl group, a 1-(carboxymethoxy)-2,2,2-trifluoroethyl group, a 1-(2-amino-2-oxoethoxy)-2,2,2-trifluoroethyl group, a 2,2,2-trifluoro-1-((methylsulfonyl)methoxy)ethyl group, a 2,2,2-trifluoro-1-(sulfamoylmethoxy)ethyl group, a 1-((2H-tetrazol-5-yl)methoxy)-2,2,2-trifluoroethyl group, a 1-((2H-tetrazol-5-yl)methoxy)-2,2-difluoroethyl group, a 1-hydroxy-3-(methylsulfonyl)propyl group, a 3-(ethylsulfonyl)-1-hydroxypropyl group, a 1-hydroxy-3-(isopropylsulfonyl) propyl group, a 2,2,2-trifluoro-1-(2-morpholino-2-oxoethoxy)ethyl group, a 1-carboxy-2,2-difluoro-1-hydroxyethyl group, a 2,2-difluoro-1-hydroxy-1-(2H-tetrazol-5-yl)ethyl group, a phenyl group, a thiazol-2-yl group, an acetamide group, a methoxy group, a trifluoromethoxy group, a cyanomethoxy group, a carboxymethoxy group, a 2-hydroxyethoxy group, a 2-methoxyethoxy group, a 2-hydroxypropoxy group, a 2-hydroxy-2-methylpropoxy group, a (1-hydroxycyclopropyl)methoxy group, a 1,1-difluoro-2-hydroxy-2-methylpropoxy group, a difluoro(1-hydroxycyclopropyl)methoxy group, a 1,1-difluoro-2-hydroxyethoxy group, a 3,3,3-trifluoro-2-hydroxypropoxy group, a 2,2-difluoro-2-hydroxyethoxy group, a 2-(trifluoromethoxy) ethoxy group, a 1,1-difluoro-2-hydroxypropoxy group, a (1,1,1-trifluoro-3-hydroxybutan-2-yl)oxy group, a cyclobutoxy group, a (methylsulfonyl)methoxy group, a (ethylsulfonyl)methoxy group, a (isopropylsulfonyl)methoxy group, a (2H-tetrazol-5-yl)methoxy group, a 2-amino-2-oxoethoxy group, a carboxydifluoromethoxy group, a 2-carboxyethoxy group, a 2-cyanoethoxy group, a 2-(methylsulfonyl)ethoxy group, a 2-morpholinoethoxy group, a 3-hydroxycyclobutoxy group, a 3-cyanocyclobutoxy group, a 3-carboxycyclobutoxy group, a 3-(methylsulfonyl)cyclobutoxy group, a 3-(2H-tetrazol-5-yl)cyclobutoxy group, a (4-hydroxycyclohexyl)oxy group, a 2-hydroxy-3-methoxypropoxy group, a benzyloxy group, an acetyl group, a carbamoyl group, a dimethylcarbamoyl group, a morpholine-4-carbonyl group, a piperidine-1-carbonyl group, a methoxycarbonyl group, an ethoxycarbonyl group, a (tetrahydro-2H-pyran-4-yl)oxy group, a 1-(1,1-difluoro-2-hydroxyethoxy)-2,2,2-trifluoroethyl group, a tetrahydro-2H-pyran-3-yl)oxy group, a difluoromethoxy group, a 3-(2-hydroxypropan-2-yl)cyclobutoxy group, a (1-hydroxy-2-methylpropan-2-yl)oxy group, a 2,2,2-trifluoro-1-((3-hydroxy-2,3-dimethylbutan-2-yl)oxy) ethyl group, a 2,2,2-trifluoro-1-(2-methoxy-2-methylpropoxy)ethyl group, a 2,2,2-trifluoro-1-((1-methoxycyclopropyl)methoxy)ethyl group, a 1,1-difluoro-3-hydroxy-3-methylbutoxy group, a (1,1-dioxido tetrahydro-2H-thiopyran-4-yl)oxy) group, an oxetan-3-yl oxy group, a 1,1-difluoro-2,3-dihydroxy-2-methylpropoxy group, a (trifluoromethyl)sulfonyl group, a (5-(trifluoromethyl)pyridin-2-yl)oxy group, a pyridin-2-yloxy group, a pyrimidin-2-yloxy group, a pyrazin-2-yloxy group, a (6-methyl-4-(trifluoromethyl)pyridazin-3-yl)oxy group, a (5-(hydroxymethyl)pyridin-2-yl)oxy group, a (5-(hydroxymethyl)-3-(trifluoromethyl)pyridin-2-yl)oxy group, a (5-(trifluoromethoxy)pyridin-2-yl)oxy group, a methylsulfonyl group, a cyclopropyl group, a methylthio group, a methylsulfinyl group, a (2-hydroxyethyl)thio group, a (2-hydroxyethyl)sulfinyl group, a (2-hydroxyethyl)sulfonyl group, a (1,1-difluoroallyl)oxy group, a (5-(methylsulfonyl)pyridin-2-yl)oxy group, a (2-methoxyethyl)carbamoyl group, a (2-hydroxyethyl)carbamoyl group, a (2-hydroxyethyl) (methyl)carbamoyl group, a cyclopropylcarbamoyl group, an ethylcarbamoyl group, a pyrrolidine-1-carbonyl group, a benzylcarbamoyl group, hydroxycarbamoyl group, a 1,1-difluoro-2,3-dihydroxypropoxy group, a 3-((hydroxymethyl)pyridin-2-yl)oxy group, a 1,1-difluoro-2,2-dihydroxypropoxy group, an N-(2-hydroxyethyl)sulfamoyl group, an N-(2-methoxyethyl)sulfamoyl group, an N-(2-hydroxyethyl)-N-methylsulfamoyl group, a pyrrolidin-1-ylsulfonyl group, a morpholinosulfonyl group, a 1,1-difluoro-2-methoxyethoxy group, a 1,1-difluoro-2-methoxy-2-methylpropoxy group, a 1,1-difluoro-2-hydroxybutoxy group, a 1,1-dioxidothio morpholino group, a 1,1-difluoropropoxy group, or a 1,1-difluoro-2-hydroxy-3-methylbutoxy group.

The group represented by $R^2$ in the general formula (1) is preferably a hydrogen atom, a fluorine atom, a chlorine atom, a bromine atom, a carboxy group, a cyano group, a methyl group, an ethyl group, an isopropyl group, a trifluoromethyl group, a difluoromethyl group, a hydroxymethyl group, a methoxymethyl group, a 2-hydroxypropan-2-yl group, a morpholinomethyl group, a (dimethylamino)methyl group, a 2,2,2-trifluoro-1-hydroxyethyl group, a 2,2,2-trifluoro-1-methoxyethyl group, a 1,1,1-trifluoro-2-hydroxypropan-2-yl group, a 2,2-difluoro-1-hydroxyethyl group, a 2,2-difluoro-1-methoxyethyl group, a 1,1-difluoro-2-hydroxypropan-2-yl group, a 1,1,1-trifluoro-2-methoxypropan-2-yl group, a 1-hydroxyethyl group, a 1-hydroxypropyl group, a 1-hydroxy-2-methylpropyl group, a 1-methoxyethyl group, a 2-methoxypropan-2-yl group, a 1-acetoxy-2,2,2-trifluoroethyl group, a 2,2,2-trifluoro-1-(2,2,2-trifluoroethoxy)ethyl group, a 2,2,2-trifluoro-1-(2-methoxyethoxy)ethyl group, a 1-ethoxy-2,2,2-trifluoroethyl group, a 2,2,2-trifluoro-1-(2-hydroxyethoxy)ethyl group, a 2,2,2-trifluoro-1,1-dihydroxyethyl group, a 1-(cyanomethoxy)-2,2,2-trifluoroethyl group, a 2,2,2-trifluoro-1-(2-hydroxypropoxy)ethyl group, a 2,2,2-trifluoro-1-(2-hydroxy-2-methylpropoxy)ethyl group, a 2,2,2-trifluoro-1-((1-hydroxycyclopropyl)methoxy)ethyl group, a 2,2,2-trifluoro-1-((1-hydroxypropan-2-yl)oxy)ethyl group, a 2,2,2-trifluoro-1-((1-hydroxy-2-methylpropan-2-yl)oxy)ethyl group, a 1-(1,1-difluoro-2-hydroxypropoxy)-2,2,2-trifluoroethyl group, a 1-(1,1-difluoro-2-hydroxy-2-methylpropoxy)-2,2,2-trifluoroethyl group, a 1-(difluoro(1-hydroxycyclopropyl)methoxy)-2,2,2-trifluoroethyl group, a 1-(carboxymethoxy)-2,2,2-trifluoroethyl group, a 1-(2-amino-2-oxoethoxy)-2,2,2-trifluoroethyl group, a 2,2,2-trifluoro-1-((methylsulfonyl)methoxy)ethyl group, a 2,2,2-trifluoro-1-(sulfamoylmethoxy)ethyl group, a 1,1,1-trifluoro-3-hydroxypropan-2-yl group, a 1,1,1,4,4,4-hexafluoro-3-hydroxybutan-2-yl group, a 1-((1,3-dihydroxypropan-2-yl)oxy)-2,2,2-trifluoroethyl group, a 1,1,1-trifluoro-3-hydroxybutan-2-yl group, a 1,1,1-trifluoro-3-oxobutan-2-yl group, a 1,1,1,4,4,4-hexafluoro-3-oxobutan-2-yl group, a 1,1,1-trifluoro-3,4-dihydroxybutan-2-yl group, a 1,1,1-trifluoro-4-hydroxy-3-oxobutan-2-yl group, a 1-((2H-tetrazol-5-yl)methoxy)-2,2,2-trifluoroethyl group, a 1-((2H-tetrazol-5-yl)methoxy)-2,2-difluoroethyl group, a 1-hydroxy-3-(methylsulfonyl)propyl group, a 2,2-difluoro-1-hydroxy-3-(methylsulfonyl)propyl group, a 3-(ethylsulfonyl)-1-hydroxypropyl group, a 3-(ethylsulfonyl)-2,2-difluoro-1-hydroxypropyl group, a 1-hydroxy-3-(isopropylsulfonyl)propyl group, a 2,2-difluoro-1-hydroxy-3-(isopropylsulfonyl)propyl group, a 2,2,2-trifluoro-1-(2-morpholino-2-oxoethoxy)ethyl group, a 1-hydroxy-2-morpholinoethyl group, a 2,2-difluoro-1-hydroxy-2-morpholinoethyl group, a 1-carboxy-2,2-difluoro-1-hydroxyethyl group, a 1-carboxy-2,2,2-trifluoro-1-hydroxyethyl group, a 2,2-difluoro-1-hydroxy-1-(2H-tetrazol-5-yl)ethyl group, a 2,2,2-trifluoro-1-hydroxy-1-(2H-tetrazol-5-yl)ethyl group, a 1,1-difluoro-3-hydroxypropan-2-yl group, a 1,1-difluoro-3-hydroxy-3-methylbutan-2-yl group, a 1,1,1-trifluoro-3-hydroxy-3-methylbutan-2-yl group, a 3-cyano-1,1,1-trifluoro-2-hydroxypropan-2-yl group, a 1,3-dihydroxypropyl group, a 1-hydroxy-3-methoxypropyl group, a 4,4,4-trifluoro-1,3-dihydroxybutyl group, a 1,3-dihydroxybutyl group, a 1,3-dihydroxy-3-methylbutyl group, a cyclopropyl (hydroxy) methyl group, a carboxy(hydroxy)methyl group, a hydroxy (2H-tetrazol-5-yl)methyl group, a hydroxy (3-hydroxycyclobutyl)methyl group, a 3-amino-1-hydroxy-3-oxopropyl group, a 1-hydroxy-2-(methylsulfonamide)ethyl group, a 2-cyanoethyl group, a 1,2-dihydroxyethyl group, a 3,3,3-trifluoro-1,2-dihydroxypropyl group, a 3,3,3-trifluoro-1-hydroxy-2-oxopropyl group, a 3,3,3-trifluoro-1-hydroxypropyl group, a 3,3,3-trifluoro-2-hydroxypropyl group, a 3,3,3-trifluoro-2-oxopropyl group, a 1-hydroxy-3-oxobutyl group, a cyclopropyl group, a cyclobutyl group, a cyclopentyl group, a phenyl group, a benzyl group, a thiazol-2-yl group, a 1H-pyrazol-1-yl group, a 5-methylthiazol-2-yl group, a 5-methoxycarbonylthiazol-2-yl group, a 5-hydroxymethylthiazol-2-yl group, a 5-(1-hydroxyethyl)thiazol-2-yl group, a 5-(2-hydroxypropan-2-yl)thiazol-2-yl group, a 5-(N,N-dimethylaminomethyl)thiazol-2-yl group, a 5-methylthiazol-4-yl group, an oxazol-2-yl group, an oxazol-4-yl group, a 5-methyloxazol-4-yl group, a 1H-imidazol-1-yl group, a 2,5-dimethyl-1H-imidazol-1-yl group, a 1H-imidazol-4-yl group, a 1-methyl-1H-imidazol-2-yl group, a 1-methyl-1H-imidazol-4-yl group, a pyridin-2-yl group, a pyridin-3-yl group, a pyridin-4-yl group, a 3,5-dimethylpyridin-4-yl group, a 6-hydroxypyridin-2-yl group, a 5-hydroxypyridin-2-yl group, a 4-hydroxypyridin-2-yl group, a 3-hydroxypyridin-2-yl group, a 6-methoxypyridin-2-yl group, a 5-methoxypyridin-2-yl group, a 4-methoxypyridin-2-yl group, a 3-methoxypyridin-2-yl group, a pyrimidin-2-yl group, a pyrimidin-4-yl group, a 1,3,5-triazin-2-yl group, a tetrahydrofuran-2-yl group, a tetrahydrofuran-3-yl group, a tetrahydropyran-2-yl group, a tetrahydropyran-3-yl group, a tetrahydropyran-4-yl group, an oxetanyl group, a pyrrolidin-1-yl group, a piperidin-1-yl group, a piperazin-1-yl group, a morpholin-4-yl group, an azetidin-1-yl group, a 4-hydroxypiperidin-1-yl group, a 3-hydroxypyrrolidin-1-yl group, a 3-hydroxyazetidin-1-yl group, a dimethylamino group, a diethylamino group, a methylethylamino group, a cyclobutylamino group, a cyclopentylamino group, a cyclohexylamino group, an acetamide group, an N-methylacetamide group, an propionylamino group, a butyrylamino group, an isobutyrylamino group, a valerylamino group, an isovalerylamino group, a methoxy group, an ethoxy group, an n-propoxy group, an isopropoxy group, an n-butoxy group, an isobutoxy group, a trifluoromethoxy group, a difluoromethoxy group, a 2,2,2-trifluoroethoxy group, a cyanomethoxy group, a carboxymethoxy group, a 2-hydroxyethoxy group, a 2-methoxyethoxy group, a 2-hydroxypropoxy group, a 2-hydroxy-2-methylpropoxy group, a (1-hydroxycyclopropyl)methoxy group, a 1,1-difluoro-2-hydroxy-2-methylpropoxy group, a difluoro(1-hydroxycyclopropyl)methoxy group, a 1,1-difluoro-2-hydroxyethoxy group, a (1,1,1-trifluoro-3-hydroxypropan-2-yl)oxy group, a 3,3,3-trifluoro-2-hydroxypropoxy group, a 2,2-difluoro-2-hydroxyethoxy group, a 2-(trifluoromethoxy)ethoxy group, a (1,3-dihydroxypropan-2-yl)oxy group, a (1-hydroxy-3-(trifluoromethoxy)propan-2-yl)oxy group, a 2-oxopropoxy group, a 1,1-difluoro-2-oxopropoxy group, a (1,1,1-trifluoro-3-oxobutan-2-yl)oxy group, a 3,3,3-trifluoro-2-oxopropoxy group, a 1,1-difluoro-2-hydroxypropoxy group, a (1,1,1-trifluoro-3-hydroxybutan-2-yl)oxy group, an oxetan-3-yl methoxy group, a 3-hydroxy-2-(hydroxymethyl)propoxy group, an allyloxy group, a cyclobutoxy group, a (methylsulfonyl)methoxy group, a (ethylsulfonyl)methoxy group, a (isopropylsulfonyl)methoxy group, a (2H-tetrazol-5-yl)methoxy group, a 2-amino-2-oxoethoxy group, a cyanodifluoromethoxy group, a carboxydifluoromethoxy group, a difluoro(2H-tetrazol-5-yl)methoxy group, a difluoro(methylsulfonyl)methoxy group, a 2-carboxyethoxy group, a 2-cyanoethoxy group, a 2-(methylsulfonyl)ethoxy group, a 2-morpholinoethoxy group, a 3-hydroxycyclobutoxy group, a 3-cyanocyclobutoxy group, a 3-carboxycyclobutoxy group, a 3-(methylsulfonyl)cyclobutoxy group, a 3-(2H- tetrazol-5-yl)cyclobutoxy group, a (4-hydroxycyclohexyl) oxy group, a 2-hydroxy-3-methoxypropoxy group, a phenyloxy group, a benzyloxy group, a thiazol-5-yloxy group, a thiazol-4-yloxy group, a pyridin-4-yloxy group, a pyridin-3-yl oxy group, a methylthio group, a methylsulfonyl group, a methylsulfinyl group, a methylsulfamoyl group, a dimethylsulfamoyl group, a sulfamoyl group, an acetyl group, a 2,2-difluoroacetyl group, a 1-(methoxyimino)ethyl group, a carbamoyl group, a dimethylcarbamoyl group, a morpholine-4-carbonyl group, a piperidine-1-carbonyl group, an azetidine-1-carbonyl group, a benzylcarbamoyl group, a methylcarbamoyl group, a 3-hydroxy-3-(trifluoromethyl) azetidine-1-carbonyl group, a methoxycarbonyl group, an ethoxycarbonyl group, a 1-hydroxycyclopropyl group, or a 1-methoxycyclopropyl group, or more preferably a hydrogen atom, a chlorine atom, a carboxy group, an isopropyl group, a trifluoromethyl group, a hydroxymethyl group, a methoxymethyl group, a 2-hydroxypropan-2-yl group, a morpholinomethyl group, a (dimethylamino)methyl group, a 2,2,2-trifluoro-1-hydroxyethyl group, a 2,2,2-trifluoro-1-methoxyethyl group, a 1,1,1-trifluoro-2-hydroxypropan-2-yl group, a 2,2-difluoro-1-hydroxyethyl group, a 2,2-difluoro-1-methoxyethyl group, a 1,1-difluoro-2-hydroxypropan-2-yl group, a 1,1,1-trifluoro-2-methoxypropan-2-yl group, a 1-hydroxyethyl group, a 1-hydroxypropyl group, a 1-hydroxy-2-methylpropyl group, a 1-methoxyethyl group, a 2-methoxypropan-2-yl group, a 1-acetoxy-2,2,2-trifluoroethyl group, a 2,2,2-trifluoro-1-(2,2,2-trifluoroethoxy)ethyl group, a 2,2,2-trifluoro-1-(2-methoxyethoxy)ethyl group, a 1-ethoxy-2,2,2-trifluoroethyl group, a 2,2,2-trifluoro-1-(2-hydroxyethoxy)ethyl group, a 2,2,2-trifluoro-1,1-dihydroxyethyl group, a 1-(cyanomethoxy)-2,2,2-trifluoroethyl group, a 2,2,2-trifluoro-1-(2-hydroxypropoxy)ethyl group, a 2,2,2-trifluoro-1-(2-hydroxy-2-methylpropoxy)ethyl group, a 2,2,2-trifluoro-1-((1-hydroxycyclopropyl)methoxy)ethyl group, a 2,2,2-trifluoro-1-((1-hydroxypropan-2-yl)oxy)ethyl group, a 2,2,2-trifluoro-1-((1-hydroxy-2-methylpropan-2-yl)oxy)ethyl group, a 1-(1,1-difluoro-2-hydroxypropoxy)-2,2,2-trifluoroethyl group, a 1-(1,1-difluoro-2-hydroxy-2-methylpropoxy)-2,2,2-trifluoroethyl group, a 1-(difluoro(1-hydroxycyclopropyl)methoxy)-2,2,2-trifluoroethyl group, a 1-(carboxymethoxy)-2,2,2-trifluoroethyl group, a 1-(2-amino-2-oxoethoxy)-2,2,2-trifluoroethyl group, a 2,2,2-trifluoro-1-((methylsulfonyl)methoxy)ethyl group, a 2,2,2-trifluoro-1-((sulfamoylmethoxy)ethyl group, a 1-((2H-tetrazol-5-yl)methoxy)-2,2,2-trifluoroethyl group, a 1-((2H-tetrazol-5-yl)methoxy)-2,2-difluoroethyl group, a 1-hydroxy-3-(methylsulfonyl)propyl group, a 3-(ethylsulfonyl)-1-hydroxypropyl group, a 1-hydroxy-3-(isopropylsulfonyl) propyl group, a 2,2,2-trifluoro-1-(2-morpholino-2-oxoethoxy)ethyl group, a 1-carboxy-2,2-difluoro-1-hydroxyethyl group, a 2,2-difluoro-1-hydroxy-1-(2H-tetrazol-5-yl)ethyl group, a 1,3-dihydroxypropyl group, a 1-hydroxy-3-methoxypropyl group, a 4,4,4-trifluoro-1,3-dihydroxybutyl group, a 1,3-dihydroxybutyl group, a 1,3-dihydroxy-3-methylbutyl group, a carboxy(hydroxy)methyl group, a hydroxy (2H-tetrazol-5-yl)methyl group, a hydroxy (3-hydroxycyclobutyl)methyl group, a 1-hydroxy-2-morpholinoethyl group, a 3-amino-1-hydroxy-3-oxopropyl group, a 1-hydroxy-2-(methylsulfonamide)ethyl group, a 2-cyanoethyl group, a 1,2-dihydroxyethyl group, a 3,3,3-trifluoro-1,2-dihydroxypropyl group, a 3,3,3-trifluoro-1-hydroxy-2-oxopropyl group, a 3,3,3-trifluoro-1-hydroxypropyl group, a 3,3,3-trifluoro-2-hydroxypropyl group, a 3,3,3-trifluoro-2-oxopropyl group, a 1-hydroxy-3-oxobutyl group, an acetamide group, an N-methylacetamide group, a methoxy group, an isopropoxy group, a trifluoromethoxy group, a 2,2,2-trifluoroethoxy group, a cyanomethoxy group, a carboxymethoxy group, a 2-hydroxyethoxy group, a 2-methoxyethoxy group, a 2-hydroxypropoxy group, a 2-hydroxy-2-methylpropoxy group, a (1-hydroxycyclopropyl)methoxy group, a 1,1-difluoro-2-hydroxy-2-methylpropoxy group, a difluoro(1-hydroxycyclopropyl)methoxy group, a 1,1-difluoro-2-hydroxyethoxy group, a 3,3,3-trifluoro-2-hydroxypropoxy group, a 2,2-difluoro-2-hydroxyethoxy group, a 2-(trifluoromethoxy)ethoxy group, a 1,1-difluoro-2-hydroxypropoxy group, a (1,1,1-trifluoro-3-hydroxybutan-2-yl)oxy group, an oxetan-3-ylmethoxy group, a 3-hydroxy-2-(hydroxymethyl)propoxy group, an allyloxy group, a cyclobutoxy group, a (methylsulfonyl) methoxy group, a (ethylsulfonyl)methoxy group, a (isopropylsulfonyl)methoxy group, a (2H-tetrazol-5-yl)methoxy group, a 2-amino-2-oxoethoxy group, a carboxydifluoromethoxy group, a 2-carboxyethoxy group, a 2-cyanoethoxy group, a 2-(methylsulfonyl)ethoxy group, a 2-morpholinoethoxy group, a 3-hydroxycyclobutoxy group, a 3-cyanocyclobutoxy group, a 3-carboxycyclobutoxy group, a 3-(methylsulfonyl)cyclobutoxy group, a 3-(2H-tetrazol-5-yl)cyclobutoxy group, a (4-hydroxycyclohexyl)oxy group, a 2-hydroxy-3-methoxypropoxy group, a benzyloxy group, a methylthio group, a methylsulfonyl group, a methylsulfinyl group, a methylsulfamoyl group, a dimethylsulfamoyl group, a sulfamoyl group, an acetyl group, a 1-(methoxyimino)ethyl group, a carbamoyl group, a dimethylcarbamoyl group, a morpholine-4-carbonyl group, a piperidine-1-carbonyl group, an azetidine-1-carbonyl group, a benzylcarbamoyl group, a methylcarbamoyl group, a 3-hydroxy-3-(trifluoromethyl)azetidine-1-carbonyl group, a methoxycarbonyl group, an ethoxycarbonyl group, a 1-hydroxycyclopropyl group, or a 1-methoxycyclopropyl group.

In the present invention, the group represented by $R^3$ in the general formula (1) is a hydrogen atom.

In the present invention, the group represented by $R^4$ in the general formula (1) is an optionally substituted 4- to 10-membered monocyclic heterocyclic group containing 1 to 4 heteroatoms selected from an oxygen atom, a nitrogen atom, and a sulfur atom, and may be aromatic and nonaromatic. In addition, if $R^4$ is to be substituted with the substituent described above, the substitution may take place at any position. The group represented by $R^4$ in the general formula (1) is preferably an oxazolyl group, an isoxazolyl group, an oxadiazolyl group, a thiazolyl group, a chlorothiazolyl group, a cyanothiazolyl group, a methylthiazolyl group, a hydroxymethylthiazolyl group, a carbamoylthiazolyl group, a nitrothiazolyl group, a fluorothiazolyl group, a difluorothiazolyl group, a deuterated thiazolyl group, an isothiazolyl group, an imidazolyl group, a methylimidazolyl group, a triazolyl group, a pyridyl group, a chloropyridyl group, a fluoropyridyl group, a cyanopyridyl group, a methylpyridyl group, a pyrimidinyl group, a tetrazolyl group, or a furanyl group, more preferably an oxazolyl group, a thiazolyl group, a fluorothiazolyl group, a difluorothiazolyl group, a deuterated thiazolyl group, an isothiazolyl group, a pyridyl group, a fluoropyridyl group, or a furanyl group, or still more preferably a thiazol-2-yl group, a thiazol-4-yl group, a pyridin-2-yl group, an oxazol-2-yl group, a 1H-pyrazol-1-yl group, a 4-methylthiazol-2-yl group, a 5-fluoropyridin-2-yl group, a 2H-1,2,3-triazol-2-yl group, a 1,2,4-thiadiazol-5-yl group, a 1-methyl-1H-pyrazol-3-yl group, a pyrimidin-2-yl group, an isothiazol-3-yl group, a 3-methyl-1,2,4-thiadiazol-5-yl group, or a 5-chloropyridin-2-yl group.

In the present invention, X in the general formula (1) represents a group represented by the formulae: —$CH_2$—, —$CH_2$—$CH_2$—, —$CH_2$—$CH_2$—$CH_2$—, or —$CH_2$—O—$CH_2$—.

In the present invention, Z in the general formula (1) represents a hydrogen atom or a hydroxyl group.

Examples of a more preferable embodiment of the compound or the pharmacologically acceptable salt thereof according to the present invention can include an embodiment in which the compound represented by the general formula (1) is the following compounds (1a) to (1j).

Compound (1a)

A compound in which, in the general formula (1),
$R^1$ represents, among the above, a hydrogen atom, a halogen atom, a hydroxyl group, a carboxy group, a cyano group, an optionally substituted $C_{1-6}$ alkyl group, an optionally substituted $C_{3-7}$ cycloalkyl group, an optionally substituted 4- to 10-membered monocyclic aromatic heterocyclic group containing 1 to 4 heteroatoms selected from an oxygen atom, a nitrogen atom, and a sulfur atom, an optionally substituted 4- to 10-membered monocyclic nonaromatic heterocyclic group containing 1 to 4 heteroatoms selected from an oxygen atom, a nitrogen atom, and a sulfur atom, an optionally substituted $C_{1-6}$ acylamino group, an optionally substituted $C_{1-6}$ alkyloxy group, an optionally substituted $C_{1-6}$ alkyloxy-$C_{1-6}$ alkyl group, an optionally substituted $C_{3-7}$ cycloalkyloxy group, an optionally substituted 4- to 10-membered monocyclic aromatic heterocyclyloxy group containing 1 to 4 heteroatoms selected from an oxygen atom, a nitrogen atom, and a sulfur atom, an optionally substituted 4- to 10-membered monocyclic nonaromatic heterocyclyloxy group containing 1 to 4 heteroatoms selected from an oxygen atom, a nitrogen atom, and a sulfur atom, an optionally substituted $C_{1-6}$ alkylthio group, an optionally substituted $C_{1-6}$ alkylsulfonyl group, an optionally substituted $C_{1-6}$ alkylsulfinyl group, an optionally substituted mono-$C_{1-6}$ alkylsulfamoyl group, an optionally substituted di-$C_{1-6}$ alkylsulfamoyl group [two $C_{1-6}$ alkyl groups in the di-$C_{1-6}$ alkylsulfamoyl group may form a pyrrolidin-1-yl group or a morpholino group with an adjacent nitrogen atom], a sulfamoyl group, an optionally substituted $C_{1-6}$ alkylcarbonyl group, an optionally substituted 1-($C_{1-6}$ alkyloxy)imino-$C_{1-6}$ alkyl group, an aminocarbonyl group, an optionally substituted mono-$C_{1-6}$ alkylaminocarbonyl group, an optionally substituted di-$C_{1-6}$ alkylaminocarbonyl group, an optionally substituted $C_{3-7}$ cycloalkylaminocarbonyl group, an optionally substituted $C_{7-11}$ monocyclic aralkylaminocarbonyl group, an optionally substituted $C_{1-6}$ alkyloxycarbonyl group, or an optionally substituted hydroxyaminocarbonyl group, and
$R^2$ represents, among the above, a hydrogen atom, a halogen atom, a hydroxyl group, a carboxy group, a cyano group, an optionally substituted $C_{1-6}$ alkyl group, an optionally substituted 4- to 10-membered monocyclic aromatic heterocyclic group containing 1 to 4 heteroatoms selected from an oxygen atom, a nitrogen atom, and a sulfur atom, an optionally substituted 4- to 10-membered monocyclic nonaromatic heterocyclic group containing 1 to 4 heteroatoms selected from an oxygen atom, a nitrogen atom, and a sulfur atom, an optionally substituted $C_{1-6}$ acylamino group, an optionally substituted $C_{1-6}$ alkyloxy group, an optionally substituted $C_{2-6}$ alkenyloxy group, an optionally substituted $C_{1-6}$ alkyloxy-$C_{1-6}$ alkyl group, an optionally substituted $C_{3-7}$ cycloalkyloxy group, an optionally substituted 4- to 10-membered monocyclic aromatic heterocyclyloxy group containing 1 to 4 heteroatoms selected from an oxygen atom, a nitrogen atom, and a sulfur atom, an optionally substituted 4- to 10-membered monocyclic nonaromatic heterocyclyloxy group containing 1 to 4 heteroatoms selected from an oxygen atom, a nitrogen atom, and a sulfur atom, an optionally substituted $C_{1-6}$ alkylthio group, an optionally substituted $C_{1-6}$ alkylsulfonyl group, an optionally substituted $C_{1-6}$ alkylsulfinyl group, an optionally substituted mono-$C_{1-6}$ alkylsulfamoyl group, an optionally substituted di-$C_{1-6}$ alkylsulfamoyl group, a sulfamoyl group, an optionally substituted $C_{1-6}$ alkylcarbonyl group, an optionally substituted 1-($C_{1-6}$ alkyloxy)imino-$C_{1-6}$ alkyl group, an aminocarbonyl group, an optionally substituted mono-$C_{1-6}$ alkylaminocarbonyl group, an optionally substituted di-$C_{1-6}$ alkylaminocarbonyl group, an optionally substituted $C_{3-7}$ cycloalkylaminocarbonyl group, an optionally substituted $C_{7-11}$ monocyclic or polycyclic aralkylaminocarbonyl group, or an optionally substituted $C_{1-6}$ alkyloxycarbonyl group.

Compound (1b)

A compound in which, in the general formula (1),
$R^1$ represents, among the above, a hydrogen atom, a halogen atom, a hydroxyl group, a carboxy group, a cyano group, an optionally substituted $C_{1-6}$ alkyl group, an optionally substituted $C_{3-7}$ cycloalkyl group, an optionally substituted 4- to 10-membered monocyclic aromatic heterocyclic group containing 1 to 4 heteroatoms selected from an oxygen atom, a nitrogen atom, and a sulfur atom, an optionally substituted 4- to 10-membered monocyclic nonaromatic heterocyclic group containing 1 to 4 heteroatoms selected from an oxygen atom, a nitrogen atom(s), and a sulfur atom, an optionally substituted $C_{1-6}$ acylamino group, an optionally substituted $C_{1-6}$ alkyloxy group, an optionally substituted $C_{1-6}$ alkyloxy-$C_{1-6}$ alkyl group, an optionally substituted $C_{3-7}$ cycloalkyloxy group, an optionally substituted 4- to 10-membered monocyclic aromatic heterocyclyloxy group containing 1 to 4 heteroatoms selected from an oxygen atom, a nitrogen atom, and a sulfur atom, an optionally substituted 4- to 10-membered monocyclic nonaromatic heterocyclyloxy group containing 1 to 4 heteroatoms selected from an oxygen atom, a nitrogen atom, and a sulfur atom, an optionally substituted $C_{1-6}$ alkylthio group, an optionally substituted $C_{1-6}$ alkylsulfonyl group, an optionally substituted $C_{1-6}$ alkylsulfinyl group, an optionally substituted mono-$C_{1-6}$ alkylsulfamoyl group, an optionally substituted di-$C_{1-6}$ alkylsulfamoyl group [two $C_{1-6}$ alkyl groups in the di-$C_{1-6}$ alkylsulfamoyl group may form a pyrrolidin-1-yl group or a morpholino group with an adjacent nitrogen atom], a sulfamoyl group, an optionally substituted $C_{1-6}$ alkylcarbonyl group, an optionally substituted 1-($C_{1-6}$ alkyloxy)imino-$C_{1-6}$ alkyl group, an aminocarbonyl group, an optionally substituted mono-$C_{1-6}$ alkylaminocarbonyl group, an optionally substituted di-$C_{1-6}$ alkylaminocarbonyl group, an optionally substituted $C_{7-11}$ monocyclic aralkylaminocarbonyl group, an optionally substituted $C_{3-7}$ cycloalkylaminocarbonyl group, an optionally substituted $C_{1-6}$ alkyloxycarbonyl group, or an optionally substituted hydroxyaminocarbonyl group, and $R^2$ represents, among the above, a hydrogen atom.

Compound (1c)

A compound in which, in the general formula (1), $R^1$ represents, among the above, a hydrogen atom, and $R^2$ represents, among the above, a hydrogen atom, a halogen atom, a hydroxyl group, a carboxy group, a cyano group, an optionally substituted $C_{1-6}$ alkyl group, an optionally substituted 4- to 10-membered monocyclic aromatic heterocyclic group containing 1 to 4 heteroatoms selected from an oxygen atom, a nitrogen atom, and a sulfur atom, an optionally substituted $C_{1-6}$ acylamino group, an optionally substituted $C_{1-6}$ alkyloxy group, an optionally substituted $C_{2-6}$ alkenyloxy group, an optionally substituted $C_{1-6}$ alkyloxy-$C_{1-6}$ alkyl group, an optionally substituted $C_{3-7}$ cycloalkyloxy group, an optionally substituted 4- to 10-membered monocyclic aromatic heterocyclyloxy group containing 1 to 4 heteroatoms selected from an oxygen atom, a nitrogen atom, and a sulfur atom, an optionally substituted 4- to 10-membered monocyclic nonaromatic heterocyclyloxy group containing 1 to 4 heteroatoms selected from an oxygen atom, a nitrogen atom, and a sulfur atom, an optionally substituted $C_{1-6}$ alkylthio group, an optionally substituted $C_{1-6}$ alkylsulfonyl group, an optionally substituted $C_{1-6}$ alkylsulfinyl group, an optionally substituted mono-$C_{1-6}$ alkylsulfamoyl group, an optionally substituted di-$C_{1-6}$ alkylsulfamoyl group, a sulfamoyl group, an optionally substituted $C_{1-6}$ alkylcarbonyl group, an optionally substituted 1-($C_{1-6}$ alkyloxy)imino-$C_{1-6}$ alkyl group, an aminocarbonyl group, an optionally substituted mono-$C_{1-6}$ alkylaminocarbonyl group, an optionally substituted di-$C_{1-6}$ alkylaminocarbonyl group, an optionally substituted $C_{3-7}$ cycloalkylaminocarbonyl group, an optionally substituted $C_{7-11}$ monocyclic or polycyclic aralkylaminocarbonyl group, or an optionally substituted $C_{1-6}$ alkyloxycarbonyl group.

Compound (1d)

A compound in which, in the general formula (1), the groups represented by $R^1$ and $R^2$ may be the same or different and each of them is, among the above, a hydrogen atom, a halogen atom, a hydroxyl group, a carboxy group, a cyano group, an optionally substituted $C_{1-6}$ alkyl group, an optionally substituted $C_{3-7}$ cycloalkyl group, an optionally substituted $C_{6-10}$ monocyclic or polycyclic aryl group, an optionally substituted $C_{7-11}$ monocyclic or polycyclic aralkyl group, an optionally substituted 4- to 10-membered monocyclic or bicyclic aromatic heterocyclic group containing 1 to 4 heteroatoms selected from an oxygen atom, a nitrogen atom, and a sulfur atom, an optionally substituted 4- to 10-membered monocyclic or bicyclic nonaromatic heterocyclic group containing 1 to 4 heteroatoms selected from an oxygen atom, a nitrogen atom, and a sulfur atom, a di-$C_{1-6}$ alkyl amino group, an optionally substituted $C_{3-7}$ cycloalkyl amino group, an optionally substituted $C_{1-6}$ acylamino group, an optionally substituted $C_{1-6}$ alkyloxy group, an optionally substituted $C_{2-6}$ alkenyloxy group, an optionally substituted $C_{1-6}$ alkyloxy-$C_{1-6}$ alkyl group, an optionally substituted $C_{3-7}$ cycloalkyloxy group, an optionally substituted $C_{6-10}$ monocyclic or polycyclic aryloxy group, an optionally substituted $C_{7-11}$ monocyclic or polycyclic aralkyloxy group, an optionally substituted 4- to 10-membered monocyclic or bicyclic aromatic heterocyclyloxy group containing 1 to 4 heteroatoms selected from an oxygen atom, a nitrogen atom, and a sulfur atom, an optionally substituted 4- to 10-membered monocyclic or bicyclic nonaromatic heterocyclyloxy group containing 1 to 4 heteroatoms selected from an oxygen atom, a nitrogen atom, and a sulfur atom, an optionally substituted $C_{1-6}$ alkylthio group, an optionally substituted $C_{1-6}$ alkylsulfonyl group, an optionally substituted $C_{1-6}$ alkylsulfinyl group, an optionally substituted mono-$C_{1-6}$ alkylsulfamoyl group, an optionally substituted di-$C_{1-6}$ alkylsulfamoyl group, a sulfamoyl group [two $C_{1-6}$ alkyl groups in the di-$C_{1-6}$ alkylsulfamoyl group may form a pyrrolidin-1-yl group or a morpholino group with an adjacent nitrogen atom], a sulfamoyl group, an optionally substituted $C_{1-6}$ alkylcarbonyl group, an optionally substituted 1-($C_{1-6}$ alkyloxy)imino-$C_{1-6}$ alkyl group, an aminocarbonyl group, an optionally substituted mono-$C_{1-6}$ alkylaminocarbonyl group, an optionally substituted di-$C_{1-6}$ alkylaminocarbonyl group, an optionally substituted $C_{3-7}$ cycloalkylaminocarbonyl group, an optionally substituted $C_{7-11}$ monocyclic or polycyclic aralkylaminocarbonyl group, or an optionally substituted $C_{1-6}$ alkyloxycarbonyl group.

Compound (1e)

A compound in which, in the general formula (1), the group represented by $R^1$ is, among the above, a hydrogen atom; a halogen atom; a hydroxyl group; a carboxy group; a cyano group; a $C_{1-3}$ alkyl group optionally substituted with one or more substituents selected from a fluorine atom, a hydroxyl group, a methyl group, a methoxy group, an oxo group, and a 4- to 6-membered monocyclic nonaromatic heterocyclic group containing 1 to 3 heteroatoms selected from an oxygen atom and a nitrogen atom; a $C_{3-6}$ cycloalkyl group; a 4- to 6-membered monocyclic aromatic heterocyclic group containing 1 to 3 heteroatoms selected from a nitrogen atom and a sulfur atom; a 4- to 6-membered monocyclic nonaromatic heterocyclic group containing one or two heteroatoms selected from an oxygen atom and a nitrogen atom; a $C_{1-3}$ acylamino group; a $C_{1-5}$ alkyloxy group optionally substituted with one or more substituents selected from a fluorine atom, a hydroxyl group, a methyl group, an ethyl group, a cyano group, and a methoxy group; a $C_{1-3}$ alkyloxy-$C_{1-3}$ alkyl group optionally substituted with one or more substituents selected from a fluorine atom, a hydroxyl group, a cyano group, a carboxy group, a carbamoyl group, a methyl group, a tetrazolyl group, a methoxy group, and a cyclopropyl group; a $C_{3-6}$ cycloalkyloxy group optionally substituted with one or more substituents selected from a $C_{1-3}$ alkyl group optionally substituted with a hydroxyl group, a hydroxyl group, and a cyano group; a 5- or 6-membered monocyclic aromatic heterocyclyloxy group containing 1 to 4 heteroatoms selected from an oxygen atom, a nitrogen atom, and a sulfur atom, which may be optionally substituted with one or more substituents selected from a $C_{1-3}$ alkyl group optionally substituted with a hydroxyl group, a $C_{1-3}$ alkyl group, a trifluoromethyl group, and a $C_{1-3}$ alkylsulfonyl group; a 4- to 6-membered monocyclic nonaromatic heterocyclyloxy group which contains 1 to 3 heteroatoms selected from an oxygen atom and a sulfur atom and which, if containing a sulfur atom, may have one or more oxo groups bonded to the sulfur atom; a $C_{1-3}$ alkylthio group optionally substituted with a hydroxyl group; a $C_{1-3}$ alkylsulfonyl group optionally substituted with one or more substituents selected from a hydroxyl group and a fluorine atom; a $C_{1-3}$ alkylsulfinyl group optionally substituted with one or more substituents selected from a hydroxyl group and a fluorine atom; a sulfamoyl group; a $C_{1-3}$ alkylcarbonyl group; an aminocarbonyl group; a mono-$C_{1-3}$ alkylaminocarbonyl group optionally substituted with one or more substituents selected from a hydroxyl group, a $C_{1-3}$ alkyloxy group, and a phenyl group; a di-$C_{1-3}$ alkylaminocarbonyl group optionally substituted with a hydroxyl group; a $C_{3-6}$ cycloalkyl amino group; a $C_{7-9}$ monocyclic aralkylaminocarbonyl group; or a $C_{1-3}$ alkyloxycarbonyl group, the group represented by $R^2$ is, among the above, a hydrogen atom; a halogen atom; hydroxyl group; a carboxy group; a $C_{1-3}$ alkyl group optionally substituted with one or more substituents selected from a fluorine atom, a hydroxyl group, a methyl group, a methoxy group, an oxo group, a dimethylamino group, and a 4- to 6-membered monocyclic nonaromatic heterocyclic group containing 1 to 3 heteroatoms selected from an oxygen atom and a nitrogen atom; a $C_{3-6}$ cycloalkyl group; a di-$C_{1-3}$ alkyl amino group optionally substituted with an oxo group; a $C_{1-3}$ acylamino group; a $C_{1-5}$ alkyloxy group optionally substituted with one or more substituents selected from a fluorine atom, a hydroxyl group, a methyl group, an ethyl group, a cyano group, a methoxy group, an oxetan-3-yl group, a hydroxymethyl group, a vinyl group, and a carboxy group; a $C_{1-3}$ alkyloxy-$C_{1-3}$ alkyl group optionally substituted with one or more substituents selected from a fluorine atom, a hydroxyl group, a cyano group, a methyl group, an oxo group, and a methoxy group; a $C_{3-6}$ cycloalkyloxy group optionally substituted with one or more substituents selected from a $C_{1-3}$ alkyl group optionally substituted with a hydroxyl group, a hydroxyl group, and a cyano group; a 4- to 6-membered monocyclic nonaromatic heterocyclyloxy group which contains 1 to 3 heteroatoms selected from an oxygen atom and a sulfur atom and which, if containing a sulfur atom, may have one or more oxo groups bonded to the sulfur atom; a $C_{1-3}$ alkylthio group; a $C_{1-3}$ alkylsulfonyl group optionally substituted with one or more substituents selected from a hydroxyl group and a fluorine atom; a $C_{1-3}$ alkylsulfinyl group optionally substituted with one or more substituents selected from a hydroxyl group and a fluorine atom; a sulfamoyl group; a $C_{1-3}$ alkylcarbonyl group; an aminocarbonyl group; a mono-$C_{1-3}$ alkylaminocarbonyl group; a di-$C_{1-3}$ alkylaminocarbonyl group optionally substituted with a hydroxyl group; a $C_{3-6}$ cycloalkyl amino group; a $C_{7-9}$ monocyclic aralkylaminocarbonyl group; or a $C_{1-3}$ alkyloxycarbonyl group, and the group represented by $R^4$ is, among the above, an oxazolyl group, a thiazolyl group, a methylthiazolyl group, an isothiazolyl group, a pyrazolyl group, a methylpyrazolyl group, a triazolyl group, a 1,2,4-thiadiazolyl, a methyl-1,2,4-thiadiazolyl, a pyridyl group, a chloropyridyl group, a fluoropyridyl group, a pyrimidinyl group, or a furanyl group, all of which may be optionally substituted at any position.

Compound (1f)

A compound in which, in the general formula (1), the group represented by $R^1$ is, among the above, a hydrogen atom, a fluorine atom, a chlorine atom, a carboxy group, a cyano group, a methyl group, an ethyl group, an isopropyl group, a trifluoromethyl group, a difluoromethyl group, a hydroxymethyl group, a methoxymethyl group, a 2-hydroxypropan-2-yl group, a morpholinomethyl group, a (dimethylamino)methyl group, a 2,2,2-trifluoro-1-hydroxyethyl group, a 2,2,2-trifluoro-1-methoxyethyl group, a 1,1,1-trifluoro-2-hydroxypropan-2-yl group, a 2,2-difluoro-1-hydroxyethyl group, a 2,2-difluoro-1-methoxyethyl group, a 1,1-difluoro-2-hydroxypropan-2-yl group, a 1,1,1-trifluoro-2-methoxypropan-2-yl group, a 1-hydroxyethyl group, a 1-hydroxypropyl group, a 1-hydroxy-2-methylpropyl group, a 1-methoxyethyl group, a 2-methoxypropan-2-yl group, a 1-acetoxy-2,2,2-trifluoroethyl group, a 2,2,2-trifluoro-1-(2,2,2-trifluoroethoxy)ethyl group, a 2,2,2-trifluoro-1-(2-methoxyethoxy)ethyl group, a 1-ethoxy-2,2,2-trifluoroethyl group, a 2,2,2-trifluoro-1-(2-hydroxyethoxy)ethyl group, a 2,2,2-trifluoro-1,1-dihydroxyethyl group, a 1-(cyanomethoxy)-2,2,2-trifluoroethyl group, a 2,2,2-trifluoro-1-(2-hydroxypropoxy)ethyl group, a 2,2,2-trifluoro-1-(2-hydroxy-2-methylpropoxy)ethyl group, a 2,2,2-trifluoro-1-((1-hydroxycyclopropyl)methoxy)ethyl group, a 2,2,2-trifluoro-1-((1-hydroxypropan-2-yl)oxy)ethyl group, a 2,2,2-trifluoro-1-((1-hydroxy-2-methylpropan-2-yl)oxy)ethyl group, a 1-(1,1-difluoro-2-hydroxypropoxy)-2,2,2-trifluoroethyl group, a 1-(1,1-difluoro-2-hydroxy-2-methylpropoxy)-2,2,2-trifluoroethyl group, a 1-(difluoro(1-hydroxycyclopropyl)methoxy)-2,2,2-trifluoroethyl group, a 1-(carboxymethoxy)-2,2,2-trifluoroethyl group, a 1-(2-amino-2-oxoethoxy)-2,2,2-trifluoroethyl group, a 2,2,2-trifluoro-1-((methylsulfonyl)methoxy)ethyl group, a 2,2,2-trifluoro-1-(sulfamoylmethoxy)ethyl group, a 1,1,1-trifluoro-3-hydroxypropan-2-yl group, a 1,1,1,4,4,4-hexafluoro-3-hydroxybutan-2-yl group, a 1-((1,3-dihydroxypropan-2-yl)oxy)-2,2,2-trifluoroethyl group, a 1,1,1-trifluoro-3-hydroxybutan-2-yl group, a 1,1,1-trifluoro-3-oxobutan-2-yl group, a 1,1,1,4,4,4-hexafluoro-3-oxobutan-2-yl group, a 1,1,1-trifluoro-3,4-dihydroxybutan-2-yl group, a 1,1,1-trifluoro-4-hydroxy-3-oxobutan-2-yl group, a 1-((2H-tetrazol-5-yl)methoxy)-2,2,2-trifluoroethyl group, a 1-((2H-tetrazol-5-yl)methoxy)-2,2-difluoroethyl group, a 1-hydroxy-3-(methylsulfonyl)propyl group, a 2,2-difluoro-1-hydroxy-3-(methylsulfonyl)propyl group, a 3-(ethylsulfonyl)-1-hydroxypropyl group, a 3-(ethylsulfonyl)-2,2-difluoro-1-hydroxypropyl group, a 1-hydroxy-3-(isopropylsulfonyl)propyl group, a 2,2-difluoro-1-hydroxy-3-(isopropylsulfonyl)propyl group, a 2,2,2-trifluoro-1-(2-morpholino-2-oxoethoxy)ethyl group, a 1-hydroxy-2-morpholinoethyl group, a 2,2-difluoro-1-hydroxy-2-morpholinoethyl group, a 1-carboxy-2,2-difluoro-1-hydroxyethyl group, a 1-carboxy-2,2,2-trifluoro-1-hydroxyethyl group, a 2,2-difluoro-1-hydroxy-1-(2H-tetrazol-5-yl)ethyl group, a 2,2,2-trifluoro-1-hydroxy-1-(2H-tetrazol-5-yl)ethyl group, a 1,1-difluoro-3-hydroxypropan-2-yl group, a 1,1-difluoro-3-hydroxy-3-methylbutan-2-yl group, a 1,1,1-trifluoro-3-hydroxy-3-methylbutan-2-yl group, a 3-cyano-1,1,1-trifluoro-2-hydroxypropan-2-yl group, a 1,3-dihydroxypropyl group, a 1-hydroxy-3-methoxypropyl group, a 4,4,4-trifluoro-1,3-dihydroxybutyl group, a 1,3-dihydroxybutyl group, a 1,3-dihydroxy-3-methylbutyl group, a cyclopropyl (hydroxy)methyl group, a carboxy(hydroxy)methyl group, a hydroxy (2H-tetrazol-5-yl)methyl group, a hydroxy (3-hydroxycyclobutyl)methyl group, a 3-amino-1-hydroxy-3-oxopropyl group, a 1-hydroxy-2-(methylsulfonamide)ethyl group, a 2-cyanoethyl group, a 1,2-dihydroxyethyl group, a 3,3,3-trifluoro-1,2-dihydroxypropyl group, a 3,3,3-trifluoro-1-hydroxy-2-oxopropyl group, a 3,3,3-trifluoro-1-hydroxypropyl group, a 3,3,3-trifluoro-2-hydroxypropyl group, a 3,3,3-trifluoro-2-oxopropyl group, a 1-hydroxy-3-oxobutyl group, a cyclopropyl group, a cyclobutyl group, a cyclopentyl group, a phenyl group, a benzyl group, a thiazol-2-yl group, a 1H-pyrazol-1-yl group, a 5-methylthiazol-2-yl group, a 5-methoxycarbonylthiazol-2-yl group, a 5-hydroxymethylthiazol-2-yl group, a 5-(1-hydroxyethyl)thiazol-2-yl group, a 5-(2-hydroxypropan-2-yl)thiazol-2-yl group, a 5-(N,N-dimethylaminomethyl)thiazol-2-yl group, a 5-methylthiazol-4-yl group, an oxazol-2-yl group, an oxazol-4-yl group, a 5-methyloxazol-4-yl group, a 1H-imidazol-1-yl group, a 2,5-dimethyl-1H-imidazol-1-yl group, a 1H-imidazol-4-yl group, a 1-methyl-1H-imidazol-2-yl group, a 1-methyl-1H-imidazol-4-yl group, a pyridin-2-yl group, a pyridin-3-yl group, a pyridin-4-yl group, a 3,5-dimethylpyridin-4-yl group, a 6-hydroxypyridin-2-yl group, a 5-hydroxypyridin-2-yl group, a 4-hydroxypyridin-2-yl group, a 3-hydroxypyridin-2-yl group, a 6-methoxypyridin-2-yl group, a 5-methoxypyridin-2-yl group, a 4-methoxypyridin-2-yl group, a 3-methoxypyridin-2-yl group, a pyrimidin-2-yl group, a pyrimidin-4-yl group, a 1,3,5-triazin-2-yl group, a tetrahydrofuran-2-yl group, a tetrahydrofuran-3-yl group, a tetrahydropyran-2-yl group, a tetrahydropyran-3-yl group, a tetrahydropyran-4-yl group, an oxetanyl group, a pyrrolidin-1-yl group, a piperidin-1-yl group, a piperazin-1-yl group, a morpholin-4-yl group, an azetidin-1-yl group, a 4-hydroxypiperidin-1-yl group, a 3-hydroxypyrrolidin-1-yl group, a 3-hydroxyazetidin-1-yl group, a dimethylamino group, a diethylamino group, a methylethylamino group, a cyclobutylamino group, a cyclopentylamino group, a cyclohexylamino group, an acetamide group, an N-methylacetamide group, an propionylamino group, a butyrylamino group, an isobutyrylamino group, a valerylamino group, an isovalerylamino group, a methoxy group, an ethoxy group, an n-propoxy group, an isopropoxy group, an n-butoxy group, an isobutoxy group, a trifluoromethoxy group, a difluoromethoxy group, a 2,2,2-trifluoroethoxy group, a cyanomethoxy group, a carboxymethoxy group, a 2-hydroxyethoxy group, a 2-methoxyethoxy group, a 2-hydroxypropoxy group, a 2-hydroxy-2-methylpropoxy group, a (1-hydroxycyclopropyl)methoxy group, a 1,1-difluoro-2-hydroxy-2-methylpropoxy group, a difluoro(1-hydroxycyclopropyl)methoxy group, a 1,1-difluoro-2-hydroxyethoxy group, a (1,1,1-trifluoro-3-hydroxypropan-2-yl)oxy group, a 3,3,3-trifluoro-2-hydroxypropoxy group, a 2,2-difluoro-2-hydroxyethoxy group, a 2-(trifluoromethoxy)ethoxy group, a (1,3-dihydroxypropan-2-yl)oxy group, a (1-hydroxy-3-(trifluoromethoxy)propan-2-yl)oxy group, a 2-oxopropoxy group, a 1,1-difluoro-2-oxopropoxy group, a (1,1,1-trifluoro-3-oxobutan-2-yl)oxy group, a 3,3,3-trifluoro-2-oxopropoxy group, a 1,1-difluoro-2-hydroxypropoxy group, a (1,1,1-trifluoro-3-hydroxybutan-2-yl)oxy group, an oxetan-3-ylmethoxy group, a 3-hydroxy-2-(hydroxymethyl)propoxy group, an allyloxy group, a cyclobutoxy group, a (methylsulfonyl)methoxy group, a (ethylsulfonyl)methoxy group, a (isopropylsulfonyl)methoxy group, a (2H-tetrazol-5-yl)methoxy group, a 2-amino-2-oxoethoxy group, a cyanodifluoromethoxy group, a carboxydifluoromethoxy group, a difluoro(2H-tetrazol-5-yl)methoxy group, a difluoro(methylsulfonyl)methoxy group, a 2-carboxyethoxy group, a 2-cyanoethoxy group, a 2-(methylsulfonyl)ethoxy group, a 2-morpholinoethoxy group, a 3-hydroxycyclobutoxy group, a 3-cyanocyclobutoxy group, a 3-carboxycyclobutoxy group, a 3-(methylsulfonyl)cyclobutoxy group, a 3-(2H-tetrazol-5-yl)cyclobutoxy group, a (4-hydroxycyclohexyl)oxy group, a 2-hydroxy-3-methoxypropoxy group, a phenyloxy group, a benzyloxy group, a thiazol-5-yloxy group, a thiazol-4-yloxy group, a pyridin-4-yloxy group, a pyridin-3-yloxy group, a methylthio group, a methylsulfonyl group, a methylsulfinyl group, a methylsulfamoyl group, a dimethylsulfamoyl group, a sulfamoyl group, an acetyl group, a 2,2-difluoroacetyl group, a 1-(methoxyimino)ethyl group, a carbamoyl group, a dimethylcarbamoyl group, a morpholine-4-carbonyl group, a piperidine-1-carbonyl group, an azetidine-1-carbonyl group, a benzylcarbamoyl group, a methylcarbamoyl group, a 3-hydroxy-3-(trifluoromethyl)azetidine-1-carbonyl group, a methoxycarbonyl group, an ethoxycarbonyl group, a (tetrahydro-2H-pyran-4-yl)oxy group, a 1-(1,1-difluoro-2-hydroxyethoxy)-2,2,2-trifluoroethyl group, a (tetrahydro-2H-pyran-3-yl)oxy group, a difluoromethoxy group, a 3-(2-hydroxypropan-2-yl)cyclobutoxy group, a (1-hydroxy-2-methylpropan-2-yl)oxy group, a 2,2,2-trifluoro-1-((3-hydroxy-2,3-dimethylbutan-2-yl)oxy)ethyl group, a 2,2,2-trifluoro-1-(2-methoxy-2-methylpropoxy)ethyl group, a 2,2,2-trifluoro-1-((1-methoxycyclopropyl)methoxy)ethyl group, a 1,1-difluoro-3-hydroxy-3-methylbutoxy group, a (1,1-dioxido tetrahydro-2H-thiopyran-4-yl)oxy) group, an oxetan-3-yloxy group, a 1,1-difluoro-2,3-dihydroxy-2-methylpropoxy group, a (trifluoromethyl)sulfonyl group, a (5-(trifluoromethyl)pyridin-2-yl)oxy group, a pyridin-2-yloxy group, a pyrimidin-2-yloxy group, a pyrazin-2-yloxy group, a (6-methyl-4-(trifluoromethyl)pyridazin-3-yl)oxy group, a (5-(hydroxymethyl)pyridin-2-yl)oxy group, a (5-(hydroxymethyl)-3-(trifluoromethyl)pyridin-2-yl)oxy group, a (5-(trifluoromethoxy)pyridin-2-yl)oxy group, a (2-hydroxyethyl)thio group, a (2-hydroxyethyl)sulfinyl group, a (2-hydroxyethyl)sulfonyl group, a (1,1-difluoroallyl)oxy group, a (5-(methylsulfonyl)pyridin-2-yl)oxy group, a (2-methoxyethyl)carbamoyl group, a (2-hydroxyethyl)carbamoyl group, a (2-hydroxyethyl)(methyl)carbamoyl group, a cyclopropylcarbamoyl group, an ethylcarbamoyl group, a pyrrolidine-1-carbonyl group, hydroxy carbamoyl group, a 1,1-difluoro-2,3-dihydroxypropoxy group, a 3-((hydroxymethyl)pyridin-2-yl)oxy group, a 1,1-difluoro-2,2-dihydroxypropoxy group, an N-(2-hydroxyethyl)sulfamoyl group, an N-(2-methoxyethyl)sulfamoyl group, an N-(2-hydroxyethyl)-N-methylsulfamoyl group, a pyrrolidin-1-ylsulfonyl group, a morpholinosulfonyl group, a 1,1-difluoro-2-methoxyethoxy group, a 1,1-difluoro-2-methoxy-2-methylpropoxy group, a 1,1-difluoro-2-hydroxybutoxy group, a 1,1-dioxidothiomorpholino group, a 1,1-difluoropropoxy group, a 1,1-difluoro-2-hydroxy-3-methylbutoxy group, a benzo[d]oxazol-2-yldifluoromethoxy group, a (1,1-difluoro-3-(pyridin-3-yl)aryl)oxy group, a 1,1-difluoro-2-((hydroxyethyl) (methyl)amino)-2-oxoethoxy group, a 2-(dimethylamino)-1,1-difluoro-2-oxoethoxy group, a 1,1-difluoro-2-morpholino-2-oxoethoxy group, a 2-amino-1,1-difluoro-2-oxoethoxy group, a 1,1-difluoro-2-((2-hydroxyethyl)amino)-2-oxoethoxy group, a 1,1-difluoro-2-(3-hydroxyazetidin-1-yl)-2-oxoethoxy group, or cyclobutyl group, the group represented by $R^2$ is, among the above, a hydrogen atom, a fluorine atom, a chlorine atom, a bromine atom, a carboxy group, a cyano group, a methyl group, an ethyl group, an isopropyl group, a trifluoromethyl group, a difluoromethyl group, a hydroxymethyl group, a methoxymethyl group, a 2-hydroxypropan-2-yl group, a morpholinomethyl group, a (dimethylamino)methyl group, a 2,2,2-trifluoro-1-hydroxyethyl group, a 2,2,2-trifluoro-1-methoxyethyl group, a 1,1,1-trifluoro-2-hydroxypropan-2-yl group, a 2,2-difluoro-1-hydroxyethyl group, a 2,2-difluoro-1-methoxyethyl group, a 1,1-difluoro-2-hydroxypropan-2-yl group, a 1,1,1-trifluoro-2-methoxypropan-2-yl group, a 1-hydroxyethyl group, a 1-hydroxypropyl group, a 1-hydroxy-2-methylpropyl group, a 1-methoxyethyl group, a 2-methoxypropan-2-yl group, a 1-acetoxy-2,2,2-trifluoroethyl group, a 2,2,2-trifluoro-1-(2,2,2-trifluoroethoxy)ethyl group, a 2,2,2-trifluoro-1-(2-methoxyethoxy)ethyl group, a 1-ethoxy-2,2,2-trifluoroethyl group, a 2,2,2-trifluoro-1-(2-hydroxyethoxy)ethyl group, a 2,2,2-trifluoro-1,1-dihydroxyethyl group, a 1-(cyanomethoxy)-2,2,2-trifluoroethyl group, a 2,2,2-trifluoro-1-(2-hydroxypropoxy)ethyl group, a 2,2,2-trifluoro-1-(2-hydroxy-2-methylpropoxy)ethyl group, a 2,2,2-trifluoro-1-((1-hydroxycyclopropyl)methoxy)ethyl group, a 2,2,2-trifluoro-1-((1-hydroxypropan-2-yl)oxy)ethyl group, a 2,2,2-trifluoro-1-((1-hydroxy-2-methylpropan-2-yl)oxy)ethyl group, a 1-(1,1-difluoro-2-hydroxypropoxy)-2,2,2-trifluoroethyl group, a 1-(1,1-difluoro-2-hydroxy-2-methylpropoxy)-2,2,2-trifluoroethyl group, a 1-(difluoro(1-hydroxycyclopropyl)methoxy)-2,2,2-trifluoroethyl group, a 1-(carboxymethoxy)-2,2,2-trifluoroethyl group, a 1-(2-amino-2-oxoethoxy)-2,2,2-trifluoroethyl group, a 2,2,2-trifluoro-1-((methylsulfonyl)methoxy)ethyl group, a 2,2,2-trifluoro-1-(sulfamoylmethoxy)ethyl group, a 1,1,1-trifluoro-3-hydroxypropan-2-yl group, a 1,1,1,4,4,4-hexafluoro-3-hydroxybutan-2-yl group, a 1-((1,3-dihydroxypropan-2-yl)oxy)-2,2,2-trifluoroethyl group, a 1,1,1-trifluoro-3-hydroxybutan-2-yl group, a 1,1,1-trifluoro-3-oxobutan-2-yl group, a 1,1,1,4,4,4-hexafluoro-3-oxobutan-2-yl group, a 1,1,1-trifluoro-3,4-dihydroxybutan-2-yl group, a 1,1,1-trifluoro-4-hydroxy-3-oxobutan-2-yl group, a 1-((2H-tetrazol-5-yl)methoxy)-2,2,2-trifluoroethyl group, a 1-((2H-tetrazol-5-yl)methoxy)-2,2-difluoroethyl group, a 1-hydroxy-3-(methylsulfonyl)propyl group, a 2,2-difluoro-1-hydroxy-3-(methylsulfonyl)propyl group, a 3-(ethylsulfonyl)-1-hydroxypropyl group, a 3-(ethylsulfonyl)-2,2-difluoro-1-hydroxypropyl group, a 1-hydroxy-3-(isopropylsulfonyl)propyl group, a 2,2-difluoro-1-hydroxy-3-(isopropylsulfonyl)propyl group, a 2,2,2-trifluoro-1-(2-morpholino-2-oxoethoxy)ethyl group, a 1-hydroxy-2-morpholinoethyl group, a 2,2-difluoro-1-hydroxy-2-morpholinoethyl group, a 1-carboxy-2,2-difluoro-1-hydroxyethyl group, a 1-carboxy-2,2,2-trifluoro-1-hydroxyethyl group, a 2,2-difluoro-1-hydroxy-1-(2H-tetrazol-5-yl)ethyl group, a 2,2,2-trifluoro-1-hydroxy-1-(2H-tetrazol-5-yl)ethyl group, a 1,1-difluoro-3-hydroxypropan-2-yl group, a 1,1-difluoro-3-hydroxy-3-methylbutan-2-yl group, a 1,1,1-trifluoro-3-hydroxy-3-methylbutan-2-yl group, a 3-cyano-1,1,1-trifluoro-2-hydroxypropan-2-yl group, a 1,3-dihydroxypropyl group, a 1-hydroxy-3-methoxypropyl group, a 4,4,4-trifluoro-1,3-dihydroxybutyl group, a 1,3-dihydroxybutyl group, a 1,3-dihydroxy-3-methylbutyl group, a cyclopropyl (hydroxy)methyl group, a carboxy(hydroxy)methyl group, a hydroxy (2H-tetrazol-5-yl)methyl group, a hydroxy (3-hydroxycyclobutyl)methyl group, a 3-amino-1-hydroxy-3-oxopropyl group, a 1-hydroxy-2-(methylsulfonamide)ethyl group, a 2-cyanoethyl group, a 1,2-dihydroxyethyl group, a 3,3,3-trifluoro-1,2-dihydroxypropyl group, a 1-hydroxycyclopropyl group, a 1-methoxycyclopropyl group, a 3,3,3-trifluoro-1-hydroxy-2-oxopropyl group, a 3,3,3-trifluoro-1-hydroxypropyl group, a 3,3,3-trifluoro-2-hydroxypropyl group, a 3,3,3-trifluoro-2-oxopropyl group, a 1-hydroxy-3-oxobutyl group, a cyclopropyl group, a cyclobutyl group, a cyclopentyl group, a phenyl group, a benzyl group, a thiazol-2-yl group, a 1H-pyrazol-1-yl group, a 5-methylthiazol-2-yl group, a 5-methoxycarbonylthiazol-2-yl group, a 5-hydroxymethylthiazol-2-yl group, a 5-(1-hydroxyethyl)thiazol-2-yl group, a 5-(2-hydroxypropan-2-yl)thiazol-2-yl group, a 5-(N,N-dimethylaminomethyl)thiazol-2-yl group, a 5-methylthiazol-4-yl group, an oxazol-2-yl group, an oxazol-4-yl group, a 5-methyloxazol-4-yl group, a 1H-imidazol-1-yl group, a 2,5-dimethyl-1H-imidazol-1-yl group, a 1H-imidazol-4-yl group, a 1-methyl-1H-imidazol-2-yl group, a 1-methyl-1H-imidazol-4-yl group, a pyridin-2-yl group, a pyridin-3-yl group, a pyridin-4-yl group, a 3,5-dimethylpyridin-4-yl group, a 6-hydroxypyridin-2-yl group, a 5-hydroxypyridin-2-yl group, a 4-hydroxypyridin-2-yl group, a 3-hydroxypyridin-2-yl group, a 6-methoxypyridin-2-yl group, a 5-methoxypyridin-2-yl group, a 4-methoxypyridin-2-yl group, a 3-methoxypyridin-2-yl group, a pyrimidin-2-yl group, a pyrimidin-4-yl group, a 1,3,5-triazin-2-yl group, a tetrahydrofuran-2-yl group, a tetrahydrofuran-3-yl group, a tetrahydropyran-2-yl group, a tetrahydropyran-3-yl group, a tetrahydropyran-4-yl group, an oxetanyl group, a pyrrolidin-1-yl group, a piperidin-1-yl group, a piperazin-1-yl group, a morpholin-4-yl group, an azetidin-1-yl group, a 4-hydroxypiperidin-1-yl group, a 3-hydroxypyrrolidin-1-yl group, a 3-hydroxyazetidin-1-yl group, a dimethylamino group, a diethylamino group, a methylethylamino group, a cyclobutylamino group, a cyclopentylamino group, a cyclohexylamino group, an acetamide group, an N-methylacetamide group, an propionylamino group, a butyrylamino group, an isobutyrylamino group, a valerylamino group, an isovalerylamino group, a methoxy group, an ethoxy group, an n-propoxy group, an isopropoxy group, an n-butoxy group, an isobutoxy group, a trifluoromethoxy group, a difluoromethoxy group, a 2,2,2-trifluoroethoxy group, a cyanomethoxy group, a carboxymethoxy group, a 2-hydroxyethoxy group, a 2-methoxyethoxy group, a 2-hydroxypropoxy group, a 2-hydroxy-2-methylpropoxy group, a (1-hydroxycyclopropyl)methoxy group, a 1,1-difluoro-2-hydroxy-2-methylpropoxy group, a difluoro(1-hydroxycyclopropyl)methoxy group, a 1,1-difluoro-2-hydroxyethoxy group, a (1,1,1-trifluoro-3-hydroxypropan-2-yl)oxy group, a 3,3,3-trifluoro-2-hydroxypropoxy group, a 2,2-difluoro-2-hydroxyethoxy group, a 2-(trifluoromethoxy)ethoxy group, a (1,3-dihydroxypropan-2-yl)oxy group, a (1-hydroxy-3-(trifluoromethoxy)propan-2-yl)oxy group, a 2-oxopropoxy group, a 1,1-difluoro-2-oxopropoxy group, a (1,1,1-trifluoro-3-oxobutan-2-yl)oxy group, a 3,3,3-trifluoro-2-oxopropoxy group, a 1,1-difluoro-2-hydroxypropoxy group, a (1,1,1-trifluoro-3-hydroxybutan-2-yl)oxy group, an oxetan-3-ylmethoxy group, a 3-hydroxy-2-(hydroxymethyl)propoxy group, an allyloxy group, a cyclobutoxy group, a (methylsulfonyl)methoxy group, a (ethylsulfonyl)methoxy group, a (isopropylsulfonyl)methoxy group, a (2H-tetrazol-5-yl)methoxy group, a 2-amino-2-oxoethoxy group, a cyanodifluoromethoxy group, a carboxydifluoromethoxy group, a difluoro(2H-tetrazol-5-yl)methoxy group, a difluoro(methylsulfonyl)methoxy group, a 2-carboxyethoxy group, a 2-cyanoethoxy group, a 2-(methylsulfonyl)ethoxy group, a 2-morpholinoethoxy group, a 3-hydroxycyclobutoxy group, a 3-cyanocyclobutoxy group, a 3-carboxycyclobutoxy group, a 3-(methylsulfonyl)cyclobutoxy group, a 3-(2H-tetrazol-5-yl)cyclobutoxy group, a (4-hydroxycyclohexyl)oxy group, a 2-hydroxy-3-methoxypropoxy group, a phenyloxy group, a benzyloxy group, a thiazol-5-yloxy group, a thiazol-4-yloxy group, a pyridin-4-yloxy group, a pyridin-3-yloxy group, a methylthio group, a methylsulfonyl group, a methylsulfinyl group, a methylsulfamoyl group, a dimethylsulfamoyl group, a sulfamoyl group, an acetyl group, a 2,2-difluoroacetyl group, a 1-(methoxyimino)ethyl group, a carbamoyl group, a dimethylcarbamoyl group, a morpholine-4-carbonyl group, a piperidine-1-carbonyl group, an azetidine-1-carbonyl group, a benzylcarbamoyl group, a methylcarbamoyl group, a 3-hydroxy-3-(trifluoromethyl)azetidine-1-carbonyl group, a methoxycarbonyl group, an ethoxycarbonyl group, a (5-(trifluoromethyl)pyridin-2-yl)oxy group, or a (5-(hydroxymethyl)pyridin-2-yl)oxy group, and the group represented by $R^4$ is, among the above, an oxazolyl group, an isoxazolyl group, an oxadiazolyl group, a thiazolyl group, a chlorothiazolyl group, a cyanothiazolyl group, a methylthiazolyl group, a hydroxymethylthiazolyl group, a carbamoylthiazolyl group, a nitrothiazolyl group, a fluorothiazolyl group, a difluorothiazolyl group, a deuterated thiazolyl group, an isothiazolyl group, an imidazolyl group, a methylimidazolyl group, a triazolyl group, a pyridyl group, a chloropyridyl group, a fluoropyridyl group, a cyanopyridyl group, a methylpyridyl group, a pyrimidinyl group, a tetrazolyl group, or a furanyl group.

Compound (1g)

A compound in which, in the general formula (1), the group represented by $R^1$ is, among the above, a hydrogen atom, a chlorine atom, a cyano group, a carboxy group, a methyl group, a trifluoromethyl group, a hydroxymethyl group, a 2-hydroxypropan-2-yl group, a 2,2,2-trifluoro-1-hydroxyethyl group, a 2,2,2-trifluoro-1-methoxyethyl group, a 1,1,1-trifluoro-2-hydroxypropan-2-yl group, a 2,2-difluoro-1-hydroxyethyl group, a 2,2-difluoro-1-methoxyethyl group, a 1,1-difluoro-2-hydroxypropan-2-yl group, a 1,1,1-trifluoro-2-methoxypropan-2-yl group, a 1-hydroxyethyl group, a 1-methoxyethyl group, a 2-methoxypropan-2-yl group, a 2,2,2-trifluoro-1-(2,2,2-trifluoroethoxy)ethyl group, a 2,2,2-trifluoro-1-(2-methoxyethoxy)ethyl group, a 1-ethoxy-2,2,2-trifluoroethyl group, a 2,2,2-trifluoro-1-(2-hydroxyethoxy)ethyl group, a 2,2,2-trifluoro-1,1-dihydroxyethyl group, a 1-(cyanomethoxy)-2,2,2-trifluoroethyl group, a 2,2,2-trifluoro-1-(2-hydroxypropoxy)ethyl group, a 2,2,2-trifluoro-1-(2-hydroxy-2-methylpropoxy)ethyl group, a 2,2,2-trifluoro-1-((1-hydroxycyclopropyl)methoxy)ethyl group, a 2,2,2-trifluoro-1-((1-hydroxypropan-2-yl)oxy)ethyl group, a 2,2,2-trifluoro-1-((1-hydroxy-2-methylpropan-2-yl)oxy)ethyl group, a 1-(1,1-difluoro-2-hydroxypropoxy)-2,2,2-trifluoroethyl group, a 1-(1,1-difluoro-2-hydroxy-2-methylpropoxy)-2,2,2-trifluoroethyl group, a 1-(difluoro(1-hydroxycyclopropyl)methoxy)-2,2,2-trifluoroethyl group, a 1-(carboxymethoxy)-2,2,2-trifluoroethyl group, a 1-(2-amino-2-oxoethoxy)-2,2,2-trifluoroethyl group, a 2,2,2-trifluoro-1-((methylsulfonyl)methoxy)ethyl group, a 2,2,2-trifluoro-1-(sulfamoylmethoxy)ethyl group, a 1-((2H-tetrazol-5-yl)methoxy)-2,2,2-trifluoroethyl group, a 1-((2H-tetrazol-5-yl)methoxy)-2,2-difluoroethyl group, a 1-hydroxy-3-(methylsulfonyl)propyl group, a 3-(ethylsulfonyl)-1-hydroxypropyl group, a 1-hydroxy-3-(isopropylsulfonyl)propyl group, a 2,2,2-trifluoro-1-(2-morpholino-2-oxoethoxy)ethyl group, a 1-carboxy-2,2-difluoro-1-hydroxyethyl group, a 2,2-difluoro-1-hydroxy-1-(2H-tetrazol-5-yl)ethyl group, a phenyl group, a thiazol-2-yl group, an acetamide group, a methoxy group, a trifluoromethoxy group, a cyanomethoxy group, a carboxymethoxy group, a 2-hydroxyethoxy group, a 2-methoxyethoxy group, a 2-hydroxypropoxy group, a 2-hydroxy-2-methylpropoxy group, a (1-hydroxycyclopropyl)methoxy group, a 1,1-difluoro-2-hydroxy-2-methylpropoxy group, a difluoro(1-hydroxycyclopropyl)methoxy group, a 1,1-difluoro-2-hydroxyethoxy group, a 3,3,3-trifluoro-2-hydroxypropoxy group, a 2,2-difluoro-2-hydroxyethoxy group, a 2-(trifluoromethoxy)ethoxy group, a 1,1-difluoro-2-hydroxypropoxy group, a (1,1,1-trifluoro-3-hydroxybutan-2-yl)oxy group, a cyclobutoxy group, a (methylsulfonyl)methoxy group, a (ethylsulfonyl)methoxy group, a (isopropylsulfonyl)methoxy group, a (2H-tetrazol-5-yl)methoxy group, a 2-amino-2-oxoethoxy group, a carboxydifluoromethoxy group, a 2-carboxyethoxy group, a 2-cyanoethoxy group, a 2-(methylsulfonyl)ethoxy group, a 2-morpholinoethoxy group, a 3-hydroxycyclobutoxy group, a 3-cyanocyclobutoxy group, a 3-carboxycyclobutoxy group, a 3-(methylsulfonyl)cyclobutoxy group, a 3-(2H-tetrazol-5-yl)cyclobutoxy group, a (4-hydroxycyclohexyl)oxy group, a 2-hydroxy-3-methoxypropoxy group, a benzyloxy group, an acetyl group, a carbamoyl group, a dimethylcarbamoyl group, a morpholine-4-carbonyl group, a piperidine-1-carbonyl group, a methoxycarbonyl group, an ethoxycarbonyl group, a (tetrahydro-2H-pyran-4-yl)oxy group, a 1-(1,1-difluoro-2-hydroxyethoxy)-2,2,2-trifluoroethyl group, a tetrahydro-2H-pyran-3-yl)oxy group, a difluoromethoxy group, a 3-(2-hydroxypropan-2-yl)cyclobutoxy group, a (1-hydroxy-2-methylpropan-2-yl)oxy group, a 2,2,2-trifluoro-1-((3-hydroxy-2,3-dimethylbutan-2-yl)oxy)ethyl group, a 2,2,2-trifluoro-1-(2- methoxy-2-methylpropoxy)ethyl group, a 2,2,2-trifluoro-1-((1-methoxycyclopropyl)methoxy)ethyl group, a 1,1-difluoro-3-hydroxy-3-methylbutoxy group, a (1,1-dioxido tetrahydro-2H-thiopyran-4-yl)oxy) group, an oxetan-3-yloxy group, a 1,1-difluoro-2,3-dihydroxy-2-methylpropoxy group, a (trifluoromethyl)sulfonyl group, a (5-(trifluoromethyl)pyridin-2-yl)oxy group, a pyridin-2-yloxy group, a pyrimidin-2-yloxy group, a pyrazin-2-yloxy group, a (6-methyl-4-(trifluoromethyl)pyridazin-3-yl)oxy group, a (5-(hydroxymethyl)pyridin-2-yl)oxy group, a (5-(hydroxymethyl)-3-(trifluoromethyl)pyridin-2-yl)oxy group, a (5-(trifluoromethoxy)pyridin-2-yl)oxy group, a methylsulfonyl group, a cyclopropyl group, a methylthio group, a methylsulfinyl group, a (2-hydroxyethyl)thio group, a (2-hydroxyethyl)sulfinyl group, a (2-hydroxyethyl)sulfonyl group, a (1,1-difluoroallyl)oxy group, a (5-(methylsulfonyl)pyridin-2-yl)oxy group, a (2-methoxyethyl)carbamoyl group, a (2-hydroxyethyl)carbamoyl group, a (2-hydroxyethyl) (methyl)carbamoyl group, a cyclopropylcarbamoyl group, an ethylcarbamoyl group, a pyrrolidine-1-carbonyl group, a benzylcarbamoyl group, hydroxy carbamoyl group, a 1,1-difluoro-2,3-dihydroxypropoxy group, a 3-((hydroxymethyl)pyridin-2-yl)oxy group, a 1,1-difluoro-2,2-dihydroxypropoxy group, an N-(2-hydroxyethyl)sulfamoyl group, an N-(2-methoxyethyl)sulfamoyl group, an N-(2-hydroxyethyl)-N-methylsulfamoyl group, a pyrrolidin-1-ylsulfonyl group, a morpholinosulfonyl group, a 1,1-difluoro-2-methoxyethoxy group, a 1,1-difluoro-2-methoxy-2-methylpropoxy group, a 1,1-difluoro-2-hydroxybutoxy group, a 1,1-dioxidothio morpholino group, a 1,1-difluoropropoxy group, a 1,1-difluoro-2-hydroxy-3-methylbutoxy group, a benzo[d]oxazol-2-yldifluoromethoxy group, a (1,1-difluoro-3-(pyridin-3-yl)aryl)oxy group, a 1,1-difluoro-2-((hydroxyethyl) (methyl)amino)-2-oxoethoxy group, a 2-(dimethylamino)-1,1-difluoro-2-oxoethoxy group, a 1,1-difluoro-2-morpholino-2-oxoethoxy group, a 2-amino-1,1-difluoro-2-oxoethoxy group, a 1,1-difluoro-2-((2-hydroxyethyl)amino)-2-oxoethoxy group, a 1,1-difluoro-2-(3-hydroxyazetidin-1-yl)-2-oxoethoxy group, or cyclobutyl group, the group represented by $R^2$ is, among the above, a hydrogen atom, a chlorine atom, a bromine atom, a carboxy group, an isopropyl group, a trifluoromethyl group, a hydroxymethyl group, a methoxymethyl group, a 2-hydroxypropan-2-yl group, a morpholinomethyl group, a (dimethylamino)methyl group, a 2,2,2-trifluoro-1-hydroxyethyl group, a 2,2,2-trifluoro-1-methoxyethyl group, a 1,1,1-trifluoro-2-hydroxypropan-2-yl group, a 2,2-difluoro-1-hydroxyethyl group, a 2,2-difluoro-1-methoxyethyl group, a 1,1-difluoro-2-hydroxypropan-2-yl group, a 1,1,1-trifluoro-2-methoxypropan-2-yl group, a 1-hydroxyethyl group, a 1-hydroxypropyl group, a 1-hydroxy-2-methylpropyl group, a 1-methoxyethyl group, a 2-methoxypropan-2-yl group, a 1-acetoxy-2,2,2-trifluoroethyl group, a 2,2,2-trifluoro-1-(2,2,2-trifluoroethoxy)ethyl group, a 2,2,2-trifluoro-1-(2-methoxyethoxy)ethyl group, a 1-ethoxy-2,2,2-trifluoroethyl group, a 2,2,2-trifluoro-1-(2-hydroxyethoxy)ethyl group, a 2,2,2-trifluoro-1,1-dihydroxyethyl group, a 1-(cyanomethoxy)-2,2,2-trifluoroethyl group, a 2,2,2-trifluoro-1-(2-hydroxypropoxy)ethyl group, a 2,2,2-trifluoro-1-(2-hydroxy-2-methylpropoxy)ethyl group, a 2,2,2-trifluoro-1-((1-hydroxycyclopropyl)methoxy) ethyl group, a 2,2,2-trifluoro-1-((1-hydroxypropan-2-yl)oxy)ethyl group, a 2,2,2-trifluoro-1-((1-hydroxy-2-methylpropan-2-yl)oxy)ethyl group, a 1-(1,1-difluoro-2-hydroxypropoxy)-2,2,2-trifluoroethyl group, a 1-(1,1-difluoro-2-hydroxy-2-methylpropoxy)-2,2,2-trifluoroethyl group, a 1-(difluoro(1-hydroxycyclopropyl)methoxy)-2,2,2-trifluoroethyl group, a 1-(carboxymethoxy)-2,2,2-trifluoroethyl group, a 1-(2-amino-2-oxoethoxy)-2,2,2-trifluoroethyl group, a 2,2,2-trifluoro-1-((methylsulfonyl)methoxy) ethyl group, a 2,2,2-trifluoro-1-(sulfamoylmethoxy) ethyl group, a 1-((2H-tetrazol-5-yl)methoxy)-2,2,2-trifluoroethyl group, a 1-((2H-tetrazol-5-yl)methoxy)-2,2-difluoroethyl group, a 1-hydroxy-3-(methylsulfonyl) propyl group, a 3-(ethylsulfonyl)-1-hydroxypropyl group, a 1-hydroxy-3-(isopropylsulfonyl)propyl group, a 2,2,2-trifluoro-1-(2-morpholino-2-oxoethoxy)ethyl group, a 1-carboxy-2,2-difluoro-1-hydroxyethyl group, a 2,2-difluoro-1-hydroxy-1-(2H-tetrazol-5-yl)ethyl group, a 1,3-dihydroxypropyl group, a 1-hydroxy-3-methoxypropyl group, a 4,4,4-trifluoro-1,3-dihydroxybutyl group, a 1,3-dihydroxybutyl group, a 1,3-dihydroxy-3-methylbutyl group, a carboxy(hydroxy)methyl group, a hydroxy (2H-tetrazol-5-yl)methyl group, a hydroxy (3-hydroxycyclobutyl)methyl group, a 1-hydroxy-2-morpholinoethyl group, a 3-amino-1-hydroxy-3-oxopropyl group, a 1-hydroxy-2-(methylsulfonamide)ethyl group, a 2-cyanoethyl group, a 1,2-dihydroxyethyl group, a 3,3,3-trifluoro-1,2-dihydroxypropyl group, a 1-hydroxycyclopropyl group, 1-methoxycyclopropyl group, a 3,3,3-trifluoro-1-hydroxy-2-oxopropyl group, a 3,3,3-trifluoro-1-hydroxypropyl group, a 3,3,3-trifluoro-2-hydroxypropyl group, a 3,3,3-trifluoro-2-oxopropyl group, a 1-hydroxy-3-oxobutyl group, an acetamide group, an N-methylacetamide group, a methoxy group, an isopropoxy group, a trifluoromethoxy group, a 2,2,2-trifluoroethoxy group, a cyanomethoxy group, a carboxymethoxy group, a 2-hydroxyethoxy group, a 2-methoxyethoxy group, a 2-hydroxypropoxy group, a (1-hydroxycyclopropyl)methoxy group, a 1,1-difluoro-2-hydroxy-2-methylpropoxy group, a difluoro(1-hydroxycyclopropyl)methoxy group, a 1,1-difluoro-2-hydroxyethoxy group, a 3,3,3-trifluoro-2-hydroxypropoxy group, a 2,2-difluoro-2-hydroxyethoxy group, a 2-(trifluoromethoxy)ethoxy group, a 1,1-difluoro-2-hydroxypropoxy group, a (1,1,1-trifluoro-3-hydroxybutan-2-yl)oxy group, an oxetan-3-ylmethoxy group, a 3-hydroxy-2-(hydroxymethyl) propoxy group, an allyloxy group, a cyclobutoxy group, a (methylsulfonyl)methoxy group, a (ethylsulfonyl)methoxy group, a (isopropylsulfonyl)methoxy group, a (2H-tetrazol-5-yl)methoxy group, a 2-amino-2-oxoethoxy group, a carboxydifluoromethoxy group, a 2-carboxyethoxy group, a 2-cyanoethoxy group, a 2-(methylsulfonyl)ethoxy group, a 2-morpholinoethoxy group, a 3-hydroxycyclobutoxy group, a 3-cyanocyclobutoxy group, a 3-carboxycyclobutoxy group, a 3-(methylsulfonyl)cyclobutoxy group, a 3-(2H-tetrazol-5-yl)cyclobutoxy group, a (4-hydroxycyclohexyl) oxy group, a 2-hydroxy-3-methoxypropoxy group, a benzyloxy group, a methylthio group, a methylsulfonyl group, a methylsulfinyl group, a methylsulfamoyl group, a dimethylsulfamoyl group, a sulfamoyl group, an acetyl group, a 1-(methoxyimino)ethyl group, a carbamoyl group, a dimethylcarbamoyl group, a morpholine-4-carbonyl group, a piperidine-1-carbonyl group, an azetidine-1-carbonyl group, a benzylcarbamoyl group, a methylcarbamoyl group, a 3-hydroxy-3-(trifluoromethyl)azetidine-1-carbonyl group, a methoxycarbonyl group, an ethoxycarbonyl group, a (5-(trifluoromethyl)pyridin-2-yl)oxy group, or a (5-(hydroxymethyl)pyridin-2-yl)oxy group, and the group represented by $R^4$ is, among the above, a thiazol-2-yl group, a thiazol-4-yl group, a pyridin-2-yl group, an oxazol-2-yl group, a 1H-pyrazol-1-yl group, a 4-methylthiazol-2-yl group, a 5-fluoropyridin-2-yl group, a 2H-1,2,3-triazol-2-yl group, a 1,2,4-thiadiazol-5-yl group, a 1-methyl-1H-pyrazol-3-yl group, a pyrimidin-2-yl group, an isothiazol-3-yl group, a 3-methyl-1,2,4-thiadiazol-5-yl group, or a 5-chloropyridin-2-yl group.

Compound (1h)

A compound in which, in the general formula (1), the group represented by $R^1$ is, among the above, a hydrogen atom, a chlorine atom, a cyano group, a carboxy group, a methyl group, a trifluoromethyl group, a hydroxymethyl group, a 2-hydroxypropan-2-yl group, a 2,2,2-trifluoro-1-hydroxyethyl group, a 2,2,2-trifluoro-1-methoxyethyl group, a 1,1,1-trifluoro-2-hydroxypropan-2-yl group, a 2,2-difluoro-1-hydroxyethyl group, a 2,2-difluoro-1-methoxyethyl group, a 1,1-difluoro-2-hydroxypropan-2-yl group, a 1,1,1-trifluoro-2-methoxypropan-2-yl group, a 1-hydroxyethyl group, a 1-methoxyethyl group, a 2-methoxypropan-2-yl group, a 2,2,2-trifluoro-1-(2,2,2-trifluoroethoxy)ethyl group, a 2,2,2-trifluoro-1-(2-methoxyethoxy)ethyl group, a 1-ethoxy-2,2,2-trifluoroethyl group, a 2,2,2-trifluoro-1-(2-hydroxyethoxy)ethyl group, a 2,2,2-trifluoro-1,1-dihydroxyethyl group, a 1-(cyanomethoxy)-2,2,2-trifluoroethyl group, a 2,2,2-trifluoro-1-(2-hydroxypropoxy)ethyl group, a 2,2,2-trifluoro-1-(2-hydroxy-2-methylpropoxy)ethyl group, a 2,2,2-trifluoro-1-((1-hydroxycyclopropyl)methoxy)ethyl group, a 2,2,2-trifluoro-1-((1-hydroxypropan-2-yl)oxy)ethyl group, a 2,2,2-trifluoro-1-((1-hydroxy-2-methylpropan-2-yl)oxy)ethyl group, a 1-(1,1-difluoro-2-hydroxypropoxy)-2,2,2-trifluoroethyl group, a 1-(1,1-difluoro-2-hydroxy-2-methylpropoxy)-2,2,2-trifluoroethyl group, a 1-(difluoro(1-hydroxycyclopropyl)methoxy)-2,2,2-trifluoroethyl group, a 1-(carboxymethoxy)-2,2,2-trifluoroethyl group, a 1-(2-amino-2-oxoethoxy)-2,2,2-trifluoroethyl group, a 2,2,2-trifluoro-1-((methylsulfonyl)methoxy)ethyl group, a 2,2,2-trifluoro-1-(sulfamoylmethoxy)ethyl group, a 1-((2H-tetrazol-5-yl)methoxy)-2,2,2-trifluoroethyl group, a 1-((2H-tetrazol-5-yl)methoxy)-2,2-difluoroethyl group, a 1-hydroxy-3-(methylsulfonyl)propyl group, a 3-(ethylsulfonyl)-1-hydroxypropyl group, a 1-hydroxy-3-(isopropylsulfonyl)propyl group, a 2,2,2-trifluoro-1-(2-morpholino-2-oxoethoxy)ethyl group, a 1-carboxy-2,2-difluoro-1-hydroxyethyl group, a 2,2-difluoro-1-hydroxy-1-(2H-tetrazol-5-yl)ethyl group, a phenyl group, a thiazol-2-yl group, an acetamide group, a methoxy group, a trifluoromethoxy group, a cyanomethoxy group, a carboxymethoxy group, a 2-hydroxyethoxy group, a 2-methoxyethoxy group, a 2-hydroxypropoxy group, a 2-hydroxy-2-methylpropoxy group, a (1-hydroxycyclopropyl)methoxy group, a 1,1-difluoro-2-hydroxy-2-methylpropoxy group, a difluoro(1-hydroxycyclopropyl)methoxy group, a 1,1-difluoro-2-hydroxyethoxy group, a 3,3,3-trifluoro-2-hydroxypropoxy group, a 2,2-difluoro-2-hydroxyethoxy group, a 2-(trifluoromethoxy)ethoxy group, a 1,1-difluoro-2-hydroxypropoxy group, a (1,1,1-trifluoro-3-hydroxybutan-2-yl)oxy group, a cyclobutoxy group, a (methylsulfonyl)methoxy group, a (ethylsulfonyl)methoxy group, a (isopropylsulfonyl)methoxy group, a (2H-tetrazol-5-yl)methoxy group, a 2-amino-2-oxoethoxy group, a carboxydifluoromethoxy group, a 2-carboxyethoxy group, a 2-cyanoethoxy group, a 2-(methylsulfonyl)ethoxy group, a 2-morpholinoethoxy group, a 3-hydroxycyclobutoxy group, a 3-cyanocyclobutoxy group, a 3-carboxycyclobutoxy group, a 3-(methylsulfonyl)cyclobutoxy group, a 3-(2H-tetrazol-5-yl)cyclobutoxy group, a (4-hydroxycyclohexyl)oxy group, a 2-hydroxy-3-methoxypropoxy group, a benzyloxy group, an acetyl group, a carbamoyl group, a dimethylcarbamoyl group, a morpholine-4-carbonyl group, a piperidine-1-carbonyl group, a methoxycarbonyl group, an ethoxycarbonyl group, a (tetrahydro-2H-pyran-4-yl)oxy group, a 1-(1,1-difluoro-2-hydroxyethoxy)-2,2,2-trifluoroethyl group, a tetrahydro-2H-pyran-3-yl)oxy group, a difluoromethoxy group, a 3-(2-hydroxypropan-2-yl)cyclobutoxy group, a (1-hydroxy-2-methylpropan-2-yl)oxy group, a 2,2,2-trifluoro-1-((3-hydroxy-2,3-dimethylbutan-2-yl)oxy)ethyl group, a 2,2,2-trifluoro-1-(2-methoxy-2-methylpropoxy)ethyl group, a 2,2,2-trifluoro-1-((1-methoxycyclopropyl)methoxy)ethyl group, a 1,1-difluoro-3-hydroxy-3-methylbutoxy group, a (1,1-dioxidotetrahydro-2H-thiopyran-4-yl)oxy) group, an oxetan-3-yloxy group, a 1,1-difluoro-2,3-dihydroxy-2-methylpropoxy group, a (trifluoromethyl)sulfonyl group, a (5-(trifluoromethyl)pyridin-2-yl)oxy group, a pyridin-2-yloxy group, a pyrimidin-2-yloxy group, a pyrazin-2-yloxy group, a (6-methyl-4-(trifluoromethyl)pyridazin-3-yl)oxy group, a (5-(hydroxymethyl)pyridin-2-yl)oxy group, a (5-(hydroxymethyl)-3-(trifluoromethyl)pyridin-2-yl)oxy group, a (5-(trifluoromethoxy)pyridin-2-yl)oxy group, a methylsulfonyl group, a cyclopropyl group, a methylthio group, a methylsulfinyl group, a (2-hydroxyethyl)thio group, a (2-hydroxyethyl)sulfinyl group, a (2-hydroxyethyl)sulfonyl group, a (1,1-difluoroallyl)oxy group, a (5-(methylsulfonyl)pyridin-2-yl)oxy group, a (2-methoxyethyl)carbamoyl group, a (2-hydroxyethyl)carbamoyl group, a (2-hydroxyethyl) (methyl)carbamoyl group, a cyclopropylcarbamoyl group, an ethylcarbamoyl group, a pyrrolidine-1-carbonyl group, a benzylcarbamoyl group, hydroxy carbamoyl group, a 1,1-difluoro-2,3-dihydroxypropoxy group, a 3-((hydroxymethyl)pyridin-2-yl)oxy group, a 1,1-difluoro-2,2-dihydroxypropoxy group, an N-(2-hydroxyethyl)sulfamoyl group, an N-(2-methoxyethyl)sulfamoyl group, an N-(2-hydroxyethyl)-N-methylsulfamoyl group, a pyrrolidin-1-ylsulfonyl group, a morpholinosulfonyl group, a 1,1-difluoro-2-methoxyethoxy group, a 1,1-difluoro-2-methoxy-2-methylpropoxy group, a 1,1-difluoro-2-hydroxybutoxy group, a 1,1-dioxidothio morpholino group, a 1,1-difluoropropoxy group, a 1,1-difluoro-2-hydroxy-3-methylbutoxy group, a benzo[d]oxazol-2-yldifluoromethoxy group, a (1,1-difluoro-3-(pyridin-3-yl)aryl)oxy group, a 1,1-difluoro-2-((hydroxyethyl) (methyl)amino)-2-oxoethoxy group, a 2-(dimethylamino)-1,1-difluoro-2-oxoethoxy group, a 1,1-difluoro-2-morpholino-2-oxoethoxy group, a 2-amino-1,1-difluoro-2-oxoethoxy group, a 1,1-difluoro-2-((2-hydroxyethyl)amino)-2-oxoethoxy group, a 1,1-difluoro-2-(3-hydroxyazetidin-1-yl)-2-oxoethoxy group, or cyclobutyl group, the group represented by $R^2$ is, among the above, a hydrogen atom, and the group represented by $R^4$ is, among the above, a thiazol-2-yl group, a thiazol-4-yl group, a pyridin-2-yl group, an oxazol-2-yl group, a 1H-pyrazol-1-yl group, a 4-methylthiazol-2-yl group, a 5-fluoropyridin-2-yl group, a 2H-1,2,3-triazol-2-yl group, a 1,2,4-thiadiazol-5-yl group, a 1-methyl-1H-pyrazol-3-yl group, a pyrimidin-2-yl group, an isothiazol-3-yl group, a 3-methyl-1,2,4-thiadiazol-5-yl group, or a 5-chloropyridin-2-yl group.

Compound (1i)

A compound in which, in the general formula (1), the group represented by $R^1$ is, among the above, a hydrogen atom, the group represented by $R^2$ is, among the above, a chlorine atom, a carboxy group, an isopropyl group, a trifluoromethyl group, a hydroxymethyl group, a methoxymethyl group, a 2-hydroxypropan-2-yl group, a morpholinomethyl group, a (dimethylamino)methyl group, a 2,2,2-trifluoro-1-hydroxyethyl group, a 2,2,2-trifluoro-1-methoxyethyl group, a 1,1,1-trifluoro-2-hydroxypropan-2-yl group, a 2,2-difluoro-1-hydroxyethyl group, a 2,2-difluoro-1-methoxyethyl group, a 1,1-difluoro-2-hydroxypropan-2-yl group, a 1,1,1-trifluoro-2-methoxypropan-2-yl group, a 1-hydroxyethyl group, a 1-hydroxypropyl group, a 1-hydroxy-2-methylpropyl group, a 1-methoxyethyl group, a 2-methoxypropan-2-yl group, a 1-acetoxy-2,2,2-trifluoroethyl group, a 2,2,2-trifluoro-1-(2,2,2-trifluoroethoxy)ethyl group, a 2,2,2-trifluoro-1-(2-methoxyethoxy)ethyl group, a 1-ethoxy-2,2,2-trifluoroethyl group, a 2,2,2-trifluoro-1-(2-hydroxyethoxy)ethyl group, a 2,2,2-trifluoro-1,1-dihydroxyethyl group, a 1-(cyanomethoxy)-2,2,2-trifluoroethyl group, a 2,2,2-trifluoro-1-(2-hydroxypropoxy)ethyl group, a 2,2,2-trifluoro-1-(2-hydroxy-2-methylpropoxy)ethyl group, a 2,2,2-trifluoro-1-((1-hydroxycyclopropyl)methoxy)ethyl group, a 2,2,2-trifluoro-1-((1-hydroxypropan-2-yl)oxy)ethyl group, a 2,2,2-trifluoro-1-((1-hydroxy-2-methylpropan-2-yl)oxy)ethyl group, a 1-(1,1-difluoro-2-hydroxypropoxy)-2,2,2-trifluoroethyl group, a 1-(1,1-difluoro-2-hydroxy-2-methylpropoxy)-2,2,2-trifluoroethyl group, a 1-(difluoro(1-hydroxycyclopropyl)methoxy)-2,2,2-trifluoroethyl group, a 1-(carboxymethoxy)-2,2,2-trifluoroethyl group, a 1-(2-amino-2-oxoethoxy)-2,2,2-trifluoroethyl group, a 2,2,2-trifluoro-1-((methylsulfonyl)methoxy)ethyl group, a 2,2,2-trifluoro-1-(sulfamoylmethoxy)ethyl group, a 1-((2H-tetrazol-5-yl)methoxy)-2,2,2-trifluoroethyl group, a 1-((2H-tetrazol-5-yl)methoxy)-2,2-difluoroethyl group, a 1-hydroxy-3-(methylsulfonyl)propyl group, a 3-(ethylsulfonyl)-1-hydroxypropyl group, a 1-hydroxy-3-(isopropylsulfonyl)propyl group, a 2,2,2-trifluoro-1-(2-morpholino-2-oxoethoxy)ethyl group, a 1-carboxy-2,2-difluoro-1-hydroxyethyl group, a 2,2-difluoro-1-hydroxy-1-(2H-tetrazol-5-yl)ethyl group, a 1,3-dihydroxypropyl group, a 1-hydroxy-3-methoxypropyl group, a 4,4,4-trifluoro-1,3-dihydroxybutyl group, a 1,3-dihydroxybutyl group, a 1,3-dihydroxy-3-methylbutyl group, a carboxy(hydroxy)methyl group, a hydroxy (2H-tetrazol-5-yl)methyl group, a hydroxy (3-hydroxycyclobutyl)methyl group, a 1-hydroxy-2-morpholinoethyl group, a 3-amino-1-hydroxy-3-oxopropyl group, a 1-hydroxy-2-(methylsulfonamide)ethyl group, a 2-cyanoethyl group, a 1,2-dihydroxyethyl group, a 3,3,3-trifluoro-1,2-dihydroxypropyl group, a 1-hydroxycyclopropyl group, a 1-methoxycyclopropyl group, a 3,3,3-trifluoro-1-hydroxy-2-oxopropyl group, a 3,3,3-trifluoro-1-hydroxypropyl group, a 3,3,3-trifluoro-2-hydroxypropyl group, a 3,3,3-trifluoro-2-oxopropyl group, a 1-hydroxy-3-oxobutyl group, an acetamide group, an N-methylacetamide group, a methoxy group, an isopropoxy group, a trifluoromethoxy group, a 2,2,2-trifluoroethoxy group, a cyanomethoxy group, a carboxymethoxy group, a 2-hydroxyethoxy group, a 2-methoxyethoxy group, a 2-hydroxypropoxy group, a (1-hydroxycyclopropyl)methoxy group, a 1,1-difluoro-2-hydroxy-2-methylpropoxy group, a difluoro(1-hydroxycyclopropyl)methoxy group, a 1,1-difluoro-2-hydroxyethoxy group, a 3,3,3-trifluoro-2-hydroxypropoxy group, a 2,2-difluoro-2-hydroxyethoxy group, a 2-(trifluoromethoxy)ethoxy group, a 1,1-difluoro-2-hydroxypropoxy group, a (1,1,1-trifluoro-3-hydroxybutan-2-yl)oxy group, an oxetan-3-ylmethoxy group, a 3-hydroxy-2-(hydroxymethyl)propoxy group, an allyloxy group, a cyclobutoxy group, a (methylsulfonyl)methoxy group, a (ethylsulfonyl)methoxy group, a (isopropylsulfonyl)methoxy group, a (2H-tetrazol-5-yl)methoxy group, a 2-amino-2-oxoethoxy group, a carboxydifluoromethoxy group, a 2-carboxyethoxy group, a 2-cyanoethoxy group, a 2-(methylsulfonyl)ethoxy group, a 2-morpholinoethoxy group, a 3-hydroxycyclobutoxy group, a 3-cyanocyclobutoxy group, a 3-carboxycyclobutoxy group, a 3-(methylsulfonyl)cyclobutoxy group, a 3-(2H-tetrazol-5-yl)cyclobutoxy group, a (4-hydroxycyclohexyl)oxy group, a 2-hydroxy-3-methoxypropoxy group, a benzyloxy group, a methylthio group, a methylsulfonyl group, a methylsulfinyl group, a methylsulfamoyl group, a dimethylsulfamoyl group, a sulfamoyl group, an acetyl group, a 1-(methoxyimino)ethyl group, a carbamoyl group, a dimethylcarbamoyl group, a morpholine-4-carbonyl group, a piperidine-1-carbonyl group, an azetidine-1-carbonyl group, a benzylcarbamoyl group, a methylcarbamoyl group, a 3-hydroxy-3-(trifluoromethyl)azetidine-1-carbonyl group, a methoxycarbonyl group, an ethoxycarbonyl group, a (5-(trifluoromethyl)pyridin-2-yl)oxy group, or a (5-(hydroxymethyl)pyridin-2-yl)oxy group, and the group represented by $R^4$ is, among the above, a thiazol-2-yl group or a 1H-pyrazol-1-yl group.

Compound (1j)

A compound represented by the following general formula (11).

[Chem. 4]

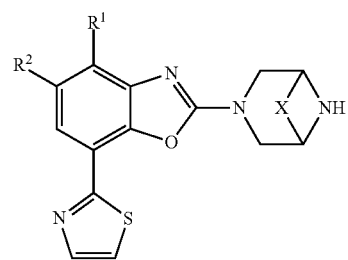

(11)

[in the formula (11), among the above, the group represented by R¹ is an optionally substituted $C_{1-6}$ alkyl group, or an optionally substituted $C_{1-6}$ alkyloxy group, among the above, the group represented by R² is a hydrogen atom, a halogen atom, an optionally substituted $C_{1-6}$ alkyl group, or an optionally substituted $C_{1-6}$ alkylcarbonyl group, and among the above, the group represented by X is a group represented by the following formula: —CH₂—, —CH₂—CH₂—, —CH₂—CH₂—CH₂—, or —CH₂—O—CH₂—].

In the general formula (11), when each group is substituted, the substituent is preferably a halogen atom (more preferably a fluorine atom or a chlorine atom), a hydroxyl group, and a $C_{1-6}$ alkyloxy group (more preferably a methoxy group), and one of these may be used alone or in combination of two or more kinds.

Examples of a further specific embodiment of the compound according to the present invention or the pharmacologically acceptable salt thereof include an embodiment in which the compound represented by the general formula (1) is the following compounds.

2-(3,8-diazabicyclo[3.2.1]octan-3-yl)-5-chloro-7-(thiazol-2-yl)-4-(trifluoromethoxy)benzo[d]oxazole,
2-(3,9-diazabicyclo[3.3.1]nonan-3-yl)-5-chloro-7-(thiazol-2-yl)-4-(trifluoromethoxy)benzo[d]oxazole,
2-(3,6-diazabicyclo[3.1.1]heptan-3-yl)-5-chloro-7-(thiazol-2-yl)-4-(trifluoromethoxy)benzo[d]oxazole,
7-(5-chloro-7-(thiazol-2-yl)-4-(trifluoromethoxy)benzo[d]oxazol-2-yl)-3-oxa-7,9-diazabicyclo[3.3.1]nonane,
2-(3,8-diazabicyclo[3.2.1]octan-3-yl)-5-chloro-7-(1H-pyrazol-1-yl)-4-(trifluoromethoxy)benzo[d]oxazole,
2-(3,8-diazabicyclo[3.2.1]octan-3-yl)-5-chloro-7-(furan-2-yl)-4-(trifluoromethoxy)benzo[d]oxazole,
2-(3,8-diazabicyclo[3.2.1]octan-3-yl)-5-chloro-7-(pyridin-2-yl)-4-(trifluoromethoxy)benzo[d]oxazole,
2-(3,8-diazabicyclo[3.2.1]octan-3-yl)-5-chloro-7-(thiazol-4-yl)-4-(trifluoromethoxy)benzo[d]oxazole,
2-(3,8-diazabicyclo[3.2.1]octan-3-yl)-5-chloro-7-(oxazol-2-yl)-4-(trifluoromethoxy)benzo[d]oxazole,
2-(3,8-diazabicyclo[3.2.1]octan-3-yl)-5-chloro-7-(5-fluoropyridin-2-yl)-4-(trifluoromethoxy)benzo[d]oxazole,
2-(3,8-diazabicyclo[3.2.1]octan-3-yl)-5-chloro-7-(pyridin-2-yl)-4-(trifluoromethyl)benzo[d]oxazole,
2-(3,9-diazabicyclo[3.3.1]nonan-3-yl)-5-chloro-7-(pyridin-2-yl)-4-(trifluoromethyl)benzo[d]oxazole,
2-(3,6-diazabicyclo[3.1.1]heptan-3-yl)-5-chloro-7-(pyridin-2-yl)-4-(trifluoromethyl)benzo[d]oxazole,
7-(5-chloro-7-(pyridin-2-yl)-4-(trifluoromethyl)benzo[d]oxazol-2-yl)-3-oxa-7,9-diazabicyclo[3.3.1]nonane,
2-(3,8-diazabicyclo[3.2.1]octan-3-yl)-5-chloro-7-(1H-pyrazol-1-yl)-4-(trifluoromethyl)benzo[d]oxazole,
2-(3,9-diazabicyclo[3.3.1]nonan-3-yl)-5-chloro-7-(1H-pyrazol-1-yl)-4-(trifluoromethyl)benzo[d]oxazole,
2-(3,6-diazabicyclo[3.1.1]heptan-3-yl)-5-chloro-7-(1H-pyrazol-1-yl)-4-(trifluoromethyl)benzo[d]oxazole,
7-(5-chloro-7-(1H-pyrazol-1-yl)-4-(trifluoromethyl)benzo[d]oxazol-2-yl)-3-oxa-7,9-diazabicyclo[3.3.1]nonane,
7-(5-chloro-7-(thiazol-2-yl)-4-(trifluoromethyl)benzo[d]oxazol-2-yl)-3-oxa-7,9-diazabicyclo[3.3.1]nonane,
2-(3,8-diazabicyclo[3.2.1]octan-3-yl)-5-chloro-7-(thiazol-2-yl)-4-(trifluoromethyl)benzo[d]oxazole,
2-(3,8-diazabicyclo[3.2.1]octan-3-yl)-5-isopropyl-7-(thiazol-2-yl)benzo[d]oxazole,
2-(3,6-diazabicyclo[3.1.1]heptan-3-yl)-5-isopropyl-7-(thiazol-2-yl)benzo[d]oxazole,
7-(5-isopropyl-7-(thiazol-2-yl)benzo[d]oxazol-2-yl)-3-oxa-7,9-diazabicyclo[3.3.1]nonane,
2-(3,9-diazabicyclo[3.3.1]nonan-3-yl)-5-isopropyl-7-(thiazol-2-yl)benzo[d]oxazole,
2-(3,8-diazabicyclo[3.2.1]octan-3-yl)-4-methyl-7-(thiazol-2-yl)benzo[d]oxazole,
2-(3,6-diazabicyclo[3.1.1]heptan-3-yl)-4-methyl-7-(thiazol-2-yl)benzo[d]oxazole,
2-(3,9-diazabicyclo[3.3.1]nonan-3-yl)-4-methyl-7-(thiazol-2-yl)benzo[d]oxazole,
2-(3,8-diazabicyclo[3.2.1]octan-3-yl)-7-(thiazol-2-yl)-4-(trifluoromethoxy)benzo[d]oxazole,
2-(3,6-diazabicyclo[3.1.1]heptan-3-yl)-7-(thiazol-2-yl)-4-(trifluoromethoxy)benzo[d]oxazole,
2-(3,9-diazabicyclo[3.3.1]nonan-3-yl)-7-(thiazol-2-yl)-4-(trifluoromethoxy)benzo[d]oxazole,
2-(3,8-diazabicyclo[3.2.1]octan-3-yl)-7-(thiazol-2-yl)-4-(trifluoromethyl)benzo[d]oxazole,
2-(3,6-diazabicyclo[3.1.1]heptan-3-yl)-7-(thiazol-2-yl)-4-(trifluoromethyl)benzo[d]oxazole,
2-(3,9-diazabicyclo[3.3.1]nonan-3-yl)-7-(thiazol-2-yl)-4-(trifluoromethyl)benzo[d]oxazole,
N-(2-(3,9-diazabicyclo[3.3.1]nonan-3-yl)-7-(thiazol-2-yl)benzo[d]oxazol-4-yl)acetamide,
N-(2-(3,6-diazabicyclo[3.1.1]heptan-3-yl)-7-(thiazol-2-yl)benzo[d]oxazol-4-yl)acetamide,
2-(3,8-diazabicyclo[3.2.1]octan-3-yl)-4-chloro-7-(thiazol-2-yl)benzo[d]oxazole,
2-(3,6-diazabicyclo[3.1.1]heptan-3-yl)-4-chloro-7-(thiazol-2-yl)benzo[d]oxazole,
2-(3,9-diazabicyclo[3.3.1]nonan-3-yl)-4-chloro-7-(thiazol-2-yl)benzo[d]oxazole,
2-(3,8-diazabicyclo[3.2.1]octan-3-yl)-5-(methylthio)-7-(thiazol-2-yl)benzo[d]oxazole,
2-(3,6-diazabicyclo[3.1.1]heptan-3-yl)-5-(methylthio)-7-(thiazol-2-yl)benzo[d]oxazole,
2-(3,9-diazabicyclo[3.3.1]nonan-3-yl)-5-(methylthio)-7-(thiazol-2-yl)benzo[d]oxazole,
2-(3,8-diazabicyclo[3.2.1]octan-3-yl)-5-(methylsulfonyl)-7-(thiazol-2-yl)benzo[d]oxazole,
2-(3,6-diazabicyclo[3.1.1]heptan-3-yl)-5-(methylsulfonyl)-7-(thiazol-2-yl)benzo[d]oxazole,
2-(3,9-diazabicyclo[3.3.1]nonan-3-yl)-5-(methylsulfonyl)-7-(thiazol-2-yl)benzo[d]oxazole,
2-(3,8-diazabicyclo[3.2.1]octan-3-yl)-5-(methylsulfinyl)-7-(thiazol-2-yl)benzo[d]oxazole,
2-(3,6-diazabicyclo[3.1.1]heptan-3-yl)-5-(methylsulfinyl)-7-(thiazol-2-yl)benzo[d]oxazole,
2-(3,9-diazabicyclo[3.3.1]nonan-3-yl)-5-(methylsulfinyl)-7-(thiazol-2-yl)benzo[d]oxazole,
N-(2-(3,9-diazabicyclo[3.3.1]nonan-3-yl)-7-(thiazol-2-yl)benzo[d]oxazol-5-yl)acetamide,
N-(2-(3,6-diazabicyclo[3.1.1]heptan-3-yl)-7-(thiazol-2-yl)benzo[d]oxazol-5-yl)acetamide,
N-(2-(3,8-diazabicyclo[3.2.1]octan-3-yl)-7-(thiazol-2-yl)benzo[d]oxazol-5-yl)acetamide,
2-(3,8-diazabicyclo[3.2.1]octan-3-yl)-7-(thiazol-2-yl)-5-(trifluoromethyl)benzo[d]oxazole,
2-(3,6-diazabicyclo[3.1.1]heptan-3-yl)-7-(thiazol-2-yl)-5-(trifluoromethyl)benzo[d]oxazole,
2-(3,9-diazabicyclo[3.3.1]nonan-3-yl)-7-(thiazol-2-yl)-5-(trifluoromethyl)benzo[d]oxazole,
2-(3,8-diazabicyclo[3.2.1]octan-3-yl)-7-(thiazol-2-yl)-5-(trifluoromethoxy)benzo[d]oxazole,
2-(3,9-diazabicyclo[3.3.1]nonan-3-yl)-7-(thiazol-2-yl)-5-(trifluoromethoxy)benzo[d]oxazole, 2-(3,6-diazabicyclo[3.1.1]heptan-3-yl)-7-(thiazol-2-yl)-5-(trifluoromethoxy)benzo[d]oxazole,
2-(3,8-diazabicyclo[3.2.1]octan-3-yl)-7-(thiazol-2-yl)benzo[d]oxazole-5-sulfonamide,
2-(3,6-diazabicyclo[3.1.1]heptan-3-yl)-7-(thiazol-2-yl)benzo[d]oxazole-5-sulfonamide,
2-(3,9-diazabicyclo[3.3.1]nonan-3-yl)-7-(thiazol-2-yl)benzo[d]oxazole-5-sulfonamide,
2-(3,8-diazabicyclo[3.2.1]octan-3-yl)-5-methoxy-7-(thiazol-2-yl)benzo[d]oxazole,
2-(3,6-diazabicyclo[3.1.1]heptan-3-yl)-5-methoxy-7-(thiazol-2-yl)benzo[d]oxazole,
2-(3,9-diazabicyclo[3.3.1]nonan-3-yl)-5-methoxy-7-(thiazol-2-yl)benzo[d]oxazole,
2-(3,8-diazabicyclo[3.2.1]octan-3-yl)-7-(thiazol-2-yl)benzo[d]oxazol-5-ol,
2-(3,6-diazabicyclo[3.1.1]heptan-3-yl)-7-(thiazol-2-yl)benzo[d]oxazol-5-ol,
2-(3,9-diazabicyclo[3.3.1]nonan-3-yl)-7-(thiazol-2-yl)benzo[d]oxazol-5-ol,
2-(3,8-diazabicyclo[3.2.1]octan-3-yl)-7-(thiazol-2-yl)-5-(2,2,2-trifluoroethoxy)benzo[d]oxazole,
2-(3,6-diazabicyclo[3.1.1]heptan-3-yl)-7-(thiazol-2-yl)-5-(2,2,2-trifluoroethoxy)benzo[d]oxazole,
2-(3,8-diazabicyclo[3.2.1]octan-3-yl)-5-isopropoxy-7-(thiazol-2-yl)benzo[d]oxazole,
2-(3,8-diazabicyclo[3.2.1]octan-3-yl)-5-(2-methoxyethoxy)-7-(thiazol-2-yl)benzo[d]oxazole,
2-(3,8-diazabicyclo[3.2.1]octan-3-yl)-5-(oxetan-3-ylmethoxy)-7-(thiazol-2-yl)benzo[d]oxazole,
2-(((2-(3,8-diazabicyclo[3.2.1]octan-3-yl)-7-(thiazol-2-yl)benzo[d]oxazol-5-yl)oxy)methyl)propane-1,3-diol,
5-(allyloxy)-2-(3,8-diazabicyclo[3.2.1]octan-3-yl)-7-(thiazol-2-yl)benzo[d]oxazole,
2-((2-(3,8-diazabicyclo[3.2.1]octan-3-yl)-7-(thiazol-2-yl)benzo[d]oxazol-5-yl)oxy)acetonitrile,
2-((2-(3,8-diazabicyclo[3.2.1]octan-3-yl)-7-(thiazol-2-yl)benzo[d]oxazol-5-yl)oxy)acetic acid,
2-(3,8-diazabicyclo[3.2.1]octan-3-yl)-4-methoxy-7-(thiazol-2-yl)benzo[d]oxazole,
2-(3,6-diazabicyclo[3.1.1]heptan-3-yl)-4-methoxy-7-(thiazol-2-yl)benzo[d]oxazole,
2-(3,9-diazabicyclo[3.3.1]nonan-3-yl)-4-methoxy-7-(thiazol-2-yl)benzo[d]oxazole,
2-(3,8-diazabicyclo[3.2.1]octan-3-yl)-7-(thiazol-2-yl)benzo[d]oxazol-4-ol,
2-(3,6-diazabicyclo[3.1.1]heptan-3-yl)-7-(thiazol-2-yl)benzo[d]oxazol-4-ol,
2-(3,9-diazabicyclo[3.3.1]nonan-3-yl)-7-(thiazol-2-yl)benzo[d]oxazol-4-ol,
2-(3,8-diazabicyclo[3.2.1]octan-3-yl)-4-cyclobutoxy-7-(thiazol-2-yl)benzo[d]oxazole,
2-((2-(3,8-diazabicyclo[3.2.1]octan-3-yl)-7-(thiazol-2-yl)benzo[d]oxazol-4-yl)oxy)acetonitrile,
1-((2-(3,8-diazabicyclo[3.2.1]octan-3-yl)-7-(thiazol-2-yl)benzo[d]oxazol-4-yl)oxy)-3-methoxypropan-2-ol,
2-(3,8-diazabicyclo[3.2.1]octan-3-yl)-4-((tetrahydrofuran-3-yl)oxy)-7-(thiazol-2-yl)benzo[d]oxazole,
2-(3,8-diazabicyclo[3.2.1]octan-3-yl)-4,7-di(thiazol-2-yl)benzo[d]oxazole,
ethyl 2-(3,8-diazabicyclo[3.2.1]octan-3-yl)-7-(thiazol-2-yl)benzo[d]oxazole-5-carboxylate,
ethyl 2-(3,6-diazabicyclo[3.1.1]heptan-3-yl)-7-(thiazol-2-yl)benzo[d]oxazole-5-carboxylate,
ethyl 2-(3-oxa-7,9-diazabicyclo[3.3.1]nonan-7-yl)-7-(thiazol-2-yl)benzo[d]oxazole-5-carboxylate,
ethyl 2-(3,9-diazabicyclo[3.3.1]nonan-3-yl)-7-(thiazol-2-yl)benzo[d]oxazole-5-carboxylate,
ethyl 2-(3,8-diazabicyclo[3.2.1]octan-3-yl)-7-(1H-pyrazol-1-yl)benzo[d]oxazole-5-carboxylate,
ethyl 2-(3,6-diazabicyclo[3.1.1]heptan-3-yl)-7-(1H-pyrazol-1-yl)benzo[d]oxazole-5-carboxylate,
ethyl 2-(3-oxa-7,9-diazabicyclo[3.3.1]nonan-7-yl)-7-(1H-pyrazol-1-yl)benzo[d]oxazole-5-carboxylate,
ethyl 2-(3,9-diazabicyclo[3.3.1]nonan-3-yl)-7-(1H-pyrazol-1-yl)benzo[d]oxazole-5-carboxylate,
2-(2-(3,8-diazabicyclo[3.2.1]octan-3-yl)-7-(thiazol-2-yl)benzo[d]oxazol-5-yl)propan-2-ol,
2-(2-(3,6-diazabicyclo[3.1.1]heptan-3-yl)-7-(thiazol-2-yl)benzo[d]oxazol-5-yl)propan-2-ol,
2-(3,6-diazabicyclo[3.1.1]heptan-3-yl)-5-(2-methoxypropan-2-yl)-7-(thiazol-2-yl)benzo[d]oxazole,
2-(3,8-diazabicyclo[3.2.1]octan-3-yl)-5-(2-methoxypropan-2-yl)-7-(thiazol-2-yl)benzo[d]oxazole,
2-(3,8-diazabicyclo[3.2.1]octan-3-yl)-N,N-dimethyl-7-(thiazol-2-yl)benzo[d]oxazole-5-carboxamide,
(2-(3,8-diazabicyclo[3.2.1]octan-3-yl)-7-(thiazol-2-yl)benzo[d]oxazol-5-yl)(morpholino)methanone,
(2-(3,8-diazabicyclo[3.2.1]octan-3-yl)-7-(thiazol-2-yl)benzo[d]oxazol-5-yl)(piperidin-1-yl)methanone,
(2-(3,8-diazabicyclo[3.2.1]octan-3-yl)-7-(thiazol-2-yl)benzo[d]oxazol-5-yl)(azetidin-1-yl)methanone,
N-benzyl-2-(3,8-diazabicyclo[3.2.1]octan-3-yl)-7-(thiazol-2-yl)benzo[d]oxazole-5-carboxamide,
2-(3,8-diazabicyclo[3.2.1]octan-3-yl)-7-(thiazol-2-yl)benzo[d]oxazole-5-carboxamide,
2-(3,8-diazabicyclo[3.2.1]octan-3-yl)-N-methyl-7-(thiazol-2-yl)benzo[d]oxazole-5-carboxamide,
N-(2-(3,8-diazabicyclo[3.2.1]octan-3-yl)-7-(thiazol-2-yl)benzo[d]oxazol-5-yl)-N-methylacetamide,
2-(3,8-diazabicyclo[3.2.1]octan-3-yl)-5-(morpholinomethyl)-7-(thiazol-2-yl)benzo[d]oxazole,
1-(2-(3,8-diazabicyclo[3.2.1]octan-3-yl)-7-(thiazol-2-yl)benzo[d]oxazol-5-yl)-N,N-dimethylmethanamine,
2-(3,8-diazabicyclo[3.2.1]octan-3-yl)-7-(thiazol-2-yl)-5-(1,1,1-trifluoro-2-methoxypropan-2-yl)benzo[d]oxazole,
2-(3,6-diazabicyclo[3.1.1]heptan-3-yl)-7-(thiazol-2-yl)-5-(1,1,1-trifluoro-2-methoxypropan-2-yl)benzo[d]oxazole,
1-(2-(3,8-diazabicyclo[3.2.1]octan-3-yl)-7-(thiazol-2-yl)benzo[d]oxazol-5-yl)ethan-1-one,
1-(2-(3,6-diazabicyclo[3.1.1]heptan-3-yl)-7-(thiazol-2-yl)benzo[d]oxazol-5-yl)ethan-1-one,
1-(2-(3,8-diazabicyclo[3.2.1]octan-3-yl)-7-(thiazol-2-yl)benzo[d]oxazol-5-yl)-2,2-difluoroethan-1-ol,
2-(3,8-diazabicyclo[3.2.1]octan-3-yl)-5-(2,2-difluoro-1-methoxyethyl)-7-(thiazol-2-yl)benzo[d]oxazole,
1-(2-(3,8-diazabicyclo[3.2.1]octan-3-yl)-7-(thiazol-2-yl)benzo[d]oxazol-5-yl)ethan-1-ol,
1-(2-(3,6-diazabicyclo[3.1.1]heptan-3-yl)-7-(thiazol-2-yl)benzo[d]oxazol-5-yl)ethan-1-ol,
2-(3,8-diazabicyclo[3.2.1]octan-3-yl)-5-(1-methoxyethyl)-7-(thiazol-2-yl)benzo[d]oxazole,
2-(3,6-diazabicyclo[3.1.1]heptan-3-yl)-5-(1-methoxyethyl)-7-(thiazol-2-yl)benzo[d]oxazole,
(2-(3,9-diazabicyclo[3.3.1]nonan-3-yl)-7-(thiazol-2-yl)benzo[d]oxazol-4-yl)methanol,
(2-(3,6-diazabicyclo[3.1.1]hepan-3-yl)-7-(thiazol-2-yl)benzo[d]oxazol-4-yl)methanol,
(2-(3,8-diazabicyclo[3.2.1]octan-3-yl)-7-(thiazol-2-yl)benzo[d]oxazol-4-yl)methanol,
ethyl 2-(3,8-diazabicyclo[3.2.1]octan-3-yl)-7-(thiazol-2-yl)benzo[d]oxazole-4-carboxylate, ethyl 2-(3,6-diazabicyclo[3.1.1]heptan-3-yl)-7-(thiazol-2-yl)benzo[d]oxazole-4-carboxylate,
ethyl 2-(3,9-diazabicyclo[3.3.1]nonan-3-yl)-7-(thiazol-2-yl)benzo[d]oxazole-4-carboxylate,
2-(3,8-diazabicyclo[3.2.1]octan-3-yl)-N,N-dimethyl-7-(thiazol-2-yl)benzo[d]oxazole-4-carboxamide,
(2-(3,8-diazabicyclo[3.2.1]octan-3-yl)-7-(thiazol-2-yl)benzo[d]oxazol-4-yl) (morpholino)methanone,
(2-(3,8-diazabicyclo[3.2.1]octan-3-yl)-7-(thiazol-2-yl)benzo[d]oxazol-4-yl)(piperidin-1-yl)methanone,
1-(2-(3,8-diazabicyclo[3.2.1]octan-3-yl)-7-(thiazol-2-yl)benzo[d]oxazol-4-yl)-2,2,2-trifluoroethan-1-ol,
(R)-1-(2-(3,8-diazabicyclo[3.2.1]octan-3-yl)-7-(thiazol-2-yl)benzo[d]oxazol-4-yl)-2,2,2-trifluoroethan-1-ol,
(S)-1-(2-(3,8-diazabicyclo[3.2.1]octan-3-yl)-7-(thiazol-2-yl)benzo[d]oxazol-4-yl)-2,2,2-trifluoroethan-1-ol,
1-(2-(3,6-diazabicyclo[3.1.1]heptan-3-yl)-7-(thiazol-2-yl)benzo[d]oxazol-4-yl)-2,2,2-trifluoroethan-1-ol,
(R)-1-(2-(3,6-diazabicyclo[3.1.1]heptan-3-yl)-7-(thiazol-2-yl)benzo[d]oxazol-4-yl)-2,2,2-trifluoroethan-1-ol,
(S)-1-(2-(3,6-diazabicyclo[3.1.1]heptan-3-yl)-7-(thiazol-2-yl)benzo[d]oxazol-4-yl)-2,2,2-trifluoroethan-1-ol,
2-(3,6-diazabicyclo[3.1.1]heptan-3-yl)-7-(thiazol-2-yl)-4-(2,2,2-trifluoro-1-methoxyethyl)benzo[d]oxazole,
(R)-2-(3,6-diazabicyclo[3.1.1]heptan-3-yl)-7-(thiazol-2-yl)-4-(2,2,2-trifluoro-1-methoxyethyl)benzo[d]oxazole,
(S)-2-(3,6-diazabicyclo[3.1.1]heptan-3-yl)-7-(thiazol-2-yl)-4-(2,2,2-trifluoro-1-methoxyethyl)benzo[d]oxazole,
1-(2-(3,6-diazabicyclo[3.1.1]heptan-3-yl)-7-(thiazol-2-yl)benzo[d]oxazol-4-yl)-2,2-difluoroethan-1-ol,
2-(2-(3,6-diazabicyclo[3.1.1]heptan-3-yl)-7-(thiazol-2-yl)benzo[d]oxazol-4-yl)-1,1-difluoropropan-2-ol,
(R)-2-(2-(3,6-diazabicyclo[3.1.1]heptan-3-yl)-7-(thiazol-2-yl)benzo[d]oxazol-4-yl)-1,1-difluoropropan-2-ol,
(S)-2-(2-(3,6-diazabicyclo[3.1.1]heptan-3-yl)-7-(thiazol-2-yl)benzo[d]oxazol-4-yl)-1,1-difluoropropan-2-ol,
1-(1-(2-(3,6-diazabicyclo[3.1.1]heptan-3-yl)-7-(thiazol-2-yl)benzo[d]oxazol-4-yl)-2,2-difluoroethoxy)-2-methylpropan-2-ol,
1-(2-(3,8-diazabicyclo[3.2.1]octan-3-yl)-7-(thiazol-2-yl)benzo[d]oxazol-4-yl)-2,2-difluoroethan-1-ol,
2-(2-(3,8-diazabicyclo[3.2.1]octan-3-yl)-7-(thiazol-2-yl)benzo[d]oxazol-4-yl)-1,1-difluoropropan-2-ol,
2-(3,6-diazabicyclo[3.1.1]heptan-3-yl)-4-(2,2-difluoro-1-methoxyethyl)-7-(thiazol-2-yl)benzo[d]oxazole,
2-(3,8-diazabicyclo[3.2.1]octan-3-yl)-4-(2,2-difluoro-1-methoxyethyl)-7-(thiazol-2-yl)benzo[d]oxazole,
1-(2-(3,8-diazabicyclo[3.2.1]octan-3-yl)-7-(thiazol-2-yl)benzo[d]oxazol-4-yl)ethan-1-ol,
1-(2-(3,6-diazabicyclo[3.1.1]heptan-3-yl)-7-(thiazol-2-yl)benzo[d]oxazol-5-yl)-2,2,2-trifluoroethan-1-ol,
1-(2-(3,9-diazabicyclo[3.3.1]nonan-3-yl)-7-(thiazol-2-yl)benzo[d]oxazol-5-yl)-2,2,2-trifluoroethan-1-ol,
1-(2-(3,8-diazabicyclo[3.2.1]octan-3-yl)-7-(thiazol-2-yl)benzo[d]oxazol-5-yl)-2,2,2-trifluoroethan-1-ol,
(R)-1-(2-(3,8-diazabicyclo[3.2.1]octan-3-yl)-7-(thiazol-2-yl)benzo[d]oxazol-5-yl)-2,2,2-trifluoroethan-1-ol,
(S)-1-(2-(3,8-diazabicyclo[3.2.1]octan-3-yl)-7-(thiazol-2-yl)benzo[d]oxazol-5-yl)-2,2,2-trifluoroethan-1-ol,
1-(2-(3,8-diazabicyclo[3.2.1]octan-3-yl)-7-(1H-pyrazol-1-yl)benzo[d]oxazol-5-yl)-2,2,2-trifluoroethan-1-ol,
1-(2-(3,8-diazabicyclo[3.2.1]octan-3-yl)-7-(thiazol-2-yl)benzo[d]oxazol-5-yl)-2,2,2-trifluoroethyl acetate,
2-(3,8-diazabicyclo[3.2.1]octan-3-yl)-7-(thiazol-2-yl)-5-(2,2,2-trifluoro-1-methoxyethyl)benzo[d]oxazole,
(R)-2-(3,8-diazabicyclo[3.2.1]octan-3-yl)-7-(thiazol-2-yl)-5-(2,2,2-trifluoro-1-methoxyethyl)benzo[d]oxazole,
(S)-2-(3,8-diazabicyclo[3.2.1]octan-3-yl)-7-(thiazol-2-yl)-5-(2,2,2-trifluoro-1-methoxyethyl)benzo[d]oxazole,
2-(3,6-diazabicyclo[3.1.1]heptan-3-yl)-7-(thiazol-2-yl)-5-(2,2,2-trifluoro-1-methoxyethyl)benzo[d]oxazole,
2-(3,9-diazabicyclo[3.3.1]nonan-3-yl)-7-(thiazol-2-yl)-5-(2,2,2-trifluoro-1-methoxyethyl)benzo[d]oxazole,
2-(3,8-diazabicyclo[3.2.1]octan-3-yl)-7-(thiazol-2-yl)-5-(2,2,2-trifluoro-1-(2,2,2-trifluoroethoxy)ethyl)benzo[d]oxazole,
2-(3,8-diazabicyclo[3.2.1]octan-3-yl)-7-(thiazol-2-yl)-5-(2,2,2-trifluoro-1-(2-methoxyethoxy)ethyl)benzo[d]oxazole,
2-(3,8-diazabicyclo[3.2.1]octan-3-yl)-5-(1-ethoxy-2,2,2-trifluoroethyl)-7-(thiazol-2-yl)benzo[d]oxazole,
2-(1-(2-(3,8-diazabicyclo[3.2.1]octan-3-yl)-7-(thiazol-2-yl)benzo[d]oxazol-5-yl)-2,2,2-trifluoroethoxy)ethan-1-ol,
2-(3,6-diazabicyclo[3.1.1]heptan-3-yl)-5-(1-ethoxy-2,2,2-trifluoroethyl)-7-(thiazol-2-yl)benzo[d]oxazole,
2-(3,6-diazabicyclo[3.1.1]heptan-3-yl)-7-(thiazol-2-yl)-5-(2,2,2-trifluoro-1-(2,2,2-trifluoroethoxy)ethyl)benzo[d]oxazole,
2-(1-(2-(3,6-diazabicyclo[3.1.1]heptan-3-yl)-7-(thiazol-2-yl)benzo[d]oxazol-5-yl)-2,2,2-trifluoroethoxy)acetonitrile,
2-(1-(2-(3,8-diazabicyclo[3.2.1]octan-3-yl)-7-(thiazol-2-yl)benzo[d]oxazol-5-yl)-2,2,2-trifluoroethoxy)acetonitrile,
2-(3,6-diazabicyclo[3.1.1]heptan-3-yl)-7-(thiazol-2-yl)-5-(2,2,2-trifluoro-1-(2-methoxyethoxy)ethyl)benzo[d]oxazole,
1-(1-(2-(3,8-diazabicyclo[3.2.1]octan-3-yl)-7-(thiazol-2-yl)benzo[d]oxazol-5-yl)-2,2,2-trifluoroethoxy)propan-2-ol,
1-(2-(3,9-diazabicyclo[3.3.1]nonan-3-yl)-7-(thiazol-2-yl)benzo[d]oxazol-5-yl)-2,2,2-trifluoroethane-1,1-diol,
1-(2-(3,8-diazabicyclo[3.2.1]octan-3-yl)-7-(thiazol-2-yl)benzo[d]oxazol-5-yl)-2,2,2-trifluoroethane-1,1-diol,
1-(2-(3,6-diazabicyclo[3.1.1]heptan-3-yl)-7-(thiazol-2-yl)benzo[d]oxazol-5-yl)-2,2,2-trifluoroethane-1,1-diol,
2-(2-(3,8-diazabicyclo[3.2.1]octan-3-yl)-7-(thiazol-2-yl)benzo[d]oxazol-5-yl)-1,1,1-trifluoropropan-2-ol,
2-(2-(3,6-diazabicyclo[3.1.1]heptan-3-yl)-7-(thiazol-2-yl)benzo[d]oxazol-5-yl)-1,1,1-trifluoropropan-2-ol,
2-(2-(3,9-diazabicyclo[3.3.1]nonan-3-yl)-7-(thiazol-2-yl)benzo[d]oxazol-5-yl)-1,1,1-trifluoropropan-2-ol,
2-(2-(3,9-diazabicyclo[3.3.1]nonan-3-yl)-7-(thiazol-2-yl)-5-(1,1,1-trifluoro-2-methoxypropan-2-yl)benzo[d]oxazole,
ethyl 2-(3,8-diazabicyclo[3.2.1]octan-3-yl)-7-(thiazol-2-yl)-4-(trifluoromethyl)benzo[d]oxazole-5-carboxylate,
ethyl 2-(3,9-diazabicyclo[3.3.1]nonan-3-yl)-7-(thiazol-2-yl)-4-(trifluoromethyl)benzo[d]oxazole-5-carboxylate,
ethyl 2-(3,6-diazabicyclo[3.1.1]heptan-3-yl)-7-(thiazol-2-yl)-4-(trifluoromethyl)benzo[d]oxazole-5-carboxylate,
2-(2-(3,9-diazabicyclo[3.3.1]nonan-3-yl)-7-(thiazol-2-yl)-4-(trifluoromethyl)benzo[d]oxazol-5-yl)propan-2-ol,
2-(3,8-diazabicyclo[3.2.1]octan-3-yl)-5-(methoxymethyl)-7-(thiazol-2-yl)-4-(trifluoromethyl)benzo[d]oxazole,
(2-(3,8-diazabicyclo[3.2.1]octan-3-yl)-7-(thiazol-2-yl)-4-(trifluoromethyl)benzo[d]oxazol-5-yl)methanol,
2-(3,8-diazabicyclo[3.2.1]octan-3-yl)-5-(2-methoxypropan-2-yl)-7-(thiazol-2-yl)-4-(trifluoromethyl)benzo[d]oxazole,
2-(3,6-diazabicyclo[3.1.1]heptan-3-yl)-5-(2-methoxypropan-2-yl)-7-(thiazol-2-yl)-4-(trifluoromethyl)benzo[d]oxazole,
2-(2-(3,8-diazabicyclo[3.2.1]octan-3-yl)-7-(thiazol-2-yl)-4-(trifluoromethyl)benzo[d]oxazol-5-yl)propan-2-ol,
2-(2-(3,6-diazabicyclo[3.1.1]heptan-3-yl)-7-(thiazol-2-yl)-4-(trifluoromethyl)benzo[d]oxazol-5-yl)propan-2-ol 1-(2-(3,8-diazabicyclo[3.2.1]octan-3-yl)-7-(thiazol-2-yl)-4-(trifluoromethyl)benzo[d]oxazol-5-yl)ethan-1-one,
1-(2-(3,6-diazabicyclo[3.1.1]heptan-3-yl)-7-(thiazol-2-yl)-4-(trifluoromethyl)benzo[d]oxazol-5-yl)ethan-1-one,
1-(2-(3,8-diazabicyclo[3.2.1]octan-3-yl)-7-(thiazol-2-yl)-4-(trifluoromethyl)benzo[d]oxazol-5-yl)ethan-1-ol,
1-(2-(3,6-diazabicyclo[3.1.1]heptan-3-yl)-7-(thiazol-2-yl)-4-(trifluoromethyl)benzo[d]oxazol-5-yl)ethan-1-ol
1-(2-(3,8-diazabicyclo[3.2.1]octan-3-yl)-7-(thiazol-2-yl)-4-(trifluoromethyl)benzo[d]oxazol-5-yl)-2,2-difluoroethan-1-ol,
2-(3,8-diazabicyclo[3.2.1]octan-3-yl)-5-(1-methoxyethyl)-7-(thiazol-2-yl)-4-(trifluoromethyl)benzo[d]oxazole,
2-(3,6-diazabicyclo[3.1.1]heptan-3-yl)-5-(1-methoxyethyl)-7-(thiazol-2-yl)-4-(trifluoromethyl)benzo[d]oxazole,
ethyl 2-(3,8-diazabicyclo[3.2.1]octan-3-yl)-7-(thiazol-2-yl)-4-(trifluoromethoxy)benzo[d]oxazole-5-carboxylate,
ethyl 2-(3,6-diazabicyclo[3.1.1]heptan-3-yl)-7-(thiazol-2-yl)-4-(trifluoromethoxy)benzo[d]oxazole-5-carboxylate,
ethyl 2-(3,9-diazabicyclo[3.3.1]nonan-3-yl)-7-(thiazol-2-yl)-4-(trifluoromethoxy)benzo[d]oxazole-5-carboxylate,
2-(3,8-diazabicyclo[3.2.1]octan-3-yl)-7-(thiazol-2-yl)-4-(trifluoromethoxy)benzo[d]oxazole-5-carboxylic acid,
2-(3,6-diazabicyclo[3.1.1]heptan-3-yl)-7-(thiazol-2-yl)-4-(trifluoromethoxy)benzo[d]oxazole-5-carboxylic acid,
2-(3,9-diazabicyclo[3.3.1]nonan-3-yl)-7-(thiazol-2-yl)-4-(trifluoromethoxy)benzo[d]oxazole-5-carboxylic acid,
2-(2-(3,8-diazabicyclo[3.2.1]octan-3-yl)-7-(thiazol-2-yl)-4-(trifluoromethoxy)benzo[d]oxazol-5-yl)propan-2-ol,
2-(2-(3,6-diazabicyclo[3.1.1]heptan-3-yl)-7-(thiazol-2-yl)-4-(trifluoromethoxy)benzo[d]oxazol-5-yl)propan-2-ol,
2-(2-(3,9-diazabicyclo[3.3.1]nonan-3-yl)-7-(thiazol-2-yl)-4-(trifluoromethoxy)benzo[d]oxazol-5-yl)propan-2-ol
2-(3,8-diazabicyclo[3.2.1]octan-3-yl)-5-(2-methoxypropan-2-yl)-7-(thiazol-2-yl)-4-(trifluoromethoxy)benzo[d]oxazole,
2-(3,6-diazabicyclo[3.1.1]heptan-3-yl)-5-(2-methoxypropan-2-yl)-7-(thiazol-2-yl)-4-(trifluoromethoxy)benzo[d]oxazole,
2-(3,9-diazabicyclo[3.3.1]nonan-3-yl)-5-(2-methoxypropan-2-yl)-7-(thiazol-2-yl)-4-(trifluoromethoxy)benzo[d]oxazole,
(2-(3,8-diazabicyclo[3.2.1]octan-3-yl)-7-(thiazol-2-yl)-4-(trifluoromethoxy)benzo[d]oxazol-5-yl)(azetidin-1-yl)methanone,
2-(3,8-diazabicyclo[3.2.1]octan-3-yl)-N-(2-hydroxyethyl)-N-methyl-7-(thiazol-2-yl)-4-(trifluoromethoxy)benzo[d]oxazole-5-carboxamide,
(2-(3,8-diazabicyclo[3.2.1]octan-3-yl)-7-(thiazol-2-yl)-4-(trifluoromethoxy)benzo[d]oxazol-5-yl)(3-hydroxy-3-(trifluoromethyl)azetidin-1-yl)methanone,
(2-(3,8-diazabicyclo[3.2.1]octan-3-yl)-7-(thiazol-2-yl)-4-(trifluoromethoxy)benzo[d]oxazol-5-yl)methanol,
1-(2-(3,8-diazabicyclo[3.2.1]octan-3-yl)-7-(thiazol-2-yl)-4-(trifluoromethoxy)benzo[d]oxazol-5-yl)ethan-1-ol,
1-(2-(3,6-diazabicyclo[3.1.1]heptan-3-yl)-7-(thiazol-2-yl)-4-(trifluoromethoxy)benzo[d]oxazol-5-yl)ethan-1-01,
(R)-1-(2-(3,6-diazabicyclo[3.1.1]heptan-3-yl)-7-(thiazol-2-yl)-4-(trifluoromethoxy)benzo[d]oxazol-5-yl)ethan-1-ol,
(S)-1-(2-(3,6-diazabicyclo[3.1.1]heptan-3-yl)-7-(thiazol-2-yl)-4-(trifluoromethoxy)benzo[d]oxazol-5-yl)ethan-1-ol,
1-(2-(3,8-diazabicyclo[3.2.1]octan-3-yl)-7-(thiazol-2-yl)-4-(trifluoromethoxy)benzo[d]oxazol-5-yl)propan-1-ol,
1-(2-(3,8-diazabicyclo[3.2.1]octan-3-yl)-7-(thiazol-2-yl)-4-(trifluoromethoxy)benzo[d]oxazol-5-yl)-2-methylpropan-1-ol,
1-(2-(3,8-diazabicyclo[3.2.1]octan-3-yl)-7-(thiazol-2-yl)-4-(trifluoromethoxy)benzo[d]oxazol-5-yl)-2,2-difluoroethan-1-ol,
(R)-1-(2-(3,8-diazabicyclo[3.2.1]octan-3-yl)-7-(thiazol-2-yl)-4-(trifluoromethoxy)benzo[d]oxazol-5-yl)-2,2-difluoroethan-1-ol,
(S)-1-(2-(3,8-diazabicyclo[3.2.1]octan-3-yl)-7-(thiazol-2-yl)-4-(trifluoromethoxy)benzo[d]oxazol-5-yl)-2,2-difluoroethan-1-ol,
1-(2-(3,6-diazabicyclo[3.1.1]heptan-3-yl)-7-(thiazol-2-yl)-4-(trifluoromethoxy)benzo[d]oxazol-5-yl)-2,2-difluoroethan-1-ol,
(R)-1-(2-(3,6-diazabicyclo[3.1.1]heptan-3-yl)-7-(thiazol-2-yl)-4-(trifluoromethoxy)benzo[d]oxazol-5-yl)-2,2-difluoroethan-1-ol,
(S)-1-(2-(3,6-diazabicyclo[3.1.1]heptan-3-yl)-7-(thiazol-2-yl)-4-(trifluoromethoxy)benzo[d]oxazol-5-yl)-2,2-difluoroethan-1-ol,
2-(3,6-diazabicyclo[3.1.1]heptan-3-yl)-5-(2,2-difluoro-1-methoxyethyl)-7-(thiazol-2-yl)-4-(trifluoromethoxy)benzo[d]oxazole,
2-(3,8-diazabicyclo[3.2.1]octan-3-yl)-5-(2,2-difluoro-1-methoxyethyl)-7-(thiazol-2-yl)-4-(trifluoromethoxy)benzo[d]oxazole,
2-(3,8-diazabicyclo[3.2.1]octan-3-yl)-5-(1-methoxyethyl)-7-(thiazol-2-yl)-4-(trifluoromethoxy)benzo[d]oxazole,
2-(3,6-diazabicyclo[3.1.1]heptan-3-yl)-5-(1-methoxyethyl)-7-(thiazol-2-yl)-4-(trifluoromethoxy)benzo[d]oxazole,
1-(2-(3,6-diazabicyclo[3.1.1]heptan-3-yl)-7-(thiazol-2-yl)-4-(trifluoromethoxy)benzo[d]oxazol-5-yl)ethan-1-one,
1-(2-(3,8-diazabicyclo[3.2.1]octan-3-yl)-7-(thiazol-2-yl)-4-(trifluoromethoxy)benzo[d]oxazol-5-yl)ethan-1-one,
2-(3,6-diazabicyclo[3.1.1]heptan-3-yl)-7-(thiazol-2-yl)-5-(1,1,1-trifluoro-2-methoxypropan-2-yl)-4-(trifluoromethoxy)benzo[d]oxazole,
2-(3,8-diazabicyclo[3.2.1]octan-3-yl)-7-(thiazol-2-yl)-5-(1,1,1-trifluoro-2-methoxypropan-2-yl)-4-(trifluoromethoxy)benzo[d]oxazole,
2-(2-(3,6-diazabicyclo[3.1.1]heptan-3-yl)-7-(thiazol-2-yl)-4-(trifluoromethoxy)benzo[d]oxazol-5-yl)-1,1,1-trifluoropropan-2-ol,
2-(2-(3,8-diazabicyclo[3.2.1]octan-3-yl)-7-(thiazol-2-yl)-4-(trifluoromethoxy)benzo[d]oxazol-5-yl)-1,1,1-trifluoropropan-2-ol,
(E)-1-(2-(3,8-diazabicyclo[3.2.1]octan-3-yl)-7-(thiazol-2-yl)-4-(trifluoromethoxy)benzo[d]oxazol-5-yl)ethan-1-one O-methyloxime,
(Z)-1-(2-(3,8-diazabicyclo[3.2.1]octan-3-yl)-7-(thiazol-2-yl)-4-(trifluoromethoxy)benzo[d]oxazol-5-yl)ethan-1-one O-methyloxime,
(E)-1-(2-(3,6-diazabicyclo[3.1.1]heptan-3-yl)-7-(thiazol-2-yl)-4-(trifluoromethoxy)benzo[d]oxazol-5-yl)ethan-1-one O-methyloxime,
(Z)-1-(2-(3,6-diazabicyclo[3.1.1]heptan-3-yl)-7-(thiazol-2-yl)-4-(trifluoromethoxy)benzo[d]oxazol-5-yl)ethan-1-one O-methyloxime,
2-(3,8-diazabicyclo[3.2.1]octan-3-yl)-4-(1-ethoxy-2,2,2-trifluoroethyl)-7-(thiazol-2-yl)benzo[d]oxazole,
2-(3,8-diazabicyclo[3.2.1]octan-3-yl)-7-(thiazol-2-yl)-4-(2,2,2-trifluoro-1-(2,2,2-trifluoroethoxy)ethyl)benzo[d]oxazole,
2-(3,8-diazabicyclo[3.2.1]octan-3-yl)-7-(thiazol-2-yl)-4-(2,2,2-trifluoro-1-methoxyethyl)benzo[d]oxazole,
2-(3,6-diazabicyclo[3.1.1]heptan-3-yl)-7-(thiazol-2-yl)-4-(2,2,2-trifluoro-1-(2,2,2-trifluoroethoxy)ethyl)benzo[d]oxazole, 2-(3,6-diazabicyclo[3.1.1]heptan-3-yl)-4-(1-ethoxy-2,2,2-trifluoroethyl)-7-(thiazol-2-yl)benzo[d]oxazole,
2-(1-(2-(3,8-diazabicyclo[3.2.1]octan-3-yl)-7-(thiazol-2-yl)benzo[d]oxazol-4-yl)-2,2,2-trifluoroethoxy)ethan-1-ol,
2-(1-(2-(3,6-diazabicyclo[3.1.1]heptan-3-yl)-7-(thiazol-2-yl)benzo[d]oxazol-4-yl)-2,2,2-trifluoroethoxy)acetonitrile,
2-(1-(2-(3,6-diazabicyclo[3.1.1]heptan-3-yl)-7-(thiazol-2-yl)benzo[d]oxazol-4-yl)-2,2,2-trifluoroethoxy)ethan-1-ol,
2-(1-(2-(3,8-diazabicyclo[3.2.1]octan-3-yl)-7-(thiazol-2-yl)benzo[d]oxazol-4-yl)-2,2,2-trifluoroethoxy)acetonitrile,
2-(3,6-diazabicyclo[3.1.1]heptan-3-yl)-7-(thiazol-2-yl)-4-(2,2,2-trifluoro-1-(2-methoxyethoxy)ethyl)benzo[d]oxazole,
4-(1-((1H-tetrazol-5-yl)methoxy)-2,2,2-trifluoroethyl)-2-(3,8-diazabicyclo[3.2.1]octan-3-yl)-7-(thiazol-2-yl)benzo[d]oxazole,
4-(1-((1H-tetrazol-5-yl)methoxy)-2,2,2-trifluoroethyl)-2-(3,6-diazabicyclo[3.1.1]heptan-3-yl)-7-(thiazol-2-yl)benzo[d]oxazole,
1-((1-(2-(3,6-diazabicyclo[3.1.1]heptan-3-yl)-7-(thiazol-2-yl)benzo[d]oxazol-4-yl)-2,2,2-trifluoroethoxy)methyl)cyclopropan-1-ol,
1-(2-(3,8-diazabicyclo[3.2.1]octan-3-yl)-7-(thiazol-2-yl)benzo[d]oxazol-4-yl)-2,2,2-trifluoroethane-1,1-diol,
2-(2-(3,6-diazabicyclo[3.1.1]heptan-3-yl)-7-(thiazol-2-yl)benzo[d]oxazol-4-yl)-1,1,1-trifluoropropan-2-ol,
(R)-2-(2-(3,6-diazabicyclo[3.1.1]heptan-3-yl)-7-(thiazol-2-yl)benzo[d]oxazol-4-yl)-1,1,1-trifluoropropan-2-ol,
(S)-2-(2-(3,6-diazabicyclo[3.1.1]heptan-3-yl)-7-(thiazol-2-yl)benzo[d]oxazol-4-yl)-1,1,1-trifluoropropan-2-ol,
2-(3,6-diazabicyclo[3.1.1]heptan-3-yl)-7-(thiazol-2-yl)-4-(1,1,1-trifluoro-2-methoxypropan-2-yl)benzo[d]oxazole,
2-(2-(3,8-diazabicyclo[3.2.1]octan-3-yl)-7-(thiazol-2-yl)benzo[d]oxazol-4-yl)-1,1,1-trifluoropropan-2-ol,
methyl 2-(3,8-diazabicyclo[3.2.1]octan-3-yl)-7-(thiazol-2-yl)benzo[d]oxazole-4-carboxylate,
2-(3,8-diazabicyclo[3.2.1]octan-3-yl)-7-(thiazol-2-yl)benzo[d]oxazole-4-carboxylic acid,
2-(2-(3,6-diazabicyclo[3.1.1]heptan-3-yl)-7-(thiazol-2-yl)benzo[d]oxazol-4-yl)propan-2-ol,
2-(2-(3,8-diazabicyclo[3.2.1]octan-3-yl)-7-(thiazol-2-yl)benzo[d]oxazol-4-yl)propan-2-ol,
1-(2-(3,9-diazabicyclo[3.3.1]nonan-3-yl)-7-(thiazol-2-yl)benzo[d]oxazol-4-yl)ethan-1-ol,
1-(2-(3,6-diazabicyclo[3.1.1]heptan-3-yl)-7-(thiazol-2-yl)benzo[d]oxazol-4-yl)ethan-1-ol,
2-(3,6-diazabicyclo[3.1.1]heptan-3-yl)-4-(1-methoxyethyl)-7-(thiazol-2-yl)benzo[d]oxazole,
2-(3,8-diazabicyclo[3.2.1]octan-3-yl)-4-(1-methoxyethyl)-7-(thiazol-2-yl)benzo[d]oxazole,
2-(3,9-diazabicyclo[3.3.1]nonan-3-yl)-4-(1-methoxyethyl)-7-(thiazol-2-yl)benzo[d]oxazole,
1-(2-(3,6-diazabicyclo[3.1.1]heptan-3-yl)-7-(thiazol-2-yl)benzo[d]oxazol-4-yl)ethan-1-one,
1-(2-(3,8-diazabicyclo[3.2.1]octan-3-yl)-7-(thiazol-2-yl)benzo[d]oxazol-4-yl)ethan-1-one,
1-((2-(3,6-diazabicyclo[3.1.1]heptan-3-yl)-7-(thiazol-2-yl)benzo[d]oxazol-4-yl)oxy)-1,1-difluoro-2-methylpropan-2-ol,
2-((2-(3,6-diazabicyclo[3.1.1]heptan-3-yl)-7-(thiazol-2-yl)benzo[d]oxazol-4-yl)oxy)-2,2-difluoroethan-1-ol,
1-((2-(3,6-diazabicyclo[3.1.1]heptan-3-yl)-7-(thiazol-2-yl)benzo[d]oxazol-4-yl)oxy)-1,1-difluoropropan-2-ol,
(R)-1-((2-(3,6-diazabicyclo[3.1.1]heptan-3-yl)-7-(thiazol-2-yl)benzo[d]oxazol-4-yl)oxy)-1,1-difluoropropan-2-ol,
(S)-1-((2-(3,6-diazabicyclo[3.1.1]heptan-3-yl)-7-(thiazol-2-yl)benzo[d]oxazol-4-yl)oxy)-1,1-difluoropropan-2-ol,
2-(1-(2-(3,6-diazabicyclo[3.1.1]heptan-3-yl)-7-(thiazol-2-yl)benzo[d]oxazol-4-yl)-2,2,2-trifluoroethoxy)acetic acid,
2-(3,8-diazabicyclo[3.2.1]octan-3-yl)-4-((tetrahydro-2H-pyran-4-yl)oxy)-7-(thiazol-2-yl)benzo[d]oxazole,
1-(1-(2-(3,6-diazabicyclo[3.1.1]heptan-3-yl)-7-(thiazol-2-yl)benzo[d]oxazol-4-yl)-2,2,2-trifluoroethoxy)-2-methylpropan-2-ol,
2-(1-(2-(3,6-diazabicyclo[3.1.1]heptan-3-yl)-7-(thiazol-2-yl)benzo[d]oxazol-4-yl)-2,2,2-trifluoroethoxy)acetamide,
1-(1-(2-(3,6-diazabicyclo[3.1.1]heptan-3-yl)-7-(thiazol-2-yl)benzo[d]oxazol-4-yl)-2,2,2-trifluoroethoxy)-1,1-difluoro-2-methylpropan-2-ol,
2-(1-(2-(3,6-diazabicyclo[3.1.1]heptan-3-yl)-7-(thiazol-2-yl)benzo[d]oxazol-4-yl)-2,2,2-trifluoroethoxy)-2,2-difluoroethan-1-ol,
1-((2-(3,6-diazabicyclo[3.1.1]heptan-3-yl)-7-(thiazol-2-yl)benzo[d]oxazol-4-yl)oxy)propan-2-ol,
1-(1-(2-(3,6-diazabicyclo[3.1.1]heptan-3-yl)-7-(thiazol-2-yl)benzo[d]oxazol-4-yl)-2,2,2-trifluoroethoxy)propan-2-ol,
2-(3,8-diazabicyclo[3.2.1]octan-3-yl)-4-((tetrahydro-2H-pyran-3-yl)oxy)-7-(thiazol-2-yl)benzo[d]oxazole,
2-(3,8-diazabicyclo[3.2.1]octan-3-yl)-4-(difluoromethoxy)-7-(thiazol-2-yl)benzo[d]oxazole,
1-((2-(3,8-diazabicyclo[3.2.1]octan-3-yl)-7-(thiazol-2-yl)benzo[d]oxazol-4-yl)oxy)-2-methylpropan-2-ol,
1-(1-(2-(3,6-diazabicyclo[3.1.1]heptan-3-yl)-7-(thiazol-2-yl)benzo[d]oxazol-4-yl)-2,2,2-trifluoroethoxy)-1,1-difluoropropan-2-ol,
3-((2-(3,6-diazabicyclo[3.1.1]heptan-3-yl)-7-(thiazol-2-yl)benzo[d]oxazol-4-yl)oxy)cyclobutane-1-carbonitrile,
2-(3-((2-(3,6-diazabicyclo[3.1.1]heptan-3-yl)-7-(thiazol-2-yl)benzo[d]oxazol-4-yl)oxy)cyclobutyl)propan-2-ol,
2-((2-(3,6-diazabicyclo[3.1.1]heptan-3-yl)-7-(thiazol-2-yl)benzo[d]oxazol-4-yl)oxy)-2-methylpropan-1-ol,
1-(2-(3,6-diazabicyclo[3.1.1]heptan-3-yl)-7-(thiazol-2-yl)-4-(trifluoromethoxy)benzo[d]oxazol-5-yl)cyclopropan-1-ol,
1-(2-(3,8-diazabicyclo[3.2.1]octan-3-yl)-7-(thiazol-2-yl)-4-(trifluoromethoxy)benzo[d]oxazol-5-yl)cyclopropan-1-ol,
3-((2-(3,6-diazabicyclo[3.1.1]heptan-3-yl)-7-(thiazol-2-yl)benzo[d]oxazol-4-yl)oxy)-1,1,1-trifluoropropan-2-ol,
2-(3,6-diazabicyclo[3.1.1]heptan-3-yl)-4-(difluoromethoxy)-7-(thiazol-2-yl)benzo[d]oxazole,
1-((2-(3,6-diazabicyclo[3.1.1]heptan-3-yl)-7-(thiazol-2-yl)benzo[d]oxazol-4-yl)oxy)-2-methylpropan-2-ol,
3-(1-(2-(3,6-diazabicyclo[3.1.1]heptan-3-yl)-7-(thiazol-2-yl)benzo[d]oxazol-4-yl)-2,2,2-trifluoroethoxy)-2,3-dimethylbutan-2-ol,
2-(3,6-diazabicyclo[3.1.1]heptan-3-yl)-7-(thiazol-2-yl)-4-(2,2,2-trifluoro-1-(2-methoxy-2-methylpropoxy)ethyl)benzo[d]oxazole,
2-(3,6-diazabicyclo[3.1.1]heptan-3-yl)-7-(thiazol-2-yl)-4-(2,2,2-trifluoro-1-((1-methoxycyclopropyl)methoxy)ethyl)benzo[d]oxazole,
2-(3,6-diazabicyclo[3.1.1]heptan-3-yl)-5-(1-methoxycyclopropyl)-7-(thiazol-2-yl)-4-(trifluoromethoxy)benzo[d]oxazole,
1-(1-(2-(3,6-diazabicyclo[3.1.1]heptan-3-yl)-7-(thiazol-4-yl)benzo[d]oxazol-4-yl)-2,2,2-trifluoroethoxy)-2-methylpropan-2-ol,
3-((2-(3,6-diazabicyclo[3.1.1]heptan-3-yl)-7-(thiazol-2-yl)benzo[d]oxazol-4-yl)oxy)cyclobutan-1-ol, 1-((1-(2-(3,6-diazabicyclo[3.1.1]heptan-3-yl)-7-(thiazol-4-yl)benzo[d]oxazol-4-yl)-2,2,2-trifluoroethoxy)methyl)cyclopropan-1-ol,
2-(3,6-diazabicyclo[3.1.1]heptan-3-yl)-5-(2-methoxypropan-2-yl)-7-(thiazol-4-yl)-4-(trifluoromethoxy)benzo[d]oxazole,
2-(2-(3,6-diazabicyclo[3.1.1]heptan-3-yl)-7-(thiazol-4-yl)-4-(trifluoromethoxy)benzo[d]oxazol-5-yl)propan-2-ol,
1-((2-(3,6-diazabicyclo[3.1.1]heptan-3-yl)-7-(pyridin-2-yl)benzo[d]oxazol-4-yl)oxy)-1,1-difluoro-2-methylpropan-2-ol,
1-((2-(3,6-diazabicyclo[3.1.1]heptan-3-yl)-7-(oxazol-2-yl)benzo[d]oxazol-4-yl)oxy)-1,1-difluoro-2-methylpropan-2-ol,
2-(2-(3,8-diazabicyclo[3.2.1]octan-3-yl)-7-(thiazol-4-yl)-4-(trifluoromethoxy)benzo[d]oxazol-5-yl)propan-2-ol,
2-(3,6-diazabicyclo[3.1.1]heptan-3-yl)-4-((tetrahydro-2H-pyran-4-yl)oxy)-7-(thiazol-2-yl)benzo[d]oxazole,
4-((2-(3,6-diazabicyclo[3.1.1]heptan-3-yl)-7-(thiazol-2-yl)benzo[d]oxazol-4-yl)oxy)-4,4-difluoro-2-methylbutan-2-ol,
2-(3,8-diazabicyclo[3.2.1]octan-3-yl)-5-(2-methoxypropan-2-yl)-7-(thiazol-4-yl)-4-(trifluoromethoxy)benzo[d]oxazole,
1-(2-(3,6-diazabicyclo[3.1.1]heptan-3-yl)-7-(thiazol-4-yl)-4-(trifluoromethoxy)benzo[d]oxazol-5-yl)cyclopropan-1-ol,
1-(2-(3,6-diazabicyclo[3.1.1]heptan-3-yl)-7-(thiazol-4-yl)-4-(trifluoromethoxy)benzo[d]oxazol-5-yl)-2,2-difluoroethan-1-ol,
(R)-1-(2-(3,6-diazabicyclo[3.1.1]heptan-3-yl)-7-(thiazol-4-yl)-4-(trifluoromethoxy)benzo[d]oxazol-5-yl)-2,2-difluoroethan-1-ol,
(S)-1-(2-(3,6-diazabicyclo[3.1.1]heptan-3-yl)-7-(thiazol-4-yl)-4-(trifluoromethoxy)benzo[d]oxazol-5-yl)-2,2-difluoroethan-1-ol,
1-(2-(3,8-diazabicyclo[3.2.1]octan-3-yl)-7-(thiazol-4-yl)-4-(trifluoromethoxy)benzo[d]oxazol-5-yl)-2,2-difluoroethan-1-ol,
(R)-1-(2-(3,8-diazabicyclo[3.2.1]octan-3-yl)-7-(thiazol-4-yl)-4-(trifluoromethoxy)benzo[d]oxazol-5-yl)-2,2-difluoroethan-1-ol,
(S)-1-(2-(3,8-diazabicyclo[3.2.1]octan-3-yl)-7-(thiazol-4-yl)-4-(trifluoromethoxy)benzo[d]oxazol-5-yl)-2,2-difluoroethan-1-ol,
1-((2-(3,6-diazabicyclo[3.1.1]heptan-3-yl)-7-(1H-pyrazol-1-yl)benzo[d]oxazol-4-yl)oxy)-1,1-difluoro-2-methylpropan-2-ol,
4-((2-(3,6-diazabicyclo[3.1.1]heptan-3-yl)-7-(thiazol-2-yl)benzo[d]oxazol-4-yl)oxy)cyclohexan-1-ol,
1-((2-(3,6-diazabicyclo[3.1.1]heptan-3-yl)-7-(4-methylthiazol-2-yl)benzo[d]oxazol-4-yl)oxy)-1,1-difluoro-2-methylpropan-2-ol,
1-((2-(3,6-diazabicyclo[3.1.1]heptan-3-yl)-7-(thiazol-4-yl)benzo[d]oxazol-4-yl)oxy)-1,1-difluoro-2-methylpropan-2-ol,
1-((2-(3,8-diazabicyclo[3.2.1]octan-3-yl)-7-(thiazol-4-yl)benzo[d]oxazol-4-yl)oxy)-1,1-difluoro-2-methylpropan-2-ol,
1-((2-(3,6-diazabicyclo[3.1.1]heptan-3-yl)-7-(thiazol-4-yl)benzo[d]oxazol-4-yl)oxy)-1,1-difluoropropan-2-ol,
1-((2-(3,8-diazabicyclo[3.2.1]octan-3-yl)-7-(thiazol-4-yl)benzo[d]oxazol-4-yl)oxy)-1,1-difluoropropan-2-ol,
2-((2-(3,6-diazabicyclo[3.1.1]heptan-3-yl)-7-(thiazol-4-yl)benzo[d]oxazol-4-yl)oxy)-2,2-difluoroethan-1-ol,
2-((2-(3,8-diazabicyclo[3.2.1]octan-3-yl)-7-(thiazol-4-yl)benzo[d]oxazol-4-yl)oxy)-2,2-difluoroethan-1-ol,
3-((2-(3,6-diazabicyclo[3.1.1]heptan-3-yl)-7-(thiazol-2-yl)benzo[d]oxazol-4-yl)oxy)-4,4,4-trifluoro-2-methylbutan-2-ol,
4-((2-(3,6-diazabicyclo[3.1.1]heptan-3-yl)-7-(thiazol-2-yl)benzo[d]oxazol-4-yl)oxy)tetrahydro-2H-thiopyran 1,1-dioxide,
2-((2-(3,6-diazabicyclo[3.1.1]heptan-3-yl)-7-(pyridin-2-yl)benzo[d]oxazol-4-yl)oxy)-2,2-difluoroethan-1-ol,
1-((2-(3,8-diazabicyclo[3.2.1]octan-3-yl)-7-(1H-pyrazol-1-yl)benzo[d]oxazol-4-yl)oxy)-1,1-difluoro-2-methylpropan-2-ol,
1-((2-(3,8-diazabicyclo[3.2.1]octan-3-yl)-7-(pyridin-2-yl)benzo[d]oxazol-4-yl)oxy)-1,1-difluoro-2-methylpropan-2-ol,
1-((2-(3,8-diazabicyclo[3.2.1]octan-3-yl)-7-(4-methylthiazol-2-yl)benzo[d]oxazol-4-yl)oxy)-1,1-difluoro-2-methylpropan-2-ol,
2-((2-(3,6-diazabicyclo[3.1.1]heptan-3-yl)-7-(5-fluoropyridin-2-yl)benzo[d]oxazol-4-yl)oxy)-2,2-difluoroethan-1-ol,
2-((2-(3,6-diazabicyclo[3.1.1]heptan-3-yl)-7-(1H-pyrazol-1-yl)benzo[d]oxazol-4-yl)oxy)-2,2-difluoroethan-1-ol,
1-((2-(3,8-diazabicyclo[3.2.1]octan-3-yl)-7-(oxazol-2-yl)benzo[d]oxazol-4-yl)oxy)-1,1-difluoro-2-methylpropan-2-ol,
1-((2-(3,8-diazabicyclo[3.2.1]octan-3-yl)-7-(2H-1,2,3-triazol-2-yl)benzo[d]oxazol-4-yl)oxy)-1,1-difluoro-2-methylpropan-2-ol,
2-(3,6-diazabicyclo[3.1.1]heptan-3-yl)-4-(((S)-tetrahydrofuran-3-yl)oxy)-7-(thiazol-2-yl)benzo[d]oxazole,
2-(3,6-diazabicyclo[3.1.1]heptan-3-yl)-4-(((R)-tetrahydrofuran-3-yl)oxy)-7-(thiazol-2-yl)benzo[d]oxazole,
2-(3,6-diazabicyclo[3.1.1]heptan-3-yl)-4-(oxetan-3-yloxy)-7-(thiazol-2-yl)benzo[d]oxazole,
3-((2-(3,6-diazabicyclo[3.1.1]heptan-3-yl)-7-(thiazol-2-yl)benzo[d]oxazol-4-yl)oxy)-3,3-difluoro-2-methylpropane-1,2-diol,
1-((2-(3,8-diazabicyclo[3.2.1]octan-3-yl)-7-(1,2,4-thiadiazol-5-yl)benzo[d]oxazol-4-yl)oxy)-1,1-difluoro-2-methylpropan-2-ol,
1-((2-(3,8-diazabicyclo[3.2.1]octan-3-yl)-7-(1-methyl-1H-pyrazol-3-yl)benzo[d]oxazol-4-yl)oxy)-1,1-difluoro-2-methylpropan-2-ol,
1-((2-(3,6-diazabicyclo[3.1.1]heptan-3-yl)-7-(5-fluoropyridin-2-yl)benzo[d]oxazol-4-yl)oxy)-1,1-difluoro-2-methylpropan-2-ol,
1-((2-(3,8-diazabicyclo[3.2.1]octan-3-yl)-7-(pyrimidin-2-yl)benzo[d]oxazol-4-yl)oxy)-1,1-difluoro-2-methylpropan-2-ol,
1-((2-(3,8-diazabicyclo[3.2.1]octan-3-yl)-7-(isothiazol-3-yl)benzo[d]oxazol-4-yl)oxy)-1,1-difluoro-2-methylpropan-2-ol,
1-((2-(3,8-diazabicyclo[3.2.1]octan-3-yl)-7-(5-fluoropyridin-2-yl)benzo[d]oxazol-4-yl)oxy)-1,1-difluoro-2-methylpropan-2-ol,
1-((2-(3,8-diazabicyclo[3.2.1]octan-3-yl)-7-(3-methyl-1,2,4-thiadiazol-5-yl)benzo[d]oxazol-4-yl)oxy)-1,1-difluoro-2-methylpropan-2-ol,
2-(3,6-diazabicyclo[3.1.1]heptan-3-yl)-7-(thiazol-2-yl)-4-((trifluoromethyl)sulfonyl)benzo[d]oxazole,
2-(3,6-diazabicyclo[3.1.1]heptan-3-yl)-7-(thiazol-2-yl)benzo[d]oxazole-4-carbonitrile,
2-(3,6-diazabicyclo[3.1.1]heptan-3-yl)-7-(thiazol-2-yl)-4-((5-(trifluoromethyl)pyridin-2-yl)oxy)benzo[d]oxazole,
2-(3,6-diazabicyclo[3.1.1]heptan-3-yl)-4-(pyridin-2-yloxy)-7-(thiazol-2-yl)benzo[d]oxazole, 2-(3,6-diazabicyclo[3.1.1]heptan-3-yl)-4-(pyrimidin-2-yloxy)-7-(thiazol-2-yl)benzo[d]oxazole,
2-(3,6-diazabicyclo[3.1.1]heptan-3-yl)-4-(pyrazin-2-yloxy)-7-(thiazol-2-yl)benzo[d]oxazole,
2-(3,6-diazabicyclo[3.1.1]heptan-3-yl)-4-((6-methyl-4-(trifluoromethyl)pyridazin-3-yl)oxy)-7-(thiazol-2-yl)benzo[d]oxazole,
(6-((2-(3,6-diazabicyclo[3.1.1]heptan-3-yl)-7-(thiazol-2-yl)benzo[d]oxazol-4-yl)oxy)pyridin-3-yl)methanol,
(6-((2-(3,6-diazabicyclo[3.1.1]heptan-3-yl)-7-(thiazol-2-yl)benzo[d]oxazol-4-yl)oxy)-5-(trifluoromethyl)pyridin-3-yl)methanol,
2-(3,6-diazabicyclo[3.1.1]heptan-3-yl)-7-(thiazol-2-yl)-4-((5-(trifluoromethoxy)pyridin-2-yl)oxy)benzo[d]oxazole,
2-(3,6-diazabicyclo[3.1.1]heptan-3-yl)-4-cyclopropyl-7-(thiazol-2-yl)benzo[d]oxazole,
2-(3,6-diazabicyclo[3.1.1]heptan-3-yl)-4-(methylthio)-7-(thiazol-2-yl)benzo[d]oxazole,
2-(3,6-diazabicyclo[3.1.1]heptan-3-yl)-4-(methylsulfinyl)-7-(thiazol-2-yl)benzo[d]oxazole,
2-(3,6-diazabicyclo[3.1.1]heptan-3-yl)-4-(methylsulfonyl)-7-(thiazol-2-yl)benzo[d]oxazole,
2-((2-(3,6-diazabicyclo[3.1.1]heptan-3-yl)-7-(thiazol-2-yl)benzo[d]oxazol-4-yl)thio)ethan-1-ol,
2-((2-(3,6-diazabicyclo[3.1.1]heptan-3-yl)-7-(thiazol-2-yl)benzo[d]oxazol-4-yl)sulfinyl)ethan-1-ol,
2-((2-(3,6-diazabicyclo[3.1.1]heptan-3-yl)-7-(thiazol-2-yl)benzo[d]oxazol-4-yl)sulfonyl)ethan-1-ol,
2-(3,6-diazabicyclo[3.1.1]heptan-3-yl)-4-((1,1-difluoroallyl)oxy)-7-(thiazol-2-yl)benzo[d]oxazole,
2-(3,6-diazabicyclo[3.1.1]heptan-3-yl)-4-((5-(methylsulfonyl)pyridin-2-yl)oxy)-7-(thiazol-2-yl)benzo[d]oxazole,
2-(3,6-diazabicyclo[3.1.1]heptan-3-yl)-N-(2-methoxyethyl)-7-(thiazol-2-yl)benzo[d]oxazole-4-carboxamide,
2-(3,6-diazabicyclo[3.1.1]heptan-3-yl)-7-(thiazol-2-yl)benzo[d]oxazole-4-carboxamide,
2-(3,6-diazabicyclo[3.1.1]heptan-3-yl)-N-(2-hydroxyethyl)-7-(thiazol-2-yl)benzo[d]oxazole-4-carboxamide,
2-(3,6-diazabicyclo[3.1.1]heptan-3-yl)-N-(2-hydroxyethyl)-N-methyl-7-(thiazol-2-yl)benzo[d]oxazole-4-carboxamide,
2-(3,6-diazabicyclo[3.1.1]heptan-3-yl)-N-cyclopropyl-7-(thiazol-2-yl)benzo[d]oxazole-4-carboxamide,
2-(3,6-diazabicyclo[3.1.1]heptan-3-yl)-N-ethyl-7-(thiazol-2-yl)benzo[d]oxazole-4-carboxamide,
(2-(3,6-diazabicyclo[3.1.1]heptan-3-yl)-7-(thiazol-2-yl)benzo[d]oxazol-4-yl)(morpholino)methanone,
(2-(3,6-diazabicyclo[3.1.1]heptan-3-yl)-7-(thiazol-2-yl)benzo[d]oxazol-4-yl)(pyrrolidin-1-yl)methanone,
N-benzyl-2-(3,6-diazabicyclo[3.1.1]heptan-3-yl)-7-(thiazol-2-yl)benzo[d]oxazole-4-carboxamide,
1-((2-(3,6-diazabicyclo[3.1.1]heptan-3-yl)-7-(thiazol-2-yl)benzo[d]oxazol-4-yl)oxy)-1,1-difluoro-3-methylbutan-2-ol,
1-((2-(3,6-diazabicyclo[3.1.1]heptan-3-yl)-7-(5-chloropyridin-2-yl)benzo[d]oxazol-4-yl)oxy)-1,1-difluoro-2-methylpropan-2-ol,
(R)-3-((2-(3,6-diazabicyclo[3.1.1]heptan-3-yl)-7-(thiazol-2-yl)benzo[d]oxazol-4-yl)oxy)-3,3-difluoro-2-methylpropane-1,2-diol,
(S)-3-((2-(3,6-diazabicyclo[3.1.1]heptan-3-yl)-7-(thiazol-2-yl)benzo[d]oxazol-4-yl)oxy)-3,3-difluoro-2-methylpropane-1,2-diol,
2-(3,6-diazabicyclo[3.1.1]heptan-3-yl)-7-(thiazol-2-yl)benzo[d]oxazole-4-carboxylic acid,
2-(3,6-diazabicyclo[3.1.1]heptan-3-yl)-N-hydroxy-7-(thiazol-2-yl)benzo[d]oxazole-4-carboxamide,
3-(5-(2-hydroxypropan-2-yl)-7-(thiazol-2-yl)-4-(trifluoromethoxy)benzo[d]oxazol-2-yl)-3,8-diazabicyclo[3.2.1]octan-8-ol,
2-(3,6-diazabicyclo[3.1.1]heptan-3-yl)-4-morpholino-7-(thiazol-2-yl)benzo[d]oxazole,
3-((2-(3,6-diazabicyclo[3.1.1]heptan-3-yl)-7-(thiazol-2-yl)benzo[d]oxazol-4-yl)oxy)-3,3-difluoropropane-1,2-diol,
3-(4-(1,1-difluoro-2-hydroxy-2-methylpropoxy)-7-(thiazol-2-yl)benzo[d]oxazol-2-yl)-3,6-diazabicyclo[3.1.1]heptan-6-ol,
(R)-3-(4-(1,1-difluoro-2-hydroxypropoxy)-7-(thiazol-2-yl)benzo[d]oxazol-2-yl)-3,6-diazabicyclo[3.1.1]heptan-6-ol,
(S)-3-(4-(1,1-difluoro-2-hydroxypropoxy)-7-(thiazol-2-yl)benzo[d]oxazol-2-yl)-3,6-diazabicyclo[3.1.1]heptan-6-ol,
3-(4-(1,1-difluoro-2-hydroxyethoxy)-7-(thiazol-2-yl)benzo[d]oxazol-2-yl)-3,6-diazabicyclo[3.1.1]heptan-6-ol,
3-(5-chloro-7-(thiazol-2-yl)-4-(trifluoromethoxy)benzo[d]oxazol-2-yl)-3,8-diazabicyclo[3.2.1]octan-8-ol,
(2-((2-(3,6-diazabicyclo[3.1.1]heptan-3-yl)-7-(thiazol-2-yl)benzo[d]oxazol-4-yl)oxy)pyridin-3-yl)methanol,
1-((2-(3,6-diazabicyclo[3.1.1]heptan-3-yl)-7-(thiazol-2-yl)benzo[d]oxazol-4-yl)oxy)-1,1-difluoropropane-2,2-diol,
(R)-3-(7-(thiazol-2-yl)-4-(2,2,2-trifluoro-1-hydroxyethyl)benzo[d]oxazol-2-yl)-3,8-diazabicyclo[3.2.1]octan-8-ol,
(S)-3-(7-(thiazol-2-yl)-4-(2,2,2-trifluoro-1-hydroxyethyl)benzo[d]oxazol-2-yl)-3,8-diazabicyclo[3.2.1]octan-8-ol,
3-(7-(thiazol-2-yl)-4-(trifluoromethoxy)benzo[d]oxazol-2-yl)-3,6-diazabicyclo[3.1.1]heptan-6-ol,
3-(5-(2-hydroxypropan-2-yl)-7-(thiazol-2-yl)-4-(trifluoromethyl)benzo[d]oxazol-2-yl)-3,8-diazabicyclo[3.2.1]octan-8-ol,
2-(3,6-diazabicyclo[3.1.1]heptan-3-yl)-7-(thiazol-2-yl)benzo[d]oxazole,
3-(5-(1-hydroxyethyl)-7-(thiazol-2-yl)-4-(trifluoromethoxy)benzo[d]oxazol-2-yl)-3,8-diazabicyclo[3.2.1]octan-8-ol,
3-(5-(1-hydroxyethyl)-7-(thiazol-2-yl)-4-(trifluoromethyl)benzo[d]oxazol-2-yl)-3,8-diazabicyclo[3.2.1]octan-8-ol,
2-(3,6-diazabicyclo[3.1.1]heptan-3-yl)-N-(2-hydroxyethyl)-7-(thiazol-2-yl)benzo[d]oxazole-4-sulfonamide,
2-(3,6-diazabicyclo[3.1.1]heptan-3-yl)-N-methyl-7-(thiazol-2-yl)benzo[d]oxazole-4-sulfonamide,
2-(3,6-diazabicyclo[3.1.1]heptan-3-yl)-N-(2-methoxyethyl)-7-(thiazol-2-yl)benzo[d]oxazole-4-sulfonamide,
2-(3,6-diazabicyclo[3.1.1]heptan-3-yl)-N,N-dimethyl-7-(thiazol-2-yl)benzo[d]oxazole-4-sulfonamide,
2-(3,6-diazabicyclo[3.1.1]heptan-3-yl)-N-(2-hydroxyethyl)-N-methyl-7-(thiazol-2-yl)benzo[d]oxazole-4-sulfonamide,
2-(3,6-diazabicyclo[3.1.1]heptan-3-yl)-4-(pyrrolidin-1-ylsulfonyl)-7-(thiazol-2-yl)benzo[d]oxazole,
2-(3,6-diazabicyclo[3.1.1]heptan-3-yl)-4-(morpholinosulfonyl)-7-(thiazol-2-yl)benzo[d]oxazole,
2-(3,6-diazabicyclo[3.1.1]heptan-3-yl)-4-(1,1-difluoro-2-methoxyethoxy)-7-(thiazol-2-yl)benzo[d]oxazole,
2-(3,6-diazabicyclo[3.1.1]heptan-3-yl)-4-(1,1-difluoro-2-methoxy-2-methylpropoxy)-7-(thiazol-2-yl)benzo[d]oxazole,
1-((2-(3,6-diazabicyclo[3.1.1]heptan-3-yl)-7-(1-methyl-1H-pyrazol-3-yl)benzo[d]oxazol-4-yl)oxy)-1,1-difluoro-2-methylpropan-2-ol,
1-((2-(3,6-diazabicyclo[3.1.1]heptan-3-yl)-7-(thiazol-2-yl)benzo[d]oxazol-4-yl)oxy)-1,1-difluorobutan-2-ol,
2-(3,6-diazabicyclo[3.1.1]heptan-3-yl)-7-(thiazol-2-yl)benzo[d]oxazole-4-sulfonamide,
1-(2-(3,6-diazabicyclo[3.1.1]heptan-3-yl)-7-(thiazol-2-yl)benzo[d]oxazol-4-yl)piperidin-4-ol, 4-(2-(3,6-diazabicyclo[3.1.1]heptan-3-yl)-7-(thiazol-2-yl)benzo[d]oxazol-4-yl)thiomorpholine 1,1-dioxide, 1-((2-(3,6-diazabicyclo[3.1.1]heptan-3-yl)-5-bromo-7-(thiazol-2-yl)benzo[d]oxazol-4-yl)oxy)-1,1-difluoro-2-methylpropan-2-ol, 1-((2-(3,6-diazabicyclo[3.1.1]heptan-3-yl)-5-chloro-7-(thiazol-2-yl)benzo[d]oxazol-4-yl)oxy)-1,1-difluoro-2-methylpropan-2-ol, 2-((2-(3,6-diazabicyclo[3.1.1]heptan-3-yl)-5-chloro-7-(thiazol-2-yl)benzo[d]oxazol-4-yl)oxy)-2,2-difluoroethan-1-ol, 2-(3,6-diazabicyclo[3.1.1]heptan-3-yl)-4-(1,1-difluoropropoxy)-7-(thiazol-2-yl)benzo[d]oxazole, 4-(benzo[d]oxazol-2-yldifluoromethoxy)-2-(3,6-diazabicyclo[3.1.1]heptan-3-yl)-7-(thiazol-2-yl)benzo[d]oxazole, 2-((2-(3,8-diazabicyclo[3.2.1]octan-3-yl)-7-(thiazol-2-yl)benzo[d]oxazol-4-yl)oxy)-2,2-difluoroethan-1-ol, 1-((2-(3,8-diazabicyclo[3.2.1]octan-3-yl)-7-(thiazol-2-yl)benzo[d]oxazol-4-yl)oxy)-1,1-difluoro-2-methylpropan-2-ol, 2-(3,6-diazabicyclo[3.1.1]heptan-3-yl)-4-((1,1-difluoro-3-(pyridin-3-yl)allyl)oxy)-7-(thiazol-2-yl)benzo[d]oxazole, 2-((2-(3,6-diazabicyclo[3.1.1]heptan-3-yl)-7-(thiazol-2-yl)benzo[d]oxazol-4-yl)oxy)-2,2-difluoro-N-(2-hydroxyethyl)-N-methylacetamide, 2-((2-(3,6-diazabicyclo[3.1.1]heptan-3-yl)-7-(thiazol-2-yl)benzo[d]oxazol-4-yl)oxy)-2,2-difluoro-N,N-dimethylacetamide, 2-((2-(3,6-diazabicyclo[3.1.1]heptan-3-yl)-7-(thiazol-2-yl)benzo[d]oxazol-4-yl)oxy)-2,2-difluoro-1-morpholinoethan-1-one, 2-((2-(3,6-diazabicyclo[3.1.1]heptan-3-yl)-7-(thiazol-2-yl)benzo[d]oxazol-4-yl)oxy)-2,2-difluoroacetamide, 2-((2-(3,6-diazabicyclo[3.1.1]heptan-3-yl)-7-(thiazol-2-yl)benzo[d]oxazol-4-yl)oxy)-2,2-difluoro-N-(2-hydroxyethyl)acetamide, 2-((2-(3,6-diazabicyclo[3.1.1]heptan-3-yl)-7-(thiazol-2-yl)benzo[d]oxazol-4-yl)oxy)-2,2-difluoro-1-(3-hydroxyazetidin-1-yl)ethan-1-one, 2-(3,6-diazabicyclo[3.1.1]heptan-3-yl)-7-(thiazol-2-yl)-5-((5-(trifluoromethyl)pyridin-2-yl)oxy)benzo[d]oxazole, 2-(3,6-diazabicyclo[3.1.1]heptan-3-yl)-4-cyclobutyl-7-(thiazol-2-yl)benzo[d]oxazole, 2-(3,6-diazabicyclo[3.1.1]heptan-3-yl)-4-(pyrrolidin-1-yl)-7-(thiazol-2-yl)benzo[d]oxazole, (6-((2-(3,6-diazabicyclo[3.1.1]heptan-3-yl)-7-(thiazol-2-yl)benzo[d]oxazol-5-yl)oxy)pyridin-3-yl)methanol, 2-(3,6-diazabicyclo[3.1.1]heptan-3-yl)-7-(thiazol-2-yl)benzo[d]oxazole-5-carbonitrile, 2-(3,6-diazabicyclo[3.1.1]heptan-3-yl)-5-(pyridin-3-yl)-7-(thiazol-2-yl)benzo[d]oxazole, 2-(3,6-diazabicyclo[3.1.1]heptan-3-yl)-5-cyclobutoxy-7-(thiazol-2-yl)benzo[d]oxazole.

In the present invention, the compound represented by the general formula (1) may be in the form of a free base (educt) and may also be a pharmacologically acceptable salt thereof. The pharmacologically acceptable salt is preferably in the form of an acid addition salt. The acid of the acid addition salt is, for example, a salt of hydrohalic acid such as hydrofluoric acid, hydrochloric acid, hydrobromic acid, or hydroiodic acid; a salt of inorganic acid such as sulfuric acid, nitric acid, phosphoric acid, hydrogen peroxide acid, or carbonic acid; a salt of organic carboxylic acid such as acetic acid, trichloroacetic acid, trifluoroacetic acid, hydroxyacetic acid, lactic acid, citric acid, tartaric acid, oxalic acid, benzoic acid, mandelic acid, butyric acid, maleic acid, propionic acid, formic acid, or malic acid; acidic amino acid such as aspartic acid or glutamic acid; alkyl sulfonic acid such as methanesulfonic acid; or aryl sulfonic acid such as p-toluenesulfonic acid.

Besides, although there is a case where the compound represented by the general formula (1) or the pharmacologically acceptable salt thereof of the present invention has one or more asymmetric carbon atoms depending on the type of substituent, the scope of the general formula (1) or the pharmacologically acceptable salt thereof of the present invention encompasses, e.g., optically active substances based on one or more asymmetric carbon atoms, diastereomers, geometrical isomers, tautomers, any mixture thereof, and racemates. In addition, the compound represented by the general formula (1) or the pharmacologically acceptable salt thereof of the present invention includes corresponding hydrates and solvates. The solvates include, for example, 2-propanol solvate.

Furthermore, the compound represented by the general formula (1) or the pharmacologically acceptable salt thereof of the present invention includes corresponding radioisotopes and labeled compounds with nonradioisotope; and hydrates, and solvates thereof.

In the present description, when the compound has isometric(s) or isotope(s) and there is not a reference about it in particular in their name, the name of compound means isometric(s), isotope(s) or mixture thereof, or racemate(s).

Among these compounds represented by the general formula (1) or pharmacologically acceptable salts thereof, the therapeutic agent of the present invention preferably contains at least one selected from the group consisting of the compound represented by the general formula (11) and pharmacologically acceptable salts thereof as an active ingredient, especially from the viewpoint of being effective in treating inflammatory diseases, autoimmune diseases, fibrotic diseases, and cancer diseases (further preferably, inflammatory diseases, autoimmune diseases, and fibrotic diseases).

Moreover, in the therapeutic agent of the present invention, the compound represented by the general formula (11) is more preferably the following compound: a compound in which the group represented by $R^1$ is, among the above, a $C_{1-3}$ alkyl group optionally substituted with at least one of a halogen atom, a hydroxyl group, and a $C_{1-3}$ alkyloxy group; or a $C_{1-4}$ alkyloxy group optionally substituted with at least one of a halogen atom and a hydroxyl group, and the group represented by $R^2$ is, among the above, a hydrogen atom; a halogen atom; a $C_{1-3}$ alkyl group optionally substituted with at least one of a halogen atom, a hydroxyl group, and a $C_{1-3}$ alkyloxy group; or an acetyl group, from the viewpoint that it tends to be more effective in treating at least one disease selected from the group consisting of psoriasis (such as psoriatic arthritis and psoriasis vulgaris), rhinitis, atopic dermatitis, allergic conjunctivitis, dry eye, asthma, COPD, Behcet's disease, inflammatory bowel diseases (such as Crohn's disease and ulcerative colitis), rheumatoid arthritis, idiopathic pulmonary fibrosis, non-alcoholic steatohepatitis, muscular dystrophy, alopecia areata, vitiligo, hidradenitis suppurativa, lichen planus, colorectal cancer, lung cancer, blood cancer, and brain tumors. Further preferable is the following compound: a compound in which the group represented by $R^1$ is, among the above, a $C_{1-4}$ alkyloxy group optionally substituted with at least one of a halogen atom and a hydroxyl group, and the group represented by $R^2$ is, among the above, a hydrogen atom, from the viewpoint that it tends to be more effective in treating psoriasis (such as psoriatic arthritis and psoriasis vulgaris), atopic dermatitis, allergic conjunctivitis, asthma, COPD, rheumatoid arthritis, idiopathic pulmonary fibrosis, ulcerative colitis, non-alcoholic steatohepatitis, muscular dystrophy, alopecia areata, vitiligo, hidradenitis suppurativa, lichen planus, colorectal cancer, lung cancer, blood cancer, and brain tumors, and that it tends to have excellent metabolic stability.

In addition, as the therapeutic agent of the present invention, the PDE4 inhibitory activity of the at least one compound selected from the group consisting of the compound represented by the general formula (1) and the pharmacologically acceptable salts thereof is preferably 11 nM or less, and more preferably 1 nM or less, at a concentration (IC50) that inhibits PDE4 activity by 50%. When the IC50 exceeds the upper limit, the treatment effect on inflammatory diseases, autoimmune diseases, fibrotic diseases, and cancer diseases tends to decrease.

In the present invention, the PDE4 inhibitory activity of a compound (including a salt) can be measured by a scintillation proximity assay, and more specifically, it can be determined as follows. To 10 µL of the test compound diluted with a reaction buffer solution (preferably 50 mM Tris-HCl, pH 7.4, 8.3 prosi mM $MgCl_2$, 1.7 mM EGTA, 3 mg/mL bovine serum albumin), 50 µL of PDE4 diluted 375-fold with the reaction buffer solution was added. After that, 40 µL of [2,8-$^3$H]-Adenosine-3',5'-cyclic phosphate triethylammonium salt (substrate) diluted 1000-fold with the reaction buffer solution was added, and the PDE4 reaction product was measured after standing at room temperature for 120 minutes. The one added only with the reaction buffer solution without adding PDE4 was defined as blank, and the one added with only with dimethyl sulfoxide instead of the test compound was defined as the control, and the following formula:

Inhibition Rate={1−(Value at Addition of Each Test Compound−Blank Value)/(Control Value−Blank Value)}×100 was used to determine the test compound concentration when the inhibition rate becomes 50% from the inhibition curves obtained from various concentrations of the test compound and the inhibition rate as the concentration (IC50) that inhibits PDE4 activity by 50%.

In addition, more specifically, the therapeutic agent of the present invention preferably contains at least one selected from the group consisting of
2-(3,6-diazabicyclo[3.1.1]heptan-3-yl)-5-chloro-7-(thiazol-2-yl)-4-(trifluoromethoxy)benzo[d]oxazole,
7-(5-chloro-7-(thiazol-2-yl)-4-(trifluoromethoxy)benzo[d]oxazole-2-yl)-3-oxa-7,9-diazabicyclo[3.3.1]nonane,
2-(3,8-diazabicyclo[3.2.1]octan-3-yl)-4-methyl-7-(thiazol-2-yl)benzo[d]oxazole,
2-(3,6-diazabicyclo[3.1.1]heptan-3-yl)-7-(thiazol-2-yl)-4-(trifluoromethoxy)benzo[d]oxazole,
2-(3,9-diazabicyclo[3.3.1]nonan-3-yl)-7-(thiazol-2-yl)-4-(trifluoromethoxy)benzo[d]oxazole,
2-(3,6-diazabicyclo[3.1.1]heptan-3-yl)-7-(thiazol-2-yl)-4-(trifluoromethyl)benzo[d]oxazole,
2-(3,8-diazabicyclo[3.2.1]octan-3-yl)-4-methoxy-7-(thiazol-2-yl)benzo[d]oxazole,
1-(2-(3,8-diazabicyclo[3.2.1]octan-3-yl)-7-(thiazol-2-yl)benzo[d]oxazole-4-yl)-2,2,2-trifluoroethan-1-ol,
1-(2-(3,6-diazabicyclo[3.1.1]heptan-3-yl)-7-(thiazol-2-yl)benzo[d]oxazole-4-yl)-2,2,2-trifluoroethan-1-ol,
2-(3,6-diazabicyclo[3.1.1]heptan-3-yl)-5-(2-methoxypropan-2-yl)-7-(thiazol-2-yl)-4-(trifluoromethyl)benzo[d]oxazole,
2-(2-(3,8-diazabicyclo[3.2.1]octan-3-yl)-7-(thiazol-2-yl)-4-(trifluoromethyl)benzo[d]oxazole-5-yl)propan-2-ol,
2-(2-(3,8-diazabicyclo[3.2.1]octan-3-yl)-7-(thiazol-2-yl)-4-(trifluoromethoxy)benzo[d]oxazole-5-yl)propan-2-ol,
2-(3,8-diazabicyclo[3.2.1]octan-3-yl)-5-(2-methoxypropan-2-yl)-7-(thiazol-2-yl)-4-(trifluoromethoxy)benzo[d]oxazole,
2-(3,6-diazabicyclo[3.1.1]heptan-3-yl)-5-(2-methoxypropan-2-yl)-7-(thiazol-2-yl)-4-(trifluoromethoxy)benzo[d]oxazole,
1-(2-(3,6-diazabicyclo[3.1.1]heptan-3-yl)-7-(thiazol-2-yl)-4-(trifluoromethoxy)benzo[d]oxazole-5-yl)ethan-1-ol,
2-(3,6-diazabicyclo[3.1.1]heptan-3-yl)-5-(2,2-difluoro-1-methoxyethyl)-7-(thiazol-2-yl)-4-(trifluoromethoxy)benzo[d]oxazole,
1-(2-(3,6-diazabicyclo[3.1.1]heptan-3-yl)-7-(thiazol-2-yl)-4-(trifluoromethoxy)benzo[d]oxazole-5-yl)ethan-1-one,
2-(2-(3,6-diazabicyclo[3.1.1]heptan-3-yl)-7-(thiazol-2-yl)benzo[d]oxazole-4-yl)-1,1,1-trifluoropropan-2-ol,
2-(3,6-diazabicyclo[3.1.1]heptan-3-yl)-7-(thiazol-2-yl)-4-(1,1,1-trifluoro-2-methoxypropan-2-yl)benzo[d]oxazole,
1-((2-(3,6-diazabicyclo[3.1.1]heptan-3-yl)-7-(thiazol-2-yl)benzo[d]oxazole-4-yl)oxy)-1,1-difluoro-2-methylpropan-2-ol,
2-((2-(3,6-diazabicyclo[3.1.1]heptan-3-yl)-7-(thiazol-2-yl)benzo[d]oxazole-4-yl)oxy)-2,2-difluoroethan-1-ol,
1-((2-(3,6-diazabicyclo[3.1.1]heptan-3-yl)-7-(thiazol-2-yl)benzo[d]oxazole-4-yl)oxy)-1,1-difluoropropan-2-ol,
2-(2-(3,6-diazabicyclo[3.1.1]heptan-3-yl)-7-(thiazol-2-yl)benzo[d]oxazole-4-yl)-1,1-difluoropropan-2-ol,
and pharmacologically acceptable salts thereof, and particularly preferably contains 1-((2-(3,6-diazabicyclo[3.1.1]heptan-3-yl)-7-(thiazol-2-yl)benzo[d]oxazole-4-yl)oxy)-1,1-difluoro-2-methylpropan-2-ol as an active ingredient from the viewpoint that it tends to be more effective in treating at least one disease selected from the group consisting of psoriasis (such as psoriatic arthritis and psoriasis vulgaris), atopic dermatitis, allergic conjunctivitis, dry eye, asthma, COPD, rheumatoid arthritis, idiopathic pulmonary fibrosis, ulcerative colitis, non-alcoholic steatohepatitis, muscular dystrophy, alopecia areata, vitiligo, hidradenitis suppurativa, lichen planus, colorectal cancer, lung cancer, blood cancer, and brain tumor, and that it tends to have excellent metabolic stability.

The method for producing the above-mentioned compound according to the present invention (the compound represented by the general formula (1), the same applies hereinafter) and the pharmacologically acceptable salt thereof is not particularly limited. With starting materials, precursors, reagents, and solvents which are commercially available or synthesizable by a method known to those skilled in the art, it is possible to produce compounds of the present invention and the pharmacologically acceptable salt thereof by a combination of e.g. methods such as a wide variety of synthesizing methods known to those skilled in the art and methods which are, if necessary, an improved version of those methods. For example, it is possible to produce them by representative methods indicated as follows.

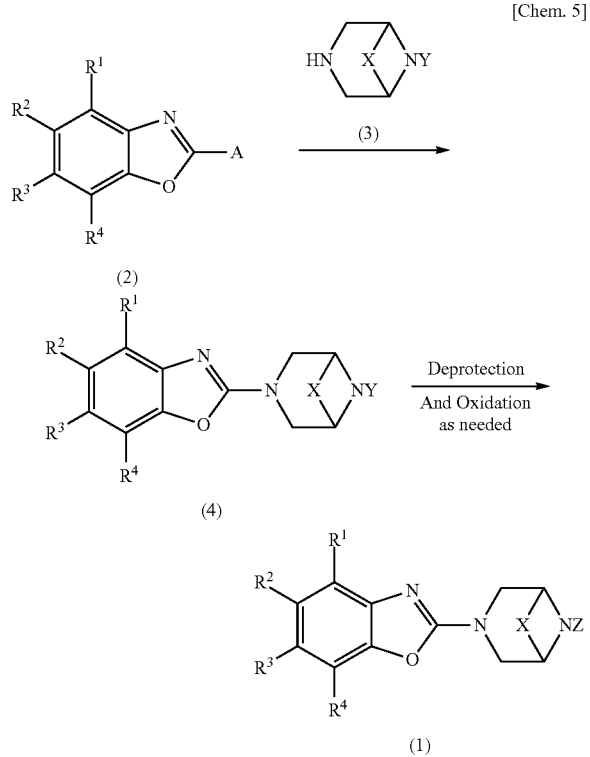

[Chem. 5]

In the above general formulae (2) to (4), $R^1$, $R^2$, $R^3$, $R^4$, and X have the same meanings as those of $R^1$, $R^2$, $R^3$, $R^4$, and X in the general formula (1), including preferred embodiments. In the above general formula (2), A represents a leaving group such as a halogen atom, a thiol group, a p-toluenesulfonyloxy group, a trifluoromethanesulfonyloxy group, or a phenoxy group. In the above general formula (3), Y represents a protecting group of amino group. In the above general formula (4), Y represents the same group as Y in the general formula (3). As the protecting group of amino group, it is possible to use, for example, a tert-butoxycarbonyl group and a benzyloxycarbonyl group described in "Protective Groups in Organic Synthesis (John Wiley and Sons, 1991)," written by T. W. Greene.

First, in a solvent, the compound represented by the general formula (4) was obtained from the compound represented by the general formula (2) with the treatment of 1 to 50 equivalents of the bicyclic diamine represented by the general formula (3) with respect to the number of moles of the compound represented by the general formula (2). Next, it is possible to obtain the compound represented by the general formula (1) by removing the protecting group Y (deprotection) and subsequently performing oxidation when necessary. In the present manufacture method, in the compound represented by the general formula (4) obtained in the above reaction, deprotection of the protecting group Y affords a compound in which Z in the general formula (1) is a hydrogen atom, and subsequent oxidation affords a compound in which Z in the general formula (1) is a hydroxyl group.

The solvent used for the above reaction is, for example, dichloromethane, chloroform, benzene, toluene, xylene, tetrahydrofuran, diethylether, dimethoxyethane, N,N-dimethylformamide, or dimethyl sulfoxide. In the above reaction, the reaction temperature is selected from a range of −78 to 200° C., preferably of −78 to 150° C., and the reaction time is in a range of 5 minutes to 48 hours, preferably 30 minutes to 20 hours. Additionally, for the purpose of promoting the above reaction or performing reaction under milder conditions, appropriate additives (for example, triethylamine or N,N-diisopropylethylamine) can be added to the above reaction.

Moreover, in the present manufacture method, in the compound represented by the general formula (4) obtained by the above reaction, it is possible to perform transformation of functional group on each of the substituents ($R^1$, $R^2$, $R^3$, and $R^4$) and convert it to another compound within the scope of the present invention. For example, functional groups are introduced by various coupling reactions with metal catalysts (for example, the Kumada-Tamao-Corriu coupling, the Migita-Kosugi-Stille coupling, the Suzuki-Miyaura coupling, the Negishi coupling, and the Buchwald-Hartwig coupling), oxidation reaction, reduction reaction, amidation reaction, hydrolysis reaction, nucleophilic reaction on a carbonyl compound, alkylation reaction, and dealkylation reaction.

The therapeutic agent of the present invention contains the above-mentioned compound according to the present invention or the pharmacologically acceptable salts thereof as an active ingredient. Since these compounds have particularly excellent PDE4 inhibitory activity, they are useful as therapeutic agents for diseases caused by PDE4, and particularly useful as therapeutic agents for at least one disease selected from the group consisting of inflammatory diseases, autoimmune diseases, fibrotic diseases, and cancer diseases. Examples of the inflammatory diseases include allergic conjunctivitis, dry eye, rhinitis, atopic dermatitis, asthma, COPD, alopecia areata, and lichen planus, examples of the autoimmune diseases include psoriasis (such as psoriatic arthritis and psoriasis vulgaris), Behcet's disease, inflammatory bowel diseases (such as Crohn's disease and ulcerative colitis), systemic lupus erythematosus, multiple sclerosis, rheumatoid arthritis, systemic scleroderma, vitiligo, and hidradenitis suppurativa, examples of the fibrotic diseases include interstitial pneumonia, idiopathic pulmonary fibrosis, non-alcoholic steatohepatitis, and muscular dystrophy, and examples of the cancer diseases include colorectal cancer, lung cancer, blood cancer, and brain tumor. Among these, the therapeutic agent of the present invention is more preferable as a therapeutic agent for treating at least one disease selected from the group consisting of psoriasis (such as psoriatic arthritis and psoriasis vulgaris), rhinitis, atopic dermatitis, allergic conjunctivitis, dry eye, asthma, COPD, Behcet's disease, inflammatory bowel diseases (such as Crohn's disease and ulcerative colitis), rheumatoid arthritis, idiopathic pulmonary fibrosis, non-alcoholic steatohepatitis, muscular dystrophy, alopecia areata, vitiligo, hidradenitis suppurativa, lichen planus, colorectal cancer, lung cancer, blood cancer, and brain tumor, and particularly preferable as a therapeutic agent for treating at least one disease selected from the group consisting of psoriasis (such as psoriatic arthritis and psoriasis vulgaris), atopic dermatitis, allergic conjunctivitis, asthma, COPD, rheumatoid arthritis, idiopathic pulmonary fibrosis, ulcerative colitis, non-alcoholic steatohepatitis, muscular dystrophy, alopecia areata, vitiligo, hidradenitis suppurativa, lichen planus, colorectal cancer, lung cancer, blood cancer, and brain tumor.

The therapeutic agent of the present invention may be administered in any of an oral administration route and a non-oral administration route, and can be administered to humans and animals other than humans. Thus, the therapeutic agent of the present invention can be a preparation of appropriate dosage form depending on the administration route. To be more specific, the preparation is, for example, an oral preparation such as a tablet, a pill, a capsule, a granule, a powder, an elixir, a suspension, an emulsion, or a syrup, or a non-oral preparation such as an injection, an inhalant, a preparation for rectal administration, a suppository, a lotion, a spray, an ointment, a cream, a patch, or a preparation for sustained release.

These types of preparations can be produced in a usual manner by use of carriers, surfactants, dispersants, and other preparation aids (such as excipients, disintegrators, binders, lubricants, and colorants) usually used as appropriate in the pharmaceutical field, and therefore, the therapeutic agent of the present invention may further contain one of these or two or more thereof in combination.

Examples of the carriers include solid carriers, liquid carriers, and gaseous carriers. Examples of the solid carriers include calcium carbonate. Examples of the liquid carriers include alcohols such as methanol, n-hexanol, and ethylene glycol; ketones such as acetone, methylethyl ketone, and cyclohexanone; aliphatic hydrocarbons such as n-hexane; aromatic hydrocarbons such as toluene, xylene, and methylnaphthalene; ethers such as diethyl ether, dioxane, and tetrahydrofuran; esters such as ethyl acetate; nitriles such as acetonitrile and isobutyronitrile; acid amides such as dimethylformamide and dimethylacetamide; vegetable oils such as soybean oil and cottonseed oil; dimethyl sulfoxide; and water. In addition, examples of the gaseous carriers include air, nitrogen, and carbon dioxide gas.

Examples of surfactants and dispersants for emulsification, dispersion, spreading, and the like include alkyl sulfate esters, alkyl (aryl) sulfonates, polyoxyalkylene alkyl (aryl) ethers, polyhydric alcohol esters, and lignin sulfonates.

In addition, examples of the auxiliary agent for improving the properties of the preparation include carboxymethyl cellulose, gum arabic, polyethylene glycol, calcium stearate, excipients, disintegrators, binders, lubricants, and colorants.

In the therapeutic agent of the present invention, the content of the compound according to the present invention or the pharmacologically acceptable salt thereof (the content of the compound according to the present invention, the content of the pharmacologically acceptable salt thereof, or, in the case of a mixture thereof, the total content of the mixture) cannot be generally specified because it is adjusted as appropriate depending on the administration purpose and the dosage form of the preparation. Nonetheless, the content is usually, in terms of educt, 0.01 to 70% by mass, preferably 0.05 to 50% by mass with respect to the total mass of the therapeutic agent.

In addition, the amount of the therapeutic agent of the present invention administered cannot be generally specified because it is determined as appropriate case by case in consideration of e.g. the ages, weights, sexes, and the difference in symptom of the patients. Nonetheless, the amount administered to an adult is usually, in terms of educt of the compound according to the present invention or the pharmacologically acceptable salt thereof (the compound according to the present invention, the pharmacologically acceptable salt thereof, or, in the case of a mixture thereof, the total thereof), 0.01 to 1000 mg, preferably 0.1 to 300 mg per day, and it is possible to administer the compound of the present invention or the pharmacologically acceptable salt thereof in one or several times a day.

EXAMPLES

The present invention is hereinafter described in further detail using Examples. Note that the present invention is not limited to these examples. Also, methods of manufacturing a raw compound used in Examples are described as reference examples. Note that these are also examples for specific explanation of the embodiments of the present invention. These examples do not limit the scope of the present invention, and it is apparent that various applications, variations, modifications, etc. can be made within a scope not departing from the scope of the present invention.

In the following description, the abbreviations in Examples and Reference Examples mean as listed below:
M: mol/L
DMSO: dimethyl sulfoxide
DMPU: N,N'-dimethylpropyleneurea
ESI: electrospray ionization
ee: enantiomeric excess
HPLC: high performance liquid chromatography
mCPBA: meta-chloroperoxybenzoic acid
MS: mass spectrum
n: normal
sec: secondary
tert: tertiary
TLC: thin-layer chromatography
UV: ultraviolet
LC-MS: liquid chromatography-mass spectrometry Reference Example 1

7-Bromo-5-isopropylbenzo[d]oxazole-2-thiol (a) 2-Bromo-4-isopropyl-6-nitrophenol 2.5 g of 2-bromo-4-isopropylphenol was dissolved in dichloromethane (50 mL), then concentrated sulfuric acid (0.8 mL, 1.3 equivalents) was added dropwise thereto at 0° C. over 5 minutes, and thereafter 70% nitric acid (0.7 mL, 1.0 equivalent) was added thereto over 5 minutes, followed by stirring at room temperature for 2 hours. The formation of the product was confirmed by TLC, and then solid sodium hydrogen carbonate was added to adjust the pH to 7. The reaction mixture was filtered and the filtrate was extracted using ethyl acetate. Thereafter, the organic phase was dried over anhydrous magnesium sulfate, followed by filtration, and thus obtaining as a crude product 2.8 g of the title compound obtained by vacuum concentration of the filtrate.
MS (ESI) m/z: 260 (M−H)⁻

(b) 2-Amino-6-bromo-4-isopropylphenol

Sodium dithionite (9.4 g, 5 equivalents) was dissolved in distilled water (32 mL) at 0° C., and ethanol (12 mL) solution of 2.8 g of 2-bromo-4-isopropyl-6-nitrophenol obtained in Reference Example 1(a) was added dropwise thereto over 10 minutes. Stirring was performed after the temperature rose to room temperature, and the formation of the product was confirmed by TLC. The reaction mixture was filtered and the solid was washed by ethanol. 20 mL of distilled water was added to the residue obtained by vacuum concentration of the filtrate, followed by stirring at 0° C. for 15 minutes. The obtained solid was filtered and washed by distilled water, followed by vacuum drying, thus obtaining 1.9 g of the title compound.
MS (ESI) m/z: 228 (M−H)⁻

(c) 7-Bromo-5-isopropylbenzo[d]oxazole-2-thiol 1.9 g of the 2-amino-6-bromo-4-isopropylphenol obtained in Reference Example 1(b) was dissolved in ethanol (14 mL), and then 0.5 M potassium hydroxide solution in ethanol (7.4 mL) and carbon disulfide (2.3 mL, 5 equivalents) were added thereto, followed by heating at 50° C. for 4 hours. The formation of the product was confirmed by TLC, and then distilled water (4 mL) and 6 M hydrochloric acid (4 mL) were added thereto at room temperature. The obtained solid was filtered, followed by vacuum drying, thus obtaining 1.5 g of the title compound.

Reference Example 2

7-Bromo-4-methylbenzo[d]oxazole-2-thiol (a) 6-Bromo-3-methyl-2-nitrophenol 1.5 g of the title compound was obtained from 2.5 g of 2-bromo-5-methylphenol using a similar method to Reference Example 1(a) except that the crude product was refined by silica gel column chromatography (hexane:ethyl acetate=95:5).
MS (ESI) m/z: 230 (M–H)⁻

(b) 2-Amino-6-bromo-3-methylphenol 610 mg of the title compound was obtained from 1.5 g of 6-bromo-3-methyl-2-nitrophenol obtained in Reference Example 2 (a), using a similar method to Reference Example 1(b).
MS (ESI) m/z: 200 (M–H)⁻

(c) 7-Bromo-4-methylbenzo[d]oxazole-2-thiol 360 mg of the title compound was obtained from 610 mg of 2-amino-6-bromo-3-methylphenol obtained in Reference Example 2 (b), using a similar method to Reference Example 1(c).

Reference Example 3

7-Bromo-4-(trifluoromethoxy)benzo[d]oxazole-2-thiol (a) 6-Bromo-2-nitro-3-(trifluoromethoxy)phenol 36 g of the title compound was obtained as a crude product from 30 g of 2-bromo-5-(trifluoromethoxy)phenol using a similar method to Reference Example 1(a).
MS (ESI) m/z: 300 (M–H)⁻

(b) 2-Amino-6-bromo-3-(trifluoromethoxy)phenol 18 g of the title compound was obtained from 36 g of 6-bromo-2-nitro-3-(trifluoromethoxy)phenol obtained in Reference Example 3(a), using a similar method to Reference Example 1(b).
MS (ESI) m/z: 272 (M+H)⁺

(c) 7-Bromo-4-(trifluoromethoxy)benzo[d]oxazole-2-thiol 9.5 g of the title compound was obtained from 21 g of 2-amino-6-bromo-3-(trifluoromethoxy)phenol obtained in Reference Example 3 (b), using a similar method to Reference Example 1(c).

Reference Example 4

7-Bromo-4-(trifluoromethyl)benzo[d]oxazole-2-thiol (a) 6-Bromo-2-nitro-3-(trifluoromethyl)phenol 5.2 g of the title compound was obtained as a crude product from 5 g of 2-bromo-5-(trifluoromethyl)phenol using a similar method to Reference Example 1(a).
MS (ESI) m/z: 284 (M–H)⁻

(b) 2-Amino-6-bromo-3-(trifluoromethyl)phenol 1.7 g of the title compound was obtained from 5.2 g of 6-bromo-2-nitro-3-(trifluoromethyl)phenol obtained in Reference Example 4(a), using a similar method to Reference Example 1(b).
MS (ESI) m/z: 256 (M+H)⁺

(c) 7-Bromo-4-(trifluoromethyl)benzo[d]oxazole-2-thiol 400 mg of the title compound was obtained from 1.7 g of 2-amino-6-bromo-3-(trifluoromethyl)phenol obtained in Reference Example 4(b), using a similar method to Reference Example 1(c).

Reference Example 5

N-(7-bromo-2-mercaptobenzo[d]oxazol-4-yl)acetamide (a) N-(4-bromo-3-hydroxyphenyl)acetamide 10 g of N-(3-hydroxyphenyl)acetamide was dissolved in acetic acid (80 mL), and then acetic acid solution (4.1 mL, 1.2 equivalents) of bromine was added thereto, followed by stirring at room temperature for 16 hours. The formation of the product was confirmed by TLC, then the reaction mixture was poured into distilled water under ice-cooling, followed by filtration, and thus obtaining 4 g of the title compound by purification of the residue obtained by vacuum concentration of the filtrate through silica gel column chromatography (hexane:ethyl acetate=3:2).
MS (ESI) m/z: 230 (M+H)⁺

(b) N-(4-bromo-3-hydroxy-2-nitrophenyl)acetamide 6.1 g of N-(4-bromo-3-hydroxyphenyl)acetamide obtained in Reference Example 5(a) was dissolved in concentrated sulfuric acid (140 mL), and then a liquid mixture of concentrated sulfuric acid (71 mL) and 70% nitric acid (1.4 mL, 1.2 equivalents) was added thereto at 0° C. over 25 minutes, followed by stirring at room temperature for 2 hours. The formation of the product was confirmed by TLC, and then the reaction mixture was poured into distilled water under ice-cooling, followed by extraction using ethyl acetate. Thereafter, the organic phase was dried over anhydrous magnesium sulfate, followed by filtration, and thus obtaining 6.9 g of the title compound as a crude product obtained by vacuum concentration of the filtrate.
MS (ESI) m/z: 273 (M–H)⁻

(c) N-(2-amino-4-bromo-3-hydroxyphenyl)acetamide 5 g of the title compound was obtained from 6.9 g of N-(4-bromo-3-hydroxy-2-nitrophenyl)acetamide obtained in Reference Example 5(b), using a similar method to Reference Example 1(b).
MS (ESI) m/z: 245 (M+H)⁺

(d) N-(7-bromo-2-mercaptobenzo[d]oxazol-4-yl) acetamide 2.5 g of the title compound was obtained from 5 g of N-(2-amino-4-bromo-3-hydroxyphenyl)acetamide obtained in Reference Example 5 (c), using a similar method to Reference Example 1(c).

Reference Example 6

7-Bromo-4-chlorobenzo[d]oxazole-2-thiol (a) 6-Bromo-3-chloro-2-nitrophenol 3.1 g of the title compound was obtained as a crude product from 2.5 g of 2-bromo-5-chlorophenol using a similar method to Reference Example 1(a).
MS (ESI) m/z: 252 (M+H)$^+$ (b) 2-Amino-6-bromo-3-chlorophenol 3.3 g of the title compound was obtained from 3.1 g of 6-bromo-3-chloro-2-nitrophenol obtained in Reference Example 6(a), using a similar method to Reference Example 1(b).
MS (ESI) m/z: 222 (M+H)$^+$ (c) 7-Bromo-4-chlorobenzo[d]oxazole-2-thiol 1.8 g of the title compound was obtained from 3.3 g of 2-amino-6-bromo-3-chlorophenol obtained in Reference Example 6(b), using a similar method to Reference Example 1(c).

Reference Example 7

7-Bromo-5-(methylthio)benzo[d]oxazole-2-thiol (a) 2-Bromo-4-(methylthio)phenol 2.5 g of 4-(methylthio)phenol was dissolved in dichloromethane (50 mL), then 47% hydrobromic acid (7.8 mL, 8 equivalents) was added thereto, followed by heating to 45° C., and 30% hydrogen peroxide solution (0.84 mL, 2 equivalents) was added dropwise thereto, followed by stirring at that temperature for 6 hours. The formation of the product was confirmed by TLC, and then the reaction mixture was poured into distilled water under ice-cooling, followed by extraction using ethyl acetate. Thereafter, the organic phase was dried over anhydrous sodium sulfate, followed by filtration, and thus obtaining 3.5 g of the title compound as a crude product obtained by vacuum concentration of the filtrate.
MS (ESI) m/z: 219 (M+H)$^+$ (b) 2-Bromo-4-(methylthio)-6-nitrophenol 1.5 g of the title compound was obtained as a crude product from 3.5 g of 2-bromo-4-(methylthio)phenol obtained in Reference Example 7(a), using a similar method to Reference Example 1(a).
MS (ESI) m/z: 264 (M+H)$^+$ (c) 2-Amino-6-bromo-4-(methylthio)phenol 3.2 g of the title compound was obtained from 3.8 g of 2-bromo-4-(methylthio)-6-nitrophenol obtained in Reference Example 7 (b), using a similar method to Reference Example 1(b).
MS (ESI) m/z: 234 (M+H)$^+$ (d) 7-Bromo-5-(methylthio)benzo[d]oxazole-2-thiol 2.4 g of the title compound was obtained from 3.2 g of 2-amino-6-bromo-4-(methylthio)phenol obtained in Reference Example 7 (c), using a similar method to Reference Example 1(c).

Reference Example 8

7-Bromo-5-(methylsulfinyl)benzo[d]oxazole-2-thiol (a) 2-Bromo-4-(methylsulfinyl)phenol 300 mg of the title compound was obtained from 1 g of 4-(methylsulfinyl)phenol using a similar method to Reference Example 9(a) except that the crude product was refined by silica gel column chromatography.
MS (ESI) m/z: 235 (M+H)$^+$ (b) 2-Bromo-4-(methylsulfinyl)-6-nitrophenol 2 g of the title compound was obtained as a crude product from 3.5 g of 2-bromo-4-(methylsulfinyl)phenol obtained in Reference Example 8 (a), using a similar method to Reference Example 1(a).
MS (ESI) m/z: 281 (M+2H)$^+$ (c) 2-Amino-6-bromo-4-(methylsulfinyl)phenol 3.2 g of the title compound was obtained from 3.8 g of 2-bromo-4-(methylsulfinyl)-6-nitrophenol obtained in Reference Example 8(b), using a similar method to Reference Example 1(b).
MS (ESI) m/z: 250 (M+H)$^+$ (d) 7-Bromo-5-(methylsulfinyl)benzo[d]oxazole-2-thiol 2.5 g of the title compound was obtained from 3.2 g of 2-amino-6-bromo-4-(methylsulfinyl)phenol obtained in Reference Example 8(c), using a similar method to Reference Example 1(c).

Reference Example 9

N-(7-bromo-2-mercaptobenzo[d]oxazol-5-yl)acetamide (a) N-(3-bromo-4-hydroxyphenyl)acetamide 1 g of N-(4-hydroxyphenyl)acetamide and chlorotrimethylsilane (0.16 mL, 0.2 equivalent) were dissolved in acetonitrile (20 mL), and then N-bromosuccinimide (1.29 g, 1.1 equivalents) was added thereto at 0° C., followed by stirring at room temperature for 14 hours. The formation of the product was confirmed by TLC, and then the reaction mixture was poured into distilled water under ice-cooling, followed by extraction using ethyl acetate. Thereafter, the organic phase was dried over anhydrous magnesium sulfate, followed by filtration, and thus obtaining 1 g of the title compound by purification of the residue obtained by vacuum concentration of the filtrate through silica gel column chromatography (hexane:ethyl acetate=3:2).

MS (ESI) m/z: 230 (M+H)$^+$ (b) N-(3-bromo-4-hydroxy-5-nitrophenyl)acetamide 2 g of the title compound was obtained as a crude product from 1.6 g of N-(3-bromo-4-hydroxyphenyl)acetamide obtained in Reference Example 9(a), using a similar method to Reference Example 1(a).

MS (ESI) m/z: 275 (M+H)$^+$ (c) N-(3-amino-5-bromo-4-hydroxyphenyl)acetamide 1.2 g of the title compound was obtained from 2 g of N-(3-bromo-4-hydroxy-5-nitrophenyl)acetamide obtained in Reference Example 9(b), using a similar method to Reference Example 1(b).

MS (ESI) m/z: 245 (M+H)$^+$ (d) N-(7-bromo-2-mercaptobenzo[d]oxazol-5-yl)acetamide 650 mg of the title compound was obtained from 1.2 g of N-(3-amino-5-bromo-4-hydroxyphenyl)acetamide obtained in Reference Example 9(c), using a similar method to Reference Example 1(c).

Reference Example 10

7-Bromo-5-(trifluoromethoxy)benzo[d]oxazole-2-thiol (a) 2-Bromo-6-nitro-4-(trifluoromethoxy)phenol 5.8 g of the title compound was obtained as a crude product from 5.2 g of 2-bromo-4-(trifluoromethoxy)phenol using a similar method to Reference Example 1(a).

MS (ESI) m/z: 300 (M–H)$^+$ (b) 2-Amino-6-bromo-4-(trifluoromethoxy)phenol 4.4 g of the title compound was obtained from 5.8 g of 2-bromo-6-nitro-4-(trifluoromethoxy)phenol obtained in Reference Example 10(a), using a similar method to Reference Example 1(b).

MS (ESI) m/z: 272 (M+H)$^+$ (c) 7-Bromo-5-(trifluoromethoxy)benzo[d]oxazole-2-thiol 5.0 g of the title compound was obtained from 4.4 g of 2-amino-6-bromo-4-(trifluoromethoxy)phenol obtained in Reference Example 10(b), using a similar method to Reference Example 1(c).

Reference Example 11

7-Bromo-2-mercaptobenzo[d]oxazole-5-sulfonamide (a) 3-Bromo-4-methoxybenzenesulfonyl chloride 10 g of 1-bromo-2-methoxybenzene was dissolved in chloroform (56 mL), and then chlorosulfuric acid (11 mL, 3 equivalents) was added thereto at –10° C., followed by stirring at room temperature for 1 hour. The formation of the product was confirmed by TLC, and then the reaction mixture was poured into distilled water under ice-cooling, followed by extraction using ethyl acetate. Thereafter, the organic phase was dried over anhydrous magnesium sulfate, followed by filtration, and thus obtaining as a crude product 14 g of the title compound by vacuum concentration of the filtrate.

MS (ESI) m/z: 285 (M+H)$^+$ (b) 3-Bromo-4-methoxybenzenesulfonamide 14 g of 3-bromo-4-methoxybenzenesulfonyl chloride obtained in Reference Example 11(a) was dissolved in dichloromethane (1000 mL), and then 0.5 M ammonia solution in 1,4-dioxane (518 mL) and triethylamine (26 mL) were added thereto at 0° C., followed by stirring at room temperature for 2 hours. The formation of the product was confirmed by TLC, and 5% aqueous solution of citric acid was added to stop the reaction, followed by extraction using ethyl acetate. Thereafter, the organic phase was dried over anhydrous magnesium sulfate, followed by filtration, and thus obtaining 11.4 g of the title compound as a crude product by vacuum concentration of the filtrate.

MS (ESI) m/z: 266 (M+H)$^+$ (c) 3-Bromo-4-hydroxybenzenesulfonamide 5 g of 3-bromo-4-methoxybenzenesulfonamide obtained in Reference Example 11(b) was dissolved in dichloromethane (1000 mL), and then 1 M boron tribromide solution in dichloromethane (56 mL, 3 equivalents) was added thereto at –78° C., followed by stirring at room temperature for 36 hours. The formation of the product was confirmed by TLC, and then distilled water was added to stop the reaction. Thereafter, the organic phase was dried over anhydrous magnesium sulfate, followed by filtration, and thus obtaining as a crude product 4 g of the title compound by vacuum concentration of the filtrate.

MS (ESI) m/z: 252 (M+H)$^+$ (d) 3-Bromo-4-hydroxy-5-nitrobenzenesulfonamide 2.4 g of the title compound was obtained as a crude product from 2.5 g of 3-bromo-4-hydroxybenzenesulfonamide obtained in Reference Example 11(c), using a similar method to Reference Example 5 (b).

MS (ESI) m/z: 297 (M+H)$^+$ (e) 3-Amino-5-bromo-4-hydroxybenzenesulfonamide 1.5 g of the title compound was obtained as a crude product from 5.6 g of 3-bromo-4-hydroxy-5-nitrobenzenesulfonamide obtained in Reference Example 11(d), using a similar method to Reference Example 1(b).

MS (ESI) m/z: 267 (M+H)$^+$ (f) 7-Bromo-2-mercaptobenzo[d]oxazole-5-sulfonamide 600 mg of the title compound was obtained from 1.5 g of 3-amino-5-bromo-4-hydroxybenzenesulfonamide obtained in Reference Example 11(e), using a similar method to Reference Example 1(c).

Reference Example 12

7-Bromo-5-methoxybenzo[d]oxazole-2-thiol (a) 2-Bromo-4-methoxy-6-nitrophenol 2.5 g of 2-bromo-4-methoxyphenol was dissolved in ethyl acetate (125 mL), and then 70% nitric acid (0.8 mL, 1.0 equivalent) was added thereto at 0° C. over 10 minutes, followed by stirring at room temperature for 10 hours. The formation of the product was confirmed by TLC, and then solid sodium hydrogen carbonate was added to adjust the pH to 7. The reaction mixture was filtered and the filtrate was extracted using ethyl acetate. Thereafter, the organic phase was dried over anhydrous magnesium sulfate, followed by filtration, and thus obtaining as a crude product 2.8 g of the title compound obtained by vacuum concentration of the filtrate.
MS (ESI) m/z: 248 (M+H)$^+$ (b) 2-Amino-6-bromo-4-methoxyphenol 1 g of the title compound was obtained from 1.2 g of 2-bromo-4-methoxy-6-nitrophenol obtained in Reference Example 12 (a), using a similar method to Reference Example 1(b).
MS (ESI) m/z: 218 (M+H)$^+$ (c) 7-Bromo-5-methoxybenzo[d]oxazole-2-thiol 600 mg of the title compound was obtained from 1 g of 2-amino-6-bromo-4-methoxyphenol obtained in Reference Example 12 (b), using a similar method to Reference Example 1(c).

Reference Example 13

7-Bromo-5-(2,2,2-trifluoroethoxy)benzo[d]oxazole-2-thiol (a) 1-(Benzyloxy)-4-(2,2,2-trifluoroethoxy)benzene 5 g of 4-(benzyloxy)phenol was dissolved in N,N-dimethylformamide (40 mL), and then potassium carbonate (10.3 g, 3 equivalents) and 2,2,2-trifluoroethyl p-toluenesulfonate (6.3 g, 2 equivalents) were added thereto, followed by stirring at 110° C. for 22 hours. The formation of the product was confirmed by TLC, and then distilled water was added to stop the reaction, followed by extraction using ethyl acetate. The organic phase was washed by distilled water and then dried over anhydrous magnesium sulfate, followed by filtration, and thus obtaining 4 g of the title compound by purification of the residue obtained by vacuum concentration of the filtrate through silica gel column chromatography (hexane:ethyl acetate=98:2).
MS (ESI) m/z: 283 (M+H)$^+$ (b) 4-(2,2,2-Trifluoroethoxy)phenol 500 mg of 1-(benzyloxy)-4-(2,2,2-trifluoroethoxy)benzene obtained in Reference Example 13(a) was dissolved in ethanol (10 mL), and then 10% Pd/C (300 mg) was added thereto under argon atmosphere. The reaction mixture was stirred under a hydrogen atmosphere (1 atm) at room temperature for 17 hours. The formation of the product was confirmed by TLC, and the reaction mixture was filtered through Celite®, thus obtaining the title compound as a crude product by vacuum concentration of the filtrate.
MS (ESI) m/z: 191 (M−H)$^−$ (c) 2-Bromo-4-(2,2,2-trifluoroethoxy)phenol 1.9 g of the title compound was obtained as a crude product from 1.2 g of 4-(2,2,2-trifluoroethoxy)phenol obtained in Reference Example 13 (b), using a similar method to Reference Example 9(a).
MS (ESI) m/z: 271 (M+H)$^+$ (d) 2-Bromo-6-nitro-4-(2,2,2-trifluoroethoxy)phenol 5.2 g of the title compound was obtained as a crude product from 5.1 g of 2-bromo-4-(2,2,2-trifluoroethoxy)phenol obtained in Reference Example 13(c), using a similar method to Reference Example 1(a).
MS (ESI) m/z: 314 (M−H)$^−$ (e) 2-Amino-6-bromo-4-(2,2,2-trifluoroethoxy)phenol 400 mg of the title compound was obtained from 634 mg of 2-bromo-6-nitro-4-(2,2,2-trifluoroethoxy)phenol obtained in Reference Example 13(d), using a similar method to Reference Example 1(b).
MS (ESI) m/z: 286 (M+H)$^+$ (f) 7-Bromo-5-(2,2,2-trifluoroethoxy)benzo[d]oxazole-2-thiol 2.1 g of the title compound was obtained from 4 g of 2-amino-6-bromo-4-(2,2,2-trifluoroethoxy)phenol obtained in Reference Example 13(e), using a similar method to Reference Example 1(c).

Reference Example 14

7-Bromo-4-methoxybenzo[d]oxazole-2-thiol (a) 3-Methoxy-2-nitrophenol 5 g of 2-nitrobenzene-1,3-diol was dissolved in N,N-dimethylformamide (75 mL), and then potassium carbonate (1.3 g, 0.3 equivalent) and methyl iodide (2.23 mL, 1.1 equivalents) were added thereto at 0° C., followed by stirring at room temperature for 30 minutes. The formation of the product was confirmed by TLC, and then distilled water was added to stop the reaction, followed by extraction using ethyl acetate. The organic phase was washed by 2 M hydrochloric acid (20 mL) and then dried over anhydrous magnesium sulfate, followed by filtration, and thus obtaining 1.6 g of the title compound by purification of the residue obtained by vacuum concentration of the filtrate through silica gel column chromatography (hexane:ethyl acetate=85:15).
MS (ESI) m/z: 168 (M−H)$^−$ (b) 6-Bromo-3-methoxy-2-nitrophenol 166 mg of the title compound was obtained from 250 mg of 3-methoxy-2-nitrophenol obtained in Reference Example 14 (a), using a similar method to Reference Example 9(a).
MS (ESI) m/z: 248 (M+H)$^+$ (c) 2-Amino-6-bromo-3-methoxyphenol 1 g of the title compound was obtained from 6.7 g of 6-bromo-3-methoxy-2-nitrophenol obtained in Reference Example 14 (b), using a similar method to Reference Example 1(b).

MS (ESI) m/z: 218 (M+H)$^+$ (d) 7-Bromo-4-methoxybenzo[d]oxazole-2-thiol 635 mg of the title compound was obtained from 1 g of 2-amino-6-bromo-3-methoxyphenol obtained in Reference Example 14(c), using a similar method to Reference Example 1(c).

Reference Example 15

Ethyl 7-bromo-2-mercaptobenzo[d]oxazole-5-carboxylate (a) Ethyl 3-bromo-4-hydroxybenzoate 5 g of 3-bromo-4-hydroxybenzoic acid was dissolved in ethanol (60 mL), and then concentrated sulfuric acid (7.3 mL, 6 equivalents) was added thereto at 0° C., followed by stirring at 90° C. for 24 hours. The formation of the product was confirmed by TLC, and the reaction mixture was subjected to vacuum concentration. The obtained residue was dissolved in ethyl acetate, and then saturated sodium hydrogen carbonate aqueous solution was added thereto. Thereafter, the organic phase was dried over anhydrous magnesium sulfate, followed by filtration, and thus obtaining 5.4 g of the title compound by purification of the residue obtained by vacuum concentration of the filtrate through silica gel column chromatography (hexane:ethyl acetate=70:30).

MS (ESI) m/z: 245 (M+H)$^+$ (b) Ethyl 3-bromo-4-hydroxy-5-nitrobenzoate 6.0 g of the title compound was obtained as a crude product from 5.4 g of ethyl 3-bromo-4-hydroxybenzoate obtained in Reference Example 15 (a), using a similar method to Reference Example 1(a).

MS (ESI) m/z: 290 (M+H)$^+$ (c) Ethyl 3-amino-5-bromo-4-hydroxybenzoate 4.0 g of the title compound was obtained from 6.0 g of ethyl 3-bromo-4-hydroxy-5-nitrobenzoate obtained in Reference Example 15 (b), using a similar method to Reference Example 1(b).

MS (ESI) m/z: 260 (M+H)$^+$ (d) Ethyl 7-bromo-2-mercaptobenzo[d]oxazole-5-carboxylate 4.1 g of the title compound was obtained from 4.0 g of ethyl 3-amino-5-bromo-4-hydroxybenzoate obtained in Reference Example 15(c), using a similar method to Reference Example 1(c).

Reference Example 16

Ethyl 7-bromo-2-mercaptobenzo[d]oxazole-4-carboxylate (a) 4-Bromo-3-hydroxy-2-nitrobenzoic acid 2.7 g of the title compound was obtained as a crude product from 2.5 g of 4-bromo-3-hydroxybenzoic acid using a similar method to Reference Example 5 (b).

MS (ESI) m/z: 262 (M+H)$^+$ (b) Ethyl 4-bromo-3-hydroxy-2-nitrobenzoate 1.3 g of the title compound was obtained as a crude product from 2.7 g of 4-bromo-3-hydroxy-2-nitrobenzoic acid obtained in Reference Example 16(a), using a similar method to Reference Example 15(a).

MS (ESI) m/z: 288 (M−H)$^−$ (c) Ethyl 2-amino-4-bromo-3-hydroxybenzoate 580 mg of the title compound was obtained from 1.3 g of ethyl 4-bromo-3-hydroxy-2-nitrobenzoate obtained in Reference Example 16(b), using a similar method to Reference Example 1(b).

MS (ESI) m/z: 260 (M+H)$^+$ (d) Ethyl 7-bromo-2-mercaptobenzo[d]oxazole-4-carboxylate 245 mg of the title compound was obtained from 580 mg of ethyl 2-amino-4-bromo-3-hydroxybenzoate obtained in Reference Example 16(c), using a similar method to Reference Example 1(c).

Reference Example 17

(7-Bromo-2-mercaptobenzo[d]oxazol-4-yl)methanol 500 mg of ethyl 7-bromo-2-mercaptobenzo[d]oxazole-4-carboxylate obtained in Reference Example 16 was dissolved in 10 mL of tetrahydrofuran, and then 1.0 M solution of lithium aluminum hydride in tetrahydrofuran (2.4 mL, 1.5 equivalents) was added thereto at 0° C., followed by stirring at room temperature for 2 hours. The formation of the product was confirmed by TLC, and saturated aqueous solution of sodium sulfate was added to stop the reaction, followed by extraction using ethyl acetate. The aqueous layer was rendered acidic using 1 M aqueous solution of hydrochloric acid, followed by extraction using ethyl acetate. Thereafter, the obtained organic phase was mixed, washed by distilled water, and dried over anhydrous magnesium sulfate, followed by filtration, and thus obtaining 240 mg of the title compound as a crude product by vacuum concentration of the filtrate.

Reference Example 18

1-(7-Bromo-2-mercaptobenzo[d]oxazol-5-yl)-2,2,2-trifluoroethan-1-ol (a) 1-(3-Bromo-4-methoxyphenyl)-2,2,2-trifluoroethanone 1 g of 2,2,2-trifluoro-1-(4-methoxyphenyl)ethan-1-one was dissolved in carbon tetrachloride (9.5 mL), and then silver oxide (II) (72 mg, 0.12 equivalent), concentrated sulfuric acid (0.47 mL), and bromine (0.26 mL, 1.03 equivalents) were added thereto, followed by stirring at 65° C. for 17 hours. The formation of the product was confirmed by TLC, and then the reaction mixture was poured into distilled water under ice-cooling, followed by extraction using dichloromethane. Thereafter, the organic phase was dried over anhydrous sodium sulfate, followed by filtration, and thus obtaining 1.3 g of the title compound by purification of the residue obtained by vacuum concentration of the filtrate through silica gel column chromatography (hexane:ethyl acetate=95:5).

MS (ESI) m/z: 283 (M+H)$^+$ (b) 1-(3-Bromo-4-hydroxyphenyl)-2,2,2-trifluoroethanone 1.3 g of 1-(3-bromo-4-methoxyphenyl)-2,2,2-trifluoroethanone obtained in Reference Example 18(a) was dissolved in N,N-dimethylformamide (13 mL), and then lithium chloride (701 mg, 3.6 equivalents) was added thereto, followed by stirring at 140° C. for 2 hours. The formation of the product was confirmed by TLC, and the reaction mixture was subjected to vacuum concentration. The obtained residue was dissolved in methanol, and then the pH was adjusted to 3 using methanol solution of hydrochloric acid. The liquid mixture was subjected to vacuum concentration again, thus obtaining 1.1 g of the title compound by purification of the obtained residue through silica gel column chromatography (hexane:ethyl acetate=4:1).

MS (ESI) m/z: 269 (M+H)$^+$ (c) 1-(3-Bromo-4-hydroxy-5-nitrophenyl)-2,2,2-trifluoroethanone 1.0 g of the title compound was obtained as a crude product from 1.1 g of 1-(3-bromo-4-hydroxyphenyl)-2,2,2-trifluoroethanone obtained in Reference Example 18 (b), using a similar method to Reference Example 1(a).

MS (ESI) m/z: 312 (M−H)$^-$ (d) 2-Bromo-6-nitro-4-(2,2,2-trifluoro-1-hydroxyethyl)phenol 1.0 g of 1-(3-bromo-4-hydroxy-5-nitrophenyl)-2,2,2-trifluoroethanone obtained in Reference Example 18(c) was dissolved in methanol (10 mL), and then sodium borohydride (129 mg, 1.1 equivalents) was added thereto at 0° C., followed by stirring at that temperature for 1 hour. The formation of the product was confirmed by TLC, and then distilled water under ice-cooling was added to stop the reaction, followed by extraction using ethyl acetate. Thereafter, the organic phase was dried over anhydrous magnesium sulfate, followed by filtration, and thus obtaining as a crude product 900 mg of the title compound by vacuum concentration of the filtrate.

MS (ESI) m/z: 314 (M−H)$^-$ (e) 2-Amino-6-bromo-4-(2,2,2-trifluoro-1-hydroxyethyl)phenol 650 mg of the title compound was obtained from 900 mg of 2-bromo-6-nitro-4-(2,2,2-trifluoro-1-hydroxyethyl)phenol obtained in Reference Example 18 (d), using a similar method to Reference Example 1(b).

MS (ESI) m/z: 284 (M+H)$^+$ (f) 1-(7-Bromo-2-mercaptobenzo[d]oxazol-5-yl)-2,2,2-trifluoroethan-1-ol 700 mg of the title compound was obtained from 925 mg of 2-amino-6-bromo-4-(2,2,2-trifluoro-1-hydroxyethyl)phenol obtained in Reference Example 18(e), using a similar method to Reference Example 1(c).

Reference Example 19

Ethyl 7-bromo-2-mercapto-4-(trifluoromethyl)benzo[d]oxazole-5-carboxylate (a) 5-Bromo-4-hydroxy-2-(trifluoromethyl)benzoic acid 3.8 g of the title compound was obtained as a crude product from 5.0 g of 4-hydroxy-2-(trifluoromethyl)benzoic acid using a similar method to Reference Example 7 (a).

MS (ESI) m/z: 283 (M−H)$^-$ (b) Ethyl 5-bromo-4-hydroxy-2-(trifluoromethyl)benzoate 3.8 g of the title compound was obtained as a crude product from 3.8 g of 5-bromo-4-hydroxy-2-(trifluoromethyl)benzoic acid obtained in Reference Example 19(a), using a similar method to Reference Example 15(a) except that the purification by silica gel column chromatography was not performed.

(c) Ethyl 5-bromo-4-hydroxy-3-nitro-2-(trifluoromethyl)benzoate 3.8 g of the title compound was obtained as a crude product from 3.8 g of ethyl 5-bromo-4-hydroxy-2-(trifluoromethyl)benzoate obtained in Reference Example 19(b), using a similar method to Reference Example 1(a).

MS (ESI) m/z: 359 (M+2H)$^+$ (d) Ethyl 3-amino-5-bromo-4-hydroxy-2-(trifluoromethyl)benzoate 2.7 g of the title compound was obtained from 3.8 g of ethyl 5-bromo-4-hydroxy-3-nitro-2-(trifluoromethyl)benzoate obtained in Reference Example 19(c), using a similar method to Reference Example 1(b).

MS (ESI) m/z: 328 (M+H)$^+$ (e) Ethyl 7-bromo-2-mercapto-4-(trifluoromethyl)benzo[d]oxazole-5-carboxylate 1.6 g of the title compound was obtained from 2.7 g of ethyl 3-amino-5-bromo-4-hydroxy-2-(trifluoromethyl)benzoate obtained in Reference Example 19(d), using a similar method to Reference Example 1(c).

Reference Example 20

Ethyl 7-bromo-2-mercapto-4-(trifluoromethoxy)benzo[d]oxazole-5-carboxylate (a) Triisopropyl (3-(trifluoromethoxy)phenoxy)silane 5 g of 3-(trifluoromethoxy)phenol and imidazole (5.7 g, 3 equivalents) were dissolved in N,N-dimethylformamide (13 mL), and then chlorotriisopropylsilane (12 mL, 2 equivalents) was added thereto, followed by stirring at room temperature for 4 hours. The formation of the product was confirmed by TLC, and then ice-cooled distilled water was added to stop the reaction, followed by extraction using ethyl acetate. Thereafter, the organic phase was dried over anhydrous magnesium sulfate, followed by filtration, and thus obtaining 8.1 g of the title compound by purification of the residue obtained by vacuum concentration of the filtrate through silica gel column chromatography (hexane).

(b) 2-(Trifluoromethoxy)-4-((triisopropylsilyl)oxy) benzoic acid 8.1 g of triisopropyl (3-(trifluoromethoxy)phenoxy)silane obtained in Reference Example 20(a) and N,N,N',N'-tetramethylethylenediamine (3.6 mL, 1 equivalent) were dissolved in tetrahydrofuran (162 mL), and then 1.5 M solution of sec-butyllithium in cyclohexane (24 mL, 1.5 equivalents) was added dropwise thereto at −78° C. over 20 minutes. Stirring was performed at that temperature for 2 hours, followed by further stirring at −40° C. for 1 hour. The reaction mixture was cooled to −78° C., and carbon dioxide gas was added thereto over 2 hours. After the temperature was raised to 0° C., the formation of the product was confirmed by TLC. Thereafter, saturated aqueous solution of ammonium chloride was added to stop the reaction, and the pH was adjusted to 2 using 6 M hydrochloric acid. The reaction mixture was extracted using ethyl acetate, and the organic phase was washed by distilled water and dried over anhydrous magnesium sulfate, followed by filtration, thus obtaining 9 g of the title compound as a crude product by vacuum concentration of the filtrate.

MS (ESI) m/z: 377 (M−H)⁻

(c) Ethyl 4-hydroxy-2-(trifluoromethoxy)benzoate 2.3 g of the title compound was obtained from 9 g of 2-(trifluoromethoxy)-4-((triisopropylsilyl)oxy)benzoic acid obtained in Reference Example 20 (b), using a similar method to Reference Example 15 (a).

MS (ESI) m/z: 248 (M−2H)⁻

(d) Ethyl 5-bromo-4-hydroxy-2-(trifluoromethoxy)benzoate 3.1 g of the title compound was obtained from 3.6 g of ethyl 4-hydroxy-2-(trifluoromethoxy)benzoate obtained in Reference Example 20(c), using a similar method to Reference Example 9(a).

MS (ESI) m/z: 326 (M−2H)⁻

(e) Ethyl 5-bromo-4-hydroxy-3-nitro-2-(trifluoromethoxy)benzoate 2.4 g of the title compound was obtained as a crude product from 1.4 g of ethyl 5-bromo-4-hydroxy-2-(trifluoromethoxy)benzoate obtained in Reference Example 20(d), using a similar method to Reference Example 1(a).

MS (ESI) m/z: 372 (M−H)⁻

(f) Ethyl 3-amino-5-bromo-4-hydroxy-2-(trifluoromethoxy)benzoate 1.5 g of the title compound was obtained from 2.4 g of ethyl 5-bromo-4-hydroxy-3-nitro-2-(trifluoromethoxy)benzoate obtained in Reference Example 20(e), using a similar method to Reference Example 1(b).

MS (ESI) m/z: 344 (M+H)⁺

(g) Ethyl 7-bromo-2-mercapto-4-(trifluoromethoxy) benzo[d]oxazole-5-carboxylate 980 mg of the title compound was obtained from 1.5 g of ethyl 3-amino-5-bromo-4-hydroxy-2-(trifluoromethoxy) benzoate obtained in Reference Example 20(f), using a similar method to Reference Example 1(c).

Reference Example 21

1-(7-Bromo-2-mercaptobenzo[d]oxazol-4-yl)-2,2,2-trifluoroethan-1-ol (a) Methyl 4-bromo-3-hydroxybenzoate 52 g of the title compound was obtained from 50 g of 4-bromo-3-hydroxybenzoic acid using a similar method to Reference Example 15 (a) except that methanol was used instead of ethanol.

MS (ESI) m/z: 231 (M+H)⁺

(b) 2-Bromo-5-(hydroxymethyl)phenol 26.8 g of methyl 4-bromo-3-hydroxybenzoate obtained in Reference Example 21(a) was dissolved in tetrahydrofuran (537 mL), and then lithium aluminum hydride (6.6 g, 1.5 equivalents) was added thereto at 0° C. over 15 minutes, followed by stirring at room temperature for 17 hours. After the formation of the product was confirmed by TLC, saturated aqueous solution of sodium sulfate was added at 0° C. to stop the reaction, and the pH was adjusted to 2 using 6 M hydrochloric acid. The reaction mixture was extracted using ethyl acetate, and the organic phase was washed by distilled water and dried over anhydrous magnesium sulfate, followed by filtration, thus obtaining 20 g of the title compound by purification of the residue obtained by vacuum concentration of the filtrate through silica gel column chromatography (hexane:ethyl acetate=7:3).

MS (ESI) m/z: 201 (M−H)⁻

(c) 4-Bromo-3-hydroxybenzaldehyde 40 g of 2-bromo-5-(hydroxymethyl)phenol obtained in Reference Example 21(b) was dissolved in dichloromethane (4000 mL), and then Celite® (150 g) and pyridinium chlorochromate (106 g, 2.5 equivalents) were added thereto at 0° C. over 45 minutes, followed by stirring at room temperature for 2 hours. The formation of the product was confirmed by TLC, and then the reaction mixture was filtered and washed by dichloromethane, thus obtaining 28 g of the title compound by purification of the residue obtained by vacuum concentration of the filtrate through silica gel column chromatography (hexane:ethyl acetate=7:3).

MS (ESI) m/z: 201 (M+H)⁺

(d) 2-Bromo-5-(2,2,2-trifluoro-1-hydroxyethyl)phenol 15 g of 4-bromo-3-hydroxybenzaldehyde obtained in Reference Example 21(c) was dissolved in N,N-dimethylformamide (300 mL), and then trifluoromethyltrimethylsilane (33 mL, 3 equivalents) and potassium carbonate (3.1 g, 0.3 equivalent) were added thereto at 0° C., followed by stirring at room temperature for 2.5 hours. The formation of the product was confirmed by TLC, and then distilled water was added thereto at 0° C., followed by stirring at room temperature for 15 hours. After the reaction mixture was extracted using ethyl acetate, the organic phase was washed by distilled water and dried over anhydrous magnesium sulfate, followed by filtration, and thus obtaining 16 g of the title compound by purification of the residue obtained by vacuum concentration of the filtrate through silica gel column chromatography (hexane:ethyl acetate=7:3).
MS (ESI) m/z: 271 (M+H)$^+$ (e) 6-Bromo-2-nitro-3-(2,2,2-trifluoro-1-hydroxyethyl)phenol 18 g of the title compound was obtained as a crude product from 25 g of 2-bromo-5-(2,2,2-trifluoro-1-hydroxyethyl)phenol obtained in Reference Example 21(d), using a similar method to Reference Example 1(a).
MS (ESI) m/z: 316 (M+H)$^+$ (f) 2-Amino-6-bromo-3-(2,2,2-trifluoro-1-hydroxyethyl)phenol 11.6 g of the title compound was obtained from 18 g of 6-bromo-2-nitro-3-(2,2,2-trifluoro-1-hydroxyethyl)phenol obtained in Reference Example 21(e), using a similar method to Reference Example 1(b).
MS (ESI) m/z: 286 (M+H)$^+$ (g) 1-(7-Bromo-2-mercaptobenzo[d]oxazol-4-yl)-2,2,2-trifluoroethan-1-ol 6.3 g of the title compound was obtained from 11.6 g of 2-amino-6-bromo-3-(2,2,2-trifluoro-1-hydroxyethyl)phenol obtained in Reference Example 21(f), using a similar method to Reference Example 1(c).

Reference Example 22

Methyl 7-bromo-2-mercaptobenzo[d]oxazole-4-carboxylate (a) Methyl 4-bromo-3-hydroxy-2-nitrobenzoate 12.7 g of the title compound was obtained as a crude product from 13 g of 4-bromo-3-hydroxy-2-nitrobenzoic acid obtained in Reference Example 16(a), using a similar method to Reference Example 15(a) except that methanol was used instead of ethanol.
MS (ESI) m/z: 276 (M+H)$^+$ (b) Methyl 2-amino-4-bromo-3-hydroxybenzoate 5.4 g of the title compound was obtained from 12.7 g of methyl 4-bromo-3-hydroxy-2-nitrobenzoate obtained in Reference Example 22(a), using a similar method to Reference Example 1(b).
MS (ESI) m/z: 246 (M+H)$^+$ (c) Methyl 7-bromo-2-mercaptobenzo[d]oxazole-4-carboxylate 2.5 g of the title compound was obtained from 5.4 g of methyl 2-amino-4-bromo-3-hydroxybenzoate obtained in Reference Example 22 (b), using a similar method to Reference Example 1(c).

Reference Example 23

4-(Benzyloxy)-7-bromobenzo[d]oxazole-2-thiol (a) (((2-Nitro-1,3-phenylene)bis(oxy))bis(methylene))dibenzene 5 g of 2-nitroresorcinol was dissolved in N,N-dimethylformamide (88 mL), and then benzylbromide (8.4 mL, 2.2 equivalents) and caesium carbonate (25 g, 2.4 equivalents) were added thereto, followed by stirring at room temperature for 12 hours. The formation of the product was confirmed by TLC, and then ethyl acetate was added thereto. The organic phase was washed by 1% aqueous solution of hydrochloric acid and then washed again by distilled water. The organic phase was dried over anhydrous magnesium sulfate, followed by filtration. Hexane was added to the residue obtained by vacuum concentration of the filtrate and the precipitated solid was collected by filtration, thus obtaining 10 g of the title compound.
MS (ESI) m/z: 336 (M+H)$^+$ (b) 3-(Benzyloxy)-2-nitrophenol 10 g of (((2-nitro-1,3-phenylene)bis(oxy))bis(methylene))dibenzene obtained in Reference Example 23(a) was dissolved in dichloromethane (270 mL), and then 1.0 M solution of boron trichloride in heptane (45 mL, 1.5 equivalents) was added thereto at −78° C., followed by stirring at −78° C. for 1 hour. After the formation of the product was confirmed by TLC, methanol was added thereto over 10 minutes, the temperature was raised to room temperature, and distilled water was added thereto. This mixture was extracted twice using dichloromethane and the organic phase was dried over anhydrous magnesium sulfate, followed by filtration, and thus obtaining 4.7 g of the title compound by purification of the residue obtained by vacuum concentration of the filtrate through silica gel column chromatography (hexane:ethyl acetate=9.5:0.5).
MS (ESI) m/z: 244 (M−H)$^-$ (c) 3-(Benzyloxy)-6-bromo-2-nitrophenol 22 g of the title compound was obtained from 20 g of 3-(benzyloxy)-2-nitrophenol obtained in Reference Example 23 (b), using a similar method to Reference Example 9(a).
MS (ESI) m/z: 322 (M−H)$^-$ (d) 2-Amino-3-(benzyloxy)-6-bromophenol 28 g of the title compound was obtained from 22 g of 3-(benzyloxy)-6-bromo-2-nitrophenol obtained in Reference Example 23(c), using a similar method to Reference Example 1(b).
MS (ESI) m/z: 292 (M−H)$^-$ (e) 4-(Benzyloxy)-7-bromobenzo[d]oxazole-2-thiol 28 g of the title compound was obtained from 25 g of 2-amino-3-(benzyloxy)-6-bromophenol obtained in Reference Example 23 (d), using a similar method to Reference Example 1(c).

Reference Example 24

7-Bromo-4-((tert-butyldimethylsilyl)oxy)benzo[d]oxazole-2-thiol

(a) 3-((tert-Butyldimethylsilyl)oxy)-2-nitrophenol 5.0 g of 2-nitroresorcinol and imidazole (2.7 g, 1.2 equivalents) were dissolved in tetrahydrofuran (160 mL), and then tert-butyldimethylchlorosilane (4.9 g, 1.0 equivalent) was added thereto at 0° C., followed by stirring at room temperature for 30 minutes and thereafter by stirring at 65° C. for 3 hours. The formation of the product was confirmed by TLC, and then distilled water was added over 10 minutes to stop the reaction, followed by extraction using ethyl acetate three times. Thereafter, the organic phase was dried over anhydrous magnesium sulfate, followed by filtration, and thus obtaining 4.0 g of the title compound by purification of the residue obtained by vacuum concentration of the filtrate through silica gel column chromatography (hexane:ethyl acetate=9:1).

MS (ESI) m/z: 268 (M−H)⁻

(b) 6-Bromo-3-((tert-butyldimethylsilyl)oxy)-2-nitrophenol 3.6 g of the title compound was obtained from 4.0 g of 3-((tert-butyldimethylsilyl)oxy)-2-nitrophenol obtained in Reference Example 24 (a), using a similar method to Reference Example 9(a).

MS (ESI) m/z: 346 (M−H)⁻

(c) 2-Amino-6-bromo-3-((tert-butyldimethylsilyl)oxy)phenol 3.0 g of the title compound was obtained from 3.6 g of 6-bromo-3-((tert-butyldimethylsilyl)oxy)-2-nitrophenol obtained in Reference Example 24 (b), using a similar method to Reference Example 1(b).

MS (ESI) m/z: 318 (M+H)⁺

(d) 7-Bromo-4-((tert-butyldimethylsilyl)oxy)benzo[d]oxazole-2-thiol 2.5 g of the title compound was obtained from 3.0 g of 2-amino-6-bromo-3-((tert-butyldimethylsilyl)oxy)phenol obtained in Reference Example 24(c), using a similar method to Reference Example 1(c).

Example 1

2-(3,8-Diazabicyclo[3.2.1]octan-3-yl)-5-chloro-7-(thiazol-2-yl)-4-(trifluoromethoxy)benzo[d]oxazole

(a) tert-Butyl 3-(7-bromo-5-chloro-4-(trifluoromethoxy)benzo[d]oxazol-2-yl)-3,8-diazabicyclo[3.2.1]octane-8-carboxylate 700 mg of 7-bromo-5-chloro-4-(trifluoromethoxy)benzo[d]oxazole-2-thiol (the compound of Reference Example 12 in International Publication No. Wo 2015/005429) and tert-butyl 3,8-diazabicyclo[3.2.1]octane-8-carboxylate (512 mg, 1.2 equivalents) were dissolved in m-xylene (5 mL), followed by stirring overnight in an oil bath at 120° C. The formation of the product was confirmed by TLC (eluent, hexane:ethyl acetate=1:1), and then 1 M aqueous solution of sodium hydroxide was added thereto, followed by extraction using ethyl acetate. Thereafter, the organic phase was dried over anhydrous magnesium sulfate, followed by filtration, and thus obtaining 967 mg of the title compound by purification of the residue obtained by vacuum concentration of the filtrate through silica gel column chromatography (hexane; then hexane:ethyl acetate=4:1).

(b) tert-Butyl 3-(5-chloro-7-(thiazol-2-yl)-4-(trifluoromethoxy)benzo[d]oxazol-2-yl)-3,8-diazabicyclo[3.2.1]octane-8-carboxylate 500 mg of tert-butyl 3-(7-bromo-5-chloro-4-(trifluoromethoxy)benzo[d]oxazol-2-yl)-3,8-diazabicyclo[3.2.1]octane-8-carboxylate obtained in Example 1(a) was dissolved in toluene (3.2 mL), and 0.5 M solution of 2-thiazolylzinc bromide in tetrahydrofuran (3.8 mL, 2 equivalents) and [1,1'-bis(diphenylphosphino)ferrocene]palladium(II) dichloride·dichloromethane complex (155 mg, 0.2 equivalent) were added thereto, followed by stirring for 6 hours in an oil bath at 90° C. under an argon atmosphere. Saturated sodium hydrogen carbonate aqueous solution was added to the reaction mixture, and the mixture was filtered through Celite®. After the filtrate was extracted using ethyl acetate, the organic phase was dried over anhydrous magnesium sulfate, followed by filtration, and thus obtaining 424 mg of the title compound by purification of the residue obtained by vacuum concentration of the filtrate through silica gel column chromatography (hexane; then hexane:ethyl acetate=4:1).

(c) 2-(3,8-Diazabicyclo[3.2.1]octan-3-yl)-5-chloro-7-(thiazol-2-yl)-4-(trifluoromethoxy)benzo[d]oxazole 420 mg of tert-butyl 3-(5-chloro-7-(thiazol-2-yl)-4-(trifluoromethoxy)benzo[d]oxazol-2-yl)-3,8-diazabicyclo[3.2.1]octane-8-carboxylate obtained in Example 1(b) was dissolved in chloroform (7.9 mL) and trifluoroacetic acid (3 mL), followed by stirring at room temperature for 3 hours. Saturated sodium hydrogen carbonate aqueous solution was added to the reaction mixture, followed by extraction using ethyl acetate. Thereafter, the organic phase was dried over anhydrous magnesium sulfate, followed by filtration, and thus obtaining 340 mg of the title compound by purification of the residue obtained by vacuum concentration of the filtrate through silica gel column chromatography (chloroform; then chloroform:methanol:aqueous solution of ammonia=4:1:0.1).

Example 2

2-(3,9-Diazabicyclo[3.3.1]nonan-3-yl)-5-chloro-7-(thiazol-2-yl)-4-(trifluoromethoxy)benzo[d]oxazole

(a) tert-Butyl 3-(7-bromo-5-chloro-4-(trifluoromethoxy)benzo[d]oxazol-2-yl)-3,9-diazabicyclo[3.3.1]nonane-9-carboxylate 280 mg of the title compound was obtained from 250 mg of 7-bromo-5-chloro-4-(trifluoromethoxy)benzo[d]oxazole-2-thiol using a similar method to Example 1(a) except that tert-butyl 3,9-diazabicyclo[3.3.1]nonane-9-carboxylate was used instead of tert-butyl 3,8-diazabicyclo[3.2.1]octane-8-carboxylate.

(b) tert-Butyl 3-(5-chloro-7-(thiazol-2-yl)-4-(trifluoromethoxy)benzo[d]oxazol-2-yl)-3,9-diazabicyclo[3.3.1]nonane-9-carboxylate 150 mg of tert-butyl 3-(7-bromo-5-chloro-4-(trifluoromethoxy)benzo[d]oxazol-2-yl)-3,9-diazabicyclo[3.3.1]nonane-9-carboxylate obtained in Example 2(a), bis(triphenylphosphine)palladium(II) dichloride (19 mg, 0.1 equivalent), and 2-(tributylstannyl)thiazole (0.12 mL, 2.0 equivalents) were dissolved in 1,4-dioxane, followed by stirring for 29 hours in an oil bath at 130° C. under an argon atmosphere. The reaction mixture was filtered through Celite®, thus obtaining 100 mg of the title compound by purification of the residue obtained by vacuum concentration of the filtrate through silica gel column chromatography (hexane:ethyl acetate=93:7).

(c) 2-(3,9-Diazabicyclo[3.3.1]nonan-3-yl)-5-chloro-7-(thiazol-2-yl)-4-(trifluoromethoxy)benzo[d]oxazole 100 mg of the title compound was obtained from 200 mg of tert-butyl 3-(5-chloro-7-(thiazol-2-yl)-4-(trifluoromethoxy)benzo[d]oxazol-2-yl)-3,9-diazabicyclo[3.3.1]nonane-9-carboxylate obtained in Example 2 (b), using a similar method to Example 1(c).

Example 3

2-(3,6-Diazabicyclo[3.1.1]heptan-3-yl)-5-chloro-7-(thiazol-2-yl)-4-(trifluoromethoxy)benzo[d]oxazole (a) tert-Butyl 3-(7-bromo-5-chloro-4-(trifluoromethoxy)benzo[d]oxazol-2-yl)-3,6-diazabicyclo[3.1.1]heptane-6-carboxylate 347 mg of the title compound was obtained from 300 mg of 7-bromo-5-chloro-4-(trifluoromethoxy)benzo[d]oxazole-2-thiol using a similar method to Example 1(a) except that tert-butyl 3,6-diazabicyclo[3.1.1]heptane-6-carboxylate was used instead of tert-butyl 3,8-diazabicyclo[3.2.1]octane-8-carboxylate.

(b) tert-Butyl 3-(5-chloro-7-(thiazol-2-yl)-4-(trifluoromethoxy)benzo[d]oxazol-2-yl)-3,6-diazabicyclo[3.1.1]heptane-6-carboxylate 275 mg of the title compound was obtained from 347 mg of tert-butyl 3-(7-bromo-5-chloro-4-(trifluoromethoxy)benzo[d]oxazol-2-yl)-3,6-diazabicyclo[3.1.1]heptane-6-carboxylate obtained in Example 3 (a), using a similar method to Example 1(b).

(c) 2-(3,6-Diazabicyclo[3.1.1]heptan-3-yl)-5-chloro-7-(thiazol-2-yl)-4-(trifluoromethoxy)benzo[d]oxazole 157 mg of the title compound was obtained from 275 mg of tert-butyl 3-(5-chloro-7-(thiazol-2-yl)-4-(trifluoromethoxy)benzo[d]oxazol-2-yl)-3,6-diazabicyclo[3.1.1]heptane-6-carboxylate obtained in Example 3 (b), using a similar method to Example 1(c).

Example 4

7-(5-Chloro-7-(thiazol-2-yl)-4-(trifluoromethoxy)benzo[d]oxazol-2-yl)-3-oxa-7,9-diazabicyclo[3.3.1]nonane (a) tert-Butyl 7-(7-bromo-5-chloro-4-(trifluoromethoxy)benzo[d]oxazol-2-yl)-3-oxa-7,9-diazabicyclo[3.3.1]nonane-9-carboxylate 280 mg of the title compound was obtained from 250 mg of 7-bromo-5-chloro-4-(trifluoromethoxy)benzo[d]oxazole-2-thiol using a similar method to Example 1(a) except that tert-butyl 3-oxa-7,9-diazabicyclo[3.3.1]nonane-9-carboxylate was used instead of tert-butyl 3,8-diazabicyclo[3.2.1]octane-8-carboxylate.

(b) tert-Butyl 7-(5-chloro-7-(thiazol-2-yl)-4-(trifluoromethoxy)benzo[d]oxazol-2-yl)-3-oxa-7,9-diazabicyclo[3.3.1]nonane-9-carboxylate 100 mg of the title compound was obtained from 200 mg of tert-butyl 7-(7-bromo-5-chloro-4-(trifluoromethoxy)benzo[d]oxazol-2-yl)-3-oxa-7,9-diazabicyclo[3.3.1]nonane-9-carboxylate obtained in Example 4 (a), using a similar method to Example 2 (b).

(c) 7-(5-Chloro-7-(thiazol-2-yl)-4-(trifluoromethoxy)benzo[d]oxazol-2-yl)-3-oxa-7,9-diazabicyclo[3.3.1]nonane 80 mg of the title compound was obtained from 150 mg of tert-butyl 7-(5-chloro-7-(thiazol-2-yl)-4-(trifluoromethoxy)benzo[d]oxazol-2-yl)-3-oxa-7,9-diazabicyclo[3.3.1]nonane-9-carboxylate obtained in Example 4 (b), using a similar method to Example 1(c).

Example 5

2-(3,8-Diazabicyclo[3.2.1]octan-3-yl)-5-chloro-7-(1H-pyrazol-1-yl)-4-(trifluoromethoxy)benzo[d]oxazole (a) tert-Butyl 3-(5-chloro-7-(1H-pyrazol-1-yl)-4-(trifluoromethoxy)benzo[d]oxazol-2-yl)-3,8-diazabicyclo[3.2.1]octane-8-carboxylate 55 mg of tert-butyl 3-(7-bromo-5-chloro-4-(trifluoromethoxy)benzo[d]oxazol-2-yl)-3,8-diazabicyclo[3.2.1]octane-8-carboxylate obtained in Example 1(a), 1H-pyrazole (14 mg, 2 equivalents), tris(dibenzylideneacetone)dipalladium(0) (9.5 mg, 0.1 equivalent), 2-di-tert-butylphosphino-3,4,5,6-tetramethyl-2',4',6'-triisopropylbiphenyl (12.5 mg, 0.25 equivalent), and potassium phosphate (44 mg, 2 equivalents) were dissolved in toluene (1.0 mL), followed by stirring for 25 hours in an oil bath at 90° C. Distilled water was added to the reaction mixture, followed by extraction using ethyl acetate. Thereafter, the organic phase was dried over anhydrous magnesium sulfate, followed by filtration, and thus obtaining 10 mg of the title compound by purification of the residue obtained by vacuum concentration of the filtrate through silica gel column chromatography (hexane; then hexane:ethyl acetate=4:1).

(b) 2-(3,8-Diazabicyclo[3.2.1]octan-3-yl)-5-chloro-7-(1H-pyrazol-1-yl)-4-(trifluoromethoxy)benzo[d]oxazole 3.8 mg of the title compound was obtained from 10 mg of tert-butyl 3-(5-chloro-7-(1H-pyrazol-1-yl)-4-(trifluoromethoxy)benzo[d]oxazol-2-yl)-3,8-diazabicyclo[3.2.1]octane-8-carboxylate obtained in Example 5 (a), using a similar method to Example 1(c).

Example 6

2-(3,8-Diazabicyclo[3.2.1]octan-3-yl)-5-chloro-7-(furan-2-yl)-4-(trifluoromethoxy)benzo[d]oxazole (a) tert-Butyl 3-(5-chloro-7-(furan-2-yl)-4-(trifluoromethoxy)benzo[d]oxazol-2-yl)-3,8-diazabicyclo[3.2.1]octane-8-carboxylate 53 mg of tert-butyl 3-(7-bromo-5-chloro-4-(trifluoromethoxy)benzo[d]oxazol-2-yl)-3,8-diazabicyclo[3.2.1]octane-8-carboxylate obtained in Example 1(a), 2-(tributylstannyl)furan (47.2 µL, 1.5 equivalents), and tetrakis(triphenylphosphine)palladium(0) (11.6 mg, 0.1 equivalent) were dissolved in N,N-dimethylformamide (0.5 mL), followed by stirring using a microwave reactor (manufactured by Biotage, conditions: 100° C., 1 hour). Distilled water was added to the reaction mixture, followed by extraction using ethyl acetate. Thereafter, the organic phase was dried over anhydrous magnesium sulfate, followed by filtration, and thus obtaining 56 mg of the title compound by purification of the residue obtained by vacuum concentration of the filtrate through silica gel column chromatography (hexane; then hexane:ethyl acetate=4:1).

(b) 2-(3,8-Diazabicyclo[3.2.1]octan-3-yl)-5-chloro-7-(furan-2-yl)-4-(trifluoromethoxy)benzo[d]oxazole 35 mg of the title compound was obtained from 56 mg of tert-butyl 3-(5-chloro-7-(furan-2-yl)-4-(trifluoromethoxy)benzo[d]oxazol-2-yl)-3,8-diazabicyclo[3.2.1]octane-8-carboxylate obtained in Example 6(a), using a similar method to Example 1(c).

Example 7

2-(3,8-Diazabicyclo[3.2.1]octan-3-yl)-5-chloro-7-(pyridin-2-yl)-4-(trifluoromethoxy)benzo[d]oxazole (a) tert-Butyl 3-(5-chloro-7-(pyridin-2-yl)-4-(trifluoromethoxy)benzo[d]oxazol-2-yl)-3,8-diazabicyclo[3.2.1]octane-8-carboxylate 46 mg of the title compound was obtained from 53 mg of tert-butyl 3-(7-bromo-5-chloro-4-(trifluoromethoxy)benzo[d]oxazol-2-yl)-3,8-diazabicyclo[3.2.1]octane-8-carboxylate obtained in Example 1(a), using a similar method to Example 6(a) except that 2-(tributylstannyl)pyridine was used instead of 2-(tributylstannyl)furan.

(b) 2-(3,8-Diazabicyclo[3.2.1]octan-3-yl)-5-chloro-7-(pyridin-2-yl)-4-(trifluoromethoxy)benzo[d]oxazole 31 mg of the title compound was obtained from 46 mg of tert-butyl 3-(5-chloro-7-(pyridin-2-yl)-4-(trifluoromethoxy)benzo[d]oxazol-2-yl)-3,8-diazabicyclo[3.2.1]octane-8-carboxylate obtained in Example 7 (a), using a similar method to Example 1(c).

Example 8

2-(3,8-Diazabicyclo[3.2.1]octan-3-yl)-5-chloro-7-(thiazol-4-yl)-4-(trifluoromethoxy)benzo[d]oxazole (a) tert-Butyl 3-(5-chloro-7-(thiazol-4-yl)-4-(trifluoromethoxy)benzo[d]oxazol-2-yl)-3,8-diazabicyclo[3.2.1]octane-8-carboxylate 60 mg of the title compound was obtained from 53 mg of tert-butyl 3-(7-bromo-5-chloro-4-(trifluoromethoxy)benzo[d]oxazol-2-yl)-3,8-diazabicyclo[3.2.1]octane-8-carboxylate obtained in Example 1(a), using a similar method to Example 6(a) except that 4-(tributylstannyl)thiazole was used instead of 2-(tributylstannyl)furan.

(b) 2-(3,8-Diazabicyclo[3.2.1]octan-3-yl)-5-chloro-7-(thiazol-4-yl)-4-(trifluoromethoxy)benzo[d]oxazole 40 mg of the title compound was obtained from 60 mg of tert-butyl 3-(5-chloro-7-(thiazol-4-yl)-4-(trifluoromethoxy)benzo[d]oxazol-2-yl)-3,8-diazabicyclo[3.2.1]octane-8-carboxylate obtained in Example 8 (a), using a similar method to Example 1(c).

Example 9

2-(3,8-Diazabicyclo[3.2.1]octan-3-yl)-5-chloro-7-(oxazol-2-yl)-4-(trifluoromethoxy)benzo[d]oxazole (a) tert-Butyl 3-(5-chloro-7-(oxazol-2-yl)-4-(trifluoromethoxy)benzo[d]oxazol-2-yl)-3,8-diazabicyclo[3.2.1]octane-8-carboxylate 55 mg of the title compound was obtained from 53 mg of tert-butyl 3-(7-bromo-5-chloro-4-(trifluoromethoxy)benzo[d]oxazol-2-yl)-3,8-diazabicyclo[3.2.1]octane-8-carboxylate obtained in Example 1(a), using a similar method to Example 6(a) except that 2-(tributylstannyl) oxazole was used instead of 2-(tributylstannyl)furan.

(b) 2-(3,8-Diazabicyclo[3.2.1]octan-3-yl)-5-chloro-7-(oxazol-2-yl)-4-(trifluoromethoxy)benzo[d]oxazole 38 mg of the title compound was obtained from 55 mg of tert-butyl 3-(5-chloro-7-(oxazol-2-yl)-4-(trifluoromethoxy)benzo[d]oxazol-2-yl)-3,8-diazabicyclo[3.2.1]octane-8-carboxylate obtained in Example 9(a), using a similar method to Example 1(c).

Example 10

2-(3,8-Diazabicyclo[3.2.1]octan-3-yl)-5-chloro-7-(5-fluoropyridin-2-yl)-4-(trifluoromethoxy)benzo[d]oxazole (a) tert-Butyl 3-(5-chloro-7-(4,4,5,5-tetramethyl-1,3,2-dioxaborolan-2-yl)-4-(trifluoromethoxy)benzo[d]oxazol-2-yl)-3,8-diazabicyclo[3.2.1]octane-8-carboxylate 263 mg of tert-butyl 3-(7-bromo-5-chloro-4-(trifluoromethoxy)benzo[d]oxazol-2-yl)-3,8-diazabicyclo[3.2.1]

octane-8-carboxylate obtained in Example 1(a), bis(pinacolato)diboron (190 mg, 1.5 equivalents), potassium acetate (147 mg, 3 equivalents), and [1,1'-bis(diphenylphosphino)ferrocene]palladium(II) dichloride·dichloromethane complex (41 mg, 0.1 equivalent) were dissolved in 1,4-dioxane (2.5 mL), followed by stirring for 5 hours in an oil bath at 90° C. under an argon atmosphere. Distilled water was added to the reaction mixture, followed by Celite® filtration. After the filtrate was extracted using ethyl acetate, the organic phase was dried over anhydrous magnesium sulfate, followed by filtration, and thus obtaining 234 mg of the title compound by purification of the residue obtained by vacuum concentration of the filtrate through silica gel column chromatography (hexane; hexane:ethyl acetate=4:1; then hexane:ethyl acetate:methanol=4:1:0.5).

(b) tert-Butyl 3-(5-chloro-7-(5-fluoropyridin-2-yl)-4-(trifluoromethoxy)benzo[d]oxazol-2-yl)-3,8-diazabicyclo[3.2.1]octane-8-carboxylate 57 mg of tert-butyl 3-(5-chloro-7-(4,4,5,5-tetramethyl-1,3,2-dioxaborolan-2-yl)-4-(trifluoromethoxy)benzo[d]oxazol-2-yl)-3,8-diazabicyclo[3.2.1]octane-8-carboxylate obtained in Example 10(a), tetrakis(triphenylphosphine)palladium(0) (11.6 mg, 0.1 equivalent), potassium carbonate (55 mg, 4 equivalents), and 2-bromo-5-fluoropyridine (35 mg, 2 equivalents) were dissolved in a mixture solvent of 1,4-dioxane (0.4 mL) and distilled water (0.1 mL), followed by stirring for 4 hours in an oil bath at 100° C. under an argon atmosphere. Distilled water was added to the reaction mixture, followed by Celite® filtration. After the filtrate was extracted using ethyl acetate, the organic phase was dried over anhydrous magnesium sulfate, followed by filtration, and thus obtaining 47 mg of the title compound by purification of the residue obtained by vacuum concentration of the filtrate through silica gel column chromatography (hexane; then hexane:ethyl acetate=4:1).

(c) 2-(3,8-Diazabicyclo[3.2.1]octan-3-yl)-5-chloro-7-(5-fluoropyridin-2-yl)-4-(trifluoromethoxy)benzo[d]oxazole 33 mg of the title compound was obtained from 47 mg of tert-butyl 3-(5-chloro-7-(5-fluoropyridin-2-yl)-4-(trifluoromethoxy)benzo[d]oxazol-2-yl)-3,8-diazabicyclo[3.2.1]octane-8-carboxylate obtained in Example 10(b), using a similar method to Example 1(c).

Example 11

2-(3,8-Diazabicyclo[3.2.1]octan-3-yl)-5-chloro-7-(pyridin-2-yl)-4-(trifluoromethyl)benzo[d]oxazole (a) tert-Butyl 3-(7-bromo-5-chloro-4-(trifluoromethyl)benzo[d]oxazol-2-yl)-3,8-diazabicyclo[3.2.1]octane-8-carboxylate 345 mg of the title compound was obtained from 250 mg of 7-bromo-5-chloro-4-(trifluoromethyl)benzo[d]oxazole-2-thiol (the compound of Reference Example 10 in International Publication No. Wo 2015/005429) and tert-butyl 3,8-diazabicyclo[3.2.1]octane-8-carboxylate using a similar method to Example 1(a).

(b) tert-Butyl 3-(5-chloro-7-(pyridin-2-yl)-4-(trifluoromethyl)benzo[d]oxazol-2-yl)-3,8-diazabicyclo[3.2.1]octane-8-carboxylate 340 mg of tert-butyl 3-(7-bromo-5-chloro-4-(trifluoromethyl)benzo[d]oxazol-2-yl)-3,8-diazabicyclo[3.2.1]octane-8-carboxylate obtained in Example 11(a), 2-(tributylstannyl)pyridine (0.32 mL, 1.5 equivalents), and bis(triphenylphosphine)palladium(II) dichloride (46 mg, 0.1 equivalent) were dissolved in 1,4-dioxane (7 mL), followed by stirring for 4 hours in an oil bath at 110° C. The reaction mixture was subjected to Celite® filtration, thus obtaining 400 mg of the title compound by purification of the residue obtained by vacuum concentration of the filtrate through silica gel column chromatography (hexane:ethyl acetate=93:7).

(c) 2-(3,8-Diazabicyclo[3.2.1]octan-3-yl)-5-chloro-7-(pyridin-2-yl)-4-(trifluoromethyl)benzo[d]oxazole 154 mg of the title compound was obtained from 400 mg of tert-butyl 3-(5-chloro-7-(pyridin-2-yl)-4-(trifluoromethyl)benzo[d]oxazol-2-yl)-3,8-diazabicyclo[3.2.1]octane-8-carboxylate obtained in Example 11(b), using a similar method to Example 1(c).

Example 12

2-(3,9-Diazabicyclo[3.3.1]nonan-3-yl)-5-chloro-7-(pyridin-2-yl)-4-(trifluoromethyl)benzo[d]oxazole (a) tert-Butyl 3-(7-bromo-5-chloro-4-(trifluoromethyl)benzo[d]oxazol-2-yl)-3,9-diazabicyclo[3.3.1]nonane-9-carboxylate 860 mg of the title compound was obtained from 600 mg of 7-bromo-5-chloro-4-(trifluoromethyl)benzo[d]oxazole-2-thiol using a similar method to Example 1(a) except that tert-butyl 3,9-diazabicyclo[3.3.1]nonane-9-carboxylate was used instead of tert-butyl 3,8-diazabicyclo[3.2.1]octane-8-carboxylate.

(b) tert-Butyl 3-(5-chloro-7-(pyridin-2-yl)-4-(trifluoromethyl)benzo[d]oxazol-2-yl)-3,9-diazabicyclo[3.3.1]nonane-9-carboxylate 333 mg of the title compound was obtained as a crude product from 300 mg of tert-butyl 3-(7-bromo-5-chloro-4-(trifluoromethyl)benzo[d]oxazol-2-yl)-3,9-diazabicyclo[3.3.1]nonane-9-carboxylate obtained in Example 12 (a), using a similar method to Example 11(b).

(c) 2-(3,9-Diazabicyclo[3.3.1]nonan-3-yl)-5-chloro-7-(pyridin-2-yl)-4-(trifluoromethyl)benzo[d]oxazole 150 mg of the title compound was obtained from 330 mg of tert-butyl 3-(5-chloro-7-(pyridin-2-yl)-4-(trifluoromethyl)benzo[d]oxazol-2-yl)-3,9-diazabicyclo[3.3.1]nonane-9-carboxylate obtained in Example 12 (b), using a similar method to Example 1(c).

Example 13

2-(3,6-Diazabicyclo[3.1.1]heptan-3-yl)-5-chloro-7-(pyridin-2-yl)-4-(trifluoromethyl)benzo[d]oxazole (a) tert-Butyl 3-(7-bromo-5-chloro-4-(trifluoromethyl)benzo[d]oxazol-2-yl)-3,6-diazabicyclo[3.1.1]heptane-6-carboxylate 700 mg of the title compound was obtained from 650 mg of 7-bromo-5-chloro-4-(trifluoromethyl)benzo[d]oxazole-2-thiol using a similar method to Example 1(a) except that tert-butyl 3,6-diazabicyclo[3.1.1]heptane-6-carboxylate was used instead of tert-butyl 3,8-diazabicyclo[3.2.1]octane-8-carboxylate.

(b) tert-Butyl 3-(5-chloro-7-(pyridin-2-yl)-4-(trifluoromethyl)benzo[d]oxazol-2-yl)-3,6-diazabicyclo [3.1.1]heptane-6-carboxylate 340 mg of the title compound was obtained as a crude product from 300 mg of tert-butyl 3-(7-bromo-5-chloro-4-(trifluoromethyl)benzo[d]oxazol-2-yl)-3,6-diazabicyclo [3.1.1]heptane-6-carboxylate obtained in Example 13(a), using a similar method to Example 11 (b).

(c) 2-(3,6-Diazabicyclo[3.1.1]heptan-3-yl)-5-chloro-7-(pyridin-2-yl)-4-(trifluoromethyl)benzo[d]oxazole 160 mg of the title compound was obtained from 340 mg of tert-butyl 3-(5-chloro-7-(pyridin-2-yl)-4-(trifluoromethyl)benzo[d]oxazol-2-yl)-3,6-diazabicyclo[3.1.1]heptane-6-carboxylate obtained in Example 13 (b), using a similar method to Example 1(c).

Example 14

7-(5-Chloro-7-(pyridin-2-yl)-4-(trifluoromethyl) benzo[d]oxazol-2-yl)-3-oxa-7,9-diazabicyclo[3.3.1] nonane (a) tert-Butyl 7-(7-bromo-5-chloro-4-(trifluoromethyl)benzo[d]oxazol-2-yl)-3-oxa-7,9-diazabicyclo [3.3.1]nonane-9-carboxylate 914 mg of the title compound was obtained from 650 mg of 7-bromo-5-chloro-4-(trifluoromethyl)benzo[d]oxazole-2-thiol using a similar method to Example 1(a) except that tert-butyl 3-oxa-7,9-diazabicyclo[3.3.1]nonane-9-carboxylate was used instead of tert-butyl 3,8-diazabicyclo[3.2.1] octane-8-carboxylate.

(b) tert-Butyl 7-(5-chloro-7-(pyridin-2-yl)-4-(trifluoromethyl)benzo[d]oxazol-2-yl)-3-oxa-7,9-diazabicyclo[3.3.1]nonane-9-carboxylate 214 mg of the title compound was obtained from 300 mg of tert-butyl 7-(7-bromo-5-chloro-4-(trifluoromethyl)benzo [d]oxazol-2-yl)-3-oxa-7,9-diazabicyclo[3.3.1]nonane-9-carboxylate obtained in Example 14(a), using a similar method to Example 11(b).

(c) 7-(5-Chloro-7-(pyridin-2-yl)-4-(trifluoromethyl) benzo[d]oxazol-2-yl)-3-oxa-7,9-diazabicyclo[3.3.1] nonane 150 mg of the title compound was obtained from 214 mg of tert-butyl 7-(5-chloro-7-(pyridin-2-yl)-4-(trifluoromethyl)benzo[d]oxazol-2-yl)-3-oxa-7,9-diazabicyclo[3.3.1] nonane-9-carboxylate obtained in Example 14 (b), using a similar method to Example 1(c).

Example 15

2-(3,8-Diazabicyclo[3.2.1]octan-3-yl)-5-chloro-7-(1H-pyrazol-1-yl)-4-(trifluoromethyl)benzo[d]oxazole (a) tert-Butyl 3-(5-chloro-7-(1H-pyrazol-1-yl)-4-(trifluoromethyl)benzo[d]oxazol-2-yl)-3,8-diazabicyclo[3.2.1]octane-8-carboxylate 570 mg of tert-butyl 3-(7-bromo-5-chloro-4-(trifluoromethyl)benzo[d]oxazol-2-yl)-3,8-diazabicyclo[3.2.1]octane-8-carboxylate obtained in Example 11(a), 1H-pyrazole (91 mg, 1.2 equivalents), copper(I) iodide (21 mg, 0.1 equivalent), trans-N,N'-dimethylcyclohexane-1,2-diamine (31 mg, 0.2 equivalent), and potassium phosphate (498 mg, 2.1 equivalents) were dissolved in toluene (18 mL), followed by stirring at 130° C. for 24 hours. Saturated sodium hydrogen carbonate aqueous solution was added to the reaction mixture, followed by extraction using ethyl acetate. Thereafter, the organic phase was dried over anhydrous magnesium sulfate, followed by filtration, and thus obtaining 140 mg of the title compound by purification of the residue obtained by vacuum concentration of the filtrate through silica gel column chromatography (hexane; then hexane:ethyl acetate=94:6).

(b) 2-(3,8-Diazabicyclo[3.2.1]octan-3-yl)-5-chloro-7-(1H-pyrazol-1-yl)-4-(trifluoromethyl)benzo[d] oxazole 98 mg of the title compound was obtained from 140 mg of tert-butyl 3-(5-chloro-7-(1H-pyrazol-1-yl)-4-(trifluoromethyl)benzo[d]oxazol-2-yl)-3,8-diazabicyclo[3.2.1]octane-8-carboxylate obtained in Example 15(a), using a similar method to Example 1(c).

Example 16

2-(3,9-Diazabicyclo[3.3.1]nonan-3-yl)-5-chloro-7-(1H-pyrazol-1-yl)-4-(trifluoromethyl)benzo[d]oxazole (a) tert-Butyl 3-(5-chloro-7-(1H-pyrazol-1-yl)-4-(trifluoromethyl)benzo[d]oxazol-2-yl)-3,9-diazabicyclo[3.3.1]nonane-9-carboxylate The title compound was obtained in an amount of 190 mg from 375 mg of tert-butyl 3-(7-bromo-5-chloro-4-(trifluoromethyl)benzo[d]oxazol-2-yl)-3,9-diazabicyclo[3.3.1] nonane-9-carboxylate obtained in Example 12 (a) by a similar method to Example 15 (a).

(b) 2-(3,9-Diazabicyclo[3.3.1]nonan-3-yl)-5-chloro-7-(1H-pyrazol-1-yl)-4-(trifluoromethyl)benzo[d] oxazole The title compound was obtained in an amount of 140 mg from 190 mg of tert-butyl 3-(5-chloro-7-(1H-pyrazol-1-yl)-4-(trifluoromethyl)benzo[d]oxazol-2-yl)-3,9-diazabicyclo [3.3.1]nonane-9-carboxylate obtained in Example 16(a) by a similar method to Example 1(c).

Example 17

2-(3,6-Diazabicyclo[3.1.1]heptan-3-yl)-5-chloro-7-(1H-pyrazol-1-yl)-4-(trifluoromethyl)benzo[d]oxazole (a) tert-Butyl 3-(5-chloro-7-(1H-pyrazol-1-yl)-4-(trifluoromethyl)benzo[d]oxazol-2-yl)-3,6-diazabicyclo[3.1.1]heptane-6-carboxylate The title compound was obtained in an amount of 240 mg from 400 mg of tert-butyl 3-(7-bromo-5-chloro-4-(trifluoromethyl)benzo[d]oxazol-2-yl)-3,6-diazabicyclo[3.1.1]heptane-6-carboxylate obtained in Example 13(a) by a similar method to Example 15 (a).

(b) 2-(3,6-Diazabicyclo[3.1.1]heptan-3-yl)-5-chloro-7-(1H-pyrazol-1-yl)-4-(trifluoromethyl)benzo[d]oxazole The title compound was obtained in an amount of 176 mg from 240 mg of tert-butyl 3-(5-chloro-7-(1H-pyrazol-1-yl)-4-(trifluoromethyl)benzo[d]oxazol-2-yl)-3,6-diazabicyclo[3.1.1]heptane-6-carboxylate obtained in Example 17 (a) by a similar method to Example 1(c).

Example 18

7-(5-Chloro-7-(1H-pyrazol-1-yl)-4-(trifluoromethyl)benzo[d]oxazol-2-yl)-3-oxa-7,9-diazabicyclo[3.3.1]nonane (a) tert-Butyl 7-(5-chloro-7-(1H-pyrazol-1-yl)-4-(trifluoromethyl)benzo[d]oxazol-2-yl)-3-oxa-7,9-diazabicyclo[3.3.1]nonane-9-carboxylate The title compound was obtained in an amount of 170 mg from 270 mg of tert-butyl 7-(7-bromo-5-chloro-4-(trifluoromethyl)benzo[d]oxazol-2-yl)-3-oxa-7,9-diazabicyclo[3.3.1]nonane-9-carboxylate obtained in Example 14(a) by a similar method to Example 15 (a).

(b) 7-(5-Chloro-7-(1H-pyrazol-1-yl)-4-(trifluoromethyl)benzo[d]oxazol-2-yl)-3-oxa-7,9-diazabicyclo[3.3.1]nonane The title compound was obtained in an amount of 120 mg from 170 mg of tert-butyl 7-(5-chloro-7-(1H-pyrazol-1-yl)-4-(trifluoromethyl)benzo[d]oxazol-2-yl)-3-oxa-7,9-diazabicyclo[3.3.1]nonane-9-carboxylate obtained in Example 18 (a) by a similar method to Example 1(c).

Example 19

7-(5-Chloro-7-(thiazol-2-yl)-4-(trifluoromethyl)benzo[d]oxazol-2-yl)-3-oxa-7,9-diazabicyclo[3.3.1]nonane (a) tert-Butyl 7-(5-chloro-7-(thiazol-2-yl)-4-(trifluoromethyl)benzo[d]oxazol-2-yl)-3-oxa-7,9-diazabicyclo[3.3.1]nonane-9-carboxylate The title compound was obtained in an amount of 62 mg from 135 mg of tert-butyl 7-(7-bromo-5-chloro-4-(trifluoromethyl)benzo[d]oxazol-2-yl)-3-oxa-7,9-diazabicyclo[3.3.1]nonane-9-carboxylate obtained in Example 14 (a) by a similar method to Example 1(b).

(b) 7-(5-Chloro-7-(thiazol-2-yl)-4-(trifluoromethyl)benzo[d]oxazol-2-yl)-3-oxa-7,9-diazabicyclo[3.3.1]nonane The title compound was obtained in an amount of 41 mg from 62 mg of tert-butyl 7-(5-chloro-7-(thiazol-2-yl)-4-(trifluoromethyl)benzo[d]oxazol-2-yl)-3-oxa-7,9-diazabicyclo[3.3.1]nonane-9-carboxylate obtained in Example 19(a) by a similar method to Example 1(c).

Example 20

2-(3,8-Diazabicyclo[3.2.1]octan-3-yl)-5-chloro-7-(thiazol-2-yl)-4-(trifluoromethyl)benzo[d]oxazole (a) tert-Butyl 3-(5-chloro-7-(thiazol-2-yl)-4-(trifluoromethyl)benzo[d]oxazol-2-yl)-3,8-diazabicyclo[3.2.1]octane-8-carboxylate The title compound was obtained in an amount of 202 mg from 300 mg of tert-butyl 3-(7-bromo-5-chloro-4-(trifluoromethyl)benzo[d]oxazol-2-yl)-3,8-diazabicyclo[3.2.1]octane-8-carboxylate obtained in Example 11(a) by a similar method to Example 1(b).

(b) 2-(3,8-Diazabicyclo[3.2.1]octan-3-yl)-5-chloro-7-(thiazol-2-yl)-4-(trifluoromethyl)benzo[d]oxazole The title compound was obtained in an amount of 94 mg from 202 mg of tert-butyl 3-(5-chloro-7-(thiazol-2-yl)-4-(trifluoromethyl)benzo[d]oxazol-2-yl)-3,8-diazabicyclo[3.2.1]octane-8-carboxylate obtained in Example 20(a) by a similar method to Example 1(c).

Example 21

2-(3,8-Diazabicyclo[3.2.1]octan-3-yl)-5-isopropyl-7-(thiazol-2-yl)benzo[d]oxazole (a) tert-Butyl 3-(7-bromo-5-isopropylbenzo[d]oxazol-2-yl)-3,8-diazabicyclo[3.2.1]octane-8-carboxylate The title compound was obtained in an amount of 140 mg from 100 mg of 7-bromo-5-isopropylbenzo[d]oxazole-2-thiol obtained in Reference Example 1 and tert-butyl 3,8-diazabicyclo[3.2.1]octane-8-carboxylate by a similar method to Example 1(a).

(b) tert-Butyl 3-(5-isopropyl-7-(thiazol-2-yl)benzo[d]oxazol-2-yl)-3,8-diazabicyclo[3.2.1]octane-8-carboxylate The title compound was obtained as a crude product in an amount of 350 mg from 240 mg of tert-butyl 3-(7-bromo-5-isopropylbenzo[d]oxazol-2-yl)-3,8-diazabicyclo[3.2.1]octane-8-carboxylate obtained in Example 21(a) by a similar method to Example 2(b) except that toluene was used instead of 1,4-dioxane.

(c) 2-(3,8-Diazabicyclo[3.2.1]octan-3-yl)-5-isopropyl-7-(thiazol-2-yl)benzo[d]oxazole The title compound was obtained in an amount of 200 mg from 350 mg of tert-butyl 3-(5-isopropyl-7-(thiazol-2-yl)benzo[d]oxazol-2-yl)-3,8-diazabicyclo[3.2.1]octane-8-carboxylate obtained in Example 21(b) by a similar method to Example 1(c).

Example 22

2-(3,6-Diazabicyclo[3.1.1]heptan-3-yl)-5-isopropyl-7-(thiazol-2-yl)benzo[d]oxazole (a) tert-Butyl 3-(7-bromo-5-isopropylbenzo[d]oxazol-2-yl)-3,6-diazabicyclo[3.1.1]heptane-6-carboxylate The title compound was obtained in an amount of 290 mg from 200 mg of 7-bromo-5-isopropylbenzo[d]oxazole-2-thiol obtained in Reference Example 1 by a similar method to Example 1(a) except that tert-butyl 3,6-diazabicyclo[3.1.1]heptane-6-carboxylate was used instead of tert-butyl 3,8-diazabicyclo[3.2.1]octane-8-carboxylate.

(b) tert-Butyl 3-(5-isopropyl-7-(thiazol-2-yl)benzo[d]oxazol-2-yl)-3,6-diazabicyclo[3.1.1]heptane-6-carboxylate The title compound was obtained as a crude product in an amount of 409 mg from 240 mg of tert-butyl 3-(7-bromo-5-isopropylbenzo[d]oxazol-2-yl)-3,6-diazabicyclo[3.1.1]heptane-6-carboxylate obtained in Example 22(a) by a similar method to Example 2(b) except that toluene was used instead of 1,4-dioxane.

(c) 2-(3,6-Diazabicyclo[3.1.1]heptan-3-yl)-5-isopropyl-7-(thiazol-2-yl)benzo[d]oxazole The title compound was obtained in an amount of 160 mg from 409 mg of tert-butyl 3-(5-isopropyl-7-(thiazol-2-yl)benzo[d]oxazol-2-yl)-3,6-diazabicyclo[3.1.1]heptane-6-carboxylate obtained in Example 22 (b) by a similar method to Example 1(c).

Example 23

7-(5-Isopropyl-7-(thiazol-2-yl)benzo[d]oxazol-2-yl)-3-oxa-7,9-diazabicyclo[3.3.1]nonane (a) tert-Butyl 7-(7-bromo-5-isopropylbenzo[d]oxazol-2-yl)-3-oxa-7,9-diazabicyclo[3.3.1]nonane-9-carboxylate The title compound was obtained in an amount of 260 mg from 200 mg of 7-bromo-5-isopropylbenzo[d]oxazole-2-thiol obtained in Reference Example 1 by a similar method to Example 1(a) except that tert-butyl 3-oxa-7,9-diazabicyclo[3.3.1]nonane-9-carboxylate was used instead of tert-butyl 3,8-diazabicyclo[3.2.1]octane-8-carboxylate.

(b) tert-Butyl 7-(5-isopropyl-7-(thiazol-2-yl)benzo[d]oxazol-2-yl)-3-oxa-7,9-diazabicyclo[3.3.1]nonane-9-carboxylate The title compound was obtained as a crude product in an amount of 380 mg from 260 mg of tert-butyl 7-(7-bromo-5-isopropylbenzo[d]oxazol-2-yl)-3-oxa-7,9-diazabicyclo[3.3.1]nonane-9-carboxylate obtained in Example 23(a) by a similar method to Example 2(b) except that toluene was used instead of 1,4-dioxane.

(c) 7-(5-Isopropyl-7-(thiazol-2-yl)benzo[d]oxazol-2-yl)-3-oxa-7,9-diazabicyclo[3.3.1]nonane The title compound was obtained in an amount of 155 mg from 380 mg of tert-butyl 7-(5-isopropyl-7-(thiazol-2-yl)benzo[d]oxazol-2-yl)-3-oxa-7,9-diazabicyclo[3.3.1]nonane-9-carboxylate obtained in Example 23 (b) by a similar method to Example 1(c).

Example 24

2-(3,9-Diazabicyclo[3.3.1]nonan-3-yl)-5-isopropyl-7-(thiazol-2-yl)benzo[d]oxazole (a) tert-Butyl 3-(7-bromo-5-isopropylbenzo[d]oxazol-2-yl)-3,9-diazabicyclo[3.3.1]nonane-9-carboxylate The title compound was obtained in an amount of 320 mg from 200 mg of 7-bromo-5-isopropylbenzo[d]oxazole-2-thiol obtained in Reference Example 1 by a similar method to Example 1(a) except that tert-butyl 3,9-diazabicyclo[3.3.1]nonane-9-carboxylate was used instead of tert-butyl 3,8-diazabicyclo[3.2.1]octane-8-carboxylate.

(b) tert-Butyl 3-(5-isopropyl-7-(thiazol-2-yl)benzo[d]oxazol-2-yl)-3,9-diazabicyclo[3.3.1]nonane-9-carboxylate The title compound was obtained as a crude product in an amount of 340 mg from 260 mg of tert-butyl 3-(7-bromo-5-isopropylbenzo[d]oxazol-2-yl)-3,9-diazabicyclo[3.3.1]nonane-9-carboxylate obtained in Example 24(a) by a similar method to Example 2(b) except that toluene was used instead of 1,4-dioxane.

(c) 2-(3,9-Diazabicyclo[3.3.1]nonan-3-yl)-5-isopropyl-7-(thiazol-2-yl)benzo[d]oxazole The title compound was obtained in an amount of 160 mg from 340 mg of tert-butyl 3-(5-isopropyl-7-(thiazol-2-yl)benzo[d]oxazol-2-yl)-3,9-diazabicyclo[3.3.1]nonane-9-carboxylate obtained in Example 24 (b) by a similar method to Example 1(c).

Example 25

2-(3,8-Diazabicyclo[3.2.1]octan-3-yl)-4-methyl-7-(thiazol-2-yl)benzo[d]oxazole (a) tert-Butyl 3-(7-bromo-4-methylbenzo[d]oxazol-2-yl)-3,8-diazabicyclo[3.2.1]octane-8-carboxylate The title compound was obtained in an amount of 210 mg from 150 mg of 7-bromo-4-methylbenzo[d]oxazole-2-thiol obtained in Reference Example 2 and tert-butyl 3,8-diazabicyclo[3.2.1]octane-8-carboxylate by a similar method to Example 1(a).

(b) tert-Butyl 3-(4-methyl-7-(thiazol-2-yl)benzo[d]oxazol-2-yl)-3,8-diazabicyclo[3.2.1]octane-8-carboxylate The title compound was obtained in an amount of 178 mg from 210 mg of tert-butyl 3-(7-bromo-4-methylbenzo[d]oxazol-2-yl)-3,8-diazabicyclo[3.2.1]octane-8-carboxylate obtained in Example 25(a) by a similar method to Example 2(b) except that toluene was used instead of 1,4-dioxane.

(c) 2-(3,8-Diazabicyclo[3.2.1]octan-3-yl)-4-methyl-7-(thiazol-2-yl)benzo[d]oxazole The title compound was obtained in an amount of 120 mg from 175 mg of tert-butyl 3-(4-methyl-7-(thiazol-2-yl)benzo

[d]oxazol-2-yl)-3,8-diazabicyclo[3.2.1]octane-8-carboxylate obtained in Example 25 (b) by a similar method to Example 1(c).

Example 26

2-(3,6-Diazabicyclo[3.1.1]heptan-3-yl)-4-methyl-7-(thiazol-2-yl)benzo[d]oxazole (a) tert-Butyl 3-(7-bromo-4-methylbenzo[d]oxazol-2-yl)-3,6-diazabicyclo[3.1.1]heptane-6-carboxylate The title compound was obtained in an amount of 205 mg from 150 mg of 7-bromo-4-methylbenzo[d]oxazole-2-thiol obtained in Reference Example 2 by a similar method to Example 1(a) except that tert-butyl 3,6-diazabicyclo[3.1.1]heptane-6-carboxylate was used instead of tert-butyl 3,8-diazabicyclo[3.2.1]octane-8-carboxylate.

(b) tert-Butyl 3-(4-methyl-7-(thiazol-2-yl)benzo[d]oxazol-2-yl)-3,6-diazabicyclo[3.1.1]heptane-6-carboxylate The title compound was obtained as a crude product in an amount of 250 mg from 205 mg of tert-butyl 3-(7-bromo-4-methylbenzo[d]oxazol-2-yl)-3,6-diazabicyclo[3.1.1]heptane-6-carboxylate obtained in Example 26(a) by a similar method to Example 2(b) except that toluene was used instead of 1,4-dioxane.

(c) 2-(3,6-Diazabicyclo[3.1.1]heptan-3-yl)-4-methyl-7-(thiazol-2-yl)benzo[d]oxazole The title compound was obtained in an amount of 140 mg from 250 mg of tert-butyl 3-(4-methyl-7-(thiazol-2-yl)benzo[d]oxazol-2-yl)-3,6-diazabicyclo[3.1.1]heptane-6-carboxylate obtained in Example 26(b) by a similar method to Example 1(c).

Example 27

2-(3,9-Diazabicyclo[3.3.1]nonan-3-yl)-4-methyl-7-(thiazol-2-yl)benzo[d]oxazole (a) tert-Butyl 3-(7-bromo-4-methylbenzo[d]oxazol-2-yl)-3,9-diazabicyclo[3.3.1]nonane-9-carboxylate The title compound was obtained in an amount of 220 mg from 150 mg of 7-bromo-4-methylbenzo[d]oxazole-2-thiol obtained in Reference Example 2 by a similar method to Example 1(a) except that tert-butyl 3,9-diazabicyclo[3.3.1]nonane-9-carboxylate was used instead of tert-butyl 3,8-diazabicyclo[3.2.1]octane-8-carboxylate.

(b) tert-Butyl 3-(4-methyl-7-(thiazol-2-yl)benzo[d]oxazol-2-yl)-3,9-diazabicyclo[3.3.1]nonane-9-carboxylate The title compound was obtained as a crude product in an amount of 235 mg from 210 mg of tert-butyl 3-(7-bromo-4-methylbenzo[d]oxazol-2-yl)-3,9-diazabicyclo[3.3.1]nonane-9-carboxylate obtained in Example 27(a) by a similar method to Example 2(b) except that toluene was used instead of 1,4-dioxane.

(c) 2-(3,9-Diazabicyclo[3.3.1]nonan-3-yl)-4-methyl-7-(thiazol-2-yl)benzo[d]oxazole The title compound was obtained in an amount of 119 mg from 235 mg of tert-butyl 3-(4-methyl-7-(thiazol-2-yl)benzo[d]oxazol-2-yl)-3,9-diazabicyclo[3.3.1]nonane-9-carboxylate obtained in Example 27 (b) by a similar method to Example 1(c).

Example 28

2-(3,8-Diazabicyclo[3.2.1]octan-3-yl)-7-(thiazol-2-yl)-4-(trifluoromethoxy)benzo[d]oxazole (a) tert-Butyl 3-(7-bromo-4-(trifluoromethoxy)benzo[d]oxazol-2-yl)-3,8-diazabicyclo[3.2.1]octane-8-carboxylate The title compound was obtained in an amount of 140 mg from 100 mg of 7-bromo-4-(trifluoromethoxy)benzo[d]oxazole-2-thiol obtained in Reference Example 3 and tert-butyl 3,8-diazabicyclo[3.2.1]octane-8-carboxylate by a similar method to Example 1(a).

(b) tert-Butyl 3-(7-(thiazol-2-yl)-4-(trifluoromethoxy)benzo[d]oxazol-2-yl)-3,8-diazabicyclo[3.2.1]octane-8-carboxylate The title compound was obtained in an amount of 120 mg from 140 mg of tert-butyl 3-(7-bromo-4-(trifluoromethoxy)benzo[d]oxazol-2-yl)-3,8-diazabicyclo[3.2.1]octane-8-carboxylate obtained in Example 28(a) by a similar method to Example 2(b) except that toluene was used instead of 1,4-dioxane.

(c) 2-(3,8-Diazabicyclo[3.2.1]octan-3-yl)-7-(thiazol-2-yl)-4-(trifluoromethoxy)benzo[d]oxazole The title compound was obtained in an amount of 90 mg from 120 mg of tert-butyl 3-(7-(thiazol-2-yl)-4-(trifluoromethoxy)benzo[d]oxazol-2-yl)-3,8-diazabicyclo[3.2.1]octane-8-carboxylate obtained in Example 28 (b) by a similar method to Example 1(c).

Example 29

2-(3,6-Diazabicyclo[3.1.1]heptan-3-yl)-7-(thiazol-2-yl)-4-(trifluoromethoxy)benzo[d]oxazole (a) tert-Butyl 3-(7-bromo-4-(trifluoromethoxy)benzo[d]oxazol-2-yl)-3,6-diazabicyclo[3.1.1]heptane-6-carboxylate The title compound was obtained in an amount of 200 mg from 150 mg of 7-bromo-4-(trifluoromethoxy)benzo[d]oxazole-2-thiol obtained in Reference Example 3 by a similar method to Example 1(a) except that tert-butyl 3,6-diazabicyclo[3.1.1]heptane-6-carboxylate was used instead of tert-butyl 3,8-diazabicyclo[3.2.1]octane-8-carboxylate.

(b) tert-Butyl 3-(7-(thiazol-2-yl)-4-(trifluoromethoxy)benzo[d]oxazol-2-yl)-3,6-diazabicyclo[3.1.1]heptane-6-carboxylate The title compound was obtained as a crude product in an amount of 250 mg from 200 mg of tert-butyl 3-(7-bromo-4-(trifluoromethoxy)benzo[d]oxazol-2-yl)-3,6-diazabicyclo[3.1.1]heptane-6-carboxylate obtained in Example 29(a) by a similar method to Example 2 (b) except that toluene was used instead of 1,4-dioxane.

(c) 2-(3,6-Diazabicyclo[3.1.1]heptan-3-yl)-7-(thiazol-2-yl)-4-(trifluoromethoxy)benzo[d]oxazole The title compound was obtained in an amount of 140 mg from 250 mg of tert-butyl 3-(7-(thiazol-2-yl)-4-(trifluoromethoxy)benzo[d]oxazol-2-yl)-3,6-diazabicyclo[3.1.1]heptane-6-carboxylate obtained in Example 29(b) by a similar method to Example 1(c).

Example 30

2-(3,9-Diazabicyclo[3.3.1]nonan-3-yl)-7-(thiazol-2-yl)-4-(trifluoromethoxy)benzo[d]oxazole (a) tert-Butyl 3-(7-bromo-4-(trifluoromethoxy)benzo[d]oxazol-2-yl)-3,9-diazabicyclo[3.3.1]nonane-9-carboxylate The title compound was obtained in an amount of 220 mg from 150 mg of 7-bromo-4-(trifluoromethoxy)benzo[d]oxazole-2-thiol obtained in Reference Example 3 by a similar method to Example 1(a) except that tert-butyl 3,9-diazabicyclo[3.3.1]nonane-9-carboxylate was used instead of tert-butyl 3,8-diazabicyclo[3.2.1]octane-8-carboxylate.

(b) tert-Butyl 3-(7-(thiazol-2-yl)-4-(trifluoromethoxy)benzo[d]oxazol-2-yl)-3,9-diazabicyclo[3.3.1]nonane-9-carboxylate The title compound was obtained as a crude product in an amount of 300 mg from 220 mg of tert-butyl 3-(7-bromo-4-(trifluoromethoxy)benzo[d]oxazol-2-yl)-3,9-diazabicyclo[3.3.1]nonane-9-carboxylate obtained in Example 30(a) by a similar method to Example 2 (b) except that toluene was used instead of 1,4-dioxane.

(c) 2-(3,9-Diazabicyclo[3.3.1]nonan-3-yl)-7-(thiazol-2-yl)-4-(trifluoromethoxy)benzo[d]oxazole The title compound was obtained in an amount of 140 mg from 300 mg of tert-butyl 3-(7-(thiazol-2-yl)-4-(trifluoromethoxy)benzo[d]oxazol-2-yl)-3,9-diazabicyclo[3.3.1]nonane-9-carboxylate obtained in Example 30(b) by a similar method to Example 1(c).

Example 31

2-(3,8-Diazabicyclo[3.2.1]octan-3-yl)-7-(thiazol-2-yl)-4-(trifluoromethyl)benzo[d]oxazole (a) tert-Butyl 3-(7-bromo-4-(trifluoromethyl)benzo[d]oxazol-2-yl)-3,8-diazabicyclo[3.2.1]octane-8-carboxylate The title compound was obtained in an amount of 200 mg from 150 mg of 7-bromo-4-(trifluoromethyl)benzo[d]oxazole-2-thiol obtained in Reference Example 4 and tert-butyl 3,8-diazabicyclo[3.2.1]octane-8-carboxylate by a similar method to Example 1(a).

(b) tert-Butyl 3-(7-(thiazol-2-yl)-4-(trifluoromethyl)benzo[d]oxazol-2-yl)-3,8-diazabicyclo[3.2.1]octane-8-carboxylate The title compound was obtained as a crude product in an amount of 130 mg from 130 mg of tert-butyl 3-(7-bromo-4-(trifluoromethyl)benzo[d]oxazol-2-yl)-3,8-diazabicyclo[3.2.1]octane-8-carboxylate obtained in Example 31(a) by a similar method to Example 2(b) except that toluene was used instead of 1,4-dioxane and tetrakis(triphenylphosphine)palladium(0) was used instead of bis(triphenylphosphine)palladium(II) dichloride.

(c) 2-(3,8-Diazabicyclo[3.2.1]octan-3-yl)-7-(thiazol-2-yl)-4-(trifluoromethyl)benzo[d]oxazole The title compound was obtained in an amount of 100 mg from 130 mg of tert-butyl 3-(7-(thiazol-2-yl)-4-(trifluoromethyl)benzo[d]oxazol-2-yl)-3,8-diazabicyclo[3.2.1]octane-8-carboxylate obtained in Example 31(b) by a similar method to Example 1(c).

Example 32

2-(3,6-Diazabicyclo[3.1.1]heptan-3-yl)-7-(thiazol-2-yl)-4-(trifluoromethyl)benzo[d]oxazole (a) tert-Butyl 3-(7-bromo-4-(trifluoromethyl)benzo[d]oxazol-2-yl)-3,6-diazabicyclo[3.1.1]heptane-6-carboxylate The title compound was obtained in an amount of 190 mg from 150 mg of 7-bromo-4-(trifluoromethyl)benzo[d]oxazole-2-thiol obtained in Reference Example 4 by a similar method to Example 1(a) except that tert-butyl 3,6-diazabicyclo[3.1.1]heptane-6-carboxylate was used instead of tert-butyl 3,8-diazabicyclo[3.2.1]octane-8-carboxylate.

(b) tert-Butyl 3-(7-(thiazol-2-yl)-4-(trifluoromethyl)benzo[d]oxazol-2-yl)-3,6-diazabicyclo[3.1.1]heptane-6-carboxylate The title compound was obtained as a crude product in an amount of 170 mg from 130 mg of tert-butyl 3-(7-bromo-4-(trifluoromethyl)benzo[d]oxazol-2-yl)-3,6-diazabicyclo[3.1.1]heptane-6-carboxylate obtained in Example 32 (a) by a similar method to Example 2 (b) except that toluene was used instead of 1,4-dioxane and tetrakis(triphenylphosphine)palladium(0) was used instead of bis(triphenylphosphine)palladium(II) dichloride.

(c) 2-(3,6-Diazabicyclo[3.1.1]heptan-3-yl)-7-(thiazol-2-yl)-4-(trifluoromethyl)benzo[d]oxazole The title compound was obtained in an amount of 98 mg from 170 mg of tert-butyl 3-(7-(thiazol-2-yl)-4-(trifluoromethyl)benzo[d]oxazol-2-yl)-3,6-diazabicyclo[3.1.1]heptane-6-carboxylate obtained in Example 32 (b) by a similar method to Example 1(c).

Example 33

2-(3,9-Diazabicyclo[3.3.1]nonan-3-yl)-7-(thiazol-2-yl)-4-(trifluoromethyl)benzo[d]oxazole (a) tert-Butyl 3-(7-bromo-4-(trifluoromethyl)benzo[d]oxazol-2-yl)-3,9-diazabicyclo[3.3.1]nonane-9-carboxylate The title compound was obtained in an amount of 210 mg from 150 mg of 7-bromo-4-(trifluoromethyl)benzo[d]oxazole-2-thiol obtained in Reference Example 4 by a similar method to Example 1(a) except that tert-butyl 3,9-diazabicyclo[3.3.1]nonane-9-carboxylate was used instead of tert-butyl 3,8-diazabicyclo[3.2.1]octane-8-carboxylate.

(b) tert-Butyl 3-(7-(thiazol-2-yl)-4-(trifluoromethyl)benzo[d]oxazol-2-yl)-3,9-diazabicyclo[3.3.1]nonane-9-carboxylate The title compound was obtained as a crude product in an amount of 100 mg from 100 mg of tert-butyl 3-(7-bromo-4-(trifluoromethyl)benzo[d]oxazol-2-yl)-3,9-diazabicyclo[3.3.1]nonane-9-carboxylate obtained in Example 33(a) by a similar method to Example 2(b) except that toluene was used instead of 1,4-dioxane and tetrakis(triphenylphosphine)palladium(0) was used instead of bis(triphenylphosphine)palladium(II) dichloride.

(c) 2-(3,9-Diazabicyclo[3.3.1]nonan-3-yl)-7-(thiazol-2-yl)-4-(trifluoromethyl)benzo[d]oxazole The title compound was obtained in an amount of 50 mg from 100 mg of tert-butyl 3-(7-(thiazol-2-yl)-4-(trifluoromethyl)benzo[d]oxazol-2-yl)-3,9-diazabicyclo[3.3.1]nonane-9-carboxylate obtained in Example 33 (b) by a similar method to Example 1(c).

Example 34

N-(2-(3,9-Diazabicyclo[3.3.1]nonan-3-yl)-7-(thiazol-2-yl)benzo[d]oxazol-4-yl)acetamide (a) tert-Butyl 3-(4-acetamido-7-bromobenzo[d]oxazol-2-yl)-3,9-diazabicyclo[3.3.1]nonane-9-carboxylate The title compound was obtained in an amount of 28 mg from 250 mg of N-(7-bromo-2-mercaptobenzo[d]oxazol-4-yl)acetamide obtained in Reference Example 5 by a similar method to Example 1(a) except that tert-butyl 3,9-diazabicyclo[3.3.1]nonane-9-carboxylate was used instead of tert-butyl 3,8-diazabicyclo[3.2.1]octane-8-carboxylate.

(b) tert-Butyl 3-(4-acetamido-7-(thiazol-2-yl)benzo[d]oxazol-2-yl)-3,9-diazabicyclo[3.3.1]nonane-9-carboxylate The title compound was obtained in an amount of 19 mg from tert-butyl 3-(4-acetamido-7-bromobenzo[d]oxazol-2-yl)-3,9-diazabicyclo[3.3.1]nonane-9-carboxylate obtained in Example 34(a) by a similar method to Example 1(b) except that a solution of 6 equivalents of 0.5M solution of 2-thiazolylzinc bromide in tetrahydrofuran was used instead of the 2 equivalents of 0.5M solution of 2-thiazolylzinc bromide in tetrahydrofuran.

(c) N-(2-(3,9-Diazabicyclo[3.3.1]nonan-3-yl)-7-(thiazol-2-yl)benzo[d]oxazol-4-yl)acetamide The title compound was obtained in an amount of 8.3 mg from 19 mg of tert-butyl 3-(4-acetamido-7-(thiazol-2-yl)benzo[d]oxazol-2-yl)-3,9-diazabicyclo[3.3.1]nonane-9-carboxylate obtained in Example 34 (b) by a similar method to Example 1(c).

Example 35

N-(2-(3,6-diazabicyclo[3.1.1]heptan-3-yl)-7-(thiazol-2-yl)benzo[d]oxazol-4-yl)acetamide (a) tert-Butyl 3-(4-acetamido-7-bromobenzo[d]oxazol-2-yl)-3,6-diazabicyclo[3.1.1]heptane-6-carboxylate The title compound was obtained in an amount of 33 mg from 250 mg of N-(7-bromo-2-mercaptobenzo[d]oxazol-4-yl)acetamide obtained in Reference Example 5 by a similar method to Example 1(a) except that tert-butyl 3,6-diazabicyclo[3.1.1]heptane-6-carboxylate was used instead of tert-butyl 3,8-diazabicyclo[3.2.1]octane-8-carboxylate.

(b) tert-Butyl 3-(4-acetamido-7-(thiazol-2-yl)benzo[d]oxazol-2-yl)-3,6-diazabicyclo[3.1.1]heptane-6-carboxylate The title compound was obtained in an amount of 21 mg from tert-butyl 3-(4-acetamido-7-bromobenzo[d]oxazol-2-yl)-3,6-diazabicyclo[3.1.1]heptane-6-carboxylate obtained in Example 35(a) by a similar method to Example 1(b) except that 6 equivalents of 0.5M solution of 2-thiazolylzinc bromide in tetrahydrofuran was used instead of the 2 equivalents of 0.5M solution of 2-thiazolylzinc bromide in tetrahydrofuran.

(c) N-(2-(3,6-diazabicyclo[3.1.1]heptan-3-yl)-7-(thiazol-2-yl)benzo[d]oxazol-4-yl)acetamide The title compound was obtained in an amount of 14 mg from 21 mg of tert-butyl 3-(4-acetamido-7-(thiazol-2-yl)benzo[d]oxazol-2-yl)-3,6-diazabicyclo[3.1.1]heptane-6-carboxylate obtained in Example 35 (b) by a similar method to Example 1(c).

Example 36

2-(3,8-Diazabicyclo[3.2.1]octan-3-yl)-4-chloro-7-(thiazol-2-yl)benzo[d]oxazole (a) tert-Butyl 3-(7-bromo-4-chlorobenzo[d]oxazol-2-yl)-3,8-diazabicyclo[3.2.1]octane-8-carboxylate The title compound was obtained in an amount of 150 mg from 100 mg of 7-bromo-4-chlorobenzo[d]oxazole-2-thiol obtained in Reference Example 6 and tert-butyl 3,8-diazabicyclo[3.2.1]octane-8-carboxylate by a similar method to Example 1(a).

(b) tert-Butyl 3-(4-chloro-7-(thiazol-2-yl)benzo[d]oxazol-2-yl)-3,8-diazabicyclo[3.2.1]octane-8-carboxylate The title compound was obtained in an amount of 130 mg from 130 mg of tert-butyl 3-(7-bromo-4-chlorobenzo[d]oxazol-2-yl)-3,8-diazabicyclo[3.2.1]octane-8-carboxylate obtained in Example 36(a) by a similar method to Example 2(b) except that toluene was used instead of 1,4-dioxane and tetrakis(triphenylphosphine)palladium(0) was used instead of bis(triphenylphosphine)palladium(II) dichloride.

(c) 2-(3,8-Diazabicyclo[3.2.1]octan-3-yl)-4-chloro-7-(thiazol-2-yl)benzo[d]oxazole The title compound was obtained in an amount of 85 mg from 130 mg of tert-butyl 3-(4-chloro-7-(thiazol-2-yl)benzo

[d]oxazol-2-yl)-3,8-diazabicyclo[3.2.1]octane-8-carboxylate obtained in Example 36(b) by a similar method to Example 1(c).

Example 37

2-(3,6-Diazabicyclo[3.1.1]heptan-3-yl)-4-chloro-7-(thiazol-2-yl)benzo[d]oxazole (a) tert-Butyl 3-(7-bromo-4-chlorobenzo[d]oxazol-2-yl)-3,6-diazabicyclo[3.1.1]heptane-6-carboxylate The title compound was obtained in an amount of 135 mg from 100 mg of 7-bromo-4-chlorobenzo[d]oxazole-2-thiol obtained in Reference Example 6 by a similar method to Example 1(a) except that tert-butyl 3,6-diazabicyclo[3.1.1]heptane-6-carboxylate was used instead of tert-butyl 3,8-diazabicyclo[3.2.1]octane-8-carboxylate.

(b) tert-Butyl 3-(4-chloro-7-(thiazol-2-yl)benzo[d]oxazol-2-yl)-3,6-diazabicyclo[3.1.1]heptane-6-carboxylate The title compound was obtained as a crude product in an amount of 200 mg from 130 mg of tert-butyl 3-(7-bromo-4-chlorobenzo[d]oxazol-2-yl)-3,6-diazabicyclo[3.1.1]heptane-6-carboxylate obtained in Example 37(a) by a similar method to Example 2(b) except that toluene was used instead of 1,4-dioxane and tetrakis(triphenylphosphine)palladium(0) was used instead of bis(triphenylphosphine)palladium(II) dichloride.

(c) 2-(3,6-Diazabicyclo[3.1.1]heptan-3-yl)-4-chloro-7-(thiazol-2-yl)benzo[d]oxazole The title compound was obtained in an amount of 90 mg from 200 mg of tert-butyl 3-(4-chloro-7-(thiazol-2-yl)benzo[d]oxazol-2-yl)-3,6-diazabicyclo[3.1.1]heptane-6-carboxylate obtained in Example 37 (b) by a similar method to Example 1(c).

Example 38

2-(3,9-Diazabicyclo[3.3.1]nonan-3-yl)-4-chloro-7-(thiazol-2-yl)benzo[d]oxazole (a) tert-Butyl 3-(7-bromo-4-chlorobenzo[d]oxazol-2-yl)-3,9-diazabicyclo[3.3.1]nonane-9-carboxylate The title compound was obtained in an amount of 160 mg from 100 mg of 7-bromo-4-chlorobenzo[d]oxazole-2-thiol obtained in Reference Example 6 by a similar method to Example 1(a) except that tert-butyl 3,9-diazabicyclo[3.3.1]nonane-9-carboxylate was used instead of tert-butyl 3,8-diazabicyclo[3.2.1]octane-8-carboxylate.

(b) tert-Butyl 3-(4-chloro-7-(thiazol-2-yl)benzo[d]oxazol-2-yl)-3,9-diazabicyclo[3.3.1]nonane-9-carboxylate The title compound was obtained as a crude product in an amount of 180 mg from 130 mg of tert-butyl 3-(7-bromo-4-chlorobenzo[d]oxazol-2-yl)-3,9-diazabicyclo[3.3.1]nonane-9-carboxylate obtained in Example 38(a) by a similar method to Example 2(b) except that toluene was used instead of 1,4-dioxane and tetrakis(triphenylphosphine)palladium(0) was used instead of bis(triphenylphosphine)palladium(II) dichloride.

(c) 2-(3,9-Diazabicyclo[3.3.1]nonan-3-yl)-4-chloro-7-(thiazol-2-yl)benzo[d]oxazole The title compound was obtained in an amount of 90 mg from 180 mg of tert-butyl 3-(4-chloro-7-(thiazol-2-yl)benzo[d]oxazol-2-yl)-3,9-diazabicyclo[3.3.1]nonane-9-carboxylate obtained in Example 38 (b) by a similar method to Example 1(c).

Example 39

2-(3,8-Diazabicyclo[3.2.1]octan-3-yl)-5-(methylthio)-7-(thiazol-2-yl)benzo[d]oxazole (a) tert-Butyl 3-(7-bromo-5-(methylthio)benzo[d]oxazol-2-yl)-3,8-diazabicyclo[3.2.1]octane-8-carboxylate The title compound was obtained in an amount of 153 mg from 100 mg of 7-bromo-5-(methylthio)benzo[d]oxazole-2-thiol obtained in Reference Example 7 and tert-butyl 3,8-diazabicyclo[3.2.1]octane-8-carboxylate by a similar method to Example 1(a).

(b) tert-Butyl 3-(5-(methiylthio)-7-(thiazol-2-yl)benzo[d]oxazol-2-yl)-3,8-diazabicyclo[3.2.1]octane-8-carboxylate The title compound was obtained as a crude product in an amount of 300 mg from 150 mg of tert-butyl 3-(7-bromo-5-(methylthio)benzo[d]oxazol-2-yl)-3,8-diazabicyclo[3.2.1]octane-8-carboxylate obtained in Example 39(a) by a similar method to Example 2(b) except that toluene was used instead of 1,4-dioxane and tetrakis(triphenylphosphine)palladium(0) was used instead of bis(triphenylphosphine)palladium(II) dichloride.

(c) 2-(3,8-Diazabicyclo[3.2.1]octan-3-yl)-5-(methylthio)-7-(thiazol-2-yl)benzo[d]oxazole The title compound was obtained in an amount of 58 mg from 300 mg of tert-butyl 3-(5-(methiylthio)-7-(thiazol-2-yl)benzo[d]oxazol-2-yl)-3,8-diazabicyclo[3.2.1]octane-8-carboxylate obtained in Example 39(b) by a similar method to Example 1(c).

Example 40

2-(3,6-Diazabicyclo[3.1.1]heptan-3-yl)-5-(methylthio)-7-(thiazol-2-yl)benzo[d]oxazole (a) tert-Butyl 3-(7-bromo-5-(methylthio)benzo[d]oxazol-2-yl)-3,6-diazabicyclo[3.1.1]heptane-6-carboxylate The title compound was obtained in an amount of 120 mg from 100 mg of 7-bromo-5-(methylthio)benzo[d]oxazole-2-thiol obtained in Reference Example 7 by a similar method to Example 1(a) except that tert-butyl 3,6-diazabicyclo[3.1.1]heptane-6-carboxylate was used instead of tert-butyl 3,8-diazabicyclo[3.2.1]octane-8-carboxylate.

(b) tert-Butyl 3-(5-(methylthio)-7-(thiazol-2-yl)
benzo[d]oxazol-2-yl)-3,6-diazabicyclo[3.1.1]heptane-6-carboxylate The title compound was obtained in an amount of 106 mg from 110 mg of tert-butyl 3-(7-bromo-5-(methylthio)benzo[d]oxazol-2-yl)-3,6-diazabicyclo[3.1.1]heptane-6-carboxylate obtained in Example 40(a) by a similar method to Example 2(b) except that toluene was used instead of 1,4-dioxane and tetrakis(triphenylphosphine)palladium(0) was used instead of bis(triphenylphosphine)palladium(II) dichloride.

(c) 2-(3,6-Diazabicyclo[3.1.1]heptan-3-yl)-5-(methylthio)-7-(thiazol-2-yl)benzo[d]oxazole The title compound was obtained in an amount of 65 mg from 103 mg of tert-butyl 3-(5-(methylthio)-7-(thiazol-2-yl)benzo[d]oxazol-2-yl)-3,6-diazabicyclo[3.1.1]heptane-6-carboxylate obtained in Example 40(b) by a similar method to Example 1(c).

Example 41

2-(3,9-Diazabicyclo[3.3.1]nonan-3-yl)-5-(methylthio)-7-(thiazol-2-yl)benzo[d]oxazole (a) tert-Butyl 3-(7-bromo-5-(methylthio)benzo[d]oxazol-2-yl)-3,9-diazabicyclo[3.3.1]nonane-9-carboxylate The title compound was obtained in an amount of 100 mg from 100 mg of 7-bromo-5-(methylthio)benzo[d]oxazole-2-thiol obtained in Reference Example 7 by a similar method to Example 1(a) except that tert-butyl 3,9-diazabicyclo[3.3.1]nonane-9-carboxylate was used instead of tert-butyl 3,8-diazabicyclo[3.2.1]octane-8-carboxylate.

(b) tert-Butyl 3-(5-(methylthio)-7-(thiazol-2-yl)benzo[d]oxazol-2-yl)-3,9-diazabicyclo[3.3.1]nonane-9-carboxylate The title compound was obtained in an amount of 70 mg from 80 mg of tert-butyl 3-(7-bromo-5-(methylthio)benzo[d]oxazol-2-yl)-3,9-diazabicyclo[3.3.1]nonane-9-carboxylate obtained in Example 41(a) by a similar method to Example 2(b) except that toluene was used instead of 1,4-dioxane and tetrakis(triphenylphosphine)palladium(0) was used instead of bis(triphenylphosphine)palladium(II) dichloride.

(c) 2-(3,9-Diazabicyclo[3.3.1]nonan-3-yl)-5-(methylthio)-7-(thiazol-2-yl)benzo[d]oxazole The title compound was obtained in an amount of 40 mg from 65 mg of tert-butyl 3-(5-(methylthio)-7-(thiazol-2-yl)benzo[d]oxazol-2-yl)-3,9-diazabicyclo[3.3.1]nonane-9-carboxylate obtained in Example 41(b) by a similar method to Example 1(c).

Example 42

2-(3,8-Diazabicyclo[3.2.1]octan-3-yl)-5-(methylsulfinyl)-7-(thiazol-2-yl)benzo[d]oxazole (a) tert-Butyl 3-(7-bromo-5-(methylsulfinyl)benzo[d]oxazol-2-yl)-3,8-diazabicyclo[3.2.1]octane-8-carboxylate The title compound was obtained in an amount of 200 mg from 150 mg of 7-bromo-5-(methylsulfinyl)benzo[d]oxazole-2-thiol obtained in Reference Example 8 and tert-butyl 3,8-diazabicyclo[3.2.1]octane-8-carboxylate by a similar method to Example 1(a).

(b) tert-Butyl 3-(5-(methylsulfinyl)-7-(thiazol-2-yl)benzo[d]oxazol-2-yl)-3,8-diazabicyclo[3.2.1]octane-8-carboxylate The title compound was obtained as a crude product in an amount of 220 mg from 200 mg of tert-butyl 3-(7-bromo-5-(methylsulfinyl)benzo[d]oxazol-2-yl)-3,8-diazabicyclo[3.2.1]octane-8-carboxylate obtained in Example 42 (a) by a similar method to Example 2(b) except that toluene was used instead of 1,4-dioxane and tetrakis(triphenylphosphine)palladium(0) was used instead of bis(triphenylphosphine)palladium(II) dichloride.

(c) 2-(3,8-Diazabicyclo[3.2.1]octan-3-yl)-5-(methylsulfinyl)-7-(thiazol-2-yl)benzo[d]oxazole The title compound was obtained in an amount of 45 mg from 90 mg of tert-butyl 3-(5-(methylsulfinyl)-7-(thiazol-2-yl)benzo[d]oxazol-2-yl)-3,8-diazabicyclo[3.2.1]octane-8-carboxylate obtained in Example 42 (b) by a similar method to Example 1(c).

Example 43

2-(3,6-Diazabicyclo[3.1.1]heptan-3-yl)-5-(methylsulfinyl)-7-(thiazol-2-yl)benzo[d]oxazole (a) tert-Butyl 3-(7-bromo-5-(methylsulfinyl)benzo[d]oxazol-2-yl)-3,6-diazabicyclo[3.1.1]heptane-6-carboxylate The title compound was obtained in an amount of 200 mg from 150 mg of 7-bromo-5-(methylsulfinyl)benzo[d]oxazole-2-thiol obtained in Reference Example 8 by a similar method to Example 1(a) except that tert-butyl 3,6-diazabicyclo[3.1.1]heptane-6-carboxylate was used instead of tert-butyl 3,8-diazabicyclo[3.2.1]octane-8-carboxylate.

(b) tert-Butyl 3-(5-(methylsulfinyl)-7-(thiazol-2-yl)benzo[d]oxazol-2-yl)-3,6-diazabicyclo[3.1.1]heptane-6-carboxylate The title compound was obtained in an amount of 200 mg from 200 mg of tert-butyl 3-(7-bromo-5-(methylsulfinyl)benzo[d]oxazol-2-yl)-3,6-diazabicyclo[3.1.1]heptane-6-carboxylate obtained in Example 43(a) by a similar method to Example 2(b) except that toluene was used instead of 1,4-dioxane and tetrakis(triphenylphosphine)palladium(0) was used instead of bis(triphenylphosphine)palladium(II) dichloride.

(c) 2-(3,6-Diazabicyclo[3.1.1]heptan-3-yl)-5-(methylsulfinyl)-7-(thiazol-2-yl)benzo[d]oxazole The title compound was obtained in an amount of 42 mg from 80 mg of tert-butyl 3-(5-(methylsulfinyl)-7-(thiazol-2-yl)benzo[d]oxazol-2-yl)-3,6-diazabicyclo[3.1.1]heptane-6-carboxylate obtained in Example 43 (b) by a similar method to Example 1(c).

Example 44

2-(3,9-Diazabicyclo[3.3.1]nonan-3-yl)-5-(methylsulfinyl)-7-(thiazol-2-yl)benzo[d]oxazole (a) tert-Butyl 3-(7-bromo-5-(methylsulfinyl)benzo[d]oxazol-2-yl)-3,9-diazabicyclo[3.3.1]nonane-9-carboxylate The title compound was obtained in an amount of 100 mg from 100 mg of 7-bromo-5-(methylsulfinyl)benzo[d]oxazole-2-thiol obtained in Reference Example 8 by a similar method to Example 1(a) except that tert-butyl 3,9-diazabicyclo[3.3.1]nonane-9-carboxylate was used instead of tert-butyl 3,8-diazabicyclo[3.2.1]octane-8-carboxylate.

(b) tert-Butyl 3-(5-(methylsulfinyl)-7-(thiazol-2-yl)benzo[d]oxazol-2-yl)-3,9-diazabicyclo[3.3.1]nonane-9-carboxylate The title compound was obtained as in an amount of 150 mg from 165 mg of tert-butyl 3-(7-bromo-5-(methylsulfinyl)benzo[d]oxazol-2-yl)-3,9-diazabicyclo[3.3.1]nonane-9-carboxylate obtained in Example 44(a) by a similar method to Example 2(b) except that toluene was used instead of 1,4-dioxane and tetrakis(triphenylphosphine)palladium(0) was used instead of bis(triphenylphosphine)palladium(II) dichloride.

(c) 2-(3,9-Diazabicyclo[3.3.1]nonan-3-yl)-5-(methylsulfinyl)-7-(thiazol-2-yl)benzo[d]oxazole The title compound was obtained in an amount of 39 mg from 80 mg of tert-butyl 3-(5-(methylsulfinyl)-7-(thiazol-2-yl)benzo[d]oxazol-2-yl)-3,9-diazabicyclo[3.3.1]nonane-9-carboxylate obtained in Example 44 (b) by a similar method to Example 1(c).

Example 45

2-(3,8-Diazabicyclo[3.2.1]octan-3-yl)-5-(methylsulfonyl)-7-(thiazol-2-yl)benzo[d]oxazole (a) tert-Butyl 3-(5-(methylsulfonyl)-7-(thiazol-2-yl)benzo[d]oxazol-2-yl)-3,8-diazabicyclo[3.2.1]octane-8-carboxylate 120 mg of tert-butyl 3-(5-(methylsulfinyl)-7-(thiazol-2-yl)benzo[d]oxazol-2-yl)-3,8-diazabicyclo[3.2.1]octane-8-carboxylate obtained in Example 42(b) and mCPBA (174 mg, 4 equivalents) were dissolved in dichloromethane (50 mL), followed by reaction at room temperature for 1 hour. The formation of the product was confirmed by TLC, and then saturated sodium hydrogen carbonate aqueous solution was added thereto, followed by extraction using dichloromethane. Thereafter, the organic phase was washed by distilled water and dried over anhydrous magnesium sulfate, followed by filtration, and thus obtaining as a crude product 130 mg of the title compound by vacuum concentration of the filtrate.

(b) 2-(3,8-Diazabicyclo[3.2.1]octan-3-yl-5-(methylsulfonyl)-7-(thiazol-2-yl)benzo[d]oxazole The title compound was obtained in an amount of 40 mg from 80 mg of tert-butyl 3-(5-(methylsulfonyl)-7-(thiazol-2-yl)benzo[d]oxazol-2-yl)-3,8-diazabicyclo[3.2.1]octane-8-carboxylate obtained in Example 45(a) by a similar method to Example 1(c).

Example 46

2-(3,6-Diazabicyclo[3.1.1]heptan-3-yl)-5-(methylsulfonyl)-7-(thiazol-2-yl)benzo[d]oxazole (a) tert-Butyl 3-(5-(methylsulfonyl)-7-(thiazol-2-yl)benzo[d]oxazol-2-yl)-3,6-diazabicyclo[3.1.1]heptane-6-carboxylate The title compound was obtained in an amount of 90 mg from 115 mg of tert-butyl 3-(5-(methylsulfinyl)-7-(thiazol-2-yl)benzo[d]oxazol-2-yl)-3,6-diazabicyclo[3.1.1]heptane-6-carboxylate obtained in Example 43 (b) by a similar method to Example 45 (a).

(b) 2-(3,6-Diazabicyclo[3.1.1]heptan-3-yl)-5-(methylsulfonyl)-7-(thiazol-2-yl)benzo[d]oxazole The title compound was obtained in an amount of 49 mg from 80 mg of tert-butyl 3-(5-(methylsulfonyl)-7-(thiazol-2-yl)benzo[d]oxazol-2-yl)-3,6-diazabicyclo[3.1.1]heptane-6-carboxylate obtained in Example 46(a) by a similar method to Example 1(c).

Example 47

2-(3,9-Diazabicyclo[3.3.1]nonan-3-yl)-5-(methylsulfonyl)-7-(thiazol-2-yl)benzo[d]oxazole (a) tert-Butyl 3-(5-(methylsulfonyl)-7-(thiazol-2-yl)benzo[d]oxazol-2-yl)-3,9-diazabicyclo[3.3.1]nonane-9-carboxylate The title compound was obtained in an amount of 80 mg from 85 mg of tert-butyl 3-(5-(methylsulfinyl)-7-(thiazol-2-yl)benzo[d]oxazol-2-yl)-3,9-diazabicyclo[3.3.1]nonane-9-carboxylate obtained in Example 44(b) by a similar method to Example 45(a).

(b) 2-(3,9-Diazabicyclo[3.3.1]nonan-3-yl)-5-(methylsulfonyl)-7-(thiazol-2-yl)benzo[d]oxazole The title compound was obtained in an amount of 48 mg from 80 mg of tert-butyl 3-(5-(methylsulfonyl)-7-(thiazol-2-yl)benzo[d]oxazol-2-yl)-3,9-diazabicyclo[3.3.1]nonane-9-carboxylate obtained in Example 47(a) by a similar method to Example 1(c).

Example 48

N-(2-(3,9-diazabicyclo[3.3.1]nonan-3-yl)-7-(thiazol-2-yl)benzo[d]oxazol-5-yl)acetamide (a) tert-Butyl 3-(5-acetamido-7-bromobenzo[d]oxazol-2-yl)-3,9-diazabicyclo[3.3.1]nonane-9-carboxylate The title compound was obtained in an amount of 362 mg from 300 mg of N-(7-bromo-2-mercaptobenzo[d]oxazol-5-yl)acetamide obtained in Reference Example 9 by a similar method to Example 1(a) except that tert-butyl 3,9-diazabicyclo[3.3.1]nonane-9-carboxylate was used instead of tert-butyl 3,8-diazabicyclo[3.2.1]octane-8-carboxylate.

(b) tert-Butyl 3-(5-acetamido-7-(thiazol-2-yl)benzo[d]oxazol-2-yl)-3,9-diazabicyclo[3.3.1]nonane-9-carboxylate The title compound was obtained in an amount of 89 mg from 100 mg of tert-butyl 3-(5-acetamido-7-bromobenzo[d]oxazol-2-yl)-3,9-diazabicyclo[3.3.1]nonane-9-carboxylate obtained in Example 48(a) by a similar method to Example 1(b) except that a solution of 5 equivalents of 0.5M solution of 2-thiazolylzinc bromide in tetrahydrofuran and 0.3 equivalent of 1,1'-Bis(diphenylphosphino)ferrocene palladium(II) dichloride dichloromethane complex were used.

(c) N-(2-(3,9-diazabicyclo[3.3.1]nonan-3-yl)-7-(thiazol-2-yl)benzo[d]oxazol-5-yl)acetamide The title compound was obtained in an amount of 45 mg from 88 mg of tert-butyl 3-(5-acetamido-7-(thiazol-2-yl)benzo[d]oxazol-2-yl)-3,9-diazabicyclo[3.3.1]nonane-9-carboxylate obtained in Example 48 (b) by a similar method to Example 1(c).

Example 49

N-(2-(3,6-diazabicyclo[3.1.1]heptan-3-yl)-7-(thiazol-2-yl)benzo[d]oxazol-5-yl)acetamide (a) tert-Butyl 3-(5-acetamido-7-bromobenzo[d]oxazol-2-yl)-3,6-diazabicyclo[3.1.1]heptane-6-carboxylate The title compound was obtained in an amount of 136 mg from 200 mg of N-(7-bromo-2-mercaptobenzo[d]oxazol-5-yl)acetamide obtained in Reference Example 9 by a similar method to Example 1(a) except that tert-butyl 3,6-diazabicyclo[3.1.1]heptane-6-carboxylate was used instead of tert-butyl 3,8-diazabicyclo[3.2.1]octane-8-carboxylate.

(b) tert-Butyl 3-(5-acetamido-7-(thiazol-2-yl)benzo[d]oxazol-2-yl)-3,6-diazabicyclo[3.1.1]heptane-6-carboxylate The title compound was obtained in an amount of 100 mg from 100 mg of tert-butyl 3-(5-acetamido-7-bromobenzo[d]oxazol-2-yl)-3,6-diazabicyclo[3.1.1]heptane-6-carboxylate obtained in Example 49(a) by a similar method to Example 1(b) except that a solution of 5 equivalents of 0.5M solution of 2-thiazolylzinc bromide in tetrahydrofuran and 0.3 equivalent of 1,1'-bis(diphenylphosphino)ferrocene palladium(II) dichloride·dichloromethane complex were used.

(c) N-(2-(3,6-diazabicyclo[3.1.1]heptan-3-yl)-7-(thiazol-2-yl)benzo[d]oxazol-5-yl)acetamide The title compound was obtained in an amount of 27 mg from 100 mg of tert-butyl 3-(5-acetamido-7-(thiazol-2-yl)benzo[d]oxazol-2-yl)-3,6-diazabicyclo[3.1.1]heptane-6-carboxylate obtained in Example 49(b) by a similar method to Example 1(c).

Example 50

N-(2-(3,8-diazabicyclo[3.2.1]octan-3-yl)-7-(thiazol-2-yl)benzo[d]oxazol-5-yl)acetamide (a) tert-Butyl 3-(5-acetamido-7-bromobenzo[d]oxazol-2-yl)-3,8-diazabicyclo[3.2.1]octane-8-carboxylate The title compound was obtained in an amount of 107 mg from 120 mg of N-(7-bromo-2-mercaptobenzo[d]oxazol-5-yl)acetamide obtained in Reference Example 9 and tert-butyl 3,8-diazabicyclo[3.2.1]octane-8-carboxylate by a similar method to Example 1(a).

(b) tert-Butyl 3-(5-acetamido-7-(thiazol-2-yl)benzo[d]oxazol-2-yl)-3,8-diazabicyclo[3.2.1]octane-8-carboxylate The title compound was obtained in an amount of 54 mg from 60 mg of tert-butyl 3-(5-acetamido-7-bromobenzo[d]oxazol-2-yl)-3,8-diazabicyclo[3.2.1]octane-8-carboxylate obtained in Example 50(a) by a similar method to Example 1(b) except that 6 equivalents of 0.5M solution of 2-thiazolylzinc bromide in tetrahydrofuran was used instead of 2 equivalents of 0.5M solution of 2-thiazolylzinc bromide in tetrahydrofuran.

(c) N-(2-(3,8-diazabicyclo[3.2.1]octan-3-yl)-7-(thiazol-2-yl)benzo[d]oxazol-5-yl)acetamide The title compound was obtained in an amount of 18 mg from 54 mg of tert-butyl 3-(5-acetamido-7-(thiazol-2-yl)benzo[d]oxazol-2-yl)-3,8-diazabicyclo[3.2.1]octane-8-carboxylate obtained in Example 50(b) by a similar method to Example 1(c).

Example 51

2-(3,8-Diazabicyclo[3.2.1]octan-3-yl)-7-(thiazol-2-yl)-5-(trifluoromethyl)benzo[d]oxazole (a) tert-Butyl 3-(7-bromo-5-(trifluoromethyl)benzo[d]oxazol-2-yl)-3,8-diazabicyclo[3.2.1]octane-8-carboxylate The title compound was obtained in an amount of 109 mg by a similar method to Example 1(a) except that 101 mg of 7-bromo-5-(trifluoromethyl)benzo[d]oxazole-2-thiol (a compound disclosed in International Publication No. WO2015/005429) was used.

(b) tert-Butyl 3-(7-(thiazol-2-yl)-5-(trifluoromethyl)benzo[d]oxazol-2-yl)-3,8-diazabicyclo[3.2.1]octane-8-carboxylate The title compound was obtained in an amount of 65 mg from 132 mg of tert-butyl 3-(7-bromo-5-(trifluoromethyl)benzo[d]oxazol-2-yl)-3,8-diazabicyclo[3.2.1]octane-8-carboxylate obtained in Example 51(a) by a similar method to Example 1(b) except that 3.5 equivalents of 0.5M solution of 2-thiazolylzinc bromide in tetrahydrofuran and 0.3 equivalent of 1,1'-bis(diphenylphosphino)ferrocene palladium(II) dichloride·dichloromethane complex were used.

(c) 2-(3,8-Diazabicyclo[3.2.1]octan-3-yl)-7-(thiazol-2-yl)-5-(trifluoromethyl)benzo[d]oxazole The title compound was obtained in an amount of 43 mg from 65 mg of tert-butyl 3-(7-(thiazol-2-yl)-5-(trifluoromethyl)benzo[d]oxazol-2-yl)-3,8-diazabicyclo[3.2.1]octane-8-carboxylate obtained in Example 51(b) by a similar method to Example 1(c).

Example 52

2-(3,6-Diazabicyclo[3.1.1]heptan-3-yl)-7-(thiazol-2-yl)-5-(trifluoromethyl)benzo[d]oxazole (a) tert-Butyl 3-(7-bromo-5-(trifluoromethyl)benzo[d]oxazol-2-yl)-3,6-diazabicyclo[3.1.1]heptane-6-carboxylate The title compound was obtained in an amount of 134 mg from 150 mg of 7-bromo-5-(trifluoromethyl)benzo[d]oxazole-2-thiol by a similar method to Example 1(a) except that tert-butyl 3,6-diazabicyclo[3.1.1]heptane-6-carboxylate was used instead of tert-butyl 3,8-diazabicyclo[3.2.1]octane-8-carboxylate.

(b) tert-Butyl 3-(7-(thiazol-2-yl)-5-(trifluoromethyl)benzo[d]oxazol-2-yl)-3,6-diazabicyclo[3.1.1]heptane-6-carboxylate The title compound was obtained in an amount of 77 mg from 134 mg of tert-butyl 3-(7-bromo-5-(trifluoromethyl)benzo[d]oxazol-2-yl)-3,6-diazabicyclo[3.1.1]heptane-6-carboxylate obtained in Example 52 (a) by a similar method to Example 1(b).

(c) 2-(3,6-Diazabicyclo[3.1.1]heptan-3-yl)-7-(thiazol-2-yl)-5-(trifluoromethyl)benzo[d]oxazole The title compound was obtained in an amount of 26 mg from 77 mg of tert-butyl 3-(7-(thiazol-2-yl)-5-(trifluoromethyl)benzo[d]oxazol-2-yl)-3,6-diazabicyclo[3.1.1]heptane-6-carboxylate obtained in Example 52 (b) by a similar method to Example 1(c).

Example 53

2-(3,9-Diazabicyclo[3.3.1]nonan-3-yl)-7-(thiazol-2-yl)-5-(trifluoromethyl)benzo[d]oxazole (a) tert-Butyl 3-(7-bromo-5-(trifluoromethyl)benzo[d]oxazol-2-yl)-3,9-diazabicyclo[3.3.1]nonane-9-carboxylate The title compound was obtained in an amount of 139 mg from 150 mg of 7-bromo-5-(trifluoromethyl)benzo[d]oxazole-2-thiol by a similar method to Example 1(a) except that tert-butyl 3,9-diazabicyclo[3.3.1]nonane-9-carboxylate was used instead of tert-butyl 3,8-diazabicyclo[3.2.1]octane-8-carboxylate.

(b) tert-Butyl 3-(7-(thiazol-2-yl)-5-(trifluoromethyl)benzo[d]oxazol-2-yl)-3,9-diazabicyclo[3.3.1]nonane-9-carboxylate The title compound was obtained in an amount of 95.4 mg from 139 mg of tert-butyl 3-(7-bromo-5-(trifluoromethyl)benzo[d]oxazol-2-yl)-3,9-diazabicyclo[3.3.1]nonane-9-carboxylate obtained in Example 53(a) by a similar method to Example 1(b).

(c) 2-(3,9-Diazabicyclo[3.3.1]nonan-3-yl)-7-(thiazol-2-yl)-5-(trifluoromethyl)benzo[d]oxazole The title compound was obtained in an amount of 49.8 mg from 95.4 mg of tert-butyl 3-(7-(thiazol-2-yl)-5-(trifluoromethyl)benzo[d]oxazol-2-yl)-3,9-diazabicyclo[3.3.1]nonane-9-carboxylate obtained in Example 53 (b) by a similar method to Example 1(c).

Example 54

2-(3,8-Diazabicyclo[3.2.1]octan-3-yl)-7-(thiazol-2-yl)-5-(trifluoromethoxy)benzo[d]oxazole (a) tert-Butyl 3-(7-bromo-5-(trifluoromethoxy)benzo[d]oxazol-2-yl)-3,8-diazabicyclo[3.2.1]octane-8-carboxylate The title compound was obtained in an amount of 192 mg from 150 mg of 7-bromo-5-(trifluoromethoxy)benzo[d]oxazole-2-thiol obtained in Reference Example 10 and tert-butyl 3,8-diazabicyclo[3.2.1]octane-8-carboxylate by a similar method to Example 1(a).

(b) tert-Butyl 3-(7-(thiazol-2-yl)-5-(trifluoromethoxy)benzo[d]oxazol-2-yl)-3,8-diazabicyclo[3.2.1]octane-8-carboxylate The title compound was obtained in an amount of 77 mg from 192 mg of tert-butyl 3-(7-bromo-5-(trifluoromethoxy)benzo[d]oxazol-2-yl)-3,8-diazabicyclo[3.2.1]octane-8-carboxylate obtained in Example 54(a) by a similar method to Example 1(b) except that a microwave reactor (by Biotage, 100° C., 20 min) was used.

(c) 2-(3,8-Diazabicyclo[3.2.1]octan-3-yl)-7-(thiazol-2-yl)-5-(trifluoromethoxy)benzo[d]oxazole The title compound was obtained in an amount of 49 mg from 74 mg of tert-butyl 3-(7-(thiazol-2-yl)-5-(trifluoromethoxy)benzo[d]oxazol-2-yl)-3,8-diazabicyclo[3.2.1]octane-8-carboxylate obtained in Example 54 (b) by a similar method to Example 1(c).

Example 55

2-(3,9-Diazabicyclo[3.3.1]nonan-3-yl)-7-(thiazol-2-yl)-5-(trifluoromethoxy)benzo[d]oxazole (a) tert-Butyl 3-(7-bromo-5-(trifluoromethoxy)benzo[d]oxazol-2-yl)-3,9-diazabicyclo[3.3.1]nonane-9-carboxylate The title compound was obtained in an amount of 195 mg from 150 mg of 7-bromo-5-(trifluoromethoxy)benzo[d]oxazole-2-thiol obtained in Reference Example 10 by a similar method to Example 1(a) except that tert-butyl 3,9-diazabicyclo[3.3.1]nonane-9-carboxylate was used instead of tert-butyl 3,8-diazabicyclo[3.2.1]octane-8-carboxylate.

(b) tert-Butyl 3-(7-(thiazol-2-yl)-5-(trifluoromethoxy)benzo[d]oxazol-2-yl)-3,9-diazabicyclo[3.3.1]nonane-9-carboxylate The title compound was obtained in an amount of 158 mg from 195 mg of tert-butyl 3-(7-bromo-5-(trifluoromethoxy)benzo[d]oxazol-2-yl)-3,9-diazabicyclo[3.3.1]nonane-9-carboxylate obtained in Example 55(a) by a similar method to Example 1(b) except that the microwave reactor (by Biotage, 100° C., 20 min) was used.

(c) 2-(3,9-Diazabicyclo[3.3.1]nonan-3-yl)-7-(thiazol-2-yl)-5-(trifluoromethoxy)benzo[d]oxazole The title compound was obtained in an amount of 114 mg from 158 mg of tert-butyl 3-(7-(thiazol-2-yl)-5-(trifluoromethoxy)benzo[d]oxazol-2-yl)-3,9-diazabicyclo[3.3.1]nonane-9-carboxylate obtained in Example 55 (b) by a similar method to Example 1(c).

Example 56

2-(3,6-Diazabicyclo[3.1.1]heptan-3-yl)-7-(thiazol-2-yl)-5-(trifluoromethoxy)benzo[d]oxazole (a) tert-Butyl 3-(7-bromo-5-(trifluoromethoxy)benzo[d]oxazol-2-yl)-3,6-diazabicyclo[3.1.1]heptane-6-carboxylate The title compound was obtained in an amount of 196 mg from 150 mg of 7-bromo-5-(trifluoromethoxy)benzo[d]oxazole-2-thiol obtained in Reference Example 10 by a similar method to Example 1(a) except that tert-butyl 3,6-diazabicyclo[3.1.1]heptane-6-carboxylate was used instead of tert-butyl 3,8-diazabicyclo[3.2.1]octane-8-carboxylate and the microwave reactor (by Biotage, 120° C., 40 min) was used.

(b) tert-Butyl 3-(7-(thiazol-2-yl)-5-(trifluoromethoxy)benzo[d]oxazol-2-yl)-3,6-diazabicyclo[3.1.1]heptane-6-carboxylate The title compound was obtained in an amount of 133 mg from 194 mg of tert-butyl 3-(7-bromo-5-(trifluoromethoxy)benzo[d]oxazol-2-yl)-3,6-diazabicyclo[3.1.1]heptane-6-carboxylate obtained in Example 56(a) by a similar method to Example 1(b) except that the microwave reactor (by Biotage, 100° C., 80 min) and 2-thiazolylzinc bromide (1.62 mL, 4 equivalents) was used.

(c) 2-(3,6-Diazabicyclo[3.1.1]heptan-3-yl)-7-(thiazol-2-yl)-5-(trifluoromethoxy)benzo[d]oxazole The title compound was obtained in an amount of 103 mg from 133 mg of tert-butyl 3-(7-(thiazol-2-yl)-5-(trifluoromethoxy)benzo[d]oxazol-2-yl)-3,6-diazabicyclo[3.1.1]heptane-6-carboxylate obtained in Example 56(b) by a similar method to Example 1(c).

Example 57

2-(3,8-Diazabicyclo[3.2.1]octan-3-yl)-7-(thiazol-2-yl)benzo[d]oxazole-5-sulfonamide (a) tert-Butyl 3-(7-bromo-5-sulfamoylbenzo[d]oxazol-2-yl)-3,8-diazabicyclo[3.2.1]octane-8-carboxylate The title compound was obtained in an amount of 45 mg from 51 mg of 7-bromo-2-mercaptobenzo[d]oxazole-5-sulfonamide obtained in Reference Example 11 and tert-butyl 3,8-diazabicyclo[3.2.1]octane-8-carboxylate by a similar method to Example 1(a).

(b) tert-Butyl 3-(5-sulfamoyl-7-(thiazol-2-yl)benzo[d]oxazol-2-yl)-3,8-diazabicyclo[3.2.1]octane-8-carboxylate The title compound was obtained in an amount of 12 mg from 45 mg of tert-butyl 3-(7-bromo-5-sulfamoylbenzo[d]oxazol-2-yl)-3,8-diazabicyclo[3.2.1]octane-8-carboxylate obtained in Example 57(a) by a similar method to Example 1(b) except that 6.0 equivalents of 0.5M solution of 2-thiazolylzinc bromide in tetrahydrofuran and 0.4 equivalent of 1,1'-bis(diphenylphosphino)ferrocene palladium(II) dichloride·dichloromethane complex were used.

(c) 2-(3,8-Diazabicyclo[3.2.1]octan-3-yl)-7-(thiazol-2-yl)benzo[d]oxazole-5-sulfonamide The title compound was obtained in an amount of 4.8 mg from 11 mg of tert-butyl 3-(5-sulfamoyl-7-(thiazol-2-yl)benzo[d]oxazol-2-yl)-3,8-diazabicyclo[3.2.1]octane-8-carboxylate obtained in Example 57 (b) by a similar method to Example 1(c).

Example 58

2-(3,6-Diazabicyclo[3.1.1]heptan-3-yl)-7-(thiazol-2-yl)benzo[d]oxazole-5-sulfonamide (a) tert-Butyl 3-(7-bromo-5-sulfamoylbenzo[d]oxazol-2-yl)-3,6-diazabicyclo[3.1.1]heptane-6-carboxylate The title compound was obtained in an amount of 170 mg from 200 mg of 7-bromo-2-mercaptobenzo[d]oxazole-5-sulfonamide obtained in Reference Example 11 by a similar method to Example 1(a) except that tert-butyl 3,6-diazabicyclo[3.1.1]heptane-6-carboxylate was used instead of tert-butyl 3,8-diazabicyclo[3.2.1]octane-8-carboxylate.

(b) tert-Butyl 3-(5-sulfamoyl-7-(thiazol-2-yl)benzo[d]oxazol-2-yl)-3,6-diazabicyclo[3.1.1]heptane-6-carboxylate The title compound was obtained in an amount of 32 mg from 100 mg of tert-butyl 3-(7-bromo-5-sulfamoylbenzo[d]oxazol-2-yl)-3,6-diazabicyclo[3.1.1]heptane-6-carboxylate obtained in Example 58(a) by a similar method to Example 1(b) except that 9 equivalents of 0.5M solution of 2-thiazolylzinc bromide in tetrahydrofuran and 0.6 equivalent of 1,1'-bis(diphenylphosphino)ferrocene palladium(II) dichloride·dichloromethane complex were used.

(c) 2-(3,6-Diazabicyclo[3.1.1]heptan-3-yl)-7-(thiazol-2-yl)benzo[d]oxazole-5-sulfonamide The title compound was obtained in an amount of 12 mg from 32 mg of tert-butyl 3-(5-sulfamoyl-7-(thiazol-2-yl)benzo[d]oxazol-2-yl)-3,6-diazabicyclo[3.1.1]heptane-6-carboxylate obtained in Example 58 (b) by a similar method to Example 1(c).

Example 59

2-(3,9-Diazabicyclo[3.3.1]nonan-3-yl)-7-(thiazol-2-yl)benzo[d]oxazole-5-sulfonamide (a) tert-Butyl 3-(7-bromo-5-sulfamoylbenzo[d]oxazol-2-yl)-3,9-diazabicyclo[3.3.1]nonane-9-carboxylate The title compound was obtained in an amount of 56 mg from 202 mg of 7-bromo-2-mercaptobenzo[d]oxazole-5-sulfonamide obtained in Reference Example 11 by a similar method to Example 1(a) except that tert-butyl 3,9-diazabicyclo[3.3.1]nonane-9-carboxylate was used instead of tert-butyl 3,8-diazabicyclo[3.2.1]octane-8-carboxylate.

(b) tert-Butyl 3-(5-sulfamoyl-7-(thiazol-2-yl)benzo[d]oxazol-2-yl)-3,9-diazabicyclo[3.3.1]nonane-9-carboxylate The title compound was obtained in an amount of 30 mg from 56 mg of tert-butyl 3-(7-bromo-5-sulfamoylbenzo[d]oxazol-2-yl)-3,9-diazabicyclo[3.3.1]nonane-9-carboxylate obtained in Example 59(a) by a similar method to Example 1(b) except that 6 equivalents of 0.5M solution of 2-thiazolylzinc bromide in tetrahydrofuran and 0.4 equivalent of 1,1'-bis(diphenylphosphino)ferrocene palladium(II) dichloride·dichloromethane complex were used.

(c) 2-(3,9-Diazabicyclo[3.3.1]nonan-3-yl)-7-(thiazol-2-yl)benzo[d]oxazole-5-sulfonamide The title compound was obtained in an amount of 10 mg from 30 mg of tert-butyl 3-(5-sulfamoyl-7-(thiazol-2-yl)benzo[d]oxazol-2-yl)-3,9-diazabicyclo[3.3.1]nonane-9-carboxylate obtained in Example 59(b) by a similar method to Example 1(c).

Example 60

2-(3,8-Diazabicyclo[3.2.1]octan-3-yl)-5-methoxy-7-(thiazol-2-yl)benzo[d]oxazole (a) tert-Butyl 3-(7-bromo-5-methoxybenzo[d]oxazol-2-yl)-3,8-diazabicyclo[3.2.1]octane-8-carboxylate The title compound was obtained in an amount of 70 mg from 50 mg of 7-bromo-5-methoxybenzo[d]oxazole-2-thiol obtained in Reference Example 12 and tert-butyl 3,8-diazabicyclo[3.2.1]octane-8-carboxylate by a similar method to Example 1(a).

(b) tert-Butyl 3-(5-methoxy-7-(thiazol-2-yl)benzo[d]oxazol-2-yl)-3,8-diazabicyclo[3.2.1]octane-8-carboxylate The title compound was obtained as a crude product in an amount of 125 mg from 70 mg of tert-butyl 3-(7-bromo-5-methoxybenzo[d]oxazol-2-yl)-3,8-diazabicyclo[3.2.1]octane-8-carboxylate obtained in Example 60(a) by a similar method to Example 2(b) except that toluene was used instead of 1,4-dioxane.

(c) 2-(3,8-Diazabicyclo[3.2.1]octan-3-yl)-5-methoxy-7-(thiazol-2-yl)benzo[d]oxazole The title compound was obtained in an amount of 30 mg from 120 mg of tert-butyl 3-(5-methoxy-7-(thiazol-2-yl)benzo[d]oxazol-2-yl)-3,8-diazabicyclo[3.2.1]octane-8-carboxylate obtained in Example 60(b) by a similar method to Example 1(c).

Example 61

2-(3,6-Diazabicyclo[3.1.1]heptan-3-yl)-5-methoxy-7-(thiazol-2-yl)benzo[d]oxazole (a) tert-Butyl 3-(7-bromo-5-methoxybenzo[d]oxazol-2-yl)-3,6-diazabicyclo[3.1.1]heptane-6-carboxylate The title compound was obtained in an amount of 230 mg from 175 mg of 7-bromo-5-methoxybenzo[d]oxazole-2-thiol obtained in Reference Example 12 by a similar method to Example 1(a) except that tert-butyl 3,6-diazabicyclo[3.1.1]heptane-6-carboxylate was used instead of tert-butyl 3,8-diazabicyclo[3.2.1]octane-8-carboxylate.

(b) tert-Butyl 3-(5-methoxy-7-(thiazol-2-yl)benzo[d]oxazol-2-yl)-3,6-diazabicyclo[3.1.1]heptane-6-carboxylate The title compound was obtained as a crude product in an amount of 245 mg from 225 mg of tert-butyl 3-(7-bromo-5-methoxybenzo[d]oxazol-2-yl)-3,6-diazabicyclo[3.1.1]heptane-6-carboxylate obtained in Example 61(a) by a similar method to Example 2(b) except that toluene was used instead of 1,4-dioxane.

(c) 2-(3,6-Diazabicyclo[3.1.1]heptan-3-yl)-5-methoxy-7-(thiazol-2-yl)benzo[d]oxazole The title compound was obtained in an amount of 140 mg from 245 mg of tert-butyl 3-(5-methoxy-7-(thiazol-2-yl)benzo[d]oxazol-2-yl)-3,6-diazabicyclo[3.1.1]heptane-6-carboxylate obtained in Example 61(b) by a similar method to Example 1(c).

Example 62

2-(3,9-Diazabicyclo[3.3.1]nonan-3-yl)-5-methoxy-7-(thiazol-2-yl)benzo[d]oxazole (a) tert-Butyl 3-(7-bromo-5-methoxybenzo[d]oxazol-2-yl)-3,9-diazabicyclo[3.3.1]nonane-9-carboxylate The title compound was obtained in an amount of 150 mg from 100 mg of 7-bromo-5-methoxybenzo[d]oxazole-2-thiol obtained in Reference Example 12 by a similar method to Example 1(a) except that tert-butyl 3,9-diazabicyclo[3.3.1]nonane-9-carboxylate was used instead of tert-butyl 3,8-diazabicyclo[3.2.1]octane-8-carboxylate.

(b) tert-Butyl 3-(5-methoxy-7-(thiazol-2-yl)benzo[d]oxazol-2-yl)-3,9-diazabicyclo[3.3.1]nonane-9-carboxylate The title compound was obtained as a crude product in an amount of 173 mg from 150 mg of tert-butyl 3-(7-bromo-5-methoxybenzo[d]oxazol-2-yl)-3,9-diazabicyclo[3.3.1]nonane-9-carboxylate obtained in Example 62(a) by a similar method to Example 2(b) except that toluene was used instead of 1,4-dioxane.

(c) 2-(3,9-Diazabicyclo[3.3.1]nonan-3-yl)-5-methoxy-7-(thiazol-2-yl)benzo[d]oxazole The title compound was obtained in an amount of 240 mg from 450 mg of tert-butyl 3-(5-methoxy-7-(thiazol-2-yl)benzo[d]oxazol-2-yl)-3,9-diazabicyclo[3.3.1]nonane-9-carboxylate obtained in Example 62 (b) by a similar method to Example 1(c).

Example 63

2-(3,8-Diazabicyclo[3.2.1]octan-3-yl)-7-(thiazol-2-yl)benzo[d]oxazol-5-ol 130 mg of tert-butyl 3-(5-methoxy-7-(thiazol-2-yl)benzo[d]oxazol-2-yl)-3,8-diazabicyclo[3.2.1]octane-8-carboxylate obtained in Example 60(b) was dissolved in dichloromethane (10 mL), and then 1.0 M solution of boron tribromide in dichloromethane (2.1 mL, 7.5 equivalents) was added thereto at −78° C., followed by stirring at room temperature for 18 hours. The formation of the product was confirmed by TLC, and then distilled water was added to stop the reaction. Thereafter, the organic phase was dried over anhydrous magnesium sulfate, followed by filtration, and thus obtaining 65 mg of the title compound by vacuum concentration of the filtrate.

Example 64

2-(3,6-Diazabicyclo[3.1.1]heptan-3-yl)-7-(thiazol-2-yl)benzo[d]oxazol-5-ol

The title compound was obtained in an amount of 65 mg from 140 mg of tert-butyl 3-(5-methoxy-7-(thiazol-2-yl)benzo[d]oxazol-2-yl)-3,6-diazabicyclo[3.1.1]heptane-6-carboxylate obtained in Example 61(b) by a similar method to Example 63.

Example 65

2-(3,9-Diazabicyclo[3.3.1]nonan-3-yl)-7-(thiazol-2-yl)benzo[d]oxazol-5-ol

The title compound was obtained in an amount of 40 mg from 340 mg of tert-butyl 3-(5-methoxy-7-(thiazol-2-yl)benzo[d]oxazol-2-yl)-3,9-diazabicyclo[3.3.1]nonane-9-carboxylate obtained in Example 62(b) by a similar method to Example 63.

Example 66

2-(3,8-Diazabicyclo[3.2.1]octan-3-yl)-7-(thiazol-2-yl)-5-(2,2,2-trifluoroethoxy)benzo[d]oxazole (a) tert-Butyl 3-(7-bromo-5-(2,2,2-trifluoroethoxy)benzo[d]oxazol-2-yl)-3,8-diazabicyclo[3.2.1]octane-8-carboxylate The title compound was obtained in an amount of 131 mg from 131 mg of 7-bromo-5-(2,2,2-trifluoroethoxy)benzo[d]oxazole-2-thiol obtained in Reference Example 13 and tert-butyl 3,8-diazabicyclo[3.2.1]octane-8-carboxylate by a similar method to Example 1(a).

(b) tert-Butyl 3-(7-(thiazol-2-yl)-5-(2,2,2-trifluoroethoxy)benzo[d]oxazol-2-yl)-3,8-diazabicyclo[3.2.1]octane-8-carboxylate The title compound was obtained in an amount of 39 mg from 47 mg of tert-butyl 3-(7-bromo-5-(2,2,2-trifluoroethoxy)benzo[d]oxazol-2-yl)-3,8-diazabicyclo[3.2.1]octane-8-carboxylate obtained in Example 66(a) by a similar method to Example 2 (b).

(c) 2-(3,8-Diazabicyclo[3.2.1]octan-3-yl)-7-(thiazol-2-yl)-5-(2,2,2-trifluoroethoxy)benzo[d]oxazole The title compound was obtained in an amount of 33 mg from 39 mg of tert-butyl 3-(7-(thiazol-2-yl)-5-(2,2,2-trifluoroethoxy)benzo[d]oxazol-2-yl)-3,8-diazabicyclo[3.2.1]octane-8-carboxylate obtained in Example 66(b) by a similar method to Example 1(c).

Example 67

2-(3,6-Diazabicyclo[3.1.1]heptan-3-yl)-7-(thiazol-2-yl)-5-(2,2,2-trifluoroethoxy)benzo[d]oxazole (a) tert-Butyl 3-(7-bromo-5-(2,2,2-trifluoroethoxy)benzo[d]oxazol-2-yl)-3,6-diazabicyclo[3.1.1]heptane-6-carboxylate The title compound was obtained in an amount of 168 mg from 164 mg of 7-bromo-5-(2,2,2-trifluoroethoxy)benzo[d]oxazole-2-thiol obtained in Reference Example 13 by a similar method to Example 1(a) except that tert-butyl 3,6-diazabicyclo[3.1.1]heptane-6-carboxylate was used instead of tert-butyl 3,8-diazabicyclo[3.2.1]octane-8-carboxylate.

(b) tert-Butyl 3-(7-(thiazol-2-yl)-5-(2,2,2-trifluoroethoxy)benzo[d]oxazol-2-yl)-3,6-diazabicyclo[3.1.1]heptane-6-carboxylate The title compound was obtained in an amount of 29 mg from 89 mg of tert-butyl 3-(7-bromo-5-(2,2,2-trifluoroethoxy)benzo[d]oxazol-2-yl)-3,6-diazabicyclo[3.1.1]heptane-6-carboxylate obtained in Example 67 (a) by a similar method to Example 2 (b).

(c) 2-(3,6-Diazabicyclo[3.1.1]heptan-3-yl)-7-(thiazol-2-yl)-5-(2,2,2-trifluoroethoxy)benzo[d]oxazole The title compound was obtained in an amount of 21 mg from 29 mg of tert-butyl 3-(7-(thiazol-2-yl)-5-(2,2,2-trifluoroethoxy)benzo[d]oxazol-2-yl)-3,6-diazabicyclo[3.1.1]heptane-6-carboxylate obtained in Example 67 (b) by a similar method to Example 1(c).

Example 68

2-(3,8-Diazabicyclo[3.2.1]octan-3-yl)-5-isopropoxy-7-(thiazol-2-yl)benzo[d]oxazole (a) tert-Butyl 3-(5-hydroxy-7-(thiazol-2-yl)benzo[d]oxazol-2-yl)-3,8-diazabicyclo[3.2.1]octane-8-carboxylate 332 mg of tert-butyl 3-(5-methoxy-7-(thiazol-2-yl)benzo[d]oxazol-2-yl)-3,8-diazabicyclo[3.2.1]octane-8-carboxylate obtained in Example 60(b) was dissolved in N,N-dimethylformamide (3.3 mL), and then sodium tert-butoxide (505 mg, 7 equivalents) and 2-(dimethylamino)ethane-1-thiol hydrochloride (319 mg, 3 equivalents) were added thereto, followed by stirring using a microwave reactor (manufactured by Biotage) for 15 minutes at 160° C. under an argon atmosphere. 1 M hydrochloric acid was added to the reaction mixture, followed by extraction using ethyl acetate. Thereafter, the organic phase was dried over anhydrous sodium sulfate, followed by filtration, and thus obtaining 134 mg of the title compound by purification of the residue obtained by vacuum concentration of the filtrate through silica gel column chromatography (hexane, hexane:ethyl acetate=1:2).

(b) tert-Butyl 3-(5-isopropoxy-7-(thiazol-2-yl)benzo[d]oxazol-2-yl)-3,8-diazabicyclo[3.2.1]octane-8-carboxylate Triphenylphosphine (18 mg, 1.5 equivalents), 2.2 M toluene solution (32 mL, 1.5 equivalents) of diethyl azodicarboxylate, and 2-propanol (5.4 µL, 1.5 equivalents) were dissolved in toluene (0.5 mL), and then 20 mg of tert-butyl 3-(5-hydroxy-7-(thiazol-2-yl)benzo[d]oxazol-2-yl)-3,8-diazabicyclo[3.2.1]octane-8-carboxylate obtained in Example 68(a) was added thereto, followed by stirring at room temperature for 17 hours under an argon atmosphere, and thus obtaining 17 mg of the title compound by preparative TLC (eluent, hexane:ethyl acetate=1:1).

(c) 2-(3,8-Diazabicyclo[3.2.1]octan-3-yl)-5-isopropoxy-7-(thiazol-2-yl)benzo[d]oxazole 12 mg of the title compound was obtained from 17 mg of tert-butyl 3-(5-isopropoxy-7-(thiazol-2-yl)benzo[d]oxazol-2-yl)-3,8-diazabicyclo[3.2.1]octane-8-carboxylate obtained in Example 68 (b), using a similar method to Example 1(c).

Example 69

2-(3,8-Diazabicyclo[3.2.1]octan-3-yl)-5-(2-methoxyethoxy)-7-(thiazol-2-yl)benzo[d]oxazole (a) tert-Butyl 3-(5-(2-methoxyethoxy)-7-(thiazol-2-yl)benzo[d]oxazol-2-yl)-3,8-diazabicyclo[3.2.1]octane-8-carboxylate The title compound was obtained as a crude product in an amount of 90 mg from 20 mg of tert-butyl 3-(5-hydroxy-7-(thiazol-2-yl)benzo[d]oxazol-2-yl)-3,8-diazabicyclo[3.2.1]octane-8-carboxylate obtained in Example 68(a) by a similar method to Example 68(b) except that 2-methoxyethanol (42 µL, 11.5 equivalents), triphenylphosphine (144 mg, 11.5 equivalents), and a 2.2M solution of diethyl azodicarboxylate in toluene (244 µL, 11.5 equivalents) were used instead of 2-propanol.

(b) 2-(3,8-Diazabicyclo[3.2.1]octan-3-yl)-5-(2-methoxyethoxy)-7-(thiazol-2-yl)benzo[d]oxazole The title compound was obtained in an amount of 6.4 mg from 90 mg of the crude product of tert-butyl 3-(5-(2-methoxyethoxy)-7-(thiazol-2-yl)benzo[d]oxazol-2-yl)-3,8-diazabicyclo[3.2.1]octane-8-carboxylate obtained in Example 69(a) by a similar method to Example 1(c).

Example 70

2-(3,8-Diazabicyclo[3.2.1]octan-3-yl)-5-(oxetan-3-ylmethoxy)-7-(thiazol-2-yl)benzo[d]oxazole (a) tert-Butyl 3-(5-(oxetan-3-ylmethoxy)-7-(thiazol-2-yl)benzo[d]oxazol-2-yl)-3,8-diazabicyclo[3.2.1]octane-8-carboxylate 20 mg of tert-butyl 3-(5-hydroxy-7-(thiazol-2-yl)benzo[d]oxazol-2-yl)-3,8-diazabicyclo[3.2.1]octane-8-carboxylate obtained in Example 68 (a), 3-(iodomethyl)oxetane (20 mg, 2.1 equivalents) and sodium hydride (6.1 mg, 3 equivalents) were dissolved in a mixed solvent consisting of N,N-dimethylformamide (0.5 mL)-tetrahydrofuran (0.5 mL), followed by stirring at 90° C. for 10 hours. The formation of the product was confirmed by TLC, and then saturated ammonium chloride aqueous solution was added and the organic phase was dried over anhydrous magnesium sulfate, followed by filtration and vacuum concentration of the filtrate, and thus obtaining 19 mg of the title compound by purification of the residue by preparative TLC (eluent, hexane:ethyl acetate=1:1).

(b) 2-(3,8-Diazabicyclo[3.2.1]octan-3-yl)-5-(oxetan-3-ylmethoxy)-7-(thiazol-2-yl)benzo[d]oxazole The title compound was obtained in an amount of 6.0 mg from 12 mg of tert-butyl 3-(5-(oxetan-3-ylmethoxy)-7-(thiazol-2-yl)benzo[d]oxazol-2-yl)-3,8-diazabicyclo[3.2.1]octane-8-carboxylate obtained in Example 70(a) by a similar method to Example 1(c).

Example 71

2-(((2-(3,8-Diazabicyclo[3.2.1]octan-3-yl)-7-(thiazol-2-yl)benzo[d]oxazol-5-yl)oxy)methyl)propane-1,3-diol The title compound was obtained in an amount of 4.0 mg from 12 mg of tert-butyl 3-(5-(oxetan-3-ylmethoxy)-7-(thiazol-2-yl)benzo[d]oxazol-2-yl)-3,8-diazabicyclo[3.2.1]octane-8-carboxylate obtained in Example 70(a) by a similar method to Example 1(c).

Example 72

5-(Allyloxy)-2-(3,8-diazabicyclo[3.2.1]octan-3-yl)-7-(thiazol-2-yl)benzo[d]oxazole (a) tert-Butyl 3-(5-(allyloxy)-7-(thiazol-2-yl)benzo[d]oxazol-2-yl)-3,8-diazabicyclo[3.2.1]octane-8-carboxylate The title compound was obtained in an amount of 7.4 mg from 20 mg of tert-butyl 3-(5-hydroxy-7-(thiazol-2-yl)benzo[d]oxazol-2-yl)-3,8-diazabicyclo[3.2.1]octane-8-carboxylate obtained in Example 68(a) by a similar method to Example 70(a) except that cyclopropyl bromide was used instead of 3-(iodomethyl)oxetane.

(b) 5-(Allyloxy)-2-(3,8-diazabicyclo[3.2.1]octan-3-yl)-7-(thiazol-2-yl)benzo[d]oxazole The title compound was obtained in an amount of 5.4 mg from 6.9 mg of tert-butyl 3-(5-(allyloxy)-7-(thiazol-2-yl)benzo[d]oxazol-2-yl)-3,8-diazabicyclo[3.2.1]octane-8-carboxylate obtained in Example 72 (a) by a similar method to Example 1(c).

Example 73

2-((2-(3,8-Diazabicyclo[3.2.1]octan-3-yl)-7-(thiazol-2-yl)benzo[d]oxazol-5-yl)oxy)acetonitrile (a) tert-Butyl 3-(5-(cyanomethoxy)-7-(thiazol-2-yl)benzo[d]oxazol-2-yl)-3,8-diazabicyclo[3.2.1]octane-8-carboxylate 10 mg of tert-butyl 3-(5-hydroxy-7-(thiazol-2-yl)benzo[d]oxazol-2-yl)-3,8-diazabicyclo[3.2.1]octane-8-carboxylate obtained in Example 68(a) was dissolved in N,N-dimethylformamide (230 µL), and then potassium carbonate (8 mg, 2.4 equivalents) and bromoacetonitrile (4 µL, 2.4 equivalents) were added thereto at room temperature, followed by stirring overnight. The formation of the product was confirmed by TLC (eluent, hexane:ethyl acetate=1:1), and the organic phase was extracted using water and ethyl acetate. Thereafter, the organic phase was dried over anhydrous magnesium sulfate, followed by filtration and vacuum concentration of the filtrate, and thus obtaining 5.4 mg of the title compound by purification of the residue by preparative TLC (eluent, hexane:ethyl acetate=1:1).

(b) 2-((2-(3,8-Diazabicyclo[3.2.1]octan-3-yl)-7-(thiazol-2-yl)benzo[d]oxazol-5-yl)oxy)acetonitrile 9 mg of tert-butyl 3-(5-(cyanomethoxy)-7-(thiazol-2-yl)benzo[d]oxazol-2-yl)-3,8-diazabicyclo[3.2.1]octane-8-carboxylate obtained in Example 73(a) was dissolved in chloroform (0.2 mL) and trifluoroacetic acid (63 μL). A reaction mixture was obtained by stirring thereof for 3 hours at room temperature. A precipitate was obtained by adding diethyl ether to a residue obtained by vacuum concentration of the reaction mixture. A trifuluoroacetic acid salt of the title compound was obtained in an amount of 3 mg by filtration of the precipitate.

Example 74

2-((2-(3,8-Diazabicyclo[3.2.1]octan-3-yl)-7-(thiazol-2-yl)benzo[d]oxazol-5-yl)oxy)acetic acid (a) tert-Butyl 3-(5-(2-(tert-butoxy)-2-oxoethoxy-7-(thiazol-2-yl)benzo[d]oxazol-2-yl)-3,8-diazabicyclo[3.2.1]octane-8-carboxylate The title compound was obtained in an amount of 9 mg from 10 mg of tert-butyl 3-(5-hydroxy-7-(thiazol-2-yl)benzo[d]oxazol-2-yl)-3,8-diazabicyclo[3.2.1]octane-8-carboxylate obtained in Example 68(a) by a similar method to Example 73(a) except that tert-butyl 2-bromoacetate was used instead of bromoacetonitrile.

(b) 2-((2-(3,8-Diazabicyclo[3.2.1]octan-3-yl)-7-(thiazol-2-yl)benzo[d]oxazol-5-yl)oxy)acetic acid A trifluoroacetic acid salt of the title compound was obtained in an amount of 7 mg from 9 mg of tert-butyl 3-(5-(2-(tert-butoxy)-2-oxoethoxy-7-(thiazol-2-yl)benzo[d]oxazol-2-yl)-3,8-diazabicyclo[3.2.1]octane-8-carboxylate obtained in Example 74 (a) by a similar method to Example 73 (b).

Example 75

2-(3,8-Diazabicyclo[3.2.1]octan-3-yl)-4-methoxy-7-(thiazol-2-yl)benzo[d]oxazole (a) tert-Butyl 3-(7-bromo-4-methoxybenzo[d]oxazol-2-yl)-3,8-diazabicyclo[3.2.1]octane-8-carboxylate The title compound was obtained in an amount of 300 mg from 200 mg of 7-bromo-4-methoxybenzo[d]oxazole-2-thiol obtained in Reference Example 14 and tert-butyl 3,8-diazabicyclo[3.2.1]octane-8-carboxylate by a similar method to Example 1(a).

(b) tert-Butyl 3-(4-methoxy-7-(thiazol-2-yl)benzo[d]oxazol-2-yl)-3,8-diazabicyclo[3.2.1]octane-8-carboxylate The title compound was obtained in an amount of 300 mg from 250 mg of tert-butyl 3-(7-bromo-4-methoxybenzo[d]oxazol-2-yl)-3,8-diazabicyclo[3.2.1]octane-8-carboxylate obtained in Example 75(a) by a similar method to Example 2(b) except that toluene was used instead of 1,4-dioxane and tetrakis(triphenylphosphine)palladium(0) was used instead of Bis(triphenylphosphine)palladium(II) dichloride.

(c) 2-(3,8-Diazabicyclo[3.2.1]octan-3-yl)-4-methoxy-7-(thiazol-2-yl)benzo[d]oxazole The title compound was obtained in an amount of 150 mg from 300 mg of tert-butyl 3-(4-methoxy-7-(thiazol-2-yl)benzo[d]oxazol-2-yl)-3,8-diazabicyclo[3.2.1]octane-8-carboxylate obtained in Example 75 (b) by a similar method to Example 1(c).

Example 76

2-(3,6-Diazabicyclo[3.1.1]heptan-3-yl)-4-methoxy-7-(thiazol-2-yl)benzo[d]oxazole (a) tert-Butyl 3-(7-bromo-4-methoxybenzo[d]oxazol-2-yl)-3,6-diazabicyclo[3.1.1]heptane-6-carboxylate The title compound was obtained in an amount of 289 mg from 200 mg of 7-bromo-4-methoxybenzo[d]oxazole-2-thiol obtained in Reference Example 14 by a similar method to Example 1(a) except that tert-butyl 3,6-diazabicyclo[3.1.1]heptane-6-carboxylate was used instead of tert-butyl 3,8-diazabicyclo[3.2.1]octane-8-carboxylate.

(b) tert-Butyl 3-(4-methoxy-7-(thiazol-2-yl)benzo[d]oxazol-2-yl)-3,6-diazabicyclo[3.1.1]heptane-6-carboxylate The title compound was obtained in an amount of 300 mg from 280 mg of tert-butyl 3-(7-bromo-4-methoxybenzo[d]oxazol-2-yl)-3,6-diazabicyclo[3.1.1]heptane-6-carboxylate obtained in Example 76(a) by a similar method to Example 2(b) except that toluene was used instead of 1,4-dioxane and tetrakis(triphenylphosphine)palladium(0) was used instead of Bis(triphenylphosphine)palladium(II) dichloride.

(c) 2-(3,6-Diazabicyclo[3.1.1]heptan-3-yl)-4-methoxy-7-(thiazol-2-yl)benzo[d]oxazole The title compound was obtained in an amount of 178 mg from 300 mg of tert-butyl 3-(4-methoxy-7-(thiazol-2-yl)benzo[d]oxazol-2-yl)-3,6-diazabicyclo[3.1.1]heptane-6-carboxylate obtained in Example 76(b) by a similar method to Example 1(c).

Example 77

2-(3,9-Diazabicyclo[3.3.1]nonan-3-yl)-4-methoxy-7-(thiazol-2-yl)benzo[d]oxazole (a) tert-Butyl 3-(7-bromo-4-methoxybenzo[d]oxazol-2-yl)-3,9-diazabicyclo[3.3.1]nonane-9-carboxylate The title compound was obtained in an amount of 320 mg from 200 mg of 7-bromo-4-methoxybenzo[d]oxazole-2-thiol obtained in Reference Example 14 by a similar method to Example 1(a) except that tert-butyl 3,9-diazabicyclo

[3.3.1]nonane-9-carboxylate was used instead of tert-butyl 3,8-diazabicyclo[3.2.1]octane-8-carboxylate.

(b) tert-Butyl 3-(4-methoxy-7-(thiazol-2-yl)benzo[d] oxazol-2-yl)-3,9-diazabicyclo[3.3.1]nonane-9-carboxylate The title compound was obtained in an amount of 180 mg from 279 mg of tert-butyl 3-(7-bromo-4-methoxybenzo[d]oxazol-2-yl)-3,9-diazabicyclo[3.3.1]nonane-9-carboxylate obtained in Example 77(a) by a similar method to Example 2(b) except that toluene was used instead of 1,4-dioxane and tetrakis(triphenylphosphine)palladium(0) was used instead of Bis(triphenylphosphine)palladium(II) dichloride.

(c) 2-(3,9-Diazabicyclo[3.3.1]nonan-3-yl)-4-methoxy-7-(thiazol-2-yl)benzo[d]oxazole The title compound was obtained in an amount of 40 mg from 180 mg of tert-butyl 3-(4-methoxy-7-(thiazol-2-yl)benzo[d]oxazol-2-yl)-3,9-diazabicyclo[3.3.1]nonane-9-carboxylate obtained in Example 77 (b) by a similar method to Example 1(c).

Example 78

2-(3,8-Diazabicyclo[3.2.1]octan-3-yl)-7-(thiazol-2-yl)benzo[d]oxazol-4-ol 100 mg of tert-butyl 3-(4-methoxy-7-(thiazol-2-yl)benzo[d]oxazol-2-yl)-3,8-diazabicyclo[3.2.1]octane-8-carboxylate obtained in Example 75(b) was dissolved in dichloromethane (10 mL), and then 1.0 M solution of boron tribromide in dichloromethane (2.9 mL, 10 equivalents) was added thereto at −78° C., followed by stirring at room temperature for 16 hours. The formation of the product was confirmed by TLC, and then distilled water was added to stop the reaction. Thereafter, the organic phase was dried over anhydrous magnesium sulfate, followed by filtration, and thus obtaining 40 mg of the title compound by vacuum concentration of the filtrate.

Example 79

2-(3,6-Diazabicyclo[3.1.1]heptan-3-yl)-7-(thiazol-2-yl)benzo[d]oxazol-4-ol

The title compound was obtained in an amount of 24 mg from 189 mg of tert-butyl 3-(4-methoxy-7-(thiazol-2-yl)benzo[d]oxazol-2-yl)-3,6-diazabicyclo[3.1.1]heptane-6-carboxylate obtained in Example 76(b) by a similar method to Example 78.

Example 80

2-(3,9-Diazabicyclo[3.3.1]nonan-3-yl)-7-(thiazol-2-yl)benzo[d]oxazol-4-ol

The title compound was obtained in an amount of 25 mg from 200 mg of tert-butyl 3-(4-methoxy-7-(thiazol-2-yl)benzo[d]oxazol-2-yl)-3,9-diazabicyclo[3.3.1]nonane-9-carboxylate obtained in Example 77(b) by a similar method to Example 78.

Example 81

2-(3,8-Diazabicyclo[3.2.1]octan-3-yl)-4-cyclobutoxy-7-(thiazol-2-yl)benzo[d]oxazole (a) tert-Butyl 3-(4-hydroxy-7-(thiazol-2-yl)benzo[d]oxazol-2-yl)-3,8-diazabicyclo[3.2.1]octane-8-carboxylate 400 mg of tert-butyl 3-(4-methoxy-7-(thiazol-2-yl)benzo[d]oxazol-2-yl)-3,8-diazabicyclo[3.2.1]octane-8-carboxylate obtained in Example 75(b) was dissolved in N,N-dimethylformamide (4.0 mL), and then sodium tert-butoxide (608 mg, 7 equivalents) and 2-(dimethylamino)ethane-1-thiol hydrochloride (384 mg, 3 equivalents) were added thereto, followed by stirring using a microwave reactor (manufactured by Biotage) for 15 minutes at 160° C. under an argon atmosphere. 1 M hydrochloric acid was added to the reaction mixture, followed by extraction using ethyl acetate. Thereafter, the organic phase was dried over anhydrous sodium sulfate, followed by filtration, and thus obtaining 280 mg of the title compound by purification of the residue obtained by vacuum concentration of the filtrate through silica gel column chromatography (hexane, hexane: ethyl acetate=1:2).

(b) tert-Butyl 3-(4-cyclobutoxy-7-(thiazol-2-yl) benzo[d]oxazol-2-yl)-3,8-diazabicyclo[3.2.1]octane-8-carboxylate The title compound was obtained in an amount of 11 mg from 20 mg of tert-butyl 3-(4-hydroxy-7-(thiazol-2-yl)benzo[d]oxazol-2-yl)-3,8-diazabicyclo[3.2.1]octane-8-carboxylate obtained in Example 81(a) by a similar method to Example 68(b) except that triphenylphosphine (74 mg, 6.0 equivalents), diethyl azodicarboxylate (44 μL, 6.0 equivalents), cyclobutanol (22 μL, 6.0 equivalents) and toluene (0.5 mL)-tetrahydrofuran (1.0 mL) were used.

(c) 2-(3,8-Diazabicyclo[3.2.1]octan-3-yl)-4-cyclobutoxy-7-(thiazol-2-yl)benzo[d]oxazole The title compound was obtained in an amount of 8.9 mg from 11 mg of tert-butyl 3-(4-cyclobutoxy-7-(thiazol-2-yl)benzo[d]oxazol-2-yl)-3,8-diazabicyclo[3.2.1]octane-8-carboxylate obtained in Example 81(b) by a similar method to Example 1(c).

Example 82

2-((2-(3,8-Diazabicyclo[3.2.1]octan-3-yl)-7-(thiazol-2-yl)benzo[d]oxazol-4-yl)oxy)acetonitrile (a) tert-Butyl 3-(4-cyanomethoxy-7-(thiazol-2-yl) benzo[d]oxazol-2-yl)-3,8-diazabicyclo[3.2.1]octane-8-carboxylate The title compound was obtained in an amount of 22 mg from 20 mg of tert-butyl 3-(4-hydroxy-7-(thiazol-2-yl)benzo[d]oxazol-2-yl)-3,8-diazabicyclo[3.2.1]octane-8-carboxylate obtained in Example 81(a) by a similar method to Example 70(a) except that bromoacetonitrile was used instead of 3-(iodomethyl)oxetane.

(b) 2-((2-(3,8-Diazabicyclo[3.2.1]octan-3-yl)-7-(thiazol-2-yl)benzo[d]oxazol-4-yl)oxy)acetonitrile The title compound was obtained in an amount of 17 mg from 22 mg of tert-butyl 3-(4-cyanomethoxy-7-(thiazol-2- yl)benzo[d]oxazol-2-yl)-3,8-diazabicyclo[3.2.1]octane-8-carboxylate obtained in Example 82 (a) by a similar method to Example 1(c).

Example 83

1-((2-(3,8-Diazabicyclo[3.2.1]octan-3-yl)-7-(thiazol-2-yl)benzo[d]oxazol-4-yl)oxy)-3-methoxypropan-2-ol (a) tert-Butyl 3-(4-oxiran-2-ylmethoxy)-7-(thiazol-2-yl)benzo[d]oxazol-2-yl)-3,8-diazabicyclo[3.2.1]octane-8-carboxylate The title compound was obtained in an amount of 17 mg from 20 mg of tert-butyl 3-(4-hydroxy-7-(thiazol-2-yl)benzo[d]oxazol-2-yl)-3,8-diazabicyclo[3.2.1]octane-8-carboxylate obtained in Example 81(a) by a similar method to Example 70(a) except that oxetan-3-yltrifluoromethanesulfonate was used instead of 3-(iodomethyl)oxetane and reacted at room temperature.

(b) tert-Butyl 3-(4-(2-hydroxy-3-methoxypropoxy)-7-(thiazol-2-yl)benzo[d]oxazol-2-yl)-3,8-diazabicyclo[3.2.1]octane-8-carboxylate 17 mg of tert-butyl 3-(4-oxiran-2-ylmethoxy)-7-(thiazol-2-yl)benzo[d]oxazol-2-yl)-3,8-diazabicyclo[3.2.1]octane-8-carboxylate obtained in Example 83(a) was dissolved in methanol (0.5 mL), then 4.1M solution of sodium methoxide (17 μL, 2 equivalents) in methanol was added thereto, followed by heat refluxing for 30 min under an argon atmosphere. Sodium hydrogen carbonate aqueous solution was added to the reaction mixture, followed by extraction using ethyl acetate. Thereafter, the organic phase was dried over anhydrous sodium sulfate, followed by filtration, and thus obtaining 13 mg of the title compound by purification of the residue obtained by vacuum concentration of the filtrate by preparative TLC (eluent, hexane:ethyl acetate=1:2).

(c) 1-((2-(3,8-Diazabicyclo[3.2.1]octan-3-yl)-7-(thiazol-2-yl)benzo[d]oxazol-4-yl)oxy)-3-methoxypropan-2-ol The title compound was obtained in an amount of 10 mg from 13 mg of tert-butyl 3-(4-(2-hydroxy-3-methoxypropoxy-7-(thiazol-2-yl)benzo[d]oxazol-2-yl)-3,8-diazabicyclo[3.2.1]octane-8-carboxylate obtained in Example 83 (b) by a similar method to Example 1(c).

Example 84

2-(3,8-Diazabicyclo[3.2.1]octan-3-yl)-4-((tetrahydrofuran-3-yl)oxy)-7-(thiazol-2-yl)benzo[d]oxazole (a) tert-Butyl 3-(4-((tetrahydrofuran-3-yl)oxy)-7-(thiazol-2-yl)benzo[d]oxazol-2-yl)-3,8-diazabicyclo[3.2.1]octane-8-carboxylate The title compound was obtained in an amount of 10 mg from 20 mg of tert-butyl 3-(4-hydroxy-7-(thiazol-2-yl)benzo[d]oxazol-2-yl)-3,8-diazabicyclo[3.2.1]octane-8-carboxylate obtained in Example 81(a) by a similar method to Example 70(a) except that tetrahydrofuran-3-yl trifluoromethanesulfonate was used instead of 3-(iodomethyl)oxetane and reacted at room temperature.

(b) 2-(3,8-Diazabicyclo[3.2.1]octan-3-yl)-4-((tetrahydrofuran-3-yl)oxy)-7-(thiazol-2-yl)benzo[d]oxazole The title compound was obtained in an amount of 5.5 mg from 10 mg of tert-butyl 3-(4-((tetrahydrofuran-3-yl)oxy)-7-(thiazol-2-yl)benzo[d]oxazol-2-yl)-3,8-diazabicyclo[3.2.1]octane-8-carboxylate obtained in Example 84(a) by a similar method to Example 1(c).

Example 85

2-(3,8-Diazabicyclo[3.2.1]octan-3-yl)-4,7-di(thiazol-2-yl)benzo[d]oxazole (a) tert-Butyl 3-(7-(thiazol-2-yl)-4-(((trifluoromethyl)sulfonyl)oxy)benzo[d]oxazol-2-yl)-3,8-diazabicyclo[3.2.1]octane-8-carboxylate 20 mg of tert-butyl 3-(4-hydroxy-7-(thiazol-2-yl)benzo[d]oxazol-2-yl)-3,8-diazabicyclo[3.2.1]octane-8-carboxylate obtained in Example 81(a) was dissolved in dichloromethane (0.47 mL), and then diisopropylethylamine (12 μL, 1.5 equivalents) and trifluoromethanesulfonic anhydride were sequentially added thereto, followed by stirring at −30° C. for 30 minutes under an argon atmosphere. After that, the temperature was caused to rise to 0° C., followed by stirring for 1 hour. Saturated sodium hydrogen carbonate aqueous solution was added to the reaction mixture, followed by extraction using chloroform. Thereafter, the organic phase was dried over anhydrous sodium sulfate, followed by filtration, and thus obtaining 24 mg of the title compound by purification of the residue obtained by vacuum concentration of the filtrate by preparative TLC (eluent, hexane:ethyl acetate=1:1).

(b) tert-Butyl 3-(4,7-di(thiazol-2-yl)benzo[d]oxazol-2-yl)-3,8-diazabicyclo[3.2.1]octane-8-carboxylate 23 mg of tert-butyl 3-(7-(thiazol-2-yl)-4-(((trifluoromethyl)sulfonyl)oxy)benzo[d]oxazol-2-yl)-3,8-diazabicyclo[3.2.1]octane-8-carboxylate obtained in Example 85(a) was dissolved in toluene (0.14 mL), and then tetrahydrofuran solution (409 μL, 5 equivalents) of 0.5 M 2-thiazolylzinc bromide and [1,1'-bis(diphenylphosphino)ferrocene]palladium(II) dichloride·dichloromethane complex (6.7 mg, 0.2 equivalent) were added thereto, followed by stirring using a microwave reactor (manufactured by Biotage) for 20 minutes at 100° C. under an argon atmosphere. Saturated sodium hydrogen carbonate aqueous solution was added to the reaction mixture, followed by Celite® filtration. After the filtrate was extracted using ethyl acetate, the organic phase was dried over anhydrous magnesium sulfate, followed by filtration, and thus obtaining 9.0 mg of the title compound by purification of the residue obtained by vacuum concentration of the filtrate by preparative TLC (eluent, hexane:ethyl acetate=1:1).

(c) 2-(3,8-Diazabicyclo[3.2.1]octan-3-yl)-4,7-di(thiazol-2-yl)benzo[d]oxazole 4.7 mg of the title compound was obtained from 9.0 mg of tert-butyl 3-(4,7-di(thiazol-2-yl)benzo[d]oxazol-2-yl)-3, 8-diazabicyclo[3.2.1]octane-8-carboxylate obtained in Example 85 (b), using a similar method to Example 1(c).

Example 86

Ethyl 2-(3,8-diazabicyclo[3.2.1]octan-3-yl)-7-(thiazol-2-yl)benzo[d]oxazole-5-carboxylate (a) Ethyl 7-bromo-2-(8-(tert-butoxycarbonyl)-3,8-diazabicyclo[3.2.1]octan-3-yl)benzo[d]oxazole-5-carboxylate The title compound was obtained in an amount of 145 mg from 100 mg of ethyl 7-bromo-2-methoxybenzo[d]oxazole-5-carboxylate obtained in Reference Example 15 and tert-butyl 3,8-diazabicyclo[3.2.1]octane-8-carboxylate by a similar method to Example 1(a).

(b) Ethyl 2-(8-(tert-butoxycarbonyl)-3,8-diazabicyclo[3.2.1]octan-3-yl)-7-(thiazol-2-yl)benzo[d]oxazole-5-carboxylate The title compound was obtained as a crude product in an amount of 350 mg from 240 mg of ethyl 7-bromo-2-(8-(tert-butoxycarbonyl)-3,8-diazabicyclo[3.2.1]octan-3-yl)benzo[d]oxazole-5-carboxylate obtained in Example 86(a) by a similar method to Example 2 (b).

(c) Ethyl 2-(3,8-diazabicyclo[3.2.1]octan-3-yl)-7-(thiazol-2-yl)benzo[d]oxazole-5-carboxylate The title compound was obtained in an amount of 105 mg from 350 mg of ethyl 2-(8-(tert-butoxycarbonyl)-3,8-diazabicyclo[3.2.1]octan-3-yl)-7-(thiazol-2-yl)benzo[d]oxazole-5-carboxylate obtained in Example 86(b) by a similar method to Example 1(c).

Example 87

Ethyl 2-(3,6-diazabicyclo[3.1.1]heptan-3-yl)-7-(thiazol-2-yl)benzo[d]oxazole-5-carboxylate (a) Ethyl 7-bromo-2-(6-(tert-butoxycarbonyl)-3,6-diazabicyclo[3.1.1]heptan-3-yl)benzo[d]oxazole-5-carboxylate The title compound was obtained in an amount of 140 mg from 100 mg of ethyl 7-bromo-2-mercaptobenzo[d]oxazole-5-carboxylate obtained in Reference Example 15 by a similar method to Example 1(a) except that tert-butyl 3,6-diazabicyclo[3.1.1]heptane-6-carboxylate was used instead of tert-butyl 3,8-diazabicyclo[3.2.1]octane-8-carboxylate.

(b) Ethyl 2-(6-(tert-butoxycarbonyl)-3,6-diazabicyclo[3.1.1]heptan-3-yl)-7-(thiazol-2-yl)benzo[d]oxazole-5-carboxylate The title compound was obtained in an amount of 26 mg from 140 mg of ethyl 7-bromo-2-(6-(tert-butoxycarbonyl)-3,6-diazabicyclo[3.1.1]heptan-3-yl)benzo[d]oxazole-5-carboxylate obtained in Example 87 (a) by a similar method to Example 2 (b).

(c) Ethyl 2-(3,6-diazabicyclo[3.1.1]heptan-3-yl)-7-(thiazol-2-yl)benzo[d]oxazole-5-carboxylate The title compound was obtained in an amount of 120 mg from 295 mg of ethyl 2-(6-(tert-butoxycarbonyl)-3,6-diazabicyclo[3.1.1]heptan-3-yl)-7-(thiazol-2-yl)benzo[d]oxazole-5-carboxylate obtained in Example 87 (b) by a similar method to Example 1(c).

Example 88

Ethyl 2-(3-oxa-7,9-diazabicyclo[3.3.1]nonan-7-yl)-7-(thiazol-2-yl)benzo[d]oxazole-5-carboxylate (a) tert-Butyl 7-(7-bromo-5-(ethoxycarbonyl)benzo[d]oxazol-2-yl)-3-oxa-7,9-diazabicyclo[3.3.1]nonane-9-carboxylate The title compound was obtained in an amount of 440 mg from 300 mg of ethyl 7-bromo-2-mercaptobenzo[d]oxazole-5-carboxylate obtained in Reference Example 15 by a similar method to Example 1(a) except that tert-butyl 3-oxa-7,9-diazabicyclo[3.3.1]nonane-9-carboxylate was used instead of tert-butyl 3,8-diazabicyclo[3.2.1]octane-8-carboxylate.

(b) tert-Butyl 7-(5-(ethoxycarbonyl)-7-(thiazol-2-yl)benzo[d]oxazol-2-yl)-3-oxa-7,9-diazabicyclo[3.3.1]nonane-9-carboxylate The title compound was obtained in an amount of 300 mg from 400 mg of tert-butyl 7-(7-bromo-5-(ethoxycarbonyl)benzo[d]oxazol-2-yl)-3-oxa-7,9-diazabicyclo[3.3.1]nonane-9-carboxylate obtained in Example 88 (a) by a similar method to Example 2 (b).

(c) Ethyl 2-(3-oxa-7,9-diazabicyclo[3.3.1]nonan-7-yl)-7-(thiazol-2-yl)benzo[d]oxazole-5-carboxylate The title compound was obtained in an amount of 200 mg from 300 mg of tert-butyl 7-(5-(ethoxycarbonyl)-7-(thiazol-2-yl)benzo[d]oxazol-2-yl)-3-oxa-7,9-diazabicyclo[3.3.1]nonane-9-carboxylate obtained in Example 88 (b) by a similar method to Example 1(c).

Example 89

Ethyl 2-(3,9-diazabicyclo[3.3.1]nonan-3-yl)-7-(thiazol-2-yl)benzo[d]oxazole-5-carboxylate (a) Ethyl 7-bromo-2-(9-(tert-butoxycarbonyl)-3,9-diazabicyclo[3.3.1]nonan-3-yl)benzo[d]oxazole-5-carboxylate The title compound was obtained in an amount of 310 mg from 200 mg of ethyl 7-bromo-2-mercaptobenzo[d]oxazole-5-carboxylate obtained in Reference Example 15 by a similar method to Example 1(a) except that tert-butyl 3,9-diazabicyclo[3.3.1]nonane-9-carboxylate was used instead of tert-butyl 3,8-diazabicyclo[3.2.1]octane-8-carboxylate.

(b) Ethyl 2-(9-(tert-butoxycarbonyl)-3,9-diazabicyclo[3.3.1]nonan-3-yl)-7-(thiazol-2-yl)benzo[d]oxazole-5-carboxylate The title compound was obtained as a crude product in an amount of 280 mg from 400 mg of ethyl 7-bromo-2-(9-(tert-butoxycarbonyl)-3,9-diazabicyclo[3.3.1]nonan-3-yl)benzo[d]oxazole-5-carboxylate obtained in Example 89(a) by a similar method to Example 2 (b).

(c) Ethyl 2-(3,9-diazabicyclo[3.3.1]nonan-3-yl)-7-(thiazol-2-yl)benzo[d]oxazole-5-carboxylate The title compound was obtained in an amount of 130 mg from 360 mg of ethyl 2-(9-(tert-butoxycarbonyl)-3,9-diazabicyclo[3.3.1]nonan-3-yl)-7-(thiazol-2-yl)benzo[d]oxazole-5-carboxylate obtained in Example 89(b) by a similar method to Example 1(c).

Example 90

Ethyl 2-(3,8-diazabicyclo[3.2.1]octan-3-yl)-7-(1H-pyrazol-1-yl)benzo[d]oxazole-5-carboxylate (a) Ethyl 2-(8-(tert-butoxycarbonyl)-3,8-diazabicyclo[3.2.1]octan-3-yl)-7-(1H-pyrazol-1-yl)benzo[d]oxazole-5-carboxylate The title compound was obtained in an amount of 140 mg from 300 mg of ethyl 7-bromo-2-(8-(tert-butoxycarbonyl)-3,8-diazabicyclo[3.2.1]octan-3-yl)benzo[d]oxazole-5-carboxylate obtained in Example 86(a) by a similar method to Example 15(a).

(b) Ethyl 2-(3,8-diazabicyclo[3.2.1]octan-3-yl)-7-(1H-pyrazol-1-yl)benzo[d]oxazole-5-carboxylate The title compound was obtained in an amount of 90 mg from 140 mg of ethyl 2-(8-(tert-butoxycarbonyl)-3,8-diazabicyclo[3.2.1]octan-3-yl)-7-(1H-pyrazol-1-yl)benzo[d]oxazole-5-carboxylate obtained in Example 90(a) by a similar method to Example 1(c).

Example 91

Ethyl 2-(3,6-diazabicyclo[3.1.1]heptan-3-yl)-7-(1H-pyrazol-1-yl)benzo[d]oxazole-5-carboxylate (a) Ethyl 2-(6-(tert-butoxycarbonyl)-3,6-diazabicyclo[3.1.1]heptan-3-yl)-7-(1H-pyrazol-1-yl)benzo[d]oxazole-5-carboxylate The title compound was obtained in an amount of 160 mg from 300 mg of ethyl 7-bromo-2-(6-(tert-butoxycarbonyl)-3,6-diazabicyclo[3.1.1]heptan-3-yl)benzo[d]oxazole-5-carboxylate obtained in Example 87 (a) by a similar method to Example 15 (a).

(b) Ethyl 2-(3,6-diazabicyclo[3.1.1]heptan-3-yl)-7-(1H-pyrazol-1-yl)benzo[d]oxazole-5-carboxylate The title compound was obtained in an amount of 110 mg from 160 mg of ethyl 2-(6-(tert-butoxycarbonyl)-3,6-diazabicyclo[3.1.1]heptan-3-yl)-7-(1H-pyrazol-1-yl)benzo[d]oxazole-5-carboxylate obtained in Example 91(a) by a similar method to Example 1(c).

Example 92

Ethyl 2-(3-oxa-7,9-diazabicyclo[3.3.1]nonan-7-yl)-7-(1H-pyrazol-1-yl)benzo[d]oxazole-5-carboxylate (a) tert-Butyl 7-(5-(ethoxycarbonyl)-7-(1H-pyrazol-1-yl)benzo[d]oxazol-2-yl)-3-oxa-7,9-diazabicyclo[3.3.1]nonane-9-carboxylate The title compound was obtained in an amount of 170 mg from 210 mg of tert-butyl 7-(7-bromo-5-(ethoxycarbonyl)benzo[d]oxazol-2-yl)-3-oxa-7,9-diazabicyclo[3.3.1]nonane-9-carboxylate obtained in Example 88 (a) by a similar method to Example 15 (a).

(b) Ethyl 2-(3-oxa-7,9-diazabicyclo[3.3.1]nonan-7-yl)-7-(1H-pyrazol-1-yl)benzo[d]oxazol-5-carboxylate The title compound was obtained in an amount of 144 mg from 220 mg of tert-butyl 7-(5-(ethoxycarbonyl)-7-(1H-pyrazol-1-yl)benzo[d]oxazol-2-yl)-3-oxa-7,9-diazabicyclo[3.3.1]nonane-9-carboxylate obtained in Example 92 (a) by a similar method to Example 1(c).

Example 93

Ethyl 2-(3,9-diazabicyclo[3.3.1]nonan-3-yl)-7-(1H-pyrazol-1-yl)benzo[d]oxazole-5-carboxylate (a) Ethyl 2-(9-(tert-butoxycarbonyl)-3,9-diazabicyclo[3.3.1]nonan-3-yl)-7-(1H-pyrazol-1-yl)benzo[d]oxazole-5-carboxylate The title compound was obtained in an amount of 160 mg from 300 mg of ethyl 7-bromo-2-(9-(tert-butoxycarbonyl)-3,9-diazabicyclo[3.3.1]nonan-3-yl)benzo[d]oxazole-5-carboxylate obtained in Example 89(a) by a similar method to Example 15(a).

(b) Ethyl 2-(3,9-diazabicyclo[3.3.1]nonan-3-yl)-7-(1H-pyrazol-1-yl)benzo[d]oxazole-5-carboxylate The title compound was obtained in an amount of 100 mg from 160 mg of ethyl 2-(9-(tert-butoxycarbonyl)-3,9-diazabicyclo[3.3.1]nonan-3-yl)-7-(1H-pyrazol-1-yl)benzo[d]oxazole-5-carboxylate obtained in Example 93(a) by a similar method to Example 1(c).

Example 94

2-(3,8-Diazabicyclo[3.2.1]octan-3-yl)-N,N-dimethyl-7-(thiazol-2-yl)benzo[d]oxazole-5-carboxamide (a) 2-(8-(tert-Butoxycarbonyl)-3,8-diazabicyclo[3.2.1]octan-3-yl)-7-(thiazol-2-yl)benzo[d]oxazole-5-carboxylic acid 250 mg of ethyl 2-(8-(tert-butoxycarbonyl)-3,8-diazabicyclo[3.2.1]octan-3-yl)-7-(thiazol-2-yl)benzo[d]oxazole-5-carboxylate obtained in Example 86(b) was dissolved in tetrahydrofuran:methanol:water=3:6:1 (2.0 mL), and then 1M sodium hydroxide aqueous solution (1 mL, 2 equivalents) was added thereto, followed by stirring for 7 days at room temperature. 1M hydrochloric acid (1 mL) was added to the reaction mixture, followed by extraction using chloroform:methanol=10:1. Thereafter, the organic phase was dried over anhydrous magnesium sulfate, followed by filtration, and thus obtaining 220 mg of the title compound by purification of the residue obtained by vacuum concentration of the filtrate through silica gel column chromatography (chloroform-chloroform:methanol=10:1).

(b) tert-Butyl 3-(5-(dimethylcarbamoyl)-7-(thiazol-2-yl)benzo[d]oxazol-2-yl)-3,8-diazabicyclo[3.2.1]octane-8-carboxylate 13 mg of 2-(8-(tert-butoxycarbonyl)-3,8-diazabicyclo[3.2.1]octan-3-yl)-7-(thiazol-2-yl)benzo[d]oxazole-5-carboxylic acid obtained in Example 94(a) was dissolved in N,N-dimethylformamide (0.5 mL), and then 4-(4,6-dimethoxy-1,3,5-triazin-2-yl)-4-methylmorpholinium chloride n-Hydrate (content 82.2%, 16 mg, 2 equivalents) and 2M solution of dimethylamine (28 μL, 2 equivalents) in methanol were added, followed by stirring at room temperature for 19 hours. 10 mg of the title compound was obtained by vacuum concentration of the reaction mixture and purification by preparative TLC (eluent, chloroform:methanol=10:1).

(c) 2-(3,8-Diazabicyclo[3.2.1]octan-3-yl)-N,N-dimethyl-7-(thiazol-2-yl)benzo[d]oxazole-5-carboxamide The title compound was obtained in an amount of 7.4 mg from 10 mg of tert-butyl 3-(5-(dimethylcarbamoyl)-7-(thiazol-2-yl)benzo[d]oxazol-2-yl)-3,8-diazabicyclo[3.2.1]octane-8-carboxylate obtained in Example 94 (b) by a similar method to Example 1(c).

Example 95

(2-(3,8-Diazabicyclo[3.2.1]octan-3-yl)-7-(thiazol-2-yl)benzo[d]oxazol-5-yl) (morpholino)methanone (a) tert-Butyl 3-(5-(morpholine-4-carbonyl)-7-(thiazol-2-yl)benzo[d]oxazol-2-yl)-3,8-diazabicyclo[3.2.1]octane-8-carboxylate The title compound was obtained in an amount of 28 mg from 24 mg of 2-(8-(tert-butoxycarbonyl)-3,8-diazabicyclo[3.2.1]octan-3-yl)-7-(thiazol-2-yl)benzo[d]oxazole-5-carboxylic acid obtained in Example 94(a) by a similar method to Example 94(b) except that morpholine (9 μL, 2 equivalents) was used instead of 2M dimethylamine solution in methanol.

(b) (2-(3,8-Diazabicyclo[3.2.1]octan-3-yl)-7-(thiazol-2-yl)benzo[d]oxazol-5-yl) (morpholino)methanone The title compound was obtained in an amount of 20 mg from 28 mg of tert-butyl 3-(5-(morpholine-4-carbonyl)-7-(thiazol-2-yl)benzo[d]oxazol-2-yl)-3,8-diazabicyclo[3.2.1]octane-8-carboxylate obtained in Example 95(a) by a similar method to Example 1(c).

Example 96

(2-(3,8-Diazabicyclo[3.2.1]octan-3-yl)-7-(thiazol-2-yl)benzo[d]oxazol-5-yl)(piperidin-1-yl)methanone (a) tert-Butyl 3-(5-(piperidine-1-carbonyl)-7-(thiazol-2-yl)benzo[d]oxazol-2-yl)-3,8-diazabicyclo[3.2.1]octane-8-carboxylate The title compound was obtained in an amount of 27 mg from 24 mg of 2-(8-(tert-butoxycarbonyl)-3,8-diazabicyclo[3.2.1]octan-3-yl)-7-(thiazol-2-yl)benzo[d]oxazole-5-carboxylic acid obtained in Example 94(a) by a similar method to Example 94(b) except that piperidine (10 μL, 2 equivalents) was used instead of 2M dimethylamine solution in methanol.

(b) (2-(3,8-Diazabicyclo[3.2.1]octan-3-yl)-7-(thiazol-2-yl)benzo[d]oxazol-5-yl)(piperidin-1-yl)methanone The title compound was obtained in an amount of 18 mg from 28 mg of tert-butyl 3-(5-(piperidine-1-carbonyl)-7-(thiazol-2-yl)benzo[d]oxazol-2-yl)-3,8-diazabicyclo[3.2.1]octane-8-carboxylate obtained in Example 96(a) by a similar method to Example 1(c).

Example 97

(2-(3,8-Diazabicyclo[3.2.1]octan-3-yl)-7-(thiazol-2-yl)benzo[d]oxazol-5-yl)(azetidin-1-yl)methanone (a) tert-Butyl 3-(5-(azetidine-1-carbonyl)-7-(thiazol-2-yl)benzo[d]oxazol-2-yl)-3,8-diazabicyclo[3.2.1]octane-8-carboxylate The title compound was obtained in an amount of 9.8 mg from 25 mg of 2-(8-(tert-butoxycarbonyl)-3,8-diazabicyclo[3.2.1]octan-3-yl)-7-(thiazol-2-yl)benzo[d]oxazole-5-carboxylic acid obtained in Example 94(a) by a similar method to Example 94(b) except that azetidine hydrochloride (10 μL, 2 equivalents) and diisopropylethylamine (19 μL, 2 equivalents) were used instead of 2M dimethylamine solution in methanol.

(b) (2-(3,8-Diazabicyclo[3.2.1]octan-3-yl)-7-(thiazol-2-yl)benzo[d]oxazol-5-yl)(azetidin-1-yl)methanone The title compound was obtained in an amount of 7.0 mg from 9.8 mg of tert-butyl 3-(5-(azetidine-1-carbonyl)-7-(thiazol-2-yl)benzo[d]oxazol-2-yl)-3,8-diazabicyclo[3.2.1]octane-8-carboxylate obtained in Example 97(a) by a similar method to Example 1(c).

Example 98

N-benzyl-2-(3,8-diazabicyclo[3.2.1]octan-3-yl)-7-(thiazol-2-yl)benzo[d]oxazole-5-carboxamide (a) tert-Butyl 3-(5-(benzylcarbamoyl)-7-(thiazol-2-yl)benzo[d]oxazol-2-yl)-3,8-diazabicyclo[3.2.1]octane-8-carboxylate The title compound was obtained as a crude product in an amount of 39 mg from 25 mg of 2-(8-(tert-butoxycarbonyl)-3,8-diazabicyclo[3.2.1]octan-3-yl)-7-(thiazol-2-yl)benzo[d]oxazole-5-carboxylic acid obtained in Example 94 (a) by a similar method to Example 94(b) except that benzylamine (12 μL, 2 equivalents) was used instead of 2M dimethylamine solution in methanol.

(b) N-benzyl-2-(3,8-diazabicyclo[3.2.1]octan-3-yl)-7-(thiazol-2-yl)benzo[d]oxazole-5-carboxamide The title compound was obtained in an amount of 24 mg from 39 mg of tert-butyl 3-(5-(benzylcarbamoyl)-7-(thiazol-2-yl)benzo[d]oxazol-2-yl)-3,8-diazabicyclo[3.2.1]octane-8-carboxylate obtained in Example 98 (a) by a similar method to Example 1(c).

Example 99

2-(3,8-Diazabicyclo[3.2.1]octan-3-yl)-7-(thiazol-2-yl)benzo[d]oxazole-5-carboxamide (a) tert-Butyl 3-(5-carbamoyl-7-(thiazol-2-yl)benzo[d]oxazol-2-yl)-3,8-diazabicyclo[3.2.1]octane-8-carboxylate The title compound was obtained as a crude product in an amount of 28 mg from 25 mg of 2-(8-(tert-butoxycarbonyl)-3,8-diazabicyclo[3.2.1]octan-3-yl)-7-(thiazol-2-yl)benzo[d]oxazole-5-carboxylic acid obtained in Example 94 (a) by a similar method to Example 94(b) except that 28% ammonia water (0.1 mL, 30 equivalents) was used instead of 2M dimethylamine solution in methanol.

(b) 2-(3,8-Diazabicyclo[3.2.1]octan-3-yl)-7-(thiazol-2-yl)benzo[d]oxazole-5-carboxamide The title compound was obtained in an amount of 15 mg from 28 mg of tert-butyl 3-(5-carbamoyl-7-(thiazol-2-yl)benzo[d]oxazol-2-yl)-3,8-diazabicyclo[3.2.1]octane-8-carboxylate obtained in Example 99(a) by a similar method to Example 1(c).

Example 100

2-(3,8-Diazabicyclo[3.2.1]octan-3-yl)-N-methyl-7-(thiazol-2-yl)benzo[d]oxazole-5-carboxamide (a) tert-Butyl 3-(5-(methylcarbamoyl)-7-(thiazol-2-yl)benzo[d]oxazol-2-yl)-3,8-diazabicyclo[3.2.1]octane-8-carboxylate The title compound was obtained as a crude product in an amount of 29 mg from 25 mg of 2-(8-(tert-butoxycarbonyl)-3,8-diazabicyclo[3.2.1]octan-3-yl)-7-(thiazol-2-yl)benzo[d]oxazole-5-carboxylic acid obtained in Example 94 (a) by a similar method to Example 94 (b) except that 2M methylamine in tetrahydrofuran (55 μL, 2 equivalents) was used instead of 2M dimethylamine solution in methanol.

(b) 2-(3,8-Diazabicyclo[3.2.1]octan-3-yl)-N-methyl-7-(thiazol-2-yl)benzo[d]oxazole-5-carboxamide The title compound was obtained in an amount of 19 mg from 29 mg of tert-butyl 3-(5-(methylcarbamoyl)-7-(thiazol-2-yl)benzo[d]oxazol-2-yl)-3,8-diazabicyclo[3.2.1]octane-8-carboxylate obtained in Example 100(a) by a similar method to Example 1(c).

Example 101

N-(2-(3,8-diazabicyclo[3.2.1]octan-3-yl)-7-(thiazol-2-yl)benzo[d]oxazol-5-yl)-N-methylacetamide (a) tert-Butyl 3-(5-(N-methylacetamide)-7-(thiazol-2-yl)benzo[d]oxazol-2-yl)-3,8-diazabicyclo[3.2.1]octane-8-carboxylate The title compound was obtained in an amount of 22 mg from 30 mg of tert-butyl 3-(5-acetamido-7-(thiazol-2-yl)benzo[d]oxazol-2-yl)-3,8-diazabicyclo[3.2.1]octane-8-carboxylate obtained in Example 50(b) by a similar method to Example 70(a) except that methyl iodide was used instead of 3-(iodomethyl)oxetane and only N,N-dimethylformamide was used as the solvent.

(b) N-(2-(3,8-diazabicyclo[3.2.1]octan-3-yl)-7-(thiazol-2-yl)benzo[d]oxazol-5-yl)-N-methylacetamide The title compound was obtained in an amount of 13 mg from 22 mg of tert-butyl 3-(5-(N-methylacetamido)-7-(thiazol-2-yl)benzo[d]oxazol-2-yl)-3,8-diazabicyclo[3.2.1]octane-8-carboxylate obtained in Example 101(a) by a similar method to Example 1(c).

Example 102

2-(3,8-Diazabicyclo[3.2.1]octan-3-yl)-7-(thiazol-2-yl)-5-(1,1,1-trifluoro-2-methoxypropan-2-yl)benzo[d]oxazole (a) tert-Butyl 3-(5-formyl-7-(thiazol-2-yl)benzo[d]oxazol-2-yl)-3,8-diazabicyclo[3.2.1]octane-8-carboxylate 498 mg of ethyl 2-(8-(tert-butoxycarbonyl)-3,8-diazabicyclo[3.2.1]octan-3-yl)-7-(thiazol-2-yl)benzo[d]oxazole-5-carboxylate obtained in Example 86(b) was dissolved in toluene (10 mL), and then 1.0 M toluene solution (5.2 mL, 5 equivalents) of diisobutylaluminum hydride was added thereto at −78° C., followed by stirring for 30 minutes. The formation of the product was confirmed by TLC (eluent, hexane:ethyl acetate=1:1), and then saturated aqueous solution of ammonium chloride was added thereto, followed by Celite® filtration. Thereafter, the organic phase extracted with ethyl acetate was washed by distilled water and dried over anhydrous magnesium sulfate, followed by filtration, and thus obtaining a crude product by vacuum concentration of the filtrate. The obtained crude product and Dess-Martin periodinane (864 mg, 2 equivalents) were dissolved in chloroform (10 mL), followed by stirring at 0° C. for 90 minutes. The formation of the product was confirmed by TLC (eluent, hexane:ethyl acetate=1:1), and then saturated sodium hydrogen carbonate aqueous solution and saturated aqueous solution of sodium thiosulfate were added thereto, followed by extraction using ethyl acetate. Thereafter, the organic phase was dried over anhydrous magnesium sulfate, followed by filtration, and thus obtaining 372 mg of the title compound by purification of the residue obtained by vacuum concentration of the filtrate through silica gel column chromatography (hexane, hexane:ethyl acetate=6:4).

(b) tert-Butyl 3-(5-(1-hydroxyethyl)-7-(thiazol-2-yl)benzo[d]oxazol-2-yl)-3,8-diazabicyclo[3.2.1]octane-8-carboxylate 150 mg of tert-butyl 3-(5-formyl-7-(thiazol-2-yl)benzo[d]oxazol-2-yl)-3,8-diazabicyclo[3.2.1]octane-8-carboxylate obtained in Example 102 (a) was dissolved in tetrahydrofuran (3.4 mL), and then 0.92 M tetrahydrofuran solution (0.8 mL, 2 equivalents) of methylmagnesium bromide was added thereto at −78° C., followed by stirring at 0° C. for 2 hours. The formation of the product was confirmed by TLC (eluent, hexane:ethyl acetate=1:1), and then saturated aqueous solution of ammonium chloride was added thereto, followed by extraction using ethyl acetate. Thereafter, the organic phase was dried over anhydrous magnesium sulfate, followed by filtration, and thus obtaining 146 mg of the title compound by purification of the residue obtained by vacuum concentration of the filtrate through silica gel column chromatography (hexane, hexane:ethyl acetate=3:7).

(c) tert-Butyl 3-(5-acetyl-7-(thiazol-2-yl)benzo[d]oxazol-2-yl)-3,8-diazabicyclo[3.2.1]octane-8-carboxylate 146 mg of tert-butyl 3-(5-(1-hydroxyethyl)-7-(thiazol-2-yl)benzo[d]oxazol-2-yl)-3,8-diazabicyclo[3.2.1]octane-8-carboxylate obtained in Example 102 (b) and Dess-Martin periodinane (274 mg, 2 equivalents) were dissolved in chloroform (3.2 mL), followed by stirring at 0° C. for 1 hour. The temperature was caused to rise to room temperature, followed by further stirring for 1 hour. The formation of the product was confirmed by TLC (eluent, hexane:ethyl acetate=1:1), and then saturated sodium hydrogen carbonate aqueous solution and saturated aqueous solution of sodium thiosulfate were added thereto, followed by extraction using ethyl acetate. Thereafter, the organic phase was dried over anhydrous magnesium sulfate, followed by filtration, and thus obtaining 109 mg of the title compound by purification of the residue obtained by vacuum concentration of the filtrate through silica gel column chromatography (hexane, hexane:ethyl acetate=5:5).

(d) tert-Butyl 3-(7-(thiazol-2-yl)-5-(1,1,1-trifluoro-2-hydroxypropan-2-yl)benzo[d]oxazol-2-yl)-3,8-diazabicyclo[3.2.1]octane-8-carboxylate 70 mg of tert-butyl 3-(5-acetyl-7-(thiazol-2-yl)benzo[d]oxazol-2-yl)-3,8-diazabicyclo[3.2.1]octane-8-carboxylate obtained in Example 102 (c), trifluoromethyltrimethylsilane (138 µL, 6 equivalents), and caesium carbonate (2.6 mg, 0.1 equivalent) were dissolved in tetrahydrofuran (3.2 mL), followed by stirring at 0° C. for 2 hours. The formation of the product was confirmed by TLC (eluent, hexane:ethyl acetate=1:1), and then saturated sodium hydrogen carbonate aqueous solution was added thereto, followed by extraction using ethyl acetate. Thereafter, the organic phase was dried over anhydrous magnesium sulfate, followed by filtration, and thus obtaining a crude product by vacuum concentration of the filtrate. The obtained crude product was dissolved in tetrahydrofuran (1.5 mL), and then 1.0 M tetrabutylammonium fluoride solution in tetrahydrofuran (308 µL, 2 equivalents) was added thereto, followed by stirring at 0° C. for 1 hour. The formation of the product was confirmed by TLC (eluent, hexane:ethyl acetate=1:1), and then saturated aqueous solution of ammonium chloride was added thereto, followed by extraction using ethyl acetate. Thereafter, the organic phase was dried over anhydrous magnesium sulfate, followed by filtration, and thus obtaining 76 mg of the title compound by purification of the residue obtained by vacuum concentration of the filtrate through silica gel column chromatography (hexane, hexane:ethyl acetate=6:4).

(e) tert-Butyl 3-(7-(thiazol-2-yl)-5-(1,1,1-trifluoro-2-methoxypropan-2-yl)benzo[d]oxazol-2-yl)-3,8-diazabicyclo[3.2.1]octane-8-carboxylate 41 mg of tert-butyl 3-(7-(thiazol-2-yl)-5-(1,1,1-trifluoro-2-hydroxypropan-2-yl)benzo[d]oxazol-2-yl)-3,8-diazabicyclo[3.2.1]octane-8-carboxylate obtained in Example 102 (d), methyl iodide (20 µL, 4 equivalents), and sodium hydride (15.9 mg, 4.4 equivalents) were dissolved in tetrahydrofuran (780 µL), followed by stirring at room temperature for 10 hours. The formation of the product was confirmed by TLC (eluent, hexane:ethyl acetate=1:1), and then saturated aqueous solution of ammonium chloride was added thereto, followed by extraction using ethyl acetate. Thereafter, the organic phase was dried over anhydrous magnesium sulfate, followed by filtration, and thus obtaining 29 mg of the title compound by purification of the residue obtained by vacuum concentration of the filtrate by preparative TLC (eluent, hexane:ethyl acetate=1:1).

(f) 2-(3,8-Diazabicyclo[3.2.1]octan-3-yl)-7-(thiazol-2-yl)-5-(1,1,1-trifluoro-2-methoxypropan-2-yl)benzo[d]oxazole 18 mg of the title compound was obtained from 29 mg of tert-butyl 3-(7-(thiazol-2-yl)-5-(1,1,1-trifluoro-2-methoxypropan-2-yl)benzo[d]oxazol-2-yl)-3,8-diazabicyclo[3.2.1]octane-8-carboxylate obtained in Example 102 (e), using a similar method to Example 1(c).

Example 103

2-(3,6-Diazabicyclo[3.1.1]heptan-3-yl)-7-(thiazol-2-yl)-5-(1,1,1-trifluoro-2-methoxypropan-2-yl)benzo[d]oxazole (a) tert-Butyl 3-(5-(methoxy(methyl)carbamoyl)-7-(thiazol-2-yl)benzo[d]oxazol-2-yl)-3,6-diazabicyclo[3.1.1]heptane-6-carboxylate 91 mg of ethyl 7-bromo-2-(6-(tert-butoxycarbonyl)-3,6-diazabicyclo[3.1.1]heptan-3-yl)benzo[d]oxazole-5-carboxylate obtained in Example 87(a) and N,O-dimethylhydroxylamine hydrochloride (59 mg, 3 equivalents) were dissolved in tetrahydrofuran (965 µL), and then 2.0 M solution of isopropylmagnesium chloride in tetrahydrofuran (580 µL, 6 equivalents) was added thereto at 0° C., followed by stirring for 30 min. The formation of the product was confirmed by TLC (eluent, hexane:ethyl acetate=1:1), and then saturated aqueous solution of ammonium chloride was added thereto, followed by extraction using ethyl acetate. Thereafter, the organic phase was dried over anhydrous magnesium sulfate, followed by filtration, and thus obtaining 82 mg of the title compound by purification of the residue obtained by vacuum concentration of the filtrate through silica gel column chromatography (hexane, hexane:ethyl acetate=1:9).

(b) tert-Butyl 3-(5-acetyl-7-(thiazol-2-yl)benzo[d]oxazol-2-yl)-3,6-diazabicyclo[3.1.1]heptane-6-carboxylate 67 mg of tert-butyl 3-(5-(methoxy(methyl)carbamoyl)-7-(thiazol-2-yl)benzo[d]oxazol-2-yl)-3,6-diazabicyclo[3.1.1]heptane-6-carboxylate obtained in Example 103(a) was dissolved in tetrahydrofuran (0.7 mL), and then 0.92 M solution of methylmagnesium bromide in tetrahydrofuran (1.5 mL, 10 equivalents) was added thereto at 0° C., followed by stirring for 30 min at room temperature. The formation of the product was confirmed by TLC (eluent, hexane:ethyl acetate=1:4), and then saturated aqueous solution of ammonium chloride was added thereto, followed by extraction using ethyl acetate. Thereafter, the organic phase was dried over anhydrous magnesium sulfate, followed by filtration, and thus obtaining 61 mg of the title compound as a crude product by vacuum concentration of the residue.

(c) tert-Butyl 3-(7-(thiazol-2-yl)-5-(1,1,1-trifluoro-2-hydroxypropan-2-yl)benzo[d]oxazol-2-yl)-3,6-diazabicyclo[3.1.1]heptane-6-carboxylate The title compound was obtained as a crude product in an amount of 70 mg from 61 mg of tert-butyl 3-(5-acetyl-7-(thiazol-2-yl)benzo[d]oxazol-2-yl)-3,6-diazabicyclo[3.1.1]heptane-6-carboxylate obtained in Example 103(b) by a similar method to Example 102(d) except that the purification by the Silica gel column chromatography was not carried out.

(d) tert-Butyl 3-(7-(thiazol-2-yl)-5-(1,1,1-trifluoro-2-methoxypropan-2-yl)benzo[d]oxazol-2-yl)-3,6-diazabicyclo[3.1.1]heptane-6-carboxylate The title compound was obtained as a crude product in an amount of 17 mg from 35 mg of tert-butyl 3-(7-(thiazol-2-yl)-5-(1,1,1-trifluoro-2-hydroxypropan-2-yl)benzo[d]oxazol-2-yl)-3,6-diazabicyclo[3.1.1]heptane-6-carboxylate obtained in Example 103(c) by a similar method to Example 102(e) except that the purification by the Silica gel column chromatography was not carried out.

(e) 2-(3,6-Diazabicyclo[3.1.1]heptan-3-yl)-7-(thiazol-2-yl)-5-(1,1,1-trifluoro-2-methoxypropan-2-yl)benzo[d]oxazole The title compound was obtained in an amount of 11 mg from 17 mg of tert-butyl 3-(7-(thiazol-2-yl)-5-(1,1,1-trifluoro-2-methoxypropan-2-yl)benzo[d]oxazol-2-yl)-3,6-diazabicyclo[3.1.1]heptane-6-carboxylate obtained in Example 103(d) by a similar method to Example 1(c).

Example 104

1-(2-(3,8-Diazabicyclo[3.2.1]octan-3-yl)-7-(thiazol-2-yl)benzo[d]oxazol-5-yl)-2,2-difluoroethan-1-ol (a) tert-Butyl 3-(5-(2,2-difluoro-1-hydroxyethyl)-7-(thiazol-2-yl)benzo[d]oxazol-2-yl)-3,8-diazabicyclo[3.2.1]octane-8-carboxylate 44 mg of tert-butyl 3-(5-formyl-7-(thiazol-2-yl)benzo[d]oxazol-2-yl)-3,8-diazabicyclo[3.2.1]octane-8-carboxylate obtained in Example 102 (a), (difluoromethyl)trimethylsilane (54 μL, 4 equivalents), and caesium fluoride (63 mg, 4 equivalents) were dissolved in N,N-dimethylformamide (1.0 mL), and stirred them for 20 hours at room temperature. Saturated aqueous sodium bicarbonate solution was added and organic phase was extracted by ethyl acetate. A filtrate was obtained by drying the extracted organic phase by anhydrous magnesium sulfate and filtering them. The title compound was obtained in an amount of 21 mg by silica gel column chromatography purification (amino silica, hexane-hexane:ethyl acetate=1:4) of residue obtained by vacuum concentration of the filtrate.

(b) 1-(2-(3,8-Diazabicyclo[3.2.1]octan-3-yl)-7-(thiazol-2-yl)benzo[d]oxazol-5-yl)-2,2-difluoroethan-1-ol The title compound was obtained in an amount of 4.8 mg from 6.6 mg of tert-butyl 3-(5-(2,2-difluoro-1-hydroxyethyl)-7-(thiazol-2-yl)benzo[d]oxazol-2-yl)-3,8-diazabicyclo[3.2.1]octane-8-carboxylate obtained in Example 104 (a) by a similar method to Example 1(c).

Example 105

2-(3,8-Diazabicyclo[3.2.1]octan-3-yl)-5-(2,2-difluoro-1-methoxyethyl)-7-(thiazol-2-yl)benzo[d]oxazole (a) tert-Butyl 3-(5-(2,2-difluoro-1-methoxyethyl)-7-(thiazol-2-yl)benzo[d]oxazol-2-yl)-3,8-diazabicyclo[3.2.1]octane-8-carboxylate The title compound was obtained in an amount of 9.0 mg from 10 mg of tert-butyl 3-(5-(2,2-difluoro-1-hydroxyethyl)-7-(thiazol-2-yl)benzo[d]oxazol-2-yl)-3,8-diazabicyclo[3.2.1]octane-8-carboxylate obtained in Example 104 (a) by a similar method to Example 102 (a).

(b) 2-(3,8-Diazabicyclo[3.2.1]octan-3-yl)-5-(2,2-difluoro-1-methoxyethyl)-7-(thiazol-2-yl)benzo[d]oxazole The title compound was obtained in an amount of 6.9 mg from 9.0 mg of tert-butyl 3-(5-(2,2-difluoro-1-methoxyethyl)-7-(thiazol-2-yl)benzo[d]oxazol-2-yl)-3,8-diazabicyclo[3.2.1]octane-8-carboxylate obtained in Example 105 (a) by a similar method to Example 1(c).

Example 106

1-(2-(3,8-Diazabicyclo[3.2.1]octan-3-yl)-7-(thiazol-2-yl)benzo[d]oxazol-5-yl)ethan-1-ol The title compound was obtained in an amount of 17 mg from 41 mg of tert-butyl 3-(5-(1-hydroxyethyl)-7-(thiazol-2-yl)benzo[d]oxazol-2-yl)-3,8-diazabicyclo[3.2.1]octane-8-carboxylate obtained in Example 102(b) by a similar method to Example 1(c)

Example 107

1-(2-(3,6-Diazabicyclo[3.1.1]heptan-3-yl)-7-(thiazol-2-yl)benzo[d]oxazol-5-yl)ethan-1-ol (a) tert-Butyl 3-(5-(hydroxymethyl)-7-(thiazol-2-yl)benzo[d]oxazol-2-yl)-3,6-diazabicyclo[3.1.1]heptane-6-carboxylate 150 mg of ethyl 2-(6-(tert-butoxycarbonyl)-3,6-diazabicyclo[3.1.1]heptan-3-yl)-7-(thiazol-2-yl)benzo[d]oxazole-5-carboxylate obtained in Example 87(b) was dissolved in dichloromethane (3.8 mL), and then 1.0 M solution of diisobutylaluminum hydride in toluene (1.5 mL, 4 equivalents) was added thereto at −78° C., followed by stirring for 1 hour. Saturated aqueous solution of ammonium chloride was added thereto to stop the reaction. Thereafter, the organic phase extracted using ethyl acetate was dried over anhydrous magnesium sulfate, followed by filtration, and thus obtaining a crude product of the title compound by vacuum concentration of the filtrate.

(b) tert-Butyl 3-(5-formyl-7-(thiazol-2-yl)benzo[d]oxazol-2-yl)-3,6-diazabicyclo[3.1.1]heptane-6-carboxylate Curude tert-butyl 3-(5-(hydroxymethyl)-7-(thiazol-2-yl)benzo[d]oxazol-2-yl)-3,6-diazabicyclo[3.1.1]heptane-6-carboxylate obtained in Example 107 (a) and Dess-Martin Periodinane (322 mg, 2 equivalents) were dissolved in chloroform (3.8 mL), and stirred them for 1 hour at room temperature. After confirming a reaction product by TLC (eluent, hexane:ethyl acetate=1:1), saturated aqueous sodium bicarbonate and saturated aqueous sodium thiosulfate were added and organic phase was extracted by ethyl acetate. A filtrate was obtained by drying the extracted organic phase by anhydrous magnesium sulfate and filtering them. The title compound was obtained in an amount of 108 mg by preparative TLC (hexane:ethyl acetate=1:3) of residue obtained by vacuum concentration of the filtrate.

(c) tert-Butyl 3-(5-(1-hydroxyethyl)-7-(thiazol-2-yl)benzo[d]oxazol-2-yl)-3,6-diazabicyclo[3.1.1]heptane-6-carboxylate The title compound was obtained in an amount of 55 mg from 108 mg of tert-butyl 3-(5-formyl-7-(thiazol-2-yl)benzo[d]oxazol-2-yl)-3,6-diazabicyclo[3.1.1]heptane-6-carboxylate obtained in Example 107 (b) by a similar method to Example 102 (d).

(d) 1-(2-(3,6-Diazabicyclo[3.1.1]heptan-3-yl)-7-(thiazol-2-yl)benzo[d]oxazol-5-yl)ethan-1-ol The title compound was obtained in an amount of 21 mg from 28 mg of tert-butyl 3-(5-(1-hydroxyethyl)-7-(thiazol-2-yl)benzo[d]oxazol-2-yl)-3,6-diazabicyclo[3.1.1]heptane-6-carboxylate obtained in Example 107 (c) by a similar method to Example 1(c).

Example 108

1-(2-(3,8-Diazabicyclo[3.2.1]octan-3-yl)-7-(thiazol-2-yl)benzo[d]oxazol-5-yl)ethan-1-one The title compound was obtained in an amount of 9.0 mg from 17.2 mg of tert-butyl 3-(5-acetyl-7-(thiazol-2-yl)benzo[d]oxazol-2-yl)-3,8-diazabicyclo[3.2.1]octane-8-carboxylate obtained in Example 102 (c) by a similar method to Example 1(c).

Example 109

1-(2-(3,6-Diazabicyclo[3.1.1]heptan-3-yl)-7-(thiazol-2-yl)benzo[d]oxazol-5-yl)ethan-1-one The title compound was obtained in an amount of 7.6 mg from 46 mg of tert-butyl 3-(5-acetyl-7-(thiazol-2-yl)benzo[d]oxazol-2-yl)-3,6-diazabicyclo[3.1.1]heptane-6-carboxylate obtained in Example 103 (b) by a similar method to Example 1(c).

Example 110

2-(3,8-Diazabicyclo[3.2.1]octan-3-yl)-5-(1-methoxyethyl)-7-(thiazol-2-yl)benzo[d]oxazole (a) tert-Butyl 3-(5-(1-methoxyethyl)-7-(thiazol-2-yl)benzo[d]oxazol-2-yl)-3,8-diazabicyclo[3.2.1]octane-8-carboxylate The title compound was obtained in an amount of 15 mg from 25 mg of tert-butyl 3-(5-(1-hydroxyethyl)-7-(thiazol-2-yl)benzo[d]oxazol-2-yl)-3,8-diazabicyclo[3.2.1]octane-8-carboxylate obtained in Example 102 (b) by a similar method to Example 102 (e).

(b) 2-(3,8-Diazabicyclo[3.2.1]octan-3-yl)-5-(1-methoxyethyl)-7-(thiazol-2-yl)benzo[d]oxazole The title compound was obtained in an amount of 10 mg from 15 mg of tert-butyl 3-(5-(1-methoxyethyl)-7-(thiazol-2-yl)benzo[d]oxazol-2-yl)-3,8-diazabicyclo[3.2.1]octane-8-carboxylate obtained in Example 110(a) by a similar method to Example 1(c).

Example 111

2-(3,6-Diazabicyclo[3.1.1]heptan-3-yl)-5-(1-methoxyethyl)-7-(thiazol-2-yl)benzo[d]oxazole (a) tert-Butyl 3-(5-(1-methoxyethyl)-7-(thiazol-2-yl)benzo[d]oxazol-2-yl)-3,6-diazabicyclo[3.1.1]heptane-6-carboxylate The title compound was obtained in an amount of 25 mg from 28 mg of tert-butyl 3-(5-(1-hydroxyethyl)-7-(thiazol-2-yl)benzo[d]oxazol-2-yl)-3,6-diazabicyclo[3.1.1]heptane-6-carboxylate obtained in Example 107 (c) by a similar method to Example 102 (e).

(b) 2-(3,6-Diazabicyclo[3.1.1]heptan-3-yl)-5-(1-methoxyethyl)-7-(thiazol-2-yl)benzo[d]oxazole The title compound was obtained in an amount of 21 mg from 25 mg of tert-butyl 3-(5-(1-methoxyethyl)-7-(thiazol-2-yl)benzo[d]oxazol-2-yl)-3,6-diazabicyclo[3.1.1]heptane-6-carboxylate obtained in Example 111(a) by a similar method to Example 1(c).

Example 112

Ethyl 2-(3,8-diazabicyclo[3.2.1]octan-3-yl)-7-(thiazol-2-yl)benzo[d]oxazole-4-carboxylate (a) Ethyl 7-bromo-2-(8-(tert-butoxycarbonyl)-3,8-diazabicyclo[3.2.1]octan-3-yl)benzo[d]oxazole-4-carboxylate The title compound was obtained in an amount of 195 mg from 150 mg of ethyl 7-bromo-2-mercaptobenzo[d]oxazole-4-carboxylate obtained in Reference Example 16 and tert-butyl 3,8-diazabicyclo[3.2.1]octane-8-carboxylate by a similar method to Example 1(a).

(b) Ethyl 2-(8-(tert-butoxycarbonyl)-3,8-diazabicyclo[3.2.1]octan-3-yl)-7-(thiazol-2-yl)benzo[d]oxazole-4-carboxylate The title compound was obtained as a crude product in an amount of 250 mg from 195 mg of ethyl 7-bromo-2-(8-(tert-butoxycarbonyl)-3,8-diazabicyclo[3.2.1]octan-3-yl)benzo[d]oxazole-4-carboxylate obtained in Example 112 (a) by a similar method to Example 2(b) except that toluene was used instead of 1,4-dioxane.

(c) Ethyl 2-(3,8-diazabicyclo[3.2.1]octan-3-yl)-7-(thiazol-2-yl)benzo[d]oxazole-4-carboxylate The title compound was obtained in an amount of 125 mg from 250 mg of ethyl 2-(8-(tert-butoxycarbonyl)-3,8-diazabicyclo[3.2.1]octan-3-yl)-7-(thiazol-2-yl)benzo[d]oxazole-4-carboxylate obtained in Example 112 (b) by a similar method to Example 1(c).

Example 113

Ethyl 2-(3,6-diazabicyclo[3.1.1]heptan-3-yl)-7-(thiazol-2-yl)benzo[d]oxazole-4-carboxylate (a) Ethyl 7-bromo-2-(6-(tert-butoxycarbonyl)-3,6-diazabicyclo[3.1.1]heptan-3-yl)benzo[d]oxazole-4-carboxylate The title compound was obtained in an amount of 164 mg from 150 mg of ethyl 7-bromo-2-mercaptobenzo[d]oxazole-4-carboxylate obtained in Reference Example 16 by a similar method to Example 1(a) except that tert-butyl 3,6-diazabicyclo[3.1.1]heptane-6-carboxylate was used instead of tert-butyl 3,8-diazabicyclo[3.2.1]octane-8-carboxylate.

(b) Ethyl 2-(6-(tert-butoxycarbonyl)-3,6-diazabicyclo[3.1.1]heptan-3-yl)-7-(thiazol-2-yl)benzo[d]oxazole-4-carboxylate The title compound was obtained as a crude product in an amount of 270 mg from 160 mg of ethyl 7-bromo-2-(6-(tert-butoxycarbonyl)-3,6-diazabicyclo[3.1.1]heptan-3-yl)benzo[d]oxazole-4-carboxylate obtained in Example 113(a) by a similar method to Example 2(b) except that toluene was used instead of 1,4-dioxane.

(c) Ethyl 2-(3,6-diazabicyclo[3.1.1]heptan-3-yl)-7-(thiazol-2-yl)benzo[d]oxazole-4-carboxylate The title compound was obtained in an amount of 98 mg from 270 mg of ethyl 2-(6-(tert-butoxycarbonyl)-3,6-diazabicyclo[3.1.1]heptan-3-yl)-7-(thiazol-2-yl)benzo[d]oxazole-4-carboxylate obtained in Example 113 (b) by a similar method to Example 1(c).

Example 114

Ethyl 2-(3,9-diazabicyclo[3.3.1]nonan-3-yl)-7-(thiazol-2-yl)benzo[d]oxazole-4-carboxylate (a) Ethyl 7-bromo-2-(9-(tert-butoxycarbonyl)-3,9-diazabicyclo[3.3.1]nonan-3-yl)benzo[d]oxazole-4-carboxylate The title compound was obtained in an amount of 186 mg from 150 mg of ethyl 7-bromo-2-mercaptobenzo[d]oxazole-4-carboxylate obtained in Reference example 16 by a similar method to Example 1(a) except that tert-butyl 3,9-diazabicyclo[3.3.1]nonane-9-carboxylate was used instead of tert-butyl 3,8-diazabicyclo[3.2.1]octane-8-carboxylate.

(b) Ethyl 2-(9-(tert-butoxycarbonyl)-3,9-diazabicyclo[3.3.1]nonan-3-yl)-7-(thiazol-2-yl)benzo[d]oxazole-4-carboxylate The title compound was obtained as a crude product in an amount of 300 mg from 180 mg of ethyl 7-bromo-2-(9-(tert-butoxycarbonyl)-3,9-diazabicyclo[3.3.1]nonan-3-yl)benzo[d]oxazole-4-carboxylate obtained in Example 114 (a) by a similar method to Example 2 (b) except that toluene was used instead of 1,4-dioxane.

(c) Ethyl 2-(3,9-diazabicyclo[3.3.1]nonan-3-yl)-7-(thiazol-2-yl)benzo[d]oxazole-4-carboxylate The title compound was obtained in an amount of 100 mg from 300 mg of ethyl 2-(9-(tert-butoxycarbonyl)-3,9-diazabicyclo[3.3.1]nonan-3-yl)-7-(thiazol-2-yl)benzo[d]oxazole-4-carboxylate obtained in Example 114 (b) by a similar method to Example 1(c).

Example 115

2-(3,8-Diazabicyclo[3.2.1]octan-3-yl)-N,N-dimethyl-7-(thiazol-2-yl)benzo[d]oxazole-4-carboxamide (a) 2-(8-(tert-Butoxycarbonyl)-3,8-diazabicyclo[3.2.1]octan-3-yl)-7-(thiazol-2-yl)benzo[d]oxazole-4-carboxylic acid The title compound was obtained in an amount of 45 mg from 48 mg of ethyl 2-(8-(tert-butoxycarbonyl)-3,8-diazabicyclo[3.2.1]octan-3-yl)-7-(thiazol-2-yl)benzo[d]oxazole-4-carboxylate obtained in Example 112 (b) by a similar method to Example 94 (a).

(b) tert-Butyl 3-(4-(dimethylcarbamoyl)-7-(thiazol-2-yl)benzo[d]oxazol-2-yl)-3,8-diazabicyclo[3.2.1]octane-8-carboxylate The title compound was obtained in an amount of 13 mg from 13 mg of 2-(8-(tert-butoxycarbonyl)-3,8-diazabicyclo[3.2.1]octan-3-yl)-7-(thiazol-2-yl)benzo[d]oxazole-4-carboxylic acid obtained in Example 115 (a) by a similar method to Example 94 (b).

(c) 2-(3,8-Diazabicyclo[3.2.1]octan-3-yl)-N,N-dimethyl-7-(thiazol-2-yl)benzo[d]oxazole-4-carboxamide The title compound was obtained in an amount of 10 mg from 13 mg of tert-butyl 3-(4-(dimethylcarbamoyl)-7-(thiazol-2-yl)benzo[d]oxazol-2-yl)-3,8-diazabicyclo[3.2.1]octane-8-carboxylate obtained in Example 115(b) by a similar method to Example 1(c).

Example 116

(2-(3,8-Diazabicyclo[3.2.1]octan-3-yl)-7-(thiazol-2-yl)benzo[d]oxazol-4-yl) (morpholino)methanone (a) tert-Butyl 3-(4-(morpholine-4-carbonyl)-7-(thiazol-2-yl)benzo[d]oxazol-2-yl)-3,8-diazabicyclo[3.2.1]octane-8-carboxylate The title compound was obtained in an amount of 20 mg from 17 mg of 2-(8-tert-butoxycarbonyl-3,8-diazabicyclo[3.2.1]octan-3-yl)-7-(thiazol-2-yl)benzo[d]oxazol-4-carboxylic acid obtained in Example 115(a) by a similar method to Example 94(b) except that morpholine (64 μL, 2 equivalents) was used instead of 2M dimethylamine solution in methanol.

(b) (2-(3,8-Diazabicyclo[3.2.1]octan-3-yl)-7-(thiazol-2-yl)benzo[d]oxazol-4-yl) (morpholino)methanone The title compound was obtained in an amount of 16 mg from 20 mg of tert-butyl 3-(4-(morpholine-4-carbonyl)-7-

(thiazol-2-yl)benzo[d]oxazol-2-yl)-3,8-diazabicyclo[3.2.1]octane-8-carboxylate obtained in Example 116(a) by a similar method to Example 1(c).

Example 117

(2-(3,8-Diazabicyclo[3.2.1]octan-3-yl)-7-(thiazol-2-yl)benzo[d]oxazol-4-yl)(piperidin-1-yl)methanone (a) tert-Butyl 3-(4-(piperidine-1-carbonyl)-7-(thiazol-2-yl)benzo[d]oxazol-2-yl)-3,8-diazabicyclo[3.2.1]octane-8-carboxylate The title compound was obtained in an amount of 18 mg from 15 mg of 2-(8-tert-butoxycarbonyl-3,8-diazabicyclo[3.2.1]octan-3-yl)-7-(thiazol-2-yl)benzo[d]oxazol-4-carboxylic acid obtained in Example 115(a) by a similar method to Example 94(b) except that piperidine (6.6 μL, 2 equivalents) was used instead of 2M dimethylamine solution in methanol.

(b) (2-(3,8-Diazabicyclo[3.2.1]octan-3-yl)-7-(thiazol-2-yl)benzo[d]oxazol-4-yl)(piperidin-1-yl)methanone The title compound was obtained in an amount of 14 mg from 18 mg of tert-butyl 3-(4-(piperidine-1-carbonyl)-7-(thiazol-2-yl)benzo[d]oxazol-2-yl)-3,8-diazabicyclo[3.2.1]octane-8-carboxylate obtained in Example 117 (a) by a similar method to Example 1(c).

Example 118

1-(2-(3,8-Diazabicyclo[3.2.1]octan-3-yl)-7-(thiazol-2-yl)benzo[d]oxazol-4-yl)-2,2,2-trifluoroethan-1-ol (Optically Active)

(a) tert-Butyl 3-(4-formyl-7-(thiazol-2-yl)benzo[d]oxazol-2-yl)-3,8-diazabicyclo[3.2.1]octane-8-carboxylate The title compound was obtained in an amount of 130 mg from 169 mg of ethyl 2-(8-tert-butoxycarbonyl-3,8-diazabicyclo[3.2.1]octan-3-yl)-7-(thiazol-2-yl)benzo[d]oxazol-4-carboxylate obtained in Example 112 (b) by a similar method to Example 102 (a).

(b) tert-Butyl 3-(7-(thiazol-2-yl)-4-(2,2,2-trifluoro-1-hydroxyethyl)benzo[d]oxazol-2-yl)-3,8-diazabicyclo[3.2.1]octane-8-carboxylate (racemic)

38 mg of tert-butyl 3-(4-formyl-7-(thiazol-2-yl)benzo[d]oxazol-2-yl)-3,8-diazabicyclo[3.2.1]octane-8-carboxylate obtained in Example 118 (a), trifluoromethyltrimethylsilane (51 μL, 4 equivalents), and 1.0M tetrabutylammonium fluoride solution in tetrahydrofuran (17.2 μL, 0.2 equivalent) were dissolved in tetrahydrofuran (860 μL), and stirred them for 2 hours at 0° C. After confirming a reaction product by TLC (eluent, hexane:ethyl acetate=1:1), 2M methanolic hydrochloric acid was added and stirred them for 30 min at room temperature. After stirring, saturated aqueous sodium bicarbonate solution was added and organic phase was extracted by ethyl acetate. A filtrate was obtained by drying the extracted organic phase by anhydrous magnesium sulfate and filtering them. The title compound was obtained in an amount of 21 mg by silica gel column chromatography purification (hexane-hexane:ethyl acetate=1:1) of residue obtained by vacuum concentration of the filtrate.

(c) tert-Butyl 3-(7-(thiazol-2-yl)-4-(2,2,2-trifluoro-1-hydroxyethyl)benzo[d]oxazol-2-yl)-3,8-diazabicyclo[3.2.1]octane-8-carboxylate (Optically Active)

157 mg of racemic tert-butyl 3-(7-(thiazol-2-yl)-4-(2,2,2-trifluoro-1-hydroxyethyl)benzo[d]oxazol-2-yl)-3,8-diazabicyclo[3.2.1]octane-8-carboxylate obtained in Example 118 (b) was purified by a preparative HPLC (Gilson, column: DAICEL CHIRALPAK IA (particle diameter: 5 μm, column diameter: 2 cm, column length: 25 cm), eluent, hexane:isopropyl alcohol=95:5-80:20, flow rate: 15 mL/min, detection: UV254 nm) and the title compound was obtained in an amount of 72 mg by concentrating fractions with the shorter retention time peak. 96% ee. Analysis conditions: HPLC (HITACHI, column: DAICEL CHIRALPAK IA (particle diameter: 5 μm, column diameter: 0.46 cm, column length: 25 cm), eluent, hexane:isopropyl alcohol=90:10, flow rate: 1 mL/min, detection: UV254 nm, temperature: 25° C., retention time: 11.7 min).

(d) 1-(2-(3,8-Diazabicyclo[3.2.1]octan-3-yl)-7-(thiazol-2-yl)benzo[d]oxazol-4-yl)-2,2,2-trifluoroethan-1-ol (Optically Active)

The title compound was obtained in an amount of 49 mg from 72 mg of tert-butyl 3-(7-(thiazol-2-yl)-4-(2,2,2-trifluoro-1-hydroxyethyl)benzo[d]oxazol-2-yl)-3,8-diazabicyclo[3.2.1]octane-8-carboxylate (optically active) obtained in Example 118 (b) by a similar method to Example 1(c). 95% ee. Analysis conditions: HPLC (HITACHI, column: DAICEL CHIRALPAK ID (particle diameter: 5 μm, column diameter: 0.46 cm, column length: 25 cm), eluent, hexane:isopropyl alcohol:diethylamine=80:20:0.1, flow rate: 1 mL/min, detection: UV254 nm, temperature: 25° C., retention time: 12.0 min).

Example 119

1-(2-(3,8-Diazabicyclo[3.2.1]octan-3-yl)-7-(thiazol-2-yl)benzo[d]oxazol-4-yl)-2,2,2-trifluoroethan-1-ol (Optically Active, Enantiomer of Example 118)

(a) tert-Butyl 3-(7-(thiazol-2-yl)-4-(2,2,2-trifluoro-1-hydroxyethyl)benzo[d]oxazol-2-yl)-3,8-diazabicyclo[3.2.1]octane-8-carboxylate (Optically Active, Enantiomer of Example 118 (c))

157 mg of racemic tert-butyl 3-(7-(thiazol-2-yl)-4-(2,2,2-trifluoro-1-hydroxyethyl)benzo[d]oxazol-2-yl)-3,8-diazabicyclo[3.2.1]octane-8-carboxylate obtained in Example 118 (b) was purified by a preparative HPLC (Gilson, column: DAICEL CHIRALPAK IA (particle diameter: 5 μm, column diameter: 2 cm, column length: 25 cm), eluent, hexane:isopropyl alcohol=95:5-80:20, flow rate: 15 mL/min, detection: UV254 nm) and the title compound was obtained in an amount of 70 mg by concentrating fractions with the longer retention time peak. 98% ee. Analysis conditions: HPLC (HITACHI, column: DAICEL CHIRALPAK IA (particle diameter: 5 μm, column diameter: 2 cm, column length: 25 cm), eluent, hexane:isopropyl alcohol=90:10, flow rate: 1 mL/min, detection: UV254 nm, temperature: 25° C., retention time: 15.5 min).

(b) 1-(2-(3,8-Diazabicyclo[3.2.1]octan-3-yl)-7-(thiazol-2-yl)benzo[d]oxazol-4-yl)-2,2,2-trifluoroethan-1-ol (Optically Active, Enantiomer of Example 118)

The title compound was obtained in an amount of 50 mg from 70 mg of tert-butyl 3-(7-(thiazol-2-yl)-4-(2,2,2-trifluoro-1-hydroxyethyl)benzo[d]oxazol-2-yl)-3,8-diazabicyclo[3.2.1]octane-8-carboxylate (Optically Active, Enantiomer of Example 118) obtained in Example 119(a) by a similar method to Example 1(c). 98% ee. Analysis conditions: HPLC (HITACHI, column: DAICEL CHIRALPAK IA (particle diameter: 5 µm, column diameter: 2 cm, column length: 25 cm), eluent, hexane:isopropyl alcohol:diethylamine=80:20:0.1, flow rate: 1 mL/min, detection: UV254 nm, temperature: 25° C., retention time: 13.8 min).

Example 120

1-(2-(3,6-Diazabicyclo[3.1.1]heptan-3-yl)-7-(thiazol-2-yl)benzo[d]oxazol-4-yl)-2,2,2-trifluoroethan-1-ol (Optically Active)

(a) tert-Butyl 3-(4-formyl-7-(thiazol-2-yl)benzo[d]oxazol-2-yl)-3,6-diazabicyclo[3.1.1]heptane-6-carboxylate The title compound was obtained in an amount of 323 mg from 440 mg of ethyl 2-(6-(tert-butoxycarbonyl)-3,6-diazabicyclo[3.1.1]heptan-3-yl)-7-(thiazol-2-yl)benzo[d]oxazol-4-carboxylate obtained in Example 113(b) by a similar method to Example 102 (a).

(b) tert-Butyl 3-(7-(thiazol-2-yl)-4-(2,2,2-trifluoro-1-hydroxyethyl)benzo[d]oxazol-2-yl)-3,6-diazabicyclo[3.1.1]heptane-6-carboxylate (racemic)

100 mg of tert-Butyl 3-(4-formyl-7-(thiazol-2-yl)benzo[d]oxazol-2-yl)-3,6-diazabicyclo[3.1.1]heptane-6-carboxylate obtained in Example 120(a), (trifluoromethyl)trimethylsilane (140 µL, 4 equivalents), and caesium fluoride (3.6 mg, 0.1 equivalent) were dissolved in tetrahydrofuran (2.3 mL), and stirred them for 30 min at 0° C. After confirming a reaction product by TLC (eluent, hexane:ethyl acetate=1:1), 2M methanolic hydrochloric acid was added and stirred them for 2 hours at room temperature. After stirring, saturated aqueous sodium bicarbonate solution was added and organic phase was extracted by ethyl acetate. A filtrate was obtained by drying the extracted organic phase by anhydrous magnesium sulfate and filtering them. The title compound was obtained in an amount of 70 mg by silica gel column chromatography purification (hexane-hexane:ethyl acetate=7:3) of residue obtained by vacuum concentration of the filtrate.

(c) tert-Butyl 3-(7-(thiazol-2-yl)-4-(2,2,2-trifluoro-1-hydroxyethyl)benzo[d]oxazol-2-yl)-3,6-diazabicyclo[3.1.1]heptane-6-carboxylate (Optically Active)

145 mg of racemic tert-butyl 3-(7-(thiazol-2-yl)-4-(2,2,2-trifluoro-1-hydroxyethyl)benzo[d]oxazol-2-yl)-3,6-diazabicyclo[3.1.1]heptane-6-carboxylate obtained in Example 120 (b) was purified by a preparative HPLC (Gilson, column: DAICEL CHIRALPAK IA (particle diameter: 5 µm, column diameter: 2 cm, column length: 25 cm), eluent, hexane:isopropyl alcohol=95:5-80:20, flow rate: 15 mL/min, detection: UV254 nm) and the title compound was obtained in an amount of 63 mg by concentrating fractions with the shorter retention time peak. 98% ee. Analysis conditions: HPLC (HITACHI, column: DAICEL CHIRALPAK IA (particle diameter: 5 µm, column diameter: 0.46 cm, column length: 25 cm), eluent, hexane:isopropyl alcohol=90:10, flow rate: 1 mL/min, detection: UV254 nm, temperature: 25° C., retention time: 23.1 min).

(d) 1-(2-(3,6-Diazabicyclo[3.1.1]heptan-3-yl)-7-(thiazol-2-yl)benzo[d]oxazol-4-yl)-2,2,2-trifluoroethan-1-ol (Optically Active)

The title compound was obtained in an amount of 28 mg from 40 mg of tert-butyl 3-(7-(thiazol-2-yl)-4-(2,2,2-trifluoro-1-hydroxyethyl)benzo[d]oxazol-2-yl)-3,6-diazabicyclo[3.1.1]heptane-6-carboxylate (optically active) obtained in Example 120(c) by a similar method to Example 1(c). 99% ee. Analysis conditions: HPLC (HITACHI, column: DAICEL CHIRALPAK IC (particle diameter: 5 µm, column diameter: 0.46 cm, column length: 25 cm), eluent, hexane:isopropyl alcohol:diethylamine=70:30:0.1, flow rate: 1 mL/min, detection: UV254 nm, temperature: 25° C., retention time: 19.0 min).

Example 121

1-(2-(3,6-Diazabicyclo[3.1.1]heptan-3-yl)-7-(thiazol-2-yl)benzo[d]oxazol-4-yl)-2,2,2-trifluoroethan-1-ol (Optically Active, Enantiomer of Example 120)

(a) tert-Butyl 3-(7-(thiazol-2-yl)-4-(2,2,2-trifluoro-1-hydroxyethyl)benzo[d]oxazol-2-yl)-3,6-diazabicyclo[3.1.1]heptane-6-carboxylate (Optically Active, Enantiomer of Example 120(c))

145 mg of racemic tert-butyl 3-(7-(thiazol-2-yl)-4-(2,2,2-trifluoro-1-hydroxyethyl)benzo[d]oxazol-2-yl)-3,6-diazabicyclo[3.1.1]heptane-6-carboxylate obtained in Example 120 (b) was purified by a preparative HPLC (Gilson, column: DAICEL CHIRALPAK IA (particle diameter: 5 µm, column diameter: 2 cm, column length: 25 cm), eluent, hexane:isopropyl alcohol=95:5-80:20, flow rate: 15 mL/min, detection: UV254 nm) and the title compound was obtained in an amount of 64 mg by concentrating fractions with the longer retention time peak. 98% ee. Analysis conditions: HPLC (HITACHI, column: DAICEL CHIRALPAK IA (particle diameter: 5 µm, column diameter: 0.46 cm, column length: 25 cm), eluent, hexane:isopropyl alcohol=90:10, flow rate: 1 mL/min, detection: UV254 nm, temperature: 25° C., retention time: 28.6 min).

(b) 1-(2-(3,6-Diazabicyclo[3.1.1]heptan-3-yl)-7-(thiazol-2-yl)benzo[d]oxazol-4-yl)-2,2,2-trifluoroethan-1-ol (Optically Active, Enantiomer of Example 120)

The title compound was obtained in an amount of 27 mg from 40 mg of tert-butyl 3-(7-(thiazol-2-yl)-4-(2,2,2-trifluoro-1-hydroxyethyl)benzo[d]oxazol-2-yl)-3,6-diazabicyclo[3.1.1]heptane-6-carboxylate (Optically Active, Enantiomer of Example 120(c)) obtained in Example 121(a) by a similar method to Example 1(c). 97% ee. Analysis conditions: HPLC (HITACHI, column: DAICEL CHIRALPAK IC (particle diameter: 5 µm, column diameter: 0.46 cm, column length: 25 cm), eluent, hexane:isopropyl alcohol:

diethylamine=70:30:0.1, flow rate: 1 mL/min, detection: UV254 nm, temperature: 25° C., retention time: 23.8 min).

Example 122

2-(3,6-Diazabicyclo[3.1.1]heptan-3-yl)-7-(thiazol-2-yl)-4-(2,2,2-trifluoro-1-methoxyethyl)benzo[d]oxazole (Optically Active)

(a) tert-Butyl 3-(7-(thiazol-2-yl)-4-(2,2,2-trifluoro-1-methoxyethyl)benzo[d]oxazol-2-yl)-3,6-diazabicyclo [3.1.1]heptane-6-carboxylate (Optically Active)

The title compound was obtained in an amount of 16 mg from 19 mg of optically active tert-butyl 3-(7-(thiazol-2-yl)-4-(2,2,2-trifluoro-1-hydroxyethyl)benzo[d]oxazol-2-yl)-3,6-diazabicyclo[3.1.1]heptane-6-carboxylate obtained in Example 120(c) by a similar method to Example 102 (e).

(b) 2-(3,6-Diazabicyclo[3.1.1]heptan-3-yl)-7-(thiazol-2-yl)-4-(2,2,2-trifluoro-1-methoxyethyl)benzo [d]oxazole (Optically Active)

The title compound was obtained in an amount of 12 mg from 16 mg of tert-butyl 3-(7-(thiazol-2-yl)-4-(2,2,2-trifluoro-1-methoxyethyl)benzo[d]oxazol-2-yl)-3,6-diazabicyclo[3.1.1]heptane-6-carboxylate (optically active) obtained in Example 122 (a) by a similar method to Example 1(c). 99% ee. Analysis conditions: HPLC (HITACHI, column: DAICEL CHIRALPAK ID (particle diameter: 5 μm, column diameter: 0.46 cm, column length: 25 cm), eluent, hexane:isopropyl alcohol:diethylamine=70:30:0.1, flow rate: 1 mL/min, detection: UV254 nm, temperature: 25° C., retention time: 9.6 min).

Example 123

2-(3,6-Diazabicyclo[3.1.1]heptan-3-yl)-7-(thiazol-2-yl)-4-(2,2,2-trifluoro-1-methoxyethyl)benzo[d]oxazole (Optically Active, Enantiomer of Example 122)

(a) tert-Butyl 3-(7-(thiazol-2-yl)-4-(2,2,2-trifluoro-1-methoxyethyl)benzo[d]oxazol-2-yl)-3,6-diazabicyclo [3.1.1]heptane-6-carboxylate (Optically Active, Enantiomer of Example 122(a))

The title compound was obtained in an amount of 17 mg from 19 mg of tert-butyl 3-(7-(thiazol-2-yl)-4-(2,2,2-trifluoro-1-hydroxyethyl)benzo[d]oxazol-2-yl)-3,6-diazabicyclo[3.1.1]heptane-6-carboxylate (Optically Active, Enantiomer of Example 120(c)) obtained in Example 121(a) by a similar method to Example 102 (e).

(b) 2-(3,6-Diazabicyclo[3.1.1]heptan-3-yl)-7-(thiazol-2-yl)-4-(2,2,2-trifluoro-1-methoxyethyl)benzo [d]oxazole (Optically Active, Enantiomer of Example 122)

The title compound was obtained in an amount of 13 mg from 17 mg of tert-butyl 3-(7-(thiazol-2-yl)-4-(2,2,2-trifluoro-1-methoxyethyl)benzo[d]oxazol-2-yl)-3,6-diazabicyclo[3.1.1]heptane-6-carboxylate (Optically Active, Enantiomer of Example 122 (a)) obtained in Example 123(a) by a similar method to Example 1(c). 98% ee. Analysis conditions: HPLC (HITACHI, column: DAICEL CHIRALPAK ID (particle diameter: 5 μm, column diameter: 0.46 cm, column length: 25 cm), eluent, hexane:isopropyl alcohol:diethylamine=70:30:0.1, flow rate: 1 mL/min, detection: UV254 nm, temperature: 25° C., retention time: 11.6 min).

Example 124

1-(2-(3,8-Diazabicyclo[3.2.1]octan-3-yl)-7-(thiazol-2-yl)benzo[d]oxazol-4-yl)ethan-1-ol 41 mg of tert-butyl 3-(4-formyl-7-(thiazol-2-yl)benzo[d]oxazol-2-yl)-3,8-diazabicyclo[3.2.1]octane-8-carboxylate obtained in Example 118 (a) was dissolved in tetrahydrofuran (924 μL). 0.92M Methylmagnesium bromide solution in tetrahydrofuran (0.2 mL, 2 equivalents) was added at −78° C. and stirred for 2 hours. After confirming a reaction product by TLC (eluent, hexane:ethyl acetate=1:1), saturated aqueous sodium bicarbonate solution was added and organic phase was extracted by ethyl acetate. A crude product was obtained by drying the extracted organic phase by anhydrous magnesium sulfate and filtering them. The title compound was obtained in an amount of 20 mg from the crude product by a similar method to Example 1(c).

Example 125

1-(2-(3,6-Diazabicyclo[3.1.1]heptan-3-yl)-7-(thiazol-2-yl)benzo[d]oxazol-4-yl)-2,2-difluoroethan-1-ol (a) tert-Butyl 3-(4-(2,2-difluoro-1-hyroxyethyl)-7-(thiazol-2-yl)benzo[d]oxazol-2-yl)-3,6-diazabicyclo [3.1.1]heptane-6-carboxylate The title compound was obtained as a crude product from 10 mg of tert-butyl 3-(4-formyl-7-(thiazol-2-yl)benzo[d]oxazol-2-yl)-3,6-diazabicyclo[3.1.1]heptane-6-carboxylate obtained in Example 120(a) by a similar method to Example 104(a) except that tetrahydrofuran was used instead of N,N-dimethylformamide and potassium tert-butoxide was used instead of caesium fluoride.

(b) 1-(2-(3,6-Diazabicyclo[3.1.1]heptan-3-yl)-7-(thiazol-2-yl)benzo[d]oxazol-4-yl)-2,2-difluoroethan-1-ol The title compound was obtained in an amount of 1.4 mg from tert-butyl 3-(4-(2,2-difluoro-1-hyroxyethyl)-7-(thiazol-2-yl)benzo[d]oxazol-2-yl)-3,6-diazabicyclo[3.1.1]heptane-6-carboxylate obtained in Example 125 (a) by a similar method to Example 1(c).

Example 126

2-(2-(3,6-Diazabicyclo[3.1.1]heptan-3-yl)-7-(thiazol-2-yl)benzo[d]oxazol-4-yl)-1,1-difluoropropan-2-ol (a) tert-Butyl 3-(4-(2,2-difluoroacetyl)-7-(thiazol-2-yl)benzo[d]oxazol-2-yl)-3,6-diazabicyclo[3.1.1]heptane-6-carboxylate 48 mg of tert-butyl 3-(4-(2,2-difluoro-1-hydroxyethyl)-7-(thiazol-2-yl)benzo[d]oxazol-2-yl)-3,6-diazabicyclo[3.1.1] heptane-6-carboxylate obtained in Example 125(a) and Dess-Martin Periodinane (127 mg, 3 equivalents) were dissolved in dichloromethane (1.0 mL), and stirred them for 1 hour at 0° C. After confirming a reaction product by TLC (eluent, hexane:ethyl acetate=1:1), saturated aqueous sodium bicarbonate solution and saturated aqueous sodium thiosulfate were added and organic phase was extracted by ethyl acetate. A filtrate was obtained by drying the extracted organic phase by anhydrous magnesium sulfate and filtering them. The title compound was obtained in an amount of 32 mg by silica gel column chromatography purification (hexane-hexane:ethyl acetate=4:6) of residue obtained by vacuum concentration of the filtrate.

(b) tert-Butyl 3-(4-(1,1-difluoro-2-hydroxypropan-2-yl)-7-(thiazol-2-yl)benzo[d]oxazol-2-yl)-3,6-diazabicyclo[3.1.1]heptane-6-carboxylate 32 mg of tert-butyl 3-(4-(2,2-difluoroacetyl)-7-(thiazol-2-yl)benzo[d]oxazol-2-yl)-3,6-diazabicyclo[3.1.1]heptane-6-carboxylate obtained in Example 126(a) was dissolved in tetrahydrofuran (700 μL). 0.98M Methylmagnesium bromide solution in tetrahydrofuran (0.68 mL, 10 equivalents) was added at −78° C. and stirred them for 1 hour at room temperature. After confirming a reaction product by TLC, saturated ammonium chloride aqueous solution was added and organic phase was extracted by ethyl acetate. A filtrate was obtained by drying the extracted organic phase by anhydrous magnesium sulfate and filtering them. The title compound was obtained in an amount of 22 mg by preparative TLC (hexane-hexane:ethyl acetate=1:1) of residue obtained by vacuum concentration of the filtrate.

(c) 2-(2-(3,6-Diazabicyclo[3.1.1]heptan-3-yl)-7-(thiazol-2-yl)benzo[d]oxazol-4-yl)-1,1-difluoropropan-2-ol The title compound was obtained in an amount of 22 mg from 25 mg of tert-butyl 3-(4-(1,1-difluoro-2-hydroxypropan-2-yl)-7-(thiazol-2-yl)benzo[d]oxazol-2-yl)-3,6-diazabicyclo[3.1.1]heptane-6-carboxylate obtained in Example 126 (b) by a similar method to Example 1(c).

Example 127

1-(1-(2-(3,6-Diazabicyclo[3.1.1]heptan-3-yl)-7-(thiazol-2-yl)benzo[d]oxazol-4-yl)-2,2-difluoroethoxy)-2-methylpropan-2-ol (a) tert-Butyl 3-(4-(1-(2-(tert-butoxy)-2-oxoethoxy)-2,2-difluoroethyl-7-(thiazol-2-yl)benzo[d]oxazol-2-yl)-3,6-diazabicyclo[3.1.1]heptane-6-carboxylate 9.6 mg of tert-butyl 3-(4-(2,2-difluoro-1-hydroxyethyl)-7-(thiazol-2-yl)benzo[d]oxazol-2-yl)-3,6-diazabicyclo[3.1.1]heptane-6-carboxylate obtained in Example 125 (a), tetrabutylammonium chloride (0.6 mg, 0.1 equivalent), 35% sodium hydroxide aquious solution (75 μL), and tert-butyl bromoacetate (4.4 μL, 1.5 equivalents) were dissolved in dichloromethane (70 μL), and stirred them for 15 hours at room temperature. After confirming a reaction product by TLC, saturated ammonium chloride aqueous solution was added and organic phase was extracted by ethyl acetate. A filtrate was obtained by drying the extracted organic phase by anhydrous magnesium sulfate and filtering them. The title compound was obtained in an amount of 11 mg by preparative TLC (eluent, hexane:ethyl acetate=1:1) of residue obtained by vacuum concentration of the filtrate.

(b) tert-Butyl 3-(4-(2,2-difluoro-1-(2-hydroxy-2-methylpropoxy)ethyl)-7-(thiazol-2-yl)benzo[d]oxazol-2-yl)-3,6-diazabicyclo[3.1.1]heptane-6-carboxylate 10 mg of tert-butyl 3-(4-(1-(2-(tert-butoxy)-2-oxoethoxy)-2,2-difluoroethyl-7-(thiazol-2-yl)benzo[d]oxazol-2-yl)-3,6-diazabicyclo[3.1.1]heptane-6-carboxylate obtained in Example 127 (a) was dissolved in tetrahydrofuran (170 μL). 0.98M Methylmagnesium bromide solution in tetrahydrofuran (17.3 μL, 10 equivalents) was added at 0° C. and stirred them for 2 hours at room temperature. After confirming a reaction product by TLC, saturated ammonium chloride aqueous solution was added and organic phase was extracted by ethyl acetate. A filtrate was obtained by drying the extracted organic phase by anhydrous magnesium sulfate and filtering them. The title compound was obtained in an amount of 8 mg by preparative TLC (eluent, hexane:ethyl acetate=1:2) of residue obtained by vacuum concentration of the filtrate.

(c) 1-(1-(2-(3,6-Diazabicyclo[3.1.1]heptan-3-yl)-7-(thiazol-2-yl)benzo[d]oxazol-4-yl)-2,2-difluoroethoxy)-2-methylpropan-2-ol The title compound was obtained in an amount of 5 mg from 8 mg of tert-butyl 3-(4-(2,2-difluoro-1-(2-hydroxy-2-methylpropoxy)ethyl)-7-(thiazol-2-yl)benzo[d]oxazol-2-yl)-3,6-diazabicyclo[3.1.1]heptane-6-carboxylate obtained in Example 127 (b) by a similar method to Example 1(c).

Example 128

1-(2-(3,8-Diazabicyclo[3.2.1]octan-3-yl)-7-(thiazol-2-yl)benzo[d]oxazol-4-yl)-2,2-difluoroethan-1-ol (a) tert-Butyl 3-(4-(2,2-difluoro-1-hydroxyethyl)-7-(thiazol-2-yl)benzo[d]oxazol-2-yl)-3,8-diazabicyclo[3.2.1]octane-8-carboxylate The title compound was obtained in an amount of 15 mg from 44 mg of tert-butyl 3-(4-formyl-7-(thiazol-2-yl)benzo[d]oxazol-2-yl)-3,8-diazabicyclo[3.2.1]octane-8-carboxylate obtained in Example 118(a) by a similar method to Example 104(a) except that 0.2 equivalent of caesium fluoride was used.

(b) 1-(2-(3,8-Diazabicyclo[3.2.1]octan-3-yl)-7-(thiazol-2-yl)benzo[d]oxazol-4-yl)-2,2-difluoroethan-1-ol The title compound was obtained in an amount of 3.4 mg from 7 mg of tert-butyl 3-(4-(2,2-difluoro-1-hydroxyethyl)-7-(thiazol-2-yl)benzo[d]oxazol-2-yl)-3,8-diazabicyclo[3.2.1]octane-8-carboxylate obtained in Example 128 (a) by a similar method to Example 1(c).

Example 129

2-(2-(3,8-Diazabicyclo[3.2.1]octan-3-yl)-7-(thiazol-2-yl)benzo[d]oxazol-4-yl)-1,1-difluoropropan-2-ol (a) tert-Butyl 3-(4-(2,2-difluoroacetyl)-7-(thiazol-2-yl)benzo[d]oxazol-2-yl)-3,8-diazabicyclo[3.2.1]octane-8-carboxylate The title compound was obtained in an amount of 59 mg from 49 mg tert-butyl 3-(4-(2,2-difluoro-1-hydroxyethyl)-7-

(thiazol-2-yl)benzo[d]oxazol-2-yl)-3,8-diazabicyclo[3.2.1]octane-8-carboxylate obtained in Example 128 (a) by a similar method to Example 126(a).

(b) tert-Butyl 3-(4-(1,1-difluoro-2-hydroxypropan-2-yl)-7-(thiazol-2-yl)benzo[d]oxazol-2-yl)-3,8-diazabicyclo[3.2.1]octane-8-carboxylate The title compound was obtained in an amount of 44 mg from 58 mg of tert-butyl 3-(4-(2,2-difluoroacetyl)-7-(thiazol-2-yl)benzo[d]oxazol-2-yl)-3,8-diazabicyclo[3.2.1]octane-8-carboxylate obtained in Example 129(a) by a similar method to Example 126 (b).

(c) 2-(2-(3,8-Diazabicyclo[3.2.1]octan-3-yl)-7-(thiazol-2-yl)benzo[d]oxazol-4-yl)-1,1-difluoropropan-2-ol The title compound was obtained in an amount of 29 mg from 43 mg of tert-butyl 3-(4-(1,1-difluoro-2-hydroxypropan-2-yl)-7-(thiazol-2-yl)benzo[d]oxazol-2-yl)-3,8-diazabicyclo[3.2.1]octane-8-carboxylate obtained in Example 129 (b) by a similar method to Example 1(c).

Example 130

2-(3,6-Diazabicyclo[3.1.1]heptan-3-yl)-4-(2,2-difluoro-1-methoxyethyl)-7-(thiazol-2-yl)benzo[d]oxazole (a) tert-Butyl 3-(4-(2,2-difluoro-1-methoxyethyl)-7-(thiazol-2-yl)benzo[d]oxazol-2-yl)-3,6-diazabicyclo[3.1.1]heptane-6-carboxylate The title compound was obtained as a crude product from 7.5 mg of tert-butyl 3-(4-(2,2-difluoro-1-hyroxyethyl)-7-(thiazol-2-yl)benzo[d]oxazol-2-yl)-3,6-diazabicyclo[3.1.1]heptane-6-carboxylate obtained in Example 125 (a) by a similar method to Example 102 (e).

(b) 2-(3,6-Diazabicyclo[3.1.1]heptan-3-yl)-4-(2,2-difluoro-1-methoxyethyl)-7-(thiazol-2-yl)benzo[d]oxazole The title compound was obtained in an amount of 2.9 mg from the crude product of tert-butyl 3-(4-(2,2-difluoro-1-methoxyethyl)-7-(thiazol-2-yl)benzo[d]oxazol-2-yl)-3,6-diazabicyclo[3.1.1]heptane-6-carboxylate obtained in Example 130(a) by a similar method to Example 1(c).

Example 131

2-(3,8-Diazabicyclo[3.2.1]octan-3-yl)-4-(2,2-difluoro-1-methoxyethyl)-7-(thiazol-2-yl)benzo[d]oxazole (a) tert-Butyl 3-(4-(2,2-difluoro-1-methoxyethyl)-7-(thiazol-2-yl)benzo[d]oxazol-2-yl)-3,8-diazabicyclo[3.2.1]octane-8-carboxylate The title compound was obtained in an amount of 5.2 mg from 7 mg of tert-butyl 3-(4-(2,2-difluoro-1-hydroxyethyl)-7-(thiazol-2-yl)benzo[d]oxazol-2-yl)-3,8-diazabicyclo[3.2.1]octane-8-carboxylate obtained in Example 128 (a) by a similar method to Example 102 (e).

(b) 2-(3,8-Diazabicyclo[3.2.1]octan-3-yl)-4-(2,2-difluoro-1-methoxyethyl)-7-(thiazol-2-yl)benzo[d]oxazole The title compound was obtained in an amount of 3.9 mg from tert-butyl 3-(4-(2,2-difluoro-1-methoxyethyl)-7-(thiazol-2-yl)benzo[d]oxazol-2-yl)-3,8-diazabicyclo[3.2.1]octane-8-carboxylate obtained in Example 131(a) by a similar method to Example 1(c).

Example 132

(2-(3,8-Diazabicyclo[3.2.1]octan-3-yl)-7-(thiazol-2-yl)benzo[d]oxazol-4-yl)methanol (a) tert-Butyl 3-(7-bromo-4-(hydroxymethyl)benzo[d]oxazol-2-yl)-3,8-diazabicyclo[3.2.1]octane-8-carboxylate The title compound was obtained in an amount of 100 mg from 100 mg of (7-bromo-2-mercaptobenzo[d]oxazol-4-yl)methanol obtained in Reference Example 17 and tert-butyl 3,8-diazabicyclo[3.2.1]octane-8-carboxylate by a similar method to Example 1(a).

(b) tert-Butyl 3-(4-(hydroxymethyl)-7-(thiazol-2-yl)benzo[d]oxazol-2-yl)-3,8-diazabicyclo[3.2.1]octane-8-carboxylate The title compound was obtained as a crude product in an amount of 60 mg from 120 mg of tert-butyl 3-(7-bromo-4-(hydroxymethyl)benzo[d]oxazol-2-yl)-3,8-diazabicyclo[3.2.1]octane-8-carboxylate obtained in Example 132(a) by a similar method to Example 2(b) except that toluene was used instead of 1,4-dioxane and tetrakis(triphenylphosphine)palladium(0) was used instead of bis(triphenylphosphine)palladium(II) dichloride.

(c) (2-(3,8-Diazabicyclo[3.2.1]octan-3-yl)-7-(thiazol-2-yl)benzo[d]oxazol-4-yl)methanol The title compound was obtained in an amount of 30 mg from 78 mg of tert-butyl 3-(4-(hydroxymethyl)-7-(thiazol-2-yl)benzo[d]oxazol-2-yl)-3,8-diazabicyclo[3.2.1]octane-8-carboxylate obtained in Example 132 (b) by a similar method to Example 1(c).

Example 133

(2-(3,6-Diazabicyclo[3.1.1]heptan-3-yl)-7-(thiazol-2-yl)benzo[d]oxazol-4-yl)methanol (a) tert-Butyl 3-(7-bromo-4-(hydroxymethyl)benzo[d]oxazol-2-yl)-3,6-diazabicyclo[3.1.1]heptane-6-carboxylate The title compound was obtained in an amount of 50 mg from 50 mg of (7-bromo-2-mercaptobenzo[d]oxazol-4-yl)methanol obtained in Reference Example 17 by a similar method to Example 1(a) except that tert-butyl 3,6-diazabicyclo[3.1.1]heptane-6-carboxylate was used instead of tert-butyl 3,8-diazabicyclo[3.2.1]octane-8-carboxylate.

(b) tert-Butyl 3-(4-(hydroxymethyl)-7-(thiazol-2-yl)benzo[d]oxazol-2-yl)-3,6-diazabicyclo[3.1.1]heptane-6-carboxylate The title compound was obtained in an amount of 60 mg from 90 mg of tert-butyl 3-(7-bromo-4-(hydroxymethyl)

benzo[d]oxazol-2-yl)-3,6-diazabicyclo[3.1.1]heptane-6-carboxylate obtained in Example 133(a) by a similar method to Example 2(b) except that tetrakis(triphenylphosphine)palladium(0) was used instead of bis(triphenylphosphine)palladium(II) dichloride.

(c) (2-(3,6-Diazabicyclo[3.1.1]heptan-3-yl)-7-(thiazol-2-yl)benzo[d]oxazol-4-yl)methanol The title compound was obtained in an amount of 20 mg from 60 mg of tert-butyl 3-(4-(hydroxymethyl)-7-(thiazol-2-yl)benzo[d]oxazol-2-yl)-3,6-diazabicyclo[3.1.1]heptane-6-carboxylate obtained in Example 133 (b) by a similar method to Example 1(c).

Example 134

(2-(3,9-Diazabicyclo[3.3.1]nonan-3-yl)-7-(thiazol-2-yl)benzo[d]oxazol-4-yl)methanol (a) tert-Butyl 3-(7-bromo-4-(hydroxymethyl)benzo[d]oxazol-2-yl)-3,9-diazabicyclo[3.3.1]nonane-9-carboxylate The title compound was obtained in an amount of 80 mg from 80 mg of (7-bromo-2-mercaptobenzo[d]oxazol-4-yl)methanol obtained in Reference Example 17 by a similar method to Example 1(a) except that tert-butyl 3,9-diazabicyclo[3.3.1]nonane-9-carboxylate was used instead of tert-butyl 3,8-diazabicyclo[3.2.1]octane-8-carboxylate.

(b) tert-Butyl 3-(4-(hydroxymethyl)-7-(thiazol-2-yl)benzo[d]oxazol-2-yl)-3,9-diazabicyclo[3.3.1]nonane-9-carboxylate The title compound was obtained in an amount of 100 mg from 110 mg of tert-butyl 3-(7-bromo-4-(hydroxymethyl)benzo[d]oxazol-2-yl)-3,9-diazabicyclo[3.3.1]nonane-9-carboxylate obtained in Example 134 (a) by a similar method to Example 2 (b) except that toluene was used instead of 1,4-dioxane and tetrakis(triphenylphosphine)palladium(0) was used instead of bis(triphenylphosphine)palladium(II) dichloride.

(c) (2-(3,9-Diazabicyclo[3.3.1]nonan-3-yl)-7-(thiazol-2-yl)benzo[d]oxazol-4-yl)methanol The title compound was obtained in an amount of 45 mg from 100 mg of tert-butyl 3-(4-(hydroxymethyl)-7-(thiazol-2-yl)benzo[d]oxazol-2-yl)-3,9-diazabicyclo[3.3.1]nonane-9-carboxylate obtained in Example 134 (b) by a similar method to Example 1(c).

Example 135

1-(2-(3,6-Diazabicyclo[3.1.1]heptan-3-yl)-7-(thiazol-2-yl)benzo[d]oxazol-5-yl)-2,2,2-trifluoroethan-1-ol (a) tert-Butyl 3-(7-bromo-5-(2,2,2-trifluoro-1-hydroxyethyl)benzo[d]oxazol-2-yl)-3,6-diazabicyclo[3.1.1]heptane-6-carboxylate The title compound was obtained in an amount of 504 mg from 400 mg of 1-(7-Bromo-2-mercaptobenzo[d]oxazol-5-yl)-2,2,2-trifluoroethan-1-ol obtained in Reference Example 18 by a similar method to Example 1(a) except that tert-butyl 3,6-diazabicyclo[3.1.1]heptane-6-carboxylate was used instead of tert-butyl 3,8-diazabicyclo[3.2.1]octane-8-carboxylate.

(b) tert-Butyl 3-(7-(thiazol-2-yl)-5-(2,2,2-trifluoro-1-hydroxyethyl)benzo[d]oxazol-2-yl)-3,6-diazabicyclo[3.1.1]heptane-6-carboxylate The title compound was obtained in an amount of 144 mg from 300 mg of tert-butyl 3-(7-bromo-5-(2,2,2-trifluoro-1-hydroxyethyl)benzo[d]oxazol-2-yl)-3,6-diazabicyclo[3.1.1]heptane-6-carboxylate obtained in Example 135 (a) by a similar method to Example 1(b).

(c) 1-(2-(3,6-Diazabicyclo[3.1.1]heptan-3-yl)-7-(thiazol-2-yl)benzo[d]oxazol-5-yl)-2,2,2-trifluoroethan-1-ol The title compound was obtained in an amount of 50 mg from 190 mg of tert-butyl 3-(7-(thiazol-2-yl)-5-(2,2,2-trifluoro-1-hydroxyethyl)benzo[d]oxazol-2-yl)-3,6-diazabicyclo[3.1.1]heptane-6-carboxylate obtained in Example 135 (b) by a similar method to Example 1(c).

Example 136

1-(2-(3,9-Diazabicyclo[3.3.1]nonan-3-yl)-7-(thiazol-2-yl)benzo[d]oxazol-5-yl)-2,2,2-trifluoroethan-1-ol (a) tert-Butyl 3-(7-bromo-5-(2,2,2-trifluoro-1-hydroxyethyl)benzo[d]oxazol-2-yl)-3,9-diazabicyclo[3.3.1]nonane-9-carboxylate The title compound was obtained in an amount of 608 mg from 400 mg of 1-(7-bromo-2-mercaptobenzo[d]oxazol-5-yl)-2,2,2-trifluoroethan-1-ol obtained in Reference Example 18 by a similar method to Example 1(a) except that tert-butyl 3,9-diazabicyclo[3.3.1]nonane-9-carboxylate was used instead of tert-butyl 3,8-diazabicyclo[3.2.1]octane-8-carboxylate.

(b) tert-Butyl 3-(7-(thiazol-2-yl)-5-(2,2,2-trifluoro-1-hydroxyethyl)benzo[d]oxazol-2-yl)-3,9-diazabicyclo[3.3.1]nonane-9-carboxylate The title compound was obtained in an amount of 244 mg from 300 mg of tert-butyl 3-(7-bromo-5-(2,2,2-trifluoro-1-hydroxyethyl)benzo[d]oxazol-2-yl)-3,9-diazabicyclo[3.3.1]nonane-9-carboxylate obtained in Example 136(a) by a similar method to Example 1(b).

(c) 1-(2-(3,9-Diazabicyclo[3.3.1]nonan-3-yl)-7-(thiazol-2-yl)benzo[d]oxazol-5-yl)-2,2,2-trifluoroethan-1-ol The title compound was obtained in an amount of 60 mg from 130 mg of tert-butyl 3-(7-(thiazol-2-yl)-5-(2,2,2-trifluoro-1-hydroxyethyl)benzo[d]oxazol-2-yl)-3,9-diazabicyclo[3.3.1]nonane-9-carboxylate obtained in Example 136 (b) by a similar method to Example 1(c).

Example 137

1-(2-(3,8-Diazabicyclo[3.2.1]octan-3-yl)-7-(thiazol-2-yl)benzo[d]oxazol-5-yl)-2,2,2-trifluoroethan-1-ol (racemic)

(a) tert-Butyl 3-(7-bromo-5-(2,2,2-trifluoro-1-hydroxyethyl)benzo[d]oxazol-2-yl)-3,8-diazabicyclo[3.2.1]octane-8-carboxylate The title compound was obtained in an amount of 359 mg from 300 mg of 1-(7-Bromo-2-mercaptobenzo[d]oxazol-5- yl)-2,2,2-trifluoroethan-1-ol obtained in Reference Example 18 and tert-butyl 3,8-diazabicyclo[3.2.1]octane-8-carboxylate by a similar method to Example 1(a).

(b) tert-Butyl 3-(7-(thiazol-2-yl)-5-(2,2,2-trifluoro-1-hydroxyethyl)benzo[d]oxazol-2-yl)-3,8-diazabicyclo[3.2.1]octane-8-carboxylate (racemic)

The title compound was obtained in an amount of 329 mg from 358 mg of tert-butyl 3-(7-bromo-5-(2,2,2-trifluoro-1-hydroxyethyl)benzo[d]oxazol-2-yl)-3,8-diazabicyclo[3.2.1]octane-8-carboxylate obtained in Example 137 (a) by a similar method to Example 2 (b).

(c) 1-(2-(3,8-Diazabicyclo[3.2.1]octan-3-yl)-7-(thiazol-2-yl)benzo[d]oxazol-5-yl)-2,2,2-trifluoroethan-1-ol (racemic)

The title compound was obtained in an amount of 220 mg from 329 mg of racemic tert-butyl 3-(7-(thiazol-2-yl)-5-(2,2,2-trifluoro-1-hydroxyethyl)benzo[d]oxazol-2-yl)-3,8-diazabicyclo[3.2.1]octane-8-carboxylate obtained in Example 137 (b) by a similar method to Example 1(c).

Example 138

1-(2-(3,8-Diazabicyclo[3.2.1]octan-3-yl)-7-(thiazol-2-yl)benzo[d]oxazol-5-yl)-2,2,2-trifluoroethan-1-ol (Optically Active)

(a) tert-Butyl 3-(7-(thiazol-2-yl)-5-(2,2,2-trifluoro-1-hydroxyethyl)benzo[d]oxazol-2-yl)-3,8-diazabicyclo[3.2.1]octane-8-carboxylate (Optically Active)

30 mg of racemic tert-butyl 3-(7-(thiazol-2-yl)-5-(2,2,2-trifluoro-1-hydroxyethyl)benzo[d]oxazol-2-yl)-3,8-diazabicyclo[3.2.1]octane-8-carboxylate obtained in Example 137 (b) was purified by a preparative HPLC (Gilson, column: DAICEL CHIRALPAK IC (particle diameter: 5 μm, column diameter: 2 cm, column length: 25 cm), eluent, hexane:isopropyl alcohol=90:10 to 80:20, flow rate: 15 mL/min, detection: UV254 nm) and the title compound was obtained in an amount of 14 mg by concentrating fractions with the shorter retention time peak. 98% ee. Analysis conditions: HPLC (HITACHI, column: DAICEL CHIRALPAK IC (particle diameter: 5 μm, column diameter: 0.46 cm, column length: 25 cm), eluent, hexane:isopropyl alcohol=90:10, flow rate: 1 mL/min, detection: UV254 nm, temperature: 25° C., retention time: 18.5 min).

(b) 1-(2-(3,8-Diazabicyclo[3.2.1]octan-3-yl)-7-(thiazol-2-yl)benzo[d]oxazol-5-yl)-2,2,2-trifluoroethan-1-ol (Optically Active)

The title compound was obtained in an amount of 8.1 mg from 14 mg of tert-butyl 3-(7-(thiazol-2-yl)-5-(2,2,2-trifluoro-1-hydroxyethyl)benzo[d]oxazol-2-yl)-3,8-diazabicyclo[3.2.1]octane-8-carboxylate (optically active) obtained in Example 138 (a) by a similar method to Example 1(c)

Example 139

1-(2-(3,8-Diazabicyclo[3.2.1]octan-3-yl)-7-(thiazol-2-yl)benzo[d]oxazol-5-yl)-2,2,2-trifluoroethan-1-ol (Optically Active, Enantiomer of Example 138)

(a) tert-Butyl 3-(7-(thiazol-2-yl)-5-(2,2,2-trifluoro-1-hydroxyethyl)benzo[d]oxazol-2-yl)-3,8-diazabicyclo[3.2.1]octane-8-carboxylate (Optically Active, Enantiomer of Example 138 (a))

30 mg of racemic tert-butyl 3-(7-(thiazol-2-yl)-5-(2,2,2-trifluoro-1-hydroxyethyl)benzo[d]oxazol-2-yl)-3,8-diazabicyclo[3.2.1]octane-8-carboxylate obtained in Example 137 (b) was purified by a preparative HPLC (Gilson, column: DAICEL CHIRALPAK IC (particle diameter: 5 μm, column diameter: 2 cm, column length: 25 cm), eluent, hexane:isopropyl alcohol=90:10 to 80:20, flow rate: 15 mL/min, detection: UV254 nm) and the title compound was obtained in an amount of 13 mg by concentrating fractions with the longer retention time peak. 99.7% ee. Analysis conditions: HPLC (HITACHI, column: DAICEL CHIRALPAK IC (particle diameter: 5 μm, column diameter: 0.46 cm, column length: 25 cm), eluent, hexane:isopropyl alcohol=90:10, flow rate: 1 mL/min, detection: UV254 nm, temperature: 25° C., retention time: 20.0 min).

(b) 1-(2-(3,8-Diazabicyclo[3.2.1]octan-3-yl)-7-(thiazol-2-yl)benzo[d]oxazol-5-yl)-2,2,2-trifluoroethan-1-ol (Optically Active, Enantiomer of Example 138)

The title compound was obtained in an amount of 7.8 mg from 13 mg of tert-butyl 3-(7-(thiazol-2-yl)-5-(2,2,2-trifluoro-1-hydroxyethyl)benzo[d]oxazol-2-yl)-3,8-diazabicyclo[3.2.1]octane-8-carboxylate (optically active) obtained in Example 139(a) by a similar method to Example 1(c)

Example 140

1-(2-(3,8-Diazabicyclo[3.2.1]octan-3-yl)-7-(1H-pyrazol-1-yl)benzo[d]oxazol-5-yl)-2,2,2-trifluoroethan-1-ol (a) tert-Butyl 3-(7-(1H-pyrazol-1-yl)-5-(2,2,2-trifluoro-1-hydroxyethyl)benzo[d]oxazol-2-yl)-3,8-diazabicyclo[3.2.1]octane-8-carboxylate The title compound was obtained in an amount of 18 mg from 100 mg of tert-butyl 3-(7-bromo-5-(2,2,2-trifluoro-1-hydroxyethyl)benzo[d]oxazol-2-yl)-3,8-diazabicyclo[3.2.1]octane-8-carboxylate obtained in Example 137 (a) by a similar method to Example 5 (a).

(b) 1-(2-(3,8-Diazabicyclo[3.2.1]octan-3-yl)-7-(1H-pyrazol-1-yl)benzo[d]oxazol-5-yl)-2,2,2-trifluoroethan-1-ol The title compound was obtained in an amount of 12 mg from 18 mg of tert-butyl 3-(7-(1H-pyrazol-1-yl)-5-(2,2,2-trifluoro-1-hydroxyethyl)benzo[d]oxazol-2-yl)-3,8-diazabicyclo[3.2.1]octane-8-carboxylate obtained in Example 140 (a) by a similar method to Example 1(c).

Example 141

1-(2-(3,8-Diazabicyclo[3.2.1]octan-3-yl)-7-(thiazol-2-yl)benzo[d]oxazol-5-yl)-2,2,2-trifluoroethyl acetate (a) tert-Butyl 3-(5-(1-acetoxy-2,2,2-trifluoroethyl-7-bromobenzo[d]oxazol-2-yl)-3,8-diazabicyclo[3.2.1]octane-8-carboxylate 165 mg of tert-butyl 3-(7-bromo-5-(2,2,2-trifluoro-1-hydroxyethyl)benzo[d]oxazol-2-yl)-3,8-diazabicyclo[3.2.1]octane-8-carboxylate obtained in Example 137 (a) was dissolved in dichloromethane (20 mL). 4-dimethylaminopyridine (8 mg, 0.2 equivalent), triethylamine (0.1 mL, 3 equivalents), and acetyl chloride (0.1 mL, 4 equivalents) were added at 0° C. and stirred for 1 hour at room temperature. After confirming a reaction product by TLC, saturated aqueous sodium bicarbonate solution was added at 0° C. to stop the reaction and organic phase was extracted by dichloromethane. A filtrate was obtained by drying the extracted organic phase by anhydrous magnesium sulfate and filtering them. The title compound was obtained as a crude product in an amount of 160 mg from the crude residue obtained by vacuum concentration of the filtrate.

(b) tert-Butyl 3-(5-(1-acetoxy-2,2,2-trifluoroethyl-7-(thiazol-2-yl)benzo[d]oxazol-2-yl)-3,8-diazabicyclo[3.2.1]octane-8-carboxylate The title compound was obtained in an amount of 80 mg from 160 mg of tert-butyl 3-(5-(1-acetoxy-2,2,2-trifluoroethyl-7-bromobenzo[d]oxazol-2-yl)-3,8-diazabicyclo[3.2.1]octane-8-carboxylate obtained in Example 141(a) by a similar method to Example 2 (b).

(c) 1-(2-(3,8-Diazabicyclo[3.2.1]octan-3-yl)-7-(thiazol-2-yl)benzo[d]oxazol-5-yl)-2,2,2-trifluoroethyl acetate The title compound was obtained in an amount of 50 mg from 70 mg of tert-butyl 3-(5-(1-acetoxy-2,2,2-trifluoroethyl-7-(thiazol-2-yl)benzo[d]oxazol-2-yl)-3,8-diazabicyclo[3.2.1]octane-8-carboxylate obtained in Example 141(b) by a similar method to Example 1(c).

Example 142

2-(3,8-Diazabicyclo[3.2.1]octan-3-yl)-7-(thiazol-2-yl)-5-(2,2,2-trifluoro-1-methoxyethyl)benzo[d]oxazole (Optically Active)

(a) tert-Butyl 3-(7-(thiazol-2-yl)-5-(2,2,2-trifluoro-1-methoxyethyl)benzo[d]oxazol-2-yl)-3,8-diazabicyclo[3.2.1]octane-8-carboxylate (racemic)

The title compound was obtained in an amount of 46 mg from 81 mg of tert-butyl 3-(7-(thiazol-2-yl)-5-(2,2,2-trifluoro-1-hydroxyethyl)benzo[d]oxazol-2-yl)-3,8-diazabicyclo[3.2.1]octane-8-carboxylate obtained in Example 137 (b) by a similar method to Example 102 (e).

(b) tert-Butyl 3-(7-(thiazol-2-yl)-5-(2,2,2-trifluoro-1-methoxyethyl)benzo[d]oxazol-2-yl)-3,8-diazabicyclo[3.2.1]octane-8-carboxylate (Optically Active)

194 mg of racemic tert-butyl 3-(7-(thiazol-2-yl)-5-(2,2,2-trifluoro-1-methoxyethyl)benzo[d]oxazol-2-yl)-3,8-diazabicyclo[3.2.1]octane-8-carboxylate obtained in Example 142 (a) was purified by a preparative HPLC (Gilson, column: DAICEL CHIRALPAK IA (particle diameter: 5 µm, column diameter: 2 cm, column length: 25 cm), eluent, hexane:isopropyl alcohol=95:5-80:20, flow rate: 15 mL/min, detection: UV254 nm) and the title compound was obtained in an amount of 79 mg by concentrating fractions with the shorter retention time peak. 98% ee. Analysis conditions: HPLC (HITACHI, column: DAICEL CHIRALPAK IA (particle diameter: 5 µm, column diameter: 0.46 cm, column length: 25 cm), eluent, hexane:isopropyl alcohol=90:10, flow rate: 1 mL/min, detection: UV254 nm, temperature: 25° C., retention time: 7.8 min).

(c) 2-(3,8-Diazabicyclo[3.2.1]octan-3-yl)-7-(thiazol-2-yl)-5-(2,2,2-trifluoro-1-methoxyethyl)benzo[d]oxazole (Optically Active)

The title compound was obtained in an amount of 64 mg from 79 mg of tert-butyl 3-(7-(thiazol-2-yl)-5-(2,2,2-trifluoro-1-methoxyethyl)benzo[d]oxazol-2-yl)-3,8-diazabicyclo[3.2.1]octane-8-carboxylate (optically active) obtained in Example 142 (b) by a similar method to Example 1(c). 98% ee. Analysis conditions: HPLC (HITACHI, column: DAICEL CHIRALPAK ID (particle diameter: 5 µm, column diameter: 0.46 cm, column length: 25 cm), eluent, hexane:isopropyl alcohol:dimethylamine=70:30:0.1, flow rate: 1 mL/min, detection: UV254 nm, temperature: 25° C., retention time: 13 min).

Example 143

2-(3,8-Diazabicyclo[3.2.1]octan-3-yl)-7-(thiazol-2-yl)-5-(2,2,2-trifluoro-1-methoxyethyl)benzo[d]oxazole (Optically Active, Enantiomer of Example 142)

(a) tert-Butyl 3-(7-(thiazol-2-yl)-5-(2,2,2-trifluoro-1-methoxyethyl)benzo[d]oxazol-2-yl)-3,8-diazabicyclo[3.2.1]octane-8-carboxylate (Optically Active, Enantiomer of Example 142 (b))

194 mg of racemic tert-butyl 3-(7-(thiazol-2-yl)-5-(2,2,2-trifluoro-1-methoxyethyl)benzo[d]oxazol-2-yl)-3,8-diazabicyclo[3.2.1]octane-8-carboxylate obtained in Example 142 (a) was purified by a preparative HPLC (Gilson, column: DAICEL CHIRALPAK IA (particle diameter: 5 µm, column diameter: 2 cm, column length: 25 cm), eluent, hexane:isopropyl alcohol=95:5-80:20, flow rate: 15 mL/min, detection: UV254 nm) and the title compound was obtained in an amount of 80 mg by concentrating fractions with the longer retention time peak. 99.5% ee. Analysis conditions: HPLC (HITACHI, column: DAICEL CHIRALPAK IA (particle diameter: 5 µm, column diameter: 0.46 cm, column length: 25 cm), eluent, hexane:isopropyl alcohol=90:10, flow rate: 1 mL/min, detection: UV254 nm, temperature: 25° C., retention time: 8.9 min).

(b) 2-(3,8-Diazabicyclo[3.2.1]octan-3-yl)-7-(thiazol-2-yl)-5-(2,2,2-trifluoro-1-methoxyethyl)benzo[d]oxazole (Optically Active, Enantiomer of Example 142)

The title compound was obtained in an amount of 66 mg from 80 mg of tert-butyl 3-(7-(thiazol-2-yl)-5-(2,2,2-trifluoro-1-methoxyethyl)benzo[d]oxazol-2-yl)-3,8-diazabicyclo[3.2.1]octane-8-carboxylate (optically active) obtained in Example 143(a) by a similar method to Example 1(c). 99.4% ee. Analysis conditions: HPLC (HITACHI, column: DAICEL CHIRALPAK ID (particle diameter: 5 µm, column diameter: 0.46 cm, column length: 25 cm), eluent, hexane:isopropyl alcohol:dimethylamine=70:30:0.1, flow rate: 1 mL/min, detection: UV254 nm, temperature: 25° C., retention time: 16 min).

Example 144

2-(3,6-Diazabicyclo[3.1.1]heptan-3-yl)-7-(thiazol-2-yl)-5-(2,2,2-trifluoro-1-methoxyethyl)benzo[d]oxazole (a) tert-Butyl 3-(7-(thiazol-2-yl)-5-(2,2,2-trifluoro-1-methoxyethyl)benzo[d]oxazol-2-yl)-3,6-diazabicyclo[3.1.1]heptane-6-carboxylate The title compound was obtained as a crude product in an amount of 51 mg from 50 mg of tert-butyl 3-(7-(thiazol-2-yl)-5-(2,2,2-trifluoro-1-hydroxyethyl)benzo[d]oxazol-2-yl)-3,6-diazabicyclo[3.1.1]heptane-6-carboxylate obtained in Example 135(b) by a similar method to Example 102(e) except that the product was not purified by preparative TLC.

(b) 2-(3,6-Diazabicyclo[3.1.1]heptan-3-yl)-7-(thiazol-2-yl)-5-(2,2,2-trifluoro-1-methoxyethyl)benzo[d]oxazole The title compound was obtained in an amount of 38 mg from 51 mg of tert-butyl 3-(7-(thiazol-2-yl)-5-(2,2,2-trifluoro-1-methoxyethyl)benzo[d]oxazol-2-yl)-3,6-diazabicyclo[3.1.1]heptane-6-carboxylate obtained in Example 144 (a) by a similar method to Example 1(c).

Example 145

2-(3,9-Diazabicyclo[3.3.1]nonan-3-yl)-7-(thiazol-2-yl)-5-(2,2,2-trifluoro-1-methoxyethyl)benzo[d]oxazole (a) tert-Butyl 3-(7-(thiazol-2-yl)-5-(2,2,2-trifluoro-1-methoxyethyl)benzo[d]oxazol-2-yl)-3,9-diazabicyclo[3.3.1]nonane-9-carboxylate The title compound was obtained as a crude product in an amount of 51 mg from 50 mg of tert-butyl 3-(7-(thiazol-2-yl)-5-(2,2,2-trifluoro-1-hydroxyethyl)benzo[d]oxazol-2-yl)-3,9-diazabicyclo[3.3.1]nonane-9-carboxylate obtained in Example 136(b) by a similar method to Example 102(e) except that the product was not purified by preparative TLC.

(b) 2-(3,9-Diazabicyclo[3.3.1]nonan-3-yl)-7-(thiazol-2-yl)-5-(2,2,2-trifluoro-1-methoxyethyl)benzo[d]oxazole The title compound was obtained in an amount of 30 mg from 51 mg of tert-butyl 3-(7-(thiazol-2-yl)-5-(2,2,2-trifluoro-1-methoxyethyl)benzo[d]oxazol-2-yl)-3,9-diazabicyclo[3.3.1]nonane-9-carboxylate obtained in Example 145 (a) by a similar method to Example 1(c).

Example 146

2-(3,8-Diazabicyclo[3.2.1]octan-3-yl)-7-(thiazol-2-yl)-5-(2,2,2-trifluoro-1-(2,2,2-trifluoroethoxy)ethyl)benzo[d]oxazole (a) tert-Butyl 3-(7-(thiazol-2-yl)-5-(2,2,2-trifluoro-1-(2,2,2-trifluoroethoxy)ethyl)benzo[d]oxazol-2-yl)-3,8-diazabicyclo[3.2.1]octane-8-carboxylate The title compound was obtained in an amount of 23 mg from 41 mg of tert-butyl 3-(7-(thiazol-2-yl)-5-(2,2,2-trifluoro-1-hydroxyethyl)benzo[d]oxazol-2-yl)-3,8-diazabicyclo[3.2.1]octane-8-carboxylate obtained in Example 137 (b) by a similar method to Example 102(e) except that 2,2,2-trifluoroethyl trifluoromethanesulfonate was used instead of methyl iodide.

(b) 2-(3,8-Diazabicyclo[3.2.1]octan-3-yl)-7-(thiazol-2-yl)-5-(2,2,2-trifluoro-1-(2,2,2-trifluoroethoxy)ethyl)benzo[d]oxazole The title compound was obtained in an amount of 11 mg from 23 mg of tert-butyl 3-(7-(thiazol-2-yl)-5-(2,2,2-trifluoro-1-(2,2,2-trifluoroethoxy)ethyl)benzo[d]oxazol-2-yl)-3,8-diazabicyclo[3.2.1]octane-8-carboxylate obtained in Example 146(a) by a similar method to Example 1(c).

Example 147

2-(3,8-Diazabicyclo[3.2.1]octan-3-yl)-7-(thiazol-2-yl)-5-(2,2,2-trifluoro-1-(2-methoxyethoxy)ethyl)benzo[d]oxazole (a) tert-Butyl 3-(7-(thiazol-2-yl)-5-(2,2,2-trifluoro-1-(2-methoxyethoxy)ethyl)benzo[d]oxazol-2-yl)-3,8-diazabicyclo[3.2.1]octane-8-carboxylate The title compound was obtained in an amount of 16 mg from 36 mg of tert-butyl 3-(7-(thiazol-2-yl)-5-(2,2,2-trifluoro-1-hydroxyethyl)benzo[d]oxazol-2-yl)-3,8-diazabicyclo[3.2.1]octane-8-carboxylate obtained in Example 137 (b) by a similar method to Example 102 (e) except that 2-bromoethyl methyl ether was used instead of methyl iodide.

(b) 2-(3,8-Diazabicyclo[3.2.1]octan-3-yl)-7-(thiazol-2-yl)-5-(2,2,2-trifluoro-1-(2-methoxyethoxy)ethyl)benzo[d]oxazole The title compound was obtained in an amount of 11 mg from 16 mg of tert-butyl 3-(7-(thiazol-2-yl)-5-(2,2,2-trifluoro-1-(2-methoxyethoxy)ethyl)benzo[d]oxazol-2-yl)-3,8-diazabicyclo[3.2.1]octane-8-carboxylate obtained in Example 147 (a) by a similar method to Example 1(c).

Example 148

2-(3,8-Diazabicyclo[3.2.1]octan-3-yl)-5-(1-ethoxy-2,2,2-trifluoroethyl)-7-(thiazol-2-yl)benzo[d]oxazole (a) tert-Butyl 3-(5-(1-ethoxy-2,2,2-trifluoroethyl-7-(thiazol-2-yl)benzo[d]oxazol-2-yl)-3,8-diazabicyclo[3.2.1]octane-8-carboxylate The title compound was obtained in an amount of 19 mg from 20 mg of tert-butyl 3-(7-(thiazol-2-yl)-5-(2,2,2-trifluoro-1-hydroxyethyl)benzo[d]oxazol-2-yl)-3,8-diazabicyclo[3.2.1]octane-8-carboxylate obtained in Example 137 (b) by a similar method to Example 102 (e) except that ethyl iodide was used instead of methyl iodide.

(b) 2-(3,8-Diazabicyclo[3.2.1]octan-3-yl)-5-(1-ethoxy-2,2,2-trifluoroethyl)-7-(thiazol-2-yl)benzo[d]oxazole The title compound was obtained in an amount of 12 mg from 30 mg of tert-butyl 3-(5-(1-ethoxy-2,2,2-trifluoroethyl-7-(thiazol-2-yl)benzo[d]oxazol-2-yl)-3,8-diazabicyclo

[3.2.1]octane-8-carboxylate obtained in Example 148 (a) by a similar method to Example 1(c).

Example 149

2-(1-(2-(3,8-Diazabicyclo[3.2.1]octan-3-yl)-7-(thiazol-2-yl)benzo[d]oxazol-5-yl)-2,2,2-trifluoroethoxy)ethan-1-ol (a) tert-Butyl 3-(7-(thiazol-2-yl)-5-(2,2,2-trifluoro-1-(2-hydroxyethoxy)ethyl)benzo[d]oxazol-2-yl)-3,8-diazabicyclo[3.2.1]octane-8-carboxylate 60 mg of tert-butyl 3-(7-(thiazol-2-yl)-5-(2,2,2-trifluoro-1-hydroxyethyl)benzo[d]oxazol-2-yl)-3,8-diazabicyclo[3.2.1]octane-8-carboxylate obtained in Example 137 (b), (2-bromorthoxy)-tert-butyldimethylsilane (930 μL, 36 equivalents), and sodium hydride (57.0 mg, 19.8 equivalents) were dissolved in tetrahydrofuran (1.2 mL), and stirred for 10 hours at room temperature. After confirming a reaction product by TLC (eluent, hexane:ethyl acetate=1:1), saturated ammonium chloride aqueous solution was added and organic phase was extracted by ethyl acetate. A filtrate was obtained by drying the extracted organic phase by anhydrous magnesium sulfate and filtering them. The title compound was obtained as a crude product in an amount of 116 mg from the residue obtained by vacuum concentration of the filtrate.

(b) 2-(1-(2-(3,8-Diazabicyclo[3.2.1]octan-3-yl)-7-(thiazol-2-yl)benzo[d]oxazol-5-yl)-2,2,2-trifluoroethoxy)ethan-1-ol The title compound was obtained in an amount of 14 mg from 116 mg of tert-butyl 3-(7-(thiazol-2-yl)-5-(2,2,2-trifluoro-1-(2-hydroxyethoxy)ethyl)benzo[d]oxazol-2-yl)-3,8-diazabicyclo[3.2.1]octane-8-carboxylate obtained in Example 149(a) by a similar method to Example 1(c).

Example 150

2-(3,6-Diazabicyclo[3.1.1]heptan-3-yl)-5-(1-ethoxy-2,2,2-trifluoroethyl)-7-(thiazol-2-yl)benzo[d]oxazole (a) tert-Butyl 3-(5-(1-ethoxy-2,2,2-trifluoroethyl-7-(thiazol-2-yl)benzo[d]oxazol-2-yl)-3,6-diazabicyclo[3.1.1]heptane-6-carboxylate The title compound was obtained in an amount of 35 mg from 40 mg of tert-butyl 3-(7-(thiazol-2-yl)-5-(2,2,2-trifluoro-1-hydroxyethyl)benzo[d]oxazol-2-yl)-3,6-diazabicyclo[3.1.1]heptane-6-carboxylate obtained in Example 135 (b) by a similar method to Example 102 (e) except that ethyl iodide was used instead of methyl iodide.

(b) 2-(3,6-Diazabicyclo[3.1.1]heptan-3-yl)-5-(1-ethoxy-2,2,2-trifluoroethyl)-7-(thiazol-2-yl)benzo[d]oxazole The title compound was obtained in an amount of 16 mg from 35 mg of tert-butyl 3-(5-(1-ethoxy-2,2,2-trifluoroethyl)-7-(thiazol-2-yl)benzo[d]oxazol-2-yl)-3,6-diazabicyclo[3.1.1]heptane-6-carboxylate obtained in Example 150 (a) by a similar method to Example 1(c).

Example 151

2-(3,6-Diazabicyclo[3.1.1]heptan-3-yl)-7-(thiazol-2-yl)-5-(2,2,2-trifluoro-1-(2,2,2-trifluoroethoxy)ethyl)benzo[d]oxazole (a) tert-Butyl 3-(7-(thiazol-2-yl)-5-(2,2,2-trifluoro-1-(2,2,2-trifluoroethoxy)ethyl)benzo[d]oxazol-2-yl)-3,6-diazabicyclo[3.1.1]heptane-6-carboxylate The title compound was obtained in an amount of 23 mg from 50 mg of tert-butyl 3-(7-(thiazol-2-yl)-5-(2,2,2-trifluoro-1-hydroxyethyl)benzo[d]oxazol-2-yl)-3,6-diazabicyclo[3.1.1]heptane-6-carboxylate obtained in Example 135 (b) by a similar method to Example 102(e) except that 2,2,2-trifluoroethyl trifluoromethanesulfonate was used instead of methyl iodide.

(b) 2-(3,6-Diazabicyclo[3.1.1]heptan-3-yl)-7-(thiazol-2-yl)-5-(2,2,2-trifluoro-1-(2,2,2-trifluoroethoxy)ethyl)benzo[d]oxazole The title compound was obtained in an amount of 7.5 mg from 23 mg of tert-butyl 3-(7-(thiazol-2-yl)-5-(2,2,2-trifluoro-1-(2,2,2-trifluoroethoxy)ethyl)benzo[d]oxazol-2-yl)-3,6-diazabicyclo[3.1.1]heptane-6-carboxylate obtained in Example 151(a) by a similar method to Example 1(c).

Example 152

2-(1-(2-(3,6-Diazabicyclo[3.1.1]heptan-3-yl)-7-(thiazol-2-yl)benzo[d]oxazol-5-yl)-2,2,2-trifluoroethoxy)acetonitrile (a) tert-Butyl 3-(5-(1-(cyanomethoxy)-2,2,2-trifluoroethyl)-7-(thiazol-2-yl)benzo[d]oxazol-2-yl)-3,6-diazabicyclo[3.1.1]heptane-6-carboxylate The title compound was obtained in an amount of 42 mg from 60 mg of tert-butyl 3-(7-(thiazol-2-yl)-5-(2,2,2-trifluoro-1-hydroxyethyl)benzo[d]oxazol-2-yl)-3,6-diazabicyclo[3.1.1]heptane-6-carboxylate obtained in Example 135 (b) by a similar method to Example 102(e) except that bromoacetonitrile was used instead of methyl iodide.

(b) 2-(1-(2-(3,6-Diazabicyclo[3.1.1]heptan-3-yl)-7-(thiazol-2-yl)benzo[d]oxazol-5-yl)-2,2,2-trifluoroethoxy)acetonitrile The title compound was obtained in an amount of 9.3 mg from 21 mg of tert-butyl 3-(5-(1-cyanomethoxy)-2,2,2-trifluoroethyl)-7-(thiazol-2-yl)benzo[d]oxazol-2-yl)-3,6-diazabicyclo[3.1.1]heptane-6-carboxylate obtained in Example 152(a) by a similar method to Example 1(c).

Example 153

2-(1-(2-(3,8-Diazabicyclo[3.2.1]octan-3-yl)-7-(thiazol-2-yl)benzo[d]oxazol-5-yl)-2,2,2-trifluoroethoxy)acetonitrile (a) tert-Butyl 3-(5-(1-cyanomethoxy)-2,2,2-trifluoroethyl)-7-(thiazol-2-yl)benzo[d]oxazol-2-yl)-3,8-diazabicyclo[3.2.1]octane-8-carboxylate The title compound was obtained in an amount of 46 mg from 61 mg of tert-butyl 3-(7-(thiazol-2-yl)-5-(2,2,2-trifluoro-1-hydroxyethyl)benzo[d]oxazol-2-yl)-3,8-diazabicyclo[3.2.1]octane-8-carboxylate obtained in Example 137 (b) by a similar method to Example 102(e) except that bromoacetonitrile was used instead of methyl iodide.

(b) 2-(1-(2-(3,8-Diazabicyclo[3.2.1]octan-3-yl)-7-(thiazol-2-yl)benzo[d]oxazol-5-yl)-2,2,2-trifluoroethoxy)acetonitrile The title compound was obtained in an amount of 13 mg from 23 mg of tert-butyl 3-(5-(1-cyanomethoxy)-(2,2,2-trifluoroethyl)-7-(thiazol-2-yl)benzo[d]oxazol-2-yl)-3,8-diazabicyclo[3.2.1]octane-8-carboxylate obtained in Example 153(a) by a similar method to Example 1(c).

Example 154

2-(3,6-Diazabicyclo[3.1.1]heptan-3-yl)-7-(thiazol-2-yl)-5-(2,2,2-trifluoro-1-(2-methoxyethoxy)ethyl)benzo[d]oxazole (a) tert-Butyl 3-(7-(thiazol-2-yl)-5-(2,2,2-trifluoro-1-(2-methoxyethoxy)ethyl)benzo[d]oxazol-2-yl)-3,6-diazabicyclo[3.1.1]heptane-6-carboxylate The title compound was obtained in an amount of 30 mg from 40 mg of tert-butyl 3-(7-(thiazol-2-yl)-5-(2,2,2-trifluoro-1-hydroxyethyl)benzo[d]oxazol-2-yl)-3,6-diazabicyclo[3.1.1]heptane-6-carboxylate obtained in Example 135 (b) by a similar method to Example 102(e) except that 2-bromoethyl methyl ether was used instead of methyl iodide.

(b) 2-(3,6-Diazabicyclo[3.1.1]heptan-3-yl)-7-(thiazol-2-yl)-5-(2,2,2-trifluoro-1-(2-methoxyethoxy)ethyl)benzo[d]oxazole The title compound was obtained in an amount of 18 mg from 30 mg of tert-butyl 3-(7-(thiazol-2-yl)-5-(2,2,2-trifluoro-1-(2-methoxyethoxy)ethyl)benzo[d]oxazol-2-yl)-3,6-diazabicyclo[3.1.1]heptane-6-carboxylate obtained in Example 154 (a) by a similar method to Example 1(c).

Example 155

1-(1-(2-(3,8-Diazabicyclo[3.2.1]octan-3-yl)-7-(thiazol-2-yl)benzo[d]oxazol-5-yl)-2,2,2-trifluoroethoxy)propan-2-ol (a) tert-Butyl 3-(5-(1-(cyanomethoxy)-2,2,2-trifluoroethyl)-7-(thiazol-2-yl)benzo[d]oxazol-2-yl)-3,8-diazabicyclo[3.2.1]octane-8-carboxylate The title compound was obtained in an amount of 230 mg from 184 mg of tert-butyl 3-(7-(thiazol-2-yl)-5-(2,2,2-trifluoro-1-hydroxyethyl)benzo[d]oxazol-2-yl)-3,8-diazabicyclo[3.2.1]octane-8-carboxylate obtained in Example 137(b) by a similar method to Example 102 (e) except that bromoacetonitrile was used instead of methyl iodide.

(b) tert-Butyl 3-(7-(thiazol-2-yl)-5-(2,2,2-trifluoro-1-(2-oxopropoxy)ethyl)benzo[d]oxazol-2-yl)-3,8-diazabicyclo[3.2.1]octane-8-carboxylate 230 mg of tert-butyl 3-(5-(1-(cyanomethoxy)-2,2,2-trifluoroethyl)-7-(thiazol-2-yl)benzo[d]oxazol-2-yl)-3,8-diazabicyclo[3.2.1]octane-8-carboxylate obtained in Example 155(a) was dissolved in diethyl ether (2.1 mL), and then 0.92 M solution of methylmagnesium bromide in tetrahydrofuran (2.9 mL, 6.5 equivalents) was added thereto at 0° C., followed by stirring at 0° C. for 5 hours. The formation of the product was confirmed by TLC (eluent, hexane:ethyl acetate=1:1), and then 1M hydrochloric acid was added thereto, followed by extraction using ethyl acetate. Thereafter, extracted organic phase was separated by using saturated aqueous sodium bicarbonate solution and the organic phase was dried over anhydrous magnesium sulfate, followed by filtration, and thus obtaining 68 mg of the title compound by purification of the residue obtained by vacuum concentration of the filtrate through silica gel column chromatography (eluent, hexane:ethyl acetate=1:1).

(c) tert-Butyl 3-(7-(thiazol-2-yl)-5-(2,2,2-trifluoro-1-(2-hydroxypropoxy)ethyl)benzo[d]oxazol-2-yl)-3,8-diazabicyclo[3.2.1]octane-8-carboxylate 27 mg of tert-butyl 3-(7-(thiazol-2-yl)-5-(2,2,2-trifluoro-1-(2-oxopropoxy)ethyl)benzo[d]oxazol-2-yl)-3,8-diazabicyclo[3.2.1]octane-8-carboxylate obtained in Example 155 (b) and sodium borohydride (3.6 mg, 2 equivalents) were dissolved in ethanol (480 μL) and stirred at 0° C. for 2 hours. The formation of the product was confirmed by TLC (eluent, hexane:ethyl acetate=1:1), and then saturated ammonium chloride aqueous solution was added thereto, followed by extraction using ethyl acetate. Thereafter, the organic phase was dried over anhydrous magnesium sulfate, followed by filtration, and thus obtaining the title compound as a crude product by vacuum concentration of the filtrate.

(d) 1-(1-(2-(3,8-Diazabicyclo[3.2.1]octan-3-yl)-7-(thiazol-2-yl)benzo[d]oxazol-5-yl)-2,2,2-trifluoroethoxy)propan-2-ol The title compound was obtained in an amount of 15 mg from tert-butyl 3-(7-(thiazol-2-yl)-5-(2,2,2-trifluoro-1-(2-hydroxypropoxy)ethyl)benzo[d]oxazol-2-yl)-3,8-diazabicyclo[3.2.1]octane-8-carboxylate obtained in Example 155(c) by a similar method to Example 1(c).

Example 156

1-(2-(3,9-Diazabicyclo[3.3.1]nonan-3-yl)-7-(thiazol-2-yl)benzo[d]oxazol-5-yl)-2,2,2-trifluoroethane-1,1-diol (a) tert-Butyl 3-(7-(thiazol-2-yl)-5-(2,2,2-trifluoro-1,1-dihydroxyethyl)benzo[d]oxazol-2-yl)-3,9-diazabicyclo[3.3.1]nonane-9-carboxylate 13 mg of tert-butyl 3-(7-(thiazol-2-yl)-5-(2,2,2-trifluoro-1-hydroxyethyl)benzo[d]oxazol-2-yl)-3,9-diazabicyclo[3.3.1]nonane-9-carboxylate obtained in Example 136(b) and Dess-Martin Periodinane (42 mg, 4 equivalents) were dissolved in chloroform (250 μL), followed by stirring at room temperature for 1 hour. The formation of the product was confirmed by TLC (eluent, hexane:ethyl acetate=1:1), and then saturated aqueous sodium bicarbonate and saturated aqueous sodium thiosulfate were added thereto, followed by extraction using ethyl acetate. Thereafter, the organic phase was dried over anhydrous magnesium sulfate, followed by filtration, and thus obtaining 13 mg of the title compound as a crude product by vacuum concentration of the filtrate.

(b) 1-(2-(3,9-Diazabicyclo[3.3.1]nonan-3-yl)-7-(thiazol-2-yl)benzo[d]oxazol-5-yl)-2,2,2-trifluoroethane-1,1-diol The title compound was obtained in an amount of 4.7 mg from 13 mg of tert-butyl 3-(7-(thiazol-2-yl)-5-(2,2,2-trifluoro-1,1-dihydroxyethyl)benzo[d]oxazol-2-yl)-3,9-diazabicyclo[3.3.1]nonane-9-carboxylate obtained in Example 156(a) by a similar method to Example 1(c).

Example 157

1-(2-(3,8-Diazabicyclo[3.2.1]octan-3-yl)-7-(thiazol-2-yl)benzo[d]oxazol-5-yl)-2,2,2-trifluoroethane-1,1-diol (a) tert-Butyl 3-(7-(thiazol-2-yl)-5-(2,2,2-trifluoro-1,1-dihydroxyethyl)benzo[d]oxazol-2-yl)-3,8-diazabicyclo[3.2.1]octane-8-carboxylate The title compound was obtained as a crude product in an amount of 110 mg from 100 mg of tert-butyl 3-(7-(thiazol-2-yl)-5-(2,2,2-trifluoro-1-hydroxyethyl)benzo[d]oxazol-2-yl)-3,8-diazabicyclo[3.2.1]octane-8-carboxylate obtained in Example 137 (b) by a similar method to Example 156(a).

(b) 1-(2-(3,8-Diazabicyclo[3.2.1]octan-3-yl)-7-(thiazol-2-yl)benzo[d]oxazol-5-yl)-2,2,2-trifluoroethane-1,1-diol The title compound was obtained in an amount of 3.7 mg from 30 mg of tert-butyl 3-(7-(thiazol-2-yl)-5-(2,2,2-trifluoro-1,1-dihydroxyethyl)benzo[d]oxazol-2-yl)-3,8-diazabicyclo[3.2.1]octane-8-carboxylate obtained in Example 157(a) by a similar method to Example 1(c).

Example 158

1-(2-(3,6-Diazabicyclo[3.1.1]heptan-3-yl)-7-(thiazol-2-yl)benzo[d]oxazol-5-yl)-2,2,2-trifluoroethane-1,1-diol (a) tert-Butyl 3-(7-(thiazol-2-yl)-5-(2,2,2-trifluoro-1,1-dihydroxyethyl)benzo[d]oxazol-2-yl)-3,6-diazabicyclo[3.1.1]heptane-6-carboxylate The title compound was obtained as a crude product in an amount of 89 mg from 84 mg of tert-butyl 3-(7-(thiazol-2-yl)-5-(2,2,2-trifluoro-1-hydroxyethyl)benzo[d]oxazol-2-yl)-3,6-diazabicyclo[3.1.1]heptane-6-carboxylate obtained in Example 135 (b) by a similar method to Example 156(a).

(b) 1-(2-(3,6-Diazabicyclo[3.1.1]heptan-3-yl)-7-(thiazol-2-yl)benzo[d]oxazol-5-yl)-2,2,2-trifluoroethane-1,1-diol The title compound was obtained in an amount of 16 mg from 30 mg of tert-butyl 3-(7-(thiazol-2-yl)-5-(2,2,2-trifluoro-1,1-dihydroxyethyl)benzo[d]oxazol-2-yl)-3,6-diazabicyclo[3.1.1]heptane-6-carboxylate obtained in Example 158(a) by a similar method to Example 1(c).

Example 159

2-(2-(3,8-Diazabicyclo[3.2.1]octan-3-yl)-7-(thiazol-2-yl)benzo[d]oxazol-5-yl)-1,1,1-trifluoropropan-2-ol (a) tert-Butyl 3-(7-(thiazol-2-yl)-5-(1,1,1-trifluoro-2-hydroxypropan-2-yl)benzo[d]oxazol-2-yl)-3,8-diazabicyclo[3.2.1]octane-8-carboxylate 53 mg of the crude product of tert-butyl 3-(7-(thiazol-2-yl)-5-(2,2,2-trifluoro-1,1-dihydroxyethyl)benzo[d]oxazol-2-yl)-3,8-diazabicyclo[3.2.1]octane-8-carboxylate obtained in Example 157(a) was dissolved in tetrahydrofuran (3.4 mL), then 0.6M solution of Lanthanum (III) chloride bis-lithium chloride complex in tetrahydrofuran (0.59 mL, 3 equivalents) and 0.92M solution of methylmagnesium bromide in tetrahydrofuran (0.32 mL, 3 equivalents) were added thereto at 0° C., followed by stirring at 0° C. for 3 hours. The formation of the product was confirmed by TLC (eluent, hexane:ethyl acetate=1:1), and then saturated ammonium chloride aqueous solution was added thereto, followed by extraction using ethyl acetate. Thereafter, the organic phase was dried over anhydrous magnesium sulfate, followed by filtration and vacuum concentration of the filtrate, and thus obtaining 38 mg of the title compound by purification of the residue by preparative TLC (eluent, hexane:ethyl acetate=1:1).

(b) 2-(2-(3,8-Diazabicyclo[3.2.1]octan-3-yl)-7-(thiazol-2-yl)benzo[d]oxazol-5-yl)-1,1,1-trifluoropropan-2-ol The title compound was obtained in an amount of 28 mg from 38 mg of tert-butyl 3-(7-(thiazol-2-yl)-5-(1,1,1-trifluoro-2-hydroxypropan-2-yl)benzo[d]oxazol-2-yl)-3,8-diazabicyclo[3.2.1]octane-8-carboxylate obtained in Example 159(a) by a similar method to Example 1(c).

Example 160

2-(2-(3,6-Diazabicyclo[3.1.1]heptan-3-yl)-7-(thiazol-2-yl)benzo[d]oxazol-5-yl)-1,1,1-trifluoropropan-2-ol (a) tert-Butyl 3-(7-(thiazol-2-yl)-5-(1,1,1-trifluoro-2-hydroxypropan-2-yl)benzo[d]oxazol-2-yl)-3,6-diazabicyclo[3.1.1]heptane-6-carboxylate The title compound was obtained in an amount of 54 mg from 59 mg of tert-butyl 3-(7-(thiazol-2-yl)-5-(2,2,2-trifluoro-1,1-dihydroxyethyl)benzo[d]oxazol-2-yl)-3,6-diazabicyclo[3.1.1]heptane-6-carboxylate obtained in Example 158(a) by a similar method to Example 159(a).

(b) 2-(2-(3,6-Diazabicyclo[3.1.1]heptan-3-yl)-7-(thiazol-2-yl)benzo[d]oxazol-5-yl)-1,1,1-trifluoropropan-2-ol The title compound was obtained in an amount of 5 mg from 53 mg of tert-butyl 3-(7-(thiazol-2-yl)-5-(1,1,1-trifluoro-2-hydroxypropan-2-yl)benzo[d]oxazol-2-yl)-3,6-diazabicyclo[3.1.1]heptane-6-carboxylate obtained in Example 160 (a) by a similar method to Example 1(c).

Example 161

2-(2-(3,9-Diazabicyclo[3.3.1]nonan-3-yl)-7-(thiazol-2-yl)benzo[d]oxazol-5-yl)-1,1,1-trifluoropropan-2-ol (a) tert-Butyl 3-(7-(thiazol-2-yl)-5-(1,1,1-trifluoro-2-hydroxypropan-2-yl)benzo[d]oxazol-2-yl)-3,9-diazabicyclo[3.3.1]nonane-9-carboxylate The title compound was obtained in an amount of 56 mg from 72 mg of tert-butyl 3-(7-(thiazol-2-yl)-5-(2,2,2-trifluoro-1,1-dihydroxyethyl)benzo[d]oxazol-2-yl)-3,9-diazabicyclo[3.3.1]nonane-9-carboxylate obtained in Example 156(a) by a similar method to Example 159(a).

(b) 2-(2-(3,9-Diazabicyclo[3.3.1]nonan-3-yl)-7-(thiazol-2-yl)benzo[d]oxazol-5-yl)-1,1,1-trifluoropropan-2-ol The title compound was obtained in an amount of 19 mg from 26 mg of tert-butyl 3-(7-(thiazol-2-yl)-5-(1,1,1-trifluoro-2-hydroxypropan-2-yl)benzo[d]oxazol-2-yl)-3,9-diazabicyclo[3.3.1]nonane-9-carboxylate obtained in Example 161 (a) by a similar method to Example 1(c).

Example 162

2-(2-(3,9-Diazabicyclo[3.3.1]nonan-3-yl)-7-(thiazol-2-yl)-5-(1,1,1-trifluoro-2-methoxypropan-2-yl)benzo[d]oxazole (a) tert-Butyl 3-(7-(thiazol-2-yl)-5-(1,1,1-trifluoro-2-methoxypropan-2-yl)benzo[d]oxazol-2-yl)-3,9-diazabicyclo[3.3.1]nonane-9-carboxylate The title compound was obtained in an amount of 19 mg from 30 mg of tert-butyl 3-(7-(thiazol-2-yl)-5-(1,1,1-trifluoro-2-hydroxypropan-2-yl)benzo[d]oxazol-2-yl)-3,9-diazabicyclo[3.3.1]nonane-9-carboxylate obtained in Example 161(a) by a similar method to Example 102 (e).

(b) 2-(2-(3,9-Diazabicyclo[3.3.1]nonan-3-yl)-7-(thiazol-2-yl)-5-(1,1,1-trifluoro-2-methoxypropan-2-yl)benzo[d]oxazole The title compound was obtained in an amount of 16 mg from 19 mg of tert-butyl 3-(7-(thiazol-2-yl)-5-(1,1,1-trifluoro-2-methoxypropan-2-yl)benzo[d]oxazol-2-yl)-3,9-diazabicyclo[3.3.1]nonane-9-carboxylate obtained in Example 162 (a) by a similar method to Example 1(c).

Example 163

Ethyl 2-(3,8-diazabicyclo[3.2.1]octan-3-yl)-7-(thiazol-2-yl)-4-(trifluoromethyl)benzo[d]oxazole-5-carboxylate (a) Ethyl 7-bromo-2-(8-(tert-butoxycarbonyl)-3,8-diazabicyclo[3.2.1]octan-3-yl)-4-(trifluoromethyl)benzo[d]oxazole-5-carboxylate The title compound was obtained in an amount of 200 mg from 150 mg of ethyl 7-bromo-2-mercapto-4-(trifluoromethyl)benzo[d]oxazole-5-carboxylate obtained in Reference Example 19 and tert-butyl-3,8-diazabicyclo[3.2.1]octane-8-carboxylate by a similar method to Example 1(a).

(b) Ethyl 2-(8-(tert-butoxycarbonyl)-3,8-diazabicyclo[3.2.1]octan-3-yl)-7-(thiazol-2-yl)-4-(trifluoromethyl)benzo[d]oxazole-5-carboxylate The title compound was obtained as a crude product in an amount of 250 mg from 200 mg of ethyl 7-bromo-2-(8-(tert-butoxycarbonyl)-3,8-diazabicyclo[3.2.1]octan-3-yl)-4-(trifluoromethyl)benzo[d]oxazole-5-carboxylate obtained in Example 163(a) by a similar method to Example 2 (b) except that toluene was used instead of 1,4-dioxane and tetrakis(triphenylphosphine)palladium(0) was used instead of bis(triphenylphosphine)palladium(II) dichloride.

(c) Ethyl 2-(3,8-diazabicyclo[3.2.1]octan-3-yl)-7-(thiazol-2-yl)-4-(trifluoromethyl)benzo[d]oxazole-5-carboxylate The title compound was obtained in an amount of 150 mg from 250 mg of ethyl 2-(8-(tert-butoxycarbonyl)-3,8-diazabicyclo[3.2.1]octan-3-yl)-7-(thiazol-2-yl)-4-(trifluoromethyl)benzo[d]oxazole-5-carboxylate obtained in Example 163(b) by a similar method to Example 1(c).

Example 164

Ethyl 2-(3,9-diazabicyclo[3.3.1]nonan-3-yl)-7-(thiazol-2-yl)-4-(trifluoromethyl)benzo[d]oxazole-5-carboxylate (a) Ethyl 7-bromo-2-(9-(tert-butoxycarbonyl)-3,9-diazabicyclo[3.3.1]nonan-3-yl)-4-(trifluoromethyl)benzo[d]oxazole-5-carboxylate The title compound was obtained in an amount of 200 mg from 150 mg of ethyl 7-bromo-2-mercapto-4-(trifluoromethyl)benzo[d]oxazole-5-carboxylate obtained in Reference Example 19 by a similar method to Example 1(a) except that tert-butyl 3,9-diazabicyclo[3.3.1]nonane-9-carboxylate was used instead of tert-butyl 3,8-diazabicyclo[3.2.1]octane-8-carboxylate.

(b) Ethyl 2-(9-(tert-butoxycarbonyl)-3,9-diazabicyclo[3.3.1]nonan-3-yl)-7-(thiazol-2-yl)-4-(trifluoromethyl)benzo[d]oxazole-5-carboxylate The title compound was obtained as a crude product in an amount of 350 mg from 200 mg of ethyl 7-bromo-2-(9-(tert-butoxycarbonyl)-3,9-diazabicyclo[3.3.1]nonan-3-yl)-4-(trifluoromethyl)benzo[d]oxazole-5-carboxylate obtained in Example 164(a) by a similar method to Example 2(b) except that toluene was used instead of 1,4-dioxane.

(c) Ethyl 2-(3,9-diazabicyclo[3.3.1]nonan-3-yl)-7-(thiazol-2-yl)-4-(trifluoromethyl)benzo[d]oxazole-5-carboxylate The title compound was obtained in an amount of 150 mg from 350 mg of ethyl 2-(9-(tert-butoxycarbonyl)-3,9-diazabicyclo[3.3.1]nonan-3-yl)-7-(thiazol-2-yl)-4-(trifluoromethyl)benzo[d]oxazole-5-carboxylate obtained in Example 164 (b) by a similar method to Example 1(c).

Example 165

Ethyl 2-(3,6-diazabicyclo[3.1.1]heptan-3-yl)-7-(thiazol-2-yl)-4-(trifluoromethyl)benzo[d]oxazole-5-carboxylate (a) Ethyl 7-bromo-2-(6-(tert-butoxycarbonyl)-3,6-diazabicyclo[3.1.1]heptan-3-yl)-4-(trifluoromethyl)benzo[d]oxazole-5-carboxylate The title compound was obtained in an amount of 200 mg from 150 mg of ethyl 7-bromo-2-mercapto-4-(trifluoromethyl)benzo[d]oxazole-5-carboxylate obtained in Reference Example 19 by a similar method to Example 1(a) except that tert-butyl 3,6-diazabicyclo[3.1.1]heptane-6-carboxylate was used instead of tert-butyl 3,8-diazabicyclo[3.2.1]octane-8-carboxylate.

(b) Ethyl 2-(6-(tert-butoxycarbonyl)-3,6-diazabicyclo[3.1.1]heptan-3-yl)-7-(thiazol-2-yl)-4-(trifluoromethyl)benzo[d]oxazole-5-carboxylate The title compound was obtained in an amount of 250 mg from 200 mg of ethyl 7-bromo-2-(6-(tert-butoxycarbonyl)-3,6-diazabicyclo[3.1.1]heptan-3-yl)-4-(trifluoromethyl)benzo[d]oxazole-5-carboxylate obtained in Example 165(a) by a similar method to Example 2(b) except that toluene was used instead of 1,4-dioxane and tetrakis(triphenylphosphine)palladium(0) was used instead of bis(triphenylphosphine)palladium(II) dichloride.

(c) Ethyl 2-(3,6-diazabicyclo[3.1.1]heptan-3-yl)-7-(thiazol-2-yl)-4-(trifluoromethyl)benzo[d]oxazole-5-carboxylate The title compound was obtained in an amount of 70 mg from 200 mg of ethyl 2-(6-(tert-butoxycarbonyl)-3,6-diazabicyclo[3.1.1]heptan-3-yl)-7-(thiazol-2-yl)-4-(trifluoromethyl)benzo[d]oxazole-5-carboxylate obtained in Example 165(b) by a similar method to Example 1(c).

Example 166

2-(2-(3,9-Diazabicyclo[3.3.1]nonan-3-yl)-7-(thiazol-2-yl)-4-(trifluoromethyl)benzo[d]oxazol-5-yl)propan-2-ol (a) tert-Butyl 3-(5-(2-hydroxypropan-2-yl)-7-(thiazol-2-yl)-4-(trifluoromethyl)benzo[d]oxazol-2-yl)-3,9-diazabicyclo[3.3.1]nonane-9-carboxylate The title compound was obtained in an amount of 6.1 mg from 26 mg of ethyl 2-(9-(tert-butoxycarbonyl)-3,9-diazabicyclo[3.3.1]nonan-3-yl)-7-(thiazol-2-yl)-4-(trifluoromethyl)benzo[d]oxazole-5-carboxylate obtained in Example 164(b) by a similar method to Example 159(a) except that 4 equivalents of 0.6M solution of Lanthanum (III) chloride bis-lithium chloride complex solution in tetrahydrofuran and 8 equivalents of 0.92M solution of methylmagnesium bromide in tetrahydrofuran were used.

(b) 2-(2-(3,9-Diazabicyclo[3.3.1]nonan-3-yl)-7-(thiazol-2-yl)-4-(trifluoromethyl)benzo[d]oxazol-5-yl)propan-2-ol The title compound was obtained in an amount of 3.7 mg from 6.1 mg of tert-butyl 3-(5-(2-hydroxypropan-2-yl)-7-(thiazol-2-yl)-4-(trifluoromethyl)benzo[d]oxazol-2-yl)-3,9-diazabicyclo[3.3.1]nonane-9-carboxylate obtained in Example 166(a) by a similar method to Example 1(c).

Example 167

2-(3,8-Diazabicyclo[3.2.1]octan-3-yl)-5-(methoxymethyl)-7-(thiazol-2-yl)-4-(trifluoromethyl)benzo[d]oxazole (a) tert-Butyl 3-(5-(hydroxymethyl)-7-(thiazol-2-yl)-4-(trifluoromethyl)benzo[d]oxazol-2-yl)-3,8-diazabicyclo[3.2.1]octane-8-carboxylate 16 mg of ethyl 2-(8-(tert-butoxycarbonyl)-3,8-diazabicyclo[3.2.1]octan-3-yl)-7-(thiazol-2-yl)-4-(trifluoromethyl)benzo[d]oxazole-5-carboxylate obtained in Example 163(b) was dissolved in toluene (290 μL), then 1.0M solution of diisobutylaluminium hydride complex in toluene (123 μL, 4.2 equivalents) was added thereto at −78° C., followed by stirring for 2 hours. The formation of the product was confirmed by TLC (eluent, hexane:ethyl acetate=1:1), and the reaction mixture was subjected to Celite® filtration. Thereafter, the organic phase extracted by ethyl acetate was dried over anhydrous magnesium sulfate, followed by filtration and vacuum concentration of the filtrate, and thus obtaining 13 mg of the title compound by purification of the residue by preparative TLC (eluent, hexane:ethyl acetate=1:1).

(b) tert-Butyl 3-(5-(methoxymethyl)-7-(thiazol-2-yl)-4-(trifluoromethyl)benzo[d]oxazol-2-yl)-3,8-diazabicyclo[3.2.1]octane-8-carboxylate The title compound was obtained in an amount of 23 mg from 35 mg of tert-butyl 3-(5-(hydroxymethyl)-7-(thiazol-2-yl)-4-(trifluoromethyl)benzo[d]oxazol-2-yl)-3,8-diazabicyclo[3.2.1]octane-8-carboxylate obtained in Example 167 (a) by a similar method to Example 102 (e).

(c) 2-(3,8-Diazabicyclo[3.2.1]octan-3-yl)-5-(methoxymethyl)-7-(thiazol-2-yl)-4-(trifluoromethyl)benzo[d]oxazole The title compound was obtained in an amount of 18 mg from 23 mg of tert-butyl 3-(5-(methoxymethyl)-7-(thiazol-2-yl)-4-(trifluoromethyl)benzo[d]oxazol-2-yl)-3,8-diazabicyclo[3.2.1]octane-8-carboxylate obtained in Example 167 (b) by a similar method to Example 1(c).

Example 168

2-(3,8-Diazabicyclo[3.2.1]octan-3-yl)-5-(morpholinomethyl)-7-(thiazol-2-yl)benzo[d]oxazole (a) tert-Butyl 3-(5-(hydroxymethyl)-7-(thiazol-2-yl)benzo[d]oxazol-2-yl)-3,8-diazabicyclo[3.2.1]octane-8-carboxylate The title compound was obtained in an amount of 141 mg from 267 mg of ethyl 2-(8-(tert-butoxycarbonyl)-3,8-diazabicyclo[3.2.1]octan-3-yl)-7-(thiazol-2-yl)benzo[d]oxazole-5-carboxylate obtained in Example 86(b) by a similar method to Example 167 (a).

(b) tert-Butyl 3-(5-(morpholinomethyl)-7-(thiazol-2-yl)benzo[d]oxazol-2-yl)-3,8-diazabicyclo[3.2.1]octane-8-carboxylate 20 mg of tert-butyl 3-(5-(hydroxymethyl)-7-(thiazol-2-yl)benzo[d]oxazol-2-yl)-3,8-diazabicyclo[3.2.1]octane-8-carboxylate obtained in Example 168 (a) was dissolved in dichloromethane (0.5 mL), then diisopropylethylamine (23.6 µL, 3 equivalents) and methanesulfonyl chloride (10.5 µL, 3 equivalents) were added thereto, followed by stirring at room temperature for 1 hour. Thereafter, the reacted solution was concentrated and dissolved in N,N-dimethylformamide (0.5 mL), and then morpholine (19.7 µL, 5 equivalents) was added thereto, followed by stirring at room temperature for 16 hours, and saturated aqueous sodium bicarbonate was added. Organic phase extracted by ethyl acetate was dried over anhydrous magnesium sulfate, followed by filtration and vacuum concentration of the filtrate, and thus obtaining 23 mg of the title compound by purification of the residue by preparative TLC (eluent, chloroform:methanol=10:1).

(c) 2-(3,8-Diazabicyclo[3.2.1]octan-3-yl)-5-(morpholinomethyl)-7-(thiazol-2-yl)benzo[d]oxazole The title compound was obtained in an amount of 16 mg from 23 mg of tert-butyl 3-(5-(morpholinomethyl)-7-(thiazol-2-yl)benzo[d]oxazol-2-yl)-3,8-diazabicyclo[3.2.1]octane-8-carboxylate obtained in Example 168(b) by a similar method to Example 1(c).

Example 169

1-(2-(3,8-Diazabicyclo[3.2.1]octan-3-yl)-7-(thiazol-2-yl)benzo[d]oxazol-5-yl)-N,N-dimethylmethanamine (a) tert-Butyl 3-(5-(dimethylamino)methyl)-7-(thiazol-2-yl)benzo[d]oxazol-2-yl)-3,8-diazabicyclo[3.2.1]octane-8-carboxylate The title compound was obtained in an amount of 10 mg from 20 mg of tert-butyl 3-(5-(hydroxymethyl)-7-(thiazol-2-yl)benzo[d]oxazol-2-yl)-3,8-diazabicyclo[3.2.1]octane-8-carboxylate obtained in Example 168(a) by a similar method to Example 168(b) except that 2M dimethylamine solution (0.46 mL, 20 equivalents) in methanol was used instead of morpholine.

(b) 1-(2-(3,8-Diazabicyclo[3.2.1]octan-3-yl)-7-(thiazol-2-yl)benzo[d]oxazol-5-yl)-N,N-dimethylmethanamine The title compound was obtained in an amount of 7.5 mg from 10 mg of tert-butyl 3-(5-(dimethylamino)methyl)-7-(thiazol-2-yl)benzo[d]oxazol-2-yl)-3,8-diazabicyclo[3.2.1]octane-8-carboxylate obtained in Example 169(a) by a similar method to Example 1(c).

Example 170

(2-(3,8-Diazabicyclo[3.2.1]octan-3-yl)-7-(thiazol-2-yl)-4-(trifluoromethyl)benzo[d]oxazol-5-yl)methanol 30 mg of ethyl 2-(3,8-diazabicyclo[3.2.1]octan-3-yl)-7-(thiazol-2-yl)-4-(trifluoromethyl)benzo[d]oxazole-5-carboxylate obtained in Example 163(c) was dissolved in tetrahydrofuran (330 µL), then lithium aluminium hydride (10 mg, 4 equivalents) was added thereto at room temperature, followed by stirring for 10 min. The formation of the product was confirmed by TLC (eluent, chloroform:methanol:ammonia water=3:1:0.1), sodium sulfate 10-hydrate, hexane, Celite® and magnesium sulfate were added, and the mixture was subjected to Celite® filtration. After vacuum concentration of the filtrate, and thus obtaining 19 mg of the title compound by purification of the residue by preparative TLC (eluent, chloroform:methanol:ammonia water=3:1:0.1).

Example 171

2-(3,8-Diazabicyclo[3.2.1]octan-3-yl)-5-(2-methoxypropan-2-yl)-7-(thiazol-2-yl)-4-(trifluoromethyl)benzo[d]oxazole (a) tert-Butyl 3-(5-formyl-7-(thiazol-2-yl)-4-(trifluoromethyl)benzo[d]oxazol-2-yl)-3,8-diazabicyclo[3.2.1]octane-8-carboxylate The title compound was obtained in an amount of 172 mg from 200 mg of ethyl 2-(8-(tert-butoxycarbonyl)-3,8-diazabicyclo[3.2.1]octan-3-yl)-7-(thiazol-2-yl)-4-(trifluoromethyl)benzo[d]oxazole-5-carboxylate obtained in Example 163(b) by a similar method to Example 102 (a).

(b) tert-Butyl 3-(5-(1-hydroxyethyl)-7-(thiazol-2-yl)-4-(trifluoromethyl)benzo[d]oxazol-2-yl)-3,8-diazabicyclo[3.2.1]octane-8-carboxylate The title compound was obtained in an amount of 165 mg from 215 mg of tert-butyl 3-(5-formyl-7-(thiazol-2-yl)-4-(trifluoromethyl)benzo[d]oxazol-2-yl)-3,8-diazabicyclo[3.2.1]octane-8-carboxylate obtained in Example 171(a) by a similar method to Example 102 (b).

(c) tert-Butyl 3-(5-acethyl)-7-(thiazol-2-yl)-4-(trifluoromethyl)benzo[d]oxazol-2-yl)-3,8-diazabicyclo[3.2.1]octane-8-carboxylate The title compound was obtained in an amount of 89 mg from 102 mg of tert-butyl 3-(5-(1-hydroxyethyl)-7-(thiazol-2-yl)-4-(trifluoromethyl)benzo[d]oxazol-2-yl)-3,8-diazabicyclo[3.2.1]octane-8-carboxylate obtained in Example 171 (b) by a similar method to Example 102 (c).

(d) tert-Butyl 3-(5-(2-hydroxypropan-2-yl)-7-(thiazol-2-yl)-4-(trifluoromethyl)benzo[d]oxazol-2-yl)-3,8-diazabicyclo[3.2.1]octane-8-carboxylate 89 mg of tert-butyl 3-(5-acethyl)-7-(thiazol-2-yl)-4-(trifluoromethyl)benzo[d]oxazol-2-yl)-3,8-diazabicyclo[3.2.1]octane-8-carboxylate obtained in Example 171(c) was dissolved in tetrahydrofuran (1.1 mL), then 0.6M solution of Lanthanum (III) chloride bis-lithium chloride complex in tetrahydrofuran (2.7 mL, 8 equivalents) and 0.92M solution of methylmagnesium bromide in tetrahydrofuran (1.5 mL, 8 equivalents) was added thereto at −78° C., followed by stirring at −78° C. for 30 min. The formation of the product was confirmed by TLC (eluent, hexane:ethyl acetate=1:1), and then saturated ammonium chloride aqueous solution were added thereto, followed by extraction using ethyl acetate. Thereafter, the organic phase was dried over anhydrous magnesium sulfate, followed by filtration and vacuum concentration of the filtrate, and thus obtaining 91 mg of the title compound by purification of the residue by preparative TLC (eluent, hexane:ethyl acetate=1:1).

(e) tert-Butyl 3-(5-(2-methoxypropan-2-yl)-7-(thiazol-2-yl)-4-(trifluoromethyl)benzo[d]oxazol-2-yl)-3,8-diazabicyclo[3.2.1]octane-8-carboxylate The title compound was obtained in an amount of 16 mg from 15 mg of the crude product of tert-butyl 3-(5-(2-hydroxypropan-2-yl)-7-(thiazol-2-yl)-4-(trifluoromethyl)benzo[d]oxazol-2-yl)-3,8-diazabicyclo[3.2.1]octane-8-carboxylate obtained in Example 171(d) by a similar method to Example 102(e) except that 25 equivalents of methyl iodide and 20 equivalents of sodium hydride were used.

(f) 2-(3,8-Diazabicyclo[3.2.1]octan-3-yl)-5-(2-methoxypropan-2-yl)-7-(thiazol-2-yl)-4-(trifluoromethyl)benzo[d]oxazole The title compound was obtained in an amount of 10 mg from 16 mg of tert-butyl 3-(5-(2-methoxypropan-2-yl)-7-(thiazol-2-yl)-4-(trifluoromethyl)benzo[d]oxazol-2-yl)-3,8-diazabicyclo[3.2.1]octane-8-carboxylate obtained in Example 171(e) by a similar method to Example 1(c).

Example 172

2-(2-(3,8-Diazabicyclo[3.2.1]octan-3-yl)-7-(thiazol-2-yl)benzo[d]oxazol-5-yl)propan-2-ol (a) tert-Butyl 3-(5-(2-hydroxypropan-2-yl)-7-(thiazol-2-yl)benzo[d]oxazol-2-yl)-3,8-diazabicyclo[3.2.1]octane-8-carboxylate The title compound was obtained in an amount of 41 mg from 52 mg of ethyl 2-(8-(tert-butoxycarbonyl)-3,8-diazabicyclo[3.2.1]octan-3-yl)-7-(thiazol-2-yl)benzo[d]oxazole-5-carboxylate obtained in Example 86(b) by a similar method to Example 171(d).

(b) 2-(2-(3,8-Diazabicyclo[3.2.1]octan-3-yl)-7-(thiazol-2-yl)benzo[d]oxazol-5-yl)propan-2-ol The title compound was obtained in an amount of 8.9 mg from 11 mg of tert-butyl 3-(5-(2-hydroxypropan-2-yl)-7-(thiazol-2-yl)benzo[d]oxazol-2-yl)-3,8-diazabicyclo[3.2.1]octane-8-carboxylate obtained in Example 172 (a) by a similar method to Example 1(c).

Example 173

2-(2-(3,6-Diazabicyclo[3.1.1]heptan-3-yl)-7-(thiazol-2-yl)benzo[d]oxazol-5-yl)propan-2-ol (a) tert-Butyl 3-(5-(2-hydroxypropan-2-yl)-7-(thiazol-2-yl)benzo[d]oxazol-2-yl)-3,6-diazabicyclo[3.1.1]heptane-6-carboxylate The title compound was obtained in an amount of 43 mg from 50 mg of ethyl 2-(6-(tert-butoxycarbonyl)-3,6-diazabicyclo[3.1.1]heptan-3-yl)-7-(thiazol-2-yl)benzo[d]oxazole-5-carboxylate obtained in Example 87 (b) by a similar method to Example 171(d).

(b) 2-(2-(3,6-Diazabicyclo[3.1.1]heptan-3-yl)-7-(thiazol-2-yl)benzo[d]oxazol-5-yl)propan-2-ol The title compound was obtained in an amount of 26 mg from 43 mg of tert-butyl 3-(5-(2-hydroxypropan-2-yl)-7-(thiazol-2-yl)benzo[d]oxazol-2-yl)-3,6-diazabicyclo[3.1.1]heptane-6-carboxylate obtained in Example 173 (a) by a similar method to Example 1(c).

Example 174

2-(3,6-Diazabicyclo[3.1.1]heptan-3-yl)-5-(2-methoxypropan-2-yl)-7-(thiazol-2-yl)benzo[d]oxazole (a) tert-Butyl 3-(5-(2-methoxypropan-2-yl)-7-(thiazol-2-yl)benzo[d]oxazol-2-yl)-3,6-diazabicyclo[3.1.1]heptane-6-carboxylate The title compound was obtained in an amount of 29 mg from 29 mg of tert-butyl 3-(5-(2-hydroxypropan-2-yl)-7-(thiazol-2-yl)benzo[d]oxazol-2-yl)-3,6-diazabicyclo[3.1.1]heptane-6-carboxylate obtained in Example 173 (a) by a similar method to Example 102 (e).

(b) 2-(3,6-Diazabicyclo[3.1.1]heptan-3-yl)-5-(2-methoxypropan-2-yl)-7-(thiazol-2-yl)benzo[d]oxazole The title compound was obtained in an amount of 16 mg from 29 mg of tert-butyl 3-(5-(2-methoxypropan-2-yl)-7-(thiazol-2-yl)benzo[d]oxazol-2-yl)-3,6-diazabicyclo[3.1.1]heptane-6-carboxylate obtained in Example 174 (a) by a similar method to Example 1(c).

Example 175

2-(3,8-Diazabicyclo[3.2.1]octan-3-yl)-5-(2-methoxypropan-2-yl)-7-(thiazol-2-yl)benzo[d]oxazole (a) tert-Butyl 3-(5-(2-methoxypropan-2-yl)-7-(thiazol-2-yl)benzo[d]oxazol-2-yl)-3,8-diazabicyclo[3.2.1]octane-8-carboxylate The title compound was obtained in an amount of 22 mg from 23 mg of tert-butyl 3-(5-(2-hydroxypropan-2-yl)-7-(thiazol-2-yl)benzo[d]oxazol-2-yl)-3,8-diazabicyclo[3.2.1]octane-8-carboxylate obtained in Example 172 (a) by a similar method to Example 102 (e).

(b) 2-(3,8-Diazabicyclo[3.2.1]octan-3-yl)-5-(2-methoxypropan-2-yl)-7-(thiazol-2-yl)benzo[d]oxazole The title compound was obtained in an amount of 15 mg from 23 mg of tert-butyl 3-(5-(2-methoxypropan-2-yl)-7-(thiazol-2-yl)benzo[d]oxazol-2-yl)-3,8-diazabicyclo[3.2.1]octane-8-carboxylate obtained in Example 175 (a) by a similar method to Example 1(c).

Example 176

2-(3,6-Diazabicyclo[3.1.1]heptan-3-yl)-5-(2-methoxypropan-2-yl)-7-(thiazol-2-yl)-4-(trifluoromethyl)benzo[d]oxazole (a) tert-Butyl 3-(5-formyl-7-(thiazol-2-yl)-4-(trifluoromethyl)benzo[d]oxazol-2-yl)-3,6-diazabicyclo[3.1.1]heptane-6-carboxylate The title compound was obtained in an amount of 166 mg from 228 mg of ethyl 2-(6-(tert-butoxycarbonyl)-3,6-diazabicyclo[3.1.1]heptan-3-yl)-7-(thiazol-2-yl)-4-(trifluoromethyl)benzo[d]oxazole-5-carboxylate obtained in Example 165(b) by a similar method to Example 102 (a).

(b) tert-Butyl 3-(5-(1-hydroxyethyl)-7-(thiazol-2-yl)-4-(trifluoromethyl)benzo[d]oxazol-2-yl)-3,6-diazabicyclo[3.1.1]heptane-6-carboxylate The title compound was obtained as a crude product in an amount of 167 mg from 166 mg of tert-butyl 3-(5-formyl-7-(thiazol-2-yl)-4-(trifluoromethyl)benzo[d]oxazol-2-yl)-3,6-diazabicyclo[3.1.1]heptane-6-carboxylate obtained in Example 176(a) by a similar method to Example 102(b) except that the product was not purified by silica gel column chromatography.

(c) tert-Butyl 3-(5-acetyl-7-(thiazol-2-yl)-4-(trifluoromethyl)benzo[d]oxazol-2-yl)-3,6-diazabicyclo[3.1.1]heptane-6-carboxylate The title compound was obtained in an amount of 100 mg from 112 mg of tert-butyl 3-(5-(1-hydroxyethyl)-7-(thiazol-2-yl)-4-(trifluoromethyl)benzo[d]oxazol-2-yl)-3,6-diazabicyclo[3.1.1]heptane-6-carboxylate obtained in Example 176 (b) by a similar method to Example 102 (c).

(d) tert-Butyl 3-(5-(2-hydroxypropan-2-yl)-7-(thiazol-2-yl)-4-(trifluoromethyl)benzo[d]oxazol-2-yl)-3,6-diazabicyclo[3.1.1]heptane-6-carboxylate The title compound was obtained as a crude product in an amount of 77 mg from 74 mg of tert-butyl 3-(5-acetyl-7-(thiazol-2-yl)-4-(trifluoromethyl)benzo[d]oxazol-2-yl)-3,6-diazabicyclo[3.1.1]heptane-6-carboxylate obtained in Example 176(c) by a similar method to Example 171(d) except that the temperature of reaction mixture was raised from −78° C. to 0° C. after stirring and further stirred for 30 min.

(e) tert-Butyl 3-(5-(2-methoxypropan-2-yl)-7-(thiazol-2-yl)-4-(trifluoromethyl)benzo[d]oxazol-2-yl)-3,6-diazabicyclo[3.1.1]heptane-6-carboxylate The title compound was obtained as a crude product in an amount of 29 mg from 29 mg of the crude product of tert-butyl 3-(5-(2-hydroxypropan-2-yl)-7-(thiazol-2-yl)-4-(trifluoromethyl)benzo[d]oxazol-2-yl)-3,6-diazabicyclo[3.1.1]heptane-6-carboxylate obtained in Example 176(d) by a similar method to Example 102 (e) except that the product was not purified by preparative TLC.

(f) 2-(3,6-Diazabicyclo[3.1.1]heptan-3-yl)-5-(2-methoxypropan-2-yl)-7-(thiazol-2-yl)-4-(trifluoromethyl)benzo[d]oxazole The title compound was obtained in an amount of 14 mg from 29 mg of tert-butyl 3-(5-(2-methoxypropan-2-yl)-7-(thiazol-2-yl)-4-(trifluoromethyl)benzo[d]oxazol-2-yl)-3,6-diazabicyclo[3.1.1]heptane-6-carboxylate obtained in Example 176(e) by a similar method to Example 1(c).

Example 177

2-(2-(3,8-Diazabicyclo[3.2.1]octan-3-yl)-7-(thiazol-2-yl)-4-(trifluoromethyl)benzo[d]oxazol-5-yl)propan-2-ol The title compound was obtained in an amount of 9.2 mg from 16 mg of tert-butyl 3-(5-hydroxypropan-2-yl)-7-(thiazol-2-yl)-4-(trifluoromethyl)benzo[d]oxazol-2-yl)-3,8-diazabicyclo[3.2.1]octane-8-carboxylate obtained in Example 171(d) by a similar method to Example 1(c).

Example 178

2-(2-(3,6-Diazabicyclo[3.1.1]heptan-3-yl)-7-(thiazol-2-yl)-4-(trifluoromethyl)benzo[d]oxazol-5-yl)propan-2-ol The title compound was obtained in an amount of 25 mg from 50 mg of tert-butyl 3-(5-(2-hydroxypropan-2-yl)-7-(thiazol-2-yl)-4-(trifluoromethyl)benzo[d]oxazol-2-yl)-3,6-diazabicyclo[3.1.1]heptane-6-carboxylate obtained in Example 176(d) by a similar method to Example 1(c).

Example 179

1-(2-(3,8-Diazabicyclo[3.2.1]octan-3-yl)-7-(thiazol-2-yl)-4-(trifluoromethyl)benzo[d]oxazol-5-yl)ethan-1-one The title compound was obtained in an amount of 18 mg from 31 mg of tert-butyl 3-(5-acetyl-7-(thiazol-2-yl)-4-(trifluoromethyl)benzo[d]oxazol-2-yl)-3,8-diazabicyclo[3.2.1]octane-8-carboxylate obtained in Example 171(c) by a similar method to Example 1(c).

Example 180

1-(2-(3,6-Diazabicyclo[3.1.1]heptan-3-yl)-7-(thiazol-2-yl)-4-(trifluoromethyl)benzo[d]oxazol-5-yl)ethan-1-one The title compound was obtained in an amount of 17 mg from 25 mg of tert-butyl 3-(5-acetyl-7-(thiazol-2-yl)-4-(trifluoromethyl)benzo[d]oxazol-2-yl)-3,6-diazabicyclo[3.1.1]heptane-6-carboxylate obtained in Example 176(c) by a similar method to Example 1(c).

Example 181

1-(2-(3,8-Diazabicyclo[3.2.1]octan-3-yl)-7-(thiazol-2-yl)-4-(trifluoromethyl)benzo[d]oxazol-5-yl)ethan-1-ol The title compound was obtained in an amount of 7.0 mg from 12 mg of tert-butyl 3-(5-(1-hydroxyethyl)-7-(thiazol-2-yl)-4-(trifluoromethyl)benzo[d]oxazol-2-yl)-3,8-diazabicyclo[3.2.1]octane-8-carboxylate obtained in Example 171 (b) by a similar method to Example 1(c).

Example 182

1-(2-(3,6-Diazabicyclo[3.1.1]heptan-3-yl)-7-(thiazol-2-yl)-4-(trifluoromethyl)benzo[d]oxazol-5-yl)ethan-1-ol The title compound was obtained in an amount of 14 mg from 28 mg of tert-butyl 3-(5-(1-hydroxyethyl)-7-(thiazol-2-yl)-4-(trifluoromethyl)benzo[d]oxazol-2-yl)-3,6-diazabicyclo[3.1.1]heptane-6-carboxylate obtained in Example 176 (b) by a similar method to Example 1(c).

Example 183

1-(2-(3,8-Diazabicyclo[3.2.1]octan-3-yl)-7-(thiazol-2-yl)-4-(trifluoromethyl)benzo[d]oxazol-5-yl)-2,2-difluoroethan-1-ol (a) tert-Butyl 3-(5-(2,2-difluoro-1-hydroxyethyl)-7-(thiazol-2-yl)-4-(trifluoromethyl)benzo[d]oxazol-2-yl)-3,8-diazabicyclo[3.2.1]octane-8-carboxylate 10 mg of tert-butyl 3-(5-formyl-7-(thiazol-2-yl)-4-(trifluoromethyl)benzo[d]oxazol-2-yl)-3,8-diazabicyclo[3.2.1]octane-8-carboxylate obtained in Example 171(a), triphenylphosphine (10.5 mg, 2 equivalents) and (bromodifluoromethyl)trimethylsilane (6.2 μL, 2 equivalents) were dissolved in DMPU (100 μL), followed by stirring at room temperature for 18 hours. 1M potassium hydroxide (0.4 mL) was added and stirred at room temperature for 1 hour. Thereafter, the organic phase extracted by ethyl acetate was dried over anhydrous magnesium sulfate, followed by filtration and vacuum concentration of the filtrate, and thus obtaining 6.4 mg of the title compound by purification of the residue by preparative TLC (eluent, hexane:ethyl acetate=1:1).

(b) 1-(2-(3,8-Diazabicyclo[3.2.1]octan-3-yl)-7-(thiazol-2-yl)-4-(trifluoromethyl)benzo[d]oxazol-5-yl)-2,2-difluoroethan-1-ol The title compound was obtained in an amount of 2.9 mg from 6.4 mg of tert-butyl 3-(5-(2,2-difluoro-1-hydroxyethyl)-7-(thiazol-2-yl)-4-(trifluoromethyl)benzo[d]oxazol-2-yl)-3,8-diazabicyclo[3.2.1]octane-8-carboxylate obtained in Example 183 (a) by a similar method to Example 1(c).

Example 184

2-(3,8-Diazabicyclo[3.2.1]octan-3-yl)-5-(1-methoxyethyl)-7-(thiazol-2-yl)-4-(trifluoromethyl)benzo[d]oxazole (a) tert-Butyl 3-(5-(1-methoxyethyl)-7-(thiazol-2-yl)-4-(trifluoromethyl)benzo[d]oxazol-2-yl)-3,8-diazabicyclo[3.2.1]octane-8-carboxylate The title compound was obtained as a crude product in an amount of 16 mg from 15 mg of tert-butyl 3-(5-(1-hydroxyethyl)-7-(thiazol-2-yl)-4-(trifluoromethyl)benzo[d]oxazol-2-yl)-3,8-diazabicyclo[3.2.1]octane-8-carboxylate obtained in Example 171(b) by a similar method to Example 102(e) except that the product was not purified by preparative TLC.

(b) 2-(3,8-Diazabicyclo[3.2.1]octan-3-yl)-5-(1-methoxyethyl)-7-(thiazol-2-yl)-4-(trifluoromethyl)benzo[d]oxazole The title compound was obtained in an amount of 12 mg from 16 mg of tert-butyl 3-(5-(1-methoxyethyl)-7-(thiazol-2-yl)-4-(trifluoromethyl)benzo[d]oxazol-2-yl)-3,8-diazabicyclo[3.2.1]octane-8-carboxylate obtained in Example 184 (a) by a similar method to Example 1(c).

Example 185

2-(3,6-Diazabicyclo[3.1.1]heptan-3-yl)-5-(1-methoxyethyl)-7-(thiazol-2-yl)-4-(trifluoromethyl)benzo[d]oxazole (a) tert-Butyl 3-(5-(1-methoxyethyl)-7-(thiazol-2-yl)-4-(trifluoromethyl)benzo[d]oxazol-2-yl)-3,6-diazabicyclo[3.1.1]heptane-6-carboxylate The title compound was obtained as a crude product in an amount of 22 mg from 21 mg of tert-butyl 3-(5-(1-hydroxyethyl)-7-(thiazol-2-yl)-4-(trifluoromethyl)benzo[d]oxazol-2-yl)-3,6-diazabicyclo[3.1.1]heptane-6-carboxylate obtained in Example 176(b) by a similar method to Example 102(e) except that the product was not purified by preparative TLC.

(b) 2-(3,6-Diazabicyclo[3.1.1]heptan-3-yl)-5-(1-methoxyethyl)-7-(thiazol-2-yl)-4-(trifluoromethyl)benzo[d]oxazole The title compound was obtained in an amount of 14 mg from 22 mg of tert-butyl 3-(5-(1-methoxyethyl)-7-(thiazol-2-yl)-4-(trifluoromethyl)benzo[d]oxazol-2-yl)-3,6-diazabicyclo[3.1.1]heptane-6-carboxylate obtained in Example 185 (a) by a similar method to Example 1(c).

Example 186

Ethyl 2-(3,8-diazabicyclo[3.2.1]octan-3-yl)-7-(thiazol-2-yl)-4-(trifluoromethoxy)benzo[d]oxazole-5-carboxylate (a) Ethyl 7-bromo-2-(8-(tert-butoxycarbonyl)-3,8-diazabicyclo[3.2.1]octan-3-yl)-4-(trifluoromethoxy)benzo[d]oxazole-5-carboxylate The title compound was obtained in an amount of 129 mg from 10 mg of ethyl 7-Bromo-2-mercapto-4-(trifluoromethoxy)benzo[d]oxazole-5-carboxylate obtained in Reference Example 20 and tert-butyl 3,8-diazabicyclo[3.2.1]octane-8-carboxylate by a similar method to Example 1(a).

(b) Ethyl 2-(8-(tert-butoxycarbonyl)-3,8-diazabicyclo[3.2.1]octan-3-yl)-7-(thiazol-2-yl)-4-(trifluoromethoxy)benzo[d]oxazole-5-carboxylate The title compound was obtained as a crude product in an amount of 600 mg from 378 mg of ethyl 7-bromo-2-(8-(tert-butoxycarbonyl)-3,8-diazabicyclo[3.2.1]octan-3-yl)-4-(trifluoromethoxy)benzo[d]oxazole-5-carboxylate obtained in Example 186(a) by a similar method to Example 2(b) except that toluene was used instead of 1,4-dioxane and tetrakis(triphenylphosphine)palladium(0) was used instead of bis(triphenylphosphine)palladium(II) dichloride.

(c) Ethyl 2-(3,8-diazabicyclo[3.2.1]octan-3-yl)-7-(thiazol-2-yl)-4-(trifluoromethoxy)benzo[d]oxazole-5-carboxylate The title compound was obtained in an amount of 115 mg from 400 mg of ethyl 2-(8-(tert-butoxycarbonyl)-3,8-diazabicyclo[3.2.1]octan-3-yl)-7-(thiazol-2-yl)-4-(trifluoromethoxy)benzo[d]oxazole-5-carboxylate obtained in Example 186(b) by a similar method to Example 1(c).

Example 187

Ethyl 2-(3,6-diazabicyclo[3.1.1]heptan-3-yl)-7-(thiazol-2-yl)-4-(trifluoromethoxy)benzo[d]oxazole-5-carboxylate (a) Ethyl 7-bromo-2-(6-(tert-butoxycarbonyl)-3,6-diazabicyclo[3.1.1]heptan-3-yl)-4-(trifluoromethoxy)benzo[d]oxazole-5-carboxylate The title compound was obtained in an amount of 110 mg from 120 mg of ethyl 7-bromo-2-mercapto-4-(trifluoromethoxy)benzo[d]oxazole-5-carboxylate obtained in Reference Example 20 by a similar method to Example 1(a) except that tert-butyl 3,6-diazabicyclo[3.1.1]heptane-6-carboxylate was used instead of tert-butyl 3,8-diazabicyclo[3.2.1]octane-8-carboxylate.

(b) Ethyl 2-(6-(tert-butoxycarbonyl)-3,6-diazabicyclo[3.1.1]heptan-3-yl)-7-(thiazol-2-yl)-4-(trifluoromethoxy)benzo[d]oxazole-5-carboxylate The title compound was obtained as a crude product in an amount of 170 mg from 110 mg of ethyl 7-bromo-2-(6-(tert-butoxycarbonyl)-3,6-diazabicyclo[3.1.1]heptan-3-yl)-4-(trifluoromethoxy)benzo[d]oxazole-5-carboxylate obtained in Example 187(a) by a similar method to Example 2(b) except that toluene was used instead of 1,4-dioxane and tetrakis(triphenylphosphine)palladium(0) was used instead of bis(triphenylphosphine)palladium(II) dichloride.

(c) Ethyl 2-(3,6-diazabicyclo[3.1.1]heptan-3-yl)-7-(thiazol-2-yl)-4-(trifluoromethoxy)benzo[d]oxazole-5-carboxylate The title compound was obtained in an amount of 75 mg from 170 mg of ethyl 2-(6-(tert-butoxycarbonyl)-3,6-diazabicyclo[3.1.1]heptan-3-yl)-7-(thiazol-2-yl)-4-(trifluoromethoxy)benzo[d]oxazole-5-carboxylate obtained in Example 187(b) by a similar method to Example 1(c).

Example 188

Ethyl 2-(3,9-diazabicyclo[3.3.1]nonan-3-yl)-7-(thiazol-2-yl)-4-(trifluoromethoxy)benzo[d]oxazole-5-carboxylate (a) Ethyl 7-bromo-2-(9-(tert-butoxycarbonyl)-3,9-diazabicyclo[3.3.1]nonan-3-yl)-4-(trifluoromethoxy)benzo[d]oxazole-5-carboxylate The title compound was obtained in an amount of 170 mg from 120 mg of ethyl 7-bromo-2-mercapto-4-(trifluoromethoxy)benzo[d]oxazole-5-carboxylate obtained in Reference Example 20 by a similar method to Example 1(a) except that tert-butyl 3,9-diazabicyclo[3.3.1]nonane-9-carboxylate was used instead of tert-butyl 3,8-diazabicyclo[3.2.1]octane-8-carboxylate.

(b) Ethyl 2-(9-(tert-butoxycarbonyl)-3,9-diazabicyclo[3.3.1]nonan-3-yl)-7-(thiazol-2-yl)-4-(trifluoromethoxy)benzo[d]oxazole-5-carboxylate The title compound was obtained as a crude product in an amount of 180 mg from 170 mg of ethyl 7-bromo-2-(9-(tert-butoxycarbonyl)-3,9-diazabicyclo[3.3.1]nonan-3-yl)-4-(trifluoromethoxy)benzo[d]oxazole-5-carboxylate obtained in Example 188(a) by a similar method to Example 2(b) except that toluene was used instead of 1,4-dioxane and tetrakis(triphenylphosphine)palladium(0) was used instead of bis(triphenylphosphine)palladium(II) dichloride.

(c) Ethyl 2-(3,9-diazabicyclo[3.3.1]nonan-3-yl)-7-(thiazol-2-yl)-4-(trifluoromethoxy)benzo[d]oxazole-5-carboxylate The title compound was obtained in an amount of 110 mg from 180 mg of ethyl 2-(9-(tert-butoxycarbonyl)-3,9-diazabicyclo[3.3.1]nonan-3-yl)-7-(thiazol-2-yl)-4-(trifluoromethoxy)benzo[d]oxazole-5-carboxylate obtained in Example 188 (b) by a similar method to Example 1(c).

Example 189

2-(3,8-Diazabicyclo[3.2.1]octan-3-yl)-7-(thiazol-2-yl)-4-(trifluoromethoxy)benzo[d]oxazole-5-carboxylic acid 54 mg of ethyl 2-(3,8-diazabicyclo[3.2.1]octan-3-yl)-7-(thiazol-2-yl)-4-(trifluoromethoxy)benzo[d]oxazole-5-carboxylate obtained in Example 186(c) was dissolved in tetrahydrofuran (3.2 mL), ethanol (3.2 mL) and distilled water (3.2 mL), and then lithium hydroxide (9 mg, 2 equivalents) was added, followed by stirring at 80° C. for 4 hours. After the formation of the product was confirmed by TLC, the pH of residue obtained by vacuum concentration of the reaction mixture was adjusted to 2 by addition of citric acid.

A solid substance formed was filtered and dried under reduced pressure to afford 40 mg of the title compound.

Example 190

2-(3,6-Diazabicyclo[3.1.1]heptan-3-yl)-7-(thiazol-2-yl)-4-(trifluoromethoxy)benzo[d]oxazole-5-carboxylic acid The title compound was obtained in an amount of 25 mg from 39 mg of ethyl 2-(3,6-diazabicyclo[3.1.1]heptan-3-yl)-7-(thiazol-2-yl)-4-(trifluoromethoxy)benzo[d]oxazole-5-carboxylate obtained in Example 187(c) by a similar method to Example 189.

Example 191

2-(3,9-Diazabicyclo[3.3.1]nonan-3-yl)-7-(thiazol-2-yl)-4-(trifluoromethoxy)benzo[d]oxazole-5-carboxylic acid The title compound was obtained in an amount of 40 mg from 62 mg of ethyl 2-(3,9-diazabicyclo[3.3.1]nonan-3-yl)-7-(thiazol-2-yl)-4-(trifluoromethoxy)benzo[d]oxazole-5-carboxylate obtained in Example 188(c) by a similar method to Example 189.

Example 192

(2-(3,8-Diazabicyclo[3.2.1]octan-3-yl)-7-(thiazol-2-yl)-4-(trifluoromethoxy)benzo[d]oxazol-5-yl)(azetidin-1-yl)methanone (a) tert-Butyl 3-(5-(azetidine-1-carbonyl)-7-(thiazol-2-yl)-4-(trifluoromethoxy)benzo[d]oxazol-2-yl)-3,8-diazabicyclo[3.2.1]octane-8-carboxylate The title compound was obtained in an amount of 26 mg from 30 mg of 2-(3,8-diazabicyclo[3.2.1]octan-3-yl)-7-(thiazol-2-yl)-4-(trifluoromethoxy)benzo[d]oxazole-5-carboxylic acid obtained in Example 189 by a similar method to Example 94(b) except that azetidine hydrochloride (21 mg, 4 equivalents) and 4-(4,6-dimethoxy-1,3,5-triazin-2-yl)-4-methylmorpholinium chloride n-hydrate (content 82.2%, 74.7 mg, 4 equivalents) were used instead of 2M solution of dimethylamine in methanol.

(b) (2-(3,8-Diazabicyclo[3.2.1]octan-3-yl)-7-(thiazol-2-yl)-4-(trifluoromethoxy)benzo[d]oxazol-5-yl) (azetidin-1-yl)methanone The title compound was obtained in an amount of 21 mg from 26 mg of tert-butyl 3-(5-(azetidine-1-carbonyl)-7-(thiazol-2-yl)-4-(trifluoromethoxy)benzo[d]oxazol-2-yl)-3,8-diazabicyclo[3.2.1]octane-8-carboxylate obtained in Example 192 (a) by a similar method to Example 1(c).

Example 193

2-(3,8-Diazabicyclo[3.2.1]octan-3-yl)-N-(2-hydroxyethyl)-N-methyl-7-(thiazol-2-yl)-4-(trifluoromethoxy)benzo[d]oxazole-5-carboxamide (a) tert-Butyl 3-(5-((2-hydroxyethyl) (methyl)carbamoyl)-7-(thiazol-2-yl)-4-(trifluoromethoxy)benzo[d]oxazol-2-yl)-3,8-diazabicyclo[3.2.1]octane-8-carboxylate The title compound was obtained in an amount of 16 mg from 16 mg of 2-(3,8-diazabicyclo[3.2.1]octan-3-yl)-7-(thiazol-2-yl)-4-(trifluoromethoxy)benzo[d]oxazole-5-carboxylic acid obtained in Example 189 by a similar method to Example 94(b) except that 2-(methylamino)ethan-1-ol (9.6 µL, 4 equivalents) and 4-(4,6-dimethoxy-1,3,5-triazin-2-yl)-4-methylmorpholinium chloride n-hydrate (content 82.2%, 40 mg, 4 equivalents) were used instead of 2M solution of dimethylamine in methanol.

(b) 2-(3,8-Diazabicyclo[3.2.1]octan-3-yl)-N-(2-hydroxyethyl)-N-methyl-7-(thiazol-2-yl)-4-(trifluoromethoxy)benzo[d]oxazole-5-carboxamide The title compound was obtained in an amount of 13 mg from 16 mg of tert-butyl 3-(5-((2-hydroxyethyl) (methyl)carbamoyl)-7-(thiazol-2-yl)-4-(trifluoromethoxy)benzo[d]oxazol-2-yl)-3,8-diazabicyclo[3.2.1]octane-8-carboxylate obtained in Example 193 (a) by a similar method to Example 1(c).

Example 194

(2-(3,8-Diazabicyclo[3.2.1]octan-3-yl)-7-(thiazol-2-yl)-4-(trifluoromethoxy)benzo[d]oxazol-5-yl)(3-hydroxy-3-(trifluoromethyl)azetidin-1-yl)methanone (a) tert-Butyl 3-(5-(3-hydroxy-3-(trifluoromethyl) azetidine-1-carbonyl)-7-(thiazol-2-yl)-4-(trifluoromethoxy)benzo[d]oxazol-2-yl)-3,8-diazabicyclo [3.2.1]octane-8-carboxylate The title compound was obtained as a crude product in an amount of 39 mg from 29 mg of 2-(3,8-diazabicyclo[3.2.1] octan-3-yl)-7-(thiazol-2-yl)-4-(trifluoromethoxy)benzo[d] oxazole-5-carboxylic acid obtained in Example 189 by a similar method to Example 94(b) except that 3-(trifluoromethyl)azetidin-3-ol hydrochloride (38 mg, 4 equivalents) and 4-(4,6-dimethoxy-1,3,5-triazin-2-yl)-4-methylmorpholinium chloride n-hydrate (content 82.2%, 71 mg, 4 equivalents) were used instead of 2M solution of dimethylamine in methanol.

(b) (2-(3,8-Diazabicyclo[3.2.1]octan-3-yl)-7-(thiazol-2-yl)-4-(trifluoromethoxy)benzo[d]oxazol-5-yl) (3-hydroxy-3-(trifluoromethyl)azetidin-1-yl)methanone The title compound was obtained in an amount of 15 mg from 39 mg of tert-butyl 3-(5-(3-hydroxy-3-(trifluoromethyl)azetidine-1-carbonyl)-7-(thiazol-2-yl)-4-(trifluoromethoxy)benzo[d]oxazol-2-yl)-3,8-diazabicyclo[3.2.1] octane-8-carboxylate obtained in Example 194 (a) by a similar method to Example 1(c).

Example 195

2-(2-(3,8-Diazabicyclo[3.2.1]octan-3-yl)-7-(thiazol-2-yl)-4-(trifluoromethoxy)benzo[d]oxazol-5-yl)propan-2-ol (a) tert-Butyl 3-(5-(2-hydroxypropan-2-yl)-7-(thiazol-2-yl)-4-(trifluoromethoxy)benzo[d]oxazol-2-yl)-3,8-diazabicyclo[3.2.1]octane-8-carboxylate The title compound was obtained as a crude product in an amount of 49 mg from 50 mg of ethyl 2-(8-(tert-butoxycarbonyl)-3,8-diazabicyclo[3.2.1]octan-3-yl)-7-(thiazol-2-yl)-4-(trifluoromethoxy)benzo[d]oxazole-5-carboxylate obtained in Example 186(b) by a similar method to Example 171(d)

(b) 2-(2-(3,8-Diazabicyclo[3.2.1]octan-3-yl)-7-(thiazol-2-yl)-4-(trifluoromethoxy)benzo[d]oxazol-5-yl) propan-2-ol The title compound was obtained in an amount of 30 mg from 49 mg of tert-butyl 3-(5-(2-hydroxypropan-2-yl)-7-(thiazol-2-yl)-4-(trifluoromethoxy)benzo[d]oxazol-2-yl)-3,8-diazabicyclo[3.2.1]octane-8-carboxylate obtained in Example 195 (a) by a similar method to Example 1(c).

Example 196

2-(2-(3,6-Diazabicyclo[3.1.1]heptan-3-yl)-7-(thiazol-2-yl)-4-(trifluoromethoxy)benzo[d]oxazol-5-yl) propan-2-ol (a) tert-Butyl 3-(5-(2-hydroxypropan-2-yl)-7-(thiazol-2-yl)-4-(trifluoromethoxy)benzo[d]oxazol-2-yl)-3,6-diazabicyclo[3.1.1]heptane-6-carboxylate The title compound was obtained in an amount of 26 mg from 49 mg of ethyl 2-(6-(tert-butoxycarbonyl)-3,6-diazabicyclo[3.1.1]heptan-3-yl)-7-(thiazol-2-yl)-4-(trifluoromethoxy)benzo[d]oxazole-5-carboxylate obtained in Example 187 (b) by a similar method to Example 171(d) except that the crude product was purified by silica gel column chromatography.

(b) 2-(2-(3,6-Diazabicyclo[3.1.1]heptan-3-yl)-7-(thiazol-2-yl)-4-(trifluoromethoxy)benzo[d]oxazol-5-yl)propan-2-ol The title compound was obtained in an amount of 11 mg from 26 mg of tert-butyl 3-(5-(2-hydroxypropan-2-yl)-7-

(thiazol-2-yl)-4-(trifluoromethoxy)benzo[d]oxazol-2-yl)-3,6-diazabicyclo[3.1.1]heptane-6-carboxylate obtained in Example 196(a) by a similar method to Example 1(c).

Example 197

2-(2-(3,9-Diazabicyclo[3.3.1]nonan-3-yl)-7-(thiazol-2-yl)-4-(trifluoromethoxy)benzo[d]oxazol-5-yl)propan-2-ol (a) tert-Butyl 3-(5-(2-hydroxypropan-2-yl)-7-(thiazol-2-yl)-4-(trifluoromethoxy)benzo[d]oxazol-2-yl)-3,9-diazabicyclo[3.3.1]nonane-9-carboxylate The title compound was obtained in an amount of 59 mg from 86 mg of ethyl 2-(9-(tert-butoxycarbonyl)-3,9-diazabicyclo[3.3.1]nonan-3-yl)-7-(thiazol-2-yl)-4-(trifluoromethoxy)benzo[d]oxazole-5-carboxylate obtained in Example 188(b) by a similar method to Example 171(d) except that the crude product was purified by silica gel column chromatography.

(b) 2-(2-(3,9-Diazabicyclo[3.3.1]nonan-3-yl)-7-(thiazol-2-yl)-4-(trifluoromethoxy)benzo[d]oxazol-5-yl)propan-2-ol The title compound was obtained in an amount of 15 mg from 26 mg of tert-butyl 3-(5-(2-hydroxypropan-2-yl)-7-(thiazol-2-yl)-4-(trifluoromethoxy)benzo[d]oxazol-2-yl)-3,9-diazabicyclo[3.3.1]nonane-9-carboxylate obtained in Example 197 (a) by a similar method to Example 1(c).

Example 198

2-(3,8-Diazabicyclo[3.2.1]octan-3-yl)-5-(2-methoxypropan-2-yl)-7-(thiazol-2-yl)-4-(trifluoromethoxy)benzo[d]oxazole (a) tert-Butyl 3-(5-(2-methoxypropan-2-yl)-7-(thiazol-2-yl)-4-(trifluoromethoxy)benzo[d]oxazol-2-yl)-3,8-diazabicyclo[3.2.1]octane-8-carboxylate The title compound was obtained in an amount of 18 mg from 30 mg of the crude product of tert-butyl 3-(5-(2-hydroxypropan-2-yl)-7-(thiazol-2-yl)-4-(trifluoromethoxy)benzo[d]oxazol-2-yl)-3,8-diazabicyclo[3.2.1]octane-8-carboxylate obtained in Example 195 (a) by a similar method to Example 102 (e).

(b) 2-(3,8-Diazabicyclo[3.2.1]octan-3-yl)-5-(2-methoxypropan-2-yl)-7-(thiazol-2-yl)-4-(trifluoromethoxy)benzo[d]oxazole The title compound was obtained in an amount of 11 mg from 18 mg of tert-butyl 3-(5-(2-methoxypropan-2-yl)-7-(thiazol-2-yl)-4-(trifluoromethoxy)benzo[d]oxazol-2-yl)-3,8-diazabicyclo[3.2.1]octane-8-carboxylate obtained in Example 198 (a) by a similar method to Example 1(c).

Example 199

2-(3,6-Diazabicyclo[3.1.1]heptan-3-yl)-5-(2-methoxypropan-2-yl)-7-(thiazol-2-yl)-4-(trifluoromethoxy)benzo[d]oxazole (a) tert-Butyl 3-(5-(2-methoxypropan-2-yl)-7-(thiazol-2-yl)-4-(trifluoromethoxy)benzo[d]oxazol-2-yl)-3,6-diazabicyclo[3.1.1]heptane-6-carboxylate The title compound was obtained in an amount of 38 mg from 71 mg of tert-butyl 3-(5-(2-hydroxypropan-2-yl)-7-(thiazol-2-yl)-4-(trifluoromethoxy)benzo[d]oxazol-2-yl)-3,6-diazabicyclo[3.1.1]heptane-6-carboxylate obtained in Example 196(a) by a similar method to Example 102 (e).

(b) 2-(3,6-Diazabicyclo[3.1.1]heptan-3-yl)-5-(2-methoxypropan-2-yl)-7-(thiazol-2-yl)-4-(trifluoromethoxy)benzo[d]oxazole The title compound was obtained in an amount of 20 mg from 38 mg of tert-butyl 3-(5-(2-methoxypropan-2-yl)-7-(thiazol-2-yl)-4-(trifluoromethoxy)benzo[d]oxazol-2-yl)-3,6-diazabicyclo[3.1.1]heptane-6-carboxylate obtained in Example 199(a) by a similar method to Example 1(c).

Example 200

2-(3,9-Diazabicyclo[3.3.1]nonan-3-yl)-5-(2-methoxypropan-2-yl)-7-(thiazol-2-yl)-4-(trifluoromethoxy)benzo[d]oxazole (a) tert-Butyl 3-(5-(2-methoxypropan-2-yl)-7-(thiazol-2-yl)-4-(trifluoromethoxy)benzo[d]oxazol-2-yl)-3,9-diazabicyclo[3.3.1]nonane-9-carboxylate The title compound was obtained in an amount of 23 mg from 32 mg of tert-butyl 3-(5-(2-hydroxypropan-2-yl)-7-(thiazol-2-yl)-4-(trifluoromethoxy)benzo[d]oxazol-2-yl)-3,9-diazabicyclo[3.3.1]nonane-9-carboxylate obtained in Example 197 (a) by a similar method to Example 102 (e).

(b) 2-(3,9-Diazabicyclo[3.3.1]nonan-3-yl)-5-(2-methoxypropan-2-yl)-7-(thiazol-2-yl)-4-(trifluoromethoxy)benzo[d]oxazole The title compound was obtained in an amount of 13 mg from 23 mg of tert-butyl 3-(5-(2-methoxypropan-2-yl)-7-(thiazol-2-yl)-4-(trifluoromethoxy)benzo[d]oxazol-2-yl)-3,9-diazabicyclo[3.3.1]nonane-9-carboxylate obtained in Example 200(a) by a similar method to Example 1(c).

Example 201

(2-(3,8-Diazabicyclo[3.2.1]octan-3-yl)-7-(thiazol-2-yl)-4-(trifluoromethoxy)benzo[d]oxazol-5-yl)methanol (a) tert-Butyl 3-(5-(hydroxymethyl)-7-(thiazol-2-yl)-4-(trifluoromethoxy)benzo[d]oxazol-2-yl)-3,8-diazabicyclo[3.2.1]octane-8-carboxylate 21 mg of ethyl 2-(8-(tert-butoxycarbonyl)-3,8-diazabicyclo[3.2.1]octan-3-yl)-7-(thiazol-2-yl)-4-(trifluoromethoxy)benzo[d]oxazole-5-carboxylate obtained in Example 186(b) was dissolved in toluene (370 μL), then 1.0M solution (0.19 mL, 5 equivalents) of diisobutylaluminium hydride in toluene was added thereto at −78° C., followed by stirring for 1 hour.

The formation of the product was confirmed by TLC (eluent, hexane:ethyl acetate=1:1), and then saturated ammonium chloride aqueous solution was added thereto, and the reaction mixture was subjected to Celite® filtration. Thereafter, the organic phase extracted by ethyl acetate was washed and dried over anhydrous magnesium sulfate, followed by filtration, and thus obtaining 20 mg of the title compound as a crude product by vacuum concentration of the filtrate.

(b) (2-(3,8-Diazabicyclo[3.2.1]octan-3-yl)-7-(thiazol-2-yl)-4-(trifluoromethoxy)benzo[d]oxazol-5-yl)methanol The title compound was obtained in an amount of 6.3 mg from 15 mg of tert-butyl 3-(5-(hydroxymethyl)-7-(thiazol-2-yl)-4-(trifluoromethoxy)benzo[d]oxazol-2-yl)-3,8-diazabicyclo[3.2.1]octane-8-carboxylate obtained in Example 201(a) by a similar method to Example 1(c).

Example 202

1-(2-(3,8-Diazabicyclo[3.2.1]octan-3-yl)-7-(thiazol-2-yl)-4-(trifluoromethoxy)benzo[d]oxazol-5-yl)ethan-1-ol (a) tert-Butyl 3-(5-formyl-7-(thiazol-2-yl)-4-(trifluoromethoxy)benzo[d]oxazol-2-yl)-3,8-diazabicyclo[3.2.1]octane-8-carboxylate 20 mg of tert-butyl 3-(5-(hydroxymethyl)-7-(thiazol-2-yl)-4-(trifluoromethoxy)benzo[d]oxazol-2-yl)-3,8-diazabicyclo[3.2.1]octane-8-carboxylate obtained in Example 201 (a) and Dess-Martin Periodinane (31 mg, 2 equivalents) were dissolved in chloroform (370 µL), followed by stirring at 0° C. for 3 hours. The formation of the product was confirmed by TLC (eluent, hexane:ethyl acetate=1:1), and then saturated aqueous sodium bicarbonate and saturated aqueous sodium thiosulfate solution were added thereto, followed by extraction using ethyl acetate. Thereafter, the organic phase was dried over anhydrous magnesium sulfate, followed by filtration, and thus obtaining 19 mg of the title compound as a crude product by vacuum concentration of the filtrate.

(b) tert-Butyl 3-(5-(1-hydroxyethyl)-7-(thiazol-2-yl)-4-(trifluoromethoxy)benzo[d]oxazol-2-yl)-3,8-diazabicyclo[3.2.1]octane-8-carboxylate The title compound was obtained as a crude product in an amount of 20 mg from 19 mg of the crude product of tert-butyl 3-(5-formyl-7-(thiazol-2-yl)-4-(trifluoromethoxy)benzo[d]oxazol-2-yl)-3,8-diazabicyclo[3.2.1]octane-8-carboxylate obtained in Example 202(a) by a similar method to Example 102(b) except that the product was not purified by silica gel column chromatography.

(c) 1-(2-(3,8-Diazabicyclo[3.2.1]octan-3-yl)-7-(thiazol-2-yl)-4-(trifluoromethoxy)benzo[d]oxazol-5-yl)ethan-1-ol The title compound was obtained in an amount of 12 mg from 20 mg of the crude product of tert-butyl 3-(5-(1-hydroxyethyl)-7-(thiazol-2-yl)-4-(trifluoromethoxy)benzo[d]oxazol-2-yl)-3,8-diazabicyclo[3.2.1]octane-8-carboxylate obtained in Example 202 (b) by a similar method to Example 1(c).

Example 203

1-(2-(3,6-Diazabicyclo[3.1.1]heptan-3-yl)-7-(thiazol-2-yl)-4-(trifluoromethoxy)benzo[d]oxazol-5-yl)ethan-1-ol (a) tert-Butyl 3-(5-formyl-7-(thiazol-2-yl)-4-(trifluoromethoxy)benzo[d]oxazol-2-yl)-3,6-diazabicyclo[3.1.1]heptane-6-carboxylate The title compound was obtained in an amount of 56 mg from 111 mg of ethyl 2-(6-(tert-butoxycarbonyl)-3,6-diazabicyclo[3.1.1]heptan-3-yl)-7-(thiazol-2-yl)-4-(trifluoromethoxy)benzo[d]oxazole-5-carboxylate obtained in Example 187(b) by a similar method to Example 102 (a).

(b) tert-Butyl 3-(5-(1-hydroxyethyl)-7-(thiazol-2-yl)-4-(trifluoromethoxy)benzo[d]oxazol-2-yl)-3,6-diazabicyclo[3.1.1]heptane-6-carboxylate The title compound was obtained in an amount of 35 mg from 54 mg of tert-butyl 3-(5-formyl-7-(thiazol-2-yl)-4-(trifluoromethoxy)benzo[d]oxazol-2-yl)-3,6-diazabicyclo[3.1.1]heptane-6-carboxylate obtained in Example 203 (a) by a similar method to Example 102 (b).

(c) 1-(2-(3,6-Diazabicyclo[3.1.1]heptan-3-yl)-7-(thiazol-2-yl)-4-(trifluoromethoxy)benzo[d]oxazol-5-yl)ethan-1-ol The title compound was obtained in an amount of 18 mg from 26 mg of tert-butyl 3-(5-(1-hydroxyethyl)-7-(thiazol-2-yl)-4-(trifluoromethoxy)benzo[d]oxazol-2-yl)-3,6-diazabicyclo[3.1.1]heptane-6-carboxylate obtained in Example 203(b) by a similar method to Example 1(c).

Example 204

1-(2-(3,8-Diazabicyclo[3.2.1]octan-3-yl)-7-(thiazol-2-yl)-4-(trifluoromethoxy)benzo[d]oxazol-5-yl)propan-1-ol (a) tert-Butyl 3-(5-(1-hydroxypropyl)-7-(thiazol-2-yl)-4-(trifluoromethoxy)benzo[d]oxazol-2-yl)-3,8-diazabicyclo[3.2.1]octane-8-carboxylate The title compound was obtained in an amount of 10 mg from 20 mg of tert-butyl 3-(5-formyl-7-(thiazol-2-yl)-4-(trifluoromethoxy)benzo[d]oxazol-2-yl)-3,8-diazabicyclo[3.2.1]octane-8-carboxylate obtained in Example 202(a) by a similar method to Example 102(b) except that 0.96 ethylmagnesium bromide solution in tetrahydrofuran (397 µL, 10 equivalents) was used instead of 0.92M methylmagnesium bromide solution in tetrahydrofuran.

(b) 1-(2-(3,8-Diazabicyclo[3.2.1]octan-3-yl)-7-(thiazol-2-yl)-4-(trifluoromethoxy)benzo[d]oxazol-5-yl)propan-1-ol The title compound was obtained in an amount of 8.4 mg from 10 mg of tert-butyl 3-(5-(1-hydroxypropyl)-7-(thiazol-2-yl)-4-(trifluoromethoxy)benzo[d]oxazol-2-yl)-3,8-diazabicyclo[3.2.1]octane-8-carboxylate obtained in Example 204 (a) by a similar method to Example 1(c).

Example 205

1-(2-(3,8-Diazabicyclo[3.2.1]octan-3-yl)-7-(thiazol-2-yl)-4-(trifluoromethoxy)benzo[d]oxazol-5-yl)-2-methylpropan-1-ol (a) tert-Butyl 3-(5-(1-hydroxy-2-methylpropyl)-7-(thiazol-2-yl)-4-(trifluoromethoxy)benzo[d]oxazol-2-yl)-3,8-diazabicyclo[3.2.1]octane-8-carboxylate The title compound was obtained in an amount of 3.6 mg from 20 mg of tert-butyl 3-(5-formyl-7-(thiazol-2-yl)-4-(trifluoromethoxy)benzo[d]oxazol-2-yl)-3,8-diazabicyclo[3.2.1]octane-8-carboxylate obtained in Example 202(a) by a similar method to Example 102(b) except that 0.74 M solution of isopropylmagnesium bromide in tetrahydrofuran (0.31 mL, 5.9 equivalents) was used instead of 0.92 M solution of methylmagnesium bromide in tetrahydrofuran.

(b) 1-(2-(3,8-Diazabicyclo[3.2.1]octan-3-yl)-7-(thiazol-2-yl)-4-(trifluoromethoxy)benzo[d]oxazol-5-yl)-2-methylpropan-1-ol The title compound was obtained in an amount of 2.0 mg from 3.6 mg of tert-butyl 3-(5-(1-hydroxy-2-methylpropyl)-7-(thiazol-2-yl)-4-(trifluoromethoxy)benzo[d]oxazol-2-yl)-3,8-diazabicyclo[3.2.1]octane-8-carboxylate obtained in Example 205 (a) by a similar method to Example 1(c).

Example 206

1-(2-(3,8-Diazabicyclo[3.2.1]octan-3-yl)-7-(thiazol-2-yl)-4-(trifluoromethoxy)benzo[d]oxazol-5-yl)-2,2-difluoroethan-1-ol (a) tert-Butyl 3-(5-(2,2-difluoro-1-hydroxyethyl)-7-(thiazol-2-yl)-4-(trifluoromethoxy)benzo[d]oxazol-2-yl)-3,8-diazabicyclo[3.2.1]octane-8-carboxylate The title compound was obtained in an amount of 15 mg from 15 mg of tert-butyl 3-(5-formyl-7-(thiazol-2-yl)-4-(trifluoromethoxy)benzo[d]oxazol-2-yl)-3,8-diazabicyclo[3.2.1]octane-8-carboxylate obtained in Example 202 (a) by a similar method to Example 183(a).

(b) 1-(2-(3,8-Diazabicyclo[3.2.1]octan-3-yl)-7-(thiazol-2-yl)-4-(trifluoromethoxy)benzo[d]oxazol-5-yl)-2,2-difluoroethan-1-ol The title compound was obtained in an amount of 6.9 mg from 15 mg of tert-butyl 3-(5-(2,2-difluoro-1-hydroxyethyl)-7-(thiazol-2-yl)-4-(trifluoromethoxy)benzo[d]oxazol-2-yl)-3,8-diazabicyclo[3.2.1]octane-8-carboxylate obtained in Example 206(a) by a similar method to Example 1(c).

Example 207

1-(2-(3,6-Diazabicyclo[3.1.1]heptan-3-yl)-7-(thiazol-2-yl)-4-(trifluoromethoxy)benzo[d]oxazol-5-yl)-2,2-difluoroethan-1-ol (a) tert-Butyl 3-(5-(2,2-difluoro-1-hydroxyethyl)-7-(thiazol-2-yl)-4-(trifluoromethoxy)benzo[d]oxazol-2-yl)-3,6-diazabicyclo[3.1.1]heptane-6-carboxylate The title compound was obtained in an amount of 40 mg from 40 mg of tert-butyl 3-(5-formyl-7-(thiazol-2-yl)-4-(trifluoromethoxy)benzo[d]oxazol-2-yl)-3,6-diazabicyclo[3.1.1]heptane-6-carboxylate obtained in Example 203 (a) by a similar method to Example 183(a).

(b) 1-(2-(3,6-Diazabicyclo[3.1.1]heptan-3-yl)-7-(thiazol-2-yl)-4-(trifluoromethoxy)benzo[d]oxazol-5-yl)-2,2-difluoroethan-1-ol The title compound was obtained in an amount of 24 mg from 40 mg of tert-butyl 3-(5-(2,2-difluoro-1-hydroxyethyl)-7-(thiazol-2-yl)-4-(trifluoromethoxy)benzo[d]oxazol-2-yl)-3,6-diazabicyclo[3.1.1]heptane-6-carboxylate obtained in Example 207 (a) by a similar method to Example 1(c).

Example 208

2-(3,6-Diazabicyclo[3.1.1]heptan-3-yl)-5-(2,2-difluoro-1-methoxyethyl)-7-(thiazol-2-yl)-4-(trifluoromethoxy)benzo[d]oxazole (a) tert-Butyl 3-(5-(2,2-difluoro-1-methoxyethyl)-7-(thiazol-2-yl)-4-(trifluoromethoxy)benzo[d]oxazol-2-yl)-3,6-diazabicyclo[3.1.1]heptane-6-carboxylate The title compound was obtained in an amount of 20 mg from 27 mg of tert-butyl 3-(5-(2,2-difluoro-1-hydroxyethyl)-7-(thiazol-2-yl)-4-(trifluoromethoxy)benzo[d]oxazol-2-yl)-3,6-diazabicyclo[3.1.1]heptane-6-carboxylate obtained in Example 207 (a) by a similar method to Example 102 (e).

(b) 2-(3,6-Diazabicyclo[3.1.1]heptan-3-yl)-5-(2,2-difluoro-1-methoxyethyl)-7-(thiazol-2-yl)-4-(trifluoromethoxy)benzo[d]oxazole The title compound was obtained in an amount of 15 mg from 19 mg of tert-butyl 3-(5-(2,2-difluoro-1-methoxyethyl)-7-(thiazol-2-yl)-4-(trifluoromethoxy)benzo[d]oxazol-2-yl)-3,6-diazabicyclo[3.1.1]heptane-6-carboxylate obtained in Example 208 (a) by a similar method to Example 1(c).

Example 209

2-(3,8-Diazabicyclo[3.2.1]octan-3-yl)-5-(2,2-difluoro-1-methoxyethyl)-7-(thiazol-2-yl)-4-(trifluoromethoxy)benzo[d]oxazole (a) tert-Butyl 3-(5-(2,2-difluoro-1-methoxyethyl)-7-(thiazol-2-yl)-4-(trifluoromethoxy)benzo[d]oxazol-2-yl)-3,8-diazabicyclo[3.2.1]octane-8-carboxylate The title compound was obtained in an amount of 25 mg from 29 mg of tert-butyl 3-(5-(2,2-difluoro-1-hydroxyethyl)-7-(thiazol-2-yl)-4-(trifluoromethoxy)benzo[d]oxazol-2-yl)-3,8-diazabicyclo[3.2.1]octane-8-carboxylate obtained in Example 206(a) by a similar method to Example 102 (e).

(b) 2-(3,8-Diazabicyclo[3.2.1]octan-3-yl)-5-(2,2-difluoro-1-methoxyethyl)-7-(thiazol-2-yl)-4-(trifluoromethoxy)benzo[d]oxazole The title compound was obtained in an amount of 18 mg from 24 mg of tert-butyl 3-(5-(2,2-difluoro-1-methoxyethyl)-7-(thiazol-2-yl)-4-(trifluoromethoxy)benzo[d]oxazol-2-yl)-3,8-diazabicyclo[3.2.1]octane-8-carboxylate obtained in Example 209(a) by a similar method to Example 1(c).

Example 210

2-(3,8-Diazabicyclo[3.2.1]octan-3-yl)-5-(1-methoxyethyl)-7-(thiazol-2-yl)-4-(trifluoromethoxy)benzo[d]oxazole (a) tert-Butyl 3-(5-(1-methoxyethyl)-7-(thiazol-2-yl)-4-(trifluoromethoxy)benzo[d]oxazol-2-yl)-3,8-diazabicyclo[3.2.1]octane-8-carboxylate The title compound was obtained in an amount of 45 mg from 57 mg of tert-butyl 3-(5-(1-hydroxyethyl)-7-(thiazol- 2-yl)-4-(trifluoromethoxy)benzo[d]oxazol-2-yl)-3,8-diazabicyclo[3.2.1]octane-8-carboxylate obtained in Example 202(b) by a similar method to Example 102 (e).

(b) 2-(3,8-Diazabicyclo[3.2.1]octan-3-yl)-5-(1-methoxyethyl)-7-(thiazol-2-yl)-4-(trifluoromethoxy) benzo[d]oxazole The title compound was obtained in an amount of 36 mg from 45 mg of tert-butyl 3-(5-(1-methoxyethyl)-7-(thiazol-2-yl)-4-(trifluoromethoxy)benzo[d]oxazol-2-yl)-3,8-diazabicyclo[3.2.1]octane-8-carboxylate obtained in Example 210(a) by a similar method to Example 1(c).

Example 211

2-(3,6-Diazabicyclo[3.1.1]heptan-3-yl)-5-(1-methoxyethyl)-7-(thiazol-2-yl)-4-(trifluoromethoxy) benzo[d]oxazole (a) tert-Butyl 3-(5-(1-methoxyethyl)-7-(thiazol-2-yl)-4-(trifluoromethoxy)benzo[d]oxazol-2-yl)-3,6-diazabicyclo[3.1.1]heptane-6-carboxylate The title compound was obtained as a crude product in an amount of 31 mg from 30 mg of the crude product of tert-butyl 3-(5-(1-hydroxyethyl)-7-(thiazol-2-yl)-4-(trifluoromethoxy)benzo[d]oxazol-2-yl)-3,6-diazabicyclo[3.1.1]heptane-6-carboxylate obtained in Example 203(b) by a similar method to Example 102 (e) except that the product was not purified by preparative TLC.

(b) 2-(3,6-Diazabicyclo[3.1.1]heptan-3-yl)-5-(1-methoxyethyl)-7-(thiazol-2-yl)-4-(trifluoromethoxy) benzo[d]oxazole The title compound was obtained in an amount of 18 mg from 31 mg of tert-butyl 3-(5-(1-methoxyethyl)-7-(thiazol-2-yl)-4-(trifluoromethoxy)benzo[d]oxazol-2-yl)-3,6-diazabicyclo[3.1.1]heptane-6-carboxylate obtained in Example 211(a) by a similar method to Example 1(c).

Example 212

1-(2-(3,6-Diazabicyclo[3.1.1]heptan-3-yl)-7-(thiazol-2-yl)-4-(trifluoromethoxy)benzo[d]oxazol-5-yl) ethan-1-one (a) tert-Butyl 3-(5-acetyl-7-(thiazol-2-yl)-4-(trifluoromethoxy)benzo[d]oxazol-2-yl)-3,6-diazabicyclo[3.1.1]heptane-6-carboxylate The title compound was obtained in an amount of 100 mg from 108 mg of tert-butyl 3-(5-(1-hydroxyethyl)-7-(thiazol-2-yl)-4-(trifluoromethoxy)benzo[d]oxazol-2-yl)-3,6-diazabicyclo[3.1.1]heptane-6-carboxylate obtained in Example 203 (b) by a similar method to Example 102 (c).

(b) 1-(2-(3,6-Diazabicyclo[3.1.1]heptan-3-yl)-7-(thiazol-2-yl)-4-(trifluoromethoxy)benzo[d]oxazol-5-yl)ethan-1-one The title compound was obtained in an amount of 10 mg from 19 mg of tert-butyl 3-(5-acetyl-7-(thiazol-2-yl)-4-(trifluoromethoxy)benzo[d]oxazol-2-yl)-3,6-diazabicyclo[3.1.1]heptane-6-carboxylate obtained in Example 212 (a) by a similar method to Example 1(c).

Example 213

1-(2-(3,8-Diazabicyclo[3.2.1]octan-3-yl)-7-(thiazol-2-yl)-4-(trifluoromethoxy)benzo[d]oxazol-5-yl) ethan-1-one (a) tert-Butyl 3-(5-acetyl-7-(thiazol-2-yl)-4-(trifluoromethoxy)benzo[d]oxazol-2-yl)-3,8-diazabicyclo[3.2.1]octane-8-carboxylate The title compound was obtained in an amount of 70 mg from 88 mg of tert-butyl 3-(5-(1-hydroxyethyl)-7-(thiazol-2-yl)-4-(trifluoromethoxy)benzo[d]oxazol-2-yl)-3,8-diazabicyclo[3.2.1]octane-8-carboxylate obtained in Example 202(b) by a similar method to Example 102 (c).

(b) 1-(2-(3,8-Diazabicyclo[3.2.1]octan-3-yl)-7-(thiazol-2-yl)-4-(trifluoromethoxy)benzo[d]oxazol-5-yl) ethan-1-one The title compound was obtained in an amount of 12 mg from 15 mg of tert-butyl 3-(5-acetyl-7-(thiazol-2-yl)-4-(trifluoromethoxy)benzo[d]oxazol-2-yl)-3,8-diazabicyclo[3.2.1]octane-8-carboxylate obtained in Example 213 (a) by a similar method to Example 1(c).

Example 214

2-(3,6-Diazabicyclo[3.1.1]heptan-3-yl)-7-(thiazol-2-yl)-5-(1,1,1-trifluoro-2-methoxypropan-2-yl)-4-(trifluoromethoxy)benzo[d]oxazole (a) tert-Butyl 3-(7-(thiazol-2-yl)-5-(1,1,1-trifluoro-2-hydroxypropan-2-yl)-4-(trifluoromethoxy)benzo[d] oxazol-2-yl)-3,6-diazabicyclo[3.1.1]heptane-6-carboxylate 23 mg of tert-butyl 3-(5-acetyl-7-(thiazol-2-yl)-4-(trifluoromethoxy)benzo[d]oxazol-2-yl)-3,6-diazabicyclo[3.1.1] heptane-6-carboxylate obtained in Example 212 (a), (trifluoromethyl)trimethylsilane (40 μL, 6 equivalents) and caesium fluoride (1.0 mg, 0.2 equivalent) were dissolved in tetrahydrofuran (440 μL), followed by stirring at 0° C. for 6 hours. The formation of the product was confirmed by TLC (eluent, hexane:ethyl acetate=1:1), and 2M hydrochloric acid/isopropyl alcohol was added, followed by stirring at room temperature for 30 min. 1M sodium hydroxide was added into the reaction mixture, and then the organic phase was extracted by ethyl acetate. The organic phase was dried over anhydrous magnesium sulfate, followed by filtration and vacuum concentration of the filtrate, and thus obtaining 14 mg of the title compound by purification of the residue by preparative TLC (eluent, hexane:ethyl acetate=1:1).

(b) tert-Butyl 3-(7-(thiazol-2-yl)-5-(1,1,1-trifluoro-2-methoxypropan-2-yl)-4-(trifluoromethoxy)benzo [d]oxazol-2-yl)-3,6-diazabicyclo[3.1.1]heptane-6-carboxylate The title compound was obtained in an amount of 7.2 mg from 14 mg of tert-butyl 3-(7-(thiazol-2-yl)-5-(1,1,1-trifluoro-2-hydroxypropan-2-yl)-4-(trifluoromethoxy)benzo[d]

oxazol-2-yl)-3,6-diazabicyclo[3.1.1]heptane-6-carboxylate obtained in Example 214 (a) by a similar method to Example 102 (e).

(c) 2-(3,6-Diazabicyclo[3.1.1]heptan-3-yl)-7-(thiazol-2-yl)-5-(1,1,1-trifluoro-2-methoxypropan-2-yl)-4-(trifluoromethoxy)benzo[d]oxazole The title compound was obtained in an amount of 5.1 mg from 7.2 mg of tert-butyl 3-(7-(thiazol-2-yl)-5-(1,1,1-trifluoro-2-methoxypropan-2-yl)-4-(trifluoromethoxy)benzo[d]oxazol-2-yl)-3,6-diazabicyclo[3.1.1]heptane-6-carboxylate obtained in Example 214 (b) by a similar method to Example 1(c).

Example 215

2-(3,8-Diazabicyclo[3.2.1]octan-3-yl)-7-(thiazol-2-yl)-5-(1,1,1-trifluoro-2-methoxypropan-2-yl)-4-(trifluoromethoxy)benzo[d]oxazole (a) tert-Butyl 3-(7-(thiazol-2-yl)-5-(1,1,1-trifluoro-2-hydroxypropan-2-yl)-4-(trifluoromethoxy)benzo[d]oxazol-2-yl)-3,8-diazabicyclo[3.2.1]octane-8-carboxylate The title compound was obtained in an amount of 33 mg from 38 mg of tert-butyl 3-(5-acetyl-7-(thiazol-2-yl)-4-(trifluoromethoxy)benzo[d]oxazol-2-yl)-3,8-diazabicyclo[3.2.1]octane-8-carboxylate obtained in Example 213(a) by a similar method to Example 102(d) except that 4 equivalents of trifluoromethyltrimethylsilane was used.

(b) tert-Butyl 3-(7-(thiazol-2-yl)-5-(1,1,1-trifluoro-2-methoxypropan-2-yl)-4-(trifluoromethoxy)benzo[d]oxazol-2-yl)-3,8-diazabicyclo[3.2.1]octane-8-carboxylate The title compound was obtained in an amount of 15 mg from 15 mg of tert-butyl 3-(7-(thiazol-2-yl)-5-(1,1,1-trifluoro-2-hydroxypropan-2-yl)-4-(trifluoromethoxy)benzo[d]oxazol-2-yl)-3,8-diazabicyclo[3.2.1]octane-8-carboxylate obtained in Example 215 (a) by a similar method to Example 102 (e).

(c) 2-(3,8-Diazabicyclo[3.2.1]octan-3-yl)-7-(thiazol-2-yl)-5-(1,1,1-trifluoro-2-methoxypropan-2-yl)-4-(trifluoromethoxy)benzo[d]oxazole The title compound was obtained in an amount of 12 mg from 15 mg of tert-butyl 3-(7-(thiazol-2-yl)-5-(1,1,1-trifluoro-2-methoxypropan-2-yl)-4-(trifluoromethoxy)benzo[d]oxazol-2-yl)-3,8-diazabicyclo[3.2.1]octane-8-carboxylate obtained in Example 215 (b) by a similar method to Example 1(c).

Example 216

2-(2-(3,6-Diazabicyclo[3.1.1]heptan-3-yl)-7-(thiazol-2-yl)-4-(trifluoromethoxy)benzo[d]oxazol-5-yl)-1,1,1-trifluoropropan-2-ol (a) tert-Butyl 3-(7-(thiazol-2-yl)-5-(1,1,1-trifluoro-2-((trimethylsilyl)oxy)propan-2-yl)-4-(trifluoromethoxy)benzo[d]oxazol-2-yl)-3,6-diazabicyclo[3.1.1]heptane-6-carboxylate 21 mg of tert-butyl 3-(5-acetyl-7-(thiazol-2-yl)-4-(trifluoromethoxy)benzo[d]oxazol-2-yl)-3,6-diazabicyclo[3.1.1]heptane-6-carboxylate obtained in Example 212 (a), (trifluoromethyl)trimethylsilane (35 μL, 6 equivalents) and caesium fluoride (1.2 mg, 0.2 equivalent) were dissolved in tetrahydrofuran (400 μL), followed by stirring at 0° C. for 3 hours. The formation of the product was confirmed by TLC (eluent, hexane:ethyl acetate=1:1), and saturated aqueous sodium bicarbonate solution was added, and then the organic phase was extracted by ethyl acetate. The organic phase was dried over anhydrous magnesium sulfate, followed by filtration and vacuum concentration of the filtrate, and thus obtaining 22 mg of the title compound by purification of the residue by preparative TLC (eluent, hexane:ethyl acetate=1:1).

(b) 2-(2-(3,6-Diazabicyclo[3.1.1]heptan-3-yl)-7-(thiazol-2-yl)-4-(trifluoromethoxy)benzo[d]oxazol-5-yl)-1,1,1-trifluoropropan-2-ol The title compound was obtained in an amount of 6.9 mg from 22 mg of tert-butyl 3-(7-(thiazol-2-yl)-5-(1,1,1-trifluoro-2-((trimethylsilyl)oxy)propan-2-yl)-4-(trifluoromethoxy)benzo[d]oxazol-2-yl)-3,6-diazabicyclo[3.1.1]heptane-6-carboxylate obtained in Example 216 (b) by a similar method to Example 1(c).

Example 217

2-(2-(3,8-Diazabicyclo[3.2.1]octan-3-yl)-7-(thiazol-2-yl)-4-(trifluoromethoxy)benzo[d]oxazol-5-yl)-1,1,1-trifluoropropan-2-ol The title compound was obtained in an amount of 13 mg from 18 mg of tert-butyl 3-(7-(thiazol-2-yl)-5-(1,1,1-trifluoro-2-hydroxypropan-2-yl)-4-(trifluoromethoxy)benzo[d]oxazol-2-yl)-3,8-diazabicyclo[3.2.1]octane-8-carboxylate obtained in Example 215 (a) by a similar method to Example 1(c).

Example 218

(E)-1-(2-(3,8-diazabicyclo[3.2.1]octan-3-yl)-7-(thiazol-2-yl)-4-(trifluoromethoxy)benzo[d]oxazol-5-yl)ethan-1-one O-methyloxime and (Z)-1-(2-(3,8-diazabicyclo[3.2.1]octan-3-yl)-7-(thiazol-2-yl)-4-(trifluoromethoxy)benzo[d]oxazol-5-yl)ethan-1-one O-methyloxime (a) tert-Butyl (E)-3-(5-(1-(methoxyimino)ethyl-7-(thiazol-2-yl)-4-(trifluoromethoxy)benzo[d]oxazol-2-yl)-3,8-diazabicyclo[3.2.1]octane-8-carboxylate and tert-butyl (Z)-3-(5-(1-(methoxyimino)ethyl-7-(thiazol-2-yl)-4-(trifluoromethoxy)benzo[d]oxazol-2-yl)-3,8-diazabicyclo[3.2.1]octane-8-carboxylate 17 mg of tert-butyl 3-(5-acetyl-7-(thiazol-2-yl)-4-(trifluoromethoxy)benzo[d]oxazol-2-yl)-3,8-diazabicyclo[3.2.1]octane-8-carboxylate obtained in Example 213(a) was dissolved in N,N-dimethylformamide (0.2 mL), then potassium carbonate (26 mg, 6 equivalents) and O-methylhydroxylamine hydrochloride (8 mg, 3 equivalents) were added thereto at room temperature followed by stirring overnight. After adding O-methylhydroxylamine hydrochloride (4 mg, 1.5 equivalents) and N,N-dimethylformamide (0.2 mL) and stirring at 60° C. for 5 hours, the formation of the product was confirmed by TLC (eluent, hexane:ethyl acetate=1:1) followed by filtration. Thereafter, 8.2 mg of the title compound was obtained by purification of the filtrate by silica gel column chromatography (eluent, hexane:ethyl acetate=1:1).

(b) (E)-1-(2-(3,8-diazabicyclo[3.2.1]octan-3-yl)-7-(thiazol-2-yl)-4-(trifluoromethoxy)benzo[d]oxazol-5-yl)ethan-1-one O-methyloxime and (Z)-1-(2-(3,8-diazabicyclo[3.2.1]octan-3-yl)-7-(thiazol-2-yl)-4-(trifluoromethoxy)benzo[d]oxazol-5-yl)ethan-1-one O-methyloxime The title compound was obtained in an amount of 8.0 mg from 5.8 mg of tert-butyl (E)-3-(5-(1-(methoxyimino)ethyl-7-(thiazol-2-yl)-4-(trifluoromethoxy)benzo[d]oxazol-2-yl)-3,8-diazabicyclo[3.2.1]octane-8-carboxylate and tert-butyl (Z)-3-(5-(1-(methoxyimino)ethyl-7-(thiazol-2-yl)-4-(trifluoromethoxy)benzo[d]oxazol-2-yl)-3,8-diazabicyclo[3.2.1]octane-8-carboxylate obtained in Example 218 (a) by a similar method to Example 1(c).

Example 219

(E)-1-(2-(3,6-diazabicyclo[3.1.1]heptan-3-yl)-7-(thiazol-2-yl)-4-(trifluoromethoxy)benzo[d]oxazol-5-yl)ethan-1-one O-methyloxime and (Z)-1-(2-(3,6-diazabicyclo[3.1.1]heptan-3-yl)-7-(thiazol-2-yl)-4-(trifluoromethoxy)benzo[d]oxazol-5-yl)ethan-1-one O-methyloxime (a) tert-Butyl (E)-3-(5-(1-(methoxyimino)ethyl-7-(thiazol-2-yl)-4-(trifluoromethoxy)benzo[d]oxazol-2-yl)-3,6-diazabicyclo[3.1.1]heptane-6-carboxylate and (Z)-3-(5-(1-(methoxyimino)ethyl-7-(thiazol-2-yl)-4-(trifluoromethoxy)benzo[d]oxazol-2-yl)-3,6-diazabicyclo[3.1.1]heptane-6-carboxylate The title compound was obtained in an amount of 10 mg from 15 mg of tert-butyl 3-(5-acetyl-7-(thiazol-2-yl)-4-(trifluoromethoxy)benzo[d]oxazol-2-yl)-3,6-diazabicyclo[3.1.1]heptane-6-carboxylate obtained in Example 212 (a) by a similar method to Example 218 (a).

(b) (E)-1-(2-(3,6-diazabicyclo[3.1.1]heptan-3-yl)-7-(thiazol-2-yl)-4-(trifluoromethoxy)benzo[d]oxazol-5-yl)ethan-1-one O-methyloxime and (Z)-1-(2-(3,6-diazabicyclo[3.1.1]heptan-3-yl)-7-(thiazol-2-yl)-4-(trifluoromethoxy)benzo[d]oxazol-5-yl)ethan-1-one O-methyloxime The title compound was obtained in an amount of 6.7 mg from 10 mg of tert-butyl (E)-3-(5-(1-(methoxyimino)ethyl-7-(thiazol-2-yl)-4-(trifluoromethoxy)benzo[d]oxazol-2-yl)-3,6-diazabicyclo[3.1.1]heptane-6-carboxylate and tert-butyl (Z)-3-(5-(1-(methoxyimino)ethyl-7-(thiazol-2-yl)-4-(trifluoromethoxy)benzo[d]oxazol-2-yl)-3,6-diazabicyclo[3.1.1]heptane-6-carboxylate obtained in Example 219(a) by a similar method to Example 1(c).

Example 220

2-(3,8-Diazabicyclo[3.2.1]octan-3-yl)-4-(1-ethoxy-2,2,2-trifluoroethyl)-7-(thiazol-2-yl)benzo[d]oxazole (a) tert-Butyl 3-(4-(1-(ethoxy-2,2,2-trifluoroethyl)-7-(thiazol-2-yl)benzo[d]oxazol-2-yl)-3,8-diazabicyclo[3.2.1]octane-8-carboxylate The title compound was obtained in an amount of 17 mg from 26 mg of tert-butyl 3-(7-(thiazol-2-yl)-4-(2,2,2-trifluoro-1-hydroxyethyl)benzo[d]oxazol-2-yl)-3,8-diazabicyclo[3.2.1]octane-8-carboxylate obtained in Example 118 (b) by a similar method to Example 102 (e) except that ethyl iodide was used instead of methyl iodide.

(b) 2-(3,8-Diazabicyclo[3.2.1]octan-3-yl)-4-(1-ethoxy-2,2,2-trifluoroethyl)-7-(thiazol-2-yl)benzo[d]oxazole The title compound was obtained in an amount of 24 mg from 35 mg of tert-butyl 3-(4-(1-ethoxy-2,2,2-trifluoroethyl)-7-(thiazol-2-yl)benzo[d]oxazol-2-yl)-3,8-diazabicyclo[3.2.1]octane-8-carboxylate obtained in Example 220(a) by a similar method to Example 1(c).

Example 221

2-(3,8-Diazabicyclo[3.2.1]octan-3-yl)-7-(thiazol-2-yl)-4-(2,2,2-trifluoro-1-(2,2,2-trifluoroethoxy)ethyl)benzo[d]oxazole (a) tert-Butyl 3-(7-(thiazol-2-yl)-4-(2,2,2-trifluoro-1-(2,2,2-trifluoroethoxy)ethyl)benzo[d]oxazol-2-yl)-3,8-diazabicyclo[3.2.1]octane-8-carboxylate The title compound was obtained in an amount of 14 mg from 51 mg of tert-butyl 3-(7-(thiazol-2-yl)-4-(2,2,2-trifluoro-1-hydroxyethyl)benzo[d]oxazol-2-yl)-3,8-diazabicyclo[3.2.1]octane-8-carboxylate obtained in Example 118 (b) by a similar method to Example 102(e) except that 2,2,2-trifluoroethyl trifluoromethanesulfonate was used instead of methyl iodide.

(b) 2-(3,8-Diazabicyclo[3.2.1]octan-3-yl)-7-(thiazol-2-yl)-4-(2,2,2-trifluoro-1-(2,2,2-trifluoroethoxy)ethyl)benzo[d]oxazole The title compound was obtained in an amount of 10 mg from 14 mg of tert-butyl 3-(7-(thiazol-2-yl)-4-(2,2,2-trifluoro-1-(2,2,2-trifluoroethoxy)ethyl)benzo[d]oxazol-2-yl)-3,8-diazabicyclo[3.2.1]octane-8-carboxylate obtained in Example 221(a) by a similar method to Example 1(c).

Example 222

2-(3,8-Diazabicyclo[3.2.1]octan-3-yl)-7-(thiazol-2-yl)-4-(2,2,2-trifluoro-1-methoxyethyl)benzo[d]oxazole (a) tert-Butyl 3-(7-(thiazol-2-yl)-4-(2,2,2-trifluoro-1-methoxyethyl)benzo[d]oxazol-2-yl)-3,8-diazabicyclo[3.2.1]octane-8-carboxylate The title compound was obtained in an amount of 48 mg from 51 mg of tert-butyl 3-(7-(thiazol-2-yl)-4-(2,2,2-trifluoro-1-hydroxyethyl)benzo[d]oxazol-2-yl)-3,8-diazabicyclo[3.2.1]octane-8-carboxylate obtained in Example 118 (b) by a similar method to Example 102 (e).

(b) 2-(3,8-Diazabicyclo[3.2.1]octan-3-yl)-7-(thiazol-2-yl)-4-(2,2,2-trifluoro-1-methoxyethyl)benzo[d]oxazole The title compound was obtained in an amount of 30 mg from 48 mg of tert-butyl 3-(7-(thiazol-2-yl)-4-(2,2,2-trifluoro-1-methoxyethyl)benzo[d]oxazol-2-yl)-3,8-diazabicyclo[3.2.1]octane-8-carboxylate obtained in Example 222 (a) by a similar method to Example 1(c).

Example 223

2-(3,6-Diazabicyclo[3.1.1]heptan-3-yl)-7-(thiazol-2-yl)-4-(2,2,2-trifluoro-1-(2,2,2-trifluoroethoxy)ethyl)benzo[d]oxazole (a) tert-Butyl 3-(7-(thiazol-2-yl)-4-(2,2,2-trifluoro-1-(2,2,2-trifluoroethoxy)ethyl)benzo[d]oxazol-2-yl)-3,6-diazabicyclo[3.1.1]heptane-6-carboxylate The title compound was obtained in an amount of 58 mg from 60 mg of tert-butyl 3-(7-(thiazol-2-yl)-4-(2,2,2-trifluoro-1-hydroxyethyl)benzo[d]oxazol-2-yl)-3,6-diazabicyclo[3.1.1]heptane-6-carboxylate obtained in Example 120 (b) by a similar method to Example 102(e) except that 36 equivalents of 2,2,2-trifluoroethyl trifluoromethanesulfonate was used instead of methyl iodide.

(b)

2-(3,6-Diazabicyclo[3.1.1]heptan-3-yl)-7-(thiazol-2-yl)-4-(2,2,2-trifluoro-1-(2,2,2-trifluoroethoxy)ethyl)benzo[d]oxazole The title compound was obtained in an amount of 35 mg from 58 mg of tert-butyl 3-(7-(thiazol-2-yl)-4-(2,2,2-trifluoro-1-(2,2,2-trifluoroethoxy)ethyl)benzo[d]oxazol-2-yl)-3,6-diazabicyclo[3.1.1]heptane-6-carboxylate obtained in Example 223 (a) by a similar method to Example 1(c).

Example 224

2-(3,6-Diazabicyclo[3.1.1]heptan-3-yl)-4-(1-ethoxy-2,2,2-trifluoroethyl)-7-(thiazol-2-yl)benzo[d]oxazole (a) tert-Butyl 3-(4-(1-ethoxy-2,2,2-trifluoroethyl-7-(thiazol-2-yl)benzo[d]oxazol-2-yl)-3,6-diazabicyclo[3.1.1]heptane-6-carboxylate The title compound was obtained in an amount of 24 mg from 50 mg of tert-butyl 3-(7-(thiazol-2-yl)-4-(2,2,2-trifluoro-1-hydroxyethyl)benzo[d]oxazol-2-yl)-3,6-diazabicyclo[3.1.1]heptane-6-carboxylate obtained in Example 120 (b) by a similar method to Example 102 (e) except that 36 equivalents of ethyl iodide and 19.8 equivalents of sodium hydride were used instead of methyl iodide.

(b) 2-(3,6-Diazabicyclo[3.1.1]heptan-3-yl)-4-(1-ethoxy-2,2,2-trifluoroethyl)-7-(thiazol-2-yl)benzo[d]oxazole The title compound was obtained in an amount of 12 mg from 24 mg of tert-butyl 3-(4-(1-ethoxy-2,2,2-trifluoroethyl-7-(thiazol-2-yl)benzo[d]oxazol-2-yl)-3,6-diazabicyclo[3.1.1]heptane-6-carboxylate obtained in Example 224 (a) by a similar method to Example 1(c).

Example 225

2-(1-(2-(3,8-Diazabicyclo[3.2.1]octan-3-yl)-7-(thiazol-2-yl)benzo[d]oxazol-4-yl)-2,2,2-trifluoroethoxy)ethan-1-ol (a) tert-Butyl 3-(7-(thiazol-2-yl)-4-(2,2,2-trifluoro-1-(2-hydroxyethoxy)ethyl)benzo[d]oxazol-2-yl)-3,8-diazabicyclo[3.2.1]octane-8-carboxylate The title compound was obtained as a crude product in an amount of 105 mg from 60 mg of tert-butyl 3-(7-(thiazol-2-yl)-4-(2,2,2-trifluoro-1-hydroxyethyl)benzo[d]oxazol-2-yl)-3,8-diazabicyclo[3.2.1]octane-8-carboxylate obtained in Example 118 (b) by a similar method to Example 149(a).

(b) 2-(1-(2-(3,8-Diazabicyclo[3.2.1]octan-3-yl)-7-(thiazol-2-yl)benzo[d]oxazol-4-yl)-2,2,2-trifluoroethoxy)ethan-1-ol The title compound was obtained in an amount of 4.2 mg from 105 mg of the crude product of tert-butyl 3-(7-(thiazol-2-yl)-4-(2,2,2-trifluoro-1-(2-hydroxyethoxy)ethyl)benzo[d]oxazol-2-yl)-3,8-diazabicyclo[3.2.1]octane-8-carboxylate obtained in Example 225 (a) by a similar method to Example 1(c).

Example 226

2-(1-(2-(3,6-Diazabicyclo[3.1.1]heptan-3-yl)-7-(thiazol-2-yl)benzo[d]oxazol-4-yl)-2,2,2-trifluoroethoxy)acetonitrile (a) tert-Butyl 3-(4-(1-(cyanomethoxy)-2,2,2-trifluoroethyl)-7-(thiazol-2-yl)benzo[d]oxazol-2-yl)-3,6-diazabicyclo[3.1.1]heptane-6-carboxylate The title compound was obtained in an amount of 54 mg from 60 mg of tert-butyl 3-(7-(thiazol-2-yl)-4-(2,2,2-trifluoro-1-hydroxyethyl)benzo[d]oxazol-2-yl)-3,6-diazabicyclo[3.1.1]heptane-6-carboxylate obtained in Example 120 (b) by a similar method to Example 102 (e) except that bromoacetonitrile was used instead of methyl iodide.

(b) 2-(1-(2-(3,6-Diazabicyclo[3.1.1]heptan-3-yl)-7-(thiazol-2-yl)benzo[d]oxazol-4-yl)-2,2,2-trifluoroethoxy)acetonitrile The title compound was obtained in an amount of 15 mg from 26 mg of tert-butyl 3-(4-(1-(cyanomethoxy)-2,2,2-trifluoroethyl)-7-(thiazol-2-yl)benzo[d]oxazol-2-yl)-3,6-diazabicyclo[3.1.1]heptane-6-carboxylate obtained in Example 226(a) by a similar method to Example 1(c).

Example 227

2-(1-(2-(3,6-Diazabicyclo[3.1.1]heptan-3-yl)-7-(thiazol-2-yl)benzo[d]oxazol-4-yl)-2,2,2-trifluoroethoxy)ethan-1-ol (a) tert-Butyl 3-(7-(thiazol-2-yl)-4-(2,2,2-trifluoro-1-(2-hydroxyethoxy)ethyl)benzo[d]oxazol-2-yl)-3,6-diazabicyclo[3.1.1]heptane-6-carboxylate The title compound was obtained as a crude product in an amount of 19 mg from 60 mg of tert-butyl 3-(7-(thiazol-2- yl)-4-(2,2,2-trifluoro-1-hydroxyethyl)benzo[d]oxazol-2-yl)-3,6-diazabicyclo[3.1.1]heptane-6-carboxylate obtained in Example 120(b) by a similar method to Example 149(a).

(b) 2-(1-(2-(3,6-Diazabicyclo[3.1.1]heptan-3-yl)-7-(thiazol-2-yl)benzo[d]oxazol-4-yl)-2,2,2-trifluoroethoxy)ethan-1-ol The title compound was obtained in an amount of 1.6 mg from 19 mg of tert-butyl 3-(7-(thiazol-2-yl)-4-(2,2,2-trifluoro-1-(2-hydroxyethoxy)ethyl)benzo[d]oxazol-2-yl)-3,6-diazabicyclo[3.1.1]heptane-6-carboxylate obtained in Example 227 (a) by a similar method to Example 1(c).

Example 228

2-(1-(2-(3,8-Diazabicyclo[3.2.1]octan-3-yl)-7-(thiazol-2-yl)benzo[d]oxazol-4-yl)-2,2,2-trifluoroethoxy)acetonitrile (a) tert-Butyl 3-(4-(1-(cyanomethoxy)-2,2,2-trifluoroethyl)-7-(thiazol-2-yl)benzo[d]oxazol-2-yl)-3,8-diazabicyclo[3.2.1]octane-8-carboxylate The title compound was obtained in an amount of 55 mg from 61 mg of tert-butyl 3-(7-(thiazol-2-yl)-4-(2,2,2-trifluoro-1-hydroxyethyl)benzo[d]oxazol-2-yl)-3,8-diazabicyclo[3.2.1]octane-8-carboxylate obtained in Example 118 (b) by a similar method to Example 102 (e) except that bromoacetonitrile was used instead of methyl iodide.

(b) 2-(1-(2-(3,8-Diazabicyclo[3.2.1]octan-3-yl)-7-(thiazol-2-yl)benzo[d]oxazol-4-yl)-2,2,2-trifluoroethoxy)acetonitrile The title compound was obtained in an amount of 12 mg from 27 mg of tert-butyl 3-(4-(1-(cyanomethoxy)-2,2,2-trifluoroethyl)-7-(thiazol-2-yl)benzo[d]oxazol-2-yl)-3,8-diazabicyclo[3.2.1]octane-8-carboxylate obtained in Example 228(a) by a similar method to Example 1(c).

Example 229

2-(3,6-Diazabicyclo[3.1.1]heptan-3-yl)-7-(thiazol-2-yl)-4-(2,2,2-trifluoro-1-(2-methoxyethoxy)ethyl)benzo[d]oxazole (a) tert-Butyl 3-(7-(thiazol-2-yl)-4-(2,2,2-trifluoro-1-(2-methoxyethoxy)ethyl)benzo[d]oxazol-2-yl)-3,6-diazabicyclo[3.1.1]heptane-6-carboxylate The title compound was obtained in an amount of 30 mg from 50 mg of tert-butyl 3-(7-(thiazol-2-yl)-4-(2,2,2-trifluoro-1-hydroxyethyl)benzo[d]oxazol-2-yl)-3,6-diazabicyclo[3.1.1]heptane-6-carboxylate obtained in Example 120 (b) by a similar method to Example 102 (e) except that 2-bromoethyl methyl ether was used instead of methyl iodide.

(b) 2-(3,6-Diazabicyclo[3.1.1]heptan-3-yl)-7-(thiazol-2-yl)-4-(2,2,2-trifluoro-1-(2-methoxyethoxy)ethyl)benzo[d]oxazole The title compound was obtained in an amount of 19 mg from 30 mg of tert-butyl 3-(7-(thiazol-2-yl)-4-(2,2,2-trifluoro-1-(2-methoxyethoxy)ethyl)benzo[d]oxazol-2-yl)-3,6-diazabicyclo[3.1.1]heptane-6-carboxylate obtained in Example 229(a) by a similar method to Example 1(c).

Example 230

4-(1-((1H-tetrazol-5-yl)methoxy)-2,2,2-trifluoroethyl)-2-(3,8-diazabicyclo[3.2.1]octan-3-yl)-7-(thiazol-2-yl)benzo[d]oxazole (a) tert-Butyl 3-(4-1-((1H-tetrazol-5-yl)methoxy)-2,2,2-trifluoroethyl)-(7-(thiazol-2-yl)benzo[d]oxazol-2-yl)-3,8-diazabicyclo[3.2.1]octane-8-carboxylate 30 mg of tert-butyl 3-(4-(1-(cyanomethoxy)-2,2,2-trifluoroethyl)-7-(thiazol-2-yl)benzo[d]oxazol-2-yl)-3,8-diazabicyclo[3.2.1]octane-8-carboxylate obtained in Example 228 (a), sodium azide (11 mg, 3 equivalents), and ammonium chloride (8.8 mg, 3 equivalents) were dissolved in N,N-dimethylformamide (0.68 mL), followed by stirring using a microwave reactor (manufactured by Biotage, conditions: 100° C., 4 hours). The formation of the product was confirmed by TLC (eluent, chloroform:methanol:aqueous solution of ammonia=4:1:0.1), and then distilled water was added thereto, and then the organic phase was extracted by ethyl acetate. Thereafter, extracted organic phase was separated by using saturated aqueous sodium bicarbonate solution and the organic phase was dried over anhydrous magnesium sulfate, followed by filtration and vacuum concentration of the filtrate, and thus obtaining 29 mg of the title compound by purification of the residue through silica gel column chromatography (chloroform:methanol:aqueous solution of ammonium=4:1:0.1).

(b) 4-(1-((1H-tetrazol-5-yl)methoxy)-2,2,2-trifluoroethyl)-2-(3,8-diazabicyclo[3.2.1]octan-3-yl)-7-(thiazol-2-yl)benzo[d]oxazole The title compound was obtained in an amount of 16 mg from 29 mg of tert-butyl 3-(4-1-((1H-tetrazol-5-yl)methoxy)-2,2,2-trifluoroethyl)-(7-(thiazol-2-yl)benzo[d]oxazol-2-yl)-3,8-diazabicyclo[3.2.1]octane-8-carboxylate obtained in Example 230(a) by a similar method to Example 1(c).

Example 231

4-(1-((1H-tetrazol-5-yl)methoxy)-2,2,2-trifluoroethyl)-2-(3,6-diazabicyclo[3.1.1]heptan-3-yl)-7-(thiazol-2-yl)benzo[d]oxazole (a) tert-Butyl 3-(4-(1-((1H-tetrazol-5-yl)methoxy)-2,2,2-trifluoroethyl)-7-(thiazol-2-yl)benzo[d]oxazol-2-yl)-3,6-diazabicyclo[3.1.1]heptane-6-carboxylate The title compound was obtained in an amount of 55 mg from 61 mg of tert-butyl 3-(4-(1-(cyanomethoxy)-2,2,2-trifluoroethyl)-7-(thiazol-2-yl)benzo[d]oxazol-2-yl)-3,6-diazabicyclo[3.1.1]heptane-6-carboxylate obtained in Example 226(a) by a similar method to Example 230(a).

(b) 4-(1-((1H-tetrazol-5-yl)methoxy)-2,2,2-trifluoroethyl)-2-(3,6-diazabicyclo[3.1.1]heptan-3-yl)-7-(thiazol-2-yl)benzo[d]oxazole The title compound was obtained in an amount of 6.4 mg from 55 mg of tert-butyl 3-(4-(1-((1H-tetrazol-5-yl)methoxy)-2,2,2-trifluoroethyl)-7-(thiazol-2-yl)benzo[d]oxazol-2-yl)-3,6-diazabicyclo[3.1.1]heptane-6-carboxylate obtained in Example 231(a) by a similar method to Example 1(c).

Example 232

1-((1-(2-(3,6-Diazabicyclo[3.1.1]heptan-3-yl)-7-(thiazol-2-yl)benzo[d]oxazol-4-yl)-2,2,2-trifluoroethoxy)methyl)cyclopropan-1-ol (a) tert-Butyl 3-(4-(1-(2-(tert-butoxy)-2-oxoethoxy)-2,2,2-trifluoroethyl)-7-(thiazol-2-yl)benzo[d]oxazol-2-yl)-3,6-diazabicyclo[3.1.1]heptane-6-carboxylate 250 mg of tert-butyl 3-(7-(thiazol-2-yl)-4-(2,2,2-trifluoro-1-hydroxyethyl)benzo[d]oxazol-2-yl)-3,6-diazabicyclo[3.1.1]heptane-6-carboxylate obtained in Example 120 (b), tetrabutylammonium chloride (13.9 mg, 0.1 equivalent), 35% aqueous sodium hydroxide solution and tert-butyl bromoacetate (10 μL, 1.5 equivalents) were dissolved in dichloromethane (2.0 mL), followed by stirring at room temperature for 19 hours. The formation of the product was confirmed by TLC, and then saturated ammonium chloride aqueous solution was added thereto, and then the organic phase was extracted by ethyl acetate. The organic phase was dried over anhydrous magnesium sulfate, followed by filtration and vacuum concentration of the filtrate, and thus obtaining 319 mg of the title compound by purification of the residue through silica gel column chromatography (hexane-hexane:ethyl acetate=1:1).

(b) tert-Butyl 3-(7-(thiazol-2-yl)-4-(2,2,2-trifluoro-1-((1-hydroxycyclopropyl)methoxy)ethyl)benzo[d]oxazol-2-yl)-3,6-diazabicyclo[3.1.1]heptane-6-carboxylate 10 mg of tert-butyl 3-(4-(1-(2-(tert-butoxy)-2-oxoethoxy)-2,2,2-trifluoroethyl)-7-(thiazol-2-yl)benzo[d]oxazol-2-yl)-3,6-diazabicyclo[3.1.1]heptane-6-carboxylate obtained in Example 232 (a) was dissolved in tetrahydrofuran (160 μL), then titanium isopropoxide (9.7 μL, 2 equivalents) and 0.97M ethylmagnesium bromide solution in tetrahydrofuran (102 μL, 6 equivalents) were added, followed by stirring at room temperature for 48 hours. Saturated ammonium chloride aqueous solution was added into the reaction mixture, and then the organic phase was extracted by ethyl acetate. The organic phase was dried over anhydrous magnesium sulfate, followed by filtration and vacuum concentration of the filtrate, and thus obtaining 1.6 mg of the title compound by purification of the residue by preparative TLC (eluent, hexane:ethyl acetate=1:1).

(c) 1-((1-(2-(3,6-Diazabicyclo[3.1.1]heptan-3-yl)-7-(thiazol-2-yl)benzo[d]oxazol-4-yl)-2,2,2-trifluoroethoxy)methyl)cyclopropan-1-ol The title compound was obtained in an amount of 2.6 mg from 2.0 mg of tert-butyl 3-(7-(thiazol-2-yl)-4-(2,2,2-trifluoro-1-((1-hydroxycyclopropyl)methoxy)ethyl)benzo[d]oxazol-2-yl)-3,6-diazabicyclo[3.1.1]heptane-6-carboxylate obtained in Example 232 (a) by a similar method to Example 1(c).

Example 233

1-(2-(3,8-Diazabicyclo[3.2.1]octan-3-yl)-7-(thiazol-2-yl)benzo[d]oxazol-4-yl)-2,2,2-trifluoroethane-1,1-diol (a) tert-butyl 3-(7-(thiazol-2-yl)-4-(2,2,2-trifluoroacetyl)benzo[d]oxazol-2-yl)-3,8-diazabicyclo[3.2.1]octane-8-carboxylate The title compound was obtained in an amount of 10 mg from 10 mg of tert-butyl 3-(7-(thiazol-2-yl)-4-(2,2,2-trifluoro-1-hydroxyethyl)benzo[d]oxazol-2-yl)-3,8-diazabicyclo[3.2.1]octane-8-carboxylate obtained in Example 118 (b) by a similar method to Example 102 (c).

(b) 1-(2-(3,8-Diazabicyclo[3.2.1]octan-3-yl)-7-(thiazol-2-yl)benzo[d]oxazol-4-yl)-2,2,2-trifluoroethane-1,1-diol The title compound was obtained in an amount of 5.7 mg from 10 mg of tert-butyl 3-(7-(thiazol-2-yl)-4-(2,2,2-trifluoroacetyl)benzo[d]oxazol-2-yl)-3,8-diazabicyclo[3.2.1]octane-8-carboxylate obtained in Example 233 (a) by a similar method to Example 1(c).

Example 234

2-(2-(3,6-Diazabicyclo[3.1.1]heptan-3-yl)-7-(thiazol-2-yl)benzo[d]oxazol-4-yl)-1,1,1-trifluoropropan-2-ol (a) tert-Butyl 3-(7-bromo-4-(2,2,2-trifluoro-1-hydroxyethyl)benzo[d]oxazol-2-yl)-3,6-diazabicyclo[3.1.1]heptane-6-carboxylate The title compound was obtained in an amount of 574 mg from 500 mg of 1-(7-bromo-2-mercaptobenzo[d]oxazol-4-yl)-2,2,2-trifluoroethan-1-ol obtained in Reference Example 21 by a similar method to Example 1(a) except that tert-butyl 3,6-diazabicyclo[3.1.1]heptane-6-carboxylate was used instead of tert-butyl 3,8-diazabicyclo[3.2.1]octane-8-carboxylate.

(b) tert-Butyl 3-(7-(thiazol-2-yl)-4-(2,2,2-trifluoro-1-hydroxyethyl)benzo[d]oxazol-2-yl)-3,6-diazabicyclo[3.1.1]heptane-6-carboxylate The title compound was obtained in an amount of 493 mg from 574 mg of tert-butyl 3-(7-bromo-4-(2,2,2-trifluoro-1-hydroxyethyl)benzo[d]oxazol-2-yl)-3,6-diazabicyclo[3.1.1]heptane-6-carboxylate obtained in Example 234 (a) by a similar method to Example 1(b).

(c) tert-Butyl 3-(7-(thiazol-2-yl)-4-(2,2,2-trifluoro-1,1-dihydroxyethyl)benzo[d]oxazol-2-yl)-3,6-diazabicyclo[3.1.1]heptane-6-carboxylate The title compound was obtained as a crude product in an amount of 26 mg from 25 mg of tert-butyl 3-(7-(thiazol-2-yl)-4-(2,2,2-trifluoro-1-hydroxyethyl)benzo[d]oxazol-2-yl)-3,6-diazabicyclo[3.1.1]heptane-6-carboxylate obtained in Example 234 (b) by a similar method to Example 156(a).

(d) tert-Butyl 3-(7-(thiazol-2-yl)-4-(1,1,1-trifluoro-2-hydroxypropan-2-yl)benzo[d]oxazol-2-yl)-3,6-diazabicyclo[3.1.1]heptane-6-carboxylate 26 mg of tert-butyl 3-(7-(thiazol-2-yl)-4-(2,2,2-trifluoro-1,1-dihydroxyethyl)benzo[d]oxazol-2-yl)-3,6-diazabicyclo

[3.1.1]heptane-6-carboxylate obtained in Example 234(c) was dissolved in tetrahydrofuran (0.5 mL), then 0.92M methylmagnesium bromide solution in tetrahydrofuran (0.54 mL, 10 equivalents) was added at 0° C. and stirred for 1 hour, followed by stirring at room temperature for 90 min. The formation of the product was confirmed by TLC (eluent, hexane:ethyl acetate=1:1), and then saturated ammonium chloride aqueous solution was added thereto, and then the organic phase was extracted by ethyl acetate. The organic phase was dried over anhydrous magnesium sulfate, followed by filtration and vacuum concentration of the filtrate, and thus obtaining 14 mg of the title compound by purification of the residue through silica gel column chromatography (aminosilica, hexane:ethyl acetate=1:4).

(e) 2-(2-(3,6-Diazabicyclo[3.1.1]heptan-3-yl)-7-(thiazol-2-yl)benzo[d]oxazol-4-yl)-1,1,1-trifluoropropan-2-ol The title compound was obtained in an amount of 4.3 mg from 14 mg of tert-butyl 3-(7-(thiazol-2-yl)-4-(1,1,1-trifluoro-2-hydroxypropan-2-yl)benzo[d]oxazol-2-yl)-3,6-diazabicyclo[3.1.1]heptane-6-carboxylate obtained in Example 234(d) by a similar method to Example 1(c).

Example 235

2-(3,6-Diazabicyclo[3.1.1]heptan-3-yl)-7-(thiazol-2-yl)-4-(1,1,1-trifluoro-2-methoxypropan-2-yl)benzo[d]oxazole (a) tert-Butyl 3-(7-(thiazol-2-yl)-4-(1,1,1-trifluoro-2-methoxypropan-2-yl)benzo[d]oxazol-2-yl)-3,6-diazabicyclo[3.1.1]heptane-6-carboxylate The title compound was obtained in an amount of 11 mg from 14 mg of tert-butyl 3-(7-(thiazol-2-yl)-4-(1,1,1-trifluoro-2-hydroxypropan-2-yl)benzo[d]oxazol-2-yl)-3,6-diazabicyclo[3.1.1]heptane-6-carboxylate obtained in Example 234(d) by a similar method to Example 102 (e).

(b) 2-(3,6-Diazabicyclo[3.1.1]heptan-3-yl)-7-(thiazol-2-yl)-4-(1,1,1-trifluoro-2-methoxypropan-2-yl)benzo[d]oxazole The title compound was obtained in an amount of 7.2 mg from 11 mg of tert-butyl 3-(7-(thiazol-2-yl)-4-(1,1,1-trifluoro-2-methoxypropan-2-yl)benzo[d]oxazol-2-yl)-3,6-diazabicyclo[3.1.1]heptane-6-carboxylate obtained in Example 235(a) by a similar method to Example 1(c).

Example 236

2-(2-(3,8-Diazabicyclo[3.2.1]octan-3-yl)-7-(thiazol-2-yl)benzo[d]oxazol-4-yl)-1,1,1-trifluoropropan-2-ol (a) tert-Butyl 3-(7-(thiazol-2-yl)-4-(1,1,1-trifluoro-2-hydroxypropan-2-yl)benzo[d]oxazol-2-yl)-3,8-diazabicyclo[3.2.1]octane-8-carboxylate The title compound was obtained in an amount of 4.2 mg from 41 mg of tert-butyl 3-(7-(thiazol-2-yl)-4-(2,2,2-trifluoroacetyl)benzo[d]oxazol-2-yl)-3,8-diazabicyclo[3.2.1]octane-8-carboxylate obtained in Example 233 (a) by a similar method to Example 102 (b).

(b) 2-(2-(3,8-Diazabicyclo[3.2.1]octan-3-yl)-7-(thiazol-2-yl)benzo[d]oxazol-4-yl)-1,1,1-trifluoropropan-2-ol The title compound was obtained in an amount of 5.2 mg from 10 mg of tert-butyl 3-(7-(thiazol-2-yl)-4-(1,1,1-trifluoro-2-hydroxypropan-2-yl)benzo[d]oxazol-2-yl)-3,8-diazabicyclo[3.2.1]octane-8-carboxylate obtained in Example 236(a) by a similar method to Example 1(c).

Example 237

Methyl 2-(3,8-diazabicyclo[3.2.1]octan-3-yl)-7-(thiazol-2-yl)benzo[d]oxazole-4-carboxylate (a) Methyl 7-bromo-2-(8-(tert-butoxycarbonyl)-3,8-diazabicyclo[3.2.1]octan-3-yl)benzo[d]oxazol-4-carboxylate The title compound was obtained in an amount of 268 mg from 200 mg of methyl 7-bromo-2-mercaptobenzo[d]oxazole-4-carboxylate obtained in Reference Example 22 and tert-butyl 3,8-diazabicyclo[3.2.1]octane-8-carboxylate by a similar method to Example 1(a).

(b) Methyl 2-(8-(tert-butoxycarbonyl)-3,8-diazabicyclo[3.2.1]octan-3-yl)-7-(thiazol-2-yl)benzo[d]oxazol-4-carboxylate The title compound was obtained in an amount of 82 mg from 221 mg of methyl 7-bromo-2-(8-(tert-butoxycarbonyl)-3,8-diazabicyclo[3.2.1]octan-3-yl)benzo[d]oxazol-4-carboxylate obtained in Example 237 (a) by a similar method to Example 1(b).

(c) Methyl 2-(3,8-diazabicyclo[3.2.1]octan-3-yl)-7-(thiazol-2-yl)benzo[d]oxazole-4-carboxylate The title compound was obtained in an amount of 12 mg from 19 mg of methyl 2-(8-(tert-butoxycarbonyl)-3,8-diazabicyclo[3.2.1]octan-3-yl)-7-(thiazol-2-yl)benzo[d]oxazol-4-carboxylate obtained in Example 237 (b) by a similar method to Example 1(c).

Example 238

2-(3,8-Diazabicyclo[3.2.1]octan-3-yl)-7-(thiazol-2-yl)benzo[d]oxazole-4-carboxylic acid The title compound was obtained in an amount of 6.8 mg from 12 mg of methyl 2-(3,8-diazabicyclo[3.2.1]octan-3-yl)-7-(thiazol-2-yl)benzo[d]oxazole-4-carboxylate obtained in Example 237 (c) by a similar method to Example 94(a).

Example 239

1-(2-(3,9-Diazabicyclo[3.3.1]nonan-3-yl)-7-(thiazol-2-yl)benzo[d]oxazol-4-yl)ethan-1-ol (a) Methyl 7-bromo-2-(9-(tert-butoxycarbonyl)-3,9-diazabicyclo[3.3.1]nonan-3-yl)benzo[d]oxazol-4-carboxylate The title compound was obtained in an amount of 566 mg from 500 mg of methyl 7-bromo-2-mercaptobenzo[d]oxazole-4-carboxylate obtained in Reference Example 22 by a similar method to Example 1(a) except that tert-butyl 3,9- diazabicyclo[3.3.1]nonane-9-carboxylate was used instead of tert-butyl 3,8-diazabicyclo[3.2.1]octane-8-carboxylate.

(b) Methyl 2-(9-(tert-butoxycarbonyl)-3,9-diazabicyclo[3.3.1]nonan-3-yl)-7-(thiazol-2-yl)benzo[d]oxazol-4-carboxylate The title compound was obtained in an amount of 312 mg from 566 mg of methyl 7-bromo-2-(9-(tert-butoxycarbonyl)-3,9-diazabicyclo[3.3.1]nonan-3-yl)benzo[d]oxazol-4-carboxylate obtained in Example 239(a) by a similar method to Example 1(b).

(c) tert-Butyl 3-(4-(hydroxymethyl)-7-(thiazol-2-yl)benzo[d]oxazol-2-yl)-3,9-Diazabicyclo[3.3.1]nonane-9-carboxylate The title compound was obtained as a crude product from 250 mg of methyl 2-(9-(tert-butoxycarbonyl)-3,9-diazabicyclo[3.3.1]nonan-3-yl)-7-(thiazol-2-yl)benzo[d]oxazol-4-carboxylate obtained in Example 239(b) by a similar method to Example 201(a).

(d) tert-Butyl 3-(4-formyl-7-(thiazol-2-yl)benzo[d]oxazol-2-yl)-3,9-diazabicyclo[3.3.1]nonane-9-carboxylate The title compound was obtained in an amount of 120 mg from the crude product of tert-butyl 3-(4-(hydroxymethyl)-7-(thiazol-2-yl)benzo[d]oxazol-2-yl)-3,9-diazabicyclo[3.3.1]nonane-9-carboxylate obtained in Example 239(c) by a similar method to Example 202 (a).

(e) tert-Butyl 3-(4-(1-hydroxyethyl)-7-(thiazol-2-yl)benzo[d]oxazol-2-yl)-3,9-diazabicyclo[3.3.1]nonane-9-carboxylate The title compound was obtained in an amount of 68 mg from 120 mg of tert-butyl 3-(4-formyl-7-(thiazol-2-yl)benzo[d]oxazol-2-yl)-3,9-diazabicyclo[3.3.1]nonane-9-carboxylate obtained in Example 239(d) by a similar method to Example 102 (b).

(f) 1-(2-(3,9-Diazabicyclo[3.3.1]nonan-3-yl)-7-(thiazol-2-yl)benzo[d]oxazol-4-yl)ethan-1-ol The title compound was obtained in an amount of 10 mg from 14 mg of tert-butyl 3-(4-(1-hydroxyethyl)-7-(thiazol-2-yl)benzo[d]oxazol-2-yl)-3,9-diazabicyclo[3.3.1]nonane-9-carboxylate obtained in Example 239(e) by a similar method to Example 1(c).

Example 240

1-(2-(3,6-Diazabicyclo[3.1.1]heptan-3-yl)-7-(thiazol-2-yl)benzo[d]oxazol-4-yl)ethan-1-ol (a) Methyl 7-bromo-2-(6-(tert-butoxycarbonyl)-3,6-diazabicyclo[3.1.1]heptan-3-yl)benzo[d]oxazol-4-carboxylate The title compound was obtained in an amount of 501 mg from 500 mg of methyl 7-bromo-2-mercaptobenzo[d]oxazole-4-carboxylate obtained in Reference Example 22 by a similar method to Example 1(a) except that tert-butyl 3,6-diazabicyclo[3.1.1]heptane-6-carboxylate was used instead of tert-butyl 3,8-diazabicyclo[3.2.1]octane-8-carboxylate.

(b) Methyl 2-(6-(tert-butoxycarbonyl)-3,6-diazabicyclo[3.1.1]heptan-3-yl)-7-(thiazol-2-yl)benzo[d]oxazol-4-carboxylate The title compound was obtained in an amount of 298 mg from 508 mg of methyl 7-bromo-2-(6-(tert-butoxycarbonyl)-3,6-diazabicyclo[3.1.1]heptan-3-yl)benzo[d]oxazol-4-carboxylate obtained in Example 240(a) by a similar method to Example 1(b).

(c) tert-Butyl 3-(4-(hydroxymethyl)-7-(thiazol-2-yl)benzo[d]oxazol-2-yl)-3,6-diazabicyclo[3.1.1]heptane-6-carboxylate The title compound was obtained as a crude product in an amount of 168 mg from 280 mg of methyl 2-(6-(tert-butoxycarbonyl)-3,6-diazabicyclo[3.1.1]heptan-3-yl)-7-(thiazol-2-yl)benzo[d]oxazol-4-carboxylate obtained in Example 240(b) by a similar method to Example 201(a) except that dichloromethane was used instead of toluene.

(d) tert-Butyl 3-(4-formyl-7-(thiazol-2-yl)benzo[d]oxazol-2-yl)-3,6-diazabicyclo[3.1.1]heptane-6-carboxylate The title compound was obtained in an amount of 163 mg from 168 mg of the crude product of tert-butyl 3-(4-(hydroxymethyl)-7-(thiazol-2-yl)benzo[d]oxazol-2-yl)-3,6-diazabicyclo[3.1.1]heptane-6-carboxylate obtained in Example 240(c) by a similar method to Example 202 (a).

(e) tert-Butyl 3-(4-(1-hydroxyethyl)-7-(thiazol-2-yl)benzo[d]oxazol-2-yl)-3,6-diazabicyclo[3.1.1]heptane-6-carboxylate The title compound was obtained in an amount of 117 mg from 175 mg of tert-butyl 3-(4-formyl-7-(thiazol-2-yl)benzo[d]oxazol-2-yl)-3,6-diazabicyclo[3.1.1]heptane-6-carboxylate obtained in Example 240(d) by a similar method to Example 102 (b).

(f) 1-(2-(3,6-Diazabicyclo[3.1.1]heptan-3-yl)-7-(thiazol-2-yl)benzo[d]oxazol-4-yl)ethan-1-ol The title compound was obtained in an amount of 6.8 mg from 13 mg of tert-butyl 3-(4-(1-hydroxyethyl)-7-(thiazol-2-yl)benzo[d]oxazol-2-yl)-3,6-diazabicyclo[3.1.1]heptane-6-carboxylate obtained in Example 240(e) by a similar method to Example 1(c).

Example 241

2-(3,6-Diazabicyclo[3.1.1]heptan-3-yl)-4-(1-methoxyethyl)-7-(thiazol-2-yl)benzo[d]oxazole (a) tert-Butyl 3-(4-(1-methoxyethyl)-7-(thiazol-2-yl)benzo[d]oxazol-2-yl)-3,6-diazabicyclo[3.1.1]heptane-6-carboxylate The title compound was obtained in an amount of 11 mg from 18 mg of tert-butyl 3-(4-(1-hydroxyethyl)-7-(thiazol-2-yl)benzo[d]oxazol-2-yl)-3,6-diazabicyclo[3.1.1]heptane-6-carboxylate obtained in Example 240(e) by a similar method to Example 102 (e).

(b) 2-(3,6-Diazabicyclo[3.1.1]heptan-3-yl)-4-(1-methoxyethyl)-7-(thiazol-2-yl)benzo[d]oxazole The title compound was obtained in an amount of 14 mg from 22 mg of tert-butyl 3-(4-(1-methoxyethyl)-7-(thiazol-2-yl)benzo[d]oxazol-2-yl)-3,6-diazabicyclo[3.1.1]heptane-6-carboxylate obtained in Example 241(a) by a similar method to Example 1(c).

Example 242

2-(3,8-Diazabicyclo[3.2.1]octan-3-yl)-4-(1-methoxyethyl)-7-(thiazol-2-yl)benzo[d]oxazole (a) tert-Butyl 3-(4-(1-methoxyethyl)-7-(thiazol-2-yl)benzo[d]oxazol-2-yl)-3,8-diazabicyclo[3.2.1]octane-8-carboxylate The title compound was obtained in an amount of 18 mg from 18 mg of the crude product of tert-butyl 3-(4-(1-hydroxyethyl)-7-(thiazol-2-yl)benzo[d]oxazol-2-yl)-3,8-diazabicyclo[3.2.1]octane-8-carboxylate obtained in Example 124 by a similar method to Example 102 (e).

(b) 2-(3,8-Diazabicyclo[3.2.1]octan-3-yl)-4-(1-methoxyethyl)-7-(thiazol-2-yl)benzo[d]oxazole The title compound was obtained in an amount of 12 mg from 18 mg of tert-butyl 3-(4-(1-methoxyethyl)-7-(thiazol-2-yl)benzo[d]oxazol-2-yl)-3,8-diazabicyclo[3.2.1]octane-8-carboxylate obtained in Example 242 (a) by a similar method to Example 1(c).

Example 243

2-(3,9-Diazabicyclo[3.3.1]nonan-3-yl)-4-(1-methoxyethyl)-7-(thiazol-2-yl)benzo[d]oxazole (a) tert-Butyl 3-(4-(1-methoxyethyl)-7-(thiazol-2-yl)benzo[d]oxazol-2-yl)-3,9-diazabicyclo[3.3.1]nonane-9-carboxylate The title compound was obtained in an amount of 13 mg from 14 mg of tert-butyl 3-(4-(1-hydroxyethyl)-7-(thiazol-2-yl)benzo[d]oxazol-2-yl)-3,9-diazabicyclo[3.3.1]nonane-9-carboxylate obtained in Example 239(e) by a similar method to Example 102 (e).

(b) 2-(3,9-Diazabicyclo[3.3.1]nonan-3-yl)-4-(1-methoxyethyl)-7-(thiazol-2-yl)benzo[d]oxazole The title compound was obtained in an amount of 8.7 mg from 13 mg of tert-butyl 3-(4-(1-methoxyethyl)-7-(thiazol-2-yl)benzo[d]oxazol-2-yl)-3,9-diazabicyclo[3.3.1]nonane-9-carboxylate obtained in Example 243 (a) by a similar method to Example 1(c).

Example 244

1-(2-(3,6-Diazabicyclo[3.1.1]heptan-3-yl)-7-(thiazol-2-yl)benzo[d]oxazol-4-yl)ethan-1-one (a) tert-Butyl 3-(4-acetyl-7-(thiazol-2-yl)benzo[d]oxazol-2-yl)-3,6-diazabicyclo[3.1.1]heptane-6-carboxylate The title compound was obtained in an amount of 71 mg from 105 mg of tert-butyl 3-(4-(1-hydroxyethyl)-7-(thiazol-2-yl)benzo[d]oxazol-2-yl)-3,6-diazabicyclo[3.1.1]heptane-6-carboxylate obtained in Example 240(e) by a similar method to Example 102 (c).

(b) 1-(2-(3,6-Diazabicyclo[3.1.1]heptan-3-yl)-7-(thiazol-2-yl)benzo[d]oxazol-4-yl)ethan-1-one The title compound was obtained in an amount of 4.0 mg from 13 mg of tert-butyl 3-(4-acetyl-7-(thiazol-2-yl)benzo[d]oxazol-2-yl)-3,6-diazabicyclo[3.1.1]heptane-6-carboxylate obtained in Example 244 (a) by a similar method to Example 1(c).

Example 245

1-(2-(3,8-Diazabicyclo[3.2.1]octan-3-yl)-7-(thiazol-2-yl)benzo[d]oxazol-4-yl)ethan-1-one (a) tert-Butyl 3-(4-acetyl-7-(thiazol-2-yl)benzo[d]oxazol-2-yl)-3,8-diazabicyclo[3.2.1]octane-8-carboxylate The title compound was obtained in an amount of 64 mg from 72 mg of the crude product of tert-butyl 3-(4-(1-hydroxyethyl)-7-(thiazol-2-yl)benzo[d]oxazol-2-yl)-3,8-diazabicyclo[3.2.1]octane-8-carboxylate obtained in Example 124 by a similar method to Example 102 (c).

(b) 1-(2-(3,8-Diazabicyclo[3.2.1]octan-3-yl)-7-(thiazol-2-yl)benzo[d]oxazol-4-yl)ethan-1-one The title compound was obtained in an amount of 4.2 mg from 14 mg of tert-butyl 3-(4-acetyl-7-(thiazol-2-yl)benzo[d]oxazol-2-yl)-3,8-diazabicyclo[3.2.1]octane-8-carboxylate obtained in Example 245 (a) by a similar method to Example 1(c).

Example 246

2-(2-(3,6-Diazabicyclo[3.1.1]heptan-3-yl)-7-(thiazol-2-yl)benzo[d]oxazol-4-yl)propan-2-ol (a) tert-Butyl 3-(4-(2-hydroxypropan-2-yl)-7-(thiazol-2-yl)benzo[d]oxazol-2-yl)-3,6-diazabicyclo[3.1.1]heptane-6-carboxylate The title compound was obtained in an amount of 37 mg from 67 mg of tert-butyl 3-(4-acetyl-7-(thiazol-2-yl)benzo[d]oxazol-2-yl)-3,6-diazabicyclo[3.1.1]heptane-6-carboxylate obtained in Example 244 (a) by a similar method to Example 171(d).

(b) 2-(2-(3,6-Diazabicyclo[3.1.1]heptan-3-yl)-7-(thiazol-2-yl)benzo[d]oxazol-4-yl)propan-2-ol The title compound was obtained in an amount of 4.0 mg from 13 mg of tert-butyl 3-(4-(2-hydroxypropan-2-yl)-7-(thiazol-2-yl)benzo[d]oxazol-2-yl)-3,6-diazabicyclo[3.1.1]

heptane-6-carboxylate obtained in Example 246(a) by a similar method to Example 1(c).

Example 247

2-(2-(3,8-Diazabicyclo[3.2.1]octan-3-yl)-7-(thiazol-2-yl)benzo[d]oxazol-4-yl)propan-2-ol (a) tert-Butyl 3-(4-(2-hydroxypropan-2-yl)-7-(thiazol-2-yl)benzo[d]oxazol-2-yl)-3,8-diazabicyclo[3.2.1]octane-8-carboxylate The title compound was obtained in an amount of 27 mg from 51 mg of tert-butyl 3-(4-acetyl-7-(thiazol-2-yl)benzo[d]oxazol-2-yl)-3,8-diazabicyclo[3.2.1]octane-8-carboxylate obtained in Example 245 (a) by a similar method to Example 171(d).

(b) 2-(2-(3,8-Diazabicyclo[3.2.1]octan-3-yl)-7-(thiazol-2-yl)benzo[d]oxazol-4-yl)propan-2-ol The title compound was obtained in an amount of 3.3 mg from 10 mg of tert-butyl 3-(4-(2-hydroxypropan-2-yl)-7-(thiazol-2-yl)benzo[d]oxazol-2-yl)-3,8-diazabicyclo[3.2.1]octane-8-carboxylate obtained in Example 247 (a) by a similar method to Example 1(c).

Example 248

1-((2-(3,6-Diazabicyclo[3.1.1]heptan-3-yl)-7-(thiazol-2-yl)benzo[d]oxazol-4-yl)oxy)-1,1-difluoro-2-methylpropan-2-ol (a) tert-Butyl 3-(4-(benzyloxyl)-7-bromobenzo[d]oxazol-2-yl)-3,6-diazabicyclo[3.1.1]heptane-6-carboxylate The title compound was obtained in an amount of 2.9 g from 2.3 g of 4-(benzyloxy)-7-bromobenzo[d]oxazole-2-thiol obtained in Reference Example 23 by a similar method to Example 1(a) except that tert-butyl 3,6-diazabicyclo[3.1.1]heptane-6-carboxylate was used instead of tert-butyl 3,8-diazabicyclo[3.2.1]octane-8-carboxylate.

(b) tert-Butyl 3-(4-(benzyloxyl)-7-(thiazol-2-yl)benzo[d]oxazol-2-yl)-3,6-diazabicyclo[3.1.1]heptane-6-carboxylate The title compound was obtained in an amount of 2.5 g from 2.9 g of tert-butyl 3-(4-(benzyloxyl)-7-bromobenzo[d]oxazol-2-yl)-3,6-diazabicyclo[3.1.1]heptane-6-carboxylate obtained in Example 248 (a) by a similar method to Example 1(b).

(c) tert-Butyl 3-(4-hydroxy-7-(thiazol-2-yl)benzo[d]oxazol-2-yl)-3,6-diazabicyclo[3.1.1]heptane-6-carboxylate 1.5 g of tert-butyl 3-(4-(benzyloxyl)-7-(thiazol-2-yl)benzo[d]oxazol-2-yl)-3,6-diazabicyclo[3.1.1]heptane-6-carboxylate obtained in Example 248 (b) was dissolved in tetrahydrofuran (60 mL), then 20% palladium hydroxide/carbon (content of water: 50%, 2.5 g) was added under an argon atmosphere, followed by filling up with hydrogen and stirring at 50° C. for 4.5 hours. After Celite® filtration of the reaction solution, 1.0 g of the title compound by purification of the residue obtained by vacuum concentration of the filtrate through silica gel column chromatography (chloroform-chloroform:methanol=94:6).

(d) tert-Butyl 3-(4-(2-ethoxy-1,1-difluoro-2-oxoethoxy)-7-(thiazol-2-yl)benzo[d]oxazol-2-yl)-3,6-diazabicyclo[3.1.1]heptane-6-carboxylate 1.0 g of tert-butyl 3-(4-hydroxy-7-(thiazol-2-yl)benzo[d]oxazol-2-yl)-3,6-diazabicyclo[3.1.1]heptane-6-carboxylate obtained in Example 248 (c) was dissolved in acetonitrile (24 mL), then 1,8-diazabicyclo[5.4.0]undec-7-ene (3.6 mL, 10 equivalents) and ethyl 2-bromo-2,2-difluoroacetate (3.1 mL, 10 equivalents) were added, followed by stirring at room temperature for 2 hours. The formation of the product was confirmed by TLC, and then saturated ammonium chloride aqueous solution was added thereto to stop the reaction, and then the organic phase was extracted by ethyl acetate 3 times. The organic phase was dried over anhydrous magnesium sulfate, followed by filtration and vacuum concentration of the filtrate, and thus obtaining 1.0 g of the title compound by purification of the residue through silica gel column chromatography (hexane-hexane:ethyl acetate=5:5).

(e) tert-Butyl 3-(4-(1,1-difluoro-2-hydroxy)-2-methylpropoxy)-7-(thiazol-2-yl)benzo[d]oxazol-2-yl)-3,6-diazabicyclo[3.1.1]heptane-6-carboxylate 92 mg of tert-butyl 3-(4-(2-ethoxy-1,1-difluoro-2-oxoethoxy)-7-(thiazol-2-yl)benzo[d]oxazol-2-yl)-3,6-diazabicyclo[3.1.1]heptane-6-carboxylate obtained in Example 248(d) was dissolved in tetrahydrofuran (1.7 mL), then 0.95M methylmagnesium bromide solution in tetrahydrofuran (0.85 mL, 5 equivalents) was added at 0° C., followed by stirring at room temperature for 1 hour. Saturated ammonium chloride aqueous solution was added thereto to stop the reaction, and then the organic phase was extracted by ethyl acetate 3 times. The organic phase was dried over anhydrous magnesium sulfate, followed by filtration and vacuum concentration of the filtrate, and thus obtaining 82 mg of the title compound by purification of the residue through silica gel column chromatography (hexane-hexane:ethyl acetate-ethyl acetate).

(f) 1-((2-(3,6-Diazabicyclo[3.1.1]heptan-3-yl)-7-(thiazol-2-yl)benzo[d]oxazol-4-yl)oxy)-1,1-difluoro-2-methylpropan-2-ol The title compound was obtained in an amount of 39 mg from 58 mg of tert-butyl 3-(4-(1,1-difluoro-2-hydroxy)-2-methylpropoxy)-7-(thiazol-2-yl)benzo[d]oxazol-2-yl)-3,6-diazabicyclo[3.1.1]heptane-6-carboxylate obtained in Example 248 (e) by a similar method to Example 1(c).

Example 249

2-((2-(3,6-Diazabicyclo[3.1.1]heptan-3-yl)-7-(thiazol-2-yl)benzo[d]oxazol-4-yl)oxy)-2,2-difluoroethan-1-ol (a) tert-Butyl 3-(4-(1,1-difluoro-2-hydroxyethoxy)-7-(thiazol-2-yl)benzo[d]oxazol-2-yl)-3,6-diazabicyclo[3.1.1]heptane-6-carboxylate 21 mg of tert-butyl 3-(4-(2-ethoxy-1,1-difluoro-2-oxoethoxy)-7-(thiazol-2-yl)benzo[d]oxazol-2-yl)-3,6-diazabicyclo[3.1.1]heptane-6-carboxylate obtained in Example 248 (d) was dissolved in tetrahydrofuran (390 μL) and methanol (390 µL), then sodium borohydride (18 mg, 12 equivalents) was added at room temperature, followed by stirring for 4 hours. Saturated ammonium chloride aqueous solution was added thereto to stop the reaction, and then the organic phase was extracted by ethyl acetate 3 times. The organic phase was dried over anhydrous magnesium sulfate, followed by filtration and vacuum concentration of the filtrate, and thus obtaining 15 mg of the title compound by purification of the residue by preparative TLC (hexane:ethyl acetate=1:2).

(b) 2-((2-(3,6-Diazabicyclo[3.1.1]heptan-3-yl)-7-(thiazol-2-yl)benzo[d]oxazol-4-yl)oxy)-2,2-difluoroethan-1-ol The title compound was obtained in an amount of 11 mg from 15 mg of tert-butyl 3-(4-(1,1-difluoro-2-hydroxyethoxy)-7-(thiazol-2-yl)benzo[d]oxazol-2-yl)-3,6-diazabicyclo[3.1.1]heptane-6-carboxylate obtained in Example 249 (a) by a similar method to Example 1(c).

Example 250

1-((2-(3,6-Diazabicyclo[3.1.1]heptan-3-yl)-7-(thiazol-2-yl)benzo[d]oxazol-4-yl)oxy)-1,1-difluoropropan-2-ol (racemic)

(a) tert-Butyl 3-(4-(1,1-difluoro-2-(methoxy(methyl)amino)-2-oxoethoxy)-7-(thiazol-2-yl)benzo[d]oxazol-2-yl)-3,6-diazabicyclo[3.1.1]heptane-6-carboxylate 200 mg of tert-butyl 3-(4-(2-ethoxy-1,1-difluoro-2-oxoethoxy)-7-(thiazol-2-yl)benzo[d]oxazol-2-yl)-3,6-diazabicyclo[3.1.1]heptane-6-carboxylate obtained in Example 248 (d) and N,O-dimethylhydroxylamine hydrochloride (110 mg, 3 equivalents) were dissolved in tetrahydrofuran (3.7 mL), and then 2M solution of isopropylmagnesium bromide in tetrahydrofuran (1.1 mL, 6 equivalents) was dropped thereto at 0° C. over 40 min, followed by stirring at 0° C. for 20 min. Saturated ammonium chloride aqueous solution was added thereto to stop the reaction, which was extracted by ethyl acetate 2 times. The organic phase was dried over anhydrous magnesium sulfate, followed by filtration and vacuum concentration of the filtrate, thus obtaining 210 mg of the title compound as a crude product.

(b) tert-Butyl 3-(4-(1,1-difluoro-2,2-dihydroxypropoxy)-7-(thiazol-2-yl)benzo[d]oxazol-2-yl)-3,6-diazabicyclo[3.1.1]heptane-6-carboxylate 210 mg of the crude product of tert-butyl 3-(4-(1,1-difluoro-2-(methoxy(methyl)amino)-2-oxoethoxy)-7-(thiazol-2-yl)benzo[d]oxazol-2-yl)-3,6-diazabicyclo[3.1.1]heptane-6-carboxylate obtained in Example 250(a) was dissolved in tetrahydrofuran (3.8 mL), and then 0.95M methylmagnesium bromide solution in tetrahydrofuran (0.81 mL, 2 equivalents) was added thereto at 0° C., followed by stirring for 30 min. Saturated ammonium chloride aqueous solution was added thereto to stop the reaction, which was extracted by ethyl acetate 2 times. The organic phase was dried over anhydrous magnesium sulfate, followed by filtration and vacuum concentration of the filtrate, and thus obtaining 200 mg of the title compound as a crude product.

(c) tert-Butyl 3-(4-(1,1-difluoro-2-hydroxypropoxy)-7-(thiazol-2-yl)benzo[d]oxazol-2-yl)-3,6-diazabicyclo[3.1.1]heptane-6-carboxylate (racemic)

195 mg of tert-butyl 3-(4-(1,1-difluoro-2,2-dihydroxypropoxy)-7-(thiazol-2-yl)benzo[d]oxazol-2-yl)-3,6-diazabicyclo[3.1.1]heptane-6-carboxylate obtained in Example 250 (b) was dissolved in tetrahydrofuran (3.7 mL) and methanol (3.7 mL), and then sodium borohydride (113 mg, 8 equivalents) was added thereto at 0° C., followed by stirring for 30 min at room temperature. Saturated ammonium chloride aqueous solution was added thereto to stop the reaction, which was extracted by ethyl acetate 2 times. The organic phase was dried over anhydrous magnesium sulfate, followed by filtration and vacuum concentration of the filtrate Ethyl acetate (1 mL) was added to the residue and the formed precipitate was collected by filteration to give 150 mg of the title compound.

(d) 1-((2-(3,6-Diazabicyclo[3.1.1]heptan-3-yl)-7-(thiazol-2-yl)benzo[d]oxazol-4-yl)oxy)-1,1-difluoropropan-2-ol (racemic)

The title compound was obtained in an amount of 31 mg from 41 mg of tert-butyl 3-(4-(1,1-difluoro-2-hydroxypropoxy)-7-(thiazol-2-yl)benzo[d]oxazol-2-yl)-3,6-diazabicyclo[3.1.1]heptane-6-carboxylate obtained in Example 250 (c) by a similar method to Example 1(c).

Example 251

1-((2-(3,6-Diazabicyclo[3.1.1]heptan-3-yl)-7-(thiazol-2-yl)benzo[d]oxazol-4-yl)oxy)-1,1-difluoropropan-2-ol (Optically Active)

(a) tert-Butyl 3-(4-(1,1-difluoro-2-hydroxypropoxy)-7-(thiazol-2-yl)benzo[d]oxazol-2-yl)-3,6-diazabicyclo[3.1.1]heptane-6-carboxylate (Optically Active)

1.4 g of racemic tert-butyl 3-(4-(1,1-difluoro-2-hydroxypropoxy)-7-(thiazol-2-yl)benzo[d]oxazol-2-yl)-3,6-diazabicyclo[3.1.1]heptane-6-carboxylate obtained in Example 250 (c) was purified by a Multiple preparative HPLC (YMC, LC-forte/R, column: DAICEL CHIRALPAK IC (particle diameter: 5 µm, column diameter: 2 cm, column length: 25 cm), eluent, hexane:isopropyl alcohol=70:30, flow rate: 19.8 mL/min, detection: UV254 nm) and the title compound was obtained in an amount of 687 mg by concentrating fractions with the shorter retention time peak. 99.9% ee. Analysis conditions: HPLC (HITACHI, column: DAICEL CHIRALPAK IC (particle diameter: 5 µm, column diameter: 0.46 cm, column length: 25 cm), eluent, hexane:isopropyl alcohol=70:30, flow rate: 1 mL/min, detection: UV254 nm, temperature: 25° C., retention time: 9.84 min).

(b) 1-((2-(3,6-Diazabicyclo[3.1.1]heptan-3-yl)-7-(thiazol-2-yl)benzo[d]oxazol-4-yl)oxy)-1,1-difluoropropan-2-ol (Optically Active)

The title compound was obtained in an amount of 474 mg from 687 mg of tert-butyl 3-(4-(1,1-difluoro-2-hydroxypropoxy)-7-(thiazol-2-yl)benzo[d]oxazol-2-yl)-3,6-diazabicyclo[3.1.1]heptane-6-carboxylate (Optically Active) Obtained in Example 251(a) by a similar method to Example 1(c). 99.9% ee. Analysis conditions: HPLC (HITACHI, column: DAICEL CHIRALPAK IC (particle diameter: 5 µm, column diameter: 0.46 cm, column length: 25 cm),

Example 252

1-((2-(3,6-Diazabicyclo[3.1.1]heptan-3-yl)-7-(thiazol-2-yl)benzo[d]oxazol-4-yl)oxy)-1,1-difluoropropan-2-ol (Optically Active, Enantiomer of Example 251)

(a) tert-Butyl 3-(4-(1,1-difluoro-2-hydroxypropoxy)-7-(thiazol-2-yl)benzo[d]oxazol-2-yl)-3,6-diazabicyclo[3.1.1]heptane-6-carboxylate (Optically Active, Enantiomer of Example 251(a))

1.4 g of racemic tert-butyl 3-(4-(1,1-difluoro-2-hydroxypropoxy)-7-(thiazol-2-yl)benzo[d]oxazol-2-yl)-3,6-diazabicyclo[3.1.1]heptane-6-carboxylate obtained in Example 250 (c) was purified by a Multiple preparative HPLC (YMC, LC-forte/R, column: DAICEL CHIRALPAK IC (particle diameter: 5 µm, column diameter: 2 cm, column length: 25 cm), eluent, hexane:isopropyl alcohol=70:30, flow rate: 19.8 mL/min, detection: UV254 nm) and the title compound was obtained in an amount of 688 mg by concentrating fractions with the longer retention time peak. 99.0% ee. Analysis conditions: HPLC (HITACHI, column: DAICEL CHIRALPAK IC (particle diameter: 5 µm, column diameter: 0.46 cm, column length: 25 cm), eluent, hexane:isopropyl alcohol=70:30, flow rate: 1 mL/min, detection: UV254 nm, temperature: 25° C., retention time: 12.3 min).

(b) 1-((2-(3,6-Diazabicyclo[3.1.1]heptan-3-yl)-7-(thiazol-2-yl)benzo[d]oxazol-4-yl)oxy)-1,1-difluoropropan-2-ol (Optically Active, Enantiomer of Example 251)

The title compound was obtained in an amount of 447 mg from 627 mg of tert-butyl 3-(4-(1,1-difluoro-2-hydroxypropoxy)-7-(thiazol-2-yl)benzo[d]oxazol-2-yl)-3,6-diazabicyclo[3.1.1]heptane-6-carboxylate (Optically Active, Enantiomer of Example 251(a)) obtained in Example 252(a) by a similar method to Example 1(c). 99.0% ee. Analysis conditions: HPLC (HITACHI, column: DAICEL CHIRALPAK IC (particle diameter: 5 µm, column diameter: 0.46 cm, column length: 25 cm), eluent, hexane:isopropyl alcohol:diethylamine=70:30:0.1, flow rate: 1 mL/min, detection: UV254 nm, temperature: 25° C., retention time: 14.6 min).

Example 253

2-(1-(2-(3,6-Diazabicyclo[3.1.1]heptan-3-yl)-7-(thiazol-2-yl)benzo[d]oxazol-4-yl)-2,2,2-trifluoroethoxy)acetic acid The title compound was obtained as a crude product from 30 mg of tert-butyl 3-(4-(1-(2-(tert-butoxy)-2-oxoethoxy)-2,2,2-trifluoroethyl)-7-(thiazol-2-yl)benzo[d]oxazol-2-yl)-3,6-diazabicyclo[3.1.1]heptane-6-carboxylate obtained in Example 232 (a) by a similar method to Example 1(c).

The crude product was purified by a preparative HPLC (Gilson, column: Sepax GP-C18 (particle diameter: 5 µm, column diameter: 2.12 cm, column length: 10 cm), eluent, 0.1% formic acid in water: 0.1% formic acid in acetonitrile=90:10-10:90, flow rate: 15 mL/min, detection: UV254 nm) and the title compound was obtained in an amount of 21 mg by freeze drying of the purified product.

Example 254

2-(3,8-Diazabicyclo[3.2.1]octan-3-yl)-4-((tetrahydro-2H-pyran-4-yl)oxy)-7-(thiazol-2-yl)benzo[d]oxazole The title compound was obtained in an amount of 5.5 mg from 20.0 mg of tert-butyl 3-(4-hydroxy-7-(thiazol-2-yl)benzo[d]oxazol-2-yl)-3,8-diazabicyclo[3.2.1]octane-8-carboxylate obtained in Example 81(a) by a similar method to Example 102(e) except that tetrahydro-2H-pyran-4-yl trifluoromethanesulfonate (0.10 mg, 9.1 equivalents) was used instead of methyl iodide.

Example 255

1-(1-(2-(3,6-Diazabicyclo[3.1.1]heptan-3-yl)-7-(thiazol-2-yl)benzo[d]oxazol-4-yl)-(2,2,2-trifluoroethoxy)-2-methylpropan-2-ol (a) tert-Butyl 3-(7-(thiazol-2-yl)-4-(2,2,2-trifluoro-1-(2-hydroxy-2-methylpropoxy)ethyl)benzo[d]oxazol-2-yl)-3,6-diazabicyclo[3.1.1]heptane-6-carboxylate The title compound was obtained in an amount of 33 mg from 40 mg of tert-butyl 3-(4-(1-(2-(tert-butoxy)-2-oxoethoxy)-2,2,2-trifluoroethyl)-7-(thiazol-2-yl)benzo[d]oxazol-2-yl)-3,6-diazabicyclo[3.1.1]heptane-6-carboxylate obtained in Example 232 (a) by a similar method to Example 248 (e).

(b) 1-(1-(2-(3,6-Diazabicyclo[3.1.1]heptan-3-yl)-7-(thiazol-2-yl)benzo[d]oxazol-4-yl)-(2,2,2-trifluoroethoxy)-2-methylpropan-2-ol The title compound was obtained in an amount of 7.9 mg from 33 mg of tert-butyl 3-(7-(thiazol-2-yl)-4-(2,2,2-trifluoro-1-(2-hydroxy-2-methylpropoxy)ethyl)benzo[d]oxazol-2-yl)-3,6-diazabicyclo[3.1.1]heptane-6-carboxylate obtained in Example 255 (a) by a similar method to Example 1(C).

Example 256

2-(1-(2-(3,6-Diazabicyclo[3.1.1]heptan-3-yl)-7-(thiazol-2-yl)benzo[d]oxazol-4-yl)-2,2,2-trifluoroethoxy)acetamide (a) Methyl 2-(1-(2-(3,6-diazabicyclo[3.1.1]heptan-3-yl)-7-(thiazol-2-yl)benzo[d]oxazol-4-yl)-2,2,2-trifluoroethoxy)acetate To 44 mg of tert-butyl 3-(4-(1-(2-(tert-butoxy)-2-oxoethoxy)-2,2,2-trifluoroethyl)-7-(thiazol-2-yl)benzo[d]oxazol-2-yl)-3,6-diazabicyclo[3.1.1]heptane-6-carboxylate obtained in Example 232 (a) was added 2M methanolic hydrochloric acid (2.0 mL), followed by stirring at room temperature for 4 days. The formation of the product was confirmed by TLC. The residue obtained by vacuum concentration of the reaction mixture was dissolved in ethyl acetate, then saturated aqueous sodium bicarbonate was added. The organic phase was dried over anhydrous sodium (b) tert-Butyl 3-(7-(thiazol-2-yl)-4-(2,2,2-trifluoro-1-(2-methoxy-2-oxoethoxy)ethyl)benzo[d]oxazol-2-yl)-3,6-diazabicyclo[3.1.1]heptane-6-carboxylate The title compound was obtained in an amount of 16.8 mg from the crude product of methyl 2-(1-(2-(3,6-diazabicyclo[3.1.1]heptan-3-yl)-7-(thiazol-2-yl)benzo[d]oxazol-4-yl)-2,2,2-trifluoroethoxy)acetate obtained in Example 256(a) by a similar method to Example 85(a) except that di-tert-butyl dicarbonate was used instead of trifluoromethanesulfonic anhydride.

(c) 2-(1-(2-(6-(tert-Butoxycarbonyl)-3,6-diazabicyclo[3.1.1]heptan-3-yl)-7-(thiazol-2-yl)benzo[d]oxazol-4-yl)-2,2,2-trifluoroethoxy)acetic acid The title compound was obtained as a crude product from 16.8 mg of tert-butyl 3-(7-(thiazol-2-yl)-4-(2,2,2-trifluoro-1-(2-methoxy-2-oxoethoxy)ethyl)benzo[d]oxazol-2-yl)-3,6-diazabicyclo[3.1.1]heptane-6-carboxylate obtained in Example 256 (b) by a similar method to Example 94 (a).

(d) tert-Butyl 3-(4-(1-(2-amino-2-oxoethoxy)-2,2,2-trifluoroethyl)-7-(thiazol-2-yl)benzo[d]oxazol-2-yl)-3,6-diazabicyclo[3.1.1]heptane-6-carboxylate 1-ethyl-3-(3-dimethylaminopropyl)carbodiimide hydrochloride (11.5 mg, 2 equivalents), 1-hydroxybenzotriazole monohydrate (8.1 mg, 2 equivalents), N,N-dimethylformamide (0.5 mL) and 7M solution (71 µL, 17 equivalents) of ammonia in methanol were added to 2-(1-(2-(6-(tert-butoxycarbonyl)-3,6-diazabicyclo[3.1.1]heptan-3-yl)-7-(thiazol-2-yl)benzo[d]oxazol-4-yl)-2,2,2-trifluoroethoxy)acetic acid obtained in Example 256(c), followed by stirring at room temperature for 3 days. 7M solution (100 µL, 33 equivalents) of ammonia in methanol was added thereto again, followed by stirring at room temperature for 2.5 hours. The formation of the product was confirmed by TLC and ethyl acetate and water were added to the reaction mixture. Thereafter, the organic phase was dried over anhydrous sodium sulfate, followed by filtration and vacuum concentration of the filtrate, and thus obtaining 10.7 mg of the title compound by purification of the residue by amino silica gel column chromatography (hexane-ethyl acetate-methanol:ethyl acetate=1:4).

(e) 2-(1-(2-(3,6-Diazabicyclo[3.1.1]heptan-3-yl)-7-(thiazol-2-yl)benzo[d]oxazol-4-yl)-2,2,2-trifluoroethoxy)acetamide 8.9 mg of the title compound was obtained from 10.7 mg of tert-butyl 3-(4-(1-(2-amino-2-oxoethoxy)-2,2,2-trifluoroethyl)-7-(thiazol-2-yl)benzo[d]oxazol-2-yl)-3,6-diazabicyclo[3.1.1]heptane-6-carboxylate obtained in Example 256 (d), by a similar method to Example 1(c).

Example 257

1-(1-(2-(3,6-Diazabicyclo[3.1.1]heptan-3-yl)-7-(thiazol-2-yl)benzo[d]oxazol-4-yl)-2,2,2-trifluoroethoxy)-1,1-difluoro-2-methylpropan-2-ol (a) tert-Butyl 3-(4-(1-(2-ethoxy-1,1-difluoro-2-oxoethoxy)-2,2,2-trifluoroethyl)-7-(thiazol-2-yl)benzo[d]oxazol-2-yl)-3,6-diazabicyclo[3.1.1]heptane-6-carboxylate 100 mg of tert-butyl 3-(7-(thiazol-2-yl)-4-(2,2,2-trifluoro-1-hydroxyethyl)benzo[d]oxazol-2-yl)-3,6-diazabicyclo[3.1.1]heptane-6-carboxylate obtained in Example 120(b) was dissolved in N,N-dimethylformamide (1.0 mL), 7-methyl-1,5,7-triazabicyclo[4.4.0]dec-5-ene (143 µL, 5 equivalents) and ethyl 2-bromo-2,2-difluoroacetate (51 µL, 2 equivalents) were added thereto, followed by stirring at 50° C. for 1 hour. 7-methyl-1,5,7-triazabicyclo[4.4.0]dec-5-ene (143 µL, 5 equivalents) and ethyl 2-bromo-2,2-difluoroacetate (102 µL, 4 equivalents) were added thereto again, followed by stirring at 50° C. for an additional 1 hour. Saturated aqueous sodium bicarbonate and ethyl acetate were added to the reaction mixture. Thereafter, the organic phase was dried over anhydrous sodium sulfate, followed by filtration and vacuum concentration of the filtrate, and thus obtaining 19 mg of the title compound by purification of the residue through preparative TLC (ethyl acetate:chloroform=1:6).

(b) tert-Butyl 3-(4-(1-(1,1-difluoro-2-hydroxy-2-methylpropoxy)-2,2,2-trifluoroethyl)-7-(thiazol-2-yl)benzo[d]oxazol-2-yl)-3,6-diazabicyclo[3.1.1]heptane-6-carboxylate 16.4 mg of the title compound was obtained from 23 mg of tert-butyl 3-(4-(1-(2-ethoxy-1,1-difluoro-2-oxoethoxy)-2,2,2-trifluoroethyl)-7-(thiazol-2-yl)benzo[d]oxazol-2-yl)-3,6-diazabicyclo[3.1.1]heptane-6-carboxylate obtained in Example 257 (a) by a similar method to Example 248 (d).

(c) 1-(1-(2-(3,6-Diazabicyclo[3.1.1]heptan-3-yl)-7-(thiazol-2-yl)benzo[d]oxazol-4-yl)-2,2,2-trifluoroethoxy)-1,1-difluoro-2-methylpropan-2-ol 11.2 mg of the title compound was obtained from 16.4 mg of tert-butyl 3-(4-(1-(1,1-difluoro-2-hydroxy-2-methylpropoxy)-2,2,2-trifluoroethyl)-7-(thiazol-2-yl)benzo[d]oxazol-2-yl)-3,6-diazabicyclo[3.1.1]heptane-6-carboxylate obtained in Example 257 (b) by a similar method to Example 1(c).

Example 258

2-(1-(2-(3,6-Diazabicyclo[3.1.1]heptan-3-yl)-7-(thiazol-2-yl)benzo[d]oxazol-4-yl)-2,2,2-trifluoroethoxy)-2,2-difluoroethan-1-ol (a) tert-Butyl 3-(4-(1-(1,1-difluoro-2-hydroxyethoxy)-2,2,2-trifluoroethyl)-7-(thiazol-2-yl)benzo[d]oxazol-2-yl)-3,6-diazabicyclo[3.1.1]heptane-6-carboxylate 6.1 mg of the title compound was obtained from 10 mg of tert-butyl 3-(4-(1-(2-ethoxy-1,1-difluoro-2-oxoethoxy)-2,2,2-trifluoroethyl)-7-(thiazol-2-yl)benzo[d]oxazol-2-yl)-3,6-diazabicyclo[3.1.1]heptane-6-carboxylate obtained in Example 257 (a) by a similar method to Example 250(c).

(b) 2-(1-(2-(3,6-Diazabicyclo[3.1.1]heptan-3-yl)-7-(thiazol-2-yl)benzo[d]oxazol-4-yl)-2,2,2-trifluoroethoxy)-2,2-difluoroethan-1-ol 16.9 mg of the title compound was obtained from 24 mg of tert-butyl 3-(4-(1-(1,1-difluoro-2-hydroxyethoxy)-2,2,2-trifluoroethyl)-7-(thiazol-2-yl)benzo[d]oxazol-2-yl)-3,6-diazabicyclo[3.1.1]heptane-6-carboxylate obtained in Example 258 (a) by a similar method to Example 1(c).

Example 259

(2R)-1-((2-(3,6-diazabicyclo[3.1.1]heptan-3-yl)-7-(thiazol-2-yl)benzo[d]oxazol-4-yl)oxy)propan-2-ol (a) tert-Butyl 3-(4-((R)-2-hydroxypropoxy)-7-(thiazol-2-yl)benzo[d]oxazol-2-yl)-3,6-diazabicyclo[3.1.1]heptane-6-carboxylate 26 mg of tert-butyl 3-(4-hydroxy-7-(thiazol-2-yl)benzo[d]oxazol-2-yl)-3,6-diazabicyclo[3.1.1]heptane-6-carboxylate obtained in Example 248(c) was dissolved in N,N-dimethylformamide (0.6 mL), then 7-methyl-1,5,7-triazabicyclo[4.4.0]dec-5-ene (9.1 µL, 1 equivalent) and (R)-propylene oxide (17.6 µL, 4 equivalents) were added thereto, followed by stirring using a microwave reactor (manufactured by Biotage, conditions: 150° C., 2 hours). Distilled water, saturated ammonium chloride aqueous solution and ethyl acetate were added to the reaction mixture. Thereafter, the organic phase was dried over anhydrous sodium sulfate, followed by filtration and vacuum concentration of the filtrate, and thus obtaining 22 mg of the title compound by purification of the residue by preparative TLC (methanol:chloroform=8:92).

(b) (2R)-1-((2-(3,6-diazabicyclo[3.1.1]heptan-3-yl)-7-(thiazol-2-yl)benzo[d]oxazol-4-yl)oxy)propan-2-ol (Optically Active)

13.4 mg of the title compound was obtained from 22 mg of tert-butyl 3-(4-((R)-2-hydroxypropoxy)-7-(thiazol-2-yl)benzo[d]oxazol-2-yl)-3,6-diazabicyclo[3.1.1]heptane-6-carboxylate obtained in Example 259(a) by a similar method to Example 1(c).

Example 260

(2S)-1-((2-(3,6-diazabicyclo[3.1.1]heptan-3-yl)-7-(thiazol-2-yl)benzo[d]oxazol-4-yl)oxy)propan-2-ol (a) tert-Butyl 3-(4-((S)-2-hydroxypropoxy)-7-(thiazol-2-yl)benzo[d]oxazol-2-yl)-3,6-diazabicyclo[3.1.1]heptane-6-carboxylate 21 mg of the title compound was obtained from 25 mg of tert-butyl 3-(4-hydroxy-7-(thiazol-2-yl)benzo[d]oxazol-2-yl)-3,6-diazabicyclo[3.1.1]heptane-6-carboxylate obtained in Example 248(c) by a similar method to Example 259(a) except that (S)-propylene oxide was used instead of (R)-propylene oxide.

(b) (2S)-1-((2-(3,6-diazabicyclo[3.1.1]heptan-3-yl)-7-(thiazol-2-yl)benzo[d]oxazol-4-yl)oxy)propan-2-ol 11.6 mg of the title compound was obtained from 21 mg of tert-butyl 3-(4-((S)-2-hydroxypropoxy)-7-(thiazol-2-yl)benzo[d]oxazol-2-yl)-3,6-diazabicyclo[3.1.1]heptane-6-carboxylate obtained in Example 260(a) by a similar method to Example 1(c).

Example 261

1-(1-(2-(3,6-Diazabicyclo[3.1.1]heptan-3-yl)-7-(thiazol-2-yl)benzo[d]oxazol-4-yl)-2,2,2-trifluoroethoxy)propan-2-ol (a) tert-Butyl 3-(7-(thiazol-2-yl)-4-(2,2,2-trifluoro-1-(2-oxoethoxy)ethyl)benzo[d]oxazol-2-yl)-3,6-diazabicyclo[3.1.1]heptane-6-carboxylate 31 mg of the title compound was obtained from 97 mg of tert-butyl 3-(7-(thiazol-2-yl)-4-(2,2,2-trifluoro-1-(2-hydroxyethoxy)ethyl)benzo[d]oxazol-2-yl)-3,6-diazabicyclo[3.1.1]heptane-6-carboxylate obtained in Example 227(a) by a similar method to Example 102 (c).

(b) tert-Butyl 3-(7-(thiazol-2-yl)-4-(2,2,2-trifluoro-1-(2-hydroxypropoxy)ethyl)benzo[d]oxazol-2-yl)-3,6-diazabicyclo[3.1.1]heptane-6-carboxylate 9.6 mg of the title compound was obtained from 31 mg of tert-butyl 3-(7-(thiazol-2-yl)-4-(2,2,2-trifluoro-1-(2-oxoethoxy)ethyl)benzo[d]oxazol-2-yl)-3,6-diazabicyclo[3.1.1]heptane-6-carboxylate obtained in Example 261(a) by a similar method to Example 102 (b).

(c) 1-(1-(2-(3,6-Diazabicyclo[3.1.1]heptan-3-yl)-7-(thiazol-2-yl)benzo[d]oxazol-4-yl)-2,2,2-trifluoroethoxy)propan-2-ol 5.1 mg of the title compound was obtained from 9.6 mg of tert-butyl 3-(7-(thiazol-2-yl)-4-(2,2,2-trifluoro-1-(2-hydroxypropoxy)ethyl)benzo[d]oxazol-2-yl)-3,6-diazabicyclo[3.1.1]heptane-6-carboxylate obtained in Example 261(b) by a similar method to Example 1(c).

Example 262

2-(3,8-Diazabicyclo[3.2.1]octan-3-yl)-4-((tetrahydro-2H-pyran-3-yl)oxy)-7-(thiazol-2-yl)benzo[d]oxazole (a) tert-Butyl 3-(4-((tetrahydro-2H-pyran-3-yl)oxy-7-(thiazol-2-yl)benzo[d]oxazol-2-yl)-3,8-diazabicyclo[3.2.1]octane-8-carboxylate 9.3 mg of the title compound was obtained from 20.0 mg of tert-butyl 3-(4-hydroxy-7-(thiazol-2-yl)benzo[d]oxazol-2-yl)-3,8-diazabicyclo[3.2.1]octane-8-carboxylate obtained in Example 81(a) by a similar method to Reference Example 23 (a) except that tetrahydro-2H-pyran-3-yl 4-methylbenzenesulfonate (3 equivalents) was used instead of benzyl bromide and stirred at 90° C. for 5 hours using 3.5 equivalents of caesium carbonate.

(b) 2-(3,8-Diazabicyclo[3.2.1]octan-3-yl)-4-((tetrahydro-2H-pyran-3-yl)oxy)-7-(thiazol-2-yl)benzo[d]oxazole 1.0 mg of the title compound was obtained from 9.3 mg of tert-butyl 3-(4-((tetrahydro-2H-pyran-3-yl)oxy-7-(thiazol-2-yl)benzo[d]oxazol-2-yl)-3,8-diazabicyclo[3.2.1]octane-8-carboxylate obtained in Example 262 (a) by a similar method to Example 1(c).

Example 263

2-(3,8-Diazabicyclo[3.2.1]octan-3-yl)-4-(difluoromethoxy)-7-(thiazol-2-yl)benzo[d]oxazole (a) tert-Butyl 3-(4-(difluoromethoxy)-7-(thiazol-2-yl)benzo[d]oxazol-2-yl)-3,8-diazabicyclo[3.2.1]octane-8-carboxylate 11.8 mg of the title compound was obtained from 20.0 mg of tert-butyl 3-(4-hydroxy-7-(thiazol-2-yl)benzo[d]oxazol-2-yl)-3,8-diazabicyclo[3.2.1]octane-8-carboxylate obtained in Example 81(a) by a similar method to Example 262 (a)

except that ethyl 2-bromo-2,2-difluoroacetate (47.4 mg, 5 equivalents) was used instead of tetrahydro-2H-pyran-3-yl 4-methylbenzenesulfonate.

(b) 2-(3,8-Diazabicyclo[3.2.1]octan-3-yl)-4-(difluoromethoxy)-7-(thiazol-2-yl)benzo[d]oxazole 8.6 mg of the title compound was obtained from 11.8 mg of tert-butyl 3-(4-(difluoromethoxy)-7-(thiazol-2-yl)benzo[d]oxazol-2-yl)-3,8-diazabicyclo[3.2.1]octane-8-carboxylate obtained in Example 263 (a) by a similar method to Example 1(c).

Example 264

1-((2-(3,8-Diazabicyclo[3.2.1]octan-3-yl)-7-(thiazol-2-yl)benzo[d]oxazol-4-yl)oxy)-2-methylpropan-2-ol (a) tert-Butyl 3-(4-(2-methoxy-2-oxoethoxy)-7-(thiazol-2-yl)benzo[d]oxazol-2-yl)-3,8-diazabicyclo[3.2.1]octane-8-carboxylate 21.5 mg of the title compound was obtained from 20.0 mg of tert-butyl 3-(4-hydroxy-7-(thiazol-2-yl)benzo[d]oxazol-2-yl)-3,8-diazabicyclo[3.2.1]octane-8-carboxylate obtained in Example 81(a) by a similar method to Example 262 (a) except that methyl 2-bromoacetate was used instead of tetrahydro-2H-pyran-3-yl 4-methylbenzenesulfonate.

(b) tert-Butyl 3-(4-(2-hydroxy-2-methylpropoxy)-7-(thiazol-2-yl)benzo[d]oxazol-2-yl)-3,8-diazabicyclo[3.2.1]octane-8-carboxylate 16.1 mg of the title compound was obtained from 21.5 mg of tert-butyl 3-(4-(2-methoxy-2-oxoethoxy)-7-(thiazol-2-yl)benzo[d]oxazol-2-yl)-3,8-diazabicyclo[3.2.1]octane-8-carboxylate obtained in Example 264 (a) by a similar method to Example 248 (e).

(c) 1-((2-(3,8-Diazabicyclo[3.2.1]octan-3-yl)-7-(thiazol-2-yl)benzo[d]oxazol-4-yl)oxy)-2-methylpropan-2-ol 12.0 mg of the title compound was obtained from 16.1 mg of tert-butyl 3-(4-(2-hydroxy-2-methylpropoxy)-7-(thiazol-2-yl)benzo[d]oxazol-2-yl)-3,8-diazabicyclo[3.2.1]octane-8-carboxylate obtained in Example 264 (b) by a similar method to Example 1(c).

Example 265

1-(1-(2-(3,6-Diazabicyclo[3.1.1]heptan-3-yl)-7-(thiazol-2-yl)benzo[d]oxazol-4-yl)-2,2,2-trifluoroethoxy)-1,1-difluoropropan-2-ol (a) tert-Butyl 3-(4-(1-(1,1-difluoro-2-(methoxy(methyl)amino)-2-oxoethoxy)-2,2,2-trifluoroethyl)-7-(thiazol-2-yl)benzo[d]oxazol-2-yl)-3,6-diazabicyclo[3.1.1]heptane-6-carboxylate 7.4 mg of the title compound was obtained from 30 mg of tert-butyl 3-(4-(1-(2-ethoxy-1,1-difluoro-2-oxoethoxy)-2,2,2-trifluoroethyl)-7-(thiazol-2-yl)benzo[d]oxazol-2-yl)-3,6-diazabicyclo[3.1.1]heptane-6-carboxylate obtained in Example 257 (a) by a similar method to Example 250(a).

(b) tert-Butyl 3-(4-(1-(1,1-difluoro-2-oxopropoxy)-2,2,2-trifluoroethyl)-7-(thiazol-2-yl)benzo[d]oxazol-2-yl)-3,6-diazabicyclo[3.1.1]heptane-6-carboxylate The title compound was obtained as a crude product from 7.4 mg of tert-butyl 3-(4-(1-(1,1-difluoro-2-(methoxy(methyl)amino)-2-oxoethoxy)-2,2,2-trifluoroethyl)-7-(thiazol-2-yl)benzo[d]oxazol-2-yl)-3,6-diazabicyclo[3.1.1]heptane-6-carboxylate obtained in Example 265(a) by a similar method to Example 250 (b).

(c) tert-Butyl 3-(4-(1-(1,1-difluoro-2-hydroxypropoxy)-2,2,2-trifluoroethyl)-7-(thiazol-2-yl)benzo[d]oxazol-2-yl)-3,6-diazabicyclo[3.1.1]heptane-6-carboxylate 6.5 mg of the title compound was obtained from the crude product of tert-butyl 3-(4-(1-(1,1-difluoro-2-oxopropoxy)-2,2,2-trifluoroethyl)-7-(thiazol-2-yl)benzo[d]oxazol-2-yl)-3,6-diazabicyclo[3.1.1]heptane-6-carboxylate obtained in Example 265 (b) by a similar method to Example 250(c).

(d) 1-(1-(2-(3,6-Diazabicyclo[3.1.1]heptan-3-yl)-7-(thiazol-2-yl)benzo[d]oxazol-4-yl)-2,2,2-trifluoroethoxy)-1,1-difluoropropan-2-ol 3.4 mg of the title compound was obtained from 6.5 mg of tert-butyl 3-(4-(1-(1,1-difluoro-2-hydroxypropoxy)-2,2,2-trifluoroethyl)-7-(thiazol-2-yl)benzo[d]oxazol-2-yl)-3,6-diazabicyclo[3.1.1]heptane-6-carboxylate obtained in Example 265 (c) by a similar method to Example 1(c).

Example 266

3-((2-(3,6-Diazabicyclo[3.1.1]heptan-3-yl)-7-(thiazol-2-yl)benzo[d]oxazol-4-yl)oxy)cyclobutane-1-carbonitrile (a) tert-Butyl 3-(4-(3-cyanocyclobutoxy)-7-(thiazol-2-yl)benzo[d]oxazol-2-yl)-3,6-diazabicyclo[3.1.1]heptane-6-carboxylate 33 mg of the title compound was obtained as a crude product from 20 mg of tert-butyl 3-(4-hydroxy-7-(thiazol-2-yl)benzo[d]oxazol-2-yl)-3,6-diazabicyclo[3.1.1]heptane-6-carboxylate obtained in Example 248 (c) by a similar method to Reference Example 23(a) except that 3-cyanocyclobutyl 4-methylbenzenesulfonate was used instead of benzyl bromide and stirred at 60° C.

(b) 3-((2-(3,6-Diazabicyclo[3.1.1]heptan-3-yl)-7-(thiazol-2-yl)benzo[d]oxazol-4-yl)oxy)cyclobutane-1-carbonitrile 7.4 mg of the title compound was obtained from 15 mg of tert-butyl 3-(4-(3-cyanocyclobutoxy)-7-(thiazol-2-yl)benzo[d]oxazol-2-yl)-3,6-diazabicyclo[3.1.1]heptane-6-carboxylate obtained in Example 266(a) by a similar method to Example 1(c).

Example 267

2-(3-((2-(3,6-Diazabicyclo[3.1.1]heptan-3-yl)-7-(thiazol-2-yl)benzo[d]oxazol-4-yl)oxy)cyclobutyl)propan-2-ol (a) tert-Butyl 3-(4-(3-(ethoxycarbonyl)cyclobutoxy)-7-(thiazol-2-yl)benzo[d]oxazol-2-yl)-3,6-diazabicyclo[3.1.1]heptane-6-carboxylate 52 mg of the title compound was obtained from 45 mg of tert-butyl 3-(4-hydroxy-7-(thiazol-2-yl)benzo[d]oxazol-2- yl)-3,6-diazabicyclo[3.1.1]heptane-6-carboxylate obtained in Example 248 (c) by a similar method to Reference Example 23(a) except that 3-(tosyloxy)cyclobutane-1-carboxylate was used instead of benzyl bromide and stirred at 60° C.

(b) tert-Butyl 3-(4-(3-(2-hydroxypropan-2-yl)cyclobutoxy)-7-(thiazol-2-yl)benzo[d]oxazol-2-yl)-3,6-diazabicyclo[3.1.1]heptane-6-carboxylate The title compound was obtained as crude product from 52 mg of tert-butyl 3-(4-(3-(ethoxycarbonyl)cyclobutoxy)-7-(thiazol-2-yl)benzo[d]oxazol-2-yl)-3,6-diazabicyclo[3.1.1]heptane-6-carboxylate obtained in Example 267 (a) by a similar method to Example 248 (e).

(c) 2-(3-((2-(3,6-Diazabicyclo[3.1.1]heptan-3-yl)-7-(thiazol-2-yl)benzo[d]oxazol-4-yl)oxy)cyclobutyl)propan-2-ol 7.2 mg of the title compound was obtained from tert-butyl 3-(4-(3-(2-hydroxypropan-2-yl)cyclobutoxy)-7-(thiazol-2-yl)benzo[d]oxazol-2-yl)-3,6-diazabicyclo[3.1.1]heptane-6-carboxylate obtained in Example 267 (b) by a similar method to Example 1(c).

Example 268

2-((2-(3,6-Diazabicyclo[3.1.1]heptan-3-yl)-7-(thiazol-2-yl)benzo[d]oxazol-4-yl)oxy)-2-methylpropan-1-ol (a) tert-Butyl 3-(4-((1-ethoxy-2-methyl-1-oxopropan-2-yl)oxy)-7-(thiazol-2-yl)benzo[d]oxazol-2-yl)-3,6-diazabicyclo[3.1.1]heptane-6-carboxylate 1.0 g of tert-butyl 3-(4-hydroxy-7-(thiazol-2-yl)benzo[d]oxazol-2-yl)-3,6-diazabicyclo[3.1.1]heptane-6-carboxylate obtained in Example 248(c) was dissolved in acetonitrile (2.4 mL), then potassium carbonate (66 mg, 2 equivalents) and ethyl 2-bromo-2-methylpropanoate (71 μL, 2 equivalents) were added, followed by stirring at 80° C. for 17 hours. The formation of the product was confirmed by TLC, and then saturated aqueous sodium bicarbonate was added thereto to stop the reaction, which was extracted by ethyl acetate 3 times. The organic phase was dried over anhydrous magnesium sulfate, followed by filtration and vacuum concentration of the filtrate, and thus obtaining 109 mg of the title compound by purification of the residue by preparative TLC (hexane:ethyl acetate=1:1).

(b) tert-Butyl 3-(4-((1-hydroxy-2-methylpropan-2-yl)oxy)-7-(thiazol-2-yl)benzo[d]oxazol-2-yl)-3,6-diazabicyclo[3.1.1]heptane-6-carboxylate 16 mg of the title compound was obtained from 20 mg of tert-butyl 3-(4-((1-ethoxy-2-methyl-1-oxopropan-2-yl)oxy)-7-(thiazol-2-yl)benzo[d]oxazol-2-yl)-3,6-diazabicyclo[3.1.1]heptane-6-carboxylate obtained in Example 268(a) by a similar method to Example 250(c) except that 31 equivalents of sodium borohydride was used.

(c) 2-((2-(3,6-Diazabicyclo[3.1.1]heptan-3-yl)-7-(thiazol-2-yl)benzo[d]oxazol-4-yl)oxy)-2-methylpropan-1-ol 11 mg of the title compound was obtained from 16 mg of tert-butyl 3-(4-((1-hydroxy-2-methylpropan-2-yl)oxy)-7-(thiazol-2-yl)benzo[d]oxazol-2-yl)-3,6-diazabicyclo[3.1.1]heptane-6-carboxylate obtained in Example 268 (b) by a similar method to Example 1(c).

Example 269

1-(2-(3,6-Diazabicyclo[3.1.1]heptan-3-yl)-7-(thiazol-2-yl)-4-(trifluoromethoxy)benzo[d]oxazol-5-yl)cyclopropan-1-ol (a) tert-Butyl 3-(5-(1-hydroxycyclopropyl)-7-(thiazol-2-yl)-4-(trifluoromethoxy)benzo[d]oxazol-2-yl)-3,6-diazabicyclo[3.1.1]heptane-6-carboxylate 13.4 mg of the title compound was obtained from 55 mg of ethyl 2-(6-(tert-butoxycarbonyl)-3,6-diazabicyclo[3.1.1]heptan-3-yl)-7-(thiazol-2-yl)-4-(trifluoromethoxy)benzo[d]oxazole-5-carboxylate obtained in Example 187(b) by a similar method to Example 232(b) except that 0.98M methylmagnesium bromide solution in tetrahydrofuran (4 equivalents) and 0.97M ethylmagnesium bromide solution in tetrahydrofuran (6 equivalents) were used instead of 0.97M ethylmagnesium bromide solution in tetrahydrofuran (6 equivalents) and stirred at room temperature for 40 min.

(b) 1-(2-(3,6-Diazabicyclo[3.1.1]heptan-3-yl)-7-(thiazol-2-yl)-4-(trifluoromethoxy)benzo[d]oxazol-5-yl)cyclopropan-1-ol 6.5 mg of the title compound was obtained from 13 mg of tert-butyl 3-(5-(1-hydroxycyclopropyl)-7-(thiazol-2-yl)-4-(trifluoromethoxy)benzo[d]oxazol-2-yl)-3,6-diazabicyclo[3.1.1]heptane-6-carboxylate obtained in Example 269(a) by a similar method to Example 1(c).

Example 270

2-(2-(3,6-Diazabicyclo[3.1.1]heptan-3-yl)-7-(thiazol-2-yl)benzo[d]oxazol-4-yl)-1,1,1-trifluoropropan-2-ol (Optically Active)

(a) tert-Butyl 3-(7-(thiazol-2-yl)-4-(1,1,1-trifluoro-2-hydroxypropan-2-yl)benzo[d]oxazol-2-yl)-3,6-diazabicyclo[3.1.1]heptane-6-carboxylate (Optically Active)

72 mg of racemic tert-butyl 3-(7-(thiazol-2-yl)-4-(1,1,1-trifluoro-2-hydroxypropan-2-yl)benzo[d]oxazol-2-yl)-3,6-diazabicyclo[3.1.1]heptane-6-carboxylate obtained in Example 234 (d) was purified by a preparative HPLC (Gilson, column: DAICEL CHIRALPAK IA (particle diameter: 5 μm, column diameter: 2 cm, column length: 25 cm), eluent, hexane:isopropyl alcohol=95:5-80:20, flow rate: 15 mL/min, detection: UV254 nm) and the title compound was obtained in an amount of 28 mg by concentrating fractions with the shorter retention time peak. 99.9% ee. Analysis conditions: HPLC (HITACHI, column: DAICEL CHIRALPAK IA (particle diameter: 5 μm, column diameter: 0.46 cm, column length: 25 cm), eluent, hexane:isopropyl alcohol=90:10, flow rate: 1 mL/min, detection: UV254 nm, temperature: 25° C., retention time: 12.7 min).

(b) 2-(2-(3,6-Diazabicyclo[3.1.1]heptan-3-yl)-7-(thiazol-2-yl)benzo[d]oxazol-4-yl)-1,1,1-trifluoropropan-2-ol (Optically Active)

The title compound was obtained in an amount of 19 mg from 28 mg of tert-butyl 3-(7-(thiazol-2-yl)-4-(1,1,1-trifluoro-2-hydroxypropan-2-yl)benzo[d]oxazol-2-yl)-3,6-diazabicyclo[3.1.1]heptane-6-carboxylate (Optically Active) Obtained in Example 270(a) by a similar method to Example 1(c).

Example 271

2-(2-(3,6-Diazabicyclo[3.1.1]heptan-3-yl)-7-(thiazol-2-yl)benzo[d]oxazol-4-yl)-1,1,1-trifluoropropan-2-ol (Optically Active, Enantiomer of Example 270)

(a) tert-Butyl 3-(7-(thiazol-2-yl)-4-(1,1,1-trifluoro-2-hydroxypropan-2-yl)benzo[d]oxazol-2-yl)-3,6-diazabicyclo[3.1.1]heptane-6-carboxylate (Optically Active, Enantiomer of Example 270(a))

The title compound was obtained in an amount of 31 mg by concentrating fractions with the longer retention time peak obtained in Example 270(a). 99.0% ee. Analysis conditions: HPLC (HITACHI, column: DAICEL CHIRALPAK IA (particle diameter: 5 μm, column diameter: 0.46 cm, column length: 25 cm), eluent, hexane:isopropyl alcohol=90:10, flow rate: 1 mL/min, detection: UV254 nm, temperature: 25° C., retention time: 16.8 min).

(b) 2-(2-(3,6-Diazabicyclo[3.1.1]heptan-3-yl)-7-(thiazol-2-yl)benzo[d]oxazol-4-yl)-1,1,1-trifluoropropan-2-ol (Optically Active, Enantiomer of Example 270)

The title compound was obtained in an amount of 20 mg from 31 mg of tert-butyl 3-(7-(thiazol-2-yl)-4-(1,1,1-trifluoro-2-hydroxypropan-2-yl)benzo[d]oxazol-2-yl)-3,6-diazabicyclo[3.1.1]heptane-6-carboxylate (Optically Active, Enantiomer of Example 270(a)) obtained in Example 271(a) by a similar method to Example 1(c).

Example 272

1-(2-(3,6-Diazabicyclo[3.1.1]heptan-3-yl)-7-(thiazol-2-yl)-4-(trifluoromethoxy)benzo[d]oxazol-5-yl)ethan-1-ol (Optically Active)

(a) tert-Butyl 3-(5-(1-hydroxyethyl)-7-(thiazol-2-yl)-4-(trifluoromethoxy)benzo[d]oxazol-2-yl)-3,6-diazabicyclo[3.1.1]heptane-6-carboxylate (Optically Active)

84.9 mg of racemic tert-butyl 3-(5-(1-hydroxyethyl)-7-(thiazol-2-yl)-4-(trifluoromethoxy)benzo[d]oxazol-2-yl)-3,6-diazabicyclo[3.1.1]heptane-6-carboxylate obtained in Example 203(b) was purified by a preparative HPLC (Gilson, column: DAICEL CHIRALPAK IA (particle diameter: 5 μm, column diameter: 2 cm, column length: 25 cm), eluent, hexane:isopropyl alcohol=80:20, flow rate: 15 mL/min, detection: UV254 nm) and the title compound was obtained in an amount of 32.7 mg by concentrating fractions with the shorter retention time peak.

(b) 1-(2-(3,6-Diazabicyclo[3.1.1]heptan-3-yl)-7-(thiazol-2-yl)-4-(trifluoromethoxy)benzo[d]oxazol-5-yl)ethan-1-ol (Optically Active)

The title compound was obtained in an amount of 19.3 mg from 32.7 mg of tert-butyl 3-(5-(1-hydroxyethyl)-7-(thiazol-2-yl)-4-(trifluoromethoxy)benzo[d]oxazol-2-yl)-3,6-diazabicyclo[3.1.1]heptane-6-carboxylate (optically active) obtained in Example 272 (a) by a similar method to Example 1(c). >99.5% ee. Analysis conditions: HPLC (HITACHI, column: DAICEL CHIRALPAK IA (particle diameter: 5 μm, column diameter: 0.46 cm, column length: 25 cm), eluent, hexane:isopropyl alcohol:diethylamine=70:30:0.1, flow rate: 1 mL/min, detection: UV254 nm, temperature: 25° C., retention time: 11.6 min).

Example 273

1-(2-(3,6-Diazabicyclo[3.1.1]heptan-3-yl)-7-(thiazol-2-yl)-4-(trifluoromethoxy)benzo[d]oxazol-5-yl)ethan-1-ol (Optically Active, Enantiomer of Example 272)

(a) tert-Butyl 3-(5-(1-hydroxyethyl)-7-(thiazol-2-yl)-4-(trifluoromethoxy)benzo[d]oxazol-2-yl)-3,6-diazabicyclo[3.1.1]heptane-6-carboxylate (Optically Active, Enantiomer of Example 272 (a))

The title compound was obtained in an amount of 35.4 mg by concentrating fractions with the longer retention time peak obtained in Example 272 (a).

(b) 1-(2-(3,6-Diazabicyclo[3.1.1]heptan-3-yl)-7-(thiazol-2-yl)-4-(trifluoromethoxy)benzo[d]oxazol-5-yl)ethan-1-ol (Optically Active, Enantiomer of Example 272)

The title compound was obtained in an amount of 19.7 mg from 35.4 mg of tert-butyl 3-(5-(1-hydroxyethyl)-7-(thiazol-2-yl)-4-(trifluoromethoxy)benzo[d]oxazol-2-yl)-3,6-diazabicyclo[3.1.1]heptane-6-carboxylate (Optically Active, Enantiomer of Example 272 (a)) obtained in Example 273 (a) by a similar method to Example 1(c). 89.7% ee. Analysis conditions: HPLC (HITACHI, column: DAICEL CHIRALPAK IA (particle diameter: 5 μm, column diameter: 0.46 cm, column length: 25 cm), eluent, hexane:isopropyl alcohol:diethylamine=70:30:0.1, flow rate: 1 mL/min, detection: UV254 nm, temperature: 25° C., retention time: 15.4 min).

Example 274

1-(2-(3,8-Diazabicyclo[3.2.1]octan-3-yl)-7-(thiazol-2-yl)-4-(trifluoromethoxy)benzo[d]oxazol-5-yl)cyclopropan-1-ol (a) tert-Butyl 3-(5-(1-hydroxycyclopropyl)-7-(thiazol-2-yl)-4-(trifluoromethoxy)benzo[d]oxazol-2-yl)-3,8-diazabicyclo[3.2.1]octane-8-carboxylate 10.6 mg of the title compound was obtained from 57 mg of ethyl 2-(8-(tert-butoxycarbonyl)-3,8-diazabicyclo[3.2.1]octan-3-yl)-7-(thiazol-2-yl)-4-(trifluoromethoxy)benzo[d]oxazole-5-carboxylate obtained in Example 186(b) by a similar method to Example 232(b) except that 0.98M methylmagnesium bromide solution in tetrahydrofuran (4 equivalents) and 0.97M ethylmagnesium bromide solution in tetrahydrofuran (6 equivalents) were used instead of 0.97M ethylmagnesium bromide solution in tetrahydrofuran (6 equivalents) and stirred at room temperature for 1 hour.

(b) 1-(2-(3,8-Diazabicyclo[3.2.1]octan-3-yl)-7-(thiazol-2-yl)-4-(trifluoromethoxy)benzo[d]oxazol-5-yl)cyclopropan-1-ol 10.8 mg of the title compound was obtained from 10 mg of tert-butyl 3-(5-(1-hydroxycyclopropyl)-7-(thiazol-2-yl)-

4-(trifluoromethoxy)benzo[d]oxazol-2-yl)-3,8-diazabicyclo[3.2.1]octane-8-carboxylate obtained in Example 274(a) by a similar method to Example 1(c).

Example 275

1-(2-(3,8-Diazabicyclo[3.2.1]octan-3-yl)-7-(thiazol-2-yl)-4-(trifluoromethoxy)benzo[d]oxazol-5-yl)-2,2-difluoroethan-1-ol (Optically Active)

(a) tert-Butyl 3-(5-(2,2-difluoro-1-hydroxyethyl)-7-(thiazol-2-yl)-4-(trifluoromethoxy)benzo[d]oxazol-2-yl)-3,8-diazabicyclo[3.2.1]octane-8-carboxylate (Optically Active)

21 mg of racemic tert-butyl 3-(5-(2,2-difluoro-1-hydroxyethyl)-7-(thiazol-2-yl)-4-(trifluoromethoxy)benzo[d]oxazol-2-yl)-3,8-diazabicyclo[3.2.1]octane-8-carboxylate obtained in Example 206(a) was purified by a preparative HPLC (Gilson, column: DAICEL CHIRALPAK IA (particle diameter: 5 μm, column diameter: 2 cm, column length: 25 cm), eluent, hexane:isopropyl alcohol=90:10-70:30, flow rate: 15 mL/min, detection: UV254 nm) and the title compound was obtained in an amount of 9.9 mg by concentrating fractions with the shorter retention time peak. >99.5% ee. Analysis conditions: HPLC (HITACHI, column: DAICEL CHIRALPAK IA (particle diameter: 5 μm, column diameter: 0.46 cm, column length: 25 cm), eluent, hexane:isopropyl alcohol=80:20, flow rate: 1 mL/min, detection: UV254 nm, temperature: 25° C., retention time: 5.8 min).

(b) 1-(2-(3,8-Diazabicyclo[3.2.1]octan-3-yl)-7-(thiazol-2-yl)-4-(trifluoromethoxy)benzo[d]oxazol-5-yl)-2,2-difluoroethan-1-ol (Optically Active)

The title compound was obtained in an amount of 5.3 mg from 8.0 mg of tert-butyl 3-(5-(2,2-difluoro-1-hydroxyethyl)-7-(thiazol-2-yl)-4-(trifluoromethoxy)benzo[d]oxazol-2-yl)-3,8-diazabicyclo[3.2.1]octane-8-carboxylate (optically active) obtained in Example 275(a) by a similar method to Example 1(c).

Example 276

1-(2-(3,8-Diazabicyclo[3.2.1]octan-3-yl)-7-(thiazol-2-yl)-4-(trifluoromethoxy)benzo[d]oxazol-5-yl)-2,2-difluoroethan-1-ol (enantiomer of Example 275)

(a) tert-Butyl 3-(5-(2,2-difluoro-1-hydroxyethyl)-7-(thiazol-2-yl)-4-(trifluoromethoxy)benzo[d]oxazol-2-yl)-3,8-diazabicyclo[3.2.1]octane-8-carboxylate (Optically Active, Enantiomer of Example 275(a))

The title compound was obtained in an amount of 10.9 mg by concentrating fractions with the longer retention time peak obtained in Example 275 (a). >99.5% ee. Analysis conditions: HPLC (HITACHI, column: DAICEL CHIRALPAK IA (particle diameter: 5 μm, column diameter: 0.46 cm, column length: 25 cm), eluent, hexane:isopropyl alcohol=80:20, flow rate: 1 mL/min, detection: UV254 nm, temperature: 25° C., retention time: 11.6 min).

(b) 1-(2-(3,8-Diazabicyclo[3.2.1]octan-3-yl)-7-(thiazol-2-yl)-4-(trifluoromethoxy)benzo[d]oxazol-5-yl)-2,2-difluoroethan-1-ol (enantiomer of Example 275)

The title compound was obtained in an amount of 5.7 mg from 9.5 mg of tert-butyl 3-(5-(2,2-difluoro-1-hydroxyethyl)-7-(thiazol-2-yl)-4-(trifluoromethoxy)benzo[d]oxazol-2-yl)-3,8-diazabicyclo[3.2.1]octane-8-carboxylate (Optically Active, Enantiomer of Example 275(a)) obtained in Example 276(a) by a similar method to Example 1(c).

Example 277

3-((2-(3,6-Diazabicyclo[3.1.1]heptan-3-yl)-7-(thiazol-2-yl)benzo[d]oxazol-4-yl)oxy)-1,1,1-trifluoropropan-2-ol (a) tert-Butyl 3-(7-(thiazol-2-yl)-4-(3,3,3-trifluoro-2-hydroxypropoxy)benzo[d]oxazol-2-yl)-3,6-diazabicyclo[3.1.1]heptane-6-carboxylate 3.5 mg of the title compound was obtained from 20.0 mg of tert-butyl 3-(4-hydroxy-7-(thiazol-2-yl)benzo[d]oxazol-2-yl)-3,6-diazabicyclo[3.1.1]heptane-6-carboxylate obtained in Example 248(c) by a similar method to Example 262(a) except that 3-bromo-1,1,1-trifluoropropan-2-ol was used instead of tetrahydro-2H-pyran-3-yl 4-methylbenzenesulfonate.

(b) 3-((2-(3,6-Diazabicyclo[3.1.1]heptan-3-yl)-7-(thiazol-2-yl)benzo[d]oxazol-4-yl)oxy)-1,1,1-trifluoropropan-2-ol 2.8 mg of the title compound was obtained from 3.5 mg of tert-butyl 3-(7-(thiazol-2-yl)-4-(3,3,3-trifluoro-2-hydroxypropoxy)benzo[d]oxazol-2-yl)-3,6-diazabicyclo[3.1.1]heptane-6-carboxylate obtained in Example 277 (a) by a similar method to Example 1(c).

Example 278

2-(3,6-Diazabicyclo[3.1.1]heptan-3-yl)-4-(difluoromethoxy)-7-(thiazol-2-yl)benzo[d]oxazole (a) tert-Butyl 3-(4-(difluoromethoxy)-7-(thiazol-2-yl)benzo[d]oxazol-2-yl)-3,6-diazabicyclo[3.1.1]heptane-6-carboxylate 12.0 mg of the title compound was obtained from 20.0 mg of tert-butyl 3-(4-hydroxy-7-(thiazol-2-yl)benzo[d]oxazol-2-yl)-3,6-diazabicyclo[3.1.1]heptane-6-carboxylate obtained in Example 248(c) by a similar method to Example 262(a) except that ethyl 2-bromo-2,2-difluoroacetate was used instead of tetrahydro-2H-pyran-3-yl 4-methylbenzenesulfonate.

(b) 2-(3,6-Diazabicyclo[3.1.1]heptan-3-yl)-4-(difluoromethoxy)-7-(thiazol-2-yl)benzo[d]oxazole 9.1 mg of the title compound was obtained from 12.0 mg of tert-butyl 3-(4-(difluoromethoxy)-7-(thiazol-2-yl)benzo[d]oxazol-2-yl)-3,6-diazabicyclo[3.1.1]heptane-6-carboxylate obtained in Example 278 (a) by a similar method to Example 1(c).

Example 279

1-((2-(3,6-Diazabicyclo[3.1.1]heptan-3-yl)-7-(thiazol-2-yl)benzo[d]oxazol-4-yl)oxy)-2-methylpropan-2-ol (a) tert-Butyl 3-(4-(2-methoxy-2-oxoethoxy)-7-(thiazol-2-yl)benzo[d]oxazol-2-yl)-3,6-diazabicyclo[3.1.1]heptane-6-carboxylate 20.4 mg of the title compound was obtained from 20.0 mg of tert-butyl 3-(4-hydroxy-7-(thiazol-2-yl)benzo[d]oxazol- 2-yl)-3,6-diazabicyclo[3.1.1]heptane-6-carboxylate obtained in Example 248(c) by a similar method to Example 262(a) except that methyl 2-bromoacetate was used instead of tetrahydro-2H-pyran-3-yl 4-methylbenzenesulfonate.

(b) tert-Butyl 3-(4-(2-hydroxy-2-methylpropoxy)-7-(thiazol-2-yl)benzo[d]oxazol-2-yl)-3,6-diazabicyclo [3.1.1]heptane-6-carboxylate 20.0 mg of the title compound was obtained from 20.4 mg of tert-butyl 3-(4-(2-methoxy-2-oxoethoxy)-7-(thiazol-2-yl)benzo[d]oxazol-2-yl)-3,6-diazabicyclo[3.1.1]heptane-6-carboxylate obtained in Example 279(a) by a similar method to Example 248 (e).

(c) 1-((2-(3,6-Diazabicyclo[3.1.1]heptan-3-yl)-7-(thiazol-2-yl)benzo[d]oxazol-4-yl)oxy)-2-methylpropan-2-ol 15.3 mg of the title compound was obtained from 20.0 mg of tert-butyl 3-(4-(2-hydroxy-2-methylpropoxy)-7-(thiazol-2-yl)benzo[d]oxazol-2-yl)-3,6-diazabicyclo[3.1.1]heptane-6-carboxylate obtained in Example 279(b) by a similar method to Example 1(c).

Example 280

3-(1-(2-(3,6-Diazabicyclo[3.1.1]heptan-3-yl)-7-(thiazol-2-yl)benzo[d]oxazol-4-yl)-2,2,2-trifluoroethoxy)-2,3-dimethylbutan-2-ol (a) tert-Butyl 3-(4-(1-((1-ethoxy-2-methyl-1-oxopropan-2-yl)oxy)-2,2,2-trifluoroethyl)-7-(thiazol-2-yl)benzo[d]oxazol-2-yl)-3,6-diazabicyclo[3.1.1]heptane-6-carboxylate 33 mg of the title compound was obtained from 40 mg of tert-butyl 3-(7-(thiazol-2-yl)-4-(2,2,2-trifluoro-1-hydroxyethyl)benzo[d]oxazol-2-yl)-3,6-diazabicyclo[3.1.1]heptane-6-carboxylate obtained in Example 120(b) by a similar method to Example 271(a) except that 9 equivalents of potassium carbonate and 9 equivalents of ethyl 2-bromo-2-methylpropanoate were used.

(b) tert-Butyl 3-(7-(thiazol-2-yl)-4-(2,2,2-trifluoro-1-((3-hydroxy-2,3-dimethylbutan-2-yl)oxy)ethyl)benzo[d]oxazol-2-yl)-3,6-diazabicyclo[3.1.1]heptane-6-carboxylate 15 mg of the title compound was obtained from 33 mg of tert-butyl 3-(4-(1-((1-ethoxy-2-methyl-1-oxopropan-2-yl)oxy)-2,2,2-trifluoroethyl)-7-(thiazol-2-yl)benzo[d]oxazol-2-yl)-3,6-diazabicyclo[3.1.1]heptane-6-carboxylate obtained in Example 280(a) by a similar method to Example 248 (e).

(c) 3-(1-(2-(3,6-Diazabicyclo[3.1.1]heptan-3-yl)-7-(thiazol-2-yl)benzo[d]oxazol-4-yl)-2,2,2-trifluoroethoxy)-2,3-dimethylbutan-2-ol 11 mg of the title compound was obtained from 15 mg of tert-butyl 3-(7-(thiazol-2-yl)-4-(2,2,2-trifluoro-1-((3-hydroxy-2,3-dimethylbutan-2-yl)oxy)ethyl)benzo[d]oxazol-2-yl)-3,6-diazabicyclo[3.1.1]heptane-6-carboxylate obtained in Example 280 (b) by a similar method to Example 1(c).

Example 281

2-(3,6-Diazabicyclo[3.1.1]heptan-3-yl)-7-(thiazol-2-yl)-4-(2,2,2-trifluoro-1-(2-methoxy-2-methylpropoxy)ethyl)benzo[d]oxazole (a) tert-Butyl 3-(7-(thiazol-2-yl)-4-(2,2,2-trifluoro-1-(2-methoxy-2-methylpropoxy)ethyl)benzo[d]oxazol-2-yl)-3,6-diazabicyclo[3.1.1]heptane-6-carboxylate 25 mg of the title compound was obtained from 42 mg of tert-butyl 3-(7-(thiazol-2-yl)-4-(2,2,2-trifluoro-1-(2-hydroxy-2-methylpropoxy)ethyl)benzo[d]oxazol-2-yl)-3,6-diazabicyclo[3.1.1]heptane-6-carboxylate obtained in Example 255 (a) by a similar method to Example 102 (e).

(b) 2-(3,6-Diazabicyclo[3.1.1]heptan-3-yl)-7-(thiazol-2-yl)-4-(2,2,2-trifluoro-1-(2-methoxy-2-methylpropoxy)ethyl)benzo[d]oxazole 16 mg of the title compound was obtained from 25 mg of tert-butyl 3-(7-(thiazol-2-yl)-4-(2,2,2-trifluoro-1-(2-methoxy-2-methylpropoxy)ethyl)benzo[d]oxazol-2-yl)-3,6-diazabicyclo[3.1.1]heptane-6-carboxylate obtained in Example 281(a) by a similar method to Example 1(c).

Example 282

2-(3,6-Diazabicyclo[3.1.1]heptan-3-yl)-7-(thiazol-2-yl)-4-(2,2,2-trifluoro-1-((1-methoxycyclopropyl)methoxy)ethyl)benzo[d]oxazole (a) tert-Butyl 3-(7-(thiazol-2-yl)-4-(2,2,2-trifluoro-1-((1-methoxycyclopropyl)methoxy)ethyl)benzo[d]oxazol-2-yl)-3,6-diazabicyclo[3.1.1]heptane-6-carboxylate 30 mg of the title compound was obtained from 36 mg of tert-butyl 3-(7-(thiazol-2-yl)-4-(2,2,2-trifluoro-1-((1-hydroxycyclopropyl)methoxy)ethyl)benzo[d]oxazol-2-yl)-3,6-diazabicyclo[3.1.1]heptane-6-carboxylate obtained in Example 232 (b) by a similar method to Example 102 (e).

(b) 2-(3,6-Diazabicyclo[3.1.1]heptan-3-yl)-7-(thiazol-2-yl)-4-(2,2,2-trifluoro-1-((1-methoxycyclopropyl)methoxy)ethyl)benzo[d]oxazole 12 mg of the title compound was obtained from 30 mg of tert-butyl 3-(7-(thiazol-2-yl)-4-(2,2,2-trifluoro-1-((1-methoxycyclopropyl)methoxy)ethyl)benzo[d]oxazol-2-yl)-3,6-diazabicyclo[3.1.1]heptane-6-carboxylate obtained in Example 282 (a) by a similar method to Example 1(c).

Example 283

2-(3,6-Diazabicyclo[3.1.1]heptan-3-yl)-5-(1-methoxycyclopropyl)-7-(thiazol-2-yl)-4-(trifluoromethoxy)benzo[d]oxazole (a) tert-Butyl 3-(5-(1-methoxycyclopropyl)-7-(thiazol-2-yl)-4-(trifluoromethoxy)benzo[d]oxazol-2-yl)-3,6-diazabicyclo[3.1.1]heptane-6-carboxylate 10.8 mg of the title compound was obtained from 15 mg of tert-butyl 3-(5-(1-hydroxycyclopropyl)-7-(thiazol-2-yl)-4-(trifluoromethoxy)benzo[d]oxazol-2-yl)-3,6-diazabicyclo[3.1.1]heptane-6-carboxylate obtained in Example 269(a) by a similar method to Example 102 (e) except that 6 equivalents of sodium hydride was used.

(b) 2-(3,6-Diazabicyclo[3.1.1]heptan-3-yl)-5-(1-methoxycyclopropyl)-7-(thiazol-2-yl)-4-(trifluoromethoxy)benzo[d]oxazole 8.6 mg of the title compound was obtained from 10.8 mg of tert-butyl 3-(5-(1-methoxycyclopropyl)-7-(thiazol-2-yl)-4-(trifluoromethoxy)benzo[d]oxazol-2-yl)-3,6-diazabicyclo[3.1.1]heptane-6-carboxylate obtained in Example 283(a) by a similar method to Example 1(c).

Example 284

1-(1-(2-(3,6-Diazabicyclo[3.1.1]heptan-3-yl)-7-(thiazol-4-yl)benzo[d]oxazol-4-yl)-2,2,2-trifluoroethoxy)-2-methylpropan-2-ol (a) tert-Butyl 3-(7-(thiazol-2-yl)-4-(2,2,2-trifluoro-1-hydroxyethyl)benzo[d]oxazol-2-yl)-3,6-diazabicyclo[3.1.1]heptane-6-carboxylate 10.8 mg of the title compound was obtained from 15 mg of tert-butyl 3-(5-(1-hydroxycyclopropyl)-7-(thiazol-2-yl)-4-(trifluoromethoxy)benzo[d]oxazol-2-yl)-3,6-diazabicyclo[3.1.1]heptane-6-carboxylate obtained in Example 269(a) by a similar method to Example 8 (a).

(b) tert-Butyl 3-(7-(thiazol-2-yl)-4-(2,2,2-trifluoro-1-(2-methoxy-2-oxoethoxy)ethyl)benzo[d]oxazol-2-yl)-3,6-diazabicyclo[3.1.1]heptane-6-carboxylate 136 mg of the title compound was obtained from 182 mg of tert-butyl 3-(7-(thiazol-2-yl)-4-(2,2,2-trifluoro-1-hydroxyethyl)benzo[d]oxazol-2-yl)-3,6-diazabicyclo[3.1.1]heptane-6-carboxylate obtained in Example 284(a) by a similar method to Example 73(a) except that methyl bromoacetate was used instead of bromoacetonitrile and stirred at 50° C.

(c) tert-Butyl 3-(7-(thiazol-2-yl)-4-(2,2,2-trifluoro-1-(2-hydroxy-2-methylpropoxy)ethyl)benzo[d]oxazol-2-yl)-3,6-diazabicyclo[3.1.1]heptane-6-carboxylate 46 mg of the title compound was obtained from 67 mg of tert-butyl 3-(7-(thiazol-2-yl)-4-(2,2,2-trifluoro-1-(2-methoxy-2-oxoethoxy)ethyl)benzo[d]oxazol-2-yl)-3,6-diazabicyclo[3.1.1]heptane-6-carboxylate obtained in Example 284 (b) by a similar method to Example 248 (e).

(d) 1-(1-(2-(3,6-Diazabicyclo[3.1.1]heptan-3-yl)-7-(thiazol-4-yl)benzo[d]oxazol-4-yl)-2,2,2-trifluoroethoxy)-2-methylpropan-2-ol 33 mg of the title compound was obtained from 45 mg of tert-butyl 3-(7-(thiazol-2-yl)-4-(2,2,2-trifluoro-1-(2-hydroxy-2-methylpropoxy)ethyl)benzo[d]oxazol-2-yl)-3,6-diazabicyclo[3.1.1]heptane-6-carboxylate obtained in Example 284 (c) by a similar method to Example 1(c).

Example 285

3-((2-(3,6-Diazabicyclo[3.1.1]heptan-3-yl)-7-(thiazol-2-yl)benzo[d]oxazol-4-yl)oxy)cyclobutan-1-ol (a) tert-Butyl 3-(4-(3-benzyloxy)cyclobutoxy)-7-(thiazol-2-yl)benzo[d]oxazol-2-yl)-3,6-diazabicyclo[3.1.1]heptane-6-carboxylate 83 mg of the title compound was obtained from 100 mg of tert-butyl 3-(4-hydroxy-7-(thiazol-2-yl)benzo[d]oxazol-2-yl)-3,6-diazabicyclo[3.1.1]heptane-6-carboxylate obtained in Example 248 (c) by a similar method to Reference Example 23(a) except that 3-(benzyloxy)cyclobutyl 4-methylbenzenesulfonate was used instead of benzyl bromide and stirred at 60° C.

(b) tert-Butyl 3-(4-(3-hydroxycyclobutoxy)-7-(thiazol-2-yl)benzo[d]oxazol-2-yl)-3,6-diazabicyclo[3.1.1]heptane-6-carboxylate 24 mg of the title compound was obtained from 83 mg of tert-butyl 3-(4-(3-benzyloxy)cyclobutoxy)-7-(thiazol-2-yl)benzo[d]oxazol-2-yl)-3,6-diazabicyclo[3.1.1]heptane-6-carboxylate obtained in Example 285 (a) by a similar method to Example 248 (c).

(c) 3-((2-(3,6-Diazabicyclo[3.1.1]heptan-3-yl)-7-(thiazol-2-yl)benzo[d]oxazol-4-yl)oxy)cyclobutan-1-ol 11 mg of the title compound was obtained from 24 mg of tert-butyl 3-(4-(3-hydroxycyclobutoxy)-7-(thiazol-2-yl)benzo[d]oxazol-2-yl)-3,6-diazabicyclo[3.1.1]heptane-6-carboxylate obtained in Example 285 (b) by a similar method to Example 1(c).

Example 286

1-((1-(2-(3,6-Diazabicyclo[3.1.1]heptan-3-yl)-7-(thiazol-4-yl)benzo[d]oxazol-4-yl)-2,2,2-trifluoroethoxy)methyl)cyclopropan-1-ol (a) tert-Butyl 3-(7-(thiazol-4-yl)-4-(2,2,2-trifluoro-1-((1-hydroxycyclopropyl)methoxy)ethyl)benzo[d]oxazol-2-yl)-3,6-diazabicyclo[3.1.1]heptane-6-carboxylate 34 mg of the title compound was obtained from 63 mg of tert-butyl 3-(7-(thiazol-2-yl)-4-(2,2,2-trifluoro-1-methoxy-2-oxoethoxy)ethyl)benzo[d]oxazol-2-yl)-3,6-diazabicyclo[3.1.1]heptane-6-carboxylate obtained in Example 284(b) by a similar method to Example 232 (b).

(b) 1-((1-(2-(3,6-Diazabicyclo[3.1.1]heptan-3-yl)-7-(thiazol-4-yl)benzo[d]oxazol-4-yl)-2,2,2-trifluoroethoxy)methyl)cyclopropan-1-ol 18 mg of the title compound was obtained from 34 mg of tert-butyl 3-(7-(thiazol-4-yl)-4-(2,2,2-trifluoro-1-((1-hydroxycyclopropyl)methoxy)ethyl)benzo[d]oxazol-2-yl)-3,6-diazabicyclo[3.1.1]heptane-6-carboxylate obtained in Example 286(a) by a similar method to Example 1(c).

Example 287

2-(3,6-Diazabicyclo[3.1.1]heptan-3-yl)-5-(2-methoxypropan-2-yl)-7-(thiazol-4-yl)-4-(trifluoromethoxy)benzo[d]oxazole (a) Ethyl 2-(6-(tert-butoxycarbonyl)-3,6-diazabicyclo[3.1.1]heptan-3-yl)-7-(thiazol-4-yl)-4-(trifluoromethoxy)benzo[d]oxazole-5-carboxylate 250 mg of the title compound was obtained from 275 mg of ethyl 7-bromo-2-(6-(tert-butoxycarbonyl)-3,6-diazabicyclo[3.1.1]heptan-3-yl)-4-(trifluoromethoxy)benzo[d]oxazole-5-carboxylate obtained in Example 187(a) by a similar method to Example 8 (a).

(b) tert-Butyl 3-(5-(2-hydroxypropan-2-yl)-7-(thiazol-4-yl)-4-(trifluoromethoxy)benzo[d]oxazol-2-yl)-3,6-diazabicyclo[3.1.1]heptane-6-carboxylate 120 mg of the title compound was obtained from 97 mg of ethyl 2-(6-(tert-butoxycarbonyl)-3,6-diazabicyclo[3.1.1]heptan-3-yl)-7-(thiazol-4-yl)-4-(trifluoromethoxy)benzo[d]oxazole-5-carboxylate obtained in Example 287(a) by a similar method to Example 126 (b).

(c) tert-Butyl 3-(5-(2-methoxypropan-2-yl)-7-(thiazol-4-yl)-4-(trifluoromethoxy)benzo[d]oxazol-2-yl)-3,6-diazabicyclo[3.1.1]heptane-6-carboxylate 38 mg of the title compound was obtained from 45 mg of tert-butyl 3-(5-(2-hydroxypropan-2-yl)-7-(thiazol-4-yl)-4-(trifluoromethoxy)benzo[d]oxazol-2-yl)-3,6-diazabicyclo[3.1.1]heptane-6-carboxylate obtained in Example 287(b) by a similar method to Example 102 (e).

(d) 2-(3,6-Diazabicyclo[3.1.1]heptan-3-yl)-5-(2-methoxypropan-2-yl)-7-(thiazol-4-yl)-4-(trifluoromethoxy)benzo[d]oxazole 31 mg of the title compound was obtained from 37 mg of tert-butyl 3-(5-(2-methoxypropan-2-yl)-7-(thiazol-4-yl)-4-(trifluoromethoxy)benzo[d]oxazol-2-yl)-3,6-diazabicyclo[3.1.1]heptane-6-carboxylate obtained in Example 287(c) by a similar method to Example 1(c).

Example 288

2-(2-(3,6-Diazabicyclo[3.1.1]heptan-3-yl)-7-(thiazol-4-yl)-4-(trifluoromethoxy)benzo[d]oxazol-5-yl)propan-2-ol 37 mg of the title compound was obtained from 37 mg of tert-butyl 3-(5-(2-hydroxypropan-2-yl)-7-(thiazol-4-yl)-4-(trifluoromethoxy)benzo[d]oxazol-2-yl)-3,6-diazabicyclo[3.1.1]heptane-6-carboxylate obtained in Example 287(b) by a similar method to Example 1(c).

Example 289

1-((2-(3,6-Diazabicyclo[3.1.1]heptan-3-yl)-7-(pyridin-2-yl)benzo[d]oxazol-4-yl)oxy)-1,1-difluoro-2-methylpropan-2-ol (a) tert-Butyl 3-(4-(benzyloxy)-7-(pyridin-2-yl)benzo[d]oxazol-2-yl)-3,6-diazabicyclo[3.1.1]heptane-6-carboxylate 50 mg of the title compound was obtained from 60 mg of tert-butyl 3-(4-(benzyloxyl)-7-bromobenzo[d]oxazol-2-yl)-3,6-diazabicyclo[3.1.1]heptane-6-carboxylate obtained in Example 248 (a) by a similar method to Example 7 (a) except that tetrakis(triphenylphosphine)palladium(0) (0.2 equivalent), 2-(tributylstannyl)pyridine (8.0 equivalents), and a microwave reactor (by Biotage, 120° C., 2 hours) were used.

(b) tert-Butyl 3-(4-hydroxy-7-(pyridin-2-yl)benzo[d]oxazol-2-yl)-3,6-diazabicyclo[3.1.1]heptane-6-carboxylate 94 mg of the title compound was obtained as a crude product from 110 mg of tert-butyl 3-(4-(benzyloxy)-7-(pyridin-2-yl)benzo[d]oxazol-2-yl)-3,6-diazabicyclo[3.1.1]heptane-6-carboxylate obtained in Example 289(a) by a similar method to Example 248 (c).

(c) tert-Butyl 3-(4-(2-ethoxy-1,1-difluoro-2-oxoethoxy)-7-(pyridin-2-yl)benzo[d]oxazol-2-yl)-3,6-diazabicyclo[3.1.1]heptane-6-carboxylate 42 mg of the title compound was obtained from 94 mg of the crude product of tert-butyl 3-(4-hydroxy-7-(pyridin-2-yl)benzo[d]oxazol-2-yl)-3,6-diazabicyclo[3.1.1]heptane-6-carboxylate obtained in Example 289(b) by a similar method to Example 248 (d).

(d) tert-Butyl 3-(4-(1,1-difluoro-2-hydroxy-2-methylpropoxy)-7-(pyridin-2-yl)benzo[d]oxazol-2-yl)-3,6-diazabicyclo[3.1.1]heptane-6-carboxylate The title compound was obtained as a crude product from 42 mg of tert-butyl 3-(4-(2-ethoxy-1,1-difluoro-2-oxoethoxy)-7-(pyridin-2-yl)benzo[d]oxazol-2-yl)-3,6-diazabicyclo[3.1.1]heptane-6-carboxylate obtained in Example 289(c) by a similar method to Example 248(e) except that 0.95M methylmagnesium bromide solution in tetrahydrofuran (6 equivalents) was used.

(e) 1-((2-(3,6-Diazabicyclo[3.1.1]heptan-3-yl)-7-(pyridin-2-yl)benzo[d]oxazol-4-yl)oxy)-1,1-difluoro-2-methylpropan-2-ol 24 mg of the title compound was obtained from the crude product of tert-butyl 3-(4-(1,1-difluoro-2-hydroxy-2-methylpropoxy)-7-(pyridin-2-yl)benzo[d]oxazol-2-yl)-3,6-diazabicyclo[3.1.1]heptane-6-carboxylate obtained in Example 289(d) by a similar method to Example 1(c).

Example 290

1-((2-(3,6-Diazabicyclo[3.1.1]heptan-3-yl)-7-(oxazol-2-yl)benzo[d]oxazol-4-yl)oxy)-1,1-difluoro-2-methylpropan-2-ol (a) tert-Butyl 3-(4-(benzyloxy)-7-(oxazol-2-yl)benzo[d]oxazol-2-yl)-3,6-diazabicyclo[3.1.1]heptane-6-carboxylate 31 mg of the title compound was obtained from 50 mg of tert-butyl 3-(4-(benzyloxyl)-7-bromobenzo[d]oxazol-2-yl)-3,6-diazabicyclo[3.1.1]heptane-6-carboxylate obtained in Example 248 (a) by a similar method to Example 9(a).

(b) tert-Butyl 3-(4-hydroxy-7-(oxazol-2-yl)benzo[d]oxazol-2-yl)-3,6-diazabicyclo[3.1.1]heptane-6-carboxylate 26 mg of the title compound was obtained from 30 mg of tert-butyl 3-(4-(benzyloxy)-7-(oxazol-2-yl)benzo[d]oxazol-2-yl)-3,6-diazabicyclo[3.1.1]heptane-6-carboxylate obtained in Example 290(a) by a similar method to Example 248 (c).

(c) tert-Butyl 3-(4-(2-ethoxy-1,1-difluoro-2-oxoethoxy)-7-(oxazol-2-yl)benzo[d]oxazol-2-yl)-3,6-diazabicyclo[3.1.1]heptane-6-carboxylate 14 mg of the title compound was obtained from 26 mg of tert-butyl 3-(4-hydroxy-7-(oxazol-2-yl)benzo[d]oxazol-2-yl)-3,6-diazabicyclo[3.1.1]heptane-6-carboxylate obtained in Example 290 (b) by a similar method to Example 248 (d).

(d) tert-Butyl 3-(4-(1,1-difluoro-2-hydroxy)-2-hydroxy-2-methylpropoxy)-7-(oxazol-2-yl)benzo[d]oxazol-2-yl)-3,6-diazabicyclo[3.1.1]heptane-6-carboxylate 9.9 mg of the title compound was obtained from 14 mg of tert-butyl 3-(4-(2-ethoxy-1,1-difluoro-2-oxoethoxy)-7-(oxazol-2-yl)benzo[d]oxazol-2-yl)-3,6-diazabicyclo[3.1.1]heptane-6-carboxylate obtained in Example 290(c) by a similar method to Example 248 (e).

(e) 1-((2-(3,6-Diazabicyclo[3.1.1]heptan-3-yl)-7-(oxazol-2-yl)benzo[d]oxazol-4-yl)oxy)-1,1-difluoro-2-methylpropan-2-ol 5.2 mg of the title compound was obtained from 9.9 mg of tert-butyl 3-(4-(1,1-difluoro-2-hydroxy)-2-hydroxy-2-methylpropoxy)-7-(oxazol-2-yl)benzo[d]oxazol-2-yl)-3,6-diazabicyclo[3.1.1]heptane-6-carboxylate obtained in Example 290(d) by a similar method to Example 1(c).

Example 291

2-(2-(3,8-Diazabicyclo[3.2.1]octan-3-yl)-7-(thiazol-4-yl)-4-(trifluoromethoxy)benzo[d]oxazol-5-yl)propan-2-ol (a) Ethyl 2-(8-(tert-butoxycarbonyl)-3,8-diazabicyclo[3.2.1]octan-3-yl)-7-(thiazol-4-yl)-4-(trifluoromethoxy)benzo[d]oxazole-5-carboxylate 553 mg of the title compound was obtained from 564 mg of ethyl 7-bromo-2-(8-(tert-butoxycarbonyl)-3,8-diazabicyclo[3.2.1]octan-3-yl)-4-(trifluoromethoxy)benzo[d]oxazole-5-carboxylate obtained in Example 186(a) by a similar method to Example 8 (a).

(b) tert-Butyl 3-(5-hydroxypropan-2-yl)-7-(thiazol-4-yl)-4-(trifluoromethoxy)benzo[d]oxazol-2-yl)-3,8-diazabicyclo[3.2.1]octane-8-carboxylate 179 mg of the title compound was obtained from 200 mg of ethyl 2-(8-(tert-butoxycarbonyl)-3,8-diazabicyclo[3.2.1]octan-3-yl)-7-(thiazol-4-yl)-4-(trifluoromethoxy)benzo[d]oxazole-5-carboxylate obtained in Example 291(a) by a similar method to Example 248 (e).

(c) 2-(2-(3,8-Diazabicyclo[3.2.1]octan-3-yl)-7-(thiazol-4-yl)-4-(trifluoromethoxy)benzo[d]oxazol-5-yl)propan-2-ol 64 mg of the title compound was obtained from 79 mg of tert-butyl 3-(5-hydroxypropan-2-yl)-7-(thiazol-4-yl)-4-(trifluoromethoxy)benzo[d]oxazol-2-yl)-3,8-diazabicyclo[3.2.1]octane-8-carboxylate obtained in Example 291(b) by a similar method to Example 1(c).

Example 292

1-(2-(3,6-Diazabicyclo[3.1.1]heptan-3-yl)-7-(thiazol-2-yl)-4-(trifluoromethoxy)benzo[d]oxazol-5-yl)-2,2-difluoroethan-1-ol (Optically Active)

(a) tert-Butyl 3-(5-(2,2-difluoro-1-hydroxyethyl)-7-(thiazol-2-yl)-4-(trifluoromethoxy)benzo[d]oxazol-2-yl)-3,6-diazabicyclo[3.1.1]heptane-6-carboxylate (Optically Active)

101 mg of racemic tert-butyl 3-(5-(2,2-difluoro-1-hydroxyethyl)-7-(thiazol-2-yl)-4-(trifluoromethoxy)benzo[d]oxazol-2-yl)-3,6-diazabicyclo[3.1.1]heptane-6-carboxylate obtained in Example 207 (a) was purified by a preparative HPLC (Gilson, column: DAICEL CHIRALPAK IA (particle diameter: 5 μm, column diameter: 2 cm, column length: 25 cm), eluent, hexane:isopropyl alcohol=80:20, flow rate: 15 mL/min, detection: UV254 nm) and the title compound was obtained in an amount of 32 mg by concentrating fractions with the shorter retention time peak. 99.9% ee. Analysis conditions: HPLC (HITACHI, column: DAICEL CHIRALPAK IA (particle diameter: 5 μm, column diameter: 0.46 cm, column length: 25 cm), eluent, hexane:isopropyl alcohol=80:20, flow rate: 1 mL/min, detection: UV254 nm, temperature: 25° C., retention time: 7.8 min).

(b) 1-(2-(3,6-Diazabicyclo[3.1.1]heptan-3-yl)-7-(thiazol-2-yl)-4-(trifluoromethoxy)benzo[d]oxazol-5-yl)-2,2-difluoroethan-1-ol (Optically Active)

The title compound was obtained in an amount of 26 mg from 32 mg of tert-butyl 3-(5-(2,2-difluoro-1-hydroxyethyl)-7-(thiazol-2-yl)-4-(trifluoromethoxy)benzo[d]oxazol-2-yl)-3,6-diazabicyclo[3.1.1]heptane-6-carboxylate (optically active) obtained in Example 292 (a) by a similar method to Example 1(c)

Example 293

1-(2-(3,6-Diazabicyclo[3.1.1]heptan-3-yl)-7-(thiazol-2-yl)-4-(trifluoromethoxy)benzo[d]oxazol-5-yl)-2,2-difluoroethan-1-ol (enantiomer of Example 292)

(a) tert-Butyl 3-(5-(2,2-difluoro-1-hydroxyethyl)-7-(thiazol-2-yl)-4-(trifluoromethoxy)benzo[d]oxazol-2-yl)-3,6-diazabicyclo[3.1.1]heptane-6-carboxylate (enantiomer of Example 292 (a))

The title compound was obtained in an amount of 29 mg by concentrating fractions with the longer retention time peak obtained in Example 292 (a). 99.9% ee. Analysis conditions: HPLC (HITACHI, column: DAICEL CHIRALPAK IA (particle diameter: 5 μm, column diameter: 0.46 cm, column length: 25 cm), eluent, hexane:isopropyl alcohol=80:20, flow rate: 1 mL/min, detection: UV254 nm, temperature: 25° C., retention time: 20.4 min).

(b) 1-(2-(3,6-Diazabicyclo[3.1.1]heptan-3-yl)-7-(thiazol-2-yl)-4-(trifluoromethoxy)benzo[d]oxazol-5-yl)-2,2-difluoroethan-1-ol (enantiomer of Example 292)

The title compound was obtained in an amount of 22 mg from 29 mg of tert-butyl 3-(5-(2,2-difluoro-1-hydroxyethyl)-7-(thiazol-2-yl)-4-(trifluoromethoxy)benzo[d]oxazol-2-yl)-3,6-diazabicyclo[3.1.1]heptane-6-carboxylate (optically active) obtained in Example 293(a) by a similar method to Example 1(c)

Example 294

2-(3,6-Diazabicyclo[3.1.1]heptan-3-yl)-4-((tetrahydro-2H-pyran-4-yl)oxy)-7-(thiazol-2-yl)benzo[d]oxazole (a) tert-Butyl 3-(4-((tetrahydro-2H-pyran-4-yl)oxy)-7-(thiazol-2-yl)benzo[d]oxazol-2-yl)-3,6-diazabicyclo[3.1.1]heptane-6-carboxylate 59.4 mg of the title compound was obtained from 50.0 mg of tert-butyl 3-(4-hydroxy-7-(thiazol-2-yl)benzo[d]oxazol-2-yl)-3,6-diazabicyclo[3.1.1]heptane-6-carboxylate obtained in Example 248(c) by a similar method to Example 262(a) except that tetrahydro-2H-pyran-4-yl 4-methylbenzenesulfonate was used instead of tetrahydro-2H-pyran-3-yl 4-methylbenzenesulfonate.

(b) 2-(3,6-Diazabicyclo[3.1.1]heptan-3-yl)-4-((tetrahydro-2H-pyran-4-yl)oxy)-7-(thiazol-2-yl)benzo[d]oxazole 39.7 mg of the title compound was obtained from 59.4 mg of tert-butyl 3-(4-((tetrahydro-2H-pyran-4-yl)oxy)-7-(thiazol-2-yl)benzo[d]oxazol-2-yl)-3,6-diazabicyclo[3.1.1]heptane-6-carboxylate obtained in Example 294 (a) by a similar method to Example 1(c).

Example 295

4-((2-(3,6-Diazabicyclo[3.1.1]heptan-3-yl)-7-(thiazol-2-yl)benzo[d]oxazol-4-yl)oxy)-4,4-difluoro-2-methylbutan-2-ol (a) tert-Butyl 3-(4-(3-ethoxy-1,1-difluoro-3-oxopropoxy)-7-(thiazol-2-yl)benzo[d]oxazol-2-yl)-3,6-diazabicyclo[3.1.1]heptane-6-carboxylate 41.3 mg of the title compound was obtained from 50.0 mg of tert-butyl 3-(4-hydroxy-7-(thiazol-2-yl)benzo[d]oxazol-2-yl)-3,6-diazabicyclo[3.1.1]heptane-6-carboxylate obtained in Example 248(c) by a similar method to Example 248(d) except that ethyl 3-bromo-3,3-difluoropropanoate was used instead of ethyl 2-bromo-2,2-difluoroacetate.

(b) tert-Butyl 3-(4-(1,1-difluoro-3-hydroxy-3-methylbutoxy)-7-(thiazol-2-yl)benzo[d]oxazol-2-yl)-3,6-diazabicyclo[3.1.1]heptane-6-carboxylate 14.4 mg of the title compound was obtained from 41.3 mg of tert-butyl 3-(4-(3-ethoxy-1,1-difluoro-3-oxopropoxy)-7-(thiazol-2-yl)benzo[d]oxazol-2-yl)-3,6-diazabicyclo[3.1.1]heptane-6-carboxylate obtained in Example 295 (a) by a similar method to Example 248 (e).

(c) 4-((2-(3,6-Diazabicyclo[3.1.1]heptan-3-yl)-7-(thiazol-2-yl)benzo[d]oxazol-4-yl)oxy)-4,4-difluoro-2-methylbutan-2-ol 9.2 mg of the title compound was obtained from 14.4 mg of tert-butyl 3-(4-(1,1-difluoro-3-hydroxy-3-methylbutoxy)-7-(thiazol-2-yl)benzo[d]oxazol-2-yl)-3,6-diazabicyclo[3.1.1]heptane-6-carboxylate obtained in Example 295 (b) by a similar method to Example 1(c).

Example 296

2-(2-(3,6-Diazabicyclo[3.1.1]heptan-3-yl)-7-(thiazol-2-yl)benzo[d]oxazol-4-yl)-1,1-difluoropropan-2-ol (Optically Active)

(a) tert-Butyl 3-(4-(1,1-difluoro-2-hydroxypropan-2-yl)-7-(thiazol-2-yl)benzo[d]oxazol-2-yl)-3,6-diazabicyclo[3.1.1]heptane-6-carboxylate (Optically Active)

45 mg of racemic tert-butyl 3-(4-(1,1-difluoro-2-hydroxypropan-2-yl)-7-(thiazol-2-yl)benzo[d]oxazol-2-yl)-3,6-diazabicyclo[3.1.1]heptane-6-carboxylate obtained in Example 126(b) was purified by a preparative HPLC (Gilson, column: DAICEL CHIRALPAK IA (particle diameter: 5 μm, column diameter: 2 cm, column length: 25 cm), eluent, hexane:isopropyl alcohol=80:20-50:50, flow rate: 15 mL/min, detection: UV254 nm) and the title compound was obtained in an amount of 19 mg by concentrating fractions with the shorter retention time peak. >99.5% ee. Analysis conditions: HPLC (HITACHI, column: DAICEL CHIRALPAK IA (particle diameter: 5 μm, column diameter: 0.46 cm, column length: 25 cm), eluent, hexane:ethanol=80:20, flow rate: 1 mL/min, detection: UV254 nm, temperature: 25° C., retention time: 8.2 min).

(b) 2-(2-(3,6-Diazabicyclo[3.1.1]heptan-3-yl)-7-(thiazol-2-yl)benzo[d]oxazol-4-yl)-1,1-difluoropropan-2-ol (Optically Active)

The title compound was obtained in an amount of 15 mg from 19 mg of tert-butyl 3-(4-(1,1-difluoro-2-hydroxypropan-2-yl)-7-(thiazol-2-yl)benzo[d]oxazol-2-yl)-3,6-diazabicyclo[3.1.1]heptane-6-carboxylate (Optically Active) Obtained in Example 296(a) by a similar method to Example 1(c).

Example 297

2-(2-(3,6-Diazabicyclo[3.1.1]heptan-3-yl)-7-(thiazol-2-yl)benzo[d]oxazol-4-yl)-1,1-difluoropropan-2-ol (Optically Active, Enantiomer of Example 296)

(a) tert-Butyl 3-(4-(1,1-difluoro-2-hydroxypropan-2-yl)-7-(thiazol-2-yl)benzo[d]oxazol-2-yl)-3,6-diazabicyclo[3.1.1]heptane-6-carboxylate (Optically Active, Enantiomer of Example 296(a))

The title compound was obtained in an amount of 18 mg by concentrating fractions with the longer retention time peak obtained in Example 296(a). >99.5% ee. Analysis conditions: HPLC (HITACHI, column: DAICEL CHIRALPAK IA (particle diameter: 5 μm, column diameter: 0.46 cm, column length: 25 cm), eluent, hexane:ethanol=80:20, flow rate: 1 mL/min, detection: UV254 nm, temperature: 25° C., retention time: 11.2 min).

(b) 2-(2-(3,6-Diazabicyclo[3.1.1]heptan-3-yl)-7-(thiazol-2-yl)benzo[d]oxazol-4-yl)-1,1-difluoropropan-2-ol (Optically Active, Enantiomer of Example 296)

The title compound was obtained in an amount of 14 mg from 18 mg of tert-butyl 3-(4-(1,1-difluoro-2-hydroxypropan-2-yl)-7-(thiazol-2-yl)benzo[d]oxazol-2-yl)-3,6-diazabicyclo[3.1.1]heptane-6-carboxylate (Optically Active, Enantiomer of Example 296(a)) obtained in Example 297(a) by a similar method to Example 1(c).

Example 298

2-(3,8-Diazabicyclo[3.2.1]octan-3-yl)-5-(2-methoxypropan-2-yl)-7-(thiazol-4-yl)-4-(trifluoromethoxy)benzo[d]oxazole (a) tert-Butyl 3-(5-(2-methoxypropan-2-yl)-7-(thiazol-4-yl)-4-(trifluoromethoxy)benzo[d]oxazol-2-yl)-3,8-diazabicyclo[3.2.1]octane-8-carboxylate 95 mg of the title compound was obtained from 98 mg of tert-butyl 3-(5-hydroxypropan-2-yl)-7-(thiazol-4-yl)-4-(trifluoromethoxy)benzo[d]oxazol-2-yl)-3,8-diazabicyclo[3.2.1]octane-8-carboxylate obtained in Example 291(b) by a similar method to Example 102 (e).

(b) 2-(3,8-Diazabicyclo[3.2.1]octan-3-yl)-5-(2-methoxypropan-2-yl)-7-(thiazol-4-yl)-4-(trifluoromethoxy)benzo[d]oxazole 54 mg of the title compound was obtained from 95 mg of tert-butyl 3-(5-(2-methoxypropan-2-yl)-7-(thiazol-4-yl)-4-(trifluoromethoxy)benzo[d]oxazol-2-yl)-3,8-diazabicyclo[3.2.1]octane-8-carboxylate obtained in Example 298(a) by a similar method to Example 1(c).

Example 299

1-(2-(3,6-Diazabicyclo[3.1.1]heptan-3-yl)-7-(thiazol-4-yl)-4-(trifluoromethoxy)benzo[d]oxazol-5-yl)cyclopropan-1-ol (a) tert-Butyl 3-(5-(2-hydroxycyclopropyl)-7-(thiazol-4-yl)-4-(trifluoromethoxy)benzo[d]oxazol-2-yl)-3,6-diazabicyclo[3.1.1]heptane-6-carboxylate 19 mg of the title compound was obtained from 80 mg of ethyl 2-(6-(tert-butoxycarbonyl)-3,6-diazabicyclo[3.1.1]heptan-3-yl)-7-(thiazol-4-yl)-4-(trifluoromethoxy)benzo[d]oxazole-5-carboxylate obtained in Example 287(a) by a similar method to Example 232 (b).

(b) 1-(2-(3,6-Diazabicyclo[3.1.1]heptan-3-yl)-7-(thiazol-4-yl)-4-(trifluoromethoxy)benzo[d]oxazol-5-yl)cyclopropan-1-ol 16 mg of the title compound was obtained from 25 mg of tert-butyl 3-(5-(2-hydroxycyclopropyl)-7-(thiazol-4-yl)-4-(trifluoromethoxy)benzo[d]oxazol-2-yl)-3,6-diazabicyclo[3.1.1]heptane-6-carboxylate obtained in Example 299(a) by a similar method to Example 1(c).

Example 300

1-(2-(3,6-Diazabicyclo[3.1.1]heptan-3-yl)-7-(thiazol-4-yl)-4-(trifluoromethoxy)benzo[d]oxazol-5-yl)-2,2-difluoroethan-1-ol (Optically Active)

(a) tert-Butyl 3-(5-(hydroxycymethyl)-7-(thiazol-4-yl)-4-(trifluoromethoxy)benzo[d]oxazol-2-yl)-3,6-diazabicyclo[3.1.1]heptane-6-carboxylate 152 mg of the title compound was obtained as a crude product from 270 mg of ethyl 2-(6-(tert-butoxycarbonyl)-3,6-diazabicyclo[3.1.1]heptan-3-yl)-7-(thiazol-4-yl)-4-(trifluoromethoxy)benzo[d]oxazole-5-carboxylate obtained in Example 287 (a) by a similar method to Example 201(a).

(b) tert-Butyl 3-(5-formyl-7-(thiazol-4-yl)-4-(trifluoromethoxy)benzo[d]oxazol-2-yl)-3,6-diazabicyclo[3.1.1]heptane-6-carboxylate 114 mg of the title compound was obtained from 151 mg of the crude product of tert-butyl 3-(5-(hydroxycymethyl)-7-(thiazol-4-yl)-4-(trifluoromethoxy)benzo[d]oxazol-2-yl)-3,6-diazabicyclo[3.1.1]heptane-6-carboxylate obtained in Example 300 (a) by a similar method to Example 202 (a).

(c) tert-Butyl 3-(5-(2,2-difluoro-1-hydroxyethyl)-7-(thiazol-4-yl)-4-(trifluoromethoxy)benzo[d]oxazol-2-yl)-3,6-diazabicyclo[3.1.1]heptane-6-carboxylate 77 mg of the title compound was obtained from 114 mg of tert-butyl 3-(5-formyl-7-(thiazol-4-yl)-4-(trifluoromethoxy)benzo[d]oxazol-2-yl)-3,6-diazabicyclo[3.1.1]heptane-6-carboxylate obtained in Example 300 (b) by a similar method to Example 183 (a).

(d) tert-Butyl 3-(5-(2,2-difluoro-1-hydroxyethyl)-7-(thiazol-4-yl)-4-(trifluoromethoxy)benzo[d]oxazol-2-yl)-3,6-diazabicyclo[3.1.1]heptane-6-carboxylate (Optically Active)

76 mg of racemic tert-butyl 3-(5-(2,2-difluoro-1-hydroxyethyl)-7-(thiazol-4-yl)-4-(trifluoromethoxy)benzo[d]oxazol-2-yl)-3,6-diazabicyclo[3.1.1]heptane-6-carboxylate obtained in Example 300(c) was purified by a preparative HPLC (Gilson, column: DAICEL CHIRALPAK IA (particle diameter: 5 μm, column diameter: 2 cm, column length: 25 cm), eluent, hexane:isopropyl alcohol=70:30, flow rate: 15 mL/min, detection: UV254 nm) and the title compound was obtained in an amount of 32 mg by concentrating fractions with the shorter retention time peak. 99.9% ee. Analysis conditions: HPLC (HITACHI, column: DAICEL CHIRALPAK IA (particle diameter: 5 μm, column diameter: 0.46 cm, column length: 25 cm), eluent, hexane:isopropyl alcohol=70:30, flow rate: 1 mL/min, detection: UV254 nm, temperature: 25° C., retention time: 5.9 min).

(e) 1-(2-(3,6-Diazabicyclo[3.1.1]heptan-3-yl)-7-(thiazol-4-yl)-4-(trifluoromethoxy)benzo[d]oxazol-5-yl)-2,2-difluoroethan-1-ol (Optically Active)

23 mg of the title compound was obtained from 32 mg of tert-butyl 3-(5-(2,2-difluoro-1-hydroxyethyl)-7-(thiazol-4-yl)-4-(trifluoromethoxy)benzo[d]oxazol-2-yl)-3,6-diazabicyclo[3.1.1]heptane-6-carboxylate (Optically Active) Obtained in Example 300(d) by a similar method to Example 1(c).

Example 301

1-(2-(3,6-Diazabicyclo[3.1.1]heptan-3-yl)-7-(thiazol-4-yl)-4-(trifluoromethoxy)benzo[d]oxazol-5-yl)-2,2-difluoroethan-1-ol (enantiomer of Example 300)

(a) tert-Butyl 3-(5-(2,2-difluoro-1-hydroxyethyl)-7-(thiazol-4-yl)-4-(trifluoromethoxy)benzo[d]oxazol-2-yl)-3,6-diazabicyclo[3.1.1]heptane-6-carboxylate (enantiomer of Example 300(d))

The title compound was obtained in an amount of 31 mg by concentrating fractions with the longer retention time peak obtained in Example 300(c). 99.9% ee. Analysis conditions: HPLC (HITACHI, column: DAICEL CHIRALPAK IA (particle diameter: 5 μm, column diameter: 0.46 cm, column length: 25 cm), eluent, hexane:isopropyl alcohol=70:30, flow rate: 1 mL/min, detection: UV254 nm, temperature: 25° C., retention time: 17.3 min).

(b) 1-(2-(3,6-Diazabicyclo[3.1.1]heptan-3-yl)-7-(thiazol-4-yl)-4-(trifluoromethoxy)benzo[d]oxazol-5-yl)-2,2-difluoroethan-1-ol (enantiomer of Example 300)

The title compound was obtained in an amount of 23 mg from 31 mg of tert-butyl 3-(5-(2,2-difluoro-1-hydroxyethyl)-7-(thiazol-4-yl)-4-(trifluoromethoxy)benzo[d]oxazol-2-yl)-3,6-diazabicyclo[3.1.1]heptane-6-carboxylate (enantiomer of Example 300(d)) obtained in Example 301(a) by a similar method to Example 1(c).

Example 302

1-(2-(3,8-Diazabicyclo[3.2.1]octan-3-yl)-7-(thiazol-4-yl)-4-(trifluoromethoxy)benzo[d]oxazol-5-yl)-2,2-difluoroethan-1-ol (Optically Active)

(a) tert-Butyl 3-(5-formyl-7-(thiazol-4-yl)-4-(trifluoromethoxy)benzo[d]oxazol-2-yl)-3,8-diazabicyclo [3.2.1]octane-8-carboxylate 241 mg of the title compound was obtained as a crude product from 350 mg of ethyl 2-(8-(tert-butoxycarbonyl)-3,8-diazabicyclo[3.2.1]octan-3-yl)-7-(thiazol-4-yl)-4-(trifluoromethoxy)benzo[d]oxazole-5-carboxylate obtained in Example 291(a) by a similar method to Example 102 (a).

(b) tert-Butyl 3-(5-(2,2-difluoro-1-hydroxyethyl)-7-(thiazol-4-yl)-4-(trifluoromethoxy)benzo[d]oxazol-2-yl)-3,8-diazabicyclo[3.2.1]octane-8-carboxylate 196 mg of the title compound was obtained from 240 mg of the crude product of tert-butyl 3-(5-formyl-7-(thiazol-4-yl)-4-(trifluoromethoxy)benzo[d]oxazol-2-yl)-3,8-diazabicyclo[3.2.1]octane-8-carboxylate obtained in Example 302 (a) by a similar method to Example 183(a) except that 4 equivalents of triphenylphosphine and 4 equivalents of (bromodifluoromethyl)trimethylsilane were used.

(c) tert-Butyl 3-(5-(2,2-difluoro-1-hydroxyethyl)-7-(thiazol-4-yl)-4-(trifluoromethoxy)benzo[d]oxazol-2-yl)-3,8-diazabicyclo[3.2.1]octane-8-carboxylate (Optically Active)

103 mg of racemic tert-butyl 3-(5-(2,2-difluoro-1-hydroxyethyl)-7-(thiazol-4-yl)-4-(trifluoromethoxy)benzo[d]oxazol-2-yl)-3,8-diazabicyclo[3.2.1]octane-8-carboxylate obtained in Example 302 (b) was purified by a preparative HPLC (Gilson, column: DAICEL CHIRALPAK IA (particle diameter: 5 μm, column diameter: 2 cm, column length: 25 cm), eluent, hexane:isopropyl alcohol=80:20-70:30, flow rate: 15 mL/min, detection: UV254 nm) and the title compound was obtained in an amount of 52 mg by concentrating fractions with the shorter retention time peak. >99.5% ee. Analysis conditions: HPLC (HITACHI, column: DAICEL CHIRALPAK IA (particle diameter: 5 μm, column diameter: 0.46 cm, column length: 25 cm), eluent, hexane:isopropyl alcohol=80:20, flow rate: 1 mL/min, detection: UV254 nm, temperature: 25° C., retention time: 5.9 min).

(d) 1-(2-(3,8-Diazabicyclo[3.2.1]octan-3-yl)-7-(thiazol-4-yl)-4-(trifluoromethoxy)benzo[d]oxazol-5-yl)-2,2-difluoroethan-1-ol (Optically Active)

27 mg of the title compound was obtained from 52 mg of tert-butyl 3-(5-(2,2-difluoro-1-hydroxyethyl)-7-(thiazol-4-yl)-4-(trifluoromethoxy)benzo[d]oxazol-2-yl)-3,8-diazabicyclo[3.2.1]octane-8-carboxylate (Optically Active) Obtained in Example 302 (c) by a similar method to Example 1(c).

Example 303

1-(2-(3,8-Diazabicyclo[3.2.1]octan-3-yl)-7-(thiazol-4-yl)-4-(trifluoromethoxy)benzo[d]oxazol-5-yl)-2,2-difluoroethan-1-ol (Optically Active, Enantiomer of Example 302)

(a) tert-Butyl 3-(5-formyl-7-(thiazol-4-yl)-4-(trifluoromethoxy)benzo[d]oxazol-2-yl)-3,8-diazabicyclo [3.2.1]octane-8-carboxylate (Optically Active, Enantiomer of Example 302 (c))

The title compound was obtained in an amount of 50 mg by concentrating fractions with the longer retention time peak obtained in Example 302 (c). >99.5% ee. Analysis conditions: HPLC (HITACHI, column: DAICEL CHIRALPAK IA (particle diameter: 5 μm, column diameter: 0.46 cm, column length: 25 cm), eluent, hexane:isopropyl alcohol=80:20, flow rate: 1 mL/min, detection: UV254 nm, temperature: 25° C., retention time: 15.1 min).

(b) 1-(2-(3,8-Diazabicyclo[3.2.1]octan-3-yl)-7-(thiazol-4-yl)-4-(trifluoromethoxy)benzo[d]oxazol-5-yl)-2,2-difluoroethan-1-ol (Optically Active, Enantiomer of Example 302)

25 mg of the title compound was obtained from 50 mg of tert-butyl 3-(5-formyl-7-(thiazol-4-yl)-4-(trifluoromethoxy) benzo[d]oxazol-2-yl)-3,8-diazabicyclo[3.2.1]octane-8-carboxylate (Optically Active, Enantiomer of Example 302 (c)) obtained in Example 303 (a) by a similar method to Example 1(c).

Example 304

1-((2-(3,6-Diazabicyclo[3.1.1]heptan-3-yl)-7-(1H-pyrazol-1-yl)benzo[d]oxazol-4-yl)oxy)-1,1-difluoro-2-methylpropan-2-ol (a) tert-Butyl 3-(4-(benzyloxy)-7-(1H-pyrazol-1-yl) benzo[d]oxazol-2-yl)-3,6-diazabicyclo[3.1.1]heptane-6-carboxylate The title compound was obtained in an amount of 25 mg from 100 mg of tert-butyl 3-(4-(benzyloxy)-7-bromobenzo [d]oxazol-2-yl)-3,6-diazabicyclo[3.1.1]heptane-6-carboxylate obtained in Example 248(a) by a similar method to Example 5(a) except that the reaction mixture was stirred at 120° C. for 15 hours.

(b) tert-Butyl 3-(4-hydroxy-7-(1H-pyrazol-1-yl) benzo[d]oxazol-2-yl)-3,6-diazabicyclo[3.1.1]heptane-6-carboxylate The title compound was obtained in an amount of 9.7 mg from 38 mg of tert-butyl 3-(4-(benzyloxyl)-7-(1H-pyrazol- 1-yl)benzo[d]oxazol-2-yl)-3,6-diazabicyclo[3.1.1]heptane-6-carboxylate obtained in Example 304 (a) by a similar method to Example 248 (c).

(c) 2-((2-(6-(tert-Butoxycarbonyl)-3,6-diazabicyclo [3.1.1]heptan-3-yl-7-(1H-pyrazol-1-yl)benzo[d]oxazol-4-yl)oxy)-2,2-difluoro acetic acid The title compound was obtained in an amount of 91 mg from 90 mg of tert-butyl 3-(4-hydroxy-7-(1H-pyrazol-1-yl)benzo[d]oxazol-2-yl)-3,6-diazabicyclo[3.1.1]heptane-6-carboxylate obtained in Example 304(b) by a similar method to Example 248(d) except that chloroform-chloroform:methanol: ammonia water=4:1:0.1 was used as the eluent of silica gel column chromatography.

(d) tert-Butyl 3-(4-(2-ethoxy-1,1-difluoro-2-oxoethoxy)-7-(1H-pyrazol-1-yl)benzo[d]oxazol-2-yl)-3,6-diazabicyclo[3.1.1]heptane-6-carboxylate 69 mg of 2-((2-(6-(tert-butoxycarbonyl)-3,6-diazabicyclo [3.1.1]heptan-3-yl-7-(1H-pyrazol-1-yl)benzo[d]oxazol-4-yl)oxy)-2,2-difluoro acetic acid obtained in Example 304(c) was dissolved in chloroform/ethanol=1:1 (2.8 mL), then trifluoroacetic acid (320 µL, 30 equivalents) was added under an argon atmosphere, followed by stirring at 60° C. for 24 hours. The formation of the product was confirmed by TLC, and then saturated sodium hydrogen carbonate aqueous solution was added thereto to stop the reaction, and then the organic phase was extracted by ethyl acetate 3 times. The organic phase was dried over anhydrous magnesium sulfate, followed by filtration and vacuum concentration of the filtrate, and thus obtaining 35 mg of the title compound by purification of the residue through silica gel column chromatography (ethyl acetate:hexane=1:9-1:1).

(e) tert-Butyl 3-(4-(1,1-difluoro-2-hydroxy-2-methylpropoxy)-7-(1H-pyrazol-1-yl)benzo[d]oxazol-2-yl)-3,6-diazabicyclo[3.1.1]heptane-6-carboxylate The title compound was obtained in an amount of 9.0 mg from 35 mg of tert-butyl 3-(4-(2-ethoxy-1,1-difluoro-2-oxoethoxy)-7-(1H-pyrazol-1-yl)benzo[d]oxazol-2-yl)-3,6-diazabicyclo[3.1.1]heptane-6-carboxylate obtained in Example 304 (d) by a similar method to Example 248 (e).

(f) 1-((2-(3,6-Diazabicyclo[3.1.1]heptan-3-yl)-7-(1H-pyrazol-1-yl)benzo[d]oxazol-4-yl)oxy)-1,1-difluoro-2-methylpropan-2-ol The title compound was obtained in an amount of 4.1 mg from 9.0 mg of tert-butyl 3-(4-(1,1-difluoro-2-hydroxy-2-methylpropoxy)-7-(1H-pyrazol-1-yl)benzo[d]oxazol-2-yl)-3,6-diazabicyclo[3.1.1]heptane-6-carboxylate obtained in Example 304 (e) by a similar method to Example 1(c).

Example 305

4-((2-(3,6-Diazabicyclo[3.1.1]heptan-3-yl)-7-(thiazol-2-yl)benzo[d]oxazol-4-yl)oxy)cyclohexan-1-ol (a) tert-Butyl 3-(4-((4-oxocyclohexyl)oxy)-7-(thiazol-2-yl)benzo[d]oxazol-2-yl)-3,6-diazabicyclo [3.1.1]heptane-6-carboxylate The title compound was obtained in an amount of 35 mg from 41 mg of tert-butyl 3-(4-hydroxy-7-(thiazol-2-yl)benzo [d]oxazol-2-yl)-3,6-diazabicyclo[3.1.1]heptane-6-carboxylate obtained in Example 248 (c) by a similar method to Reference Example 23(a) except that 4-oxocyclohexyl 4-methylbenzenesulfonate was used instead of benzyl bromide and the reaction mixture was stirred at 60° C.

(b) tert-Butyl 3-(4-((4-hydroxycyclohexyl)oxy)-7-(thiazol-2-yl)benzo[d]oxazol-2-yl)-3,6-diazabicyclo [3.1.1]heptane-6-carboxylate The title compound was obtained in an amount of 22 mg from 41 mg of tert-butyl 3-(4-((4-oxocyclohexyl)oxy)-7-(thiazol-2-yl)benzo[d]oxazol-2-yl)-3,6-diazabicyclo[3.1.1] heptane-6-carboxylate obtained in Example 305(a) by a similar method to Example 155(c) except that 1 equivalent of sodium borohydride was used.

(c) 4-((2-(3,6-Diazabicyclo[3.1.1]heptan-3-yl)-7-(thiazol-2-yl)benzo[d]oxazol-4-yl)oxy)cyclohexan-1-ol The title compound was obtained in an amount of 7.5 mg from 22 mg of tert-butyl 3-(4-((4-hydroxycyclohexyl)oxy)-7-(thiazol-2-yl)benzo[d]oxazol-2-yl)-3,6-diazabicyclo [3.1.1]heptane-6-carboxylate obtained in Example 305(b) by a similar method to Example 1(c).

Example 306

1-((2-(3,6-Diazabicyclo[3.1.1]heptan-3-yl)-7-(4-methylthiazol-2-yl)benzo[d]oxazol-4-yl)oxy)-1,1-difluoro-2-methylpropan-2-ol (a) tert-Butyl 3-(4-(benzyloxy)-7-(4-methylthiazol-2-yl)benzo[d]oxazol-2-yl)-3,6-diazabicyclo[3.1.1] heptane-6-carboxylate The title compound was obtained in an amount of 209 mg from 200 mg of tert-butyl 3-(4-(benzyloxyl)-7-bromobenzo [d]oxazol-2-yl)-3,6-diazabicyclo[3.1.1]heptane-6-carboxylate obtained in Example 248(a) by a similar method to Example 6(a) except that 4-methyl-2-(tributylstannyl)thiazole was used instead of 2-(tributylstannyl)furan.

(b) tert-Butyl 3-(4-hydroxy-7-(4-methylthiazol-2-yl) benzo[d]oxazol-2-yl)-3,6-diazabicyclo[3.1.1]heptane-6-carboxylate The title compound was obtained in an amount of 107 mg from 209 mg of tert-butyl 3-(4-(benzyloxy)-7-(methylthiazol-2-yl)benzo[d]oxazol-2-yl)-3,6-diazabicyclo[3.1.1]heptane-6-carboxylate obtained in Example 306(a) by a similar method to Example 248 (c).

(c) tert-Butyl 3-(4-(2-ethoxy-1,1-difluoro-2-oxoethoxy)-7-(4-methylthiazol-2-yl)benzo[d]oxazol-2-yl)-3,6-diazabicyclo[3.1.1]heptane-6-carboxylate The title compound was obtained in an amount of 98 mg from 107 mg of tert-butyl 3-(4-hydroxy-7-(4-methylthiazol-2-yl)benzo[d]oxazol-2-yl)-3,6-diazabicyclo[3.1.1]heptane-6-carboxylate obtained in Example 306 (b) by a similar method to Example 248 (b).

(d) tert-Butyl 3-(4-(1,1-difluoro-2-hydroxy-2-methylpropoxy)-7-(4-methylthiazol-2-yl)benzo[d]oxazol-2-yl)-3,6-diazabicyclo[3.1.1]heptane-6-carboxylate The title compound was obtained in an amount of 75 mg from 98 mg of tert-butyl 3-(4-(2-ethoxy-1,1-difluoro-2-oxoethoxy)-7-(4-methylthiazol-2-yl)benzo[d]oxazol-2-yl)-3,6-diazabicyclo[3.1.1]heptane-6-carboxylate obtained in Example 306(c) by a similar method to Example 248 (e).

(e) 1-((2-(3,6-Diazabicyclo[3.1.1]heptan-3-yl)-7-(4-methylthiazol-2-yl)benzo[d]oxazol-4-yl)oxy)-1,1-difluoro-2-methylpropan-2-ol The title compound was obtained in an amount of 34 mg from 75 mg of tert-butyl 3-(4-(1,1-difluoro-2-hydroxy-2-methylpropoxy)-7-(4-methylthiazol-2-yl)benzo[d]oxazol-2-yl)-3,6-diazabicyclo[3.1.1]heptane-6-carboxylate obtained in Example 306(d) by a similar method to Example 1(c).

Example 307

1-((2-(3,6-Diazabicyclo[3.1.1]heptan-3-yl)-7-(thiazol-4-yl)benzo[d]oxazol-4-yl)oxy)-1,1-difluoro-2-methylpropan-2-ol (a) tert-Butyl 3-(7-bromo-4-((tert-butyldimethylsilyl)oxy)benzo[d]oxazol-2-yl)-3,6-diazabicyclo[3.1.1]heptane-6-carboxylate The title compound was obtained in an amount of 590 mg from 1.0 g of 7-bromo-4-((tert-butyldimethylsilyl)oxy)benzo[d]oxazole-2-thiol obtained in Reference Example 24 by a similar method to Example 3 (a).

(b) tert-Butyl 3-(4-((tert-butyldimethylsilyl)oxy)-7-(thiazol-4-yl)benzo[d]oxazol-2-yl)-3,6-diazabicyclo[3.1.1]heptane-6-carboxylate The title compound was obtained in an amount of 212 mg from 300 mg of tert-butyl 3-(7-bromo-4-((tert-butyldimethylsilyl)oxy)benzo[d]oxazol-2-yl)-3,6-diazabicyclo[3.1.1]heptane-6-carboxylate obtained in Example 307 (a) by a similar method to Example 8 (a).

(c) tert-Butyl 3-(4-hydroxy-7-(thiazol-4-yl)benzo[d]oxazol-2-yl)-3,6-diazabicyclo[3.1.1]heptane-6-carboxylate 212 mg of tert-butyl 3-(4-((tert-butyldimethylsilyl)oxy)-7-(thiazol-4-yl)benzo[d]oxazol-2-yl)-3,6-diazabicyclo[3.1.1]heptane-6-carboxylate obtained in Example 307(b) was dissolved in tetrahydrofuran (4.0 mL), then 1.0 M solution of tetrabutylammonium fluoride in tetrahydrofuran (0.8 mL, 2 equivalents) was added, followed by stirring at 0° C. for 1 hour. The formation of the product was confirmed by TLC, and then saturated ammonium chloride aqueous solution was added thereto to stop the reaction, and then the organic phase was extracted by ethyl acetate three times. The organic phase was dried over anhydrous magnesium sulfate, followed by filtration and vacuum concentration of the filtrate, and thus obtaining 145 mg of the title compound by purification of the residue through silica gel column chromatography (hexane-ethyl acetate:hexane: =1:1).

(d) tert-Butyl 3-(4-(2-ethoxy-1,1-difluoro-2-oxoethoxy)-7-(thiazol-4-yl)benzo[d]oxazol-2-yl)-3,6-diazabicyclo[3.1.1]heptane-6-carboxylate The title compound was obtained in an amount of 107 mg from 145 mg of tert-butyl 3-(4-hydroxy-7-(thiazol-4-yl)benzo[d]oxazol-2-yl)-3,6-diazabicyclo[3.1.1]heptane-6-carboxylate obtained in Example 307 (c) by a similar method to Example 248 (d).

(e) tert-Butyl 3-(4-(1,1-difluoro-2-hydroxy-2-methylpropoxy)-7-(thiazol-4-yl)benzo[d]oxazol-2-yl)-3,6-diazabicyclo[3.1.1]heptane-6-carboxylate The title compound was obtained in an amount of 34 mg from 54 mg of tert-butyl 3-(4-(2-ethoxy-1,1-difluoro-2-oxoethoxy)-7-(thiazol-4-yl)benzo[d]oxazol-2-yl)-3,6-diazabicyclo[3.1.1]heptane-6-carboxylate obtained in Example 307 (d) by a similar method to Example 248 (e).

(f) 1-((2-(3,6-Diazabicyclo[3.1.1]heptan-3-yl)-7-(thiazol-4-yl)benzo[d]oxazol-4-yl)oxy)-1,1-difluoro-2-methylpropan-2-ol The title compound was obtained in an amount of 9.8 mg from 34 mg of tert-butyl 3-(4-(1,1-difluoro-2-hydroxy-2-methylpropoxy)-7-(thiazol-4-yl)benzo[d]oxazol-2-yl)-3,6-diazabicyclo[3.1.1]heptane-6-carboxylate obtained in Example 307 (e) by a similar method to Example 1(c).

Example 308

1-((2-(3,8-Diazabicyclo[3.2.1]octan-3-yl)-7-(thiazol-4-yl)benzo[d]oxazol-4-yl)oxy)-1,1-difluoro-2-methylpropan-2-ol (a) tert-Butyl 3-(7-bromo-4-((tert-butyldimethylsilyl)oxy)benzo[d]oxazol-2-yl)-3,8-diazabicyclo[3.2.1]octane-8-carboxylate The title compound was obtained in an amount of 884 mg from 1.0 g of 7-bromo-4-((tert-butyldimethylsilyl)oxy)benzo[d]oxazole-2-thiol obtained in Reference Example 24 by a similar method to Example 1(a).

(b) tert-Butyl 3-(4-((tert-butyldimethylsilyl)oxy)-7-(thiazol-4-yl)benzo[d]oxazol-2-yl)-3,8-diazabicyclo[3.2.1]octane-8-carboxylate The title compound was obtained in an amount of 189 mg from 442 mg of tert-butyl 3-(7-bromo-4-((tert-butyldimethylsilyl)oxy)benzo[d]oxazol-2-yl)-3,8-diazabicyclo[3.2.1]octane-8-carboxylate obtained in Example 308 (a) by a similar method to Example 8 (a).

(c) tert-Butyl 3-(4-hydroxy-7-(thiazol-4-yl)benzo[d]oxazol-2-yl)-3,8-diazabicyclo[3.2.1]octane-8-carboxylate The title compound was obtained in an amount of 115 mg from 189 mg of tert-butyl 3-(4-((tert-butyldimethylsilyl)oxy)-7-(thiazol-4-yl)benzo[d]oxazol-2-yl)-3,8-diazabicyclo[3.2.1]octane-8-carboxylate obtained in Example 308 (b) by a similar method to Example 307 (c).

(d) tert-Butyl 3-(4-(2-ethoxy-1,1-difluoro-2-oxoethoxy)-7-(thiazol-4-yl)benzo[d]oxazol-2-yl)-3,8-diazabicyclo[3.2.1]octane-8-carboxylate The title compound was obtained in an amount of 111 mg from 115 mg of tert-butyl 3-(4-hydroxy-7-(thiazol-4-yl)

benzo[d]oxazol-2-yl)-3,8-diazabicyclo[3.2.1]octane-8-carboxylate obtained in Example 308 (c) by a similar method to Example 248 (d).

(e) tert-Butyl 3-(4-(1,1-difluoro-2-hydroxy-2-methylpropoxy)-7-(thiazol-4-yl)benzo[d]oxazol-2-yl)-3,8-diazabicyclo[3.2.1]octane-8-carboxylate The title compound was obtained in an amount of 36 mg from 56 mg of tert-butyl 3-(4-(2-ethoxy-1,1-difluoro-2-oxoethoxy)-7-(thiazol-4-yl)benzo[d]oxazol-2-yl)-3,8-diazabicyclo[3.2.1]octane-8-carboxylate obtained in Example 308 (d) by a similar method to Example 248 (e).

(f) 1-((2-(3,8-Diazabicyclo[3.2.1]octan-3-yl)-7-(thiazol-4-yl)benzo[d]oxazol-4-yl)oxy)-1,1-difluoro-2-methylpropan-2-ol The title compound was obtained in an amount of 14 mg from 36 mg of tert-butyl 3-(4-(1,1-difluoro-2-hydroxy-2-methylpropoxy)-7-(thiazol-4-yl)benzo[d]oxazol-2-yl)-3,8-diazabicyclo[3.2.1]octane-8-carboxylate obtained in Example 308 (e) by a similar method to Example 1(c).

Example 309

1-((2-(3,6-Diazabicyclo[3.1.1]heptan-3-yl)-7-(thiazol-4-yl)benzo[d]oxazol-4-yl)oxy)-1,1-difluoropropan-2-ol (a) tert-Butyl 3-(4-(1,1-difluoro-2-(methoxy(methyl)amino)-2-oxoethoxy)-7-(thiazol-4-yl)benzo[d]oxazol-2-yl)-3,6-diazabicyclo[3.1.1]heptane-6-carboxylate The title compound was obtained in an amount of 29 mg from 54 mg of tert-butyl 3-(4-(2-ethoxy-1,1-difluoro-2-oxoethoxy)-7-(thiazol-4-yl)benzo[d]oxazol-2-yl)-3,6-diazabicyclo[3.1.1]heptane-6-carboxylate obtained in Example 307 (d) by a similar method to Example 250(a).

(b) tert-Butyl 3-(4-(1,1-difluoro-2-oxopropoxy)-7-(thiazol-4-yl)benzo[d]oxazol-2-yl)-3,6-diazabicyclo[3.1.1]heptane-6-carboxylate The title compound was obtained in an amount of 16 mg from 29 mg of tert-butyl 3-(4-(1,1-difluoro-2-(methoxy(methyl)amino)-2-oxoethoxy)-7-(thiazol-4-yl)benzo[d]oxazol-2-yl)-3,6-diazabicyclo[3.1.1]heptane-6-carboxylate obtained in Example 309(a) by a similar method to Example 250(b).

(c) tert-Butyl 3-(4-(1,1-difluoro-2-hydroxypropoxy)-7-(thiazol-4-yl)benzo[d]oxazol-2-yl)-3,6-diazabicyclo[3.1.1]heptane-6-carboxylate The title compound was obtained in an amount of 16 mg from 16 mg of tert-butyl 3-(4-(1,1-difluoro-2-oxopropoxy)-7-(thiazol-4-yl)benzo[d]oxazol-2-yl)-3,6-diazabicyclo[3.1.1]heptane-6-carboxylate obtained in Example 309(b) by a similar method to Example 250(c).

(d) 1-((2-(3,6-Diazabicyclo[3.1.1]heptan-3-yl)-7-(thiazol-4-yl)benzo[d]oxazol-4-yl)oxy)-1,1-difluoropropan-2-ol The title compound was obtained in an amount of 7.6 mg from 16 mg of tert-butyl 3-(4-(1,1-difluoro-2-hydroxypropoxy)-7-(thiazol-4-yl)benzo[d]oxazol-2-yl)-3,6-diazabicyclo[3.1.1]heptane-6-carboxylate obtained in Example 309 (c) by a similar method to Example 1(c).

Example 310

1-((2-(3,8-Diazabicyclo[3.2.1]octan-3-yl)-7-(thiazol-4-yl)benzo[d]oxazol-4-yl)oxy)-1,1-difluoropropan-2-ol (a) tert-Butyl 3-(4-(1,1-difluoro-2-(methoxy(methyl)amino)-2-oxoethoxy)-7-(thiazol-4-yl)benzo[d]oxazol-2-yl)-3,8-diazabicyclo[3.2.1]octane-8-carboxylate The title compound was obtained in an amount of 29 mg from 54 mg of tert-butyl 3-(4-(2-ethoxy-1,1-difluoro-2-oxoethoxy)-7-(thiazol-4-yl)benzo[d]oxazol-2-yl)-3,8-diazabicyclo[3.2.1]octane-8-carboxylate obtained in Example 308 (d) by a similar method to Example 250 (a).

(b) tert-Butyl 3-(4-(1,1-difluoro-2-oxopropoxy)-7-(thiazol-4-yl)benzo[d]oxazol-2-yl)-3,8-diazabicyclo[3.2.1]octane-8-carboxylate The title compound was obtained in an amount of 16 mg from 29 mg of tert-butyl 3-(4-(1,1-difluoro-2-(methoxy(methyl)amino)-2-oxoethoxy)-7-(thiazol-4-yl)benzo[d]oxazol-2-yl)-3,8-diazabicyclo[3.2.1]octane-8-carboxylate obtained in Example 310(a) by a similar method to Example 250 (b).

(c) tert-Butyl 3-(4-(1,1-difluoro-2-hydroxypropoxy)-7-(thiazol-4-yl)benzo[d]oxazol-2-yl)-3,8-diazabicyclo[3.2.1]octane-8-carboxylate The title compound was obtained in an amount of 21 mg from 39 mg of tert-butyl 3-(4-(1,1-difluoro-2-oxopropoxy)-7-(thiazol-4-yl)benzo[d]oxazol-2-yl)-3,8-diazabicyclo[3.2.1]octane-8-carboxylate obtained in Example 310 (b) by a similar method to Example 250(c).

(d) 1-((2-(3,8-Diazabicyclo[3.2.1]octan-3-yl)-7-(thiazol-4-yl)benzo[d]oxazol-4-yl)oxy)-1,1-difluoropropan-2-ol The title compound was obtained in an amount of 1.9 mg from 14 mg of tert-butyl 3-(4-(1,1-difluoro-2-hydroxypropoxy)-7-(thiazol-4-yl)benzo[d]oxazol-2-yl)-3,8-diazabicyclo[3.2.1]octane-8-carboxylate obtained in Example 310 (c) by a similar method to Example 1(c).

Example 311

2-((2-(3,6-Diazabicyclo[3.1.1]heptan-3-yl)-7-(thiazol-4-yl)benzo[d]oxazol-4-yl)oxy)-2,2-difluoroethan-1-ol (a) tert-Butyl 3-(4-(1,1-difluoro-2-hydroxyethoxy)-7-(thiazol-4-yl)benzo[d]oxazol-2-yl)-3,6-diazabicyclo[3.1.1]heptane-6-carboxylate The title compound was obtained in an amount of 35 mg from 54 mg of the crude product of tert-butyl 3-(4-(2-ethoxy-1,1-difluoro-2-oxoethoxy)-7-(thiazol-4-yl)benzo[d]

oxazol-2-yl)-3,6-diazabicyclo[3.1.1]heptane-6-carboxylate obtained in Example 307 (d) by a similar method to Example 249(a).

(b) 2-((2-(3,6-Diazabicyclo[3.1.1]heptan-3-yl)-7-(thiazol-4-yl)benzo[d]oxazol-4-yl)oxy)-2,2-difluoro-ethan-1-ol The title compound was obtained in an amount of 11 mg from 31 mg of tert-butyl 3-(4-(1,1-difluoro-2-hydroxy-ethoxy)-7-(thiazol-4-yl)benzo[d]oxazol-2-yl)-3,6-diazabi-cyclo[3.1.1]heptane-6-carboxylate obtained in Example 311 (a) by a similar method to Example 1(c).

Example 312

2-((2-(3,8-Diazabicyclo[3.2.1]octan-3-yl)-7-(thiazol-4-yl)benzo[d]oxazol-4-yl)oxy)-2,2-difluoroethan-1-ol (a) tert-Butyl 3-(4-(1,1-difluoro-2-hydroxyethoxy)-7-(thiazol-4-yl)benzo[d]oxazol-2-yl)-3,8-diazabicy-clo[3.2.1]octane-8-carboxylate The title compound was obtained in an amount of 37 mg from 68 mg of tert-butyl 3-(4-(2-ethoxy-1,1-difluoro-2-oxo-ethoxy)-7-(thiazol-4-yl)benzo[d]oxazol-2-yl)-3,8-diazabi-cyclo[3.2.1]octane-8-carboxylate obtained in Example 308 (d) by a similar method to Example 249 (a).

(b) 2-((2-(3,8-Diazabicyclo[3.2.1]octan-3-yl)-7-(thi-azol-4-yl)benzo[d]oxazol-4-yl)oxy)-2,2-difluoro-ethan-1-ol The title compound was obtained in an amount of 11 mg from 31 mg of tert-butyl 3-(4-(1,1-difluoro-2-hydroxy-ethoxy)-7-(thiazol-4-yl)benzo[d]oxazol-2-yl)-3,8-diazabi-cyclo[3.2.1]octane-8-carboxylate obtained in Example 312 (a) by a similar method to Example 1(c).

Example 313

3-((2-(3,6-Diazabicyclo[3.1.1]heptan-3-yl)-7-(thi-azol-2-yl)benzo[d]oxazol-4-yl)oxy)-4,4,4-trifluoro-2-methylbutan-2-ol (a) tert-Butyl 3-(4-((2-bromo-3-ethoxy-1,1,1-trif-luoro-3-oxopropan-2-yl)oxy)-7-(thiazol-2-yl)benzo[d]oxazol-2-yl)-3,6-diazabicyclo[3.1.1]heptane-6-carboxylate The title compound was obtained in an amount of 75.8 mg from 50.0 mg of tert-butyl 3-(4-hydroxy-7-(thiazol-2-yl)benzo[d]oxazol-2-yl)-3,6-diazabicyclo[3.1.1]heptane-6-car-boxylate obtained in Example 248(c) by a similar method to Example 248(d) except that ethyl 2-bromo-2,3,3,3-tetrafluo-ropropanoate was used instead of ethyl 2-bromo-2,2-difluo-roacetate.

(b) tert-Butyl 3-(4-((3-ethoxy-1,1,1-trifluoro-3-oxo-propan-2-yl)oxy)-7-(thiazol-2-yl)benzo[d]oxazol-2-yl)-3,6-diazabicyclo[3.1.1]heptane-6-carboxylate The title compound was obtained in an amount of 39.4 mg from 75.8 mg of tert-butyl 3-(4-((2-bromo-3-ethoxy-1,1,1-trifluoro-3-oxopropan-2-yl)oxy)-7-(thiazol-2-yl)benzo[d]oxazol-2-yl)-3,6-diazabicyclo[3.1.1]heptane-6-carboxylate obtained in Example 313(a) by a similar method to Example 248(c) except that 10% palladium/carbon (50 mg) was used.

(c) tert-Butyl 3-(7-(thiazol-2-yl)-4-((1,1,1-trifluoro-3-hydroxy-3-methylbutan-2-yl)oxy)benzo[d]oxazol-2-yl)-3,6-diazabicyclo[3.1.1]heptane-6-carboxylate The title compound was obtained in an amount of 31.1 mg from 39.4 mg of tert-butyl 3-(4-((3-ethoxy-1,1,1-trifluoro-3-oxopropan-2-yl)oxy)-7-(thiazol-2-yl)benzo[d]oxazol-2-yl)-3,6-diazabicyclo[3.1.1]heptane-6-carboxylate obtained in Example 313 (b) by a similar method to Example 248 (e).

(d) 3-((2-(3,6-Diazabicyclo[3.1.1]heptan-3-yl)-7-(thiazol-2-yl)benzo[d]oxazol-4-yl)oxy)-4,4,4-trif-luoro-2-methylbutan-2-ol The title compound was obtained in an amount of 5.2 mg from 6.4 mg of tert-butyl 3-(7-(thiazol-2-yl)-4-((1,1,1-trif-luoro-3-hydroxy-3-methylbutan-2-yl)oxy)benzo[d]oxazol-2-yl)-3,6-diazabicyclo[3.1.1]heptane-6-carboxylate obtained in Example 313 (c) by a similar method to Example 1(c).

Example 314

4-((2-(3,6-Diazabicyclo[3.1.1]heptan-3-yl)-7-(thi-azol-2-yl)benzo[d]oxazol-4-yl)oxy)tetrahydro-2H-thiopyran 1,1-dioxide (a) tert-Butyl 3-(4-((1,1-dioxidotetrahydro-2H-thio-pyran-4-yl)oxy-7-(thiazol-2-yl)benzo[d]oxazol-2-yl)-3,6-diazabicyclo[3.1.1]heptane-6-carboxylate The title compound was obtained in an amount of 65.5 mg from 50.0 mg of tert-butyl 3-(4-hydroxy-7-(thiazol-2-yl)benzo[d]oxazol-2-yl)-3,6-diazabicyclo[3.1.1]heptane-6-car-boxylate obtained in Example 248(c) by a similar method to Example 262(a) except that 1,1-dioxidotetrahydro-2H-thio-pyran-4-yl 4-methylbenzenesulfonate was used instead of tetrahydro-2H-pyran-3-yl 4-methylbenzenesulfonate.

(b) 4-((2-(3,6-Diazabicyclo[3.1.1]heptan-3-yl)-7-(thiazol-2-yl)benzo[d]oxazol-4-yl)oxy)tetrahydro-2H-thiopyran 1,1-dioxide The title compound was obtained in an amount of 52.5 mg from 65.5 mg of tert-butyl 3-(4-((1,1-dioxidotetrahydro-2H-thiopyran-4-yl)oxy-7-(thiazol-2-yl)benzo[d]oxazol-2-yl)-3,6-diazabicyclo[3.1.1]heptane-6-carboxylate obtained in Example 314 (a) by a similar method to Example 1(c).

Example 315

2-((2-(3,6-Diazabicyclo[3.1.1]heptan-3-yl)-7-(pyri-din-2-yl)benzo[d]oxazol-4-yl)oxy)-2,2-difluoro-ethan-1-ol (a) tert-Butyl 3-(4-(benzyloxy)-7-(pyridin-2-yl)benzo[d]oxazol-2-yl)-3,6-diazabicyclo[3.1.1]hep-tane-6-carboxylate The title compound was obtained in an amount of 930 mg from 1.4 g of tert-butyl 3-(4-(benzyloxyl)-7-bromobenzo[d]oxazol-2-yl)-3,6-diazabicyclo[3.1.1]heptane-6-carboxylate obtained in Example 248 (a) by a similar method to Example 7 (a).

(b) tert-Butyl 3-(4-hydroxy-7-(pyridin-2-yl)benzo[d]oxazol-2-yl)-3,6-diazabicyclo[3.1.1]heptane-6-carboxylate The title compound was obtained as a crude product in an amount of 650 mg from 900 mg of tert-butyl 3-(4-(benzyloxy)-7-(pyridin-2-yl)benzo[d]oxazol-2-yl)-3,6-diazabicyclo[3.1.1]heptane-6-carboxylate obtained in Example 315 (a) by a similar method to Example 248 (c) except that 10% palladium/carbon was used instead of 20% palladium hydroxide/carbon (content of water: 50%), ethanol and ethyl acetate were used instead of tetrahydrofuran, and the reaction mixture was stirred at room temperature.

(c) tert-Butyl 3-(4-(2-ethoxy-1,1-difluoro-2-oxoethoxy)-7-(pyridin-2-yl)benzo[d]oxazol-2-yl)-3,6-diazabicyclo[3.1.1]heptane-6-carboxylate The title compound was obtained in an amount of 350 mg from 680 mg of the crude product of tert-butyl 3-(4-hydroxy-7-(pyridin-2-yl)benzo[d]oxazol-2-yl)-3,6-diazabicyclo[3.1.1]heptane-6-carboxylate obtained in Example 315 (b) by a similar method to Example 248 (d).

(d) tert-Butyl 3-(4-(1,1-difluoro-2-hydroxyethoxy)-7-(pyridin-2-yl)benzo[d]oxazol-2-yl)-3,6-diazabicyclo[3.1.1]heptane-6-carboxylate The title compound was obtained in an amount of 180 mg from 300 mg of tert-butyl 3-(4-(2-ethoxy-1,1-difluoro-2-oxoethoxy)-7-(pyridin-2-yl)benzo[d]oxazol-2-yl)-3,6-diazabicyclo[3.1.1]heptane-6-carboxylate obtained in Example 315(c) by a similar method to Example 155(c) except that the reaction mixture was stirred at room temperature.

(e) 2-((2-(3,6-Diazabicyclo[3.1.1]heptan-3-yl)-7-(pyridin-2-yl)benzo[d]oxazol-4-yl)oxy)-2,2-difluoroethan-1-ol The title compound was obtained in an amount of 100 mg from 180 mg of tert-butyl 3-(4-(1,1-difluoro-2-hydroxyethoxy)-7-(pyridin-2-yl)benzo[d]oxazol-2-yl)-3,6-diazabicyclo[3.1.1]heptane-6-carboxylate obtained in Example 315 (d) by a similar method to Example 1(c) except that dichloromethane was used instead of chloroform.

Example 316

1-((2-(3,8-Diazabicyclo[3.2.1]octan-3-yl)-7-(1H-pyrazol-1-yl)benzo[d]oxazol-4-yl)oxy)-1,1-difluoro-2-methylpropan-2-ol (a) tert-Butyl 3-(4-(benzyloxy)-7-bromobenzo[d]oxazol-2-yl)-3,8-diazabicyclo[3.2.1]octane-8-carboxylate The title compound was obtained in an amount of 3.0 g from 2.0 g of 4-(benzyloxy)-7-bromobenzo[d]oxazole-2-thiol obtained in Reference Example 23 by a similar method to Example 1(a).

(b) tert-Butyl 3-(4-(benzyloxy)-7-(1H-pyrazol-1-yl)benzo[d]oxazol-2-yl)-3,8-diazabicyclo[3.2.1]octane-8-carboxylate The title compound was obtained in an amount of 40 mg from 101 mg of tert-butyl 3-(4-(benzyloxy)-7-bromobenzo[d]oxazol-2-yl)-3,8-diazabicyclo[3.2.1]octane-8-carboxylate obtained in Example 316(a) by a similar method to Example 5 (a).

(c) tert-Butyl 3-(4-hydroxy-7-(1H-pyrazol-1-yl)benzo[d]oxazol-2-yl)-3,8-diazabicyclo[3.2.1]octane-8-carboxylate The title compound was obtained in an amount of 31 mg from 40 mg of tert-butyl 3-(4-(benzyloxy)-7-(1H-pyrazol-1-yl)benzo[d]oxazol-2-yl)-3,8-diazabicyclo[3.2.1]octane-8-carboxylate obtained in Example 316 (b) by a similar method to Example 248 (c).

(d) tert-Butyl 3-(4-(2-ethoxy-1,1-difluoro-2-oxoethoxy)-7-(1H-pyrazol-1-yl)benzo[d]oxazol-2-yl)-3,8-diazabicyclo[3.2.1]octane-8-carboxylate The title compound was obtained in an amount of 34 mg from 31 mg of tert-butyl 3-(4-hydroxy-7-(1H-pyrazol-1-yl)benzo[d]oxazol-2-yl)-3,8-diazabicyclo[3.2.1]octane-8-carboxylate obtained in Example 316(c) by a similar method to Example 248 (d).

(e) tert-Butyl 3-(4-(1,1-difluoro-2-hydroxy-2-methylpropoxy)-7-(1H-pyrazol-1-yl)benzo[d]oxazol-2-yl)-3,8-diazabicyclo[3.2.1]octane-8-carboxylate The title compound was obtained in an amount of 16 mg from 34 mg of tert-butyl 3-(4-(2-ethoxy-1,1-difluoro-2-oxoethoxy)-7-(1H-pyrazol-1-yl)benzo[d]oxazol-2-yl)-3,8-diazabicyclo[3.2.1]octane-8-carboxylate obtained in Example 316(d) by a similar method to Example 248 (e).

(f) 1-((2-(3,8-Diazabicyclo[3.2.1]octan-3-yl)-7-(1H-pyrazol-1-yl)benzo[d]oxazol-4-yl)oxy)-1,1-difluoro-2-methylpropan-2-ol The title compound was obtained in an amount of 9.9 mg from 16 mg of tert-butyl 3-(4-(1,1-difluoro-2-hydroxy-2-methylpropoxy)-7-(1H-pyrazol-1-yl)benzo[d]oxazol-2-yl)-3,8-diazabicyclo[3.2.1]octane-8-carboxylate obtained in Example 316(e) by a similar method to Example 1(c).

Example 317

1-((2-(3,8-Diazabicyclo[3.2.1]octan-3-yl)-7-(pyridin-2-yl)benzo[d]oxazol-4-yl)oxy)-1,1-difluoro-2-methylpropan-2-ol (a) tert-Butyl 3-(4-(benzyloxy)-7-(pyridin-2-yl)benzo[d]oxazol-2-yl)-3,8-diazabicyclo[3.2.1]octane-8-carboxylate The title compound was obtained in an amount of 82 mg from 101 mg of tert-butyl 3-(4-(benzyloxy)-7-bromobenzo[d]oxazol-2-yl)-3,8-diazabicyclo[3.2.1]octane-8-carboxylate obtained in Example 316(a) by a similar method to Example 7 (a).

(b) tert-Butyl 3-(4-hydroxy-7-(pyridin-2-yl)benzo[d]oxazol-2-yl)-3,8-diazabicyclo[3.2.1]octane-8-carboxylate The title compound was obtained in an amount of 51 mg from 82 mg of tert-butyl 3-(4-(benzyloxy)-7-(pyridin-2-yl)

benzo[d]oxazol-2-yl)-3,8-diazabicyclo[3.2.1]octane-8-carboxylate obtained in Example 317 (b) by a similar method to Example 248 (c).

(c) tert-Butyl 3-(4-(2-ethoxy-1,1-difluoro-2-oxoethoxy)-7-(pyridin-2-yl)benzo[d]oxazol-2-yl)-3,8-diazabicyclo[3.2.1]octane-8-carboxylate The title compound was obtained in an amount of 42 mg from 51 mg of tert-butyl 3-(4-hydroxy-7-(pyridin-2-yl)benzo[d]oxazol-2-yl)-3,8-diazabicyclo[3.2.1]octane-8-carboxylate obtained in Example 317 (b) by a similar method to Example 248 (d).

(d) tert-Butyl 3-(4-(1,1-difluoro-2-hydroxy-2-methylpropoxy)-7-(pyridin-2-yl)benzo[d]oxazol-2-yl)-3,8-diazabicyclo[3.2.1]octane-8-carboxylate The title compound was obtained in an amount of 37 mg from 42 mg of tert-butyl 3-(4-(2-ethoxy-1,1-difluoro-2-oxoethoxy)-7-(pyridin-2-yl)benzo[d]oxazol-2-yl)-3,8-diazabicyclo[3.2.1]octane-8-carboxylate obtained in Example 317 (c) by a similar method to Example 248 (e).

(e) 1-((2-(3,8-Diazabicyclo[3.2.1]octan-3-yl)-7-(pyridin-2-yl)benzo[d]oxazol-4-yl)oxy)-1,1-difluoro-2-methylpropan-2-ol The title compound was obtained in an amount of 22 mg from 37 mg of tert-butyl 3-(4-(1,1-difluoro-2-hydroxy-2-methylpropoxy)-7-(pyridin-2-yl)benzo[d]oxazol-2-yl)-3,8-diazabicyclo[3.2.1]octane-8-carboxylate obtained in Example 317 (d) by a similar method to Example 1(c).

Example 318

1-((2-(3,8-Diazabicyclo[3.2.1]octan-3-yl)-7-(4-methylthiazol-2-yl)benzo[d]oxazol-4-yl)oxy)-1,1-difluoro-2-methylpropan-2-ol (a) tert-Butyl 3-(4-(benzyloxy)-7-(4-methylthiazol-2-yl)benzo[d]oxazol-2-yl)-3,8-diazabicyclo[3.2.1]octane-8-carboxylate The title compound was obtained in an amount of 101 mg from 100 mg of tert-butyl 3-(4-(benzyloxy)-7-bromobenzo[d]oxazol-2-yl)-3,8-diazabicyclo[3.2.1]octane-8-carboxylate obtained in Example 316(a) by a similar method to Example 306(a).

(b) tert-Butyl 3-(4-hydroxy-7-(4-methylthiazol-2-yl)benzo[d]oxazol-2-yl)-3,8-diazabicyclo[3.2.1]octane-8-carboxylate The title compound was obtained in an amount of 69 mg from 101 mg of tert-butyl 3-(4-(benzyloxy)-7-(4-methylthiazol-2-yl)benzo[d]oxazol-2-yl)-3,8-diazabicyclo[3.2.1]octane-8-carboxylate obtained in Example 318 (a) by a similar method to Example 248 (c).

(c) tert-Butyl 3-(4-(2-ethoxy-1,1-difluoro-2-oxoethoxy)-7-(4-methylthiazol-2-yl)benzo[d]oxazol-2-yl)-3,8-diazabicyclo[3.2.1]octane-8-carboxylate The title compound was obtained in an amount of 66 mg from 69 mg of tert-butyl 3-(4-hydroxy-7-(4-methylthiazol-2-yl)benzo[d]oxazol-2-yl)-3,8-diazabicyclo[3.2.1]octane-8-carboxylate obtained in Example 318 (b) by a similar method to Example 248 (d).

(d) tert-Butyl 3-(4-(1,1-difluoro-2-hydroxy-2-methylpropoxy)-7-(4-methylthiazol-2-yl)benzo[d]oxazol-2-yl)-3,8-diazabicyclo[3.2.1]octane-8-carboxylate The title compound was obtained in an amount of 14 mg from 66 mg of tert-butyl 3-(4-(2-ethoxy-1,1-difluoro-2-oxoethoxy)-7-(4-methylthiazol-2-yl)benzo[d]oxazol-2-yl)-3,8-diazabicyclo[3.2.1]octane-8-carboxylate obtained in Example 318 (c) by a similar method to Example 248 (e).

(e) 1-((2-(3,8-Diazabicyclo[3.2.1]octan-3-yl)-7-(4-methylthiazol-2-yl)benzo[d]oxazol-4-yl)oxy)-1,1-difluoro-2-methylpropan-2-ol The title compound was obtained in an amount of 5.7 mg from 14 mg of tert-butyl 3-(4-(1,1-difluoro-2-hydroxy-2-methylpropoxy)-7-(4-methylthiazol-2-yl)benzo[d]oxazol-2-yl)-3,8-diazabicyclo[3.2.1]octane-8-carboxylate obtained in Example 318 (d) by a similar method to Example 1(c).

Example 319

2-((2-(3,6-Diazabicyclo[3.1.1]heptan-3-yl)-7-(5-fluoropyridin-2-yl)benzo[d]oxazol-4-yl)oxy)-2,2-difluoroethan-1-ol (a) tert-Butyl 3-(4-(benzyloxy)-7-(5-fluoropyridin-2-yl)benzo[d]oxazol-2-yl)-3,6-diazabicyclo[3.1.1]heptane-6-carboxylate The title compound was obtained in an amount of 30 mg by a similar method to Example 10 (b) except that (5-fluoropyridin-2-yl)boronic acid was used instead of tert-butyl 3-(5-chloro-7-(4,4,5,5-tetramethyl-1,3,2-dioxaborolan-2-yl)-4-(trifluoromethoxy)benzo[d]oxazol-2-yl)-3,8-diazabicyclo[3.2.1]octane-8-carboxylate, caesium carbonate was used instead of potassium carbonate, 50 mg of tert-butyl 3-(4-(benzyloxyl)-7-bromobenzo[d]oxazol-2-yl)-3,6-diazabicyclo[3.1.1]heptane-6-carboxylate obtained in Example 248(a) was used instead of 2-bromo-5-fluoropyridine, and stirred the mixture in N,N-dimethylformamide.

(b) tert-Butyl 3-(7-(5-fluoropyridin-2-yl)-4-hydroxybenzo[d]oxazol-2-yl)-3,6-diazabicyclo[3.1.1]heptane-6-carboxylate The title compound was obtained as a crude product in an amount of 310 mg from 360 mg of tert-butyl 3-(4-(benzyloxy)-7-(5-fluoropyridin-2-yl)benzo[d]oxazol-2-yl)-3,6-diazabicyclo[3.1.1]heptane-6-carboxylate obtained in Example 319(a) by a similar method to Example 315 (b).

(c) tert-Butyl 3-(4-(2-ethoxy-1,1-difluoro-2-oxoethoxy)-7-(5-fluoropyridin-2-yl)benzo[d]oxazol-2-yl)-3,6-diazabicyclo[3.1.1]heptane-6-carboxylate The title compound was obtained in an amount of 170 mg from 260 mg of the crude product of tert-butyl 3-(7-(5-fluoropyridin-2-yl)-4-hydroxybenzo[d]oxazol-2-yl)-3,6-diazabicyclo[3.1.1]heptane-6-carboxylate obtained in Example 319(b) by a similar method to Example 248 (d).

(d) tert-Butyl 3-(4-(1,1-difluoro-2-hydroxy-2-methylpropoxy)-7-(5-fluoropyridin-2-yl)benzo[d]oxazol-2-yl)-3,6-diazabicyclo[3.1.1]heptane-6-carboxylate The title compound was obtained in an amount of 110 mg from 170 mg of tert-butyl 3-(4-(2-ethoxy-1,1-difluoro-2-oxoethoxy)-7-(5-fluoropyridin-2-yl)benzo[d]oxazol-2-yl)-3,6-diazabicyclo[3.1.1]heptane-6-carboxylate obtained in Example 319(c) by a similar method to Example 155(c) except that the reaction mixture was stirred at room temperature.

(e) 2-((2-(3,6-Diazabicyclo[3.1.1]heptan-3-yl)-7-(5-fluoropyridin-2-yl)benzo[d]oxazol-4-yl)oxy)-2,2-difluoroethan-1-ol The title compound was obtained in an amount of 60 mg from 110 mg of tert-butyl 3-(4-(1,1-difluoro-2-hydroxy-2-methylpropoxy)-7-(5-fluoropyridin-2-yl)benzo[d]oxazol-2-yl)-3,6-diazabicyclo[3.1.1]heptane-6-carboxylate obtained in Example 319(d) by a similar method to Example 1(c).

Example 320

2-((2-(3,6-Diazabicyclo[3.1.1]heptan-3-yl)-7-(1H-pyrazol-1-yl)benzo[d]oxazol-4-yl)oxy)-2,2-difluoroethan-1-ol (a) tert-Butyl 3-(4-(benzyloxy)-7-(1H-pyrazol-1-yl)benzo[d]oxazol-2-yl)-3,6-diazabicyclo[3.1.1]heptane-6-carboxylate The title compound was obtained in an amount of 1.3 g from 2.0 g of tert-butyl 3-(4-(benzyloxyl)-7-bromobenzo[d]oxazol-2-yl)-3,6-diazabicyclo[3.1.1]heptane-6-carboxylate obtained in Example 248 (a) by a similar method to Example 15 (a).

(b) tert-Butyl 3-(4-hydroxy-7-(1H-pyrazol-1-yl)benzo[d]oxazol-2-yl)-3,6-diazabicyclo[3.1.1]heptane-6-carboxylate The title compound was obtained as a crude product in an amount of 250 mg from 900 mg of tert-butyl 3-(4-(benzyloxy)-7-(1H-pyrazol-1-yl)benzo[d]oxazol-2-yl)-3,6-diazabicyclo[3.1.1]heptane-6-carboxylate obtained in Example 320(a) by a similar method to Example 315 (b).

(c) tert-Butyl 3-(4-(2-ethoxy-1,1-difluoro-2-oxoethoxy)-7-(1H-pyrazol-1-yl)benzo[d]oxazol-2-yl)-3,6-diazabicyclo[3.1.1]heptane-6-carboxylate The title compound was obtained in an amount of 1.0 g from 1.4 g of the crude product of tert-butyl 3-(4-hydroxy-7-(1H-pyrazol-1-yl)benzo[d]oxazol-2-yl)-3,6-diazabicyclo[3.1.1]heptane-6-carboxylate obtained in Example 320(b) by a similar method to Example 248 (d).

(d) tert-Butyl 3-(4-(1,1-difluoro-2-hydroxyethoxy)-7-(1H-pyrazol-1-yl)benzo[d]oxazol-2-yl)-3,6-diazabicyclo[3.1.1]heptane-6-carboxylate The title compound was obtained in an amount of 250 mg from 350 mg of tert-butyl 3-(4-(2-ethoxy-1,1-difluoro-2-oxoethoxy)-7-(1H-pyrazol-1-yl)benzo[d]oxazol-2-yl)-3,6-diazabicyclo[3.1.1]heptane-6-carboxylate obtained in Example 320(c) by a similar method to Example 155(c) except that the reaction mixture was stirred at room temperature.

(e) 2-((2-(3,6-Diazabicyclo[3.1.1]heptan-3-yl)-7-(1H-pyrazol-1-yl)benzo[d]oxazol-4-yl)oxy)-2,2-difluoroethan-1-ol The title compound was obtained in an amount of 130 mg from 250 mg of tert-butyl 3-(4-(1,1-difluoro-2-hydroxyethoxy)-7-(1H-pyrazol-1-yl)benzo[d]oxazol-2-yl)-3,6-diazabicyclo[3.1.1]heptane-6-carboxylate obtained in Example 320(d) by a similar method to Example 1(c).

Example 321

1-((2-(3,8-Diazabicyclo[3.2.1]octan-3-yl)-7-(oxazol-2-yl)benzo[d]oxazol-4-yl)oxy)-1,1-difluoro-2-methylpropan-2-ol (a) tert-Butyl 3-(4-(benzyloxy)-7-(oxazol-2-yl)benzo[d]oxazol-2-yl)-3,8-diazabicyclo[3.2.1]octane-8-carboxylate The title compound was obtained in an amount of 98 mg from 150 mg of tert-butyl 3-(4-(benzyloxy)-7-bromobenzo[d]oxazol-2-yl)-3,8-diazabicyclo[3.2.1]octane-8-carboxylate obtained in Example 316(a) by a similar method to Example 9(a).

(b) tert-Butyl 3-(4-hydroxy-7-(oxazol-2-yl)benzo[d]oxazol-2-yl)-3,8-diazabicyclo[3.2.1]octane-8-carboxylate The title compound was obtained in an amount of 72 mg from 98 mg of tert-butyl 3-(4-(benzyloxy)-7-(oxazol-2-yl)benzo[d]oxazol-2-yl)-3,8-diazabicyclo[3.2.1]octane-8-carboxylate obtained in Example 321(a) by a similar method to Example 248 (c).

(c) tert-Butyl 3-(4-(2-ethoxy-1,1-difluoro-2-oxoethoxy)-7-(oxazol-2-yl)benzo[d]oxazol-2-yl)-3,8-diazabicyclo[3.2.1]octane-8-carboxylate The title compound was obtained in an amount of 68 mg from 72 mg of tert-butyl 3-(4-hydroxy-7-(oxazol-2-yl)benzo[d]oxazol-2-yl)-3,8-diazabicyclo[3.2.1]octane-8-carboxylate obtained in Example 321(b) by a similar method to Example 248 (d).

(d) tert-Butyl 3-(4-(1,1-difluoro-2-hydroxy-2-methylpropoxy)-7-(oxazol-2-yl)benzo[d]oxazol-2-yl)-3,8-diazabicyclo[3.2.1]octane-8-carboxylate The title compound was obtained in an amount of 65 mg from 68 mg of tert-butyl 3-(4-(2-ethoxy-1,1-difluoro-2-oxoethoxy)-7-(oxazol-2-yl)benzo[d]oxazol-2-yl)-3,8-diazabicyclo[3.2.1]octane-8-carboxylate obtained in Example 321 (c) by a similar method to Example 248 (e).

(e) 1-((2-(3,8-Diazabicyclo[3.2.1]octan-3-yl)-7-(oxazol-2-yl)benzo[d]oxazol-4-yl)oxy)-1,1-difluoro-2-methylpropan-2-ol The title compound was obtained in an amount of 54 mg from 65 mg of tert-butyl 3-(4-(1,1-difluoro-2-hydroxy-2-methylpropoxy)-7-(oxazol-2-yl)benzo[d]oxazol-2-yl)-3,8- diazabicyclo[3.2.1]octane-8-carboxylate obtained in Example 321(d) by a similar method to Example 1(c).

Example 322

1-((2-(3,8-Diazabicyclo[3.2.1]octan-3-yl)-7-(2H-1,2,3-triazol-2-yl)benzo[d]oxazol-4-yl)oxy)-1,1-difluoro-2-methylpropan-2-ol (a) tert-Butyl 3-(4-(benzyloxy)-7-(2H-1,2,3-triazol-2-yl)benzo[d]oxazol-2-yl)-3,8-diazabicyclo[3.2.1]octane-8-carboxylate The title compound was obtained in an amount of 100 mg from 150 mg of tert-butyl 3-(4-(benzyloxy)-7-bromobenzo[d]oxazol-2-yl)-3,8-diazabicyclo[3.2.1]octane-8-carboxylate obtained in Example 316(a) by a similar method to Example 5(a) except that 1H-1,2,3-triazole was used instead of 1H-pyrazole.

(b) tert-Butyl 3-(4-hydroxy-7-(2H-1,2,3-triazol-2-yl)benzo[d]oxazol-2-yl)-3,8-diazabicyclo[3.2.1]octane-8-carboxylate The title compound was obtained in an amount of 74 mg from 56 mg of tert-butyl 3-(4-(benzyloxy)-7-(2H-1,2,3-triazol-2-yl)benzo[d]oxazol-2-yl)-3,8-diazabicyclo[3.2.1]octane-8-carboxylate obtained in Example 322 (a) by a similar method to Example 248 (c).

(c) tert-Butyl 3-(4-(2-ethoxy-1,1-difluoro-2-oxoethoxy)-7-(2H-1,2,3-triazol-2-yl)benzo[d]oxazol-2-yl)-3,8-diazabicyclo[3.2.1]octane-8-carboxylate The title compound was obtained in an amount of 84 mg from 74 mg of tert-butyl 3-(4-hydroxy-7-(2H-1,2,3-triazol-2-yl)benzo[d]oxazol-2-yl)-3,8-diazabicyclo[3.2.1]octane-8-carboxylate obtained in Example 322 (b) by a similar method to Example 248 (d).

(d) tert-Butyl 3-(4-(1,1-difluoro-2-hydroxy-2-methylpropoxy)-7-(2H-1,2,3-triazol-2-yl)benzo[d]oxazol-2-yl)-3,8-diazabicyclo[3.2.1]octane-8-carboxylate The title compound was obtained in an amount of 56 mg from 84 mg of tert-butyl 3-(4-(2-ethoxy-1,1-difluoro-2-oxoethoxy)-7-(2H-1,2,3-triazol-2-yl)benzo[d]oxazol-2-yl)-3,8-diazabicyclo[3.2.1]octane-8-carboxylate obtained in Example 322 (c) by a similar method to Example 248 (e).

(e) 1-((2-(3,8-Diazabicyclo[3.2.1]octan-3-yl)-7-(2H-1,2,3-triazol-2-yl)benzo[d]oxazol-4-yl)oxy)-1,1-difluoro-2-methylpropan-2-ol The title compound was obtained in an amount of 32 mg from 56 mg of tert-butyl 3-(4-(1,1-difluoro-2-hydroxy-2-methylpropoxy)-7-(2H-1,2,3-triazol-2-yl)benzo[d]oxazol-2-yl)-3,8-diazabicyclo[3.2.1]octane-8-carboxylate obtained in Example 322 (d) by a similar method to Example 1(c).

Example 323

2-(3,6-Diazabicyclo[3.1.1]heptan-3-yl)-4-(((S)-tetrahydrofuran-3-yl)oxy)-7-(thiazol-2-yl)benzo[d]oxazole (a) tert-Butyl 3-(4-(((S)-tetrahydrofuran-3-yl)oxy)-7-(thiazol-2-yl)benzo[d]oxazol-2-yl)-3,6-diazabicyclo[3.1.1]heptane-6-carboxylate The title compound was obtained in an amount of 33 mg from 30 mg of tert-butyl 3-(4-hydroxy-7-(thiazol-2-yl)benzo[d]oxazol-2-yl)-3,6-diazabicyclo[3.1.1]heptane-6-carboxylate obtained in Example 248 (c) by a similar method to Reference Example 23(a) except that (R)-tetrahydrofuran-3-yl 4-methylbenzenesulfonate was used instead of benzyl bromide and the reaction mixture was stirred at 60° C.

(b) 2-(3,6-Diazabicyclo[3.1.1]heptan-3-yl)-4-(((S)-tetrahydrofuran-3-yl)oxy)-7-(thiazol-2-yl)benzo[d]oxazole The title compound was obtained in an amount of 19 mg from 33 mg of tert-butyl 3-(4-(((S)-tetrahydrofuran-3-yl)oxy)-7-(thiazol-2-yl)benzo[d]oxazol-2-yl)-3,6-diazabicyclo[3.1.1]heptane-6-carboxylate obtained in Example 323 (a) by a similar method to Example 1(c).

Example 324

2-(3,6-Diazabicyclo[3.1.1]heptan-3-yl)-4-(((R)-tetrahydrofuran-3-yl)oxy)-7-(thiazol-2-yl)benzo[d]oxazole (a) tert-Butyl 3-(4-(((R)-tetrahydrofuran-3-yl)oxy)-7-(thiazol-2-yl)benzo[d]oxazol-2-yl)-3,6-diazabicyclo[3.1.1]heptane-6-carboxylate The title compound was obtained in an amount of 34 mg from 31 mg of tert-butyl 3-(4-hydroxy-7-(thiazol-2-yl)benzo[d]oxazol-2-yl)-3,6-diazabicyclo[3.1.1]heptane-6-carboxylate obtained in Example 248 (c) by a similar method to Reference Example 23(a) except that (S)-tetrahydrofuran-3-yl 4-methylbenzenesulfonate was used instead of benzyl bromide and the reaction mixture was stirred at 60° C.

(b) 2-(3,6-Diazabicyclo[3.1.1]heptan-3-yl)-4-(((R)-tetrahydrofuran-3-yl)oxy)-7-(thiazol-2-yl)benzo[d]oxazole The title compound was obtained in an amount of 21 mg from 32 mg of tert-butyl 3-(4-(((R)-tetrahydrofuran-3-yl)oxy)-7-(thiazol-2-yl)benzo[d]oxazol-2-yl)-3,6-diazabicyclo[3.1.1]heptane-6-carboxylate obtained in Example 324 (a) by a similar method to Example 1(c).

Example 325

2-(3,6-Diazabicyclo[3.1.1]heptan-3-yl)-4-(oxetan-3-yloxy)-7-(thiazol-2-yl)benzo[d]oxazole (a) tert-Butyl 3-(4-(oxetan-3-yloxy)-7-(thiazol-2-yl)benzo[d]oxazol-2-yl)-3,6-diazabicyclo[3.1.1]heptane-6-carboxylate The title compound was obtained in an amount of 26 mg from 30 mg of tert-butyl 3-(4-hydroxy-7-(thiazol-2-yl)benzo[d]oxazol-2-yl)-3,6-diazabicyclo[3.1.1]heptane-6-carboxylate obtained in Example 248 (c) by a similar method to Reference Example 23(a) except that oxetan-3-yl 4-methylbenzenesulfonate was used instead of benzyl bromide and the reaction mixture was stirred at 60° C.

(b) 2-(3,6-Diazabicyclo[3.1.1]heptan-3-yl)-4-(oxetan-3-yloxy)-7-(thiazol-2-yl)benzo[d]oxazole The title compound was obtained in an amount of 8.9 mg from 26 mg of tert-butyl 3-(4-(oxetan-3-yloxy)-7-(thiazol- 2-yl)benzo[d]oxazol-2-yl)-3,6-diazabicyclo[3.1.1]heptane-6-carboxylate obtained in Example 325 (a) by a similar method to Example 1(c).

Example 326

3-((2-(3,6-Diazabicyclo[3.1.1]heptan-3-yl)-7-(thiazol-2-yl)benzo[d]oxazol-4-yl)oxy)-3,3-difluoro-2-methylpropane-1,2-diol (a) tert-Butyl 3-(4-(difluoro(2-methyloxiran-2-yl)methoxy)-7-(thiazol-2-yl)benzo[d]oxazol-2-yl)-3,6-diazabicyclo[3.1.1]heptane-6-carboxylate 101.3 mg of tert-butyl 3-(4-(1,1-difluoro-2,2-dihydroxypropoxy)-7-(thiazol-2-yl)benzo[d]oxazol-2-yl)-3,6-diazabicyclo[3.1.1]heptane-6-carboxylate obtained in Example 250 (b) was dissolved in DMSO (1 mL), then trimethylsulfonium iodide (52.8 mg, 1.2 equivalents) and potassium tert-butoxide (26.9 mg, 1.2 equivalents) were added, followed by stirring at room temperature for 1 hour. Saturated ammonium chloride aqueous solution and ethyl acetate were added thereto, and then the organic phase was dried over anhydrous sodium sulfate, followed by filtration and vacuum concentration of the filtrate, and thus obtaining 64.3 mg of the title compound by purification of the residue through silica gel column chromatography (hexane:ethyl acetate=1:1).

(b) 3-((2-(3,6-Diazabicyclo[3.1.1]heptan-3-yl)-7-(thiazol-2-yl)benzo[d]oxazol-4-yl)oxy)-3,3-difluoro-2-methylpropane-1,2-diol The title compound was obtained in an amount of 48.9 mg from 64.3 mg of tert-butyl 3-(4-(difluoro(2-methyloxiran-2-yl)methoxy)-7-(thiazol-2-yl)benzo[d]oxazol-2-yl)-3,6-diazabicyclo[3.1.1]heptane-6-carboxylate obtained in Example 326(a) by a similar method to Example 1(c) except that the reaction mixture was stirred at room temperature overnight.

Example 327

1-((2-(3,8-Diazabicyclo[3.2.1]octan-3-yl)-7-(1,2,4-thiadiazol-5-yl)benzo[d]oxazol-4-yl)oxy)-1,1-difluoro-2-methylpropan-2-ol (a) tert-Butyl 3-(4-(benzyloxy)-7-(4,4,5,5-tetramethyl-1,3,2-dioxaborolan-2-yl)benzo[d]oxazol-2-yl)-3,8-diazabicyclo[3.2.1]octane-8-carboxylate The title compound was obtained in an amount of 695 mg from 1.0 g of tert-butyl 3-(4-(benzyloxy)-7-bromobenzo[d]oxazol-2-yl)-3,8-diazabicyclo[3.2.1]octane-8-carboxylate obtained in Example 316(a) by a similar method to Example 10(a).

(b) tert-Butyl 3-(4-(benzyloxy)-7-(1,2,4-thiadiazol-5-yl)benzo[d]oxazol-2-yl)-3,8-diazabicyclo[3.2.1]octane-8-carboxylate The title compound was obtained in an amount of 60 mg from 101 mg of tert-butyl 3-(4-(benzyloxy)-7-(4,4,5,5-tetramethyl-1,3,2-dioxaborolan-2-yl)benzo[d]oxazol-2-yl)-3,8-diazabicyclo[3.2.1]octane-8-carboxylate obtained in Example 327 (a) by a similar method to Example 10(b) except that 5-bromo-1,2,4-thiadiazole was used instead of 2-bromo-5-fluoropyridine.

(c) tert-Butyl 3-(4-hydroxy-7-(1,2,4-thiadiazol-5-yl)benzo[d]oxazol-2-yl)-3,8-diazabicyclo[3.2.1]octane-8-carboxylate The title compound was obtained in an amount of 24 mg from 59 mg of tert-butyl 3-(4-(benzyloxy)-7-(1,2,4-thiadiazol-5-yl)benzo[d]oxazol-2-yl)-3,8-diazabicyclo[3.2.1]octane-8-carboxylate obtained in Example 327(b) by a similar method to Example 248(c) except that methanol was used instead of tetrahydrofuran and ammonium formate was used instead of hydrogen.

(d) tert-Butyl 3-(4-(2-ethoxy-1,1-difluoro-2-oxoethoxy)-7-(1,2,4-thiadiazol-5-yl)benzo[d]oxazol-2-yl)-3,8-diazabicyclo[3.2.1]octane-8-carboxylate The title compound was obtained in an amount of 20 mg from 23 mg of tert-butyl 3-(4-hydroxy-7-(1,2,4-thiadiazol-5-yl)benzo[d]oxazol-2-yl)-3,8-diazabicyclo[3.2.1]octane-8-carboxylate obtained in Example 327 (c) by a similar method to Example 248 (d).

(e) tert-Butyl 3-(4-(1,1-difluoro-2-hydroxy-2-methylpropoxy)-7-(1,2,4-thiadiazol-5-yl)benzo[d]oxazol-2-yl)-3,8-diazabicyclo[3.2.1]octane-8-carboxylate A solution (0.5 mL) of 19 mg of tert-butyl 3-(4-(2-ethoxy-1,1-difluoro-2-oxoethoxy)-7-(1,2,4-thiadiazol-5-yl)benzo[d]oxazol-2-yl)-3,8-diazabicyclo[3.2.1]octane-8-carboxylate obtained in Example 327 (d) in tetrahydrofuran was added to 0.95 M solution of methylmagnesium bromide in tetrahydrofuran (0.36 mL, 10 equivalents) at 0° C. The mixture was allowed to warm to room temperature, and stirred at room temperature for 2.5 hours. Saturated aqueous solution of ammonium chloride was added thereto to stop the reaction and then the organic phase was extracted by ethyl acetate three times. 19 mg of the title compound as a crude product was obtained by vacuum concentration of the organic phase.

(f) 1-((2-(3,8-Diazabicyclo[3.2.1]octan-3-yl)-7-(1,2,4-thiadiazol-5-yl)benzo[d]oxazol-4-yl)oxy)-1,1-difluoro-2-methylpropan-2-ol The title compound was obtained in an amount of 11 mg from 19 mg of the crude product of tert-butyl 3-(4-(1,1-difluoro-2-hydroxy-2-methylpropoxy)-7-(1,2,4-thiadiazol-5-yl)benzo[d]oxazol-2-yl)-3,8-diazabicyclo[3.2.1]octane-8-carboxylate obtained in Example 327(e) by a similar method to Example 1(c) except that the reaction mixture was stirred at room temperature overnight.

Example 328

1-((2-(3,8-Diazabicyclo[3.2.1]octan-3-yl)-7-(1-methyl-1H-pyrazol-3-yl)benzo[d]oxazol-4-yl)oxy)-1,1-difluoro-2-methylpropan-2-ol (a) tert-Butyl 3-(4-(benzyloxy)-7-(1-methyl-1H-pyrazol-3-yl)benzo[d]oxazol-2-yl)-3,8-diazabicyclo[3.2.1]octane-8-carboxylate The title compound was obtained in an amount of 70 mg from 91 mg of tert-butyl 3-(4-(benzyloxy)-7-(4,4,5,5-tetramethyl-1,3,2-dioxaborolan-2-yl)benzo[d]oxazol-2-yl)-3,8-diazabicyclo[3.2.1]octane-8-carboxylate obtained in Example 327 (a) by a similar method to Example 10(b)

except that 3-bromo-1-methyl-1H-pyrazole was used instead of 2-bromo-5-fluoropyridine.

(b) tert-Butyl 3-(4-hydroxy-7-(1-methyl-1H-pyrazol-3-yl)benzo[d]oxazol-2-yl)-3,8-diazabicyclo[3.2.1]octane-8-carboxylate The title compound was obtained in an amount of 46 mg from 70 mg of tert-butyl 3-(4-(benzyloxy)-7-(1-methyl-1H-pyrazol-3-yl)benzo[d]oxazol-2-yl)-3,8-diazabicyclo[3.2.1]octane-8-carboxylate obtained in Example 328 (a) by a similar method to Example 327(c).

(c) tert-Butyl 3-(4-(2-ethoxy-1,1-difluoro-2-oxoethoxy)-7-(1-methyl-1H-pyrazol-3-yl)benzo[d]oxazol-2-yl)-3,8-diazabicyclo[3.2.1]octane-8-carboxylate The title compound was obtained in an amount of 31 mg from 46 mg of tert-butyl 3-(4-hydroxy-7-(1-methyl-1H-pyrazol-3-yl)benzo[d]oxazol-2-yl)-3,8-diazabicyclo[3.2.1]octane-8-carboxylate obtained in Example 328 (b) by a similar method to Example 248 (d).

(d) tert-Butyl 3-(4-(1,1-difluoro-2-hydroxy-2-methylpropoxy)-7-(1-methyl-1H-pyrazol-3-yl)benzo[d]oxazol-2-yl)-3,8-diazabicyclo[3.2.1]octane-8-carboxylate The title compound was obtained as a crude product in an amount of 29 mg from 29 mg of tert-butyl 3-(4-(2-ethoxy-1,1-difluoro-2-oxoethoxy)-7-(1-methyl-1H-pyrazol-3-yl)benzo[d]oxazol-2-yl)-3,8-diazabicyclo[3.2.1]octane-8-carboxylate obtained in Example 328 (c) by a similar method to Example 327(e).

(e) 1-((2-(3,8-Diazabicyclo[3.2.1]octan-3-yl)-7-(1-methyl-1H-pyrazol-3-yl)benzo[d]oxazol-4-yl)oxy)-1,1-difluoro-2-methylpropan-2-ol The title compound was obtained in an amount of 17 mg from 28 mg of the crude product of tert-butyl 3-(4-(1,1-difluoro-2-hydroxy-2-methylpropoxy)-7-(1-methyl-1H-pyrazol-3-yl)benzo[d]oxazol-2-yl)-3,8-diazabicyclo[3.2.1]octane-8-carboxylate obtained in Example 328 (d) by a similar method to Example 1(c).

Example 329

1-((2-(3,6-Diazabicyclo[3.1.1]heptan-3-yl)-7-(5-fluoropyridin-2-yl)benzo[d]oxazol-4-yl)oxy)-1,1-difluoro-2-methylpropan-2-ol (a) tert-Butyl 3-(4-(1,1-difluoro-2-hydroxy-2-methylpropoxy)-7-(5-fluoropyridin-2-yl)benzo[d]oxazol-2-yl)-3,6-diazabicyclo[3.1.1]heptane-6-carboxylate The title compound was obtained in an amount of 670 mg from 930 mg of tert-butyl 3-(7-(5-fluoropyridin-2-yl)-4-hydroxybenzo[d]oxazol-2-yl)-3,6-diazabicyclo[3.1.1]heptane-6-carboxylate obtained in Example 319(b) by a similar method to Example 248(e) except that 3M methylmagnesium bromide solution in diethyl ether was used instead of 0.95M methylmagnesium bromide solution in tetrahydrofuran.

(b) 1-((2-(3,6-Diazabicyclo[3.1.1]heptan-3-yl)-7-(5-fluoropyridin-2-yl)benzo[d]oxazol-4-yl)oxy)-1,1-difluoro-2-methylpropan-2-ol The title compound was obtained in an amount of 80 mg from 150 mg of tert-butyl 3-(4-(1,1-difluoro-2-hydroxy-2-methylpropoxy)-7-(5-fluoropyridin-2-yl)benzo[d]oxazol-2-yl)-3,6-diazabicyclo[3.1.1]heptane-6-carboxylate obtained in Example 329(a) by a similar method to Example 315(e).

Example 330

1-((2-(3,8-Diazabicyclo[3.2.1]octan-3-yl)-7-(pyrimidin-2-yl)benzo[d]oxazol-4-yl)oxy)-1,1-difluoro-2-methylpropan-2-ol (a) tert-Butyl 3-(7-bromo-4-hydroxybenzo[d]oxazol-2-yl)-3,8-diazabicyclo[3.2.1]octane-8-carboxylate 996 mg of tert-butyl 3-(4-(benzyloxy)-7-bromobenzo[d]oxazol-2-yl)-3,8-diazabicyclo[3.2.1]octane-8-carboxylate obtained in Example 316(a) was dissolved in chloroform (10 mL), then 1.0 M solution of boron trichloride in heptane (9.7 mL, 5 equivalents) was added thereto at 0° C., and the mixture was stirred for 1 hour at 0° C. Methanol and water were added, then 5N sodium hydroxide aqueous solution (4.4 mL) and di-tert-butyl dicarbonate (0.49 mL, 1.1 equivalents) were added thereto, followed by stirring at room temperature overnight. 5N sodium hydroxide aqueous solution (1.6 mL) was added thereto again, followed by stirring at room temperature for 3 hours. 5% sodium potassium hydrogen sulfate was added thereto, and then the organic phase was extracted using chloroform, followed by vacuum concentration thereof, and thus obtaining 589 mg of the title compound by purification of the residue through silica gel column chromatography (haxane; thenhexane:ethyl acetate=1:1).

(b) tert-Butyl 3-(7-bromo-4-(2-ethoxy-1,1-difluoro-2-oxoethoxy)benzo[d]oxazol-2-yl)-3,8-diazabicyclo[3.2.1]octane-8-carboxylate The title compound was obtained in an amount of 192 mg from 99 mg of tert-butyl 3-(7-bromo-4-hydroxybenzo[d]oxazol-2-yl)-3,8-diazabicyclo[3.2.1]octane-8-carboxylate obtained in Example 330(a) by a similar method to Example 248 (d).

(c) tert-Butyl 3-(7-bromo-4-(1,1-difluoro-2-hydroxy-2-methylpropoxy)benzo[d]oxazol-2-yl)-3,8-diazabicyclo[3.2.1]octane-8-carboxylate The title compound was obtained in an amount of 58 mg from 192 mg of tert-butyl 3-(7-bromo-4-(2-ethoxy-1,1-difluoro-2-oxoethoxy)benzo[d]oxazol-2-yl)-3,8-diazabicyclo[3.2.1]octane-8-carboxylate obtained in Example 330(b) by a similar method to Example 327 (e).

(d) tert-Butyl 3-(4-(1,1-difluoro-2-hydroxy-2-methylpropoxy)-7-(pyrimidin-2-yl)benzo[d]oxazol-2-yl)-3,8-diazabicyclo[3.2.1]octane-8-carboxylate The title compound was obtained in an amount of 15 mg from 20 mg of tert-butyl 3-(7-bromo-4-(1,1-difluoro-2-hydroxy-2-methylpropoxy)benzo[d]oxazol-2-yl)-3,8-diazabicyclo[3.2.1]octane-8-carboxylate obtained in Example 330

(c) by a similar method to Example 6(a) except that 2-(tributylstannyl)pyridine was used instead of 2-(tributylstannyl)furan.

(e) 1-((2-(3,8-Diazabicyclo[3.2.1]octan-3-yl)-7-(pyrimidin-2-yl)benzo[d]oxazol-4-yl)oxy)-1,1-difluoro-2-methylpropan-2-ol The title compound was obtained in an amount of 7.6 mg from 14 mg of tert-butyl 3-(4-(1,1-difluoro-2-hydroxy-2-methylpropoxy)-7-(pyrimidin-2-yl)benzo[d]oxazol-2-yl)-3,8-diazabicyclo[3.2.1]octane-8-carboxylate obtained in Example 330(d) by a similar method to Example 1(c).

Example 331

1-((2-(3,8-Diazabicyclo[3.2.1]octan-3-yl)-7-(isothiazol-3-yl)benzo[d]oxazol-4-yl)oxy)-1,1-difluoro-2-methylpropan-2-ol (a) tert-Butyl 3-(4-(1,1-difluoro-2-hydroxy-2-methylpropoxy)-7-(4,4,5,5-tetramethyl-1,3,2-dioxaboroloran-2-yl)benzo[d]oxazol-2-yl)-3,8-diazabicyclo[3.2.1]octane-8-carboxylate The title compound was obtained in an amount of 361 mg from 299 mg of tert-butyl 3-(7-bromo-4-(1,1-difluoro-2-hydroxy-2-methylpropoxy)benzo[d]oxazol-2-yl)-3,8-diazabicyclo[3.2.1]octane-8-carboxylate obtained in Example 330(c) by a similar method to Example 10(a).

(b) tert-Butyl 3-(4-(1,1-difluoro-2-hydroxy-2-methylpropoxy)-7-(isothiazol-3-yl)benzo[d]oxazol-2-yl)-3,8-diazabicyclo[3.2.1]octane-8-carboxylate The title compound was obtained in an amount of 12 mg from 42 mg of tert-butyl 3-(4-(1,1-difluoro-2-hydroxy-2-methylpropoxy)-7-(4,4,5,5-tetramethyl-1,3,2-dioxaboroloran-2-yl)benzo[d]oxazol-2-yl)-3,8-diazabicyclo[3.2.1]octane-8-carboxylate obtained in Example 331(a) by a similar method to Example 10(b) except that 3-bromo-isothiazole was used instead of 2-bromo-5-fluoropyridine.

(c) 1-((2-(3,8-Diazabicyclo[3.2.1]octan-3-yl)-7-(isothiazol-3-yl)benzo[d]oxazol-4-yl)oxy)-1,1-difluoro-2-methylpropan-2-ol The title compound was obtained in an amount of 5.0 mg from 12 mg of tert-butyl 3-(4-(1,1-difluoro-2-hydroxy-2-methylpropoxy)-7-(isothiazol-3-yl)benzo[d]oxazol-2-yl)-3,8-diazabicyclo[3.2.1]octane-8-carboxylate obtained in Example 331(b) by a similar method to Example 1(c).

Example 332

1-((2-(3,8-Diazabicyclo[3.2.1]octan-3-yl)-7-(5-fluoropyridin-2-yl)benzo[d]oxazol-4-yl)oxy)-1,1-difluoro-2-methylpropan-2-ol (a) tert-Butyl 3-(4-(1,1-difluoro-2-hydroxy-2-methylpropoxy)-7-(5-fluoropyridin-2-yl)benzo[d]oxazol-2-yl)-3,8-diazabicyclo[3.2.1]octane-8-carboxylate The title compound was obtained in an amount of 11 mg from 40 mg of the crude product of tert-butyl 3-(4-(1,1-difluoro-2-hydroxy-2-methylpropoxy)-7-(4,4,5,5-tetramethyl-1,3,2-dioxaboroloran-2-yl)benzo[d]oxazol-2-yl)-3,8-diazabicyclo[3.2.1]octane-8-carboxylate obtained in Example 331(a) by a similar method to Example 10 (b).

(b) 1-((2-(3,8-Diazabicyclo[3.2.1]octan-3-yl)-7-(5-fluoropyridin-2-yl)benzo[d]oxazol-4-yl)oxy)-1,1-difluoro-2-methylpropan-2-ol The title compound was obtained in an amount of 8.3 mg from 10 mg of tert-butyl 3-(4-(1,1-difluoro-2-hydroxy-2-methylpropoxy)-7-(5-fluoropyridin-2-yl)benzo[d]oxazol-2-yl)-3,8-diazabicyclo[3.2.1]octane-8-carboxylate obtained in Example 332 (a) by a similar method to Example 1(c).

Example 333

1-((2-(3,8-Diazabicyclo[3.2.1]octan-3-yl)-7-(3-methyl-1,2,4-thiadiazol-5-yl)benzo[d]oxazol-4-yl)oxy)-1,1-difluoro-2-methylpropan-2-ol (a) tert-Butyl 3-(4-(1,1-difluoro-2-hydroxy-2-methylpropoxy)-7-(3-methyl-1,2,4-thiadiazol-5-yl)benzo[d]oxazol-2-yl)-3,8-diazabicyclo[3.2.1]octane-8-carboxylate The title compound was obtained in an amount of 17 mg from 36 mg of the crude product of tert-butyl 3-(4-(1,1-difluoro-2-hydroxy-2-methylpropoxy)-7-(4,4,5,5-tetramethyl-1,3,2-dioxaboroloran-2-yl)benzo[d]oxazol-2-yl)-3,8-diazabicyclo[3.2.1]octane-8-carboxylate obtained in Example 331(a) by a similar method to Example 10(b) except that 5-bromo-3-methyl-1,2,4-thiadiazole was used instead of 2-bromo-5-fluoropyridine.

(b) 1-((2-(3,8-Diazabicyclo[3.2.1]octan-3-yl)-7-(3-methyl-1,2,4-thiadiazol-5-yl)benzo[d]oxazol-4-yl)oxy)-1,1-difluoro-2-methylpropan-2-ol The title compound was obtained in an amount of 7.0 mg from 16 mg of tert-butyl 3-(4-(1,1-difluoro-2-hydroxy-2-methylpropoxy)-7-(3-methyl-1,2,4-thiadiazol-5-yl)benzo[d]oxazol-2-yl)-3,8-diazabicyclo[3.2.1]octane-8-carboxylate obtained in Example 333 (a) by a similar method to Example 1(c).

Example 334

2-(3,6-Diazabicyclo[3.1.1]heptan-3-yl)-7-(thiazol-2-yl)-4-((trifluoromethyl)sulfonyl)benzo[d]oxazole (a) tert-Butyl 3-(7-(thiazol-2-yl)-4-(((trifluoromethyl)sulfonyl)oxy)benzo[d]oxazol-2-yl)-3,6-diazabicyclo[3.1.1]heptane-6-carboxylate The title compound was obtained in an amount of 2.26 mg from 2.03 mg of tert-butyl 3-(4-hydroxy-7-(thiazol-2-yl)benzo[d]oxazol-2-yl)-3,6-diazabicyclo[3.1.1]heptane-6-carboxylate obtained in Example 248 (c) by a similar method to Example 85 (a).

(b) tert-Butyl 3-(7-(thiazol-2-yl)-4-((trifluoromethyl)sulfonyl)benzo[d]oxazol-2-yl)-3,6-diazabicyclo[3.1.1]heptane-6-carboxylate 4.7 mg of tert-butyl 3-(7-(thiazol-2-yl)-4-(((trifluoromethyl)sulfonyl)oxy)benzo[d]oxazol-2-yl)-3,6-diazabicyclo[3.1.1]heptane-6-carboxylate obtained in Example 334(a) was dissolved in toluene (2.5 mL), then sodium trifluoromethansulfinate (31.2 mg, 2 equivalents), tris(dibenzylideneacetone)dipalladium(0) (4.6 mg, 0.05 equivalent), 2-di(tert-butyl)phosphino-2',4',6'-triisopropyl-3-methoxy-6-methyl-biphenyl (5.6 mg, 0.12 equivalent) and tris[2-(2-methoxyethoxy)ethyl]amine (3 µL, 0.1 equivalent) were added thereto, followed by stirring using a microwave reactor (manufactured by Biotage, conditions: 150° C., 1 hour). Saturated ammonium chloride aqueous solution and ethyl acetate were added to the cooled reaction mixture. Thereafter, reaction mixture was subjected to Celite® filtration, the organic phase was dried over anhydrous sodium sulfate, followed by filtration and vacuum concentration of the filtrate, and thus obtaining 19.7 mg of the title compound by purification of the residue through silica gel column chromatography (hexane:ethyl acetate=1:1).

(c) 2-(3,6-Diazabicyclo[3.1.1]heptan-3-yl)-7-(thiazol-2-yl)-4-((trifluoromethyl)sulfonyl)benzo[d]oxazole The title compound was obtained in an amount of 12.2 mg from 19.7 mg of tert-butyl 3-(7-(thiazol-2-yl)-4-((trifluoromethyl)sulfonyl)benzo[d]oxazol-2-yl)-3,6-diazabicyclo[3.1.1]heptane-6-carboxylate obtained in Example 334 (b) by a similar method to Example 1(c).

Example 335

2-(3,6-Diazabicyclo[3.1.1]heptan-3-yl)-7-(thiazol-2-yl)benzo[d]oxazole-4-carbonitrile (a) tert-Butyl 3-(4-cyano-7-(thiazol-2-yl)benzo[d]oxazol-2-yl)-3,6-diazabicyclo[3.1.1]heptane-6-carboxylate 4.6 mg of tert-butyl 3-(7-(thiazol-2-yl)-4-(((trifluoromethyl)sulfonyl)oxy)benzo[d]oxazol-2-yl)-3,6-diazabicyclo[3.1.1]heptane-6-carboxylate obtained in Example 334(a) was dissolved in N,N-dimethylformamide (1 mL), then zinc cyanide (23.5 mg, 2 equivalents) and tetrakis(triphenylphosphine)palladium(0) (11.6 mg, 0.1 equivalent) were added thereto, followed by stirring using a microwave reactor (manufactured by Biotage, conditions: 30° C., 30 min). Distilled water and ethyl acetate were added to the reaction mixture. Thereafter, reaction mixture was subjected to Celite® filtration, the separated organic phase was dried over anhydrous sodium sulfate, followed by filtration and vacuum concentration of the filtrate, and thus obtaining 28.8 mg of the title compound by purification of the residue through silica gel column chromatography (hexane:ethyl acetate=1:1).

(b) 2-(3,6-Diazabicyclo[3.1.1]heptan-3-yl)-7-(thiazol-2-yl)benzo[d]oxazole-4-carbonitrile The title compound was obtained in an amount of 28.8 mg from 20.7 mg of tert-butyl 3-(4-cyano-7-(thiazol-2-yl)benzo[d]oxazol-2-yl)-3,6-diazabicyclo[3.1.1]heptane-6-carboxylate obtained in Example 335 (a) by a similar method to Example 1(c).

Example 336

2-(3,6-Diazabicyclo[3.1.1]heptan-3-yl)-7-(thiazol-2-yl)-4-((5-(trifluoromethyl)pyridin-2-yl)oxy)benzo[d]oxazole (a) tert-Butyl 3-(7-(thiazol-2-yl)-4-((5-(trifluoromethyl)pyridin-2-yl)oxy)benzo[d]oxazol-2-yl)-3,6-diazabicyclo[3.1.1]heptane-6-carboxylate The title compound was obtained in an amount of 25 mg from 21 mg of tert-butyl 3-(4-hydroxy-7-(thiazol-2-yl)benzo[d]oxazol-2-yl)-3,6-diazabicyclo[3.1.1]heptane-6-carboxylate obtained in Example 248 (c) by a similar method to Reference Example 23(a) except that 2-chloro-5-trifluoromethylpyridine was used instead of benzyl bromide.

(b) 2-(3,6-Diazabicyclo[3.1.1]heptan-3-yl)-7-(thiazol-2-yl)-4-((5-(trifluoromethyl)pyridin-2-yl)oxy)benzo[d]oxazole The title compound was obtained in an amount of 19 mg from 24 mg of tert-butyl 3-(7-(thiazol-2-yl)-4-((5-(trifluoromethyl)pyridin-2-yl)oxy)benzo[d]oxazol-2-yl)-3,6-diazabicyclo[3.1.1]heptane-6-carboxylate obtained in Example 336(a) by a similar method to Example 1(c).

Example 337

2-(3,6-Diazabicyclo[3.1.1]heptan-3-yl)-4-(pyridin-2-yloxy)-7-(thiazol-2-yl)benzo[d]oxazole (a) tert-Butyl 3-(4-(pyridin-2-yloxy)-7-(thiazol-2-yl)benzo[d]oxazol-2-yl)-3,6-diazabicyclo[3.1.1]heptane-6-carboxylate The title compound was obtained as a crude product in an amount of 18 mg from 21 mg of tert-butyl 3-(4-hydroxy-7-(thiazol-2-yl)benzo[d]oxazol-2-yl)-3,6-diazabicyclo[3.1.1]heptane-6-carboxylate obtained in Example 248 (c) by a similar method to Reference Example 23(a) except that 2-fluoropyridine was used instead of benzyl bromide, the reaction mixture was stirred at 90° C. for 2.5 hours and at 100° C. for 3 days, and further the reaction mixture was stirred at 120° C. for 1.5 hours using a microwave reactor.

(b) 2-(3,6-Diazabicyclo[3.1.1]heptan-3-yl)-4-(pyridin-2-yloxy)-7-(thiazol-2-yl)benzo[d]oxazole The title compound was obtained in an amount of 3.8 mg from 16 mg of the crude product of tert-butyl 3-(4-(pyridin-2-yloxy)-7-(thiazol-2-yl)benzo[d]oxazol-2-yl)-3,6-diazabicyclo[3.1.1]heptane-6-carboxylate obtained in Example 337 (a) by a similar method to Example 1(c).

Example 338

2-(3,6-Diazabicyclo[3.1.1]heptan-3-yl)-4-(pyrimidin-2-yloxy)-7-(thiazol-2-yl)benzo[d]oxazole (a) tert-Butyl 3-(4-(pyrimidin-2-yloxy)-7-(thiazol-2-yl)benzo[d]oxazol-2-yl)-3,6-diazabicyclo[3.1.1]heptane-6-carboxylate The title compound was obtained in an amount of 12 mg from 20 mg of tert-butyl 3-(4-hydroxy-7-(thiazol-2-yl)benzo[d]oxazol-2-yl)-3,6-diazabicyclo[3.1.1]heptane-6-carboxylate obtained in Example 248 (c) by a similar method to Reference Example 23(a) except that 2-bromopyrimidine was used instead of benzyl bromide.

(b) 2-(3,6-Diazabicyclo[3.1.1]heptan-3-yl)-4-(pyrimidin-2-yloxy)-7-(thiazol-2-yl)benzo[d]oxazole The title compound was obtained in an amount of 7.1 mg from 11 mg of tert-butyl 3-(4-(pyrimidin-2-yloxy)-7-(thiazol-2-yl)benzo[d]oxazol-2-yl)-3,6-diazabicyclo[3.1.1]heptane-6-carboxylate obtained in Example 338 (a) by a similar method to Example 1(c).

Example 339

2-(3,6-Diazabicyclo[3.1.1]heptan-3-yl)-4-(pyrazin-2-yloxy)-7-(thiazol-2-yl)benzo[d]oxazole (a) tert-Butyl 3-(4-(pyrazin-2-yloxy)-7-(thiazol-2-yl)benzo[d]oxazol-2-yl)-3,6-diazabicyclo[3.1.1]heptane-6-carboxylate The title compound was obtained in an amount of 24 mg from 22 mg of tert-butyl 3-(4-hydroxy-7-(thiazol-2-yl)benzo[d]oxazol-2-yl)-3,6-diazabicyclo[3.1.1]heptane-6-carboxylate obtained in Example 248 (c) by a similar method to Reference Example 23(a) except that 2-iodopyrazine was used instead of benzyl bromide and the reaction mixture was stirred at 90° C. for 1.5 hours and at 115° C. for 3 hours.

(b) 2-(3,6-Diazabicyclo[3.1.1]heptan-3-yl)-4-(pyrazin-2-yloxy)-7-(thiazol-2-yl)benzo[d]oxazole The title compound was obtained in an amount of 11 mg from 24 mg of tert-butyl 3-(4-(pyrazin-2-yloxy)-7-(thiazol-2-yl)benzo[d]oxazol-2-yl)-3,6-diazabicyclo[3.1.1]heptane-6-carboxylate obtained in Example 339(a) by a similar method to Example 1(c).

Example 340

2-(3,6-Diazabicyclo[3.1.1]heptan-3-yl)-4-((6-methyl-4-(trifluoromethyl)pyridazin-3-yl)oxy)-7-(thiazol-2-yl)benzo[d]oxazole (a) tert-Butyl 3-(4-((6-methyl-4-(trifluoromethyl)pyridazin-3-yl)oxy)-7-(thiazol-2-yl)benzo[d]oxazol-2-yl)-3,6-diazabicyclo[3.1.1]heptane-6-carboxylate The title compound was obtained in an amount of 17 mg from 21 mg of tert-butyl 3-(4-hydroxy-7-(thiazol-2-yl)benzo[d]oxazol-2-yl)-3,6-diazabicyclo[3.1.1]heptane-6-carboxylate obtained in Example 248 (c) by a similar method to Reference Example 23(a) except that 3-chloro-6-methyl-4-(trifluoromethyl)pyridazin was used instead of benzyl bromide and the reaction mixture was stirred at 90° C.

(b) 2-(3,6-Diazabicyclo[3.1.1]heptan-3-yl)-4-((6-methyl-4-(trifluoromethyl)pyridazin-3-yl)oxy)-7-(thiazol-2-yl)benzo[d]oxazole The title compound was obtained in an amount of 6.8 mg from 16 mg of tert-butyl 3-(4-((6-methyl-4-(trifluoromethyl)pyridazin-3-yl)oxy)-7-(thiazol-2-yl)benzo[d]oxazol-2-yl)-3,6-diazabicyclo[3.1.1]heptane-6-carboxylate obtained in Example 340(a) by a similar method to Example 1(c).

Example 341

(6-((2-(3,6-Diazabicyclo[3.1.1]heptan-3-yl)-7-(thiazol-2-yl)benzo[d]oxazol-4-yl)oxy)pyridin-3-yl)methanol (a) tert-Butyl 3-(4-((5-(methoxycarbonyl)pyridin-2-yl)oxy)-7-(thiazol-2-yl)benzo[d]oxazol-2-yl)-3,6-diazabicyclo[3.1.1]heptane-6-carboxylate The title compound was obtained in an amount of 26 mg from 19 mg of tert-butyl 3-(4-hydroxy-7-(thiazol-2-yl)benzo[d]oxazol-2-yl)-3,6-diazabicyclo[3.1.1]heptane-6-carboxylate obtained in Example 248 (c) by a similar method to Reference Example 23(a) except that methyl 6-chloronicotinate was used instead of benzyl bromide and the reaction mixture was stirred at 90° C.

(b) tert-Butyl 3-(4-((5-(hydroxymethyl)pyridin-2-yl)oxy)-7-(thiazol-2-yl)benzo[d]oxazol-2-yl)-3,6-diazabicyclo[3.1.1]heptane-6-carboxylate The title compound was obtained in an amount of 17 mg from 26 mg of tert-butyl 3-(4-((5-(methoxycarbonyl)pyridin-2-yl)oxy)-7-(thiazol-2-yl)benzo[d]oxazol-2-yl)-3,6-diazabicyclo[3.1.1]heptane-6-carboxylate obtained in Example 341(a) by a similar method to Example 250(c).

(c) (6-((2-(3,6-Diazabicyclo[3.1.1]heptan-3-yl)-7-(thiazol-2-yl)benzo[d]oxazol-4-yl)oxy)pyridin-3-yl)methanol The title compound was obtained in an amount of 12 mg from 16 mg of tert-butyl 3-(4-((5-(hydroxymethyl)pyridin-2-yl)oxy)-7-(thiazol-2-yl)benzo[d]oxazol-2-yl)-3,6-diazabicyclo[3.1.1]heptane-6-carboxylate obtained in Example 341 (b) by a similar method to Example 1(c).

Example 342

(6-((2-(3,6-Diazabicyclo[3.1.1]heptan-3-yl)-7-(thiazol-2-yl)benzo[d]oxazol-4-yl)oxy)-5-(trifluoromethyl)pyridin-3-yl)methanol (a) tert-Butyl 3-(4-((5-(methoxycarbonyl)-3-(trifluoromethyl)pyridin-2-yl)oxy)-7-(thiazol-2-yl)benzo[d]oxazol-2-yl)-3,6-diazabicyclo[3.1.1]heptane-6-carboxylate The title compound was obtained in an amount of 39 mg from 30 mg of tert-butyl 3-(4-hydroxy-7-(thiazol-2-yl)benzo[d]oxazol-2-yl)-3,6-diazabicyclo[3.1.1]heptane-6-carboxylate obtained in Example 248 (c) by a similar method to Reference Example 23(a) except that methyl 6-chloro-5-(trifluoromethyl)nicotinate was used instead of benzyl bromide and the reaction mixture was stirred at 90° C.

(b) tert-Butyl 3-(4-((5-(hydroxymethyl)-3-(trifluoromethyl)pyridin-2-yl)oxy)-7-(thiazol-2-yl)benzo[d]oxazol-2-yl)-3,6-diazabicyclo[3.1.1]heptane-6-carboxylate The title compound was obtained in an amount of 10 mg from 39 mg of tert-butyl 3-(4-((5-(methoxycarbonyl)-3-(trifluoromethyl)pyridin-2-yl)oxy)-7-(thiazol-2-yl)benzo[d]

oxazol-2-yl)-3,6-diazabicyclo[3.1.1]heptane-6-carboxylate obtained in Example 342 (a) by a similar method to Example 250(c).

(c) (6-((2-(3,6-Diazabicyclo[3.1.1]heptan-3-yl)-7-(thiazol-2-yl)benzo[d]oxazol-4-yl)oxy)-5-(trifluoromethyl)pyridin-3-yl)methanol The title compound was obtained in an amount of 7.1 mg from 8.8 mg of tert-butyl 3-(4-((5-(hydroxymethyl)-3-(trifluoromethyl)pyridin-2-yl)oxy)-7-(thiazol-2-yl)benzo[d]oxazol-2-yl)-3,6-diazabicyclo[3.1.1]heptane-6-carboxylate obtained in Example 342 (b) by a similar method to Example 1(c).

Example 343

2-(3,6-Diazabicyclo[3.1.1]heptan-3-yl)-7-(thiazol-2-yl)-4-((5-(trifluoromethoxy)pyridin-2-yl)oxy)benzo[d]oxazole (a) tert-Butyl 3-(7-(thiazol-2-yl)-4-((5-(trifluoromethoxy)pyridin-2-yl)oxy)benzo[d]oxazol-2-yl)-3,6-diazabicyclo[3.1.1]heptane-6-carboxylate The title compound was obtained in an amount of 18 mg from 21 mg of tert-butyl 3-(4-hydroxy-7-(thiazol-2-yl)benzo[d]oxazol-2-yl)-3,6-diazabicyclo[3.1.1]heptane-6-carboxylate obtained in Example 248 (c) by a similar method to Reference Example 23(a) except that 2-chloro-5-(trifluoromethoxy)pyridine was used instead of benzyl bromide and the reaction mixture was stirred at 90° C.

(b) 2-(3,6-Diazabicyclo[3.1.1]heptan-3-yl)-7-(thiazol-2-yl)-4-((5-(trifluoromethoxy)pyridin-2-yl)oxy)benzo[d]oxazole The title compound was obtained in an amount of 6.8 mg from 16 mg of tert-butyl 3-(7-(thiazol-2-yl)-4-((5-(trifluoromethoxy)pyridin-2-yl)oxy)benzo[d]oxazol-2-yl)-3,6-diazabicyclo[3.1.1]heptane-6-carboxylate obtained in Example 343(a) by a similar method to Example 1(c).

Example 344

2-(3,6-Diazabicyclo[3.1.1]heptan-3-yl)-4-cyclopropyl-7-(thiazol-2-yl)benzo[d]oxazole (a) tert-Butyl 3-(4-cyclopropyl-7-(thiazol-2-yl)benzo[d]oxazol-2-yl)-3,6-diazabicyclo[3.1.1]heptane-6-carboxylate 54.6 mg of tert-butyl 3-(7-(thiazol-2-yl)-4-(((trifluoromethyl)sulfonyl)oxy)benzo[d]oxazol-2-yl)-3,6-diazabicyclo[3.1.1]heptane-6-carboxylate obtained in Example 334(a) was dissolved in 1,4-dioxane (1 mL), then cyclobutylboronic acid (12.9 mg, 1.5 equivalents) and tetrakis(triphenylphosphine)palladium(0) (5.8 mg, 0.05 equivalent) were added thereto, followed by stirring at 100° C. for 4 hours. Distilled water and ethyl acetate were added to the reaction mixture.

Thereafter, reaction mixture was subjected to Celite® filtration, the organic phase was dried over anhydrous sodium sulfate, followed by filtration and vacuum concentration of the filtrate, and thus obtaining 38.5 mg of the title compound by purification of the residue through silica gel column chromatography (hexane:ethyl acetate=1:1).

(b) 2-(3,6-Diazabicyclo[3.1.1]heptan-3-yl)-4-cyclopropyl-7-(thiazol-2-yl)benzo[d]oxazole The title compound was obtained in an amount of 7.8 mg from 38.5 mg of tert-butyl 3-(4-cyclopropyl-7-(thiazol-2-yl)benzo[d]oxazol-2-yl)-3,6-diazabicyclo[3.1.1]heptane-6-carboxylate obtained in Example 344 (a) by a similar method to Example 1(c).

Example 345

2-(3,6-Diazabicyclo[3.1.1]heptan-3-yl)-4-(methylthio)-7-(thiazol-2-yl)benzo[d]oxazole (a) tert-Butyl 3-(4-(methylthio)-7-(thiazol-2-yl)benzo[d]oxazol-2-yl)-3,6-diazabicyclo[3.1.1]heptane-6-carboxylate 109.3 mg of tert-butyl 3-(7-(thiazol-2-yl)-4-(((trifluoromethyl)sulfonyl)oxy)benzo[d]oxazol-2-yl)-3,6-diazabicyclo[3.1.1]heptane-6-carboxylate obtained in Example 334(a) was dissolved in 1,4-dioxane (2 mL), then sodium thiomethoxide (28.0 mg, 2 equivalents), tris(dibenzylideneacetone)dipalladium(0) (18.3 mg, 0.1 equivalent) and 4,5-bis(diphenylphosphino)-9,9-dimethylxanthene (23.1 mg, 0.2 equivalent) were added thereto, followed by stirring using a microwave reactor (manufactured by Biotage, conditions: 150° C., 1 hour). Distilled water and ethyl acetate were added to the reaction mixture. Thereafter, reaction mixture was subjected to Celite® filtration, the organic phase was dried over anhydrous sodium sulfate, followed by filtration and vacuum concentration of the filtrate, and thus obtaining 58.1 mg of the title compound by purification of the residue through silica gel column chromatography (hexane:ethyl acetate=2:1).

(b) 2-(3,6-Diazabicyclo[3.1.1]heptan-3-yl)-4-(methylthio)-7-(thiazol-2-yl)benzo[d]oxazole The title compound was obtained in an amount of 28.7 mg from 44.5 mg of tert-butyl 3-(4-(methylthio)-7-(thiazol-2-yl)benzo[d]oxazol-2-yl)-3,6-diazabicyclo[3.1.1]heptane-6-carboxylate obtained in Example 345 (a) by a similar method to Example 1(c).

Example 346

2-(3,6-Diazabicyclo[3.1.1]heptan-3-yl)-4-(methylsulfinyl)-7-(thiazol-2-yl)benzo[d]oxazole (a) tert-Butyl 3-(4-(methysulfinyl)-7-(thiazol-2-yl)benzo[d]oxazol-2-yl)-3,6-diazabicyclo[3.1.1]heptane-6-carboxylate 53.0 mg of tert-butyl 3-(4-(methylthio)-7-(thiazol-2-yl)benzo[d]oxazol-2-yl)-3,6-diazabicyclo[3.1.1]heptane-6-carboxylate obtained in Example 345(a) was dissolved in chloroform (1 mL), then mCPBA (29.3 mg, 1 equivalent) was added thereto, followed by stirring at room temperature for 1 hour. Sodium hydrogen carbonate aqueous solution was added to the reaction mixture. Thereafter, the organic phase was extracted using chloroform and dried over anhydrous sodium sulfate, followed by filtration and vacuum concentration of the filtrate, and thus obtaining 50.2 mg of the title compound by purification of the residue through silica gel column chromatography (ethyl acetate:methanol=9:1).

(b) 2-(3,6-Diazabicyclo[3.1.1]heptan-3-yl)-4-(methylsulfinyl)-7-(thiazol-2-yl)benzo[d]oxazole The title compound was obtained in an amount of 27.5 mg from 50.2 mg of tert-butyl 3-(4-(methylsulfinyl)-7-(thiazol-2-yl)benzo[d]oxazol-2-yl)-3,6-diazabicyclo[3.1.1]heptane-6-carboxylate obtained in Example 346(a) by a similar method to Example 1(c).

Example 347

2-(3,6-Diazabicyclo[3.1.1]heptan-3-yl)-4-(methylsulfonyl)-7-(thiazol-2-yl)benzo[d]oxazole (a) tert-Butyl 3-(4-(methylsulfonyl)-7-(thiazol-2-yl)benzo[d]oxazol-2-yl)-3,6-diazabicyclo[3.1.1]heptane-6-carboxylate The title compound was obtained in an amount of 71.2 mg from 79.3 mg of tert-butyl 3-(4-(methylthio)-7-(thiazol-2-yl)benzo[d]oxazol-2-yl)-3,6-diazabicyclo[3.1.1]heptane-6-carboxylate obtained in Example 345(a) by a similar method to Example 346(a) except that 2 equivalents of mCPBA was used.

(b) 2-(3,6-Diazabicyclo[3.1.1]heptan-3-yl)-4-(methylsulfonyl)-7-(thiazol-2-yl)benzo[d]oxazole The title compound was obtained in an amount of 54.9 mg from 71.2 mg of tert-butyl 3-(4-(methylsulfonyl)-7-(thiazol-2-yl)benzo[d]oxazol-2-yl)-3,6-diazabicyclo[3.1.1]heptane-6-carboxylate obtained in Example 347 (a) by a similar method to Example 1(c).

Example 348

2-((2-(3,6-Diazabicyclo[3.1.1]heptan-3-yl)-7-(thiazol-2-yl)benzo[d]oxazol-4-yl)thio)ethan-1-ol (a) tert-Butyl 3-(4-((2-hydroxyethyl)thio)-7-(thiazol-2-yl)benzo[d]oxazol-2-yl)-3,6-diazabicyclo[3.1.1]heptane-6-carboxylate The title compound was obtained in an amount of 49.5 mg from 54.6 mg of tert-butyl 3-(7-(thiazol-2-yl)-4-(((trifluoromethyl)sulfonyl)oxy)benzo[d]oxazol-2-yl)-3,6-diazabicyclo[3.1.1]heptane-6-carboxylate obtained in Example 334 (a) by a similar method to Example 345(a) except that 2-mercaptoethanol and triethylamine were used instead of sodium thiomethoxide.

(b) 2-((2-(3,6-Diazabicyclo[3.1.1]heptan-3-yl)-7-(thiazol-2-yl)benzo[d]oxazol-4-yl)thio)ethan-1-ol The title compound was obtained in an amount of 24.0 mg from 38.0 mg of tert-butyl 3-(4-((2-hydroxyethyl)thio)-7-(thiazol-2-yl)benzo[d]oxazol-2-yl)-3,6-diazabicyclo[3.1.1]heptane-6-carboxylate obtained in Example 348(a) by a similar method to Example 1(c).

Example 349

2-((2-(3,6-Diazabicyclo[3.1.1]heptan-3-yl)-7-(thiazol-2-yl)benzo[d]oxazol-4-yl)sulfinyl)ethan-1-ol (a) tert-Butyl 3-(4-((2-hydroxyethyl)sulfinyl)-7-(thiazol-2-yl)benzo[d]oxazol-2-yl)-3,6-diazabicyclo[3.1.1]heptane-6-carboxylate The title compound was obtained in an amount of 43.7 mg from 47.5 mg of tert-butyl 3-(4-((2-hydroxyethyl)thio)-7-(thiazol-2-yl)benzo[d]oxazol-2-yl)-3,6-diazabicyclo[3.1.1]heptane-6-carboxylate obtained in Example 348(a) by a similar method to Example 346(a).

(b) 2-((2-(3,6-Diazabicyclo[3.1.1]heptan-3-yl)-7-(thiazol-2-yl)benzo[d]oxazol-4-yl)sulfinyl)ethan-1-ol The title compound was obtained in an amount of 25.8 mg from 43.7 mg of tert-butyl 3-(4-((2-hydroxyethyl)sulfinyl)-7-(thiazol-2-yl)benzo[d]oxazol-2-yl)-3,6-diazabicyclo[3.1.1]heptane-6-carboxylate obtained in Example 349(a) by a similar method to Example 1(c).

Example 350

2-((2-(3,6-Diazabicyclo[3.1.1]heptan-3-yl)-7-(thiazol-2-yl)benzo[d]oxazol-4-yl)sulfonyl)ethan-1-ol (a) tert-Butyl 3-(4-((2-hydroxyethyl)sulfonyl)-7-(thiazol-2-yl)benzo[d]oxazol-2-yl)-3,6-diazabicyclo[3.1.1]heptane-6-carboxylate The title compound was obtained in an amount of 42.8 mg from 54.6 mg of tert-butyl 3-(4-((2-hydroxyethyl)thio)-7-(thiazol-2-yl)benzo[d]oxazol-2-yl)-3,6-diazabicyclo[3.1.1]heptane-6-carboxylate obtained in Example 348(a) by a similar method to Example 347 (a).

(b) 2-((2-(3,6-Diazabicyclo[3.1.1]heptan-3-yl)-7-(thiazol-2-yl)benzo[d]oxazol-4-yl)sulfonyl)ethan-1-ol The title compound was obtained in an amount of 27.9 mg from 42.8 mg of tert-butyl 3-(4-((2-hydroxyethyl)sulfonyl)-7-(thiazol-2-yl)benzo[d]oxazol-2-yl)-3,6-diazabicyclo[3.1.1]heptane-6-carboxylate obtained in Example 350(a) by a similar method to Example 1(c).

Example 351

2-(3,6-Diazabicyclo[3.1.1]heptan-3-yl)-4-((1,1-difluoroallyl)oxy)-7-(thiazol-2-yl)benzo[d]oxazole (a) tert-Butyl 3-(4-((1,1-difluoroallyl)oxy)-7-(thiazol-2-yl)benzo[d]oxazol-2-yl)-3,6-diazabicyclo[3.1.1]heptane-6-carboxylate 124.3 mg of tert-butyl 3-(4-hydroxy-7-(thiazol-2-yl)benzo[d]oxazol-2-yl)-3,6-diazabicyclo[3.1.1]heptane-6-carboxylate obtained in Example 248 (c) was dissolved in tetrahydrofuran (3 mL), then 3-bromo-3,3-difluoropropene (71 µL, 1.5 equivalents), sodium hydride (18 mg, 1.5 equivalents), palladium (II) acetate (6.7 mg, 0.1 equivalent) and triphenylphosphine (26.9 mg, 0.4 equivalent) were added thereto, followed by stirring at room temperature for 1 hour. Distilled water and ethyl acetate were added to the reaction mixture. Thereafter, reaction mixture was subjected to Celite® filtration, the organic phase was dried over anhydrous sodium sulfate, followed by filtration and vacuum concentration of the filtrate, and thus obtaining 132.7 mg of the title compound by purification of the residue through silica gel column chromatography (hexane:ethyl acetate=1:1).

(b) 2-(3,6-Diazabicyclo[3.1.1]heptan-3-yl)-4-((1,1-difluoroallyl)oxy)-7-(thiazol-2-yl)benzo[d]oxazole The title compound was obtained in an amount of 11.8 mg from 30.0 mg of tert-butyl 3-(4-((1,1-difluoroallyl)oxy)-7-(thiazol-2-yl)benzo[d]oxazol-2-yl)-3,6-diazabicyclo[3.1.1]heptane-6-carboxylate obtained in Example 351(a) by a similar method to Example 1(c).

Example 352

2-(3,6-Diazabicyclo[3.1.1]heptan-3-yl)-4-((5-(methylsulfonyl)pyridin-2-yl)oxy)-7-(thiazol-2-yl)benzo[d]oxazole (a) tert-Butyl 3-(4-((5-(methylsulfonyl)pyridin-2-yl)oxy)-7-(thiazol-2-yl)benzo[d]oxazol-2-yl)-3,6-diazabicyclo[3.1.1]heptane-6-carboxylate The title compound was obtained in an amount of 29 mg from 20 mg of tert-butyl 3-(4-hydroxy-7-(thiazol-2-yl)benzo[d]oxazol-2-yl)-3,6-diazabicyclo[3.1.1]heptane-6-carboxylate obtained in Example 248 (c) by a similar method to Reference Example 23(a) except that 2-bromo-5-(methylsulfonyl)pyridin was used instead of benzylbromide and the reaction mixture was stirred at 90° C.

(b) 2-(3,6-Diazabicyclo[3.1.1]heptan-3-yl)-4-((5-(methylsulfonyl)pyridin-2-yl)oxy)-7-(thiazol-2-yl)benzo[d]oxazole The title compound was obtained in an amount of 9.6 mg from 28 mg of tert-butyl 3-(4-((5-(methylsulfonyl)pyridin-2-yl)oxy)-7-(thiazol-2-yl)benzo[d]oxazol-2-yl)-3,6-diazabicyclo[3.1.1]heptane-6-carboxylate obtained in Example 352 (a) by a similar method to Example 1(c).

Example 353

2-(3,6-Diazabicyclo[3.1.1]heptan-3-yl)-N-(2-methoxyethyl)-7-(thiazol-2-yl)benzo[d]oxazole-4-carboxamide (a) tert-butyl (a) 2,4,6-Trichlorophenyl 2-(6-(tert-butoxycarbonyl)-3,6-diazabicyclo[3.1.1]heptan-3-yl)-7-(thiazol-2-yl)benzo[d]oxazole-4-carboxylate 100 mg of tert-butyl 3-(7-(thiazol-2-yl)-4-(((trifluoromethyl)sulfonyl)oxy)benzo[d]oxazol-2-yl)-3,6-diazabicyclo[3.1.1]heptane-6-carboxylate obtained in Example 334(a) and 2,4,6-trichlorophenyl formate (85 mg, 2 equivalents), palladium (II) acetate (3.5 mg, 0.05 equivalent), 4,5-bis(diphenylphosphino)-9,9-dimethylxanthene (12.1 mg, 0.1 equivalent) were dissolved in toluene (2 mL), then triethylamine (51 μL, 2 equivalents) was added thereto, followed by stirring using a microwave reactor (manufactured by Biotage, conditions: 150° C., 1 hour). Distilled water was added to the reaction mixture. Thereafter, the organic phase was extracted using ethyl acetate, washed using distilled water, and dried over anhydrous sodium sulfate, followed by filtration and vacuum concentration of the filtrate, and thus obtaining 28 mg of the title compound by purification of the residue through silica gel column chromatography (hexane:ethyl acetate=1:0-1:1).

(b) tert-Butyl 3-(4-((2-methoxyethyl)carbamoyl)-7-(thiazol-2-yl)benzo[d]oxazol-2-yl)-3,6-diazabicyclo[3.1.1]heptane-6-carboxylate 28 mg of 2,4,6-trichlorophenyl 2-(6-(tert-butoxycarbonyl)-3,6-diazabicyclo[3.1.1]heptan-3-yl)-7-(thiazol-2-yl)benzo[d]oxazole-4-carboxylate obtained in Example 353(a) was dissolved in acetonitrile (0.5 mL), then 2-methoxyethan-1-amine (8 μL, 2 equivalents) was added thereto, followed by heat refluxing for 2 hours. Ethyl acetate and distilled water were added to the reaction mixture. Thereafter, 25 mg of the title compound as a crude product by vacuum concentration of the organic phase.

(c) 2-(3,6-Diazabicyclo[3.1.1]heptan-3-yl)-N-(2-methoxyethyl)-7-(thiazol-2-yl)benzo[d]oxazole-4-carboxamide (a) tert-butyl The title compound was obtained in an amount of 12 mg from 23 mg of the crude product of tert-butyl 3-(4-((2-methoxyethyl)carbamoyl)-7-(thiazol-2-yl)benzo[d]oxazol-2-yl)-3,6-diazabicyclo[3.1.1]heptane-6-carboxylate obtained in Example 353 (b) by a similar method to Example 1(c).

Example 354

2-(3,6-Diazabicyclo[3.1.1]heptan-3-yl)-7-(thiazol-2-yl)benzo[d]oxazole-4-carboxamide (a) tert-Butyl 3-(4-carbamoyl-7-(thiazol-2-yl)benzo[d]oxazol-2-yl)-3,6-diazabicyclo[3.1.1]heptane-6-carboxylate The title compound was obtained as a crude product in an amount of 20 mg from 20 mg of tert-butyl 3-(7-(thiazol-2-yl)-4-((2,4,6-trichlorobenzoyl)oxy)benzo[d]oxazol-2-yl)-3,6-diazabicyclo[3.1.1]heptane-6-carboxylate obtained in Example 353(a) by a similar method to Example 353(b) except that 7N solution of ammonia in methanol was used instead of 2-methoxyethan-1-amine.

(b) 2-(3,6-Diazabicyclo[3.1.1]heptan-3-yl)-7-(thiazol-2-yl)benzo[d]oxazole-4-carboxamide The title compound was obtained in an amount of 7.7 mg from 19 mg of tert-butyl 3-(4-carbamoyl-7-(thiazol-2-yl)benzo[d]oxazol-2-yl)-3,6-diazabicyclo[3.1.1]heptane-6-carboxylate obtained in Example 354 (a) by a similar method to Example 1(c).

Example 355

2-(3,6-Diazabicyclo[3.1.1]heptan-3-yl)-N-(2-hydroxyethyl)-7-(thiazol-2-yl)benzo[d]oxazole-4-carboxamide (a) tert-Butyl 3-(4-((2-hydroxyethyl)carbamoyl)-7-(thiazol-2-yl)benzo[d]oxazol-2-yl)-3,6-diazabicyclo[3.1.1]heptane-6-carboxylate The title compound was obtained as a crude product in an amount of 16 mg from 20 mg of tert-butyl 3-(7-(thiazol-2- yl)-4-((2,4,6-trichlorobenzoyl)oxy)benzo[d]oxazol-2-yl)-3,6-diazabicyclo[3.1.1]heptane-6-carboxylate obtained in Example 353(a) by a similar method to Example 353(b) except that 2-aminoethan-1-ol was used instead of 2-methoxyethan-1-amine.

(b) 2-(3,6-Diazabicyclo[3.1.1]heptan-3-yl)-N-(2-hydroxyethyl)-7-(thiazol-2-yl)benzo[d]oxazole-4-carboxamide The title compound was obtained in an amount of 6.2 mg from 16 mg of the crude product of tert-butyl 3-(4-((2-hydroxyethyl)carbamoyl)-7-(thiazol-2-yl)benzo[d]oxazol-2-yl)-3,6-diazabicyclo[3.1.1]heptane-6-carboxylate obtained in Example 355 (a) by a similar method to Example 1(c).

Example 356

2-(3,6-Diazabicyclo[3.1.1]heptan-3-yl)-N-(2-hydroxyethyl)-N-methyl-7-(thiazol-2-yl)benzo[d]oxazole-4-carboxamide (a) tert-Butyl 3-(4-((2-hydroxyethyl)(methyl)carbamoyl)-7-(thiazol-2-yl)benzo[d]oxazol-2-yl)-3,6-diazabicyclo[3.1.1]heptane-6-carboxylate The title compound was obtained as a crude product in an amount of 16 mg from 20 mg of tert-butyl 3-(7-(thiazol-2-yl)-4-((2,4,6-trichlorobenzoyl)oxy)benzo[d]oxazol-2-yl)-3,6-diazabicyclo[3.1.1]heptane-6-carboxylate obtained in Example 353(a) by a similar method to Example 353(b) except that 2-(methylamino)ethan-1-ol was used instead of 2-methoxyethan-1-amine.

(b) 2-(3,6-Diazabicyclo[3.1.1]heptan-3-yl)-N-(2-hydroxyethyl)-N-methyl-7-(thiazol-2-yl)benzo[d]oxazole-4-carboxamide The title compound was obtained in an amount of 11 mg from 16 mg of the crude product of tert-butyl 3-(4-((2-hydroxyethyl)(methyl)carbamoyl)-7-(thiazol-2-yl)benzo[d]oxazol-2-yl)-3,6-diazabicyclo[3.1.1]heptane-6-carboxylate obtained in Example 356(a) by a similar method to Example 1(c).

Example 357

2-(3,6-Diazabicyclo[3.1.1]heptan-3-yl)-N-cyclopropyl-7-(thiazol-2-yl)benzo[d]oxazole-4-carboxamide (a) tert-Butyl 3-(4-(cyclopropylcarbamoyl)-7-(thiazol-2-yl)benzo[d]oxazol-2-yl)-3,6-diazabicyclo[3.1.1]heptane-6-carboxylate The title compound was obtained as a crude product in an amount of 22 mg from 20 mg of tert-butyl 3-(7-(thiazol-2-yl)-4-((2,4,6-trichlorobenzoyl)oxy)benzo[d]oxazol-2-yl)-3,6-diazabicyclo[3.1.1]heptane-6-carboxylate obtained in Example 353(a) by a similar method to Example 353(b) except that cyclopropanamine was used instead of 2-methoxyethan-1-amine.

(b) 2-(3,6-Diazabicyclo[3.1.1]heptan-3-yl)-N-cyclopropyl-7-(thiazol-2-yl)benzo[d]oxazole-4-carboxamide The title compound was obtained in an amount of 4.3 mg from 20 mg of the crude product of tert-butyl 3-(4-(cyclopropylcarbamoyl)-7-(thiazol-2-yl)benzo[d]oxazol-2-yl)-3,6-diazabicyclo[3.1.1]heptane-6-carboxylate obtained in Example 357 (a) by a similar method to Example 1(c).

Example 358

2-(3,6-Diazabicyclo[3.1.1]heptan-3-yl)-N-ethyl-7-(thiazol-2-yl)benzo[d]oxazole-4-carboxamide (a) tert-Butyl 3-(4-(ethylcarbamoyl)-7-(thiazol-2-yl)benzo[d]oxazol-2-yl)-3,6-diazabicyclo[3.1.1]heptane-6-carboxylate The title compound was obtained as a crude product in an amount of 22 mg from 20 mg of tert-butyl 3-(7-(thiazol-2-yl)-4-((2,4,6-trichlorobenzoyl)oxy)benzo[d]oxazol-2-yl)-3,6-diazabicyclo[3.1.1]heptane-6-carboxylate obtained in Example 353(a) by a similar method to Example 353(b) except that ethanamine was used instead of 2-methoxyethan-1-amine.

(b) 2-(3,6-Diazabicyclo[3.1.1]heptan-3-yl)-N-ethyl-7-(thiazol-2-yl)benzo[d]oxazole-4-carboxamide The title compound was obtained in an amount of 6.4 mg from 21 mg of the crude product of tert-butyl 3-(4-(ethylcarbamoyl)-7-(thiazol-2-yl)benzo[d]oxazol-2-yl)-3,6-diazabicyclo[3.1.1]heptane-6-carboxylate obtained in Example 358(a) by a similar method to Example 1(c).

Example 359

(2-(3,6-Diazabicyclo[3.1.1]heptan-3-yl)-7-(thiazol-2-yl)benzo[d]oxazol-4-yl)(morpholino)methanone (a) tert-Butyl 3-(4-(morpholine-4-carbonyl)-7-(thiazol-2-yl)benzo[d]oxazol-2-yl)-3,6-diazabicyclo[3.1.1]heptane-6-carboxylate The title compound was obtained as a crude product in an amount of 38 mg from 16 mg of tert-butyl 3-(7-(thiazol-2-yl)-4-((2,4,6-trichlorobenzoyl)oxy)benzo[d]oxazol-2-yl)-3,6-diazabicyclo[3.1.1]heptane-6-carboxylate obtained in Example 353(a) by a similar method to Example 353(b) except that morpholine was used instead of 2-methoxyethan-1-amine.

(b) (2-(3,6-Diazabicyclo[3.1.1]heptan-3-yl)-7-(thiazol-2-yl)benzo[d]oxazol-4-yl)(morpholino)methanone The title compound was obtained in an amount of 9.9 mg from 38 mg of the crude product of tert-butyl 3-(4-(morpholine-4-carbonyl)-7-(thiazol-2-yl)benzo[d]oxazol-2-yl)-3,6-diazabicyclo[3.1.1]heptane-6-carboxylate obtained in Example 359(a) by a similar method to Example 1(c).

Example 360

(2-(3,6-Diazabicyclo[3.1.1]heptan-3-yl)-7-(thiazol-2-yl)benzo[d]oxazol-4-yl)(pyrrolidin-1-yl)methanone (a) tert-Butyl 3-(4-(pyrrolidin-1-carbonyl)-7-(thiazol-2-yl)benzo[d]oxazol-2-yl)-3,6-diazabicyclo[3.1.1]heptane-6-carboxylate The title compound was obtained as a crude product in an amount of 22 mg from 19 mg of tert-butyl 3-(7-(thiazol-2- yl)-4-((2,4,6-trichlorobenzoyl)oxy)benzo[d]oxazol-2-yl)-3,6-diazabicyclo[3.1.1]heptane-6-carboxylate obtained in Example 353(a) by a similar method to Example 353(b) except that pyrrolidine was used instead of 2-methoxyethan-1-amine.

(b) (2-(3,6-Diazabicyclo[3.1.1]heptan-3-yl)-7-(thiazol-2-yl)benzo[d]oxazol-4-yl) (pyrrolidin-1-yl)methanone The title compound was obtained in an amount of 9.5 mg from 22 mg of the crude product of tert-butyl 3-(4-(pyrrolidin-1-carbonyl)-7-(thiazol-2-yl)benzo[d]oxazol-2-yl)-3,6-diazabicyclo[3.1.1]heptane-6-carboxylate obtained in Example 360(a) by a similar method to Example 1(c).

Example 361

N-benzyl-2-(3,6-diazabicyclo[3.1.1]heptan-3-yl)-7-(thiazol-2-yl)benzo[d]oxazole-4-carboxamide (a) tert-Butyl 3-(4-(benzylcarbamoyl)-7-(thiazol-2-yl)benzo[d]oxazol-2-yl)-3,6-diazabicyclo[3.1.1]heptane-6-carboxylate The title compound was obtained as a crude product in an amount of 26 mg from 19 mg of tert-butyl 3-(7-(thiazol-2-yl)-4-((2,4,6-trichlorobenzoyl)oxy)benzo[d]oxazol-2-yl)-3,6-diazabicyclo[3.1.1]heptane-6-carboxylate obtained in Example 353(a) by a similar method to Example 353(b) except that phenylmethanamine was used instead of 2-methoxyethan-1-amine.

(b) N-benzyl-2-(3,6-diazabicyclo[3.1.1]heptan-3-yl)-7-(thiazol-2-yl)benzo[d]oxazole-4-carboxamide The title compound was obtained in an amount of 11 mg from 26 mg of the crude product of tert-butyl 3-(4-(benzylcarbamoyl)-7-(thiazol-2-yl)benzo[d]oxazol-2-yl)-3,6-diazabicyclo[3.1.1]heptane-6-carboxylate obtained in Example 361(a) by a similar method to Example 1(c).

Example 362

1-((2-(3,6-Diazabicyclo[3.1.1]heptan-3-yl)-7-(thiazol-2-yl)benzo[d]oxazol-4-yl)oxy)-1,1-difluoro-3-methylbutan-2-ol (a) tert-Butyl 3-(4-(1,1-difluoro-2-hydroxy-3-methylbutoxy)-7-(thiazol-2-yl)benzo[d]oxazol-2-yl)-3,6-diazabicyclo[3.1.1]heptane-6-carboxylate The title compound was obtained in an amount of 150 mg from 200 mg of tert-butyl 3-(4-(2-ethoxy-1,1-difluoro-2-oxoethoxy)-7-(thiazol-2-yl)benzo[d]oxazol-2-yl)-3,6-diazabicyclo[3.1.1]heptane-6-carboxylate obtained in Example 248(d) by a similar method to Example 248 (e) except that 3M isopropylmagnesium chloride solution in diethyl ether was used instead of 0.95M methylmagnesium bromide solution in tetrahydrofuran.

(b) 1-((2-(3,6-Diazabicyclo[3.1.1]heptan-3-yl)-7-(thiazol-2-yl)benzo[d]oxazol-4-yl)oxy)-1,1-difluoro-3-methylbutan-2-ol The title compound was obtained in an amount of 90 mg from 150 mg of tert-butyl 3-(4-(1,1-difluoro-2-hydroxy-3-methylbutoxy)-7-(thiazol-2-yl)benzo[d]oxazol-2-yl)-3,6-diazabicyclo[3.1.1]heptane-6-carboxylate obtained in Example 362 (a) by a similar method to Example 1(c).

Example 363

1-((2-(3,6-Diazabicyclo[3.1.1]heptan-3-yl)-7-(5-chloropyridin-2-yl)benzo[d]oxazol-4-yl)oxy)-1,1-difluoro-2-methylpropan-2-ol (a) tert-Butyl 3-(4-(benxyloxy)-7-(5-chloropyridin-2-yl)benzo[d]oxazol-2-yl)-3,6-diazabicyclo[3.1.1]heptane-6-carboxylate The title compound was obtained in an amount of 500 mg from 1 g of tert-butyl 3-(4-(benzyloxyl)-7-bromobenzo[d]oxazol-2-yl)-3,6-diazabicyclo[3.1.1]heptane-6-carboxylate obtained in Example 248(a) by a similar method to Example 319(a) except that (5-chloropyridin-2-yl)boronic acid was used instead of (5-fluoropyridin-2-yl)boronic acid, palladium (II) acetate was used instead of tetrakis(triphenylphosphine)palladium(0), and further copper (I) chloride (1 equivalent) and 1,1'-bis(diphenylphosphino)ferrocene (0.1 equivalent) were added thereto.

(b) tert-Butyl 3-(7-(5-chloropyridin-2-yl)-4-hydroxybenzo[d]oxazol-2-yl)-3,6-diazabicyclo[3.1.1]heptane-6-carboxylate The title compound was obtained as a crude product in an amount of 200 mg from 180 mg of tert-butyl 3-(4-(benxyloxy)-7-(5-chloropyridin-2-yl)benzo[d]oxazol-2-yl)-3,6-diazabicyclo[3.1.1]heptane-6-carboxylate obtained in Example 363 (a) by a similar method to Example 330(a).

(c) tert-Butyl 3-(7-(5-chloropyridin-2-yl)-4-(2-ethoxy-1,1-difluoro-2-oxoethoxy)benzo[d]oxazol-2-yl)-3,6-diazabicyclo[3.1.1]heptane-6-carboxylate The title compound was obtained in an amount of 45 mg from 200 mg of the crude product of tert-butyl 3-(7-(5-chloropyridin-2-yl)-4-hydroxybenzo[d]oxazol-2-yl)-3,6-diazabicyclo[3.1.1]heptane-6-carboxylate obtained in Example 363(b) by a similar method to Example 248 (d).

(d) tert-Butyl 3-(7-(5-chloropyridin-2-yl)-4-(2-ethoxy-1,1-difluoro-2-hydroxy-3-methylpropoxy)benzo[d]oxazol-2-yl)-3,6-diazabicyclo[3.1.1]heptane-6-carboxylate The title compound was obtained in an amount of 20 mg from 45 mg of tert-butyl 3-(7-(5-chloropyridin-2-yl)-4-(2-ethoxy-1,1-difluoro-2-oxoethoxy)benzo[d]oxazol-2-yl)-3,6-diazabicyclo[3.1.1]heptane-6-carboxylate obtained in Example 363(c) by a similar method to Example 248(e) except that 3M methylmagnesium bromide solution in diethyl ether was used instead of 0.95M methylmagnesium bromide solution in tetrahydrofuran.

(e) 1-((2-(3,6-Diazabicyclo[3.1.1]heptan-3-yl)-7-(5-chloropyridin-2-yl)benzo[d]oxazol-4-yl)oxy)-1,1-difluoro-2-methylpropan-2-ol The title compound was obtained in an amount of 8 mg from 20 mg of tert-butyl 3-(7-(5-chloropyridin-2-yl)-4-(2-ethoxy-1,1-difluoro-2-hydroxy-3-methylpropoxy)benzo[d]

oxazol-2-yl)-3,6-diazabicyclo[3.1.1]heptane-6-carboxylate obtained in Example 363 (d) by a similar method to Example 315(e).

Example 364

3-((2-(3,6-Diazabicyclo[3.1.1]heptan-3-yl)-7-(thiazol-2-yl)benzo[d]oxazol-4-yl)oxy)-3,3-difluoro-2-methylpropane-1,2-diol (Optically Active)

109.0 mg of racemic 3-((2-(3,6-diazabicyclo[3.1.1]heptan-3-yl)-7-(thiazol-2-yl)benzo[d]oxazol-4-yl)oxy)-3,3-difluoro-2-methylpropane-1,2-diol obtained in Example 326(b) was resolved by a preparative HPLC (YMC, Multiple preparative HPLC (LC-forte/R) column: DAICEL CHIRALPAK IC (particle diameter: 5 μm, column diameter: 2 cm, column length: 25 cm), eluent, hexane:isopropyl alcohol: diethyamine=50:50:0.1, flow rate: 19.8 mL/min, detection: UV 254 nm) and the title compound was obtained in an amount of 26.8 mg by concentrating fractions with the shorter retention time peak.

Example 365

3-((2-(3,6-Diazabicyclo[3.1.1]heptan-3-yl)-7-(thiazol-2-yl)benzo[d]oxazol-4-yl)oxy)-3,3-difluoro-2-methylpropane-1,2-diol (Optically Active, Enantiomer of Example 364)

The title compound was obtained in an amount of 27.3 mg by concentrating the fractions with the longer retention time peak obtained in Example 364.

Example 366

2-(3,6-Diazabicyclo[3.1.1]heptan-3-yl)-7-(thiazol-2-yl)benzo[d]oxazole-4-carboxylic acid 16 mg of ethyl 2-(3,6-diazabicyclo[3.1.1]heptan-3-yl)-7-(thiazol-2-yl)benzo[d]oxazole-4-carboxylate obtained in Example 113 and lithium hydroxide monohydrate (17 mg, 10 equivalents) were dissolved in tetrahydrofuran (0.2 mL) and distilled water (0.2 mL), followed by stirring at room temperature for 4 days. The residue obtained by vacuum concentration of the reaction mixture was purified by a preparative HPLC (Gilson, column: Sepax GP-C18 (particle diameter: 5 μm, column diameter: 2.12 cm, column length: 10 cm), eluent, water:acetonitrile=90:10-10:90, flow rate: 15 mL/min, detection: UV254 nm) to afford 14 mg of the title compound.

Example 367

2-(3,6-Diazabicyclo[3.1.1]heptan-3-yl)-N-hydroxy-7-(thiazol-2-yl)benzo[d]oxazole-4-carboxamide (a) tert-Butyl 3-(4-(hydroxycarbamoyl)-7-(thiazol-2-yl)benzo[d]oxazol-2-yl)-3,6-diazabicyclo[3.1.1]heptane-6-carboxylate The title compound was obtained as a crude product in an amount of 20 mg from 20 mg of tert-butyl 3-(7-(thiazol-2-yl)-4-((2,4,6-trichlorobenzoyl)oxy)benzo[d]oxazol-2-yl)-3,6-diazabicyclo[3.1.1]heptane-6-carboxylate obtained in Example 353(a) by a similar method to Example 353(b) except that hydroxylamine monohydrate was used instead of 2-methoxyethan-1-amine and further triethylamine (2 equivalents) was added thereto.

(b) 2-(3,6-Diazabicyclo[3.1.1]heptan-3-yl)-N-hydroxy-7-(thiazol-2-yl)benzo[d]oxazole-4-carboxamide The title compound was obtained in an amount of 11 mg from 20 mg of the crude product of tert-butyl 3-(4-(hydroxycarbamoyl)-7-(thiazol-2-yl)benzo[d]oxazol-2-yl)-3,6-diazabicyclo[3.1.1]heptane-6-carboxylate obtained in Example 367(a) by a similar method to Example 1(c).

Example 368

3-(5-(2-Hydroxypropan-2-yl)-7-(thiazol-2-yl)-4-(trifluoromethoxy)benzo[d]oxazol-2-yl)-3,8-diazabicyclo[3.2.1]octan-8-ol 20 mg of 2-(2-(3,8-diazabicyclo[3.2.1]octan-3-yl)-7-(thiazol-2-yl)-4-(trifluoromethoxy)benzo[d]oxazol-5-yl)propan-2-ol obtained in Example 195 was dissolved in chloroform (0.5 mL), then mCPBA (content of water: about 30%) (17.1 mg, 1.5 equivalents) was added thereto, followed by stirring at room temperature for 1.5 hours. mCPBA (content of water: about 30%) (16.5 mg, 1.5 equivalents) was added thereto again, followed by stirring at room temperature for 1.5 hours. Furthermore, Methanol (0.5 mL) and potassium carbonate (36 mg, 6 equivalents) were added thereto, followed by stirring overnight. Distilled water and chloroform were added to the reaction mixture. Thereafter, the organic phase was dried over anhydrous sodium sulfate, followed by filtration and vacuum concentration of the filtrate, and thus obtaining 9.7 mg of the title compound by purification of the residue through silica gel column chromatography (ethyl acetate:methanol=9:1).

Example 369

2-(3,6-Diazabicyclo[3.1.1]heptan-3-yl)-4-morpholino-7-(thiazol-2-yl)benzo[d]oxazole (a) tert-Butyl 3-(4-morpholino-7-(thiazol-2-yl)benzo[d]oxazol-2-yl)-3,6-diazabicyclo[3.1.1]heptane-6-carboxylate 28 mg of tert-butyl 3-(7-(thiazol-2-yl)-4-(((trifluoromethyl)sulfonyl)oxy)benzo[d]oxazol-2-yl)-3,6-diazabicyclo[3.1.1]heptane-6-carboxylate obtained in Example 334(a), caesium carbonate (28 mg, 1.5 equivalents), palladium (II) acetate (2.0 mg, 0.1 equivalent) and 2,2'-bis(diphenylphosphanyl)-1,1'-binaphthalene (4.1 mg, 0.1 equivalent) were dissolved in toluene (0.5 mL), then morpholine (6 μL, 1.2 equivalents) was added thereto, followed by heat refluxing overnight. Thereafter, reaction mixture was subjected to Celite® filtration, followed by vacuum concentration of the filtrate, and thus obtaining 10 mg of the title compound by purification of the residue through silica gel column chromatography (hexane:ethyl acetate=1:0-1:1).

(b) 2-(3,6-Diazabicyclo[3.1.1]heptan-3-yl)-4-morpholino-7-(thiazol-2-yl)benzo[d]oxazole The title compound was obtained in an amount of 6.0 mg from 10 mg of tert-butyl 3-(4-morpholino-7-(thiazol-2-yl)

benzo[d]oxazol-2-yl)-3,6-diazabicyclo[3.1.1]heptane-6-carboxylate obtained in Example 369 (a) by a similar method to Example 1(c).

Example 370

3-((2-(3,6-Diazabicyclo[3.1.1]heptan-3-yl)-7-(thiazol-2-yl)benzo[d]oxazol-4-yl)oxy)-3,3-difluoropropane-1,2-diol (a) tert-Butyl 3-(4-(1,1-difluoro-2,3-difluoropropoxy)-7-(thiazol-2-yl)benzo[d]oxazol-2-yl)-3,6-diazabicyclo[3.1.1]heptane-6-carboxylate 24.5 mg of tert-butyl 3-(4-((1,1-difluoroallyl)oxy)-7-(thiazol-2-yl)benzo[d]oxazol-2-yl)-3,6-diazabicyclo[3.1.1]heptane-6-carboxylate obtained in Example 351(a) was dissolved in acetone-water (1 mL), then 4-methylmorpholine N-oxide (8.8 mg, 1.5 equivalents) and osmium tetroxide (4% in water) (25 μL, 0.05 equivalent) were added thereto, followed by stirring at room temperature for 24 hours. Distilled water and ethyl acetate were added to the reaction mixture. Thereafter, reaction mixture was subjected to Celite® filtration, the organic phase was dried over anhydrous sodium sulfate, followed by filtration and vacuum concentration of the filtrate, and thus obtaining 19.4 mg of the title compound by purification of the residue through silica gel column chromatography (hexane:ethyl acetate=1:4).

(b) 3-((2-(3,6-Diazabicyclo[3.1.1]heptan-3-yl)-7-(thiazol-2-yl)benzo[d]oxazol-4-yl)oxy)-3,3-difluoropropane-1,2-diol The title compound was obtained in an amount of 16.4 mg from 22.8 mg of tert-butyl 3-(4-(1,1-difluoro-2,3-difluoropropoxy)-7-(thiazol-2-yl)benzo[d]oxazol-2-yl)-3,6-diazabicyclo[3.1.1]heptane-6-carboxylate obtained in Example 370 (a) by a similar method to Example 1(c).

Example 371

3-(4-(1,1-Difluoro-2-hydroxy-2-methylpropoxy)-7-(thiazol-2-yl)benzo[d]oxazol-2-yl)-3,6-diazabicyclo[3.1.1]heptan-6-ol 211.2 mg of 1-((2-(3,6-diazabicyclo[3.1.1]heptan-3-yl)-7-(thiazol-2-yl)benzo[d]oxazol-4-yl)oxy)-1,1-difluoro-2-methylpropan-2-ol obtained in Example 248 was dissolved in chloroform (5 mL), then mCPBA (content of water: about 30%) (184.9 mg, 1.5 equivalents) was added thereto, followed by stirring at room temperature for 1 hour. Further, Methanol (5 mL) and potassium carbonate (207.3 mg, 3 equivalents) were added thereto, followed by stirring for 1 hour. Distilled water and chloroform were added to the reaction mixture. Thereafter, the organic phase was dried over anhydrous sodium sulfate, followed by filtration and vacuum concentration of the filtrate, and thus obtaining 83.3 mg of the title compound by purification of the residue through silica gel column chromatography (ethyl acetate:methanol=9:1).

Example 372

3-(4-(1,1-Difluoro-2-hydroxypropoxy)-7-(thiazol-2-yl)benzo[d]oxazol-2-yl)-3,6-diazabicyclo[3.1.1]heptan-6-ol (Optically Active)

The title compound was obtained in an amount of 13.5 mg from 40.8 mg of 1-((2-(3,6-diazabicyclo[3.1.1]heptan-3-yl)-7-(thiazol-2-yl)benzo[d]oxazol-4-yl)oxy)-1,1-difluoropropan-2-ol (Optically Active) Obtained in Example 251 by a similar method to Example 371.

Example 373

3-(4-(1,1-Difluoro-2-hydroxypropoxy)-7-(thiazol-2-yl)benzo[d]oxazol-2-yl)-3,6-diazabicyclo[3.1.1]heptan-6-ol (enantiomer of Example 372)

The title compound was obtained in an amount of 16.9 mg from 40.8 mg of 1-((2-(3,6-diazabicyclo[3.1.1]heptan-3-yl)-7-(thiazol-2-yl)benzo[d]oxazol-4-yl)oxy)-1,1-difluoropropan-2-ol (Optically Active, Enantiomer of Example 251) obtained in Example 252 by a similar method to Example 371.

Example 374

3-(4-(1,1-Difluoro-2-hydroxyethoxy)-7-(thiazol-2-yl)benzo[d]oxazol-2-yl)-3,6-diazabicyclo[3.1.1]heptan-6-ol The title compound was obtained in an amount of 9.3 mg from 39.4 mg of 2-((2-(3,6-diazabicyclo[3.1.1]heptan-3-yl)-7-(thiazol-2-yl)benzo[d]oxazol-4-yl)oxy)-2,2-difluoroethan-1-ol obtained in Example 249 by a similar method to Example 371.

Example 375

3-(5-Chloro-7-(thiazol-2-yl)-4-(trifluoromethoxy)benzo[d]oxazol-2-yl)-3,8-diazabicyclo[3.2.1]octan-8-ol The title compound was obtained in an amount of 16.9 mg from 43.0 mg of 2-(3,8-diazabicyclo[3.2.1]octan-3-yl)-5-chloro-7-(thiazol-2-yl)-4-(trifluoromethoxy)benzo[d]oxazole obtained in Example 1 by a similar method to Example 371.

Example 376

(2-((2-(3,6-Diazabicyclo[3.1.1]heptan-3-yl)-7-(thiazol-2-yl)benzo[d]oxazol-4-yl)oxy)pyridin-3-yl)methanol (a) tert-Butyl 3-(4-((3-(methoxycarbonyl)pyridin-2-yl)oxy)-7-(thiazol-2-yl)benzo[d]oxazol-2-yl)-3,6-diazabicyclo[3.1.1]heptane-6-carboxylate The title compound was obtained in an amount of 26 mg from 51 mg of tert-butyl 3-(4-hydroxy-7-(thiazol-2-yl)benzo[d]oxazol-2-yl)-3,6-diazabicyclo[3.1.1]heptane-6-carboxylate obtained in Example 248 (c) by a similar method to Reference Example 23(a) except that except that methyl 2-chloronicotinate was used instead of benzyl bromide and stirred at 120° C.

(b) Methyl (2-((2-(3,6-diazabicyclo[3.1.1]heptan-3-yl)-7-(thiazol-2-yl)benzo[d]oxazol-4-yl)oxy)nicotinate The title compound was obtained in an amount of 11 mg from 18 mg of tert-butyl 3-(4-((3-(methoxycarbonyl)pyridin-2-yl)oxy)-7-(thiazol-2-yl)benzo[d]oxazol-2-yl)-3,6-diazabicyclo[3.1.1]heptane-6-carboxylate obtained in Example 376(a) by a similar method to Example 1(c).

(c) (2-((2-(3,6-Diazabicyclo[3.1.1]heptan-3-yl)-7-(thiazol-2-yl)benzo[d]oxazol-4-yl)oxy)pyridin-3-yl)methanol The title compound was obtained in an amount of 11 mg from 4.6 mg of methyl (2-((2-(3,6-diazabicyclo[3.1.1]heptan-3-yl)-7-(thiazol-2-yl)benzo[d]oxazol-4-yl)oxy)nicotinate obtained in Example 376 (b) by a similar method to Example 250(c).

Example 377

1-((2-(3,6-Diazabicyclo[3.1.1]heptan-3-yl)-7-(thiazol-2-yl)benzo[d]oxazol-4-yl)oxy)-1,1-difluoropropane-2,2-diol The title compound was obtained in an amount of 16.1 mg from 30.0 mg of tert-butyl 3-(4-(1,1-difluoro-2,2-dihydroxypropoxy)-7-(thiazol-2-yl)benzo[d]oxazol-2-yl)-3,6-diazabicyclo[3.1.1]heptane-6-carboxylate obtained in Example 250(b) by a similar method to Example 250(c)

Example 378

3-(7-(Thiazol-2-yl)-4-(2,2,2-trifluoro-1-hydroxyethyl)benzo[d]oxazol-2-yl)-3,8-diazabicyclo[3.2.1]octan-8-ol (Optically Active)

The title compound was obtained in an amount of 16.4 mg from 41.0 mg of 1-(2-(3,8-diazabicyclo[3.2.1]octan-3-yl)-7-(thiazol-2-yl)benzo[d]oxazol-4-yl)-2,2,2-trifluoroethan-1-ol (Optically Active) Obtained in Example 118 by a similar method to Example 371.

Example 379

3-(7-(Thiazol-2-yl)-4-(2,2,2-trifluoro-1-hydroxyethyl)benzo[d]oxazol-2-yl)-3,8-diazabicyclo[3.2.1]octan-8-ol (enantiomer of Example 378)

The title compound was obtained in an amount of 15.7 mg from 41.0 mg of 1-(2-(3,8-diazabicyclo[3.2.1]octan-3-yl)-7-(thiazol-2-yl)benzo[d]oxazol-4-yl)-2,2,2-trifluoroethan-1-ol (Optically Active, Enantiomer of Example 118) obtained in Example 119 by a similar method to Example 371.

Example 380

3-(7-(Thiazol-2-yl)-4-(trifluoromethoxy)benzo[d]oxazol-2-yl)-3,6-diazabicyclo[3.1.1]heptan-6-ol The title compound was obtained in an amount of 4.4 mg from 20 mg of 2-(3,6-diazabicyclo[3.1.1]heptan-3-yl)-7-(thiazol-2-yl)-4-(trifluoromethoxy)benzo[d]oxazole obtained in Example 29 by a similar method to Example 371.

Example 381

3-(5-(2-Hydroxypropan-2-yl)-7-(thiazol-2-yl)-4-(trifluoromethyl)benzo[d]oxazol-2-yl)-3,8-diazabicyclo[3.2.1]octan-8-ol The title compound was obtained in an amount of 6.0 mg from 21 mg of 2-(2-(3,8-diazabicyclo[3.2.1]octan-3-yl)-7-(thiazol-2-yl)-4-(trifluoromethyl)benzo[d]oxazol-5-yl)propan-2-ol obtained in Example 177 by a similar method to Example 371.

Example 382

2-(3,6-Diazabicyclo[3.1.1]heptan-3-yl)-7-(thiazol-2-yl)benzo[d]oxazole (a) tert-Butyl 3-(7-(thiazol-2-yl)benzo[d]oxazol-2-yl)-3,6-diazabicyclo[3.1.1]heptane-6-carboxylate The title compound was obtained in an amount of 23 mg from 30 mg of tert-butyl 3-(7-(thiazol-2-yl)-4-(((trifluoromethyl)sulfonyl)oxy)benzo[d]oxazol-2-yl)-3,6-diazabicyclo[3.1.1]heptane-6-carboxylate obtained in Example 334 (a) by a similar method to Example 369(a) except that cyclopropanamine was used instead of morpholine, further 0.2 equivalent of palladium (II) acetate was added thereto, and a microwave reactor (by Biotage, 120° C., 1 hour) was used.

(b) 2-(3,6-Diazabicyclo[3.1.1]heptan-3-yl)-7-(thiazol-2-yl)benzo[d]oxazole

The title compound was obtained in an amount of 8.8 mg from 20 mg of tert-butyl 3-(7-(thiazol-2-yl)benzo[d]oxazol-2-yl)-3,6-diazabicyclo[3.1.1]heptane-6-carboxylate obtained in Example 382 (a) by a similar method to Example 1(c).

Example 383

3-(5-(1-Hydroxyethyl)-7-(thiazol-2-yl)-4-(trifluoromethoxy)benzo[d]oxazol-2-yl)-3,8-diazabicyclo[3.2.1]octan-8-ol The title compound was obtained in an amount of 6.2 mg from 20 mg of 1-(2-(3,8-diazabicyclo[3.2.1]octan-3-yl)-7-(thiazol-2-yl)-4-(trifluoromethoxy)benzo[d]oxazol-5-yl)ethan-1-ol obtained in Example 202 by a similar method to Example 371.

Example 384

3-(5-(1-Hydroxyethyl)-7-(thiazol-2-yl)-4-(trifluoromethyl)benzo[d]oxazol-2-yl)-3,8-diazabicyclo[3.2.1]octan-8-ol The title compound was obtained in an amount of 6.9 mg from 20 mg of 1-(2-(3,8-diazabicyclo[3.2.1]octan-3-yl)-7-(thiazol-2-yl)-4-(trifluoromethyl)benzo[d]oxazol-5-yl)ethan-1-ol obtained in Example 181 by a similar method to Example 371.

Example 385

2-(3,6-Diazabicyclo[3.1.1]heptan-3-yl)-N-(2-hydroxyethyl)-7-(thiazol-2-yl)benzo[d]oxazole-4-sulfonamide (a) tert-Butyl 3-(4-(chlorosulfonyl)-7-(thiazol-2-yl)benzo[d]oxazol-2-yl)-3,6-diazabicyclo[3.1.1]heptane-6-carboxylate 566.8 mg of tert-butyl 3-(7-(thiazol-2-yl)-4-(((trifluoromethyl)sulfonyl)oxy)benzo[d]oxazol-2-yl)-3,6-diazabicyclo[3.1.1]heptane-6-carboxylate obtained in Example 334(a)

was dissolved in 1,4-dioxane (10 mL), and then triisopropylsilanethiol (444 µL, 2 equivalents), triethylamine (289 µL, 2 equivalents), tris(dibenzylideneacetone)dipalladium (0) (95.0 mg, 0.1 equivalent) and 4,5-bis(diphenylphosphino)-9,9-dimethylxanthene (120.0 mg, 0.2 equivalent) were added thereto, followed by stirring using a microwave reactor (manufactured by Biotage, conditions: 150° C., 1 hour). Distilled water and ethyl acetate were added to the reaction mixture. Thereafter, reaction mixture was subjected to Celite® filtration, the organic phase was dried over anhydrous sodium sulfate, followed by filtration and vacuum concentration of the filtrate. The residue was dissolved in acetonitrile (10 ml), and 1M aqueous hydrochloric acid solution (2 mL) and N-chlorosuccinimide (553.9 mg, 4 equivalents) were added to the residue followed by stirring at room temperature for 1 hour. Sodium hydrogen carbonate aqueous solution was added to the reaction mixture. The organic phase was extracted using chloroform and dried over anhydrous sodium sulfate, followed by filtration and vacuum concentration of the filtrate, and thus obtaining 364.2 mg of the title compound by purification of the residue through silica gel column chromatography (hexane:ethyl acetate=1:1).

(b) tert-Butyl 3-(4-(N-(2-hydroxyethyl)sulfamoyl)-7-(thiazol-2-yl)benzo[d]oxazol-2-yl)-3,6-diazabicyclo[3.1.1]heptane-6-carboxylate 24.8 mg of tert-butyl 3-(4-(chlorosulfonyl)-7-(thiazol-2-yl)benzo[d]oxazol-2-yl)-3,6-diazabicyclo[3.1.1]heptane-6-carboxylate obtained in Example 385 (a) was dissolved in acetonitrile (1 mL), then 2-aminoethanol (9 µL, 3 equivalents) was added thereto, followed by stirring at room temperature for 1 hour. Distilled water and ethyl acetate were added to the reaction mixture. The organic phase was dried over anhydrous sodium sulfate, followed by filtration and vacuum concentration of the filtrate, and thus obtaining 26.1 mg of the title compound by purification of the residue through silica gel column chromatography (hexane:ethyl acetate=1:4).

(c) 2-(3,6-Diazabicyclo[3.1.1]heptan-3-yl)-N-(2-hydroxyethyl)-7-(thiazol-2-yl)benzo[d]oxazole-4-sulfonamide The title compound was obtained in an amount of 13.8 mg from 26.1 mg of tert-butyl 3-(4-(N-(2-hydroxyethyl)sulfamoyl)-7-(thiazol-2-yl)benzo[d]oxazol-2-yl)-3,6-diazabicyclo[3.1.1]heptane-6-carboxylate obtained in Example 385 (b) by a similar method to Example 1(c).

Example 386

2-(3,6-Diazabicyclo[3.1.1]heptan-3-yl)-N-methyl-7-(thiazol-2-yl)benzo[d]oxazole-4-sulfonamide (a) tert-Butyl 3-(4-(N-methylsulfamoyl)-7-(thiazol-2-yl)benzo[d]oxazol-2-yl)-3,6-diazabicyclo[3.1.1] heptane-6-carboxylate The title compound was obtained in an amount of 24.6 mg from 24.8 mg of tert-butyl 3-(4-(chlorosulfonyl)-7-(thiazol-2-yl)benzo[d]oxazol-2-yl)-3,6-diazabicyclo[3.1.1]heptane-6-carboxylate obtained in Example 385 (a) by a similar method to Example 385(b) except that 40% methanolic solution of methylamine was used instead of 2-aminoethanol.

(b) 2-(3,6-Diazabicyclo[3.1.1]heptan-3-yl)-N-methyl-7-(thiazol-2-yl)benzo[d]oxazole-4-sulfonamide The title compound was obtained in an amount of 17.1 mg from 24.6 mg of tert-butyl 3-(4-(N-methylsulfamoyl)-7-(thiazol-2-yl)benzo[d]oxazol-2-yl)-3,6-diazabicyclo[3.1.1] heptane-6-carboxylate obtained in Example 386(a) by a similar method to Example 1(c).

Example 387

2-(3,6-Diazabicyclo[3.1.1]heptan-3-yl)-N-(2-methoxyethyl)-7-(thiazol-2-yl)benzo[d]oxazole-4-sulfonamide (a) tert-Butyl 3-(4-(N-(2-methoxyethyl)sulfamoyl)-7-(thiazol-2-yl)benzo[d]oxazol-2-yl)-3,6-diazabicyclo[3.1.1]heptane-6-carboxylate The title compound was obtained in an amount of 26.8 mg from 24.8 mg of tert-butyl 3-(4-(chlorosulfonyl)-7-(thiazol-2-yl)benzo[d]oxazol-2-yl)-3,6-diazabicyclo[3.1.1]heptane-6-carboxylate obtained in Example 385 (a) by a similar method to Example 385 (b) except that 2-methoxyethylamine was used instead of 2-aminoethanol.

(b) 2-(3,6-Diazabicyclo[3.1.1]heptan-3-yl)-N-(2-methoxyethyl)-7-(thiazol-2-yl)benzo[d]oxazole-4-sulfonamide The title compound was obtained in an amount of 19.8 mg from 26.8 mg of tert-butyl 3-(4-(N-(2-methoxyethyl)sulfamoyl)-7-(thiazol-2-yl)benzo[d]oxazol-2-yl)-3,6-diazabicyclo[3.1.1]heptane-6-carboxylate obtained in Example 387 (a) by a similar method to Example 1(c).

Example 388

2-(3,6-Diazabicyclo[3.1.1]heptan-3-yl)-N,N-dimethyl-7-(thiazol-2-yl)benzo[d]oxazole-4-sulfonamide (a) tert-Butyl 3-(4-(N,N-dimethylsulfamoyl)-7-(thiazol-2-yl)benzo[d]oxazol-2-yl)-3,6-diazabicyclo [3.1.1]heptane-6-carboxylate The title compound was obtained in an amount of 25.3 mg from 24.8 mg of tert-butyl 3-(4-(chlorosulfonyl)-7-(thiazol-2-yl)benzo[d]oxazol-2-yl)-3,6-diazabicyclo[3.1.1]heptane-6-carboxylate obtained in Example 385 (a) by a similar method to Example 385 (b) except that dimethylamine hydrochloride was used instead of 2-aminoethanol, and further 1.5 equivalents of triethylamine was added thereto.

(b) 2-(3,6-Diazabicyclo[3.1.1]heptan-3-yl)-N,N-dimethyl-7-(thiazol-2-yl)benzo[d]oxazole-4-sulfonamide The title compound was obtained in an amount of 15.9 mg from 25.3 mg of tert-butyl 3-(4-(N,N-dimethylsulfamoyl)-7-(thiazol-2-yl)benzo[d]oxazol-2-yl)-3,6-diazabicyclo [3.1.1]heptane-6-carboxylate obtained in Example 388(a) by a similar method to Example 1(c).

Example 389

2-(3,6-Diazabicyclo[3.1.1]heptan-3-yl)-N-(2-hydroxyethyl)-N-methyl-7-(thiazol-2-yl)benzo[d]oxazole-4-sulfonamide (a) tert-Butyl 3-(4-(N-(2-hydroxyethyl)-N-methylsulfamoyl-7-(thiazol-2-yl)benzo[d]oxazol-2-yl)-3,6-diazabicyclo[3.1.1]heptane-6-carboxylate The title compound was obtained in an amount of 25.3 mg from 24.8 mg of tert-butyl 3-(4-(chlorosulfonyl)-7-(thiazol-2-yl)benzo[d]oxazol-2-yl)-3,6-diazabicyclo[3.1.1]heptane-6-carboxylate obtained in Example 385 (a) by a similar method to Example 385(b) except that 2-(methylamino)ethanol was used instead of 2-aminoethanol.

(b) 2-(3,6-Diazabicyclo[3.1.1]heptan-3-yl)-N-(2-hydroxyethyl)-N-methyl-7-(thiazol-2-yl)benzo[d]oxazole-4-sulfonamide The title compound was obtained in an amount of 19.5 mg from 25.3 mg of tert-butyl 3-(4-(N-(2-hydroxyethyl)-N-methylsulfamoyl-7-(thiazol-2-yl)benzo[d]oxazol-2-yl)-3,6-diazabicyclo[3.1.1]heptane-6-carboxylate obtained in Example 389(a) by a similar method to Example 1(c).

Example 390

2-(3,6-Diazabicyclo[3.1.1]heptan-3-yl)-4-(pyrrolidin-1-ylsulfonyl)-7-(thiazol-2-yl)benzo[d]oxazole (a) tert-Butyl 3-(4-(pyrrolidin-1-ylsulfonyl)-7-(thiazol-2-yl)benzo[d]oxazol-2-yl)-3,6-diazabicyclo[3.1.1]heptane-6-carboxylate The title compound was obtained in an amount of 26.6 mg from 24.8 mg of tert-butyl 3-(4-(chlorosulfonyl)-7-(thiazol-2-yl)benzo[d]oxazol-2-yl)-3,6-diazabicyclo[3.1.1]heptane-6-carboxylate obtained in Example 385 (a) by a similar method to Example 385(b) except that pyrrolidine was used instead of 2-aminoethanol.

(b) 2-(3,6-Diazabicyclo[3.1.1]heptan-3-yl)-4-(pyrrolidin-1-ylsulfonyl)-7-(thiazol-2-yl)benzo[d]oxazole The title compound was obtained in an amount of 18.8 mg from 26.6 mg of tert-butyl 3-(4-(pyrrolidin-1-ylsulfonyl)-7-(thiazol-2-yl)benzo[d]oxazol-2-yl)-3,6-diazabicyclo[3.1.1]heptane-6-carboxylate obtained in Example 390(a) by a similar method to Example 1(c).

(Example 391) 2-(3,6-Diazabicyclo[3.1.1]heptan-3-yl)-4-(morpholinosulfonyl)-7-(thiazol-2-yl)benzo[d]oxazole (a) tert-Butyl 3-(4-(morpholinosulfonyl)-7-(thiazol-2-yl)benzo[d]oxazol-2-yl)-3,6-diazabicyclo[3.1.1]heptane-6-carboxylate The title compound was obtained in an amount of 27.4 mg from 24.8 mg of tert-butyl 3-(4-(chlorosulfonyl)-7-(thiazol-2-yl)benzo[d]oxazol-2-yl)-3,6-diazabicyclo[3.1.1]heptane-6-carboxylate obtained in Example 385 (a) by a similar method to Example 385(b) except that morpholine was used instead of 2-aminoethanol.

(b) 2-(3,6-Diazabicyclo[3.1.1]heptan-3-yl)-4-(morpholinosulfonyl)-7-(thiazol-2-yl)benzo[d]oxazole The title compound was obtained in an amount of 20.6 mg from 27.4 mg of tert-butyl 3-(4-(morpholinosulfonyl)-7-(thiazol-2-yl)benzo[d]oxazol-2-yl)-3,6-diazabicyclo[3.1.1]heptane-6-carboxylate obtained in Example 391(a) by a similar method to Example 1(c).

Example 392

2-(3,6-Diazabicyclo[3.1.1]heptan-3-yl)-4-(1,1-difluoro-2-methoxyethoxy)-7-(thiazol-2-yl)benzo[d]oxazole (a) tert-Butyl 3-(4-(1,1-difluoro-2-methoxyethoxy)-7-(thiazol-2-yl)benzo[d]oxazol-2-yl)-3,6-diazabicyclo[3.1.1]heptane-6-carboxylate The title compound was obtained in an amount of 28 mg from 30 mg of tert-butyl 3-(4-(1,1-difluoro-2-hydroxyethoxy)-7-(thiazol-2-yl)benzo[d]oxazol-2-yl)-3,6-diazabicyclo[3.1.1]heptane-6-carboxylate obtained in Example 249 (a) by a similar method to Example 102 (e).

(b) 2-(3,6-Diazabicyclo[3.1.1]heptan-3-yl)-4-(1,1-difluoro-2-methoxyethoxy)-7-(thiazol-2-yl)benzo[d]oxazole The title compound was obtained in an amount of 19 mg from 26 mg of tert-butyl 3-(4-(1,1-difluoro-2-methoxyethoxy)-7-(thiazol-2-yl)benzo[d]oxazol-2-yl)-3,6-diazabicyclo[3.1.1]heptane-6-carboxylate obtained in Example 392 (a) by a similar method to Example 1(c).

Example 393

2-(3,6-Diazabicyclo[3.1.1]heptan-3-yl)-4-(1,1-difluoro-2-methoxy-2-methylpropoxy)-7-(thiazol-2-yl)benzo[d]oxazole (a) tert-Butyl 3-(4-(1,1-difluoro-2-methoxy-2-methylpropoxy)-7-(thiazol-2-yl)benzo[d]oxazol-2-yl)-3,6-diazabicyclo[3.1.1]heptane-6-carboxylate The title compound was obtained in an amount of 30 mg from 31 mg of tert-butyl 3-(4-(1,1-difluoro-2-hydroxy)-2-methylpropoxy)-7-(thiazol-2-yl)benzo[d]oxazol-2-yl)-3,6-diazabicyclo[3.1.1]heptane-6-carboxylate obtained in Example 248 (e) by a similar method to Example 102 (e).

(b) 2-(3,6-Diazabicyclo[3.1.1]heptan-3-yl)-4-(1,1-difluoro-2-methoxy-2-methylpropoxy)-7-(thiazol-2-yl)benzo[d]oxazole The title compound was obtained in an amount of 9.5 mg from 29 mg of tert-butyl 3-(4-(1,1-difluoro-2-methoxy-2-methylpropoxy)-7-(thiazol-2-yl)benzo[d]oxazol-2-yl)-3,6-diazabicyclo[3.1.1]heptane-6-carboxylate obtained in Example 393 (a) by a similar method to Example 1(c).

Example 394

1-((2-(3,6-Diazabicyclo[3.1.1]heptan-3-yl)-7-(1-methyl-1H-pyrazol-3-yl)benzo[d]oxazol-4-yl)oxy)-1,1-difluoro-2-methylpropan-2-ol (a) tert-Butyl 3-(4-(benzyloxy)-7-(1-methyl-1H-pyrazol-3-yl)benzo[d]oxazol-2-yl)-3,6-diazabicyclo[3.1.1]heptane-6-carboxylate The title compound was obtained in an amount of 80 mg from 100 mg of tert-butyl 3-(4-(benzyloxyl)-7-bromobenzo

[d]oxazol-2-yl)-3,6-diazabicyclo[3.1.1]heptane-6-carboxylate obtained in Example 248(a) by a similar method to Example 363(a) except that 1-methyl-3-(4,4,5,5-tetramethyl-1,3,2-dioxaborolan-2-yl)-1H-pyrazole was used instead of (5-chloropyridin-2-yl)boronic acid.

(b) tert-Butyl 3-(4-hydroxy-7-(1-methyl-1H-pyrazol-3-yl)benzo[d]oxazol-2-yl)-3,6-diazabicyclo[3.1.1]heptane-6-carboxylate The title compound was obtained in an amount of 50 mg from 80 mg of tert-butyl 3-(4-(benzyloxy)-7-(1-methyl-1H-pyrazol-3-yl)benzo[d]oxazol-2-yl)-3,6-diazabicyclo[3.1.1]heptane-6-carboxylate obtained in Example 394 (a) by a similar method to Example 315 (b).

(c) tert-Butyl 3-(4-(2-ethoxy-1,1-difluoro-2-oxoethoxy)-7-(1-methyl-1H-pyrazol-3-yl)benzo[d]oxazol-2-yl)-3,6-diazabicyclo[3.1.1]heptane-6-carboxylate The title compound was obtained in an amount of 30 mg from 50 mg of tert-butyl 3-(4-hydroxy-7-(1-methyl-1H-pyrazol-3-yl)benzo[d]oxazol-2-yl)-3,6-diazabicyclo[3.1.1]heptane-6-carboxylate obtained in Example 394 (b) by a similar method to Example 248 (d).

(d) tert-Butyl 3-(4-(1,1-difluoro-2-hydroxy)-2-methylpropoxy)-7-(1-methyl-1H-pyrazol-3-yl)benzo[d]oxazol-2-yl)-3,6-diazabicyclo[3.1.1]heptane-6-carboxylate The title compound was obtained in an amount of 120 mg from 120 mg of tert-butyl 3-(4-(2-ethoxy-1,1-difluoro-2-oxoethoxy)-7-(1-methyl-1H-pyrazol-3-yl)benzo[d]oxazol-2-yl)-3,6-diazabicyclo[3.1.1]heptane-6-carboxylate obtained in Example 394 (c) by a similar method to Example 248 (e).

(e) 1-((2-(3,6-Diazabicyclo[3.1.1]heptan-3-yl)-7-(1-methyl-1H-pyrazol-3-yl)benzo[d]oxazol-4-yl)oxy)-1,1-difluoro-2-methylpropan-2-ol The title compound was obtained in an amount of 50 mg from 120 mg of tert-butyl 3-(4-(1,1-difluoro-2-hydroxy)-2-methylpropoxy)-7-(1-methyl-1H-pyrazol-3-yl)benzo[d]oxazol-2-yl)-3,6-diazabicyclo[3.1.1]heptane-6-carboxylate obtained in Example 394 (d) by a similar method to Example 315(e).

Example 395

1-((2-(3,6-Diazabicyclo[3.1.1]heptan-3-yl)-7-(thiazol-2-yl)benzo[d]oxazol-4-yl)oxy)-1,1-difluorobutan-2-ol (a) tert-Butyl 3-(4-(1,1-difluoro-2-hydroxybutoxy)-7-(thiazol-2-yl)benzo[d]oxazol-2-yl)-3,6-diazabicyclo[3.1.1]heptane-6-carboxylate The title compound was obtained in an amount of 90 mg from 100 mg of tert-butyl 3-(4-(2-ethoxy-1,1-difluoro-2-oxoethoxy)-7-(thiazol-2-yl)benzo[d]oxazol-2-yl)-3,6-diazabicyclo[3.1.1]heptane-6-carboxylate obtained in Example 248(d) by a similar method to Example 248 (e) except that 3M ethylmagnesium bromide solution in diethyl ether (20 equivalents) was used instead of 0.95M methylmagnesium bromide solution in tetrahydrofuran.

(b) 1-((2-(3,6-Diazabicyclo[3.1.1]heptan-3-yl)-7-(thiazol-2-yl)benzo[d]oxazol-4-yl)oxy)-1,1-difluorobutan-2-ol The title compound was obtained in an amount of 50 mg from 90 mg of tert-butyl 3-(4-(1,1-difluoro-2-hydroxybutoxy)-7-(thiazol-2-yl)benzo[d]oxazol-2-yl)-3,6-diazabicyclo[3.1.1]heptane-6-carboxylate obtained in Example 395 (a) by a similar method to Example 315 (e).

Example 396

2-(3,6-Diazabicyclo[3.1.1]heptan-3-yl)-7-(thiazol-2-yl)benzo[d]oxazole-4-sulfonamide (a) tert-Butyl 3-(4-(sulfamoyl-7-(thiazol-2-yl)benzo[d]oxazol-2-yl)-3,6-diazabicyclo[3.1.1]heptane-6-carboxylate The title compound was obtained in an amount of 20.1 mg from 23.4 mg of tert-butyl 3-(4-(chlorosulfonyl)-7-(thiazol-2-yl)benzo[d]oxazol-2-yl)-3,6-diazabicyclo[3.1.1]heptane-6-carboxylate obtained in Example 385 (a) by a similar method to Example 385(b) except that 28% ammonia water was used instead of 2-aminoethanol.

(b) 2-(3,6-Diazabicyclo[3.1.1]heptan-3-yl)-7-(thiazol-2-yl)benzo[d]oxazole-4-sulfonamide The title compound was obtained in an amount of 15.9 mg from 20.1 mg of tert-butyl 3-(4-(sulfamoyl-7-(thiazol-2-yl)benzo[d]oxazol-2-yl)-3,6-diazabicyclo[3.1.1]heptane-6-carboxylate obtained in Example 396(a) by a similar method to Example 1(c).

Example 397

1-(2-(3,6-Diazabicyclo[3.1.1]heptan-3-yl)-7-(thiazol-2-yl)benzo[d]oxazol-4-yl)piperidin-4-ol (a) tert-Butyl 3-(4-(4-hydroxypiperidin-1-yl)-7-(thiazol-2-yl)benzo[d]oxazol-2-yl)-3,6-diazabicyclo[3.1.1]heptane-6-carboxylate The title compound was obtained in an amount of 20.7 mg from 54.7 mg of tert-butyl 3-(7-(thiazol-2-yl)-4-(((trifluoromethyl)sulfonyl)oxy)benzo[d]oxazol-2-yl)-3,6-diazabicyclo[3.1.1]heptane-6-carboxylate obtained in Example 334 (a) by a similar method to Example 369(a) except that 4-hydroxypiperidine was used instead of morpholine.

(b) 1-(2-(3,6-Diazabicyclo[3.1.1]heptan-3-yl)-7-(thiazol-2-yl)benzo[d]oxazol-4-yl)piperidin-4-ol The title compound was obtained in an amount of 9.9 mg from 20.7 mg of tert-butyl 3-(4-(4-hydroxypiperidin-1-yl)-7-(thiazol-2-yl)benzo[d]oxazol-2-yl)-3,6-diazabicyclo[3.1.1]heptane-6-carboxylate obtained in Example 397(a) by a similar method to Example 1(c).

Example 398

4-(2-(3,6-Diazabicyclo[3.1.1]heptan-3-yl)-7-(thiazol-2-yl)benzo[d]oxazol-4-yl)thiomorpholine 1,1-dioxide (a) tert-Butyl 3-(4-(1,1-dioxidothiomorpholino)-7-(thiazol-2-yl)benzo[d]oxazol-2-yl)-3,6-diazabicyclo[3.1.1]heptane-6-carboxylate The title compound was obtained in an amount of 68.2 mg from 82.0 mg of tert-butyl 3-(7-(thiazol-2-yl)-4-(((trifluoromethyl)sulfonyl)oxy)benzo[d]oxazol-2-yl)-3,6-diazabicyclo[3.1.1]heptane-6-carboxylate obtained in Example 334 (a) by a similar method to Example 369(a) except that thiomorpholine 1,1-dioxide was used instead of morpholine.

(b) 4-(2-(3,6-Diazabicyclo[3.1.1]heptan-3-yl)-7-(thiazol-2-yl)benzo[d]oxazol-4-yl)thiomorpholine 1,1-dioxide The title compound was obtained in an amount of 40.4 mg from 68.2 mg of tert-butyl 3-(4-(1,1-dioxidothiomorpholino)-7-(thiazol-2-yl)benzo[d]oxazol-2-yl)-3,6-diazabicyclo[3.1.1]heptane-6-carboxylate obtained in Example 398 (a) by a similar method to Example 1(c).

Example 399

1-((2-(3,6-Diazabicyclo[3.1.1]heptan-3-yl)-5-bromo-7-(thiazol-2-yl)benzo[d]oxazol-4-yl)oxy)-1,1-difluoro-2-methylpropan-2-ol (a) tert-Butyl 3-(5-bromo-4-hydroxy-7-(thiazol-2-yl)benzo[d]oxazol-2-yl)-3,6-diazabicyclo[3.1.1]heptane-6-carboxylate 99 mg of tert-butyl 3-(4-hydroxy-7-(thiazol-2-yl)benzo[d]oxazol-2-yl)-3,6-diazabicyclo[3.1.1]heptane-6-carboxylate obtained in Example 248 (c) was dissolved in tetrahydrofuran (2 mL), then N-bromosuccinimide (51 mg, 1.1 equivalents) was added thereto, followed by stirring at room temperature for 3.5 hours. Distilled water was added to the reaction mixture. Thereafter, the organic phase was extracted using ethyl acetate, followed by vacuum concentration of the organic phase, and thus obtaining 60 mg of the title compound by purification of the residue through silica gel column chromatography (hexane:ethyl acetate=1:0-1:4).

(b) tert-Butyl 3-(5-bromo-4-(2-ethoxy-1,1-difluoro-2-oxoethoxy)-7-(thiazol-2-yl)benzo[d]oxazol-2-yl)-3,6-diazabicyclo[3.1.1]heptane-6-carboxylate The title compound was obtained in an amount of 45 mg from 60 mg of tert-butyl 3-(5-bromo-4-hydroxy-7-(thiazol-2-yl)benzo[d]oxazol-2-yl)-3,6-diazabicyclo[3.1.1]heptane-6-carboxylate obtained in Example 399(a) by a similar method to Example 248 (d).

(c) tert-Butyl 3-(5-bromo-4-(1,1-difluoro-2-hydroxy-2-methylpropoxy)-7-(thiazol-2-yl)benzo[d]oxazol-2-yl)-3,6-diazabicyclo[3.1.1]heptane-6-carboxylate The title compound was obtained in an amount of 36 mg from 45 mg of tert-butyl 3-(5-bromo-4-(2-ethoxy-1,1-difluoro-2-oxoethoxy)-7-(thiazol-2-yl)benzo[d]oxazol-2-yl)-3,6-diazabicyclo[3.1.1]heptane-6-carboxylate obtained in Example 399(b) by a similar method to Example 327 (e).

(d) 1-((2-(3,6-Diazabicyclo[3.1.1]heptan-3-yl)-5-bromo-7-(thiazol-2-yl)benzo[d]oxazol-4-yl)oxy)-1,1-difluoro-2-methylpropan-2-ol The title compound was obtained in an amount of 7.7 mg from 12 mg of tert-butyl 3-(5-bromo-4-(1,1-difluoro-2-hydroxy-2-methylpropoxy)-7-(thiazol-2-yl)benzo[d]oxazol-2-yl)-3,6-diazabicyclo[3.1.1]heptane-6-carboxylate obtained in Example 399(c) by a similar method to Example 1(c).

Example 400

1-((2-(3,6-Diazabicyclo[3.1.1]heptan-3-yl)-5-chloro-7-(thiazol-2-yl)benzo[d]oxazol-4-yl)oxy)-1,1-difluoro-2-methylpropan-2-ol (a) tert-Butyl 3-(5-chloro-4-(1,1-difluoro-2-hydroxy-2-methylpropoxy)-7-(thiazol-2-yl)benzo[d]oxazol-2-yl)-3,6-diazabicyclo[3.1.1]heptane-6-carboxylate The title compound was obtained in an amount of 58 mg from 60 mg of tert-butyl 3-(4-(1,1-difluoro-2-hydroxy)-2-methylpropoxy)-7-(thiazol-2-yl)benzo[d]oxazol-2-yl)-3,6-diazabicyclo[3.1.1]heptane-6-carboxylate obtained in Example 248(e) by a similar method to Example 399(a) except that N-chlorosuccinimide was used instead of N-bromosuccinimide, and further 0.1 equivalent of p-toluenesulfonic acid monohydrate was added thereto.

(b) 1-((2-(3,6-Diazabicyclo[3.1.1]heptan-3-yl)-5-chloro-7-(thiazol-2-yl)benzo[d]oxazol-4-yl)oxy)-1,1-difluoro-2-methylpropan-2-ol The title compound was obtained in an amount of 37 mg from 57 mg of tert-butyl 3-(5-chloro-4-(1,1-difluoro-2-hydroxy-2-methylpropoxy)-7-(thiazol-2-yl)benzo[d]oxazol-2-yl)-3,6-diazabicyclo[3.1.1]heptane-6-carboxylate obtained in Example 400(a) by a similar method to Example 1(c).

Example 401

2-((2-(3,6-Diazabicyclo[3.1.1]heptan-3-yl)-5-chloro-7-(thiazol-2-yl)benzo[d]oxazol-4-yl)oxy)-2,2-difluoroethan-1-ol (a) tert-Butyl 3-(5-chloro-4-(2-ethoxy-1,1-difluoro-2-oxoethoxy)-7-(thiazol-2-yl)benzo[d]oxazol-2-yl)-3,6-diazabicyclo[3.1.1]heptane-6-carboxylate The title compound was obtained in an amount of 64 mg from 60 mg of tert-butyl 3-(4-(1,1-difluoro-2-hydroxyethoxy)-7-(thiazol-2-yl)benzo[d]oxazol-2-yl)-3,6-diazabicyclo[3.1.1]heptane-6-carboxylate obtained in Example 249 (a) by a similar method to Example 400 (a).

(b) 2-((2-(3,6-Diazabicyclo[3.1.1]heptan-3-yl)-5-chloro-7-(thiazol-2-yl)benzo[d]oxazol-4-yl)oxy)-2,2-difluoroethan-1-ol The title compound was obtained in an amount of 25 mg from 62 mg of tert-butyl 3-(5-chloro-4-(2-ethoxy-1,1-difluoro-2-oxoethoxy)-7-(thiazol-2-yl)benzo[d]oxazol-2-yl)-3, 6-diazabicyclo[3.1.1]heptane-6-carboxylate obtained in Example 401(a) by a similar method to Example 1(c).

Example 402

2-(3,6-Diazabicyclo[3.1.1]heptan-3-yl)-4-(1,1-difluoropropoxy)-7-(thiazol-2-yl)benzo[d]oxazole (a) tert-Butyl 3-(4-(1,1-difluoropropoxy)-7-(thiazol-2-yl)benzo[d]oxazol-2-yl)-3,6-diazabicyclo[3.1.1]heptane-6-carboxylate The title compound was obtained as a crude product in an amount of 17 mg from 20 mg of tert-butyl 3-(4-((1,1-difluoroallyl)oxy)-7-(thiazol-2-yl)benzo[d]oxazol-2-yl)-3,6-diazabicyclo[3.1.1]heptane-6-carboxylate obtained in Example 351(a) by a similar method to Example 315(b) except that methanol was used instead of ethanol and ethyl acetate, and 10 weight % of palladium/carbon was used.

(b) 2-(3,6-Diazabicyclo[3.1.1]heptan-3-yl)-4-(1,1-difluoropropoxy)-7-(thiazol-2-yl)benzo[d]oxazole The title compound was obtained in an amount of 11 mg from 16 mg of the crude product of tert-butyl 3-(4-(1,1-difluoropropoxy)-7-(thiazol-2-yl)benzo[d]oxazol-2-yl)-3,6-diazabicyclo[3.1.1]heptane-6-carboxylate obtained in Example 402 (a) by a similar method to Example 1(c).

Example 403

4-(Benzo[d]oxazol-2-yldifluoromethoxy)-2-(3,6-diazabicyclo[3.1.1]heptan-3-yl)-7-(thiazol-2-yl)benzo[d]oxazole (a) tert-Butyl 3-(4-(benzo[d]oxazol-2-yldifluoromethoxy)-7-(thiazol-2-yl)benzo[d]oxazol-2-yl)-3,6-diazabicyclo[3.1.1]heptane-6-carboxylate The title compound was obtained in an amount of 23 mg from 31 mg of tert-butyl 3-(4-hydroxy-7-(thiazol-2-yl)benzo[d]oxazol-2-yl)-3,6-diazabicyclo[3.1.1]heptane-6-carboxylate obtained in Example 248(c) by a similar method to Example 262(a) except that 2-(bromodifluoromethyl)benzo[d]oxazole was used instead of tetrahydro-2H-pyran-3-yl 4-methylbenzenesulfonate.

(b) 4-(Benzo[d]oxazol-2-yldifluoromethoxy)-2-(3,6-diazabicyclo[3.1.1]heptan-3-yl)-7-(thiazol-2-yl)benzo[d]oxazole The title compound was obtained in an amount of 11 mg from 23 mg of tert-butyl 3-(4-(benzo[d]oxazol-2-yldifluoromethoxy)-7-(thiazol-2-yl)benzo[d]oxazol-2-yl)-3,6-diazabicyclo[3.1.1]heptane-6-carboxylate obtained in Example 403(a) by a similar method to Example 1(c).

Example 404

2-((2-(3,8-Diazabicyclo[3.2.1]octan-3-yl)-7-(thiazol-2-yl)benzo[d]oxazol-4-yl)oxy)-2,2-difluoroethan-1-ol (a) tert-Butyl 3-(4-(2-ethoxy-1,1-difluoro-2-oxoethoxy)-7-(thiazol-2-yl)benzo[d]oxazol-2-yl)-3,8-diazabicyclo[3.2.1]octane-8-carboxylate The title compound was obtained in an amount of 77 mg from 72 mg of tert-butyl 3-(4-hydroxy-7-(thiazol-2-yl)benzo[d]oxazol-2-yl)-3,8-diazabicyclo[3.2.1]octane-8-carboxylate obtained in Example 81(a) by a similar method to Example 248 (d).

(b) tert-Butyl 3-(4-(1,1-difluoro-2-hydroxyethoxy)-7-(thiazol-2-yl)benzo[d]oxazol-2-yl)-3,8-diazabicyclo[3.2.1]octane-8-carboxylate The title compound was obtained in an amount of 34 mg from 49 mg of tert-butyl 3-(4-(2-ethoxy-1,1-difluoro-2-oxoethoxy)-7-(thiazol-2-yl)benzo[d]oxazol-2-yl)-3,8-diazabicyclo[3.2.1]octane-8-carboxylate obtained in Example 404 (a) by a similar method to Example 250(c).

(c) 2-((2-(3,8-Diazabicyclo[3.2.1]octan-3-yl)-7-(thiazol-2-yl)benzo[d]oxazol-4-yl)oxy)-2,2-difluoroethan-1-ol The title compound was obtained in an amount of 21 mg from 32 mg of tert-butyl 3-(4-(1,1-difluoro-2-hydroxyethoxy)-7-(thiazol-2-yl)benzo[d]oxazol-2-yl)-3,8-diazabicyclo[3.2.1]octane-8-carboxylate obtained in Example 404 (b) by a similar method to Example 1(c).

Example 405

1-((2-(3,8-Diazabicyclo[3.2.1]octan-3-yl)-7-(thiazol-2-yl)benzo[d]oxazol-4-yl)oxy)-1,1-difluoro-2-methylpropan-2-ol (a) tert-Butyl 3-(4-(1,1-difluoro-2-hydroxy-2-methylpropoxy)-7-(thiazol-2-yl)benzo[d]oxazol-2-yl)-3,8-diazabicyclo[3.2.1]octane-8-carboxylate The title compound was obtained in an amount of 25 mg from 44 mg of tert-butyl 3-(4-(2-ethoxy-1,1-difluoro-2-oxoethoxy)-7-(thiazol-2-yl)benzo[d]oxazol-2-yl)-3,8-diazabicyclo[3.2.1]octane-8-carboxylate obtained in Example 404 (a) by a similar method to Example 327 (e).

(b) 1-((2-(3,8-Diazabicyclo[3.2.1]octan-3-yl)-7-(thiazol-2-yl)benzo[d]oxazol-4-yl)oxy)-1,1-difluoro-2-methylpropan-2-ol The title compound was obtained in an amount of 14 mg from 23 mg of tert-butyl 3-(4-(1,1-difluoro-2-hydroxy-2-methylpropoxy)-7-(thiazol-2-yl)benzo[d]oxazol-2-yl)-3,8-diazabicyclo[3.2.1]octane-8-carboxylate obtained in Example 405(a) by a similar method to Example 1(c).

Example 406

(E)-2-(3,6-diazabicyclo[3.1.1]heptan-3-yl)-4-((1,1-difluoro-3-(pyridin-3-yl)allyl)oxy)-7-(thiazol-2-yl)benzo[d]oxazole (a) tert-Butyl (E)-3-(4-(1,1-difluoro-3-(pyridin-3-yl)allyl)oxy)-7-(thiazol-2-yl)benzo[d]oxazol-2-yl)-3,6-diazabicyclo[3.1.1]heptane-6-carboxylate Tris(dibenzylideneacetone)dipalladium(0) (2.0 mg, 0.015 equivalent) and tri-tert-butylphosphonium tetrafluoroborate (1.6 mg, 0.03 equivalent) were dissolved in 1,4-dioxane (1 mL), and then 52 mg of tert-butyl 3-(4-((1,1-difluoroallyl)oxy)-7-(thiazol-2-yl)benzo[d]oxazol-2-yl)-3,6-diazabicyclo[3.1.1]heptane-6-carboxylate obtained in Example 351(a), 3-bromopyridine (9.9 µL, 1 equivalent) and N,N-dicyclohexylmethylamine (24 μL, 1.1 equivalents) were added thereto, followed by stirring at room temperature overnight. After stirring at 40° C. for 3 hours, at 80° C. for 3 hours, at 100° C. for 3 days, and heat refluxing for 2 days, distilled water and ethyl acetate were added to the reaction mixture. The title compound was obtained as a crude product in an amount of 46 mg by purification of the residue obtained by vacuum concentration of the organic phase by preparative TLC (eluent, hexane:ethyl acetate=1:1).

(b) (E)-2-(3,6-diazabicyclo[3.1.1]heptan-3-yl)-4-((1, 1-difluoro-3-(pyridin-3-yl)allyl)oxy)-7-(thiazol-2-yl) benzo[d]oxazole The title compound was obtained in an amount of 3.7 mg from 46 mg of the crude product of tert-butyl (E)-3-(4-(1, 1-difluoro-3-(pyridin-3-yl)allyl)oxy)-7-(thiazol-2-yl)benzo [d]oxazol-2-yl)-3,6-diazabicyclo[3.1.1]heptane-6-carboxylate obtained in Example 406(a) by a similar method to Example 1(c).

Example 407

2-((2-(3,6-Diazabicyclo[3.1.1]heptan-3-yl)-7-(thiazol-2-yl)benzo[d]oxazol-4-yl)oxy)-2,2-difluoro-N-(2-hydroxyethyl)-N-methylacetamide (a) tert-Butyl 3-(4-(1,1-difluoro-2-((2-hydroxyethyl) (methyl)amino)-2-oxoethoxy)-7-(thiazol-2-yl)benzo [d]oxazol-2-yl)-3,6-diazabicyclo[3.1.1]heptane-6-carboxylate 21 mg of tert-butyl 3-(4-(2-ethoxy-1,1-difluoro-2-oxoethoxy)-7-(thiazol-2-yl)benzo[d]oxazol-2-yl)-3,6-diazabicyclo [3.1.1]heptane-6-carboxylate obtained in Example 248(d) was dissolved in methanol (0.4 mL), and then 2-(methylamino)ethan-1-ol (30 μL, 10 equivalents) was added thereto, followed by stirring at room temperature for 1.5 hours. Distilled water and ethyl acetate were added to the reaction mixture. The title compound was obtained as a crude product in an amount of 22 mg by vacuum concentration of the organic phase.

(b) 2-((2-(3,6-Diazabicyclo[3.1.1]heptan-3-yl)-7-(thiazol-2-yl)benzo[d]oxazol-4-yl)oxy)-2,2-difluoro-N-(2-hydroxyethyl)-N-methylacetamide The title compound was obtained in an amount of 6.5 mg from 22 mg of the crude product of tert-butyl 3-(4-(1,1-difluoro-2-((2-hydroxyethyl) (methyl)amino)-2-oxoethoxy)-7-(thiazol-2-yl)benzo[d]oxazol-2-yl)-3,6-diazabicyclo [3.1.1]heptane-6-carboxylate obtained in Example 407 (a) by a similar method to Example 1(c).

Example 408

2-((2-(3,6-Diazabicyclo[3.1.1]heptan-3-yl)-7-(thiazol-2-yl)benzo[d]oxazol-4-yl)oxy)-2,2-difluoro-N, N-dimethylacetamide (a) tert-Butyl 3-(4-(2-(dimethylamino)-1,1-difluoro-2-oxoethoxy)-7-(thiazol-2-yl)benzo[d]oxazol-2-yl)-3,6-diazabicyclo[3.1.1]heptane-6-carboxylate The title compound was obtained as a crude product in an amount of 24 mg from 20 mg of tert-butyl 3-(4-(2-ethoxy-1,1-difluoro-2-oxoethoxy)-7-(thiazol-2-yl)benzo[d]oxazol-2-yl)-3,6-diazabicyclo[3.1.1]heptane-6-carboxylate obtained in Example 248(d) by a similar method to Example 407(a) except that 2.0M of dimethylamine solution in tetrahydrofuran was used instead of 2-(methylamino)ethan-1-ol, and tetrahydrofuran was used instead of methanol.

(b) 2-((2-(3,6-Diazabicyclo[3.1.1]heptan-3-yl)-7-(thiazol-2-yl)benzo[d]oxazol-4-yl)oxy)-2,2-difluoro-N,N-dimethylacetamide The title compound was obtained in an amount of 17 mg from 22 mg of the crude product of tert-butyl 3-(4-(2-(dimethylamino)-1,1-difluoro-2-oxoethoxy)-7-(thiazol-2-yl)benzo[d]oxazol-2-yl)-3,6-diazabicyclo[3.1.1]heptane-6-carboxylate obtained in Example 408 (a) by a similar method to Example 1(c).

Example 409

2-((2-(3,6-Diazabicyclo[3.1.1]heptan-3-yl)-7-(thiazol-2-yl)benzo[d]oxazol-4-yl)oxy)-2,2-difluoro-1-morpholinoethan-1-one (a) tert-Butyl 3-(4-(1,1-difluoro-2-morpholino-2-oxoethoxy)-7-(thiazol-2-yl)benzo[d]oxazol-2-yl)-3, 6-diazabicyclo[3.1.1]heptane-6-carboxylate The title compound was obtained in an amount of 14 mg from 19 mg of tert-butyl 3-(4-(2-ethoxy-1,1-difluoro-2-oxoethoxy)-7-(thiazol-2-yl)benzo[d]oxazol-2-yl)-3,6-diazabicyclo[3.1.1]heptane-6-carboxylate obtained in Example 248 (d) by a similar method to Example 407 (a) except that morpholine was used instead of 2-(methylamino)ethan-1-ol, and acetonitrile was used instead of methanol.

(b) 2-((2-(3,6-Diazabicyclo[3.1.1]heptan-3-yl)-7-(thiazol-2-yl)benzo[d]oxazol-4-yl)oxy)-2,2-difluoro-1-morpholinoethan-1-one The title compound was obtained in an amount of 5.4 mg from 14 mg of tert-butyl 3-(4-(1,1-difluoro-2-morpholino-2-oxoethoxy)-7-(thiazol-2-yl)benzo[d]oxazol-2-yl)-3,6-diazabicyclo[3.1.1]heptane-6-carboxylate obtained in Example 409(a) by a similar method to Example 1(c).

Example 410

2-((2-(3,6-Diazabicyclo[3.1.1]heptan-3-yl)-7-(thiazol-2-yl)benzo[d]oxazol-4-yl)oxy)-2,2-difluoroacetamide (a) tert-Butyl 3-(4-(2-amino-1,1-difluoro-2-oxoethoxy)-7-(thiazol-2-yl)benzo[d]oxazol-2-yl)-3,6-diazabicyclo[3.1.1]heptane-6-carboxylate The title compound was obtained as a crude product in an amount of 22 mg from 20 mg of tert-butyl 3-(4-(2-ethoxy-1,1-difluoro-2-oxoethoxy)-7-(thiazol-2-yl)benzo[d]oxazol-2-yl)-3,6-diazabicyclo[3.1.1]heptane-6-carboxylate obtained in Example 248(d) by a similar method to Example 407(a) except that 7N ammonia solution in methanol was used instead of 2-(methylamino)ethan-1-ol.

(b) 2-((2-(3,6-Diazabicyclo[3.1.1]heptan-3-yl)-7-(thiazol-2-yl)benzo[d]oxazol-4-yl)oxy)-2,2-difluoroacetamide The title compound was obtained in an amount of 7.6 mg from 20 mg of the crude product of tert-butyl 3-(4-(2-amino- 1,1-difluoro-2-oxoethoxy)-7-(thiazol-2-yl)benzo[d]oxazol-2-yl)-3,6-diazabicyclo[3.1.1]heptane-6-carboxylate obtained in Example 410(a) by a similar method to Example 1(c).

Example 411

2-((2-(3,6-Diazabicyclo[3.1.1]heptan-3-yl)-7-(thiazol-2-yl)benzo[d]oxazol-4-yl)oxy)-2,2-difluoro-N-(2-hydroxyethyl)acetamide (a) tert-Butyl 3-(4-(1,1-difluoro-2-((2-hydroxyethyl)amino)-2-oxoethoxy)-7-(thiazol-2-yl)benzo[d]oxazol-2-yl)-3,6-diazabicyclo[3.1.1]heptane-6-carboxylate The title compound was obtained as a crude product in an amount of 25 mg from 21 mg of tert-butyl 3-(4-(2-ethoxy-1,1-difluoro-2-oxoethoxy)-7-(thiazol-2-yl)benzo[d]oxazol-2-yl)-3,6-diazabicyclo[3.1.1]heptane-6-carboxylate obtained in Example 248(d) by a similar method to Example 409(a) except that 2-aminoethan-1-ol was used instead of morpholine.

(b) 2-((2-(3,6-Diazabicyclo[3.1.1]heptan-3-yl)-7-(thiazol-2-yl)benzo[d]oxazol-4-yl)oxy)-2,2-difluoro-N-(2-hydroxyethyl)acetamide The title compound was obtained in an amount of 12 mg from 25 mg of the crude product of tert-butyl 3-(4-(1,1-difluoro-2-((2-hydroxyethyl)amino)-2-oxoethoxy)-7-(thiazol-2-yl)benzo[d]oxazol-2-yl)-3,6-diazabicyclo[3.1.1]heptane-6-carboxylate obtained in Example 411(a) by a similar method to Example 1(c).

Example 412

2-((2-(3,6-Diazabicyclo[3.1.1]heptan-3-yl)-7-(thiazol-2-yl)benzo[d]oxazol-4-yl)oxy)-2,2-difluoro-1-(3-hydroxyazetidin-1-yl)ethan-1-one (a) tert-Butyl 3-(4-(1,1-difluoro-2-(3-hydroxyazetidin-1-yl)-2-oxoethoxy)-7-(thiazol-2-yl)benzo[d]oxazol-2-yl)-3,6-diazabicyclo[3.1.1]heptane-6-carboxylate The title compound was obtained as a crude product in an amount of 24 mg from 20 mg of tert-butyl 3-(4-(2-ethoxy-1,1-difluoro-2-oxoethoxy)-7-(thiazol-2-yl)benzo[d]oxazol-2-yl)-3,6-diazabicyclo[3.1.1]heptane-6-carboxylate obtained in Example 248(d) by a similar method to Example 407(a) except that azetidin-3-ol hydrochloride (2 equivalents) was used instead of 2-(methylamino)ethan-1-ol.

(b) 2-((2-(3,6-Diazabicyclo[3.1.1]heptan-3-yl)-7-(thiazol-2-yl)benzo[d]oxazol-4-yl)oxy)-2,2-difluoro-1-(3-hydroxyazetidin-1-yl)ethan-1-one The title compound was obtained in an amount of 14 mg from 24 mg of the crude product of tert-butyl 3-(4-(1,1-difluoro-2-(3-hydroxyazetidin-1-yl)-2-oxoethoxy)-7-(thiazol-2-yl)benzo[d]oxazol-2-yl)-3,6-diazabicyclo[3.1.1]heptane-6-carboxylate obtained in Example 412 (a) by a similar method to Example 1(c).

Example 413

2-(3,6-Diazabicyclo[3.1.1]heptan-3-yl)-7-(thiazol-2-yl)-5-((5-(trifluoromethyl)pyridin-2-yl)oxy)benzo[d]oxazole (a) tert-Butyl 3-(5-hydroxy-7-(thiazol-2-yl)benzo[d]oxazol-2-yl)-3,6-diazabicyclo[3.1.1]heptane-6-carboxylate The title compound was obtained in an amount of 500 mg from 480 mg of 2-(3,6-diazabicyclo[3.1.1]heptan-3-yl)-7-(thiazol-2-yl)benzo[d]oxazol-5-ol obtained in Example 64 by a similar method to Example 256(b) except that triethylamine was used instead of diisopropylethylamine, and dichloromethane-tetrahydrofuran (1:1) was used as the reaction solvent.

(b) tert-Butyl 3-(7-(thiazol-2-yl)-5-((5-(trifluoromethyl)pyridin-2-yl)oxy)benzo[d]oxazol-2-yl)-3,6-diazabicyclo[3.1.1]heptane-6-carboxylate The title compound was obtained in an amount of 50 mg from 100 mg of tert-butyl 3-(5-hydroxy-7-(thiazol-2-yl)benzo[d]oxazol-2-yl)-3,6-diazabicyclo[3.1.1]heptane-6-carboxylate obtained in Example 413(a) by a similar method to Example 262(a) except that 2-chloro-5-(trifluoromethyl)pyridine was used instead of tetrahydro-2H-pyran-3-yl 4-methylbenzenesulfonate, and stirred at 110° C.

(c) 2-(3,6-Diazabicyclo[3.1.1]heptan-3-yl)-7-(thiazol-2-yl)-5-((5-(trifluoromethyl)pyridin-2-yl)oxy)benzo[d]oxazole The title compound was obtained in an amount of 25 mg from 50 mg of tert-butyl 3-(7-(thiazol-2-yl)-5-((5-(trifluoromethyl)pyridin-2-yl)oxy)benzo[d]oxazol-2-yl)-3,6-diazabicyclo[3.1.1]heptane-6-carboxylate obtained in Example 413(b) by a similar method to Example 1(c).

Example 414

2-(3,6-Diazabicyclo[3.1.1]heptan-3-yl)-4-cyclobutyl-7-(thiazol-2-yl)benzo[d]oxazole (a) tert-Butyl 3-(4-cyclobutyl-7-(thiazol-2-yl)benzo[d]oxazol-2-yl)-3,6-diazabicyclo[3.1.1]heptane-6-carboxylate The title compound was obtained in an amount of 19.9 mg from 54.6 mg of tert-butyl 3-(7-(thiazol-2-yl)-4-(((trifluoromethyl)sulfonyl)oxy)benzo[d]oxazol-2-yl)-3,6-diazabicyclo[3.1.1]heptane-6-carboxylate obtained in Example 334 (a) by a similar method to Example 344 (a) except that cyclobutylboronic acid was used instead of cyclobutylboronic acid.

(b) 2-(3,6-Diazabicyclo[3.1.1]heptan-3-yl)-4-cyclobutyl-7-(thiazol-2-yl)benzo[d]oxazole The title compound was obtained in an amount of 13.4 mg from 19.9 mg of tert-butyl 3-(4-cyclobutyl-7-(thiazol-2-yl)benzo[d]oxazol-2-yl)-3,6-diazabicyclo[3.1.1]heptane-6-carboxylate obtained in Example 414 (a) by a similar method to Example 1(c).

Example 415

2-(3,6-Diazabicyclo[3.1.1]heptan-3-yl)-4-(pyrrolidin-1-yl)-7-(thiazol-2-yl)benzo[d]oxazole (a) tert-Butyl 3-(4-(pyrrolidin-1-yl)-7-(thiazol-2-yl)benzo[d]oxazol-2-yl)-3,6-diazabicyclo[3.1.1]heptane-6-carboxylate The title compound was obtained in an amount of 15.6 mg from 82.0 mg of tert-butyl 3-(7-(thiazol-2-yl)-4-(((trifluoromethyl)sulfonyl)oxy)benzo[d]oxazol-2-yl)-3,6-diazabicyclo[3.1.1]heptane-6-carboxylate obtained in Example 334 (a) by a similar method to Example 369(a) except that pyrrolidine was used instead of morpholine.

(b) 2-(3,6-Diazabicyclo[3.1.1]heptan-3-yl)-4-(pyrrolidin-1-yl)-7-(thiazol-2-yl)benzo[d]oxazole The title compound was obtained in an amount of 12.4 mg from 15.6 mg of tert-butyl 3-(4-(pyrrolidin-1-yl)-7-(thiazol-2-yl)benzo[d]oxazol-2-yl)-3,6-diazabicyclo[3.1.1]heptane-6-carboxylate obtained in Example 415 (a) by a similar method to Example 1(c).

Example 416

(6-((2-(3,6-Diazabicyclo[3.1.1]heptan-3-yl)-7-(thiazol-2-yl)benzo[d]oxazol-5-yl)oxy)pyridin-3-yl)methanol (a) tert-Butyl 3-(5-((5-(methoxycarbonyl)pyridin-2-yl)oxy)-7-(thiazol-2-yl)benzo[d]oxazol-2-yl)-3,6-diazabicyclo[3.1.1]heptane-6-carboxylate The title compound was obtained in an amount of 100 mg from 150 mg of tert-butyl 3-(5-hydroxy-7-(thiazol-2-yl)benzo[d]oxazol-2-yl)-3,6-diazabicyclo[3.1.1]heptane-6-carboxylate obtained in Example 413(a) by a similar method to Example 262(a) except that methyl 6-chloronicotinate was used instead of tetrahydro-2H-pyran-3-yl 4-methylbenzenesulfonate, and stirred at 110° C.

(b) tert-Butyl 3-(5-((5-(hydroxymethyl)pyridin-2-yl)oxy)-7-(thiazol-2-yl)benzo[d]oxazol-2-yl)-3,6-diazabicyclo[3.1.1]heptane-6-carboxylate The title compound was obtained in an amount of 60 mg from 100 mg of tert-butyl 3-(5-((5-(methoxycarbonyl)pyridin-2-yl)oxy)-7-(thiazol-2-yl)benzo[d]oxazol-2-yl)-3,6-diazabicyclo[3.1.1]heptane-6-carboxylate obtained in Example 416(a) by a similar method to Reference Example 17.

(c) (6-((2-(3,6-Diazabicyclo[3.1.1]heptan-3-yl)-7-(thiazol-2-yl)benzo[d]oxazol-5-yl)oxy)pyridin-3-yl)methanol The title compound was obtained in an amount of 10 mg from 60 mg of tert-butyl 3-(5-((5-(hydroxymethyl)pyridin-2-yl)oxy)-7-(thiazol-2-yl)benzo[d]oxazol-2-yl)-3,6-diazabicyclo[3.1.1]heptane-6-carboxylate obtained in Example 416 (b) by a similar method to Example 1(c).

Example 417

2-(3,6-Diazabicyclo[3.1.1]heptan-3-yl)-7-(thiazol-2-yl)benzo[d]oxazole-5-carbonitrile (a) tert-Butyl 3-(7-(thiazol-2-yl)-5-(((trifluoromethyl)sulfonyl)oxy)benzo[d]oxazol-2-yl)-3,6-diazabicyclo[3.1.1]heptane-6-carboxylate The title compound was obtained in an amount of 270 mg from 250 mg of tert-butyl 3-(5-hydroxy-7-(thiazol-2-yl)benzo[d]oxazol-2-yl)-3,6-diazabicyclo[3.1.1]heptane-6-carboxylate obtained in Example 413(a) by a similar method to Example 85(a) except that triethylamine was used instead of diisopropylamine.

(b) tert-Butyl 3-(5-cyano-7-(thiazol-2-yl)benzo[d]oxazol-2-yl)-3,6-diazabicyclo[3.1.1]heptane-6-carboxylate The title compound was obtained in an amount of 40 mg from 100 mg of tert-butyl 3-(7-(thiazol-2-yl)-5-(((trifluoromethyl)sulfonyl)oxy)benzo[d]oxazol-2-yl)-3,6-diazabicyclo[3.1.1]heptane-6-carboxylate obtained in Example 417 (a) by a similar method to Example 335 (a).

(c) 2-(3,6-Diazabicyclo[3.1.1]heptan-3-yl)-7-(thiazol-2-yl)benzo[d]oxazole-5-carbonitrile The title compound was obtained in an amount of 11 mg from 35 mg of tert-butyl 3-(5-cyano-7-(thiazol-2-yl)benzo[d]oxazol-2-yl)-3,6-diazabicyclo[3.1.1]heptane-6-carboxylate obtained in Example 417 (b) by a similar method to Example 1(c).

Example 418

2-(3,6-Diazabicyclo[3.1.1]heptan-3-yl)-5-(pyridin-3-yl)-7-(thiazol-2-yl)benzo[d]oxazole (a) tert-Butyl 3-(5-(pyridin-3-yl)-7-(thiazol-2-yl)benzo[d]oxazol-2-yl)-3,6-diazabicyclo[3.1.1]heptane-6-carboxylate The title compound was obtained in an amount of 85 mg by a similar method to Example 10 (b) except that pyridin-3-ylbronic acid was used instead of tert-butyl 3-(5-chloro-7-(4,4,5,5-tetramethyl-1,3,2-dioxaborolan-2-yl)-4-(trifluoromethoxy)benzo[d]oxazol-2-yl)-3,8-diazabicyclo[3.2.1]octane-8-carboxylate, 270 mg of tert-butyl 3-(7-(thiazol-2-yl)-5-(((trifluoromethyl)sulfonyl)oxy)benzo[d]oxazol-2-yl)-3,6-diazabicyclo[3.1.1]heptane-6-carboxylate obtained in Example 417 (a) was used instead of 2-bromo-5-fluoropyridine, and stirred at 120° C.

(b) 2-(3,6-Diazabicyclo[3.1.1]heptan-3-yl)-5-(pyridin-3-yl)-7-(thiazol-2-yl)benzo[d]oxazole The title compound was obtained in an amount of 33 mg from 100 mg of tert-butyl 3-(5-(pyridin-3-yl)-7-(thiazol-2-yl)benzo[d]oxazol-2-yl)-3,6-diazabicyclo[3.1.1]heptane-6-carboxylate obtained in Example 418 (a) by a similar method to Example 1(c).

Example 419

2-(3,6-Diazabicyclo[3.1.1]heptan-3-yl)-5-cyclobutoxy-7-(thiazol-2-yl)benzo[d]oxazole

(a) tert-Butyl 3-(5-cyclobutoxy-7-(thiazol-2-yl)benzo[d]oxazol-2-yl)-3,6-diazabicyclo[3.1.1]heptane-6-carboxylate The title compound was obtained in an amount of 90 mg from 100 mg of tert-butyl 3-(5-hydroxy-7-(thiazol-2-yl)benzo[d]oxazol-2-yl)-3,6-diazabicyclo[3.1.1]heptane-6-carboxylate obtained in Example 413(a) by a similar method to Example 262(a) except that bromocyclobutane was used instead of tetrahydro-2H-pyran-3-yl 4-methylbenzenesulfonate, and stirred at 65° C.

(b) 2-(3,6-Diazabicyclo[3.1.1]heptan-3-yl)-5-cyclobutoxy-7-(thiazol-2-yl)benzo[d]oxazole The title compound was obtained in an amount of 25 mg from 90 mg of tert-butyl 3-(5-cyclobutoxy-7-(thiazol-2-yl)benzo[d]oxazol-2-yl)-3,6-diazabicyclo[3.1.1]heptane-6-carboxylate obtained in Example 419(a) by a similar method to Example 1(c).

Tables 1 to 3 show compounds obtained in Reference Examples, Tables 4 to 56 show compounds obtained in Examples. The Tables also show analysis data of each compound obtained by ESI-MS and 1H NMR.

TABLE 1

| Ex. No. | structural formula | compound name | ESI MS m/z | $^1$H NMR, δ (ppm) | deuterated solvent |
|---|---|---|---|---|---|
| 1 | | 7-bromo-5-isopropylbenzo[d]oxazole-2-thiol | 272 (M + H)$^+$ | 1.19 (d, J = 6.8 Hz, 6H), 2.91-3.02 (m, 1H), 7.05 (d, J = 1.2 Hz, 1H), 7.34 (d, J = 1.2 Hz, 1H), 14.08 (brs, 1H) | DMSO-d$_6$ |
| 2 | | 7-bromo-4-methylbenzo[d]oxazole-2-thiol | 245 (M + 2H)$^+$ | 2.33 (s, 3H), 7.07 (d, J = 8.4 Hz, 1H), 7.36 (d, J = 8.4 Hz, 1H), 14.23 (brs, 1H) | DMSO-d$_6$ |
| 3 | | 7-bromo-4-(trifluoromethoxy)benzo[d]oxazole-2-thiol | 312 (M − H)$^−$ | 7.31 (dq, J = 9.0, 1.3 Hz, 1H), 7.54 (d, J = 9.0 Hz, 1H) | DMSO-d$_6$ |
| 4 | | 7-bromo-4-(trifluoromethyl)benzo[d]oxazole-2-thiol | 298 (M + H)$^+$ | 3.7 (brs, 1H), 7.54 (d, J = 8.8 Hz, 1H), 7.64 (d, J = 8.8 Hz, 1H) | DMSO-d$_6$ |
| 5 | | N-(7-bromo-2-mercaptobenzo[d]oxazol-4-yl)acetamide | 275 (M − H)$^−$ | 2.06 (s, 3H), 7.23 (d, J = 8.8 Hz, 1H), 7.43 (d, J = 8.8 Hz, 1H), 9.93 (brs, 1H), 13.6 (brs, 1H) | DMSO-d$_6$ |

TABLE 1-continued

| Ex. No. | structural formula | compound name | ESI MS m/z | $^1$H NMR, δ (ppm) | deuterated solvent |
|---|---|---|---|---|---|
| 6 | (structure: 4-chloro-7-bromo-benzoxazole-2-thiol) | 7-bromo-4-chlorobenzo[d]oxazole-2-thiol | 264 (M + H)$^+$ | 7.34 (d, J = 8.4 Hz, 1H), 7.48 (d, J = 8.4 Hz, 1H) | DMSO-d$_6$ |
| 7 | (structure: 5-MeS-7-Br-benzoxazole-2-thiol) | 7-bromo-5-(methylthio)benzo[d]oxazole-2-thiol | 274 (M − H)$^−$ | 2.52 (s, 3H), 7.50 (d, J = 1.2 Hz, 1H), 7.75 (d, J = 1.2 Hz, 1H), 14.3 (brs, 1H) | DMSO-d$_6$ |
| 8 | (structure: 5-methylsulfinyl-7-Br-benzoxazole-2-thiol) | 7-bromo-5-(methylsulfinyl)benzo[d]oxazole-2-thiol | 292 (M + H)$^+$ | 2.80 (s, 3H), 3.41 (brs, 1H), 7.50 (d, J = 1.2 Hz, 1H), 7.75 (d, J = 1.2 Hz, 1H) | DMSO-d$_6$ |

TABLE 2

| Ex. No. | structural formula | compound name | ESI MS m/z | $^1$H NMR, δ (ppm) | deuterated solvent |
|---|---|---|---|---|---|
| 9 | (structure: 5-AcHN-7-Br-benzoxazole-2-thiol) | N-(7-bromo-2-mercaptobenzo[d]oxazol-5-yl)acetamide | 288 (M + 2H)$^+$ | 2.06 (s, 3H), 7.57 (d, J = 2 Hz, 1H), 7.64 (d, J = 2 Hz, 1H), 10.22 (brs, 1H), 14.02 (brs, 1H) | DMSO-d$_6$ |
| 10 | (structure: 5-F$_3$CO-7-Br-benzoxazole-2-thiol) | 7-bromo-5-(trifluoromethoxy)benzo[d]oxazole-2-thiol | 312 (M − H)$^−$ | 7.28-7.29 (m, 1H), 7.60-7.61 (m, 1H), 10.22 (brs, 1H), 14.22 (brs, 1H) | DMSO-d$_6$ |
| 11 | (structure: 5-H$_2$NO$_2$S-7-Br-benzoxazole-2-thiol) | 7-bromo-2-mercaptobenzo[d]oxazole-5-sulfonamide | 309 (M + H)$^+$ | 7.62 (d, J = 1.6 Hz, 1H), 7.91 (d, J = 1.6 Hz, 1H) | CD$_3$OD |
| 12 | (structure: 5-MeO-7-Br-benzoxazole-2-thiol) | 7-bromo-5-methoxybenzo[d]oxazole-2-thiol | 260 (M + H)$^+$ | 3.79 (s, 3H), 6.76 (d, J = 2.4 Hz, 1H), 7.07 (d, J = 2.4 Hz, 1H), 14.08 (brs, 1H) | DMSO-d$_6$ |
| 13 | (structure: 5-(CF$_3$CH$_2$O)-7-Br-benzoxazole-2-thiol) | 7-bromo-5-(2,2,2-trifluoroethoxy)benzo[d]oxazole-2-thiol | 328 (M + H)$^+$ | 4.85 (q, J = 9.2 Hz, 2H), 6.94 (d, J = 2.4 Hz, 1H), 7.23 (d, J = 2.4 Hz, 1H), 14.2 (brs, 1H) | DMSO-d$_6$ |

TABLE 2-continued

| Ex. No. | structural formula | compound name | ESI MS m/z | $^1$H NMR, δ (ppm) | deuterated solvent |
|---|---|---|---|---|---|
| 14 | (structure: 7-bromo-4-methoxy benzoxazole-2-thiol with OMe, Br, SH) | 7-bromo-4-methoxybenzo[d]oxazole-2-thiol | 258 (M − H)$^-$ | 3.90 (s, 3H), 6.97 (d, J = 8.8 Hz, 1H), 7.42 (d, J = 8.8 Hz, 1H), 14.3 (brs, 1H) | DMSO-d$_6$ |
| 15 | (structure with EtO$_2$C, Br, SH) | ethyl 7-bromo-2-mercaptobenzo[d]oxazole-5-carboxylate | 302 (M + H)$^+$ | 1.33 (t, J = 7.2 Hz, 3H), 4.36 (q, J = 7.2 Hz, 2H), 7.61 (d, J = 1.6 Hz, 1H), 7.96 (d, J = 1.6 Hz, 1H) | DMSO-d$_6$ |
| 16 | (structure with CO$_2$Et, Br, SH) | ethyl 7-bromo-2-mercaptobenzo[d]oxazole-4-carboxylate | 300 (M − H)$^-$ | 1.35 (t, J = 6.8 Hz, 3H), 4.44 (q, J = 6.8 Hz, 2H), 7.59 (d, J = 8.4 Hz, 1H), 7.71 (d, J = 8.4 Hz, 1H), 14.03 (brs, 1H) | DMSO-d$_6$ |
| 17 | (structure with CH$_2$OH, Br, SH) | (7-bromo-2-mercaptobenzo[d]oxazol-4-yl)methanol | 258 (M − H)$^-$ | 4.59 (s, 2H), 5.37 (s, 1H), 7.25 (d, J = 8.8 Hz, 1H), 7.45 (d, J = 8.8 Hz, 1H), 14.16 (brs, 1H) | DMSO-d$_6$ |

TABLE 3

| Ex. No. | structural formula | compound name | ESI MS m/z | $^1$H NMR, δ (ppm) | deuterated solvent |
|---|---|---|---|---|---|
| 18 | (structure with OH, F$_3$C, Br, SH) | 1-(7-bromo-2-mercaptobenzo[d]oxazol-5-yl)-2,2,2-trifluoroethan-1-ol | 328 (M + H)$^+$ | 5.32-5.37 (m, 1H), 7.13 (brs, 1H), 7.33 (s, 1H), 7.58 (s, 1H), 14.24 (brs, 1H) | DMSO-d$_6$ |
| 19 | (structure with CF$_3$, EtO$_2$C, Br, SH) | ethyl 7-bromo-2-mercapto-4-(trifluoromethyl)benzo[d]oxazole-5-carboxylate | 368 (M − H)$^-$ | 1.29 (t, J = 6.8 Hz, 3H), 4.32 (q, J = 6.8 Hz, 2H), 7.79 (s, 1H) | DMSO-d$_6$ |
| 20 | (structure with OCF$_3$, EtO$_2$C, Br, SH) | ethyl 7-bromo-2-mercapto-4-(trifluoromethoxy)benzo[d]oxazole-5-carboxylate | 386 (M + H)$^+$ | 1.31 (t, J = 6.8 Hz, 3H), 4.34 (q, J = 6.8 Hz, 2H), 7.90 (s, 1H) | DMSO-d$_6$ |

TABLE 3-continued

| Ex. No. | structural formula | compound name | ESI MS m/z | ¹H NMR, δ (ppm) | deuterated solvent |
|---|---|---|---|---|---|
| 21 | (F₃C, OH; benzoxazole-SH with Br) | 1-(7-bromo-2-mercaptobenzo[d]oxazol-4-yl)-2,2,2-trifluoroethan-1-ol | 328 (M + H)⁺ | 5.46 (q, J = 6 Hz, 1H), 7.23 (brs, 1H), 7.40 (d, J = 8 Hz, 1H), 7.56 (d, J = 8 Hz, 1H), 14.3 (brs, 1H) | DMSO-d₆ |
| 22 | (CO₂Me; benzoxazole-SH with Br) | methyl 7-bromo-2-mercaptobenzo[d]oxazole-4-carboxylate | 288 (M + H)⁺ | 3.9 (s, 3H), 7.59 (d, J = 8.8 Hz, 1H), 7.71 (d, J = 8.8 Hz, 1H), 14.02 (brs, 1H) | CDCl₃ |
| 23 | (OBn; benzoxazole-SH with Br) | 4-(benzyloxy)-7-bromobenzo[d]oxazole-2-thiol | 336 (M + H)⁺ | 5.15 (s, 2H), 6.75 (d, J = 8.9 Hz, 1H), 7.25-7.27 (m, 1H), 7.37-7.43 (m, 5H), 9.51 (brs, 1H) | CDCl₃ |
| 24 | (OTBS; benzoxazole-SH with Br) | 7-bromo-4-((tert-butyldimethylsilyl)oxy)benzo[d]oxazole-2-thiol | 358 (M − H)⁻ | 0.22 (s, 6H), 0.95 (s, 9H), 6.51 (d, J = 8.8 Hz, 1H), 7.02 (d, J = 8.8 Hz, 1H) | CDCl₃ |

TABLE 4

| Ex. No. | structural formula | compound name | ESI MS m/z | ¹H NMR, δ (ppm) | deuterated solvent |
|---|---|---|---|---|---|
| 1 | (Cl, OCF₃, thiazole, 3,8-diazabicyclo[3.2.1]octane on benzoxazole) | 2-(3,8-diazabicyclo[3.2.1]octan-3-yl)-5-chloro-7-(thiazol-2-yl)-4-(trifluoromethoxy)benzo[d]oxazole | 431 (M + H)⁺ | (400 MHz): 1.88 (s, 4H), 3.46 (dd, J = 12.2, 1.7 Hz, 2H), 3.69 (s, 2H), 4.04 (dd, J = 12.2, 1.7 Hz, 2H), 7.51 (d, J = 3.3 Hz, 1H), 7.94 (s, 1H), 7.97 (dd, J = 3.3, 0.55 Hz, 1H) | CDCl₃ |
| 2 | (Cl, OCF₃, thiazole, 3,9-diazabicyclo[3.3.1]nonane on benzoxazole) | 2-(3,9-diazabicyclo[3.3.1]nonan-3-yl)-5-chloro-7-(thiazol-2-yl)-4-(trifluoromethoxy)benzo[d]oxazole | 445 (M + H)⁺ | (400 MHz): 1.60-1.69 (m, 1H), 1.88-2.07 (m, 5H), 3.24-3.30 (m, 2H), 3.63 (dd, J = 12.8, 3.9 Hz, 2H), 4.27 (d, J = 12.8 Hz, 2H), 7.52 (d, J = 3.2 Hz, 1H), 7.95 (s, 1H), 7.98 (d, J = 3.2 Hz, 1H) | CDCl₃ |

TABLE 4-continued

| Ex. No. | structural formula | compound name | ESI MS m/z | ¹H NMR, δ (ppm) | deuterated solvent |
|---|---|---|---|---|---|
| 3 | | 2-(3,6-diazabicyclo[3.1.1]heptan-3-yl)-5-chloro-7-(thiazol-2-yl)-4-(trifluoromethoxy)benzo[d]oxazole | 417 (M + H)⁺ | (400 MHz): 1.68 (d, J = 9.3 Hz, 1H), 2.87 (d, J = 9.3 Hz, 1H), 3.92 (d, J = 6.0 Hz, 2H), 3.96-4.07 (m, 4H), 7.52 (d, J = 3.3 Hz, 1H), 7.98 (d, J = 3.3 Hz, 1H), 7.99 (s, 1H) | CDCl₃ |
| 4 | | 7-(5-chloro-7-(thiazol-2-yl)-4-(trifluoromethoxy)benzo[d]oxazol-2-yl)-3-oxa-7,9-diazabicyclo[3.3.1]nonane | 447 (M + H)⁺ | (400 MHz): 3.02 (s, 2H), 3.71 (d, J = 13.0 Hz, 2H), 3.92 (dt, J = 11.5, 2.5 Hz, 2H), 4.05 (d, J = 11.5 Hz, 2H), 4.51 (d, J = 13.0 Hz, 2H), 7.50 (d, J = 3.3 Hz, 1H), 7.94 (s, 1H), 7.97 (d, J = 3.3 Hz, 1H) | CDCl₃ |
| 5 | | 2-(3,8-diazabicyclo[3.2.1]octan-3-yl)-5-chloro-7-(1H-pyrazol-1-yl)-4-(trifluoromethoxy)benzo[d]oxazole | 414 (M + H)⁺ | (400 MHz): 1.87 (d, J = 2.1 Hz, 4H), 3.43 (dd, J = 12.2, 2.1 Hz, 2H), 3.67 (s, 2H), 3.91-4.02 (m, 2H), 6.54 (dd, J = 2.6, 1.8 Hz, 1H), 7.73 (s, 1H), 7.77 (d, J = 1.8 Hz, 1H), 8.15 (d, J = 2.6 Hz, 1H) | CDCl₃ |
| 6 | | 2-(3,8-diazabicyclo[3.2.1]octan-3-yl)-5-chloro-7-(furan-2-yl)-4-(trifluoromethoxy)benzo[d]oxazole | 414 (M + H)⁺ | (400 MHz): 1.87 (d, J = 2.0 Hz, 4H), 3.42 (dd, J = 12.2, 2.0 Hz, 2H), 3.67 (s, 2H), 3.99 (dd, J = 12.2, 2.0 Hz, 2H), 6.56 (dd, J = 3.4, 1.8 Hz, 1H), 6.88 (dd, J = 3.4, 0.7 Hz, 1H), 7.49 (s, 1H), 7.55 (dd, J = 1.8, 0.7 Hz, 1H) | CDCl₃ |
| 7 | | 2-(3,8-diazabicyclo[3.2.1]octan-3-yl)-5-chloro-7-(pyridin-2-yl)-4-(trifluoromethoxy)benzo[d]oxazole | 425 (M + H)⁺ | (400 MHz): 1.87 (d, J = 2.0 Hz, 4H), 3.42 (dd, J = 12.2, 2.0 Hz, 2H), 3.67 (s, 2H), 3.98 (dd, J = 12.2, 2.0 Hz, 2H), 7.31 (ddd, J = 7.5, 4.8, 1.1 Hz, 1H), 7.83 (dt, J = 7.5, 1.8 Hz, 1H), 7.92-7.98 (m, 2H), 8.72-8.78 (m, 1H) | CDCl₃ |

TABLE 4-continued

| Ex. No. | structural formula | compound name | ESI MS m/z | ¹H NMR, δ (ppm) | deuterated solvent |
|---|---|---|---|---|---|
| 8 | | 2-(3,8-diazabicyclo[3.2.1]octan-3-yl)-5-chloro-7-(thiazol-4-yl)-4-(trifluoromethoxy)benzo[d]oxazole | 431 (M + H)⁺ | (400 MHz): 1.88 (d, J = 2.1 Hz, 4H), 3.45 (dd, J = 12.2, 2.1 Hz, 2H), 3.68 (s, 2H), 4.00 (dd, J = 12.2, 2.1 Hz, 2H), 7.87 (d, J = 2.0 Hz, 1H), 7.96 (s, 1H), 8.92 (d, J = 2.0 Hz, 1H) | CDCl₃ |
| 9 | | 2-(3,8-diazabicyclo[3.2.1]octan-3-yl)-5-chloro-7-(oxazol-2-yl)-4-(trifluoromethoxy)benzo[d]oxazole | 415 (M + H)⁺ | (400 MHz): 1.87 (d, J = 1.8 Hz, 4H), 3.43 (dd, J = 12.4, 1.8 Hz, 2H), 3.66 (s, 2H), 4.05 (dd, J = 12.4, 1.8 Hz, 2H), 7.34 (d, J = 0.7 Hz, 1H), 7.75 (s, 1H), 7.81 (d, J = 0.7 Hz, 1H) | CDCl₃ |

TABLE 5

| Ex. No. | structural formula | compound name | ESI MS m/z | ¹H NMR, δ (ppm) | deuterated solvent |
|---|---|---|---|---|---|
| 10 | | 2-(3,8-diazabicyclo[3.2.1]octan-3-yl)-5-chloro-7-(5-fluoropyridin-2-yl)-4-(trifluoromethoxy)benzo[d]oxazole | 443 (M + H)⁺ | (400 MHz): 1.87 (d, J = 1.7 Hz, 4H), 3.43 (dd, J = 12.2, 1.7 Hz, 2H), 3.67 (s, 2H), 3.97 (dd, J = 12.2, 1.7 Hz, 2H), 7.50-7.58 (m, 1H), 7.89 (s, 1H), 7.93-8.00 (m, 1H), 8.60 (d, J = 2.6 Hz, 1H) | CDCl₃ |
| 11 | | 2-(3,8-diazabicyclo[3.2.1]octan-3-yl)-5-chloro-7-(pyridin-2-yl)-4-(trifluoromethyl)benzo[d]oxazole | 409 (M + H)⁺ | (400 MHz): 1.87 (s, 4H), 3.42-3.45 (m, 2H), 3.67 (s, 2H), 3.98-4.01 (m, 2H), 7.32-7.35 (m, 1H), 7.82-7.87 (m, 1H), 7.95 (s, 1H), 7.98-8.00 (m, 1H), 8.78 (d, J = 4.0 Hz, 1H) | CDCl₃ |
| 12 | | 2-(3,9-diazabicyclo[3.3.1]nonan-3-yl)-5-chloro-7-(pyridin-2-yl)-4-(trifluoromethyl)benzo[d]oxazole | 423 (M + H)⁺ | (400 MHz): 1.62-1.64 (m, 1H), 1.91-1.93 (m, 4H), 1.96-2.07 (m, 1H), 3.27 (d, J = 2.4 Hz, 2H), 3.59-3.63 (m, 2H), 4.21-4.24 (m, 2H), 7.33-7.36 (m, 1H), 7.84-7.88 (m, 1H), 7.95 (s, 1H), 8.01-8.03 (m, 1H), 8.77-8.79 (m, 1H) | CDCl₃ |

TABLE 5-continued

| Ex. No. | structural formula | compound name | ESI MS m/z | ¹H NMR, δ (ppm) | deuterated solvent |
|---|---|---|---|---|---|
| 13 | | 2-(3,6-diazabicyclo[3.1.1]heptan-3-yl)-5-chloro-7-(pyridin-2-yl)-4-(trifluoromethyl)benzo[d]oxazole | 395 (M + H)⁺ | (400 MHz): 1.66 (d, J = 8.0 Hz, 1H), 2.83-2.89 (m, 1H), 3.90-3.92 (m, 2H), 3.95-4.03 (m, 4H), 7.33-7.36 (m, 1H), 7.82-7.86 (m, 1H), 7.99 (s, 1H), 8.06 (d, J = 8.0 Hz, 1H), 8.77-8.78 (m, 1H) | CDCl₃ |
| 14 | | 7-(5-chloro-7-(pyridin-2-yl)-4-(trifluoromethyl)benzo[d]oxazol-2-yl)-3-oxa-7,9-diazabicyclo[3.3.1]nonane | 425 (M + H)⁺ | (400 MHz): 3.03 (s, 2H), 3.67-3.72 (m, 2H), 3.90-3.94 (m, 2H), 4.03-4.05 (m, 2H), 4.44-4.47 (m, 2H), 7.32-7.35 (m, 1H), 7.81-7.86 (m, 1H), 7.92-8.01 (m, 2H), 8.76-8.78 (m, 1H) | CDCl₃ |
| 15 | | 2-(3,8-diazabicyclo[3.2.1]octan-3-yl)-5-chloro-7-(1H-pyrazol-1-yl)-4-(trifluoromethyl)benzo[d]oxazole | 398 (M + H)⁺ | (400 MHz): 1.87 (s, 4H), 3.44-3.47 (m, 2H), 3.68 (s, 2H), 3.97-4.00 (m, 2H), 6.56-6.57 (m, 1H), 7.79 (s, 2H), 8.23 (d, J = 2.4 Hz, 1H) | CDCl₃ |
| 16 | | 2-(3,9-diazabicyclo[3.3.1]nonan-3-yl)-5-chloro-7-(1H-pyrazol-1-yl)-4-(trifluoromethyl)benzo[d]oxazole | 412 (M + H)⁺ | (400 MHz): 1.65-1.67 (m, 1H), 1.91-1.93 (m, 4H), 1.96-2.05 (m, 1H), 3.28 (s, 2H), 3.60-3.64 (m, 2H), 4.20-4.23 (m, 2H), 6.58 (dd, J = 2.0, 2.0 Hz, 1H), 7.80 (s, 2H), 8.26 (d, J = 2.8 Hz, 1H) | CDCl₃ |
| 17 | | 2-(3,6-diazabicyclo[3.1.1]heptan-3-yl)-5-chloro-7-(1H-pyrazol-1-yl)-4-(trifluoromethyl)benzo[d]oxazole | 384 (M + H)⁺ | (400 MHz): 1.65-1.67 (m, 1H), 2.85-2.90 (m, 1H), 3.91-3.96 (m, 2H), 3.99-4.03 (m, 4H), 6.57 (dd, J = 2.0, 2.0 Hz, 1H), 7.81 (d, J = 4.0 Hz, 1H), 7.84 (s, 1H), 8.29 (d, J = 3.2 Hz, 1H) | CDCl₃ |

TABLE 6

| Ex. No. | structural formula | compound name | ESI MS m/z | $^1$H NMR, δ (ppm) | deuterated solvent |
|---|---|---|---|---|---|
| 18 | | 7-(5-chloro-7-(1H-pyrazol-1-yl)-4-(trifluoromethyl)benzo[d]oxazol-2-yl)-3-oxa-7,9-diazabicyclo[3.3.1]nonane | 414 (M + H)$^+$ | (400 MHz): 3.03 (s, 2H), 3.69-3.72 (m, 2H), 3.91-3.94 (m, 2H), 4.03-4.06 (m, 2H), 4.45 (brs, 2H), 6.55 (d, J = 2.4 Hz, 1H), 7.77 (s, 1H), 7.80 (s, 1H), 8.23 (d, J = 2.4 Hz, 1H) | CDCl$_3$ |
| 19 | | 7-(5-chloro-7-(thiazol-2-yl)-4-(trifluoromethyl)benzo[d]oxazol-2-yl)-3-oxa-7,9-diazabicyclo[3.3.1]nonane | 431 (M + H)$^+$ | (400 MHz, HCl塩): 3.80 (s, 2H), 3.94 (d, J = 14.6 Hz, 2H), 4.10 (d, J = 13.5 Hz, 2H), 4.18-4.25 (m, 2H), 4.56 (d, J = 14.6 Hz, 2H), 7.18 (s, 1H), 7.63 (d, J = 3.3 Hz, 1H), 7.71 (d, J = 3.3 Hz, 1H) | D$_2$O |
| 20 | | 2-(3,8-diazabicyclo[3.2.1]octan-3-yl)-5-chloro-7-(thiazol-2-yl)-4-(trifluoromethyl)benzo[d]oxazole | 415 (M + H)$^+$ | (400 MHz): 1.70-1.78 (m, 4H), 3.42 (d, J = 11.7 Hz, 2H), 3.62 (s, 2H), 3.87-3.90 (m, 2H), 7.85 (d, J = 0.64 Hz, 1H), 8.10 (d, J = 3.0 Hz, 1H), 8.13 (d, J = 3.0 Hz, 1H) | DMSO-d$_6$ |
| 21 | | 2-(3,8-diazabicyclo[3.2.1]octan-3-yl)-5-isopropyl-7-(thiazol-2-yl)benzo[d]oxazole | 355 (M + H)$^+$ | (400 MHz): 1.31 (d, J = 8.0 Hz, 6H), 1.88 (s, 4H), 3.02-3.06 (m, 1H), 3.41-3.43 (m, 2H), 3.68 (s, 2H), 3.98-4.02 (m, 2H), 7.30 (d, J = 1.6 Hz, 1H), 7.45 (d, J = 2.8 Hz, 1H), 7.73 (d, J = 1.6 Hz, 1H), 7.95 (d, J = 2.8 Hz, 1H) | CDCl$_3$ |
| 22 | | 2-(3,6-diazabicyclo[3.1.1]heptan-3-yl)-5-isopropyl-7-(thiazol-2-yl)benzo[d]oxazole | 341 (M + H)$^+$ | (400 MHz): 1.33 (d, J = 4.0 Hz, 6H), 1.69 (d, J = 9.6 Hz, 1H), 2.82-2.88 (m, 1H), 3.01-3.08 (m, 1H), 3.91-3.95 (m, 2H), 3.98-4.03 (m, 4H), 7.35 (d, J = 1.6 Hz, 1H), 7.46 (d, J = 2.8 Hz, 1H), 7.76 (d, J = 1.6 Hz, 1H), 7.96 (d, J = 2.8 Hz, 1H) | CDCl$_3$ |

TABLE 6-continued

| Ex. No. | structural formula | compound name | ESI MS m/z | ¹H NMR, δ (ppm) | deuterated solvent |
|---|---|---|---|---|---|
| 23 | | 7-(5-isopropyl-7-(thiazol-2-yl)benzo[d]oxazol-2-yl)-3-oxa-7,9-diazabicyclo[3.3.1]nonane | 371 (M + H)+ | (400 MHz): 1.31 (d, J = 7.2 Hz, 6H), 2.99-3.06 (m, 3H), 3.66-3.71 (m, 2H), 3.90-3.95 (m, 2H), 4.03-4.06 (m, 2H), 4.45-4.48 (m, 2H), 7.30 (s, 1H), 7.44 (d, J = 3.6 Hz, 1H), 7.72 (d, J = 1.6 Hz, 1H), 7.95 (d, J = 3.6 Hz, 1H) | CDCl₃ |
| 24 | | 2-(3,9-diazabicyclo[3.3.1]nonan-3-yl)-5-isopropyl-7-(thiazol-2-yl)benzo[d]oxazole | 369 (M + H)+ | (400 MHz): 1.32 (d, J = 6.4 Hz, 6H), 1.60-1.64 (m, 1H), 1.91-1.93 (m, 4H), 2.03-2.13 (m, 1H), 3.01-3.07 (m, 1H), 3.26 (s, 2H), 3.58-3.62 (m, 2H), 4.23-4.27 (m, 2H), 7.32 (d, J = 1.6 Hz, 1H), 7.46 (d, J = 4.0 Hz, 1H), 7.73 (d, J = 1.6 Hz, 1H), 7.96 (d, J = 4.0 Hz, 1H) | CDCl₃ |
| 25 | | 2-(3,8-diazabicyclo[3.2.1]octan-3-yl)-4-methyl-7-(thiazol-2-yl)benzo[d]oxazole | 327 (M + H)+ | (400 MHz): 1.85-1.92 (m, 4H), 2.52 (s, 3H), 3.41-3.44 (m, 2H), 3.67 (s, 2H), 4.01-4.04 (m, 2H), 7.09 (d, J = 8.4 Hz, 1H), 7.42 (d, J = 3.6 Hz, 1H), 7.75 (d, J = 8.4 Hz, 1H), 7.92 (d, J = 3.6 Hz, 1H) | CDCl₃ |

TABLE 7

| Ex. No. | structural formula | compound name | ESI MS m/z | ¹H NMR, δ (ppm) | deuterated solvent |
|---|---|---|---|---|---|
| 26 | | 2-(3,6-diazabicyclo[3.1.1]heptan-3-yl)-4-methyl-7-(thiazol-2-yl)benzo[d]oxazole | 313 (M + H)+ | (400 MHz): 1.69 (d, J = 10 Hz, 1H), 2.55 (s, 3H), 2.82-2.87 (m, 1H), 3.91-3.93 (m, 2H), 3.97-4.05 (m, 4H), 7.11 (d, J = 8.0 Hz, 1H), 7.43 (d, J = 2.8 Hz, 1H), 7.78 (d, J = 8.0 Hz, 1H), 7.93 (d, J = 2.8 Hz, 1H) | CDCl₃ |
| 27 | | 2-(3,9-diazabicyclo[3.3.1]nonan-3-yl)-4-methyl-7-(thiazol-2-yl)benzo[d]oxazole | 341 (M + H)+ | (400 MHz): 1.61-1.64 (m, 1H), 1.92-1.95 (m, 4H), 2.09-2.17 (m, 1H), 2.54 (s, 3H), 3.27 (d, J = 2.8 Hz, 2H), 3.58-3.62 (m, 2H), 4.25-4.28 (m, 2H), 7.10 (d, J = 8.0 Hz, 1H), 7.43 (d, J = 2.8 Hz, 1H), 7.76 (d, J = 8.0 Hz, 1H), 7.93 (d, | CDCl₃ |

TABLE 7-continued

| Ex. No. | structural formula | compound name | ESI MS m/z | $^1$H NMR, δ (ppm) | deuterated solvent |
|---|---|---|---|---|---|
| | | | | J = 2.8 Hz, 1H) | |
| 28 | | 2-(3,8-diazabicyclo[3.2.1]octan-3-yl)-7-(thiazol-2-yl)-4-(trifluoromethoxy)benzo[d]oxazole | 397 (M + H)$^+$ | (400 MHz): 1.90-1.93 (m, 4H), 3.53 (d, J = 12.6 Hz, 2H), 3.76 (s, 2H), 4.08 (d, J = 12.6 Hz, 2H), 7.15-7.22 (m, 1H), 7.48 (d, J = 3.2 Hz, 1H), 7.84 (d, J = 8.9 Hz, 1H), 7.96 (d, J = 3.2 Hz, 1H) | CDCl$_3$ |
| 29 | | 2-(3,6-diazabicyclo[3.1.1]heptan-3-yl)-7-(thiazol-2-yl)-4-(trifluoromethoxy)benzo[d]oxazole | 383 (M + H)$^+$ | (400 MHz): 1.69 (d, J = 9.3 Hz, 1H), 2.81-2.93 (m, 1H), 3.94 (d, J = 6.0 Hz, 2H), 3.98-4.10 (m, 4H), 7.17-7.24 (m, 1H), 7.48 (d, J = 3.2 Hz, 1H), 7.87 (d, J = 8.9 Hz, 1H), 7.97 (d, J = 3.2 Hz, 1H) | CDCl$_3$ |
| 30 | | 2-(3,9-diazabicyclo[3.3.1]nonan-3-yl)-7-(thiazol-2-yl)-4-(trifluoromethoxy)benzo[d]oxazole | 411 (M + H)$^+$ | (400 MHz): 1.63-1.66 (m, 1H), 1.97-2.07 (m, 5H), 3.36 (s, 2H), 3.71 (d, J = 9.9 Hz, 2H), 4.32 (d, J = 12.8 Hz, 2H), 7.18-7.21 (m, 1H), 7.48 (d, J = 3.3 Hz, 1H), 7.85 (d, J = 8.9 Hz, 1H), 7.97 (d, J = 3.3 Hz, 1H) | CDCl$_3$ |
| 31 | | 2-(3,8-diazabicyclo[3.2.1]octan-3-yl)-7-(thiazol-2-yl)-4-(trifluoromethyl)benzo[d]oxazole | 381 (M + H)$^+$ | (400 MHz): 1.89 (s, 4H), 3.45-3.49 (m, 2H), 3.69 (s, 2H), 4.07-4.10 (m, 2H), 7.50 (d, J = 8.0 Hz, 1H), 7.53 (d, J = 2.8 Hz, 1H), 7.89 (d, J = 8.0 Hz, 1H), 8.01 (d, J = 2.8 Hz, 1H) | CDCl$_3$ |
| 32 | | 2-(3,6-diazabicyclo[3.1.1]heptan-3-yl)-7-(thiazol-2-yl)-4-(trifluoromethyl)benzo[d]oxazole | 367 (M + H)$^+$ | (400 MHz): 1.69 (d, J = 9.2 Hz, 1H), 2.84-2.90 (m, 1H), 3.94 (d, J = 6.0 Hz, 2H), 4.01-4.09 (m, 4H), 7.52-7.55 (m, 2H), 7.93 (d, J = 8.4 Hz, 1H), 8.01 (d, J = 2.8 Hz, 1H) | CDCl$_3$ |

TABLE 7-continued

| Ex. No. | structural formula | compound name | ESI MS m/z | ¹H NMR, δ (ppm) | deuterated solvent |
|---|---|---|---|---|---|
| 33 | | 2-(3,9-diazabicyclo[3.3.1]nonan-3-yl)-7-(thiazol-2-yl)-4-(trifluoromethyl)benzo[d]oxazole | 395 (M + H)⁺ | (400 MHz): 1.62-1.67 (m, 1H), 1.93-1.94 (m, 4H), 2.01-2.06 (m, 1H), 3.28 (s, 2H), 3.62-3.67 (m, 2H), 4.30-4.33 (m, 2H), 7.49-7.54 (m, 2H), 7.90 (d, J = 8.8 Hz, 1H), 8.01 (d, J = 3.2 Hz, 1H) | CDCl₃ |

TABLE 8

| Ex. No. | structural formula | compound name | ESI MS m/z | ¹H NMR, δ (ppm) | deuterated solvent |
|---|---|---|---|---|---|
| 34 | | N-(2-(3,9-diazabicyclo[3.3.1]nonan-3-yl)-7-(thiazol-2-yl)benzo[d]oxazol-4-yl)acetamide | 384 (M + H)⁺ | (400 MHz): 1.64-1.68 (m, 1H), 1.92-1.95 (m, 4H), 2.02-2.10 (m, 1H), 2.28 (s, 3H), 3.28 (brs, 2H), 3.61 (dd, J = 12.3, 4.1 Hz, 2H), 4.25 (d, J = 12.3 Hz, 2H), 7.40 (d, J = 3.3 Hz, 1H), 7.81 (d, J = 8.8 Hz, 1H), 7.92 (d, J = 3.3 Hz, 1H), 8.27 (d, J = 8.8 Hz, 1H) | CDCl₃ |
| 35 | | N-(2-(3,6-diazabicyclo[3.1.1]heptan-3-yl)-7-(thiazol-2-yl)benzo[d]oxazol-4-yl)acetamide | 356 (M + H)⁺ | (400 MHz): 1.77-1.79 (m, 1H), 2.24 (s, 3H), 2.81-2.86 (m, 1H), 3.88-3.89 (m, 2H), 4.01-4.06 (m, 4H), 7.71 (d, J = 3.3 Hz, 1H), 7.76 (d, J = 8.4 Hz, 1H), 7.93 (d, J = 3.3 Hz, 1H), 8.04 (d, J = 8.4 Hz, 1H) | CD₃OD |
| 36 | | 2-(3,8-diazabicyclo[3.2.1]octan-3-yl)-4-chloro-7-(thiazol-2-yl)benzo[d]oxazole | 347 (M + H)⁺ | (400 MHz): 1.89 (s, 4H), 3.45-3.48 (m, 2H), 3.69 (s, 2H), 4.04-4.07 (m, 2H), 7.27 (d, J = 8.4 Hz, 1H), 7.47 (d, J = 2.8 Hz, 1H), 7.79 (d, J = 8.4 Hz, 1H), 7.95 (d, J = 2.8 Hz, 1H) | CDCl₃ |
| 37 | | 2-(3,6-diazabicyclo[3.1.1]heptan-3-yl)-4-chloro-7-(thiazol-2-yl)benzo[d]oxazole | 333 (M + H)⁺ | (400 MHz): 1.70 (d, J = 3.2 Hz, 1H), 2.84-2.91 (m, 1H), 3.96 (d, J = 6.0 Hz, 2H), 4.01-4.09 (m, 4H), 7.31 (d, J = 8.4 Hz, 1H), 7.48 (d, J = 3.2 Hz, 1H), 7.82 (d, J = 8.4 Hz, 1H), 7.96 (d, J = 3.2 Hz, 1H) | CDCl₃ |

TABLE 8-continued

| Ex. No. | structural formula | compound name | ESI MS m/z | ¹H NMR, δ (ppm) | deuterated solvent |
|---|---|---|---|---|---|
| 38 | | 2-(3,9-diazabicyclo[3.3.1]nonan-3-yl)-4-chloro-7-(thiazol-2-yl)benzo[d]oxazole | 361 (M + H)⁺ | (400 MHz): 1.64 (s, 1H), 1.93-1.94 (m, 4H), 2.02-2.11 (m, 1H), 3.28 (s, 2H), 3.61-3.66 (m, 2H), 4.28-4.31 (m, 2H), 7.26-7.29 (m, 1H), 7.47 (d, J = 3.6 Hz, 1H), 7.80 (d, J = 8.4 Hz, 1H), 7.96 (d, J = 3.6 Hz, 1H) | CDCl₃ |
| 39 | | 2-(3,8-diazabicyclo[3.2.1]octan-3-yl)-5-(methylthio)-7-(thiazol-2-yl)benzo[d]oxazole | 359 (M + H)⁺ | (400 MHz): 1.88 (s, 4H), 2.55 (s, 3H), 3.43 (dd, J = 12.2, 2.0 Hz, 2H), 3.67 (s, 2H), 3.99 (dd, J = 12.2, 2.0 Hz, 2H), 7.33 (d, J = 1.8 Hz, 1H), 7.47 (d, J = 3.2 Hz, 1H), 7.80 (d, J = 1.8 Hz, 1H), 7.96 (d, J = 3.2 Hz, 1H) | CDCl₃ |
| 40 | | 2-(3,6-diazabicyclo[3.1.1]heptan-3-yl)-5-(methylthio)-7-(thiazol-2-yl)benzo[d]oxazole | 345 (M + H)⁺ | (400 MHz): 1.70 (d, J = 9.2 Hz, 1H), 2.56 (s, 3H), 2.84-2.89 (m, 1H), 3.93 (d, J = 5.6 Hz, 2H), 3.96-4.03 (m, 4H), 7.38 (d, J = 1.8 Hz, 1H), 7.48 (d, J = 3.3 Hz, 1H), 7.82 (d, J = 1.8 Hz, 1H), 7.97 (d, J = 3.3 Hz, 1H) | CDCl₃ |
| 41 | | 2-(3,9-diazabicyclo[3.3.1]nonan-3-yl)-5-(methylthio)-7-(thiazol-2-yl)benzo[d]oxazole | 373 (M + H)⁺ | (400 MHz): 1.55-1.61 (m, 1H), 1.86-1.96 (m, 4H), 1.99-2.15 (m, 1H), 2.55 (s, 3H), 3.27 (brs, 2H), 3.62 (dd, J = 12.7, 3.8 Hz, 2H), 4.25 (d, J = 12.7 Hz, 2H), 7.35 (d, J = 1.8 Hz, 1H), 7.48 (d, J = 3.3 Hz, 1H), 7.80 (d, J = 1.8 Hz, 1H), 7.96 (d, J = 3.3 Hz, 1H) | CDCl₃ |

TABLE 9

| Ex. No. | structural formula | compound name | ESI MS m/z | ¹H NMR, δ (ppm) | deuterated solvent |
|---|---|---|---|---|---|
| 42 | | 2-(3,8-diazabicyclo[3.2.1]octan-3-yl)-5-(methylsulfinyl)-7-(thiazol-2-yl)benzo[d]oxazole | 375 (M + H)⁺ | (400 MHz): 1.92 (s, 4H), 2.76 (s, 3H), 3.51 (d, J = 11.9 Hz, 2H), 3.74 (s, 2H), 4.04 (d, J = 11.9 Hz, 2H), 7.52 (d, J = 3.3 Hz, 1H), 7.72 (d, J = 1.7 Hz, 1H), 7.99 (d, J = 3.3 Hz, 1H), 8.09 (d, J = 1.7 Hz, 1H) | CDCl₃ |

TABLE 9-continued

| Ex. No. | structural formula | compound name | ESI MS m/z | $^1$H NMR, δ (ppm) | deuterated solvent |
|---|---|---|---|---|---|
| 43 | | 2-(3,6-diazabicyclo[3.1.1]heptan-3-yl)-5-(methyl-sulfinyl)-7-(thiazol-2-yl)benzo[d]oxazole | 361 (M + H)⁺ | (400 MHz): 1.71 (d, J = 9.2 Hz, 1H), 2.79 (s, 3H), 2.88-2.90 (m, 1H), 3.95 (d, J = 6.0 Hz, 2H), 3.99-4.06 (m, 4H), 7.52-7.53 (m, 1H), 7.78 (d, J = 1.6 Hz, 1H), 7.98 (d, J = 3.3 Hz, 1H), 8.12 (d, J = 1.6 Hz, 1H) | CDCl₃ |
| 44 | | 2-(3,9-diazabicyclo[3.3.1]nonan-3-yl)-5-(methyl-sulfinyl)-7-(thiazol-2-yl)benzo[d]oxazole | 389 (M + H)⁺ | (400 MHz): 1.60-1.70 (m, 1H), 1.92-1.94 (m, 4H), 2.00-2.07 (m, 1H), 2.77 (s, 3H), 3.29 (s, 2H), 3.67 (dd, J = 13.4, 3.9 Hz, 2H), 4.29 (d, J = 13.4 Hz, 2H), 7.53 (d, J = 2.8 Hz, 1H), 7.73 (d, J = 1.6 Hz, 1H), 7.99 (d, J = 2.8 Hz, 1H), 8.09 (d, J = 1.6 Hz, 1H) | CDCl₃ |
| 45 | | 2-(3,8-diazabicyclo[3.2.1]octan-3-yl)-5-(methyl-sulfonyl)-7-(thiazol-2-yl)benzo[d]oxazole | 391 (M + H)⁺ | (400 MHz): 1.90 (s, 4H), 3.10 (s, 3H), 3.51 (d, J = 11.5 Hz, 2H), 3.72 (s, 2H), 4.03 (d, J = 11.5 Hz, 2H), 7.54 (d, J = 3.3 Hz, 1H), 7.90 (d, J = 1.7 Hz, 1H), 8.01 (d, J = 3.3 Hz, 1H), 8.47 (d, J = 1.7 Hz, 1H) | CDCl₃ |
| 46 | | 2-(3,6-diazabicyclo[3.1.1]heptan-3-yl)-5-(methyl-sulfonyl)-7-(thiazol-2-yl)benzo[d]oxazole | 377 (M + H)⁺ | (400 MHz): 1.71 (d, J = 9.6 Hz, 1H), 2.87-2.93 (m, 1H), 3.10 (s, 3H), 3.97 (d, J = 6.1 Hz, 2H), 4.04 (s, 4H), 7.55 (d, J = 3.2 Hz, 1H), 7.95 (d, J = 1.8 Hz, 1H), 8.01 (d, J = 3.2 Hz, 1H), 8.50 (d, J = 1.8 Hz, 1H) | CDCl₃ |
| 47 | | 2-(3,9-diazabicyclo[3.3.1]nonan-3-yl)-5-(methyl-sulfonyl)-7-(thiazol-2-yl)benzo[d]oxazole | 405 (M + H)⁺ | (400 MHz): 1.64-1.66 (m, 1H), 1.92-2.04 (m, 5H), 3.11 (s, 3H), 3.34 (s, 2H), 3.71 (dd, J = 13.0, 3.7 Hz, 2H), 4.26-4.29 (m, 2H), 7.55 (d, J = 3.3 Hz, 1H), 7.92 (d, J = 1.7 Hz, 1H), 8.02 (d, J = 3.3 Hz, 1H), 8.48 (d, J = 1.7 Hz, 1H) | CDCl₃ |

TABLE 9-continued

| Ex. No. | structural formula | compound name | ESI MS m/z | ¹H NMR, δ (ppm) | deuterated solvent |
|---|---|---|---|---|---|
| 48 | | N-(2-(3,9-diazabicyclo[3.3.1]nonan-3-yl)-7-(thiazol-2-yl)benzo[d]oxazol-5-yl)acetamide | 384 (M + H)⁺ | (400 MHz): 1.61-1.68 (m, 1H), 1.92-1.94 (m, 4H), 2.00-2.10 (m, 1H), 2.20 (s, 3H), 3.26 (s, 2H), 3.60 (dd, J = 12.6, 3.7 Hz, 2H), 4.23-4.26 (m, 2H), 7.47 (d, J = 3.3 Hz, 1H), 7.76 (d, J = 1.8 Hz, 1H), 7.81 (d, J = 1.8 Hz, 1H), 7.94 (d, J = 3.3 Hz, 1H) | CDCl₃ |
| 49 | | N-(2-(3,6-diazabicyclo[3.1.1]heptan-3-yl)-7-(thiazol-2-yl)benzo[d]oxazol-5-yl)acetamide | 356 (M + H)⁺ | (400 MHz): 1.68 (d, J = 9.1 Hz, 1H), 2.21 (s, 3H), 2.83-2.89 (m, 1H), 3.91-4.03 (m, 6H), 7.47 (d, J = 3.3 Hz, 1H), 7.79 (d, J = 1.7 Hz, 1H), 7.86 (d, J = 1.7 Hz, 1H), 7.95 (d, J = 3.3 Hz, 1H) | CDCl₃ |

TABLE 10

| Ex. No. | structural formula | compound name | ESI MS m/z | ¹H NMR, δ (ppm) | deuterated solvent |
|---|---|---|---|---|---|
| 50 | | N-(2-(3,8-diazabicyclo[3.2.1]octan-3-yl)-7-(thiazol-2-yl)benzo[d]oxazol-5-yl)acetamide | 370 (M + H)⁺ | (400 MHz): 1.89 (s, 4H), 2.20 (s, 3H), 3.43 (d, J = 12.3 Hz, 2H), 3.68 (brs, 2H), 4.00 (d, J = 12.3 Hz, 2H), 7.46 (d, J = 3.1 Hz, 1H), 7.78 (d, J = 8.8 Hz, 2H), 7.94 (d, J = 3.1 Hz, 1H) | CDCl₃ |
| 51 | | 2-(3,8-diazabicyclo[3.2.1]octan-3-yl)-7-(thiazol-2-yl)-5-(trifluoromethyl)benzo[d]oxazole | 381 (M + H)⁺ | (400 MHz): 1.89 (s, 4H), 3.47 (dd, J = 12.2, 2.1 Hz, 2H), 3.70 (s, 2H), 4.02 (dd, J = 12.2, 2.1 Hz, 2H), 7.52 (d, J = 3.3 Hz, 1H), 7.60 (d, J = 1.2 Hz, 1H), 7.99 (d, J = 3.3 Hz, 1H), 8.17 (d, J = 1.2 Hz, 1H) | CDCl₃ |
| 52 | | 2-(3,6-diazabicyclo[3.1.1]heptan-3-yl)-7-(thiazol-2-yl)-5-(trifluoromethyl)benzo[d]oxazole | 367 (M + H)⁺ | (400 MHz): 1.75-1.78 (m, 1H), 2.92-3.01 (m, 1H) 4.02-4.05 (m, 2H), 4.06-4.08 (m, 2H), 4.19 (brs, 2H), 7.53 (d, J = 3.3 Hz, 1H), 7.67 (s, 1H), 8.00 (d, J = 3.3 Hz, 1H), 8.21 (s, 1H) | CDCl₃ |

TABLE 10-continued

| Ex. No. | structural formula | compound name | ESI MS m/z | $^1$H NMR, δ (ppm) | deuterated solvent |
|---|---|---|---|---|---|
| 53 | F₃C-benzoxazole-thiazole-diazabicyclo[3.3.1]nonane | 2-(3,9-diazabicyclo[3.3.1]nonan-3-yl)-7-(thiazol-2-yl)-5-(trifluoromethyl)benzo[d]oxazole | 395 (M + H)⁺ | (400 MHz): 1.53-1.59 (m, 1H), 1.91-2.04 (m, 5H), 3.44 (brs, 2H), 3.66 (dd, J = 13.6, 3.6 Hz, 2H), 4.30 (d, J = 13.6 Hz, 2H), 7.53 (s, 1H), 7.75 (d, J = 3.2 Hz, 1H), 7.93 (d, J = 3.2 Hz, 1H), 8.03 (s, 1H) | CD₃OD |
| 54 | F₃CO-benzoxazole-thiazole-diazabicyclo[3.2.1]octane | 2-(3,8-diazabicyclo[3.2.1]octan-3-yl)-7-(thiazol-2-yl)-5-(trifluoromethoxy)benzo[d]oxazole | 397 (M + H)⁺ | (400 MHz): 1.84-1.97 (m, 4H), 3.47 (dd, J = 12.2, 2.0 Hz, 2H), 3.65-3.77 (m, 2H), 4.01 (dd, J = 12.2, 2.0 Hz, 2H), 7.24 (dd, J = 2.2, 1.0 Hz, 1H), 7.50 (d, J = 3.2 Hz, 1H), 7.75 (dd, J = 2.2, 1.0 Hz, 1H), 7.97 (d, J = 3.2 Hz, 1H) | CDCl₃ |
| 55 | F₃CO-benzoxazole-thiazole-diazabicyclo[3.3.1]nonane | 2-(3,9-diazabicyclo[3.3.1]nonan-3-yl)-7-(thiazol-2-yl)-5-(trifluoromethoxy)benzo[d]oxazole | 411 (M + H)⁺ | (400 MHz): 1.57-1.70 (m, 1H), 1.86-1.97 (m, 4H), 2.01-2.15 (m, 1H), 3.25-3.35 (m, 2H), 3.64 (dd, J = 12.8, 3.9 Hz, 2H), 4.25 (d, J = 12.8 Hz, 2H), 7.26 (dd, J = 2.2, 0.9 Hz, 1H), 7.51 (d, J = 3.2 Hz, 1H), 7.75 (dd, J = 2.2, 0.9 Hz, 1H), 7.98 (d, J = 3.2 Hz, 1H) | CDCl₃ |
| 56 | F₃CO-benzoxazole-thiazole-diazabicyclo[3.1.1]heptane | 2-(3,6-diazabicyclo[3.1.1]heptan-3-yl)-7-(thiazol-2-yl)-5-(trifluoromethoxy)benzo[d]oxazole | 383 (M + H)⁺ | (400 MHz): 1.69 (d, J = 9.1 Hz, 1H), 2.88 (dt, J = 9.1, 6.3 Hz, 1H), 3.88-4.08 (m, 6H), 7.26-7.32 (m, 1H), 7.50 (d, J = 3.3 Hz, 1H), 7.77 (dd, J = 2.3, 0.9 Hz, 1H), 7.97 (d, J = 3.3 Hz, 1H) | CDCl₃ |
| 57 | H₂NO₂S-benzoxazole-thiazole-diazabicyclo[3.2.1]octane | 2-(3,8-diazabicyclo[3.2.1]octan-3-yl)-7-(thiazol-2-yl)benzo[d]oxazole-5-sulfonamide | 392 (M + H)⁺ | (400 MHz): 1.66-1.74 (m, 4H), 3.37-3.41 (m, 2H), 3.55 (s, 2H), 3.85 (d, J = 10.3 Hz, 2H), 7.43 (s, 2H), 7.69 (d, J = 1.8 Hz, 1H), 8.02 (d, J = 3.2 Hz, 1H), 8.09 (d, J = 3.2 Hz, 1H), 8.26 (d, J = 1.8 Hz, 1H) | DMSO-d₆ |

TABLE 11

| Ex. No. | structural formula | compound name | ESI MS m/z | $^1$H NMR, δ (ppm) | deuterated solvent |
|---|---|---|---|---|---|
| 58 | | 2-(3,6-diazabicyclo[3.1.1]heptan-3-yl)-7-(thiazol-2-yl)benzo[d]oxazole-5-sulfonamide | 378 (M + H)$^+$ | (400 MHz): 1.59-1.62 (m, 1H), 2.56-2.61 (m, 1H), 3.70-3.71 (m, 2H), 3.90 (brs, 4H), 7.38 (brs, 2H), 7.75 (d, J = 1.7 Hz, 1H), 8.04 (d, J = 3.0 Hz, 1H), 8.10 (d, J = 3.0 Hz, 1H), 8.29 (d, J = 1.7 Hz, 1H) | DMSO-d$_6$ |
| 59 | | 2-(3,9-diazabicyclo[3.3.1]nonan-3-yl)-7-(thiazol-2-yl)benzo[d]oxazole-5-sulfonamide | 406 (M + H)$^+$ | (400 MHz): 1.51 (brs, 1H), 1.66-1.84 (m, 5H), 3.12 (s, 2H), 3.56 (dd, J = 12.7, 3.7 Hz, 2H), 4.10 (d, J = 12.7 Hz, 2H), 7.43 (brs, 2H), 7.70 (d, J = 1.8 Hz, 1H), 8.02 (d, J = 3.3 Hz, 1H), 8.09 (d, J = 3.3 Hz, 1H), 8.26 (d, J = 1.8 Hz, 1H) | DMSO-d$_6$ |
| 60 | | 2-(3,8-diazabicyclo[3.2.1]octan-3-yl)-5-methoxy-7-(thiazol-2-yl)benzo[d]oxazole | 343 (M + H)$^+$ | (400 MHz): 1.88 (s, 4H), 3.40-3.44 (m, 2H), 3.67 (s, 2H), 3.88 (s, 3H), 3.97-4.0 (m, 2H), 6.99 (d, J = 2.4 Hz, 1H), 7.40 (d, J = 2.4 Hz, 1H), 7.46 (d, J = 3.2 Hz, 1H), 7.95 (d, J = 3.2 Hz, 1H) | CDCl$_3$ |
| 61 | | 2-(3,6-diazabicyclo[3.1.1]heptan-3-yl)-5-methoxy-7-(thiazol-2-yl)benzo[d]oxazole | 329 (M + H)$^+$ | (400 MHz): 1.69 (d, J = 8.8 Hz, 1H), 2.83-2.88 (m, 1H), 3.90 (s, 3H), 3.90-4.03 (m, 6H), 7.04 (d, J = 2.8 Hz, 1H), 7.43 (d, J = 2.8 Hz, 1H), 7.48 (d, J = 3.6 Hz, 1H), 7.96 (d, J = 3.6 Hz, 1H) | CDCl$_3$ |
| 62 | | 2-(3,9-diazabicyclo[3.3.1]nonan-3-yl)-5-methoxy-7-(thiazol-2-yl)benzo[d]oxazole | 357 (M + H)$^+$ | (400 MHz): 1.63-1.65 (m, 1H), 1.91-1.93 (m, 4H), 2.03-2.13 (m, 1H), 3.27 (d, J = 2.8 Hz, 2H), 3.58-3.62 (m, 2H), 3.89 (s, 3H), 4.23-4.26 (m, 2H), 7.01 (d, J = 2.0 Hz, 1H), 7.40 (d, J = 2.0 Hz, 1H), 7.47 (d, J = 3.2 Hz, 1H), 7.96 (d, J = 3.2 Hz, 1H) | CDCl$_3$ |
| 63 | | 2-(3,8-diazabicyclo[3.2.1]octan-3-yl)-7-(thiazol-2-yl)benzo[d]oxazol-5-ol | 329 (M + H)$^+$ | (400 MHz): 1.84-1.88 (m, 2H), 1.90-1.94 (m, 2H), 3.40-3.43 (m, 2H), 3.65 (d, J = 1.6 Hz, 2H), 3.92-3.96 (m, 2H), 6.82 (d, J = 2.4 Hz, 1H), 7.22 (d, J = 2.4 Hz, 1H), 7.74 (d, J = 3.2 Hz, 1H), 7.95 (d, J = 3.2 Hz, 1H) | CD$_3$OD |

TABLE 11-continued

| Ex. No. | structural formula | compound name | ESI MS m/z | $^1$H NMR, δ (ppm) | deuterated solvent |
|---|---|---|---|---|---|
| 64 | 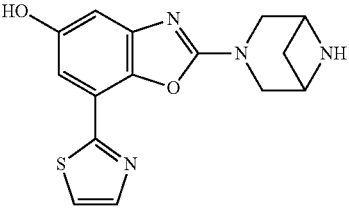 [SMILES: Oc1cc(-c2nccs2)c2oc(N3CC4CC(C3)N4)nc2c1] | 2-(3,6-diazabicyclo[3.1.1]heptan-3-yl)-7-(thiazol-2-yl)benzo[d]oxazol-5-ol | 315 (M + H)$^+$ | (400 MHz): 1.74-1.76 (m, 1H), 2.79-2.84 (m, 1H), 3.86 (d, J = 6.0 Hz, 2H), 3.96-3.97 (m, 4H), 6.84 (d, J = 2.4 Hz, 1H), 7.23 (d, J = 2.4 Hz, 1H), 7.73 (d, J = 3.2 Hz, 1H), 7.94 (d, J = 3.2 Hz, 1H) | CD$_3$OD |
| 65 | 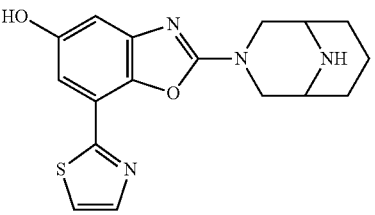 [SMILES: Oc1cc(-c2nccs2)c2oc(N3CC4CCCC(C3)N4)nc2c1] | 2-(3,9-diazabicyclo[3.3.1]nonan-3-yl)-7-(thiazol-2-yl)benzo[d]oxazol-5-ol | 343 (M + H)$^+$ | (400 MHz): 1.61-1.64 (m, 1H), 1.92-1.93 (m, 4H), 2.01-2.13 (m, 1H), 3.28 (s, 2H), 3.59-3.63 (m, 2H), 4.21-4.25 (m, 2H), 6.93 (d, J = 2.0 Hz, 1H), 7.34 (d, J = 2.0 Hz, 1H), 7.47 (d, J = 3.2 Hz, 1H), 7.94 (d, J = 3.2 Hz, 1H) | CD$_3$OD |

TABLE 12

| Ex. No. | structural formula | compound name | ESI MS m/z | $^1$H NMR, δ (ppm) | deuterated solvent |
|---|---|---|---|---|---|
| 66 | 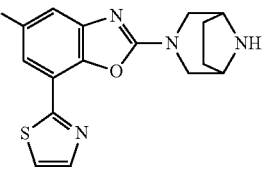 | 2-(3,8-diazabicyclo[3.2.1]octan-3-yl)-7-(thiazol-2-yl)-5-(2,2,2-trifluoroethoxy)benzo[d]oxazole | 411 (M + H)$^+$ | (400 MHz): 1.95-2.11 (m, 2H), 2.11-2.23 (m, 2H), 3.74 (d, J = 12.5 Hz, 2H), 4.00 (brs, 2H), 4.05-4.20 (m, 2H), 4.44 (q, J = 8.1 Hz, 2H), 7.04 (d, J = 2.5 Hz, 1H), 7.48 (d, J = 2.5 Hz, 1H), 7.49 (d, J = 3.3 Hz, 1H), 7.96 (d, J = 3.3 Hz, 1H) | CDCl$_3$ |
| 67 | 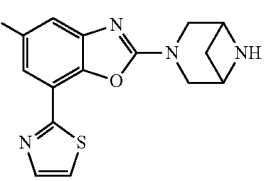 | 2-(3,6-diazabicyclo[3.1.1]heptan-3-yl)-7-(thiazol-2-yl)-5-(2,2,2-trifluoroethoxy)benzo[d]oxazole | 397 (M + H)$^+$ | (400 MHz): 1.69 (d, J = 9.3 Hz, 1H), 2.75-2.99 (m, 1H), 3.85-3.96 (m, 2H), 4.01 (brs, 4H), 4.45 (q, J = 8.1 Hz, 2H), 7.08 (d, J = 2.6 Hz, 1H), 7.48 (d, J = 2.6 Hz, 1H), 7.49 (d, J = 3.3 Hz, 1H), 7.96 (d, J = 3.3 Hz, 1H) | CDCl$_3$ |
| 68 | 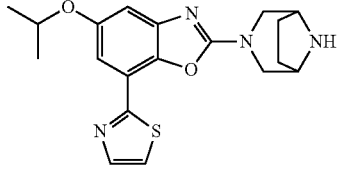 [SMILES: CC(C)Oc1cc(-c2nccs2)c2oc(N3CC4CCC(C3)N4)nc2c1] | 2-(3,8-diazabicyclo[3.2.1]octan-3-yl)-5-isopropoxy-7-(thiazol-2-yl)benzo[d]oxazole | 371 (M + H)$^+$ | (400 MHz): 1.34 (d, J = 6.0 Hz, 6H), 1.74-1.98 (m, 4H), 3.42 (dd, J = 12.3, 2.1 Hz, 2H), 3.61-3.67 (m, 2H), 3.94 (dd, J = 12.3, 2.1 Hz, 2H), 4.61 (spt, J = 6.0 Hz, 1H), 6.91 (d, J = 2.3 Hz, 1H), 7.32 (d, J = 2.3 Hz, 1H), 7.73 (d, J = 3.3 Hz, 1H), 7.94 (d, J = 3.3 Hz, 1H) | CD$_3$OD |
| 69 | 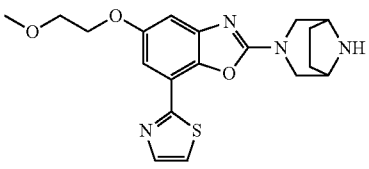 [SMILES: COCCOc1cc(-c2nccs2)c2oc(N3CC4CCC(C3)N4)nc2c1] | 2-(3,8-diazabicyclo[3.2.1]octan-3-yl)-5-(2-methoxyethoxy)-7-(thiazol-2-yl)benzo[d]oxazole | 387 (M + H)$^+$ | (400 MHz): 1.75-1.99 (m, 4H), 3.36-3.47 (m, 2H), 3.44 (s, 3H), 3.62-3.71 (m, 2H), 3.73-3.81 (m, 2H), 3.95 (dd, J = 12.3, 2.1 Hz, 2H), 4.15-4.21 (m, 2H), 6.96 (d, J = 2.4 Hz, 1H), 7.36 (d, J = 2.4 Hz, 1H), 7.74 (d, J = 3.3 Hz, 1H), 7.94 (d, J = 3.3 Hz, 1H) | CD$_3$OD |

TABLE 12-continued

| Ex. No. | structural formula | compound name | ESI MS m/z | ¹H NMR, δ (ppm) | deuterated solvent |
|---|---|---|---|---|---|
| 70 | | 2-(3,8-diazabicyclo[3.2.1]octan-3-yl)-5-(oxetan-3-ylmethoxy)-7-(thiazol-2-yl)benzo[d]oxazole | 399 (M + H)⁺ | (400 MHz): 1.85-2.05 (m, 4H), 3.43-3.54 (m, 3H), 3.75-3.82 (m, 2H), 4.01 (dd, J = 12.7, 2.0 Hz, 2H), 4.28 (d, J = 6.4 Hz, 2H), 4.63 (t, J = 6.1 Hz, 2H), 4.89 (dd, J = 7.9, 6.2 Hz, 2H), 6.99 (d, J = 2.4 Hz, 1H), 7.39 (d, J = 2.4 Hz, 1H), 7.75 (d, J = 3.3 Hz, 1H), 7.95 (d, J = 3.3 Hz, 1H) | CD₃OD |
| 71 | | 2-(((2-(3,8-diazabicyclo[3.2.1]octan-3-yl)-7-(thiazol-2-yl)benzo[d]oxazol-5-yl)oxy)methyl)propane-1,3-diol | 417 (M + H)⁺ | (400 MHz): 1.84-2.04 (m, 4H), 2.16 (q, J = 5.9 Hz, 1H), 3.47 (dd, J = 12.7, 1.7 Hz, 2H), 3.76 (d, J = 6.0 Hz, 4H), 3.75-3.83 (m, 2H), 4.01 (dd, J = 12.7, 2.0 Hz, 2H), 4.13 (d, J = 5.7 Hz, 2H), 6.98 (d, J = 2.4 Hz, 1H), 7.37 (d, J = 2.4 Hz, 1H), 7.75 (d, J = 3.3 Hz, 1H), 7.95 (d, J = 3.3 Hz, 1H) | CD₃OD |
| 72 | | 5-(allyloxy)-2-(3,8-diazabicyclo[3.2.1]octan-3-yl)-7-(thiazol-2-yl)benzo[d]oxazole | 369 (M + H)⁺ | (400 MHz): 1.83-2.02 (m, 4H), 3.46 (dd, J = 12.6, 1.9 Hz, 2H), 3.68-3.79 (m, 2H), 3.98 (dd, J = 12.6, 2.0 Hz, 2H), 4.59-4.63 (m, 2H), 5.25-5.29 (m, 1H), 5.40-5.47 (m, 1H), 6.09 (ddt, J = 17.3, 10.5, 5.2 Hz, 1H), 6.95 (d, J = 2.4 Hz, 1H), 7.35 (d, J = 2.4 Hz, 1H), 7.74 (d, J = 3.3 Hz, 1H), 7.94 (d, J = 3.3 Hz, 1H) | CD₃OD |
| 73 | | 2-((2-(3,8-diazabicyclo[3.2.1]octan-3-yl)-7-(thiazol-2-yl)benzo[d]oxazol-5-yl)oxy)acetonitrile | 368 (M + H)⁺ | (400 MHz): 1.92 (brs, 2H), 1.97-2.13 (m, 2H), 3.50 (d, J = 11.9 Hz, 2H), 3.75 (brs, 2H), 4.02 (d, J = 11.9 Hz, 2H), 4.84 (s, 2H), 7.06 (d, J = 2.6 Hz, 1H), 7.46-7.52 (m, 2H), 7.96 (d, J = 3.3 Hz, 1H) | CDCl₃ |

TABLE 13

| Ex. No. | structural formula | compound name | ESI MS m/z | ¹H NMR, δ (ppm) | deuterated solvent |
|---|---|---|---|---|---|
| 74 | | 2-((2-(3,8-diazabicyclo[3.2.1]octan-3-yl)-7-(thiazol-2-yl)benzo[d]oxazol-5-yl)oxy)acetic acid | 387 (M + H)⁺ | (400 MHz, TFA?): 2.11-2.22 (m, 4H), 3.58-3.72 (m, 2H), 4.21-4.28 (m, 4H), 4.74 (s, 2H), 7.04 (d, J = 2.5 Hz, 1H), 7.41 (d, J = 2.5 Hz, 1H), 7.77 (d, J = 3.3 Hz, 1H), 7.97 (d, J = 3.3 Hz, 1H) | CD₃OD |
| 75 | | 2-(3,8-diazabicyclo[3.2.1]octan-3-yl)-4-methoxy-7-(thiazol-2-yl)benzo[d]oxazole | 343 (M + H)⁺ | (400 MHz): 1.84-1.92 (m, 4H), 3.40-3.43 (m, 2H), 3.66 (s, 2H), 4.02 (s, 3H), 4.03-4.07 (m, 2H), 6.83 (d, J = 9.3 Hz, 1H), 7.38 (d, J = 3.2 Hz, 1H), 7.84 (d, J = 9.3 Hz, 1H), 7.90 (d, J = 3.2 Hz, 1H) | CDCl₃ |

TABLE 13-continued

| Ex. No. | structural formula | compound name | ESI MS m/z | ¹H NMR, δ (ppm) | deuterated solvent |
|---|---|---|---|---|---|
| 76 | | 2-(3,6-diazabicyclo[3.1.1]heptan-3-yl)-4-methoxy-7-(thiazol-2-yl)benzo[d]oxazole | 329 (M + H)⁺ | (400 MHz): 1.67 (d, J = 8.0 Hz, 1H), 2.81-2.87 (m, 1H), 3.92 (s, 2H), 4.04 (s, 3H), 3.98-4.06 (m, 4H), 6.86 (d, J = 8.8 Hz, 1H), 7.39 (d, J = 2.8 Hz, 1H), 7.86 (d, J = 8.8 Hz, 1H), 7.90 (d, J = 2.8 Hz, 1H) | CDCl₃ |
| 77 | | 2-(3,9-diazabicyclo[3.3.1]nonan-3-yl)-4-methoxy-7-(thiazol-2-yl)benzo[d]oxazole | 357 (M + H)⁺ | (400 MHz): 1.61-1.63 (m, 1H), 1.91-1.93 (m, 4H), 2.06-2.14 (m, 1H), 3.26 (s, 2H), 3.57-3.61 (m, 2H), 4.03 (s, 3H), 4.28-4.31 (m, 2H), 6.84 (d, J = 8.4 Hz, 1H), 7.39 (d, J = 3.2 Hz, 1H), 7.84 (d, J = 8.4 Hz, 1H), 7.90 (d, J = 3.2 Hz, 1H) | CDCl₃ |
| 78 | | 2-(3,8-diazabicyclo[3.2.1]octan-3-yl)-7-(thiazol-2-yl)benzo[d]oxazol-4-ol | 329 (M + H)⁺ | (400 MHz): 1.90 (s, 4H), 3.44-3.47 (m, 2H), 3.72 (s, 2H), 3.96-3.98 (m, 2H), 6.83 (d, J = 8.4 Hz, 1H), 7.36 (d, J = 3.6 Hz, 1H), 7.76 (d, J = 8.4 Hz, 1H), 7.89 (d, J = 3.6 Hz, 1H) | CDCl₃ |
| 79 | | 2-(3,6-diazabicyclo[3.1.1]heptan-3-yl)-7-(thiazol-2-yl)benzo[d]oxazol-4-ol | 315 (M + H)⁺ | (400 MHz): 1.95-1.98 (m, 1H), 2.88-2.91 (m, 1H), 4.11 (brs, 4H), 4.32-4.45 (m, 2H), 6.80 (d, J = 8.9 Hz, 1H), 7.67 (d, J = 8.9 Hz, 1H), 7.82 (d, J = 3.3 Hz, 1H), 7.94 (d, J = 3.3 Hz, 1H), 10.32 (brs, 1H) | DMSO-d₆ |
| 80 | | 2-(3,9-diazabicyclo[3.3.1]nonan-3-yl)-7-(thiazol-2-yl)benzo[d]oxazol-4-ol | 343 (M + H)⁺ | (400 MHz): 1.62-1.66 (m, 1H), 1.87-2.00 (m, 4H), 2.01-2.18 (m, 1H), 3.31 (s, 2H), 3.62 (d, J = 12.7, 4.0 Hz, 2H), 4.22 (d, J = 12.7 Hz, 2H), 6.84 (d, J = 8.6 Hz, 1H), 7.37 (d, J = 3.3 Hz, 1H), 7.76 (d, J = 8.6 Hz, 1H), 7.89 (d, J = 3.3 Hz, 1H) | CDCl₃ |

TABLE 13-continued

| Ex. No. | structural formula | compound name | ESI MS m/z | ¹H NMR, δ (ppm) | deuterated solvent |
|---|---|---|---|---|---|
| 81 | | 2-(3,8-diazabicyclo[3.2.1]octan-3-yl)-4-cyclobutoxy-7-(thiazol-2-yl)benzo[d]oxazole | 383 (M + H)⁺ | (400 MHz): 1.69-1.81 (m, 1H), 1.81-1.97 (m, 5H), 2.18-2.33 (m, 2H), 2.46-2.61 (m, 2H), 3.41 (dd, J = 12.3, 2.1 Hz, 2H), 3.60-3.69 (m, 2H), 3.98 (dd, J = 12.3, 2.1 Hz, 2H), 4.94 (quin, J = 7.0 Hz, 1H), 6.78 (d, J = 8.7 Hz, 1H), 7.64 (d, J = 3.3 Hz, 1H), 7.70 (d, J = 8.7 Hz, 1H), 7.88 (d, J = 3.4 Hz, 1H) | CD₃OD |

TABLE 14

| Ex. No. | structural formula | compound name | ESI MS m/z | ¹H NMR, δ (ppm) | deuterated solvent |
|---|---|---|---|---|---|
| 82 | | 2-((2-(3,8-diazabicyclo[3.2.1]octan-3-yl)-7-(thiazol-2-yl)benzo[d]oxazol-4-yl)oxy)acetonitrile | 368 (M + H)⁺ | (400 MHz): 1.79-1.98 (m, 4H), 3.43 (dd, J = 12.4, 2.1 Hz, 2H), 3.59-3.69 (m, 2H), 3.98 (dd, J = 12.4, 2.1 Hz, 2H), 5.32 (s, 2H), 7.00 (d, J = 8.7 Hz, 1H), 7.67 (d, J = 3.4 Hz, 1H), 7.74 (d, J = 8.7 Hz, 1H), 7.90 (d, J = 3.4 Hz, 1H) | CD₃OD |
| 83 | | 1-((2-(3,8-diazabicyclo[3.2.1]octan-3-yl)-7-(thiazol-2-yl)benzo[d]oxazol-4-yl)oxy)-3-methoxypropan-2-ol | 417 (M + H)⁺ | (400 MHz): 1.82-2.01 (m, 4H), 3.40 (s, 3H), 3.45 (dd, J = 12.3, 1.8 Hz, 2H), 3.54-3.64 (m, 2H), 3.65-3.75 (m, 2H), 3.98 (dd, J = 12.3, 2.0 Hz, 2H), 4.12-4.21 (m, 2H), 4.26-4.33 (m, 1H), 6.93 (d, J = 8.7 Hz, 1H), 7.65 (d, J = 3.4 Hz, 1H), 7.73 (d, J = 8.7 Hz, 1H), 7.89 (d, J = 3.4 Hz, 1H) | CD₃OD |
| 84 | | 2-(3,8-diazabicyclo[3.2.1]octan-3-yl)-4-((tetrahydrofuran-3-yl)oxy)-7-(thiazol-2-yl)benzo[d]oxazole | 399 (M + H)⁺ | (400 MHz): 1.82-2.00 (m, 4H), 2.17-2.37 (m, 2H), 3.44 (dd, J = 12.5, 1.8 Hz, 2H), 3.66-3.74 (m, 2H), 3.90 (td, J = 8.3, 4.3 Hz, 1H), 3.97-4.08 (m, 5H), 5.42 (ddt, J = 5.8, 3.8, 2.0 Hz, 1H), 6.89 (d, J = 8.7 Hz, 1H), 7.65 (d, J = 3.3 Hz, 1H), 7.73 (d, J = 8.7 Hz, 1H), 7.89 (d, J = 3.3 Hz, 1H) | CD₃OD |

TABLE 14-continued

| Ex. No. | structural formula | compound name | ESI MS m/z | $^1$H NMR, δ (ppm) | deuterated solvent |
|---|---|---|---|---|---|
| 85 | | 2-(3,8-diazabicyclo[3.2.1]octan-3-yl)-4,7-di(thiazol-2-yl)benzo[d]oxazole | 396 (M + H)$^+$ | (400 MHz): 1.89-2.00 (s, 4H), 3.52-3.59 (m, 2H), 3.72-3.79 (m, 2H), 4.16 (dd, J = 12.5, 1.7 Hz, 2H), 7.47 (d, J = 3.2 Hz, 1H), 7.49 (d, J=3.2 Hz, 1H), 7.93 (d, J = 8.5 Hz, 1H), 7.95 (d, J = 3.2 Hz, 1H), 7.99 (d, J = 3.2 Hz, 1H), 8.22 (d, J = 8.5 Hz, 1H) | CDCl$_3$ |
| 86 | | ethyl 2-(3,8-diazabicyclo[3.2.1]octan-3-yl)-7-(thiazol-2-yl)benzo[d]oxazole-5-carboxylate | 385 (M + H)$^+$ | (400 MHz): 1.43 (t, J = 6.8 Hz, 3H), 1.90 (s, 4H), 3.44-3.47 (m, 2H), 3.70 (s, 2H), 4.00-4.03 (m, 2H), 4.38-4.43 (m, 2H), 7.50 (d, J = 2.8 Hz, 1H), 8.00 (d, J = 2.8 Hz, 1H), 8.07 (d, J = 1.6 Hz, 1H), 8.58 (d, J = 1.6 Hz, 1H) | CDCl$_3$ |
| 87 | | ethyl 2-(3,6-diazabicyclo[3.1.1]heptan-3-yl)-7-(thiazol-2-yl)benzo[d]oxazole-5-carboxylate | 371 (M + H)$^+$ | (400 MHz): 1.44 (t, J = 7.2 Hz, 3H), 1.71 (d, J = 9.2 Hz, 1H), 2.85-2.90 (m, 1H), 3.94 (d, J = 5.2 Hz, 2H), 3.98-4.05 (m, 4H), 4.44 (q, J = 7.2 Hz, 2H), 7.51 (d, J = 2.8 Hz, 1H), 8.01 (d, J = 2.8 Hz, 1H), 8.13 (d, J = 1.6 Hz, 1H), 8.61 (d, J = 1.6 Hz, 1H) | CDCl$_3$ |
| 88 | | ethyl 2-(3-oxa-7,9-diazabicyclo[3.3.1]nonan-7-yl)-7-(thiazol-2-yl)benzo[d]oxazole-5-carboxylate | 401 (M + H)$^+$ | (400 MHz): 1.43 (t, J = 7.2 Hz, 3H), 3.04 (s, 2H), 3.70-3.73 (m, 2H), 3.92-3.95 (m, 2H), 4.04-4.07 (m, 2H), 4.40 (q, J = 7.2 Hz, 2H), 4.47-4.50 (m, 2H), 7.49 (d, J = 3.2 Hz, 1H), 8.00 (d, J = 3.2 Hz, 1H), 8.07 (d, J = 1.2 Hz, 1H), 8.58 (d, J = 1.2 Hz, 1H) | CDCl$_3$ |
| 89 | | ethyl 2-(3,9-diazabicyclo[3.3.1]nonan-3-yl)-7-(thiazol-2-yl)benzo[d]oxazole-5-carboxylate | 399 (M + H)$^+$ | (400 MHz): 1.44 (t, J = 7.6 Hz, 3H), 1.57-1.65 (m, 1H), 1.92-1.94 (m, 4H), 2.02-2.12 (m, 1H), 3.29 (brs, 2H), 3.62-3.66 (m, 2H), 4.25-4.28 (m, 2H), 4.44 (q, J = 7.6 Hz, 2H), 7.51 (d, J = 3.2 Hz, 1H), 8.01 (d, J = 3.2 Hz, 1H), 8.09 (d, J = 1.2 Hz, 1H), 8.59 (d, J = 1.2 Hz, 1H) | CDCl$_3$ |

TABLE 15

| Ex. No. | structural formula | compound name | ESI MS m/z | $^1$H NMR, δ (ppm) | deuterated solvent |
|---|---|---|---|---|---|
| 90 | | ethyl 2-(3,8-diazabicyclo[3.2.1]octan-3-yl)-7-(1H-pyrazol-1-yl)benzo[d]oxazole-5-carboxylate | 368 (M + H)$^+$ | (400 MHz): 1.42 (t, J = 7.2 Hz, 3H), 1.89 (s, 4H), 3.43-3.46 (m, 2H), 3.70 (s, 2H), 3.93-3.96 (m, 2H), 4.42 (q, J = 7.2 Hz, 2H), 6.54-6.55 (m, 1H), 7.80 (d, J = 1.6 Hz, 1H), 7.96 (d, J = 1.2 Hz, 1H), 8.19 (d, J = 2.4 Hz, 1H), 8.30 (d, J = 1.6 Hz, 1H) | CDCl$_3$ |

TABLE 15-continued

| Ex. No. | structural formula | compound name | ESI MS m/z | ¹H NMR, δ (ppm) | deuterated solvent |
|---|---|---|---|---|---|
| 91 | | ethyl 2-(3,6-diazabicyclo[3.1.1]heptan-3-yl)-7-(1H-pyrazol-1-yl)benzo[d]oxazole-5-carboxylate | 354 (M + H)⁺ | (400 MHz): 1.43 (t, J=6.8 Hz, 3H), 1.69 (d, J = 1.2 Hz, 1H), 2.84-2.89 (m, 1H), 3.93 (d, J = 6.0 Hz, 2H), 3.98-4.01 (m, 4H), 4.43 (q, J = 6.8 Hz, 2H), 6.54-6.55 (m, 1H), 7.81 (d, J = 1.2 Hz, 1H), 8.01 (d, J = 1.2 Hz, 1H), 8.24 (d, J = 2.4 Hz, 1H), 8.33 (d, J = 2.0 Hz, 1H) | CDCl₃ |
| 92 | | ethyl 2-(3-oxa-7,9-diazabicyclo[3.3.1]nonan-7-yl)-7-(1H-pyrazol-1-yl)benzo[d]oxazole-5-carboxylate | 384 (M + H)⁺ | (400 MHz): 1.42 (t, J = 7.2 Hz, 3H), 3.03 (s, 2H), 3.67-3.70 (m, 2H), 3.91-3.94 (m, 2H), 4.02-4.05 (m, 2H), 4.38-4.43 (m, 4H), 6.53-6.54 (m, 1H), 7.80 (d, J = 2.0 Hz, 1H), 7.95 (d, J = 1.2 Hz, 1H), 8.20 (d, J = 2.4 Hz, 1H), 8.28 (d, J = 1.2 Hz, 1H) | CDCl₃ |
| 93 | | ethyl 2-(3,9-diazabicyclo[3.3.1]nonan-3-yl)-7-(1H-pyrazol-1-yl)benzo[d]oxazole-5-carboxylate | 382 (M + H)⁺ | (400 MHz): 1.43 (t, J = 7.2 Hz, 3H), 1.60-1.65 (m, 1H), 1.91-1.93 (m, 4H), 2.09-2.11 (m, 1H), 3.27 (s, 2H), 3.59-3.63 (m, 2H), 4.17-4.20 (m, 2H), 4.43 (q, J = 7.2 Hz, 2H), 6.55-6.56 (m, 1H), 7.81 (d, J = 1.2 Hz, 1H), 7.97 (d, J = 1.2 Hz, 1H), 8.22 (d, J = 2.4 Hz, 1H), 8.31 (d, J = 2.0 Hz, 1H) | CDCl₃ |
| 94 | | 2-(3,8-diazabicyclo[3.2.1]octan-3-yl)-N,N-dimethyl-7-(thiazol-2-yl)benzo[d]oxazole-5-carboxamide | 384 (M + H)⁺ | (400 MHz): 1.76-1.95 (m, 4H), 2.97 (brs, 3H), 3.04 (brs, 3H), 3.41 (dd, J = 12.6, 1.7 Hz, 2H), 3.65-3.72 (m, 2H), 3.95 (dd, J = 12.6, 2.0 Hz, 2H), 7.31 (d, J = 1.5 Hz, 1H), 7.69 (d, J = 3.3 Hz, 1H), 7.77 (d, J = 1.5 Hz, 1H), 7.89 (d, J = 3.3 Hz, 1H) | CD₃OD |
| 95 | | (2-(3,8-diazabicyclo[3.2.1]octan-3-yl)-7-(thiazol-2-yl)benzo[d]oxazol-5-yl)(morpholino)methanone | 426 (M + H)⁺ | (400 MHz): 1.72-1.89 (m, 4H), 3.32-3.76 (m, 10H), 3.38 (dd, J = 12.4, 1.8 Hz, 2H), 3.91 (dd, J = 12.4, 1.9 Hz, 2H), 7.30 (d, J = 1.6 Hz, 1H), 7.68 (d, J = 3.2 Hz, 1H), 7.76 (d, J = 1.6 Hz, 1H), 7.88 (d, J = 3.2 Hz, 1H) | CD₃OD |
| 96 | | (2-(3,8-diazabicyclo[3.2.1]octan-3-yl)-7-(thiazol-2-yl)benzo[d]oxazol-5-yl)(piperidin-1-yl)methanone | 424 (M + H)⁺ | (400 MHz): 1.41-1.69 (m, 6H), 1.70-1.89 (m, 4H), 3.36 (dd, J = 12.3, 1.8 Hz, 4H), 3.49-3.71 (m, 4H), 3.88 (dd, J = 12.3, 1.9 Hz, 2H), 7.25 (d, J = 1.5 Hz, 1H), 7.68 (d, J = 3.3 Hz, 1H), 7.73 (d, J = 1.5 Hz, 1H), 7.87 (d, J = 3.3 Hz, 1H) | CD₃OD |
| 97 | | (2-(3,8-diazabicyclo[3.2.1]octan-3-yl)-7-(thiazol-2-yl)benzo[d]oxazol-5-yl)(azetidin-1-yl)methanone | 396 (M + H)⁺ | (400 MHz): 1.75-1.94 (m, 4H), 2.30 (quin, J = 7.8 Hz, 2H), 3.41 (dd, J = 12.7, 1.7 Hz, 2H), 3.65-3.72 (m, 2H), 3.94 (dd, J = 12.5, 1.7 Hz, 2H), 4.14 (t, J = 7.8 Hz, 2H), 4.36 (t, J = 7.8 Hz, 2H), 7.50 (d, J = 1.6 Hz, 1H), 7.69 (d, J = 3.3 Hz, 1H), 7.89 (d, J = 3.3 Hz, 1H), 7.99 (d, J = 1.6 Hz, 1H) | CD₃OD |

TABLE 16

| Ex. No. | structural formula | compound name | ESI MS m/z | $^1$H NMR, δ (ppm) | deuterated solvent |
|---|---|---|---|---|---|
| 98 | | N-benzyl-2-(3,8-diazabicyclo[3.2.1]octan-3-yl)-7-(thiazol-2-yl)benzo[d]oxazole-5-carboxamide | 446 (M + H)+ | (400 MHz): 1.78-1.98 (m, 4H), 3.43 (dd, J = 12.4, 1.6 Hz, 2H), 3.61-3.70 (m, 2H), 3.94 (dd, J = 12.4, 1.3 Hz, 2H), 4.58 (s, 2H), 7.19-7.26 (m, 1H), 7.28-7.35 (m, 2H), 7.35-7.40 (m, 2H), 7.71 (d, J = 3.3 Hz, 1H), 7.76 (d, J = 1.6 Hz, 1H), 7.93 (d, J = 3.3 Hz, 1H), 8.27 (d, J = 1.6 Hz, 1H) | CD$_3$OD |
| 99 | | 2-(3,8-diazabicyclo[3.2.1]octan-3-yl)-7-(thiazol-2-yl)benzo[d]oxazole-5-carboxamide | 356 (M + H)+ | (400 MHz): 1.86-2.04 (m, 4H), 3.51 (dd, J = 12.5, 1.8 Hz, 2H), 3.72-3.77 (m, 2H), 4.02 (dd, J = 12.5, 2.0 Hz, 2H), 7.68 (d, J = 3.2 Hz, 1H), 7.88 (d, J = 1.7 Hz, 1H), 7.99 (d, J = 3.2 Hz, 1H), 8.36 (d, J = 1.7 Hz, 1H) | CD$_3$OD |
| 100 | | 2-(3,8-diazabicyclo[3.2.1]octan-3-yl)-N-methyl-7-(thiazol-2-yl)benzo[d]oxazole-5-carboxamide | 370 (M + H)+ | (400 MHz): 1.78-2.00 (m, 4H), 2.94 (s, 3H), 3.45 (dd, J = 12.4, 1.8 Hz, 2H), 3.65-3.71 (m, 2H), 3.96 (dd, J = 12.4, 1.8 Hz, 2H), 7.71 (d, J = 1.6 Hz, 1H), 7.73 (d, J = 3.2 Hz, 1H), 7.95 (d, J = 3.2 Hz, 1H), 8.23 (d, J = 1.6 Hz, 1H) | CD$_3$OD |
| 101 | | N-(2-(3,8-diazabicyclo[3.2.1]octan-3-yl)-7-(thiazol-2-yl)benzo[d]oxazol-5-yl)-N-methylacetamide | 384 (M + H)+ | (400 MHz): 1.85-2.05 (m, 4H), 1.93 (s, 3H), 3.33 (s, 3H), 3.52 (dd, J = 12.3, 1.6 Hz, 2H), 3.54-3.56 (m, 2H), 4.05 (dd, J = 12.3, 1.5 Hz, 2H), 7.32 (d, J = 2.0 Hz, 1H), 7.73 (d, J = 2.0 Hz, 1H), 7.83 (d, J = 3.2 Hz, 1H), 8.01 (d, J = 3.2 Hz, 1H) | CD$_3$OD |
| 102 | | 2-(3,8-diazabicyclo[3.2.1]octan-3-yl)-7-(thiazol-2-yl)-5-(1,1,1-trifluoro-2-methoxypropan-2-yl)benzo[d]oxazole | 439 (M + H)+ | (400 MHz): 1.87-1.90 (m, 7H), 3.26 (s, 3H), 3.46 (dd, J = 12.2, 1.7 Hz, 2H), 3.70 (s, 2H), 4.01-4.03 (m, 2H), 7.48 (d, J = 3.3 Hz, 1H), 7.61 (d, J = 1.6 Hz, 1H), 7.98 (d, J = 3.3 Hz, 1H), 8.00 (d, J = 1.6 Hz, 1H) | CDCl$_3$ |
| 103 | | 2-(3,6-diazabicyclo[3.1.1]heptan-3-yl)-7-(thiazol-2-yl)-5-(1,1,1-trifluoro-2-methoxypropan-2-yl)benzo[d]oxazole | 425 (M + H)+ | (400 MHz): 1.69 (d, J = 9.3 Hz, 1H), 1.89 (s, 3H), 2.85-2.90 (m, 1H), 3.28 (s, 3H), 3.94 (d, J = 6.1 Hz, 2H), 3.97-4.05 (m, 4H), 7.49 (d, J = 3.3 Hz, 1H), 7.67 (d, J = 1.6 Hz, 1H), 7.80 (d, J = 1.6 Hz, 1H), 7.99 (d, J = 3.3 Hz, 1H) | CDCl$_3$ |
| 104 | | 1-(2-(3,8-diazabicyclo[3.2.1]octan-3-yl)-7-(thiazol-2-yl)benzo[d]oxazol-5-yl)-2,2-difluoroethan-1-ol | 393 (M + H)+ | (400 MHz): 1.58-1.80 (m, 4H), 3.25-3.39 (m, 2H), 3.54 (s, 2H), 3.83 (d, J = 10.1 Hz, 2H), 4.80-4.95 (m, 1H), 5.86-6.22 (m, 1H), 6.30 (d, J = 5.1 Hz, 1H), 7.39 (d, J = 1.3 Hz, 1H), 7.84 (d, J = 1.3 Hz, 1H), 7.94 (d, J = 3.2 Hz, 1H), 8.03 (d, J = 3.2 Hz, 1H) | DMSO-d$_6$ |

TABLE 16-continued

| Ex. No. | structural formula | compound name | ESI MS m/z | ¹H NMR, δ (ppm) | deuterated solvent |
|---|---|---|---|---|---|
| 105 | (structure: OMe, HF₂C group on benzoxazole with thiazole and diazabicyclo[3.2.1]octane) | 2-(3,8-diazabicyclo[3.2.1]octan-3-yl)-5-(2,2-difluoro-1-methoxyethyl)-7-(thiazol-2-yl)benzo[d]oxazole | 407 (M + H)⁺ | (400 MHz): 1.89 (d, J = 1.7 Hz, 4H), 3.38 (s, 3H), 3.45 (dd, J = 12.2, 2.1 Hz, 2H), 3.69 (s, 2H), 4.02 (dd, J = 12.2, 2.1 Hz, 2H), 4.43 (td, J = 9.9, 4.7 Hz, 1H), 5.66-5.99 (m, 1H), 7.43 (d, J = 1.5 Hz, 1H), 7.49 (d, J = 3.2 Hz, 1H), 7.87 (d, J = 1.5 Hz, 1H), 7.97 (d, J = 3.2 Hz, 1H) | CDCl₃ |

TABLE 17

| Ex. No. | structural formula | compound name | ESI MS m/z | ¹H NMR, δ (ppm) | deuterated solvent |
|---|---|---|---|---|---|
| 106 | (structure) | 1-(2-(3,8-diazabicyclo[3.2.1]octan-3-yl)-7-(thiazol-2-yl)benzo[d]oxazol-5-yl)ethan-1-ol | 357 (M + H)⁺ | (400 MHz): 1.55 (d, J = 6.5 Hz, 3H), 1.89 (s, 4H), 3.42 (d, J = 11.1 Hz, 2H), 3.68 (s, 2H), 4.00 (d, J = 9.9 Hz, 2H), 5.02 (q, J = 6.5 Hz, 1H), 7.45-7.46 (m, 2H), 7.85 (d, J = 1.2 Hz, 1H), 7.95 (d, J = 3.3 Hz, 1H) | CDCl₃ |
| 107 | (structure) | 1-(2-(3,6-diazabicyclo[3.1.1]heptan-3-yl)-7-(thiazol-2-yl)benzo[d]oxazol-5-yl)ethan-1-ol | 343 (M + H)⁺ | (400 MHz): 1.42 (d, J = 6.5 Hz, 3H), 2.02 (d, J = 10.9 Hz, 1H), 3.01-3.11 (m, 1H), 4.14-4.25 (m, 4H), 4.51 (d, J = 6.1 Hz, 2H), 4.87 (q, J = 6.5 Hz, 1H), 7.41 (s, 1H), 7.67 (d, J = 3.3 Hz, 1H), 7.77 (s, 1H), 7.88 (d, J = 3.3 Hz, 1H) | CD₃OD |
| 108 | (structure) | 1-(2-(3,8-diazabicyclo[3.2.1]octan-3-yl)-7-(thiazol-2-yl)benzo[d]oxazol-5-yl)ethan-1-one | 355 (M + H)⁺ | (400 MHz): 1.88-1.92 (m, 4H), 2.70 (s, 3H), 3.47 (dd, J = 12.2, 1.9 Hz, 2H), 3.70 (s, 2H), 3.98-4.06 (m, 2H), 7.50 (d, J = 3.3 Hz, 1H), 7.98-8.01 (m, 2H), 8.51 (s, 1H) | CDCl₃ |
| 109 | (structure) | 1-(2-(3,6-diazabicyclo[3.1.1]heptan-3-yl)-7-(thiazol-2-yl)benzo[d]oxazol-5-yl)ethan-1-one | 341 (M + H)⁺ | (400 MHz): 1.59-1.66 (m, 1H), 2.59-2.63 (m, 1H), 2.67 (s, 3H), 3.71-3.79 (m, 2H), 3.85-4.01 (m, 4H), 7.98 (s, 1H), 8.02 (d, J = 3.2 Hz, 1H), 8.09 (d, J = 3.2 Hz, 1H), 8.40 (s, 1H) | DMSO-d₆ |
| 110 | (structure) | 2-(3,8-diazabicyclo[3.2.1]octan-3-yl)-5-(1-methoxyethyl)-7-(thiazol-2-yl)benzo[d]oxazole | 371 (M + H)⁺ | (400 MHz): 1.48 (d, J = 6.5 Hz, 3H), 1.92 (s, 4H), 3.24 (s, 3H), 3.50 (d, J = 12.7 Hz, 2H), 3.75 (s, 2H), 4.04 (d, J = 12.7 Hz, 2H), 4.41 (q, J = 6.5 Hz, 1H), 7.41 (d, J = 1.5 Hz, 1H), 7.47 (d, J = 3.3 Hz, 1H), 7.79 (d, J = 1.5 Hz, 1H), 7.96 (d, J = 3.3 Hz, 1H) | CDCl₃ |

TABLE 17-continued

| Ex. No. | structural formula | compound name | ESI MS m/z | ¹H NMR, δ (ppm) | deuterated solvent |
|---|---|---|---|---|---|
| 111 | (OMe substituted benzoxazole with thiazole and 3,6-diazabicyclo[3.1.1]heptane) | 2-(3,6-diazabicyclo[3.1.1]heptan-3-yl)-5-(1-methoxyethyl)-7-(thiazol-2-yl)benzo[d]oxazole | 357 (M + H)⁺ | (400 MHz): 1.50 (d, J = 6.5 Hz, 3H), 1.72 (d, J = 9.3 Hz, 1H), 2.87-2.94 (m, 1H), 3.25 (s, 3H), 3.97-4.00 (m, 2H), 4.02-4.07 (m, 4H), 4.43 (q, J = 6.5 Hz, 1H), 7.46 (s, 1H), 7.48 (d, J = 3.3 Hz, 1H), 7.82 (s, 1H), 7.97 (d, J = 3.3 Hz, 1H) | CDCl₃ |
| 112 | (CO₂Et benzoxazole with thiazole and 3,8-diazabicyclo[3.2.1]octane) | ethyl 2-(3,8-diazabicyclo[3.2.1]octan-3-yl)-7-(thiazol-2-yl)benzo[d]oxazole-4-carboxylate | 385 (M + H)⁺ | (400 MHz): 1.46 (t, J = 7.2 Hz, 3H), 1.85-1.92 (m, 4H), 3.47-3.51 (m, 2H), 3.69 (s, 2H), 4.13 (d, J = 12.0 Hz, 2H), 4.47 (q, J = 7.2 Hz, 2H), 7.53 (d, J = 3.2 Hz, 1H), 7.85-7.91 (m, 2H), 8.01 (d, J = 3.2 Hz, 1H) | CDCl₃ |
| 113 | (CO₂Et benzoxazole with thiazole and 3,6-diazabicyclo[3.1.1]heptane) | ethyl 2-(3,6-diazabicyclo[3.1.1]heptan-3-yl)-7-(thiazol-2-yl)benzo[d]oxazole-4-carboxylate | 371 (M + H)⁺ | (400 MHz): 1.47 (t, J = 7.2 Hz, 3H), 1.66-1.68 (m, 1H), 2.84-2.89 (m, 1H), 3.93-3.94 (m, 2H), 4.04-4.14 (m, 4H), 4.49 (q, J = 7.2 Hz, 2H), 7.55 (d, J = 2.8 Hz, 1H), 7.88-7.94 (m, 2H), 8.02 (d, J = 2.8 Hz, 1H) | CDCl₃ |

TABLE 18

| Ex. No. | structural formula | compound name | ESI MS m/z | ¹H NMR, δ (ppm) | deuterated solvent |
|---|---|---|---|---|---|
| 114 | (CO₂Et benzoxazole with thiazole and 3,9-diazabicyclo[3.3.1]nonane) | ethyl 2-(3,9-diazabicyclo[3.3.1]nonan-3-yl)-7-(thiazol-2-yl)benzo[d]oxazole-4-carboxylate | 399 (M + H)⁺ | (400 MHz): 1.47 (t, J = 7.2 Hz, 3H), 1.60-1.65 (m, 1H), 1.93-1.95 (m, 4H), 2.05-2.11 (m, 1H), 3.30 (s, 2H), 3.65-3.69 (m, 2H), 4.34-4.37 (m, 2H), 4.49 (q, J = 7.2 Hz, 2H), 7.55 (d, J = 3.2 Hz, 1H), 7.86-7.92 (m, 2H), 8.02 (d, J = 3.2 Hz, 1H) | CDCl₃ |
| 115 | (N,N-dimethylcarboxamide benzoxazole with thiazole and 3,8-diazabicyclo[3.2.1]octane) | 2-(3,8-diazabicyclo[3.2.1]octan-3-yl)-N,N-dimethyl-7-(thiazol-2-yl)benzo[d]oxazole-4-carboxamide | 384 (M + H)⁺ | (400 MHz): 1.77-1.99 (m, 4H), 2.99 (s, 3H), 3.16 (s, 3H), 3.44 (dd, J = 12.4, 1.7 Hz, 2H), 3.60-3.68 (m, 2H), 4.03 (dd, J = 12.4, 2.0 Hz, 2H), 7.30 (d, J = 8.2 Hz, 1H), 7.78 (d, J = 3.2 Hz, 1H), 7.83 (d, J = 8.2 Hz, 1H), 7.98 (d, J = 3.2 Hz, 1H) | CD₃OD |

TABLE 18-continued

| Ex. No. | structural formula | compound name | ESI MS m/z | ¹H NMR, δ (ppm) | deuterated solvent |
|---|---|---|---|---|---|
| 116 | | (2-(3,8-diazabicyclo[3.2.1]octan-3-yl)-7-(thiazol-2-yl)benzo[d]oxazol-4-yl)(morpholino)methanone | 426 (M + H)⁺ | (400 MHz): 1.79-1.97 (m, 4H), 3.37-3.42 (m, 2H), 3.44 (dd, J = 12.4, 1.7 Hz, 2H), 3.62-3.67 (m, 2H), 3.67-3.73 (m, 2H), 3.80 (s, 4H), 4.02 (dd, J = 12.4, 2.1 Hz, 2H), 7.33 (d, J = 8.2 Hz, 1H), 7.77 (d, J = 3.3 Hz, 1H), 7.83 (d, J = 8.2 Hz, 1H), 7.97 (d, J = 3.3 Hz, 1H) | CD₃OD |
| 117 | | (2-(3,8-diazabicyclo[3.2.1]octan-3-yl)-7-(thiazol-2-yl)benzo[d]oxazol-4-yl)(piperidin-1-yl)methanone | 424 (M + H)⁺ | (400 MHz): 1.52-1.77 (m, 6H), 1.78-2.00 (m, 4H), 3.31-3.36 (m, 2H), 3.44 (dd, J = 12.4, 1.8 Hz, 2H), 3.65 (dd, J = 3.9, 2.1 Hz, 2H), 3.73-3.80 (m, 2H), 4.02 (dd, J = 12.4, 2.0 Hz, 2H), 7.28 (d, J = 8.2 Hz, 1H), 7.77 (d, J = 3.3 Hz, 1H), 7.82 (d, J = 8.2 Hz, 1H), 7.97 (d, J = 3.3 Hz, 1H) | CD₃OD |
| 118 | | 1-(2-(3,8-diazabicyclo[3.2.1]octan-3-yl)-7-(thiazol-2-yl)benzo[d]oxazol-4-yl)-2,2,2-trifluoroethan-1-ol (optically active) | 411 (M + H)⁺ | (400 MHz): 1.88 (d, J = 1.5 Hz, 4H), 3.37-3.51 (m, 2H), 3.68 (s, 2H), 4.00 (dd, J = 12.1, 2.1 Hz, 2H), 5.12-5.25 (m, 1H), 7.20 (d, J = 8.1 Hz, 1H), 7.48 (d, J = 3.2 Hz, 1H), 7.85 (d, J = 8.1 Hz, 1H), 7.97 (d, J = 3.2 Hz, 1H) | CDCl₃ |
| 119 | | 1-(2-(3,8-diazabicyclo[3.2.1]octan-3-yl)-7-(thiazol-2-yl)benzo[d]oxazol-4-yl)-2,2,2-trifluoroethan-1-ol (No. 118's enantiomer) | 411 (M + H)⁺ | (400 MHz): 1.88 (d, J = 1.5 Hz, 4H), 3.37-3.51 (m, 2H), 3.68 (s, 2H), 4.00 (dd, J = 12.1, 2.1 Hz, 2H), 5.12-5.25 (m, 1H), 7.20 (d, J = 8.1 Hz, 1H), 7.48 (d, J = 3.2 Hz, 1H), 7.85 (d, J = 8.1 Hz, 1H), 7.97 (d, J = 3.2 Hz, 1H) | CDCl₃ |
| 120 | | 1-(2-(3,6-diazabicyclo[3.1.1]heptan-3-yl)-7-(thiazol-2-yl)benzo[d]oxazol-4-yl)-2,2,2-trifluoroethan-1-ol (optically active) | 397 (M + H)⁺ | (400 MHz): 1.69 (d, J = 9.1 Hz, 1H), 2.85-2.91 (m, 1H), 3.93-4.05 (m, 6H), 5.17-5.24 (m, 1H), 6.14 (brs, 1H), 7.23 (d, J = 8.3 Hz, 1H), 7.50 (d, J = 3.2 Hz, 1H), 7.88 (d, J = 8.3 Hz, 1H), 7.98 (d, J = 3.2 Hz, 1H) | CDCl₃ |

TABLE 18-continued

| Ex. No. | structural formula | compound name | ESI MS m/z | ¹H NMR, δ (ppm) | deuterated solvent |
|---|---|---|---|---|---|
| 121 | | 1-(2-(3,6-diazabicyclo[3.1.1]heptan-3-yl)-7-(thiazol-2-yl)benzo[d]oxazol-4-yl)-2,2,2-trifluoroethan-1-ol (No. 120's enantiomer) | 397 (M + H)⁺ | (400 MHz): 1.69 (d, J = 9.1 Hz, 1H), 2.85-2.91 (m, 1H), 3.93-4.05 (m, 6H), 5.17-5.24 (m, 1H), 6.14 (brs, 1H), 7.23 (d, J = 8.3 Hz, 1H), 7.50 (d, J = 3.2 Hz, 1H), 7.88 (d, J = 8.3 Hz, 1H), 7.98 (d, J = 3.2 Hz, 1H) | CDCl₃ |

TABLE 19

| Ex. No. | structural formula | compound name | ESI MS m/z | ¹H NMR, δ (ppm) | deuterated solvent |
|---|---|---|---|---|---|
| 122 | | 2-(3,6-diazabicyclo[3.1.1]heptan-3-yl)-7-(thiazol-2-yl)-4-(2,2,2-trifluoro-1-methoxyethyl)benzo[d]oxazole (optically active) | 411 (M + H)⁺ | (400 MHz): 1.69 (d, J = 9.3 Hz, 1H), 2.82-2.91 (m, 1H), 3.46 (s, 3H), 3.92-4.06 (m, 6H), 5.34 (q, J = 6.7 Hz, 1H), 7.47-7.49 (m, 2H), 7.92 (d, J = 8.3 Hz, 1H), 7.98 (d, J = 3.3 Hz, 1H) | CDCl₃ |
| 123 | | 2-(3,6-diazabicyclo[3.1.1]heptan-3-yl)-7-(thiazol-2-yl)-4-(2,2,2-trifluoro-1-methoxyethyl)benzo[d]oxazole (No.122's enantiomer) | 411 (M + H)⁺ | (400 MHz): 1.69 (d, J = 9.3 Hz, 1H), 2.82-2.91 (m, 1H), 3.46 (s, 3H), 3.92-4.06 (m, 6H), 5.34 (q, J = 6.7 Hz, 1H), 7.47-7.49 (m, 2H), 7.92 (d, J = 8.3 Hz, 1H), 7.98 (d, J = 3.3 Hz, 1H) | CDCl₃ |
| 124 | | 1-(2-(3,8-diazabicyclo[3.2.1]octan-3-yl)-7-(thiazol-2-yl)benzo[d]oxazol-4-yl)ethan-1-ol | 357 (M + H)⁺ | (400 MHz): 1.63 (d, J = 6.6 Hz, 3H), 1.89 (s, 4H), 3.43 (d, J = 10.6 Hz, 2H), 3.68 (s, 2H), 4.02 (d, J = 10.6 Hz, 2H), 5.19 (brs, 1H), 7.15 (d, J = 8.6 Hz, 1H), 7.44 (d, J = 3.3 Hz, 1H), 7.80 (d, J = 8.6 Hz, 1H), 7.94 (d, J = 3.3 Hz, 1H) | CDCl₃ |
| 125 | | 1-(2-(3,6-diazabicyclo[3.1.1]heptan-3-yl)-7-(thiazol-2-yl)benzo[d]oxazol-4-yl)-2,2-difluoroethan-1-ol | 379 (M + H)⁺ | (400 MHz): 1.68 (d, J = 9.3 Hz, 1H), 2.83-2.92 (m, 1H), 3.93 (d, J = 6.0 Hz, 2H), 3.95-4.06 (m, 4H), 5.05 (td, J = 11.4, 3.7 Hz, 1H), 5.89-6.22 (m, 1H), 7.24 (d, J = 8.2 Hz, 1H), 7.48 (d, J = 3.2 Hz, 1H), 7.87 (d, J = 8.2 Hz, 1H), 7.97 (d, J = 3.2 Hz, 1H) | CDCl₃ |

TABLE 19-continued

| Ex. No. | structural formula | compound name | ESI MS m/z | ¹H NMR, δ (ppm) | deuterated solvent |
|---|---|---|---|---|---|
| 126 | | 2-(2-(3,6-diazabicyclo[3.1.1]heptan-3-yl)-7-(thiazol-2-yl)benzo[d]oxazol-4-yl)-1,1-difluoropropan-2-ol | 393 (M + H)+ | (400 MHz): 1.68 (d, J = 9.3 Hz, 1H), 1.73 (s, 3H), 2.84-2.90 (m, 1H), 3.88-4.08 (m, 6H), 5.75-6.11 (m, 1H), 7.24-7.26 (m, 1H), 7.48 (d, J = 3.2 Hz, 1H), 7.88 (d, J = 8.3 Hz, 1H), 7.97 (d, J = 3.2 Hz, 1H) | CDCl₃ |
| 127 | | 1-(1-(2-(3,6-diazabicyclo[3.1.1]heptan-3-yl)-7-(thiazol-2-yl)benzo[d]oxazol-4-yl)-2,2-difluoroethoxy)-2-methylpropan-2-ol | 451 (M + H)+ | (400 MHz): 1.15 (s, 3H), 1.27 (s, 3H), 1.68 (d, J = 9.3 Hz, 1H), 2.85 (dt, J = 9.3, 6.2 Hz, 1H), 3.35-3.51 (m, 2H), 3.92 (d, J = 6.0 Hz, 2H), 3.95-4.06 (m, 4H), 4.97-5.03 (m, 1H), 6.03-6.36 (m, 1H), 7.30 (d, J = 8.3 Hz, 1H), 7.49 (d, J = 3.3 Hz, 1H), 7.89 (d, J = 8.3 Hz, 1H), 7.97 (d, J = 3.3 Hz, 1H) | CDCl₃ |
| 128 | | 1-(2-(3,8-diazabicyclo[3.2.1]octan-3-yl)-7-(thiazol-2-yl)benzo[d]oxazol-4-yl)-2,2-difluoroethan-1-ol | 393 (M + H)+ | (400 MHz): 1.88 (s, 4H), 3.43 (ddd, J = 12.2, 4.7, 2.0 Hz, 2H), 3.68 (s, 2H), 4.00 (d, J = 12.2 Hz, 2H), 5.02 (dt, J = 11.2, 4.0 Hz, 1H), 5.84-6.23 (m, 1H), 7.21 (d, J = 8.1 Hz, 1H), 7.47 (d, J = 3.2 Hz, 1H), 7.84 (d, J = 8.1 Hz, 1H), 7.96 (d, J = 3.2 Hz, 1H) | CDCl₃ |
| 129 | | 2-(2-(3,8-diazabicyclo[3.2.1]octan-3-yl)-7-(thiazol-2-yl)benzo[d]oxazol-4-yl)-1,1-difluoropropan-2-ol | 407 (M + H)+ | (400 MHz): 1.71 (s, 3H), 1.87 (d, J = 1.7 Hz, 4H), 3.38-3.47 (m, 2H), 3.68 (s, 2H), 4.00 (dt, J = 12.4, 2.9 Hz, 2H), 5.72-6.08 (m, 1H), 7.23 (d, J = 8.3 Hz, 1H), 7.47 (d, J = 3.2 Hz, 1H), 7.85 (d, J = 8.3 Hz, 1H), 7.96 (d, J = 3.2 Hz, 1H) | CDCl₃ |

TABLE 20

| Ex. No. | structural formula | compound name | ESI MS m/z | ¹H NMR, δ (ppm) | deuterated solvent |
|---|---|---|---|---|---|
| 130 | | 2-(3,6-diazabicyclo[3.1.1]heptan-3-yl)-4-(2,2-difluoro-1-methoxyethyl)-7-(thiazol-2-yl)benzo[d]oxazole | 393 (M + H)+ | (400 MHz): 1.68 (d, J = 9.2 Hz, 1H), 2.81-2.91 (m, 1H), 3.45 (s, 3H), 3.92 (d, J = 6.0 Hz, 2H), 3.95-4.07 (m, 4H), 4.91-5.02 (m, 1H), 6.04-6.38 (m, 1H), 7.36 (d, J = 8.3 Hz, 1H), 7.48 (d, J = 3.3 Hz, 1H), 7.91 (d, J = 8.3 Hz, 1H), 7.97 (d, J = 3.3 Hz, 1H) | CDCl₃ |

TABLE 20-continued

| Ex. No. | structural formula | compound name | ESI MS m/z | $^1$H NMR, δ (ppm) | deuterated solvent |
|---|---|---|---|---|---|
| 131 | 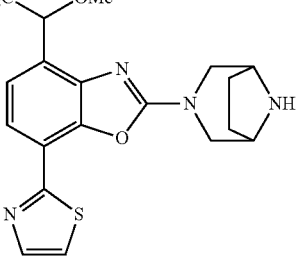 | 2-(3,8-diazabicyclo[3.2.1]octan-3-yl)-4-(2,2-difluoro-1-methoxyethyl)-7-(thiazol-2-yl)benzo[d]oxazole | 407 (M + H)$^+$ | (400 MHz): 1.85-1.91 (m, 4H), 3.39-3.42 (m, 2H), 3.44 (s, 3H), 3.68 (s, 2H), 4.03 (dt, J = 12.5, 2.9 Hz, 2H), 4.93 (ddd, 12.5, 8.1, 4.3 Hz, 1H), 6.02-6.35 (m, 1H), 7.34 (d, J = 8.2 Hz, 1H), 7.47 (d, J = 3.2 Hz, 1H), 7.87 (d, J = 8.2 Hz, 1H), 7.96 (d, J = 3.2 Hz, 1H) | CDCl$_3$ |
| 132 | 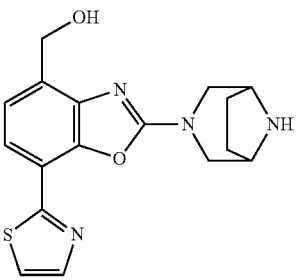 [SMILES: OCc1ccc(-c2nccs2)c2oc(N3CC4CCC(C3)N4)nc12] | (2-(3,8-diazabicyclo[3.2.1]octan-3-yl)-7-(thiazol-2-yl)benzo[d]oxazol-4-yl)methanol | 343 (M + H)$^+$ | (400 MHz): 1.89 (s, 4H), 3.44 (d, J = 12.2 Hz, 2H), 3.68 (s, 2H), 4.02 (d, J = 12.2 Hz, 2H), 4.96 (s, 2H), 7.17 (d, J = 8.1 Hz, 1H), 7.46 (d, J = 3.2 Hz, 1H), 7.80 (d, J = 8.1 Hz, 1H), 7.94 (d, J = 3.2 Hz, 1H) | CDCl$_3$ |
| 133 | 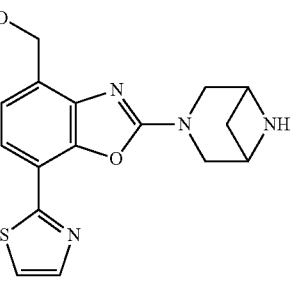 | (2-(3,6-diazabicyclo[3.1.1]heptan-3-yl)-7-(thiazol-2-yl)benzo[d]oxazol-4-yl)methanol | 329 (M + H)$^+$ | (400 MHz): 1.68 (d, J = 9.4 Hz, 1H), 2.82-2.93 (m, 1H), 3.93 (d, J = 5.9 Hz, 2H), 3.96-4.07 (m, 4H), 5.00 (s, 2H), 7.20 (d, J = 8.1 Hz, 1H), 7.46 (d, J = 3.2 Hz, 1H), 7.83 (d, J = 8.1 Hz, 1H), 7.95 (d, J = 3.2 Hz, 1H) | CDCl$_3$ |
| 134 | 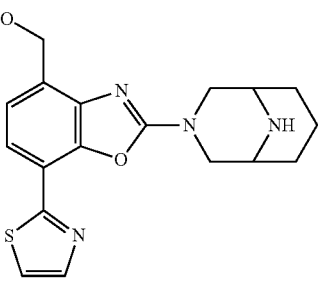 | (2-(3,9-diazabicyclo[3.3.1]nonan-3-yl)-7-(thiazol-2-yl)benzo[d]oxazol-4-yl)methanol | 357 (M + H)$^+$ | (400 MHz): 1.65-1.66 (m, 1H), 1.87-1.97 (m, 4H), 2.02-2.16 (m, 1H), 3.27 (s, 2H), 3.61 (dd, J = 12.5, 3.8 Hz, 2H), 4.26 (d, J = 12.5 Hz, 2H), 4.99 (s, 2H), 7.17 (d, J = 8.1 Hz, 1H), 7.46 (d, J = 3.2 Hz, 1H), 7.81 (d, J = 8.1 Hz, 1H), 7.95 (d, J = 3.2 Hz, 1H) | CDCl$_3$ |
| 135 | 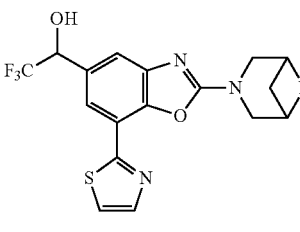 | 1-(2-(3,6-diazabicyclo[3.1.1]heptan-3-yl)-7-(thiazol-2-yl)benzo[d]oxazol-5-yl)-2,2,2-trifluoroethan-1-ol | 397 (M + H)$^+$ | (400 MHz): 1.70 (d, J = 8.0 Hz, 1H), 2.85-2.89 (m, 1H), 3.92-4.01 (m, 6H), 5.10-5.15 (m, 1H), 7.48 (d, J = 4.0 Hz, 1H), 7.54 (s, 1H), 7.96-7.97 (m, 2H) | CDCl$_3$ |
| 136 | 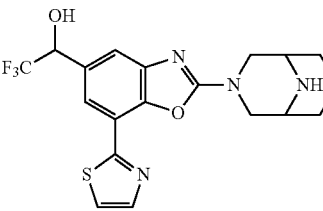 | 1-(2-(3,9-diazabicyclo[3.3.1]nonan-3-yl)-7-(thiazol-2-yl)benzo[d]oxazol-5-yl)-2,2,2-trifluoroethan-1-ol | 425 (M + H)$^+$ | (400 MHz): 1.61-1.65 (m, 1H), 1.91-1.94 (m, 4H), 2.04 (s, 1H), 3.30 (s, 2H), 3.57-3.61 (m, 2H), 4.25 (d, J = 12.6 Hz, 2H), 5.15 (q, J = 6.8 Hz, 1H), 7.49 (d, J = 3.2 Hz, 1H), 7.55 (s, 1H), 7.97-7.98 (m, 2H) | CDCl$_3$ |

TABLE 20-continued

| Ex. No. | structural formula | compound name | ESI MS m/z | $^1$H NMR, δ (ppm) | deuterated solvent |
|---|---|---|---|---|---|
| 137 | | 1-(2-(3,8-diazabicyclo[3.2.1]octan-3-yl)-7-(thiazol-2-yl)benzo[d]oxazol-5-yl)-2,2,2-trifluoroethan-1-ol (racemic) | 411 (M + H)⁺ | (400 MHz): 1.88 (s, 4H), 3.35-3.49 (m, 2H), 3.68 (s, 2H), 3.91-4.01 (m, 2H), 5.11 (q, J = 6.7 Hz, 1H), 7.47 (d, J = 3.2 Hz, 1H), 7.54 (s, 1H), 7.95 (d, J = 3.2 Hz, 1H) | CDCl₃ |

TABLE 21

| Ex. No. | structural formula | compound name | ESI MS m/z | $^1$H NMR, δ (ppm) | deuterated solvent |
|---|---|---|---|---|---|
| 138 | | 1-(2-(3,8-diazabicyclo[3.2.1]octan-3-yl)-7-(thiazol-2-yl)benzo[d]oxazol-5-yl)-2,2,2-trifluoroethan-1-ol (optically active) | 411 (M + H)⁺ | (400 MHz): 1.88 (s, 4H), 3.35-3.49 (m, 2H), 3.68 (s, 2H), 3.91-4.01 (m, 2H), 5.11 (q, J = 6.7 Hz, 1H), 7.47 (d, J = 3.2 Hz, 1H), 7.54 (s, 1H), 7.95-7.96 (m, 2H) | CDCl₃ |
| 139 | | 1-(2-(3,8-diazabicyclo[3.2.1]octan-3-yl)-7-(thiazol-2-yl)benzo[d]oxazol-5-yl)-2,2,2-trifluoroethan-1-ol (No. 138's enantiomer) | 411 (M + H)⁺ | (400 MHz): 1.88 (s, 4H), 3.35-3.49 (m, 2H), 3.68 (s, 2H), 3.91-4.01 (m, 2H), 5.11 (q, J = 6.7 Hz, 1H), 7.47 (d, J = 3.2 Hz, 1H), 7.54 (s, 1H), 7.95-7.96 (m, 2H) | CDCl₃ |
| 140 | | 1-(2-(3,8-diazabicyclo[3.2.1]octan-3-yl)-7-(1H-pyrazol-1-yl)benzo[d]oxazol-5-yl)-2,2,2-trifluoroethan-1-ol | 394 (M + H)⁺ | (400 MHz): 1.87 (s, 4H), 3.39 (t, J = 9.9 Hz, 2H), 3.67 (s, 2H), 3.91 (d, J = 12.1 Hz, 2H), 5.11 (q, J = 6.8 Hz, 1H), 6.53 (dd, J = 2.5, 1.8 Hz, 1H), 7.39 (s, 1H), 7.70-7.80 (m, 2H), 8.18 (d, J = 2.1 Hz, 1H) | CDCl₃ |
| 141 | | 1-(2-(3,8-diazabicyclo[3.2.1]octan-3-yl)-7-(thiazol-2-yl)benzo[d]oxazol-5-yl)-2,2,2-trifluoroethyl acetate | 453 (M + H)⁺ | (400 MHz): 1.88 (s, 4H), 2.20 (s, 3H), 3.45 (d, J = 12.1 Hz, 2H), 3.69 (s, 2H), 4.01 (dd, J = 12.1, 1.9 Hz, 2H), 6.24 (q, J = 6.8 Hz, 1H), 7.49-7.50 (m, 2H), 7.98-7.99 (m, 2H) | CDCl₃ |
| 142 | | 2-(3,8-diazabicyclo[3.2.1]octan-3-yl)-7-(thiazol-2-yl)-5-(2,2,2-trifluoro-1-methoxyethyl)benzo[d]oxazole (optically active) | 425 (M + H)⁺ | (400 MHz): 1.89 (d, J = 1.8 Hz, 4H), 3.39-3.49 (m, 5H), 3.69 (s, 2H), 4.02 (d, J = 11.4 Hz, 2H), 4.61 (q, J = 6.6 Hz, 1H), 7.48-7.53 (m, 2H), 7.91 (d, J = 1.5Hz, 1H), 7.98 (d, J = 3.2 Hz, 1H) | CDCl₃ |

TABLE 21-continued

| Ex. No. | structural formula | compound name | ESI MS m/z | ¹H NMR, δ (ppm) | deuterated solvent |
|---|---|---|---|---|---|
| 143 | (OMe, F₃C, benzoxazole with thiazole and 3,8-diazabicyclo[3.2.1]octane) | 2-(3,8-diazabicyclo[3.2.1]octan-3-yl)-7-(thiazol-2-yl)-5-(2,2,2-trifluoro-1-methoxyethyl)benzo[d]oxazole (No.142's enantiomer) | 425 (M + H)⁺ | (400 MHz): 1.89 (d, J = 1.8 Hz, 4H), 3.39-3.49 (m, 5H), 3.69 (s, 2H), 4.02 (d, J = 11.4 Hz, 2H), 4.61 (q, J = 6.6 Hz, 1H), 7.48-7.53 (m, 2H), 7.91 (d, J = 1.5 Hz, 1H), 7.98 (d, J = 3.2 Hz, 1H) | CDCl₃ |
| 144 | (OMe, F₃C, benzoxazole with thiazole and 3,6-diazabicyclo[3.1.1]heptane) | 2-(3,6-diazabicyclo[3.1.1]heptan-3-yl)-7-(thiazol-2-yl)-5-(2,2,2-trifluoro-1-methoxyethyl)benzo[d]oxazole | 411 (M + H)⁺ | (400 MHz): 1.69 (d, J = 9.2 Hz, 1H), 2.79-2.93 (m, 1H), 3.45 (s, 3H), 3.88-4.08 (m, 6H), 4.63 (q, J = 6.5 Hz, 1H), 7.47-7.52 (m, 1H), 7.56 (s, 1H), 7.95 (s, 1H), 7.99 (d, J = 3.2 Hz, 1H) | CDCl₃ |
| 145 | (OMe, F₃C, benzoxazole with thiazole and 3,9-diazabicyclo[3.3.1]nonane) | 2-(3,9-diazabicyclo[3.3.1]nonan-3-yl)-7-(thiazol-2-yl)-5-(2,2,2-trifluoro-1-methoxyethyl)benzo[d]oxazole | 439 (M + H)⁺ | (400 MHz): 1.59-1.70 (m, 1H), 1.86-1.97 (m, 4H), 1.99-2.15 (m, 1H), 3.28 (s, 2H), 3.43 (s, 3H), 3.63 (dd, J = 12.7, 3.9 Hz, 2H), 4.27 (d, J = 12.7 Hz, 2H), 4.62 (q, J = 6.5 Hz, 1H), 7.47-7.55 (m, 2H), 7.92 (d, J = 1.5 Hz, 1H), 7.98 (d, J = 3.2 Hz, 1H) | CDCl₃ |

TABLE 22

| Ex. No. | structural formula | compound name | ESI MS m/z | ¹H NMR, δ (ppm) | deuterated solvent |
|---|---|---|---|---|---|
| 146 | (O-CH₂-CF₃, F₃C, benzoxazole with thiazole and 3,8-diazabicyclo[3.2.1]octane) | 2-(3,8-diazabicyclo[3.2.1]octan-3-yl)-7-(thiazol-2-yl)-5-(2,2,2-trifluoro-1-(2,2,2-trifluoroethoxy)ethyl)benzo[d]oxazole | 493 (M + H)⁺ | (400 MHz): 1.89 (s, 4H), 3.45-3.48 (m, 2H), 3.70 (brs, 2H), 3.78-3.96 (m, 2H), 4.02 (q, J = 12.0 Hz, 2H), 4.89 (q, J = 6.2 Hz, 1H), 7.47-7.55 (m, 2H), 7.91 (s, 1H), 7.98 (d, J = 3.2 Hz, 1H) | CDCl₃ |
| 147 | (O-CH₂CH₂-OMe, F₃C, benzoxazole with thiazole and 3,8-diazabicyclo[3.2.1]octane) | 2-(3,8-diazabicyclo[3.2.1]octan-3-yl)-7-(thiazol-2-yl)-5-(2,2,2-trifluoro-1-(2-methoxyethoxy)ethyl)benzo[d]oxazole | 469 (M + H)⁺ | (400 MHz): 1.60-1.68 (m, 2H), 2.05-2.09 (m, 2H), 3.36 (s, 3H), 3.55-3.64 (m, 2H), 3.68-3.74 (m, 2H), 3.81 (brd, J = 14.2 Hz, 2H), 4.08 (brs, 2H), 4.19 (d, J = 14.2 Hz, 2H), 4.83-4.92 (m, 1H), 7.50 (d, J = 3.3 Hz, 1H), 7.57 (s, 1H), 7.95 (s, 1H), 7.98 (d, J = 3.3 Hz, 1H) | CDCl₃ |
| 148 | (O-Et, F₃C, benzoxazole with thiazole and 3,8-diazabicyclo[3.2.1]octane) | 2-(3,8-diazabicyclo[3.2.1]octan-3-yl)-5-(1-ethoxy-2,2,2-trifluoroethyl)-7-(thiazol-2-yl)benzo[d]oxazole | 439 (M + H)⁺ | (400 MHz): 1.22-1.29 (m, 3H), 1.91 (s, 4H), 3.49 (d, J = 11.0 Hz, 2H), 3.54-3.64 (m, 2H), 3.73 (brs, 2H), 4.03 (d, J = 11.0 Hz, 2H), 4.71 (q, J = 6.5 Hz, 1H), 7.49 (d, J = 3.3 Hz, 1H), 7.54 (s, 1H), 7.91 (s, 1H), 7.97 (d, J = 3.3 Hz, 1H) | CDCl₃ |

TABLE 22-continued

| Ex. No. | structural formula | compound name | ESI MS m/z | ¹H NMR, δ (ppm) | deuterated solvent |
|---|---|---|---|---|---|
| 149 | | 2-(1-(2-(3,8-diazabicyclo[3.2.1]octan-3-yl)-7-(thiazol-2-yl)benzo[d]oxazol-5-yl)-2,2,2-trifluoroethoxy)ethan-1-ol | 455 (M + H)⁺ | (400 MHz): 1.89 (s, 4H), 3.42-3.50 (m, 2H), 3.64-3.69 (m, 2H), 3.70-3.74 (m, 2H), 3.75-3.81 (m, 2H), 4.02 (d, J = 11.9 Hz, 2H), 4.74-4.83 (m, 1H), 7.47-7.54 (m, 2H), 7.93 (s, 1H), 7.97 (d, J = 3.2 Hz, 1H) | CDCl₃ |
| 150 | | 2-(3,6-diazabicyclo[3.1.1]heptan-3-yl)-5-(1-ethoxy-2,2,2-trifluoroethyl)-7-(thiazol-2-yl)benzo[d]oxazole | 425 (M + H)⁺ | (400 MHz): 1.26 (t, J = 7.0 Hz, 3H), 1.72 (m, 1H), 2.98 (d, J = 9.4 Hz, 1H), 3.60 (qd, J = 7.0, 2.5 Hz, 2H), 4.05-4.12 (m, 6H), 4.70-4.77 (m, 1H), 7.50 (d, J = 3.3 Hz, 1H), 7.59 (s, 1H), 7.94 (s, 1H), 7.98 (d, J = 3.3 Hz, 1H) | CDCl₃ |
| 151 | | 2-(3,6-diazabicyclo[3.1.1]heptan-3-yl)-7-(thiazol-2-yl)-5-(2,2,2-trifluoro-1-(2,2,2-trifluoroethoxy)ethyl)benzo[d]oxazole | 479 (M + H)⁺ | (400 MHz): 1.71 (d, J = 9.2 Hz, 1H), 2.91 (d, J = 9.2 Hz, 1H), 3.86-3.95 (m, 2H), 3.98 (d, J = 6.5 Hz, 2H), 4.01-4.06 (m, 4H), 4.91 (m, 1H), 7.52 (d, J = 3.2 Hz, 1H), 7.57 (s, 1H), 7.95 (s, 1H), 7.99 (d, J = 3.2 Hz, 1H) | CDCl₃ |
| 152 | | 2-(1-(2-(3,6-diazabicyclo[3.1.1]heptan-3-yl)-7-(thiazol-2-yl)benzo[d]oxazol-5-yl)-2,2,2-trifluoroethoxy)acetonitrile | 436 (M + H)⁺ | (400 MHz): 1.70 (d, J = 9.4 Hz, 1H), 2.86-2.92 (m, 1H), 3.96 (d, J = 6.2 Hz, 2H), 4.00-4.08 (m, 4H), 4.19-4.25 (m, 1H), 4.43-4.49 (m, 1H), 4.95-4.98 (m, 1H), 7.51-7.54 (m, 2H), 7.98 (s, 1H), 8.00 (d, J = 3.3 Hz, 1H) | CDCl₃ |
| 153 | | 2-(1-(2-(3,8-diazabicyclo[3.2.1]octan-3-yl)-7-(thiazol-2-yl)benzo[d]oxazol-5-yl)-2,2,2-trifluoroethoxy)acetonitrile | 450 (M + H)⁺ | (400 MHz): 1.89-1.94 (m, 4H), 3.54 (d, J = 12.0 Hz, 2H), 3.77 (s, 2H), 4.05 (d, J = 12.0 Hz, 2H), 4.16-4.24 (m, 1H), 4.41-4.47 (m, 1H), 4.90-4.98 (m, 1H), 7.48 (s, 1H), 7.52 (d, J = 3.3 Hz, 1H), 7.95 (s, 1H), 7.99 (d, J = 3.3 Hz, 1H) | CDCl₃ |

TABLE 23

| Ex. No. | compound name | ESI MS m/z | ¹H NMR, δ (ppm) | deuterated solvent |
|---|---|---|---|---|
| 154 | 2-(3,6-diazabicyclo[3.1.1]heptan-3-yl)-7-(thiazol-2-yl)-5-(2,2,2-trifluoro-1-(2-methoxyethoxy)ethyl)benzo[d]oxazole | 455 (M + H)⁺ | (400 MHz): 1.59 (d, J = 8.9 Hz, 1H), 2.55-2.61 (m, 1H), 3.23 (s, 3H), 3.45-3.54 (m, 2H), 3.60-3.68 (m, 2H), 3.70-3.75 (m, 2H), 3.82-4.00 (m, 4H), 5.33-5.36 (m, 1H), 7.46 (s, 1H), 7.92 (s, 1H), 7.98 (d, J = 3.3 Hz, 1H), 8.06 (d, J = 3.3 Hz, 1H) | DMSO-d₆ |
| 155 | 1-(1-(2-(3,8-diazabicyclo[3.2.1]octan-3-yl)-7-(thiazol-2-yl)benzo[d]oxazol-5-yl)-2,2,2-trifluoroethoxy)propan-2-ol | 469 (M + H)⁺ | (400 MHz): 1.05-1.08 (m, 3H), 1.77-1.84 (m, 4H), 3.30-3.42 (m, 4H), 3.53-3.59 (m, 2H), 3.82-3.92 (m, 3H), 4.87 (q, J = 6.6 Hz, 1H), 7.38-7.42 (m, 1H), 7.69 (d, J = 3.3 Hz, 1H), 7.82-7.85 (m, 1H), 7.89 (d, J = 3.3 Hz, 1H) | CD₃OD |
| 156 | 1-(2-(3,9-diazabicyclo[3.3.1]nonan-3-yl)-7-(thiazol-2-yl)benzo[d]oxazol-5-yl)-2,2,2-trifluoroethane-1,1-diol | 441 (M + H)⁺ | (400 MHz): 1.62-1.68 (m, 1H), 1.91-1.94 (m, 4H), 2.02-2.09 (m, 1H), 3.29 (brs, 2H), 3.61-3.69 (m, 2H), 4.25-4.29 (m, 2H), 7.49 (d, J = 3.3 Hz, 0.6H), 7.54 (d, J = 3.3 Hz, 0.4H), 7.68 (s, 0.6H), 7.99 (d, J = 3.3 Hz, 0.6H), 8.03 (d, J = 3.3 Hz, 0.4H), 8.07 (s, 0.4H), 8.22 (s, 0.6H), 8.66 (s, 0.4H) | CDCl₃ |
| 157 | 1-(2-(3,8-diazabicyclo[3.2.1]octan-3-yl)-7-(thiazol-2-yl)benzo[d]oxazol-5-yl)-2,2,2-trifluoroethane-1,1-diol | 427 (M + H)⁺ | (400 MHz): 1.89 (s, 4H), 3.30 (s, 1H), 3.44-3.50 (m, 3H), 3.71 (brs, 2H), 4.01-4.04 (m, 2H), 7.48 (d, J = 3.3 Hz, 0.5H), 7.53 (d, J = 3.3 Hz, 0.5H), 7.66 (s, 0.5H), 7.98 (d, J = 3.3 Hz, 0.5H), 8.02 (d, J = 3.3 Hz, 0.5H), 8.06 (s, 0.5H), 8.20 (d, J = 1.7 Hz, 0.5H), 8.66 (d, J = 1.7 Hz, 0.5H) | CDCl₃ |
| 158 | 1-(2-(3,6-diazabicyclo[3.1.1]heptan-3-yl)-7-(thiazol-2-yl)benzo[d]oxazol-5-yl)-2,2,2-trifluoroethane-1,1-diol | 413 (M + H)⁺ | (400 MHz): 1.71 (d, J = 9.5 Hz, 1H), 2.85-2.94 (m, 1H), 3.49 (brs, 2H), 3.95 (d, J = 6.0 Hz, 2H), 4.04-4.12 (m, 4H), 7.55 (d, J = 3.2 Hz, 1H), 8.03 (d, J = 3.2 Hz, 1H), 8.12 (s, 1H), 8.69 (s, 1H) | CDCl₃ |
| 159 | 2-(2-(3,8-diazabicyclo[3.2.1]octan-3-yl)-7-(thiazol-2-yl)benzo[d]oxazol-5-yl)-1,1,1-trifluoropropan-2-ol | 425 (M + H)⁺ | (400 MHz): 1.83-1.88 (m, 7H), 3.43 (dd, J = 12.2, 2.0 Hz, 2H), 3.68 (s, 2H), 4.00 (dd, J = 12.2, 2.0 Hz, 2H), 7.48 (d, J = 3.3 Hz, 1H), 7.64 (d, J = 1.5 Hz, 1H), 7.97 (d, J = 3.3 Hz, 1H), 8.12 (d, J = 1.5 Hz, 1H) | CDCl₃ |

TABLE 23-continued

| Ex. No. | structural formula | compound name | ESI MS m/z | $^1$H NMR, δ (ppm) | deuterated solvent |
|---|---|---|---|---|---|
| 160 | | 2-(2-(3,6-diazabicyclo[3.1.1]heptan-3-yl)-7-(thiazol-2-yl)benzo[d]oxazol-5-yl)-1,1,1-trifluoropropan-2-ol | 411 (M + H)+ | (400 MHz): 1.69 (d, J = 9.2 Hz, 1H), 1.88 (s, 3H), 2.83-2.91 (m, 1H), 3.93-4.04 (m, 6H), 7.49 (d, J = 3.3 Hz, 1H), 7.70 (s, 1H), 7.98 (d, J = 3.3 Hz, 1H), 8.15 (s, 1H) | CDCl$_3$ |
| 161 | | 2-(2-(3,9-diazabicyclo[3.3.1]nonan-3-yl)-7-(thiazol-2-yl)benzo[d]oxazol-5-yl)-1,1,1-trifluoropropan-2-ol | 439 (M + H)+ | (400 MHz): 1.62-1.67 (m, 1H), 1.87 (s, 3H), 1.90-1.98 (m, 4H), 2.02-2.10 (m, 1H), 2.62 (s, 1H), 3.30 (s, 2H), 3.64 (dd, J = 13.1, 3.6 Hz, 2H), 4.27 (d, J = 13.1 Hz, 2H), 7.49 (d, J = 3.3 Hz, 1H), 7.66 (s, 1H), 7.98 (d, J = 3.3 Hz, 1H), 8.13 (d, J = 1.6 Hz, 1H) | CDCl$_3$ |

TABLE 24

| Ex. No. | structural formula | compound name | ESI MS m/z | $^1$H NMR, δ (ppm) | deuterated solvent |
|---|---|---|---|---|---|
| 162 | | 2-(3,9-diazabicyclo[3.3.1]nonan-3-yl)-7-(thiazol-2-yl)-5-(1,1,1-trifluoro-2-methoxypropan-2-yl)benzo[d]oxazole | 453 (M + H)+ | (400 MHz): 1.60-1.69 (m, 1H), 1.87 (s, 3H), 1.90-1.98 (m, 4H), 2.00-2.15 (m, 1H), 3.27 (s, 5H), 3.63 (dd, J = 12.7, 3.8 Hz, 2H), 4.27 (d, J = 12.7 Hz, 2H), 7.49 (d, J = 3.2 Hz, 1H), 7.63 (s, 1H), 7.92-8.03 (m, 2H) | CDCl$_3$ |
| 163 | | ethyl 2-(3,8-diazabicyclo[3.2.1]octan-3-yl)-7-(thiazol-2-yl)-4-(trifluoromethyl)benzo[d]oxazole-5-carboxylate | 453 (M + H)+ | (400 MHz): 1.41 (t, J = 7.6 Hz, 3H), 1.93 (d, J = 8.8 Hz, 4H), 3.55-3.58 (m, 2H), 3.77 (s, 2H), 4.09-4.12 (m, 2H), 4.43 (q, J = 7.6 Hz, 2H), 7.56 (d, J = 3.2 Hz, 1H), 8.02 (d, J = 3.2 Hz, 1H), 8.10 (s, 1H) | CDCl$_3$ |
| 164 | | ethyl 2-(3,9-diazabicyclo[3.3.1]nonan-3-yl)-7-(thiazol-2-yl)-4-(trifluoromethyl)benzo[d]oxazole-5-carboxylate | 467 (M + H)+ | (400 MHz): 1.42 (t, J = 7.2 Hz, 3H), 1.60-1.68 (m, 1H), 1.94-2.00 (m, 4H), 2.02-2.09 (m, 1H), 3.33 (s, 2H), 3.68-3.71 (m, 2H), 4.31-4.34 (m, 2H), 4.43 (q, J = 7.2 Hz, 2H), 7.57 (d, J = 3.6 Hz, 1H), 8.02 (d, J = 3.6 Hz, 1H), 8.11 (s, 1H) | CDCl$_3$ |
| 165 | | ethyl 2-(3,6-diazabicyclo[3.1.1]heptan-3-yl)-7-(thiazol-2-yl)-4-(trifluoromethyl)benzo[d]oxazole-5-carboxylate | 439 (M + H)+ | (400 MHz): 1.41 (t, J = 7.1 Hz, 3H), 1.70 (d, J = 9.4 Hz, 1H), 2.85-2.91 (m, 1H), 3.93 (d, J = 5.8 Hz, 2H), 3.99-4.11 (m, 4H), 4.42 (q, J = 7.1 Hz, 2H), 7.57 (d, J = 3.2 Hz, 1H), 8.02 (d, J = 3.2 Hz, 1H), 8.13 (s, 1H) | CDCl$_3$ |

TABLE 24-continued

| Ex. No. | structural formula | compound name | ESI MS m/z | ¹H NMR, δ (ppm) | deuterated solvent |
|---|---|---|---|---|---|
| 166 | | 2-(2-(3,9-diazabicyclo[3.3.1]nonan-3-yl)-7-(thiazol-2-yl)-4-(trifluoromethyl)benzo[d]oxazol-5-yl)propan-2-ol | 453 (M + H)⁺ | (400 MHz): 1.60-1.69 (m, 1H), 1.80 (s, 6H), 1.89-1.98 (m, 4H), 2.03-2.10 (m, 1H), 2.17-2.18 (m, 1H), 3.27 (s, 2H), 3.62 (dd, J = 13.0, 3.7 Hz, 2H), 4.30 (d, J = 13.0 Hz, 2H), 7.54 (d, J = 3.3 Hz, 1H), 8.01 (d, J = 3.3 Hz, 1H), 8.20 (s, 1H) | CDCl₃ |
| 167 | | 2-(3,8-diazabicyclo[3.2.1]octan-3-yl)-5-(methoxymethyl)-7-(thiazol-2-yl)-4-(trifluoromethyl)benzo[d]oxazole | 425 (M + H)⁺ | (400 MHz): 1.89 (m, 4H), 3.45-3.48 (m, 5H), 3.69 (s, 2H), 4.05-4.08 (m, 2H), 4.70 (d, J = 0.73 Hz, 2H), 7.52 (d, J = 3.3 Hz, 1H), 8.01 (d, J = 3.3 Hz, 1H), 8.07 (s, 1H) | CDCl₃ |
| 168 | | 2-(3,8-diazabicyclo[3.2.1]octan-3-yl)-5-(morpholinomethyl)-7-(thiazol-2-yl)benzo[d]oxazole | 412 (M + H)⁺ | (400 MHz): 1.69-1.91 (m, 4H), 2.30-2.47 (m, 4H), 3.35 (dd, J = 12.4, 1.9 Hz, 2H), 3.51 (s, 2H), 3.55-3.65 (m, 6H), 3.88 (dd, J = 12.4, 2.0 Hz, 2H), 7.27 (d, J = 1.6 Hz, 1H), 7.64 (d, J = 3.3 Hz, 1H), 7.66 (d, J = 1.6 Hz, 1H), 7.86 (d, J = 3.3 Hz, 1H) | CD₃OD |
| 169 | | 1-(2-(3,8-diazabicyclo[3.2.1]octan-3-yl)-7-(thiazol-2-yl)benzo[d]oxazol-5-yl)-N,N-dimethylmethanamine | 370 (M + H)⁺ | (400 MHz): 1.79-2.00 (m, 4H), 2.35 (s, 6H), 3.44 (dd, J = 12.4, 1.9 Hz, 2H), 3.64-3.72 (m, 2H), 3.68 (s, 2H), 3.98 (dd, J = 12.3, 2.0 Hz, 2H), 7.37 (d, J = 1.6 Hz, 1H), 7.75 (d, J = 3.3 Hz, 1H), 7.76 (d, J = 1.6 Hz, 1H), 7.96 (d, J = 3.3 Hz, 1H) | CD₃OD |

TABLE 25

| Ex. No. | structural formula | compound name | ESI MS m/z | ¹H NMR, δ (ppm) | deuterated solvent |
|---|---|---|---|---|---|
| 170 | | (2-(3,8-diazabicyclo[3.2.1]octan-3-yl)-7-(thiazol-2-yl)-4-(trifluoromethyl)benzo[d]oxazol-5-yl)methanol | 411 (M + H)⁺ | (400 MHz): 1.90 (m, 4H), 3.46 (dd, J = 12.3, 1.9 Hz, 2H), 3.69 (s, 2H), 4.03-4.10 (m, 2H), 4.94 (d, J = 0.73 Hz, 2H), 7.53 (d, J = 3.2 Hz, 1H), 8.00 (d, J = 3.2 Hz, 1H), 8.10 (d, J = 0.73 Hz, 1H) | CDCl₃ |
| 171 | | 2-(3,8-diazabicyclo[3.2.1]octan-3-yl)-5-(2-methoxypropan-2-yl)-7-(thiazol-2-yl)-4-(trifluoromethyl)benzo[d]oxazole | 453 (M + H)⁺ | (400 MHz): 1.75 (s, 6H), 1.90 (m, 4H), 3.14 (s, 3H), 3.45-3.50 (m, 2H), 3.71 (s, 2H), 4.08 (d, J = 12.4 Hz, 2H), 7.53 (d, J = 3.2 Hz, 1H), 8.01 (d, J = 3.2 Hz, 1H), 8.03 (s, 1H) | CDCl₃ |

TABLE 25-continued

| Ex. No. | structural formula | compound name | ESI MS m/z | $^1$H NMR, δ (ppm) | deuterated solvent |
|---|---|---|---|---|---|
| 172 | | 2-(2-(3,8-diazabicyclo[3.2.1]octan-3-yl)-7-(thiazol-2-yl)benzo[d]oxazol-5-yl)propan-2-ol | 371 (M + H)+ | (400 MHz): 1.60 (s, 6H), 1.81-1.99 (m, 4H), 3.43 (dd, J = 12.3, 2.0 Hz, 2H), 3.62-3.69 (m, 2H), 3.96 (dd, J = 12.3, 2.1 Hz, 2H), 7.54 (d, J = 1.7 Hz, 1H), 7.73 (d, J = 3.3 Hz, 1H), 7.94 (d, J = 1.7 Hz, 1H), 7.95 (d, J = 3.3 Hz, 1H) | CD$_3$OD |
| 173 | | 2-(2-(3,6-diazabicyclo[3.1.1]heptan-3-yl)-7-(thiazol-2-yl)benzo[d]oxazol-5-yl)propan-2-ol | 357 (M + H)+ | (400 MHz): 1.64 (s, 6H), 1.81 (d, J = 9.4 Hz, 1H), 2.87 (dt, J = 9.4, 6.4 Hz, 1H), 3.90-4.08 (m, 6H), 7.60 (d, J = 1.7 Hz, 1H), 7.74 (d, J = 3.3 Hz, 1H), 7.97 (d, J = 3.3 Hz, 1H), 7.99 (d, J = 1.7 Hz, 1H) | CD$_3$OD |
| 174 | | 2-(3,6-diazabicyclo[3.1.1]heptan-3-yl)-5-(2-methoxypropan-2-yl)-7-(thiazol-2-yl)benzo[d]oxazole | 371 (M + H)+ | (400 MHz): 1.62 (s, 6H), 1.68 (d, J = 9.3 Hz, 1H), 2.83-2.90 (m, 1H), 3.11 (s, 3H), 3.91-3.98 (m, 2H), 4.00-4.06 (m, 4H), 7.47 (d, J = 3.3 Hz, 1H), 7.58 (s, 1H), 7.92 (s, 1H), 7.97 (d, J = 3.3 Hz, 1H) | CDCl$_3$ |
| 175 | | 2-(3,8-diazabicyclo[3.2.1]octan-3-yl)-5-(2-methoxypropan-2-yl)-7-(thiazol-2-yl)benzo[d]oxazole | 385 (M + H)+ | (400 MHz): 1.61 (s, 6H), 1.88-1.92 (m, 4H), 3.10 (s, 3H), 3.46 (d, J = 12.2 Hz, 2H), 3.71 (s, 2H), 4.02 (d, J = 12.2 Hz, 2H), 7.46 (d, J = 3.3 Hz, 1H), 7.53 (s, 1H), 7.89 (s, 1H), 7.97 (d, J = 3.3 Hz, 1H) | CDCl$_3$ |
| 176 | | 2-(3,6-diazabicyclo[3.1.1]heptan-3-yl)-5-(2-methoxypropan-2-yl)-7-(thiazol-2-yl)-4-(trifluoromethyl)benzo[d]oxazole | 439 (M + H)+ | (400 MHz): 1.69 (d, J = 9.3 Hz, 1H), 1.76 (s, 6H), 2.85-2.90 (m, 1H), 3.15 (s, 3H), 3.94 (d, J = 6.1 Hz, 2H), 4.00-4.09 (m, 4H), 7.54 (d, J = 3.2 Hz, 1H), 8.02 (d, J = 3.2 Hz, 1H), 8.07 (s, 1H) | CDCl$_3$ |
| 177 | | 2-(2-(3,8-diazabicyclo[3.2.1]octan-3-yl)-7-(thiazol-2-yl)-4-(trifluoromethyl)benzo[d]oxazol-5-yl)propan-2-ol | 439 (M + H)+ | (400 MHz): 1.79 (s, 6H), 1.88 (s, 4H), 3.45 (dd, J = 12.2, 2.0 Hz, 2H), 3.68 (s, 2H), 4.05-4.08 (m, 2H), 7.53 (d, J = 3.3 Hz, 1H), 8.00 (d, J = 3.3 Hz, 1H), 8.20 (s, 1H) | CDCl$_3$ |

TABLE 26

| Ex. No. | structural formula | compound name | ESI MS m/z | $^1$H NMR, δ (ppm) | deuterated solvent |
|---|---|---|---|---|---|
| 178 | | 2-(2-(3,6-diazabicyclo[3.1.1]heptan-3-yl)-7-(thiazol-2-yl)-4-(trifluoromethyl)benzo[d]oxazol-5-yl)propan-2-ol | 425 (M + H)+ | (400 MHz): 1.68 (d, J = 9.3 Hz, 1H), 1.81 (s, 6H), 2.84-2.89 (m, 1H), 3.93 (d, J = 6.1 Hz, 2H), 3.99-4.08 (m, 4H), 7.54 (d, J = 3.3 Hz, 1H), 8.01 (d, J = 3.3 Hz, 1H), 8.24 (s, 1H) | CDCl$_3$ |
| 179 | | 1-(2-(3,8-diazabicyclo[3.2.1]octan-3-yl)-7-(thiazol-2-yl)-4-(trifluoromethyl)benzo[d]oxazol-5-yl)ethan-1-one | 423 (M + H)+ | (400 MHz): 1.89 (s, 4H), 2.62 (s, 3H), 3.49 (d, J = 12.4 Hz, 2H), 3.70 (s, 2H), 4.08 (d, J = 12.4 Hz, 2H), 7.56 (d, J = 3.2 Hz, 1H), 7.83 (s, 1H), 8.01 (d, J = 3.2 Hz, 1H) | CDCl$_3$ |
| 180 | | 1-(2-(3,6-diazabicyclo[3.1.1]heptan-3-yl)-7-(thiazol-2-yl)-4-(trifluoromethyl)benzo[d]oxazol-5-yl)ethan-1-one | 409 (M + H)+ | (400 MHz): 1.69 (d, J = 9.3 Hz, 1H), 2.64 (s, 3H), 2.86-2.92 (m, 1H), 3.94 (d, J = 5.9 Hz, 2H), 4.02-4.10 (m, 4H), 7.58 (d, J = 3.2 Hz, 1H), 7.87 (s, 1H), 8.02 (d, J = 3.2 Hz, 1H) | CDCl$_3$ |
| 181 | | 1-(2-(3,8-diazabicyclo[3.2.1]octan-3-yl)-7-(thiazol-2-yl)-4-(trifluoromethyl)benzo[d]oxazol-5-yl)ethan-1-ol | 425 (M + H)+ | (400 MHz): 1.57 (s, 3H), 1.88 (s, 4H), 3.44-3.47 (m, 2H), 3.68 (s, 2H), 4.06 (d, J = 12.0 Hz, 2H), 5.37-5.45 (m, 1H), 7.53 (d, J = 3.2 Hz, 1H), 8.02 (d, J = 3.2 Hz, 1H), 8.28 (s, 1H) | CDCl$_3$ |
| 182 | | 1-(2-(3,6-diazabicyclo[3.1.1]heptan-3-yl)-7-(thiazol-2-yl)-4-(trifluoromethyl)benzo[d]oxazol-5-yl)ethan-1-ol | 411 (M + H)+ | (400 MHz): 1.57 (d, J = 6.2 Hz, 3H), 1.68 (d, J = 9.3 Hz, 1H), 2.84-2.90 (m, 1H), 3.49 (s, 1H), 3.93 (d, J = 6.1 Hz, 2H), 4.00-4.07 (m, 4H), 5.43-5.48 (m, 1H), 7.54 (d, J = 3.2 Hz, 1H), 8.02 (d, J = 3.2 Hz, 1H), 8.31 (s, 1H) | CDCl$_3$ |
| 183 | | 1-(2-(3,8-diazabicyclo[3.2.1]octan-3-yl)-7-(thiazol-2-yl)-4-(trifluoromethyl)benzo[d]oxazol-5-yl)-2,2-difluoroethan-1-ol | 461 (M + H)+ | (400 MHz): 1.60-1.83 (m, 4H), 3.37-3.46 (m, 2H), 3.56 (s, 2H), 3.87 (d, J = 12.2 Hz, 2H), 5.11-5.30 (m, 1H), 5.86-6.27 (m, 1H), 6.63 (d, J = 5.3 Hz, 1H), 8.06 (d, J = 3.2 Hz, 1H), 8.12 (d, J = 3.2 Hz, 1H), 8.17 (s, 1H) | DMSO-d$_6$ |

TABLE 26-continued

| Ex. No. | structural formula | compound name | ESI MS m/z | $^1$H NMR, δ (ppm) | deuterated solvent |
|---|---|---|---|---|---|
| 184 | | 2-(3,8-diazabicyclo[3.2.1]octan-3-yl)-5-(1-methoxyethyl)-7-(thiazol-2-yl)-4-(trifluoromethyl)benzo[d]oxazole | 439 (M + H)⁺ | (400 MHz): 1.49 (d, J = 6.2 Hz, 3H), 1.88 (d, J = 1.6 Hz, 4H), 3.23 (s, 3H), 3.46 (dd, J = 12.4, 2.1 Hz, 2H), 3.69 (s, 2H), 4.05-4.08 (m, 2H), 4.80-4.85 (m, 1H), 7.53 (d, J = 3.3 Hz, 1H), 8.02 (d, J = 3.3 Hz, 1H), 8.15 (s, 1H) | CDCl₃ |
| 185 | | 2-(3,6-diazabicyclo[3.1.1]heptan-3-yl)-5-(1-methoxyethyl)-7-(thiazol-2-yl)-4-(trifluoromethyl)benzo[d]oxazole | 425 (M + H)⁺ | (400 MHz): 1.51 (d, J = 6.2 Hz, 3H), 1.68 (d, J = 9.3 Hz, 1H), 2.85-2.91 (m, 1H), 3.24 (s, 3H), 3.95 (d, J = 5.9 Hz, 2H), 4.00-4.09 (m, 4H), 4.85-4.89 (m, 1H), 7.54 (d, J = 3.3 Hz, 1H), 8.03 (d, J = 3.3 Hz, 1H), 8.19 (s, 1H) | CDCl₃ |

TABLE 27

| Ex. No. | structural formula | compound name | ESI MS m/z | $^1$H NMR, δ (ppm) | deuterated solvent |
|---|---|---|---|---|---|
| 186 | | ethyl 2-(3,8-diazabicyclo[3.2.1]octan-3-yl)-7-(thiazol-2-yl)-4-(trifluoromethoxy)benzo[d]oxazole-5-carboxylate | 469 (M + H)⁺ | (400 MHz): 1.42 (t, J = 7.2 Hz, 3H), 1.89 (s, 4H), 3.45-3.49 (m, 2H), 3.69 (s, 2H), 4.05 (d, J = 10.4 Hz, 2H), 4.43 (q, J = 7.2 Hz, 2H), 7.51 (d, J = 3.3 Hz, 1H), 7.99 (d, J = 3.3 Hz, 1H), 8.45 (s, 1H) | CDCl₃ |
| 187 | | ethyl 2-(3,6-diazabicyclo[3.1.1]heptan-3-yl)-7-(thiazol-2-yl)-4-(trifluoromethoxy)benzo[d]oxazole-5-carboxylate | 455 (M + H)⁺ | (400 MHz): 1.42 (t, J = 7.2 Hz, 3H), 1.70 (d, J = 9.3 Hz, 1H), 2.85-2.90 (m, 1H), 3.93 (s, 2H), 4.00-4.07 (m, 4H), 4.44 (q, J = 7.2 Hz, 2H), 7.52 (d, J = 3.2 Hz, 1H), 8.00 (d, J = 3.2 Hz, 1H), 8.48 (s, 1H) | CDCl₃ |
| 188 | | ethyl 2-(3,9-diazabicyclo[3.3.1]nonan-3-yl)-7-(thiazol-2-yl)-4-(trifluoromethoxy)benzo[d]oxazole-5-carboxylate | 483 (M + H)⁺ | (400 MHz): 1.42 (t, J = 7.2 Hz, 3H), 1.63-1.66 (m, 1H), 1.91-1.93 (m, 4H), 1.98-2.07 (m, 1H), 3.28 (s, 2H), 3.64 (dd, J = 12.8, 4.0 Hz, 2H), 4.29 (d, J = 12.8 Hz, 2H), 4.43 (q, J = 7.2 Hz, 2H), 7.51 (d, J = 3.3 Hz, 1H), 8.00 (d, J = 3.3 Hz, 1H), 8.45 (s, 1H) | CDCl₃ |

TABLE 27-continued

| Ex. No. | structural formula | compound name | ESI MS m/z | ¹H NMR, δ (ppm) | deuterated solvent |
|---|---|---|---|---|---|
| 189 | | 2-(3,8-diazabicyclo[3.2.1]octan-3-yl)-7-(thiazol-2-yl)-4-(trifluoromethoxy)benzo[d]oxazole-5-carboxylic acid | 441 (M + H)⁺ | (400 MHz): 1.70-1.77 (m, 4H), 3.40-3.43 (m, 2H), 3.64 (s, 2H), 3.86-3.89 (m, 2H), 8.00 (d, J = 3.2 Hz, 1H), 8.08 (d, J = 3.2 Hz, 1H), 8.23 (s, 1H) | DMSO-d₆ |
| 190 | | 2-(3,6-diazabicyclo[3.1.1]heptan-3-yl)-7-(thiazol-2-yl)-4-(trifluoromethoxy)benzo[d]oxazole-5-carboxylic acid | 427 (M + H)⁺ | (400 MHz): 2.26-2.29 (m, 1H), 3.52 (d, J = 5.2 Hz, 1H), 4.54-4.58 (m, 2H), 4.69-4.72 (m, 2H), 4.91 (d, J = 6.0 Hz, 2H), 8.27 (d, J = 3.6 Hz, 1H), 8.43 (d, J = 3.6 Hz, 1H), 8.72 (s, 1H) | TFA-d |
| 191 | | 2-(3,9-diazabicyclo[3.3.1]nonan-3-yl)-7-(thiazol-2-yl)-4-(trifluoromethoxy)benzo[d]oxazole-5-carboxylic acid | 455 (M + H)⁺ | (400 MHz): 1.52 (s, 1H), 1.84-1.88 (m, 5H), 3.21-3.28 (m, 2H), 3.62-3.65 (m, 2H), 4.12-4.15 (m, 2H), 8.02 (d, J = 3.2 Hz, 1H), 8.09 (d, J = 3.2 Hz, 1H), 8.24 (s, 1H) | DMSO-d₆ |
| 192 | | (2-(3,8-diazabicyclo[3.2.1]octan-3-yl)-7-(thiazol-2-yl)-4-(trifluoromethoxy)benzo[d]oxazol-5-yl)(azetidin-1-yl)methanone | 480 (M + H)⁺ | (400 MHz): 1.76-2.00 (m, 4H), 2.36 (quin, J = 7.8 Hz, 2H), 3.47 (dd, J = 12.4, 1.7 Hz, 2H), 3.63-3.69 (m, 2H), 4.04 (dd, J = 12.4, 2.0 Hz, 2H), 4.12 (t, J = 7.8 Hz, 2H), 4.21 (t, J = 7.8 Hz, 2H), 7.80 (d, J = 3.3 Hz, 1H), 7.88 (s, 1H), 7.99 (d, J = 3.3 Hz, 1H) | CD₃OD |
| 193 | | 2-(3,8-diazabicyclo[3.2.1]octan-3-yl)-N-(2-hydroxyethyl)-N-methyl-7-(thiazol-2-yl)-4-(trifluoromethoxy)benzo[d]oxazole-5-carboxamide | 498 (M + H)⁺ | (400 MHz, 90° C.): 1.64-1.86 (m, 4H), 2.95 (brs, 3H), 3.13-3.34 (m, 1H), 3.41 (dd, J = 11.8, 1.7 Hz, 2H), 3.44-3.76 (m, 5H), 3.88 (dd, J = 11.8, 1.3 Hz, 2H), 4.40 (brs, 1H), 7.68 (s, 1H), 7.92 (d, J = 3.2 Hz, 1H), 8.03 (d, J = 3.2 Hz, 1H) | DMSO-d₆ |

TABLE 28

| Ex. No. | structural formula | compound name | ESI MS m/z | ¹H NMR, δ (ppm) | deuterated solvent |
|---|---|---|---|---|---|
| 194 | | (2-(3,8-diazabicyclo[3.2.1]octan-3-yl)-7-(thiazol-2-yl)-4-(trifluoromethoxy)benzo[d]oxazol-5-yl)(3-hydroxy-3-(trifluoromethyl)azetidin-1-yl)methanone | 564 (M + H)⁺ | (400 MHz): 1.79-2.01 (m, 4H), 3.48 (dd, J = 12.4, 1.6 Hz, 2H), 3.62-3.70 (m, 2H), 4.03 (dd, J = 12.4, 1.9 Hz, 2H), 4.10 (m, 2H), 4.35 (dd, J = 10.3, 1.1 Hz, 1H), 4.41 (dd, J = 11.3, 1.2 Hz, 1H), 7.81 (d, J = 3.2 Hz, 1H), 7.91 (s, 1H), 8.00 (d, J = 3.2 Hz, 1H) | CD₃OD |
| 195 | | 2-(2-(3,8-diazabicyclo[3.2.1]octan-3-yl)-7-(thiazol-2-yl)-4-(trifluoromethoxy)benzo[d]oxazol-5-yl)propan-2-ol | 455 (M + H)⁺ | (400 MHz): 1.72 (s, 6H), 1.83-1.92 (m, 4H), 3.43 (dd, J = 12.3, 1.9 Hz, 2H), 3.67 (s, 2H), 4.02 (dd, J = 12.3, 1.9 Hz, 2H), 7.46 (d, J = 3.3 Hz, 1H), 7.96 (d, J = 3.3 Hz, 1H), 8.15 (s, 1H) | CDCl₃ |
| 196 | | 2-(2-(3,6-diazabicyclo[3.1.1]heptan-3-yl)-7-(thiazol-2-yl)-4-(trifluoromethoxy)benzo[d]oxazol-5-yl)propan-2-ol | 441 (M + H)⁺ | (400 MHz): 1.68 (d, J = 9.2 Hz, 1H), 1.74 (s, 6H), 2.82-2.90 (m, 1H), 3.92 (d, J = 6.2 Hz, 2H), 3.96-4.05 (m, 4H), 7.48 (d, J = 3.3 Hz, 1H), 7.97 (d, J = 3.3 Hz, 1H), 8.18 (s, 1H) | CDCl₃ |
| 197 | | 2-(2-(3,9-diazabicyclo[3.3.1]nonan-3-yl)-7-(thiazol-2-yl)-4-(trifluoromethoxy)benzo[d]oxazol-5-yl)propan-2-ol | 469 (M + H)⁺ | (400 MHz): 1.61-1.65 (m, 1H), 1.73 (s, 6H), 1.92-1.94 (m, 4H), 1.97-2.10 (m, 1H), 3.28 (s, 2H), 3.62 (dd, J = 12.8, 4.0 Hz, 2H), 4.27 (d, J = 12.8 Hz, 2H), 7.47 (d, J = 3.2 Hz, 1H), 7.96 (d, J = 3.2 Hz, 1H), 8.15 (s, 1H) | CDCl₃ |
| 198 | | 2-(3,8-diazabicyclo[3.2.1]octan-3-yl)-5-(2-methoxypropan-2-yl)-7-(thiazol-2-yl)-4-(trifluoromethoxy)benzo[d]oxazole | 469 (M + H)⁺ | (400 MHz): 1.69 (s, 6H), 1.89 (d, J = 1.6 Hz, 4H), 3.16 (s, 3H), 3.45 (dd, J = 12.2, 1.8 Hz, 2H), 3.69 (s, 2H), 4.04 (dd, J = 12.2, 1.8 Hz, 2H), 7.47 (d, J = 3.3 Hz, 1H), 7.96-7.98 (m, 2H) | CDCl₃ |
| 199 | | 2-(3,6-diazabicyclo[3.1.1]heptan-3-yl)-5-(2-methoxypropan-2-yl)-7-(thiazol-2-yl)-4-(trifluoromethoxy)benzo[d]oxazole | 455 (M + H)⁺ | (400 MHz): 1.68 (d, J = 9.3 Hz, 1H), 1.71 (s, 6H), 2.84-2.89 (m, 1H), 3.17 (s, 3H), 3.92 (d, J = 6.1 Hz, 2H), 3.96-4.05 (m, 4H), 7.48 (d, J = 3.2 Hz, 1H), 7.98 (d, J = 3.2 Hz, 1H), 8.02 (s, 1H) | CDCl₃ |

TABLE 28-continued

| Ex. No. | structural formula | compound name | ESI MS m/z | ¹H NMR, δ (ppm) | deuterated solvent |
|---|---|---|---|---|---|
| 200 | | 2-(3,9-diazabicyclo[3.3.1]nonan-3-yl)-5-(2-methoxypropan-2-yl)-7-(thiazol-2-yl)-4-(trifluoromethoxy)benzo[d]oxazole | 483 (M + H)⁺ | (400 MHz): 1.61-1.65 (m, 1H), 1.70 (s, 6H), 1.93-1.95 (m, 4H), 1.99-2.12 (m, 1H), 3.17 (s, 3H), 3.30 (s, 2H), 3.64 (dd, J = 12.5, 3.4 Hz, 2H), 4.28 (d, J = 12.5 Hz, 2H), 7.48 (d, J = 3.3 Hz, 1H), 7.98 (d, J = 3.3 Hz, 1H), 7.99 (s, 1H) | CDCl₃ |
| 201 | | (2-(3,8-diazabicyclo[3.2.1]octan-3-yl)-7-(thiazol-2-yl)-4-(trifluoromethoxy)benzo[d]oxazol-5-yl)methanol | 427 (M + H)⁺ | (400 MHz): 1.92 (s, 4H), 3.51 (d, J = 13.1 Hz, 2H), 3.73 (s, 2H), 4.06 (d, J = 10.3 Hz, 2H), 4.87 (s, 2H), 7.49 (d, J = 3.3 Hz, 1H), 7.97 (d, J = 3.3 Hz, 1H), 8.00 (s, 1H) | CDCl₃ |

TABLE 29

| Ex. No. | structural formula | compound name | ESI MS m/z | ¹H NMR, δ (ppm) | deuterated solvent |
|---|---|---|---|---|---|
| 202 | | 1-(2-(3,8-diazabicyclo[3.2.1]octan-3-yl)-7-(thiazol-2-yl)-4-(trifluoromethoxy)benzo[d]oxazol-5-yl)ethan-1-ol | 441 (M + H)⁺ | (400 MHz): 1.55-1.58 (m, 3H), 1.88 (d, J = 1.5 Hz, 4H), 3.44 (d, J = 12.2 Hz, 2H), 3.68 (s, 2H), 4.03 (d, J = 12.2 Hz, 2H), 5.36 (q, J = 6.5 Hz, 1H), 7.48 (d, J = 3.3 Hz, 1H), 7.97 (d, J = 3.3 Hz, 1H), 8.08 (s, 1H) | CDCl₃ |
| 203 | | 1-(2-(3,6-diazabicyclo[3.1.1]heptan-3-yl)-7-(thiazol-2-yl)-4-(trifluoromethoxy)benzo[d]oxazol-5-yl)ethan-1-ol | 427 (M + H)⁺ | (400 MHz): 1.56 (d, J = 6.4 Hz, 3H), 1.69 (d, J = 9.2 Hz, 1H), 2.81-2.99 (m, 1H), 3.86-4.02 (m, 6H), 5.38 (q, J = 6.4 Hz, 1H), 7.49 (d, J = 3.3 Hz, 1H), 7.97 (d, J = 3.3 Hz, 1H), 8.08 (s, 1H) | CD₃OD |
| 204 | | 1-(2-(3,8-diazabicyclo[3.2.1]octan-3-yl)-7-(thiazol-2-yl)-4-(trifluoromethoxy)benzo[d]oxazol-5-yl)propan-1-ol | 455 (M + H)⁺ | (400 MHz): 0.97 (t, J = 7.4 Hz, 3H), 1.68-2.01 (m, 6H), 3.46 (dd, J = 12.5, 1.8 Hz, 2H), 3.66-3.72 (m, 2H), 4.00-4.08 (m, 2H), 5.01 (dd, J = 7.5, 5.4 Hz, 1H), 7.76 (d, J = 3.3 Hz, 1H), 7.97 (d, J = 3.3 Hz, 1H), 8.02 (s, 1H) | CD₃OD |

TABLE 29-continued

| Ex. No. | structural formula | compound name | ESI MS m/z | $^1$H NMR, δ (ppm) | deuterated solvent |
|---|---|---|---|---|---|
| 205 | | 1-(2-(3,8-diazabicyclo[3.2.1]octan-3-yl)-7-(thiazol-2-yl)-4-(trifluoromethoxy)benzo[d]oxazol-5-yl)-2-methylpropan-1-ol | 469 (M + H)+ | (400 MHz): 0.82 (d, J = 6.7 Hz, 3H), 1.04 (d, J = 6.7 Hz, 3H), 1.85-2.09 (m, 5H), 3.50 (dd, J = 12.7, 1.7 Hz, 2H), 3.75-3.85 (m, 2H), 4.09 (ddd, J = 12.7, 4.2, 2.0 Hz, 2H), 4.78 (d, J = 7.2 Hz, 1H), 7.77 (d, J = 3.3 Hz, 1H), 7.98 (d, J = 3.3 Hz, 1H), 7.99 (s, 1H) | CD$_3$OD |
| 206 | | 1-(2-(3,8-diazabicyclo[3.2.1]octan-3-yl)-7-(thiazol-2-yl)-4-(trifluoromethoxy)benzo[d]oxazol-5-yl)-2,2-difluoroethan-1-ol | 477 (M + H)+ | (400 MHz): 1.61-1.80 (m, 4H), 3.35-3.46 (m, 2H), 3.55 (s, 2H), 3.84 (d, J = 12.0 Hz, 2H), 5.03-5.17 (m, 1H) 5.95-6.31 (m, 1H), 6.58 (d, J = 5.4 Hz, 1H), 7.99 (d, J = 3.2 Hz, 1H), 8.01 (s, 1H), 8.07 (d, J = 3.2 Hz, 1H) | DMSO-d$_6$ |
| 207 | | 1-(2-(3,6-diazabicyclo[3.1.1]heptan-3-yl)-7-(thiazol-2-yl)-4-(trifluoromethoxy)benzo[d]oxazol-5-yl)-2,2-difluoroethan-1-ol | 463 (M + H)+ | (400 MHz): 1.60 (d, J = 8.8 Hz, 1H), 2.54-2.62 (m, 1H), 3.70 (d, J = 6.0 Hz, 2H), 3.88 (brs, 4H), 5.04-5.21 (m, 1H), 5.93-6.33 (m, 1H), 6.59 (d, J = 5.4 Hz, 1H), 8.01 (d, J = 3.2 Hz, 1H), 8.04 (s, 1H), 8.08 (d, J = 3.2 Hz, 1H) | DMSO-d$_6$ |
| 208 | | 2-(3,6-diazabicyclo[3.1.1]heptan-3-yl)-5-(2,2-difluoro-1-methoxyethyl)-7-(thiazol-2-yl)-4-(trifluoromethoxy)benzo[d]oxazole | 477 (M + H)+ | (400 MHz): 1.68 (d, J = 9.1 Hz, 1H), 2.87 (dt, J = 9.1, 6.3 Hz, 1H), 3.41 (s, 3H), 3.93 (d, J = 6.1 Hz, 2H), 3.96-4.08 (m, 4H), 4.82-4.96 (m, 1H), 5.71-6.08 (m, 1H), 7.51 (d, J = 3.2 Hz, 1H), 7.99 (d, J = 3.2 Hz, 1H), 8.03 (s, 1H) | CDCl$_3$ |
| 209 | | 2-(3,8-diazabicyclo[3.2.1]octan-3-yl)-5-(2,2-difluoro-1-methoxyethyl)-7-(thiazol-2-yl)-4-(trifluoromethoxy)benzo[d]oxazole | 491 (M + H)+ | (400 MHz): 1.88 (s, 4H), 3.39 (s, 3H), 3.45 (d, J = 12.2 Hz, 2H), 3.69 (s, 2H), 3.98-4.11 (m, 2H), 4.82-4.94 (m, 1H), 5.70-6.06 (m, 1H), 7.50 (d, J = 3.2 Hz, 1H), 7.96-8.00 (m, 2H) | CDCl$_3$ |

TABLE 30

| Ex. No. | structural formula | compound name | ESI MS m/z | $^1$H NMR, δ (ppm) | deuterated solvent |
|---|---|---|---|---|---|
| 210 | | 2-(3,8-diazabicyclo[3.2.1]octan-3-yl)-5-(1-methoxyethyl)-7-(thiazol-2-yl)-4-(trifluoromethoxy)benzo[d]oxazole | 455 (M + H)$^+$ | (400 MHz): 1.48 (d, J = 6.5 Hz, 3H), 1.91 (s, 4H), 3.24 (s, 3H), 3.50 (d, J = 11.3 Hz, 2H), 3.73 (s, 2H), 4.06 (d, J = 11.3 Hz, 2H), 4.81 (q, J = 6.5 Hz, 1H), 7.48 (d, J = 3.3 Hz, 1H), 7.97-7.98 (m, 2H) | CDCl$_3$ |
| 211 | | 2-(3,6-diazabicyclo[3.1.1]heptan-3-yl)-5-(1-methoxyethyl)-7-(thiazol-2-yl)-4-(trifluoromethoxy)benzo[d]oxazole | 441 (M + H)$^+$ | (400 MHz): 1.50 (d, J = 6.4 Hz, 3H), 1.68 (d, J = 9.3 Hz, 1H), 2.84-2.89 (m, 1H), 3.25 (s, 3H), 3.92 (d, J = 5.9 Hz, 2H), 3.98-4.06 (m, 4H), 4.83 (q, J = 6.4 Hz, 1H), 7.49 (d, J = 3.2 Hz, 1H), 7.99 (d, J = 3.2 Hz, 1H), 8.01 (s, 1H) | CDCl$_3$ |
| 212 | | 1-(2-(3,6-diazabicyclo[3.1.1]heptan-3-yl)-7-(thiazol-2-yl)-4-(trifluoromethoxy)benzo[d]oxazol-5-yl)ethan-1-one | 425 (M + H)$^+$ | (400 MHz): 1.70 (d, J = 9.3 Hz, 1H), 2.69 (s, 3H), 2.83-2.91 (m, 1H), 3.94 (d, J = 6.4 Hz, 2H), 3.98-4.07 (m, 4H), 7.52 (d, J = 3.3 Hz, 1H), 8.00 (d, J = 3.3 Hz, 1H), 8.24 (s, 1H) | CDCl$_3$ |
| 213 | | 1-(2-(3,8-diazabicyclo[3.2.1]octan-3-yl)-7-(thiazol-2-yl)-4-(trifluoromethoxy)benzo[d]oxazol-5-yl)ethan-1-one | 439 (M + H)$^+$ | (400 MHz): 1.90 (brs, 4H), 2.67 (s, 3H), 3.49 (d, J = 11.9 Hz, 2H), 3.72 (brs, 2H), 4.06 (d, J = 11.9 Hz, 2H), 7.51 (d, J = 3.2 Hz, 1H), 7.98 (d, J = 3.2 Hz, 1H), 8.20 (s, 1H) | CDCl$_3$ |
| 214 | | 2-(3,6-diazabicyclo[3.1.1]heptan-3-yl)-7-(thiazol-2-yl)-5-(1,1,1-trifluoro-2-methoxypropan-2-yl)-4-(trifluoromethoxy)benzo[d]oxazole | 509 (M + H)$^+$ | (400 MHz): 1.68 (d, J = 9.3 Hz, 1H), 1.99 (s, 3H), 2.84-2.89 (m, 1H), 3.33 (s, 3H), 3.92 (d, J = 6.0 Hz, 2H), 3.96-4.05 (m, 4H), 7.49 (d, J = 3.3 Hz, 1H), 7.99 (d, J = 3.3 Hz, 1H), 8.21 (s, 1H) | CDCl$_3$ |
| 215 | | 2-(3,8-diazabicyclo[3.2.1]octan-3-yl)-7-(thiazol-2-yl)-5-(1,1,1-trifluoro-2-methoxypropan-2-yl)-4-(trifluoromethoxy)benzo[d]oxazole | 523 (M + H)$^+$ | (400 MHz): 1.87 (s, 4H), 1.98 (s, 3H), 3.32 (s, 3H), 3.44 (d, J = 10.9 Hz, 2H), 3.68 (s, 2H), 4.03 (d, J = 10.9 Hz, 2H), 7.48 (d, J = 3.3 Hz, 1H), 7.98 (d, J = 3.3 Hz, 1H), 8.17 (s, 1H) | CDCl$_3$ |

TABLE 30-continued

| Ex. No. | structural formula | compound name | ESI MS m/z | ¹H NMR, δ (ppm) | deuterated solvent |
|---|---|---|---|---|---|
| 216 | | 2-(2-(3,6-diazabicyclo[3.1.1]heptan-3-yl)-7-(thiazol-2-yl)-4-(trifluoromethoxy)benzo[d]oxazol-5-yl)-1,1,1-trifluoropropan-2-ol | 495 (M + H)⁺ | (400 MHz): 1.59 (d, J = 8.3 Hz, 1H), 1.90 (s, 3H), 2.55-2.60 (m, 1H), 3.69 (d, J = 5.9 Hz, 2H), 3.88 (brs, 4H), 6.99 (s, 1H), 8.00 (d, J = 3.3 Hz, 1H), 8.07 (d, J = 3.3 Hz, 1H), 8.36 (s, 1H) | DMSO-d₆ |
| 217 | | 2-(2-(3,8-diazabicyclo[3.2.1]octan-3-yl)-7-(thiazol-2-yl)-4-(trifluoromethoxy)benzo[d]oxazol-5-yl)-1,1,1-trifluoropropan-2-ol | 509 (M + H)⁺ | (400 MHz): 1.88 (s, 4H), 1.97 (s, 3H), 3.43-3.46 (m, 2H), 3.68 (s, 2H), 4.03 (d, J = 10.3 Hz, 2H), 7.49 (d, J = 3.2 Hz, 1H), 7.97 (d, J = 3.2 Hz, 1H), 8.14 (s, 1H) | CDCl₃ |

TABLE 31

| Ex. No. | structural formula | compound name | ESI MS m/z | ¹H NMR, δ (ppm) | deuterated solvent |
|---|---|---|---|---|---|
| 218 | | (E)-1-(2-(3,8-diazabicyclo[3.2.1]octan-3-yl)-7-(thiazol-2-yl)-4-(trifluoromethoxy)benzo[d]oxazol-5-yl)ethan-1-one O-methyl oxime and (Z)-1-(2-(3,8-diazabicyclo[3.2.1]octan-3-yl)-7-(thiazol-2-yl)-4-(trifluoromethoxy)benzo[d]oxazol-5-yl)ethan-1-one O-methyl oxime | 468 (M + H)⁺ | (400 MHz): 1.88-1.97 (m, 2H), 2.10-2.23 (m, 2H), 2.24 (s, 3H), 3.48-3.56 (m, 2H), 3.75 (brs, 2H), 3.80 (s, 0.75H), 4.01 (s, 2.25H), 4.03-4.09 (m, 2H), 7.47-7.50 (m, 1H), 7.69 (s, 0.25H), 7.92 (s, 0.75H), 7.94-7.99 (m, 1H) | CDCl₃ |
| 219 | | (E)-1-(2-(3,6-diazabicyclo[3.1.1]heptan-3-yl)-7-(thiazol-2-yl)-4-(trifluoromethoxy)benzo[d]oxazol-5-yl)ethan-1-one O-methyl oxime and (Z)-1-(2-(3,6-diazabicyclo[3.1.1]heptan-3-yl)-7-(thiazol-2-yl)-4-(trifluoromethoxy)benzo[d]oxazol-5-yl)ethan-1-one O-methyl oxime | 468 (M + H)⁺ | (400 MHz): 1.64-1.77 (m, 1H), 2.26 (s, 3H), 2.86-2.93 (m, 1H), 3.81 (s, 0.75H), 3.96 (d, J = 6.0 Hz, 2H), 4.02 (s, 2.25H), 4.02-4.09 (m, 4H), 7.48-7.51 (m, 1H), 7.69-7.74 (m, 0.25H), 7.95 (s, 0.75H), 7.96-7.99 (m, 1H) | CDCl₃ |
| 220 | | 2-(3,8-diazabicyclo[3.2.1]octan-3-yl)-4-(1-ethoxy-2,2,2-trifluoroethyl)-7-(thiazol-2-yl)benzo[d]oxazole | 439 (M + H)⁺ | (400 MHz): 1.24 (t, J = 7.0 Hz, 3H), 1.90 (s, 4H), 3.35-3.47 (m, 2H), 3.55-3.72 (m, 4H), 4.03 (d, J = 12.4 Hz, 2H), 5.37 (q, J = 6.6 Hz, 1H), 7.47 (d, J = 3.3 Hz, 1H), 7.49-7.51 (m, 1H), 7.88 (d, J = 8.3 Hz, 1H), 7.95 (d, J = 3.3 Hz, 1H) | CDCl₃ |

TABLE 31-continued

| Ex. No. | structural formula | compound name | ESI MS m/z | ¹H NMR, δ (ppm) | deuterated solvent |
|---|---|---|---|---|---|
| 221 | | 2-(3,8-diazabicyclo[3.2.1]octan-3-yl)-7-(thiazol-2-yl)-4-(2,2,2-trifluoro-1-(2,2,2-trifluoroethoxy)ethyl)benzo[d]oxazole | 493 (M + H)⁺ | (400 MHz): 1.89 (s, 4H), 3.43 (d, J = 12.2 Hz, 2H), 3.69 (brs, 2H), 3.87-3.95 (m, 2H), 4.03 (d, J = 12.2 Hz, 2H), 5.54 (q, J = 6.4 Hz, 1H), 7.46 (d, J = 8.3 Hz, 1H), 7.49 (d, J = 3.2 Hz, 1H), 7.90 (d, J = 8.3 Hz, 1H), 7.98 (d, J = 3.2 Hz, 1H) | CDCl₃ |
| 222 | | 2-(3,8-diazabicyclo[3.2.1]octan-3-yl)-7-(thiazol-2-yl)-4-(2,2,2-trifluoro-1-methoxyethyl)benzo[d]oxazole | 425 (M + H)⁺ | (400 MHz): 1.89 (s, 4H), 3.44-3.49 (m, 5H), 3.69 (brs, 2H), 4.04 (d, J = 12.1 Hz, 2H), 5.23-5.32 (m, 1H), 7.45 (d, J = 8.2 Hz, 1H), 7.47 (d, J = 3.3 Hz, 1H), 7.89 (d, J = 8.2 Hz, 1H), 7.97 (d, J = 3.3 Hz, 1H) | CDCl₃ |
| 223 | | 2-(3,6-diazabicyclo[3.1.1]heptan-3-yl)-7-(thiazol-2-yl)-4-(2,2,2-trifluoro-1-(2,2,2-trifluoroethoxy)ethyl)benzo[d]oxazole | 479 (M + H)⁺ | (400 MHz): 1.69 (d, J = 9.3 Hz, 1H), 2.81-2.93 (m, 1H), 3.86-3.97 (m, 4H), 3.99-4.10 (m, 4H), 5.60 (q, J = 6.3 Hz, 1H), 7.47-7.49 (m, 1H), 7.50 (d, J = 3.3 Hz, 1H), 7.93 (d, J = 8.3 Hz, 1H), 7.99 (d, J = 3.3 Hz, 1H) | CDCl₃ |
| 224 | | 2-(3,6-diazabicyclo[3.1.1]heptan-3-yl)-4-(1-ethoxy-2,2,2-trifluoroethyl)-7-(thiazol-2-yl)benzo[d]oxazole | 425 (M + H)⁺ | (400 MHz): 1.22-1.28 (m, 3H), 1.70 (d, J = 9.2 Hz, 1H), 2.80-2.93 (m, 1H), 3.54-3.72 (m, 2H), 3.95 (d, J = 6.1 Hz, 2H), 3.99-4.08 (m, 4H), 5.34-5.52 (m, 1H), 7.48 (d, J = 3.2 Hz, 1H), 7.52 (d, J = 8.3 Hz, 1H), 7.91 (d, J = 8.3 Hz, 1H), 7.98 (d, J = 3.2 Hz, 1H) | CDCl₃ |
| 225 | | 2-(1-(2-(3,8-diazabicyclo[3.2.1]octan-3-yl)-7-(thiazol-2-yl)benzo[d]oxazol-4-yl)-2,2,2-trifluoroethoxy)ethan-1-ol | 455 (M + H)⁺ | (400 MHz): 1.85-2.06 (m, 4H), 3.50 (d, J = 13.0 Hz, 2H), 3.57-3.64 (m, 2H), 3.66-3.74 (m, 2H), 3.75-3.79 (m, 2H), 4.05-4.12 (m, 2H), 5.49 (q, J = 6.7 Hz, 1H), 7.51 (d, J = 8.3 Hz, 1H), 7.78 (d, J = 3.3 Hz, 1H), 7.83 (d, J = 8.3 Hz, 1H), 7.98 (d, J = 3.3 Hz, 1H) | CD₃OD |

TABLE 32

| Ex. No. | structural formula | compound name | ESI MS m/z | ¹H NMR, δ (ppm) | deuterated solvent |
|---|---|---|---|---|---|
| 226 | | 2-(1-(2-(3,6-diazabicyclo[3.1.1]heptan-3-yl)-7-(thiazol-2-yl)benzo[d]oxazol-4-yl)-2,2,2-trifluoroethoxy)acetonitrile | 436 (M + H)⁺ | (400 MHz): 1.78 (d, J = 9.3 Hz, 1H), 2.94-3.04 (m, 1H), 3.95-4.01 (m, 2H), 4.02-4.15 (m, 4H), 4.23-4.27 (m, 1H), 4.40-4.44 (m, 1H), 5.63-5.66 (m, 1H), 7.45 (d, J = 8.3 Hz, 1H), 7.51 (d, J = 3.2 Hz, 1H), 7.94 (d, J = 8.3 Hz, 1H), 7.99 (d, J = 3.2 Hz, 1H) | CDCl₃ |
| 227 | | 2-(1-(2-(3,6-diazabicyclo[3.1.1]heptan-3-yl)-7-(thiazol-2-yl)benzo[d]oxazol-4-yl)-2,2,2-trifluoroethoxy)ethan-1-ol | 441 (M + H)⁺ | (400 MHz): 1.66-1.74 (m, 1H), 3.26-3.34 (m, 1H), 3.63-3.74 (m, 2H), 3.81-3.86 (m, 2H), 4.23-4.28 (m, 2H), 4.37-4.43 (d, J = 12.0 Hz, 2H), 4.53-4.57 (m, 2H), 5.31-5.36 (m, 1H), 7.44 (d, J = 8.2 Hz, 1H), 7.50 (d, J = 3.3 Hz, 1H), 7.94 (d, J = 8.2 Hz, 1H), 7.98 (d, J = 3.3 Hz, 1H) | CDCl₃ |
| 228 | | 2-(1-(2-(3,8-diazabicyclo[3.2.1]octan-3-yl)-7-(thiazol-2-yl)benzo[d]oxazol-4-yl)-2,2,2-trifluoroethoxy)acetonitrile | 450 (M + H)⁺ | (400 MHz): 1.88-1.92 (m, 4H), 3.46 (d, J = 12.4 Hz, 2H), 3.70 (s, 2H), 4.02-4.06 (m, 2H), 4.21-4.27 (m, 1H), 4.37-4.43 (m, 1H), 5.60 (q, J = 6.4 Hz, 1H), 7.42 (d, J = 8.3 Hz, 1H), 7.50 (d, J = 3.3 Hz, 1H), 7.90 (d, J = 8.3 Hz, 1H), 7.98 (d, J = 3.3 Hz, 1H) | CDCl₃ |
| 229 | | 2-(3,6-diazabicyclo[3.1.1]heptan-3-yl)-7-(thiazol-2-yl)-4-(2,2,2-trifluoro-1-(2-methoxyethoxy)ethyl)benzo[d]oxazole | 455 (M + H)⁺ | (400 MHz): 1.62 (d, J = 8.9 Hz, 1H), 2.56-2.61 (m, 1H), 3.23 (s, 3H), 3.45-3.54 (m, 2H), 3.60-3.68 (m, 2H), 3.70-3.74 (m, 2H), 3.82-3.95 (m, 4H), 5.33-5.36 (m, 1H), 7.46 (d, J = 8.3 Hz, 1H), 7.92 (d, J = 8.3 Hz, 1H), 7.98 (d, J = 3.3 Hz, 1H), 8.06 (d, J = 3.3 Hz, 1H) | DMSO-d₆ |
| 230 | | 4-(1-((1H-tetrazol-5-yl)methoxy)-2,2,2-trifluoroethyl)-2-(3,8-diazabicyclo[3.2.1]octan-3-yl)-7-(thiazol-2-yl)benzo[d]oxazole | 493 (M + H)⁺ | (400 MHz): 2.14-2.21 (m, 4H), 3.62-3.69 (m, 2H), 4.19-4.27 (m, 2H), 4.29-4.34 (m, 2H), 4.79-4.93 (m, 2H), 5.48-5.56 (m, 1H), 7.55 (d, J = 8.3 Hz, 1H), 7.80 (d, J = 3.2 Hz, 1H), 7.87 (d, J = 8.3 Hz, 1H), 8.01 (d, J = 3.2 Hz, 1H) | DMSO-d₆ |

TABLE 32-continued

| Ex. No. | structural formula | compound name | ESI MS m/z | ¹H NMR, δ (ppm) | deuterated solvent |
|---|---|---|---|---|---|
| 231 | | 4-(1-((1H-tetrazol-5-yl)methoxy)-2,2,2-trifluoroethyl)-2-(3,6-diazabicyclo[3.1.1]heptan-3-yl)-7-(thiazol-2-yl)benzo[d]oxazole | 479 (M + H)⁺ | (400 MHz): 2.02-2.07 (m, 1H), 2.90-2.98 (m, 1H), 4.13-4.25 (m, 4H), 4.49-4.53 (m, 2H), 4.77-4.85 (m, 2H), 5.68-5.74 (m, 1H), 7.51 (d, J = 8.3 Hz, 1H), 7.91 (d, J = 8.3 Hz, 1H), 8.03 (d, J = 3.2 Hz, 1H), 8.09 (d, J = 3.2 Hz, 1H) | DMSO-d₆ |
| 232 | | 1-((1-(2-(3,6-diazabicyclo[3.1.1]heptan-3-yl)-7-(thiazol-2-yl)benzo[d]oxazol-4-yl)-2,2,2-trifluoroethoxy)methyl)cyclopropan-1-ol | 467 (M + H)⁺ | (400 MHz): 0.51-0.64 (m, 2H), 0.80-0.86 (m, 2H), 1.67 (d, J = 9.3 Hz, 1H), 2.86 (dt, J = 9.3, 6.3 Hz, 1H), 3.69 (d, J = 11.2 Hz, 1H), 3.85-4.05 (m, 7H), 5.59 (q, J = 6.7 Hz, 1H), 7.45 (d, J = 8.1 Hz, 1H), 7.50 (d, J = 3.3 Hz, 1H), 7.91 (d, J = 8.1 Hz, 1H), 7.98 (d, J = 3.3 Hz, 1H) | CDCl₃ |
| 233 | | 1-(2-(3,8-diazabicyclo[3.2.1]octan-3-yl)-7-(thiazol-2-yl)benzo[d]oxazol-4-yl)-2,2,2-trifluoroethane-1,1-diol | 427 (M + H)⁺ | (400 MHz): 1.89 (s, 4H), 3.47-3.55 (m, 2H), 3.72 (brs, 2H), 4.09-4.15 (m, 2H), 7.59 (d, J = 3.3 Hz, 1H), 7.83-7.86 (m, 1H), 7.89-7.92 (m, 1H), 8.05 (d, J = 3.3 Hz, 1H) | CDCl₃ |

TABLE 33

| Ex. No. | structural formula | compound name | ESI MS m/z | ¹H NMR, δ (ppm) | deuterated solvent |
|---|---|---|---|---|---|
| 1234 | | 2-(2-(3,6-diazabicyclo[3.1.1]heptan-3-yl)-7-(thiazol-2-yl)benzo[d]oxazol-4-yl)-1,1,1-trifluoropropan-2-ol | 411 (M + H)⁺ | (400 MHz): 1.68 (d, J = 9.4 Hz, 1H), 1.83 (s, 3H), 2.82-2.94 (m, 1H), 3.90-3.96 (m, 2H), 3.96-4.08 (m, 4H), 7.26 (d, J = 8.4 Hz, 1H), 7.50 (d, J = 3.2 Hz, 1H), 7.89 (d, J = 8.4 Hz, 1H), 7.98 (d, J = 3.2 Hz, 1H) | CDCl₃ |

TABLE 33-continued

| Ex. No. | structural formula | compound name | ESI MS m/z | ¹H NMR, δ (ppm) | deuterated solvent |
|---|---|---|---|---|---|
| 235 | | 2-(3,6-diazabicyclo[3.1.1]heptan-3-yl)-7-(thiazol-2-yl)-4-(1,1,1-trifluoro-2-methoxypropan-2-yl)benzo[d]oxazole | 425 (M + H)⁺ | (400 MHz): 1.69 (d, J = 9.3 Hz, 1H), 2.17 (s, 3H), 2.81-2.90 (m, 1H), 3.33 (s, 3H), 3.92 (d, J = 6.1 Hz, 2H), 3.95-4.06 (m, 4H), 7.48 (d, J = 3.2 Hz, 1H), 7.52 (d, J = 8.4 Hz, 1H), 7.90 (d, J = 8.4 Hz, 1H), 7.98 (d, J = 3.2 Hz, 1H) | CDCl₃ |
| 236 | | 2-(2-(3,8-diazabicyclo[3.2.1]octan-3-yl)-7-(thiazol-2-yl)benzo[d]oxazol-4-yl)-1,1,1-trifluoropropan-2-ol | 425 (M + H)⁺ | (400 MHz): 1.75-1.90 (m, 7H), 3.38 (d, J = 12.1 Hz, 2H), 3.63 (s, 2H), 3.96 (d, J = 12.1 Hz, 2H), 7.35 (d, J = 8.4 Hz, 1H), 7.67 (d, J = 3.3 Hz, 1H), 7.70 (d, J = 8.4 Hz, 1H), 7.88 (d, J = 3.3 Hz, 1H) | CD₃OD |
| 237 | | methyl 2-(3,8-diazabicyclo[3.2.1]octan-3-yl)-7-(thiazol-2-yl)benzo[d]oxazole-4-carboxylate | 371 (M + H)⁺ | (400 MHz): 2.09-2.21 (m, 4H), 3.78 (d, J = 13.6 Hz, 2H), 3.97 (s, 3H), 4.26 (brs, 2H), 4.38 (d, J = 13.6 Hz, 2H), 7.85 (d, J = 3.2 Hz, 1H), 7.87-7.93 (m, 2H), 8.04 (d, J = 3.2 Hz, 1H) | CD₃OD |
| 238 | | 2-(3,8-diazabicyclo[3.2.1]octan-3-yl)-7-(thiazol-2-yl)benzo[d]oxazole-4-carboxylic acid | 357 (M + H)⁺ | (400 MHz): 1.48-1.65 (m, 4H), 2.47-2.53 (m, 2H), 3.27-3.30 (m, 2H), 3.88-3.93 (m, 2H), 7.70-7.74 (m, 1H), 7.78-7.81 (m, 1H), 7.93 (d, J = 3.3 Hz, 1H), 8.03 (d, J = 3.3 Hz, 1H) | DMSO-d₆ |
| 239 | | 1-(2-(3,9-diazabicyclo[3.3.1]nonan-3-yl)-7-(thiazol-2-yl)benzo[d]oxazol-4-yl)ethan-1-ol | 371 (M + H)⁺ | (400 MHz): 1.62-1.67 (m, 4H), 1.91-1.95 (m, 4H), 2.07-2.14 (m, 1H), 3.27 (d, J = 2.9 Hz, 2H), 3.60 (dd, J = 12.8, 3.9 Hz, 2H), 4.26 (d, J = 12.8 Hz, 2H), 5.22 (q, J = 6.7 Hz, 1H), 7.16 (dd, J = 8.2, 0.61 Hz, 1H), 7.45 (d, J = 3.3 Hz, 1H), 7.81 (d, J = 8.2 Hz, 1H), 7.95 (d, J = 3.3 Hz, 1H) | CDCl₃ |

TABLE 33-continued

| Ex. No. | structural formula | compound name | ESI MS m/z | ¹H NMR, δ (ppm) | deuterated solvent |
|---|---|---|---|---|---|
| 240 | | 1-(2-(3,6-diazabicyclo[3.1.1]heptan-3-yl)-7-(thiazol-2-yl)benzo[d]oxazol-4-yl)ethan-1-ol | 343 (M + H)⁺ | (400 MHz): 1.56 (d, J = 6.5 Hz, 3H), 1.91-1.96 (m, 1H), 3.05-3.15 (m, 1H), 3.59-3.64 (m, 2H), 4.20-4.34 (m, 4H), 5.37 (q, J = 6.5 Hz, 1H), 7.47 (d, J = 8.2 Hz, 1H), 7.74 (d, J = 3.3 Hz, 1H), 7.82 (d, J = 8.2 Hz, 1H), 7.95 (d, J = 3.3 Hz, 1H) | CDCl₃ |
| 241 | | 2-(3,6-diazabicyclo[3.1.1]heptan-3-yl)-4-(1-methoxyethyl)-7-(thiazol-2-yl)benzo[d]oxazole | 357 (M + H)⁺ | (400 MHz): 1.55 (d, J = 6.5 Hz, 3H), 1.97-2.03 (m, 1H), 3.28-3.33 (m, 4H), 4.26-4.42 (m, 4H), 4.50-4.56 (m, 2H), 4.90 (q, J = 6.5 Hz, 1H), 7.36 (d, J = 8.3 Hz, 1H), 7.44 (d, J = 3.3 Hz, 1H), 7.88 (d, J = 8.3 Hz, 1H), 7.94 (d, J = 3.3 Hz, 1H) | CDCl₃ |

TABLE 34

| Ex. No. | structural formula | compound name | ESI MS m/z | ¹H NMR, δ (ppm) | deuterated solvent |
|---|---|---|---|---|---|
| 242 | | 2-(3,8-diazabicyclo[3.2.1]octan-3-yl)-4-(1-methoxyethyl)-7-(thiazol-2-yl)benzo[d]oxazole | 371 (M + H)⁺ | (400 MHz): 1.54 (d, J = 6.8 Hz, 3H), 2.06-2.20 (m, 2H), 2.25-2.38 (m, 2H), 3.31 (s, 3H), 3.88 (d, J = 13.6 Hz, 2H), 4.14-4.19 (m, 2H), 4.26 (d, J = 13.6 Hz, 2H), 4.88 (q, J = 6.8 Hz, 1H), 7.37 (d, J = 8.2 Hz, 1H), 7.45 (d, J = 3.3 Hz, 1H), 7.89 (d, J = 8.2 Hz, 1H), 7.96 (d, J = 3.3 Hz, 1H) | CDCl₃ |
| 243 | | 2-(3,9-diazabicyclo[3.3.1]nonan-3-yl)-4-(1-methoxyethyl)-7-(thiazol-2-yl)benzo[d]oxazole | 385 (M + H)⁺ | (400 MHz): 1.51-1.57 (m, 3H), 1.59-1.64 (m, 1H), 2.00-2.07 (m, 4H), 2.18-2.31 (m, 1H), 3.32 (s, 3H), 3.60-3.68 (m, 2H), 3.87 (dd, J = 13.5, 3.0 Hz, 2H), 4.40 (d, J = 13.5 Hz, 2H), 4.92 (q, J = 6.5 Hz, 1H), 7.36 (d, J = 8.2 Hz, 1H), 7.46 (d, J = 3.3 Hz, 1H), 7.88 (d, J = 8.2 Hz, 1H), 7.96 (d, J = 3.3 Hz, 1H) | CDCl₃ |
| 244 | | 1-(2-(3,6-diazabicyclo[3.1.1]heptan-3-yl)-7-(thiazol-2-yl)benzo[d]oxazol-4-yl)ethan-1-one | 341 (M + H)⁺ | (400 MHz): 1.69-1.73 (m, 1H), 2.84-2.94 (m, 4H), 3.96 (d, J = 6.1 Hz, 2H), 4.03-4.11 (m, 4H), 7.54 (d, J = 3.3 Hz, 1H), 7.88-7.91 (m, 2H), 8.01 (d, J = 3.3 Hz, 1H) | CDCl₃ |

TABLE 34-continued

| Ex. No. | structural formula | compound name | ESI MS m/z | ¹H NMR, δ (ppm) | deuterated solvent |
|---|---|---|---|---|---|
| 245 | | 1-(2-(3,8-diazabicyclo[3.2.1]octan-3-yl)-7-(thiazol-2-yl)benzo[d]oxazol-4-yl)ethan-1-one | 355 (M + H)⁺ | (400 MHz): 1.93 (s, 4H), 2.90 (s, 3H), 3.54 (d J = 12.2 Hz, 2H), 3.77 (m, 2H), 4.12 (d, J = 12.2 Hz, 2H), 7.53 (d, J = 3.3 Hz, 1H), 7.85-7.88 (m, 2H), 8.01 (d, J = 3.3 Hz, 1H) | CDCl₃ |
| 246 | | 2-(2-(3,6-diazabicyclo[3.1.1]heptan-3-yl)-7-(thiazol-2-yl)benzo[d]oxazol-4-yl)propan-2-ol | 371 (M + H)⁺ | (400 MHz): 1.65-1.74 (m, 7H), 2.84-2.95 (m, 1H), 3.93 (d, J = 6.0 Hz, 2H), 3.98-4.04 (m, 4H), 7.19 (d, J = 8.3 Hz, 1H), 7.45 (d, J = 3.3 Hz, 1H), 7.82 (d, J = 8.3 Hz, 1H), 7.96 (d, J = 3.3 Hz, 1H) | CDCl₃ |
| 247 | | 2-(2-(3,8-diazabicyclo[3.2.1]octan-3-yl)-7-(thiazol-2-yl)benzo[d]oxazol-4-yl)propan-2-ol | 371 (M + H)⁺ | (400 MHz): 1.67 (s, 6H), 1.89 (s, 4H), 3.43 (dd, J = 12.3, 2.0 Hz, 2H), 3.61-3.73 (m, 2H), 4.02 (dd, J = 12.3, 2.0 Hz, 2H), 7.16 (d, J = 8.3 Hz, 1H), 7.44 (d, J = 3.2 Hz, 1H), 7.79 (d, J = 8.3 Hz, 1H), 7.97 (d, J = 3.2 Hz, 1H) | CDCl₃ |
| 248 | | 1-((2-(3,6-diazabicyclo[3.1.1]heptan-3-yl)-7-(thiazol-2-yl)benzo[d]oxazol-4-yl)oxy)-1,1-difluoro-2-methylpropan-2-ol | 423 (M + H)⁺ | (400 MHz): 1.53 (s, 6H), 1.65 (d, J = 9.3 Hz, 1H), 2.82-2.87 (m, 1H), 3.90-4.01 (m, 7H), 7.23-7.25 (m, 1H), 7.44 (d, J = 3.3 Hz, 1H), 7.84 (d, J = 8.8 Hz, 1H), 7.94 (d, J = 3.3 Hz, 1H) | CDCl₃ |
| 249 | | 2-((2-(3,6-diazabicyclo[3.1.1]heptan-3-yl)-7-(thiazol-2-yl)benzo[d]oxazol-4-yl)oxy)-2,2-difluoroethan-1-ol | 395 (M + H)⁺ | (400 MHz): 1.68 (d, J = 9.2 Hz, 1H), 2.86-2.92 (m, 1H), 3.79 (t, J = 7.6 Hz, 2H), 3.93 (d, J = 8.0 Hz, 2H), 4.00 (brs, 4H), 7.22-7.25 (m, 1H), 7.48 (d, J = 3.2 Hz, 1H), 7.87 (d, J = 8.7 Hz, 1H), 7.97 (d, J = 3.2 Hz, 1H) | CDCl₃ |

TABLE 35

| Ex. No. | structural formula | compound name | ESI MS m/z | ¹H NMR, δ (ppm) | deuterated solvent |
|---|---|---|---|---|---|
| 250 | | 1-((2-(3,6-diazabicyclo[3.1.1]heptan-3-yl)-7-(thiazol-2-yl)benzo[d]oxazol-4-yl)oxy)-1,1-difluoropropan-2-ol (racemic) | 409 (M + H)⁺ | (400 MHz): 1.37 (d, J = 6.5 Hz, 3H), 1.67 (d, J = 9.3 Hz, 1H), 2.85-2.90 (m, 1H), 3.92 (d, J = 6.0 Hz, 2H), 3.95-4.04 (m, 5H), 7.22-7.24 (m, 1H), 7.47 (d, J = 3.2 Hz, 1H), 7.85 (d, J = 8.7 Hz, 1H), 7.96 (d, J = 3.2 Hz, 1H) | CDCl₃ |
| 251 | | 1-((2-(3,6-diazabicyclo[3.1.1]heptan-3-yl)-7-(thiazol-2-yl)benzo[d]oxazol-4-yl)oxy)-1,1-difluoropropan-2-ol (optically active) | 409 (M + H)⁺ | (400 MHz): 1.37 (d, J = 6.5 Hz, 3H), 1.67 (d, J = 9.3 Hz, 1H), 2.85-2.90 (m, 1H), 3.92 (d, J = 6.0 Hz, 2H), 3.95-4.04 (m, 5H), 7.22-7.24 (m, 1H), 7.47 (d, J = 3.2 Hz, 1H), 7.85 (d, J = 8.7 Hz, 1H), 7.96 (d, J = 3.2 Hz, 1H) | CDCl₃ |
| 252 | | 1-((2-(3,6-diazabicyclo[3.1.1]heptan-3-yl)-7-(thiazol-2-yl)benzo[d]oxazol-4-yl)oxy)-1,1-difluoropropan-2-ol (No. 251's enantiomer) | 409 (M + H)⁺ | (400 MHz): 1.37 (d, J = 6.5 Hz, 3H), 1.67 (d, J = 9.3 Hz, 1H), 2.85-2.90 (m, 1H), 3.92 (d, J = 6.0 Hz, 2H), 3.95-4.04 (m, 5H), 7.22-7.24 (m, 1H), 7.47 (d, J = 3.2 Hz, 1H), 7.85 (d, J = 8.7 Hz, 1H), 7.96 (d, J = 3.2 Hz, 1H) | CDCl₃ |
| 253 | | 2-(1-(2-(3,6-diazabicyclo[3.1.1]heptan-3-yl)-7-(thiazol-2-yl)benzo[d]oxazol-4-yl)-2,2,2-trifluoroethoxy)acetic acid | 455 (M + H)⁺ | (400 MHz): 1.72 (d, J = 9.3 Hz, 1H), 2.63-2.76 (m, 1H), 3.81-4.04 m, (8H), 3.86 (d, J = 16.3 Hz, 1H), 4.11 (d, J = 16.3 Hz, 1H), 5.82 (q, J = 6.9 Hz, 1H), 7.41 (d, J = 8.3 Hz, 1H), 7.87 (d, J = 8.3 Hz, 1H), 8.00 (d, J = 3.2 Hz, 1H), 8.07 (d, J = 3.2 Hz, 1H), 8.17 (s, 1H) | DMSO-d₆ |

TABLE 35-continued

| Ex. No. | structural formula | compound name | ESI MS m/z | ¹H NMR, δ (ppm) | deuterated solvent |
|---|---|---|---|---|---|
| 254 | | 2-(3,8-diazabicyclo[3.2.1]octan-3-yl)-4-((tetrahydro-2H-pyran-4-yl)oxy)-7-(thiazol-2-yl)benzo[d]oxazole | 413 (M + H)⁺ | (400 MHz): 1.76-1.87 (m, 2H), 1.96-2.05 (m, 4H), 2.06-2.14 (m, 2H), 3.50 (dd, J = 12.8, 1.6 Hz, 2H), 3.56-3.67 (m, 2H), 3.81-3.89 (m, 2H), 3.98-4.05 (m, 2H), 4.08 (d, J = 12.8, 2.0 Hz, 2H), 4.99 (tt, J = 8.3, 4.1 Hz, 1H), 6.98 (d, J = 8.8 Hz, 1H), 7.66 (d, J = 3.3 Hz, 1H), 7.73 (d, J = 8.8 Hz, 1H), 7.89 (d, J = 3.3 Hz, 1H) | CD₃OD |
| 255 | | 1-(1-(2-(3,6-diazabicyclo[3.1.1]heptan-3-yl)-7-(thiazol-2-yl)benzo[d]oxazol-4-yl)-2,2,2-trifluoroethoxy)-2-methylpropan-2-ol | 469 (M + H)⁺ | (400 MHz): 1.12 (s, 6H), 1.69 (d, J = 9.3 Hz, 1H), 2.70-2.79 (m, 1H), 3.22-3.36 (m, 2H), 3.76-3.82 (m, 2H), 3.92-3.98 (m, 4H), 5.43 (q, J = 6.4 Hz, 1H), 7.41 (d, J = 8.4 Hz, 1H), 7.69 (d, J = 3.3 Hz, 1H), 7.77 (d, J = 8.4 Hz, 1H), 7.89 (d, J = 3.3 Hz, 1H) | CD₃OD |
| 256 | | 2-(1-(2-(3,6-diazabicyclo[3.1.1]heptan-3-yl)-7-(thiazol-2-yl)benzo[d]oxazol-4-yl)-2,2,2-trifluoroethoxy)acetamide | 454 (M + H)⁺ | (400 MHz): 1.69 (d, J = 9.3 Hz, 1H), 2.87 (td, J = 6.2, 9.3 Hz, 1H), 3.93 (d, J = 6.0 Hz, 2H), 3.96-4.04 (m, 4H), 4.07 (d, J = 15.3 Hz, 1H), 4.12 (d, J = 15.3 Hz, 1H), 5.49 (q, J = 6.6 Hz, 1H), 6.62-6.82 (m, 2H), 7.44 (d, J = 8.3 Hz, 1H), 7.51 (d, J = 3.3 Hz, 1H), 7.93 (d, J = 8.3 Hz, 1H), 7.99 (d, J = 3.3 Hz, 1H) | CDCl₃ |
| 257 | | 1-(1-(2-(3,6-diazabicyclo[3.1.1]heptan-3-yl)-7-(thiazol-2-yl)benzo[d]oxazol-4-yl)-2,2,2-trifluoroethoxy)-1,1-difluoro-2-methylpropan-2-ol | 505 (M + H)⁺ | (400 MHz): 1.37 (s, 3H), 1.44 (s, 3H), 1.68 (d, J = 9.3 Hz, 1H), 2.80-2.91 (m, 1H), 3.50 (brs, 1H), 3.93 (d, J = 6.0 Hz, 2H), 3.95-4.05 (m, 4H), 6.01 (q, J = 6.4 Hz, 1H), 7.35 (d, J = 8.3 Hz, 1H), 7.49 (d, J = 3.2 Hz, 1H), 7.91 (d, J = 8.4 Hz, 1H), 7.98 (d, J = 3.2 Hz, 1H) | CDCl₃ |

TABLE 36

| Ex. No. | structural formula | compound name | ESI MS m/z | ¹H NMR, δ (ppm) | deuterated solvent |
|---|---|---|---|---|---|
| 258 | | 2-(1-(2-(3,6-diazabicyclo[3.1.1]heptan-3-yl)-7-(thiazol-2-yl)benzo[d]oxazol-4-yl)-2,2,2-trifluoroethoxy)-2,2-difluoroethan-1-ol | 477 (M + H)⁺ | (400 MHz): 1.71 (d, J = 9.3 Hz, 1H), 2.82-2.91 (m, 1H), 3.41 (s, 1H), 3.83-3.97 (m, 4H), 3.98-4.08 (m, 4H), 6.14 (q, J = 6.6 Hz, 1H), 7.44 (d, J = 8.3 Hz, 1H), 7.52 (d, J = 3.3 Hz, 1H), 7.90 (d, J = 8.3 Hz, 1H), 7.98 (d, J = 3.2 Hz, 1H) | CDCl₃, 3% CD₃OD |
| 259 | | (2R)-1-((2-(3,6-diazabicyclo[3.1.1]heptan-3-yl)-7-(thiazol-2-yl)benzo[d]oxazol-4-yl)oxy)propan-2-ol | 373 (M + H)⁺ | (400 MHz): 1.28 (d, J = 6.2 Hz, 3H), 1.65 (d, J = 9.3 Hz, 1H), 2.77-2.90 (m, 1H), 3.85-4.03 (m, 6H), 4.04-4.21 (m, 1H), 4.22-4.33 (m, 2H), 6.90 (d, J = 8.7 Hz, 1H), 7.38 (d, J = 3.2 Hz, 1H), 7.83 (d, J = 8.7 Hz, 1H), 7.90 (d, J = 3.3 Hz, 1H) | CDCl₃ |
| 260 | | (2S)-1-((2-(3,6-diazabicyclo[3.1.1]heptan-3-yl)-7-(thiazol-2-yl)benzo[d]oxazol-4-yl)oxy)propan-2-ol | 373 (M + H)⁺ | (400 MHz): 1.28 (d, J = 6.4 Hz, 3H), 1.65 (brd, J = 9.2 Hz, 3H), 2.77-2.91 (m, 1H), 3.85-4.03 (m, 4H), 4.04-4.16 (m, 1H), 4.21-4.34 (m, 2H), 6.90 (d, J = 8.8 Hz, 1H), 7.33-7.41 (m, 1H), 7.83 (d, J = 8.7 Hz, 1H), 7.89 (d, J = 3.2 Hz, 1H) | CDCl₃ |
| 261 | | 1-(1-(2-(3,6-diazabicyclo[3.1.1]heptan-3-yl)-7-(thiazol-2-yl)benzo[d]oxazol-4-yl)-2,2,2-trifluoroethoxy)propan-2-ol | 455 (M + H)⁺ | (400 MHz): 1.11 (d, J = 6.5 Hz, 1.5H), 1.15 (d, J = 6.5 Hz, 1.5H), 1.68-1.74 (m, 1H), 2.85-2.95 (m, 1H), 3.47-3.62 (m, 1H), 3.63-3.68 (m, 2H), 3.94-4.00 (m, 2H), 4.01-4.07 (m, 4H), 5.28 (q, J = 6.6 Hz, 0.5H), 5.41 (q, J = 6.6 Hz, 0.5H), 7.37 (d, J = 8.2 Hz, 0.5H), 7.44 (d, J = 8.2 Hz, 0.5H), 7.48-7.51 (m, 1H), 7.89-7.93 (m, 1H), 7.97-8.00 (m, 1H) | CDCl₃ |
| 262 | | 2-(3,8-diazabicyclo[3.2.1]octan-3-yl)-4-((tetrahydro-2H-pyran-3-yl)oxy)-7-(thiazol-2-yl)benzo[d]oxazole | 413 (M + H)⁺ | (400 MHz): 1.43-1.64 (m, 2H), 1.70-1.94 (m, 4H), 2.00-2.13 (m, 2H), 3.32 (dd, J = 12.9, 1.8 Hz, 2H), 3.47-3.61 (m, 4H), 3.61-3.69 (m, 1H), 3.83-3.94 (m, 3H), 4.70-4.80 (m, 1H), 6.86 (d, J = 8.9 Hz, 1H), 7.56 (d, J = 3.3 Hz, 1H), 7.62 (d, J = 8.7 Hz, 1H), 7.79 (d, J = 3.3 Hz, 1H) | CD₃OD |

TABLE 36-continued

| Ex. No. | structural formula | compound name | ESI MS m/z | ¹H NMR, δ (ppm) | deuterated solvent |
|---|---|---|---|---|---|
| 263 | | 2-(3,8-diazabicyclo[3.2.1]octan-3-yl)-4-(difluoromethoxy)-7-(thiazol-2-yl)benzo[d]oxazole | 379 (M + H)⁺ | (400 MHz): 1.74-1.89 (m, 4H), 3.37 (dd, J = 12.6, 2.0 Hz, 2H), 3.58-3.66 (m, 2H), 3.93 (dd, J = 12.6, 2.0 Hz, 2H), 6.99 (d, J = 8.7 Hz, 1H), 7.23 (t, J = 74.4 Hz, 1H), 7.63 (d, J = 3.3 Hz, 1H), 7.66 (d, J = 8.7 Hz, 1H), 7.84 (d, J = 3.3 Hz, 1H) | CD₃OD |
| 264 | | 1-((2-(3,8-diazabicyclo[3.2.1]octan-3-yl)-7-(thiazol-2-yl)benzo[d]oxazol-4-yl)oxy)-2-methylpropan-2-ol | 401 (M + H)⁺ | (400 MHz): 1.26 (s, 6H), 1.75-1.92 (m, 4H), 3.39 (dd, J = 12.5, 2.0 Hz, 2H), 3.61-3.69 (m, 2H), 3.86-3.95 (m, 4H), 6.83 (d, J = 8.7 Hz, 1H), 7.55 (d, J = 3.3 Hz, 1H), 7.64 (d, J = 8.7 Hz, 1H), 7.79 (d, J = 3.3 Hz, 1H) | CD₃OD |
| 265 | | 1-(1-(2-(3,6-diazabicyclo[3.1.1]heptan-3-yl)-7-(thiazol-2-yl)benzo[d]oxazol-4-yl)-2,2,2-trifluoroethoxy)-1,1-difluoropropan-2-ol | 491 (M + H)⁺ | (400 MHz): 1.32 (d, J = 6.6 Hz, 1.8H), 1.38 (d, J = 6.5 Hz, 1.2H), 1.68 (d, J = 9.2 Hz, 1H), 2.81-2.91 (m, 1H), 3.93 (d, J = 6.2 Hz, 2H), 3.96-4.25 (m, 5H), 5.95 (q, J = 6.7 Hz, 0.6H), 6.10 (q, J = 6.5 Hz, 0.4H), 7.32 (d, J = 8.3 Hz, 0.6H), 7.39 (d, J = 8.3 Hz, 0.4H), 7.49 (d, J = 3.2 Hz, 0.4H), 7.50 (d, J = 3.2 Hz, 0.6H), 7.92 (d, J = 8.3 Hz, 1H), 7.98 (d, J = 3.3 Hz, 1H) | CDCl₃ |

TABLE 37

| Ex. No. | structural formula | compound name | ESI MS m/z | ¹H NMR, δ (ppm) | deuterated solvent |
|---|---|---|---|---|---|
| 266 | | 3-((2-(3,6-diazabicyclo[3.1.1]heptan-3-yl)-7-(thiazol-2-yl)benzo[d]oxazol-4-yl)oxy)cyclobutane-1-carbonitrile | 394 (M + H)⁺ | (400 MHz): 1.71 (d, J = 9.4 Hz, 4H), 2.70-2.85 (m, 2H), 2.85-3.01 (m, 3H), 3.14-3.38 (m, 1H), 3.97-4.10 (m, 6H), 5.23-5.50 (m, 1H), 6.66 (d, J = 8.7 Hz, 1H), 7.40 (d, J = 3.3 Hz, 1H), 7.81 (d, J = 8.0 Hz, 1H), 7.91 (d, J = 3.3 Hz, 1H) | CDCl₃ |

TABLE 37-continued

| Ex. No. | structural formula | compound name | ESI MS m/z | ¹H NMR, δ (ppm) | deuterated solvent |
|---|---|---|---|---|---|
| 267 | 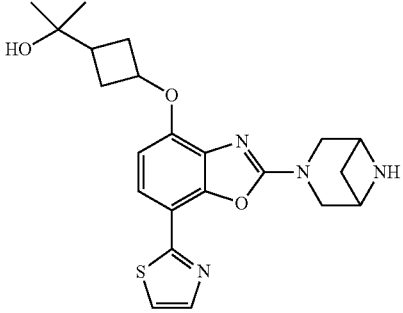 [SMILES: CC(C)(O)C1CC(Oc2ccc(-c3nccs3)c3oc(N4CC5CC(C4)N5)nc23)C1] | 2-(3-((2-(3,6-diazabicyclo[3.1.1]heptan-3-yl)-7-(thiazol-2-yl)benzo[d]oxazol-4-yl)oxy)cyclobutyl)propan-2-ol | 427 (M + H)⁺ | (400 MHz): 1.22 (s, 6H), 1.69 (d, J = 9.3 Hz, 1H), 2.41-2.55 (m, 5H), 2.85-2.92 (m, 1H), 3.99 (d, J = 5.6 Hz, 2H), 4.02-4.12 (m, 4H), 4.93-5.01 (m, 1H), 6.64 (d, J = 8.8 Hz, 1H), 7.37 (d, J = 3.3 Hz, 1H), 7.79 (d, J = 8.8 Hz, 1H), 7.89 (d, J = 3.3 Hz, 1H) | CDCl₃ |
| 268 | 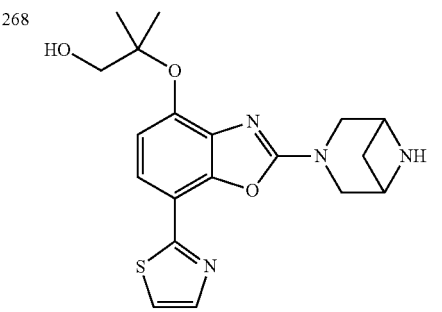 | 2-((2-(3,6-diazabicyclo[3.1.1]heptan-3-yl)-7-(thiazol-2-yl)benzo[d]oxazol-4-yl)oxy)-2-methylpropan-1-ol | 387 (M + H)⁺ | (400 MHz): 1.41 (s, 6H), 1.68 (d, J = 9.3 Hz, 1H), 2.84-2.90 (m, 1H), 3.37 (d, J = 7.3 Hz, 2H), 3.92 (d, J = 5.9 Hz, 2H), 3.96-4.10 (m, 4H), 6.19 (t, J = 7.3 Hz, 1H), 6.98 (d, J = 8.6 Hz, 1H), 7.45 (d, J = 3.3 Hz, 1H), 7.81 (d, J = 8.6 Hz, 1H), 7.95 (d, J = 3.3 Hz, 1H) | CDCl₃ |
| 269 | 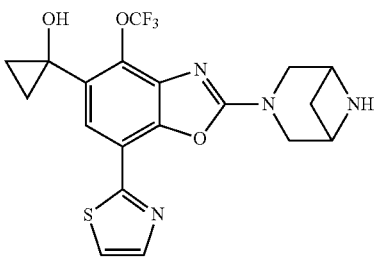 [SMILES: OC1(c2cc(-c3nccs3)c3oc(N4CC5CC(C4)N5)nc3c2OC(F)(F)F)CC1] | 1-(2-(3,6-diazabicyclo[3.1.1]heptan-3-yl)-7-(thiazol-2-yl)-4-(trifluoromethoxy)benzo[d]oxazol-5-yl)cyclopropan-1-ol | 439 (M + H)⁺ | (400 MHz): 1.07-1.13 (m, 2H), 1.22-1.29 (m, 2H), 7.99 (s, 1H), 1.69 (d, J = 9.3 Hz, 1H), 2.75 (brs, 1H), 2.82-2.91 (m, 1H), 3.92 (d, J = 6.0 Hz, 2H), 3.95-4.08 (m, 4H), 7.49 (d, J = 3.3 Hz, 1H), 7.97 (d, J = 3.3 Hz, 1H) | CDCl₃ |
| 270 | 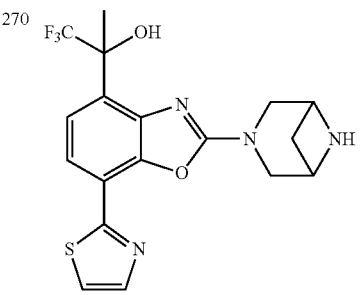 | 2-(2-(3,6-diazabicyclo[3.1.1]heptan-3-yl)-7-(thiazol-2-yl)benzo[d]oxazol-4-yl)-1,1,1-trifluoropropan-2-ol (optically active) | 411 (M + H)⁺ | (400 MHz): 1.68 (d, J = 9.4 Hz, 1H), 1.83 (s, 3H), 2.82-2.94 (m, 1H), 3.90-3.96 (m, 2H), 3.96-4.08 (m, 4H), 7.26 (d, J = 8.4 Hz, 1H), 7.50 (d, J = 3.2 Hz, 1H), 7.89 (d, J = 8.4 Hz, 1H), 7.98 (d, J = 3.2 Hz, 1H) | CDCl₃ |
| 271 | 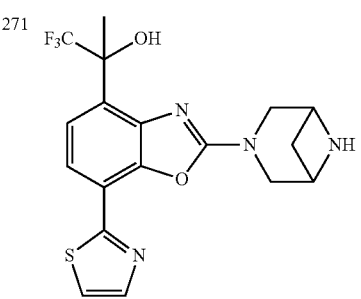 | 2-(2-(3,6-diazabicyclo[3.1.1]heptan-3-yl)-7-(thiazol-2-yl)benzo[c]oxazol-4-yl)-1,1,1-trifluoropropan-2-ol (No. 270's enantiomer) | 411 (M + H)⁺ | (400 MHz): 1.68 (d, J = 9.4 Hz, 1H), 1.83 (s, 3H), 2.82-2.94 (m, 1H), 3.90-3.96 (m, 2H), 3.96-4.08 (m, 4H), 7.26 (d, J = 8.4 Hz, 1H), 7.50 (d, J = 3.2 Hz, 1H), 7.89 (d, J = 8.4 Hz, 1H), 7.98 (d, J = 3.2 Hz, 1H) | CDCl₃ |

TABLE 37-continued

| Ex. No. | structural formula | compound name | ESI MS m/z | ¹H NMR, δ (ppm) | deuterated solvent |
|---|---|---|---|---|---|
| 272 | | 1-(2-(3,6-diazabicyclo[3.1.1]heptan-3-yl)-7-(thiazol-2-yl)-4-(trifluoromethoxy)benzo[d]oxazol-5-yl)ethan-1-ol (optically active) | 427 (M + H)+ | (400 MHz): 1.57 (d, J = 6.4 Hz, 3H), 1.71 (d, J = 9.3 Hz, 1H), 2.84-2.95 (m, 1H), 3.88-4.10 (m, 6H), 5.39 (q, J = 6.5 Hz, 1H), 7.49 (d, J = 3.2 Hz, 1H), 7.97 (d, J = 3.2 Hz, 1H), 8.10 (s, 1H) | CDCl₃ |
| 273 | | 1-(2-(3,6-diazabicyclo[3.1.1]heptan-3-yl)-7-(thiazol-2-yl)-4-(trifluoromethoxy)benzo[d]oxazol-5-yl)ethan-1-ol (No. 272's enantiomer) | 427 (M + H)+ | (400 MHz): 1.57 (d, J = 6.4 Hz, 3H), 1.71 (d, J = 9.3 Hz, 1H), 2.80-2.99 (m, 1H), 3.88-4.08 (m, 6H), 5.39 (q, J = 6.5 Hz, 1H), 7.49 (d, J = 3.2 Hz, 1H), 7.98 (d, J = 3.3 Hz, 1H), 8.11 (s, 1H) | CDCl₃ |

TABLE 38

| Ex. No. | structural formula | compound name | ESI MS m/z | ¹H NMR, δ (ppm) | deuterated solvent |
|---|---|---|---|---|---|
| 274 | | 1-(2-(3,8-diazabicyclo[3.2.1]octan-3-yl)-7-(thiazol-2-yl)-4-(trifluoromethoxy)benzo[d]oxazol-5-yl)cyclopropan-1-ol | 453 (M + H)+ | (400 MHz): 1.04-1.12 (m, 2H), 1.21-1.29 (m, 2H), 1.88 (d, J = 1.8 Hz, 4H), 2.70 (s, 1H), 3.44 (dd, J = 2.1, 12.2 Hz, 2H), 3.68 (brs, 2H), 4.04 (dd, J = 2.1, 12.2 Hz, 2H), 7.48 (d, J = 3.3 Hz, 1H), 7.96 (s, 1H), 7.96 (d, J = 3.3 Hz, 1H) | CDCl₃ |
| 275 | | 1-(2-(3,8-diazabicyclo[3.2.1]octan-3-yl)-7-(thiazol-2-yl)-4-(trifluoromethoxy)benzo[d]oxazol-5-yl)-2,2-difluoroethan-1-ol (optically active) | 477 (M + H)+ | (400 MHz): 1.90 (s, 4H), 3.38-3.58 (m, 2H), 3.71 (brs, 2H), 3.95-4.14 (m, 2H), 5.25-5.42 (m, 1H), 5.73-6.14 (m, 1H), 7.50 (d, J = 3.2 Hz, 1H), 7.98 (d, J = 3.3 Hz, 1H), 8.08 (s, 1H) | CDCl₃ |
| 276 | | 1-(2-(3,8-diazabicyclo[3.2.1]octan-3-yl)-7-(thiazol-2-yl)-4-(trifluoromethoxy)benzo[d]oxazol-5-yl)-2,2-difluoroethan-1-ol (No. 275's enantiomer) | 477 (M + H)+ | (400 MHz): 1.90 (s, 4H), 3.48 (brd, J = 12.0 Hz, 2H), 3.71 (brs, 2H), 3.97-4.11 (m, 2H), 5.34 (ddd, J = 13.0, 7.0, 4.3 Hz, 1H), 5.70-6.17 (m, 1H), 7.49 (d, J = 3.3 Hz, 1H), 7.98 (d, J = 3.2 Hz, 1H), 8.08 (s, 1H) | CDCl₃ |

TABLE 38-continued

| Ex. No. | structural formula | compound name | ESI MS m/z | ¹H NMR, δ (ppm) | deuterated solvent |
|---|---|---|---|---|---|
| 277 | | 3-((2-(3,6-diazabicyclo[3.1.1]heptan-3-yl)-7-(thiazol-2-yl)benzo[d]oxazol-4-yl)oxy)-1,1,1-trifluoropropan-2-ol | 427 (M + H)⁺ | (400 MHz): 1.72 (d, J = 9.7 Hz, 1H), 2.70-2.83 (m, 1H), 3.86 (d, J = 6.1 Hz, 2H), 3.90-4.02 (m, 4H), 4.22-4.52 (m, 3H), 6.89 (d, J = 8.7 Hz, 1H), 7.58 (d, J = 3.3 Hz, 1H), 7.67 (d, J = 8.7 Hz, 1H), 7.81 (d, J = 3.3 Hz, 1H) | CD₃OD |
| 278 | | 2-(3,6-diazabicyclo[3.1.1]heptan-3-yl)-4-(difluoromethoxy)-7-(thiazol-2-yl)benzo[d]oxazole | 365 (M + H)⁺ | (400 MHz): 1.78 (d, J = 9.5 Hz, 1H), 2.79-2.88 (m, 1H), 3.89 (brd, J = 6.0 Hz, 2H), 3.94-4.10 (m, 4H), 7.09 (d, J = 8.7 Hz, 1H), 7.32 (t, J = 74.4 Hz, 1H), 7.72 (d, J = 3.3 Hz, 1H), 7.77 (d, J = 8.7 Hz, 1H), 7.93 (d, J = 3.3 Hz, 1H) | CD₃OD |
| 279 | | 1-((2-(3,6-diazabicyclo[3.1.1]heptan-3-yl)-7-(thiazol-2-yl)benzo[d]oxazol-4-yl)oxy)-2-methylpropan-2-ol | 387 (M + H)⁺ | (400 MHz): 1.26 (s, 6H), 1.72 (d, J = 9.7 Hz, 1H), 2.72-2.81 (m, 1H), 3.85 (brd, J = 6.1 Hz, 2H), 3.88-4.03 (m, 6H), 6.82 (d, J = 8.8 Hz, 1H), 7.54 (d, J = 3.3 Hz, 1H), 7.64 (d, J = 8.8 Hz, 1H), 7.79 (d, J = 3.3 Hz, 1H) | CD₃OD |
| 280 | | 3-(1-(2-(3,6-diazabicyclo[3.1.1]heptan-3-yl)-7-(thiazol-2-yl)benzo[d]oxazol-4-yl)-2,2,2-trifluoroethoxy)-2,3-dimethylbutan-2-ol | 497 (M + H)⁺ | (400 MHz): 0.97 (s, 3H), 1.19 (s, 3H), 1.34 (d, J = 4.8 Hz, 6H), 1.71 (d, J = 9.3 Hz, 1H), 2.83-2.88 (m, 1H), 3.93-4.06 (m, 6H), 5.31-5.36 (m, 1H), 7.34 (d, J = 8.4 Hz, 1H), 7.49 (d, J = 3.2 Hz, 1H), 7.89 (d, J = 8.4 Hz, 1H), 7.98 (d, J = 3.2 Hz, 1H) | CDCl₃ |
| 281 | | 2-(3,6-diazabicyclo[3.1.1]heptan-3-yl)-7-(thiazol-2-yl)-4-(2,2,2-trifluoro-1-(2-methoxy-2-methylpropoxy)ethyl)benzo[d]oxazole | 483 (M + H)⁺ | (400 MHz): 1.17 (s, 3H), 1.22 (s, 3H), 1.72 (d, J = 9.3 Hz, 1H), 2.84-2.94 (m, 1H), 3.22 (s, 3H), 3.34-3.50 (m, 2H), 3.94-4.00 (m, 2H), 4.01-4.07 (m, 4H), 5.42-5.50 (q, J = 6.4 Hz, 1H), 7.48 (d, J = 3.3 Hz, 1H), 7.51 (d, J = 8.4 Hz, 1H), 7.91 (d, J = 8.4 Hz, 1H) | CDCl₃ |

TABLE 39

| Ex. No. | structural formula | compound name | ESI MS m/z | $^1$H NMR, δ (ppm) | deuterated solvent |
|---|---|---|---|---|---|
| 282 | | 2-(3,6-diazabicyclo[3.1.1]heptan-3-yl)-7-(thiazol-2-yl)-4-(2,2,2-trifluoro-1-((1-methoxycyclopropyl)methoxy)ethyl)benzo[d]oxazole | 481 (M + H)⁺ | (400 MHz): 0.48-0.60 (m, 2H), 0.77-0.87 (m, 2H), 1.71-1.75 (m, 1H), 2.02-2.07 (m, 1H), 3.34 (s, 3H), 3.58-3.71 (m, 2H), 4.26-4.43 (m, 4H), 4.50-4.56 (m, 2H), 5.51 (q, J = 6.8 Hz, 1H), 7.48 (d, J = 3.3 Hz, 1H), 7.56 (d, J = 8.3 Hz, 1H), 7.94 (d, J = 8.3 Hz, 1H) | CDCl₃ |
| 283 | | 2-(3,6-diazabicyclo[3.1.1]heptan-3-yl)-5-(1-methoxycyclopropyl)-7-(thiazol-2-yl)-4-(trifluoromethoxy)benzo[d]oxazole | 453 (M + H)⁺ | (400 MHz): 0.98-1.05 (m, 2H), 1.18-1.24 (m, 2H), 1.68 (d, J = 9.2 Hz, 1H), 2.82-2.92 (m, 1H), 3.18 (s, 3H), 3.92 (d, J = 6.1 Hz, 2H), 3.96-4.09 (m, 4H), 7.50 (d, J = 3.3 Hz, 1H), 7.94 (s, 1H), 7.98 (d, J = 3.3 Hz, 1H) | CDCl₃ |
| 284 | | 1-(1-(2-(3,6-diazabicyclo[3.1.1]heptan-3-yl)-7-(thiazol-4-yl)benzo[d]oxazol-4-yl)-2,2,2-trifluoroethoxy)-2-methylpropan-2-ol | 469 (M + H)⁺ | (400 MHz): 1.19 (s, 3H), 1.25 (s, 3H), 1.68 (d, J = 9.2 Hz, 1H), 2.85 (td, J = 6.2, 9.1 Hz, 1H), 3.40-3.58 (m, 3H), 3.92 (d, J = 6.0 Hz, 2H), 3.95-4.04 (m, 4H), 5.39 (q, J = 6.7 Hz, 1H), 7.42 (d, J = 8.2 Hz, 1H), 7.92 (d, J = 8.3 Hz, 1H), 7.95 (d, J = 2.0 Hz, 1H), 8.93 (d, J = 2.0 Hz, 1H) | CDCl₃ |
| 285 | | 3-((2-(3,6-diazabicyclo[3.1.1]heptan-3-yl)-7-(thiazol-2-yl)benzo[d]oxazol-4-yl)oxy)cyclobutan-1-ol | 385 (M + H)⁺ | (400 MHz): 1.62-1.68 (m, 1H), 2.46-2.56 (m, 2H), 2.65-2.76 (m, 2H), 2.81-2.89 (m, 1H), 3.90-3.95 (m, 2H), 3.97-4.09 (m, 4H), 4.67-4.75 (m, 1H), 5.14-5.22 (m, 1H), 6.66 (d, J = 8.7 Hz, 1H), 7.38 (d, J = 3.3 Hz, 1H), 7.80 (d, J = 8.7 Hz, 1H), 7.90 (d, J = 3.3 Hz, 1H) | CDCl₃ |
| 286 | | 1-((1-(2-(3,6-diazabicyclo[3.1.1]heptan-3-yl)-7-(thiazol-4-yl)benzo[d]oxazol-4-yl)-2,2,2-trifluoroethoxy)methyl)cyclopropan-1-ol | 467 (M + H)⁺ | (400 MHz): 0.52-0.63 (m, 2H), 0.78-0.87 (m, 2H), 1.67 (d, J = 9.2 Hz, 1H), 2.80-2.91 (m, 1H), 3.70 (d, J = 11.4 Hz, 1H), 3.87-4.03 (m, 7H), 5.14 (brs, 1H), 5.60 (q, J = 6.7 Hz, 1H), 7.45 (d, J = 7.7 Hz, 1H), 7.90-7.96 (m, 2H), 8.94 (d, J = 2.0 Hz, 1H) | CDCl₃ |

TABLE 39-continued

| Ex. No. | structural formula | compound name | ESI MS m/z | ¹H NMR, δ (ppm) | deuterated solvent |
|---|---|---|---|---|---|
| 287 | | 2-(3,6-diazabicyclo [3.1.1] heptan-3-yl)-5-(2-methoxypropan-2-yl)-7-(thiazol-4-yl)-4-(trifluoromethoxy)benzo[d]oxazole | 455 (M + H)⁺ | (400 MHz): 1.56 (s, 3H), 1.67 (d, J = 9.2 Hz, 1H), 1.71 (s, 3H), 2.82-2.90 (m, 1H), 3.16 (s, 3H), 3.91 (d, J = 5.9 Hz, 2H), 3.95-4.05 (m, 4H), 7.91 (d, J = 2.0 Hz, 1H), 8.04 (s, 1H), 8.94 (d, J = 2.0 Hz, 1H) | CDCl₃ |
| 288 | | 2-(2-(3,6-diazabicyclo [3.1.1]heptan-3-yl)-7-(thiazol-4-yl)-4-(trifluoromethoxy) benzo[d]oxazol-5-yl)propan-2-ol | 441 (M + H)⁺ | (400 MHz): 1.55 (s, 6H), 1.92 (brs, 1H), 2.44-2.61 (m, 1H), 3.68 (d, J = 5.7 Hz, 2H), 3.87 (brs, 4H), 5.35 (s, 1H), 8.22-8.26 (m, 2H), 9.28 (d, J = 1.8 Hz, 1H) | DMSO-d₆ |
| 289 | | 1-((2-(3,6-diazabicyclo [3.1.1]heptan-3-yl)-7-(pyridin-2-yl)benzo[d]oxazol-4-yl)oxy)-1,1-difluoro-2-methylpropan-2-ol | 417 (M + H)⁺ | (400 MHz): 1.53 (s, 6H), 1.64 (d, J = 9.4 Hz, 1H), 2.80-2.88 (m, 2H), 3.87-3.93 (m, 2H), 3.94-4.02 (m, 4H), 7.20-7.33 (m, 2H), 7.79 (dd, J = 7.7, 2.0 Hz, 1H), 7.84 (d, J = 8.7 Hz, 1H), 7.95-8.00 (m, 1H), 8.72-8.76 (m, 1H) | CDCl₃ |

TABLE 40

| Ex. No. | structural formula | compound name | ESI MS m/z | ¹H NMR, δ (ppm) | deuterated solvent |
|---|---|---|---|---|---|
| 290 | | 1-((2-(3,6-diazabicyclo[3.1.1] heptan-3-yl)-7-(oxazol-2-yl)benzo[d]oxazol-4-yl)oxy)-1,1-difluoro-2-methylpropan-2-ol | 407 (M + H)⁺ | (400 MHz): 1.54 (s, 6H), 1.63-1.66 (m, 1H), 2.82-2.87 (m, 1H), 3.89-4.03 (m, 6H), 7.24-7.26 (m, 1H), 7.33 (d, J = 0.73 Hz, 1H), 7.69 (d, J = 8.7 Hz, 1H), 7.79 (d, J = 0.73 Hz, 1H) | CDCl₃ |

TABLE 40-continued

| Ex. No. | structural formula | compound name | ESI MS m/z | ¹H NMR, δ (ppm) | deuterated solvent |
|---|---|---|---|---|---|
| 291 | | 2-(2-(3,8-diazabicyclo[3.2.1]octan-3-yl)-7-(thiazol-4-yl)-4-(trifluoromethoxy)benzo[d]oxazol-5-yl)propan-2-ol | 455 (M + H)⁺ | (400 MHz): 1.73 (s, 6H), 1.86-1.91 (m, 4H), 3.43 (dd, J = 12.2, 1.8 Hz, 2H), 3.69 (s, 2H), 4.00 (dd, J = 12.2, 1.8 Hz, 2H), 7.85 (d, J = 2.0 Hz, 1H), 8.16 (s, 1H), 8.93 (d, J = 2.0 Hz, 1H) | CDCl₃ |
| 292 | | 1-(2-(3,6-diazabicyclo[3.1.1]heptan-3-yl)-7-(thiazol-2-yl)-4-(trifluoromethoxy)benzo[d]oxazol-5-yl)-2,2-difluoroethan-1-ol (optically active) | 463 (M + H)⁺ | (400 MHz): 1.60 (d, J = 8.8 Hz, 1H), 2.54-2.62 (m, 1H), 3.70 (d, J = 6.0 Hz, 2H), 3.88 (brs, 4H), 5.04-5.21 (m, 1H), 5.93-6.33 (m, 1H), 6.59 (d, J = 5.4 Hz, 1H), 8.01 (d, J = 3.2 Hz, 1H), 8.04 (s, 1H), 8.08 (d, J = 3.2 Hz, 1H) | DMSO-d₆ |
| 293 | | 1-(2-(3,6-diazabicyclo[3.1.1]heptan-3-yl)-7-(thiazol-2-yl)-4-(trifluoromethoxy)benzo[d]oxazol-5-yl)-2,2-difluoroethan-1-ol (No. 292's enantiomer) | 463 (M + H)⁺ | (400 MHz): 1.60 (d, J = 8.8 Hz, 1H), 2.54-2.62 (m, 1H), 3.70 (d, J = 6.0 Hz, 2H), 3.88 (brs, 4H), 5.04-5.21 (m, 1H), 5.93-6.33 (m, 1H), 6.59 (d, J = 5.4 Hz, 1H), 8.01 (d, J = 3.2 Hz, 1H), 8.04 (s, 1H), 8.08 (d, J = 3.2 Hz, 1H) | DMSO-d₆ |
| 294 | | 2-(3,6-diazabicyclo[3.1.1]heptan-3-yl)-4-((tetrahydro-2H-pyran-4-yl)oxy)-7-(thiazol-2-yl)benzo[d]oxazole | 399 (M + H)⁺ | (400 MHz): 1.66 (d, J = 9.3 Hz, 1H), 1.72 (ddt, J = 13.2, 8.8, 4.5, 4.5 Hz, 2H), 1.93-2.06 (m, 2H), 2.67-2.77 (m, 1H), 3.43-3.56 (m, 2H), 3.77 (d, J = 6.1 Hz, 2H), 3.83-3.99 (m, 6H), 4.86 (tt, J = 8.3, 4.0 Hz, 1H), 6.84 (d, J = 8.8 Hz, 1H), 7.53 (d, J = 3.3 Hz, 1H), 7.61 (d, J = 8.8 Hz, 1H), 7.77 (d, J = 3.3 Hz, 1H) | CD₃OD |
| 295 | | 4-((2-(3,6-diazabicyclo[3.1.1]heptan-3-yl)-7-(thiazol-2-yl)benzo[d]oxazol-4-yl)oxy)-4,4-difluoro-2-methylbutan-2-ol | 437 (M + H)⁺ | (400 MHz): 1.34 (s, 6H), 1.86 (d, J = 10.4 Hz, 1H), 2.38-2.49 (m, 2H), 2.85-2.95 (m, 2H), 4.00-4.11 (m, 4H), 4.16 (brd, J = 6.1 Hz, 2H), 7.13-7.20 (m, 1H), 7.66 (d, J = 3.3 Hz, 1H), 7.70 (d, J = 8.7 Hz, 1H), 7.87 (d, J = 3.3 Hz, 1H) | CD₃OD |

TABLE 40-continued

| Ex. No. | structural formula | compound name | ESI MS m/z | $^1$H NMR, δ (ppm) | deuterated solvent |
|---|---|---|---|---|---|
| 296 | | 2-(2-(3,6-diazabicyclo[3.1.1]heptan-3-yl)-7-(thiazol-2-yl)benzo[d]oxazol-4-yl)-1,1-difluoropropan-2-ol (optically active) | 393 (M + H)$^+$ | (400 MHz): 1.68 (d, J = 9.3 Hz, 1H), 1.73 (s, 3H), 2.81-2.94 (m, 1H), 3.93 (brd, J = 5.9 Hz, 2H), 3.95-4.08 (m, 4H), 5.73-6.11 (m, 1H), 6.46 (s, 1H), 7.24-7.27 (m, 1H), 7.48 (d, J = 3.2 Hz, 1H), 7.88 (d, J = 8.3 Hz, 1H), 7.97 (d, J = 3.2 Hz, 1H) | CDCl$_3$ |
| 297 | | 2-(2-(3,6-diazabicyclo[3.1.1]heptan-3-yl)-7-(thiazol-2-yl)benzo[d]oxazol-4-yl)-1,1-difluoropropan-2-ol (No. 296's enantiomer) | 393 (M + H)$^+$ | (400 MHz): 1.68 (d, J = 9.3 Hz, 1H), 1.73 (s, 3H), 2.80-2.96 (m, 1H), 3.93 (d, J = 6.0 Hz, 2H), 3.95-4.08 (m, 4H), 5.70-6.13 (m, 1H), 6.46 (s, 1H), 7.24-7.27 (m, 1H), 7.48 (d, J = 3.2 Hz, 1H), 7.88 (d, J = 8.3 Hz, 1H), 7.97 (d, J = 3.3 Hz, 1H) | CDCl$_3$ |

TABLE 41

| Ex. No. | structural formula | compound name | ESI MS m/z | $^1$H NMR, δ (ppm) | deuterated solvent |
|---|---|---|---|---|---|
| 298 | | 2-(3,8-diazabicyclo[3.2.1]octan-3-yl)-5-(2-methoxypropan-2-yl)-7-(thiazol-4-yl)-4-(trifluoromethoxy)benzo[d]oxazole | 469 (M + H)$^+$ | (400 MHz): 1.71 (s, 6H), 1.86-1.91 (m, 4H), 3.16 (s, 3H), 3.43 (dd, J = 12.2, 1.9 Hz, 2H), 3.68 (s, 2H), 4.00 (dd, J = 12.2, 1.9 Hz, 2H), 7.86 (d, J = 2.0 Hz, 1H), 8.01 (s, 1H), 8.94 (d, J = 2.0 Hz, 1H) | CDCl$_3$ |
| 299 | | 1-(2-(3,6-diazabicyclo[3.1.1]heptan-3-yl)-7-(thiazol-4-yl)-4-(trifluoromethoxy)benzo[d]oxazol-5-yl)cyclopropan-1-ol | 439 (M + H)$^+$ | (400 MHz): 1.07-1.12 (m, 2H), 1.22-1.29 (m, 2H), 1.68 (d, J = 9.3 Hz, 1H), 2.73 (s, 1H), 2.81-2.91 (m, 1H), 3.92 (d, J = 6.0 Hz, 2H), 3.96-4.06 (m, 4H), 7.91 (d, J = 2.0 Hz, 1H), 8.01 (s, 1H), 8.94 (d, J = 2.0 Hz, 1H) | CDCl$_3$ |
| 300 | | 1-(2-(3,6-diazabicyclo[3.1.1]heptan-3-yl)-7-(thiazol-4-yl)-4-(trifluoromethoxy)benzo[d]oxazol-5-yl)-2,2-difluoroethan-1-ol (optically active) | 463 (M + H)$^+$ | (400 MHz): 1.58 (d, J = 8.9 Hz, 1H), 2.54-2.63 (m, 1H), 3.29 (s, 1H), 3.68 (d, J = 5.8 Hz, 2H), 3.89 (brs, 4H), 5.04-5.21 (m, 1H), 5.96-6.25 (m, 1H), 6.53 (d, J = 4.5 Hz, 1H), 8.03 (s, 1H), 8.31 (d, J = 1.8 Hz, 1H), 9.30 (d, J = 1.8 Hz, 1H) | DMSO-d$_6$ |

TABLE 41-continued

| Ex. No. | structural formula | compound name | ESI MS m/z | ¹H NMR, δ (ppm) | deuterated solvent |
|---|---|---|---|---|---|
| 301 | | 1-(2-(3,6-diazabicyclo[3.1.1]heptan-3-yl)-7-(thiazol-4-yl)-4-(trifluoromethoxy)benzo[d]oxazol-5-yl)-2,2-difluoroethan-1-ol (No. 300's enantiomer) | 463 (M + H)+ | (400 MHz): 1.58 (d, J = 8.9 Hz, 1H), 2.54-2.63 (m, 1H), 3.29 (s, 1H), 3.68 (d, J = 5.8 Hz, 2H), 3.89 (brs, 4H), 5.04-5.21 (m, 1H), 5.96-6.25 (m, 1H), 6.53 (d, J = 4.5 Hz, 1H), 8.03 (s, 1H), 8.31 (d, J = 1.8 Hz, 1H), 9.30 (d, J = 1.8 Hz, 1H) | DMSO-d₆ |
| 302 | | 1-(2-(3,8-diazabicyclo[3.2.1]octan-3-yl)-7-(thiazol-4-yl)-4-(trifluoromethoxy)benzo[d]oxazol-5-yl)-2,2-difluoroethan-1-ol (optically active) | 477 (M + H)+ | (400 MHz): 1.89 (s, 4H), 2.61 (brs, 1H), 3.38-3.54 (m, 2H), 3.70 (brs, 2H), 3.93-4.09 (m, 2H), 5.25-5.42 (m, 1H), 5.74-6.15 (m, 1H), 7.87 (d, J = 2.0 Hz, 1H), 8.08 (s, 1H), 8.93 (d, J = 2.0 Hz, 1H) | CDCl₃ |
| 303 | | 1-(2-(3,8-diazabicyclo[3.2.1]octan-3-yl)-7-(thiazol-4-yl)-4-(trifluoromethoxy)benzo[d]oxazol-5-yl)-2,2-difluoroethan-1-ol (No. 302's enantiomer) | 477 (M + H)+ | (400 MHz): 1.89 (s, 4H), 2.68 (brs, 1H), 3.38-3.55 (m, 2H), 3.70 (brs, 2H), 3.91-4.09 (m, 2H), 5.34 (ddd, J = 13.1, 6.8, 4.5 Hz, 1H), 5.71-6.17 (m, 1H), 7.87 (d, J = 2.0 Hz, 1H), 8.08 (s, 1H), 8.93 (d, J = 2.0 Hz, 1H) | CDCl₃ |
| 304 | | 1-((2-(3,6-diazabicyclo[3.1.1]heptan-3-yl)-7-(1H-pyrazol-1-yl)benzo[d]oxazol-4-yl)oxy)-1,1-difluoro-2-methylpropan-2-ol | 406 (M + H)+ | (400 MHz): 1.52 (s, 6H), 1.66 (d, J = 9.5 Hz, 1H), 2.83-2.94 (m, 1H), 3.62-3.68 (m, 2H), 3.98-4.01 (brs, 4H), 6.51 (dd, J = 2.5, 1.6 Hz, 1H), 7.22 (d, J = 8.9 Hz, 1H), 7.55 (d, J = 8.9 Hz, 1H), 7.76 (d, J = 1.6 Hz, 1H), 8.15 (d, J = 2.5 Hz, 1H) | CDCl₃ |
| 305 | | 4-((2-(3,6-diazabicyclo[3.1.1]heptan-3-yl)-7-(thiazol-2-yl)benzo[d]oxazol-4-yl)oxy)cyclohexan-1-ol | 413 (M + H)+ | (400 MHz): 1.08-1.74 (m, 6H), 1.75-1.93 (m, 2H), 2.00-2.17 (m, 1H), 2.56-2.65 (m, 1H), 3.46-4.03 (m, 7H), 4.50 (d, J = 3.7 Hz, 0.5H), 4.57-4.61 (m, 0.5H), 4.75-4.99 (m, 1H), 6.94 (d, J = 8.4 Hz, 1H), 7.70 (dd, J = 2.9, 8.7 Hz, 1H), 7.83 (dd, J = 1.1, 3.3 Hz, 1H), 7.95 (dd, J = 0.7, 3.3 Hz, 1H) | DMSO-d₆ |

TABLE 42

| Ex. No. | structural formula | compound name | ESI MS m/z | $^1$H NMR, δ (ppm) | deuterated solvent |
| --- | --- | --- | --- | --- | --- |
| 306 | | 1-((2-(3,6-diazabicyclo[3.1.1]heptan-3-yl)-7-(4-methylthiazol-2-yl)benzo[d]oxazol-4-yl)oxy)-1,1-difluoro-2-methylpropan-2-ol | 437 (M + H)$^+$ | (400 MHz): 1.51 (s, 6H), 1.63 (d, J = 9.3 Hz, 1H), 2.54 (s, 3H), 2.79-2.92 (m, 1H), 3.88-4.02 (m, 6H), 6.93-7.05 (m, 1H), 7.16-7.25 (m, 1H), 7.79-7.84 (m, 1H) | CDCl$_3$ |
| 307 | | 1-((2-(3,6-diazabicyclo[3.1.1]heptan-3-yl)-7-(thiazol-4-yl)benzo[d]oxazol-4-yl)oxy)-1,1-difluoro-2-methylpropan-2-ol | 423 (M + H)$^+$ | (400 MHz): 1.52 (s, 6H), 1.67 (d, J = 9.5 Hz, 1H), 2.83-2.92 (m, 1H), 3.94-3.98 (m, 2H), 3.98-4.02 (m, 4H), 7.23-7.25 (m, 1H), 7.83 (d, J = 2.0 Hz, 1H), 7.85 (d, J = 8.8 Hz, 1H), 8.91 (d, J = 2.0 Hz, 1H) | CDCl$_3$ |
| 308 | | 1-((2-(3,8-diazabicyclo[3.2.1]octan-3-yl)-7-(thiazol-4-yl)benzo[d]oxazol-4-yl)oxy)-1,1-difluoro-2-methylpropan-2-ol | 437 (M + H)$^+$ | (400 MHz): 1.52 (s, 6H), 1.88 (s, 4H), 3.43 (d, J = 12.1 Hz, 2H), 3.70 (s, 2H), 3.95 (d, J = 12.1 Hz, 2H), 7.22 (d, J = 8.7 Hz, 1H), 7.80 (d, J = 2.0 Hz, 1H), 7.84 (d, J = 8.8 Hz, 1H), 8.91 (d, J = 2.0 Hz, 1H) | CDCl$_3$ |
| 309 | | 1-((2-(3,6-diazabicyclo[3.1.1]heptan-3-yl)-7-(thiazol-4-yl)benzo[d]oxazol-4-yl)oxy)-1,1-difluoropropan-2-ol | 409 (M + H)$^+$ | (400 MHz): 1.36 (d, J = 6.5 Hz, 3H), 1.69 (d, J = 9.7 Hz, 1H), 2.86-2.96 (m, 1H), 3.95-4.06 (m, 7H), 7.23 (d, J = 8.6 Hz, 1H), 7.84-7.89 (m, 2H), 8.92 (d, J = 2.0 Hz, 1H) | CDCl$_3$ |

TABLE 42-continued

| Ex. No. | structural formula | compound name | ESI MS m/z | $^{1}$H NMR, δ (ppm) | deuterated solvent |
|---|---|---|---|---|---|
| 310 | | 1-((2-(3,8-diazabicyclo[3.2.1]octan-3-yl)-7-(thiazol-4-yl)benzo[d]oxazol-4-yl)oxy)-1,1-difluoropropan-2-ol | 423 (M + H)+ | (400 MHz): 1.32 (d, J = 6.6 Hz, 3H), 1.82 (s, 4H), 3.36 (d, J = 12.3 Hz, 2H), 3.58 (s, 2H), 3.90 (d, J = 12.3 Hz, 2H), 4.12 (dt, J = 8.8, 6.6 Hz, 1H), 7.13 (d, J = 8.7 Hz, 1H), 7.67 (d, J = 8.7 Hz, 1H), 7.99 (d, J = 2.0 Hz, 1H), 9.01 (d, J = 2.0 Hz, | CD$_3$OD |
| 311 | | 2-((2-(3,6-diazabicyclo[3.1.1]heptan-3-yl)-7-(thiazol-4-yl)benzo[d]oxazol-4-yl)oxy)-2,2-difluoroethan-1-ol | 395 (M + H)+ | (400 MHz): 1.77 (d, J = 9.8 Hz, 1H), 2.78-2.89 (m, 1H), 3.88-3.95 (m, 2H), 3.96-4.06 (m, 6H), 7.16 (d, J = 8.7 Hz, 1H), 7.71 (d, J = 8.7 Hz, 1H), 8.04 (d, J = 2.0 Hz, 1H), 9.02 (d, J = 2.0 Hz, 1H) | CD$_3$OD |
| 312 | | 2-((2-(3,8-diazabicyclo[3.2.1]octan-3-yl)-7-(thiazol-4-yl)benzo[d]oxazol-4-yl)oxy)-2,2-difluoroethan-1-ol | 409 (M + H)+ | (400 MHz): 1.82 (s, 4H), 3.37 (d, J = 12.4 Hz, 2H), 3.63 (s, 2H), 3.86-3.97 (m, 4H), 7.13 (d, J = 8.7 Hz, 1H), 7.68 (d, J = 8.7 Hz, 1H), 8.01 (d, J = 1.8 Hz, 1H), 9.01 (d, J = 1.8 Hz, 1H) | CD$_3$OD |
| 313 | | 3-((2-(3,6-diazabicyclo[3.1.1]heptan-3-yl)-7-(thiazol-2-yl)benzo[d]oxazol-4-yl)oxy)-4,4,4-trifluoro-2-methylbutan-2-ol | 455 (M + H)+ | (400 MHz): 1.37 (d, J = 1.2 Hz, 6H), 1.75 (d, J = 9.8 Hz, 1H), 2.73-2.85 (m, 1H), 3.83-4.07 (m, 6H), 4.58- 4.75 (m, 1H), 7.13-7.21 (m, 1H), 7.67 (d, J = 3.3 Hz, 1H), 7.72 (d, J = 8.7 Hz, 1H), 7.87 (d, J = 3.3 Hz, 1H) | CD$_3$OD |

TABLE 43

| Ex. No. | structural formula | compound name | ESI MS m/z | $^1$H NMR, δ (ppm) | deuterated solvent |
|---|---|---|---|---|---|
| 314 | | 4-((2-(3,6-diazabicyclo[3.1.1]heptan-3-yl)-7-(thiazol-2-yl)benzo[d]oxazol-4-yl)oxy)tetrahydro-2H-thiopyran 1,1-dioxide | 447 (M + H)$^+$ | (400 MHz): 1.70 (d, J = 9.2 Hz, 1H), 2.33-2.46 (m, 2H), 2.48-2.59 (m, 2H), 2.81-3.03 (m, 3H), 3.59 (td, J = 13.3, 3.5 Hz, 2H), 3.92-4.06 (m, 6H), 5.29 (tt, J = 4.4, 2.1 Hz, 1H), 6.90 (d, J = 8.7 Hz, 1H), 7.42 (d, J = 3.3 Hz, 1H), 7.82 (d, J = 8.7 Hz, 1H), 7.92 (d, J = 3.2 Hz, 1H) | CDCl$_3$ |
| 315 | | 2-((2-(3,6-diazabicyclo[3.1.1]heptan-3-yl)-7-(pyridin-2-yl)benzo[d]oxazol-4-yl)oxy)-2,2-difluoroethan-1-ol | 389 (M + H)$^+$ | (400 MHz): 1.65 (d, J = 9.5 Hz, 1H), 2.78-2.89 (m, 1H), 3.76 (t, J = 7.5 Hz, 2H), 3.91 (d, J = 6.0 Hz, 2H), 3.95 (s, 4H), 6.22 (brs, 1H), 7.20-7.25 (m, 1H), 7.25-7.30 (m, 1H), 7.77-7.84 (m, 2H), 7.95 (d, J = 7.9 Hz, 1H), 8.74 (dd, J = 4.9, 0.9 Hz, 1H) | CDCl$_3$ |
| 316 | | 1-((2-(3,8-diazabicyclo[3.2.1]octan-3-yl)-7-(1H-pyrazol-1-yl)benzo[d]oxazol-4-yl)oxy)-1,1-difluoro-2-methylpropan-2-ol | 420 (M + H)$^+$ | (400 MHz): 1.53 (s, 6H), 1.87 (s, 4H), 3.41 (dd, J = 12.1, 2.0 Hz, 2H), 3.67 (brs, 2H), 3.91 (brd, J = 12.1 Hz, 2H), 6.50-6.56 (m, 1H), 7.21 (d, J = 8.9 Hz, 1H), 7.51-7.58 (m, 1H), 7.77 (d, J = 1.5 Hz, 1H), 8.13 (d, J = 2.5 Hz, 1H) | CDCl$_3$ |
| 317 | | 1-((2-(3,8-diazabicyclo[3.2.1]octan-3-yl)-7-(pyridin-2-yl)benzo[d]oxazol-4-yl)oxy)-1,1-difluoro-2-methylpropan-2-ol | 431 (M + H)$^+$ | (400 MHz): 1.53 (s, 6H), 1.83-1.94 (m, 4H), 3.41 (dd, J = 12.1, 2.0 Hz, 2H), 3.67 (brs, 2H), 3.93 (dd, J = 12.0, 2.1 Hz, 2H), 7.24-7.29 (m, 2H), 7.77-7.85 (m, 2H), 7.94 (dt, J = 7.95, 0.98 Hz, 1H), 8.71-8.78 (m, 1H) | CDCl$_3$ |

TABLE 43-continued

| Ex. No. | structural formula | compound name | ESI MS m/z | $^1$H NMR, δ (ppm) | deuterated solvent |
|---|---|---|---|---|---|
| 318 | | 1-((2-(3,8-diazabicyclo[3.2.1]octan-3-yl)-7-(4-methylthiazol-2-yl)benzo[d]oxazol-4-yl)oxy)-1,1-difluoro-2-methylpropan-2-ol | 451 (M + H)⁺ | (400 MHz): 1.52 (s, 6H), 1.88 (s, 4H), 2.56 (s, 3H), 3.44 (brd, J = 12.1 Hz, 2H), 3.69 (brs, 2H), 3.98 (brd, J = 10.8 Hz, 2H), 7.00 (s, 1H), 7.22 (d, J = 8.7 Hz, 1H), 7.80 (d, J = 8.7 Hz, 1H) | CDCl₃ |
| 319 | | 2-((2-(3,6-diazabicyclo[3.1.1]heptan-3-yl)-7-(5-fluoropyridin-2-yl)benzo[d]oxazol-4-yl)oxy)-2,2-difluoroethan-1-ol | 407 (M + H)⁺ | (400 MHz): 1.67 (d, J = 8.8 Hz, 1H), 2.84-2.91 (m, 1H), 3.79 (t, J = 7.2 Hz, 2H), 3.96 (s, 6H), 7.20-7.28 (m, 1H), 7.49-7.55 (m, 1H), 7.77 (d, J = 8.8 Hz, 1H), 7.96 (dd, J = 3.6, 8.4 Hz, 1H), 8.59 (brs, 1H) | CDCl₃ |
| 320 | | 2-((2-(3,6-diazabicyclo[3.1.1]heptan-3-yl)-7-(1H-pyrazol-1-yl)benzo[d]oxazol-4-yl)oxy)-2,2-difluoroethan-1-ol | 378 (M + H)⁺ | (400 MHz): 1.66 (d, J = 9.5 Hz, 1H), 2.84-2.92 (m, 1H), 3.49 (s, 1H), 3.78 (t, J = 7.5 Hz, 2H), 3.92 (d, J = 6.0 Hz, 2H), 3.96 (s, 4H), 6.54 (t, J = 2.1 Hz, 1H), 7.22 (d, J = 9.0 Hz, 1H), 7.59 (d, J = 8.8 Hz, 1H), 7.78 (d, J = 1.5 Hz, 1H), 8.16 (d, J = 2.4 Hz, 1H) | CDCl₃ |
| 321 | | 1-((2-(3,8-diazabicyclo[3.2.1]octan-3-yl)-7-(oxazol-2-yl)benzo[d]oxazol-4-yl)oxy)-1,1-difluoro-2-methylpropan-2-ol | 421 (M + H)⁺ | (400 MHz): 1.52 (s, 6H), 1.83-1.92 (m, 4H), 3.42 (dd, J = 12.2, 1.9 Hz, 2H), 3.67 (brs, 2H), 4.00 (dd, J = 12.2, 2.1 Hz, 2H), 7.20-7.25 (m, 1H), 7.32 (d, J = 0.7 Hz, 1H), 7.67 (d, J = 8.7 Hz, 1H), 7.78 (d, J = 0.7 Hz, 1H) | CDCl₃ |

TABLE 44

| Ex. No. | structural formula | compound name | ESI MS m/z | ¹H NMR, δ (ppm) | deuterated solvent |
|---|---|---|---|---|---|
| 322 | | 1-((2-(3,8-diazabicyclo[3.2.1]octan-3-yl)-7-(2H-1,2,3-triazol-2-yl)benzo[d]oxazol-4-yl)oxy)-1,1-difluoro-2-methylpropan-2-ol | 421 (M + H)⁺ | (400 MHz): 1.53 (s, 6H), 1.82-1.91 (m, 4H), 3.41 (dd, J = 12.2, 2.0 Hz, 2H), 3.66 (brs, 2H), 3.97 (dd, J = 12.2, 2.3 Hz, 2H), 7.21-7.26 (m, 1H), 7.62 (d, J = 9.1 Hz, 1H), 7.89 (s, 2H) | CDCl₃ |
| 323 | | 2-(3,6-diazabicyclo[3.1.1]heptan-3-yl)-4-(((S)-tetrahydrofuran-3-yl)oxy)-7-(thiazol-2-yl)benzo[d]oxazole | 385 (M + H)⁺ | (400 MHz): 1.68 (d, J = 9.17 Hz, 1H), 2.25-2.35 (m, 2H), 2.81-2.92 (m, 1H), 3.90-4.13 (m, 10H), 5.44-5.53 (m, 1H), 6.81 (d, J = 8.80 Hz, 1H), 7.40 (d, J = 3.30 Hz, 1H), 7.82 (d, J = 8.68 Hz, 1H), 7.91 (d, J = 3.18 Hz, 1H) | CDCl₃ |
| 324 | | 2-(3,6-diazabicyclo[3.1.1]heptan-3-yl)-4-(((R)-tetrahydrofuran-3-yl)oxy)-7-(thiazol-2-yl)benzo[d]oxazole | 385 (M + H)⁺ | (400 MHz): 1.68 (d, J = 9.2 Hz, 1H), 2.24-2.34 (m, 2H), 2.81-2.91 (m, 1H), 3.88-4.15 (m, 10H), 5.45-5.53 (m, 1H), 6.81 (d, J = 8.7 Hz, 1H), 7.40 (d, J = 3.3 Hz, 1H), 7.82 (d, J = 8.7 Hz, 1H), 7.91 (d, J = 3.2 Hz, 1H) | CDCl₃ |
| 325 | | 2-(3,6-diazabicyclo[3.1.1]heptan-3-yl)-4-(oxetan-3-yloxy)-7-(thiazol-2-yl)benzo[d]oxazole | 371 (M + H)⁺ | (400 MHz): 1.69 (d, J = 9.17 Hz, 1H), 2.83-2.92 (m, 1H), 3.91-4.09 (m, 6H), 4.89-4.96 (m, 2H), 5.01-5.08 (m, 2H), 5.58 (quin, J = 5.7 Hz, 1H), 6.55 (d, J = 8.7 Hz, 1H), 7.41 (d, J = 3.3 Hz, 1H), 7.80 (d, J = 8.7 Hz, 1H), 7.92 (d, J = 3.3 Hz, 1H) | CDCl₃ |

TABLE 44-continued

| Ex. No. | structural formula | compound name | ESI MS m/z | $^1$H NMR, δ (ppm) | deuterated solvent |
|---|---|---|---|---|---|
| 326 | | 3-((2-(3,6-diazabicyclo[3.1.1]heptan-3-yl)-7-(thiazol-2-yl)benzo[d]oxazol-4-yl)oxy)-3,3-difluoro-2-methylpropane-1,2-diol | 439 (M + H)$^+$ | (400 MHz): 1.38 (s, 3H), 1.61 (d, J = 8.8 Hz, 1H), 2.54-2.61 (m, 1H), 3.57-3.73 (m, 4H), 3.79-3.94 (m, 4H), 4.97 (t, J = 6.6 Hz, 1H), 5.51 (s, 1H). 7.22 d, J = 8.7 Hz, 1H), 7.78 (d, J = 8.7 Hz, 1H), 7.95 (d, J = 3.3 Hz, 1H), 8.04 (d, J = 3.3 Hz, 1H) | DMSO-d$_6$ |
| 327 | | 1-((2-(3,8-diazabicyclo[3.2.1]octan-3-yl)-7-(1,2,4-thiadiazol-5-yl)benzo[d]oxazol-4-yl)oxy)-1,1-difluoro-2-methylpropan-2-ol | 438 (M + H)$^+$ | (400 MHz): 1.53 (s, 6H), 1.90 (brs, 4H), 3.43-3.55 (m, 2H), 3.71 (brs, 2H), 3.98 (dd, J = 12.1, 2.1 Hz, 2H), 7.29-7.36 (m, 1H), 7.88 (d, J = 8.8 Hz, 1H), 8.77 (s, 1H) | CDCl$_3$ |
| 328 | | 1-((2-(3,8-diazabicyclo[3.2.1]octan-3-yl)-7-(1-methyl-1H-pyrazol-3-yl)benzo[d]oxazol-4-yl)oxy)-1,1-difluoro-2-methylpropan-2-ol | 434 (M + H)$^+$ | (400 MHz): 1.52 (s, 6H), 1.82-1.92 (m, 4H), 3.39 (brd, J = 10.8 Hz, 2H), 3.65 (brs, 2H), 3.89-3.97 (m, 2H), 4.00 (s, 3H), 4.12 (brs, 1H), 6.73 (d, J = 2.2 Hz, 1H), 7.16 (d, J = 8.7 Hz, 1H), 7.44 (d, J = 2.2 Hz, 1H), 7.57 (d, J = 8.6 Hz, 1H) | CDCl$_3$ |
| 329 | | 1-((2-(3,6-diazabicyclo[3.1.1]heptan-3-yl)-7-(5-fluoropyridin-2-yl)benzo[d]oxazol-4-yl)oxy)-1,1-difluoro-2-methylpropan-2-ol | 435 (M + H)$^+$ | (400 MHz): 1.52 (s, 6H), 1.64 (d, J = 9.3 Hz, 1H), 2.80-2.88 (m, 1H), 3.85-3.97 (m, 6H), 7.30 (d, J = 8.8 Hz, 1H), 7.50 (td, J = 8.3, 2.9 Hz, 1H), 7.77 (t, J = 4.4 Hz, 1H), 7.95 (q, J = 4.4 Hz, 1H), 8.58 (d, J = 2.9 Hz, 1H) | CDCl$_3$ |

TABLE 45

| Ex. No. | structural formula | compound name | ESI MS m/z | $^1$H NMR, δ (ppm) | deuterated solvent |
|---|---|---|---|---|---|
| 330 | 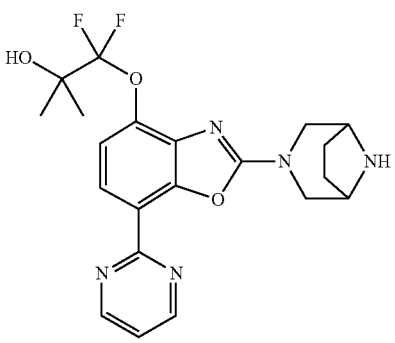 [SMILES: CC(C)(O)C(F)(F)Oc1ccc(-c2ncccn2)c2oc(N3CC4CCC(C3)N4)nc12] | 1-((2-(3,8-diazabicyclo[3.2.1]octan-3-yl)-7-(pyrimidin-2-yl)benzo[d]oxazol-4-yl)oxy)-1,1-difluoro-2-methylpropan-2-ol | 432 (M + H)$^+$ | (400 MHz): 1.53 (s, 6H), 1.81-1.94 (m, 4H), 3.40 (dd, J = 12.1, 1.7 Hz, 2H), 3.66 (brs, 2H), 3.99 (dd, J = 12.0, 2.0 Hz, 2H), 4.18 (brs, 1H), 7.21-7.25 (m, 2H), 7.97 (d, J = 8.68 Hz, 1H), 8.87 (d, J = 4.89 Hz, 2H) | CDCl$_3$ |
| 331 | 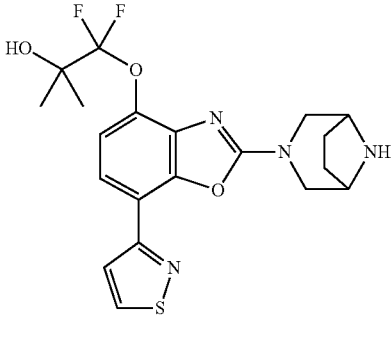 [SMILES: CC(C)(O)C(F)(F)Oc1ccc(-c2ccsn2)c2oc(N3CC4CCC(C3)N4)nc12] | 1-((2-(3,8-diazabicyclo[3.2.1]octan-3-yl)-7-(isothiazol-3-yl)benzo[d]oxazol-4-yl)oxy)-1,1-difluoro-2-methylpropan-2-ol | 437 (M + H)$^+$ | (400 MHz): 1.53 (s, 6H), 1.88 (s, 4H), 3.42 (dd, J = 12.0, 1.7 Hz, 2H), 3.68 (brs, 2H), 3.95 (dd, J = 12.0, 2.1 Hz, 2H), 7.24 (d, J = 8.6 Hz, 2H), 7.77 (d, J = 8.7 Hz, 1H), 7.82 (d, J = 4.8 Hz, 1H), 8.79 (d, J = 4.7 Hz, 1H) | CDCl$_3$ |
| 332 | 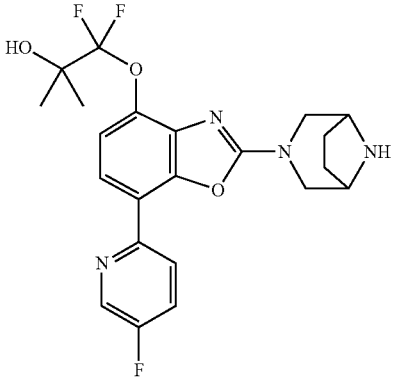 [SMILES: CC(C)(O)C(F)(F)Oc1ccc(-c2ccc(F)cn2)c2oc(N3CC4CCC(C3)N4)nc12] | 1-(2-(3,8-diazabicyclo[3.2.1]octan-3-yl)-7-(5-fluoropyridin-2-yl)benzo[d]oxazol-4-yl)oxy)-1,1-difluoro-2-methylpropan-2-ol | 449 (M + H)$^+$ | (400 MHz): 1.53 (s, 6H), 1.88 (d, J = 1.83 Hz, 4H), 3.41 (dd, J = 12.0, 2.2 Hz, 2H), 3.67 (brs, 2H), 3.92 (dd, J = 11.9, 2.1 Hz, 2H), 4.04 (brs, 1H), 7.23-7.30 (m, 1H), 7.53 (ddd, J = 8.8, 7.9, 2.9 Hz, 1H), 7.76 (d, J = 8.7 Hz, 1H), 7.95 (dd, J = 8.7, 4.3 Hz, 1H), 8.60 (d, J = 2.8 Hz, 1H) | CDCl$_3$ |
| 333 | 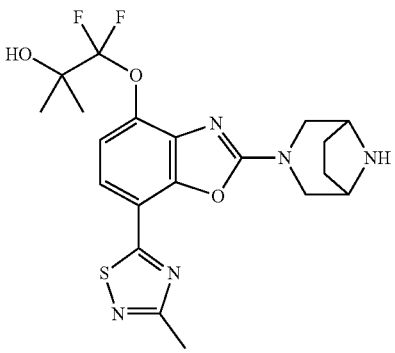 [SMILES: Cc1nsc(-c2ccc(OC(F)(F)C(C)(C)O)c3nc(N4CC5CCC(C4)N5)oc23)n1] | 1-((2-(3,8-diazabicyclo[3.2.1]octan-3-yl)-7-(3-methyl-1,2,4-thiadiazol-5-yl)benzo[d]oxazol-4-yl)oxy)-1,1-difluoro-2-methylpropan-2-ol | 452 (M + H)$^+$ | (400 MHz): 1.54 (s, 6H), 1.89 (s, 4H), 2.77 (s, 3H), 3.46 (dd, J = 12.3, 1.8 Hz, 2H), 3.55 (brs, 1H), 3.70 (brs, 2H), 3.98 (dd, J = 12.1, 2.1 Hz, 2H), 7.23-7.28 (m, 1H), 7.84 (d, J = 8.80 Hz, 1H) | CDCl$_3$ |

TABLE 45-continued

| Ex. No. | structural formula | compound name | ESI MS m/z | ¹H NMR, δ (ppm) | deuterated solvent |
|---|---|---|---|---|---|
| 334 | | 2-(3,6-diazabicyclo[3.1.1]heptan-3-yl)-7-(thiazol-2-yl)-4-((trifluoromethyl)sulfonyl)benzo[d]oxazole | 431 (M + H)⁺ | (400 MHz): 1.69 (d, J = 9.4 Hz, 1H), 2.87-2.93 (m, 1H), 3.92-3.97 (m, 2H), 4.04-4.14 (m, 4H), 7.64 (d, J = 3.3 Hz, 1H), 7.87 (d, J = 8.7 Hz, 1H), 8.03 (d, J = 8.7 Hz, 1H), 8.08 (d, J = 3.3 Hz, 1H) | CDCl₃ |
| 335 | | 2-(3,6-diazabicyclo[3.1.1]heptan-3-yl)-7-(thiazol-2-yl)benzo[d]oxazole-4-carbonitrile | 324 (M + H)⁺ | (400 MHz): 1.69 (d, J = 9.3 Hz, 1H), 2.86-2.93 (m, 1H), 3.92-3.97 (m, 2H), 4.00-4.10 (m, 4H), 7.52 (d, J = 8.4 Hz, 1H), 7.57 (d, J = 3.3 Hz, 1H), 7.89 (d, J = 8.4 Hz, 1H), 8.03 (d, J = 3.3 Hz, 1H) | CDCl₃ |
| 336 | | 2-(3,6-diazabicyclo[3.1.1]heptan-3-yl)-7-(thiazol-2-yl)-4-((5-(trifluoromethyl)pyridin-2-yl)oxy)benzo[d]oxazole | 460 (M + H)⁺ | (400 MHz): 1.65 (d, J = 9.3 Hz, 1H), 2.78-2.91 (m, 1H), 3.86-4.06 (m, 6H), 7.13 (d, J = 8.6 Hz, 1H), 7.20 (d, J = 8.7 Hz, 1H), 7.47 (d, J = 3.3 Hz, 1H), 7.89-8.01 (m, 3H), 8.43-8.45 (m, 1H) | CDCl₃ |
| 337 | | 2-(3,6-diazabicyclo[3.1.1]heptan-3-yl)-4-(pyridin-2-yloxy)-7-(thiazol-2-yl)benzo[d]oxazole | 3921 (M + H)⁺ | (400 MHz): 1.65 (d, J = 9.4 Hz, 1H), 2.79-2.88 (m, 1H), 3.89 (d, J = 6.1 Hz, 2H), 3.92-4.06 (m, 4H), 7.00-7.05 (m, 1H), 7.07-7.05 (m, 2H), 7.45 (d, J = 3.2 Hz, 1 H), 7.71-7.76 (m, 1H), 7.90 (d, J = 8.7 Hz, 1H), 7.95 (d, J = 3.3 Hz, 1H), 8.17-8.24 (m, 1H) | CDCl₃ |

TABLE 46

| Ex. No. | structural formula | compound name | ESI MS m/z | ¹H NMR, δ (ppm) | deuterated solvent |
|---|---|---|---|---|---|
| 338 | | 2-(3,6-diazabicyclo[3.1.1]heptan-3-yl)-4-(pyrimidin-2-yloxy)-7-(thiazol-2-yl)benzo[d]oxazole | 393 (M + H)⁺ | (400 MHz): 1.64 (d, J = 9.2 Hz, 2H), 2.77-2.89 (m, 1H), 3.84-4.05 (m, 6H), 7.07 (t, J = 4.8 Hz, 1H), 7.17 (d, J = 8.6 Hz, 1H), 7.46 (d, J = 3.3 Hz, 1H), 7.93 (d, J = 8.7 Hz, 1H), 7.96 (d, J = 3.3 Hz, 1H), 8.59 (d, J = 4.8 Hz, 2H) | CDCl₃ |
| 339 | | 2-(3,6-diazabicyolo[3.1.1]heptan-3-yl)-4-(pyrazin-2-yloxy)-7-(thiazol-2-yl)benzo[d]oxazole | 393 (M + H)⁺ | (400 MHz): 1.64 (d, J = 9.2 Hz, 1H), 2.77-2.89 (m, 1H), 3.83-4.05 (m, 6H), 7.13 (d, J = 8.7 Hz, 1H), 7.46 (d, J = 3.3 Hz, 1H), 7.92 (d, J = 8.7 Hz, 1H), 7.96 (d, J = 3.2 Hz, 1H), 8.11 (dd, J = 2.6, 1.4 Hz, 1H), 8.29 (d, J = 2.7 Hz, 1H), 8.58 (d, J = 1.2 Hz, 1H) | CDCl₃ |
| 340 | | 2-(3,6-diazabicyolo[3.1.1]heptan-3-yl)-4-((6-methyl-4-(trifluoromethyl)pyridazin-3-yl)oxy)-7-(thiazol-2-yl)benzo[d]oxazole | 475 (M + H)⁺ | (400 MHz): 1.63 (d, J = 9.3 Hz, 2H), 2.75 (s, 3H), 2.77-2.86 (m, 1H), 3.82-4.00 (m, 6H), 7.18 (d, J = 8.7 Hz, 1H), 7.47 (d, J = 3.3 Hz, 1H), 7.60 (s, 1H), 7.92 (d, J = 8.7 Hz, 1H), 7.96 (d, J = 3.3 Hz, 1H) | CDCl₃ |
| 341 | | (6-((2-(3,6-diazabicyolo[3.1.1]heptan-3-yl)-7-(thiazol-2-yl)benzo[d]oxazol-4-yl)oxy)pyridin-3-yl)methanol | 422 (M + H)⁺ | (400 MHz): 1.65 (d, J = 9.2 Hz, 2H), 2.77-2.90 (m, 1H), 3.89 (d, J = 6.1 Hz, 2H), 3.92-4.07 (m, 4H), 4.69 (s, 2H), 7.08 (d, J = 8.7 Hz, 1H), 7.12 (d, J = 8.6 Hz, 1H), 7.45 (d, J = 3.3 Hz, 1H), 7.79 (dd, J = 8.4, 2.5 Hz, 1H), 7.89 (d, J = 8.7 Hz, 1H), 7.95 (d, J = 3.2 Hz, 1H), 8.14-8.20 (m, 1H) | CDCl₃ |

TABLE 46-continued

| Ex. No. | structural formula | compound name | ESI MS m/z | ¹H NMR, δ (ppm) | deuterated solvent |
|---|---|---|---|---|---|
| 342 | | (6-((2-(3,6-diazabicyclo[3.1.1]heptan-3-yl)-7-(thiazol-2-yl)benzo[d]oxazol-4-yl)oxy)-5-(trifluoromethyl)pyridin-3-yl)methanol | 490 (M + H)⁺ | (400 MHz): 1.64 (d, J = 9.2 Hz, 2H), 2.78-2.88 (m, 1H), 3.83-4.03 (m, 6H), 4.74 (s, 2H), 7.09 (d, J = 8.7 Hz, 1H), 7.46 (d, J = 3.3 Hz, 1H), 7.91 (d, J = 8.6 Hz, 1H), 7.96 (d, J = 3.2 Hz, 1H), 8.08 (d, J = 1.8 Hz, 1H), 8.23-8.26 (m, 1H) | CDCl₃ |
| 343 | | 2-(3,6-diazabicyclo[3.1.l]heptan-3-yl)-7-(thiazol-2-yl)-4-((5-(trifluoromethoxy)pyridin-2-yl)oxy)benzo[d]oxazole | 476 (M + H)⁺ | (400 MHz): 1.65 (d, J = 9.3 Hz, 1H), 2.78-2.89 (m, 1H), 3.90 (d, J = 6.1 Hz, 2H), 3.92-4.06 (m, 4H), 7.11 (d, J = 8.7 Hz, 1H), 7.15 (d, J = 8.9 Hz, 1H), 7.46 (d, J = 3.3 Hz, 1H), 7.59-7.66 (m, 1H), 7.91 (d, J = 8.7 Hz, 1H), 7.96 (d, J = 3.3 Hz, 1H), 8.10 (d, J = 2.9 Hz, 1H) | CDCl₃ |

TABLE 47

| Ex. No. | structural formula | compound name | ESI MS m/z | ¹H NMR, δ (ppm) | deuterated solvent |
|---|---|---|---|---|---|
| 344 | | (3,6-diazabicycolo[3.1.1]heptan-3-yl)-4-cyclopropyl-7-(thiazol-2-yl)benzo[d]oxazole | 339 (M + H)+ | (400 MHz): 1.00-1.09 (m, 4H), 1.81 (d, J = 9.5 Hz, 1H), 2.28-2.36 (m, 1H), 2.73-280 (m, 1H), 3.98-4.06 (m, 4H), 4.08-4.13 (m, 2H), 6.91 (d, J = 8.3 Hz, 1H), 7.70 (d, J = 8.3 Hz, 1H), 7.90 (d, J = 3.3 Hz, 1H), 8.00 (d, J = 33 Hz, 1H) | DMSO-d₆ |
| 345 | | (3,6-diazabicycolo[3.1.1]heptan-3-yl)-4-(methylthio)-7-(thiazol-2-yl)benzo[d]oxazole | 345 (M + H)+ | (400 MHz): 1.07 (d, J = 9.2 Hz, 1H), 2.64 (s, 3H), 2.81-2.88 (m, 1H), 3.89-3.94 (m, 2H), 3.97-4.08 (m, 4H), 7.14 (d, J = 8.4 Hz, 1H), 7.43 (d, J = 3.3 Hz, 1H), 7.84 (d, J = 8.4 Hz, 1H), 7.93 (d, J = 3.3 Hz, 1H) | CDCl₃ |

TABLE 47-continued

| Ex. No. | structural formula | compound name | ESI MS m/z | ¹H NMR, δ (ppm) | deuterated solvent |
|---|---|---|---|---|---|
| 346 | | (3,6-diazabicyclo[3.1.1]heptan-3-yl)-4-(methylsulfinyl)-7-(thiazol-2-yl)benzo[d]oxazole | 361 (M + H)+ | (400 MHz): 1.69 (d, J = 9.3 Hz, 1H), 2.85-2.92 (m, 1H), 2.99 (s, 3H), 3.91-4.06 (m, 8H), 7.52 (d, J = 3.2 Hz, 1H), 7.77 (d, J = 8.3 Hz, 1H), 8.00 9d, J = 3.2 Hz, 1H), 8.03 (d, J = 8.3 Hz, 1H) | CDCl$_3$ |
| 347 | | (3,6-diazabicyclo[3.1.1]heptan-3-yl)-4-(methylsulfonyl)-7-(thiazol-2-yl)benzo[d]oxazole | 377 (M + H)+ | (400 MHz): 1.69 (d, J = 9.4 Hz, 1H), 2.86-2.93 (m, 1H), 3.42 (s, 3H), 3.92-3.97 (m, 2H), 4.01-4.12 (m, 4H), 7.58 (d, J = 3.2 Hz, 1H), 7.87 (d, J = 8.4 Hz, 1H), 7.96 (d, J = 8.4 Hz, 1H), 8.03 (d, J = 8.2 Hz, 1H) | CDCl$_3$ |
| 348 | | 2-((2-(3,6-diazabicyclo[3.1.1]heptan-3-yl)-7-(thiazol-2-yl)benzo[d]oxazol-4-yl)thio)ethan-1-ol | 375 (M + H)+ | (400 MHz): 1.68 (d, J = 9.3 Hz, 1H), 2.83-2.90 (m, 1H), 3.14-3.18 (m, 2H), 3.70-3.74 (m, 2H), 3.91-3.95 (m, 2H), 3.97-4.07 (m, 4H), 7.42 (d, J = 8.3 Hz, 1H), 7.48 (d, J = 3.3 HZ, 1H), 7.81 (d, J = 8.3 Hz, 1H), 7.97 (d, J = 3.3 Hz, 1H) | CDCl$_3$ |
| 349 | | 2-((2-(3,6-diazabicyclo[3.1.1]heptan-3-yl)-7-(thiazol-2-yl)benzo[d]oxazol-4-yl)sulfinyl)ethan-1-ol | 391 (M + H)+ | (400 MHz): 1.68 (d, J = 9.3 Hz, 1H), 2.85-2.92 (m, 1H), 3.42-3.46 (m, 2H), 3.91-4.03 (m, 7H), 4.07-4.15 (m, 1H), 7.54 (d, J = 3.2 Hz, 1H), 7.82 (d, J = 8.3 Hz, 1H), 8.01 (d, J = 3.2 Hz, 1H), 8.09 (d, J = 8.3 Hz, 1H) | CDCl$_3$ |
| 350 | | 2-((2-(3,6-diazabicyclo[3.1.1]heptan-3-yl)-7-(thiazol-2-yl)benzo[d]oxazol-4-yl)sulfonyl)ethan-1-ol | 407 (M + H)+ | (400 MHz): 1.63 (d, J = 9.1 Hz, 1H), 2.57-2.64 (m, 1H), 3.68-3.81 (m, 6H), 3.84-4.05 (m, 4H), 4.85 (t, J = 5.4 Hz, 1H), 7.70 (d, J = 8.4 Hz, 1H), 7.91 (d, J = 8.4 Hz, 1H), 8.10 (d, J = 3.2 Hz, 1H), 8.14 (d, J = 3.2 Hz, 1H) | DMSO-d$_6$ |

TABLE 47-continued

| Ex. No. | structural formula | compound name | ESI MS m/z | ¹H NMR, δ (ppm) | deuterated solvent |
|---|---|---|---|---|---|
| 351 | | 2-(3,6-diazabicyclo[3.1.1]heptan-3-yl)-4-((1,1-difluoroallyl)oxy)-7-(thiazol-2-yl)benzo[d]oxazole | 391 (M + H)+ | (400 MHz): 1.67 (d, J = 9.2 Hz, 1H), 2.82-2.89 (m, 1H), 3.90-3.94 (m, 2H), 3.97-4.07 (m, 4H), 5.60-5.64 (m, 1H), 5.96-6.03 (m, 1H), 6.13-6.25 (m, 1H), 7.23-7.27 (m, 1H), 7.45 (d, J = 3.3 Hz, 1H), 7.83 (d, J = 8.8 Hz, 1H), 7.95 (d, J = 3.3 Hz, 1H) | CDCl₃ |

TABLE 48

| Ex. No. | structural formula | compound name | ESI MS m/z | ¹H NMR, δ (ppm) | deuterated solvent |
|---|---|---|---|---|---|
| 352 | | 2-(3,6-diazabicyclo[3.1.1]heptan-3-yl)-4-((5-(methylsulfonyl)pyridin-2-yl)oxy)-7-(thiazol-2-yl)benzo[d]oxaole | 470 (M + H)+ | (400 MHz): 1.65 (d, J = 9.3 Hz, 1H), 2.80-2.88 (m, 1H), 3.10 (s, 3H), 3.86-4.03 (m, 6H), 5.15-5.17 (m, 1H), 7.13 (d, J = 8.7 Hz, 1H), 7.4 (dd, J = 8.7, 0.5 Hz, 1H), 7.48 (d, J = 3.2 Hz, 1H), 7.94 (d, J = 807 Hz, 1H), 7.97 (d, J = 3.3 Hz, 1H), 8.22 (dd, J = 8.8, 2.6 Hz, 1H), 8.70 (d, J = 2.0 Hz, 1H) | CDCl₃ |
| 353 | | 2-(3,6-diazabicyclo[3.1.1]heptan-3-yl)-N-(2-methoxyethyl)-7-(thiazol-2-yl)benzo[d]oxazole-4-carboxamide | 400 (M + H)+ | (400 MHz): 1.71 (d, J = 9.4 Hz, 1H), 2.85-2.98 (m, 1H), 3.44 (s, 3H), 3.61-3.69 (m, 2H), 3.76 (q, J = 5.3 Hz, 2H), 3.96 (brd, J = 6.0 Hz, 2H), 3.99-4.17 (m, 4H), 7.52 (d, J = 3.3 Hz, 1H), 7.93 (d, J = 8.4 Hz, 1H), 8.01 (d, J = 3.2 Hz, 1H), 8.11 (d, J = 8.3 Hz, 1H), 9.40 (t, J = 5.1 Hz, 1H) | CDCl₃ |
| 354 | | 2-(3,6-diazabicyclo[3.1.1]heptan-3-yl)-7-(thiazol-2-yl)benzo[d]oxazole-4-carboxamide | 342 (M + H)+ | (400 MHz): 1.71 (d, J = 9.3 Hz, 1H), 2.85-2.99 (m, 1H), 3.91-4.16 (m, 8H), 5.81 (brs, 1H), 7.54 (d, J = 3.2 Hz, 1H), 7.95 (d, J = 8.4 Hz, 1H), 8.02 (d, J = 3.3 Hz, 1H), 8.11 (d, J = 8.4 Hz, 1H), 8.90 (brs, 1H) | CDCl₃ |

TABLE 48-continued

| Ex. No. | structural formula | compound name | ESI MS m/z | ¹H NMR, δ (ppm) | deuterated solvent |
|---|---|---|---|---|---|
| 355 | | 2-(3,6-diazabicyclo[3.1.1]heptan-3-yl)-N-(2-hydroxyethyl)-7-(thiazol-2-yl)benzo[d]oxazole-4-carboxamide | 386 (M + H)+ | (400 MHz): 1.71 (d, J = 9.3 Hz, 1H), 2.86-2.96 (m, 1H), 3.15 (brs, 1H), 3.70-3.78 (m, 2H), 2.87-3.92 (m, 2H), 3.96 (brd, J = 6.0 Hz, 2H), 3.99-4.17 (m, 4H), 7.53 (d, J = 3.3 Hz, 1H), 7.94 (d, J = 8.4 Hz, 1H), 8.01 (d, J = 3.2 Hz, 1H), 8.10 (d, J = 8.4 Hz, 1H), 9.39 (brt, J = 5.4 Hz, 1H) | CDCl₃ |
| 356 | | 2-(3,6-diazabicyclo[3.1.1]heptan-3-yl)-N-(2-hydroxyethyl)-N-methyl-7-(thiazol-2-yl)benzo[d]oxazole-4-carboxamide | 400 (M + H)+ | (400 MHz): 1.69 (d, J = 9.3 Hz, 1H), 2.82-2.93 (m, 1H), 3.06 (brs, 1H), 3.20 (s, 1.65H), 3.50 (brd, 1H), 3.81 (brs, 2H), 3.91-4.07 (m, 7H), 7.72 (brs, 0.45H), 5.84 (brs, 0.55H), 7.48 (brd, J = 8.3 Hz, 1H), 7.52 (d, J = 3.3 Hz, 1H), 7.95 (brd, J = 7.2 Hz, 1H), 8.00 (d, J = 3.3 Hz, 1H) | CDCl₃ |
| 357 | | 2-(3,6-diazabicyclo[3.1.1]heptan-3-yl)-N-cyclopropyl-7-(thiazol-2-yl)benzo[d]oxazole-4-carboxamide | 382 (M + H)+ | (400 MHz): 0.63-0.72 (m, 2H), 0.87-0.98 (m, 2H), 1.71 (d, J = 9.4 Hz, 1H), 2.86-2.96 (m, 1H), 3.04 (tq, J = 7.3, 3.7 Hz, 1H), 3.92-4.14 (m, 6H), 7.52 (d, J = 3.3 Hz, 1H), 7.93 (d, J = 8.4 Hz, 1H), 8.01 (d, J = 3.3 Hz, 1H), 8.13 (d, J = 8.4 Hz, 1H), 9.14 (brs, 1H) | CDCl₃ |
| 358 | | 2-(3,6-diazabicyclo[3.1.1]heptan-3-yl)-N-ethyl-7-(thiazol-2-yl)benzo[d]oxazole-4-carboxamide | 370 (M + H)+ | (400 MHz): 1.32 (t, J = 7.3 Hz, 3H), 1.72 (d, J = 9.3 Hz, 1H), 2.88-3.00 (m, 1H), 3.59 (qd, J = 7.3, 5.5 Hz, 2H), 3.97-4.13 (m, 6H), 7.52 (d, J = 3.3 Hz, 1H), 7.92 (d, J = 8.4 Hz, 1H), 8.00 (d, J = 3.3 Hz, 1H), 8.11 (d, J = 8.3 Hz, 1H), 9.01 (brs, 1H) | CDCl₃ |

TABLE 49

| Ex. No. | structural formula | compound name | ESI MS m/z | ¹H NMR, δ (ppm) | deuterated solvent |
|---|---|---|---|---|---|
| 359 | | 2-(3,6-diazabicyclo[3.1.1]heptan-3-yl)-7-(thiazol-2-yl)benzo[d]oxazol-4-yl)(morpholino)methanone | 412 (M + H)+ | (400 MHz): 1.69 (t, J = 9.3 Hz, 1H), 2.83-2.95 (m, 1H), 3.46 (brs, 2H), 3.70-4.13 (m, 12H), 7.43 (d, J = 8.2 Hz, 1H), 7.46-7.51 (d, J = 3.3 Hz, 1H), 7.91 (d, J = 8.2 Hz, 1H), 7.99 (d, J = 3.2 Hz, 1H) | CDCl₃ |
| 360 | | 2-(3,6-diazabicyclo[3.1.1]heptan-3-yl)-7-(thiazol-2-yl)benzo[d]oxazol-yl)pyrrolidin-1-yl)methanone | 396 (M + H)+ | (400 MHz): 1.69 (t, J = 9.2 Hz, 1H), 1.85-2.05 (m, 4H), 2.81-2.93 (m, 1H), 3.51 (t, J = 6.7 Hz, 2H), 3.75 (t, J = 7.0 Hz, 2H), 3.88-4.09 (m, 6H), 7.44 (d, J = 8.2 Hz, 1H), 7.50 (d, J = 3.2 Hz, 1H), 7.89 (d, J = 8.2 Hz, 1H), 7.99 (d, J = 3.2 Hz, 1H) | CDCl₃ |
| 361 | | N-benzyl-2-(3,6-diazabicyclo[3.1.1]heptan-3-yl)-7-(thiazol-2-yl)benzo[d]oxazole-4-carboxamide | 432 (M + H)+ | (400 MHz): 1.68 (d, J = 9.3 Hz, 1H), 2.82-2.94 (m, 1H), 3.85-4.11 (m, 6H), 4.79 (d, J = 5.5 Hz, 2H), 7.29-7.41 (m, 3H), 7.43-7.48 (m, 2H), 7.52 (d, J = 3.3 Hz, 1H), 7.95 (d, J = 8.4 Hz, 1H), 8.01 (d, J = 3.3 Hz, 1H), 8.16 (d, J = 8.4 Hz, 1H), 9.49 (brs, 1H) | CDCl₃ |
| 362 | | 1-((2-(3,6-diazabicyclo[3.1.1]heptan-3-yl)-7-(thiazol-2-yl)benzo[d]oxazol-4-yl)oxy)-1,1-difluoro-3-methylbutan-2-ol | 437 (M + H)+ | (400 MHz): 1.06 (d, J = 6.9 Hz, 3H), 1.09 (d, J = 6.7 Hz, 2H), 1.70 (d, J = 9.6 Hz, 1H), 2.10-2.20 (m, 1H), 2.91 (dd, J = 15.0, 6.2 Hz, 1H), 3.66 (dd, J = 17.2, 3.6 Hz, 1H), 3.95-4.06 (m, 6H), 7.23 (d, J = 8.8 Hz, 1H), 7.46 (d, J = 3.3 Hz, 1H), 7.83 (d, J = 8.8 Hz, 1H), 7.95 (q, J = 3.3 Hz, 1H) | CDCl₃ |

TABLE 49-continued

| Ex. No. | structural formula | compound name | ESI MS m/z | ¹H NMR, δ (ppm) | deuterated solvent |
|---|---|---|---|---|---|
| 363 | | 1-((2-(3,6-diazabicyclo[3.1.1]heptan-3-yl)-7-(5-chloropyridin-2-yl)benzo[d]oxazol-4-yl)oxy)-1,1-difluoro-3-methylpropan-2-ol | 451 (M + H)+ | (400 MHz): 1.48 (s, 6H), 1.70-1.80 (m, 1H), 3.05-3.15 (m, 1H), 4.08 (d, J = 10.8 Hz, 2H), 4.20-4.50 (m, 4H), 7.20-7.30 (m, 1H), 7.70-7.80 (m, 2H), 7.80-7.85 (m, 1H), 8.62-8.70 (m, 1H) | CDCl₃ |
| 364 | | 3-((2-(3,6-diazabicyclo[3.1.1]heptan-3-yl)-7-(thiazol-2-yl)benzo[d]oxazol-4-yl)oxy)-3,3-difluoro-2-methylpropane-1,2-diol (optically active) | 439 (M + H)+ | (400 MHz): 1.38 (s, 3H), 1.61 (d, J = 8.9 Hz, 1H), 2.55-2.62 (m, 1H), 3.57-3.74 (m, 4H), 3.80-3.95 (m, 4H), 4.97 (t, J = 6.5 Hz, 1H), 5.51 (s, 1H), 7.22 (d, J = 8.7 Hz, 1H), 7.78 (d, J = 8.7 Hz, 1H), 7.95 (d, J = 3.2 Hz, 1H), 8.04 (d, J = 3.2 Hz, 1H) | DMSO-d₆ |
| 365 | | 3-((2-(3,6-diazabicyclo[3.1.1]heptan-3-yl)-7-(thiazol-2-yl)benzo[d]oxazol-4-yl)oxy)-3,3-difluoro-2-methylpropane-1,2-diol (No.364's) enantiomer) | 439 (M + H)+ | (400 MHz): 1.38 (s, 3H), 1.61 (d, J = 8.8 Hz, 1H), 2.55-2.62 (m, 1H), 3.57-3.74 (m, 4H), 3.80-3.95 (m, 4H), 4.98 (brs, 1H), 5.51 (brs, 1H), 7.22 (d, J = 8.7 Hz, 1H), 7.78 (d, J = 8.7 Hz, 1H), 7.95 (d, J = 3.2 Hz, 1H), 8.04 (d, J = 3.2 Hz, 1H) | DMSO-d₆ |
| 366 | | 2-(3,6-diazabicyclo[3.1.1]heptan-3-yl)-7-(thiazol-2-yl)benzo[d]oxazole-4-carboxylic acid | 343 (M + H)+ | (400 MHz): 1.61 (d, J = 8.9 Hz, 1H), 2.56-2.64 (m, 1H), 3.17 (s, 1H), 3.72 (brd, J = 61 Hz, 2H), 3.82-4.04 (m, 4H), 7.75-7.84 (m, 2H), 8.02 (d, J = 3.3 Hz, 1H), 8.09 (d, J = 3.1 Hz, 1H) | DMSO-d₆ |

TABLE 50

| Ex. No. | structural formula | compound name | ESI MS m/z | $^1$H NMR, δ (ppm) | deuterated solvent |
|---|---|---|---|---|---|
| 367 | | 2-(3,6-diazabicyclo[3.1.1]heptan-3-yl)-N-hydroxy-7-(thiazol-2-yl)benzo[d]oxazole-4-carboxamide | 358 (M + H)+ | (400 MHz): 1.61 (brd, J = 8.0 Hz, 1H), 2.56-2.65 (m, 1H), 3.65-3.76 (m, 2H), 3.80-4.07 (m, 5H), 4.14-4.52 (m, 1H), 7.75-7.89 (m, 2H), 7.95-8.03 (m, 1H), 8.09-8.16 (m, 1H) | DMSO-d$_3$ |
| 368 | | 3-(5-(2-hydroxypropan-2-yl)-(thiazol-2-yl)-4-(trifluoromethoxy)benzo-[d]oxazol-2-yl)-3,8-diazabicyclo[3.2.1]octan-8-ol | 471 (M + H)+ | (400 MHz): 1.73 (s, 6H), 1.75-1.83 (m, 2H), 2.18-2.27 (m, 2H), 3.50 (s, 1H), 3.54 (brd, J = 11.9 Hz, 2H), 3.66-3.75 (m, 2H), 4.03-4.15 (m, 2H), 5.24 (brs, 1H), 7.48 (d, J = 3.2 Hz, 1H), 7.97 (d, J = 3.2 Hz, 1H), 8.17 (s, 1H) | CDCl$_3$ |
| 369 | | 2-(3,6-diazabicyclo[3.1.1]heptan-3-yl)-4-morpholino-7-(thiazol-2-yl)benzo[d]oxazole | 384 (M + H)+ | (400 MHz): 1.68 (d, J = 9.1 Hz, 1H), 2.78-2.92 (m, 1H), 3.52-3.64 (m, 4H), 3.87-4.12 (m, 10H), 6.73 (d, J = 8.7 Hz, 1H), 7.37 (d, J = 3.3 Hz, 1H), 7.82 (d, J = 8.6 Hz, 1H), 7.90 (d, J = 3.2 Hz, 1H) | CDCl$_3$ |
| 370 | | 3-((2-(3,6-diazabicyclo[3.1.1]heptan-3-yl)-7-(thiazol-2-yl)benzo[d]oxazol-4-yl)oxy)-3,3-difluoropropane-1,2-diol | 425 (M + H)+ | (400 MHz): 1.61 (d, J = 8.8 Hz, 1H), 1.96 (brs, 1H), 2.55-2.62 (m, 1H), 3.54-3.62 (m, 1H), 3.68-3.73 (m, 2H), 3.81-4.02 (m, 6H), 4.94 (t, J = 6.2 Hz, 1H), 6.07 (d, J = 6.4 Hz, 1H), 7.22 (d, J = 8.7 Hz, 1H), 7.78 (d, J = 8.7 Hz, 1H), 9.96 (d, J = 3.2 Hz, 1H), 8.04 (d, J = 3.2 Hz, 1H) | DMSO-d$_3$ |
| 371 | | 3-(4-(1,1-difluoro-2-hydroxy-2-methylpropoxy)-7-(thiazol-2-yl)benzo[d]oxazol-2-yl)-3,6-diazabicyclo[3.1.1]heptan-6-ol | 439 (M + H)+ | (400 MHz): 1.52 (brs, 6H), 1.73 (d, J = 9.9 Hz, 1H), 2.19-2.26 (m, 1H), 3.76-3.82 (m, 2H), 3.92-3.96 (m, 2H), 4.21-4.27 (m, 2H), 7.26-7.30 (m, 1H), 7.45 (d, J = 3.3 Hz, 1H), 7.82 (d, J = 8.8 Hz, 1H), 7.94 (d, J = 3.3 Hz, 1H) | CDCl$_3$ |

TABLE 50-continued

| Ex. No. | structural formula | compound name | ESI MS m/z | ¹H NMR, δ (ppm) | deuterated solvent |
|---|---|---|---|---|---|
| 372 | | 3-(4-(1,1-difluoro-hydroxypropoxy)-7-(thiazol-2-yl)benzo[d]oxazol-2-yl)-3,6-diazabicyclo[3.1.1]heptan-6-ol (optically active) | 425 (M + H)+ | (400 MHz): 1.39 (d, J = 6.5 Hz, 3H), 1.76 (d, J = 10.0 Hz, 1H), 2.22-2.29 (m, 1H), 3.76-3.84 (m, 2H), 3.95-3.99 (m, 2H), 4.01-4.10 (m, 1H), 4.21-4.29 (m, 2H), 5.57 (brs, 1H), 7.22-7.27 (m, 1H), 7.47 (d, J = 3.3 Hz, 1H), 7.83 (d, J = 8.8 Hz, 1H), 7.96 (d, J = 3.3 Hz, 1H) | CDCl₃ |
| 373 | | 3-(4-(1,1-difluoro-2-hydroxypropoxy)-7-(thiazol-2-yl)benzo[d]oxazol-2-yl)-3,6-diazabicyclo[3.1.1]heptan-6-ol (No.372's enantiomer) | 425 (M + H)+ | (400 MHz): 1.39 (d, J = 6.5 Hz, 3H), 1.76 (d, J = 9.9 Hz, 1H), 2.22-2.29 (m, 1H), 3.76-3.84 (m, 2H), 3.95-3.99 (m, 2H), 4.01-4.10 (m, 1H), 4.21-4.29 (m, 2H), 5.57 (brs, 1H), 7.22-7.27 (m, 1H), 7.47 (d, J = 3.3 Hz, 1H), 7.83 (d, J = 8.8 Hz, 1H), 7.96 (d, J = 3.3 Hz, 1H) | CDCl₃ |
| 374 | | 3-(4-(1,1-difluoro-2-hydroxyethoxy)-7-(thiazol-2-yl)benzo[d]oxazol-2-yl)-3,6-diazabicyclo[3.1.1]heptan-6-ol | 411 (M + H)+ | (400 MHz): 1.76 (d, J = 9.7 Hz, 1H), 2.07-2.14 (m, 1H), 3.70-3.78 (m, 2H), 3.82-3.86 (m, 2H), 3.89-4.04 (m, 4H), 5.96 (t, J = 6.8 Hz, 1H), 7.24 (d, J = 8.7 Hz, 1H), 7.79 (d, J = 8.7 Hz, 1H), 7.92 (m, 1H), 7.96 (d, J = 3.2 Hz, 1H), 8.04 (d, J = 3.2 Hz, 1H) | DMSO-d₃ |

TABLE 51

| Ex. No. | structural formula | compound name | ESI MS m/z | ¹H NMR, δ (ppm) | deuterated solvent |
|---|---|---|---|---|---|
| 375 | | 3-(5-chloro-7-(thiazol-2-yl)-4-(trifluoromethyoxy)-benzo[d]oxazol-2-yl)-3,8-diazabicyclo[3.2.1]octan-8-ol | 447 (M + H)+ | (400 MHz): 1.73-1.80 (m, 2H), 2.20-2.27 (m, 2H), 3.52-3.58 (m, 2H), 3.68-3.72 (m, 2H), 4.07-4.13 (m, 2H), 5.86 (brs, 1H), 7.51 (d, J = 3.3 Hz, 1H), 7.96 (s, 1H), 7.97 (d, J = 3.3 Hz, 1H) | CDCl₃ |

TABLE 51-continued

| Ex. No. | structural formula | compound name | ESI MS m/z | ¹H NMR, δ (ppm) | deuterated solvent |
|---|---|---|---|---|---|
| 376 | | (2-((2-3,6-diazabicyclo[3.1.1]heptan-3-yl)-7-(thiazol-2-yl)benzo[d]oxazol-4-yl)oxy)pyridin-3-yl)methanol | 422 (M + H)+ | (400 MHz): 1.55 (d, J = 8.9 Hz, 1H), 2.53-2.58 (m, 1H), 3.59-3.93 (m, 6H), 4.71 (brd, J = 4.5 Hz, 2H), 5.43 (brt, J = 5.2 Hz, 1H), 7.06 (d, J = 8.6 Hz, 1H), 7.77 (d, J = 8.6 Hz,1H), 7.88-7.98 (m, 3H), 8.02 (d, J = 3.3 Hz, 1H) | DMSO-d₃ |
| 377 | | (2-((2-3,6-diazabicyclo[3.1.1]heptan-3-yl)-7-(thiazol-2-yl)benzo[d]oxazol-4-yl)oxy)-1,1-difluoropropane-2,2-diol | 425 (M + H)+ | (400 MHz): 1.68 (d, J = 9.3 Hz, 1H), 2.57 (s, 3H), 2.83-2.90 (m, 1H), 3.90-3.95 (m, 2H), 3.96-4.05 (m, 4H), 7.20-7.24 (m, 1H), 7.47 (d, J = 3.3 Hz, 1H), 7.85 (d, J = 8.8 Hz, 1H), 7.96 (d, J = 3.3 Hz, 1H) | CDCl₃ |
| 378 | | 3-(7-(thiazol-2-yl)-4-(2,2,2-trifluoro-1-hydroxyethyl)-benzo[d]oxazol-2-yl)-3,8-diazabicyclo[3.2.1]octan-8-ol (optically active) | 427 (M + H)+ | (400 MHz): 1.73-1.79 (m, 2H), 2.20-2.26 (m, 2H), 3.51-3.58 (m, 2H, 3.68-3.73 (m, 2H), 4.03-4.10 (m, 2H), 5.20 (q, J = 7.0 Hz, 1H), 7.21 (d, J = 8.1 Hz, 1H), 7.49 (d, J = 3.3 Hz, 1H), 7.85 (d, J = 8.1 Hz, 1H), 7.97 (d, J = 3.3 Hz, 1H) | CDCl₃ |
| 379 | | 3-(7-(thiazol-2-yl)-4-(2,2,2-trifluoro-1-hydroxyethyl)-benzo[d]oxazol-2-yl)-3,8-diazabicyclo[3.2.1]octan-8-ol (No.378's enantiomer) | 427 (M + H)+ | (400 MHz): 1.73-1.79 (m, 2H), 2.20-2.26 (m, 2H), 3.51-3.58 (m, 2H, 3.68-3.73 (m, 2H), 4.03-4.10 (m, 2H), 5.19 (q, J = 7.2 Hz, 1H), 7.21 (d, J = 8.1 Hz, 1H), 7.49 (d, J = 3.3 Hz, 1H), 7.85 (d, J = 8.1 Hz, 1H), 7.97 (d, J = 3.3 Hz, 1H) | CDCl₃ |
| 380 | | 3-(7-(thiazol-2-yl)-(trifluoromethoxy)-benzo[d]oxazol-2-yl)-3,6-diazabicyclo[3.1.1]heptan-6-ol | 399 (M + H)+ | (400 MHz): 1.79 (d, J = 9.8 Hz, 1H), 2.22-2.33 (m, 1H), 3.88 (d, J = 12.5 Hz, 2H), 4.01 (brd, J = 4.9 Hz, 2H), 4.29 (brd, J = 12.1 Hz, 2H), 4.67 (s, 1H), 7.21 (dq, J = 8.8, 1.5 Hz, 1H), 7.49 (d, J = 3.2 Hz, 1H), 7.87 (d, J = 8.8 Hz, 1H), 7.97 (d, J = 3.2 Hz, 1H) | CDCl₃ |

TABLE 51-continued

| Ex. No. | structural formula | compound name | ESI MS m/z | ¹H NMR, δ (ppm) | deuterated solvent |
|---|---|---|---|---|---|
| 381 | | 3-(5-(2-hydroxypropan-2-yl)-7-(thiazol-2-yl)-4-(trifluoromethyl)-benzo[d]oxazol-2-yl)-3,8-diazabicyclo[3.2.1]heptan-8-ol | 455 (M + H)+ | (400 MHz): 1.74-1.87 (m, 1H), 1.80 (m, 6H), 2.15-2.28 (m, 3H), 3.55 (brd, J = 12.4 Hz, 2H), 3.65-3.73 (m, 2H), 4.08-4.19 (m, 2H), 5.13 (s, 1H), 7.54 (d, J = 3.2 Hz, 1H), 8.01 (d, J = 3.3 Hz, 1H), 8.22 (s, 1H) | CDCl₃ |
| 382 | | 2-(3,6-diazabicyclo[3.1.1]heptan-3-yl)-7-(thiazol-2-yl)benzo[d]oxazole | 299 (M + H)+ | (400 MHz): 1.70 (d, J = 9.2 Hz, 1H), 2.87 (dt, J = 9.2, 6.2 Hz, 1H), 3.90-4.09 (m, 6H), 7.31 (t, J = 7.9 Hz, 1H), 7.44-7.50 (m, 2H), 7.88 (dd, J = 8.0, 1.1 Hz, 1H), 7.97 (d, J = 3.2 Hz, 1H) | CDCl₃ |

TABLE 52

| Ex. No. | structural formula | compound name | ESI MS m/z | ¹H NMR, δ (ppm) | deuterated solvent |
|---|---|---|---|---|---|
| 383 | | 3-(5-(1-hydroxyethyl)-2-7-(thiazol-2-yl)-4-(trifluoromethoxy)-benzo[d]oxazol-2-yl)-3,8-diazabicyclo[3.2.1]heptan-8-ol | 457 (M + H)+ | (400 MHz): 1.53-1.57 (m, 3H), 1.17-1.83 (m, 2H), 1.96 (brs, 1H), 2.16-2.32 (m, 2H), 3.54 (brd, J = 12.2 Hz, 2H), 3.70 (brs, 2H), 4.05-4.13 (m, 2H), 5.24 (s, 1H), 5.37 (q, J = 6.2 Hz, 1H), 7.49 (d, J = 3.12 Hz, 1H), 7.98 (d, J = 3.3 Hz, 1H), 8.10 (s, 1H) | CDCl₃ |
| 384 | | 3-(5-(1-hydroxyethyl)-2-7-(thiazol-2-yl)-4-(trifluoromethoxy)-benzo[d]oxazol-2-yl)-3,8-diazabicyclo[3.2.1]heptan-8-ol | 441 (M + H)+ | (400 MHz): 1.52-1.62 (m, 3H), 1.74-1.83 (m, 2H), 1.95-2.06 (m, 1H), 2.18-2.32 (m, 2H), 3.56 (brd, J = 12.5 Hz, 2H), 3.70 (brd, 2H), 4.12 (brdd, J = 12.8 Hz, 2.1 Hz, 2H), 5.20 (brs, 1H), 5.39-5.51 (m, 1H), 7.54 (d, J = 3.3 Hz, 1H), 8.03 (d, J = 3.2 Hz, 1H), 8.30 (s, 1H) | CDCl₃ |
| 385 | | 2-(3,6-diazabicyclo[3.1.1]heptan-3-yl)-N-(2-hydroxyethyl)-7-(thiazol-2-yl)-4-(trifluoromethoxy)-benzo[d]oxazole-4-sulfonamide | 422 (M + H)+ | (400 MHz): 1.63 (d, J = 8.9 Hz, 1H), 2.57-2.64 (m, 1H), 2.99-3.05 (m, 2H), 3.39-3.46 (m, 2H), 3.71-3.76 (m, 2H), 3.86-4.02 (m, 4H), 4.67 (t, J = 5.6 Hz, 1H), 7.19 (t, J = 5.9 Hz, 1H), 7.86 (d, J = 8.4 Hz, 1H), 8.07 (d, J = 3.2 Hz, 1H), 8.12 (d, J = 3.2 Hz, 1H) | DMSO-d₃ |

TABLE 52-continued

| Ex. No. | structural formula | compound name | ESI MS m/z | ¹H NMR, δ (ppm) | deuterated solvent |
|---|---|---|---|---|---|
| 386 | | 2-(3,6-diazabicyclo[3.1.1]heptan-3-yl)-N-methyl-7-(thiazol-2-yl)-benzo[d]oxazole-4-sulfonamide | 392 (M + H)+ | (400 MHz): 1.63 (d, J = 8.9 Hz, 1H), 2.56-2.64 (m, 4H), 3.70-3.75 (m, 2H), 3.87-4.02 (m, 4H), 7.17 (q, J = 8.4 Hz, 1H), 7.66 (d, J = 8.4 Hz, 1H), 7.86 (d, J = 8.4 Hz, 1H), 8.07 (d, J = 3.2 Hz, 1H), 8.12 (d, J = 3.2 Hz, 1H) | CDCl₃ |
| 387 | | 2-(3,6-diazabicyclo[3.1.1]heptan-3-yl)-N-(2-methoxyethyl)-2-7-(thiazol-2-yl)-benzo[d]oxazole-4-sulfonamide | 436 (M + H)+ | (400 MHz): 1.68 (d, J = 9.5 Hz, 1H), 2.87-2.94 (m, 1H), 3.06-3.11 (m, 2H), 3.26 (m, 3H), 3.46 (t, J = 5.1 Hz, 2H), 3.94-3.98 (m, 2H), 4.00-4.10 (m, 4H), 6.00 (brs, 1H), 7.56 (d, J = 3.2 Hz, 1H), 7.78 (d, J = 8.4 Hz, 1H), 7.92 (d, J = 8.4 Hz, 1H), 8.02 (d, J = 3.2 Hz, 1H) | CDCl₃ |
| 388 | | 2-(3,6-diazabicyclo[3.1.1]heptan-3-yl)-N,N-dimethyl-7-(thiazol-2-yl)-benzo[d]oxazole-4-sulfonamide | 406 (M + H)+ | (400 MHz): 1.69 (d, J = 9.4 Hz, 1H), 2.86-2.94 (m, 7H), 3.92-3.97 (m, 2H), 4.00-4.10 (m, 4H), 7.56 (d, J = 3.3 Hz, 1H), 7.76 (d, J = 8.4 Hz, 1H), 7.92 (d, J = 8.4 Hz, 1H), 8.02 (d, J = 3.3 Hz, 1H) | CDCl₃ |
| 389 | | 2-(3,6-diazabicyclo[3.1.1]heptan-3-yl)-N-(2-hydroxyethyl)-N-methyl-7-(thiazol-2-yl)-benzo[d]oxazole-4-sulfonamide | 436 (M + H)+ | (400 MHz): 1.67 (d, J = 9.4 Hz, 1H), 2.77 (s, 3H), 2.85-2.92 (m, 1H), 3.62-3.67 (m, 2H), 3.76-3.81 (m, 2H), 3.94-3.98 (m, 2H), 4.02-4.11 (m, 4H), 7.58 (d, J = 3.2 Hz, 1H), 7.80 (d, J = 8.4 Hz, 1H), 7.96 (d, J = 8.4 Hz, 1H), 8.03 (d, J = 3.2 Hz, 1H) | CDCl₃ |
| 390 | | 2-(3,6-diazabicyclo[3.1.1]heptan-3-yl)-4-(pyrrolidine-1-ylsulfonyl)7-(thiazol-2-yl)-benzo[d]oxazole | 432 (M + H)+ | (400 MHz): 1.69 (d, J = 9.3 Hz, 1H), 1.77-1.83 (m, 4H), 2.86-2.92 (m, 1H), 3.55-3.61 (m, 4H), 3.92-3.96 (m, 2H), 3.99-4.09 (m, 4H), 7.55 (d, J = 3.2 Hz, 1H), 7.82 (d, J = 8.4 Hz, 1H), 7.91 (d, J = 8.4 Hz, 1H), 8.02 (d, J = 3.2 Hz, 1H) | CDCl₃ |

TABLE 53

| Ex. No. | structural formula | compound name | ESI MS m/z | ¹H NMR, δ (ppm) | deuterated solvent |
|---|---|---|---|---|---|
| 391 | | 2-(3,6-diazabicyclo[3.1.1]heptan-3-yl)-4-(morpholinosulfonyl)-7-(thiazol-2-yl)-benzo[d]oxazole | 448 (M + H)+ | (400 MHz): 1.70 (d, J = 8.8 Hz, 1H), 2.87-2.94 (m, 1H), 3.32-3.36 (m, 4H), 3.71-3.76 (m, 4H), 3.95-3.99 (m, 2H), 4.01-4.10 (m, 4H), 7.57 (d, J = 3.2 Hz, 1H), 7.74 (d, J = 8.4 Hz, 1H), 7.93 (d, J = 8.4 Hz, 1H), 8.03 (d, J = 3.2 Hz, 1H) | CDCl₃ |
| 392 | | 2-(3,6-diazabicyclo[3.1.1]heptan-3-yl)-4-(1,1-difluoro-2-methylethoxy)-7-(thiazol-2-yl)-benzo[d]oxazole | 409 (M + H)+ | (400 MHz): 1.68 (d, J = 9.3 Hz, 1H), 2.81-2.92 (m, 1H), 3.62 (s, 4H), 3.92 (brd, J = 5.9 Hz, 2H), 3.97-4.11 (m, 6H), 7.25-7.31 (m, 1H), 7.46 (d, J = 3.3 Hz, 1H), 7.85 (d, J = 8.8 Hz, 1H), 7.96 (d, J = 3.2 Hz, 1H) | CDCl₃ |
| 393 | | 2-(3,6-diazabicyclo[3.1.1]heptan-3-yl)-4-(1,1-difluoro-2-methoxy-2-methylpropoxy)-7-(thiazol-2-yl)-benzo[d]oxazole | 437 (M + H)+ | (400 MHz): 1.54 (s, 6H), 1.68 (brd, J = 9.3 Hz, 1H), 2.78-2.92 (m, 1H), 3.53 (s, 3H), 3.84-4.12 (m, 6H), 7.22-7.26 (m, 1H), 7.46 (d, J = 3.3 Hz, 1H), 7.84 (d, J = 8.8 Hz, 1H), 7.96 (d, J = 3.3 Hz, 1H) | CDCl₃ |
| 394 | | 1-((2-(3,6-diazabicyclo[3.1.1]heptan-3-yl)-7-(1-methyl-1H-pyrazol-3-yl)benzo[d]oxazol-4-yl)oxy)-1,1-difluoro-2-methylpropan-2-ol | 420 (M + H)+ | (400 MHz): 1.51 (s, 6H), 1.64 (d, J = 9.3 Hz, 1H), 2.80-2.88 (m, 1H), 3.92-4.02 (s, 6H), 5.30 (s, 3H), 6.74 (d, J = 2.4 Hz, 1H), 7.19 (d, J = 8.6 Hz, 1H), 7.43 (d, J = 2.2 Hz, 1H), 7.59 (d, J = 8.6 Hz, 1H) | CDCl₃ |

TABLE 53-continued

| Ex. No. | structural formula | compound name | ESI MS m/z | $^1$H NMR, δ (ppm) | deuterated solvent |
|---|---|---|---|---|---|
| 395 | | 1-((2-(3,6-diazabicyclo[3.1.1]heptan-3-yl)-7-(thiazol-2-yl)benzo[d]oxazol-4-yl)oxy)-1,1-difluorobutan-2-ol | 423 (M + H)+ | (400 MHz): 1.05 (t, J = 6.0 Hz, 3H), 1.65-1.75 (m, 2H), 1.75-1.85 (m, 1H), 2.89 (brs, 1H), 3.73 (ddd, J = 16.7, 9.3 3.3 Hz, 1H), 3.90-4.10 (m, 6H), 7.24 (d, J = 9.0 Hz, 1H), 7.47 (d, J = 3.1 Hz, 1H), 7.85 (d, J = 8.6 Hz, 1H), 7.96 (d, J = 3.3 Hz, 1H) | CDCl$_3$ |
| 396 | | 2-(3,6-diazabicyclo[3.1.1]heptan-3-yl)-7-(thiazol-2-yl)benzo[d]oxazole-4-sulfonamide | 378 (M + H)+ | (400 MHz): 1.63 (d, J = 8.9 Hz, 1H), 2.58-2.65 (m, 1H), 3.72-3.77 (m, 2H), 3.90-4.02 (m, 4H), 7.23 (brs, 2H), 7.67 (d, J = 8.4 Hz, 1H), 7.85 (d, J = 8.4 Hz, 1H), 8.06 (d, J = 3.2 Hz, 1H), 8.11 (d, J = 3.2 Hz, 1H) | DMSO-d$_3$ |
| 397 | | 2-(3,6-diazabicyclo[3.1.1]heptan-3-yl)-7-(thiazol-2-yl)benzo[d]oxazol-4-yl)piperidin-4-ol | 398 (M + H)+ | (400 MHz): 1.68 (d, J = 9.3 Hz, 1H), 1.73-1.84 (m, 2H), 2.03-2.11 (m, 2H), 2.81-2.88 (m, 1H), 3.12-3.20 (m, 2H), 3.87-4.10 (m, 9H), 6.74 (d, J = 8.6 Hz, 1H), 7.34 (d, J = 3.3 Hz, 1H), 7.79 (d, J = 8.6 Hz, 1H), 7.87 (d, J = 3.3 Hz, 1H) | CDCl$_3$ |
| 398 | | 4-(2-(3,6-diazabicyclo[3.1.1]heptan-3-yl)-7-(thiazol-2-yl)benzo[d]oxazol-4-yl)thiomorpholine 1,1-dioxide | 432 (M + H)+ | (400 MHz): 1.68 (d, J = 9.3 Hz, 1H), 2.83-2.91 (m, 1H), 3.18-3.23 (m, 4H), 3.91-4.03 (m, 6H), 4.21-4.27 (m, 4H), 6.73 (d, J = 8.7 Hz, 1H), 7.39 (d, J = 3.3 Hz, 1H), 7.82 (d, J = 8.7 Hz, 1H), 7.90 (d, J = 3.3 Hz, 1H) | CDCl$_3$ |

TABLE 54

| Ex. No. | structural formula | compound name | ESI MS m/z | ¹H NMR, δ (ppm) | deuterated solvent |
|---|---|---|---|---|---|
| 399 | | 1-((2-(3,6-diazabicyclo[3.1.1]heptan-3-yl)-5-bromo-7-(thiazol-2-yl)benzo[d]oxazol-4-yl)oxy)-1,1-difluoro-2-methylpropan-2-ol | 501 (M + H)+ | (400 MHz): 1.46 (s, 6H), 1.59 (d, J = 8.4 Hz, 1H), 2.53-2.63 (m, 1H), 3.69 (brd, J = 6.0 Hz, 2H), 3.74-3.99 (m, 4H), 5.58 (s, 1H), 7.97 (s, 1H), 8.01 (d, J = 3.2 Hz, 1H), 8.07 (d, J = 3.3 Hz, 1H) | DMSO-d₃ |
| 400 | | 1-((2-(3,6-diazabicyclo[3.1.1]heptan-3-yl)-5-chloro-7-(thiazol-2-yl)benzo[d]oxazol-4-yl)oxy)-1,1-difluoro-2-methylpropan-2-ol | 457 (M + H)+ | (400 MHz): 1.40 (s, 6H), 1.53 (d, J = 8.8 Hz, 1H), 2.52-2.57 (m, 1H), 3.63 (brd, J = 6.0 Hz, 2H), 3.66-3.82 (m, 4H), 5.61 (s, 1H), 7.30 (s, 1H), 8.07 (d, J = 3.3 Hz, 1H), 8.11 (d, J = 3.2 Hz, 1H) | DMSO-d₃ |
| 401 | | 2-((2-(3,6-diazabicyclo[3.1.1]heptan-3-yl)-5-chloro-7-(thiazol-2-yl)benzo[d]oxazol-4-yl)oxy)-2,2-difluoroethan-1-ol | 429 (M + H)+ | (400 MHz): 1.53 (d, J = 8.8 Hz, 1H), 2.53-2.58 (m, 1H), 3.63 (brd, J = 6.0 Hz, 2H), 3.67-3.83 (m, 4H), 3.94 (td, J = 10.5, 6.0 Hz, 2H), 5.99 (brt, J = 6.6 Hz, 1H), 7.33 (s, 1H), 8.07 (d, J = 3.3 Hz, 1H), 8.12 (d, J = 3.3 Hz, 1H) | DMSO-d₃ |
| 402 | | 2-(3,6-diazabicyclo[3.1.1]heptan-3-yl)-4-(1,1-difluoropropoxy)-7-(thiazol-2-yl)benzo[d]oxazole | 393 (M + H)+ | (400 MHz): 1.53 (d, J = 8.8 Hz, 1H), 2.53-2.58 (m, 1H), 3.63 (brd, J = 6.0 Hz, 2H), 3.67-3.83 (m, 4H), 3.94 (td, J = 10.5, 6.0 Hz, 2H), 5.99 (brt, J = 6.6 Hz, 1H), 7.33 (s, 1H), 8.07 (d, J = 3.3 Hz, 1H), 8.12 (d, J = 3.3 Hz, 1H) | CDCl₃ |
| 403 | | benzo[d]oxazol-2-yldifluoromethoxy)-2-(3,6-diazabicyclo[3.1.1]heptan-3-yl)-7-(thiazol-2-yl)benzo[d]oxazole | 482 (M + H)+ | (400 MHz): 1.60 (brd, J = 9.2 Hz, 1H), 2.77-2.88 (m, 1H), 3.71-4.01(m, 6H), 7.34 (brd, J = 8.8 Hz, 1H), 7.41-7.56 (m, 3H), 7.68 (d, J = 7.8 Hz, 1H), 7.87 (d, J = 8.8 Hz, 2H), 7.97 (d, J = 3.2 Hz, 1H) | DMSO-d₃ |

TABLE 54-continued

| Ex. No. | structural formula | compound name | ESI MS m/z | ¹H NMR, δ (ppm) | deuterated solvent |
|---|---|---|---|---|---|
| 404 | | 2-((2-(3,8-diazabicyclo[3.2.1]octan-3-yl)-7-(thiazol-2-yl)benzo[d]oxazol-4-yl)oxy)-2,2-difluoroethan-2-ol | 409 (M + H)+ | (400 MHz): 1.84-1.97 (m, 4H), 3.48 (dd, J = 12.2, 2.0 Hz, 2H), 3.66-3.75 (m, 2H), 3.71-4.01 (m, 6H), 7.34 (brd, J = 8.8 Hz, 1H), 7.41-7.56 (m, 3H), 7.68 (d, J = 7.8 Hz, 1H), 7.87 (d, J = 8.8 Hz, 2H), 7.97 (d, J = 3.2 Hz, 1H) | CDCl3 |
| 405 | | 2-((2-(3,8-diazabicyclo[3.2.1]octan-3-yl)-7-(thiazol-2-yl)benzo[d]oxazol-4-yl)oxy)-1,1-difluoro-2-methylpropan-2-ol | 437 (M + H)+ | (400 MHz): 1.53 (s, 6H), 1.82-1.96 (m, 4H), 3.43 (dd, J = 12.2, 2.2 Hz, 2H), 7.19-7.25 (m, 1H), 7.45 (d, J = 3.3 Hz, 1H), 7.82 (d, J = 8.7 Hz, 1H), 7.82 (d, J = 8.7 Hz, 1H), 7.95 (d, J = 3.3 Hz, 1H) | CDCl₃ |
| 406 | | (E)-2-(3,6-diazabicyclo[3.1.1]heptan-3-yl)-4-((1,1-difluoro-3-(pyridin-3-yl)allyl)oxy)-7-(thiazol-2-yl)benzo[d]oxazol | 468 (M + H)+ | (400 MHz): 1.68 (d, J = 9.2 Hz, 1H), 2.81-2.92 (m, 1H), 3.92 (brd, J = 5.9 Hz, 2H), 3.96-4.10 (m, 4H), 6.58 (dt, J = 16.2, 7.2 Hz, 1H), 7.28-7.37 (m, 3H), 7.47 (d, J = 3.2 Hz, 1H), 7.80 (dt, J = 8.0, 1.8 Hz, 1H), 7.87 (d, J = 8.7 Hz, 1H), 7.97 (d, J = 3.2 Hz, 1H), 8.59 (dd, J = 4.8, 1.6 Hz, 1H), 8.71 (d, J = 2.1 Hz, 1H) | CDCl₃ |

TABLE 55

| Ex. No. | structural formula | compound name | ESI MS m/z | ¹H NMR, δ (ppm) | deuterated solvent |
|---|---|---|---|---|---|
| 407 | | 2-((2-(3,6-diazabicyclo[3.1.1]heptan-3-yl)-7-(thiazol-2-yl)benzo[d]oxazol-4-yl)oxy)-2,2-difluoro-N-(2-hydroxyethyl)-N-methylacetamide | 466 (M + H)+ | (400 MHz): 1.69 (d, J = 9.4 Hz, 1H), 2.84-2.97 (m, 1H), 3.12 (s, 2.7H), 3.54 (s, 0.3H), 3.62-3.70 (m, 0.4H), 3.79-4.12 (m, 10H), 5.48-5.59 (m, 0.5H), 7.38-7.45 (m, 1H), 7.46-7.51 (m, 1H), 7.83 (d, J = 8.8 Hz, 0.1H), 7.90 (d, J = 8.8 Hz, 0.9H), 7.96 (d, J = 3.2 Hz, 0.1H), 7.98 (d, J = 3.2 Hz, 0.9H) | CDCl₃ |

TABLE 55-continued

| Ex. No. | structural formula | compound name | ESI MS m/z | ¹H NMR, δ (ppm) | deuterated solvent |
|---|---|---|---|---|---|
| 408 | | 2-((2-(3,6-diazabicyclo[3.1.1]heptan-3-yl)-7-(thiazol-2-yl)benzo[d]oxazol-4-yl)oxy)-2,2-difluoro-N,N-dimethylacetamide | 436 (M + H)+ | (400 MHz): 1.68 (d, J = 9.5 Hz, 1H), 2.83-2.91 (m, 1H), 3.09 (s, 3H), 3.44-3.48 (m, 3H), 3.92 (brd, J = 5.9 Hz, 2H), 3.95-4.07 (m, 4H), 7.29-7.33 (m, 1H), 7.48 (d, J = 3.3 Hz, 1H), 7.86 (d, J = 8.7 Hz, 1H), 7.97 (d, J = 3.2 Hz, 1H) | CDCl₃ |
| 409 | | 2-((2-(3,6-diazabicyclo[3.1.1]heptan-3-yl)-7-(thiazol-2-yl)benzo[d]oxazol-4-yl)oxy)-2,2-difluoro-1-morpholinoethan-1-one | 478 (M + H)+ | (400 MHz): 1.69 (d, J = 9.3 Hz, 1H), 2.83-2.94 (m, 1H), 3.71-3.86 (m, 6H), 3.90-4.05 (m, 5H), 4.13-4.22 (m, 2H), 7.29-7.34 (m, 1H), 7.48 (brd, J = 3.3 Hz, 1H), 7.86 (d, J = 8.8 Hz, 1H), 7.97 (d, J = 3.3 Hz, 1H) | CDCl₃ |
| 410 | | 2-((2-(3,6-diazabicyclo[3.1.1]heptan-3-yl)-7-(thiazol-2-yl)benzo[d]oxazol-4-yl)oxy)-2,2-difluoroacetamide | 408 (M + H)+ | (400 MHz): 1.59 (d, J = 8.8 Hz, 1H), 2.54-2.63 (m, 1H), 3.69 (brd, J = 5.9 Hz, 2H), 3.56-3.59 (m, 4H), 7.24 (brd, J = 6.8 Hz, 1H), 7.79 (d, J = 8.8 Hz, 1H), 7.96 (d, J = 3.2 Hz, 1H), 8.24 (d, J = 3.3 Hz, 1H), 8.25 (brs, 1H), 8.53 (brs, 1H) | DMSO-d₃ |
| 411 | | 2-((2-(3,6-diazabicyclo[3.1.1]heptan-3-yl)-7-(thiazol-2-yl)benzo[d]oxazol-4-yl)oxy)-2,2-difluoro-N-(2-hydroxethyl)acetamide | 452 (M + H)+ | (400 MHz): 1.68 (d, J = 9.4 Hz, 1H), 2.83-2.95 (m, 1H), 3.53-3.60 (m, 2H), 3.79-3.87 (m, 2H), 3.89-4.06 (m, 8H), 7.25-7.30 (m, 1H), 7.46 (d, J = 3.3 Hz, 1H), 7.83 (d, J = 8.8 Hz, 1H), 7.94 (d, J = 3.2 Hz, 1H), 8.20-8.30 (m, 1H) | CDCl₃ |

TABLE 55-continued

| Ex. No. | structural formula | compound name | ESI MS m/z | $^1$H NMR, δ (ppm) | deuterated solvent |
|---|---|---|---|---|---|
| 412 | | 2-((2-(3,6-diazabicyclo[3.1.1]heptan-3-yl)-7-(thiazol-2-yl)benzo[d]oxazol-4-yl)oxy)-2,2-difluoro-1-(3-hydroxyazetidin-1-yl)ethan-1-one | 464 (M + H)+ | (400 MHz): 1.68 (brd, J = 9.3 Hz, 1H), 2.88 (dt, J = 9.1, 6.2 Hz, 1H), 3.93 (brd, J = 6.0 Hz, 2H), 4.00 (s, 4H), 4.05 (ddd, J = 11.4, 3.9, 1.3 Hz, 1H), 4.43 (ddd, J = 11.3, 3.9, 1.3 Hz, 1H), 4.54-4.64 (m, 1H), 4.68-4.80 (m, 1H), 4.89 (brdd, J = 10.6, 6.4 Hz, 1H), 7.18-7.25 (m, 1H), 7.47 (d, J = 3.2 Hz, 1H), 7.79 (d, J = 8.8 Hz, 1H), 7.96 (d, J = 3.2 Hz, 1H) | CDCl$_3$ |
| 413 | | 2-(3,6-diazabicyclo[3.1.1]heptan-3-yl)-7-(thiazol-2-yl)-5-((5-(trifluoromethyl)pyridin-2-yl)oxy)-benzo[d]oxazole | 460 (M + H)+ | (400 MHz): 1.50-1.80 (m, 1H), 2.85-2.95 (m, 1H), 3.80-4.30 (m, 6H), 7.05 (d, J = 8.4 Hz, 1H), 7.25 (d, J = 2.4 Hz, 1H), 7.49 (d, J = 3.6 Hz, 1H), 7.68 (d, J = 2.4 Hz, 1H), 7.90 (d, J = 8.8 Hz, 2H), 7.94 (d, J = 3.6 Hz, 1H), 8.43 (brs, 1H) | CDCl$_3$ |

TABLE 56

| Ex. No. | structural formula | compound name | ESI MS m/z | $^1$H NMR, δ (ppm) | deuterated solvent |
|---|---|---|---|---|---|
| 414 | | 2-(3,6-diazabicyclo[3.1.1]heptan-3-yl)-4-cyclobutyl-7-(thiazol-2-yl)benzo[d]oxazole | 353 (M + H)+ | (400 MHz): 1.68 (d, J = 9.2 Hz, 1H), 1.89-1.98 (m, 1H), 2.05-2.14 (m, 1H), 2.28-2.48 (m, 4H), 2.61-2.88 (m, 1H), 3.91-4.09 (m, 7H), 7.25 (d, J = 8.1 Hz, 1H), 7.41 (d, J = 3.2 Hz, 1H), 7.84 (d, J = 8.1 Hz, 1H), 7.93 (d, J = 3.2 Hz, 1H) | CDCl$_3$ |
| 415 | | 2-(3,6-diazabicyclo[3.1.1]heptan-3-yl)-4-(pyrrolindin-1-yl)-7-(thiazol-2-yl)benzo[d]oxazole | 368 (M + H)+ | (400 MHz): 1.69 (d, J = 9.3 Hz, 1H), 1.97-2.02 (m, 4H), 2.83-2.90 (m, 1H), 3.70-3.76 (m, 4H), 3.94-4.01 (m, 6H), 6.39 (d, J = 8.7 Hz, 1H), 7.25 (d, J = 3.3 Hz, 1H), 7.75 (d, J = 8.7 Hz, 1H), 7.82 (d, J = 3.3 Hz, 1H) | CDCl$_3$ |

TABLE 56-continued

| Ex. No. | structural formula | compound name | ESI MS m/z | $^1$H NMR, δ (ppm) | deuterated solvent |
|---|---|---|---|---|---|
| 416 | | (6-((2-(3,6-diazabicyclo[3.1.1]heptan-3-yl)-7-(thiazol-2-yl)benzo[d]oxazol-5-yl)oxy)pyridin-3-yl)methanol | 422 (M + H)+ | (400 MHz): 1.70 (d, J = 9.0 Hz, 1H), 2.88 (m, 1H), 3.94 (d, J = 8.2 Hz, 2H), 3.97-4.07 (m, 4H), 4.65 (s, 2H), 6.95 (d, J = 9.0 Hz, 1H), 7.24 (d, J = 2.1 Hz, 1H), 7.48 (d, J = 3.4 Hz, 1H), 7.55 (d, J = 2.1 Hz, 1H), 7.74 (dd, J = 8.6, 2.4 Hz, 1H), 7.93 (d, J = 2.8 Hz, 1H), 8.15 (d, J = 2.8 Hz, 1H) | CDCl$_3$ |
| 417 | | 2-(3,6-diazabicyclo[3.1.1]heptan-3-yl)-7-(thiazol-2-yl)benzo[d]oxazole-5-carbonitrile | 324 (M + H)+ | (400 MHz): 1.71 (d, J = 9.0 Hz, 1H), 2.91 (m, 1H), 3.97 (d, J = 8.2 Hz, 2H), 3.96-4.08 (m, 4H), 7.55 (d, J = 2.8 Hz, 1H), 7.64-7.65 (m, 1H), 8.01 (d, J = 3.4 Hz, 1H), 8.22-8.24 (m, 1H) | CDCl$_3$ |
| 418 | | 2-(3,6-diazabicyclo[3.1.1]heptan-3-yl)-5-(pyridin-3-yl)-7-(thiazol-2-yl)benzo[d]oxazole | 376 (M + H)+ | (400 MHz): 1.74 (d, J = 9.5 Hz, 1H), 2.88-2.94 (m, 1H), 3.97 (d, J = 5.5 Hz, 2H), 4.02-4.10 (m, 4H), 7.42 (s, J = 4.4 Hz, 1H), 7.54 (d, J = 3.4 Hz, 1H), 7.65 (d, J = 2.1 Hz, 1H), 7.98-8.03 (m, 2H), 8.10 (d, J = 1.4 Hz, 1H), 8.57-8.03 (m, 1H), 8.92 (d, J = 2.1 Hz, 1H) | CDCl$_3$ |
| 419 | | 2-(3,6-diazabicyclo[3.1.1]heptan-3-yl)-5-cyclobutoxy-7-(thiazol-2-yl)benzo[d]oxazole | 369 (M + H)+ | (400 MHz): 1.65-1.74 (m, 2H), 1.82-1.92 (m, 1H), 2.16-2.27 (m, 2H), 2.47-2.56 (m, 2H), 2.82-2.88 (m, 1H), 3.90-3.94 (m, 2H), 3.95-4.04 (m, 4H), 4.69-4.77 (m, 1H), 6.96 (d, J = 2.1 Hz, 1H), 7.34 (d, J = 2.1 Hz, 1H), 7.46 (d, J = 3.1 Hz, 1H), 7.95 (d, J = 3.8 Hz, 1H) | CDCl$_3$ |

Test Example 1: Evaluation of BDE4 Inhibitory Activity

The BDE4 inhibitory activity was measured using scintillation proximity assay (SPA) as follows. First, a test compound dissolved in dimethyl sulfoxide was diluted 1:10 in reaction buffer solution which contained 50 mM of Tris-HCl with pH 7.4, 8.3 mM of MgCl$_2$, 1.7 mM of EGTA, and 3 mg/mL of bovine serum albumin (BSA). Then, 10 μL of the diluted solution was added in a 96-well assay plate. Moreover, 50 μL of PDE4 (enzyme preparation) diluted 1:375 in the reaction buffer solution was added, and then 40 μL of [2,8-$^3$H]-adenosine-3',5'-cyclic phosphate triethylammonium salt diluted 1:1000 in the reaction buffer solution was added. The mixture was allowed to stand at room temperature for 120 minutes. Thereafter, 200 mM of RNA binding YSi-SPA beads suspension containing ZnSO$_4$ was added and the mixture was allowed to stand at room temperature for 15 minutes, followed by adsorption of the enzyme reaction product to the beads. After that, the radioactivity was measured using a liquid scintillation counter for a 96-well plate. The mixture without the enzyme preparation added but only the reaction buffer solution added is a blank, and the mixture with the enzyme preparation added and only dimethyl sulfoxide added instead of the test compound is a control. The inhibition rate for the control of the test compound was calculated using the calculation formula below:

Inhibition Rate={1−(Value at Addition of Each Test Compound−Blank Value)/(Control Value−Blank Value)}×100

In addition, the PDE4 inhibitory activity (concentration that inhibits PDE4 activity by 50%=concentration for the inhibition rate of 50% (IC50)) of the test compound was calculated from the inhibition curves based on the inhibition rates for various concentrations of the test compound.

The results obtained by measuring the PDE4 inhibitory activity (concentration for the inhibition rate of 50%) of the test compound by the above method were evaluated in accordance with the following evaluated basis; A: less than 100 nM, B: 100 nM or more and less than 1000 nM, and C: 1000 nM or more (Evaluation 1). The results of Evaluation 1 when the compounds obtained in Examples were used as test compounds are shown in Tables 57 to 68.

In addition, for the compounds whose results for Evaluation 1 were A, the measurement results obtained by measuring the PDE4 inhibitory activity (concentration for the inhibition rate of 50%) were further evaluated in accordance with AA: 1 nM or less, AB: more than 1 nM and 11 nM or less, and AC: more than 11 nM and less than 100 nM (Evaluation 2). Table 69 shows the results of Evaluation 2 when the compounds obtained in Examples were used as test compounds. Table 69 also shows the results obtained using apremilast or crisaborole as the test compound. Note that, in Table 69, "100<" indicates that the measurement result obtained by measuring the PDE4 inhibitory activity (concentration for the inhibition rate of 50%) was 100 nM or more.

TABLE 57

| Test compound | PDE4 Inhibitory Activity | Test compound | PDE4 Inhibitory Activity | Test compound | PDE4 Inhibitory Activity |
|---|---|---|---|---|---|
| Example 1 | A | Example 13 | A | Example 25 | A |
| Example 2 | A | Example 14 | B | Example 26 | A |
| Example 3 | A | Example 15 | A | Example 27 | A |
| Example 4 | A | Example 16 | A | Example 28 | A |
| Example 5 | A | Example 17 | A | Example 29 | A |
| Example 6 | A | Example 18 | B | Example 30 | A |
| Example 7 | A | Example 19 | A | Example 31 | A |
| Example 8 | A | Example 20 | A | Example 32 | A |
| Example 9 | A | Example 21 | A | Example 33 | A |
| Example 10 | A | Example 22 | A | Example 34 | A |
| Example 11 | A | Example 23 | B | Example 35 | B |
| Example 12 | A | Example 24 | A | Example 36 | A |

TABLE 58

| Test compound | PDE4 Inhibitory Activity | Test compound | PDE4 Inhibitory Activity | Test compound | PDE4 Inhibitory Activity |
|---|---|---|---|---|---|
| Example 37 | A | Example 49 | B | Example 61 | A |
| Example 38 | A | Example 50 | A | Example 62 | A |
| Example 39 | A | Example 51 | A | Example 63 | A |
| Example 40 | A | Example 52 | A | Example 64 | A |
| Example 41 | A | Example 53 | A | Example 65 | A |
| Example 42 | A | Example 54 | A | Example 66 | A |
| Example 43 | A | Example 55 | A | Example 67 | A |
| Example 44 | A | Example 56 | A | Example 68 | A |
| Example 45 | A | Example 57 | A | Example 69 | A |
| Example 46 | A | Example 58 | A | Example 70 | A |
| Example 47 | A | Example 59 | A | Example 71 | A |
| Example 48 | A | Example 60 | A | Example 72 | A |

TABLE 59

| Test compound | PDE4 Inhibitory Activity | Test compound | PDE4 Inhibitory Activity | Test compound | PDE4 Inhibitory Activity |
|---|---|---|---|---|---|
| Example 73 | A | Example 85 | A | Example 97 | A |
| Example 74 | A | Example 86 | A | Example 98 | A |
| Example 75 | A | Example 87 | A | Example 99 | A |
| Example 76 | A | Example 88 | B | Example 100 | A |
| Example 77 | A | Example 89 | A | Example 101 | A |
| Example 78 | A | Example 90 | B | Example 102 | A |
| Example 79 | A | Example 91 | C | Example 103 | A |
| Example 80 | A | Example 92 | C | Example 104 | A |
| Example 81 | A | Example 93 | B | Example 105 | A |
| Example 82 | A | Example 94 | A | Example 106 | A |
| Example 83 | A | Example 95 | A | Example 107 | B |
| Example 84 | A | Example 96 | A | Example 108 | A |

TABLE 60

| Test compound | PDE4 Inhibitory Activity |
|---|---|
| Example 109 | A |
| Example 110 | A |
| Example 111 | A |
| Example 112 | A |
| Example 113 | A |
| Example 114 | A |
| Example 115 | A |
| Example 116 | A |
| Example 117 | A |
| Example 118 | A |
| Example 119 | A |
| Example 120 | A |
| Example 121 | A |
| Example 122 | A |
| Example 123 | A |
| Example 124 | A |
| Example 125 | A |
| Example 126 | A |
| Example 127 | A |
| Example 128 | A |
| Example 129 | A |
| Example 130 | A |
| Example 131 | A |
| Example 132 | A |
| Example 133 | A |
| Example 134 | A |
| Example 135 | A |
| Example 136 | A |
| Example 137 | A |
| Example 138 | A |
| Example 139 | A |
| Example 140 | A |
| Example 141 | A |
| Example 142 | A |

TABLE 60-continued

| Test compound | PDE4 Inhibitory Activity |
| --- | --- |
| Example 143 | A |
| Example 144 | A |

TABLE 61

| Test compound | PDE4 Inhibitory Activity |
| --- | --- |
| Example 145 | A |
| Example 146 | A |
| Example 147 | A |
| Example 148 | A |
| Example 149 | A |
| Example 150 | A |
| Example 151 | A |
| Example 152 | A |
| Example 153 | A |
| Example 154 | A |
| Example 155 | A |
| Example 156 | A |
| Example 157 | A |
| Example 158 | B |
| Example 159 | A |
| Example 160 | A |
| Example 161 | A |
| Example 162 | A |
| Example 163 | A |
| Example 164 | A |
| Example 165 | A |
| Example 166 | A |
| Example 167 | A |
| Example 168 | A |
| Example 169 | A |
| Example 170 | A |
| Example 171 | A |
| Example 172 | A |
| Example 173 | A |
| Example 174 | A |
| Example 175 | A |
| Example 176 | A |
| Example 177 | A |
| Example 178 | A |
| Example 179 | A |
| Example 180 | A |

TABLE 62

| Test compound | PDE4 Inhibitory Activity |
| --- | --- |
| Example 181 | A |
| Example 182 | A |
| Example 183 | A |
| Example 184 | A |
| Example 185 | A |
| Example 186 | A |
| Example 187 | A |
| Example 188 | A |
| Example 189 | B |
| Example 190 | C |
| Example 191 | B |
| Example 192 | A |
| Example 193 | A |
| Example 194 | B |
| Example 195 | A |
| Example 196 | A |
| Example 197 | A |
| Example 198 | A |
| Example 199 | A |
| Example 200 | A |
| Example 201 | A |

TABLE 62-continued

| Test compound | PDE4 Inhibitory Activity |
| --- | --- |
| Example 202 | A |
| Example 203 | A |
| Example 204 | A |
| Example 205 | A |
| Example 206 | A |
| Example 207 | A |
| Example 208 | A |
| Example 209 | A |
| Example 210 | A |
| Example 211 | A |
| Example 212 | A |
| Example 213 | A |
| Example 214 | A |
| Example 215 | A |
| Example 216 | A |

TABLE 63

| Test compound | PDE4 Inhibitory Activity |
| --- | --- |
| Example 217 | A |
| Example 218 | A |
| Example 219 | A |
| Example 220 | A |
| Example 221 | A |
| Example 222 | A |
| Example 223 | A |
| Example 224 | A |
| Example 225 | A |
| Example 226 | A |
| Example 227 | A |
| Example 228 | A |
| Example 229 | A |
| Example 230 | A |
| Example 231 | A |
| Example 232 | A |
| Example 233 | A |
| Example 234 | A |
| Example 235 | A |
| Example 236 | A |
| Example 237 | A |
| Example 238 | A |
| Example 239 | A |
| Example 240 | A |
| Example 241 | A |
| Example 242 | A |
| Example 243 | A |
| Example 244 | A |
| Example 245 | A |
| Example 246 | A |
| Example 247 | A |
| Example 248 | A |
| Example 249 | A |
| Example 250 | A |
| Example 251 | A |
| Example 252 | A |

TABLE 64

| Test compound | PDE4 Inhibitory Activity |
| --- | --- |
| Example 253 | A |
| Example 254 | A |
| Example 255 | A |
| Example 256 | A |
| Example 257 | A |
| Example 258 | A |
| Example 259 | A |
| Example 260 | A |
| Example 261 | A |

TABLE 64-continued

| Test compound | PDE4 Inhibitory Activity |
|---|---|
| Example 262 | A |
| Example 263 | A |
| Example 264 | A |
| Example 265 | A |
| Example 266 | A |
| Example 267 | A |
| Example 268 | A |
| Example 269 | A |
| Example 270 | A |
| Example 271 | A |
| Example 272 | A |
| Example 273 | A |
| Example 274 | A |
| Example 275 | A |
| Example 276 | A |
| Example 277 | A |
| Example 278 | A |
| Example 279 | A |
| Example 280 | A |
| Example 281 | A |
| Example 282 | A |
| Example 283 | A |
| Example 284 | A |
| Example 285 | A |
| Example 286 | A |
| Example 287 | A |
| Example 288 | A |

TABLE 65

| Test compound | PDE4 Inhibitory Activity |
|---|---|
| Example 289 | A |
| Example 290 | A |
| Example 291 | A |
| Example 292 | A |
| Example 293 | A |
| Example 294 | A |
| Example 295 | A |
| Example 296 | A |
| Example 297 | A |
| Example 298 | A |
| Example 299 | A |
| Example 300 | A |
| Example 301 | A |
| Example 302 | A |
| Example 303 | A |
| Example 304 | A |
| Example 305 | A |
| Example 306 | B |
| Example 307 | A |
| Example 308 | A |
| Example 309 | A |
| Example 310 | A |
| Example 311 | A |
| Example 312 | A |
| Example 313 | A |
| Example 314 | A |
| Example 315 | A |
| Example 316 | A |
| Example 317 | A |
| Example 318 | A |
| Example 319 | A |
| Example 320 | A |
| Example 321 | A |
| Example 322 | A |
| Example 323 | A |
| Example 324 | A |

TABLE 66

| Test compound | PDE4 Inhibitory Activity |
|---|---|
| Example 325 | A |
| Example 326 | A |
| Example 327 | A |
| Example 328 | A |
| Example 329 | A |
| Example 330 | A |
| Example 331 | A |
| Example 332 | A |
| Example 333 | B |
| Example 334 | A |
| Example 335 | A |
| Example 336 | A |
| Example 337 | A |
| Example 338 | A |
| Example 339 | A |
| Example 340 | A |
| Example 341 | A |
| Example 342 | A |
| Example 343 | A |
| Example 344 | A |
| Example 345 | A |
| Example 346 | A |
| Example 347 | A |
| Example 348 | A |
| Example 349 | A |
| Example 350 | A |
| Example 351 | A |
| Example 352 | A |
| Example 353 | A |
| Example 354 | A |
| Example 355 | A |
| Example 356 | B |
| Example 357 | A |
| Example 358 | A |
| Example 359 | B |
| Example 360 | B |

TABLE 67

| Test compound | PDE4 Inhibitory Activity |
|---|---|
| Example 361 | A |
| Example 362 | A |
| Example 363 | A |
| Example 364 | A |
| Example 365 | A |
| Example 366 | B |
| Example 367 | A |
| Example 368 | B |
| Example 369 | A |
| Example 370 | A |
| Example 371 | A |
| Example 372 | A |
| Example 373 | A |
| Example 374 | A |
| Example 375 | A |
| Example 376 | A |
| Example 377 | A |
| Example 378 | B |
| Example 379 | A |
| Example 380 | A |
| Example 381 | C |
| Example 382 | A |
| Example 383 | C |
| Example 384 | C |
| Example 385 | A |
| Example 386 | A |
| Example 387 | A |
| Example 388 | A |
| Example 389 | A |
| Example 390 | A |
| Example 391 | A |
| Example 392 | A |

TABLE 67-continued

| Test compound | PDE4 Inhibitory Activity |
|---|---|
| Example 393 | A |
| Example 394 | B |
| Example 395 | A |
| Example 396 | A |

TABLE 68

| Test compound | PDE4 Inhibitory Activity |
|---|---|
| Example 397 | A |
| Example 398 | A |
| Example 399 | A |
| Example 400 | A |
| Example 401 | A |
| Example 402 | A |
| Example 403 | A |
| Example 404 | A |
| Example 405 | A |
| Example 406 | A |
| Example 407 | A |
| Example 408 | A |
| Example 409 | A |
| Example 410 | A |
| Example 411 | A |
| Example 412 | A |
| Example 413 | A |
| Example 414 | A |
| Example 415 | A |

TABLE 69

| Example | PDE4 Inhibitory Activity (Evaluation 2) |
|---|---|
| Example 3 | AA |
| Example 4 | AB |
| Example 25 | AA |
| Example 29 | AB |
| Example 30 | AA |
| Example 32 | AB |
| Example 75 | AB |
| Example 118 | AB |
| Example 119 | AA |
| Example 120 | AB |
| Example 176 | AB |
| Example 177 | AB |
| Example 195 | AA |
| Example 198 | AA |
| Example 199 | AB |
| Example 203 | AB |
| Example 208 | AB |
| Example 212 | AA |
| Example 234 | AA |
| Example 235 | AA |
| Example 248 | AA |
| Example 249 | AA |
| Example 251 | AA |
| Example 252 | AA |
| Example 296 | AB |
| Apremilast | AC |
| Crisaborole | 100< |

(Test Example 2: Evaluation of Hepatic Metabolic Stability (Rat Liver Microsome Method))

Metabolic stability in rat liver microsomes was evaluated by the following method. First, in 100 mM of potassium phosphate buffer solution (pH 7.4), liver microsomes (concentration at reaction: 0.5 mg/mL) and the test substance (concentration at reaction: 1 μM) were preincubated at 37° C. Five minutes later, 100 mM of potassium phosphate buffer (pH 7.4) solution of NADPH (concentration at reaction: 1 mM) was mixed thereto to start the reaction. After a predetermined time passed, acetonitrile was mixed to the reaction mixture to stop the reaction. Here, the reaction time was 0 and 30 minutes, and drug concentration measurement was performed for each time period using LC-MS. The % remaining value of the test compound was calculated from the value for 0 minutes and the value for 30 minutes, using the calculation formula below:

% Remaining=(Value for 30 Minutes/Value for 0 Minutes)×100

The results of measuring the rat liver microsome metabolic Stability (% remaining for 30-minute reaction) for the test compound by the above method were evaluated in accordance with the following evaluated basis; A: a % remaining rate of 75% or more, B: 60% or more and less than 75%, C: 45% or more and less than 60%, and D: less than 45%. The Table 70 shows the results when the compounds obtained in each example were used as test compounds.

TABLE 70

| Test compound | Residual ratio |
|---|---|
| Example 3 | B |
| Example 5 | B |
| Example 8 | A |
| Example 10 | A |
| Example 12 | B |
| Example 17 | B |
| Example 29 | B |
| Example 104 | B |
| Example 230 | A |
| Example 231 | A |
| Example 248 | A |
| Example 249 | B |
| Example 251 | A |
| Example 252 | A |
| Example 254 | A |
| Example 259 | A |
| Example 285 | A |
| Example 294 | A |
| Example 304 | A |
| Example 306 | A |
| Example 315 | A |
| Example 316 | A |
| Example 317 | A |
| Example 318 | B |
| Example 319 | A |
| Example 321 | A |
| Example 322 | A |
| Example 323 | B |
| Example 324 | A |
| Example 325 | A |
| Example 326 | A |
| Example 327 | B |
| Example 328 | A |
| Example 329 | A |
| Example 330 | A |
| Example 331 | B |
| Example 332 | A |
| Example 333 | B |
| Example 334 | B |
| Example 335 | A |
| Example 336 | B |
| Example 337 | B |
| Example 338 | A |
| Example 339 | B |
| Example 340 | A |
| Example 341 | A |
| Example 342 | B |

TABLE 70-continued

| Test compound | Residual ratio |
|---|---|
| Example 343 | B |
| Example 346 | A |
| Example 347 | A |
| Example 348 | B |
| Example 349 | A |
| Example 350 | A |
| Example 352 | A |
| Example 353 | A |
| Example 354 | A |
| Example 355 | A |
| Example 356 | A |
| Example 357 | A |
| Example 358 | A |
| Example 359 | A |
| Example 360 | A |
| Example 363 | A |
| Example 364 | A |
| Example 365 | A |
| Example 369 | B |
| Example 370 | A |
| Example 372 | B |
| Example 373 | B |
| Example 374 | B |
| Example 376 | A |
| Example 382 | B |
| Example 385 | A |
| Example 387 | A |
| Example 391 | B |
| Example 392 | B |
| Example 394 | A |
| Example 395 | B |
| Example 397 | A |
| Example 399 | B |
| Example 400 | B |
| Example 401 | A |
| Example 404 | B |
| Example 405 | B |
| Example 409 | B |
| Example 410 | A |
| Example 411 | A |
| Example 412 | A |
| Example 413 | A |

Using the compounds obtained in Examples as test compounds, the anti-inflammatory effects, anti-autoimmune effects, anti-fibrotic effects, and anti-cancer effects of the therapeutic agents containing the test compounds were evaluated by the following Test Examples 3 to 12.

(Test Example 3: Evaluation of Cytokine (TNFα, IL-17A, IL-4, and IL-5) Suppression Using Whole Human Blood)

The test compound dissolved in dimethyl sulfoxide was added to a 96-well plate, and RPMI-1640 medium and human peripheral blood containing sodium heparin were added, followed by culture at 37° C. under 5% $CO_2$ for 1 hour. A medium containing only dimethyl sulfoxide instead of the test compound was added to the control well. To each well, lipopolysaccharide (final concentration 10 ng/mL) as a TNFα production stimulant, or phytohaemagglutinin (final concentration 20 μg/mL) as an IL-17A production stimulant, or CytoStim reagent (1/100 concentration) and CD28 antibody (final concentration 2.5 ng/mL) as an IL-4 production stimulant and an IL-5 production stimulant were added, followed by culture at 37° C. under 5% $CO_2$. The culture was carried out for about 18 hours for the evaluation of the amount of TNFα, and for about 48 hours for the evaluation of the amounts of IL-17A, IL-4, and IL-5.

After collecting the culture supernatant after culturing, the amount of each cytokine was measured by the sandwich ELISA method. The cytokine production suppression rate (inhibition rate) by the test compound was calculated by the following formula from the cytokine production amount when the test compound was added, with the cytokine production amount for the control well as 100%.

Inhibition Rate={1−(Cytokine Amount at Addition of Each Test Compound)/(Cytokine Amount for Control Well)}×100

In addition, the cytokine inhibitory activity (concentration for the inhibition rate of 50%) of the test compound was calculated from the inhibition curves based on the inhibition rates for various concentrations of the test compound.

The measurement results obtained by measuring the TNFα inhibitory activity and IL-5 inhibitory activity (50% inhibitory concentration) of the test compounds by the above method were evaluated in accordance with the following evaluated basis; A: less than 100 nM, B: 100 nM or more and less than 500 nM, and C: 500 nM or more. In addition, the measurement results obtained by measuring the IL-17A inhibitory activity and IL-4 inhibitory activity (50% inhibitory concentration) of the test compounds were evaluated in accordance with the following evaluated basis; A: less than 500 nM, B: 500 nM or more and less than 5000 nM, and C: 5000 nM or more.

(Test Example 4: Evaluation of Cytokine (TNFα, IL-17A, IL-23, IL-4, IL-5, and IL-13) Suppression Using Human Peripheral Blood Mononuclear Cells)

First, peripheral blood mononuclear cells (PBMC) were separated from whole blood by specific gravity centrifugation. Then, the isolated peripheral blood mononuclear cells were added to RPMI-1640 medium (containing 10% fetal bovine serum, penicillin, streptomycin, L-glutamine, and 2-mercaptoethanol), and cultured in a 96-well plate at 37° C. under 5% $CO_2$ for 0 to 1 hour. The test compound dissolved in dimethyl sulfoxide was added to each well, followed by further culture at 37° C. under 5% $CO_2$ for 1 hour. A medium containing only dimethyl sulfoxide instead of the test compound was added to the control well. To each well, lipopolysaccharide (final concentration 1 ng/mL) as a TNFα production stimulant and an IL-23 production stimulant, or concanavalin A (final concentration 20 μg/mL) as an IL-17A production stimulant was added, followed by culture at 37° C. under 5% $CO_2$. In addition, as IL-4 production stimulus, IL-5 production stimulus, and IL-13 production stimulus, PBMC was seeded on a 96-well plate previously coated with a CD3 antibody (final concentration 3 μg/mL), and a CD28 antibody (final concentration 5 ng/mL) was added. The culture was carried out for about 18 hours for the evaluation of the amounts of TNFα and IL-23, and about 48 hours for the evaluation of the amounts of IL-17A, IL-4, IL-5, and IL-13. After collecting the culture supernatant after culturing, the amount of each cytokine was measured by the sandwich ELISA method in the same manner as in Test Example 3, and the cytokine production suppression rate (inhibition rate) and the cytokine inhibitory activity (concentration for the inhibition rate of 50%) of each test compound were calculated.

The measurement results obtained by measuring the TNFα inhibitory activity and IL-5 inhibitory activity (50% inhibitory concentration) of the test compounds by the above method were evaluated in accordance with the following evaluated basis; A: less than 10 nM, B: 10 nM or more and less than 100 nM, and C: 100 nM or more. In addition, the measurement results obtained by measuring the IL-17A inhibitory activity, IL-23 inhibitory activity, IL-4 inhibitory activity, and IL-13 inhibitory activity (50% inhibitory concentration) of the test compounds were evaluated in accordance with the following evaluated basis; A: less than 500 nM, B: 500 nM or more and less than 5000 nM, and C: 5000 nM or more.

(Test Example 5: Evaluation of Cytokine (TNFα, IL-17A, IL-5, IL-13) Suppression Using Human T Cells)

First, CD3-positive T cells were separated from whole blood by a magnetic bead method using an EasySep cell separation kit. Separated T cells suspended in RPMI-1640 medium were seeded on a 96-well plate previously coated with CD3 antibody (final concentration 3 µg/mL). Further, CD28 antibody (final concentration 5 ng/mL) was added as an IL-5 production stimulus and an IL-13 production stimulus. A test compound dissolved in dimethyl sulfoxide was added to each well, followed by culture at 37° C. under 5% $CO_2$. The culture was carried out for about 18 hours for the evaluation of the amount of TNFα, and for about 48 hours for the evaluation of the amounts of IL-17A, IL-5, and IL-13. A medium containing only dimethyl sulfoxide instead of the test compound was added to the control well. The amount of each cytokine was measured in the same manner as in Test Example 3, and the cytokine production suppression rate (inhibition rate) and the cytokine inhibitory activity (concentration for the inhibition rate of 50%) of each test compound were calculated.

The measurement results obtained by measuring the TNFα inhibitory activity (50% inhibitory concentration) of the test compounds by the above method were evaluated in accordance with the following evaluated basis; A: less than 10 nM, B: 10 nM or more and less than 100 nM, and C: 100 nM or more. In addition, the measurement results obtained by measuring the IL-17A inhibitory activity, IL-5 inhibitory activity, and IL-13 inhibitory activity (50% inhibitory concentration) of the test compounds were evaluated in accordance with the following evaluated basis; A: less than 500 nM, B: 500 nM or more and less than 5000 nM, and C: 5000 nM or more.

The results of the TNFα inhibitory activity obtained in Test Examples 3 to 5 are shown in Table 71. Note that Table 71 also shows the results obtained by using apremilast or crisaborole as the test compound. In addition, Table 72 shows the results of each IL inhibitory activity obtained in Test Examples 3 to 5 using the compound obtained in Example 248 as the test compound. Table 72 also shows the results obtained using apremilast as the test compound.

TABLE 71

| | TNFα Inhibitory Activity | | |
|---|---|---|---|
| Example | Human Whole Blood (Test Example 3) | Human PBMC (Test Example 4) | Human T-Cell (Test Example 5) |
| Example 29 | A | — | — |
| Example 118 | B | — | — |
| Example 119 | A | A | — |
| Example 176 | B | — | — |
| Example 195 | B | — | — |
| Example 198 | B | — | — |
| Example 248 | A | A | A |
| Example 249 | A | — | — |
| Example 251 | A | — | — |
| Example 252 | A | A | — |

TABLE 71-continued

| | TNFα Inhibitory Activity | | |
|---|---|---|---|
| Example | Human Whole Blood (Test Example 3) | Human PBMC (Test Example 4) | Human T-Cell (Test Example 5) |
| Apremilast | C | B | C |
| Crisaborole | — | C | — |

TABLE 72

| | Human Whole Blood (Test Example 3) | | Human PBMC (Test Example 4) | | Human T-Cell (Test Example 5) | |
|---|---|---|---|---|---|---|
| Inhibitory Activity | Example 248 | Apremilast | Example 248 | Apremilast | Example 248 | Apremilast |
| IL-17A | A | C | A | B | A | B |
| IL-23 | — | — | A | C | — | — |
| IL-4 | A | C | A | C | — | — |
| IL-5 | A | C | A | C | A | C |
| IL-13 | — | — | A | C | A | B |

Test Example 6: Evaluation of TGF-β Inhibitory Activity

The TGF-β inhibitory activity was measured using THP1 cells as follows. First, THP1 cells were seeded on a 24-well culture plate at $1 \times 10^3$ cells/well, and culture was carried out overnight at 37° C. and 5% $CO_2$ in RPMI-1640 medium (containing 10% fetal bovine serum, penicillin, and streptomycin) supplemented with 100 nM phorbol myristate acetate. After that, the cells were differentiated into macrophages by changing to RPMI-1640 medium without phorbol myristate acetate, followed by further culture at 37° C. under 5% $CO_2$ overnight. Next, the THP1 culture plate was washed once with PBS(−) 1 mL/well, and then the test compound and lipopolysaccharide (final concentration 1 µg/mL) were added, followed by culture at 37° C. under 5% $CO_2$ for about 7 hours. After culturing, the entire amount of the medium was collected, and the amount of TGF-β in the centrifuged supernatant was quantified by the sandwich ELISA method. The non-addition of lipopolysaccharide was used as a blank, and the control was obtained by adding only dimethyl sulfoxide instead of the test compound, and the inhibition rate of the test compound against the control was calculated by the following formula.

Inhibition Rate (%)={1−(Value at Addition of Each Test Compound−Blank Value)/(Control Value−Blank Value)}×100

In addition, the TGF-β inhibitory activity (concentration for the inhibition rate of 50%) of the test compound was calculated from the inhibition curves based on the inhibition rate for various concentrations of the test compound.

The measurement results obtained by measuring the TFG-β inhibitory activity (50% inhibitory concentration) of the test compounds by the above method were evaluated in accordance with the following evaluated basis; A: less than 1 µM, and B: 1 µM or more. The results are shown in Table 73. Table 73 also shows the results obtained by using apremilast as the test compound.

TABLE 73

| Example | TFG-β Inhibitory Activity (Test Example 6) |
| --- | --- |
| Example 3 | A |
| Example 4 | A |
| Example 25 | A |
| Example 29 | A |
| Example 30 | A |
| Example 32 | A |
| Example 75 | A |
| Example 120 | A |
| Example 177 | A |
| Example 195 | A |
| Example 199 | A |
| Example 203 | A |
| Example 248 | A |
| Apremilast | B |

Test Example 7: Evaluation of Antitumor Activity

As antitumor activity, 50% growth inhibitory concentration of various cancer cells (CEM-C1 (blood cancer (leukemia)), SU-DHL-4 (blood cancer (lymphoma)), A549 (lung cancer), HCT-116 (colorectal cancer), and Daoy (brain tumor)) was calculated as follows. First, each of the above cancer cells was seeded on a 384-well plate and cultured overnight at 37° C. under 5% $CO_2$. After that, the test compound was added at various concentrations on the next day, and each number of cells was measured after culturing for 5 days. The 50% growth inhibitory concentration was defined as the test compound concentration at which the number of cells measured is an intermediate value between the number of cells after culture for 5 days under the same conditions without the addition of the test compound and the number of cells at the time of seeding (before the start of culture). The measurement results obtained by measuring the 50% growth inhibitory concentration of the test compound by the above method were evaluated in accordance with the following evaluated basis; A: less than 10 μM, B: 10 μM or more and less than 50 μM, and C: 50 μM or more. As a result of using apremilast as the test compound, the evaluation was C in all cancer cells. On the other hand, as a result of using the compound obtained in Example 248 as the test compound, the evaluation was A in all cancer cells.

(Test Example 8: Hapten Repeated Application Mouse Chronic Dermatitis Model (Oral, Topical))

Evaluation was carried out using female BALB/c mice (7 to 8 weeks of age). First, the hair of the abdomen of the mice was treated with a hair clipper, and then 150 μL of a 3% oxazolone acetone/ethanol solution was applied to the abdomen as a hapten. One week later, 20 μL/ear of 1% oxazolone acetone/ethanol solution was applied to the outer surface of the auricle of both ears of the mice 3 times/week to induce inflammation. A 1% oxazolone-acetone/ethanol solution was applied every other day for 10 days from 1 week after the start of inflammation induction. In addition, for 10 days from 1 week after the start of inflammation induction, the test compound suspended in 0.5% w/v methylcellulose (0.5% MC) was orally administered at 0.3 to 10 mg/kg twice a day (10 μL/g), or 20 μL of a 0.3 to 3% test compound dissolved in an acetone/ethanol solution was applied once or twice a day (topical administration). A 1% oxazolone was not applied to the blank. The control was one in which 1% oxazolone was applied and only 0.5% MC was orally administered without using the test compound, or only an acetone/ethanol solution was applied.

After administration for 10 days, auricle thickness was measured using a dial thickness gauge, and the changes in auricular thickness before the treatment (immediately before the start of administration of the test compound) and after the treatment (after the administration of the test compound for 10 days) were used to calculate the edema suppression rate by the following formula.

Edema Suppression Rate (%)={1−(Auricle Thickness After Treatment by Test Compound−Auricle Thickness Before Treatment by Test Compound)/(Auricle Thickness After Treatment of Control−Auricle Thickness Before Treatment of Control)}×100

The measurement results obtained by measuring the edema suppression rate at the time of oral administration of each test compound by the above method were evaluated in accordance with the following evaluated basis; A: 70% or more, B: 40% or more and less than 70%, and C: less than 40%. In addition, the measurement results obtained by measuring the edema suppression rate at the time of topical administration of each test compound were evaluated in accordance with the following evaluated basis; A: 100% or more, B: 70% or more and less than 100%, and C: less than 70%. The results are shown in Table 74. Table 74 also shows the results obtained by using apremilast or crisaborole as the test compound.

TABLE 74

| Test Compound | Mouse Chronic Dermatitis Model (Test Example 8) | |
| --- | --- | --- |
| | Oral | Topical |
| Example 29 | A | A |
| Example 118 | B | — |
| Example 119 | A | — |
| Example 120 | B | — |
| Example 176 | B | — |
| Example 195 | B | — |
| Example 199 | B | — |
| Example 203 | B | — |
| Example 208 | B | — |
| Example 212 | B | — |
| Example 234 | A | — |
| Example 235 | A | — |
| Example 248 | A | A |
| Example 249 | B | — |
| Example 251 | B | A |
| Example 252 | A | A |
| Example 296 | A | — |
| Apremilast | B | — |
| Crisaborole | — | C |

Test Example 9: Histamine-Induced Mouse Vascular Hyperpermeability Model

Evaluation was carried out using male Crl:CD1 (ICR) mice (6 to 7 weeks of age). First, before conducting the test, the hair on the back of the mice was shaved with a small hair clipper under isoflurane anesthesia (an appropriate amount of about 3% with an inhalation isoflurane anesthesia machine). Next, the mice were orally administered with 10 mg/kg (10 mL/kg) of the test compound dissolved or suspended in 0.5% w/v methylcellulose (0.5% MC), and intravenously administered with 0.4% Evans blue saline (10 mL/kg) after 1 to 4 hours, and approximately 2 minutes later, 15 mM histamine saline was intradermally administered to the dorsal neck as a vascular hyperpermeability substance (20 μL/site). To the non-vascular permeability group (hereinafter, the blank group) and the vascular permeability non-treatment group (hereinafter, the control group), 0.5% MC was orally administered. In addition, in the blank group, saline containing no histamine was intradermally administered. Then, after 30 minutes, the tissues of the evaluation target site were collected, and the tissues were cut into 3×3 cm, added with 1 mL of 1 M potassium hydroxide, and were allowed to stand at 37° C. overnight. After that, 380 μL of 6 N phosphoric acid, 5 mL of acetone, and 2.5 mL of water were added, mixed well, and centrifuged. The absorption value (620/670 nm) of the supernatant after centrifugation was measured with a plate reader, and the average absorption value of the blank group was subtracted therefrom. Using the resultant as the absorption value of each tissue lysate, the vascular permeability suppression rate was calculated by the following formula.

Vascular Permeability Suppression Rate (%)={1−
(Value at Addition of Each Test Compound−
Blank Value)/(Control Value−Blank Value)}×
100

The measurement results obtained by measuring the vascular permeability suppression rate of the test compound by the above method were evaluated in accordance with the following evaluated basis; A: 90% or more, B: 80% or more and less than 90%, and C: less than 80%. As a result of using apremilast as the test compound, the evaluation was C. On the other hand, as a result of using the compound obtained in Example 248 as the test compound, the evaluation was A.

Test Example 10: Mouse CIA (Arthritis) Model

Evaluation was carried out using male DBA-1 JNCrlj mice (6 to 8 weeks of age). First, 150 μg/0.1 mL of type II collagen (bovine)/ACF emulsion was intradermally administered to the mouse ridge to cause primary sensitization. Twenty-one days later, 100 μg/0.1 mL of type II collagen (bovine)/AIF emulsion was similarly intradermally administered to the ridge to cause secondary sensitization. Note that, in the blank group, saline was intradermally administered to the ridge at the first sensitization and second sensitization. Next, for 10 days from the day of secondary sensitization, 0.1 to 20 mg/kg of the test compound dissolved or suspended in 0.5% w/v methylcellulose (0.5% MC) was orally administered once or twice a day.

The arthritis score of each limb was judged to be 0 to 4 by visual inspection and palpation (0: no symptoms, 1: one finger is red and swollen, 2: two or more fingers or in step is red and swollen, 3: fingers, in step, and heel are red and swollen, 4: movement of joints throughout the limb is poor), and the total of the limbs was used as the individual score, and the average score of the individual group administered with each test compound was calculated and used as the arthritis score. In addition, the foot volume (mL) of the left and right hind limbs was measured using a foot volume measuring device, and the edema rate was calculated by the following formula.

Edema Rate (%)={(Left and Right Added Footpad
Volume After Sensitization−Left and Right
Added Footpad Volume Before Sensitization)/
Left and Right Added Footpad Volume Before
Sensitization}×100

The arthritis score of each test compound on day 31 after the initial sensitization of type II collagen was evaluated by the above method in accordance with the following evaluated basis; A: less than 2, B: 2 or more and less than 3, and C: 3 or more. In addition, the edema rate of each test compound on day 31 after the initial sensitization of type II collagen was evaluated in accordance with the following evaluated basis; A: less than 10%, B: 10% or more and less than 20%, and C: 20% or more. As a result of using apremilast as the test compound, the arthritis score and the edema rate were both evaluated as B. On the other hand, as a result of using the compound obtained in Example 248 as the test compound, the arthritis score and the edema rate were both evaluated as A.

Test Example 11: Mouse Delayed Type Hypersensitivity (DTH) Model (Topical)

Evaluation was carried out using female BALB/c mice (7 to 8 weeks of age). First, the hair of the abdomen of the mice was treated with a hair clipper, and then 150 μL of a 3% oxazolone acetone/ethanol solution was applied to the abdomen as a hapten. Five days later, 20 μL/ear of a 1% oxazolone.acetone/ethanol solution was applied to the outer surface of the auricle of both ears of the mouse to induce inflammation. Thirty minutes after the start of inflammation induction, 20 μL of the test compound dissolved in an acetone/ethanol solution was applied to the auricle. A 1% oxazolone was not applied to the blank. The control was one in which 1% oxazolone was applied and only an acetone/ethanol solution was applied without using the test compound.

The auricle thickness 24 hours after application of the test compound was measured with a dial thickness gauge, and the value obtained by subtracting the blank value was used to calculate the edema suppression rate by the following formula.

Edema Suppression Rate (%)={1−(Value at Addition
of Each Test Compound−Blank Value)/(Control
Value−Blank Value)}×100

The measurement results obtained by measuring the edema suppression rate at the time of topical administration of each test compound by the above method were evaluated in accordance with the following evaluated basis; A: 60% or more, B: 40% or more and less than 60%, and C: less than 40%. The results are shown in Table 75. Table 75 also shows the results obtained using crisaborole as the test compound.

TABLE 75

| Test Compound | Mouse DTH Model (Test Example 11) Topical |
|---|---|
| Example 29 | A |
| Example 248 | A |
| Example 251 | B |
| Example 252 | B |
| Crisaborole | C |

Test Example 12: Mouse Bleomycin Model

Evaluation was carried out using female C57BL/6J mice (7 weeks of age). Bleomycin (BLM) at a concentration of 2 mg/kg was administered oropharyngeally under anesthesia to induce pulmonary fibrosis. Six days after BLM administration, the group was divided into experimental groups so as to achieve a uniform weight loss rate from the BLM administration day. The test compound dissolved or suspended in 0.5% w/v methylcellulose (0.5% MC) was orally administered (10 μL/g) at a concentration of 10 to 100 mg/kg once a day for 14 days from day 7 after the administration of BLM. On day 21 after BLM administration, blood was collected under anesthesia, and the lungs were fixed with a 10% neutral buffered formalin solution and treated for histological examination. To evaluate the degree of fibrosis, the concentration of serum surfactant protein D (SP-D) was measured by the ELISA method. In addition, lung tissue sections were scored and evaluated in accordance with the revised criteria by Aschcroft et al. As a result of using the compound obtained in Example 248 and the idiopathic pulmonary fibrosis therapeutic agent nintedanib as the test compounds, it was confirmed that the compound obtained in Example 248 had a serum SP-D concentration and a pulmonary fibrosis score equal to or lower than those of nintedanib, and was able to suppress the serum SP-D concentration and the pulmonary fibrosis score to levels equal to or lower than those of nintedanib.

Test Example 13: Mouse Pruritus Model

Evaluation was carried out using male ICR mice (5 to 7 weeks of age). A micro magnet was embedded under the skin of both hind limbs of the mice in advance, and the hair on the back of the mouse neck was shaved. On the day of the test, the test compound was dissolved or suspended in 0.5% w/v methylcellulose (0.5% MC) and orally administered. Two hours after administration of the test compound, 50 μL of 300 nM substance P dissolved in saline was intradermally administered to the back of the mouse neck. The blank was a non-pruritus-induced group orally administered with 0.5% MC instead of the test compound and intradermally administered with saline instead of substance P, and the pruritus induction control was a group orally administered with 0.5% MC instead of the test compound. The pruritus measurement system for small animals, MicroAct II, automatically measured pruritus behavior for 30 minutes immediately after intradermal administration. As a result of using the compound obtained in Example 248, apremilast, and a histamine H1 receptor antagonist fexofenadine as the test compounds, the compound obtained in Example 248 suppressed mouse scratching behavior at a lower concentration than apremilast. In addition, fexofenadine did not suppress scratching behavior.

Test Example 14: DSS-Induced Mouse Colitis Model

Evaluation was carried out using male C57BL/6J mice (7 weeks of age). The mice were allowed to freely drink dextran sodium sulfate (DSS) dissolved in water for 5 days, and then allowed to freely drink water for 4 to 5 days. The test compound was dissolved or suspended in 0.5% w/v methylcellulose (0.5% MC) and orally administered once a day from the first day. The blank was a non-inflammation-induced group orally administered with 0.5% MC instead of the test compound and allowed to freely drink water instead of DSS, and the inflammation-induced control was a group orally administered with 0.5% MC instead of the test compound. The colitis inhibitory effect was evaluated by the disease activity index (DAI) score. As a result of using the compound obtained in Example 248 and apremilast as the test compounds, the compound obtained in Example 248 suppressed the DAI score at a lower concentration than that of apremilast.

As shown in Tables 57 to 69, the compounds obtained in Examples 3, 4, 25, 29, 30, 32, 75, 118, 119, 120, 176, 177, 195, 198, 199, 203, 208, 212, 234, 235, 248, 249, 251, 252, and 296 have particularly excellent PDE4 inhibitory activity. In addition, from the results of Test Examples 3 to 7, it was confirmed that these compounds (particularly, the compound obtained in Example 248) exhibited excellent TNFα inhibitory activity, IL-17A inhibitory activity, IL-23 inhibitory activity, IL-4 inhibitory activity, IL-5 inhibitory activity, IL-13 inhibitory activity, TGF-β inhibitory activity, and antitumor activity. Moreover, in vivo studies in mice have confirmed that therapeutic agents containing these compounds are useful as therapeutic agents for the treatment of inflammatory diseases, autoimmune diseases, fibrotic diseases, and cancer diseases, and in particular are useful for the treatment of psoriasis (such as psoriatic arthritis and psoriasis vulgaris), atopic dermatitis, allergic conjunctivitis, asthma, COPD, rheumatoid arthritis, idiopathic pulmonary fibrosis, ulcerative colitis, non-alcoholic steatohepatitis, muscular dystrophy, alopecia areata, vitiligo, hidradenitis suppurativa, lichen planus, colorectal cancer, lung cancer, blood cancer, and brain tumor.

INDUSTRIAL APPLICABILITY

As described above, the present invention makes it possible to provide a therapeutic agent containing a compound having excellent PDE4 inhibitory activity and useful for treating inflammatory diseases, autoimmune diseases, fibrotic diseases, and cancer diseases.

The invention claimed is:
1. A therapeutic agent for treating at least one disease selected from the group consisting of inflammatory diseases, autoimmune diseases, fibrotic diseases, and cancer diseases, comprising: at least one selected from the group consisting of a compound represented by the following general formula (1) and pharmacologically acceptable salts thereof as an active ingredient,

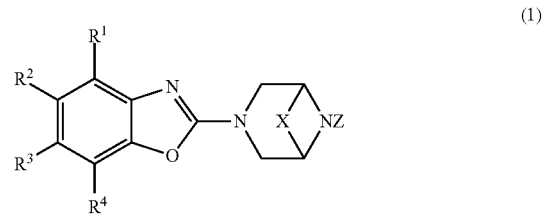

In the formula (1),
$R^1$ and $R^2$ may be the same or different and each represents a hydrogen atom; a halogen atom; a hydroxyl group; a carboxy group; a cyano group; an optionally substituted $C_{1-6}$ alkyl group; an optionally substituted $C_{3-7}$ cycloalkyl group; an optionally substituted $C_{6-10}$ monocyclic or polycyclic aryl group; an optionally substituted $C_{7-11}$ monocyclic or polycyclic aralkyl group; an optionally substituted 4- to 10-membered monocyclic or bicyclic aromatic heterocyclic group containing 1 to 4 heteroatoms selected from an oxygen atom, a nitrogen atom, and a sulfur atom; an optionally substituted 4- to 10-membered monocyclic or bicyclic nonaromatic heterocyclic group containing 1 to 4 heteroatoms selected from an oxygen atom, a nitrogen atom, and a sulfur atom; an optionally substituted di-$C_{1-6}$ alkyl amino group; an optionally substituted $C_{3-7}$ cycloalkyl amino group; an optionally substituted $C_{1-6}$ acylamino group; an optionally substituted $C_{1-6}$ alkyloxy group; an optionally substituted $C_{2-6}$ alkenyloxy group; an optionally substituted $C_{1-6}$ alkyloxy-$C_{1-6}$ alkyl group; an optionally substituted $C_{3-7}$ cycloalkyloxy group; an optionally substituted $C_{6-10}$ monocyclic or polycyclic aryloxy group; an optionally substituted $C_{7-11}$ monocyclic or polycyclic aralkyloxy group; an optionally substituted 4- to 10-membered monocyclic or bicyclic aromatic heterocyclyloxy group containing 1 to 4 heteroatoms selected from an oxygen atom, a nitrogen atom, and a sulfur atom; an optionally substituted 4- to 10-membered monocyclic or bicyclic nonaromatic heterocyclyloxy group containing 1 to 4 heteroatoms selected from an oxygen atom, a nitrogen atom, and a sulfur atom; an optionally substituted $C_{1-6}$ alkylthio group; an optionally substituted $C_{1-6}$ alkylsulfonyl group; an optionally substituted $C_{1-6}$ alkylsulfinyl group; an optionally substituted mono-$C_{1-6}$ alkylsulfamoyl group; an optionally substituted di-$C_{1-6}$ alkylsulfamoyl group wherein two $C_{1-6}$ alkyl groups in the di-$C_{1-6}$ alkylsulfamoyl group may form a pyrrolidin-1-yl group or a morpholino group with an adjacent nitrogen atom; a sulfamoyl group; an optionally substituted $C_{1-6}$ alkylcarbonyl group; an optionally substituted 1-($C_{1-6}$ alkyloxy)imino-$C_{1-6}$ alkyl group; an aminocarbonyl group; an optionally substituted mono-$C_{1-6}$ alkylaminocarbonyl group; an optionally substituted di-$C_{1-6}$ alkylaminocarbonyl group; an optionally substituted $C_{3-7}$ cycloalkylaminocarbonyl group; an optionally substituted $C_{7-11}$ monocyclic or polycyclic aralkylaminocarbonyl group; an optionally substituted $C_{1-6}$ alkyloxycarbonyl group; or an optionally substituted hydroxyaminocarbonyl group;

$R^3$ represents a hydrogen atom;

$R^4$ represents an optionally substituted 4- to 10-membered monocyclic heterocyclic group containing 1 to 4 heteroatoms selected from an oxygen atom, a nitrogen atom, and a sulfur atom;

X represents a group represented by the following formula: —$CH_2$—, —$CH_2$—$CH_2$—, —$CH_2$—$CH_2$—$CH_2$—, or —$CH_2$—O—$CH_2$—, and Z represents a hydrogen atom or a hydroxyl group.

2. The therapeutic agent according to claim 1, wherein the compound represented by the general formula (1) is a compound in which $R^1$ represents a hydrogen atom; a halogen atom; a hydroxyl group; a carboxy group; a cyano group; an optionally substituted $C_{1-6}$ alkyl group; an optionally substituted $C_{3-7}$ cycloalkyl group; an optionally substituted 4- to 10-membered monocyclic aromatic heterocyclic group containing 1 to 4 heteroatoms selected from an oxygen atom, a nitrogen atom, and a sulfur atom; an optionally substituted 4- to 10-membered monocyclic nonaromatic heterocyclic group containing 1 to 4 heteroatoms selected from an oxygen atom, a nitrogen atom, and a sulfur atom; an optionally substituted $C_{1-6}$ acylamino group; an optionally substituted $C_{1-6}$ alkyloxy group; an optionally substituted $C_{1-6}$ alkyloxy-$C_{1-6}$ alkyl group; an optionally substituted $C_{3-7}$ cycloalkyloxy group; an optionally substituted 4- to 10-membered monocyclic aromatic heterocyclyloxy group containing 1 to 4 heteroatoms selected from an oxygen atom, a nitrogen atom, and a sulfur atom; an optionally substituted 4- to 10-membered monocyclic nonaromatic heterocyclyloxy group containing 1 to 4 heteroatoms selected from an oxygen atom, a nitrogen atom, and a sulfur atom; an optionally substituted $C_{1-6}$ alkylthio group; an optionally substituted $C_{1-6}$ alkylsulfonyl group; an optionally substituted $C_{1-6}$ alkylsulfinyl group; an optionally substituted mono-$C_{1-6}$ alkylsulfamoyl group; an optionally substituted di-$C_{1-6}$ alkylsulfamoyl group wherein two $C_{1-6}$ alkyl groups in the di-$C_{1-6}$ alkylsulfamoyl group may form a pyrrolidin-1-yl group or a morpholino group with an adjacent nitrogen atom; a sulfamoyl group; an optionally substituted $C_{1-6}$ alkylcarbonyl group; an optionally substituted 1-($C_{1-6}$ alkyloxy) imino-$C_{1-6}$ alkyl group; an aminocarbonyl group; an optionally substituted mono-$C_{1-6}$ alkylaminocarbonyl group; an optionally substituted di-$C_{1-6}$ alkylaminocarbonyl group; an optionally substituted $C_{3-7}$ cycloalkylaminocarbonyl group; an optionally substituted $C_{7-11}$ monocyclic aralkylaminocarbonyl group; an optionally substituted $C_{1-6}$ alkyloxycarbonyl group; or an optionally substituted hydroxyaminocarbonyl group; and $R^2$ represents a hydrogen atom; a halogen atom; a hydroxyl group; a carboxy group; a cyano group; an optionally substituted $C_{1-6}$ alkyl group; an optionally substituted 4- to 10-membered monocyclic aromatic heterocyclic group containing 1 to 4 heteroatoms selected from an oxygen atom, a nitrogen atom, and a sulfur atom; an optionally substituted 4- to 10-membered monocyclic nonaromatic heterocyclic group containing 1 to 4 heteroatoms selected from an oxygen atom, a nitrogen atom, and a sulfur atom; an optionally substituted $C_{1-6}$ acylamino group; an optionally substituted $C_{1-6}$ alkyloxy group; an optionally substituted $C_{2-6}$ alkenyloxy group; an optionally substituted $C_{1-6}$ alkyloxy-$C_{1-6}$ alkyl group; an optionally substituted $C_{3-7}$ cycloalkyloxy group; an optionally substituted 4- to 10-membered monocyclic aromatic heterocyclyloxy group containing 1 to 4 heteroatoms selected from an oxygen atom, a nitrogen atom, and a sulfur atom; an optionally substituted 4- to 10-membered monocyclic nonaromatic heterocyclyloxy group containing 1 to 4 heteroatoms selected from an oxygen atom, a nitrogen atom, and a sulfur atom; an optionally substituted $C_{1-6}$ alkylthio group; an optionally substituted $C_{1-6}$ alkylsulfonyl group; an optionally substituted $C_{1-6}$ alkylsulfinyl group; an optionally substituted mono-$C_{1-6}$ alkylsulfamoyl group; an optionally substituted di-$C_{1-6}$ alkylsulfamoyl group; a sulfamoyl group; an optionally substituted $C_{1-6}$ alkylcarbonyl group; an optionally substituted 1-($C_{1-6}$ alkyloxy) imino-$C_{1-6}$ alkyl group; an aminocarbonyl group; an optionally substituted mono-$C_{1-6}$ alkylaminocarbonyl group; an optionally substituted di-$C_{1-6}$ alkylaminocarbonyl group; an optionally substituted $C_{3-7}$ cycloalkylaminocarbonyl group; an optionally substituted $C_{7-11}$ monocyclic or polycyclic aralkylaminocarbonyl group; or an optionally substituted $C_{1-6}$ alkyloxycarbonyl group.

3. The therapeutic agent according to claim 1, wherein the compound represented by the general formula (1) is a compound in which $R^1$ represents a hydrogen atom; a halogen atom; a hydroxyl group; a carboxy group; a cyano group; an optionally substituted $C_{1-6}$ alkyl group; an optionally substituted $C_{3-7}$ cycloalkyl group; an optionally substituted 4- to 10-membered monocyclic aromatic heterocyclic group containing 1 to 4 heteroatoms selected from an oxygen atom, a nitrogen atom, and a sulfur atom; an optionally substituted 4- to 10-membered monocyclic nonaromatic heterocyclic group containing 1 to 4 heteroatoms selected from an oxygen atom, a nitrogen atom, and a sulfur atom; an optionally substituted C₁₋₆ acylamino group; an optionally substituted C₁-6 alkyloxy group; an optionally substituted C₁₋₆ alkyloxy-C₁₋₆ alkyl group; an optionally substituted C₃₋₇ cycloalkyloxy group; an optionally substituted 4- to 10-membered monocyclic aromatic heterocyclyloxy group containing 1 to 4 heteroatoms selected from an oxygen atom, a nitrogen atom, and a sulfur atom; an optionally substituted 4- to 10-membered monocyclic nonaromatic heterocyclyloxy group containing 1 to 4 heteroatoms selected from an oxygen atom, a nitrogen atom, and a sulfur atom; an optionally substituted $C_{1-6}$ alkylthio group; an optionally substituted $C_{1-6}$ alkylsulfonyl group; an optionally substituted $C_{1-6}$ alkylsulfinyl group; an optionally substituted mono-$C_{1-6}$ alkylsulfamoyl group; an optionally substituted di-$C_{1-6}$ alkylsulfamoyl group wherein two $C_{1-6}$ alkyl groups in the di-$C_{1-6}$ alkylsulfamoyl group may form a pyrrolidin-1-yl group or a morpholino group with an adjacent nitrogen atom; a sulfamoyl group; an optionally substituted $C_{1-6}$ alkylcarbonyl group; an optionally substituted 1-($C_{1-6}$ alkyloxy) imino-$C_{1-6}$ alkyl group; an aminocarbonyl group; an optionally substituted mono-$C_{1-6}$ alkylaminocarbonyl group; an optionally substituted di-$C_{1-6}$ alkylaminocarbonyl group; an optionally substituted $C_{3-7}$ cycloalkylaminocarbonyl group; an optionally substituted $C_{7-11}$ monocyclic aralkylaminocarbonyl group; an optionally substituted $C_{1-6}$ alkyloxycarbonyl group; or an optionally substituted hydroxyaminocarbonyl group; and $R^2$ represents a hydrogen atom.

4. The therapeutic agent according to claim 1, wherein the compound represented by the general formula (1) is a compound in which $R^1$ represents a hydrogen atom; and $R^2$ represents a hydrogen atom; a halogen atom; a hydroxyl group; a carboxy group; a cyano group; an optionally substituted $C_{1-6}$ alkyl group; an optionally substituted 4- to 10-membered monocyclic aromatic heterocyclic group containing 1 to 4 heteroatoms selected from an oxygen atom, a nitrogen atom, and a sulfur atom; an optionally substituted $C_{1-6}$ acylamino group; an optionally substituted $C_{1-6}$ alkyloxy group; an optionally substituted $C_{2-6}$ alkenyloxy group; an optionally substituted $C_{1-6}$ alkyloxy-$C_{1-6}$ alkyl group; an optionally substituted $C_{3-7}$ cycloalkyloxy group; an optionally substituted 4- to 10-membered monocyclic aromatic heterocyclyloxy group containing 1 to 4 heteroatoms selected from an oxygen atom, a nitrogen atom, and a sulfur atom; an optionally substituted 4- to 10-membered monocyclic nonaromatic heterocyclyloxy group containing 1 to 4 heteroatoms selected from an oxygen atom, a nitrogen atom, and a sulfur atom; an optionally substituted $C_{1-6}$ alkylthio group; an optionally substituted $C_{1-6}$ alkylsulfonyl group; an optionally substituted $C_{1-6}$ alkylsulfinyl group; an optionally substituted mono-$C_{1-6}$ alkylsulfamoyl group; an optionally substituted di-$C_{1-6}$ alkylsulfamoyl group; a sulfamoyl group; an optionally substituted $C_{1-6}$ alkylcarbonyl group; an aminocarbonyl group; an optionally substituted 1-($C_{1-6}$ alkyloxy) imino-$C_{1-6}$ alkyl group; an aminocarbonyl group; an optionally substituted mono-$C_{1-6}$ alkylaminocarbonyl group; an optionally substituted di-$C_{1-6}$ alkylaminocarbonyl group; an optionally substituted $C_{3-7}$ cycloalkylaminocarbonyl group; an optionally substituted $C_{7-11}$ monocyclic or polycyclic aralkylaminocarbonyl group; or an optionally substituted $C_{1-6}$ alkyloxycarbonyl group.

5. The therapeutic agent according to claim 1, wherein the compound represented by the general formula (1) is a compound represented by the following general formula (11),

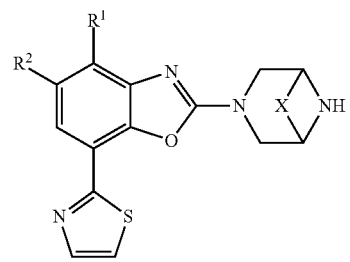

(11)

in the formula (11), $R^1$ represents an optionally substituted $C_{1-6}$ alkyl group; or an optionally substituted $C_{1-6}$ alkyloxy group;

$R^2$ represents a hydrogen atom; a halogen atom; an optionally substituted $C_{1-6}$ alkyl group; or an optionally substituted $C_{1-6}$ alkylcarbonyl group; and X represents a group represented by the following formula: —CH₂—, —CH₂—CH₂—, —CH₂—CH₂—CH₂—, or —CH₂—O—CH₂—.

6. The therapeutic agent according to claim 1, wherein PDE4 inhibitory activity of the at least one selected from the group consisting of the compound represented by the general formula (1) and the pharmacologically acceptable salts thereof is 11 nM or less at a concentration (IC50) that inhibits PDE4 activity by 50%.

7. The therapeutic agent according to claim 1, wherein the compound represented by the general formula (1) is 2-(3,8-diazabicyclo[3.2.1]octan-3-yl)-5-chloro-7-(thiazol-2-yl)-4-(trifluoromethoxy)benzo[d]oxazole;

2-(3,9-diazabicyclo[3.3.1]nonan-3-yl)-5-chloro-7-(thiazol-2-yl)-4-(trifluoromethoxy)benzo[d]oxazole;

2-(3,6-diazabicyclo[3.1.1]heptan-3-yl)-5-chloro-7-(thiazol-2-yl)-4-(trifluoromethoxy)benzo[d]oxazole;

7-(5-chloro-7-(thiazol-2-yl)-4-(trifluoromethoxy)benzo[d]oxazol-2-yl)-3-oxa-7,9-diazabicyclo[3.3.1]nonane;

2-(3,8-diazabicyclo[3.2.1]octan-3-yl)-5-chloro-7-(1H-pyrazol-1-yl)-4-(trifluoromethoxy)benzo[d]oxazole;

2-(3,8-diazabicyclo[3.2.1]octan-3-yl)-5-chloro-7-(furan-2-yl)-4-(trifluoromethoxy)benzo[d]oxazole;

2-(3,8-diazabicyclo[3.2.1]octan-3-yl)-5-chloro-7-(pyridin-2-yl)-4-(trifluoromethoxy)benzo[d]oxazole;

2-(3,8-diazabicyclo[3.2.1]octan-3-yl)-5-chloro-7-(thiazol-4-yl)-4-(trifluoromethoxy)benzo[d]oxazole;

2-(3,8-diazabicyclo[3.2.1]octan-3-yl)-5-chloro-7-(oxazol-2-yl)-4-(trifluoromethoxy)benzo[d]oxazole;

2-(3,8-diazabicyclo[3.2.1]octan-3-yl)-5-chloro-7-(5-fluoropyridin-2-yl)-4-(trifluoromethoxy)benzo[d]oxazole;

2-(3,8-diazabicyclo[3.2.1]octan-3-yl)-5-chloro-7-(pyridin-2-yl)-4-(trifluoromethyl)benzo[d]oxazole;

2-(3,9-diazabicyclo[3.3.1]nonan-3-yl)-5-chloro-7-(pyridin-2-yl)-4-(trifluoromethyl)benzo[d]oxazole;

2-(3,6-diazabicyclo[3.1.1]heptan-3-yl)-5-chloro-7-(pyridin-2-yl)-4-(trifluoromethyl)benzo[d]oxazole;

7-(5-chloro-7-(pyridin-2-yl)-4-(trifluoromethyl)benzo[d]oxazol-2-yl)-3-oxa-7,9-diazabicyclo[3.3.1]nonane;

2-(3,8-diazabicyclo[3.2.1]octan-3-yl)-5-chloro-7-(1H-pyrazol-1-yl)-4-(trifluoromethyl)benzo[d]oxazole;

2-(3,9-diazabicyclo[3.3.1]nonan-3-yl)-5-chloro-7-(1H-pyrazol-1-yl)-4-(trifluoromethyl)benzo[d]oxazole;

2-(3,6-diazabicyclo[3.1.1]heptan-3-yl)-5-chloro-7-(1H-pyrazol-1-yl)-4-(trifluoromethyl)benzo[d]oxazole;
7-(5-chloro-7-(1H-pyrazol-1-yl)-4-(trifluoromethyl)benzo[d]oxazol-2-yl)-3-oxa-7,9-diazabicyclo[3.3.1]nonane;
7-(5-chloro-7-(thiazol-2-yl)-4-(trifluoromethyl)benzo[d]oxazol-2-yl)-3-oxa-7,9-diazabicyclo[3.3.1]nonane;
2-(3,8-diazabicyclo[3.2.1]octan-3-yl)-5-chloro-7-(thiazol-2-yl)-4-(trifluoromethyl)benzo[d]oxazole;
2-(3,8-diazabicyclo[3.2.1]octan-3-yl)-5-isopropyl-7-(thiazol-2-yl)benzo[d]oxazole;
2-(3,6-diazabicyclo[3.1.1]heptan-3-yl)-5-isopropyl-7-(thiazol-2-yl)benzo[d]oxazole;
7-(5-isopropyl-7-(thiazol-2-yl)benzo[d]oxazol-2-yl)-3-oxa-7,9-diazabicyclo[3.3.1]nonane;
2-(3,9-diazabicyclo[3.3.1]nonan-3-yl)-5-isopropyl-7-(thiazol-2-yl)benzo[d]oxazole;
2-(3,8-diazabicyclo[3.2.1]octan-3-yl)-4-methyl-7-(thiazol-2-yl)benzo[d]oxazole;
2-(3,6-diazabicyclo[3.1.1]heptan-3-yl)-4-methyl-7-(thiazol-2-yl)benzo[d]oxazole;
2-(3,9-diazabicyclo[3.3.1]nonan-3-yl)-4-methyl-7-(thiazol-2-yl)benzo[d]oxazole;
2-(3,8-diazabicyclo[3.2.1]octan-3-yl)-7-(thiazol-2-yl)-4-(trifluoromethoxy)benzo[d]oxazole;
2-(3,6-diazabicyclo[3.1.1]heptan-3-yl)-7-(thiazol-2-yl)-4-(trifluoromethoxy)benzo[d]oxazole;
2-(3,9-diazabicyclo[3.3.1]nonan-3-yl)-7-(thiazol-2-yl)-4-(trifluoromethoxy)benzo[d]oxazole;
2-(3,8-diazabicyclo[3.2.1]octan-3-yl)-7-(thiazol-2-yl)-4-(trifluoromethyl)benzo[d]oxazole;
2-(3,6-diazabicyclo[3.1.1]heptan-3-yl)-7-(thiazol-2-yl)-4-(trifluoromethyl)benzo[d]oxazole;
2-(3,9-diazabicyclo[3.3.1]nonan-3-yl)-7-(thiazol-2-yl)-4-(trifluoromethyl)benzo[d]oxazole;
N-(2-(3,9-diazabicyclo[3.3.1]nonan-3-yl)-7-(thiazol-2-yl)benzo[d]oxazol-4-yl)acetamide;
N-(2-(3,6-diazabicyclo[3.1.1]heptan-3-yl)-7-(thiazol-2-yl)benzo[d]oxazol-4-yl)acetamide;
2-(3,8-diazabicyclo[3.2.1]octan-3-yl)-4-chloro-7-(thiazol-2-yl)benzo[d]oxazole;
2-(3,6-diazabicyclo[3.1.1]heptan-3-yl)-4-chloro-7-(thiazol-2-yl)benzo[d]oxazole;
2-(3,9-diazabicyclo[3.3.1]nonan-3-yl)-4-chloro-7-(thiazol-2-yl)benzo[d]oxazole;
2-(3,8-diazabicyclo[3.2.1]octan-3-yl)-5-(methylthio)-7-(thiazol-2-yl)benzo[d]oxazole;
2-(3,6-diazabicyclo[3.1.1]heptan-3-yl)-5-(methylthio)-7-(thiazol-2-yl)benzo[d]oxazole;
2-(3,9-diazabicyclo[3.3.1]nonan-3-yl)-5-(methylthio)-7-(thiazol-2-yl)benzo[d]oxazole;
2-(3,8-diazabicyclo[3.2.1]octan-3-yl)-5-(methylsulfonyl)-7-(thiazol-2-yl)benzo[d]oxazole;
2-(3,6-diazabicyclo[3.1.1]heptan-3-yl)-5-(methylsulfonyl)-7-(thiazol-2-yl)benzo[d]oxazole;
2-(3,9-diazabicyclo[3.3.1]nonan-3-yl)-5-(methylsulfonyl)-7-(thiazol-2-yl)benzo[d]oxazole;
2-(3,8-diazabicyclo[3.2.1]octan-3-yl)-5-(methylsulfinyl)-7-(thiazol-2-yl)benzo[d]oxazole;
2-(3,6-diazabicyclo[3.1.1]heptan-3-yl)-5-(methylsulfinyl)-7-(thiazol-2-yl)benzo[d]oxazole;
2-(3,9-diazabicyclo[3.3.1]nonan-3-yl)-5-(methylsulfinyl)-7-(thiazol-2-yl)benzo[d]oxazole;
N-(2-(3,9-diazabicyclo[3.3.1]nonan-3-yl)-7-(thiazol-2-yl)benzo[d]oxazol-5-yl)acetamide; N-(2-(3,6-diazabicyclo[3.1.1]heptan-3-yl)-7-(thiazol-2-yl)benzo[d]oxazol-5-yl)acetamide;
N-(2-(3,8-diazabicyclo[3.2.1]octan-3-yl)-7-(thiazol-2-yl)benzo[d]oxazol-5-yl)acetamide;
2-(3,8-diazabicyclo[3.2.1]octan-3-yl)-7-(thiazol-2-yl)-5-(trifluoromethyl)benzo[d]oxazole;
2-(3,6-diazabicyclo[3.1.1]heptan-3-yl)-7-(thiazol-2-yl)-5-(trifluoromethyl)benzo[d]oxazole;
2-(3,9-diazabicyclo[3.3.1]nonan-3-yl)-7-(thiazol-2-yl)-5-(trifluoromethyl)benzo[d]oxazole;
2-(3,8-diazabicyclo[3.2.1]octan-3-yl)-7-(thiazol-2-yl)-5-(trifluoromethoxy)benzo[d]oxazole;
2-(3,9-diazabicyclo[3.3.1]nonan-3-yl)-7-(thiazol-2-yl)-5-(trifluoromethoxy)benzo[d]oxazole;
2-(3,6-diazabicyclo[3.1.1]heptan-3-yl)-7-(thiazol-2-yl)-5-(trifluoromethoxy)benzo[d]oxazole;
2-(3,8-diazabicyclo[3.2.1]octan-3-yl)-7-(thiazol-2-yl)benzo[d]oxazole-5-sulfonamide;
2-(3,6-diazabicyclo[3.1.1]heptan-3-yl)-7-(thiazol-2-yl)benzo[d]oxazole-5-sulfonamide;
2-(3,9-diazabicyclo[3.3.1]nonan-3-yl)-7-(thiazol-2-yl)benzo[d]oxazole-5-sulfonamide;
2-(3,8-diazabicyclo[3.2.1]octan-3-yl)-5-methoxy-7-(thiazol-2-yl)benzo[d]oxazole;
2-(3,6-diazabicyclo[3.1.1]heptan-3-yl)-5-methoxy-7-(thiazol-2-yl)benzo[d]oxazole;
2-(3,9-diazabicyclo[3.3.1]nonan-3-yl)-5-methoxy-7-(thiazol-2-yl)benzo[d]oxazole;
2-(3,8-diazabicyclo[3.2.1]octan-3-yl)-7-(thiazol-2-yl)benzo[d]oxazol-5-ol;
2-(3,6-diazabicyclo[3.1.1]heptan-3-yl)-7-(thiazol-2-yl)benzo[d]oxazol-5-ol;
2-(3,9-diazabicyclo[3.3.1]nonan-3-yl)-7-(thiazol-2-yl)benzo[d]oxazol-5-ol;
2-(3,8-diazabicyclo[3.2.1]octan-3-yl)-7-(thiazol-2-yl)-5-(2,2,2-trifluoroethoxy)benzo[d]oxazole;
2-(3,6-diazabicyclo[3.1.1]heptan-3-yl)-7-(thiazol-2-yl)-5-(2,2,2-trifluoroethoxy)benzo[d]oxazole;
2-(3,8-diazabicyclo[3.2.1]octan-3-yl)-5-isopropoxy-7-(thiazol-2-yl)benzo[d]oxazole;
2-(3,8-diazabicyclo[3.2.1]octan-3-yl)-5-(2-methoxyethoxy)-7-(thiazol-2-yl)benzo[d]oxazole;
2-(3,8-diazabicyclo[3.2.1]octan-3-yl)-5-(oxetan-3-ylmethoxy)-7-(thiazol-2-yl)benzo[d]oxazole;
2-(((2-(3,8-diazabicyclo[3.2.1]octan-3-yl)-7-(thiazol-2-yl)benzo[d]oxazol-5-yl)oxy) methyl)propane-1,3-diol;
5-(allyloxy)-2-(3,8-diazabicyclo[3.2.1]octan-3-yl)-7-(thiazol-2-yl)benzo[d]oxazole;
2-((2-(3,8-diazabicyclo[3.2.1]octan-3-yl)-7-(thiazol-2-yl)benzo[d]oxazol-5-yl)oxy)acetonitrile;
2-((2-(3,8-diazabicyclo[3.2.1]octan-3-yl)-7-(thiazol-2-yl)benzo[d]oxazol-5-yl)oxy) acetic acid;
2-(3,8-diazabicyclo[3.2.1]octan-3-yl)-4-methoxy-7-(thiazol-2-yl)benzo[d]oxazole;
2-(3,6-diazabicyclo[3.1.1]heptan-3-yl)-4-methoxy-7-(thiazol-2-yl)benzo[d]oxazole;
2-(3,9-diazabicyclo[3.3.1]nonan-3-yl)-4-methoxy-7-(thiazol-2-yl)benzo[d]oxazole;
2-(3,8-diazabicyclo[3.2.1]octan-3-yl)-7-(thiazol-2-yl)benzo[d]oxazol-4-ol;
2-(3,6-diazabicyclo[3.1.1]heptan-3-yl)-7-(thiazol-2-yl)benzo[d]oxazol-4-ol;
2-(3,9-diazabicyclo[3.3.1]nonan-3-yl)-7-(thiazol-2-yl)benzo[d]oxazol-4-ol;
2-(3,8-diazabicyclo[3.2.1]octan-3-yl)-4-cyclobutoxy-7-(thiazol-2-yl)benzo[d]oxazole;
2-((2-(3,8-diazabicyclo[3.2.1]octan-3-yl)-7-(thiazol-2-yl)benzo[d]oxazol-4-yl)oxy)acetonitrile;

1-((2-(3,8-diazabicyclo[3.2.1]octan-3-yl)-7-(thiazol-2-yl)benzo[d]oxazol-4-yl)oxy)-3-methoxypropan-2-ol;
2-(3,8-diazabicyclo[3.2.1]octan-3-yl)-4-((tetrahydrofuran-3-yl)oxy)-7-(thiazol-2-yl)benzo[d]oxazole;
2-(3,8-diazabicyclo[3.2.1]octan-3-yl)-4,7-di (thiazol-2-yl)benzo[d]oxazole;
ethyl 2-(3,8-diazabicyclo[3.2.1]octan-3-yl)-7-(thiazol-2-yl)benzo[d]oxazole-5-carboxylate;
ethyl 2-(3,6-diazabicyclo[3.1.1]heptan-3-yl)-7-(thiazol-2-yl)benzo[d]oxazole-5-carboxylate;
ethyl 2-(3-oxa-7,9-diazabicyclo[3.3.1]nonan-7-yl)-7-(thiazol-2-yl)benzo[d]oxazole-5-carboxylate;
ethyl 2-(3,9-diazabicyclo[3.3.1]nonan-3-yl)-7-(thiazol-2-yl)benzo[d]oxazole-5-carboxylate;
ethyl 2-(3,8-diazabicyclo[3.2.1]octan-3-yl)-7-(1H-pyrazol-1-yl)benzo[d]oxazole-5-carboxylate;
ethyl 2-(3,6-diazabicyclo[3.1.1]heptan-3-yl)-7-(1H-pyrazol-1-yl)benzo[d]oxazole-5-carboxylate;
ethyl 2-(3-oxa-7,9-diazabicyclo[3.3.1]nonan-7-yl)-7-(1H-pyrazol-1-yl)benzo[d]oxazole-5-carboxylate;
ethyl 2-(3,9-diazabicyclo[3.3.1]nonan-3-yl)-7-(1H-pyrazol-1-yl)benzo[d]oxazole-5-carboxylate;
2-(2-(3,8-diazabicyclo[3.2.1]octan-3-yl)-7-(thiazol-2-yl)benzo[d]oxazol-5-yl)propan-2-ol;
2-(2-(3,6-diazabicyclo[3.1.1]heptan-3-yl)-7-(thiazol-2-yl)benzo[d]oxazol-5-yl)propan-2-ol;
2-(3,6-diazabicyclo[3.1.1]heptan-3-yl)-5-(2-methoxypropan-2-yl)-7-(thiazol-2-yl)benzo[d]oxazole;
2-(3,8-diazabicyclo[3.2.1]octan-3-yl)-5-(2-methoxypropan-2-yl)-7-(thiazol-2-yl)benzo[d]oxazole;
2-(3,8-diazabicyclo[3.2.1]octan-3-yl)-N,N-dimethyl-7-(thiazol-2-yl)benzo[d]oxazole-5-carboxamide;
(2-(3,8-diazabicyclo[3.2.1]octan-3-yl)-7-(thiazol-2-yl)benzo[d]oxazol-5-yl)(morpholino)methanone;
(2-(3,8-diazabicyclo[3.2.1]octan-3-yl)-7-(thiazol-2-yl)benzo[d]oxazol-5-yl)(piperidin-1-yl)methanone;
(2-(3,8-diazabicyclo[3.2.1]octan-3-yl)-7-(thiazol-2-yl)benzo[d]oxazol-5-yl)(azetidin-1-yl)methanone;
N-benzyl-2-(3,8-diazabicyclo[3.2.1]octan-3-yl)-7-(thiazol-2-yl)benzo[d]oxazole-5-carboxamide;
2-(3,8-diazabicyclo[3.2.1]octan-3-yl)-7-(thiazol-2-yl)benzo[d]oxazole-5-carboxamide;
2-(3,8-diazabicyclo[3.2.1]octan-3-yl)-N-methyl-7-(thiazol-2-yl)benzo[d]oxazole-5-carboxamide;
N-(2-(3,8-diazabicyclo[3.2.1]octan-3-yl)-7-(thiazol-2-yl)benzo[d]oxazol-5-yl)-N-methylacetamide;
2-(3,8-diazabicyclo[3.2.1]octan-3-yl)-5-(morpholinomethyl)-7-(thiazol-2-yl)benzo[d]oxazole;
1-(2-(3,8-diazabicyclo[3.2.1]octan-3-yl)-7-(thiazol-2-yl)benzo[d]oxazol-5-yl)-N,N-dimethylmethanamine;
2-(3,8-diazabicyclo[3.2.1]octan-3-yl)-7-(thiazol-2-yl)-5-(1,1,1-trifluoro-2-methoxypropan-2-yl)benzo[d]oxazole;
2-(3,6-diazabicyclo[3.1.1]heptan-3-yl)-7-(thiazol-2-yl)-5-(1,1,1-trifluoro-2-methoxypropan-2-yl)benzo[d]oxazole;
1-(2-(3,8-diazabicyclo[3.2.1]octan-3-yl)-7-(thiazol-2-yl)benzo[d]oxazol-5-yl)ethan-1-one;
1-(2-(3,6-diazabicyclo[3.1.1]heptan-3-yl)-7-(thiazol-2-yl)benzo[d]oxazol-5-yl)ethan-1-one;
1-(2-(3,8-diazabicyclo[3.2.1]octan-3-yl)-7-(thiazol-2-yl)benzo[d]oxazol-5-yl)-2,2-difluoroethan-1-ol;
2-(3,8-diazabicyclo[3.2.1]octan-3-yl)-5-(2,2-difluoro-1-methoxyethyl)-7-(thiazol-2-yl)benzo[d]oxazole;
1-(2-(3,8-diazabicyclo[3.2.1]octan-3-yl)-7-(thiazol-2-yl)benzo[d]oxazol-5-yl)ethan-1-ol;
1-(2-(3,6-diazabicyclo[3.1.1]heptan-3-yl)-7-(thiazol-2-yl)benzo[d]oxazol-5-yl)ethan-1-ol;
2-(3,8-diazabicyclo[3.2.1]octan-3-yl)-5-(1-methoxyethyl)-7-(thiazol-2-yl)benzo[d]oxazole;
2-(3,6-diazabicyclo[3.1.1]heptan-3-yl)-5-(1-methoxyethyl)-7-(thiazol-2-yl)benzo[d]oxazole;
(2-(3,9-diazabicyclo[3.3.1]nonan-3-yl)-7-(thiazol-2-yl)benzo[d]oxazol-4-yl)methanol;
(2-(3,6-diazabicyclo[3.1.1]hepan-3-yl)-7-(thiazol-2-yl)benzo[d]oxazol-4-yl)methanol;
(2-(3,8-diazabicyclo[3.2.1]octan-3-yl)-7-(thiazol-2-yl)benzo[d]oxazol-4-yl)methanol;
ethyl 2-(3,8-diazabicyclo[3.2.1]octan-3-yl)-7-(thiazol-2-yl)benzo[d]oxazole-4-carboxylate;
ethyl 2-(3,6-diazabicyclo[3.1.1]heptan-3-yl)-7-(thiazol-2-yl)benzo[d]oxazole-4-carboxylate;
ethyl 2-(3,9-diazabicyclo[3.3.1]nonan-3-yl)-7-(thiazol-2-yl)benzo[d]oxazole-4-carboxylate;
2-(3,8-diazabicyclo[3.2.1]octan-3-yl)-N,N-dimethyl-7-(thiazol-2-yl)benzo[d]oxazole-4-carboxamide;
(2-(3,8-diazabicyclo[3.2.1]octan-3-yl)-7-(thiazol-2-yl)benzo[d]oxazol-4-yl)(morpholino)methanone;
(2-(3,8-diazabicyclo[3.2.1]octan-3-yl)-7-(thiazol-2-yl)benzo[d]oxazol-4-yl)(piperidin-1-yl)methanone;
1-(2-(3,8-diazabicyclo[3.2.1]octan-3-yl)-7-(thiazol-2-yl)benzo[d]oxazol-4-yl)-2,2,2-trifluoroethan-1-ol;
(R)-1-(2-(3,8-diazabicyclo[3.2.1]octan-3-yl)-7-(thiazol-2-yl)benzo[d]oxazol-4-yl)-2,2,2-trifluoroethan-1-ol;
(S)-1-(2-(3,8-diazabicyclo[3.2.1]octan-3-yl)-7-(thiazol-2-yl)benzo[d]oxazol-4-yl)-2,2,2-trifluoroethan-1-ol;
1-(2-(3,6-diazabicyclo[3.1.1]heptan-3-yl)-7-(thiazol-2-yl)benzo[d]oxazol-4-yl)-2,2,2-trifluoroethan-1-ol;
(R)-1-(2-(3,6-diazabicyclo[3.1.1]heptan-3-yl)-7-(thiazol-2-yl)benzo[d]oxazol-4-yl)-2,2,2-trifluoroethan-1-ol;
(S)-1-(2-(3,6-diazabicyclo[3.1.1]heptan-3-yl)-7-(thiazol-2-yl)benzo[d]oxazol-4-yl)-2,2,2-trifluoroethan-1-ol;
2-(3,6-diazabicyclo[3.1.1]heptan-3-yl)-7-(thiazol-2-yl)-4-(2,2,2-trifluoro-1-methoxyethyl)benzo[d]oxazole;
(R)-2-(3,6-diazabicyclo[3.1.1]heptan-3-yl)-7-(thiazol-2-yl)-4-(2,2,2-trifluoro-1-methoxyethyl)benzo[d]oxazole;
(S)-2-(3,6-diazabicyclo[3.1.1]heptan-3-yl)-7-(thiazol-2-yl)-4-(2,2,2-trifluoro-1-methoxyethyl)benzo[d]oxazole;
1-(2-(3,6-diazabicyclo[3.1.1]heptan-3-yl)-7-(thiazol-2-yl)benzo[d]oxazol-4-yl)-2,2-difluoroethan-1-ol;
2-(2-(3,6-diazabicyclo[3.1.1]heptan-3-yl)-7-(thiazol-2-yl)benzo[d]oxazol-4-yl)-1,1-difluoropropan-2-ol;
(R)-2-(2-(3,6-diazabicyclo[3.1.1]heptan-3-yl)-7-(thiazol-2-yl)benzo[d]oxazol-4-yl)-1,1-difluoropropan-2-ol;
(S)-2-(2-(3,6-diazabicyclo[3.1.1]heptan-3-yl)-7-(thiazol-2-yl)benzo[d]oxazol-4-yl)-1,1-difluoropropan-2-ol;
1-(1-(2-(3,6-diazabicyclo[3.1.1]heptan-3-yl)-7-(thiazol-2-yl)benzo[d]oxazol-4-yl)-2,2-difluoroethoxy)-2-methylpropan-2-ol;
1-(2-(3,8-diazabicyclo[3.2.1]octan-3-yl)-7-(thiazol-2-yl)benzo[d]oxazol-4-yl)-2,2-difluoroethan-1-ol;
2-(2-(3,8-diazabicyclo[3.2.1]octan-3-yl)-7-(thiazol-2-yl)benzo[d]oxazol-4-yl)-1,1-difluoropropan-2-ol;
2-(3,6-diazabicyclo[3.1.1]heptan-3-yl)-4-(2,2-difluoro-1-methoxyethyl)-7-(thiazol-2-yl)benzo[d]oxazole;
2-(3,8-diazabicyclo[3.2.1]octan-3-yl)-4-(2,2-difluoro-1-methoxyethyl)-7-(thiazol-2-yl)benzo[d]oxazole;
1-(2-(3,8-diazabicyclo[3.2.1]octan-3-yl)-7-(thiazol-2-yl)benzo[d]oxazol-4-yl)ethan-1-ol;
1-(2-(3,6-diazabicyclo[3.1.1]heptan-3-yl)-7-(thiazol-2-yl)benzo[d]oxazol-5-yl)-2,2,2-trifluoroethan-1-ol;

1-(2-(3,9-diazabicyclo[3.3.1]nonan-3-yl)-7-(thiazol-2-yl)benzo[d]oxazol-5-yl)-2,2,2-trifluoroethan-1-ol;
1-(2-(3,8-diazabicyclo[3.2.1]octan-3-yl)-7-(thiazol-2-yl)benzo[d]oxazol-5-yl)-2,2,2-trifluoroethan-1-ol;
(R)-1-(2-(3,8-diazabicyclo[3.2.1]octan-3-yl)-7-(thiazol-2-yl)benzo[d]oxazol-5-yl)-2,2,2-trifluoroethan-1-ol;
(S)-1-(2-(3,8-diazabicyclo[3.2.1]octan-3-yl)-7-(thiazol-2-yl)benzo[d]oxazol-5-yl)-2,2,2-trifluoroethan-1-ol;
1-(2-(3,8-diazabicyclo[3.2.1]octan-3-yl)-7-(1H-pyrazol-1-yl)benzo[d]oxazol-5-yl)-2,2,2-trifluoroethan-1-ol;
1-(2-(3,8-diazabicyclo[3.2.1]octan-3-yl)-7-(thiazol-2-yl)benzo[d]oxazol-5-yl)-2,2,2-trifluoroethyl acetate;
2-(3,8-diazabicyclo[3.2.1]octan-3-yl)-7-(thiazol-2-yl)-5-(2,2,2-trifluoro-1-methoxyethyl)benzo[d]oxazole;
(R)-2-(3,8-diazabicyclo[3.2.1]octan-3-yl)-7-(thiazol-2-yl)-5-(2,2,2-trifluoro-1-methoxyethyl)benzo[d]oxazole;
(S)-2-(3,8-diazabicyclo[3.2.1]octan-3-yl)-7-(thiazol-2-yl)-5-(2,2,2-trifluoro-1-methoxyethyl)benzo[d]oxazole;
2-(3,6-diazabicyclo[3.1.1]heptan-3-yl)-7-(thiazol-2-yl)-5-(2,2,2-trifluoro-1-methoxyethyl)benzo[d]oxazole;
2-(3,9-diazabicyclo[3.3.1]nonan-3-yl)-7-(thiazol-2-yl)-5-(2,2,2-trifluoro-1-methoxyethyl)benzo[d]oxazole;
2-(3,8-diazabicyclo[3.2.1]octan-3-yl)-7-(thiazol-2-yl)-5-(2,2,2-trifluoro-1-(2,2,2-trifluoroethoxy)ethyl)benzo[d]oxazole;
2-(3,8-diazabicyclo[3.2.1]octan-3-yl)-7-(thiazol-2-yl)-5-(2,2,2-trifluoro-1-(2-methoxyethoxy)ethyl)benzo[d]oxazole;
2-(3,8-diazabicyclo[3.2.1]octan-3-yl)-5-(1-ethoxy-2,2,2-trifluoroethyl)-7-(thiazol-2-yl)benzo[d]oxazole;
2-(1-(2-(3,8-diazabicyclo[3.2.1]octan-3-yl)-7-(thiazol-2-yl)benzo[d]oxazol-5-yl)-2,2,2-trifluoroethoxy)ethan-1-ol;
2-(3,6-diazabicyclo[3.1.1]heptan-3-yl)-5-(1-ethoxy-2,2,2-trifluoroethyl)-7-(thiazol-2-yl)benzo[d]oxazole;
2-(3,6-diazabicyclo[3.1.1]heptan-3-yl)-7-(thiazol-2-yl)-5-(2,2,2-trifluoro-1-(2,2,2-trifluoroethoxy)ethyl)benzo[d]oxazole;
2-(1-(2-(3,6-diazabicyclo[3.1.1]heptan-3-yl)-7-(thiazol-2-yl)benzo[d]oxazol-5-yl)-2,2,2-trifluoroethoxy)acetonitrile;
2-(1-(2-(3,8-diazabicyclo[3.2.1]octan-3-yl)-7-(thiazol-2-yl)benzo[d]oxazol-5-yl)-2,2,2-trifluoroethoxy)acetonitrile;
2-(3,6-diazabicyclo[3.1.1]heptan-3-yl)-7-(thiazol-2-yl)-5-(2,2,2-trifluoro-1-(2-methoxyethoxy)ethyl)benzo[d]oxazole;
1-(1-(2-(3,8-diazabicyclo[3.2.1]octan-3-yl)-7-(thiazol-2-yl)benzo[d]oxazol-5-yl)-2,2,2-trifluoroethoxy)propan-2-ol;
1-(2-(3,9-diazabicyclo[3.3.1]nonan-3-yl)-7-(thiazol-2-yl)benzo[d]oxazol-5-yl)-2,2,2-trifluoroethane-1,1-diol;
1-(2-(3,8-diazabicyclo[3.2.1]octan-3-yl)-7-(thiazol-2-yl)benzo[d]oxazol-5-yl)-2,2,2-trifluoroethane-1,1-diol;
1-(2-(3,6-diazabicyclo[3.1.1]heptan-3-yl)-7-(thiazol-2-yl)benzo[d]oxazol-5-yl)-2,2,2-trifluoroethane-1,1-diol;
2-(2-(3,8-diazabicyclo[3.2.1]octan-3-yl)-7-(thiazol-2-yl)benzo[d]oxazol-5-yl)-1,1,1-trifluoropropan-2-ol;
2-(2-(3,6-diazabicyclo[3.1.1]heptan-3-yl)-7-(thiazol-2-yl)benzo[d]oxazol-5-yl)-1,1,1-trifluoropropan-2-ol;
2-(2-(3,9-diazabicyclo[3.3.1]nonan-3-yl)-7-(thiazol-2-yl)benzo[d]oxazol-5-yl)-1,1,1-trifluoropropan-2-ol;
2-(2-(3,9-diazabicyclo[3.3.1]nonan-3-yl)-7-(thiazol-2-yl)-5-(1,1,1-trifluoro-2-methoxypropan-2-yl)benzo[d]oxazole;

ethyl 2-(3,8-diazabicyclo[3.2.1]octan-3-yl)-7-(thiazol-2-yl)-4-(trifluoromethyl)benzo[d]oxazole-5-carboxylate;
ethyl 2-(3,9-diazabicyclo[3.3.1]nonan-3-yl)-7-(thiazol-2-yl)-4-(trifluoromethyl)benzo[d]oxazole-5-carboxylate;
ethyl 2-(3,6-diazabicyclo[3.1.1]heptan-3-yl)-7-(thiazol-2-yl)-4-(trifluoromethyl)benzo[d]oxazole-5-carboxylate;
2-(2-(3,9-diazabicyclo[3.3.1]nonan-3-yl)-7-(thiazol-2-yl)-4-(trifluoromethyl)benzo[d]oxazol-5-yl)propan-2-ol;
2-(3,8-diazabicyclo[3.2.1]octan-3-yl)-5-(methoxymethyl)-7-(thiazol-2-yl)-4-(trifluoromethyl)benzo[d]oxazole;
(2-(3,8-diazabicyclo[3.2.1]octan-3-yl)-7-(thiazol-2-yl)-4-(trifluoromethyl)benzo[d]oxazol-5-yl)methanol;
2-(3,8-diazabicyclo[3.2.1]octan-3-yl)-5-(2-methoxypropan-2-yl)-7-(thiazol-2-yl)-4-(trifluoromethyl)benzo[d]oxazole;
2-(3,6-diazabicyclo[3.1.1]heptan-3-yl)-5-(2-methoxypropan-2-yl)-7-(thiazol-2-yl)-4-(trifluoromethyl)benzo[d]oxazole;
2-(2-(3,8-diazabicyclo[3.2.1]octan-3-yl)-7-(thiazol-2-yl)-4-(trifluoromethyl)benzo[d]oxazol-5-yl)propan-2-ol;
2-(2-(3,6-diazabicyclo[3.1.1]heptan-3-yl)-7-(thiazol-2-yl)-4-(trifluoromethyl)benzo[d]oxazol-5-yl)propan-2-ol;
1-(2-(3,8-diazabicyclo[3.2.1]octan-3-yl)-7-(thiazol-2-yl)-4-(trifluoromethyl)benzo[d]oxazol-5-yl)ethan-1-one;
1-(2-(3,6-diazabicyclo[3.1.1]heptan-3-yl)-7-(thiazol-2-yl)-4-(trifluoromethyl)benzo[d]oxazol-5-yl)ethan-1-one;
1-(2-(3,8-diazabicyclo[3.2.1]octan-3-yl)-7-(thiazol-2-yl)-4-(trifluoromethyl)benzo[d]oxazol-5-yl)ethan-1-ol;
1-(2-(3,6-diazabicyclo[3.1.1]heptan-3-yl)-7-(thiazol-2-yl)-4-(trifluoromethyl)benzo[d]oxazol-5-yl)ethan-1-ol;
1-(2-(3,8-diazabicyclo[3.2.1]octan-3-yl)-7-(thiazol-2-yl)-4-(trifluoromethyl)benzo[d]oxazol-5-yl)-2,2-difluoroethan-1-ol;
2-(3,8-diazabicyclo[3.2.1]octan-3-yl)-5-(1-methoxyethyl)-7-(thiazol-2-yl)-4-(trifluoromethyl)benzo[d]oxazole;
2-(3,6-diazabicyclo[3.1.1]heptan-3-yl)-5-(1-methoxyethyl)-7-(thiazol-2-yl)-4-(trifluoromethyl)benzo[d]oxazole;
ethyl 2-(3,8-diazabicyclo[3.2.1]octan-3-yl)-7-(thiazol-2-yl)-4-(trifluoromethoxy)benzo[d]oxazole-5-carboxylate;
ethyl 2-(3,6-diazabicyclo[3.1.1]heptan-3-yl)-7-(thiazol-2-yl)-4-(trifluoromethoxy)benzo[d]oxazole-5-carboxylate;
ethyl 2-(3,9-diazabicyclo[3.3.1]nonan-3-yl)-7-(thiazol-2-yl)-4-(trifluoromethoxy)benzo[d]oxazole-5-carboxylate;
2-(3,8-diazabicyclo[3.2.1]octan-3-yl)-7-(thiazol-2-yl)-4-(trifluoromethoxy)benzo[d]oxazole-5-carboxylic acid;
2-(3,6-diazabicyclo[3.1.1]heptan-3-yl)-7-(thiazol-2-yl)-4-(trifluoromethoxy)benzo[d]oxazole-5-carboxylic acid;
2-(3,9-diazabicyclo[3.3.1]nonan-3-yl)-7-(thiazol-2-yl)-4-(trifluoromethoxy)benzo[d]oxazole-5-carboxylic acid;
2-(2-(3,8-diazabicyclo[3.2.1]octan-3-yl)-7-(thiazol-2-yl)-4-(trifluoromethoxy)benzo[d]oxazol-5-yl)propan-2-ol;
2-(2-(3,6-diazabicyclo[3.1.1]heptan-3-yl)-7-(thiazol-2-yl)-4-(trifluoromethoxy)benzo[d]oxazol-5-yl)propan-2-ol;
2-(2-(3,9-diazabicyclo[3.3.1]nonan-3-yl)-7-(thiazol-2-yl)-4-(trifluoromethoxy)benzo[d]oxazol-5-yl)propan-2-ol;

2-(3,8-diazabicyclo[3.2.1]octan-3-yl)-5-(2-methoxypropan-2-yl)-7-(thiazol-2-yl)-4-(trifluoromethoxy)benzo[d]oxazole;
2-(3,6-diazabicyclo[3.1.1]heptan-3-yl)-5-(2-methoxypropan-2-yl)-7-(thiazol-2-yl)-4-(trifluoromethoxy)benzo[d]oxazole;
2-(3,9-diazabicyclo[3.3.1]nonan-3-yl)-5-(2-methoxypropan-2-yl)-7-(thiazol-2-yl)-4-(trifluoromethoxy)benzo[d]oxazole;
(2-(3,8-diazabicyclo[3.2.1]octan-3-yl)-7-(thiazol-2-yl)-4-(trifluoromethoxy)benzo[d]oxazol-5-yl)(azetidin-1-yl)methanone;
2-(3,8-diazabicyclo[3.2.1]octan-3-yl)-N-(2-hydroxyethyl)-N-methyl-7-(thiazol-2-yl)-4-(trifluoromethoxy)benzo[d]oxazole-5-carboxamide;
(2-(3,8-diazabicyclo[3.2.1]octan-3-yl)-7-(thiazol-2-yl)-4-(trifluoromethoxy)benzo[d]oxazol-5-yl)(3-hydroxy-3-(trifluoromethyl)azetidin-1-yl)methanone;
(2-(3,8-diazabicyclo[3.2.1]octan-3-yl)-7-(thiazol-2-yl)-4-(trifluoromethoxy)benzo[d]oxazol-5-yl)methanol;
1-(2-(3,8-diazabicyclo[3.2.1]octan-3-yl)-7-(thiazol-2-yl)-4-(trifluoromethoxy)benzo[d]oxazol-5-yl)ethan-1-ol;
1-(2-(3,6-diazabicyclo[3.1.1]heptan-3-yl)-7-(thiazol-2-yl)-4-(trifluoromethoxy)benzo[d]oxazol-5-yl)ethan-1-ol;
(R)-1-(2-(3,6-diazabicyclo[3.1.1]heptan-3-yl)-7-(thiazol-2-yl)-4-(trifluoromethoxy)benzo[d]oxazol-5-yl)ethan-1-ol;
(S)-1-(2-(3,6-diazabicyclo[3.1.1]heptan-3-yl)-7-(thiazol-2-yl)-4-(trifluoromethoxy)benzo[d]oxazol-5-yl)ethan-1-ol;
1-(2-(3,8-diazabicyclo[3.2.1]octan-3-yl)-7-(thiazol-2-yl)-4-(trifluoromethoxy)benzo[d]oxazol-5-yl)propan-1-ol;
1-(2-(3,8-diazabicyclo[3.2.1]octan-3-yl)-7-(thiazol-2-yl)-4-(trifluoromethoxy)benzo[d]oxazol-5-yl)-2-methylpropan-1-ol;
1-(2-(3,8-diazabicyclo[3.2.1]octan-3-yl)-7-(thiazol-2-yl)-4-(trifluoromethoxy)benzo[d]oxazol-5-yl)-2,2-difluoroethan-1-ol;
(R)-1-(2-(3,8-diazabicyclo[3.2.1]octan-3-yl)-7-(thiazol-2-yl)-4-(trifluoromethoxy)benzo[d]oxazol-5-yl)-2,2-difluoroethan-1-ol;
(S)-1-(2-(3,8-diazabicyclo[3.2.1]octan-3-yl)-7-(thiazol-2-yl)-4-(trifluoromethoxy)benzo[d]oxazol-5-yl)-2,2-difluoroethan-1-ol;
1-(2-(3,6-diazabicyclo[3.1.1]heptan-3-yl)-7-(thiazol-2-yl)-4-(trifluoromethoxy)benzo[d]oxazol-5-yl)-2,2-difluoroethan-1-ol;
(R)-1-(2-(3,6-diazabicyclo[3.1.1]heptan-3-yl)-7-(thiazol-2-yl)-4-(trifluoromethoxy)benzo[d]oxazol-5-yl)-2,2-difluoroethan-1-ol;
(S)-1-(2-(3,6-diazabicyclo[3.1.1]heptan-3-yl)-7-(thiazol-2-yl)-4-(trifluoromethoxy)benzo[d]oxazol-5-yl)-2,2-difluoroethan-1-ol;
2-(3,6-diazabicyclo[3.1.1]heptan-3-yl)-5-(2,2-difluoro-1-methoxyethyl)-7-(thiazol-2-yl)-4-(trifluoromethoxy)benzo[d]oxazole;
2-(3,8-diazabicyclo[3.2.1]octan-3-yl)-5-(2,2-difluoro-1-methoxyethyl)-7-(thiazol-2-yl)-4-(trifluoromethoxy)benzo[d]oxazole;
2-(3,8-diazabicyclo[3.2.1]octan-3-yl)-5-(1-methoxyethyl)-7-(thiazol-2-yl)-4-(trifluoromethoxy)benzo[d]oxazole;
2-(3,6-diazabicyclo[3.1.1]heptan-3-yl)-5-(1-methoxyethyl)-7-(thiazol-2-yl)-4-(trifluoromethoxy)benzo[d]oxazole;
1-(2-(3,6-diazabicyclo[3.1.1]heptan-3-yl)-7-(thiazol-2-yl)-4-(trifluoromethoxy)benzo[d]oxazol-5-yl)ethan-1-one;
1-(2-(3,8-diazabicyclo[3.2.1]octan-3-yl)-7-(thiazol-2-yl)-4-(trifluoromethoxy)benzo[d]oxazol-5-yl)ethan-1-one;
2-(3,6-diazabicyclo[3.1.1]heptan-3-yl)-7-(thiazol-2-yl)-5-(1,1,1-trifluoro-2-methoxypropan-2-yl)-4-(trifluoromethoxy)benzo[d]oxazole;
2-(3,8-diazabicyclo[3.2.1]octan-3-yl)-7-(thiazol-2-yl)-5-(1,1,1-trifluoro-2-methoxypropan-2-yl)-4-(trifluoromethoxy)benzo[d]oxazole;
2-(2-(3,6-diazabicyclo[3.1.1]heptan-3-yl)-7-(thiazol-2-yl)-4-(trifluoromethoxy)benzo[d]oxazol-5-yl)-1,1,1-trifluoropropan-2-ol;
2-(2-(3,8-diazabicyclo[3.2.1]octan-3-yl)-7-(thiazol-2-yl)-4-(trifluoromethoxy)benzo[d]oxazol-5-yl)-1,1,1-trifluoropropan-2-ol;
(E)-1-(2-(3,8-diazabicyclo[3.2.1]octan-3-yl)-7-(thiazol-2-yl)-4-(trifluoromethoxy)benzo[d]oxazol-5-yl)ethan-1-one O-methyloxime;
(Z)-1-(2-(3,8-diazabicyclo[3.2.1]octan-3-yl)-7-(thiazol-2-yl)-4-(trifluoromethoxy)benzo[d]oxazol-5-yl)ethan-1-one O-methyloxime;
(E)-1-(2-(3,6-diazabicyclo[3.1.1]heptan-3-yl)-7-(thiazol-2-yl)-4-(trifluoromethoxy)benzo[d]oxazol-5-yl)ethan-1-one O-methyloxime;
(Z)-1-(2-(3,6-diazabicyclo[3.1.1]heptan-3-yl)-7-(thiazol-2-yl)-4-(trifluoromethoxy)benzo[d]oxazol-5-yl)ethan-1-one O-methyloxime;
2-(3,8-diazabicyclo[3.2.1]octan-3-yl)-4-(1-ethoxy-2,2,2-trifluoroethyl)-7-(thiazol-2-yl)benzo[d]oxazole;
2-(3,8-diazabicyclo[3.2.1]octan-3-yl)-7-(thiazol-2-yl)-4-(2,2,2-trifluoro-1-(2,2,2-trifluoroethoxy)ethyl)benzo[d]oxazole;
2-(3,8-diazabicyclo[3.2.1]octan-3-yl)-7-(thiazol-2-yl)-4-(2,2,2-trifluoro-1-methoxyethyl)benzo[d]oxazole;
2-(3,6-diazabicyclo[3.1.1]heptan-3-yl)-7-(thiazol-2-yl)-4-(2,2,2-trifluoro-1-(2,2,2-trifluoroethoxy)ethyl)benzo[d]oxazole;
2-(3,6-diazabicyclo[3.1.1]heptan-3-yl)-4-(1-ethoxy-2,2,2-trifluoroethyl)-7-(thiazol-2-yl)benzo[d]oxazole;
2-(1-(2-(3,8-diazabicyclo[3.2.1]octan-3-yl)-7-(thiazol-2-yl)benzo[d]oxazol-4-yl)-2,2,2-trifluoroethoxy)ethan-1-ol;
2-(1-(2-(3,6-diazabicyclo[3.1.1]heptan-3-yl)-7-(thiazol-2-yl)benzo[d]oxazol-4-yl)-2,2,2-trifluoroethoxy)acetonitrile;
2-(1-(2-(3,6-diazabicyclo[3.1.1]heptan-3-yl)-7-(thiazol-2-yl)benzo[d]oxazol-4-yl)-2,2,2-trifluoroethoxy)ethan-1-ol;
2-(1-(2-(3,8-diazabicyclo[3.2.1]octan-3-yl)-7-(thiazol-2-yl)benzo[d]oxazol-4-yl)-2,2,2-trifluoroethoxy)acetonitrile;
2-(3,6-diazabicyclo[3.1.1]heptan-3-yl)-7-(thiazol-2-yl)-4-(2,2,2-trifluoro-1-(2-methoxyethoxy)ethyl)benzo[d]oxazole;
4-(1-((1H-tetrazol-5-yl)methoxy)-2,2,2-trifluoroethyl)-2-(3,8-diazabicyclo[3.2.1]octan-3-yl)-7-(thiazol-2-yl)benzo[d]oxazole;
4-(1-((1H-tetrazol-5-yl)methoxy)-2,2,2-trifluoroethyl)-2-(3,6-diazabicyclo[3.1.1]heptan-3-yl)-7-(thiazol-2-yl)benzo[d]oxazole;
1-((1-(2-(3,6-diazabicyclo[3.1.1]heptan-3-yl)-7-(thiazol-2-yl)benzo[d]oxazol-4-yl)-2,2,2-trifluoroethoxy)methyl)cyclopropan-1-ol;
1-(2-(3,8-diazabicyclo[3.2.1]octan-3-yl)-7-(thiazol-2-yl)benzo[d]oxazol-4-yl)-2,2,2-trifluoroethane-1,1-diol;

2-(2-(3,6-diazabicyclo[3.1.1]heptan-3-yl)-7-(thiazol-2-yl)benzo[d]oxazol-4-yl)-1,1,1-trifluoropropan-2-ol;
(R)-2-(2-(3,6-diazabicyclo[3.1.1]heptan-3-yl)-7-(thiazol-2-yl)benzo[d]oxazol-4-yl)-1,1,1-trifluoropropan-2-ol;
(S)-2-(2-(3,6-diazabicyclo[3.1.1]heptan-3-yl)-7-(thiazol-2-yl)benzo[d]oxazol-4-yl)-1,1,1-trifluoropropan-2-ol;
2-(3,6-diazabicyclo[3.1.1]heptan-3-yl)-7-(thiazol-2-yl)-4-(1,1,1-trifluoro-2-methoxypropan-2-yl)benzo[d]oxazole;
2-(2-(3,8-diazabicyclo[3.2.1]octan-3-yl)-7-(thiazol-2-yl)benzo[d]oxazol-4-yl)-1,1,1-trifluoropropan-2-ol;
methyl 2-(3,8-diazabicyclo[3.2.1]octan-3-yl)-7-(thiazol-2-yl)benzo[d]oxazole-4-carboxylate;
2-(3,8-diazabicyclo[3.2.1]octan-3-yl)-7-(thiazol-2-yl)benzo[d]oxazole-4-carboxylic acid;
2-(2-(3,6-diazabicyclo[3.1.1]heptan-3-yl)-7-(thiazol-2-yl)benzo[d]oxazol-4-yl)propan-2-ol;
2-(2-(3,8-diazabicyclo[3.2.1]octan-3-yl)-7-(thiazol-2-yl)benzo[d]oxazol-4-yl)propan-2-ol;
1-(2-(3,9-diazabicyclo[3.3.1]nonan-3-yl)-7-(thiazol-2-yl)benzo[d]oxazol-4-yl)ethan-1-ol;
1-(2-(3,6-diazabicyclo[3.1.1]heptan-3-yl)-7-(thiazol-2-yl)benzo[d]oxazol-4-yl)ethan-1-ol;
2-(3,6-diazabicyclo[3.1.1]heptan-3-yl)-4-(1-methoxyethyl)-7-(thiazol-2-yl)benzo[d]oxazole;
2-(3,8-diazabicyclo[3.2.1]octan-3-yl)-4-(1-methoxyethyl)-7-(thiazol-2-yl)benzo[d]oxazole;
2-(3,9-diazabicyclo[3.3.1]nonan-3-yl)-4-(1-methoxyethyl)-7-(thiazol-2-yl)benzo[d]oxazole;
1-(2-(3,6-diazabicyclo[3.1.1]heptan-3-yl)-7-(thiazol-2-yl)benzo[d]oxazol-4-yl)ethan-1-one;
1-(2-(3,8-diazabicyclo[3.2.1]octan-3-yl)-7-(thiazol-2-yl)benzo[d]oxazol-4-yl)ethan-1-one;
1-((2-(3,6-diazabicyclo[3.1.1]heptan-3-yl)-7-(thiazol-2-yl)benzo[d]oxazol-4-yl)oxy)-1,1-difluoro-2-methylpropan-2-ol;
2-((2-(3,6-diazabicyclo[3.1.1]heptan-3-yl)-7-(thiazol-2-yl)benzo[d]oxazol-4-yl)oxy)-2,2-difluoroethan-1-ol;
1-((2-(3,6-diazabicyclo[3.1.1]heptan-3-yl)-7-(thiazol-2-yl)benzo[d]oxazol-4-yl)oxy)-1,1-difluoropropan-2-ol;
(R)-1-((2-(3,6-diazabicyclo[3.1.1]heptan-3-yl)-7-(thiazol-2-yl)benzo[d]oxazol-4-yl)oxy)-1,1-difluoropropan-2-ol;
(S)-1-((2-(3,6-diazabicyclo[3.1.1]heptan-3-yl)-7-(thiazol-2-yl)benzo[d]oxazol-4-yl)oxy)-1,1-difluoropropan-2-ol;
2-(1-(2-(3,6-diazabicyclo[3.1.1]heptan-3-yl)-7-(thiazol-2-yl)benzo[d]oxazol-4-yl)-2,2,2-trifluoroethoxy) acetic acid;
2-(3,8-diazabicyclo[3.2.1]octan-3-yl)-4-((tetrahydro-2H-pyran-4-yl)oxy)-7-(thiazol-2-yl)benzo[d]oxazole;
1-(1-(2-(3,6-diazabicyclo[3.1.1]heptan-3-yl)-7-(thiazol-2-yl)benzo[d]oxazol-4-yl)-2,2,2-trifluoroethoxy)-2-methylpropan-2-ol;
2-(1-(2-(3,6-diazabicyclo[3.1.1]heptan-3-yl)-7-(thiazol-2-yl)benzo[d]oxazol-4-yl)-2,2,2-trifluoroethoxy) acetamide;
1-(1-(2-(3,6-diazabicyclo[3.1.1]heptan-3-yl)-7-(thiazol-2-yl)benzo[d]oxazol-4-yl)-2,2,2-trifluoroethoxy)-1,1-difluoro-2-methylpropan-2-ol;
2-(1-(2-(3,6-diazabicyclo[3.1.1]heptan-3-yl)-7-(thiazol-2-yl)benzo[d]oxazol-4-yl)-2,2,2-trifluoroethoxy)-2,2-difluoroethan-1-ol;
1-((2-(3,6-diazabicyclo[3.1.1]heptan-3-yl)-7-(thiazol-2-yl)benzo[d]oxazol-4-yl)oxy) propan-2-ol;
1-(1-(2-(3,6-diazabicyclo[3.1.1]heptan-3-yl)-7-(thiazol-2-yl)benzo[d]oxazol-4-yl)-2,2,2-trifluoroethoxy)propan-2-ol;
2-(3,8-diazabicyclo[3.2.1]octan-3-yl)-4-((tetrahydro-2H-pyran-3-yl)oxy)-7-(thiazol-2-yl)benzo[d]oxazole;
2-(3,8-diazabicyclo[3.2.1]octan-3-yl)-4-(difluoromethoxy)-7-(thiazol-2-yl)benzo[d]oxazole;
1-((2-(3,8-diazabicyclo[3.2.1]octan-3-yl)-7-(thiazol-2-yl)benzo[d]oxazol-4-yl)oxy)-2-methylpropan-2-ol;
1-(1-(2-(3,6-diazabicyclo[3.1.1]heptan-3-yl)-7-(thiazol-2-yl)benzo[d]oxazol-4-yl)-2,2,2-trifluoroethoxy)-1,1-difluoropropan-2-ol;
3-((2-(3,6-diazabicyclo[3.1.1]heptan-3-yl)-7-(thiazol-2-yl)benzo[d]oxazol-4-yl)oxy)cyclobutane-1-carbonitrile;
2-(3-((2-(3,6-diazabicyclo[3.1.1]heptan-3-yl)-7-(thiazol-2-yl)benzo[d]oxazol-4-yl)oxy)cyclobutyl)propan-2-ol;
2-((2-(3,6-diazabicyclo[3.1.1]heptan-3-yl)-7-(thiazol-2-yl)benzo[d]oxazol-4-yl)oxy)-2-methylpropan-1-ol;
1-(2-(3,6-diazabicyclo[3.1.1]heptan-3-yl)-7-(thiazol-2-yl)-4-(trifluoromethoxy)benzo[d]oxazol-5-yl) cyclopropan-1-ol;
1-(2-(3,8-diazabicyclo[3.2.1]octan-3-yl)-7-(thiazol-2-yl)-4-(trifluoromethoxy)benzo[d]oxazol-5-yl) cyclopropan-1-ol;
3-((2-(3,6-diazabicyclo[3.1.1]heptan-3-yl)-7-(thiazol-2-yl)benzo[d]oxazol-4-yl)oxy)-1,1,1-trifluoropropan-2-ol;
2-(3,6-diazabicyclo[3.1.1]heptan-3-yl)-4-(difluoromethoxy)-7-(thiazol-2-yl)benzo[d]oxazole;
1-((2-(3,6-diazabicyclo[3.1.1]heptan-3-yl)-7-(thiazol-2-yl)benzo[d]oxazol-4-yl)oxy)-2-methylpropan-2-ol;
3-(1-(2-(3,6-diazabicyclo[3.1.1]heptan-3-yl)-7-(thiazol-2-yl)benzo[d]oxazol-4-yl)-2,2,2-trifluoroethoxy)-2,3-dimethylbutan-2-ol;
2-(3,6-diazabicyclo[3.1.1]heptan-3-yl)-7-(thiazol-2-yl)-4-(2,2,2-trifluoro-1-(2-methoxy-2-methylpropoxy)ethyl)benzo[d]oxazole;
2-(3,6-diazabicyclo[3.1.1]heptan-3-yl)-7-(thiazol-2-yl)-4-(2,2,2-trifluoro-1-((1-methoxycyclopropyl)methoxy)ethyl)benzo[d]oxazole;
2-(3,6-diazabicyclo[3.1.1]heptan-3-yl)-5-(1-methoxycyclopropyl)-7-(thiazol-2-yl)-4-(trifluoromethoxy)benzo[d]oxazole;
1-(1-(2-(3,6-diazabicyclo[3.1.1]heptan-3-yl)-7-(thiazol-4-yl)benzo[d]oxazol-4-yl)-2,2,2-trifluoroethoxy)-2-methylpropan-2-ol;
3-((2-(3,6-diazabicyclo[3.1.1]heptan-3-yl)-7-(thiazol-2-yl)benzo[d]oxazol-4-yl)oxy)cyclobutan-1-ol;
1-((1-(2-(3,6-diazabicyclo[3.1.1]heptan-3-yl)-7-(thiazol-4-yl)benzo[d]oxazol-4-yl)-2,2,2-trifluoroethoxy)methyl)cyclopropan-1-ol;
2-(3,6-diazabicyclo[3.1.1]heptan-3-yl)-5-(2-methoxypropan-2-yl)-7-(thiazol-4-yl)-4-(trifluoromethoxy)benzo[d]oxazole;
2-(2-(3,6-diazabicyclo[3.1.1]heptan-3-yl)-7-(thiazol-4-yl)-4-(trifluoromethoxy)benzo[d]oxazol-5-yl)propan-2-ol;
1-((2-(3,6-diazabicyclo[3.1.1]heptan-3-yl)-7-(pyridin-2-yl)benzo[d]oxazol-4-yl)oxy)-1,1-difluoro-2-methylpropan-2-ol;
1-((2-(3,6-diazabicyclo[3.1.1]heptan-3-yl)-7-(oxazol-2-yl)benzo[d]oxazol-4-yl)oxy)-1,1-difluoro-2-methylpropan-2-ol;
2-(2-(3,8-diazabicyclo[3.2.1]octan-3-yl)-7-(thiazol-4-yl)-4-(trifluoromethoxy)benzo[d]oxazol-5-yl)propan-2-ol;

2-(3,6-diazabicyclo[3.1.1]heptan-3-yl)-4-((tetrahydro-2H-pyran-4-yl)oxy)-7-(thiazol-2-yl)benzo[d]oxazole;

4-((2-(3,6-diazabicyclo[3.1.1]heptan-3-yl)-7-(thiazol-2-yl)benzo[d]oxazol-4-yl)oxy)-4,4-difluoro-2-methylbutan-2-ol;

2-(3,8-diazabicyclo[3.2.1]octan-3-yl)-5-(2-methoxypropan-2-yl)-7-(thiazol-4-yl)-4-(trifluoromethoxy)benzo[d]oxazole;

1-(2-(3,6-diazabicyclo[3.1.1]heptan-3-yl)-7-(thiazol-4-yl)-4-(trifluoromethoxy)benzo[d]oxazol-5-yl) cyclopropan-1-ol;

1-(2-(3,6-diazabicyclo[3.1.1]heptan-3-yl)-7-(thiazol-4-yl)-4-(trifluoromethoxy)benzo[d]oxazol-5-yl)-2,2-difluoroethan-1-ol;

(R)-1-(2-(3,6-diazabicyclo[3.1.1]heptan-3-yl)-7-(thiazol-4-yl)-4-(trifluoromethoxy)benzo[d]oxazol-5-yl)-2,2-difluoroethan-1-ol;

(S)-1-(2-(3,6-diazabicyclo[3.1.1]heptan-3-yl)-7-(thiazol-4-yl)-4-(trifluoromethoxy)benzo[d]oxazol-5-yl)-2,2-difluoroethan-1-ol;

1-(2-(3,8-diazabicyclo[3.2.1]octan-3-yl)-7-(thiazol-4-yl)-4-(trifluoromethoxy)benzo[d]oxazol-5-yl)-2,2-difluoroethan-1-ol;

(R)-1-(2-(3,8-diazabicyclo[3.2.1]octan-3-yl)-7-(thiazol-4-yl)-4-(trifluoromethoxy)benzo[d]oxazol-5-yl)-2,2-difluoroethan-1-ol;

(S)-1-(2-(3,8-diazabicyclo[3.2.1]octan-3-yl)-7-(thiazol-4-yl)-4-(trifluoromethoxy)benzo[d]oxazol-5-yl)-2,2-difluoroethan-1-ol;

1-((2-(3,6-diazabicyclo[3.1.1]heptan-3-yl)-7-(1H-pyrazol-1-yl)benzo[d]oxazol-4-yl)oxy)-1,1-difluoro-2-methylpropan-2-ol;

4-((2-(3,6-diazabicyclo[3.1.1]heptan-3-yl)-7-(thiazol-2-yl)benzo[d]oxazol-4-yl)oxy)cyclohexan-1-ol;

1-((2-(3,6-diazabicyclo[3.1.1]heptan-3-yl)-7-(4-methylthiazol-2-yl)benzo[d]oxazol-4-yl)oxy)-1,1-difluoro-2-methylpropan-2-ol;

1-((2-(3,6-diazabicyclo[3.1.1]heptan-3-yl)-7-(thiazol-4-yl)benzo[d]oxazol-4-yl)oxy)-1,1-difluoro-2-methylpropan-2-ol;

1-((2-(3,8-diazabicyclo[3.2.1]octan-3-yl)-7-(thiazol-4-yl)benzo[d]oxazol-4-yl)oxy)-1,1-difluoro-2-methylpropan-2-ol;

1-((2-(3,6-diazabicyclo[3.1.1]heptan-3-yl)-7-(thiazol-4-yl)benzo[d]oxazol-4-yl)oxy)-1,1-difluoropropan-2-ol;

1-((2-(3,8-diazabicyclo[3.2.1]octan-3-yl)-7-(thiazol-4-yl)benzo[d]oxazol-4-yl)oxy)-1,1-difluoropropan-2-ol;

2-((2-(3,6-diazabicyclo[3.1.1]heptan-3-yl)-7-(thiazol-4-yl)benzo[d]oxazol-4-yl)oxy)-2,2-difluoroethan-1-ol;

2-((2-(3,8-diazabicyclo[3.2.1]octan-3-yl)-7-(thiazol-4-yl)benzo[d]oxazol-4-yl)oxy)-2,2-difluoroethan-1-ol;

3-((2-(3,6-diazabicyclo[3.1.1]heptan-3-yl)-7-(thiazol-2-yl)benzo[d]oxazol-4-yl)oxy)-4,4,4-trifluoro-2-methylbutan-2-ol;

4-((2-(3,6-diazabicyclo[3.1.1]heptan-3-yl)-7-(thiazol-2-yl)benzo[d]oxazol-4-yl)oxy) tetrahydro-2H-thiopyran 1,1-dioxide;

2-((2-(3,6-diazabicyclo[3.1.1]heptan-3-yl)-7-(pyridin-2-yl)benzo[d]oxazol-4-yl)oxy)-2,2-difluoroethan-1-ol;

1-((2-(3,8-diazabicyclo[3.2.1]octan-3-yl)-7-(1H-pyrazol-1-yl)benzo[d]oxazol-4-yl)oxy)-1,1-difluoro-2-methylpropan-2-ol;

1-((2-(3,8-diazabicyclo[3.2.1]octan-3-yl)-7-(pyridin-2-yl)benzo[d]oxazol-4-yl)oxy)-1,1-difluoro-2-methylpropan-2-ol;

1-((2-(3,8-diazabicyclo[3.2.1]octan-3-yl)-7-(4-methylthiazol-2-yl)benzo[d]oxazol-4-yl)oxy)-1,1-difluoro-2-methylpropan-2-ol;

2-((2-(3,6-diazabicyclo[3.1.1]heptan-3-yl)-7-(5-fluoropyridin-2-yl)benzo[d]oxazol-4-yl)oxy)-2,2-difluoroethan-1-ol;

2-((2-(3,6-diazabicyclo[3.1.1]heptan-3-yl)-7-(1H-pyrazol-1-yl)benzo[d]oxazol-4-yl)oxy)-2,2-difluoroethan-1-ol;

1-((2-(3,8-diazabicyclo[3.2.1]octan-3-yl)-7-(oxazol-2-yl)benzo[d]oxazol-4-yl)oxy)-1,1-difluoro-2-methylpropan-2-ol;

1-((2-(3,8-diazabicyclo[3.2.1]octan-3-yl)-7-(2H-1,2,3-triazol-2-yl)benzo[d]oxazol-4-yl)oxy)-1,1-difluoro-2-methylpropan-2-ol;

2-(3,6-diazabicyclo[3.1.1]heptan-3-yl)-4-(((S)-tetrahydrofuran-3-yl)oxy)-7-(thiazol-2-yl)benzo[d]oxazole;

2-(3,6-diazabicyclo[3.1.1]heptan-3-yl)-4-(((R)-tetrahydrofuran-3-yl)oxy)-7-(thiazol-2-yl)benzo[d]oxazole;

2-(3,6-diazabicyclo[3.1.1]heptan-3-yl)-4-(oxetan-3-yloxy)-7-(thiazol-2-yl)benzo[d]oxazole;

3-((2-(3,6-diazabicyclo[3.1.1]heptan-3-yl)-7-(thiazol-2-yl)benzo[d]oxazol-4-yl)oxy)-3,3-difluoro-2-methylpropane-1,2-diol;

1-((2-(3,8-diazabicyclo[3.2.1]octan-3-yl)-7-(1,2,4-thiadiazol-5-yl)benzo[d]oxazol-4-yl)oxy)-1,1-difluoro-2-methylpropan-2-ol;

1-((2-(3,8-diazabicyclo[3.2.1]octan-3-yl)-7-(1-methyl-1H-pyrazol-3-yl)benzo[d]oxazol-4-yl)oxy)-1,1-difluoro-2-methylpropan-2-ol;

1-((2-(3,6-diazabicyclo[3.1.1]heptan-3-yl)-7-(5-fluoropyridin-2-yl)benzo[d]oxazol-4-yl)oxy)-1,1-difluoro-2-methylpropan-2-ol;

1-((2-(3,8-diazabicyclo[3.2.1]octan-3-yl)-7-(pyrimidin-2-yl)benzo[d]oxazol-4-yl)oxy)-1,1-difluoro-2-methylpropan-2-ol;

1-((2-(3,8-diazabicyclo[3.2.1]octan-3-yl)-7-(isothiazol-3-yl)benzo[d]oxazol-4-yl)oxy)-1,1-difluoro-2-methylpropan-2-ol;

1-((2-(3,8-diazabicyclo[3.2.1]octan-3-yl)-7-(5-fluoropyridin-2-yl)benzo[d]oxazol-4-yl)oxy)-1,1-difluoro-2-methylpropan-2-ol;

1-((2-(3,8-diazabicyclo[3.2.1]octan-3-yl)-7-(3-methyl-1,2,4-thiadiazol-5-yl)benzo[d]oxazol-4-yl)oxy)-1,1-difluoro-2-methylpropan-2-ol;

2-(3,6-diazabicyclo[3.1.1]heptan-3-yl)-7-(thiazol-2-yl)-4-((trifluoromethyl)sulfonyl)benzo[d]oxazole;

2-(3,6-diazabicyclo[3.1.1]heptan-3-yl)-7-(thiazol-2-yl)benzo[d]oxazole-4-carbonitrile;

2-(3,6-diazabicyclo[3.1.1]heptan-3-yl)-7-(thiazol-2-yl)-4-((5-(trifluoromethyl) pyridin-2-yl)oxy)benzo[d]oxazole;

2-(3,6-diazabicyclo[3.1.1]heptan-3-yl)-4-(pyridin-2-yloxy)-7-(thiazol-2-yl)benzo[d]oxazole;

2-(3,6-diazabicyclo[3.1.1]heptan-3-yl)-4-(pyrimidin-2-yloxy)-7-(thiazol-2-yl)benzo[d]oxazole;

2-(3,6-diazabicyclo[3.1.1]heptan-3-yl)-4-(pyrazin-2-yloxy)-7-(thiazol-2-yl)benzo[d]oxazole;

2-(3,6-diazabicyclo[3.1.1]heptan-3-yl)-4-((6-methyl-4-(trifluoromethyl) pyridazin-3-yl)oxy)-7-(thiazol-2-yl)benzo[d]oxazole; (6-((2-(3,6-diazabicyclo[3.1.1]heptan-3-yl)-7-(thiazol-2-yl)benzo[d]oxazol-4-yl)oxy) pyridin-3-yl)methanol;

(6-((2-(3,6-diazabicyclo[3.1.1]heptan-3-yl)-7-(thiazol-2-yl)benzo[d]oxazol-4-yl)oxy)-5-(trifluoromethyl) pyridin-3-yl)methanol;

2-(3,6-diazabicyclo[3.1.1]heptan-3-yl)-7-(thiazol-2-yl)-4-((5-(trifluoromethoxy) pyridin-2-yl)oxy)benzo[d]oxazole;

2-(3,6-diazabicyclo[3.1.1]heptan-3-yl)-4-cyclopropyl-7-(thiazol-2-yl)benzo[d]oxazole;

2-(3,6-diazabicyclo[3.1.1]heptan-3-yl)-4-(methylthio)-7-(thiazol-2-yl)benzo[d]oxazole;

2-(3,6-diazabicyclo[3.1.1]heptan-3-yl)-4-(methylsulfinyl)-7-(thiazol-2-yl)benzo[d]oxazole;

2-(3,6-diazabicyclo[3.1.1]heptan-3-yl)-4-(methylsulfonyl)-7-(thiazol-2-yl)benzo[d]oxazole;

2-((2-(3,6-diazabicyclo[3.1.1]heptan-3-yl)-7-(thiazol-2-yl)benzo[d]oxazol-4-yl)thio)ethan-1-ol;

2-((2-(3,6-diazabicyclo[3.1.1]heptan-3-yl)-7-(thiazol-2-yl)benzo[d]oxazol-4-yl)sulfinyl)ethan-1-ol;

2-((2-(3,6-diazabicyclo[3.1.1]heptan-3-yl)-7-(thiazol-2-yl)benzo[d]oxazol-4-yl)sulfonyl)ethan-1-ol;

2-(3,6-diazabicyclo[3.1.1]heptan-3-yl)-4-((1,1-difluoroallyl)oxy)-7-(thiazol-2-yl)benzo[d]oxazole;

2-(3,6-diazabicyclo[3.1.1]heptan-3-yl)-4-((5-(methylsulfonyl) pyridin-2-yl)oxy)-7-(thiazol-2-yl)benzo[d]oxazole;

2-(3,6-diazabicyclo[3.1.1]heptan-3-yl)-N-(2-methoxyethyl)-7-(thiazol-2-yl)benzo[d]oxazole-4-carboxamide;

2-(3,6-diazabicyclo[3.1.1]heptan-3-yl)-7-(thiazol-2-yl)benzo[d]oxazole-4-carboxamide;

2-(3,6-diazabicyclo[3.1.1]heptan-3-yl)-N-(2-hydroxyethyl)-7-(thiazol-2-yl)benzo[d]oxazole-4-carboxamide;

2-(3,6-diazabicyclo[3.1.1]heptan-3-yl)-N-(2-hydroxyethyl)-N-methyl-7-(thiazol-2-yl)benzo[d]oxazole-4-carboxamide;

2-(3,6-diazabicyclo[3.1.1]heptan-3-yl)-N-cyclopropyl-7-(thiazol-2-yl)benzo[d]oxazole-4-carboxamide;

2-(3,6-diazabicyclo[3.1.1]heptan-3-yl)-N-ethyl-7-(thiazol-2-yl)benzo[d]oxazole-4-carboxamide;

(2-(3,6-diazabicyclo[3.1.1]heptan-3-yl)-7-(thiazol-2-yl)benzo[d]oxazol-4-yl)(morpholino)methanone;

(2-(3,6-diazabicyclo[3.1.1]heptan-3-yl)-7-(thiazol-2-yl)benzo[d]oxazol-4-yl) (pyrrolidin-1-yl)methanone;

N-benzyl-2-(3,6-diazabicyclo[3.1.1]heptan-3-yl)-7-(thiazol-2-yl)benzo[d]oxazole-4-carboxamide;

1-((2-(3,6-diazabicyclo[3.1.1]heptan-3-yl)-7-(thiazol-2-yl)benzo[d]oxazol-4-yl)oxy)-1,1-difluoro-3-methylbutan-2-ol;

1-((2-(3,6-diazabicyclo[3.1.1]heptan-3-yl)-7-(5-chloropyridin-2-yl)benzo[d]oxazol-4-yl)oxy)-1,1-difluoro-2-methylpropan-2-ol;

(R)-3-((2-(3,6-diazabicyclo[3.1.1]heptan-3-yl)-7-(thiazol-2-yl)benzo[d]oxazol-4-yl)oxy)-3,3-difluoro-2-methylpropane-1,2-diol;

(S)-3-((2-(3,6-diazabicyclo[3.1.1]heptan-3-yl)-7-(thiazol-2-yl)benzo[d]oxazol-4-yl)oxy)-3,3-difluoro-2-methylpropane-1,2-diol;

2-(3,6-diazabicyclo[3.1.1]heptan-3-yl)-7-(thiazol-2-yl)benzo[d]oxazole-4-carboxylic acid;

2-(3,6-diazabicyclo[3.1.1]heptan-3-yl)-N-hydroxy-7-(thiazol-2-yl)benzo[d]oxazole-4-carboxamide;

3-(5-(2-hydroxypropan-2-yl)-7-(thiazol-2-yl)-4-(trifluoromethoxy)benzo[d]oxazol-2-yl)-3,8-diazabicyclo[3.2.1]octan-8-ol;

2-(3,6-diazabicyclo[3.1.1]heptan-3-yl)-4-morpholino-7-(thiazol-2-yl)benzo[d]oxazole;

3-((2-(3,6-diazabicyclo[3.1.1]heptan-3-yl)-7-(thiazol-2-yl)benzo[d]oxazol-4-yl)oxy)-3,3-difluoropropane-1,2-diol;

3-(4-(1,1-difluoro-2-hydroxy-2-methylpropoxy)-7-(thiazol-2-yl)benzo[d]oxazol-2-yl)-3,6-diazabicyclo[3.1.1]heptan-6-ol;

(R)-3-(4-(1,1-difluoro-2-hydroxypropoxy)-7-(thiazol-2-yl)benzo[d]oxazol-2-yl)-3,6-diazabicyclo[3.1.1]heptan-6-ol;

(S)-3-(4-(1,1-difluoro-2-hydroxypropoxy)-7-(thiazol-2-yl)benzo[d]oxazol-2-yl)-3,6-diazabicyclo[3.1.1]heptan-6-ol;

3-(4-(1,1-difluoro-2-hydroxyethoxy)-7-(thiazol-2-yl)benzo[d]oxazol-2-yl)-3,6-diazabicyclo[3.1.1]heptan-6-ol;

3-(5-chloro-7-(thiazol-2-yl)-4-(trifluoromethoxy)benzo[d]oxazol-2-yl)-3,8-diazabicyclo[3.2.1]octan-8-ol;

(2-((2-(3,6-diazabicyclo[3.1.1]heptan-3-yl)-7-(thiazol-2-yl)benzo[d]oxazol-4-yl)oxy)pyridin-3-yl)methanol;

1-((2-(3,6-diazabicyclo[3.1.1]heptan-3-yl)-7-(thiazol-2-yl)benzo[d]oxazol-4-yl)oxy)-1,1-difluoropropane-2,2-diol;

(R)-3-(7-(thiazol-2-yl)-4-(2,2,2-trifluoro-1-hydroxyethyl)benzo[d]oxazol-2-yl)-3,8-diazabicyclo[3.2.1]octan-8-ol;

(S)-3-(7-(thiazol-2-yl)-4-(2,2,2-trifluoro-1-hydroxyethyl)benzo[d]oxazol-2-yl)-3,8-diazabicyclo[3.2.1]octan-8-ol;

3-(7-(thiazol-2-yl)-4-(trifluoromethoxy)benzo[d]oxazol-2-yl)-3,6-diazabicyclo[3.1.1]heptan-6-ol;

3-(5-(2-hydroxypropan-2-yl)-7-(thiazol-2-yl)-4-(trifluoromethyl)benzo[d]oxazol-2-yl)-3,8-diazabicyclo[3.2.1]octan-8-ol;

2-(3,6-diazabicyclo[3.1.1]heptan-3-yl)-7-(thiazol-2-yl)benzo[d]oxazole;

3-(5-(1-hydroxyethyl)-7-(thiazol-2-yl)-4-(trifluoromethoxy)benzo[d]oxazol-2-yl)-3,8-diazabicyclo[3.2.1]octan-8-ol;

3-(5-(1-hydroxyethyl)-7-(thiazol-2-yl)-4-(trifluoromethyl)benzo[d]oxazol-2-yl)-3,8-diazabicyclo[3.2.1]octan-8-ol;

2-(3,6-diazabicyclo[3.1.1]heptan-3-yl)-N-(2-hydroxyethyl)-7-(thiazol-2-yl)benzo[d]oxazole-4-sulfonamide;

2-(3,6-diazabicyclo[3.1.1]heptan-3-yl)-N-methyl-7-(thiazol-2-yl)benzo[d]oxazole-4-sulfonamide;

2-(3,6-diazabicyclo[3.1.1]heptan-3-yl)-N-(2-methoxyethyl)-7-(thiazol-2-yl)benzo[d]oxazole-4-sulfonamide;

2-(3,6-diazabicyclo[3.1.1]heptan-3-yl)-N,N-dimethyl-7-(thiazol-2-yl)benzo[d]oxazole-4-sulfonamide;

2-(3,6-diazabicyclo[3.1.1]heptan-3-yl)-N-(2-hydroxyethyl)-N-methyl-7-(thiazol-2-yl)benzo[d]oxazole-4-sulfonamide;

2-(3,6-diazabicyclo[3.1.1]heptan-3-yl)-4-(pyrrolidin-1-ylsulfonyl)-7-(thiazol-2-yl)benzo[d]oxazole;

2-(3,6-diazabicyclo[3.1.1]heptan-3-yl)-4-(morpholinosulfonyl)-7-(thiazol-2-yl)benzo[d]oxazole;

2-(3,6-diazabicyclo[3.1.1]heptan-3-yl)-4-(1,1-difluoro-2-methoxyethoxy)-7-(thiazol-2-yl)benzo[d]oxazole;

2-(3,6-diazabicyclo[3.1.1]heptan-3-yl)-4-(1,1-difluoro-2-methoxy-2-methylpropoxy)-7-(thiazol-2-yl)benzo[d]oxazole;

1-((2-(3,6-diazabicyclo[3.1.1]heptan-3-yl)-7-(1-methyl-1H-pyrazol-3-yl)benzo[d]oxazol-4-yl)oxy)-1,1-difluoro-2-methylpropan-2-ol;

1-((2-(3,6-diazabicyclo[3.1.1]heptan-3-yl)-7-(thiazol-2-yl)benzo[d]oxazol-4-yl)oxy)-1,1-difluorobutan-2-ol;

2-(3,6-diazabicyclo[3.1.1]heptan-3-yl)-7-(thiazol-2-yl)benzo[d]oxazole-4-sulfonamide;

1-(2-(3,6-diazabicyclo[3.1.1]heptan-3-yl)-7-(thiazol-2-yl)benzo[d]oxazol-4-yl)piperidin-4-ol;

4-(2-(3,6-diazabicyclo[3.1.1]heptan-3-yl)-7-(thiazol-2-yl)benzo[d]oxazol-4-yl)thiomorpholine 1,1-dioxide;
1-((2-(3,6-diazabicyclo[3.1.1]heptan-3-yl)-5-bromo-7-(thiazol-2-yl)benzo[d]oxazol-4-yl)oxy)-1,1-difluoro-2-methylpropan-2-ol;
1-((2-(3,6-diazabicyclo[3.1.1]heptan-3-yl)-5-chloro-7-(thiazol-2-yl)benzo[d]oxazol-4-yl)oxy)-1,1-difluoro-2-methylpropan-2-ol;
2-((2-(3,6-diazabicyclo[3.1.1]heptan-3-yl)-5-chloro-7-(thiazol-2-yl)benzo[d]oxazol-4-yl)oxy)-2,2-difluoroethan-1-ol;
2-(3,6-diazabicyclo[3.1.1]heptan-3-yl)-4-(1,1-difluoropropoxy)-7-(thiazol-2-yl)benzo[d]oxazole;
4-(benzo[d]oxazol-2-yldifluoromethoxy)-2-(3,6-diazabicyclo[3.1.1]heptan-3-yl)-7-(thiazol-2-yl)benzo[d]oxazole;
2-((2-(3,8-diazabicyclo[3.2.1]octan-3-yl)-7-(thiazol-2-yl)benzo[d]oxazol-4-yl)oxy)-2,2-difluoroethan-1-ol;
1-((2-(3,8-diazabicyclo[3.2.1]octan-3-yl)-7-(thiazol-2-yl)benzo[d]oxazol-4-yl)oxy)-1,1-difluoro-2-methylpropan-2-ol;
2-(3,6-diazabicyclo[3.1.1]heptan-3-yl)-4-((1,1-difluoro-3-(pyridin-3-yl)allyl)oxy)-7-(thiazol-2-yl)benzo[d]oxazole;
2-((2-(3,6-diazabicyclo[3.1.1]heptan-3-yl)-7-(thiazol-2-yl)benzo[d]oxazol-4-yl)oxy)-2,2-difluoro-N-(2-hydroxyethyl)-N-methylacetamide;
2-((2-(3,6-diazabicyclo[3.1.1]heptan-3-yl)-7-(thiazol-2-yl)benzo[d]oxazol-4-yl)oxy)-2,2-difluoro-N,N-dimethylacetamide;
2-((2-(3,6-diazabicyclo[3.1.1]heptan-3-yl)-7-(thiazol-2-yl)benzo[d]oxazol-4-yl)oxy)-2,2-difluoro-1-morpholinoethan-1-one;
2-((2-(3,6-diazabicyclo[3.1.1]heptan-3-yl)-7-(thiazol-2-yl)benzo[d]oxazol-4-yl)oxy)-2,2-difluoroacetamide;
2-((2-(3,6-diazabicyclo[3.1.1]heptan-3-yl)-7-(thiazol-2-yl)benzo[d]oxazol-4-yl)oxy)-2,2-difluoro-N-(2-hydroxyethyl)acetamide;
2-((2-(3,6-diazabicyclo[3.1.1]heptan-3-yl)-7-(thiazol-2-yl)benzo[d]oxazol-4-yl)oxy)-2,2-difluoro-1-(3-hydroxyazetidin-1-yl)ethan-1-one;
2-(3,6-diazabicyclo[3.1.1]heptan-3-yl)-7-(thiazol-2-yl)-5-((5-(trifluoromethyl) pyridin-2-yl)oxy)benzo[d]oxazole;
2-(3,6-diazabicyclo[3.1.1]heptan-3-yl)-4-cyclobutyl-7-(thiazol-2-yl)benzo[d]oxazole;
2-(3,6-diazabicyclo[3.1.1]heptan-3-yl)-4-(pyrrolidin-1-yl)-7-(thiazol-2-yl)benzo[d]oxazole;
(6-((2-(3,6-diazabicyclo[3.1.1]heptan-3-yl)-7-(thiazol-2-yl)benzo[d]oxazol-5-yl)oxy)pyridin-3-yl)methanol;
2-(3,6-diazabicyclo[3.1.1]heptan-3-yl)-7-(thiazol-2-yl)benzo[d]oxazole-5-carbonitrile;
2-(3,6-diazabicyclo[3.1.1]heptan-3-yl)-5-(pyridin-3-yl)-7-(thiazol-2-yl)benzo[d]oxazole; or
2-(3,6-diazabicyclo[3.1.1]heptan-3-yl)-5-cyclobutoxy-7-(thiazol-2-yl)benzo[d]oxazole.

\* \* \* \* \*